(12) United States Patent
Wang et al.

(10) Patent No.: US 8,916,702 B2
(45) Date of Patent: Dec. 23, 2014

(54) COMPOUNDS FOR THE TREATMENT OF HEPATITIS C

(71) Applicant: Bristol-Myers Squibb Company, Princeton, NJ (US)

(72) Inventors: Tao Wang, Farmington, CT (US); Paul Michael Scola, Glastonbury, CT (US); Zhongxing Zhang, Madison, CT (US); Zhiwei Yin, Glastonbury, CT (US); Qian Zhao, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/758,624

(22) Filed: Feb. 4, 2013

(65) Prior Publication Data
US 2013/0203758 A1    Aug. 8, 2013

Related U.S. Application Data

(60) Provisional application No. 61/595,239, filed on Feb. 6, 2012.

(51) Int. Cl.
| | | |
|---|---|---|
| C07D 251/52 | (2006.01) | |
| A61K 31/53 | (2006.01) | |
| A61P 31/14 | (2006.01) | |
| C07D 401/14 | (2006.01) | |
| C07D 513/04 | (2006.01) | |
| C07D 405/12 | (2006.01) | |
| C07D 403/12 | (2006.01) | |
| C07D 413/12 | (2006.01) | |
| C07D 417/12 | (2006.01) | |
| C07D 401/12 | (2006.01) | |

(52) U.S. Cl.
CPC ............ *C07D 513/04* (2013.01); *C07D 401/14* (2013.01); *C07D 405/12* (2013.01); *C07D 403/12* (2013.01); *C07D 413/12* (2013.01); *C07D 251/52* (2013.01); *C07D 417/12* (2013.01); *C07D 401/12* (2013.01)
USPC .......................................... 544/212; 514/245

(58) Field of Classification Search
CPC .............................. C07D 251/52; A61K 31/53
USPC .................................... 544/211, 212; 514/245
See application file for complete search history.

(56) References Cited

U.S. PATENT DOCUMENTS

| | | | |
|---|---|---|---|
| 4,816,064 | A | 3/1989 | Konno et al. |
| 7,163,943 | B2 | 1/2007 | Timmer et al. |
| 7,169,785 | B2 | 1/2007 | Timmer et al. |
| 8,445,490 | B2 | 5/2013 | Wang et al. |
| 2009/0286778 | A1 | 11/2009 | Combs et al. |
| 2011/0086858 | A1 | 4/2011 | Wang et al. |
| 2012/0093767 | A1 | 4/2012 | Wang et al. |
| 2012/0213729 | A1 | 8/2012 | Sun et al. |
| 2013/0078214 | A1 | 3/2013 | Wang et al. |
| 2013/0095063 | A1 | 4/2013 | Sun et al. |
| 2013/0095066 | A1 | 4/2013 | Wang et al. |

FOREIGN PATENT DOCUMENTS

| | | |
|---|---|---|
| KR | 2004-0033100 | 4/2004 |
| WO | WO 2002/079187 | 10/2002 |
| WO | WO 2004/026881 | 4/2004 |
| WO | WO 2004/089286 | 10/2004 |
| WO | WO 2008/057209 | 5/2008 |
| WO | WO 2009/091388 | 7/2009 |
| WO | WO 2009/132202 | 10/2009 |
| WO | WO 2010/036896 | 4/2010 |
| WO | WO 2010/118367 | 10/2010 |

*Primary Examiner* — Venkataraman Balasubramanian
(74) *Attorney, Agent, or Firm* — James Epperson

(57) ABSTRACT

The disclosure provides compounds of formula I, including pharmaceutically acceptable salts, as well as compositions and methods of using the compounds. The compounds have activity against hepatitis C virus (HCV) and may be useful in treating those infected with HCV.

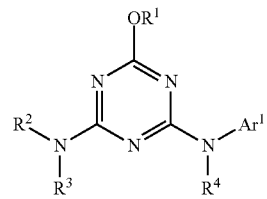

14 Claims, No Drawings

COMPOUNDS FOR THE TREATMENT OF HEPATITIS C

CROSS-REFERENCE TO RELATED APPLICATIONS

This application claims the benefit of U.S. Provisional Application Ser. No. 61/595,239 filed Feb. 6, 2012.

BACKGROUND OF THE INVENTION

The disclosure generally relates to the novel compounds of formula I including pharmaceutically acceptable salts, which have activity against hepatitis C virus (HCV) and are useful in treating those infected with HCV. The disclosure also relates to compositions and methods of using these compounds.

Hepatitis C virus (HCV) chronically infects an estimated 170 million people worldwide, with 3 to 4 million infected individuals in the United States alone (Boyer, N. and Marcellin, P. *J. Hepatology.* 2000, 32:98-112; Alter, M. J., et al. *Engl. J. Med.* 1999, 341:556-562). Prior to the mid 1990s, transfusion with infected blood products was the main route of HCV transmission. Following the introduction of blood screening methods, transmission via injection drug use became the primary risk factor. Chronic infection often leads to the development of severe liver complications, including fibrosis, cirrhosis, and hepatocellular carcinoma. HCV infection is also the leading cause of orthotopic liver transplantation in the United States. The degree to which disease progression is related to viral and cellular factors is not completely understood.

Considerable heterogeneity is found within the nucleotide and encoded amino acid sequence of the HCV genome (Simmonds, P. *J. Gen. Virology.* 2004, 85:3173-3188). Based on this sequence diversity, six major genotypes and multiple associated subtypes have been described. The genotypes of HCV differ in their worldwide distribution, and the clinical significance of the genetic heterogeneity of HCV remains elusive despite numerous studies of the possible effect of genotypes on pathogenesis and therapy.

Medical treatment for HCV is limited by the lack of a vaccine or approved therapies that specifically target the virus. Currently, patients undergo treatment with a combination of parenterally administered pegylated alpha-interferon and oral ribavirin. Genotype 1 HCV is the most difficult to treat and elimination of the virus (sustained virologic response) is achieved for only approximately 50% of patients (Fried, M. W. et al. *N. Engl. J. Med.* 2002, 347:975-982; Zeumzem, S, *Nature Clinical Practice.* 2008, 5:610-622). This poor treatment response, combined with often severe side effects induced by therapy, highlight a need for improved antiviral drugs with better efficacy and safety profiles.

HCV is a member of the Flaviviridae family of viruses with a single-stranded positive-sense RNA genome. Following infection of host cells, the 9.6 Kb genome is translated into a polyprotein precursor of approximately 3,000 amino acids (reviewed in Lindenbach, B. D. and Rice, C. M. *Nature.* 2005, 436:933-938; Moradpour, D, Penin, F., and Rice, C. M. *Nature Reviews.* 2007, 5:453-463). Post-translational processing by both cellular and viral proteases results in the generation of at least 10 separate viral proteins. The structural proteins (which by definition are found in mature virions) include core, E1, E2, and possibly p7, and originate from the amino-terminal region of the polyprotein. The core protein assembles into the viral nucleocapsid. The E1 and E2 glycoproteins form heterodimers that are found within the lipid envelope surrounding the viral particles, and mediate host cell receptor binding and entry of the virus into cells. It is unclear if p7 is a structural protein, and its role in replication has yet to be defined. However p7 is believed to form an ion channel in cellular membranes, preventing acidification of intracellular compartments in which virions are assembled, and it has been shown to be essential for viral replication and assembly. The nonstructural proteins NS2, NS3, NS4A, NS4B, NS5A, and NS5B are produced through maturational cleavages of the carboxy-terminal region of the polyprotein. NS2 along with the amino terminus of NS3 form the NS2-3 metalloprotease which cleaves at the NS2-NS3 junction. Additionally, NS2 is involved in assembly and egress of nascent virions. The NS3 protein contains both a serine protease in its amino-terminal region, and a nucleotide-dependent RNA helicase in its carboxy-terminal region. NS3 forms a heterodimer with the NS4A protein, constituting the active protease which mediates cleavages of the polyprotein downstream of NS3, both in cis, at the NS3-NS4A cleavage site, and in trans, for the remaining NS4A-NS4B, NS4B-NS5A, NS5A-NS5B sites. The complex formation of the NS3 protein with NS4A seems necessary to the processing events, enhancing the proteolytic efficiency at all of the sites. The NS3 protein also exhibits nucleoside triphosphatase and RNA helicase activities. The NS4B protein has been shown to be important for localization of HCV proteins into replication complexes in altered membranous structures within the cell. NS5B encodes an RNA-dependent RNA polymerase that is involved in the replication of HCV.

Subgenomic HCV replicons, containing the untranslated regions 5' and 3' to the coding sequence fused to the nonstructural proteins or the full-length polyprotein, are competent for translation, viral protein expression, and replication within cultured cells (Lohmann, V. et al. *Science.* 1999, 285:110-113; Moradpour, D, Penin, F., and Rice, C. M. *Nature Reviews.* 2007, 5:453-463). The replicon system has proven valuable for the identification of inhibitors targeting the nonstructural proteins associated with these functions. However, only limited subsets of HCV genotypes have been used to generate functional replicons.

Other systems have been used to study the biology of the HCV structural proteins that mediate the entry into host cells. For example, virus-like-particles made in recombinant baculovirus-infected cells with the HCV core, E1 and E2 proteins have also been used to study the function of the HCV E1 and E2 proteins (Barth, H., et al. *J. Biol. Chem.* 2003, 278:41003-41012). In addition, pseudotyping systems where the E1 and E2 glycoproteins are used to functionally replace the glycoproteins of retroviruses have been developed (Bartosch, B., Dubuisson, J. and Cosset, F.-L. *J. Exp. Med.* 2003, 197:633-642; Hsu, M. et al. *Proc. Natl. Acad. Sci. USA.* 2003, 100: 7271-7276). These systems yield HCV pseudoparticles that bind to and enter host cells in a manner which is believed to be analogous to the natural virus, thus making them a convenient tool to study the viral entry steps as well as to identify inhibitors block this process.

Recently, a full-length genotype 2a HCV clone, JFH1, was isolated and demonstrated the ability to replicate in vitro. Through repeated passage and adaptation in cell culture increased titers of infectious virus were produced (Lindenbach, B. D., et al. *Science.* 2005, 309:623-626; Wakita, T. et al. *Nature Med.* 2005, 11:791-796). In contrast to the HCV replicon or pseudotyping systems, the infectious virus is useful for studying the complete HCV replication cycle, including identifying inhibitors of not only the replication proteins, but those involved in early steps in virus infection (entry and uncoating) and production of progeny viruses (genome packaging, nucleocapsid assembly, virion envelopment and egress).

Triazines have been disclosed. See WO 2009/091388 and US 2009/0286778.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

One aspect of the invention is a compound of formula I

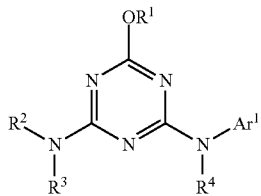

where
$R^1$ is alkyl, hydroxyalkyl, alkoxyalkyl, haloalkyl, cycloalkyl, hydroxycycloalkyl, alkoxycycloalkyl, halocycloalkyl, cycloalkenyl, indanyl, alkylcarbonyl, or benzyl wherein the benzyl moiety is substituted with 0-3 substituents selected from halo, alkyl, cycloalkyl, alkenyl, alkynyl, hydroxy, cyano, haloalkyl, alkoxy, and haloalkoxy;
$R^2$ is alkyl, cycloalkyl, $(Ar^2)$alkyl, $(Ar^2)$cycloalkyl, $((Ar^2)$cycloalkyl)alkyl, $((Ar^2)$alkyl)cycloalkyl, or $(((Ar^2)$alkyl)cycloalkyl)alkyl;
$R^3$ is hydrogen, alkyl or cycloalkyl;
$R^4$ is hydrogen, alkyl or cycloalkyl;
$R^5$ is

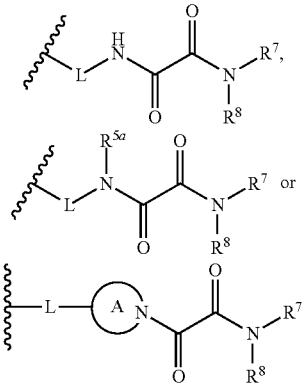

where ring A is a 4 to 7 membered alkylene ring;
$R^{5a}$ is alkyl or benzyl, and is substituted with 0-4 substituents selected from the group consisting of halo, alkyl, cycloalkyl, hydroxyalkyl, alkoxyalkyl, hydroxy, and alkoxy;
$R^6$ is hydrogen, alkyl or cycloalkyl;
$R^7$ is hydroxy, alkyloxy, phenoxy, $SO_2R^9$, $SO_2N(R^{10})(R^{11})$, CN, alkyl, cycloalkyl, benzocycloalkyl, bicyclicalkyl, (cycloalkyl)alkyl, (alkyl)cycloalkyl, ((alkyl))cycloalkyl)alkyl, or bridged bicycloalkyl, and is substituted with 0-4 substituents selected from the group consisting of halo, alkyl, cycloalkyl, benzocycloalkyl, bicyclicalkyl, hydroxyalkyl, alkoxyalkyl, hydroxy, alkoxy, benzyloxy, ether, cyclicether, benzocyclicether, bicyclicether, $CO_2R^9$, $NR^9CO_2R^{11}$, $N(R^{10})(R^{11})$, $CON(R^{10})(R^{11})$, $NR^9CON(R^{10})(R^{11})$, $SO_2N(R^{10})(R^{11})$, tetrahydrofuranyl, tetrahydropyranyl, $Ar^3$, $OAr^3$, $NR^{13}Ar^3$, $N(R^{13})COAr^3$, $N(R^{13})COAr^3$, and $N(R^{13})SO_2Ar^3$;
or $R^7$ is hydrogen, N-alkoxycarbonylpiperidinyl, piperidinonyl, or $Ar^4$;
$R^8$ is hydrogen, alkyl, or cycloalkyl, and alkyl or cycloalkyl is substituted with 0-4 substituents selected from the group consisting of halo, alkyl, cycloalkyl, fused bicyclic alkyl, bridged bicyclic alkyl, spiro bicyclic alkyl, hydroxyalkyl, alkoxyalkyl, hydroxy, alkoxy, benzyloxy, $CO_2R^9$, $N(R^{10})(R^{11})$, tetrahydrofuranyl, tetrahydropyranyl, $Ar^3$, $OAr^3$, $NR^{13}Ar^3$, $N(R^{13})COAr^3$, and $N(R^{13})SO_2Ar^3$;
or $R^8$ is substituted with biotin, flurescein or rhosamin;
or $R^7$ and $R^8$ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl or isoindolinyl, and is substituted with 0-2 substituents selected from alkyl, (aryl)alkyl, alkylcarbonyl, and alkoxycarbonyl;
$R^9$ is hydrogen, $Ar^3$, alkyl, cycloalkyl, hydroxyalkyl, alkoxyalkyl, ((hydroxyalkyl)alkoxy)alkoxy, or ((alkoxy)alkoxy)alkoxy;
$R^{10}$ is hydrogen, alkyl, cycloalkyl, alkylcarbonyl, alkoxycarbonyl, or $Ar^6$;
$R^{11}$ is hydrogen, alkyl, cycloalkyl, or $Ar^6$;
or $R^{10}$ and $R^{11}$ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl or isoindolinyl, and is substituted with 0-2 substituents selected from alkyl, (aryl)alkyl, alkylcarbonyl, and alkoxycarbonyl;
$R^{12}$ is hydrogen, alkyl, cycloalkyl, or $Ar^6$;
$R^{13}$ is hydrogen, alkyl, cycloalkyl, alkylcarbonyl, alkoxycarbonyl, or $Ar^6$, and is substituted with 0-3 substituents selected from cyano, halo, alkyl, alkyenyl, haloalkyl, alkoxy, and haloalkoxy, $N(R^{15})(R^{16})$, and alkylCO;
$R^{14}$ is hydrogen, alkyl, cycloalkyl, or $Ar^6$;
or $R^{13}$ and $R^{14}$ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl, or isoindolinyl, and is substituted with 0-2 substituents selected from alkyl, (aryl)alkyl, alkylcarbonyl, and alkoxycarbonyl;
$R^{15}$ is hydrogen, alkyl, cycloalkyl, alkylcarbonyl, or alkoxycarbonyl;
$R^{16}$ is hydrogen, alkyl, or cycloalkyl;
or $R^{15}$ and $R^{16}$ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl, or isoindolinyl, and is substituted with 0-2 substituents selected from alkyl, (aryl)alkyl, alkylcarbonyl, and alkoxycarbonyl;
L is alkylene, cycloalkylene, (cycloalkyl)alkyl, (alkyl)cycloalkyl, or alkyl(cycloalkyl)alkyl, and is substituted with 0-2 substituents selected from alkyl, alkoxy, hydroxy, $CO_2R^{12}$ and $CONR^{13}R^{14}$;
$Ar^1$ is phenyl substituted with 1 $CON(R^5)(R^6)$ and with 0-3 substituents selected from $Ar^3$, hydroxy, halo, alkyl, cycloalkyl, haloalkyl, alkoxy, and haloalkoxy;

Ar² is phenyl substituted with 0-3 substituents selected from halo, hydroxy, cyano, alkyl, cycloalkyl, alkenyl, alkynyl, haloalkyl, alkoxy, and haloalkoxy;

Ar³ is phenyl, biphenyl, terphenyl, naphthalenyl, furanyl, benzofuranyl, fluorenonyl, thiophenyl, benzothiophenyl, pyrrolyl, indolyl, indanyl, pyridinyl, quinolinyl, azaquinolinyl, isoquinolinyl, azaisoquinolinyl, quinoxalinyl, azaquinoxalinyl, pyrimidinyl, quinazolinyl, azaquinazolinyl, pyrazolyl, indazolyl, azaindolyl, oxazolyl, benzoxazolyl, azabenzoxazolyl, isoxazolyl, benzoisoxazolyl, azabenzoisoxazolyl, imidazolyl, benzoimidazolyl, azabenzoimidazolyl, thiazolyl, benzothiazolyl, azabenzothiazolyl, isothiazolyl, benzoisothiazolyl, azabenzoisothiazolyl, oxadiazolyl, thiadiazolyl, triazolyl, benzotriazolyl, azabenzotriazolyl, tetrazolyl, indolinyl, chromenonyl, or dibenzofuranyl, and is substituted with 0-5 substituents selected from cyano, halo, alkyl, cycloalkyl, alkenyl, alkynyl, haloalkyl, cycloalkyl, ($CO_2R^{12}$)alkyl, ($CO_2R^{12}$)alkenyl, ($CON(R^{13})(R^{14})$)alkyl, phenyl, hydroxy, alkoxy, $Ar^5$, $OAr^5$, $NR^{13}Ar^5$, $N(R^{13})COAr^5$, $N(R^{13})SO_2Ar^5$, alkylthio, haloalkoxy, haloalkylthio, alkylcarbonyl, $CO_2R^{12}$, $COR^{12}$, $SO_2R^{12}$, $CON(R^{13})(R^{14})$, $SO_2N(R^{13})(R^{14})$, $N(R^{13})(R^{14})$, amidine, urea, ketone, sulfone, sulfamide, and $PhCONHSO_2$; and said alkyl, alkenyl, cycloalkyl, alkynyl or $Ar^5$ is further substituted with 0-5 substituents selected from cyano, halo, alkyl, cycloalkyl, alkenyl, alkynyl, haloalkyl, cycloalkyl, ($CO_2R^{12}$)alkyl, ($CO_2R^{12}$)alkenyl, ($CON(R^{13})(R^{14})$)alkyl, phenyl, hydroxy, alkoxy, aryoxy, alkylthio, haloalkoxy, haloalkylthio, alkylcarbonyl, $CO_2R^{12}$, $COR^{12}$, $SO_2R^{12}$, $CON(R^{13})(R^{14})$, $SO_2N(R^{13})(R^{14})$, $N(R^{13})(R^{14})$, amidine, urea, ketone, sulfone, sulfamide, $PhCONHSO_2$ and $Ar^6$;

or Ar³ is phenyl substituted with 1 substituents selected from benzyl, phenoxy, pyridyloxy, pyrimidyloxy, tetrazolyloxy, thiazolyl, phenylpyrazolyl, methyloxadiazolyl, thiadiazolyl, triazolyl, methyltriazolyl, tetrazolyl, pyridinyl, dimethoxypyrimdinyl, indolyl, indolinyl, and isoindolinyl;

Ar⁴ is phenyl, indanyl, tetrahydronaphthyl, isochromanyl, benzodioxolyl, pyridinyl, pyrazolyl, imidazolyl, or triazolyl, and is substituted with 0-3 substituents selected from cyano, halo, alkyl, alkyenyl, haloalkyl, alkoxy, and haloalkoxy, $N(R^{13})(R^{14})$, and alkylCO;

Ar⁵ is phenyl, naphthalenyl, furanyl, benzofuranyl, azabenzofuranyl, thiophenyl, benzothiophenyl, azabenzothiophenyl, pyrrolyl, indolyl, azaindolyl, indanyl, pyridinyl, quinolinyl, azaquinolinyl, isoquinolinyl, azaisoquinolinyl, quinoxalinyl, azaquinoxalinyl, pyrimidinyl, quinazolinyl, azaquinazolinyl, pyrazolyl, indazolyl, azaindolyl, oxazolyl, benzoxazolyl, azabenzoxazolyl, isoxazolyl, benzoisoxazolyl, azabenzoisoxazolyl, imidazolyl, benzoimidazolyl, azabenzoimidazolyl, thiazolyl, benzothiazolyl, azabenzothiazolyl, isothiazolyl, benzoisothiazolyl, azabenzothiazolyl, oxadiazolyl, thiadiazolyl, triazolyl, benzotriazolyl, azabenzotriazolyl, tetrazolyl, or indolinyl, and is substituted with 0-5 substituents selected from cyano, halo, alkyl, cycloalkyl, alkenyl, alkynyl, haloalkyl, cycloalkyl, ($CO_2R^{12}$)alkyl, ($CO_2R^{12}$)alkenyl, ($CON(R^{13})(R^{14})$)alkyl, phenyl, hydroxy, alkoxy, $OAr^6$, $NR^{13}Ar^6$, alkylthio, haloalkoxy, haloalkylthio, alkylcarbonyl, $CO_2R^{12}$, $COR^{12}$, $SO_2R^{12}$, $CON(R^{13})(R^{14})$, $SO_2N(R^{13})(R^{14})$, $N(R^{13})(R^{14})$, amidine, urea, ketone, sulfone and sulfamide;

or Ar⁵ is substituted with biotin, flurescein or rhosamin;

Ar⁶ is phenyl, naphthalenyl, furanyl, benzofuranyl, azabenzofuranyl, thiophenyl, benzothiophenyl, azabenzothiophenyl, pyrrolyl, indolyl, azaindolyl, indanyl, pyridinyl, quinolinyl, azaquinolinyl, isoquinolinyl, azaisoquinolinyl, quinoxalinyl, azaquinoxalinyl, pyrimidinyl, quinazolinyl, azaquinazolinyl, pyrazolyl, indazolyl, azaindazolyl, oxazolyl, benzoxazolyl, azabenzoxazolyl, isoxazolyl, benzoisoxazolyl, azabenzoisoxazolyl, imidazolyl, benzoimidazolyl, azabenzoimidazolyl, thiazolyl, benzothiazolyl, azabenzothiazolyl, isothiazolyl, benzoisothiazolyl, azabenzothiazolyl, oxadiazolyl, thiadiazolyl, triazolyl, benzotriazolyl, azabenzotriazolyl, tetrazolyl, or indolinyl, and is substituted with 0-5 substituents selected from cyano, halo, alkyl, cycloalkyl, alkenyl, alkynyl, haloalkyl, cycloalkyl, phenyl, hydroxy, alkoxy, aryloxy, alkylthio, haloalkoxy, haloalkylthio, alkylcarbonyl, ester, ketone, amidine, urea, ketone, sulfone and sulfamide;

or Ar⁶ is substituted with biotin, flurescein or rhosamin;

or a pharmaceutically acceptable salt thereof.

Another aspect of the invention is a compound of formula I where:

R¹ is alkyl, hydroxyalkyl, alkoxyalkyl, haloalkyl, cycloalkyl, hydroxycycloalkyl, alkoxycycloalkyl, halocycloalkyl, cycloalkenyl, indanyl, alkylcarbonyl, or benzyl wherein the benzyl moiety is substituted with 0-3 substituents selected from halo, alkyl, haloalkyl, alkoxy, and haloalkoxy;

R² is alkyl, (Ar²)alkyl, (Ar²)cycloalkyl, ((Ar²)cycloalkyl)alkyl, ((Ar²)alkyl)cycloalkyl, or (((Ar²)alkyl)cycloalkyl)alkyl;

R³ is hydrogen or alkyl;

R⁴ is hydrogen or alkyl;

R⁵ is

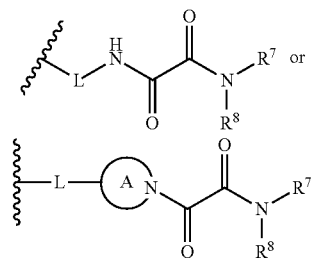

where ring A is a 4 to 7 membered alkylene ring substituted with L;

R⁶ is hydrogen or alkyl;

R⁷ is alkyl, cycloalkyl, (cycloalkyl)alkyl, (alkyl)cycloalkyl, ((alkyl))cycloalkyl)alkyl, or a bridged bicycloalkyl, and is substituted with 0-4 substituents selected from the group consisting of halo, alkyl, cycloalkyl, hydroxyalkyl, alkoxyalkyl, hydroxy, alkoxy, benzyloxy, $CO_2R^9$, $N(R^{10})(R^{11})$, tetrahydrofuranyl, tetrahydropyranyl, and $Ar^4$;

or R⁷ is hydrogen, N-alkoxycarbonylpiperidinyl, piperidinonyl, or $Ar^3$;

R⁸ is hydrogen or alkyl;

or R⁷ and R⁸ taken together with the nitrogen to which they are attached is azetidinyl, pyrrolidinyl, piperidinyl, piperazinyl, or morpholinyl, and is substituted with 0-2 substituents selected from alkyl, alkylcarbonyl, and alkoxycarbonyl;

R⁹ is hydrogen, alkyl, hydroxyalkyl, alkoxyalkyl, ((hydroxyalkyl)alkoxy)alkoxy, or ((alkoxy)alkoxy)alkoxy;

R¹⁰ is hydrogen, alkyl, cycloalkyl, alkylcarbonyl, or alkoxycarbonyl;

R¹¹ is hydrogen, alkyl;

or R¹⁰ and R¹¹ taken together with the nitrogen to which they are attached is azetidinyl, pyrrolidinyl, piperidinyl, piperazinyl, or morpholinyl, and is substituted with 0-2 substituents selected from alkyl, alkylcarbonyl, and alkoxycarbonyl;

R¹² is hydrogen or alkyl;

R¹³ is hydrogen, alkyl, cycloalkyl, alkylcarbonyl, or alkoxycarbonyl;

R¹⁴ is hydrogen or alkyl;

or R¹³ and R¹⁴ taken together with the nitrogen to which they are attached is azetidinyl, pyrrolidinyl, piperidinyl, piperazinyl, or morpholinyl, and is substituted with 0-2 substituents selected from alkyl, alkylcarbonyl, and alkoxycarbonyl;

L is alkylene, cycloalkylene, (cycloalkyl)alkyl, (alkyl)cycloalkyl, or alkyl(cycloalkyl)alkyl, and is substituted with 0-1 $CO_2R^{12}$ or $CONR^{13}R^{14}$;

$Ar^1$ is phenyl substituted with 1 $CON(R^5)(R^6)$ and with 0-3 substituents selected from halo, alkyl, haloalkyl, alkoxy, and haloalkoxy;

$Ar^2$ is phenyl substituted with 0-3 substituents selected from halo, alkyl, haloalkyl, alkoxy, and haloalkoxy;

$Ar^3$ is phenyl, indanyl, fluorenyl, biphenyl, terphenyl, pyridinyl, pyrazolyl, isoxazolyl, imidazolyl, thiazolyl, triazolyl, benzoxazolyl, indolinyl, or dibenzofuranyl, and is substituted with 0-3 substituents selected from cyano, halo, alkyl, alkenyl, haloalkyl, cycloalkyl, $(CO_2R^{12})$alkyl, $(CO_2R^{12})$alkenyl, $(CON(R^{13})(R^{14})))$alkyl, phenyl, hydroxy, alkoxy, haloalkoxy, alkylcarbonyl, $CO_2R^{12}$, $CON(R^{13})(R^{14})$, or $PhCONHSO_2$;

or $Ar^3$ is phenyl substituted with 1 substituents selected from benzyl, tetrazolyloxy, thiazolyl, phenylpyrazolyl, methyloxadiazolyl, thiadiazolyl, triazolyl, methyltriazolyl, tetrazolyl, pyridinyl, dimethoxypyrimdinyl; and $Ar^4$ is phenyl, indanyl, tetrahydronaphthyl, isochromanyl, benzodioxolyl, pyridinyl, pyrazolyl, or imidazolyl, triazolyl and is substituted with 0-3 substituents selected from cyano, halo, alkyl, alkenyl, haloalkyl, alkoxy, and haloalkoxy, $N(R^{13})(R^{14})$, and alkylCO;

or a pharmaceutically acceptable salt thereof.

Another aspect of the invention is a compound of formula I where R¹ is alkyl, hydroxyalkyl, alkoxyalkyl, haloalkyl, cycloalkyl, hydroxycycloalkyl, alkoxycycloalkyl, halocycloalkyl, cycloalkenyl, indanyl, alkylcarbonyl, or benzyl.

Another aspect of the invention is a compound of formula I where R¹ is alkyl, hydroxyalkyl, alkoxyalkyl, haloalkyl, cycloalkyl, hydroxycycloalkyl, alkoxycycloalkyl, halocycloalkyl, cycloalkenyl, benzyl, indanyl, or alkylcarbonyl.

Another aspect of the invention is a compound of formula I where R² is alkyl, cycloalkyl, $(Ar^2)$alkyl, $(Ar^2)$cycloalkyl, $((Ar^2)$cycloalkyl)alkyl, $((Ar^2)$alkyl)cycloalkyl, or $(((Ar^2)$alkyl)cycloalkyl)alkyl.

Another aspect of the invention is a compound of formula I where R² is alkyl, $(Ar^2)$alkyl, $(Ar^2)$cycloalkyl, $((Ar^2)$cycloalkyl)alkyl, $((Ar^2)$alkyl)cycloalkyl, or $(((Ar^2)$alkyl)cycloalkyl)alkyl.

Another aspect of the invention is a compound of formula I where R³ is hydrogen, alkyl or cycloalkyl.

Another aspect of the invention is a compound of formula I where R³ is hydrogen or alkyl.

Another aspect of the invention is a compound of formula I where R³ is hydrogen.

Another aspect of the invention is a compound of formula I where R⁴ is hydrogen, alkyl or cycloalkyl.

Another aspect of the invention is a compound of formula I where R⁴ is hydrogen or alkyl.

Another aspect of the invention is a compound of formula I where R⁴ is hydrogen.

Another aspect of the invention is a compound of formula I where R⁵ is

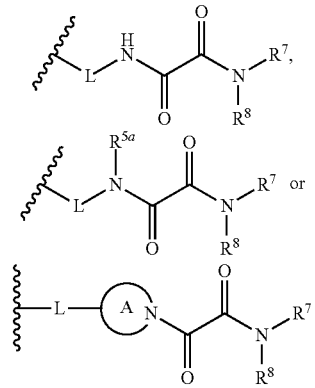

where ring A is a 4 to 7 membered alkylene ring substituted with L.

Another aspect of the invention is a compound of formula I where R⁵ is

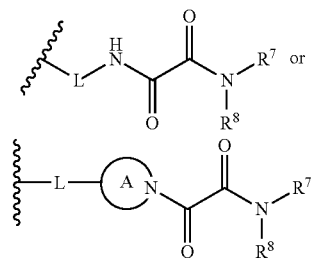

where ring A is a 4 to 7 membered alkylene ring substituted with L.

Another aspect of the invention is a compound of formula I where $R^{5a}$ is alkyl or benzyl, and is substituted with 0-4 substituents selected from the group consisting of halo, alkyl, cycloalkyl, hydroxyalkyl, alkoxyalkyl, hydroxy, and alkoxy.

Another aspect of the invention is a compound of formula I where R⁶ is hydrogen, alkyl or cycloalkyl.

Another aspect of the invention is a compound of formula I where R⁶ is hydrogen or alkyl.

Another aspect of the invention is a compound of formula I where R⁷ is hydroxy, alkyloxy, phenoxy, $SO_2R^9$, $SO_2N(R^{10})(R^{11})$, CN, alkyl, cycloalkyl, benzocycloalkyl, bicyclicalkyl, (cycloalkyl)alkyl, (alkyl)cycloalkyl, ((alkyl))cycloalkyl)alkyl, or a bridged bicycloalkyl, and is substituted with 0-4 substituents selected from the group consisting of halo, alkyl, cycloalkyl, benzocycloalkyl, bicyclicalkyl, hydroxyalkyl, alkoxyalkyl, hydroxy, alkoxy, benzyloxy, ether, cyclicether, benzocyclicether, bicyclicether, $CO_2R^9$, $NR^9CO_2R^{11}$, $N(R^{10})(R^{11})$, $CON(R^{10})(R^{11})$, $NR^9CON(R^{10})(R^{11})$, $SO_2N(R^{10})(R^{11})$, tetrahydrofuranyl, tetrahydropyranyl, $Ar^3$, $OAr^3$, $NR^{13}Ar^3$, $N(R^{13})COAr^3$, $N(R^{13})COAr^3$, and $N(R^{13})SO_2Ar^3$;

Another aspect of the invention is a compound of formula I where R⁷ is alkyl, cycloalkyl, (cycloalkyl)alkyl, (alkyl)cycloalkyl, ((alkyl))cycloalkyl)alkyl, or a bridged bicycloalkyl, and is substituted with 0-4 substituents selected from the group consisting of halo, alkyl, cycloalkyl, hydroxyalkyl, alkoxyalkyl, hydroxy, alkoxy, benzyloxy, $CO_2R^9$, $N(R^{10})(R^{11})$, tetrahydrofuranyl, tetrahydropyranyl, and $Ar^4$.

Another aspect of the invention is a compound of formula I where R⁷ is hydrogen, N-alkoxycarbonylpiperidinyl, piperidinonyl, or $Ar^4$.

Another aspect of the invention is a compound of formula I where $R^7$ is hydrogen, N-alkoxycarbonylpiperidinyl, piperidinonyl, or $Ar^3$.

Another aspect of the invention is a compound of formula I where $R^8$ is hydrogen, alkyl or cycloalkyl, and said alkyl or cycloalkyl is substituted with 0-4 substituents selected from the group consisting of halo, alkyl, cycloalkyl, fused bicyclic alkyl, bridged bicyclic alkyl, spiro bicyclic alkyl, hydroxyalkyl, alkoxyalkyl, hydroxy, alkoxy, benzyloxy, $CO_2R^9$, $N(R^{10})(R^{11})$, tetrahydrofuranyl, tetrahydropyranyl, $Ar^3$, $OAr^3$, $NR^{13}Ar^3$, $N(R^{13})COAr^3$, and $N(R^{13})SO_2Ar^3$.

Another aspect of the invention is a compound of formula I where $R^8$ is hydrogen or alkyl.

Another aspect of the invention is a compound of formula I where $R^8$ is substituted with biotin, flurescein or rhosamin.

Another aspect of the invention is a compound of formula I where $R^7$ and $R^8$ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl, or isoindolinyl, and is substituted with 0-2 substituents selected from alkyl, (aryl)alkyl, alkylcarbonyl, and alkoxycarbonyl.

Another aspect of the invention is a compound of formula I where $R^7$ and $R^8$ taken together with the nitrogen to which they are attached is azetidinyl, pyrrolidinyl, piperidinyl, piperazinyl, or morpholinyl, and is substituted with 0-2 substituents selected from alkyl, alkylcarbonyl, and alkoxycarbonyl.

Another aspect of the invention is a compound of formula I where $R^9$ is hydrogen, $Ar^3$, alkyl, cycloalkyl, hydroxyalkyl, alkoxyalkyl, ((hydroxyalkyl)alkoxy)alkoxy, or ((alkoxy)alkoxy)alkoxy.

Another aspect of the invention is a compound of formula I where $R^9$ is hydrogen, alkyl, hydroxyalkyl, alkoxyalkyl, ((hydroxyalkyl)alkoxy)alkoxy, or ((alkoxy)alkoxy)alkoxy.

Another aspect of the invention is a compound of formula I where $R^{10}$ is hydrogen, alkyl, cycloalkyl, alkylcarbonyl, alkoxycarbonyl, or $Ar^6$.

Another aspect of the invention is a compound of formula I where $R^{10}$ is hydrogen, alkyl, cycloalkyl, alkylcarbonyl, or alkoxycarbonyl.

Another aspect of the invention is a compound of formula I where $R^{11}$ is hydrogen, alkyl, cycloalkyl, or $Ar^6$.

Another aspect of the invention is a compound of formula I where $R^{11}$ is hydrogen or alkyl.

Another aspect of the invention is a compound of formula I where $R^{10}$ and $R^{11}$ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl, or isoindolinyl, and is substituted with 0-2 substituents selected from alkyl, (aryl)alkyl, alkylcarbonyl, and alkoxycarbonyl.

Another aspect of the invention is a compound of formula I where $R^{10}$ and $R^{11}$ taken together with the nitrogen to which they are attached is azetidinyl, pyrrolidinyl, piperidinyl, piperazinyl, or morpholinyl, and is substituted with 0-2 substituents selected from alkyl, alkylcarbonyl, and alkoxycarbonyl.

Another aspect of the invention is a compound of formula I where $R^{12}$ is hydrogen, alkyl, cycloalkyl, or $Ar^6$.

Another aspect of the invention is a compound of formula I where $R^{12}$ is hydrogen or alkyl.

Another aspect of the invention is a compound of formula I where $R^{13}$ is hydrogen, alkyl, cycloalkyl, alkylcarbonyl, alkoxycarbonyl, or $Ar^6$ and is substituted with 0-3 substituents selected from cyano, halo, alkyl, alkyenyl, haloalkyl, alkoxy, haloalkoxy, $N(R^{15})(R^{16})$, and alkylCO.

Another aspect of the invention is a compound of formula I where $R^{13}$ is hydrogen, alkyl, cycloalkyl, alkylcarbonyl, or alkoxycarbonyl.

Another aspect of the invention is a compound of formula I where $R^{14}$ is hydrogen, alkyl, cycloalkyl, or $Ar^6$.

Another aspect of the invention is a compound of formula I where $R^{14}$ is hydrogen or alkyl;

Another aspect of the invention is a compound of formula I where $R^{13}$ and $R^{14}$ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl, or isoindolinyl, and is substituted with 0-2 substituents selected from alkyl, (aryl)alkyl, alkylcarbonyl, and alkoxycarbonyl.

Another aspect of the invention is a compound of formula I where $R^{13}$ and $R^{14}$ taken together with the nitrogen to which they are attached is azetidinyl, pyrrolidinyl, piperidinyl, piperazinyl, or morpholinyl, and is substituted with 0-2 substituents selected from alkyl, alkylcarbonyl, and alkoxycarbonyl.

Another aspect of the invention is a compound of formula I where $R^{15}$ is hydrogen, alkyl, cycloalkyl, alkylcarbonyl, or alkoxycarbonyl.

Another aspect of the invention is a compound of formula I where $R^{16}$ is hydrogen, alkyl or cycloalkyl.

Another aspect of the invention is a compound of formula I where $R^{15}$ and $R^{16}$ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl, or isoindolinyl, and is substituted with 0-2 substituents selected from alkyl, (aryl)alkyl, alkylcarbonyl, and alkoxycarbonyl.

Another aspect of the invention is a compound of formula I where L is alkylene, cycloalkylene, (cycloalkyl)alkyl, (alkyl)cycloalkyl, or alkyl(cycloalkyl)alkyl, and is substituted with 0-2 substituents selected from alkyl, alkoxy, hydroxy, $CO_2R^{12}$ or $CONR^{13}R^{14}$.

Another aspect of the invention is a compound of formula I where L is alkylene, cycloalkylene, (cycloalkyl)alkyl, (alkyl)cycloalkyl, or alkyl(cycloalkyl)alkyl, and is substituted with 0-1 $CO_2R^{12}$ or $CONR^{13}R^{14}$.

Another aspect of the invention is a compound of formula I where $Ar^1$ is phenyl substituted with 1 $CON(R^5)(R^6)$ and with 0-3 substituents selected from $Ar^3$, hydroxy, halo, alkyl, cycloalkyl, haloalkyl, alkoxy, and haloalkoxy.

Another aspect of the invention is a compound of formula I where $Ar^2$ is phenyl substituted with 0-3 substituents selected from halo, alkyl, haloalkyl, alkoxy, and haloalkoxy.

Another aspect of the invention is a compound of formula I where $Ar^1$ is fluorophenyl substituted with 1 $CON(R^5)(R^6)$ and with 0-3 substituents selected from $Ar^3$, hydroxy, halo, alkyl, cycloalkyl, haloalkyl, alkoxy, and haloalkoxy.

Another aspect of the invention is a compound of formula I where $Ar^2$ is phenyl substituted with 0-3 substituents selected from halo, hydroxy, cyano, alkyl, cycloalkyl, alkenyl, alkynyl, haloalkyl, alkoxy, and haloalkoxy.

Another aspect of the invention is a compound of formula I where $Ar^2$ is phenyl substituted with 0-3 substituents selected from halo, alkyl, haloalkyl, alkoxy, and haloalkoxy.

Another aspect of the invention is a compound of formula I where $Ar^3$ is phenyl, biphenyl, terphenyl, naphthalenyl, furanyl, benzofuranyl, fluorenyl, fluorenonyl, thiophenyl, benzothiophenyl, pyrrolyl, indolyl, indanyl, pyridinyl, quinolinyl, azaquinolinyl, isoquinolinyl, azaisoquinolinyl, quinoxalinyl, azaquinoxalinyl, pyrimidinyl, quinazolinyl, azaquinazolinyl, pyrazolyl, indazolyl, azaindolyl, oxazolyl, benzoxazolyl, azabenzoxazolyl, isoxazolyl, benzoisoxazolyl, azabenzoisoxazolyl, imidazolyl, benzoimidazolyl, azabenzoimidazolyl, thiazolyl, benzothiazolyl, azabenzothiazolyl, isothiazolyl, benzoisothiazolyl, azabenzoisothiazolyl, oxadiazolyl, thiadiazolyl, triazolyl, benzotriazolyl, azabenzotriazolyl, tetrazolyl, indolinyl, chromenonyl, or dibenzofuranyl, and is substituted with 0-5 substituents selected from cyano, halo, alkyl, cycloalkyl, alkenyl, alkynyl, haloalkyl, cycloalkyl, $(CO_2R^{12})$alkyl, $(CO_2R^{12})$alkenyl, $(CON(R^{13})(R^{14}))$alkyl, phenyl, hydroxy, alkoxy, $Ar^5$, $OAr^5$, $NR^{13}$, $Ar^5$, $N(R^{13})COAr^5$, $N(R^{13})SO_2Ar^5$, alkylthio, haloalkoxy, haloalkylthio, alkylcarbonyl, $CO_2R^{12}$, $COR^{12}$, $SO_2R^{12}$, $CON(R^{13})(R^{14})$, $SO_2N(R^{13})(R^{14})$, $N(R^{13})(R^{14})$, amidine, urea, ketone, sulfone, sulfamide, and $PhCONHSO_2$; and said alkyl, alkenyl, cycloalkyl, alkynyl or $Ar^5$ is further substituted with 0-5 substituents selected from cyano, halo, alkyl, cycloalkyl, alkenyl, alkynyl, haloalkyl, cycloalkyl, $(CO_2R^{12})$alkyl, $(CO_2R^{12})$alkenyl, $(CON(R^{13})(R^{14}))$alkyl, phenyl, hydroxy, alkoxy, aryoxy, alkylthio, haloalkoxy, haloalkylthio, alkylcarbonyl, $CO_2R^{12}$, $COR^{12}$, $SO_2R^{12}$, $CON(R^{13})(R^{14})$, $SO_2N(R^{13})(R^{14})$, $N(R^{13})(R^{14})$, amidine, urea, ketone, sulfone, sulfamide, $PhCONHSO_2$ and $Ar^6$.

Another aspect of the invention is a compound of formula I where $Ar^3$ is phenyl, indanyl, fluorenyl, biphenyl, terphenyl, pyridinyl, pyrazolyl, isoxazolyl, imidazolyl, thiazolyl, triazolyl, benzoxazolyl, indolinyl, or dibenzofuranyl, and is substituted with 0-3 substituents selected from cyano, halo, alkyl, alkenyl, haloalkyl, cycloalkyl, $(CO_2R^{12})$alkyl, $(CO_2R^{12})$alkenyl, $(CON(R^{13})(R^{14}))$alkyl, phenyl, hydroxy, alkoxy, haloalkoxy, alkylcarbonyl, $CO_2R^{12}$, $CON(R^{13})(R^{14})$, or $PhCONHSO_2$.

Another aspect of the invention is a compound of formula I where $Ar^3$ is phenyl substituted with 1 substituents selected from benzyl, phenoxy, pyridyloxy, pyrimidyloxy, tetrazolyloxy, thiazolyl, phenylpyrazolyl, methyloxadiazolyl, thiadiazolyl, triazolyl, methyltriazolyl, tetrazolyl, pyridinyl, dimethoxypyrimdinyl, indolyl, indolinyl, and isoindolinyl.

Another aspect of the invention is a compound of formula I where $Ar^3$ is phenyl substituted with 1 substituents selected from benzyl, tetrazolyloxy, thiazolyl, phenylpyrazolyl, methyloxadiazolyl, thiadiazolyl, triazolyl, methyltriazolyl, tetrazolyl, pyridinyl, and dimethoxypyrimdinyl.

Another aspect of the invention is a compound of formula I where $Ar^4$ is phenyl, indanyl, tetrahydronaphthyl, isochromanyl, benzodioxolyl, pyridinyl, pyrazolyl, imidazolyl, or triazolyl, and is substituted with 0-3 substituents selected from cyano, halo, alkyl, alkyenyl, haloalkyl, alkoxy, and haloalkoxy, $N(R^{13})(R^{14})$, and alkylCO.

Another aspect of the invention is a compound of formula I where $Ar^5$ is phenyl, naphthalenyl, furanyl, benzofuranyl, azabenzofuranyl, thiophenyl, benzothiophenyl, azabenzothiophenyl, pyrrolyl, indolyl, azaindolyl, indanyl, pyridinyl, quinolinyl, azaquinolinyl, isoquinolinyl, azaisoquinolinyl, quinoxalinyl, azaquinoxalinyl, pyrimidinyl, quinazolinyl, azaquinazolinyl, pyrazolyl, indazolyl, azaindazolyl, oxazolyl, benzoxazolyl, azabenzoxazolyl, isoxazolyl, benzoisoxazolyl, azabenzoisoxazolyl, imidazolyl, benzoimidazolyl, azabenzoimidazolyl, thiazolyl, benzothiazolyl, azabenzothiazolyl, isothiazolyl, benzoisothiazolyl, azabenzothiazolyl, oxadiazolyl, thiadiazolyl, triazolyl, benzotriazolyl, azabenzotriazolyl, tetrazolyl, or indolinyl, and is substituted with 0-5 substituents selected from cyano, halo, alkyl, cycloalkyl, alkenyl, alkynyl, haloalkyl, cycloalkyl, $(CO_2R^{12})$alkyl, $(CO_2R^{12})$alkenyl, $(CON(R^{13})(R^{14}))$alkyl, phenyl, hydroxy, alkoxy, $OAr^6$, $NR^{13}Ar^6$, alkylthio, haloalkoxy, haloalkylthio, alkylcarbonyl, $CO_2R^{12}$, $COR^{12}$, $SO_2R^{12}$, $CON(R^{13})(R^{14})$, $SO_2N(R^{13})(R^{14})$, $N(R^{13})(R^{14})$, amidine, urea, ketone, sulfone and sulfamide.

Another aspect of the invention is a compound of formula I where $Ar^5$ is substituted with biotin, flurescein, or rhosamin.

Another aspect of the invention is a compound of formula I where $Ar^6$ is phenyl, naphthalenyl, furanyl, benzofuranyl, azabenzofuranyl, thiophenyl, benzothiophenyl, azabenzothiophenyl, pyrrolyl, indolyl, azaindolyl, indanyl, pyridinyl, quinolinyl, azaquinolinyl, isoquinolinyl, azaisoquinolinyl, quinoxalinyl, azaquinoxalinyl, pyrimidinyl, quinazolinyl, azaquinazolinyl, pyrazolyl, indazolyl, azaindazolyl, oxazolyl, benzoxazolyl, azabenzoxazolyl, isoxazolyl, benzoisoxazolyl, azabenzoisoxazolyl, imidazolyl, benzoimidazolyl, azabenzoimidazolyl, thiazolyl, benzothiazolyl, azabenzothiazolyl, isothiazolyl, benzoisothiazolyl, azabenzothiazolyl, oxadiazolyl, thiadiazolyl, triazolyl, benzotriazolyl, azabenzotriazolyl, tetrazolyl, or indolinyl, and is substituted with 0-5 substituents selected from cyano, halo, alkyl, cycloalkyl, alkenyl, alkynyl, haloalkyl, cycloalkyl, phenyl, hydroxy, alkoxy, aryloxy, alkylthio, haloalkoxy, haloalkylthio, alkylcarbonyl, ester, ketone, amidine, urea, ketone, sulfone and sulfamide Another aspect of the invention is a compound of formula I where $Ar^6$ is substituted with biotin, flurescein, or rhosamin;

Another aspect of the invention is a compound of formula I where $R^1$ is haloalkyl or a pharmaceutically acceptable salt thereof.

Another aspect of the invention is a compound of formula I where $R^1$ is trifluoroethyl or a pharmaceutically acceptable salt thereof.

Another aspect of the invention is a compound of formula I where $R^1$ is alkyl or a pharmaceutically acceptable salt thereof.

Another aspect of the invention is a compound of formula I where $R^1$ is phenylalkyl substituted with 0-5 halo, alkyl, alkenyl, haloalkyl, alkoxy or haloalkoxy or a pharmaceutically acceptable salt thereof.

Another aspect of the invention is a compound of formula I where $R^1$ is benzyl substituted with 0-5 halo, alkyl, alkenyl, haloalkyl, alkoxy or haloalkoxy or a pharmaceutically acceptable salt thereof.

Another aspect of the invention is a compound of formula I where $R^2$ is $(Ar^2)$alkyl or $(Ar^2)$cycloalkyl, or a pharmaceutically acceptable salt thereof.

Another aspect of the invention is a compound of formula I where $R^2$ is $(Ar^2)$alkyl or $(Ar^2)$cycloalkyl, or a pharmaceutically acceptable salt thereof.

Another aspect of the invention is a compound of formula I where $R^7$ is hydroxy, alkyloxy, phenoxy, $SO_2R^9$, $SO_2N(R^{10})(R^{11})$, CN, alkyl, cycloalkyl, benzocycloalkyl, bicyclicalkyl, (cycloalkyl)alkyl, (alkyl)cycloalkyl, ((alkyl))cycloalkyl)alkyl, or a bridged bicycloalkyl, and is substituted with 0-4 substituents selected from the group consisting of halo, alkyl, cycloalkyl, benzocycloalkyl, bicyclicalkyl, hydroxyalkyl, alkoxyalkyl, hydroxy, alkoxy, benzyloxy, ether, cyclicether, benzocyclicether, bicyclicether, $CO_2R^9$, $NR^9CO_2R^{11}$, $N(R^{10})(R^{11})$, $CON(R^{10})(R^{11})$, $NR^9CON(R^{10})(R^{11})$, $SO_2N(R^{10})(R^{11})$, tetrahydrofuranyl, tetrahydropyranyl, $Ar^3$, $OAr^3$, $NR^{13}Ar^3$, $N(R^{13})COAr^3$, $N(R^{13})COAr^3$, and $N(R^{13})SO_2Ar^3$.

Another aspect of the invention is a compound of formula I where $R^7$ is $Ar^4$ or a pharmaceutically acceptable salt thereof.

Another aspect of the invention is a compound of formula I where L is

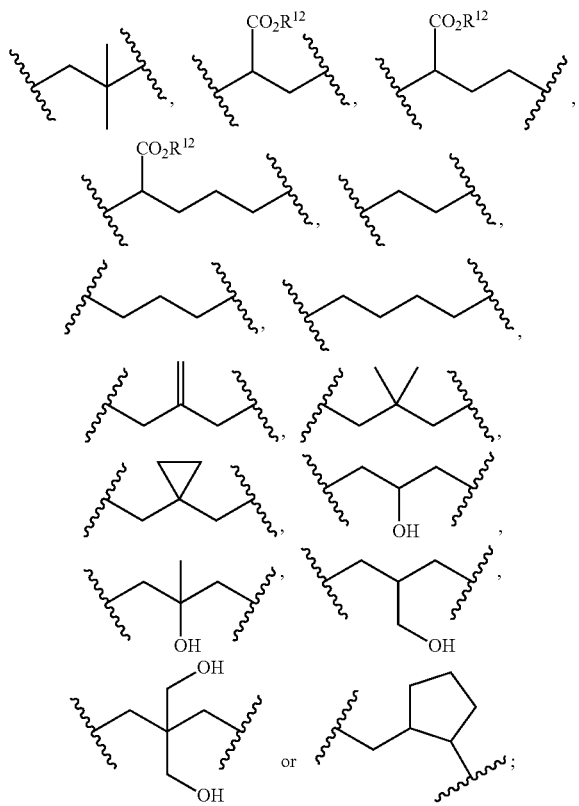

or a pharmaceutically acceptable salt thereof.

Another aspect of the invention is a compound of formula I where $Ar^1$ is phenyl para-substituted with 1 $CON(R^5)(R^6)$, or a pharmaceutically acceptable salt thereof.

Another aspect of the invention is a compound of formula I where $Ar^1$ is fluoro phenyl para-substituted with 1 $CON(R^5)(R^6)$, or a pharmaceutically acceptable salt thereof.

Any scope of any variable, including $R^1$, $R^2$, $R^3$, $R^4$, $R^5$, $R^{5a}$, $R^6$, $R^7$, $R^8$, $R^9$, $R^{10}$, $R^{11}$, $R^{12}$, $R^{13}$, $R^{14}$, $R^{15}$, $R^{16}$, L, $Ar^1$, $Ar^2$, $Ar^3$, $Ar^4$, $Ar^5$, and $Ar^6$ can be used independently with the scope of any other instance of a variable.

Unless specified otherwise, these terms have the following meanings. "Halo" means fluoro, chloro, bromo, or iodo. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 8 carbons. "Benzocycloalkyl" means a monocyclic ring system composed of 3 to 8 carbons fused to a benzene ring system. "Bicycloalkyl" means a fused bicyclic ring system wherein each ring is composed of 3 to 7 carbons, that is a [(3-7).0.(3-7)] system. "Bridged bicycloalkyl" means a [(3-7).(1-3).(3-7)] ring system. "Spirocycloalkyl" means a spirocyclic ring system wherein each ring is composed of 3 to 7 carbons. "Alkylene" means a straight or branched divalent alkyl group. "Alkenylene" means a straight or branched divalent alkyl group with at least one double bond. "Cycloalkylene" means a divalent cycloalkane moiety composed of 3 to 7 carbons and includes gem-divalency (for example 1,1-cyclopropanediyl) as well as non-gem-divalency (for example, 1,4-cyclohexanediyl). "Alkylidinyl" means a divalent alkene substituent where the divalency occurs on the same carbon of the alkene. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Phenylene is a divalent benzene ring. "1,4-Phenylene" means 1,4-benzenediyl with respect to regiochemistry for the divalent moiety. Parenthetic and multiparenthetic terms are intended to clarify bonding relationships to those skilled in the art. For example, a term such as ((R)alkyl) means an alkyl substituent further substituted with the substituent R.

The substituents described above may be attached at any suitable point of attachment unless otherwise specified. However, it is understood that the compounds encompassed by the present invention are those that are chemically stable as understood by those skilled in the art. Additionally, the compounds encompassed by the present disclosure are those that are suitably stable for use as a pharmaceutical agent.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the structures below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Infection Assays.

HCV pseudoparticles, produced using standardized methodology (Bartosch, B., Dubuisson, J. and Cosset, F.-L. *J. Exp. Med.* 2003, 197:633-642) were made via a liposome-based transfection procedure of 293T cells with plasmids expressing the murine leukemia virus capsid and polymerase proteins, an MLV genome encoding the luciferase reporter gene, and envelope glycoproteins from either HCV or vesicular stomatitis virus (VSV). The genotype 1a HCV E1 and E2 envelope coding sequences were derived from the H77C isolate (GenBank accession number AF009606). Media containing pseudoparticles was collected 3 days following transfection, filtered, and stored at −20° C. as a viral stock. Infections were performed in 384-well plates by mixing pseudovirus with $1 \times 10^4$ Huh7 cells/well in the presence or absence of test inhibitors, followed by incubation at 37° C. Luciferase activity, reflecting the degree of entry of the pseudoparticles into host cells, was measured 2 days after infection. The specificity of the compounds for inhibiting HCV was determined by evaluating inhibition of VSV pseudoparticle infection.

Compounds and Data Analysis.

Test compounds were serially diluted 3-fold in dimethyl sulfoxide (DMSO) to give a final concentration range in the assay of 50.0 μM to 0.04 μM. Maximum activity (100% of control) and background were derived from control wells containing DMSO but no inhibitor or from uninfected wells, respectively. The individual signals in each of the compound test wells were then divided by the averaged control values after background subtraction and multiplied by 100% to determine percent activity. Assays were performed in duplicate and average $EC_{50}$ values (reflecting the concentration at which 50% inhibition of virus replication was achieved) were calculated. Compound $EC_{50}$ data is expressed as A=0.01≤10 nM; B=10-1000 nM. Representative data for compounds are reported in Table 1.

TABLE 1
| Compound | Structure | EC$_{50}$ | Activity |
|---|---|---|---|
| 1001 | 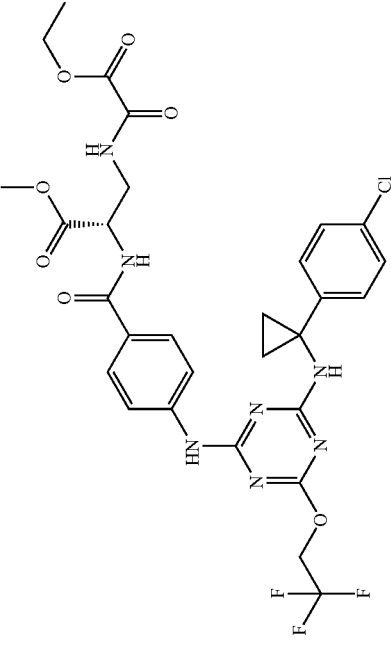 Chiral | | B |
| 1002 | 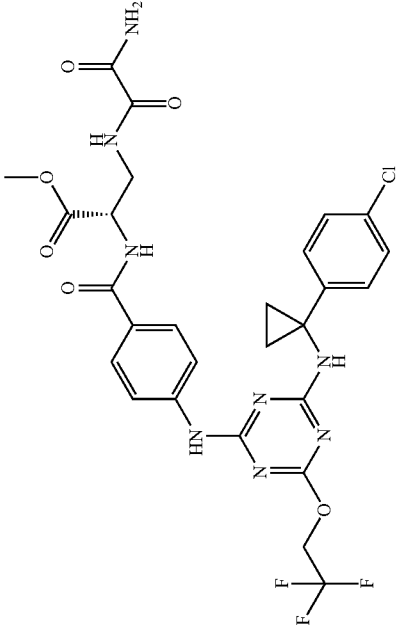 Chiral | 2.11 | A |

TABLE 1-continued
| Compound | Structure | EC$_{50}$ | Activity |
|---|---|---|---|
| 1003 | 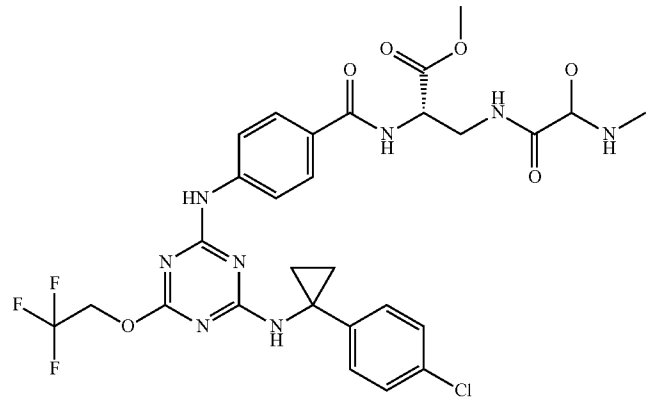 Chiral | | A |
| 1004 | 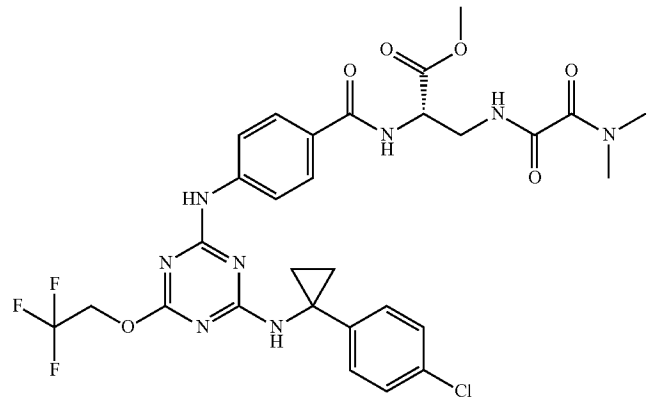 Chiral | 4.74 | A |

TABLE 1-continued
| Compound | Structure | | EC$_{50}$ | Activity |
|---|---|---|---|---|
| 1005 | Chiral 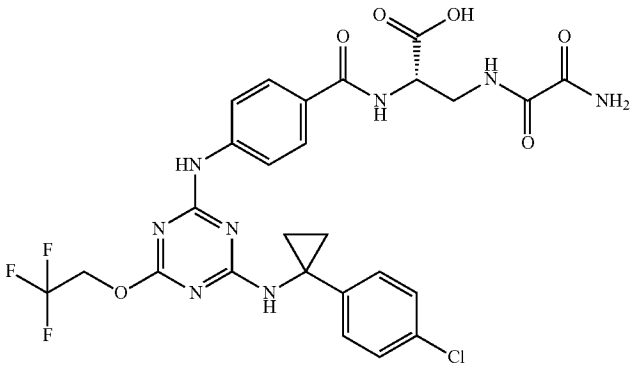 | | | A |
| 1006 | Chiral 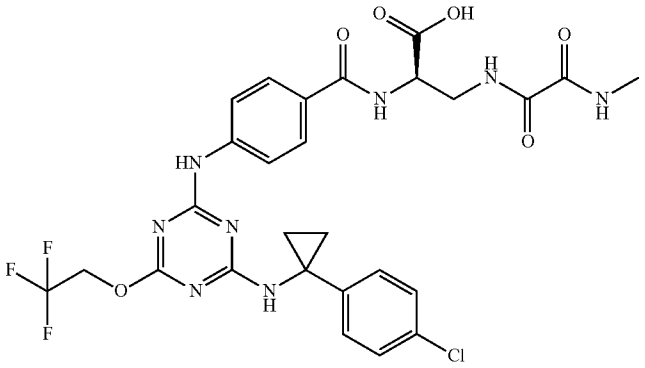 | | 0.69 | A |

TABLE 1-continued
| Compound | Structure | EC$_{50}$ | Activity |
|---|---|---|---|
| 1007 | Chiral 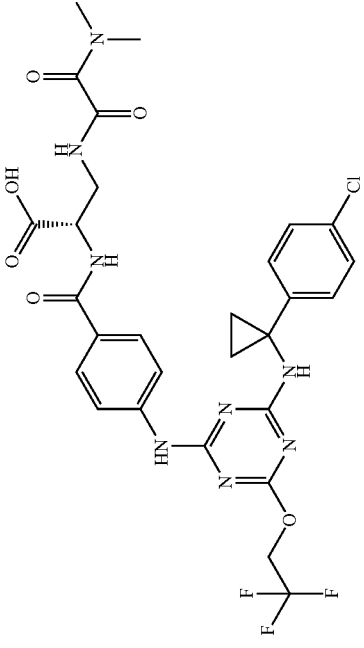 | | A |
| 1008 | 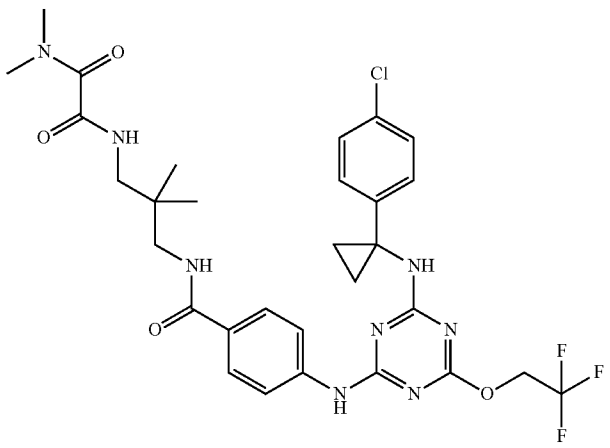 [SMILES: CN(C)C(=O)C(=O)NCC(C)(C)CNC(=O)c1ccc(Nc2nc(NC3(c4ccc(Cl)cc4)CC3)nc(OCC(F)(F)F)n2)cc1] | | A |

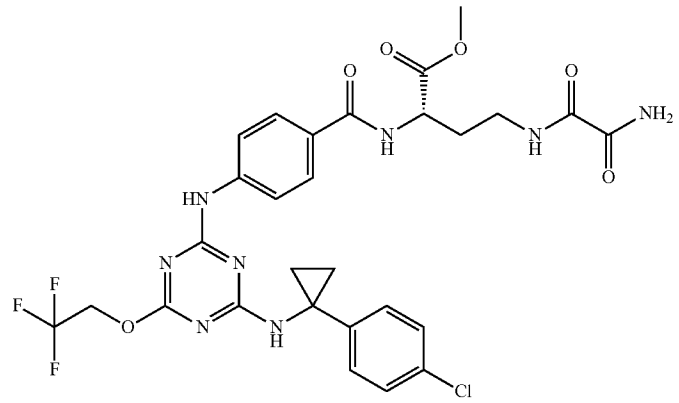

| Compound | Structure | EC$_{50}$ | Activity |
|---|---|---|---|
| 1011 | 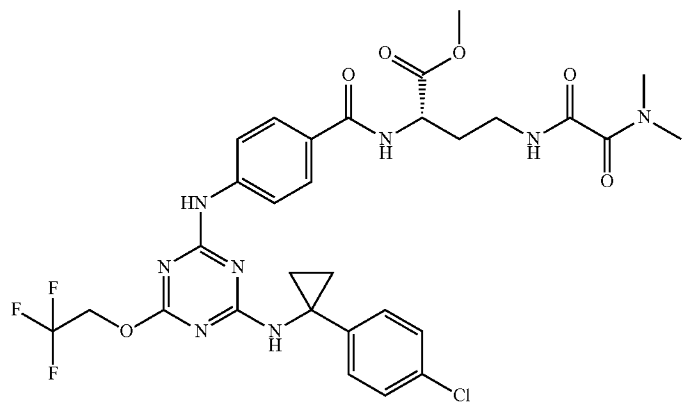 | | A |
| 1012 | 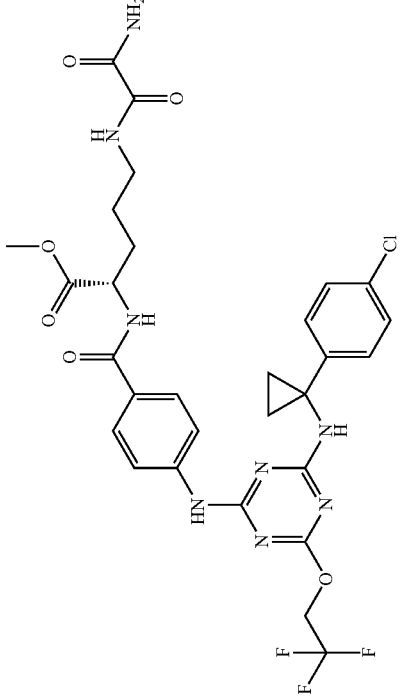 | | A |

TABLE 1-continued
| Compound | Structure | EC$_{50}$ | Activity |
|---|---|---|---|
| 1013 | 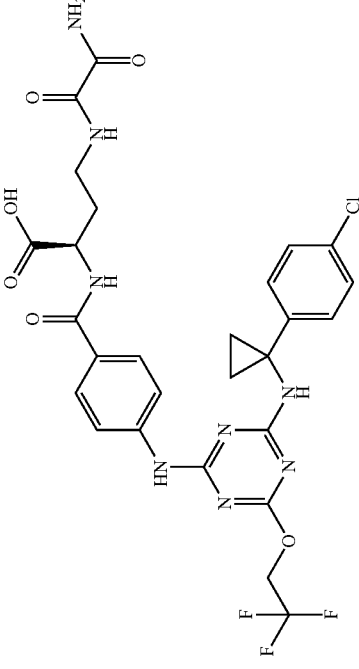 Chiral | | A |
| 1014 | 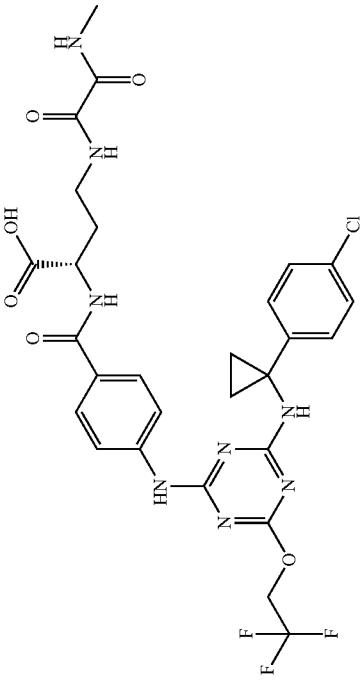 Chiral | | A |

TABLE 1-continued
| Compound | Structure | EC$_{50}$ | Activity |
|---|---|---|---|
| 1015 | 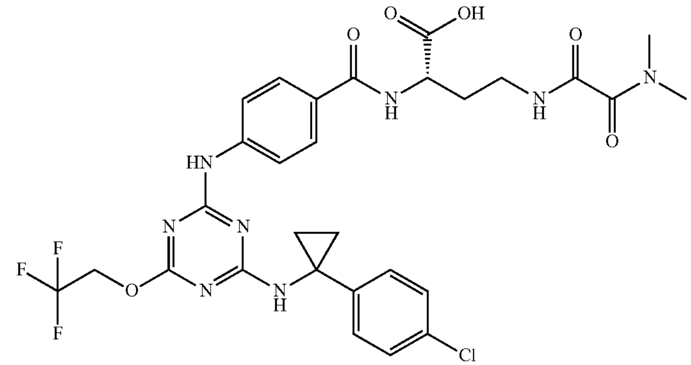 | | A |
| 1016 | 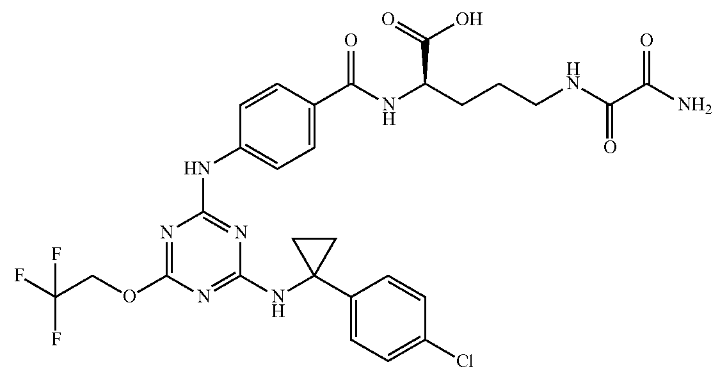 | | A |

TABLE 1-continued

| Compound | Structure | EC$_{50}$ | Activity |
|---|---|---|---|
| 1017 | (structure) | | A |
| 1018 | (structure) | | A |

TABLE 1-continued
| Compound | Structure | EC$_{50}$ | Activity |
|---|---|---|---|
| 1019 | 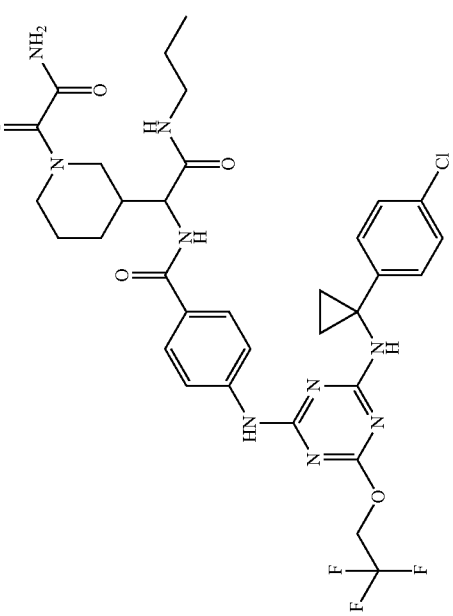 | | A |
| 1020 | 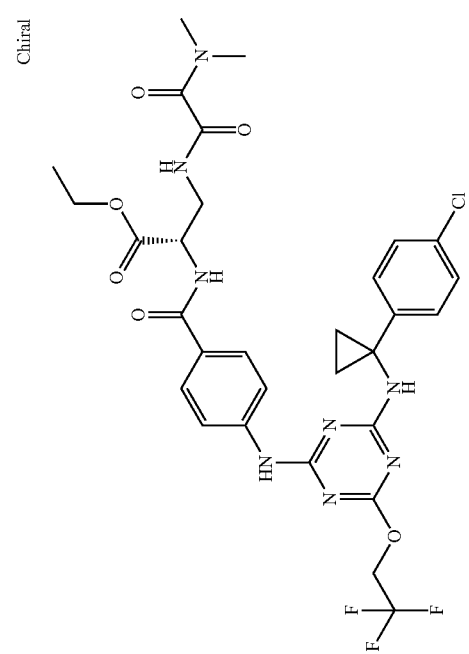 Chiral | | A |

TABLE 1-continued
| Compound | Structure | EC$_{50}$ | Activity |
|---|---|---|---|
| 1021 | 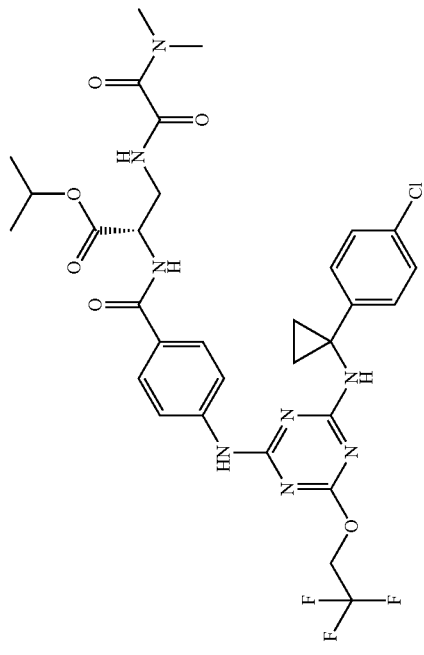 Chiral | | A |
| 1022 | 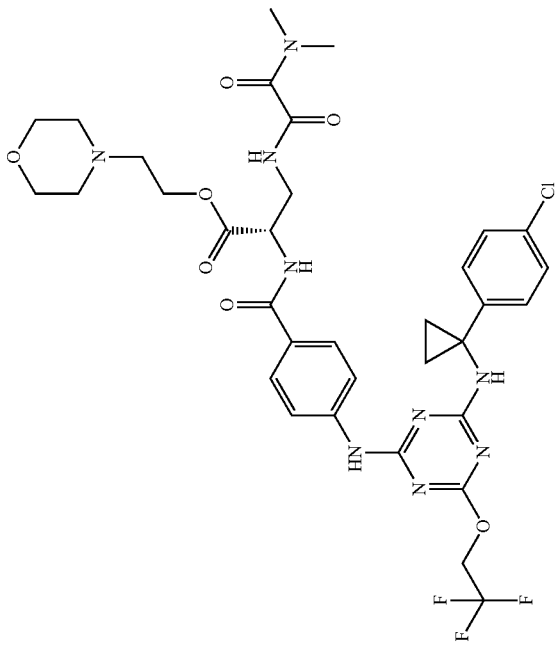 Chiral | 7.11 | A |

| Compound | Structure | EC$_{50}$ | Activity |
|---|---|---|---|
| 1023 | 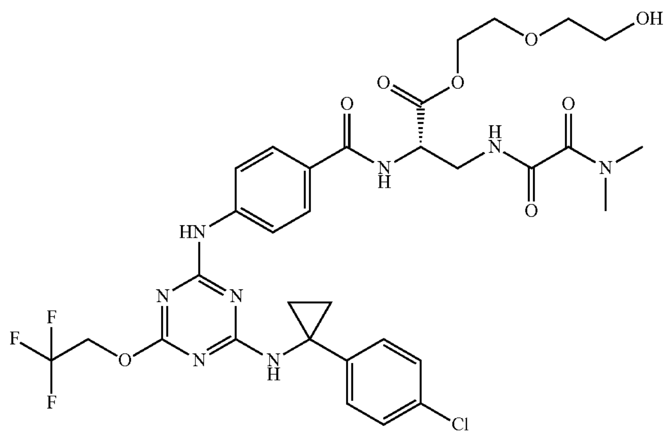 | | A |
| 1024 | 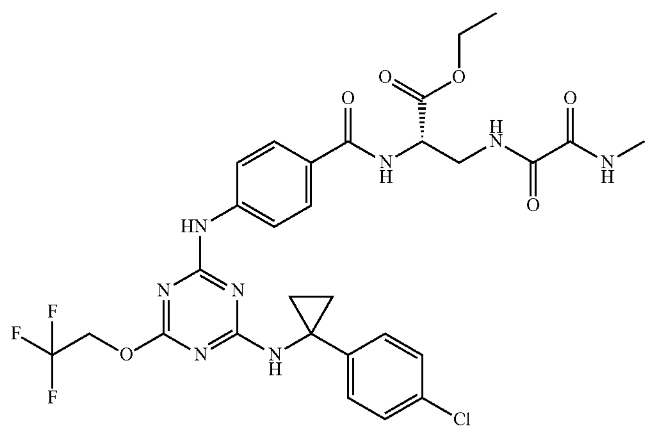 | | A |

TABLE 1-continued
| Compound | Structure | EC$_{50}$ | Activity |
|---|---|---|---|
| 1025 | 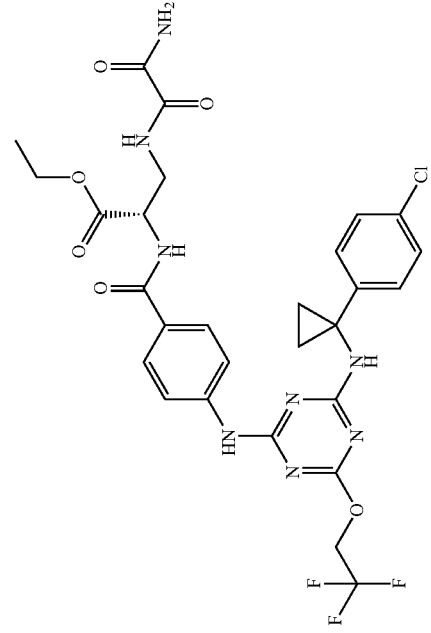 | 1.73 | A |
| 1026 | 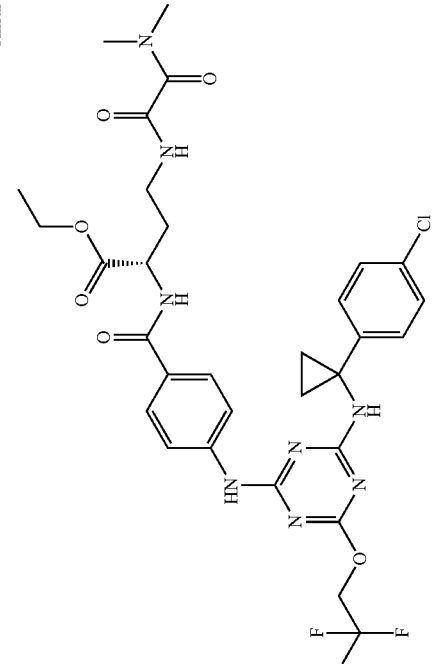 | 2.68 | A |

TABLE 1-continued
| Compound | Structure | EC$_{50}$ | Activity |
|---|---|---|---|
| 1027 | 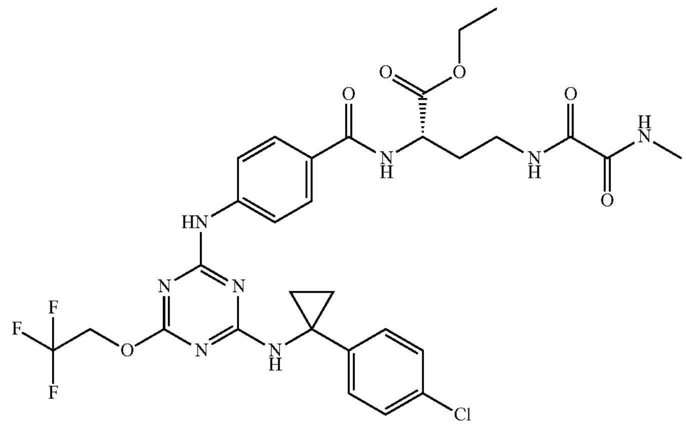 | | A |
| 1028 | 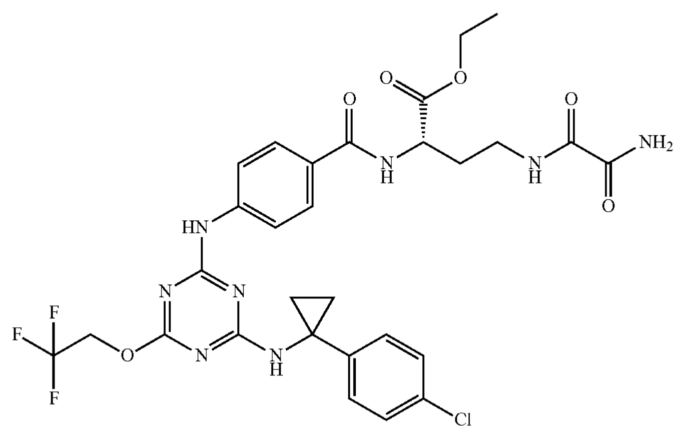 | 0.40 | A |

TABLE 1-continued
| Compound | Structure | EC$_{50}$ | Activity |
|---|---|---|---|
| 1029 | 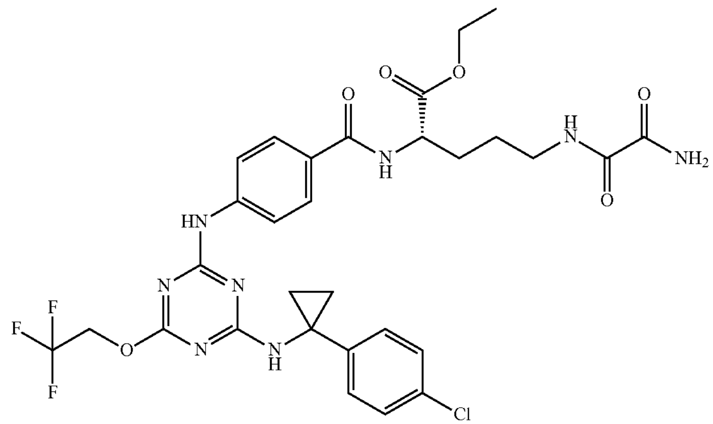 | | A |
| 1030 | 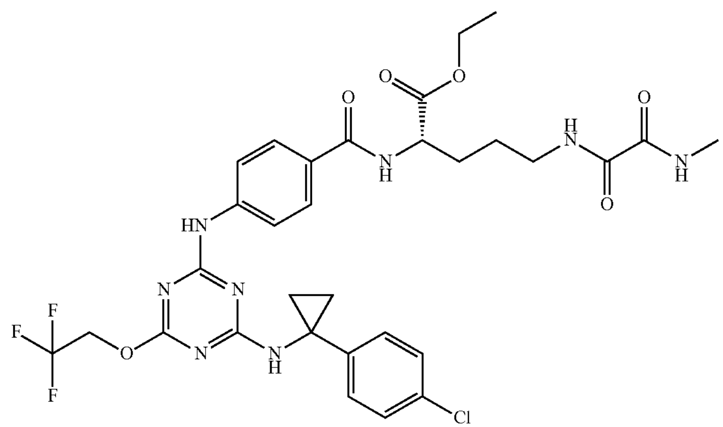 | | A |

TABLE 1-continued
| Compound | Structure | EC$_{50}$ | Activity |
|---|---|---|---|
| 1031 | 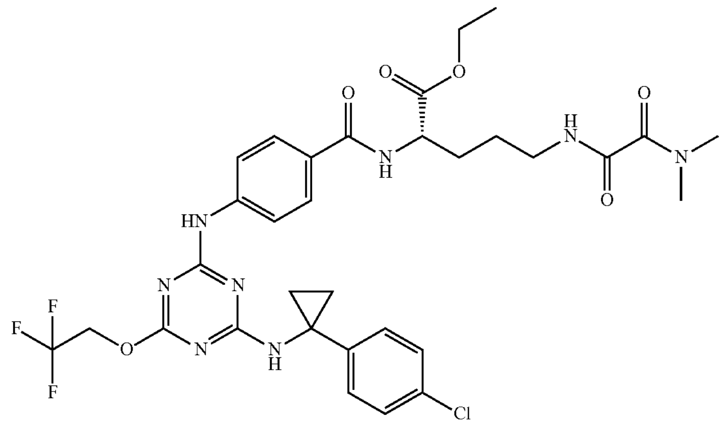 | | A |
| 1032 | 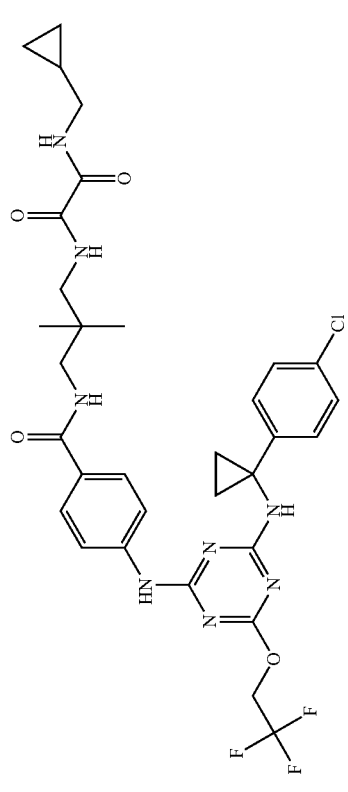 | | A |

TABLE 1-continued

| Compound | Structure | EC$_{50}$ | Activity |
|---|---|---|---|
| 1033 | (structure) | | A |
| 1034 | (structure) | | A |

TABLE 1-continued

| Compound | Structure | EC$_{50}$ | Activity |
|---|---|---|---|
| 1035 | 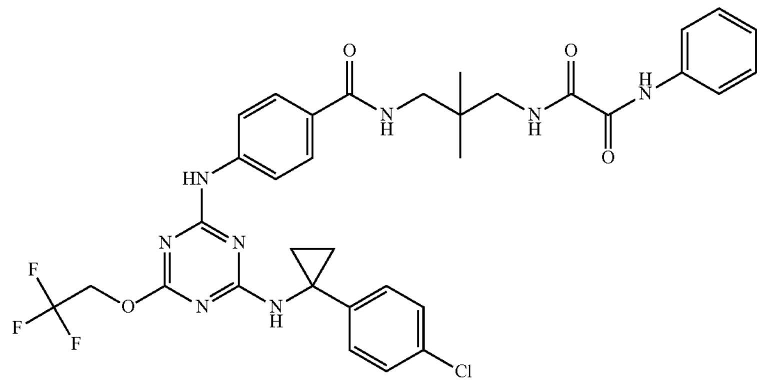 [SMILES: CC(C)(CNC(=O)C(=O)Nc1ccccc1)CNC(=O)c1ccc(Nc2nc(NC3(c4ccc(Cl)cc4)CC3)nc(OCC(F)(F)F)n2)cc1] | 0.03 | A |
| 1036 | 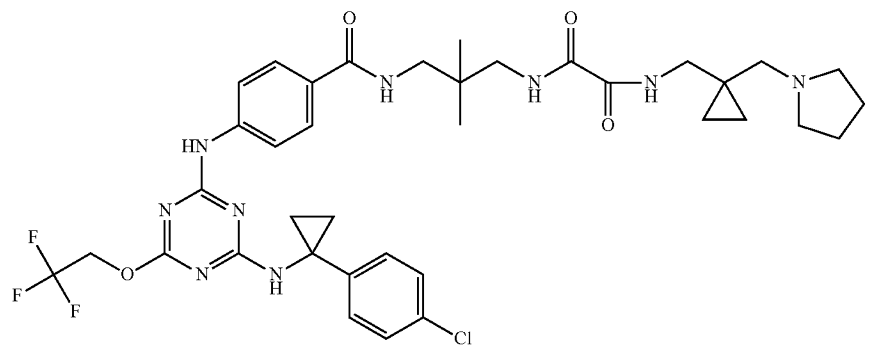 [SMILES: CC(C)(CNC(=O)C(=O)NCC1(CN2CCCC2)CC1)CNC(=O)c1ccc(Nc2nc(NC3(c4ccc(Cl)cc4)CC3)nc(OCC(F)(F)F)n2)cc1] | | A |

| Compound | Structure | EC$_{50}$ | Activity |
|---|---|---|---|
| 1037 | 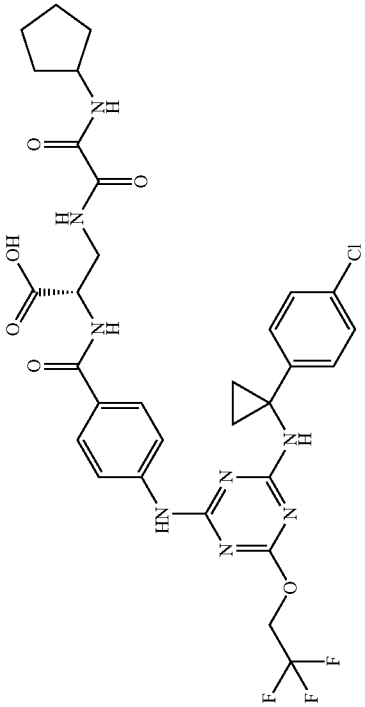 Chiral | | A |
| 1038 | 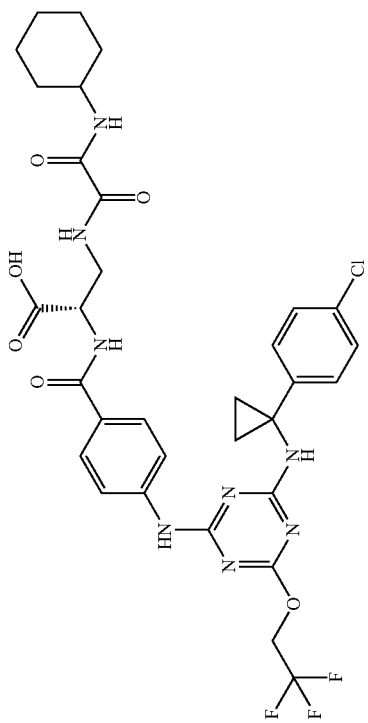 Chiral | | A |

TABLE 1-continued
| Compound | Structure | EC$_{50}$ | Activity |
|---|---|---|---|
| 1039 | 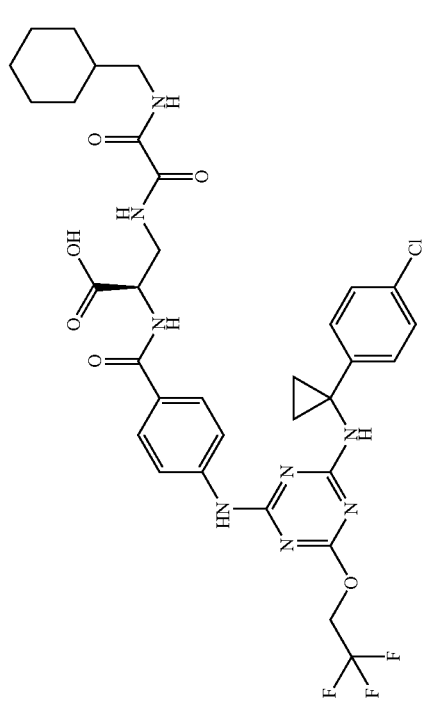 | | A |
| 1040 | 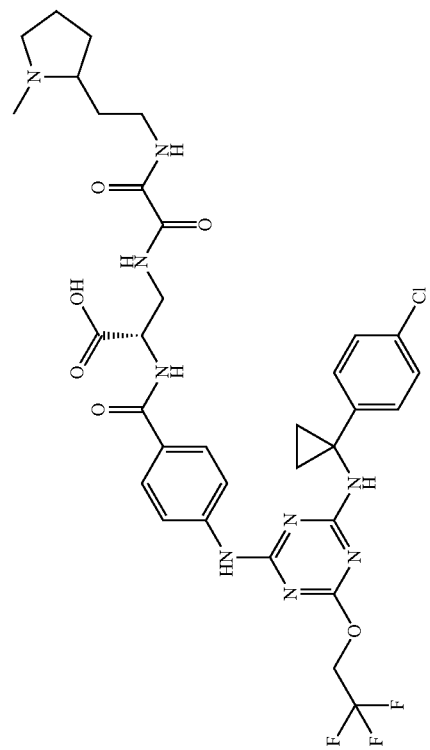 | | B |

TABLE 1-continued
| Compound | Structure | EC$_{50}$ | Activity |
|---|---|---|---|
| 1041 | Chiral  | | A |
| 1042 | 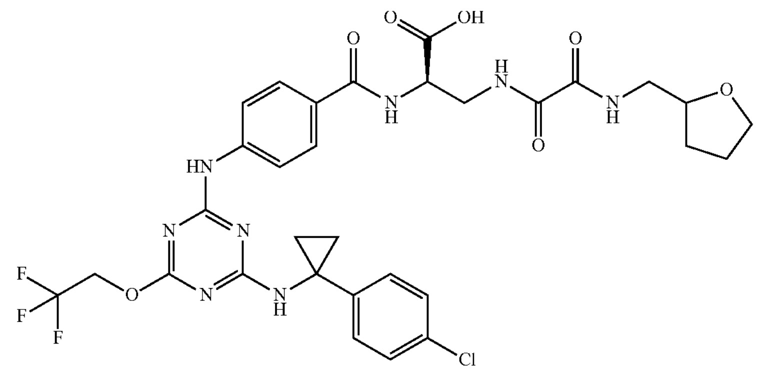 [SMILES: O=C(NCC1CCCO1)C(=O)NC[C@@H](NC(=O)c1ccc(Nc2nc(NC3(c4ccc(Cl)cc4)CC3)nc(OCC(F)(F)F)n2)cc1)C(=O)O] | | A |

TABLE 1-continued

| Compound | Structure | EC$_{50}$ | Activity |
|---|---|---|---|
| 1043 | Chiral | | A |
| 1044 | 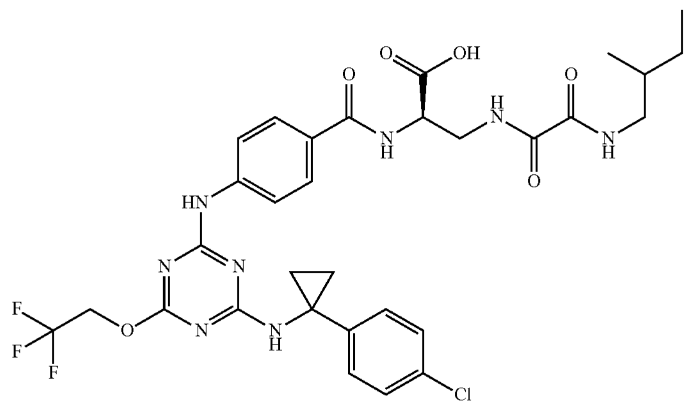 [SMILES: CCC(C)CNC(=O)C(=O)NC[C@@H](NC(=O)c1ccc(Nc2nc(NC3(c4ccc(Cl)cc4)CC3)nc(OCC(F)(F)F)n2)cc1)C(=O)O] | | A |

TABLE 1-continued
| Compound | Structure | EC$_{50}$ | Activity |
|---|---|---|---|
| 1045 | 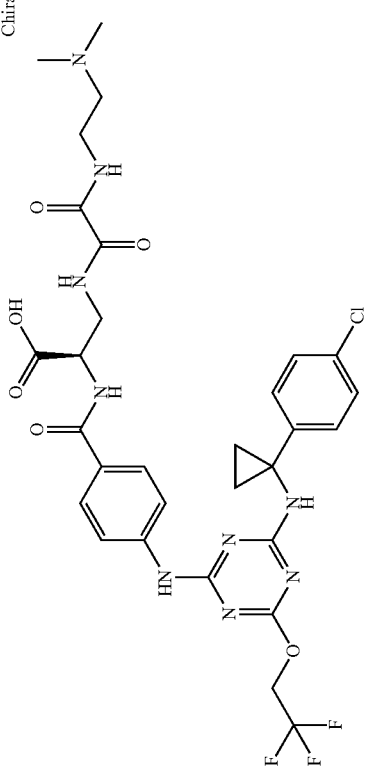 | | A |
| 1046 | 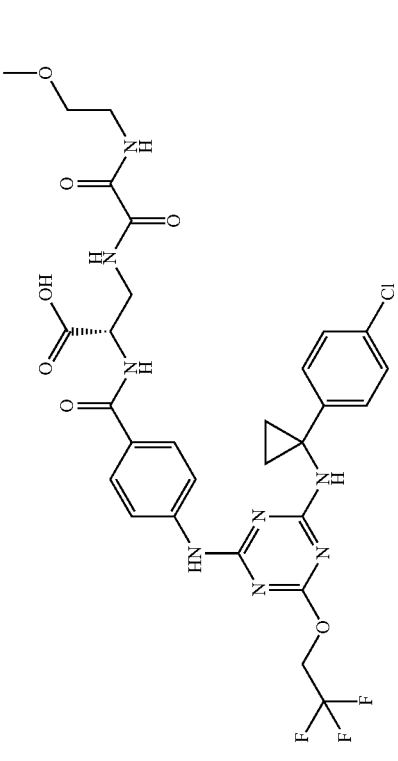 | | A |

TABLE 1-continued
| Compound | Structure | EC$_{50}$ | Activity |
|---|---|---|---|
| 1047 | 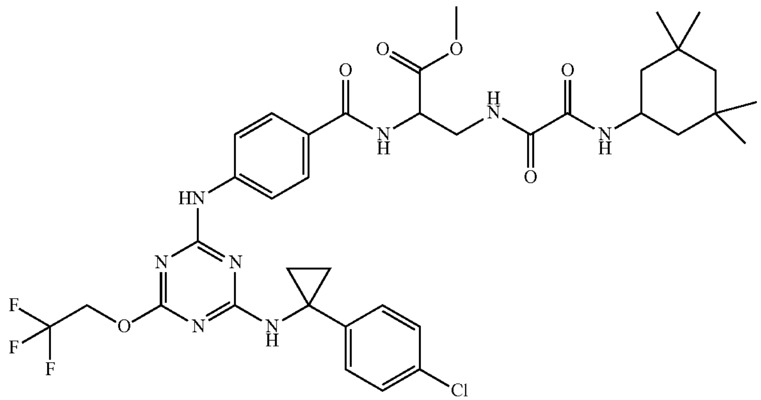 | | A |
| 1048 | 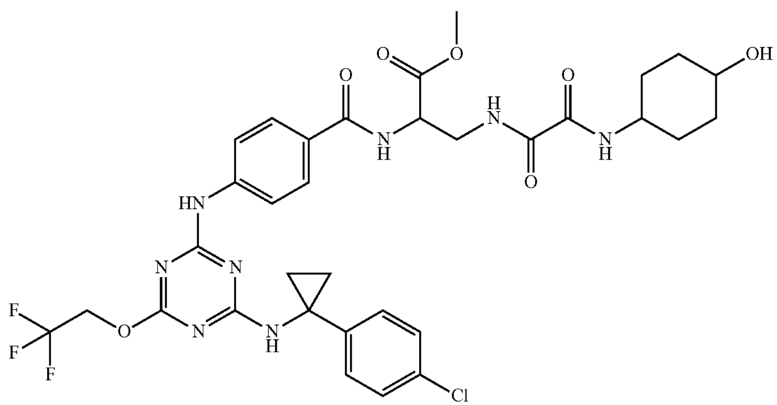 | | A |

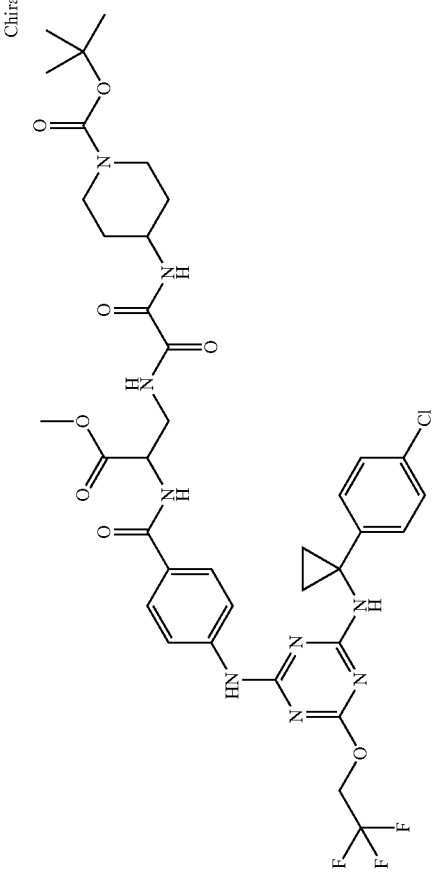
| Compound | Structure | EC$_{50}$ | Activity |
|---|---|---|---|
| 1049 | 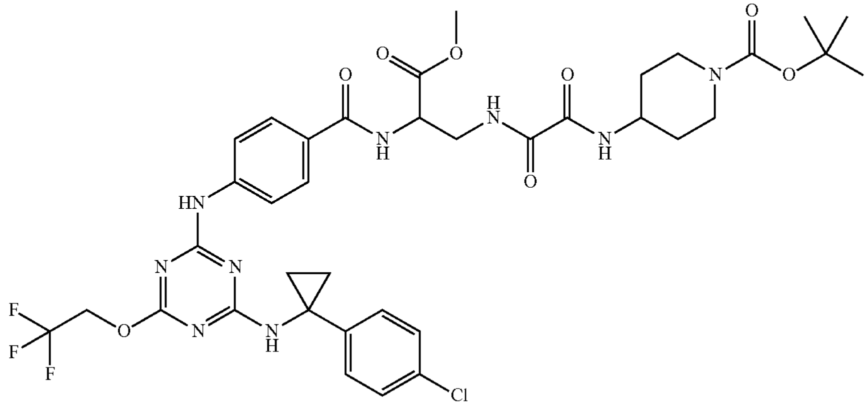 | | A |
| 1050 | 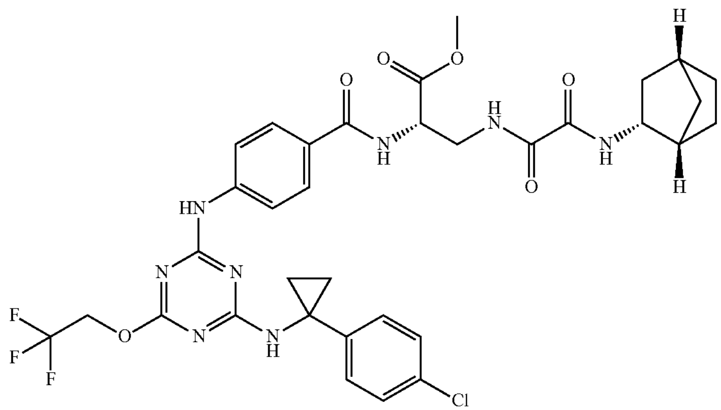 [SMILES: COC(=O)[C@H](CNC(=O)C(=O)N[C@@H]1C[C@@H]2CC[C@H]1C2)NC(=O)c1ccc(Nc2nc(NC3(c4ccc(Cl)cc4)CC3)nc(OCC(F)(F)F)n2)cc1] | | A |

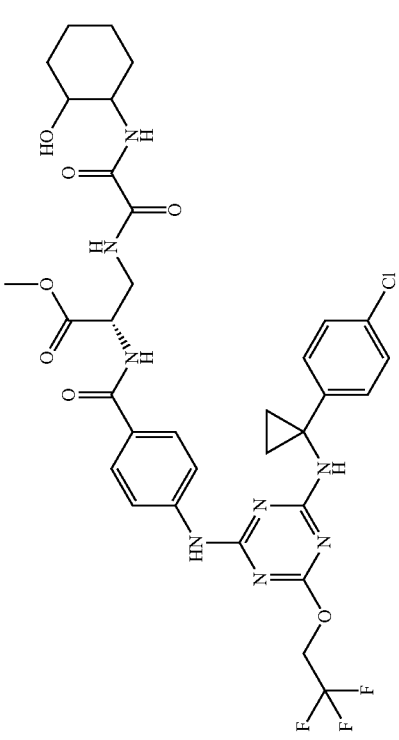
| Compound | Structure | EC$_{50}$ | Activity |
|---|---|---|---|
| 1051 | | | A |
| 1051 | | | A |

TABLE 1-continued
| Compound | Structure | EC$_{50}$ | Activity |
|---|---|---|---|
| 1053 | 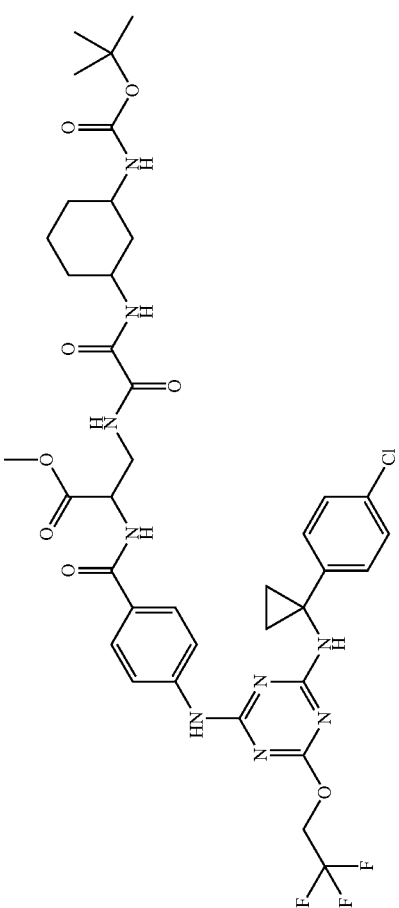 | | A |
| 1054 | 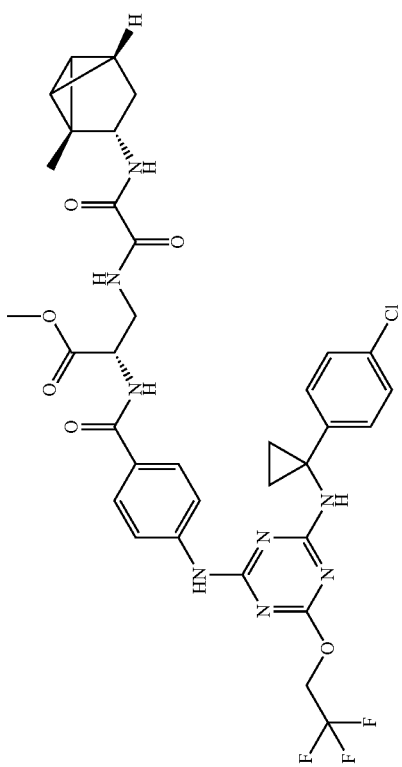 | | A |

TABLE 1-continued
| Compound | Structure | EC$_{50}$ | Activity |
|---|---|---|---|
| 1055 | 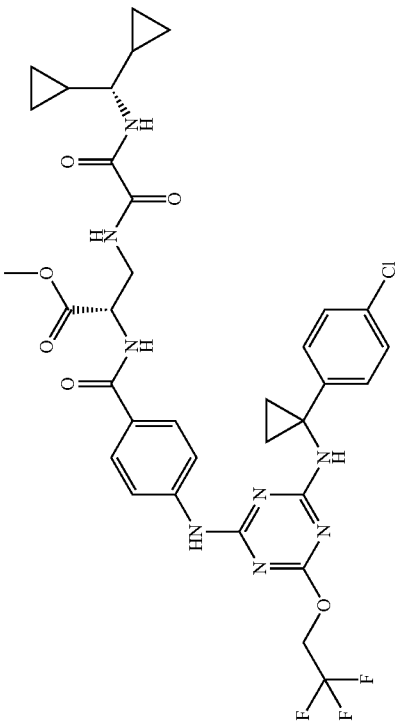 | 2.41 | A |
| 1056 | 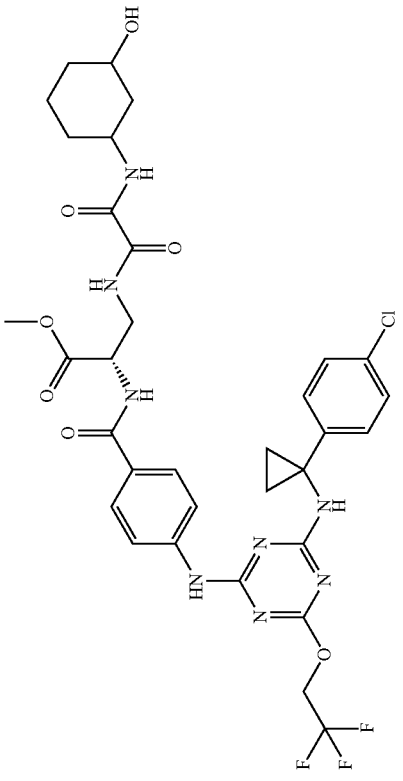 | | A |

TABLE 1-continued
| Compound | Structure | EC$_{50}$ | Activity |
|---|---|---|---|
| 1057 | 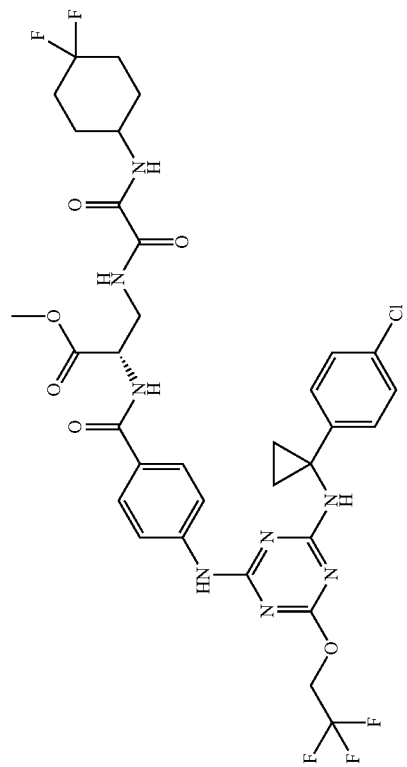 | | A |
| 1058 | 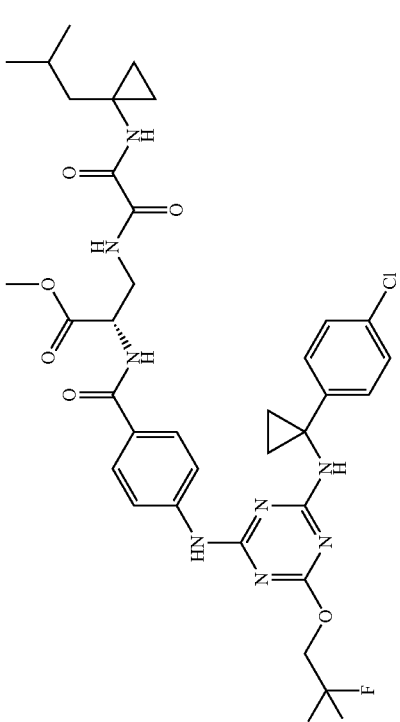 | 1.15 | A |

TABLE 1-continued

| Compound | Structure | EC₅₀ | Activity |
|---|---|---|---|
| 1059 | 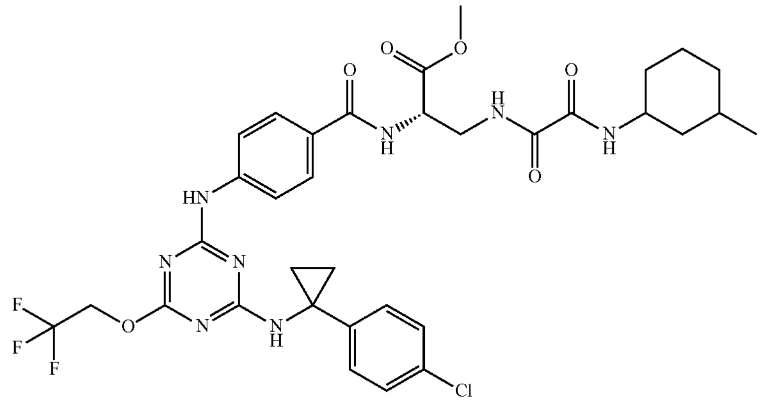 [SMILES: COC(=O)[C@H](CNC(=O)C(=O)NC1CCCC(C)C1)NC(=O)c1ccc(Nc2nc(NC3(c4ccc(Cl)cc4)CC3)nc(OCC(F)(F)F)n2)cc1] | | A |
| 1060 | 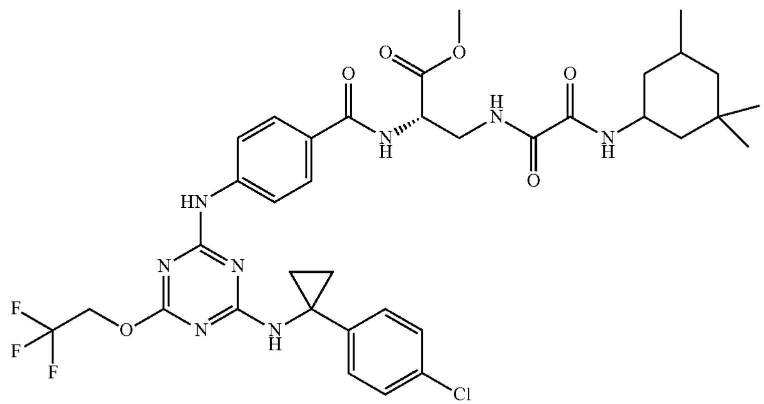 [SMILES: COC(=O)[C@H](CNC(=O)C(=O)NC1CC(C)CC(C)(C)C1)NC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 1061 | 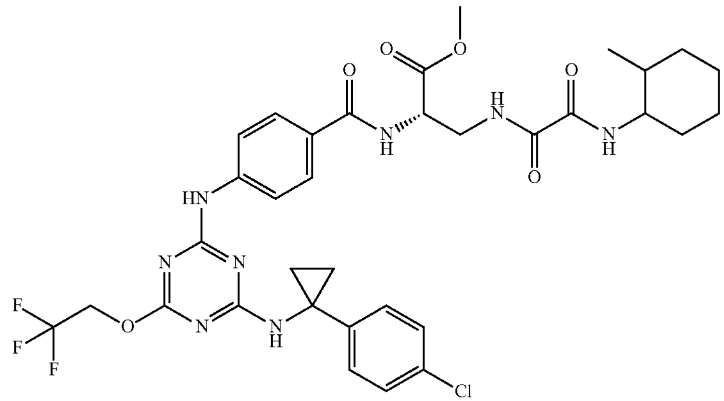 [SMILES: COC(=O)[C@H](CNC(=O)C(=O)NC1CCCCC1C)NC(=O)c1ccc(Nc2nc(NC3(c4ccc(Cl)cc4)CC3)nc(OCC(F)(F)F)n2)cc1] | 1.58 | A |
| 1062 | Chiral | | A |

TABLE 1-continued
| Compound | Structure | EC$_{50}$ | Activity |
|---|---|---|---|
| 1063 | 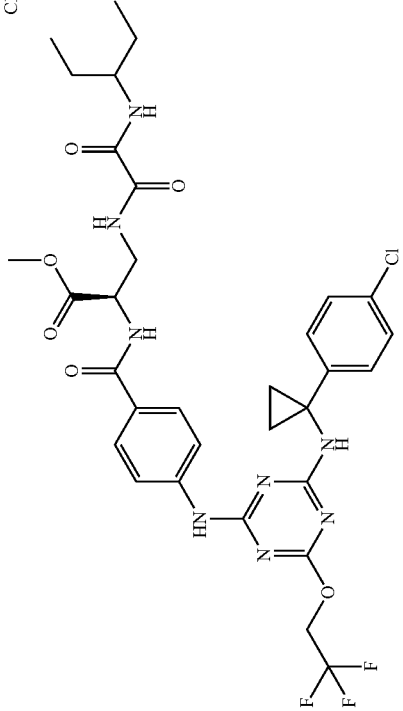 Chiral | | A |
| 1064 | 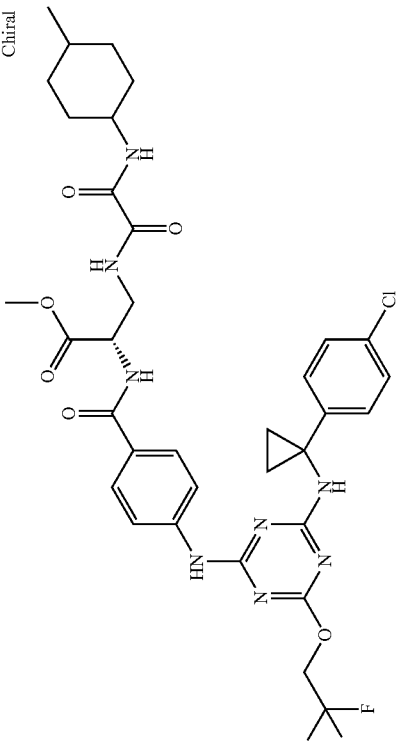 Chiral | 1.89 | A |

TABLE 1-continued
| Compound | Structure | EC$_{50}$ | Activity |
|---|---|---|---|
| 1065 | 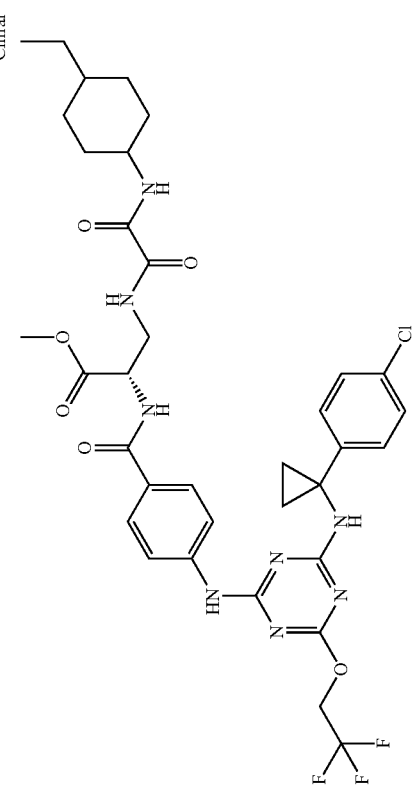 | 0.59 | A |
| 1066 | 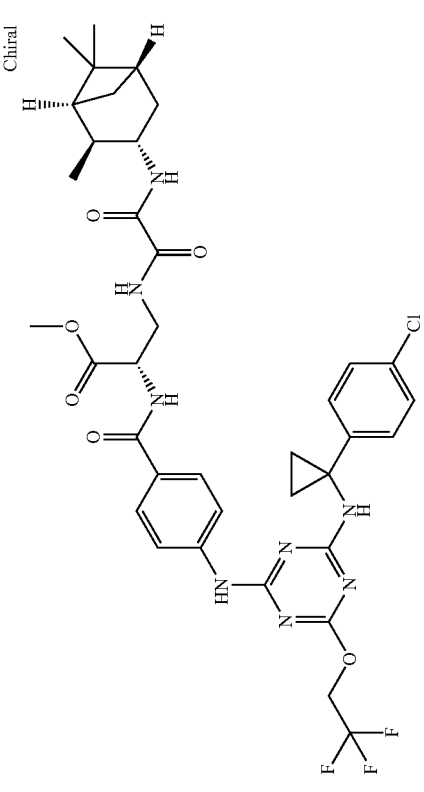 | | A |

TABLE 1-continued
| Compound | Structure | EC$_{50}$ | Activity |
|---|---|---|---|
| 1067 | 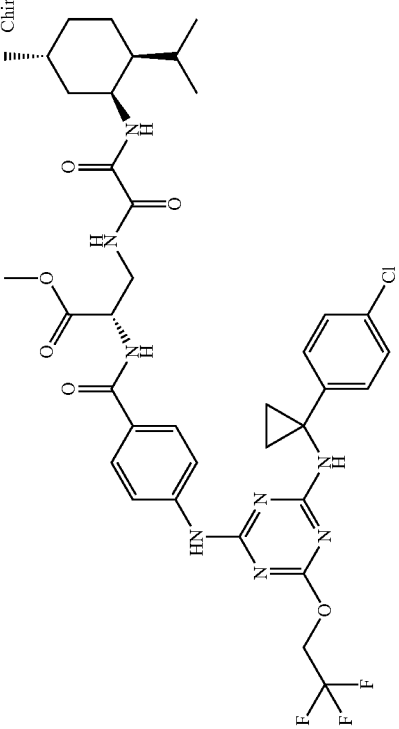 | | A |
| 1068 | 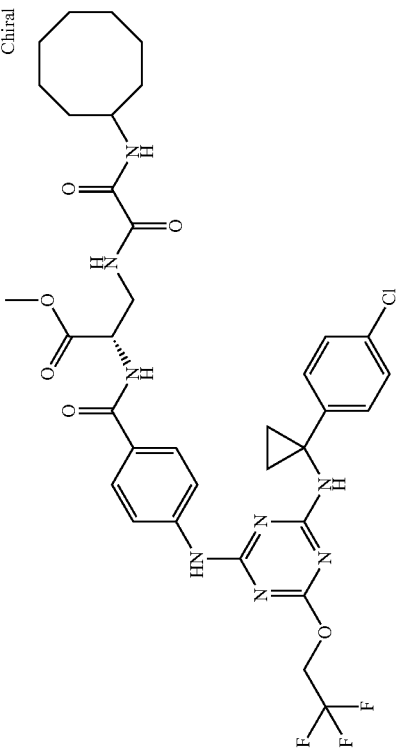 | | A |

TABLE 1-continued
| Compound | Structure | EC$_{50}$ | Activity |
|---|---|---|---|
| 1069 | 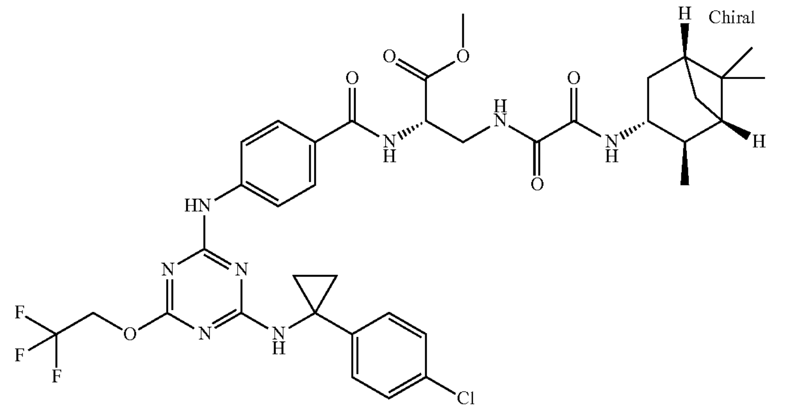 [SMILES: COC(=O)[C@H](CNC(=O)C(=O)N[C@@H]1C[C@H]2C[C@@H]([C@H]1C)C2(C)C)NC(=O)c1ccc(Nc2nc(NC3(c4ccc(Cl)cc4)CC3)nc(OCC(F)(F)F)n2)cc1] | | A |
| 1070 | 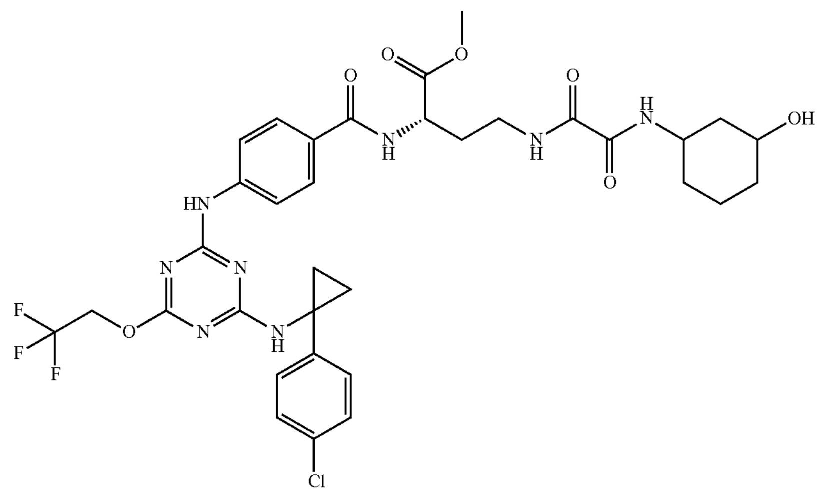 [SMILES: COC(=O)[C@H](CCNC(=O)C(=O)NC1CCCC(O)C1)NC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 1071 | Chiral | | A |
| 1072 | 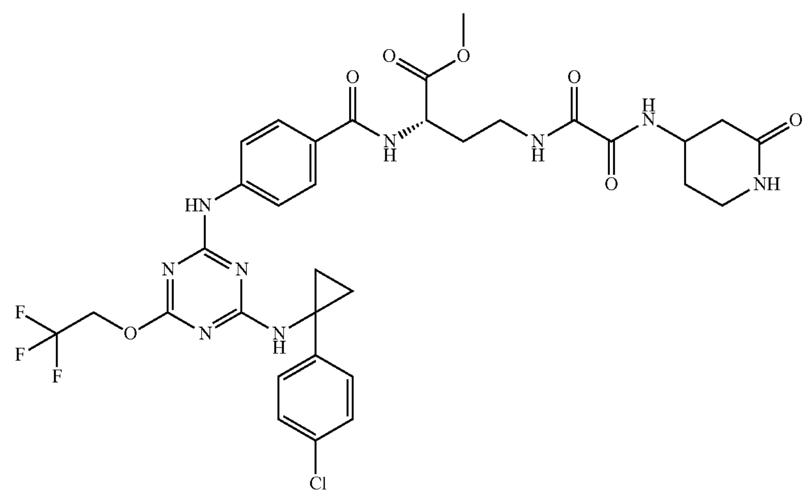 [SMILES: COC(=O)[C@H](CCNC(=O)C(=O)NC1CCNC(=O)C1)NC(=O)c1ccc(Nc2nc(NC3(c4ccc(Cl)cc4)CC3)nc(OCC(F)(F)F)n2)cc1] | | A |

| Compound | Structure | EC$_{50}$ | Activity |
|---|---|---|---|
| 1073 | 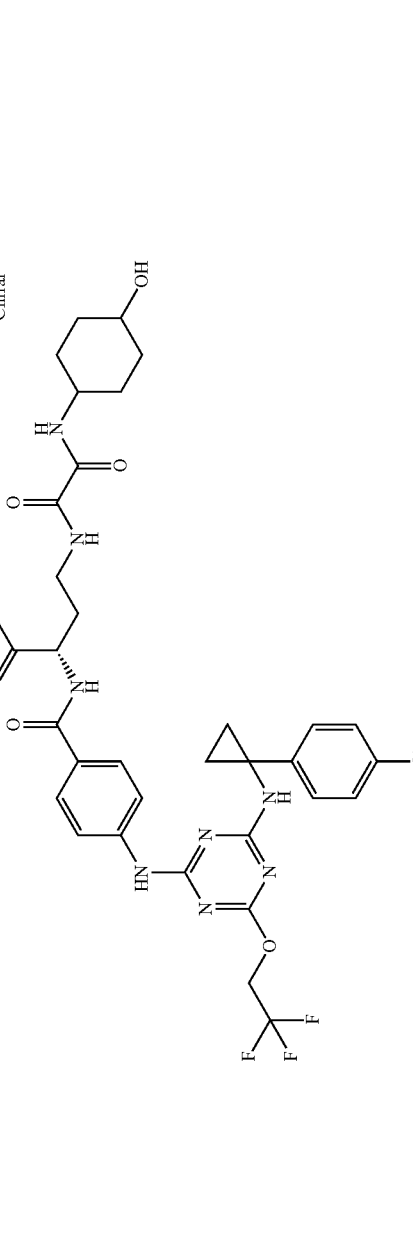 | | A |
| 1074 | 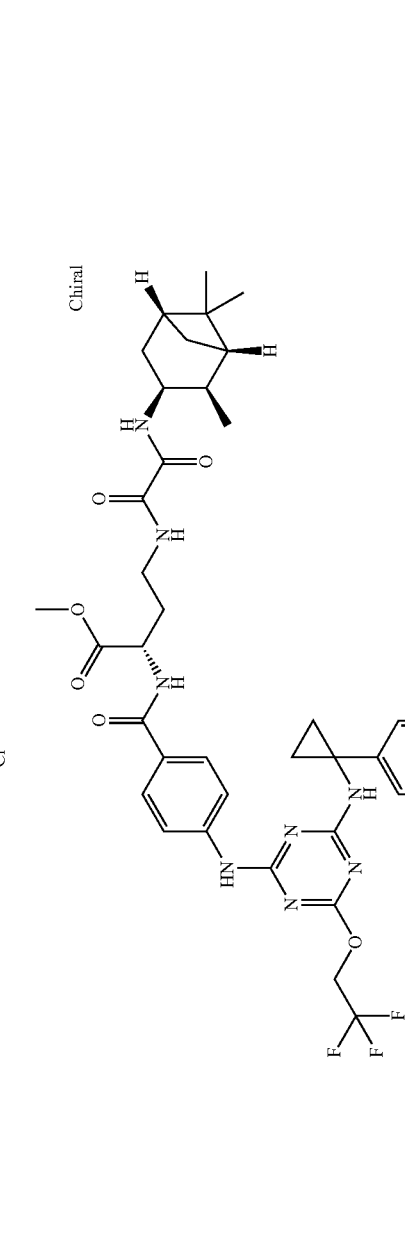 | | A |

TABLE 1-continued

| Compound | Structure | EC$_{50}$ | Activity |
|---|---|---|---|
| 1075 | 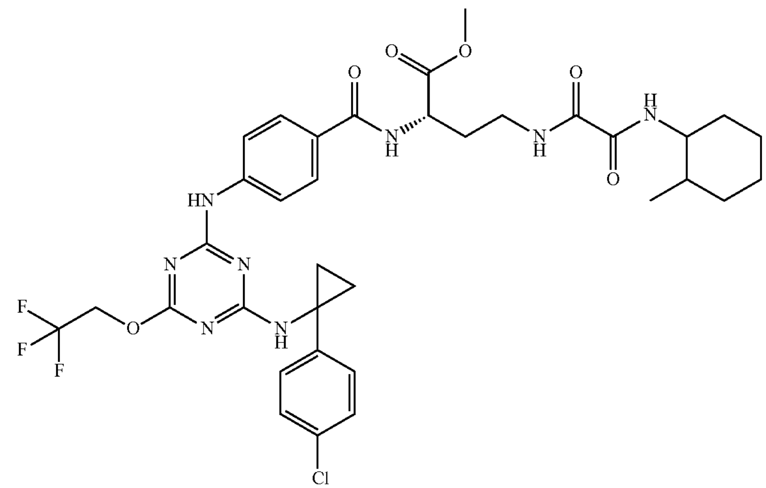 [SMILES: COC(=O)[C@H](CCNC(=O)C(=O)NC1CCCCC1C)NC(=O)c1ccc(Nc2nc(NC3(c4ccc(Cl)cc4)CC3)nc(OCC(F)(F)F)n2)cc1] | | A |
| 1076 | 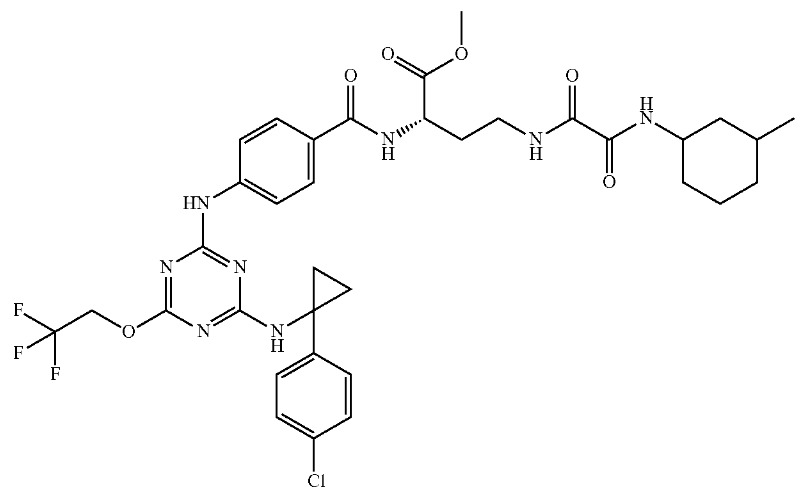 [SMILES: COC(=O)[C@H](CCNC(=O)C(=O)NC1CCCC(C)C1)NC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 1077 | (Chiral) | | A |
| 1078 | (Chiral) | 11.91 | B |

TABLE 1-continued
| Compound | Structure | EC$_{50}$ | Activity |
|---|---|---|---|
| 1079 | 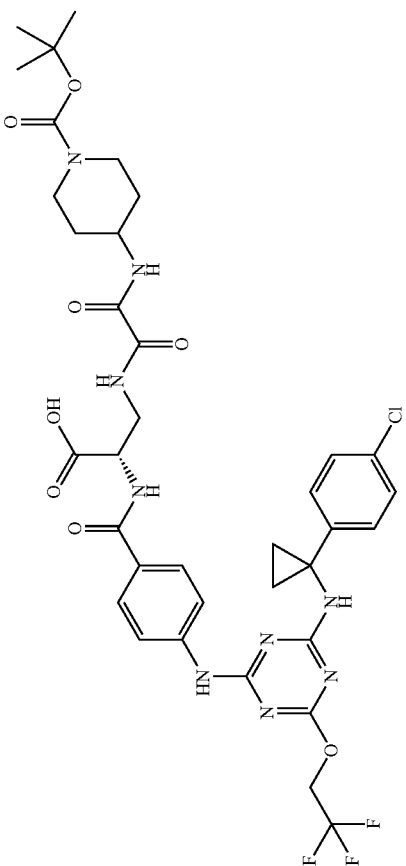 | | A |
| 1080 | 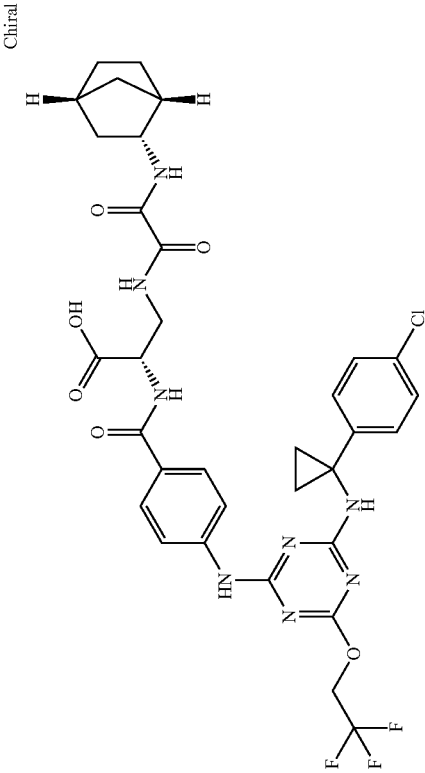 | | A |

TABLE 1-continued

| Compound | Structure | EC$_{50}$ | Activity |
|---|---|---|---|
| 1081 | 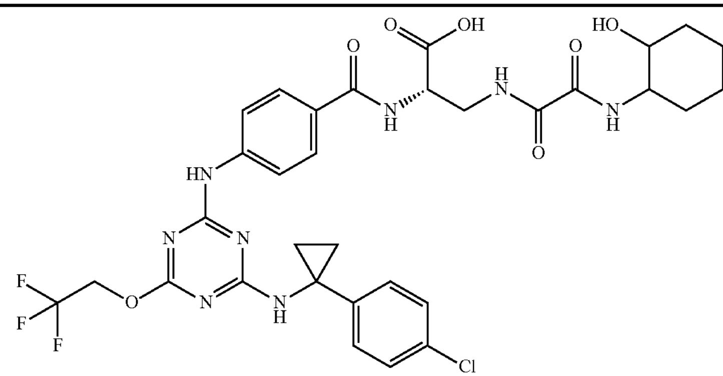 | | A |
| 1082 | 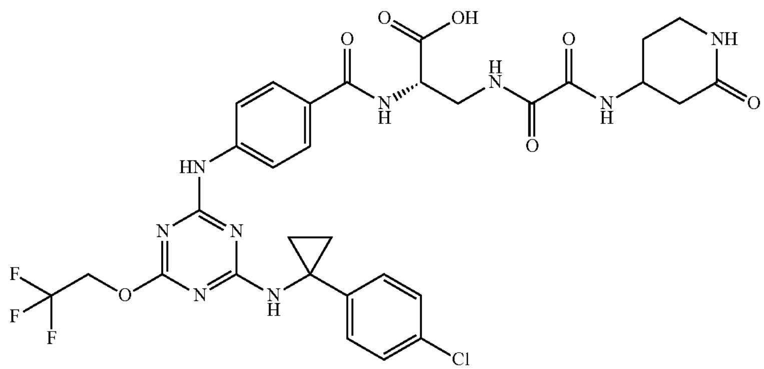 [SMILES: O=C1CC(NC(=O)C(=O)NC[C@H](NC(=O)c2ccc(Nc3nc(NC4(c5ccc(Cl)cc5)CC4)nc(OCC(F)(F)F)n3)cc2)C(=O)O)CCN1] | | A |

TABLE 1-continued

| Compound | Structure | EC$_{50}$ | Activity |
|---|---|---|---|
| 1083 | 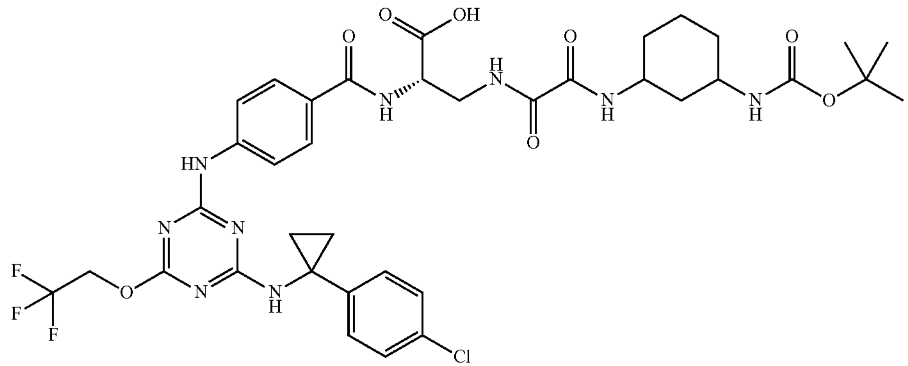 [SMILES: CC(C)(C)OC(=O)NC1CCCC(NC(=O)C(=O)NC[C@H](NC(=O)c2ccc(Nc3nc(NC4(c5ccc(Cl)cc5)CC4)nc(OCC(F)(F)F)n3)cc2)C(=O)O)C1] | 1.78 | A |
| 1084 | Chiral | 0.26 | A |

TABLE 1-continued

| Compound | Structure | EC$_{50}$ | Activity |
|---|---|---|---|
| 1085 | Chiral structure | | A |
| 1086 | structure | | A |

TABLE 1-continued

| Compound | Structure | EC$_{50}$ | Activity |
|---|---|---|---|
| 1087 | 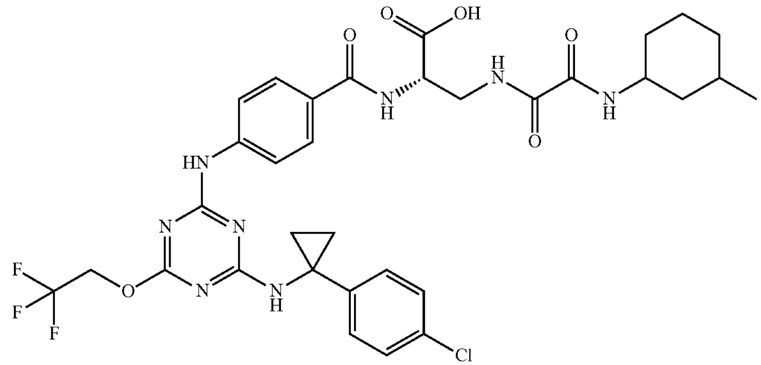 [SMILES: CC1CCCC(NC(=O)C(=O)NC[C@H](NC(=O)c2ccc(Nc3nc(NC4(c5ccc(Cl)cc5)CC4)nc(OCC(F)(F)F)n3)cc2)C(=O)O)C1] | | A |
| 1088 | 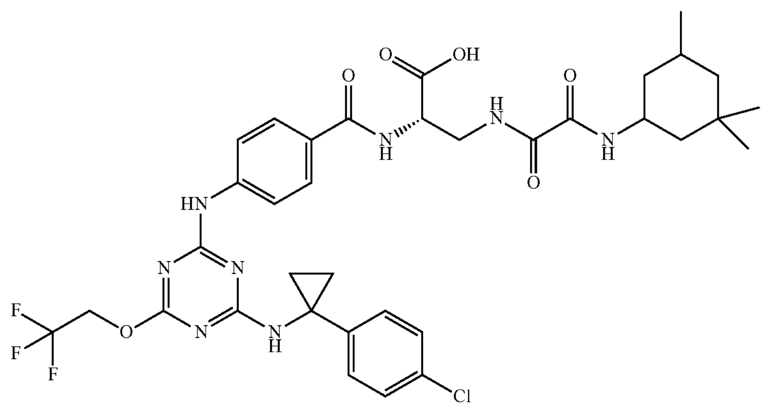 [SMILES: CC1CC(NC(=O)C(=O)NC[C@H](NC(=O)c2ccc(Nc3nc(NC4(c5ccc(Cl)cc5)CC4)nc(OCC(F)(F)F)n3)cc2)C(=O)O)CC(C)(C)C1] | | A |

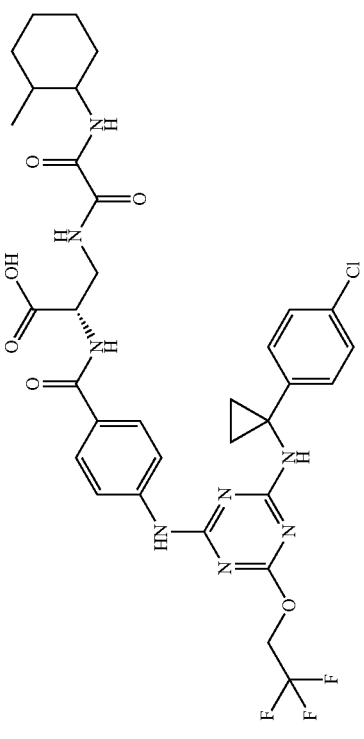

TABLE 1-continued

| Compound | Structure | EC$_{50}$ | Activity |
|---|---|---|---|
| 1091 | Chiral | | A |
| 1092 | Chiral | | A |

TABLE 1-continued
| Compound | Structure | EC$_{50}$ | Activity |
|---|---|---|---|
| 1093 | 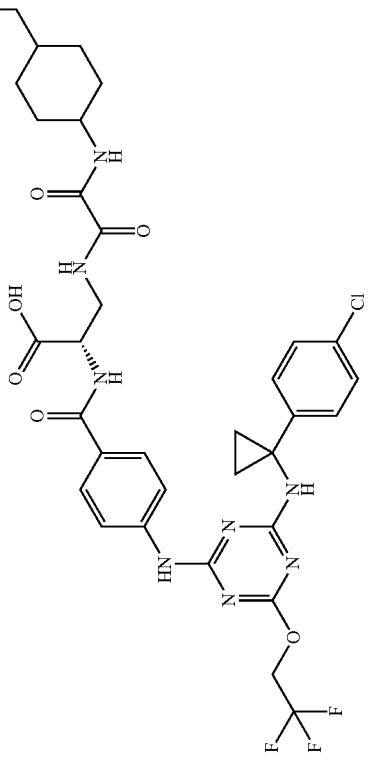 | | A |
| 1094 | 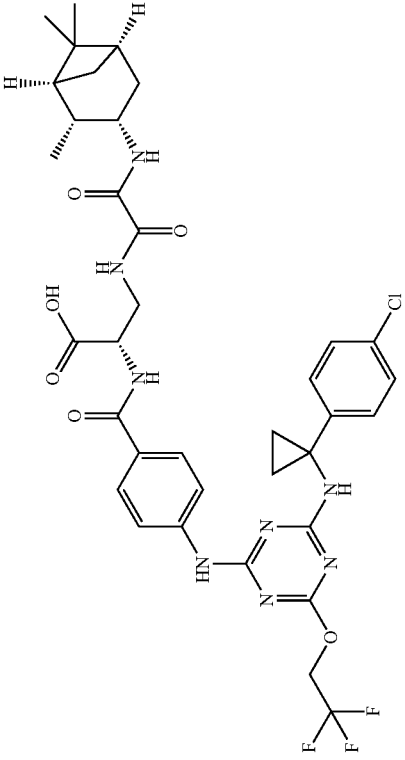 | | A |

TABLE 1-continued
| Compound | Structure | EC$_{50}$ | Activity |
|---|---|---|---|
| 1095 | 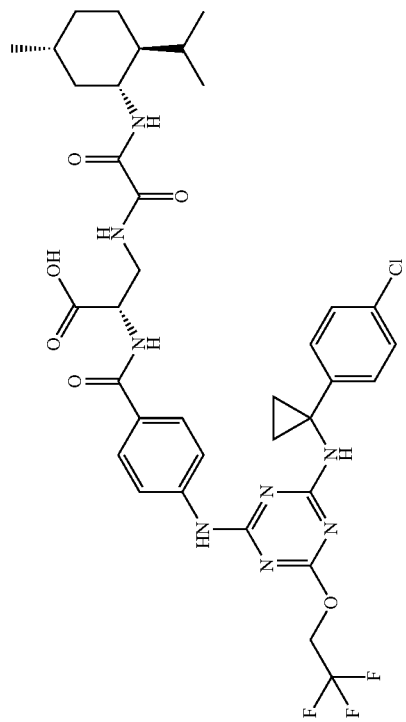 Chiral | | A |
| 1096 | 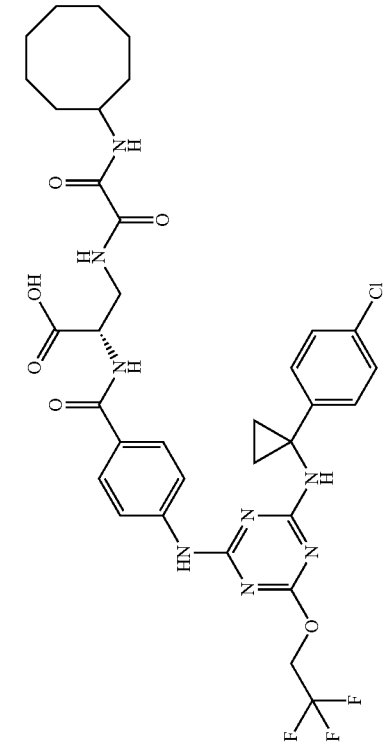 Chiral | | A |

TABLE 1-continued

| Compound | Structure | EC$_{50}$ | Activity |
|---|---|---|---|
| 1097 | 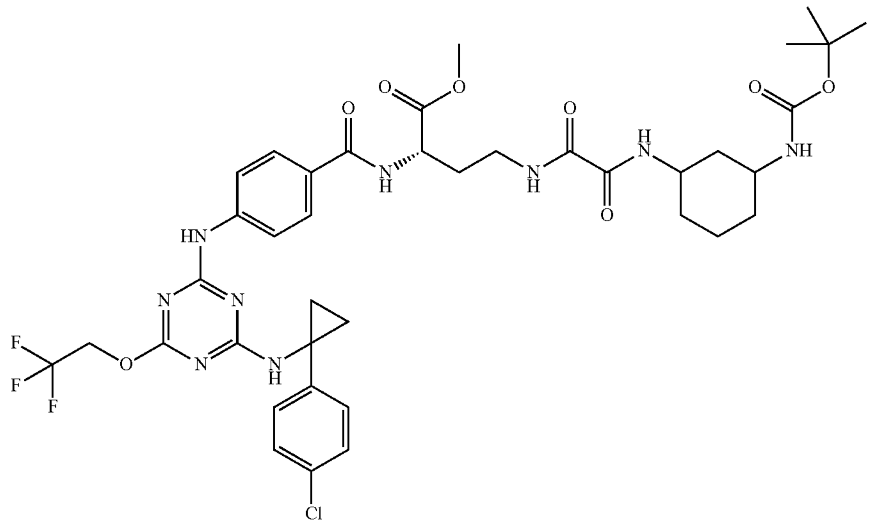 [SMILES: COC(=O)[C@H](CCNC(=O)C(=O)NC1CCCC(NC(=O)OC(C)(C)C)C1)NC(=O)c1ccc(Nc2nc(NC3(c4ccc(Cl)cc4)CC3)nc(OCC(F)(F)F)n2)cc1] | | A |
| 1098 | 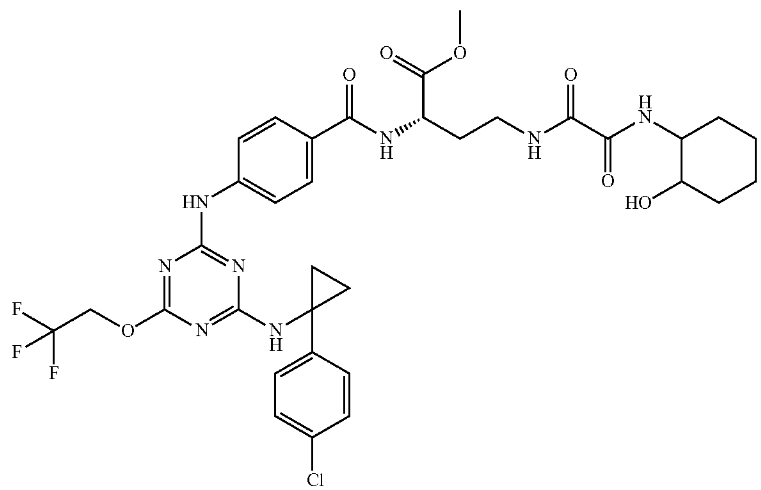 [SMILES: COC(=O)[C@H](CCNC(=O)C(=O)NC1CCCCC1O)NC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 1099 | 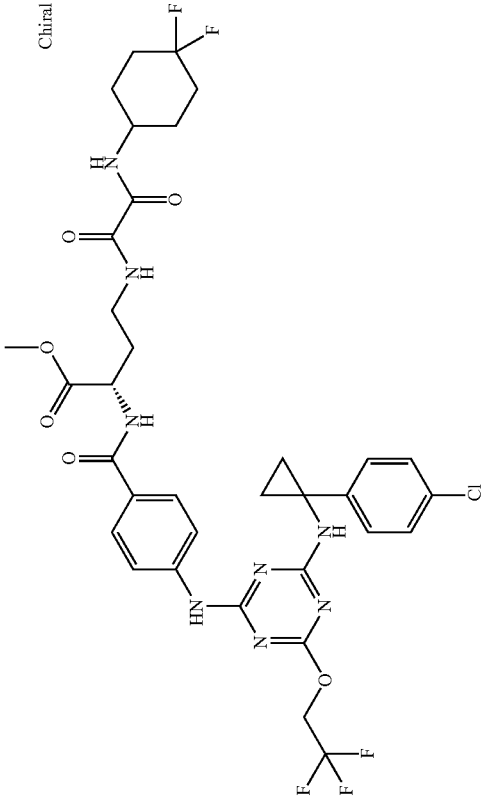 | | A |
| 1100 | 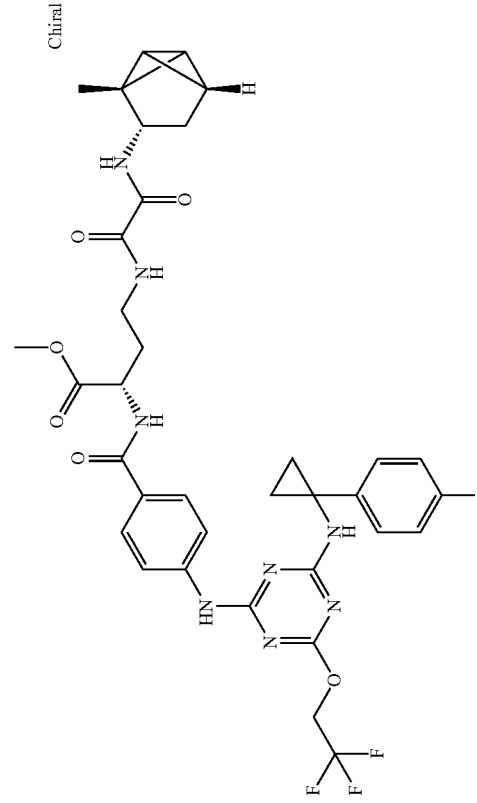 | | A |

TABLE 1-continued
| Compound | Structure | EC$_{50}$ | Activity |
|---|---|---|---|
| 1101 | 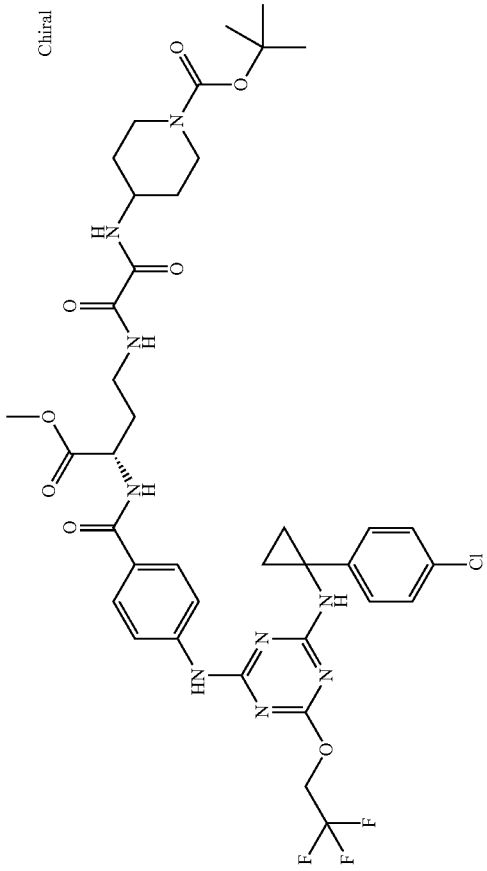 | | A |
| 1102 | 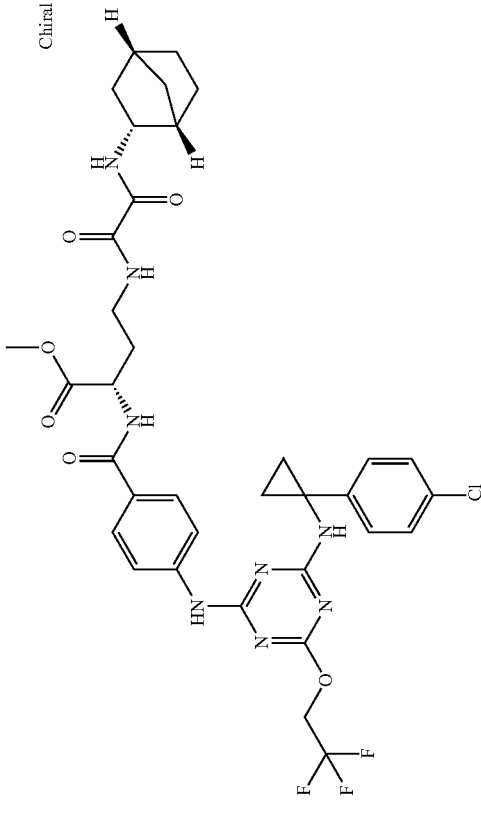 | | A |

TABLE 1-continued
| Compound | Structure | EC$_{50}$ | Activity |
|---|---|---|---|
| 1103 | 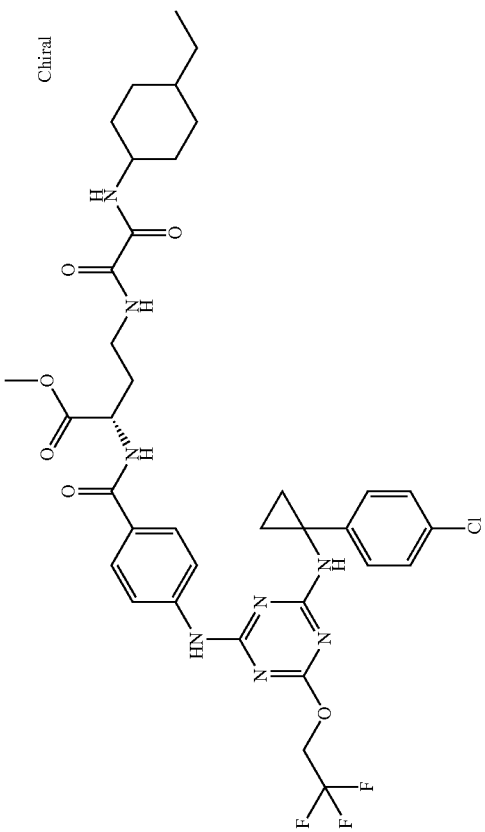 | | A |
| 1104 | 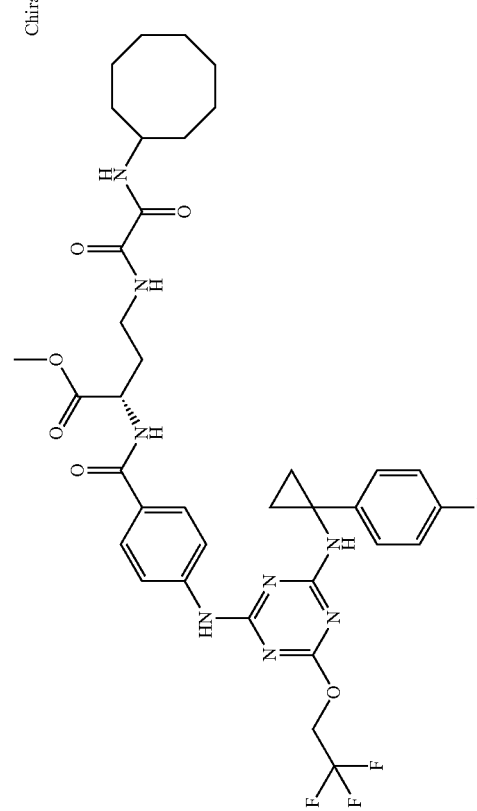 | | A |

TABLE 1-continued

| Compound | Structure | EC$_{50}$ | Activity |
|---|---|---|---|
| 1105 | Chiral | | A |
| 1106 | Chiral | | A |

TABLE 1-continued
| Compound | Structure | EC$_{50}$ | Activity |
|---|---|---|---|
| 1107 | 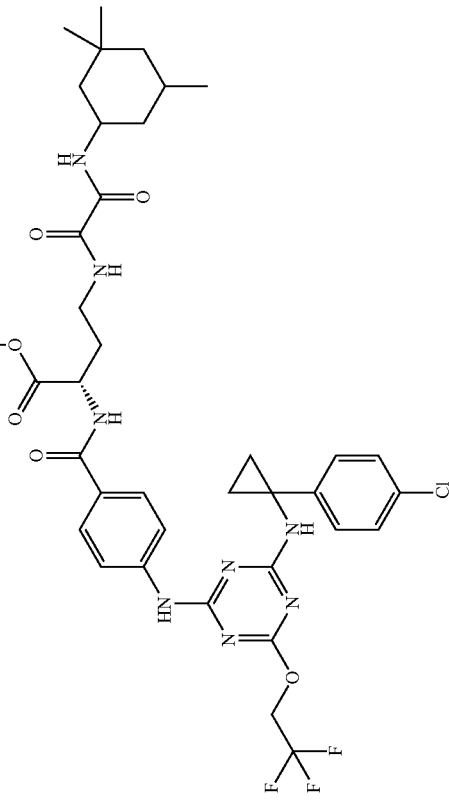 | 0.46 | A |
| 1108 | 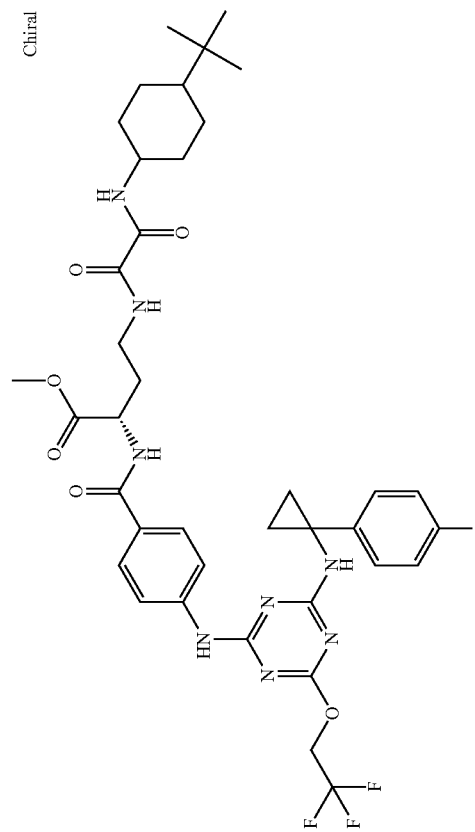 Chiral | | A |

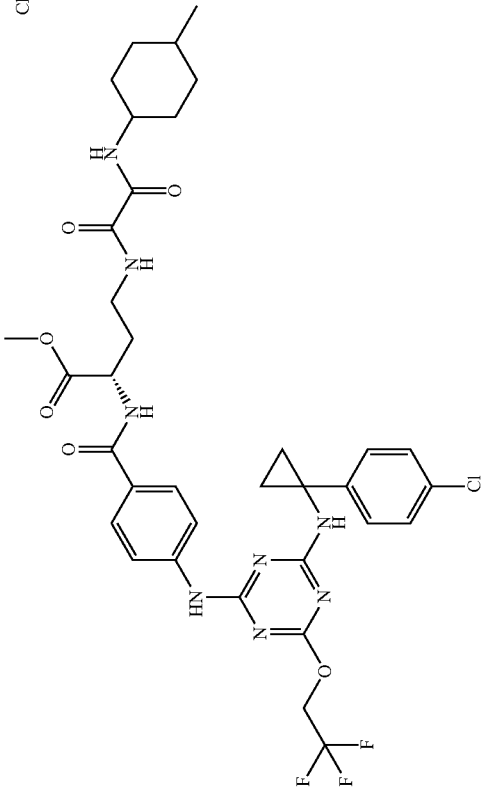

TABLE 1-continued
| Compound | Structure | EC$_{50}$ | Activity |
|---|---|---|---|
| 1111 | 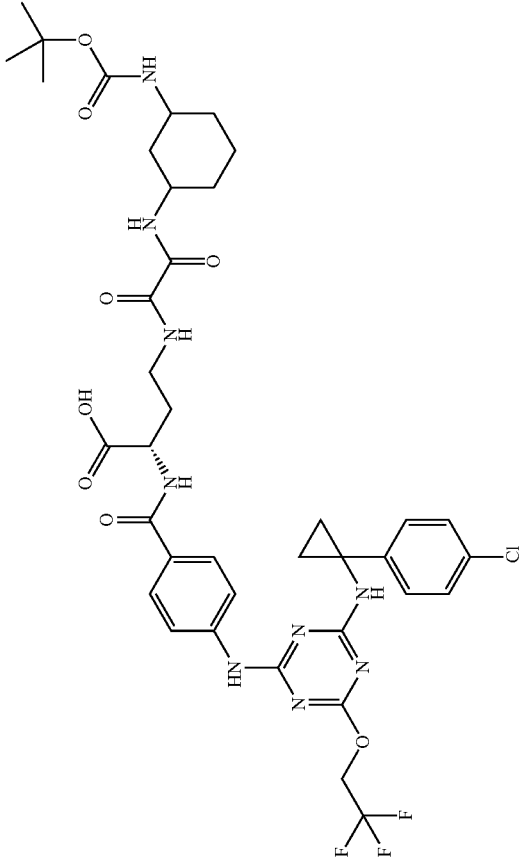 | | A |
| 1112 | 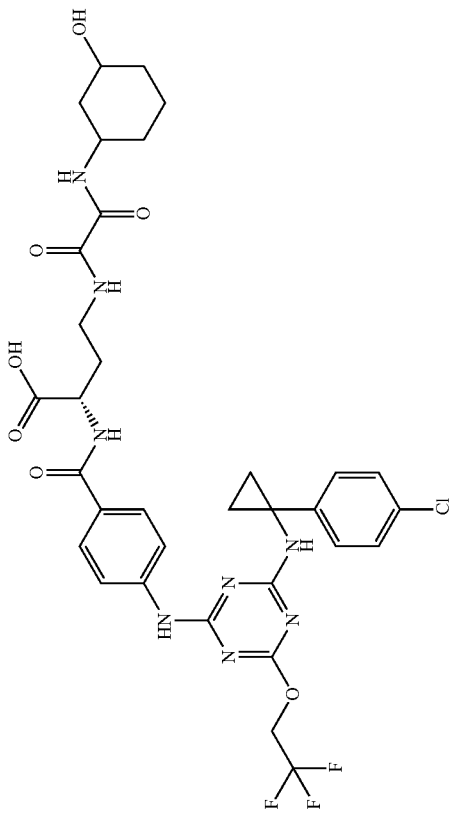 | 1.23 | A |

| Compound | Structure | EC$_{50}$ | Activity |
|---|---|---|---|
| 1113 | 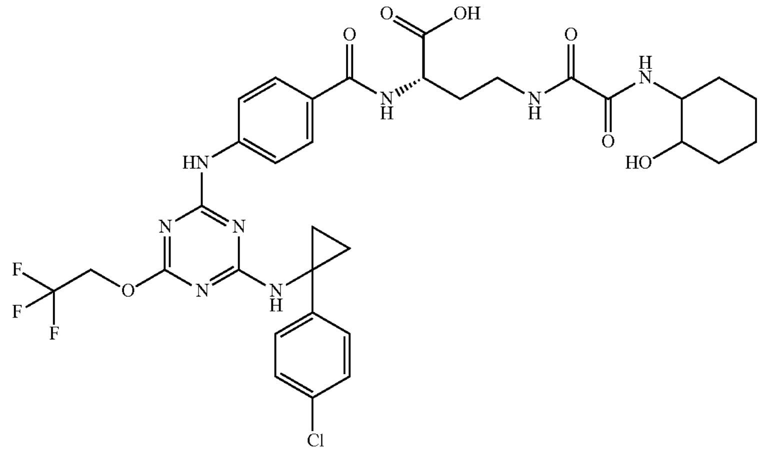 [SMILES: O=C(NCC[C@H](NC(=O)c1ccc(Nc2nc(NC3(c4ccc(Cl)cc4)CC3)nc(OCC(F)(F)F)n2)cc1)C(=O)O)C(=O)NC1CCCCC1O] | | A |
| 1114 | 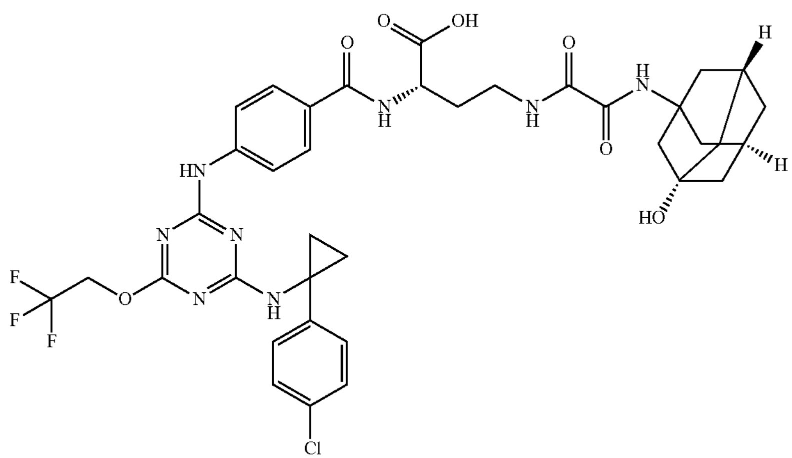 | | A |

TABLE 1-continued
| Compound | Structure | EC$_{50}$ | Activity |
|---|---|---|---|
| 1115 | 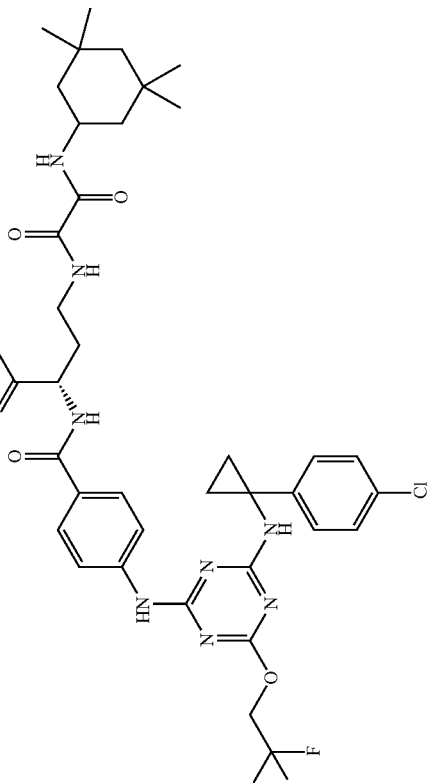 | | A |
| 1116 | 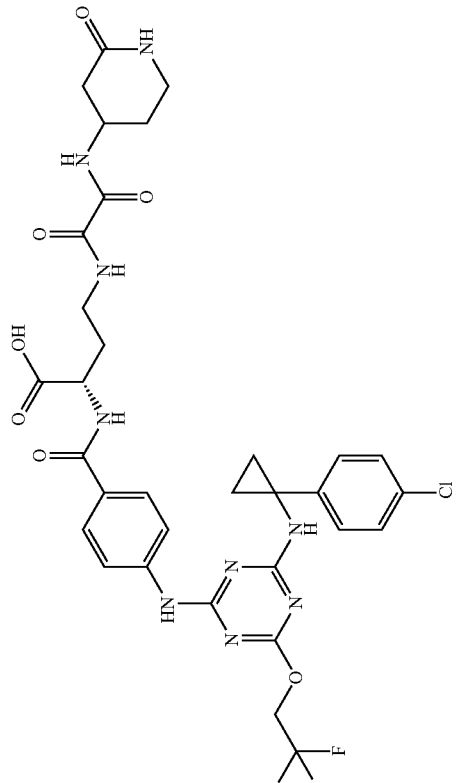 | | B |

TABLE 1-continued

| Compound | Structure | EC$_{50}$ | Activity |
|---|---|---|---|
| 1117 | Chiral | | A |
| 1118 | Chiral | | A |

TABLE 1-continued
| Compound | Structure | EC$_{50}$ | Activity |
|---|---|---|---|
| 1119 | Chiral 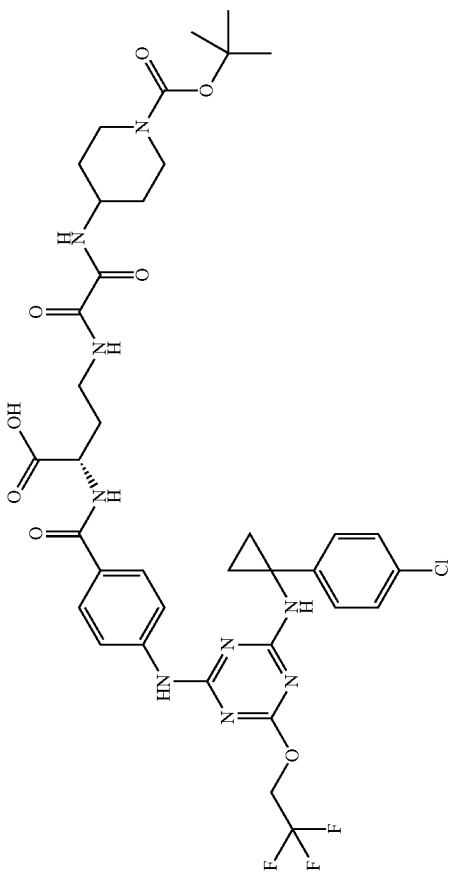 | | A |
| 1120 | Chiral 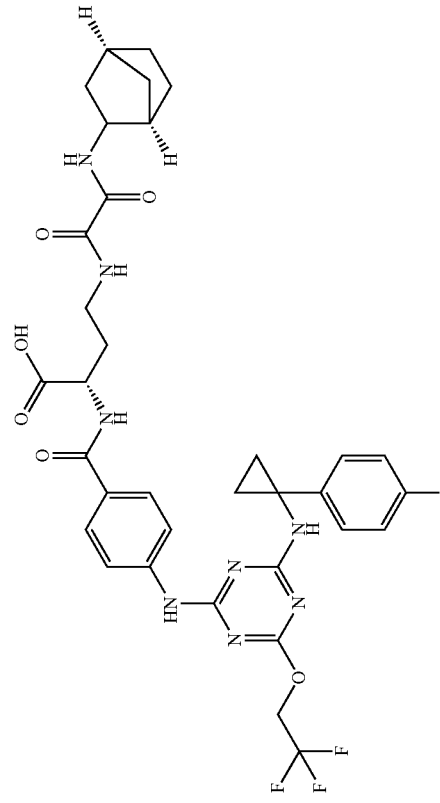 | | A |

TABLE 1-continued
| Compound | Structure | EC$_{50}$ | Activity |
|---|---|---|---|
| 1121 | 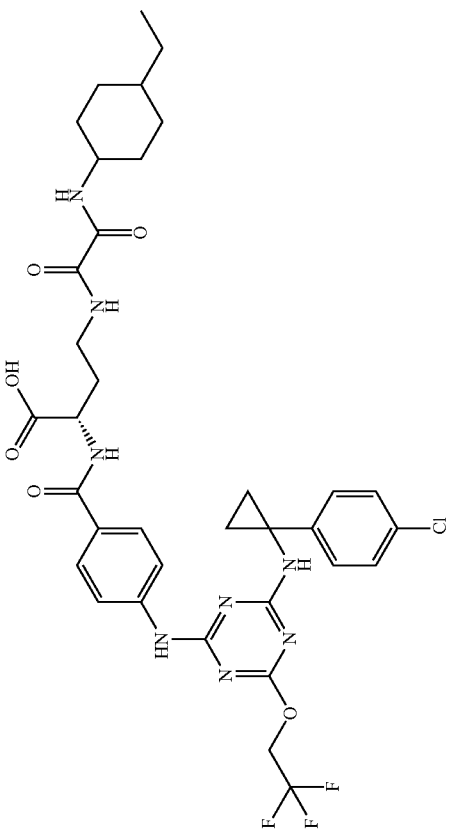 | | A |
| 1122 | 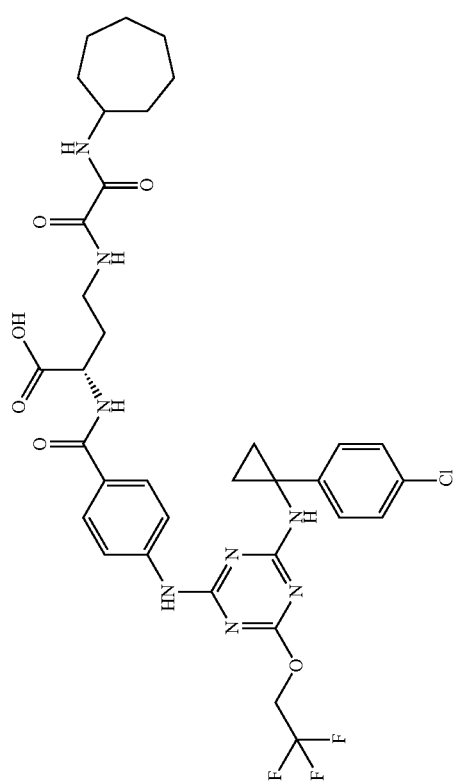 | | A |

TABLE 1-continued
| Compound | Structure | EC$_{50}$ | Activity |
|---|---|---|---|
| 1123 | 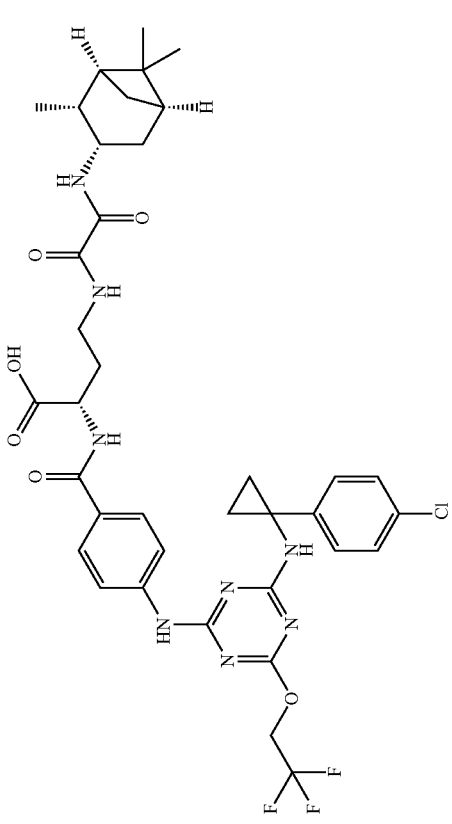 | | A |
| 1124 | 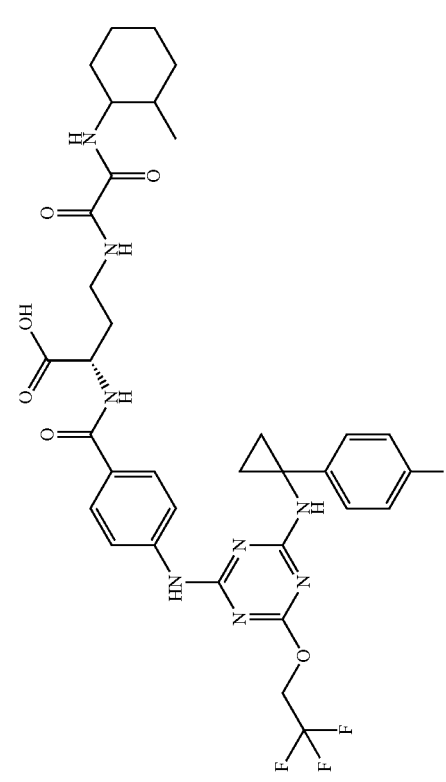 | | A |

TABLE 1-continued
| Compound | Structure | EC$_{50}$ | Activity |
|---|---|---|---|
| 1125 | 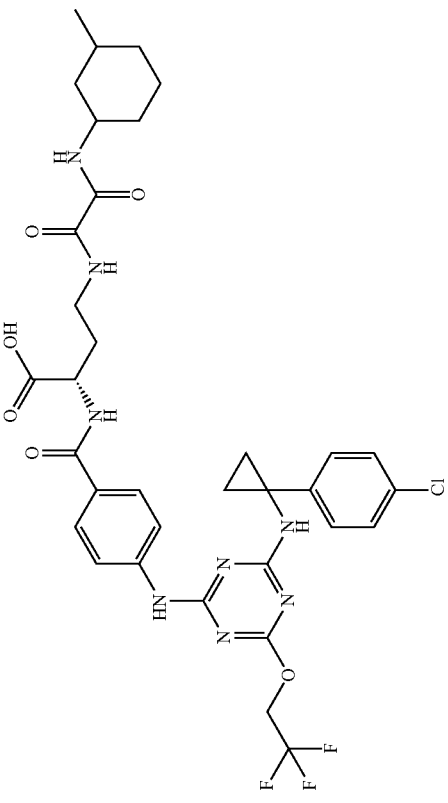 | | A |
| 1126 | 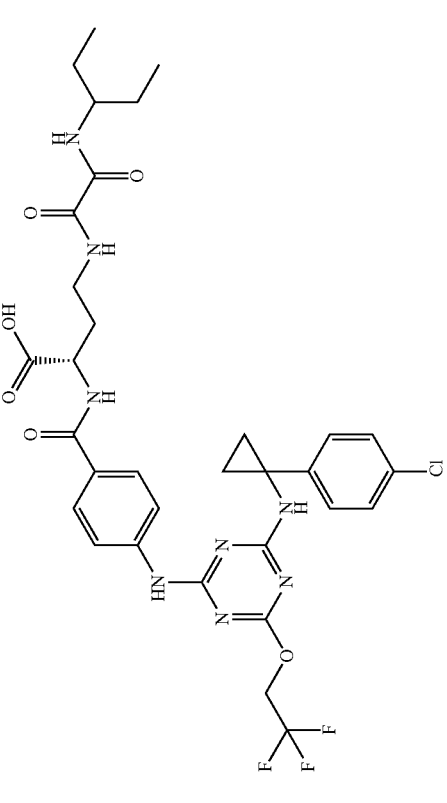 Chiral | | A |

TABLE 1-continued
| Compound | Structure | EC$_{50}$ | Activity |
|---|---|---|---|
| 1127 | 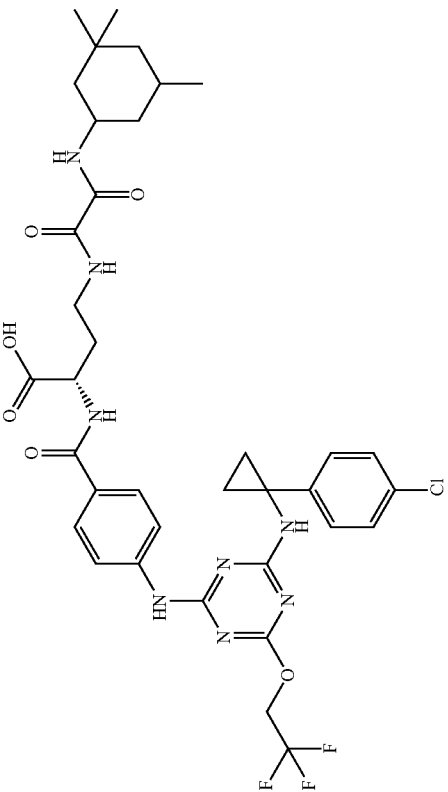 | | A |
| 1128 | 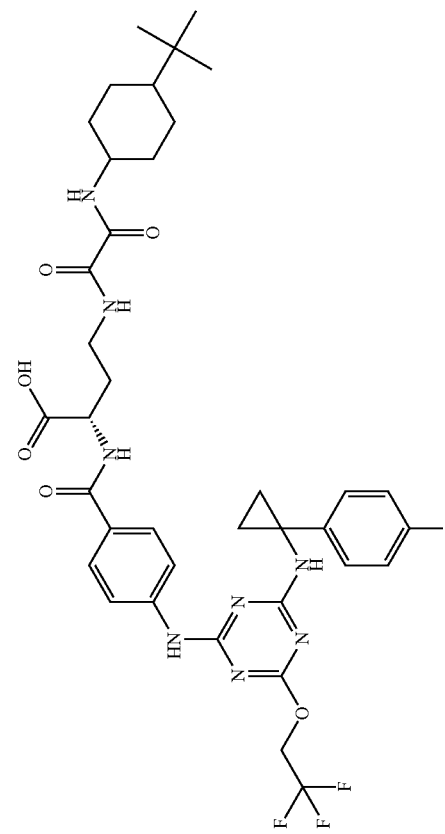 Chiral | | A |

TABLE 1-continued
| Compound | Structure | EC$_{50}$ | Activity |
|---|---|---|---|
| 1129 | Chiral | | A |
| 1130 | Chiral | 0.12 | A |
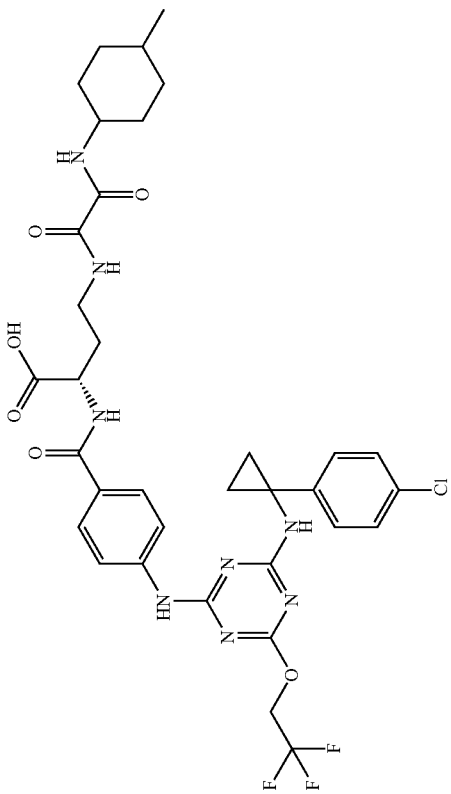
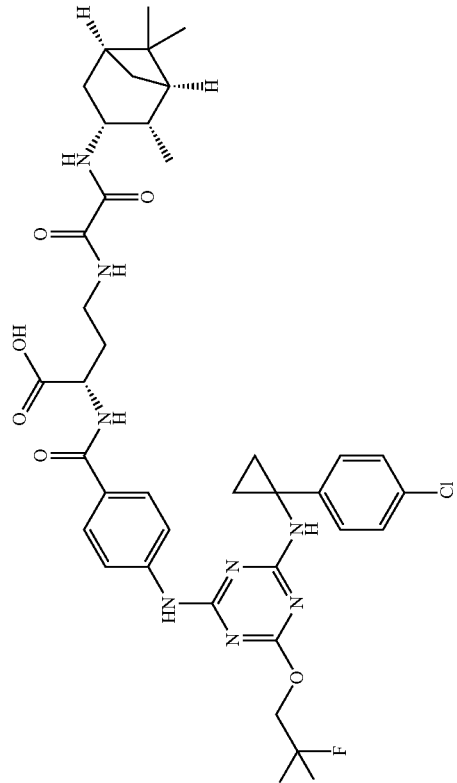

TABLE 1-continued
| Compound | Structure | EC$_{50}$ | Activity |
|---|---|---|---|
| 1131 | Chiral 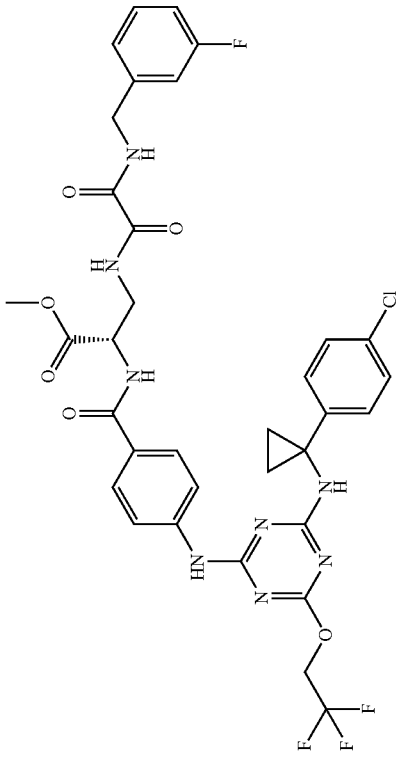 | | A |
| 1132 | Chiral 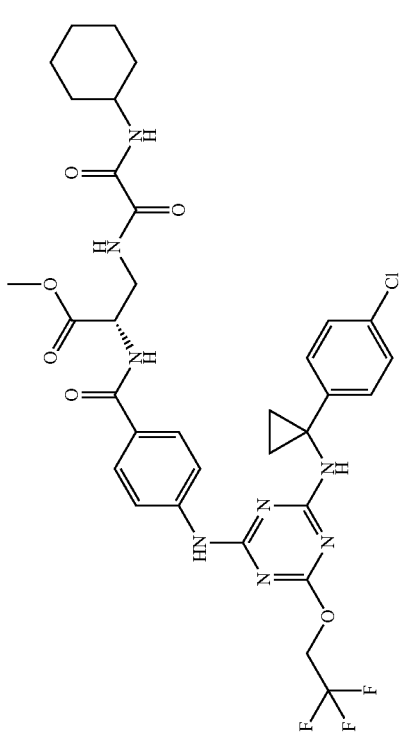 | | A |

TABLE 1-continued
| Compound | Structure | EC$_{50}$ | Activity |
|---|---|---|---|
| 1133 | Chiral 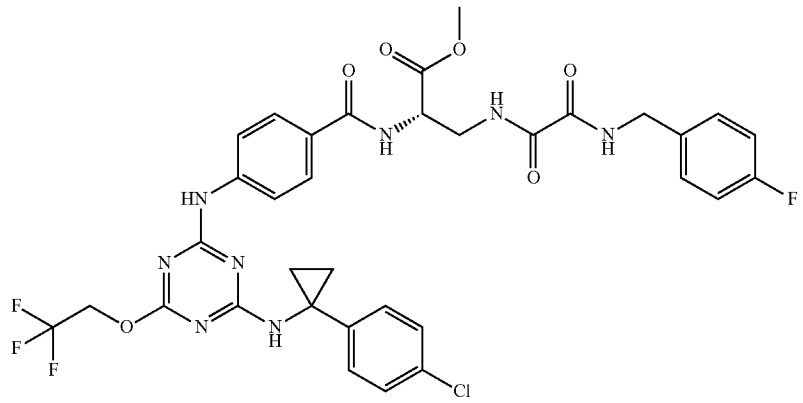 | 1.40 | A |
| 1134 | Chiral 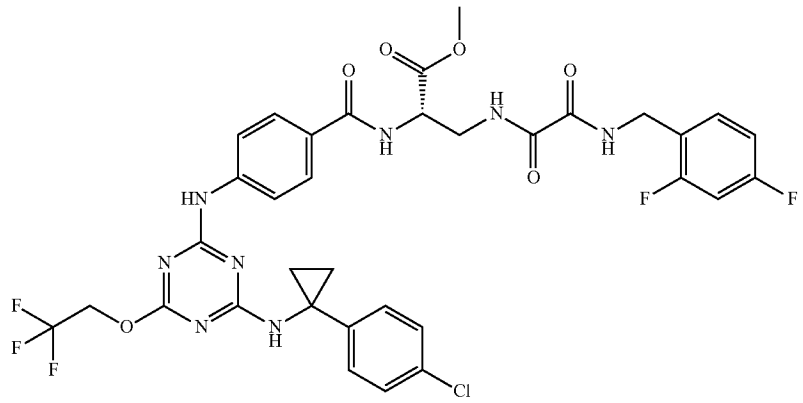 | | A |

TABLE 1-continued
| Compound | Structure | EC$_{50}$ | Activity |
|---|---|---|---|
| 1135 | 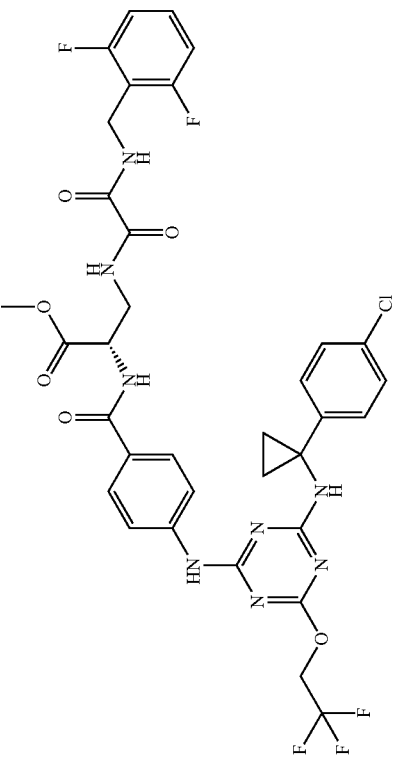 | 1.92 | A |
| 1136 | 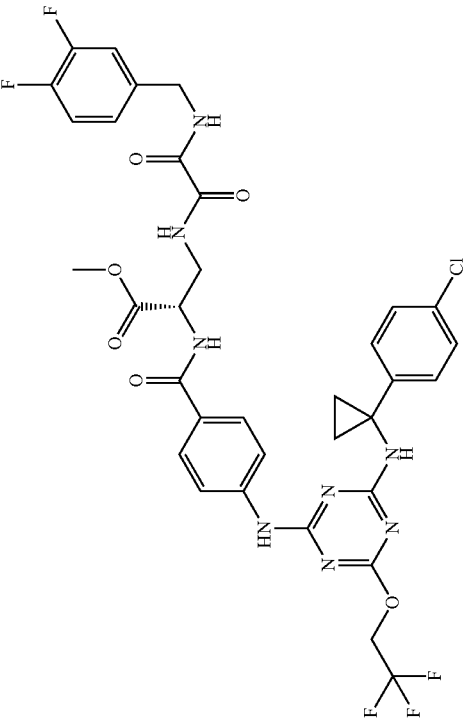 | | A |

| Compound | Structure | EC$_{50}$ | Activity |
|---|---|---|---|
| 1137 | Chiral 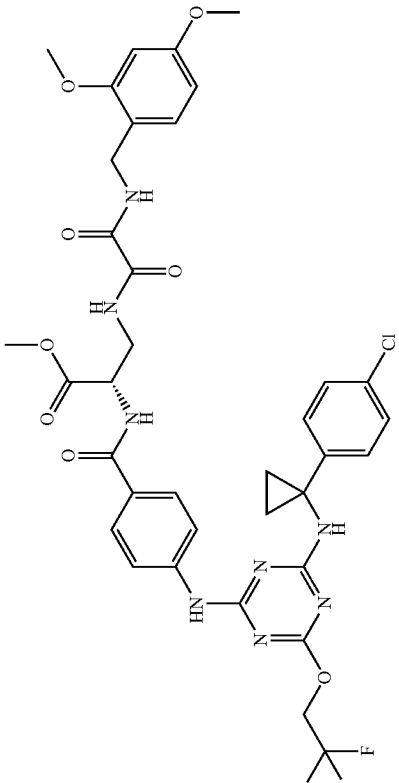 | | A |
| 1138 | Chiral 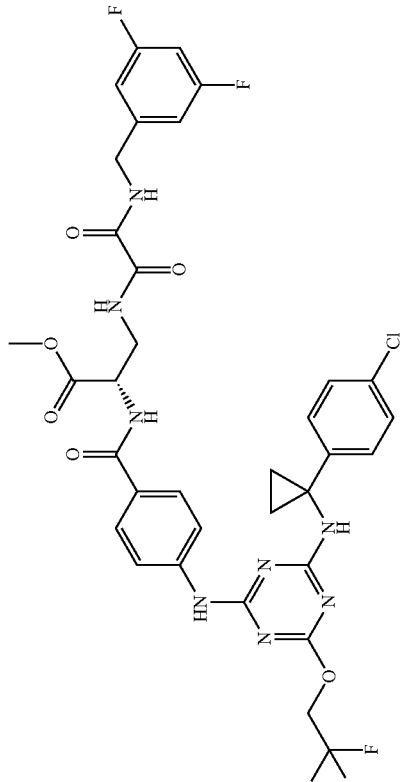 | 0.81 | A |

TABLE 1-continued
| Compound | Structure | EC$_{50}$ | Activity |
|---|---|---|---|
| 1139 | 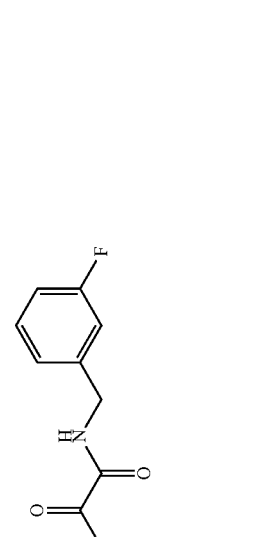 Chiral | | A |
| 1140 | 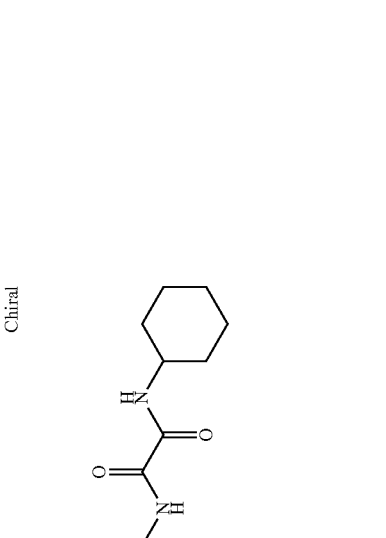 Chiral | | A |

TABLE 1-continued
| Compound | Structure | EC$_{50}$ | Activity |
|---|---|---|---|
| 1141 | Chiral 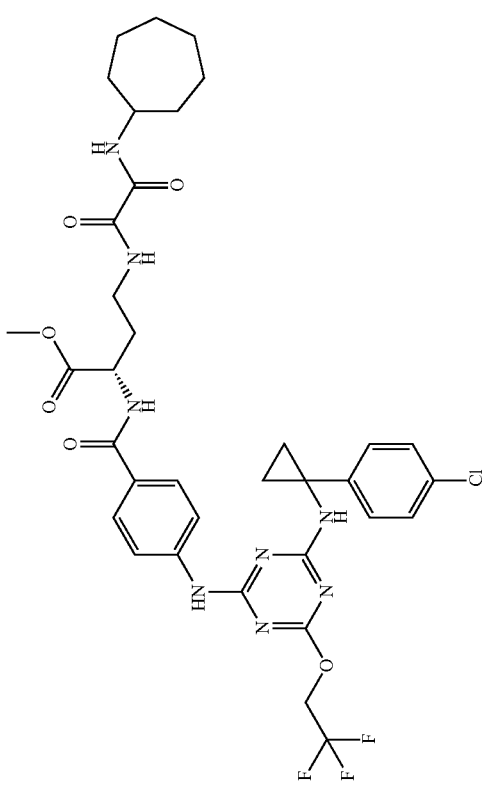 | | A |
| 1142 | Chiral 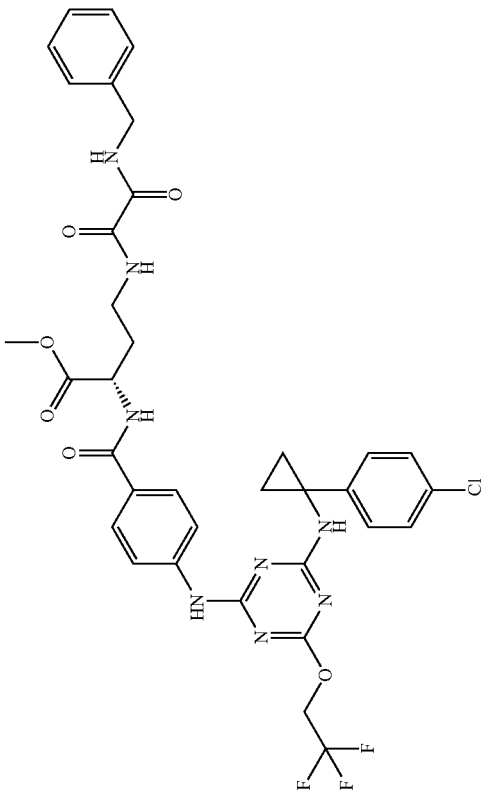 | | A |

TABLE 1-continued
| Compound | Structure | EC$_{50}$ | Activity |
|---|---|---|---|
| 1143 | 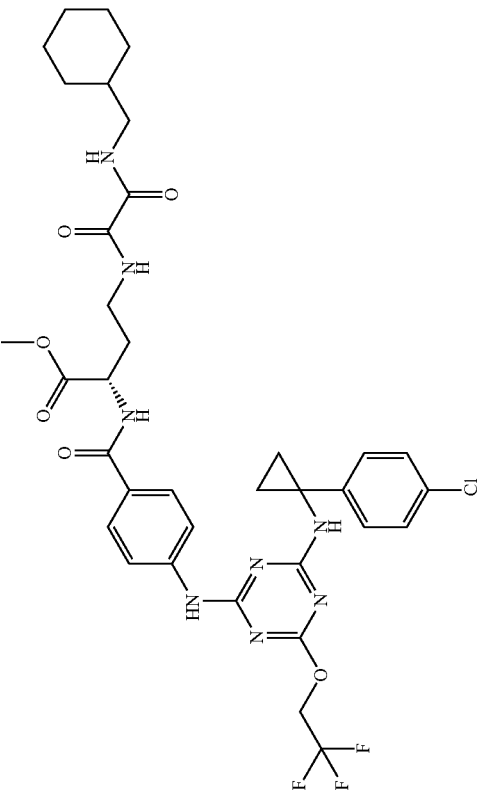 | | A |
| 1144 | 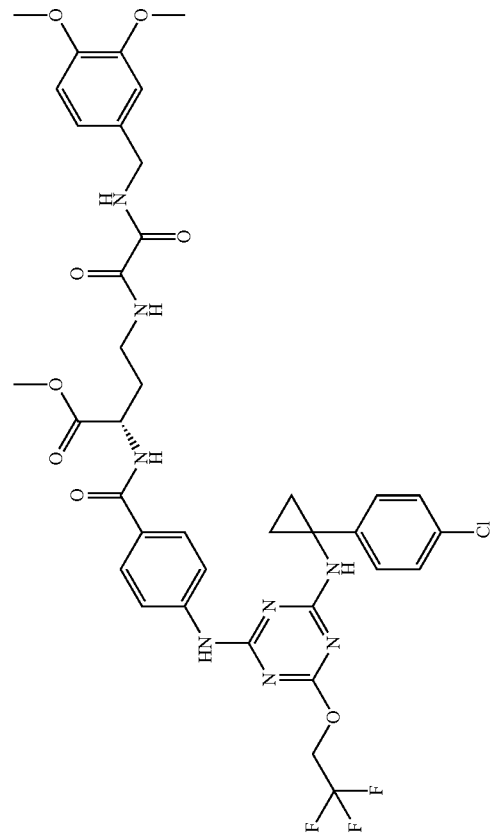 | | A |

| Compound | Structure | EC$_{50}$ | Activity |
|---|---|---|---|
| 1145 | Chiral 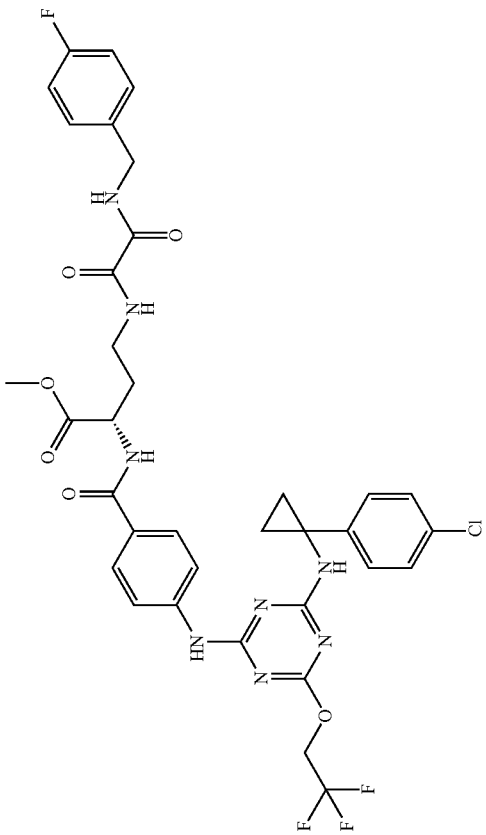 | | A |
| 1146 | Chiral 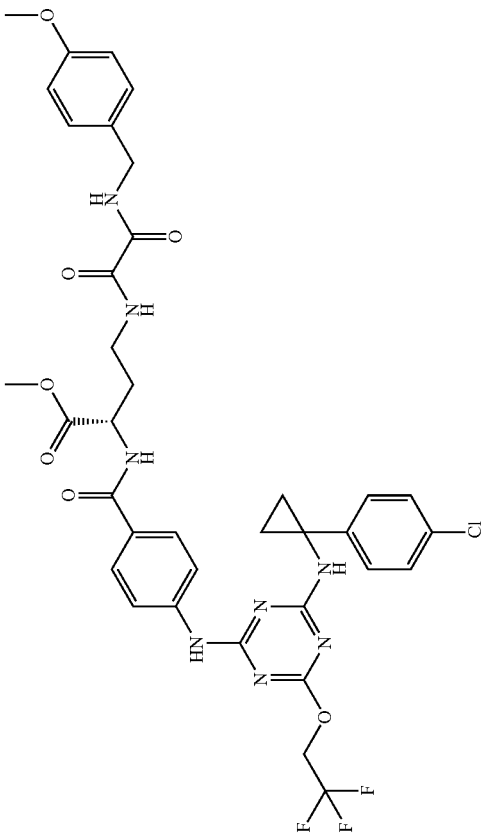 | | A |

TABLE 1-continued
| Compound | Structure | EC$_{50}$ | Activity |
|---|---|---|---|
| 1147 | 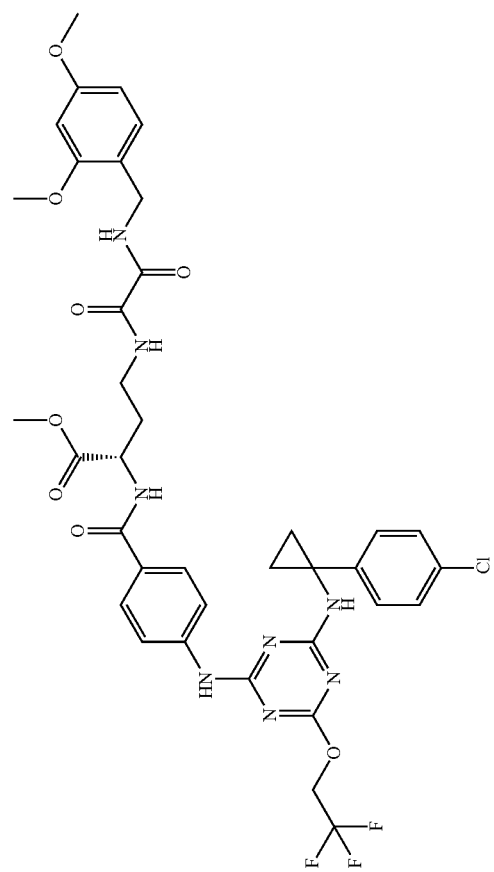 | | A |
| 1148 | 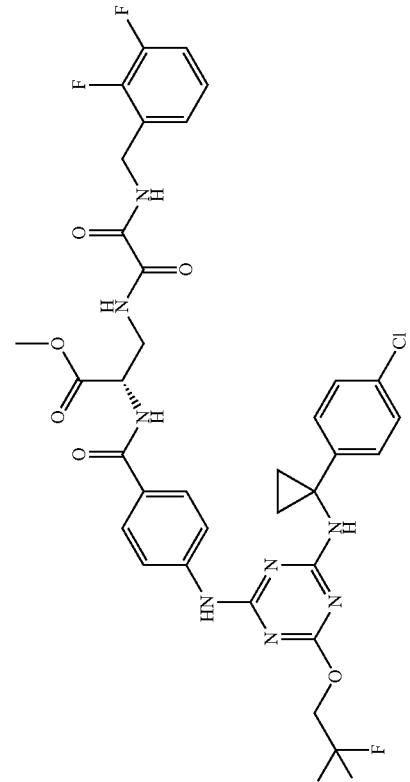 | | A |

TABLE 1-continued
| Compound | Structure | EC50 | Activity |
|---|---|---|---|
| 1149 | Chiral 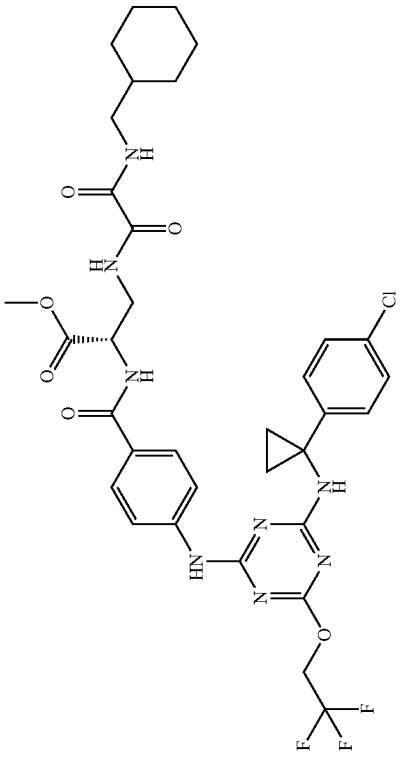 | | A |
| 1150 | Chiral 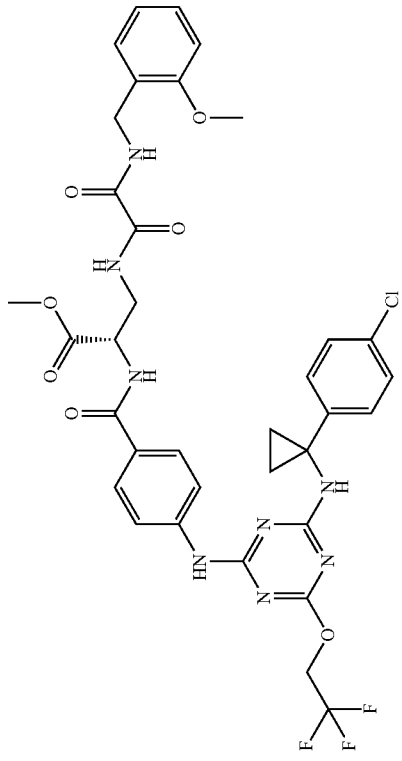 | | A |

TABLE 1-continued
| Compound | Structure | EC$_{50}$ | Activity |
|---|---|---|---|
| 1151 | 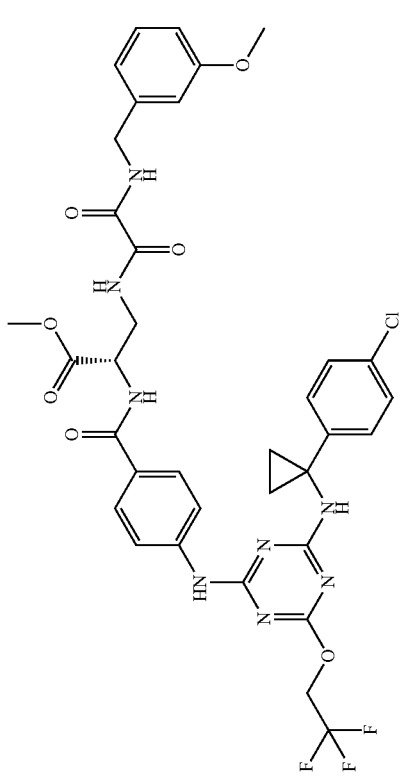 Chiral | 1.62 | A |
| 1152 | 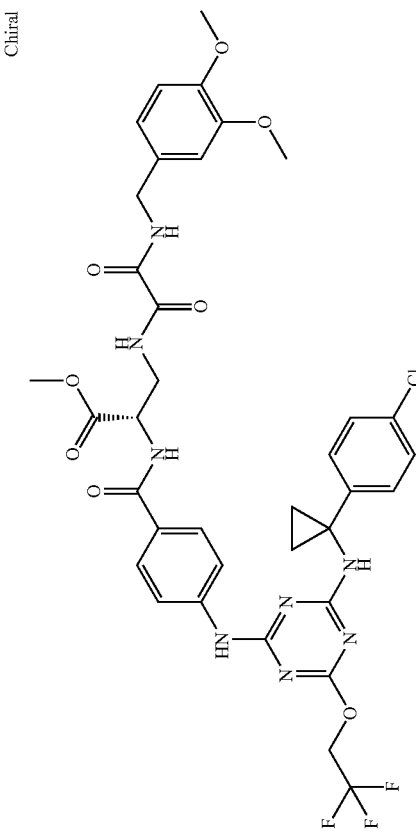 Chiral | | A |

TABLE 1-continued
| Compound | Structure | EC$_{50}$ | Activity |
|---|---|---|---|
| 1153 | 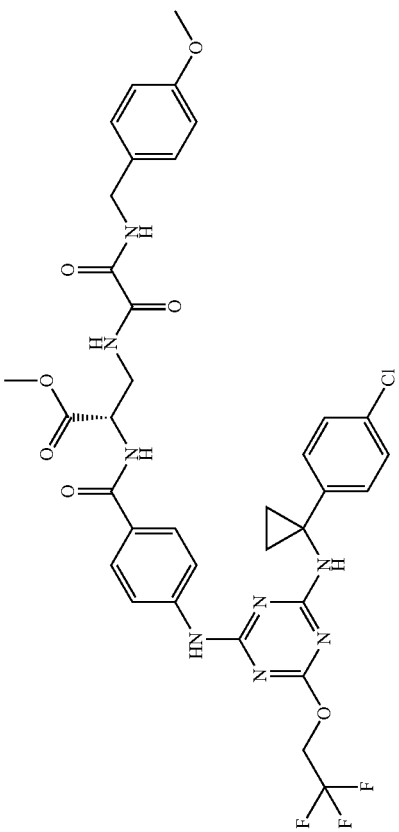 Chiral | | A |
| 1154 | 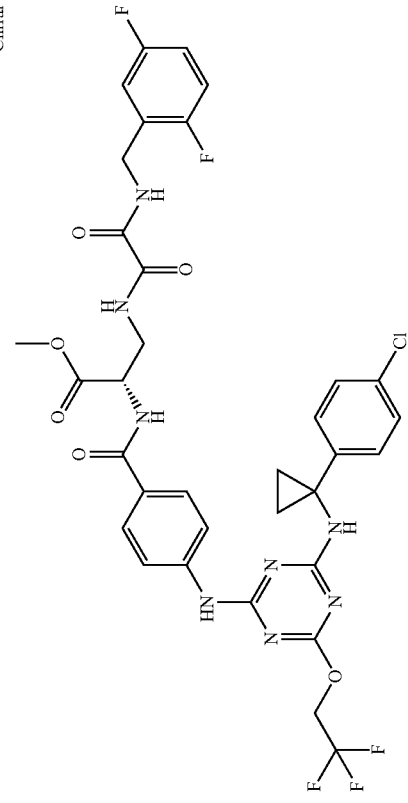 Chiral | 1.07 | A |

TABLE 1-continued
| Compound | Structure | EC$_{50}$ | Activity |
|---|---|---|---|
| 1155 | 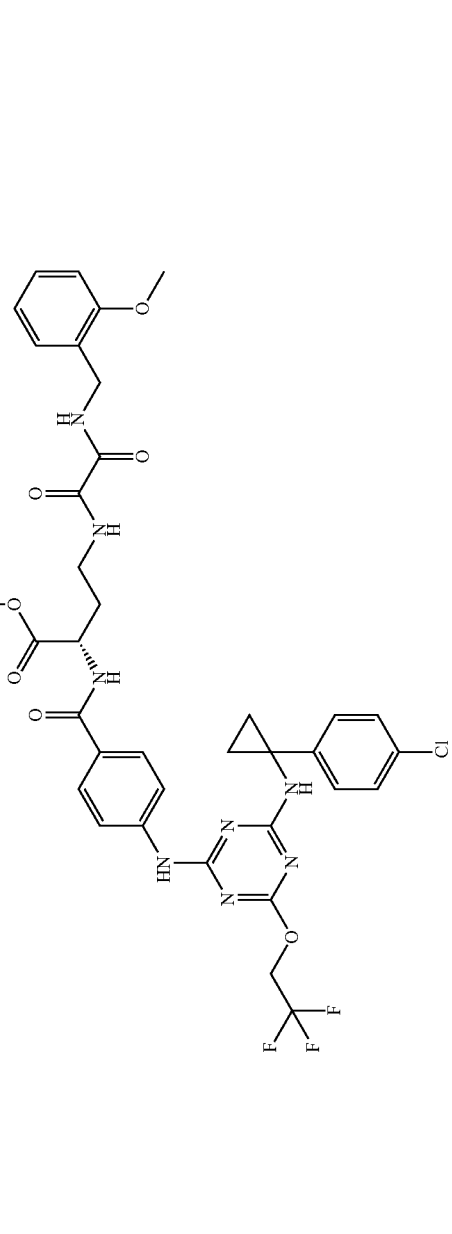 Chiral | | A |
| 1156 | 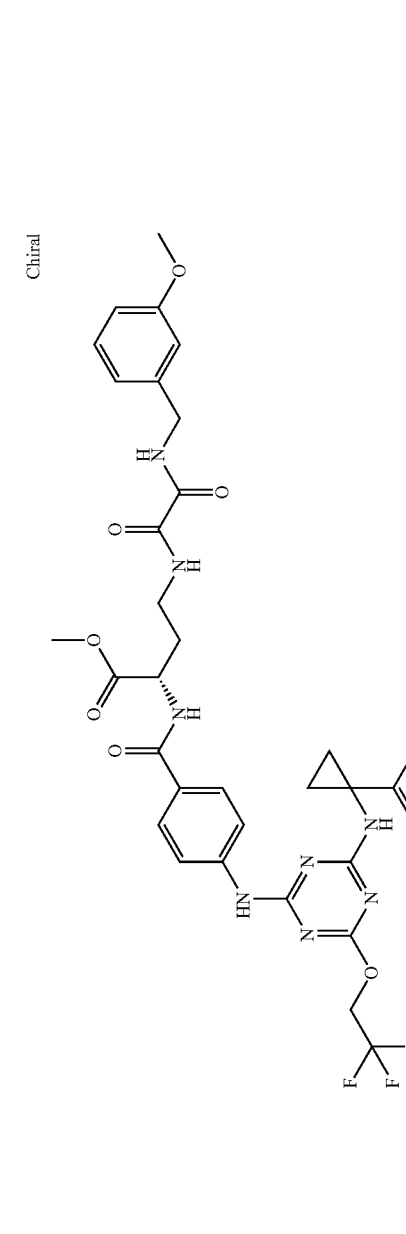 Chiral | | A |

TABLE 1-continued
| Compound | Structure | EC$_{50}$ | Activity |
|---|---|---|---|
| 1157 | 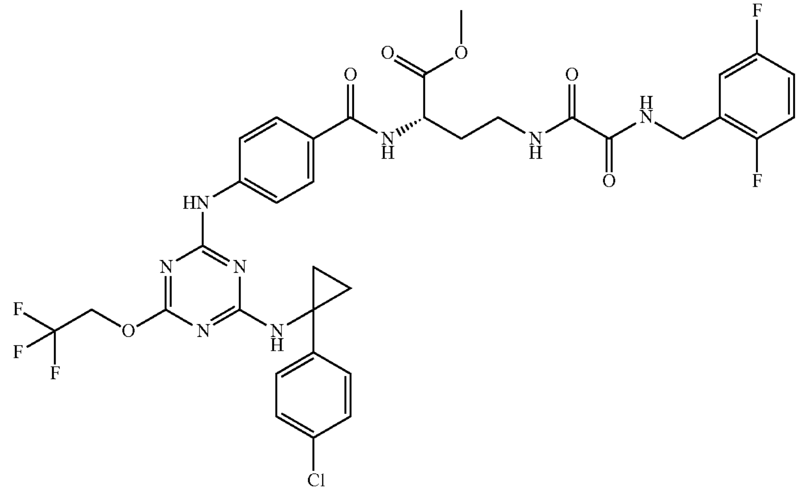 | | A |
| 1158 | 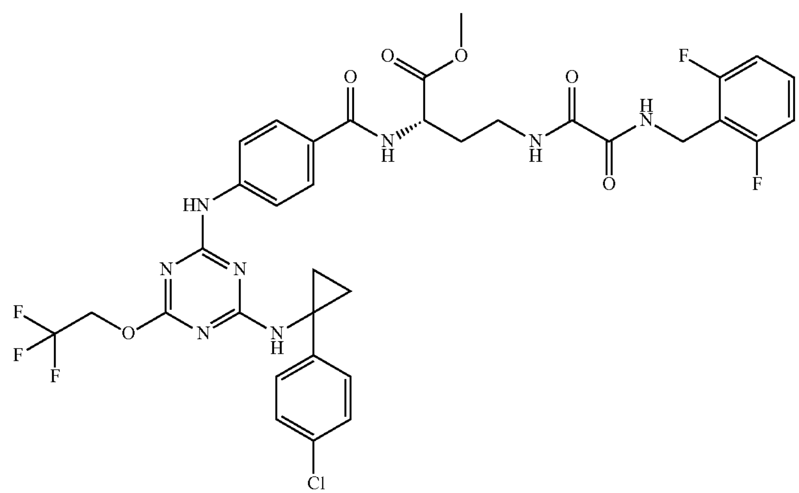 | | A |

TABLE 1-continued
| Compound | Structure | EC$_{50}$ | Activity |
|---|---|---|---|
| 1159 | Chiral 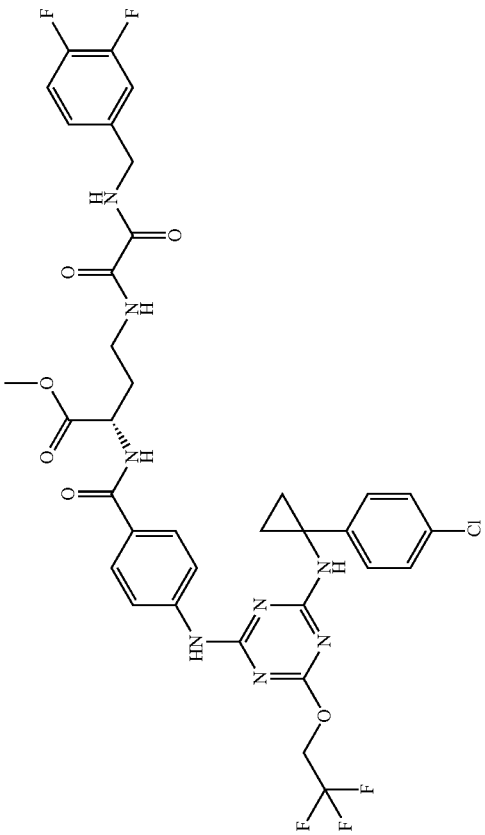 | | A |
| 1160 | Chiral 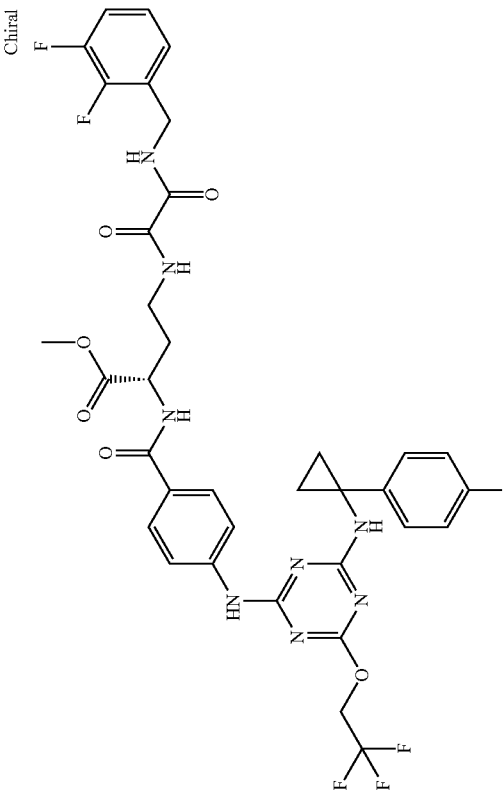 | | A |

TABLE 1-continued
| Compound | Structure | EC$_{50}$ | Activity |
|---|---|---|---|
| 1161 | Chiral 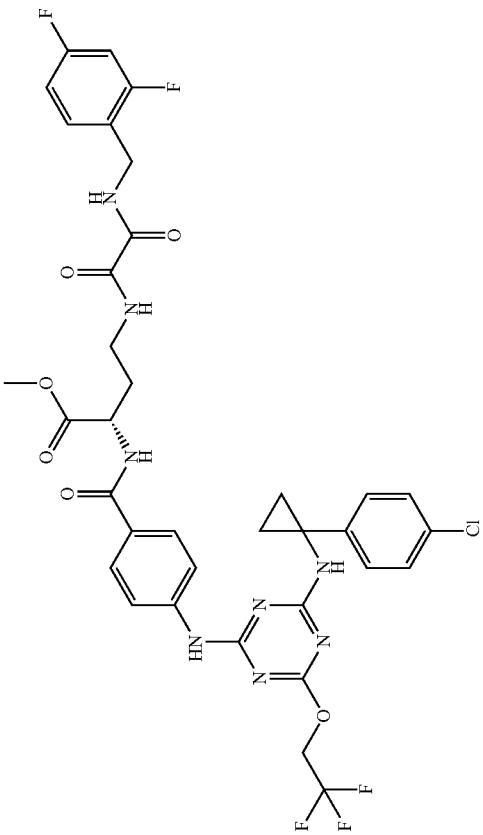 | | A |
| 1162 | Chiral 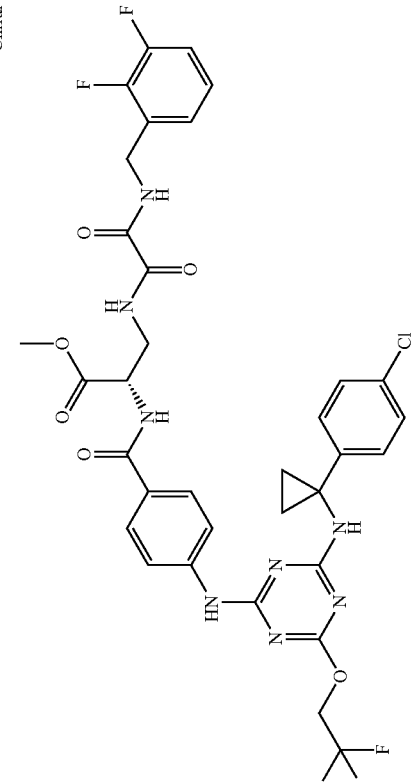 | | A |

TABLE 1-continued
| Compound | Structure | EC$_{50}$ | Activity |
|---|---|---|---|
| 1163 | Chiral 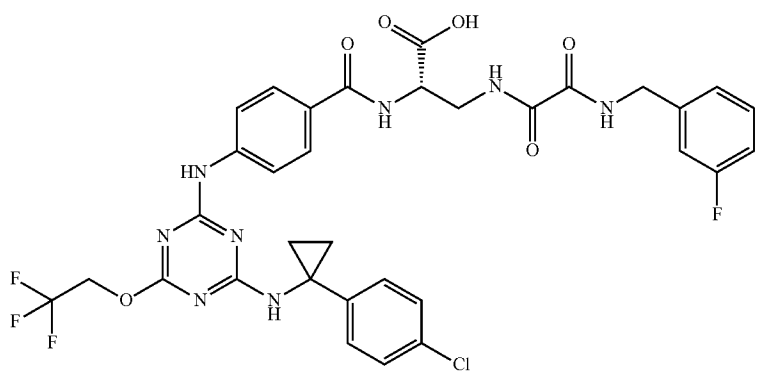 | | A |
| 1164 | Chiral 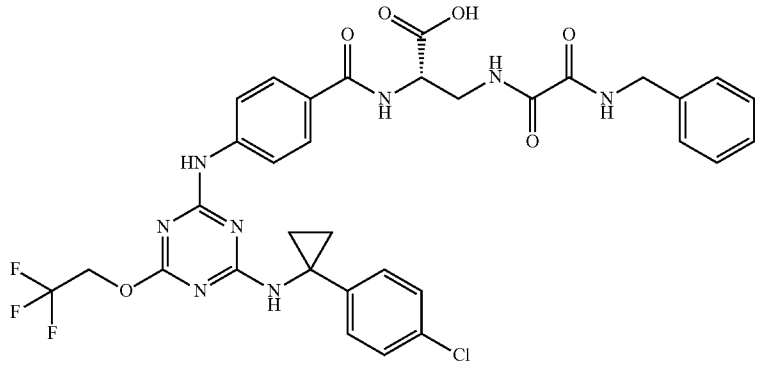 | | A |

TABLE 1-continued
| Compound | Structure | EC$_{50}$ | Activity |
|---|---|---|---|
| 1165 | 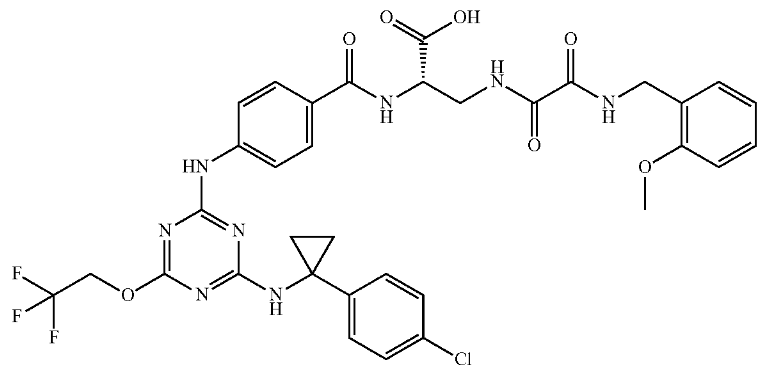 | | A |
| 1166 | 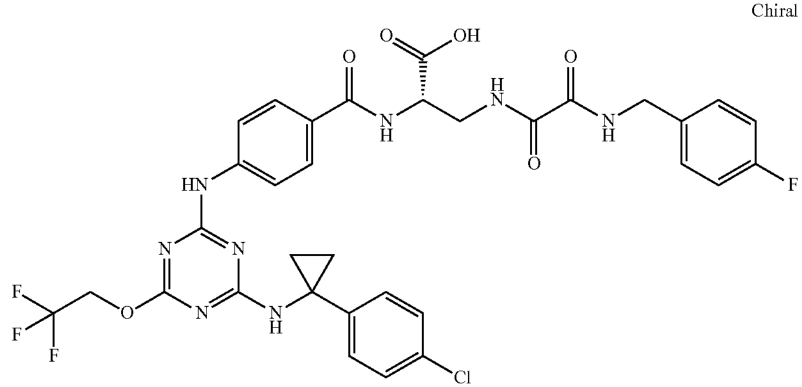 [SMILES: O=C(NCc1ccc(F)cc1)C(=O)NC[C@H](NC(=O)c1ccc(Nc2nc(NC3(c4ccc(Cl)cc4)CC3)nc(OCC(F)(F)F)n2)cc1)C(=O)O] | | A |

TABLE 1-continued
| Compound | Structure | EC$_{50}$ | Activity |
|---|---|---|---|
| 1167 | 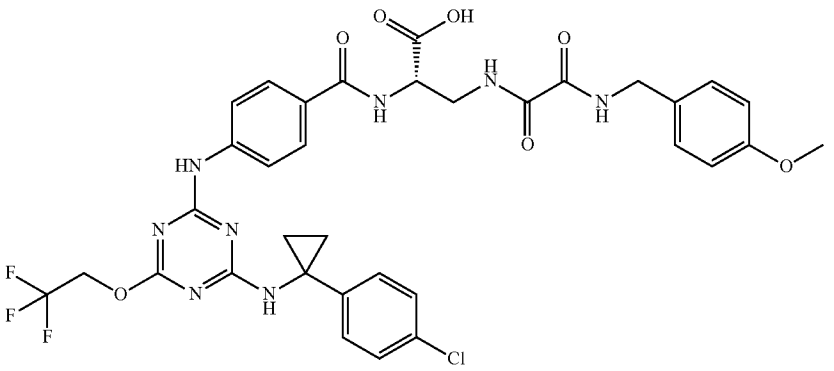 Chiral | 1.32 | A |
| 1168 | 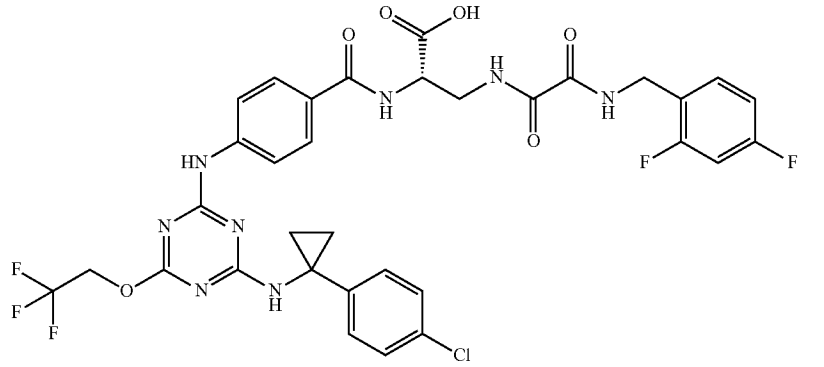 Chiral | | A |

TABLE 1-continued
| Compound | Structure | EC$_{50}$ | Activity |
|---|---|---|---|
| 1169 | 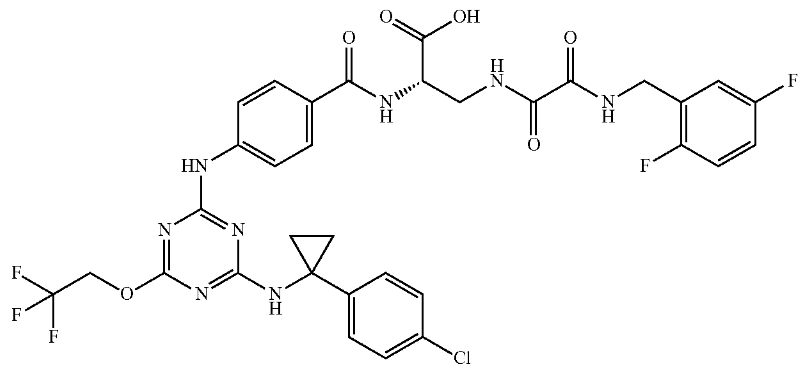 | | A |
| 1170 | 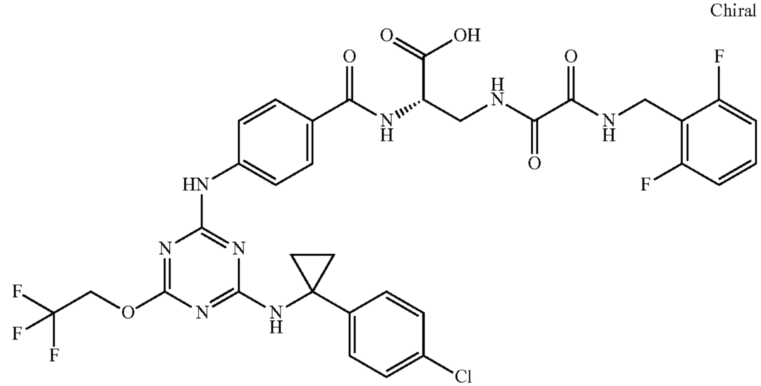 [SMILES: O=C(NCc1c(F)cccc1F)C(=O)NC[C@H](NC(=O)c1ccc(Nc2nc(NC3(c4ccc(Cl)cc4)CC3)nc(OCC(F)(F)F)n2)cc1)C(=O)O] | | A |

TABLE 1-continued
| Compound | Structure | EC$_{50}$ | Activity |
|---|---|---|---|
| 1171 | 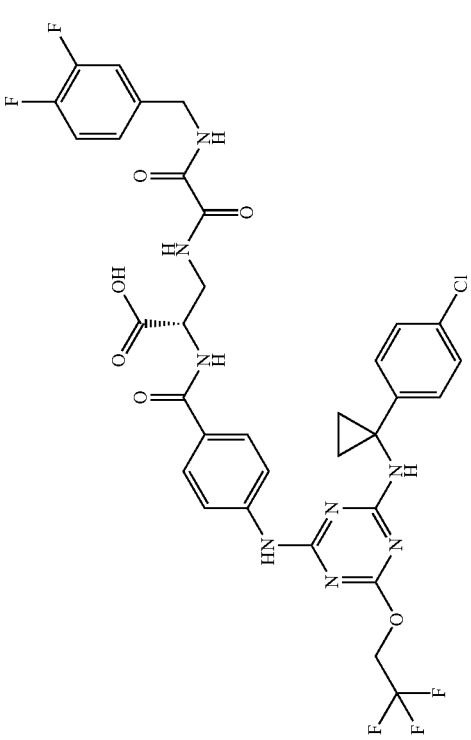 | | A |
| 1172 | 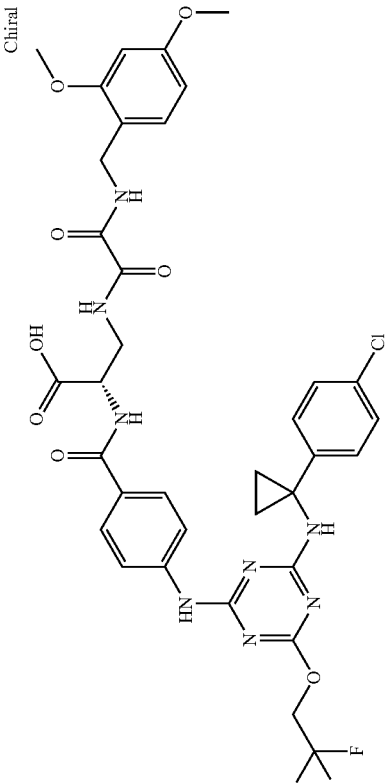 | 9.26 | A |

TABLE 1-continued
| Compound | Structure | EC$_{50}$ | Activity |
|---|---|---|---|
| 1173 | 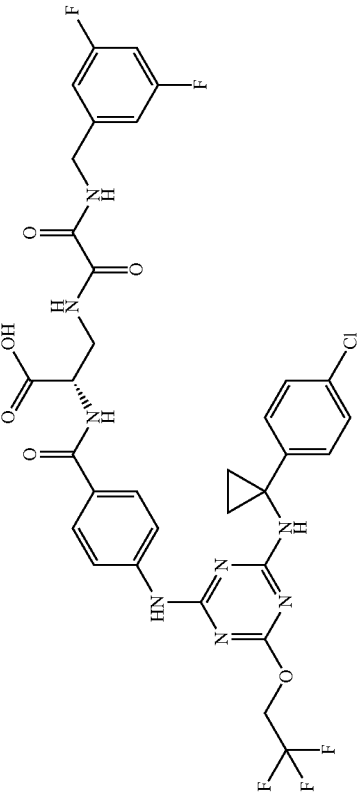 | 0.74 | A |
| 1174 | 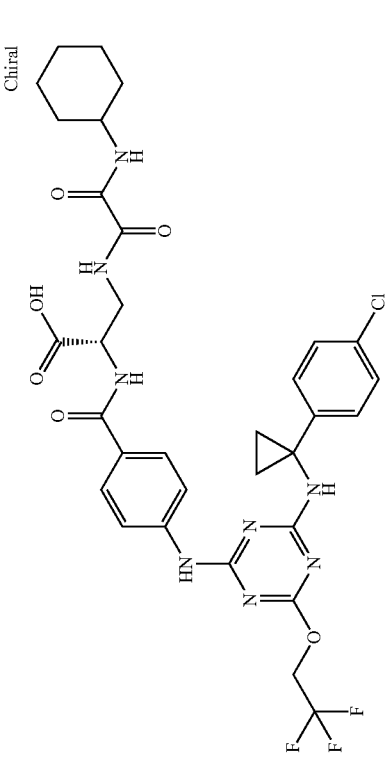 | | A |

TABLE 1-continued
| Compound | Structure | EC$_{50}$ | Activity |
|---|---|---|---|
| 1175 | 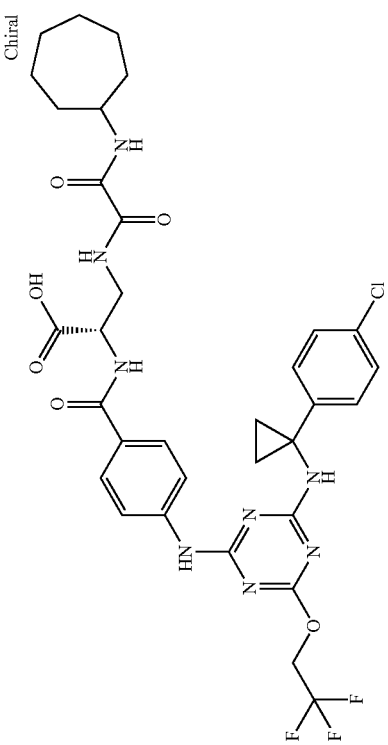 Chiral | | A |
| 1176 | 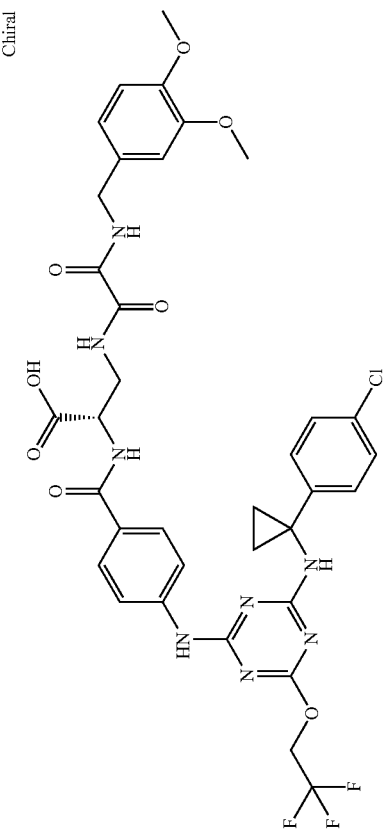 Chiral | | A |

TABLE 1-continued
| Compound | Structure | EC$_{50}$ | Activity |
|---|---|---|---|
| 1177 | 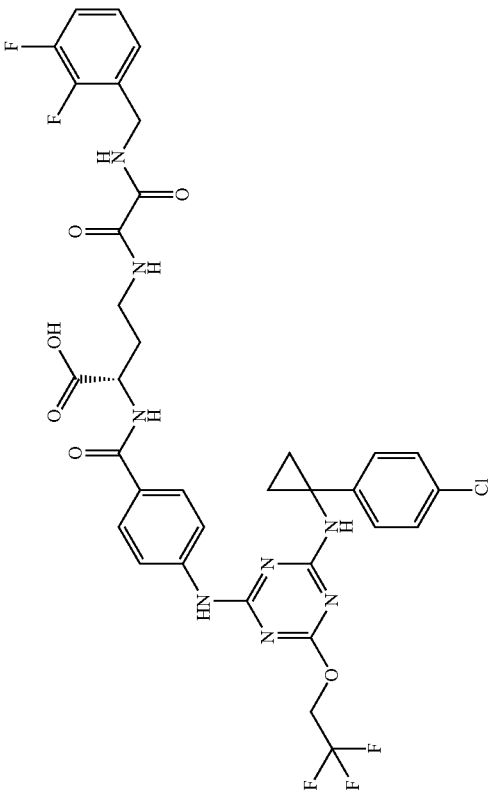 | | A |
| 1178 | 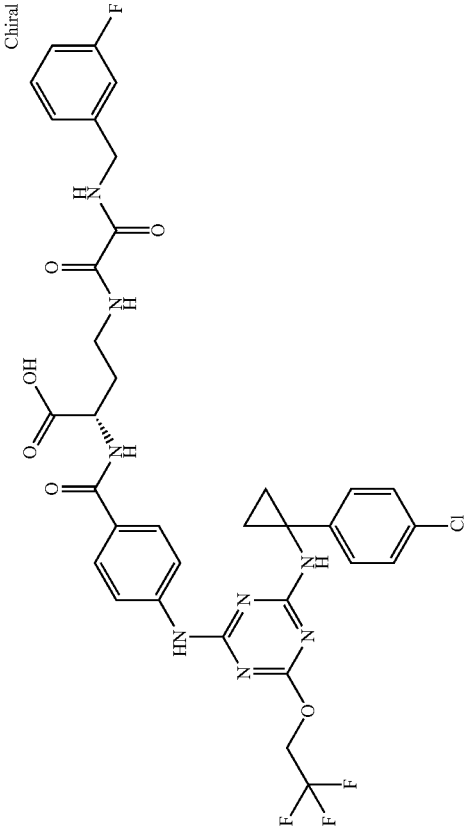 | | A |

TABLE 1-continued
| Compound | Structure | EC$_{50}$ | Activity |
|---|---|---|---|
| 1179 | Chiral 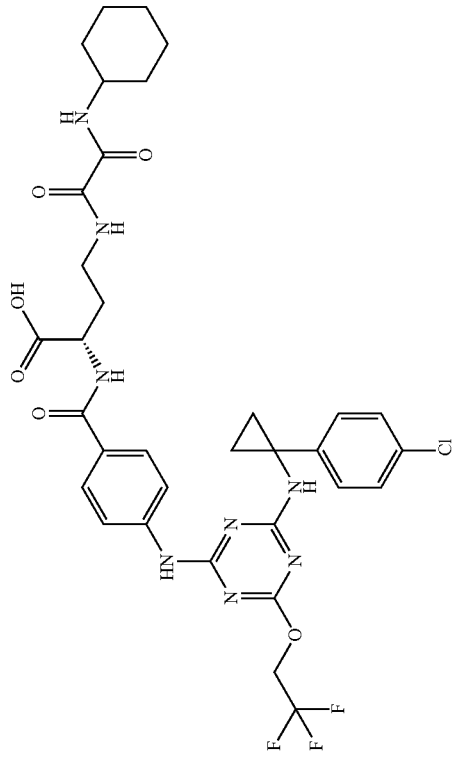 | | A |
| 1180 | Chiral 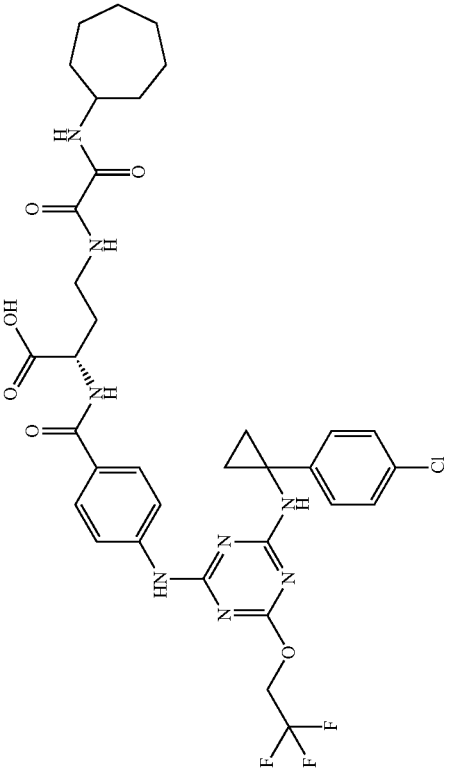 | | A |

TABLE 1-continued

| Compound | Structure | EC$_{50}$ | Activity |
|---|---|---|---|
| 1181 | Chiral | | A |
| 1182 | Chiral | | A |

TABLE 1-continued

| Compound | Structure | EC$_{50}$ | Activity |
|---|---|---|---|
| 1183 | Chiral | | A |
| 1184 | Chiral | | A |

TABLE 1-continued
| Compound | Structure | EC$_{50}$ | Activity |
|---|---|---|---|
| 1185 | 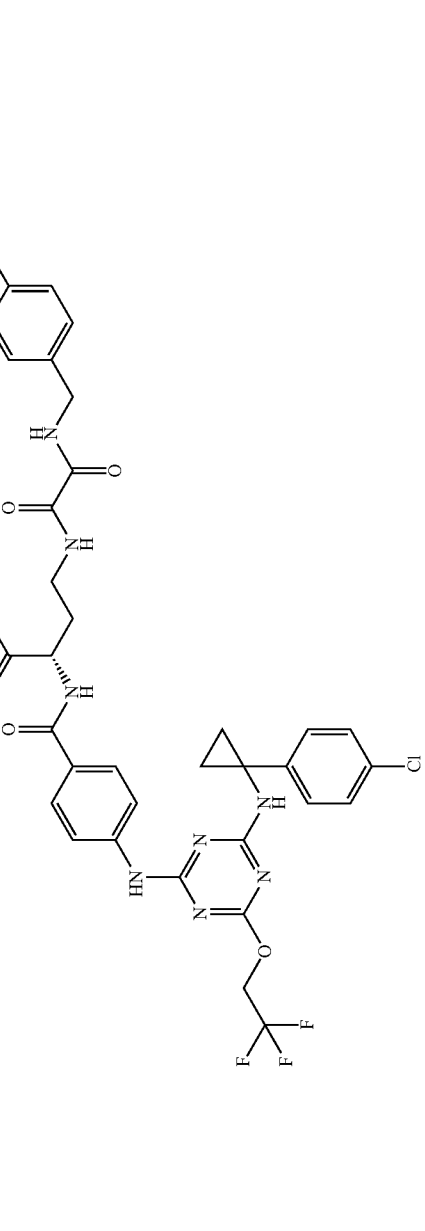 | | A |
| 1186 | 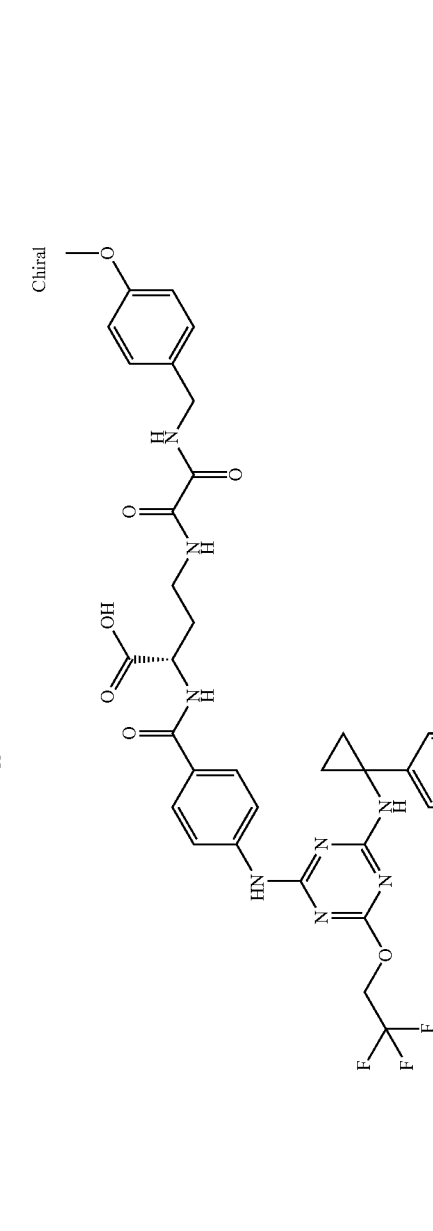 | | A |

TABLE 1-continued

| Compound | Structure | EC$_{50}$ | Activity |
|---|---|---|---|
| 1187 | Chiral | 0.08 | A |
| 1188 | Chiral | | A |

| Compound | Structure | EC$_{50}$ | Activity |
|---|---|---|---|
| 1189 | 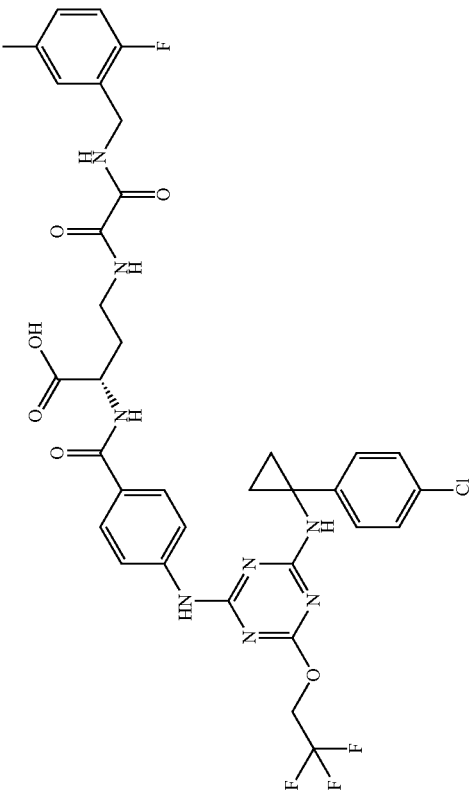 | | A |
| 1190 | 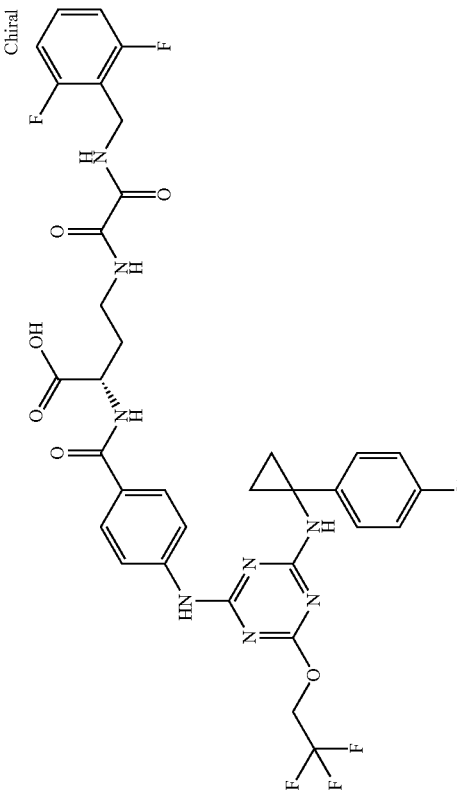 | | A |

TABLE 1-continued
| Compound | Structure | EC$_{50}$ | Activity |
|---|---|---|---|
| 1191 | 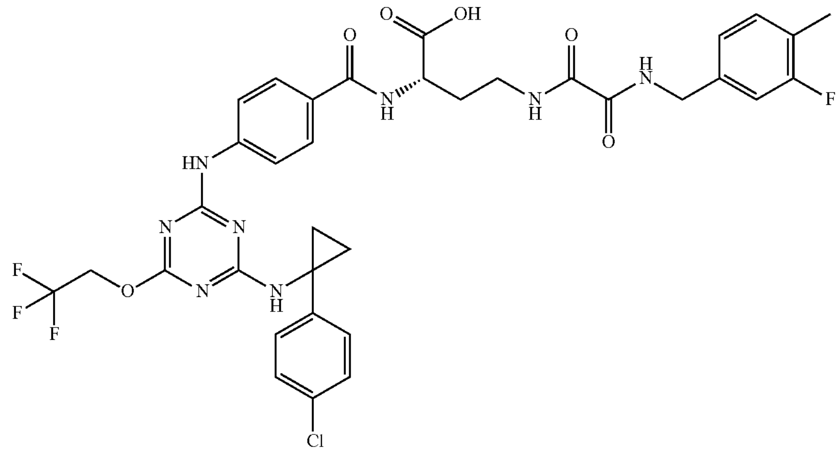 | 0.17 | A |
| 1192 | 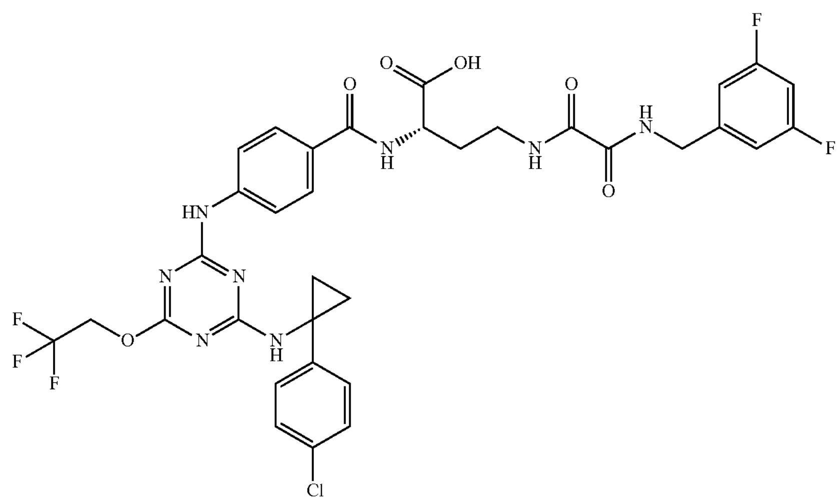 | | A |

TABLE 1-continued

| Compound | Structure | EC$_{50}$ | Activity |
|---|---|---|---|
| 1193 | Chiral (structure) | 0.52 | A |
| 1194 | Chiral (structure) |  | A |

TABLE 1-continued
| Compound | Structure | EC$_{50}$ | Activity |
|---|---|---|---|
| 1195 | Chiral 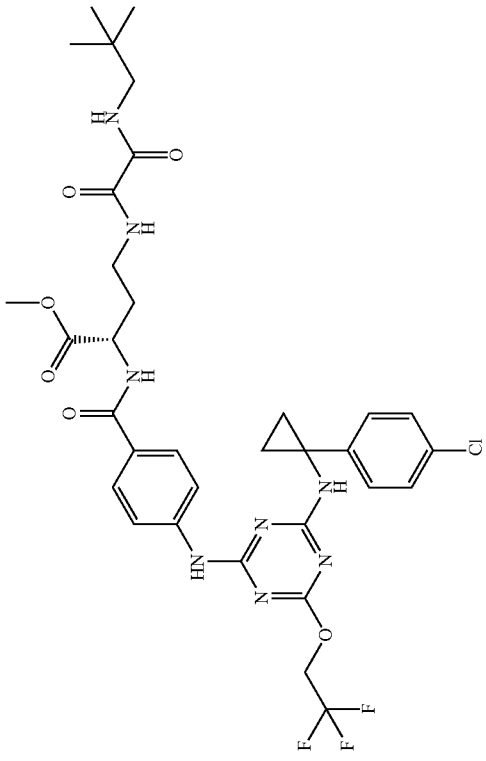 | | A |
| 1196 | Chiral 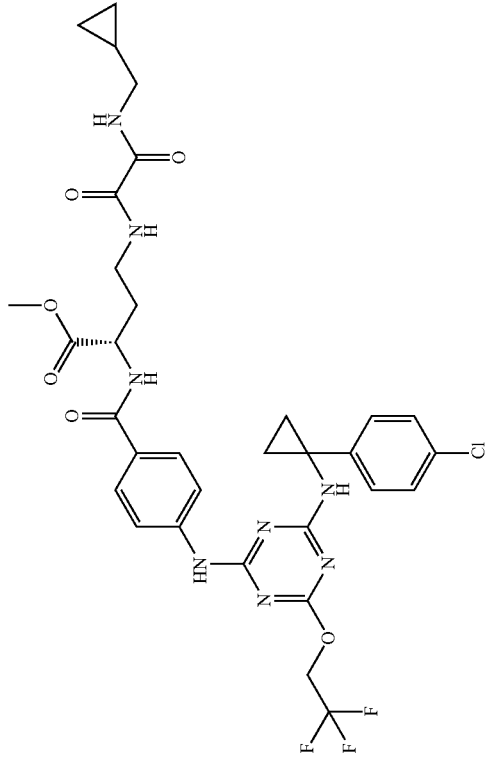 | | A |

TABLE 1-continued

| Compound | Structure | EC$_{50}$ | Activity |
|---|---|---|---|
| 1197 | 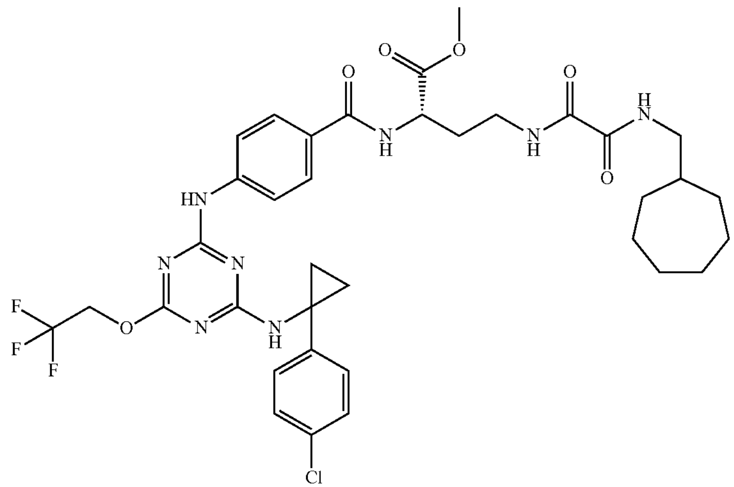 | | A |
| 1198 | 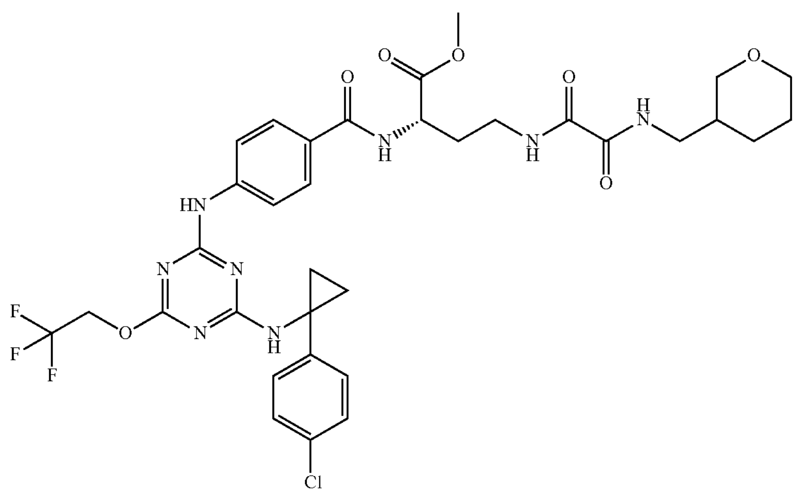 [SMILES: COC(=O)[C@H](CCNC(=O)C(=O)NCC1CCCOC1)NC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 1199 | 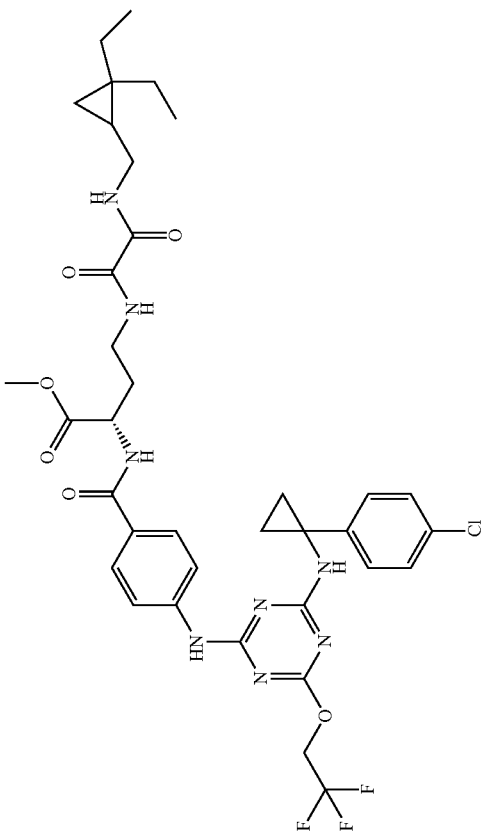 | 0.19 | A |
| 1200 | 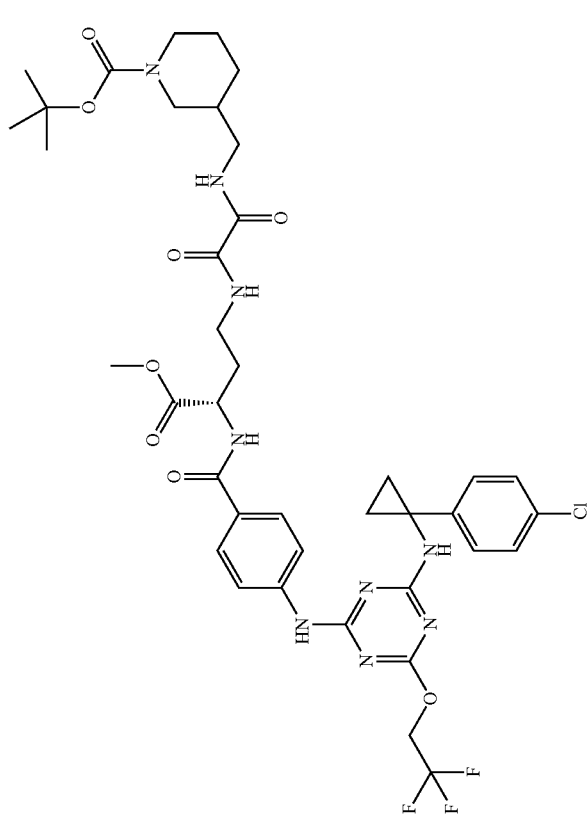 | | A |

TABLE 1-continued
| Compound | Structure | EC$_{50}$ | Activity |
|---|---|---|---|
| 1201 | 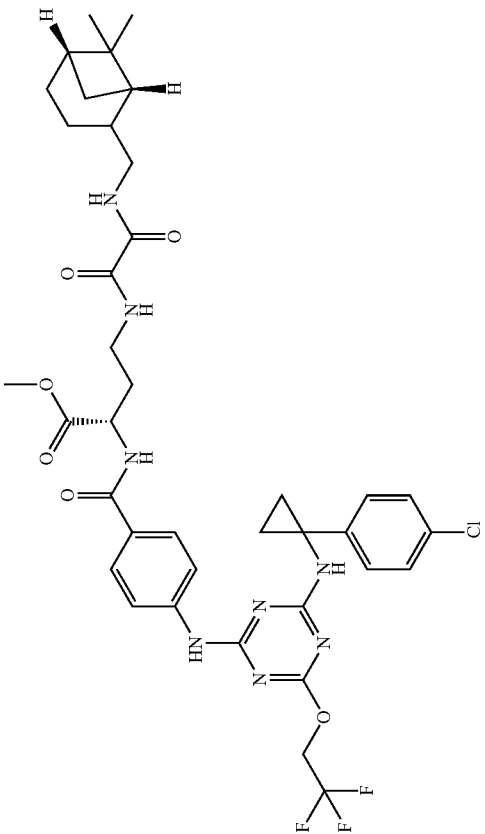 | | A |
| 1202 | 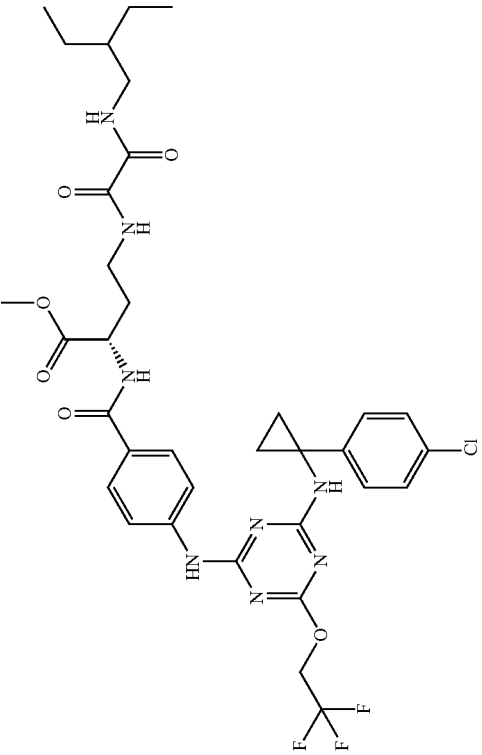 | | A |

| Compound | Structure | EC$_{50}$ | Activity |
|---|---|---|---|
| 1203 | 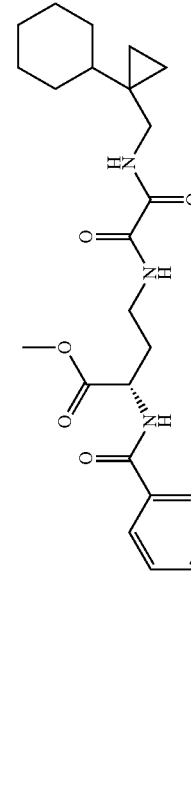 Chiral | | A |
| 1204 | 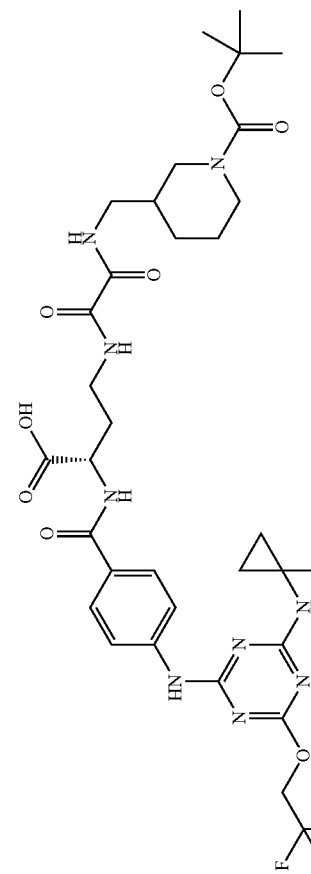 Chiral | | A |

| Compound | Structure | EC₅₀ | Activity |
|---|---|---|---|
| 1205 | Chiral | | A |
| 1206 | Chiral | | A |

TABLE 1-continued
| Compound | Structure | EC$_{50}$ | Activity |
|---|---|---|---|
| 1207 | 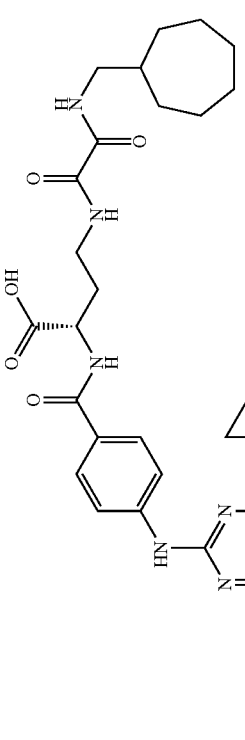 | | A |
| 1208 | 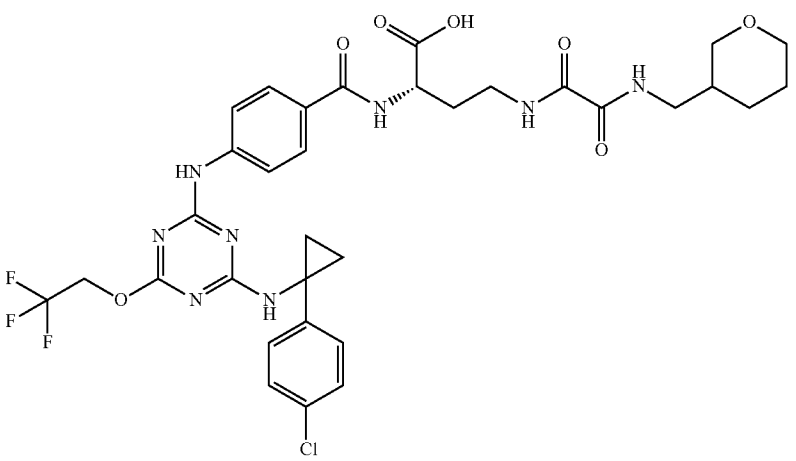 [SMILES: O=C(NCC[C@H](NC(=O)c1ccc(Nc2nc(NC3(c4ccc(Cl)cc4)CC3)nc(OCC(F)(F)F)n2)cc1)C(=O)O)C(=O)NCC1CCCOC1] | 0.21 | A |

TABLE 1-continued

| Compound | Structure | EC$_{50}$ | Activity |
|---|---|---|---|
| 1209 | 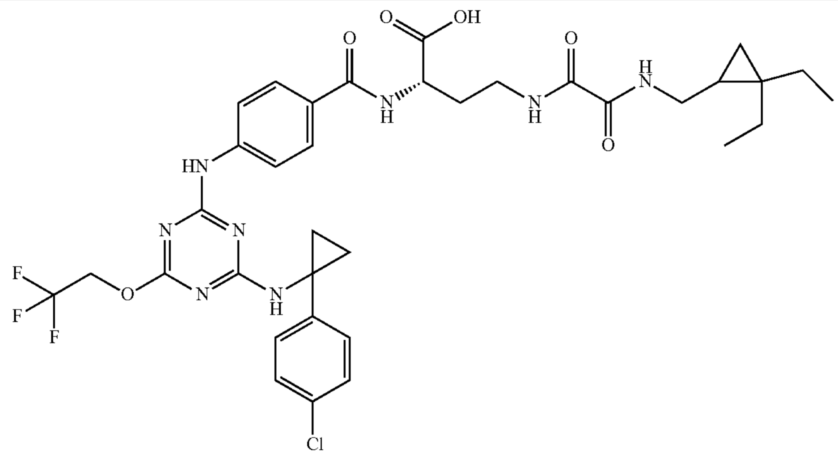 [SMILES: CCC1(CC)CC1CNC(=O)C(=O)NCC[C@H](NC(=O)c1ccc(Nc2nc(NC3(c4ccc(Cl)cc4)CC3)nc(OCC(F)(F)F)n2)cc1)C(=O)O] | | A |
| 1210 | 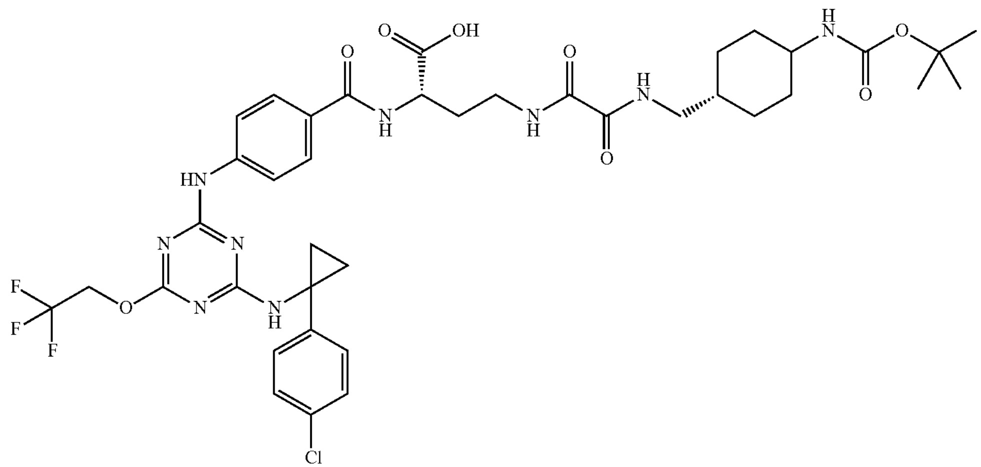 | | A |

TABLE 1-continued

| Compound | Structure | EC$_{50}$ | Activity |
|---|---|---|---|
| 1211 | 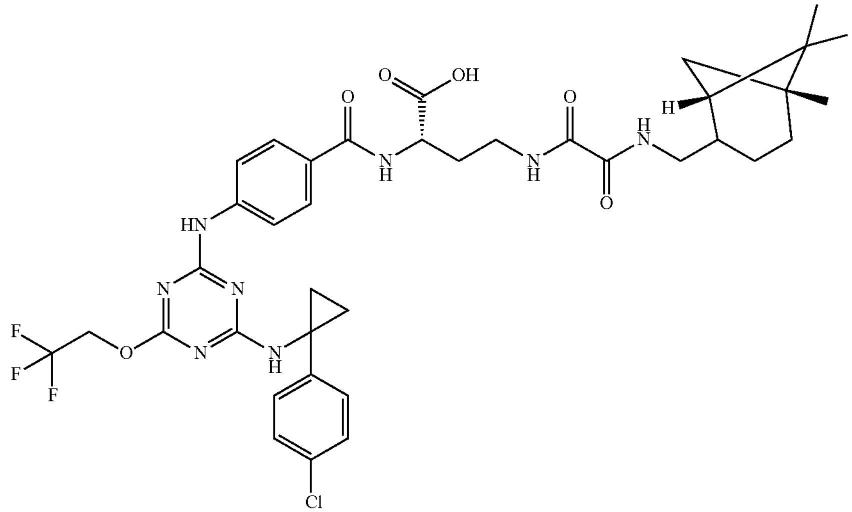 [SMILES: CC1(C)[C@H]2C[C@@]1(C)CCC2CNC(=O)C(=O)NCC[C@H](NC(=O)c1ccc(Nc2nc(NC3(c4ccc(Cl)cc4)CC3)nc(OCC(F)(F)F)n2)cc1)C(=O)O] | 0.13 | A |
| 1212 | 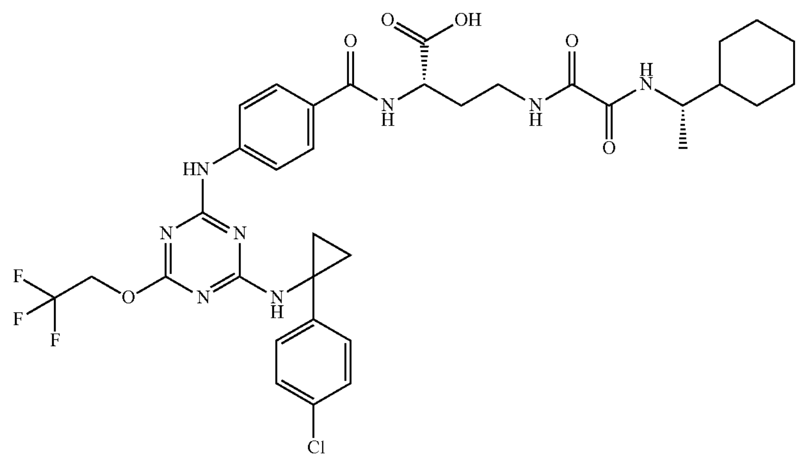 | 0.07 | A |

TABLE 1-continued

| Compound | Structure | EC$_{50}$ | Activity |
|---|---|---|---|
| 1213 | 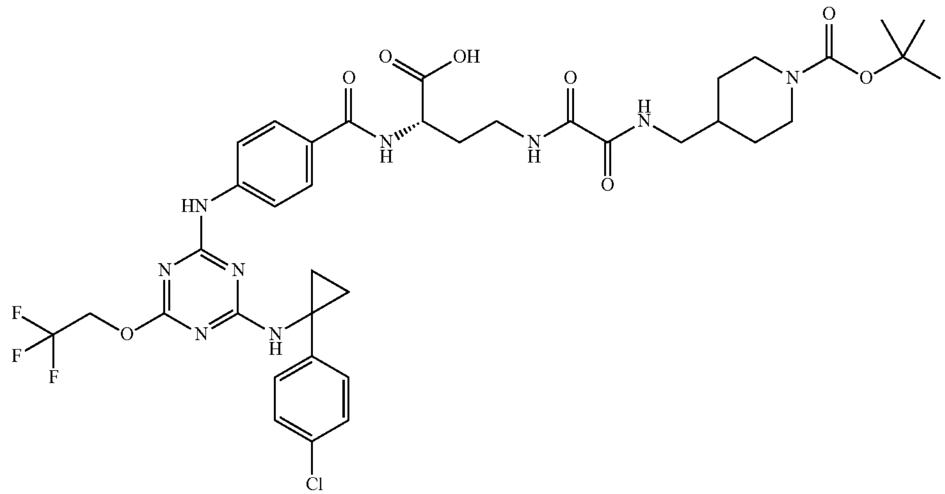 | | A |
| 1214 | 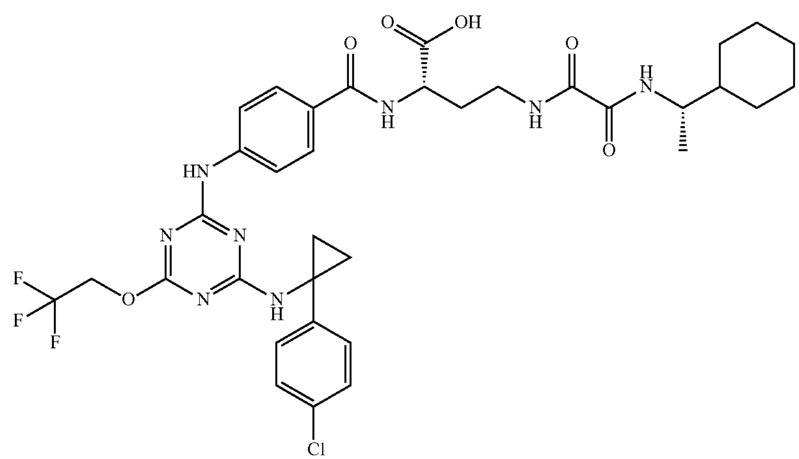 | | A |

| Compound | Structure | EC$_{50}$ | Activity |
|---|---|---|---|
| 1215 | 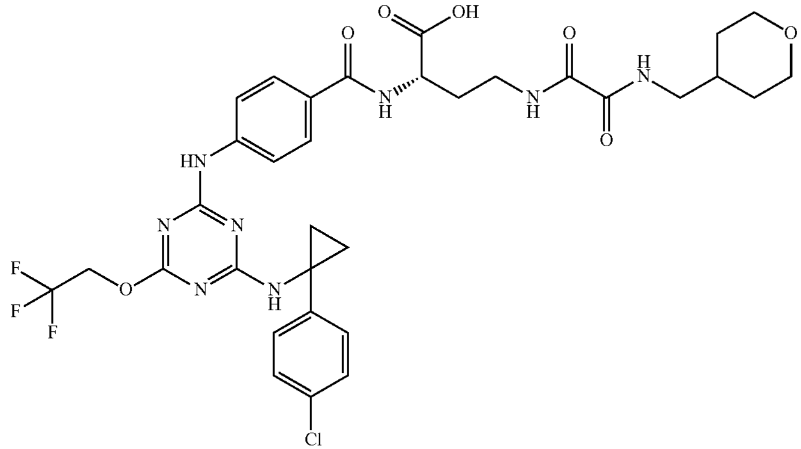 | | A |
| 1216 | 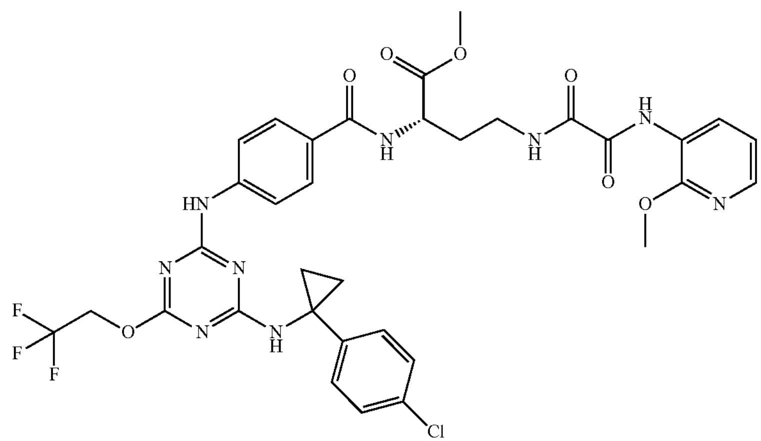 | | A |

TABLE 1-continued
| Compound | Structure | EC$_{50}$ | Activity |
|---|---|---|---|
| 1217 | 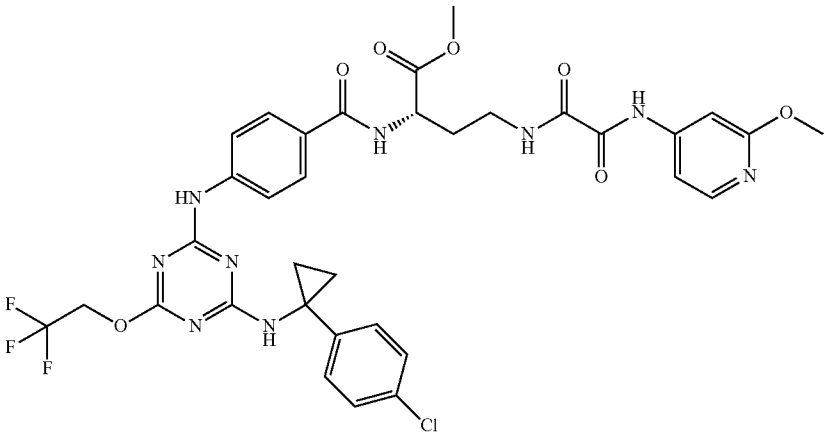 Chiral | | A |
| 1218 | 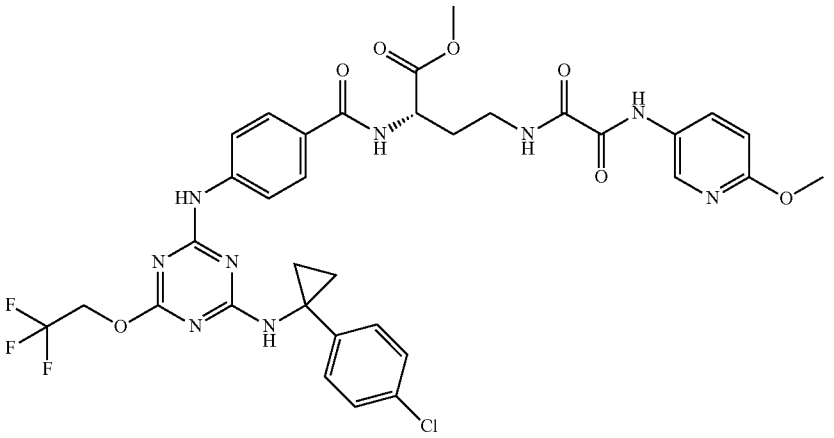 Chiral | | A |

| Compound | Structure | EC$_{50}$ | Activity |
|---|---|---|---|
| 1219 | 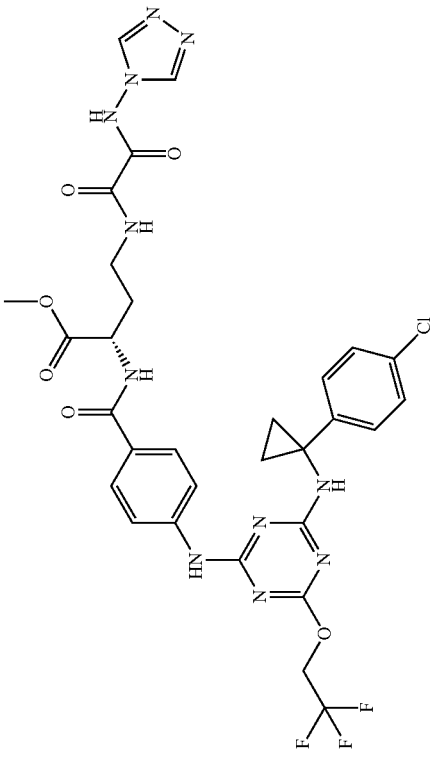 Chiral | | B |
| 1220 | 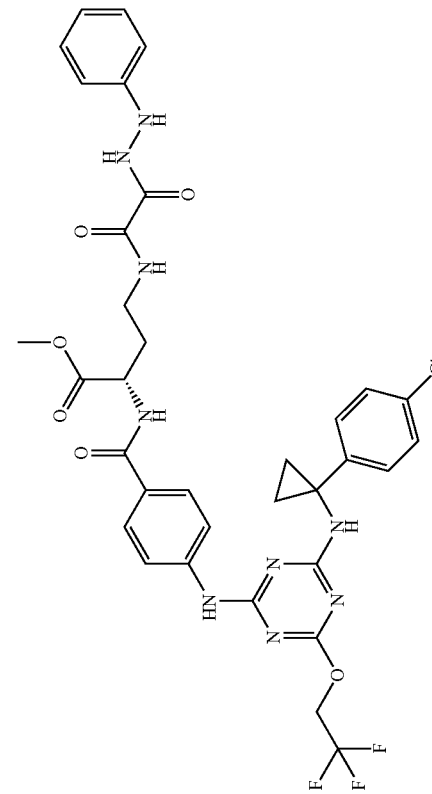 Chiral | | A |

TABLE 1-continued
| Compound | Structure | EC$_{50}$ | Activity |
|---|---|---|---|
| 1221 | 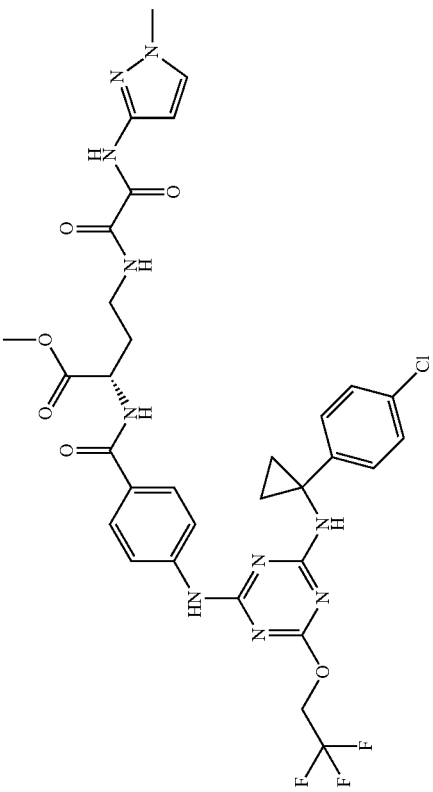 | | A |
| 1222 | 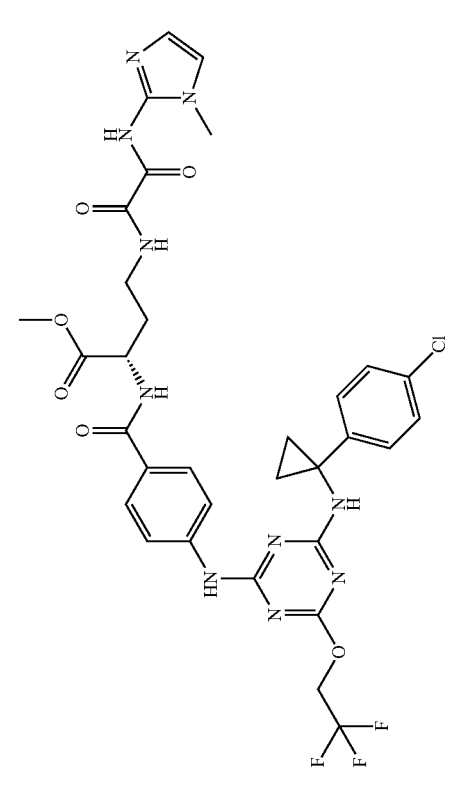 | | A |

TABLE 1-continued
| Compound | Structure | EC₅₀ | Activity |
|---|---|---|---|
| 1223 | 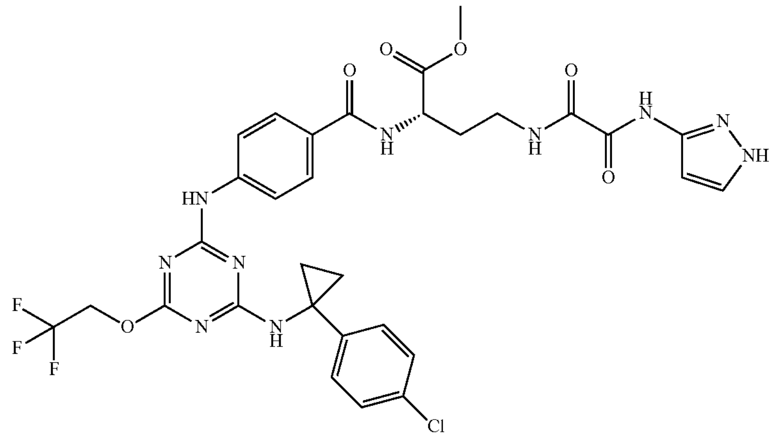 | | A |
| 1224 | 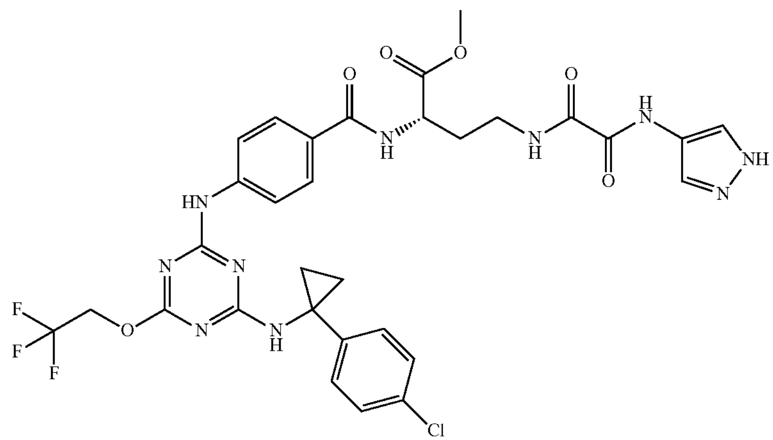 | | A |

| Compound | Structure | EC$_{50}$ | Activity |
|---|---|---|---|
| 1225 | 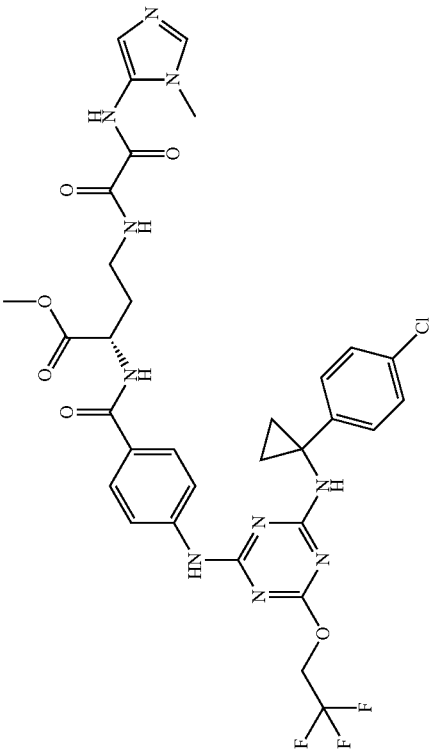 | | A |
| 1226 | 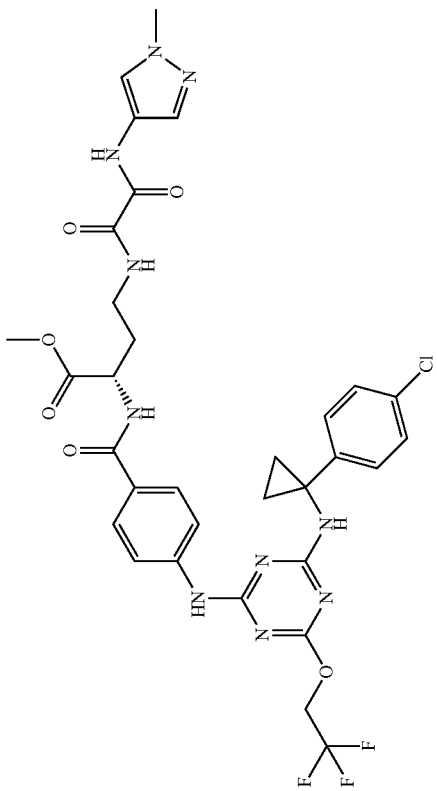 | | A |

TABLE 1-continued
| Compound | Structure | EC$_{50}$ | Activity |
|---|---|---|---|
| 1227 | Chiral 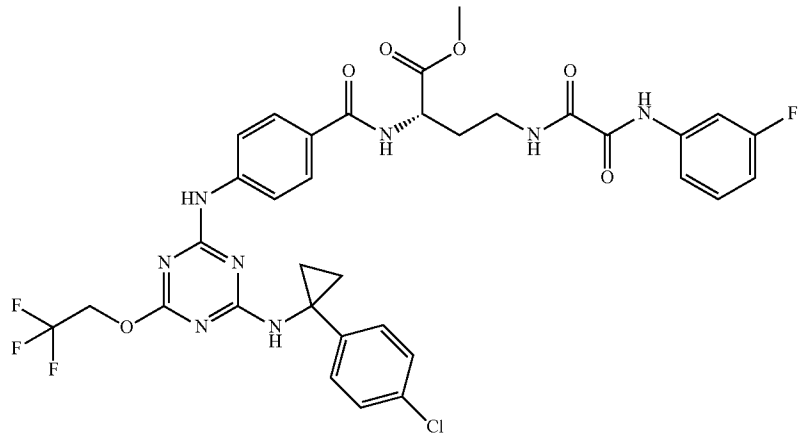 | | A |
| 1228 | Chiral 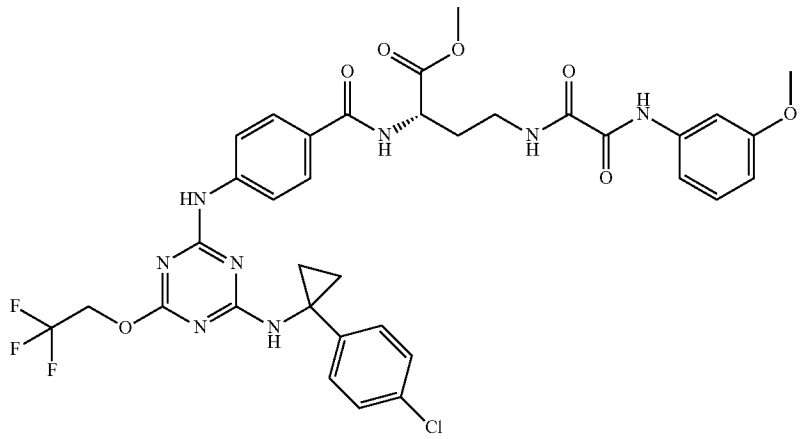 | | A |

| Compound | Structure | EC$_{50}$ | Activity |
|---|---|---|---|
| 1229 | Chiral 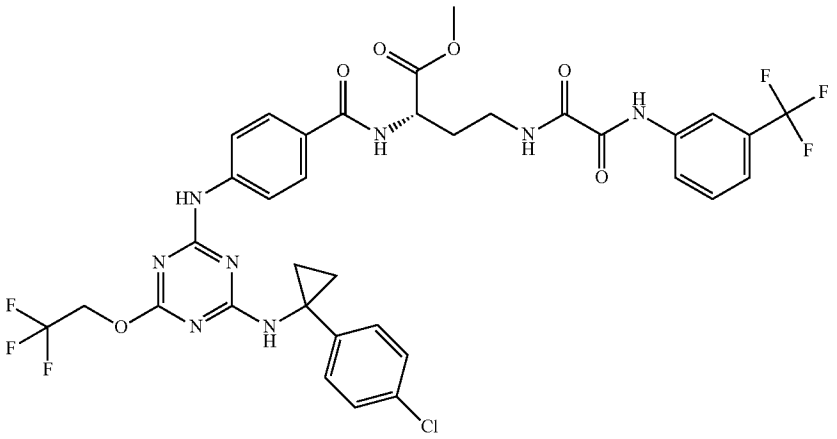 | | A |
| 1230 | Chiral 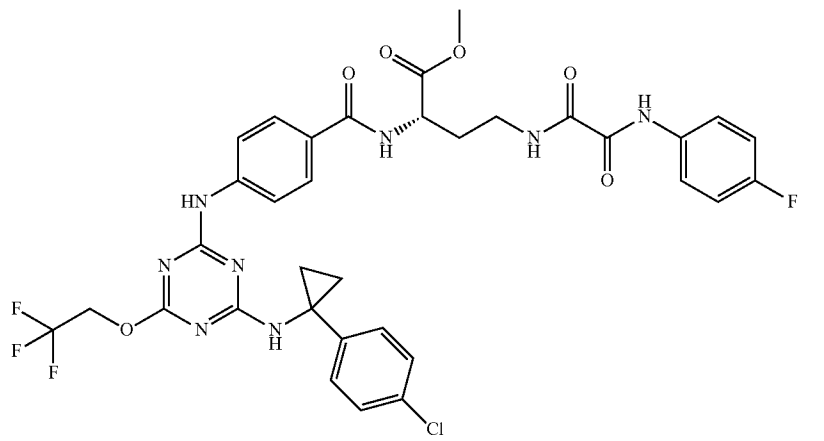 | | A |

TABLE 1-continued
| Compound | Structure | EC$_{50}$ | Activity |
|---|---|---|---|
| 1231 | Chiral 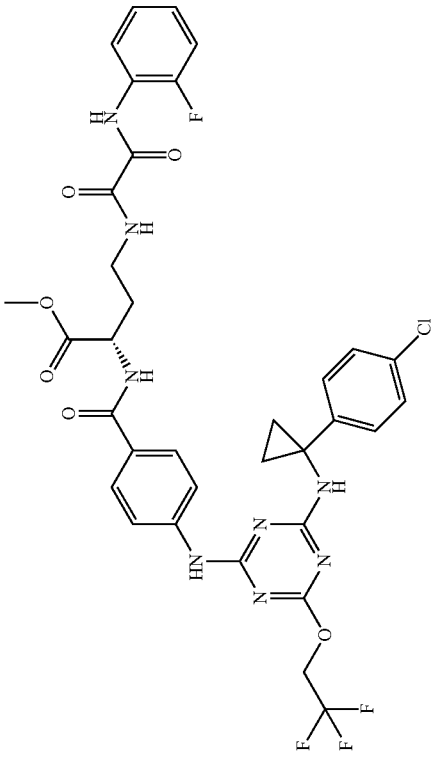 | | A |
| 1232 | Chiral 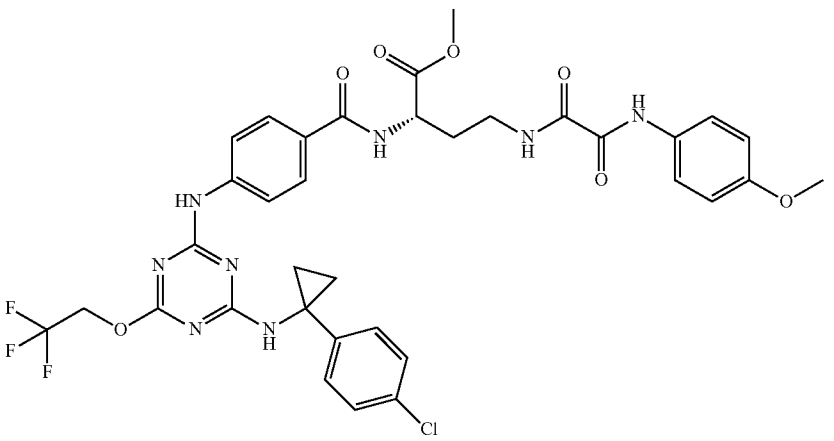 | | A |

TABLE 1-continued
| Compound | Structure | EC$_{50}$ | Activity |
|---|---|---|---|
| 1233 | 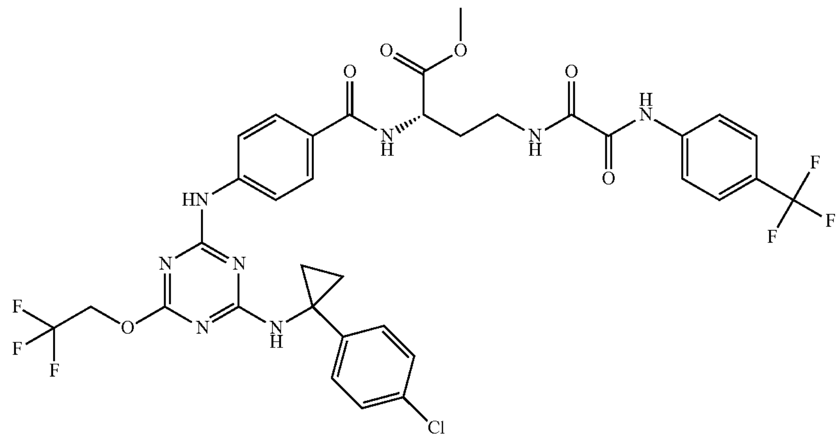 | | A |
| 1234 | 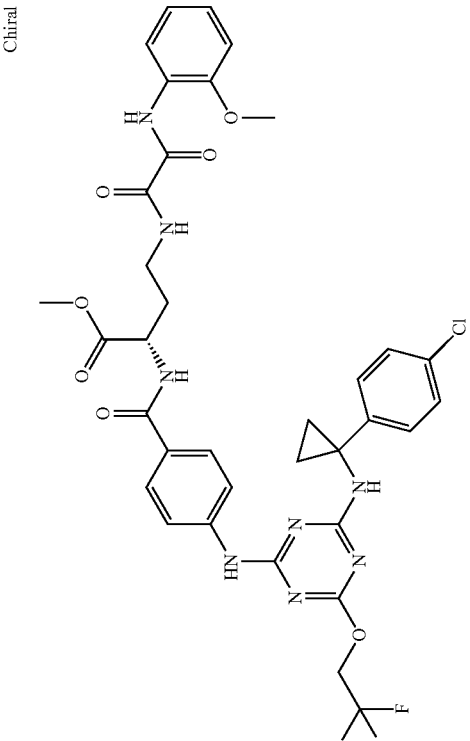 | | A |

TABLE 1-continued
| Compound | Structure | EC$_{50}$ | Activity |
|---|---|---|---|
| 1235 | Chiral 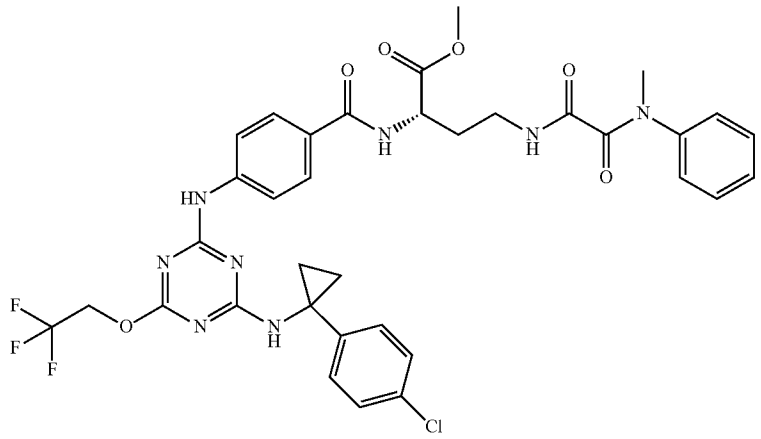 | 0.53 | A |
| 1236 | Chiral 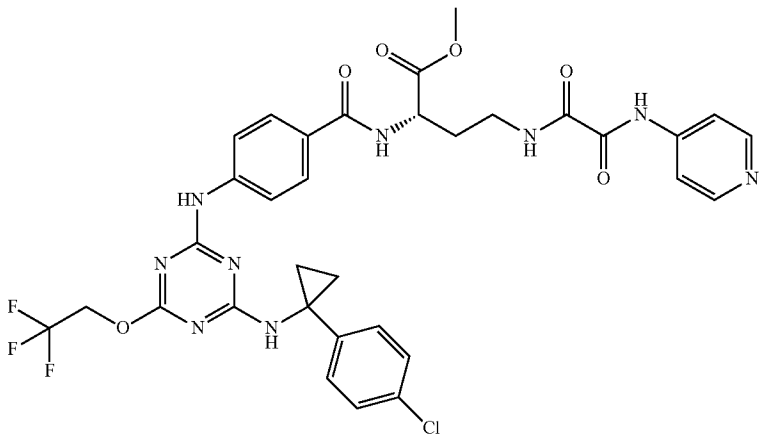 | | A |

TABLE 1-continued
| Compound | Structure | EC$_{50}$ | Activity |
|---|---|---|---|
| 1237 | 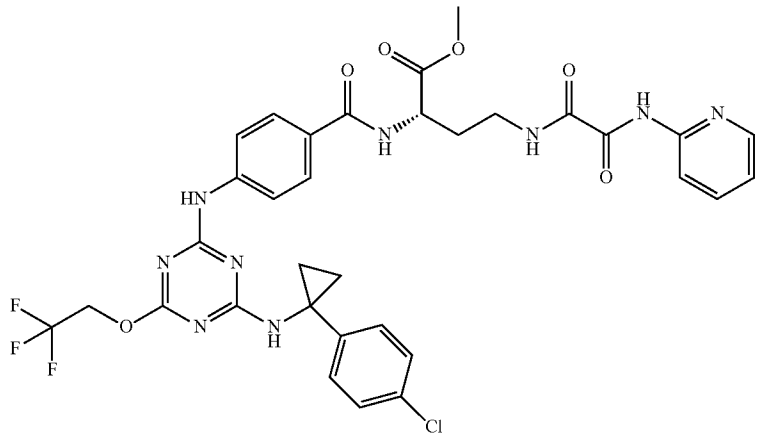 Chiral | 0.77 | A |
| 1238 | 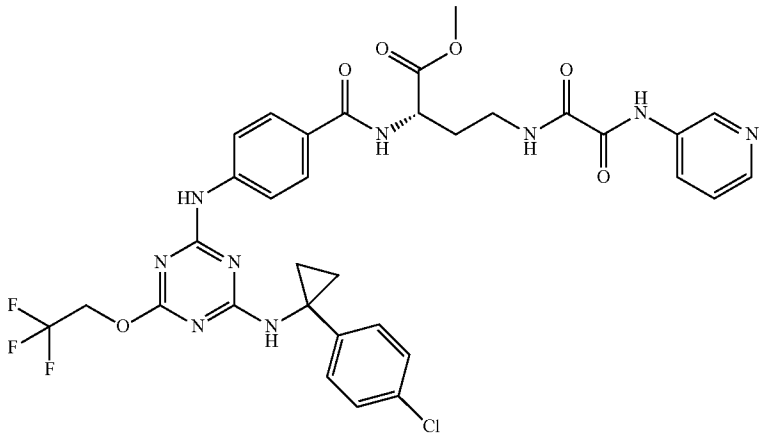 Chiral | | A |

TABLE 1-continued
| Compound | Structure | EC$_{50}$ | Activity |
|---|---|---|---|
| 1239 | 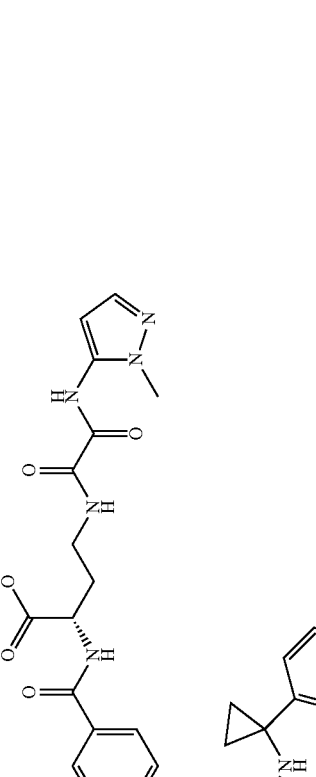 | | A |
| 1240 | 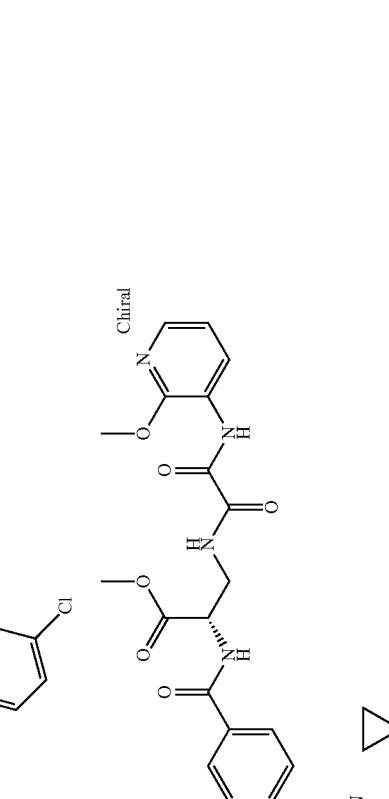 | | A |

TABLE 1-continued
| Compound | Structure | EC$_{50}$ | Activity |
|---|---|---|---|
| 1241 | 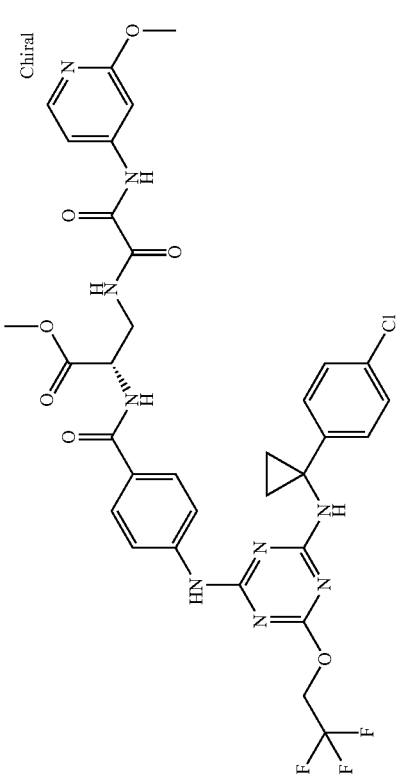 | 0.99 | A |
| 1242 | 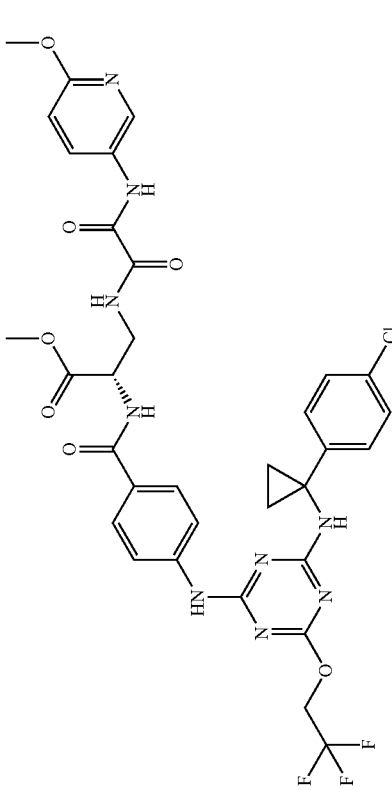 | 0.32 | A |

TABLE 1-continued
| Compound | Structure | EC$_{50}$ | Activity |
|---|---|---|---|
| 1243 | 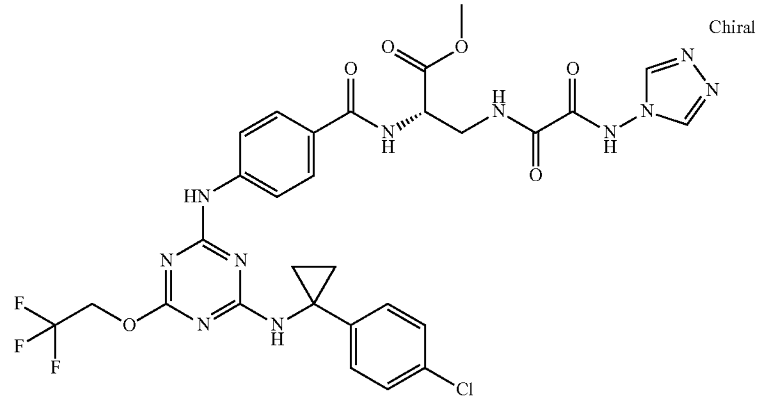 [SMILES: COC(=O)[C@H](CNC(=O)C(=O)Nn1cnnc1)NC(=O)c1ccc(Nc2nc(NC3(c4ccc(Cl)cc4)CC3)nc(OCC(F)(F)F)n2)cc1] | | B |
| 1244 | 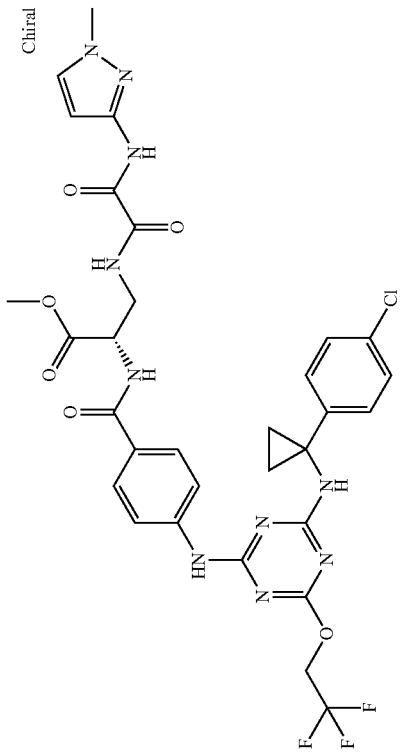 | | A |

| Compound | Structure | EC$_{50}$ | Activity |
|---|---|---|---|
| 1245 | 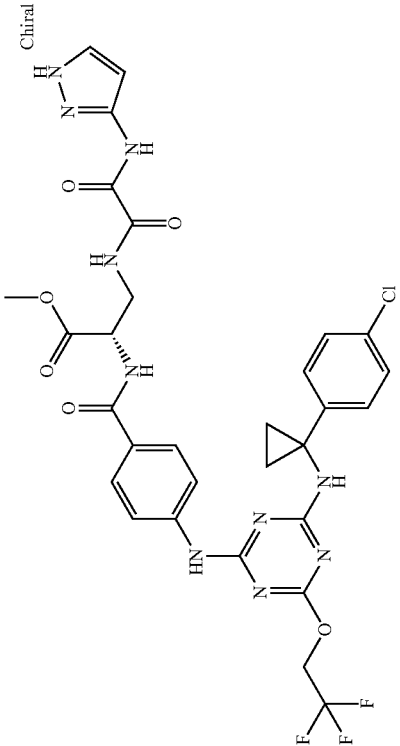 | 1.69 | A |
| 1246 | 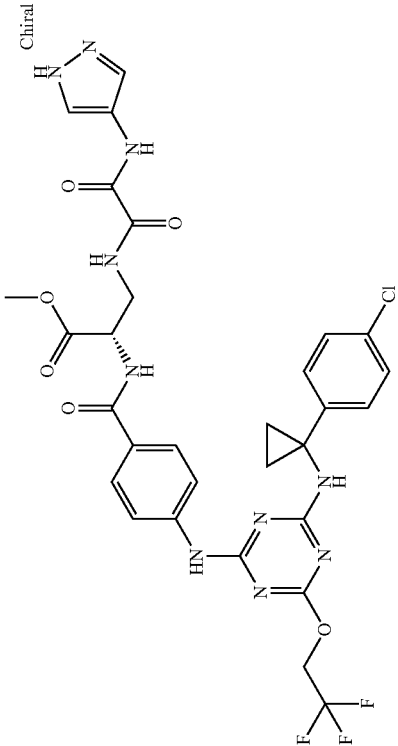 | | A |

TABLE 1-continued

| Compound | Structure | EC$_{50}$ | Activity |
|---|---|---|---|
| 1247 | 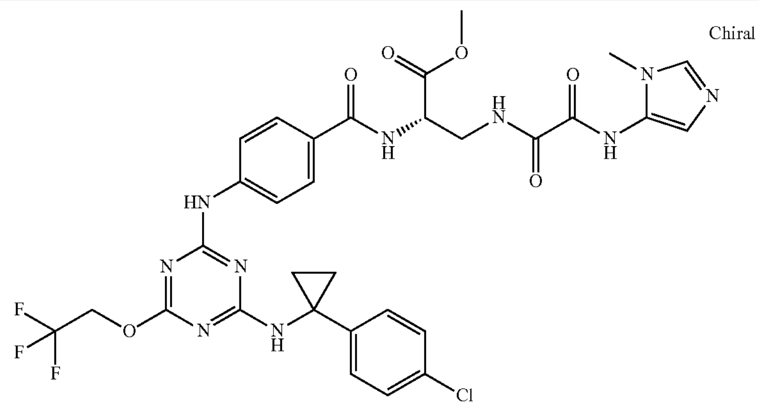 [SMILES: COC(=O)[C@H](CNC(=O)C(=O)Nc1cncn1C)NC(=O)c1ccc(Nc2nc(NC3(c4ccc(Cl)cc4)CC3)nc(OCC(F)(F)F)n2)cc1] | | A |
| 1248 | 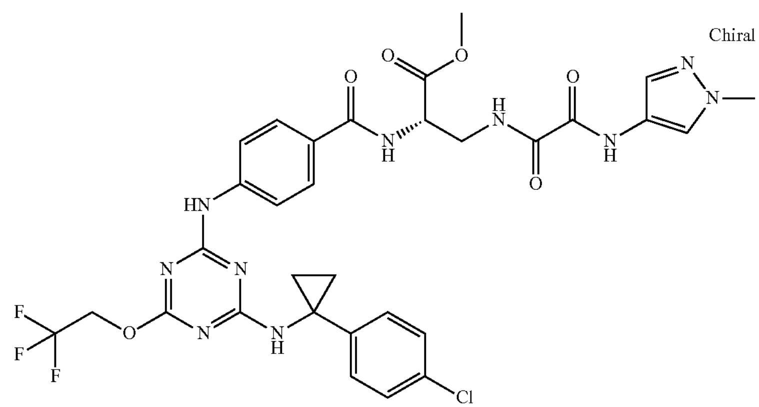 [SMILES: COC(=O)[C@H](CNC(=O)C(=O)Nc1cnn(C)c1)NC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 1249 | 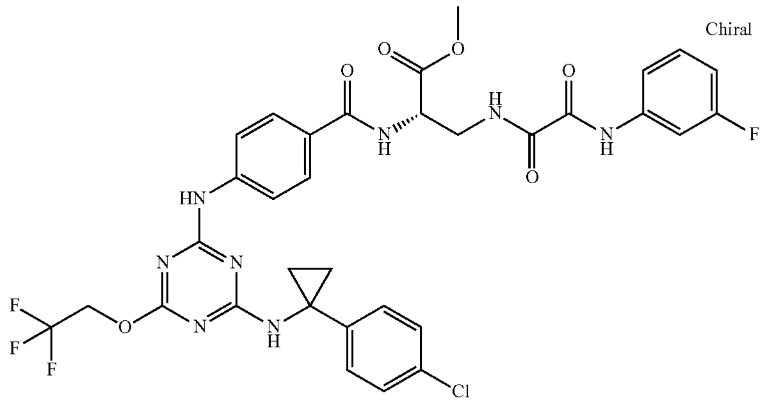 [SMILES: COC(=O)[C@H](CNC(=O)C(=O)Nc1cccc(F)c1)NC(=O)c1ccc(Nc2nc(NC3(c4ccc(Cl)cc4)CC3)nc(OCC(F)(F)F)n2)cc1] | | A |
| 1250 | 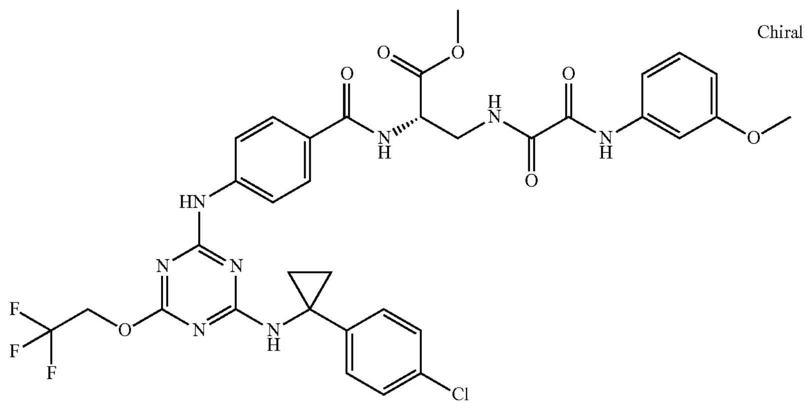 [SMILES: COC(=O)[C@H](CNC(=O)C(=O)Nc1cccc(OC)c1)NC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 1251 | 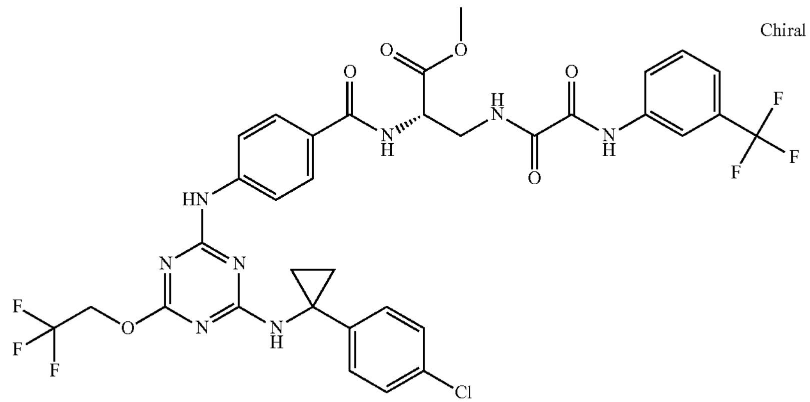 [SMILES: COC(=O)[C@H](CNC(=O)C(=O)Nc1cccc(C(F)(F)F)c1)NC(=O)c1ccc(Nc2nc(NC3(c4ccc(Cl)cc4)CC3)nc(OCC(F)(F)F)n2)cc1] | | A |
| 1252 | 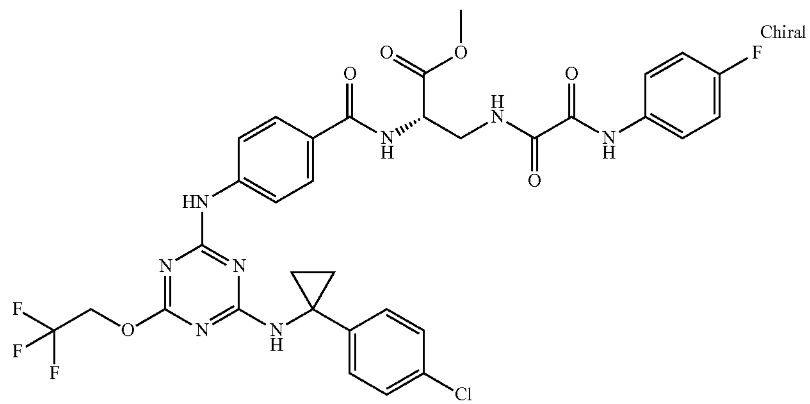 [SMILES: COC(=O)[C@H](CNC(=O)C(=O)Nc1ccc(F)cc1)NC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 1253 | 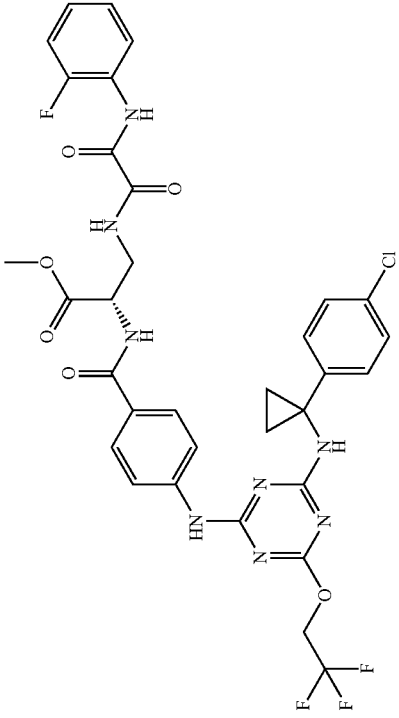 | | A |
| 1254 | 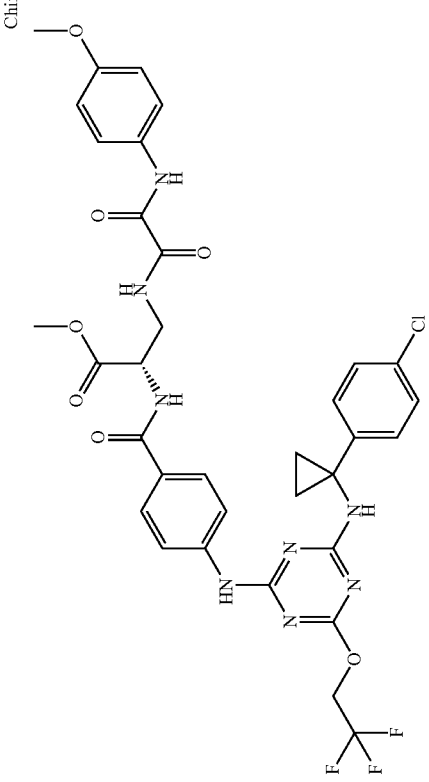 | 0.37 | A |

TABLE 1-continued
| Compound | Structure | EC$_{50}$ | Activity |
|---|---|---|---|
| 1255 | 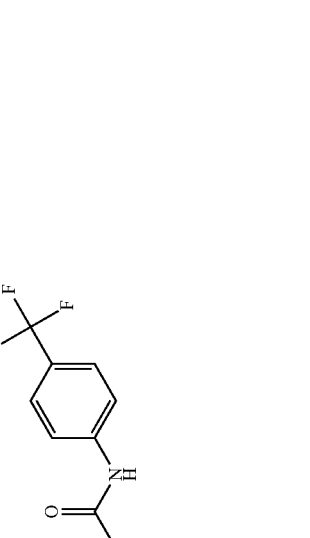 | 1.10 | A |
| 1256 | 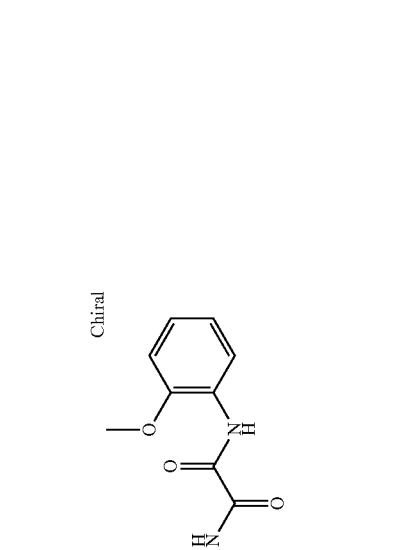 | 0.64 | A |

TABLE 1-continued
| Compound | Structure | EC$_{50}$ | Activity |
|---|---|---|---|
| 1257 | 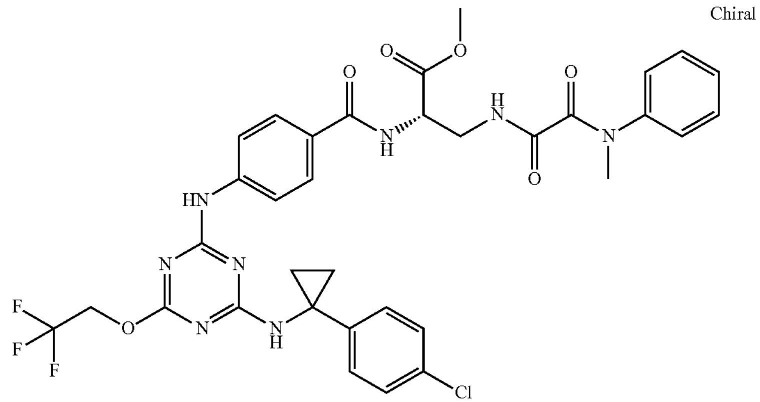 [SMILES: COC(=O)[C@H](CNC(=O)C(=O)N(C)c1ccccc1)NC(=O)c1ccc(Nc2nc(NC3(c4ccc(Cl)cc4)CC3)nc(OCC(F)(F)F)n2)cc1] | | A |
| 1258 | 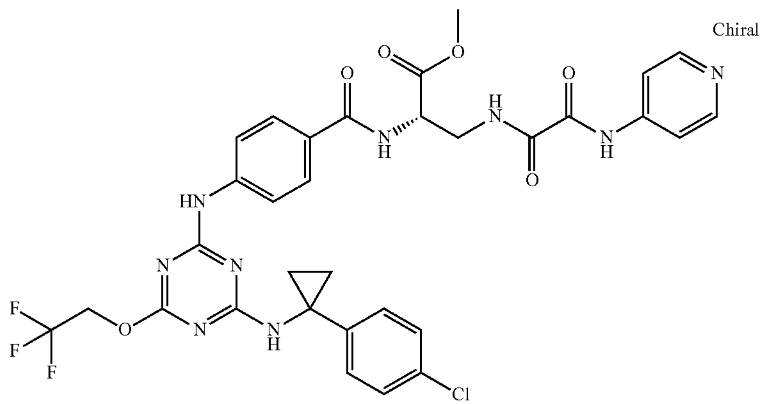 [SMILES: COC(=O)[C@H](CNC(=O)C(=O)Nc1ccncc1)NC(=O)c1ccc(Nc2nc(NC3(c4ccc(Cl)cc4)CC3)nc(OCC(F)(F)F)n2)cc1] | | A |
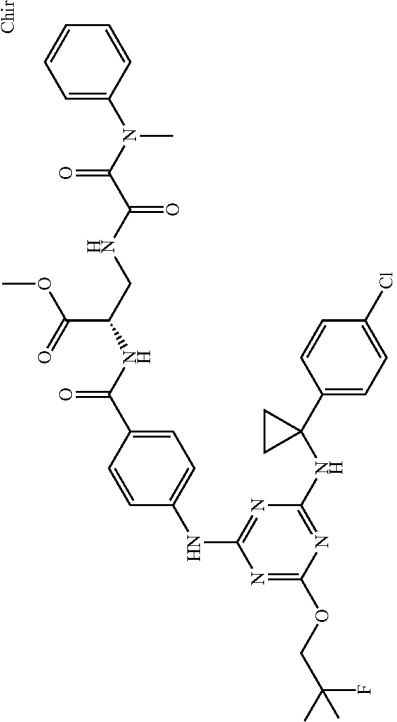

TABLE 1-continued
| Compound | Structure | EC$_{50}$ | Activity |
|---|---|---|---|
| 1259 | 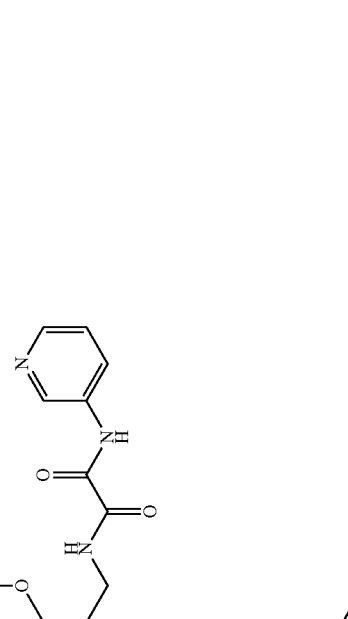 | | A |
| 1260 | 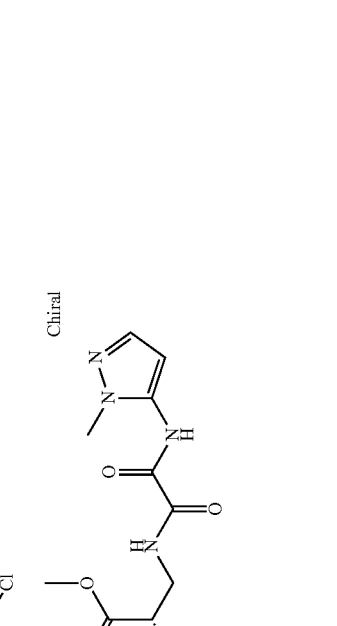 | | A |

TABLE 1-continued

| Compound | Structure | EC$_{50}$ | Activity |
|---|---|---|---|
| 1261 | Chiral | | A |
| 1262 | Chiral | | A |

TABLE 1-continued
| Compound | Structure | EC$_{50}$ | Activity |
|---|---|---|---|
| 1263 | Chiral 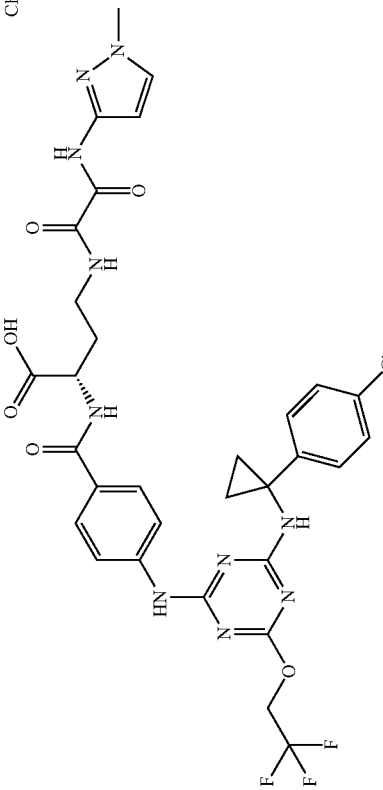 | | A |
| 1264 | Chiral 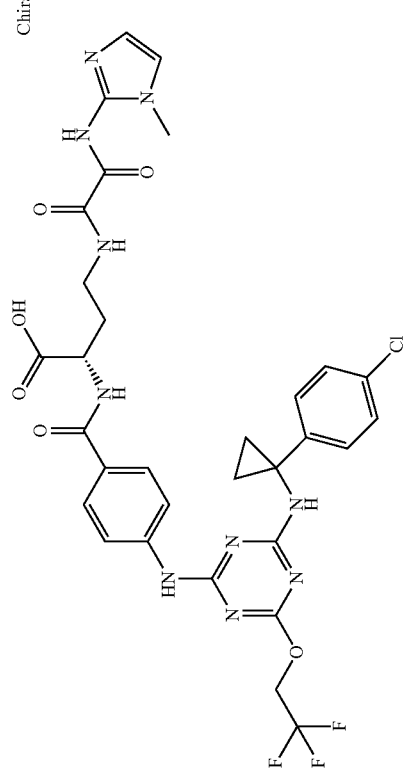 | | B |

TABLE 1-continued

| Compound | Structure | EC$_{50}$ | Activity |
|---|---|---|---|
| 1265 | Chiral | | A |
| 1266 | Chiral | | A |

TABLE 1-continued
| Compound | Structure | EC$_{50}$ | Activity |
|---|---|---|---|
| 1267 | 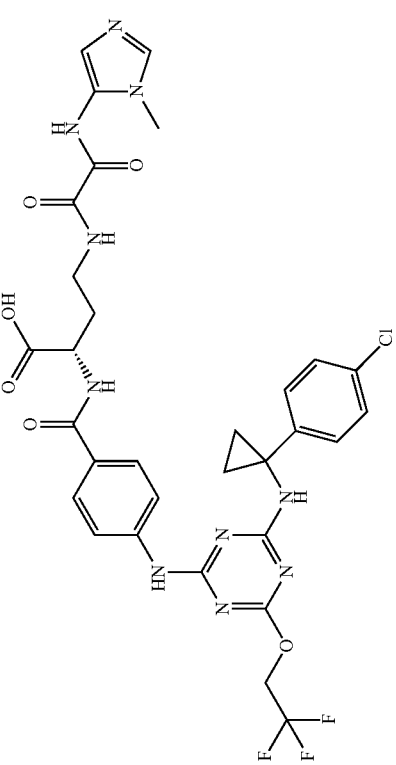 | 5.26 | A |
| 1268 | 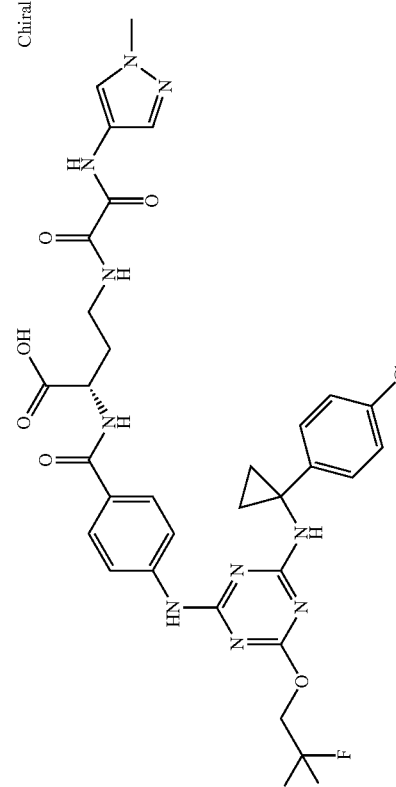 |  | A |

TABLE 1-continued
| Compound | Structure | EC$_{50}$ | Activity |
|---|---|---|---|
| 1269 | 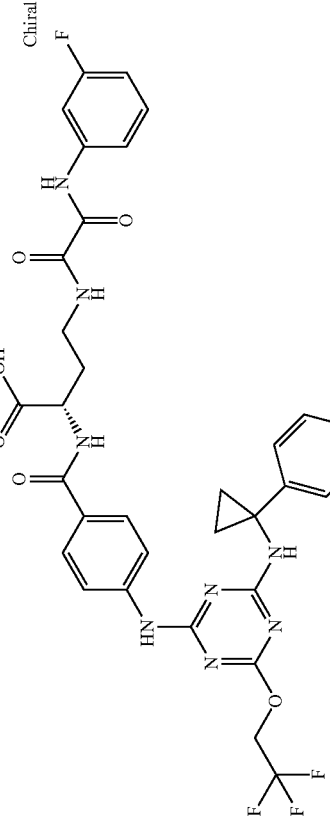 | | A |
| 1270 | 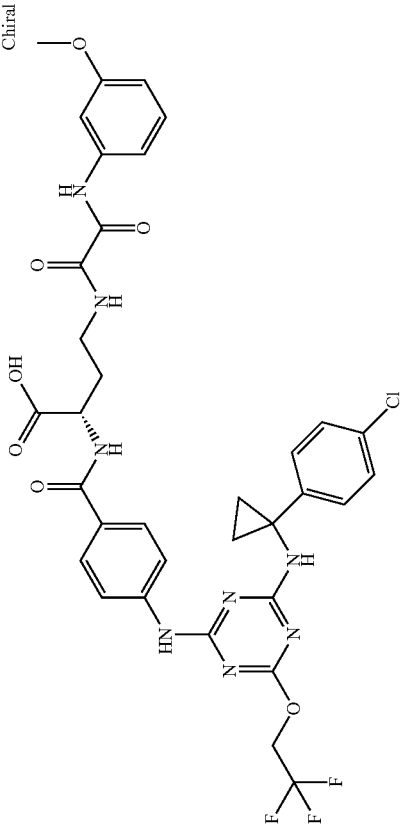 | 0.13 | A |

TABLE 1-continued
| Compound | Structure | EC$_{50}$ | Activity |
|---|---|---|---|
| 1271 | 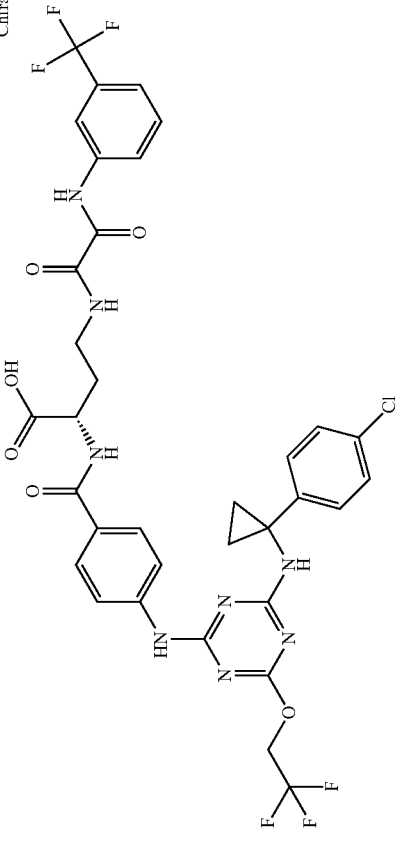 | | A |
| 1272 | 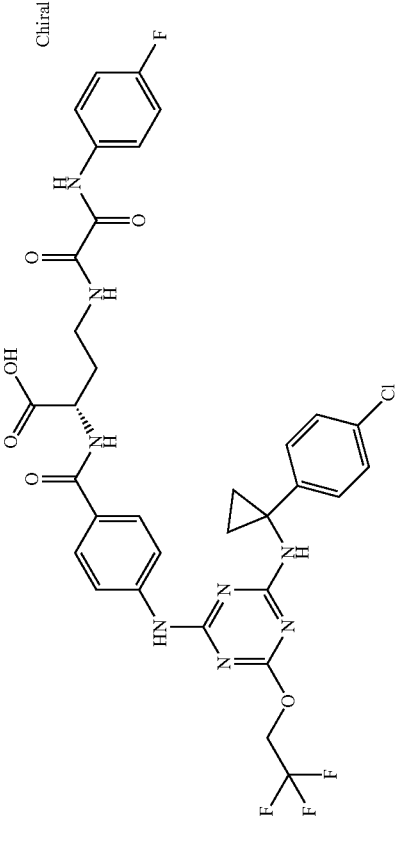 | | A |

TABLE 1-continued
| Compound | Structure | EC$_{50}$ | Activity |
|---|---|---|---|
| 1273 | 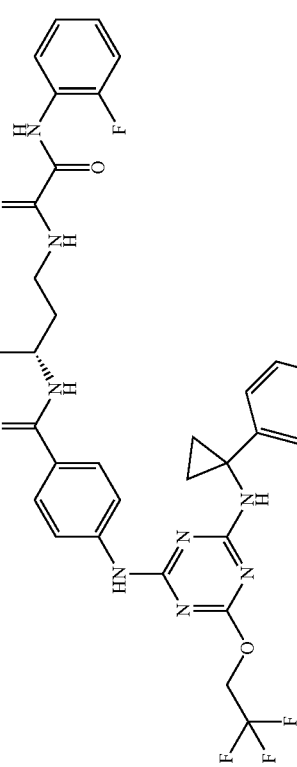 | | A |
| 1274 | 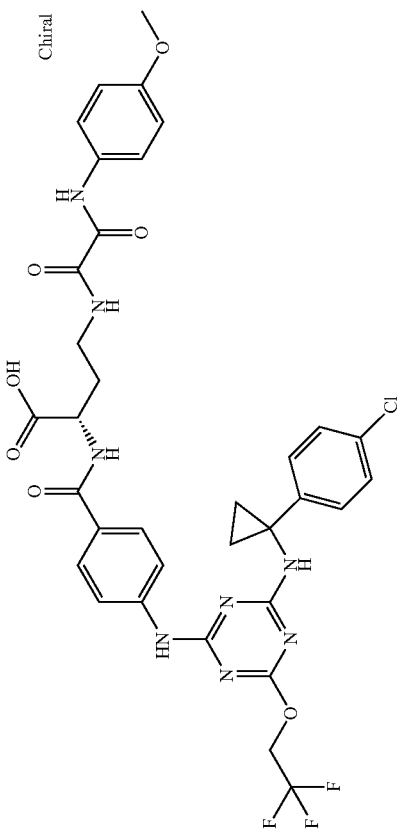 | | A |

| Compound | Structure | EC$_{50}$ | Activity |
|---|---|---|---|
| 1275 | 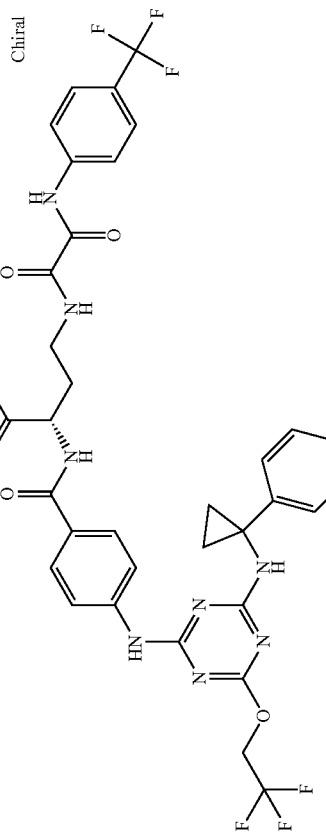 | | A |
| 1276 | 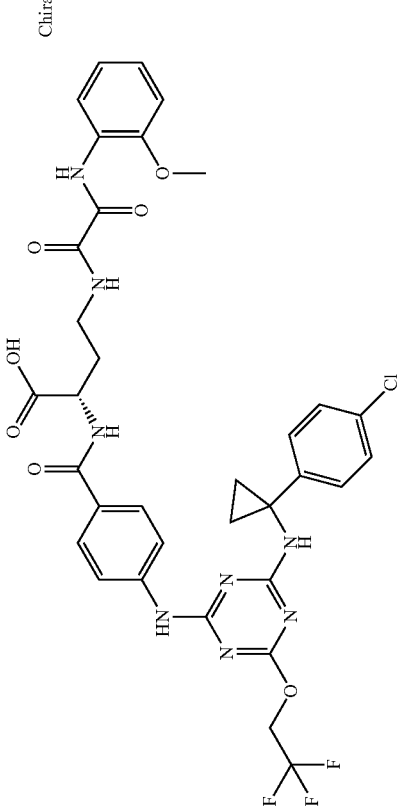 | | A |

TABLE 1-continued

| Compound | Structure | EC$_{50}$ | Activity |
|---|---|---|---|
| 1277 | 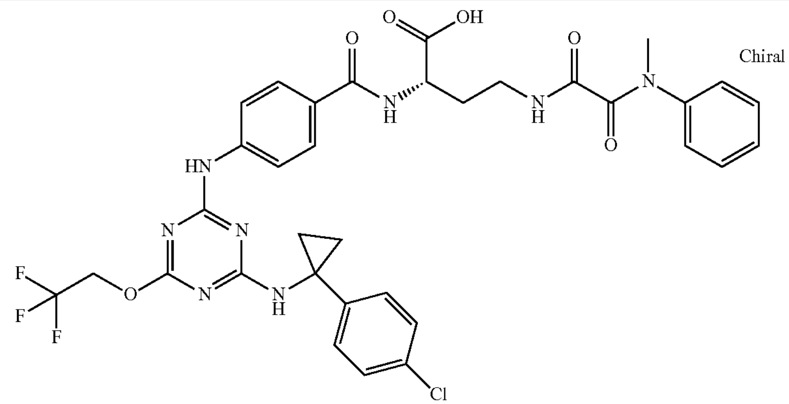 [SMILES: CN(C(=O)C(=O)NCC[C@H](NC(=O)c1ccc(Nc2nc(NC3(c4ccc(Cl)cc4)CC3)nc(OCC(F)(F)F)n2)cc1)C(=O)O)c1ccccc1] | | A |
| 1278 | 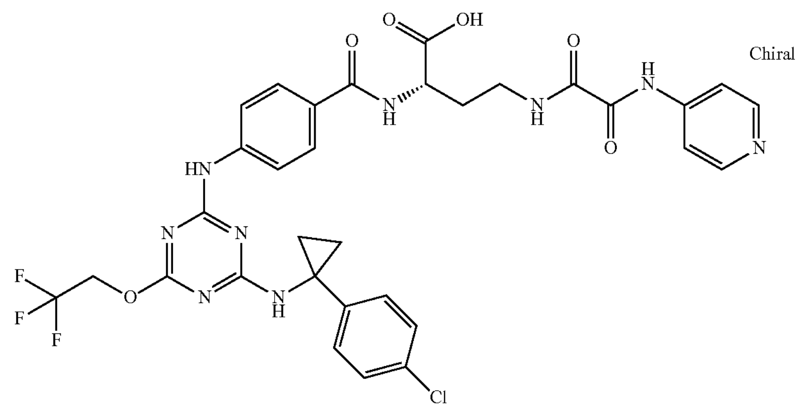 [SMILES: O=C(NCC[C@H](NC(=O)c1ccc(Nc2nc(NC3(c4ccc(Cl)cc4)CC3)nc(OCC(F)(F)F)n2)cc1)C(=O)O)C(=O)Nc1ccncc1] | | A |

TABLE 1-continued

| Compound | Structure | EC$_{50}$ | Activity |
|---|---|---|---|
| 1279 | (chiral structure with 2-pyridyl oxamide) | 1.29 | A |
| 1280 | (chiral structure with 3-pyridyl oxamide) | | A |

TABLE 1-continued

| Compound | Structure | EC$_{50}$ | Activity |
|---|---|---|---|
| 1281 | 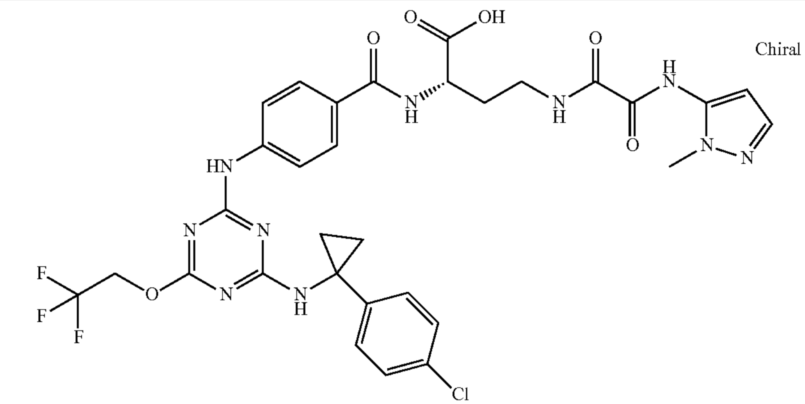 [SMILES: Cn1nccc1NC(=O)C(=O)NCC[C@H](NC(=O)c1ccc(Nc2nc(NC3(c4ccc(Cl)cc4)CC3)nc(OCC(F)(F)F)n2)cc1)C(=O)O] | | A |
| 1282 | 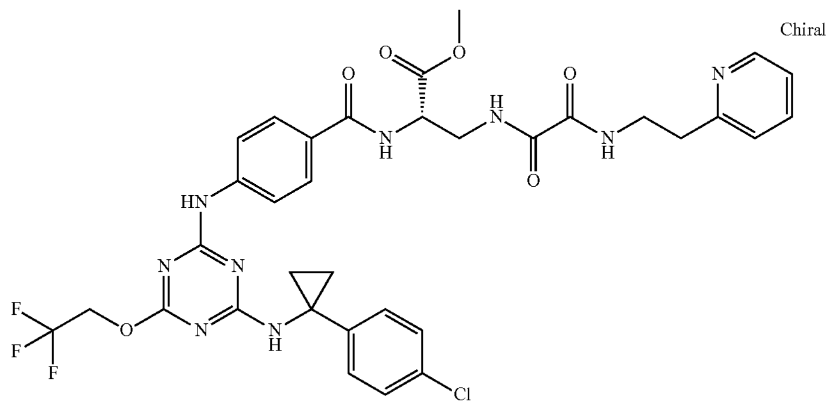 [SMILES: COC(=O)[C@H](CNC(=O)C(=O)NCCc1ccccn1)NC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 1283 | 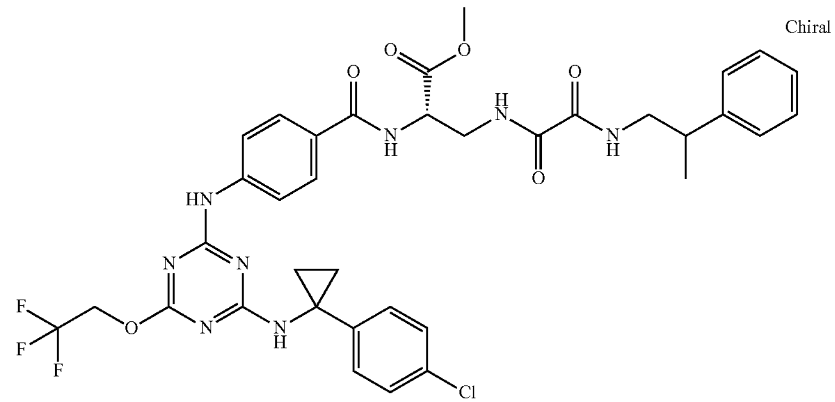 [SMILES: COC(=O)[C@H](CNC(=O)C(=O)NCC(C)c1ccccc1)NC(=O)c1ccc(Nc2nc(NC3(c4ccc(Cl)cc4)CC3)nc(OCC(F)(F)F)n2)cc1] | | A |
| 1284 | 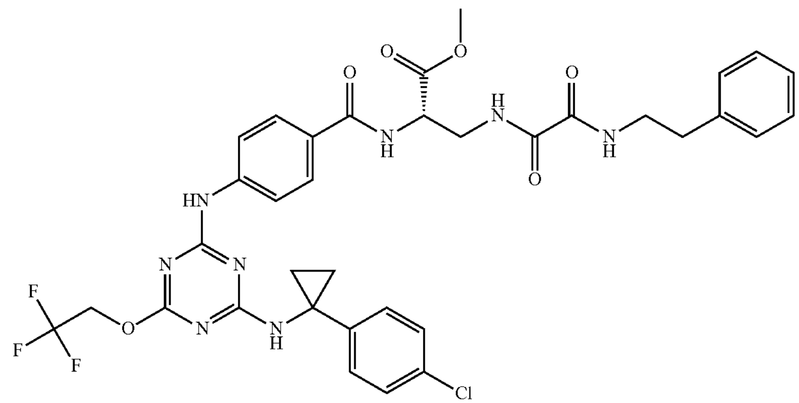 | | A |

TABLE 1-continued
| Compound | Structure | EC$_{50}$ | Activity |
|---|---|---|---|
| 1285 | Chiral 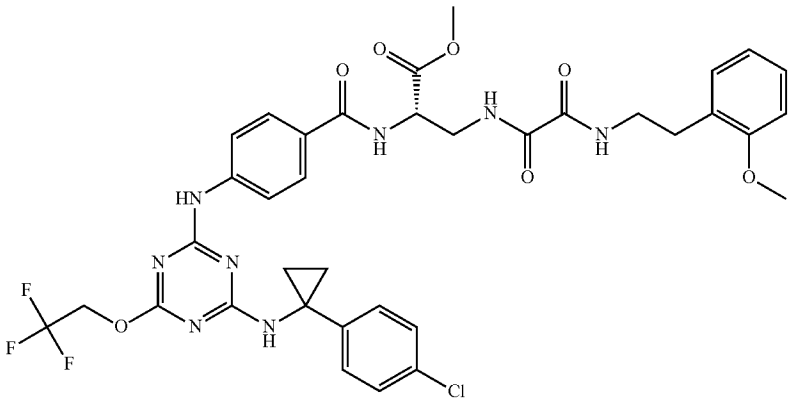 | | A |
| 1286 | Chiral 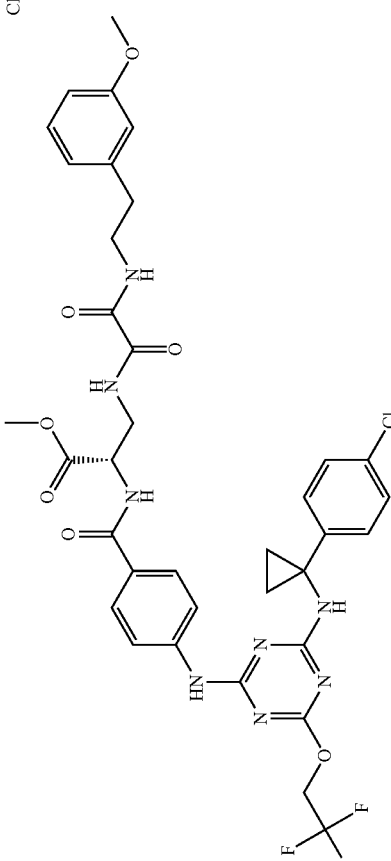 | | A |

TABLE 1-continued
| Compound | Structure | EC$_{50}$ | Activity |
|---|---|---|---|
| 1287 | 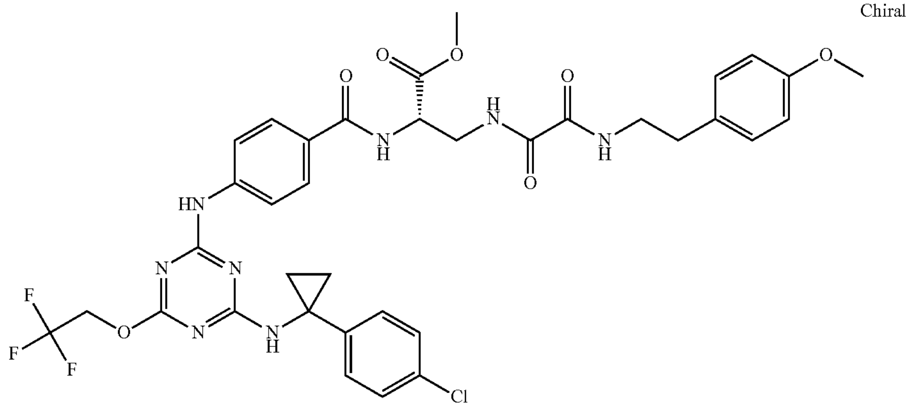 [SMILES: COC(=O)[C@H](CNC(=O)C(=O)NCCc1ccc(OC)cc1)NC(=O)c1ccc(Nc2nc(NC3(c4ccc(Cl)cc4)CC3)nc(OCC(F)(F)F)n2)cc1] | | A |
| 1288 | 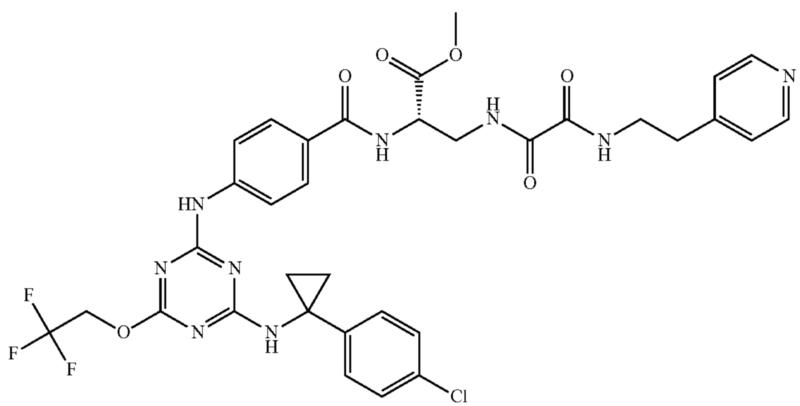 | | A |
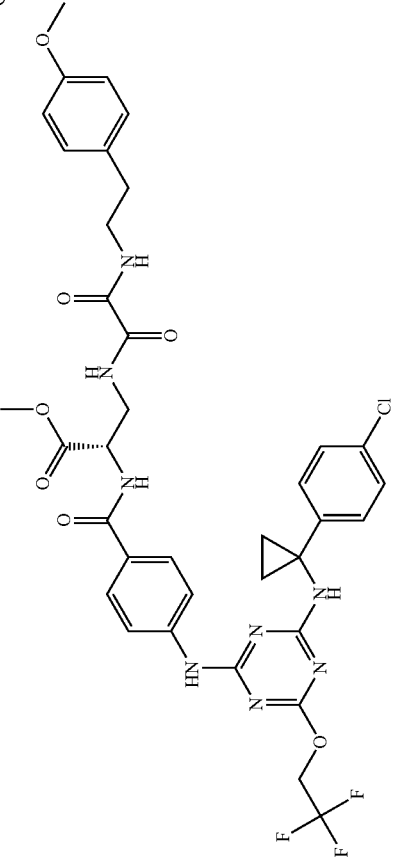

TABLE 1-continued
| Compound | Structure | EC$_{50}$ | Activity |
|---|---|---|---|
| 1289 | 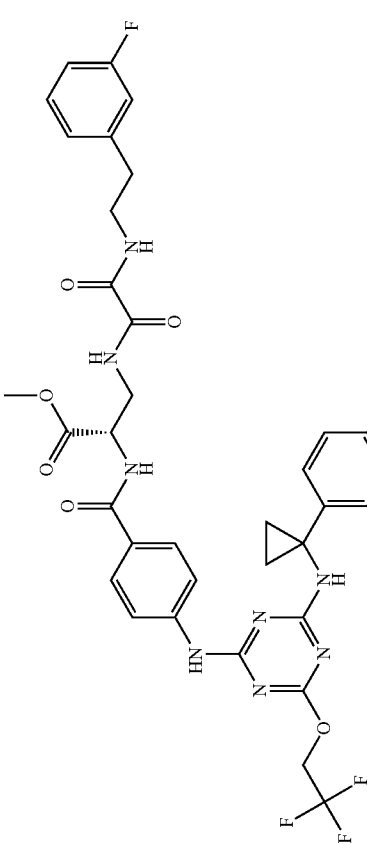 Chiral | | A |
| 1290 | 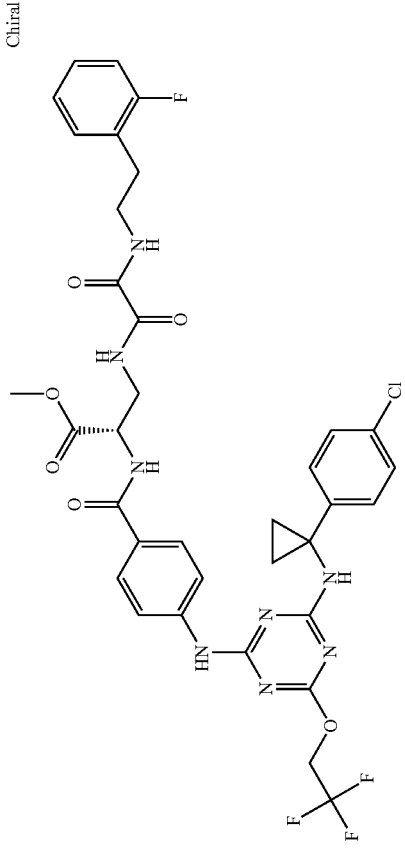 Chiral | | A |

TABLE 1-continued

| Compound | Structure | EC$_{50}$ | Activity |
|---|---|---|---|
| 1291 | Chiral | | A |
| 1292 | Chiral | | A |

TABLE 1-continued

| Compound | Structure | EC$_{50}$ | Activity |
|---|---|---|---|
| 1293 | (Chiral structure) | 4.40 | A |
| 1294 | (structure) | | A |

TABLE 1-continued
| Compound | Structure | EC$_{50}$ | Activity |
|---|---|---|---|
| 1295 | 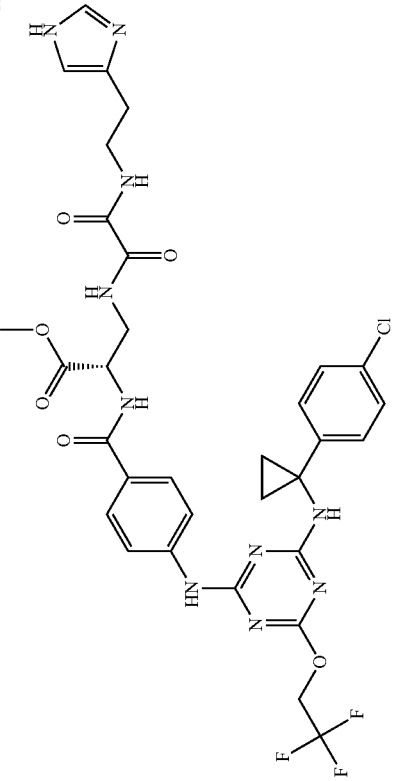 | | B |
| 1296 | 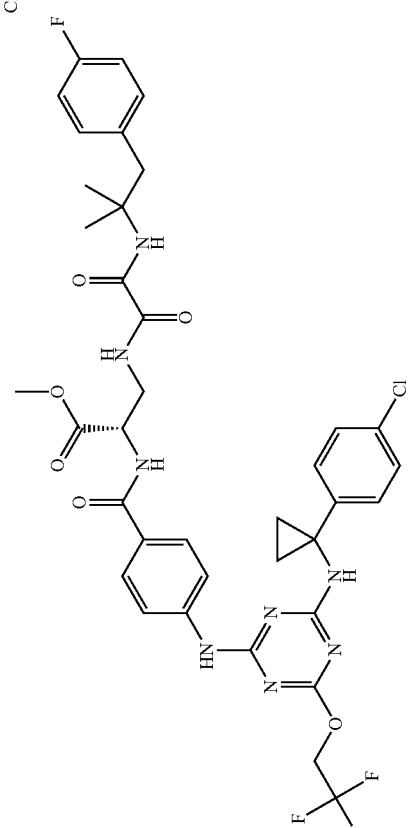 | | A |

TABLE 1-continued

| Compound | Structure | EC$_{50}$ | Activity |
|---|---|---|---|
| 1297 | 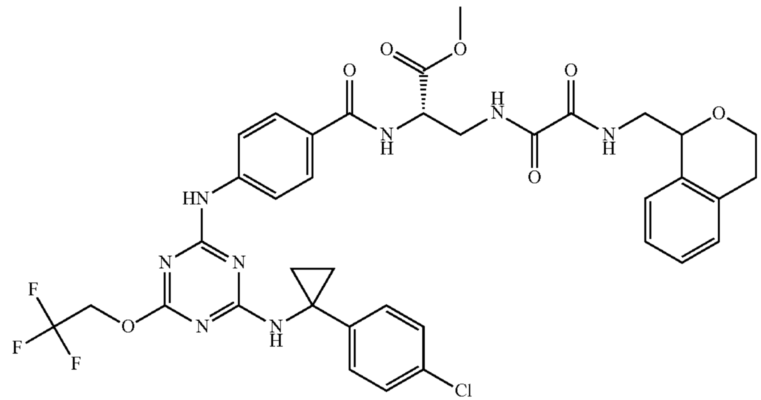 [SMILES: COC(=O)[C@H](CNC(=O)C(=O)NCC1OCCc2ccccc21)NC(=O)c1ccc(Nc2nc(NC3(c4ccc(Cl)cc4)CC3)nc(OCC(F)(F)F)n2)cc1] | | A |
| 1298 | (Chiral) | | A |

TABLE 1-continued

| Compound | Structure | EC$_{50}$ | Activity |
|---|---|---|---|
| 1299 | 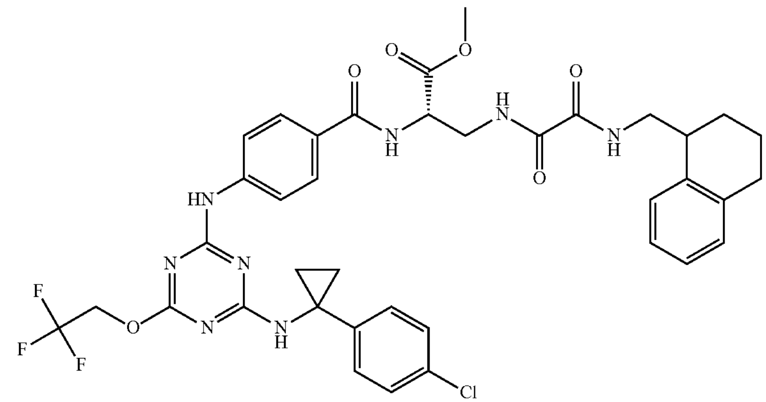 [SMILES: COC(=O)[C@H](CNC(=O)C(=O)NCC1CCCc2ccccc21)NC(=O)c1ccc(Nc2nc(NC3(c4ccc(Cl)cc4)CC3)nc(OCC(F)(F)F)n2)cc1] | | A |
| 1300 | Chiral | | A |

TABLE 1-continued
| Compound | Structure | EC$_{50}$ | Activity |
|---|---|---|---|
| 1301 | 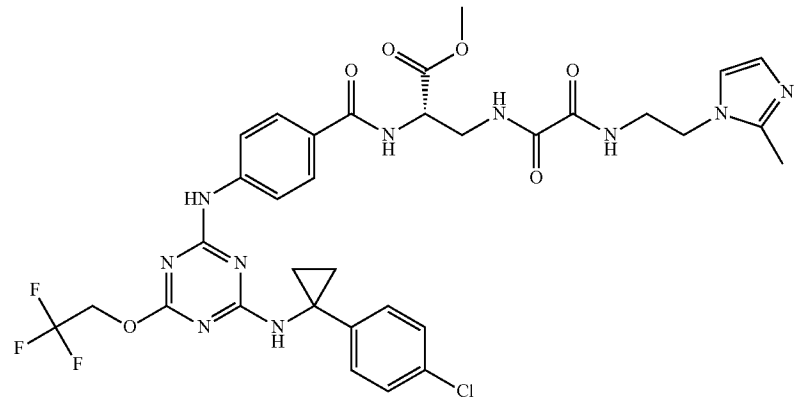 Chiral | | A |
| 1302 | 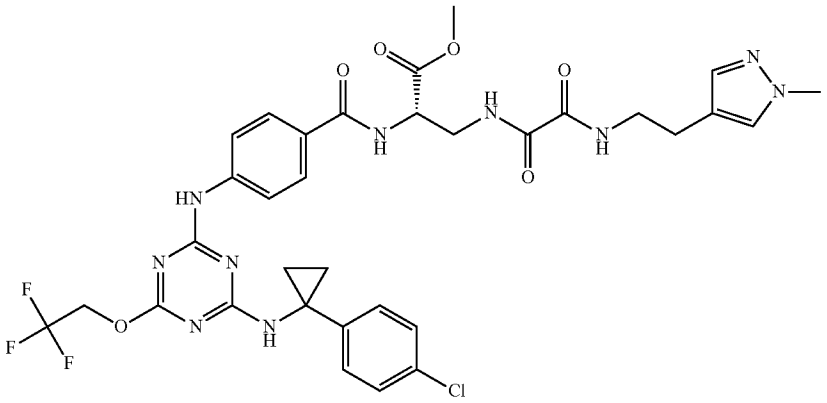 Chiral | | A |

TABLE 1-continued
| Compound | Structure | EC$_{50}$ | Activity |
|---|---|---|---|
| 1303 | 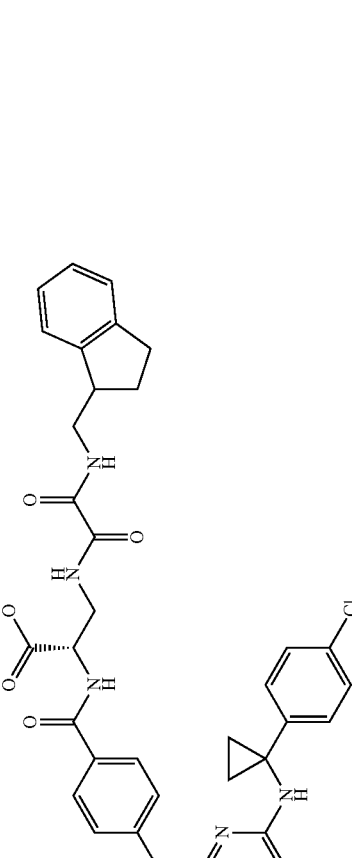 | | A |
| 1304 | 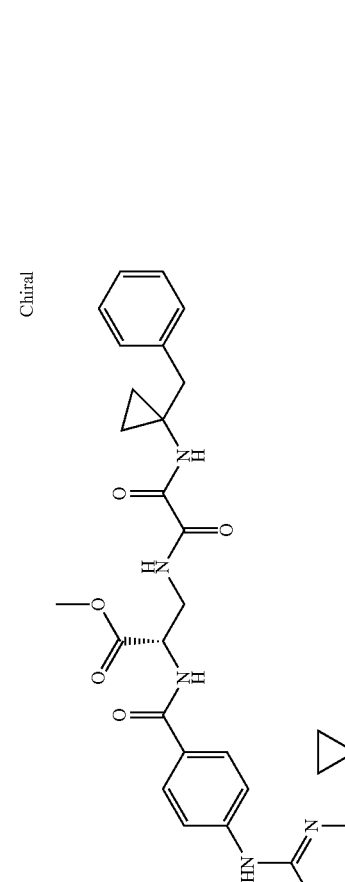 Chiral | | A |

TABLE 1-continued

| Compound | Structure | EC$_{50}$ | Activity |
|---|---|---|---|
| 1305 | 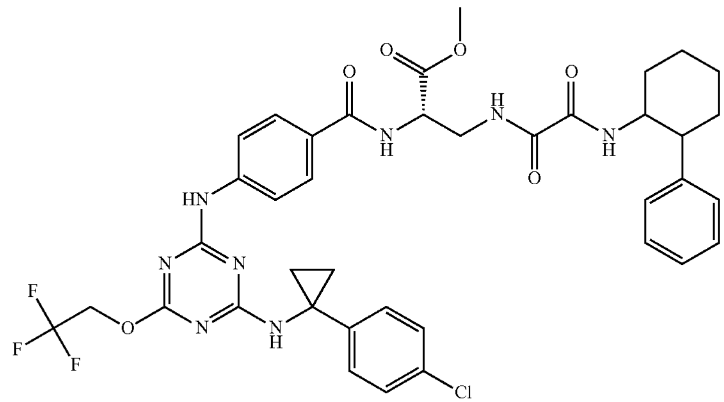 [SMILES: COC(=O)[C@H](CNC(=O)C(=O)NC1CCCCC1c1ccccc1)NC(=O)c1ccc(Nc2nc(NC3(c4ccc(Cl)cc4)CC3)nc(OCC(F)(F)F)n2)cc1] | | A |
| 1306 | 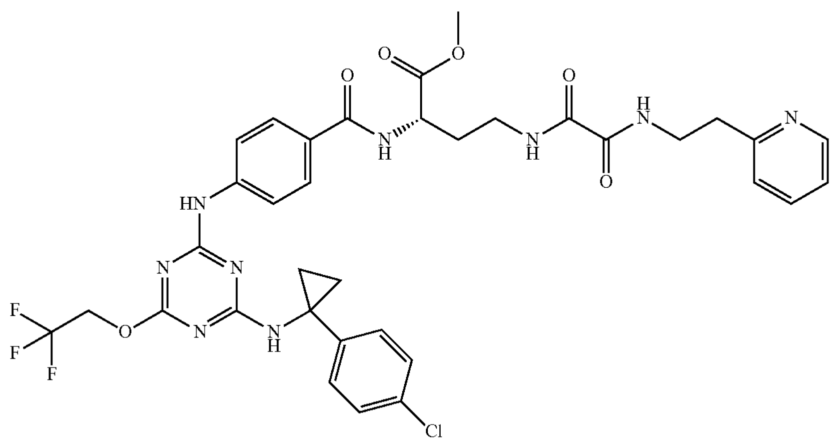 | | A |

TABLE 1-continued
| Compound | Structure | EC$_{50}$ | Activity |
|---|---|---|---|
| 1307 | 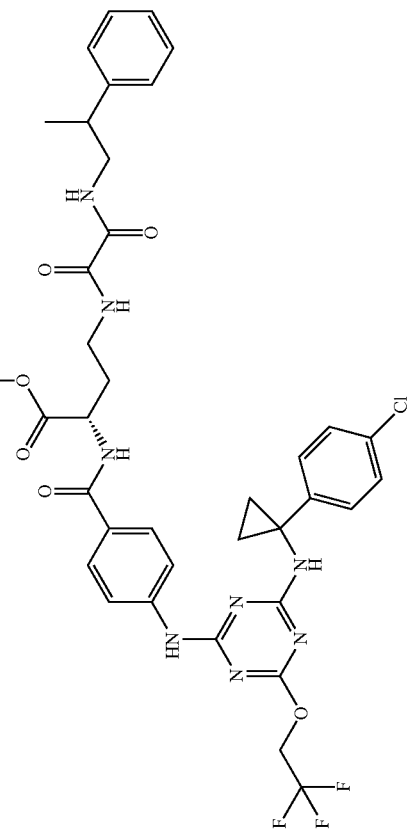 | 0.38 | A |
| 1308 | 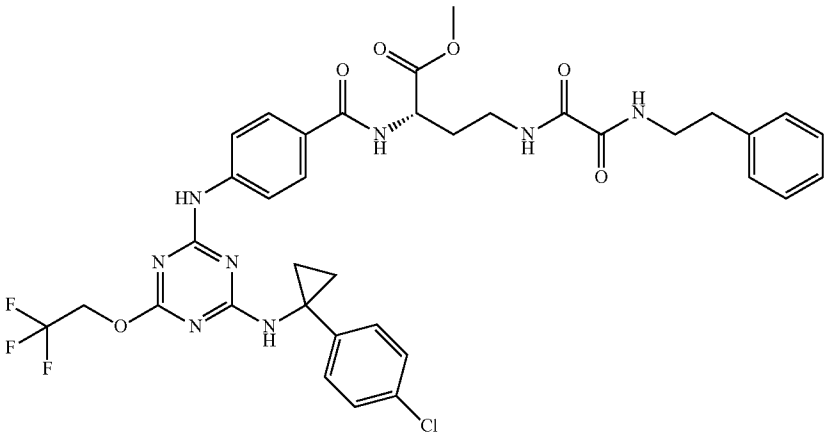 [SMILES: COC(=O)[C@H](CCNC(=O)C(=O)NCC(C)c1ccccc1)NC(=O)c1ccc(Nc2nc(NC3(c4ccc(Cl)cc4)CC3)nc(OCC(F)(F)F)n2)cc1] Chiral | | A |

TABLE 1-continued
| Compound | Structure | EC$_{50}$ | Activity |
|---|---|---|---|
| 1309 | 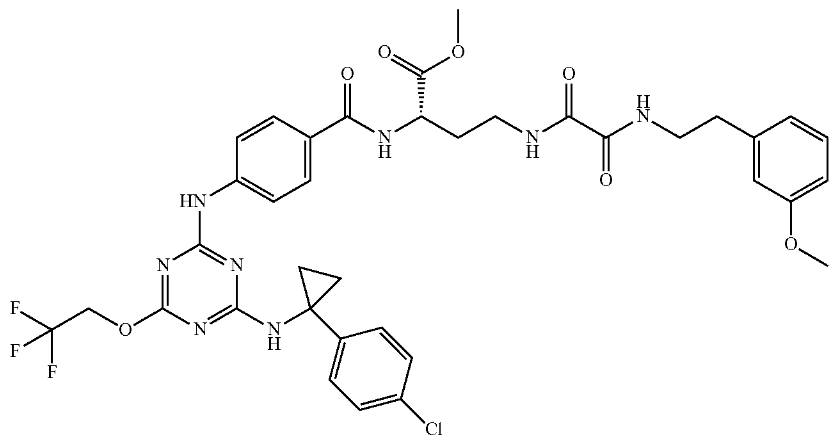 | | A |
| 1310 | 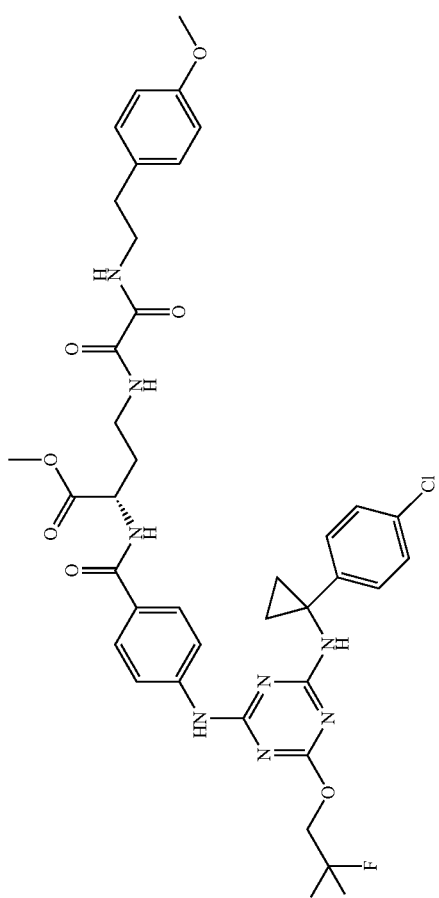 | 0.62 | A |

TABLE 1-continued

| Compound | Structure | EC$_{50}$ | Activity |
|---|---|---|---|
| 1311 | Chiral (structure) | | A |
| 1312 | Chiral (structure) | | A |

TABLE 1-continued
| Compound | Structure | EC$_{50}$ | Activity |
|---|---|---|---|
| 1313 | Chiral 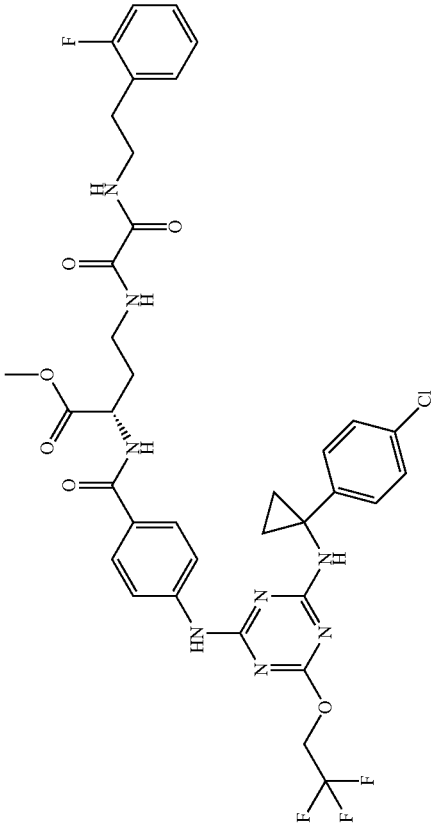 | | A |
| 1314 | Chiral 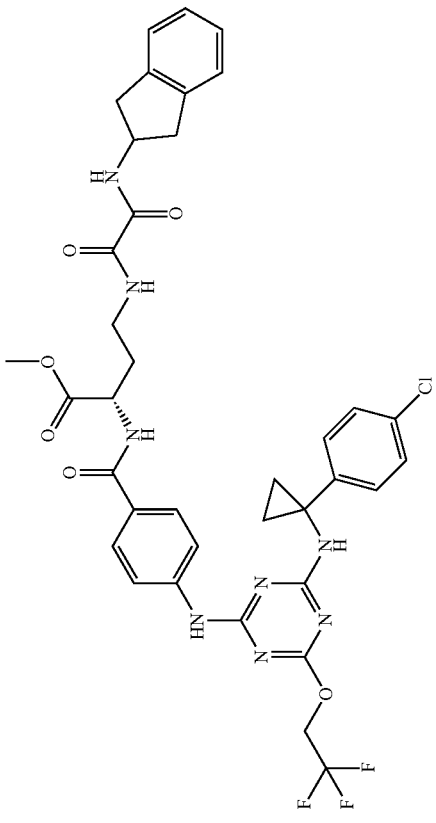 | 0.43 | A |

TABLE 1-continued
| Compound | Structure | EC$_{50}$ | Activity |
|---|---|---|---|
| 1315 | 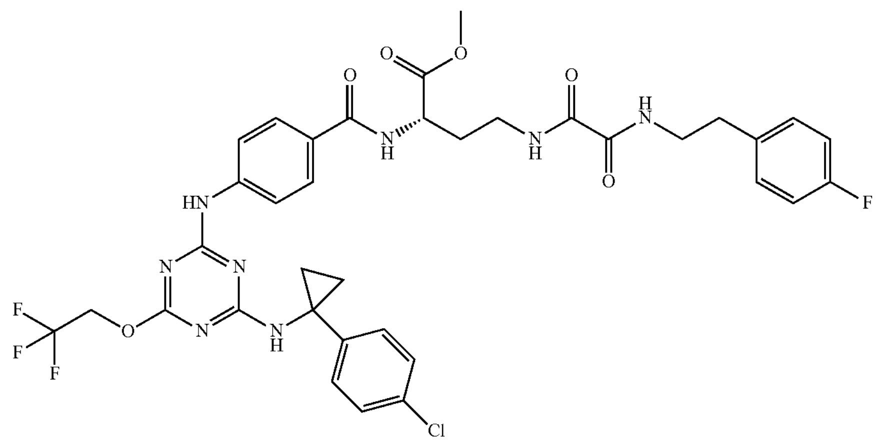 | 1.03 | A |
| 1316 | 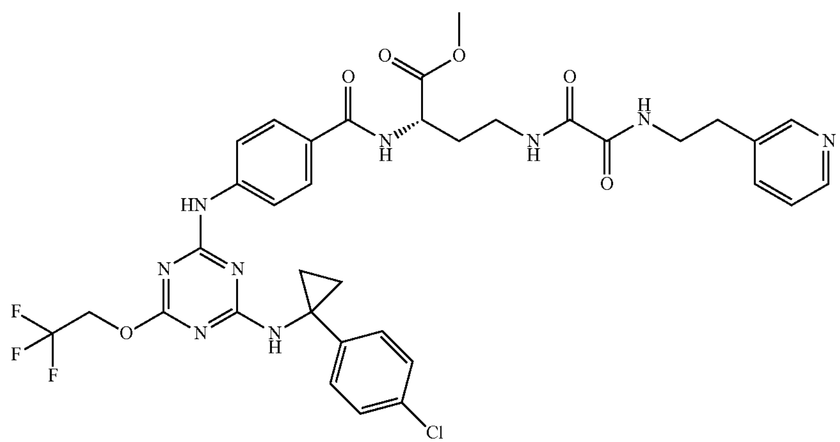 | 0.57 | A |

TABLE 1-continued
| Compound | Structure | EC$_{50}$ | Activity |
|---|---|---|---|
| 1317 | 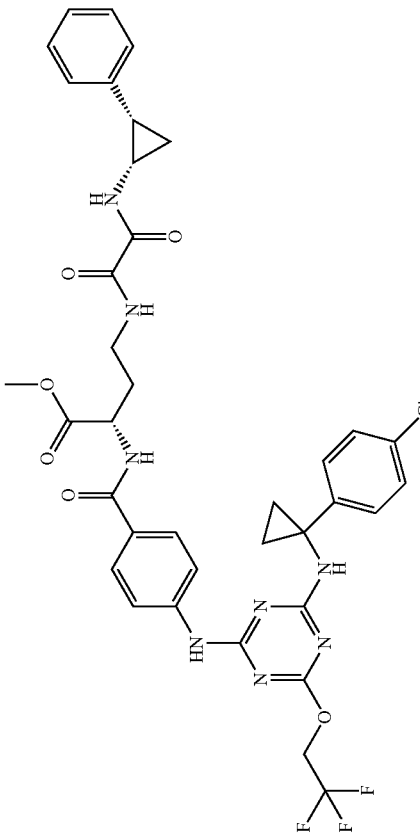 | | A |
| 1318 | 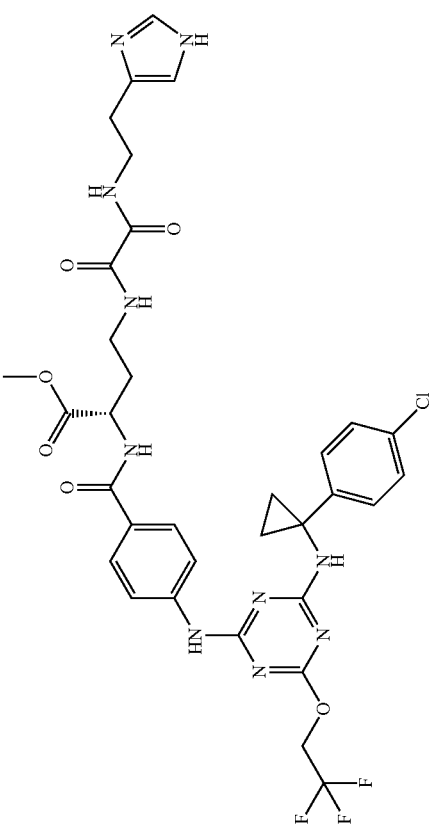 Chiral | | A |

TABLE 1-continued
| Compound | Structure | EC$_{50}$ | Activity |
|---|---|---|---|
| 1319 | 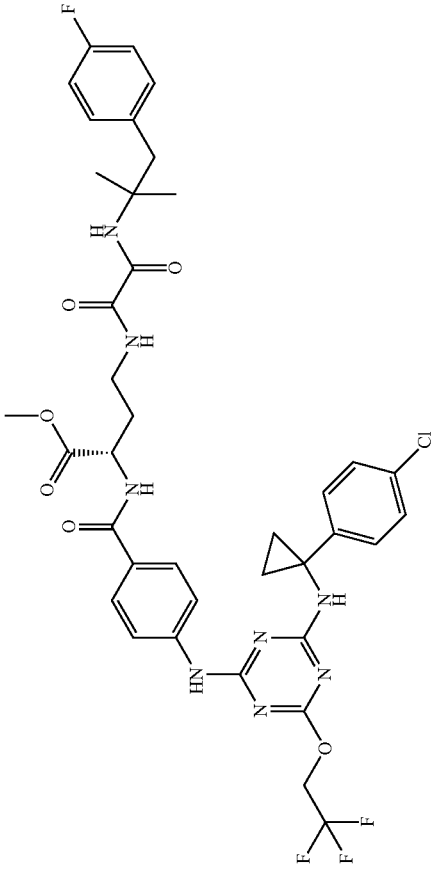 | | A |
| 1320 | 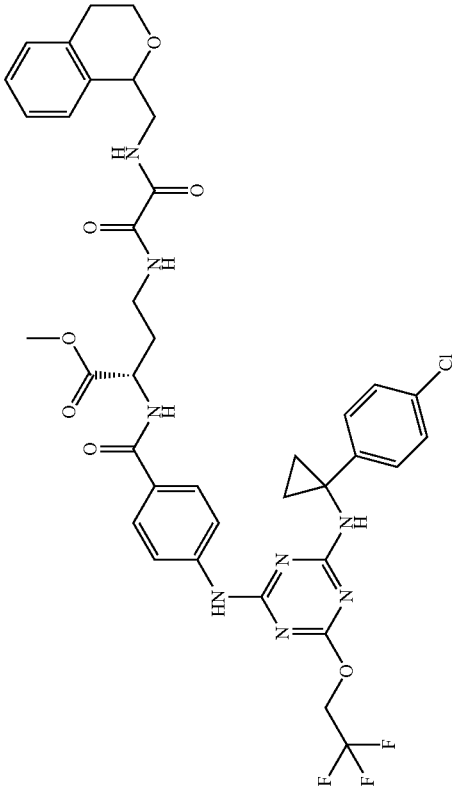 | | A |

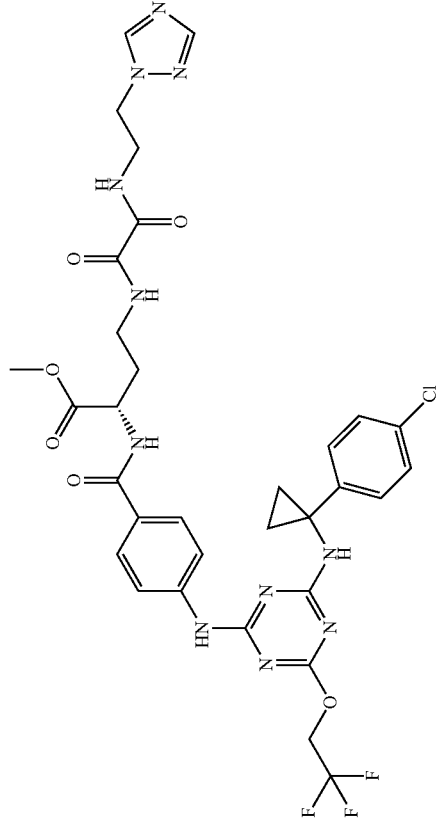

TABLE 1-continued
| Compound | Structure | EC$_{50}$ | Activity |
|---|---|---|---|
| 1323 | 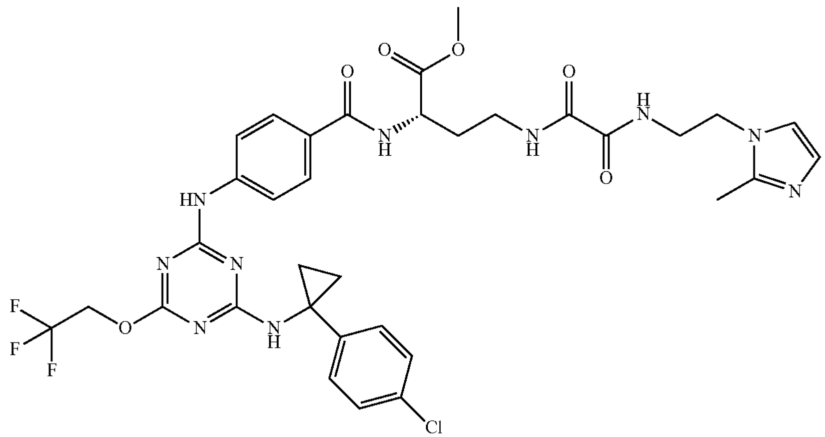 | 6.28 | A |
| 1324 | 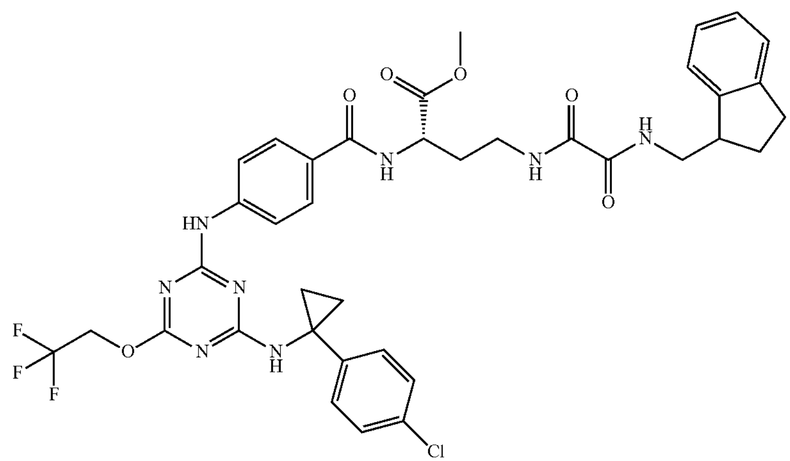 [SMILES: COC(=O)[C@H](CCNC(=O)C(=O)NCC1CCc2ccccc21)NC(=O)c1ccc(Nc2nc(NC3(c4ccc(Cl)cc4)CC3)nc(OCC(F)(F)F)n2)cc1] | | A |
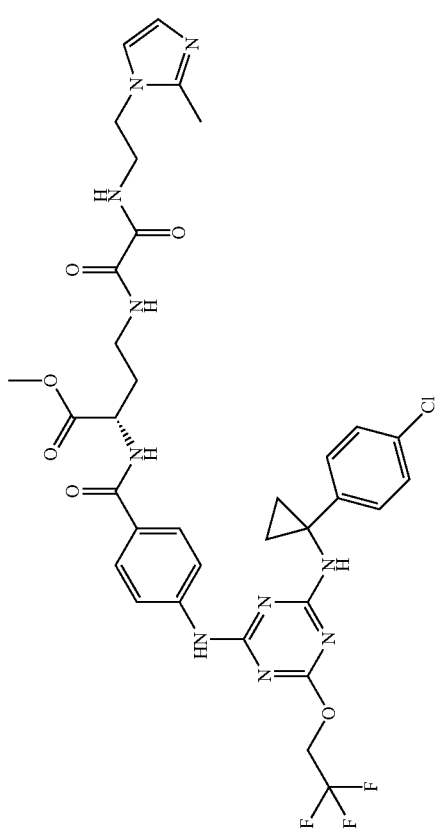

TABLE 1-continued

| Compound | Structure | EC$_{50}$ | Activity |
|---|---|---|---|
| 1325 | Chiral | | A |
| 1326 | Chiral | | A |

TABLE 1-continued

| Compound | Structure | EC$_{50}$ | Activity |
|---|---|---|---|
| 1327 | 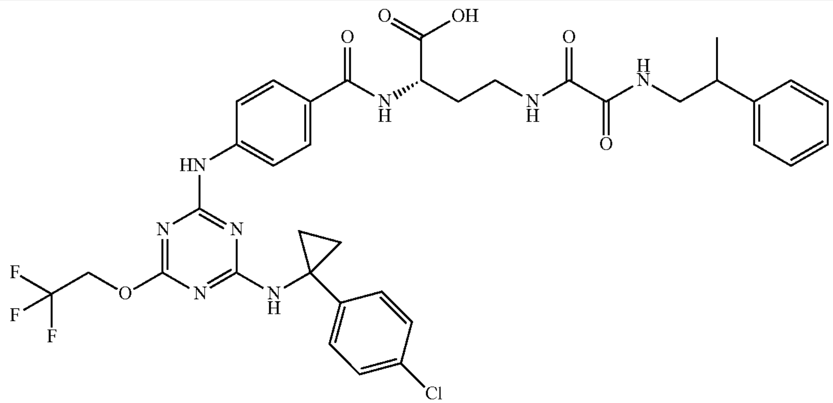 [SMILES: CC(CNC(=O)C(=O)NCC[C@H](NC(=O)c1ccc(Nc2nc(NC3(c4ccc(Cl)cc4)CC3)nc(OCC(F)(F)F)n2)cc1)C(=O)O)c1ccccc1] | | A |
| 1328 | (Chiral) | | A |

TABLE 1-continued
| Compound | Structure | EC$_{50}$ | Activity |
|---|---|---|---|
| 1329 | 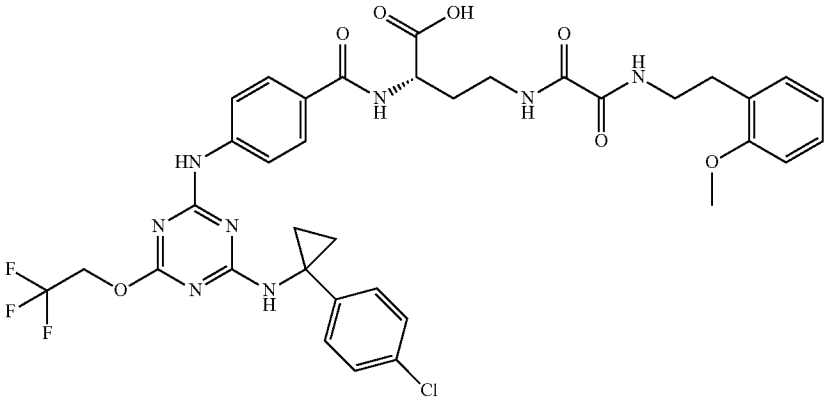 Chiral | | A |
| 1330 | 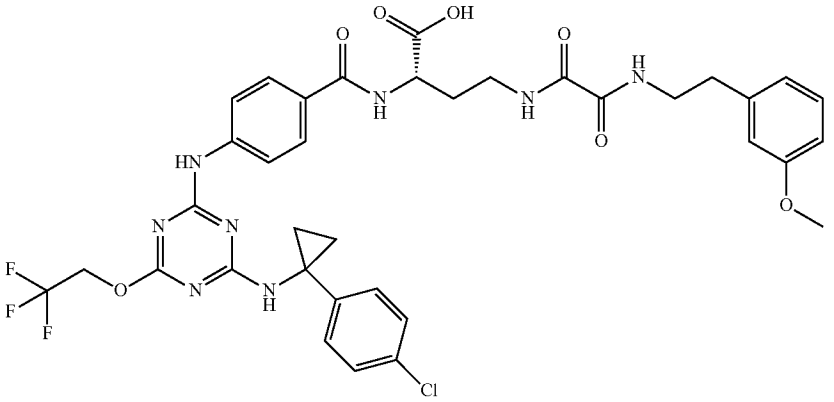 Chiral | | A |

TABLE 1-continued
| Compound | Structure | EC$_{50}$ | Activity |
|---|---|---|---|
| 1331 | 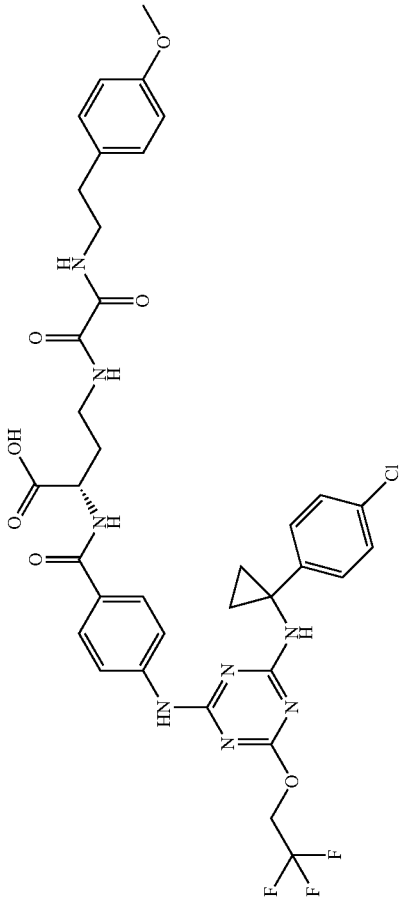 | | A |
| 1332 | 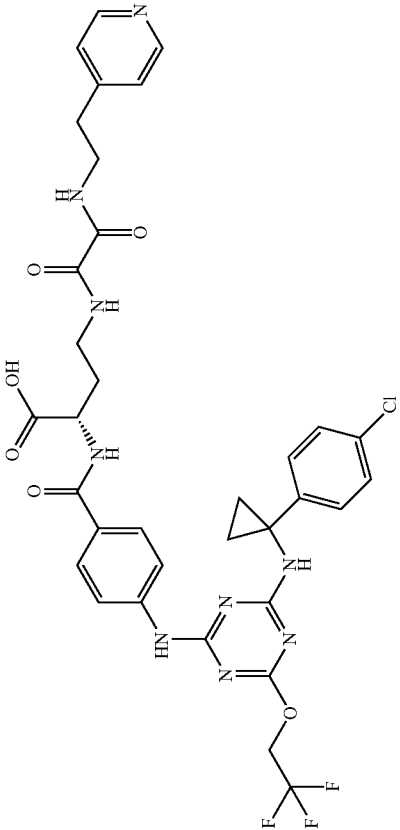 | | A |

TABLE 1-continued
| Compound | Structure | EC$_{50}$ | Activity |
|---|---|---|---|
| 1333 | Chiral 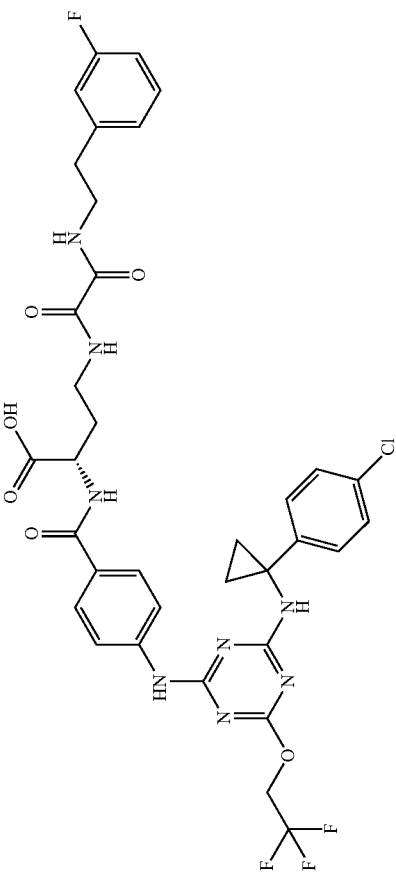 | | A |
| 1334 | Chiral 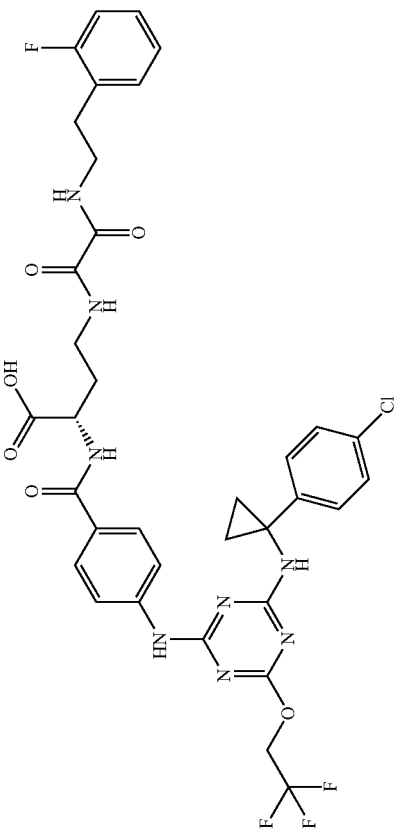 | | A |

TABLE 1-continued
| Compound | Structure | EC$_{50}$ | Activity |
|---|---|---|---|
| 1335 | Chiral | | A |
| 1336 | Chiral | 0.88 | A |
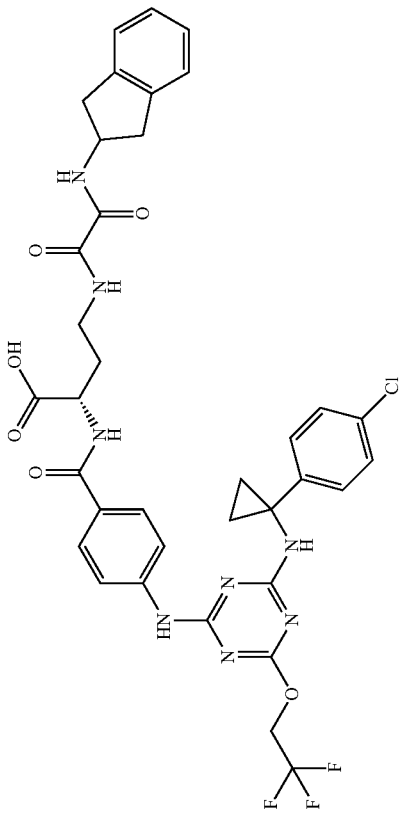
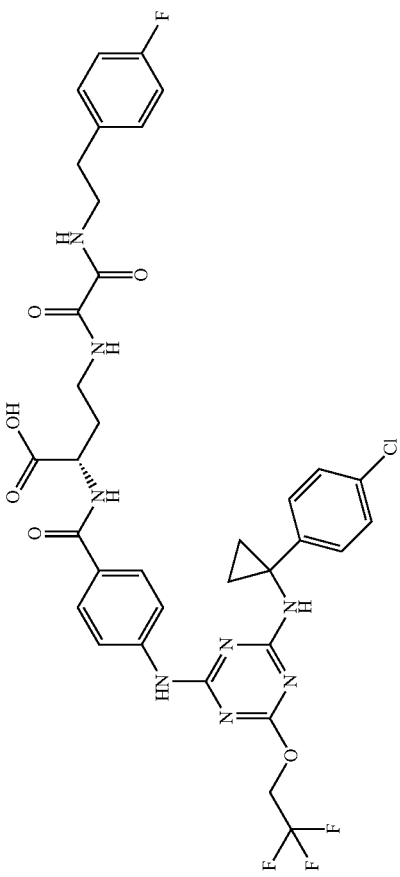

TABLE 1-continued

| Compound | Structure | EC$_{50}$ | Activity |
|---|---|---|---|
| 1337 | *(chiral structure)* | | A |
| 1338 | *(chiral structure)* | | A |

TABLE 1-continued
| Compound | Structure | EC$_{50}$ | Activity |
|---|---|---|---|
| 1339 | 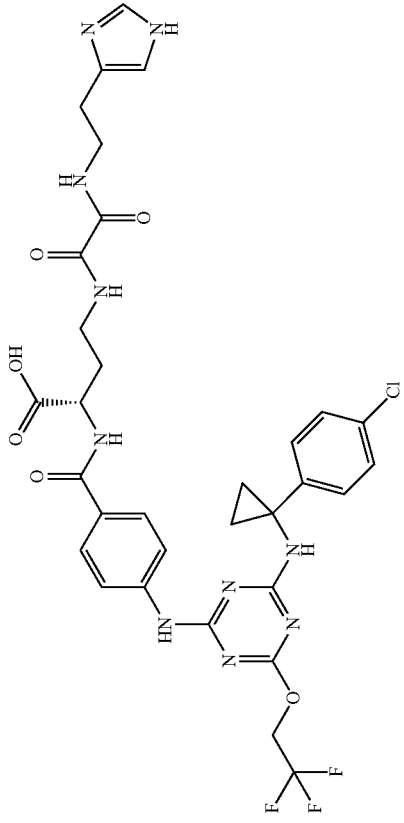 Chiral | | A |
| 1340 | 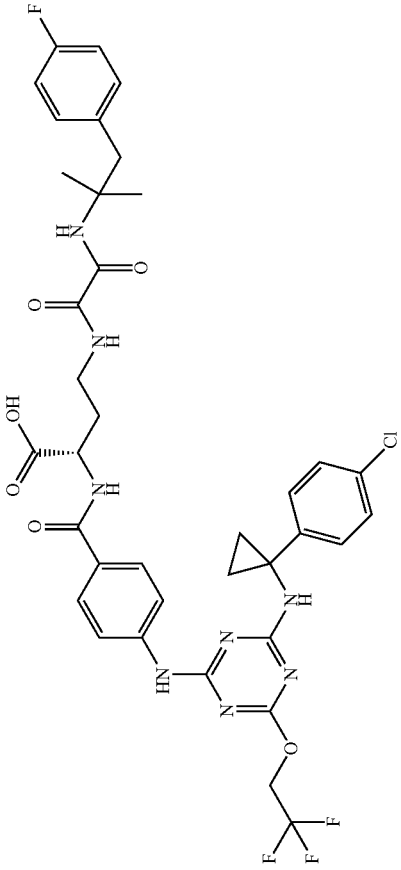 Chiral | 0.10 | A |

| Compound | Structure | EC$_{50}$ | Activity |
|---|---|---|---|
| 1341 | 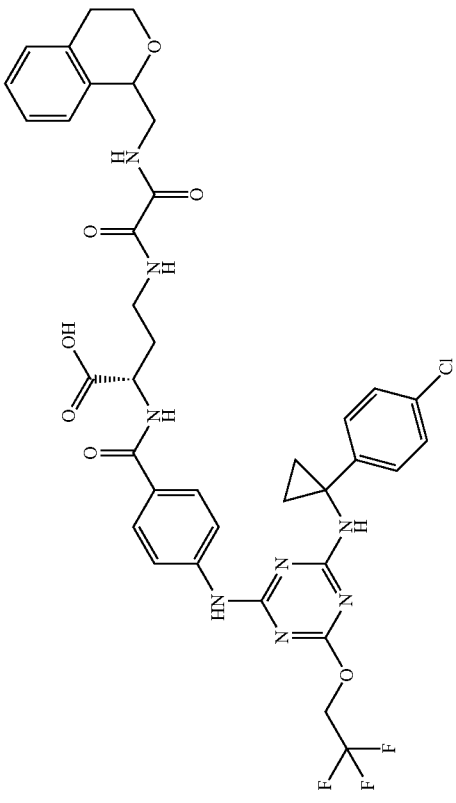 | | A |
| 1342 | 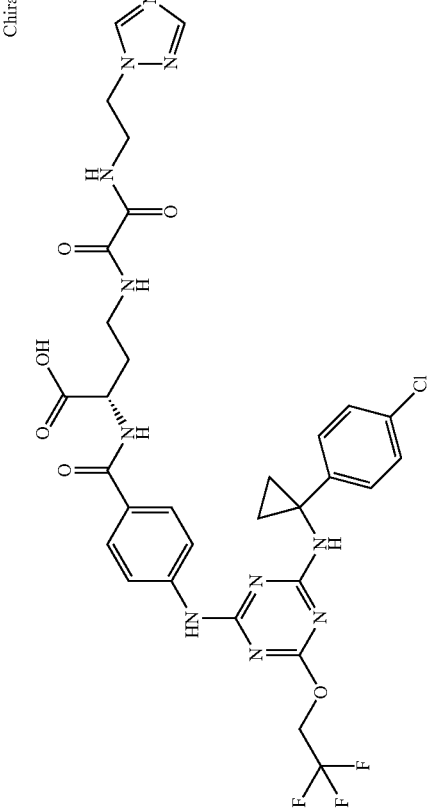 Chiral | | A |

TABLE 1-continued
| Compound | Structure | EC$_{50}$ | Activity |
|---|---|---|---|
| 1343 | 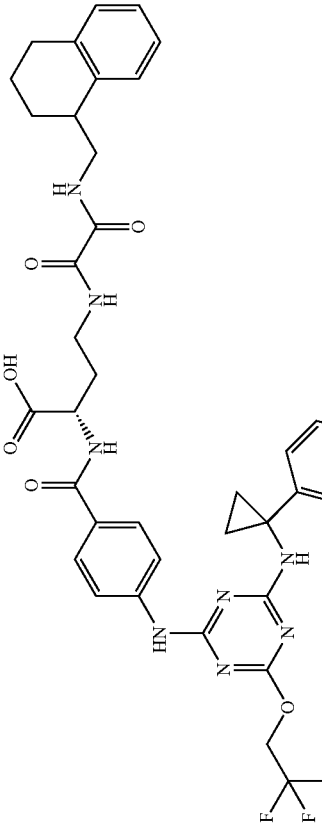 | | A |
| 1344 | 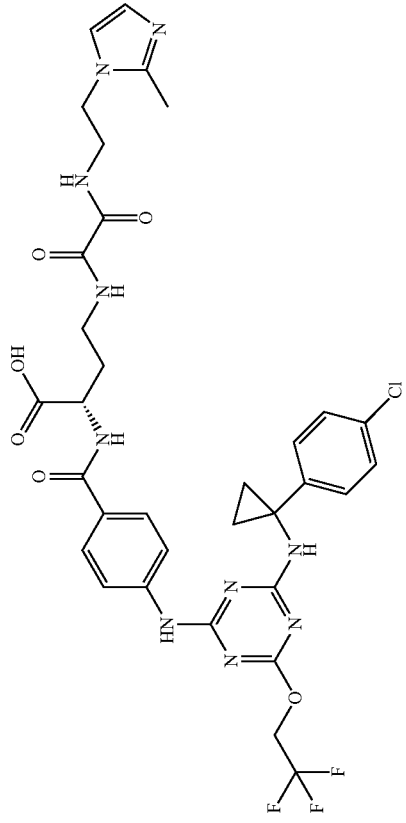 | | A |

TABLE 1-continued
| Compound | Structure | EC$_{50}$ | Activity |
|---|---|---|---|
| 1345 | 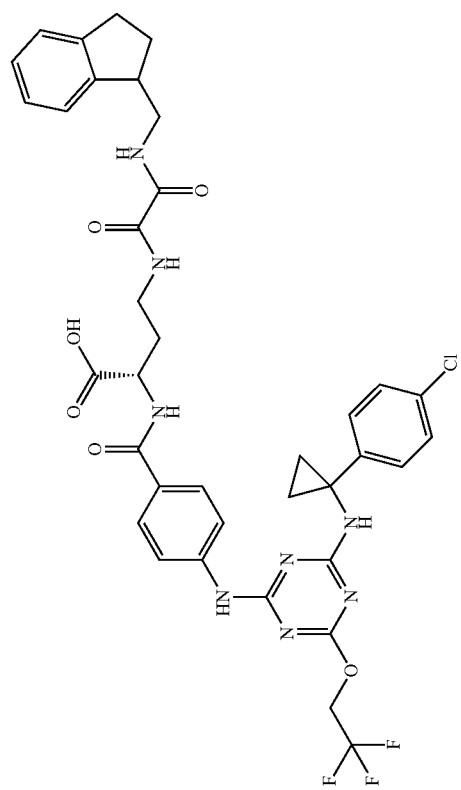 | | A |
| 1346 | 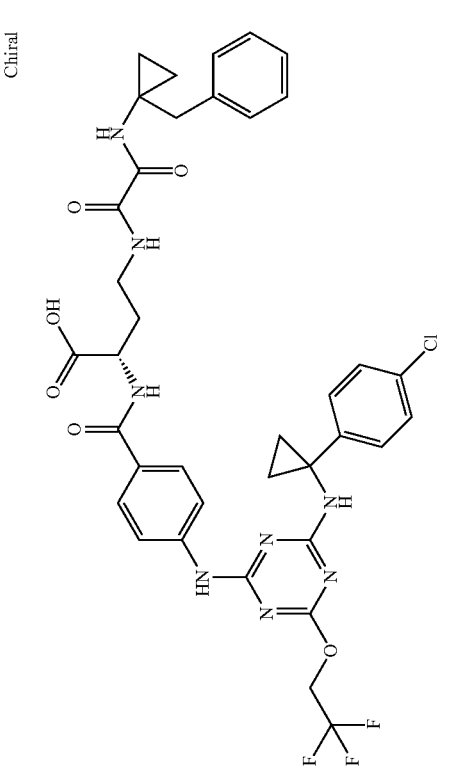 | | A |

TABLE 1-continued
| Compound | Structure | EC$_{50}$ | Activity |
|---|---|---|---|
| 1347 | Chiral | | A |
| 1348 | Chiral | 0.50 | A |

TABLE 1-continued
| Compound | Structure | EC$_{50}$ | Activity |
|---|---|---|---|
| 1349 | 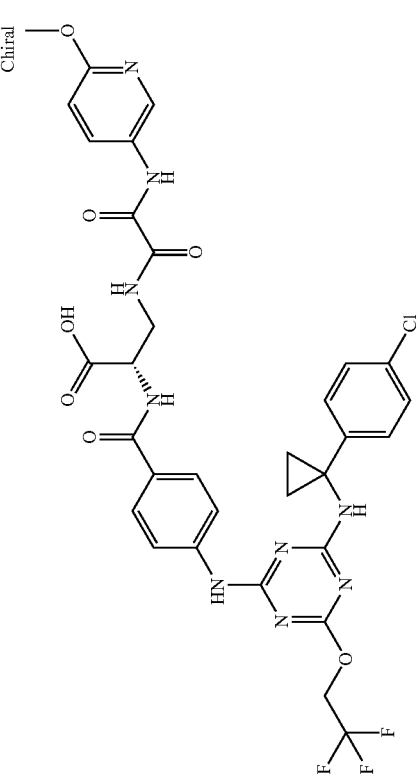 | | A |
| 1350 | 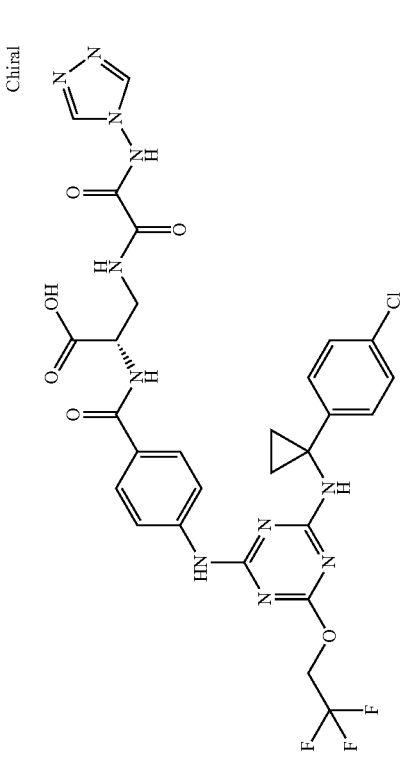 | | B |

TABLE 1-continued
| Compound | Structure | EC$_{50}$ | Activity |
|---|---|---|---|
| 1351 | 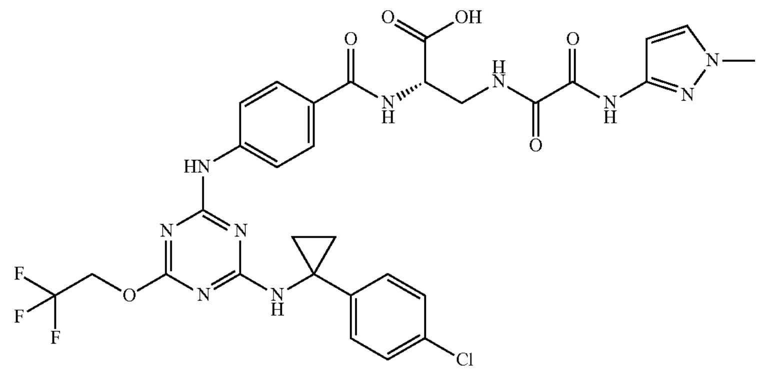 | | A |
| 1352 | 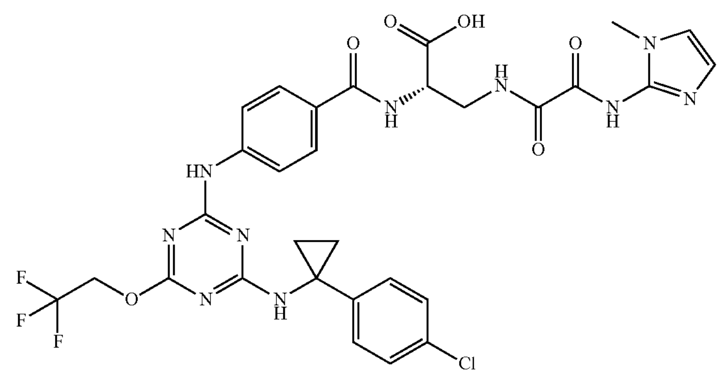 | | A |

TABLE 1-continued
| Compound | Structure | EC$_{50}$ | Activity |
|---|---|---|---|
| 1353 | 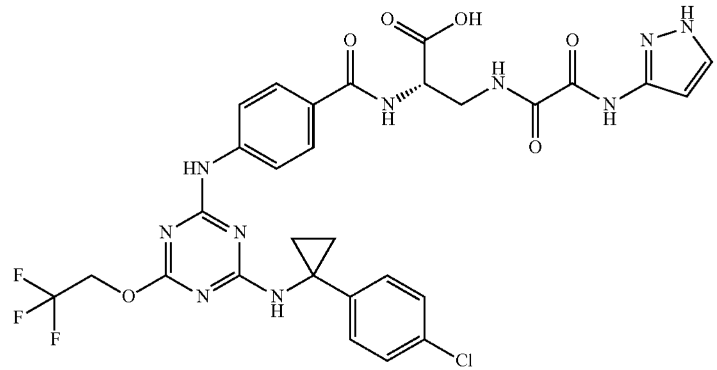 | 1.66 | A |
| 1354 | 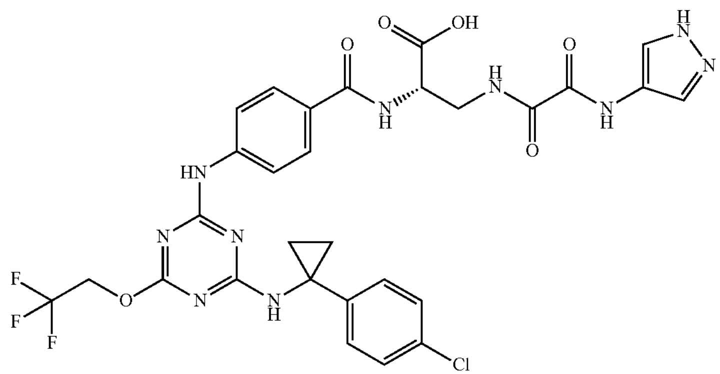 | | A |

TABLE 1-continued

| Compound | Structure | EC$_{50}$ | Activity |
|---|---|---|---|
| 1356 | (Chiral structure) | | A |
| 1357 | (Chiral structure) | | A |

TABLE 1-continued
| Compound | Structure | EC$_{50}$ | Activity |
|---|---|---|---|
| 1358 | 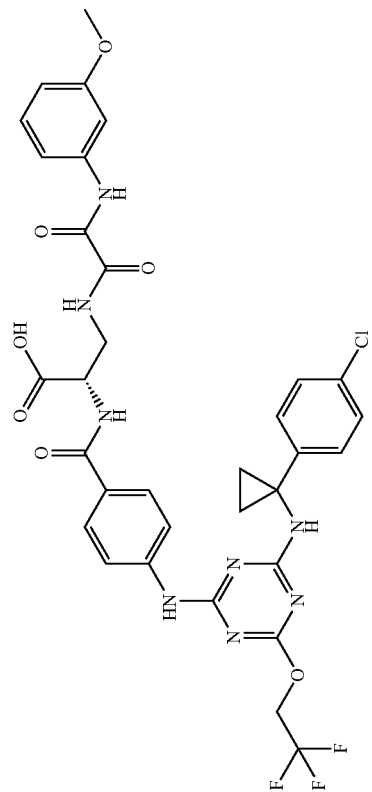 Chiral | | A |
| 1359 | 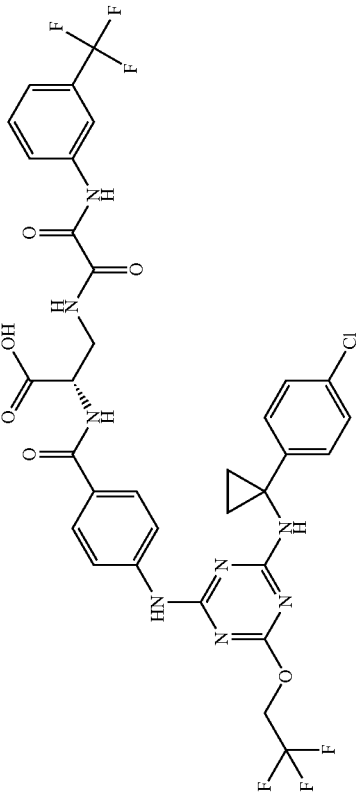 Chiral | | A |

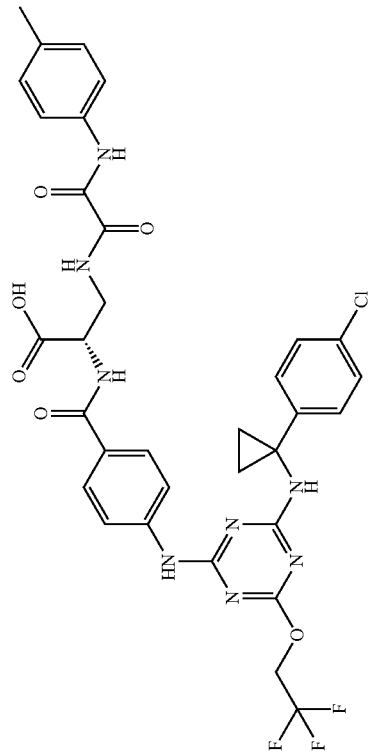

TABLE 1-continued
| Compound | Structure | EC$_{50}$ | Activity |
|---|---|---|---|
| 1362 | 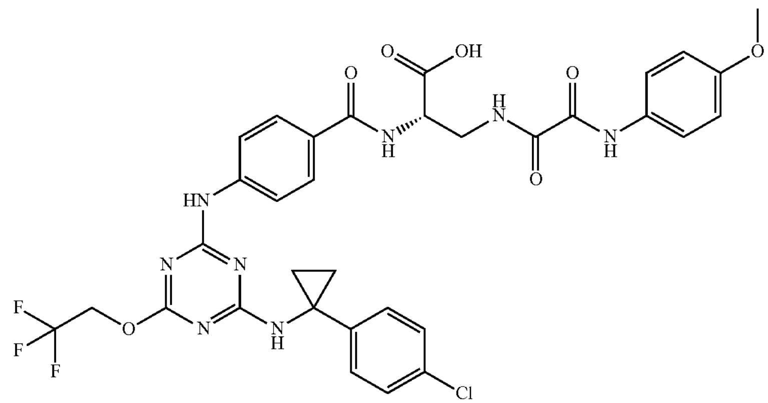 [SMILES: O=C(NC[C@H](NC(=O)c1ccc(Nc2nc(NC3(c4ccc(Cl)cc4)CC3)nc(OCC(F)(F)F)n2)cc1)C(=O)O)C(=O)Nc1cccc(F)c1] | 0.30 | A |
| 1363 | 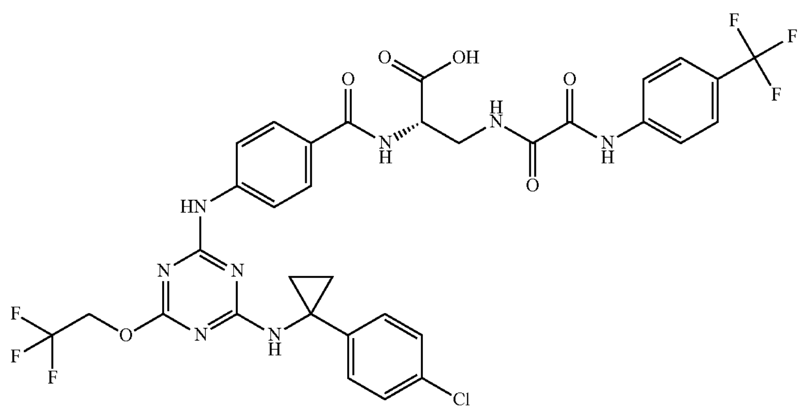 [SMILES: O=C(NC[C@H](NC(=O)c1ccc(Nc2nc(NC3(c4ccc(Cl)cc4)CC3)nc(OCC(F)(F)F)n2)cc1)C(=O)O)C(=O)Nc1cccc(C(F)(F)F)c1] | | A |

TABLE 1-continued
| Compound | Structure | EC$_{50}$ | Activity |
|---|---|---|---|
| 1364 | 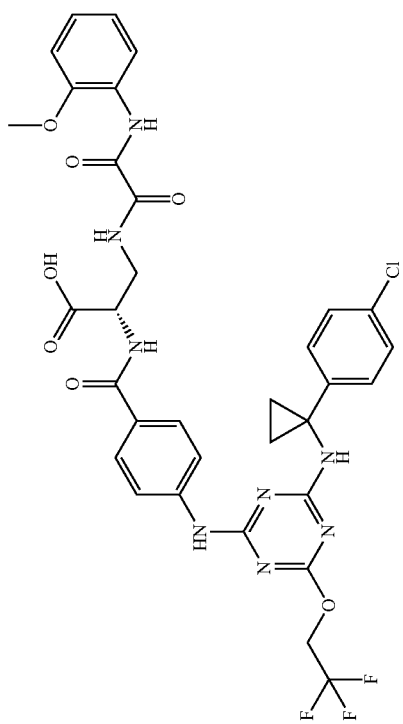 | | A |
| 1365 | 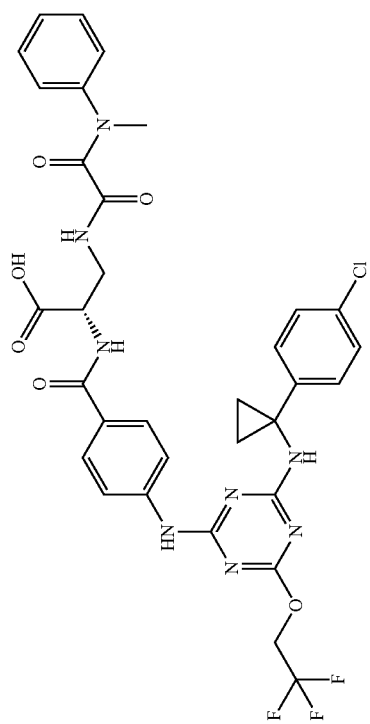 | | A |

TABLE 1-continued
| Compound | Structure | EC$_{50}$ | Activity |
|---|---|---|---|
| 1367 | 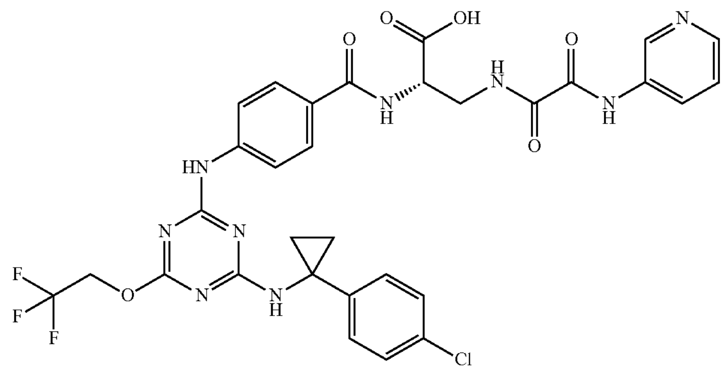 | | A |
| 1368 | 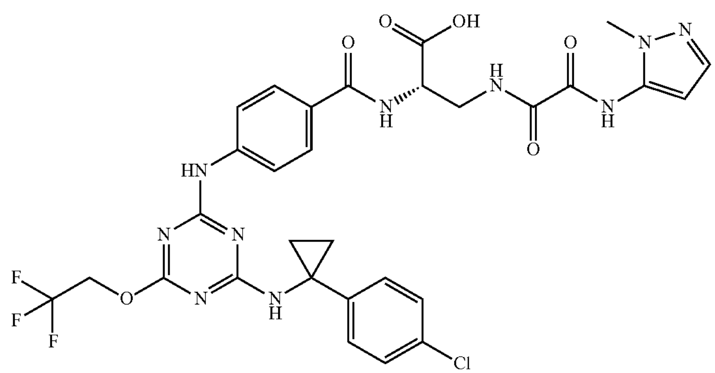 | | A |
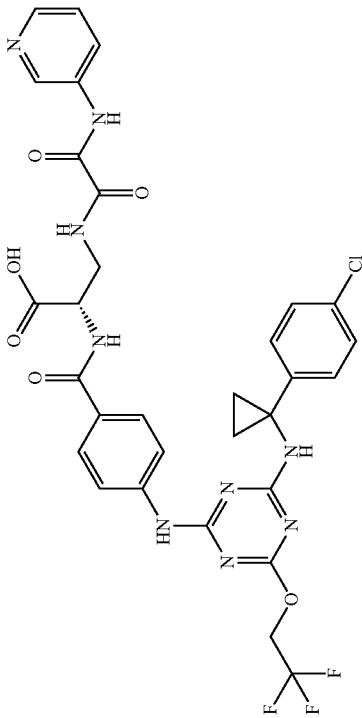

TABLE 1-continued
| Compound | Structure | EC$_{50}$ | Activity |
|---|---|---|---|
| 1369 | 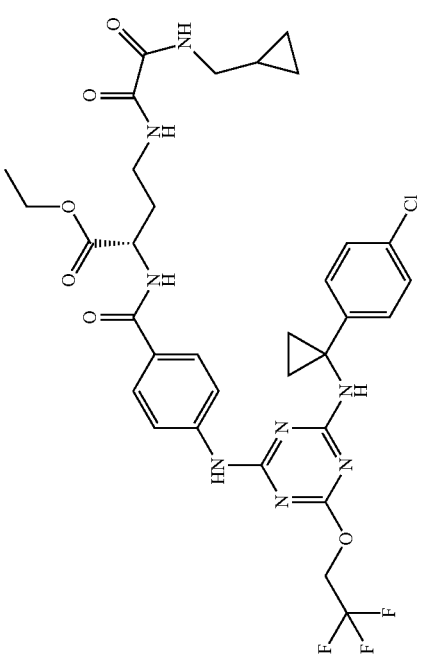 | | A |
| 1370 | 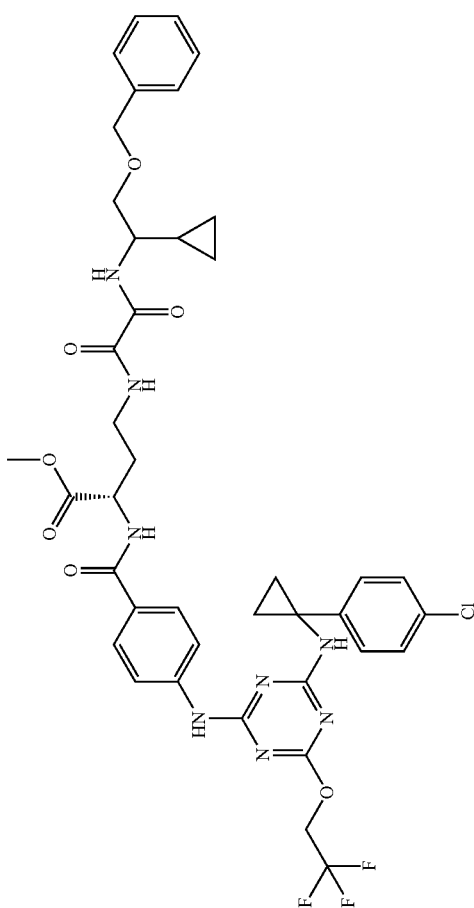 | | A |

TABLE 1-continued

| Compound | Structure | EC$_{50}$ | Activity |
|---|---|---|---|
| 1371 | 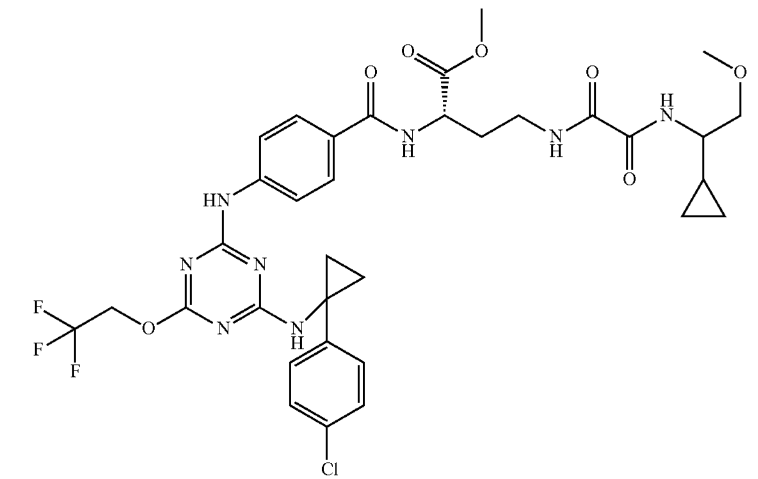 [SMILES: COCC(NC(=O)C(=O)NCC[C@H](NC(=O)c1ccc(Nc2nc(NC3(c4ccc(Cl)cc4)CC3)nc(OCC(F)(F)F)n2)cc1)C(=O)OC)C1CC1] | | A |
| 1372 | 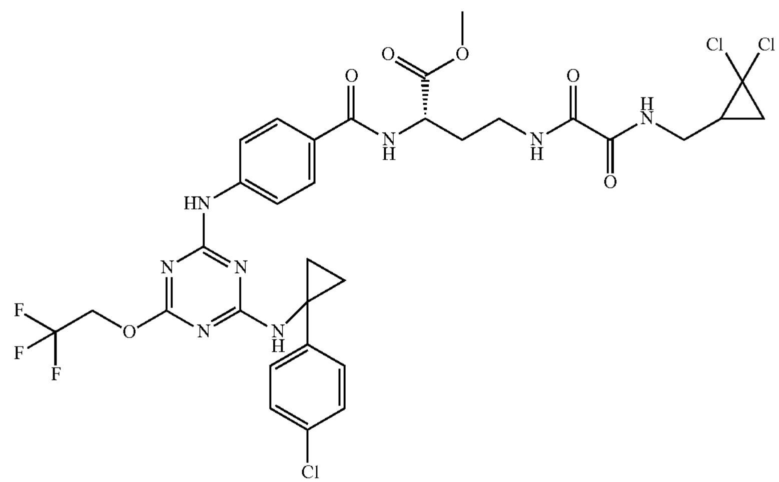 [SMILES: COC(=O)[C@H](CCNC(=O)C(=O)NCC1CC1(Cl)Cl)NC(=O)c1ccc(Nc2nc(NC3(c4ccc(Cl)cc4)CC3)nc(OCC(F)(F)F)n2)cc1] | | A |

TABLE 1-continued
| Compound | Structure | EC50 | Activity |
|---|---|---|---|
| 1373 | 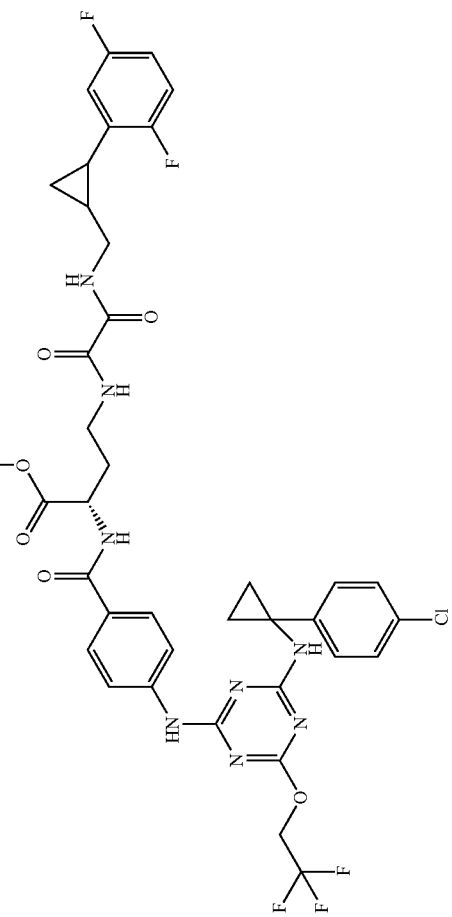 | | A |
| 1374 | 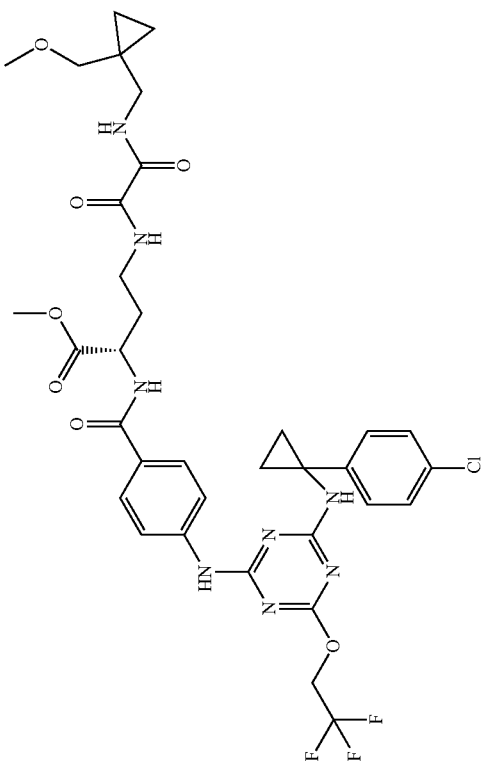 | | A |

TABLE 1-continued
| Compound | Structure | EC$_{50}$ | Activity |
|---|---|---|---|
| 1375 | 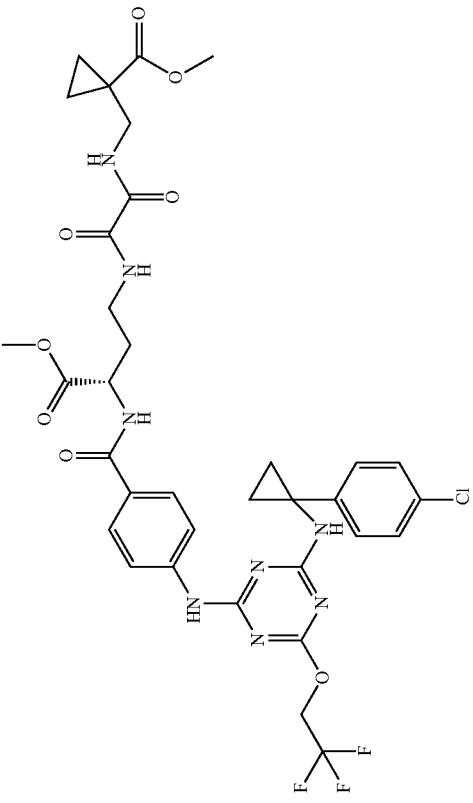 Chiral | | A |
| 1376 | 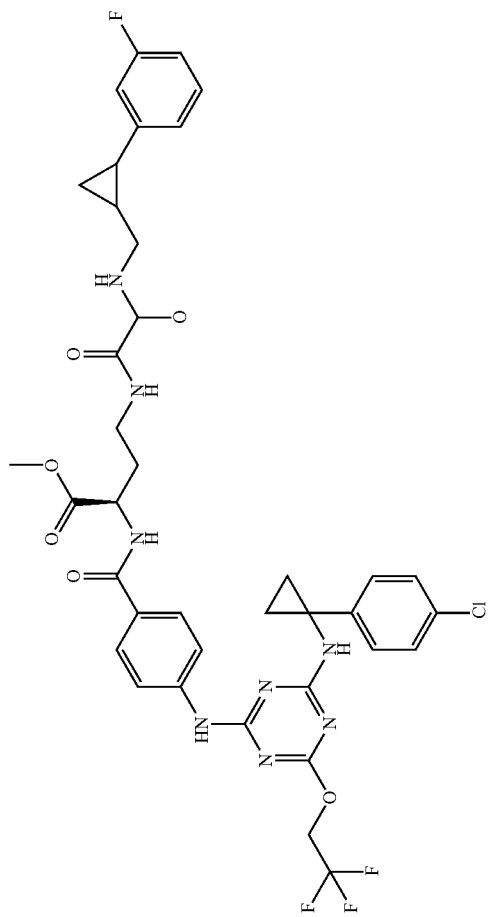 | | A |

TABLE 1-continued
| Compound | Structure | EC$_{50}$ | Activity |
|---|---|---|---|
| 1377 | 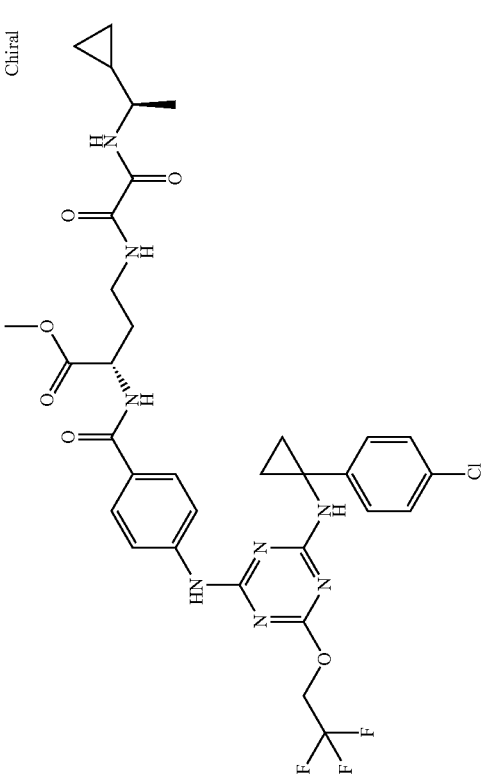 | | A |
| 1378 | 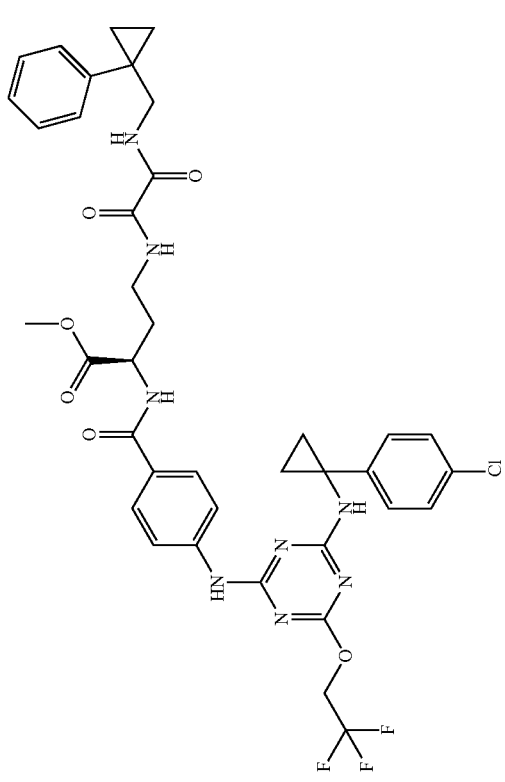 | 0.23 | A |

TABLE 1-continued
| Compound | Structure | EC$_{50}$ | Activity |
|---|---|---|---|
| 1379 | 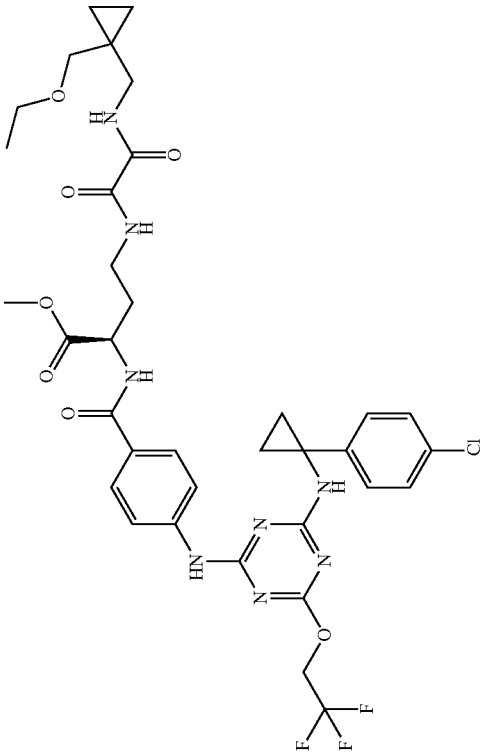 Chiral | | A |

| Compound | Structure | EC$_{50}$ | Activity |
|---|---|---|---|
| 1380 | Chiral 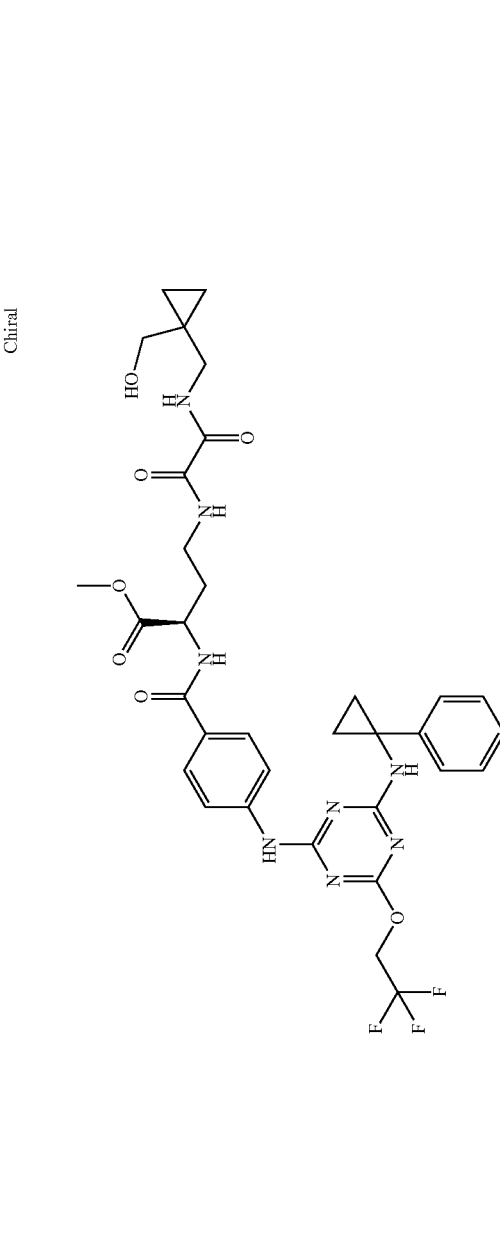 | | A |

TABLE 1-continued
| Compound | Structure | EC$_{50}$ | Activity |
|---|---|---|---|
| 1381 | 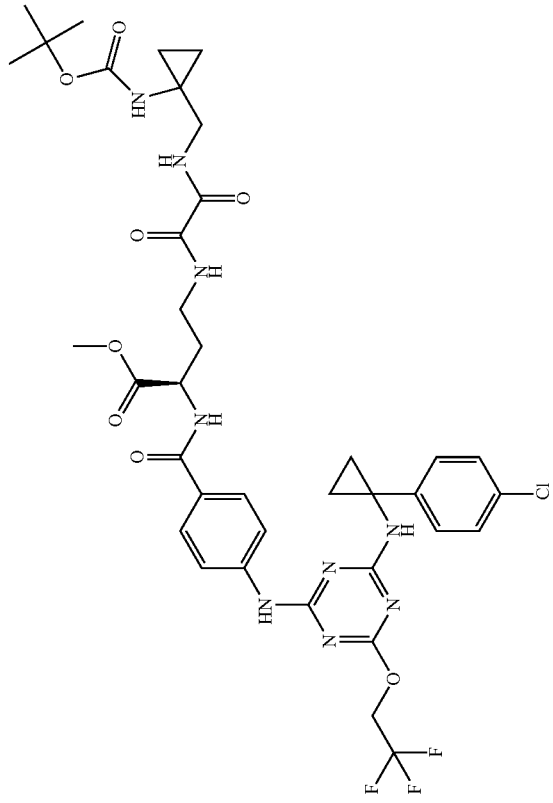 Chiral | | A |
| 1382 | 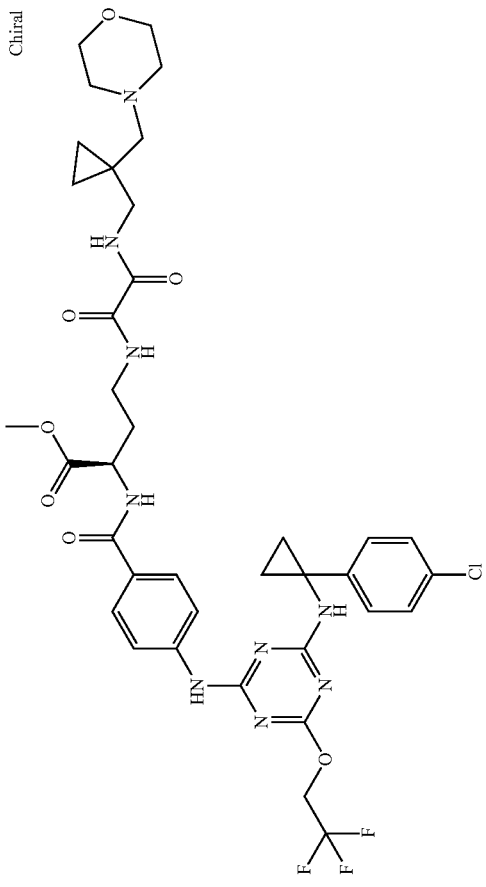 Chiral | | A |

TABLE 1-continued
| Compound | Structure | EC$_{50}$ | Activity |
|---|---|---|---|
| 1383 | 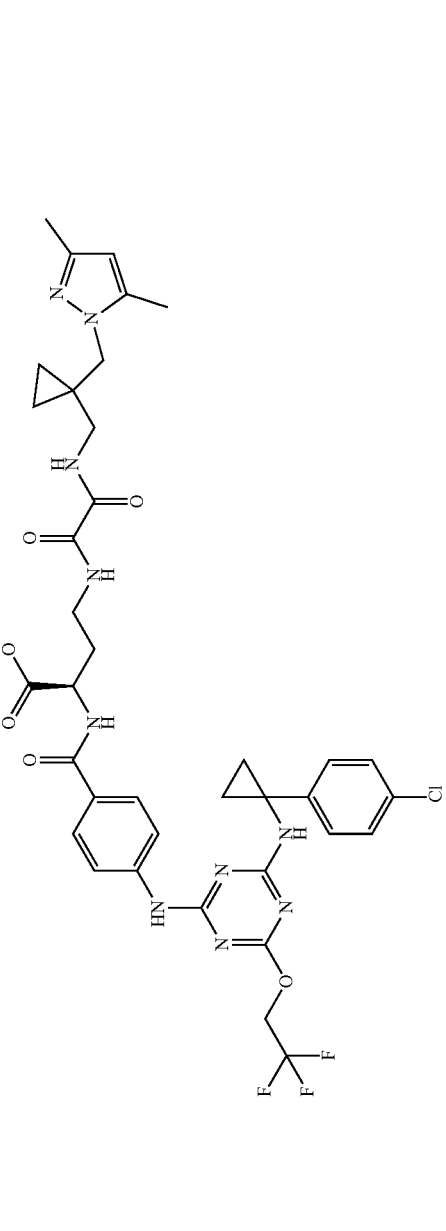 | | A |
| 1384 | 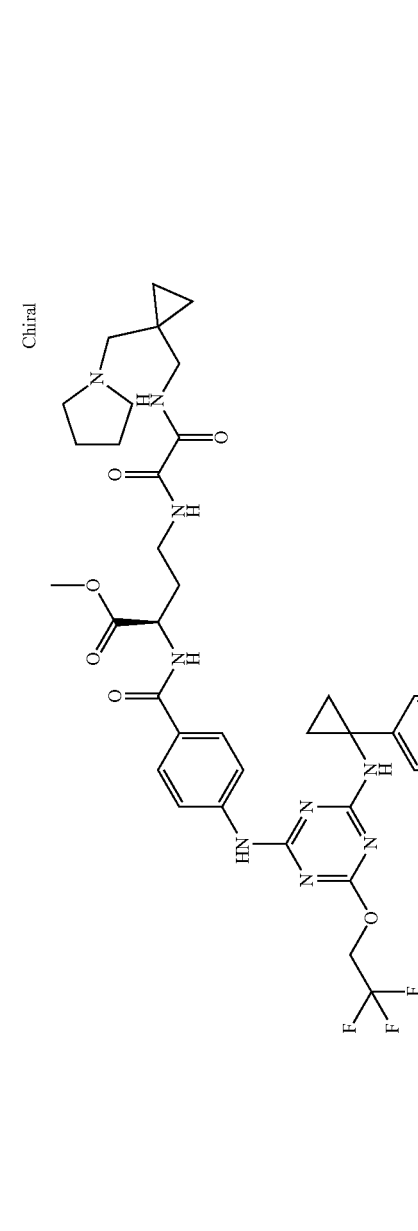 | | A |

| Compound | Structure | EC$_{50}$ | Activity |
|---|---|---|---|
| 1385 | 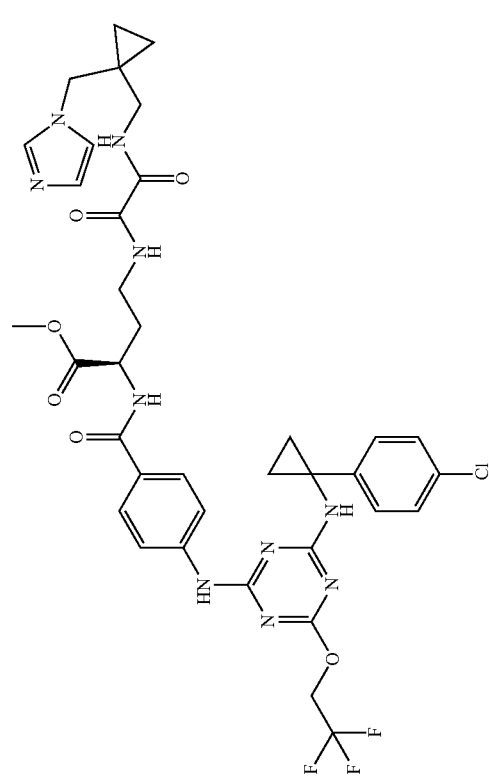 Chiral | | A |

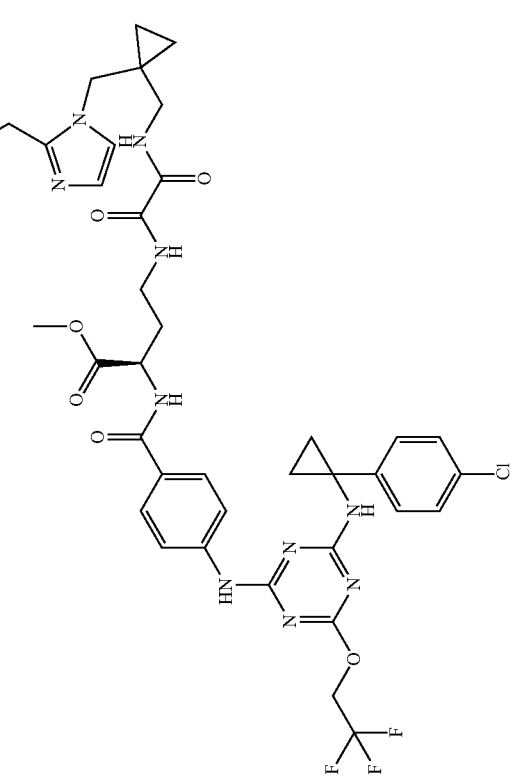

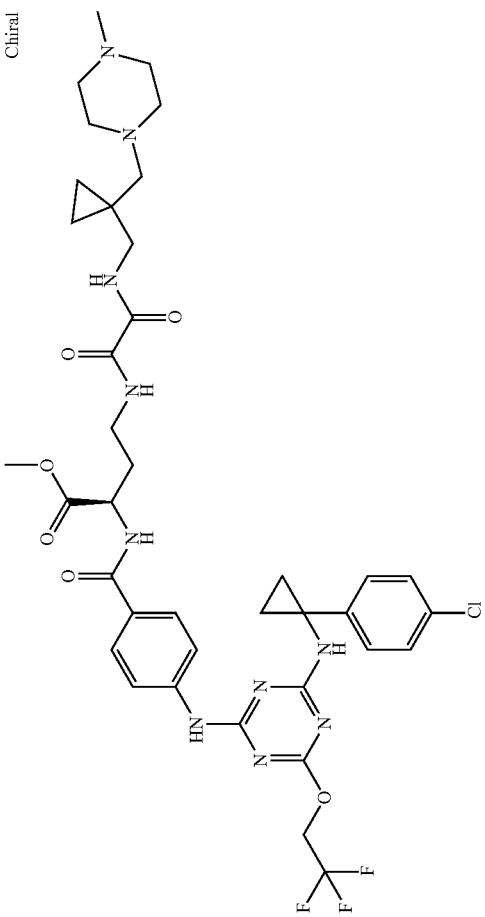

TABLE 1-continued

| Compound | Structure | EC$_{50}$ | Activity |
|---|---|---|---|
| 1390 | 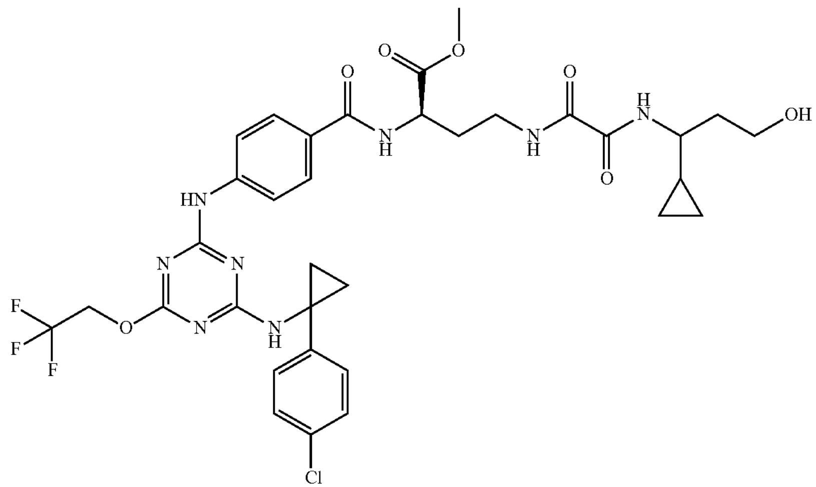 [SMILES: COC(=O)[C@@H](CCNC(=O)C(=O)NC(CCO)C1CC1)NC(=O)c1ccc(Nc2nc(NC3(c4ccc(Cl)cc4)CC3)nc(OCC(F)(F)F)n2)cc1] | | A |
| 1391 | 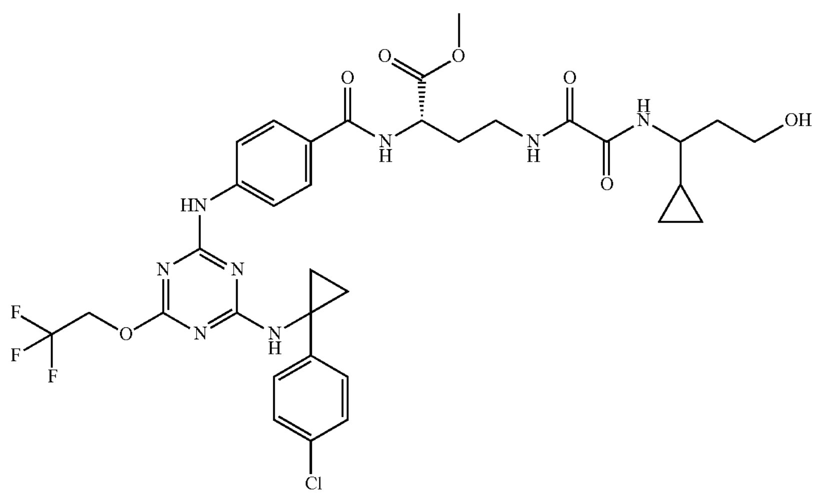 [SMILES: COC(=O)[C@H](CCNC(=O)C(=O)NC(CCO)C1CC1)NC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 1392 | 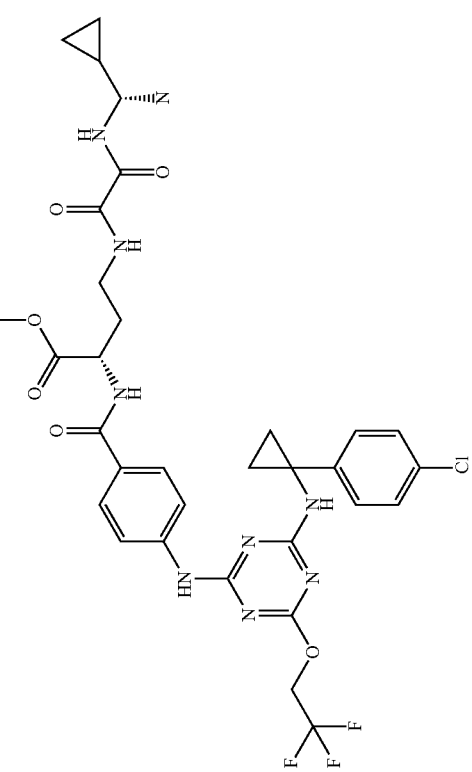 | 0.14 | A |
| 1393 | 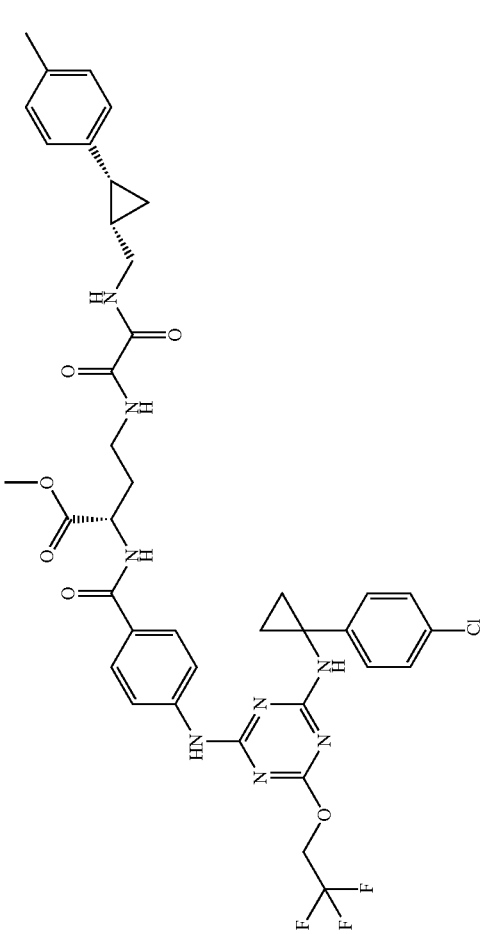 | | A |

TABLE 1-continued

| Compound | Structure | EC$_{50}$ | Activity |
|---|---|---|---|
| 1394 | Chiral | | A |
| 1395 | 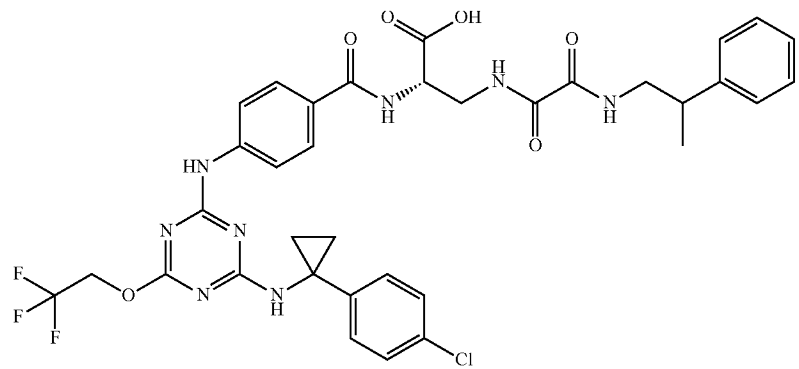 [SMILES: CC(CNC(=O)C(=O)NC[C@H](NC(=O)c1ccc(Nc2nc(NC3(c4ccc(Cl)cc4)CC3)nc(OCC(F)(F)F)n2)cc1)C(=O)O)c1ccccc1] | | A |

TABLE 1-continued
| Compound | Structure | EC$_{50}$ | Activity |
|---|---|---|---|
| 1396 | Chiral 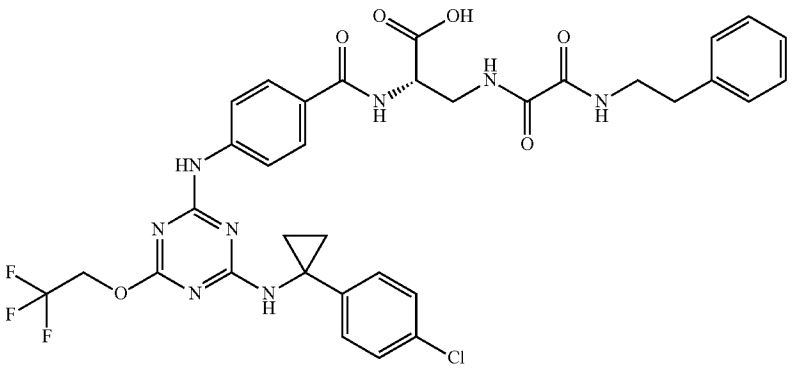 | | A |
| 1397 | Chiral 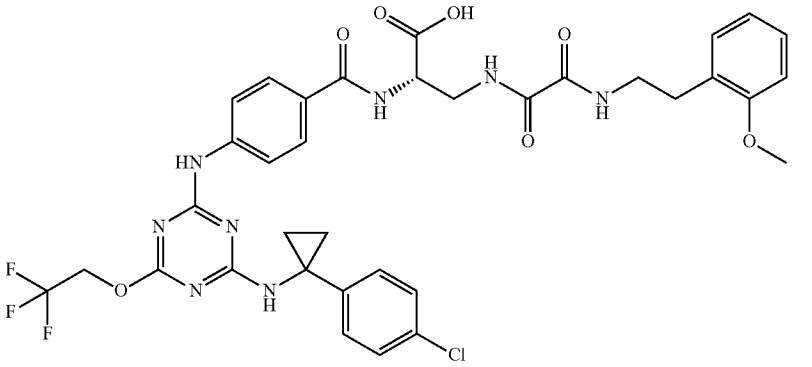 | | A |

TABLE 1-continued
| Compound | Structure | EC₅₀ | Activity |
|---|---|---|---|
| 1398 | Chiral 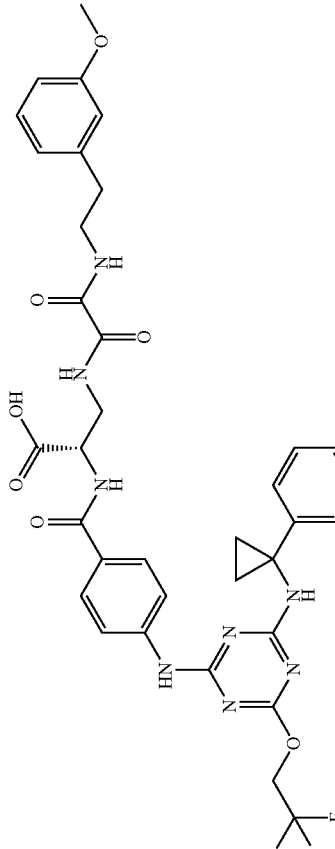 | 2.19 | A |
| 1399 | Chiral 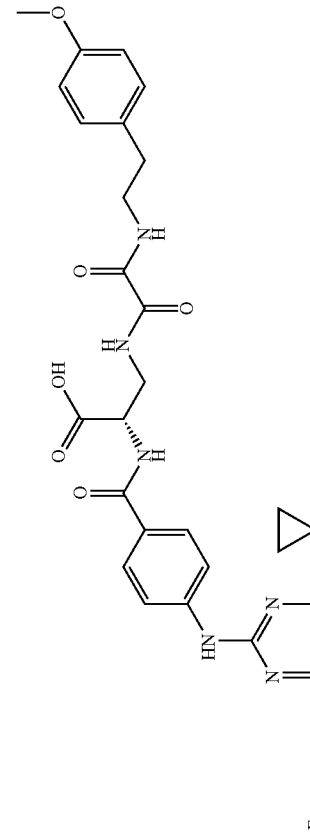 | | A |

TABLE 1-continued
| Compound | Structure | EC$_{50}$ | Activity |
|---|---|---|---|
| 1400 | 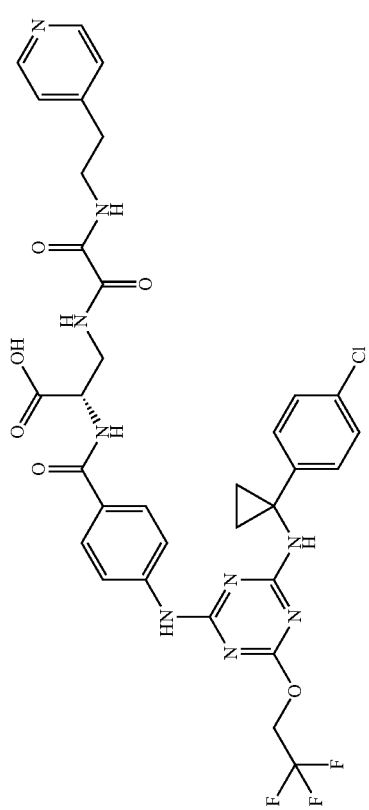 Chiral | 3.77 | A |
| 1401 | 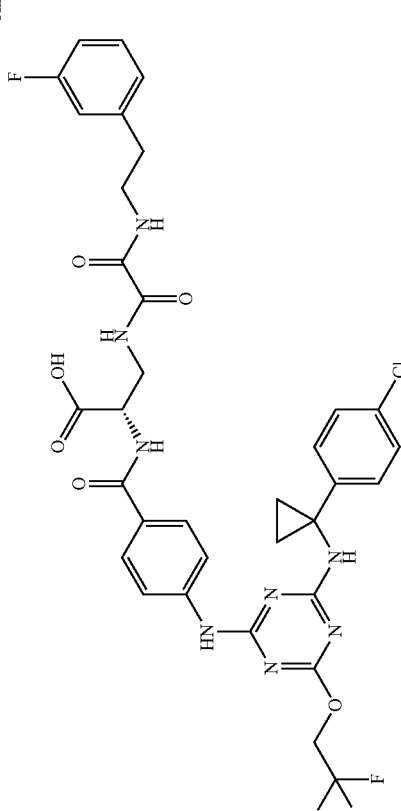 Chiral | | A |

TABLE 1-continued
| Compound | Structure | EC$_{50}$ | Activity |
|---|---|---|---|
| 1402 | Chiral 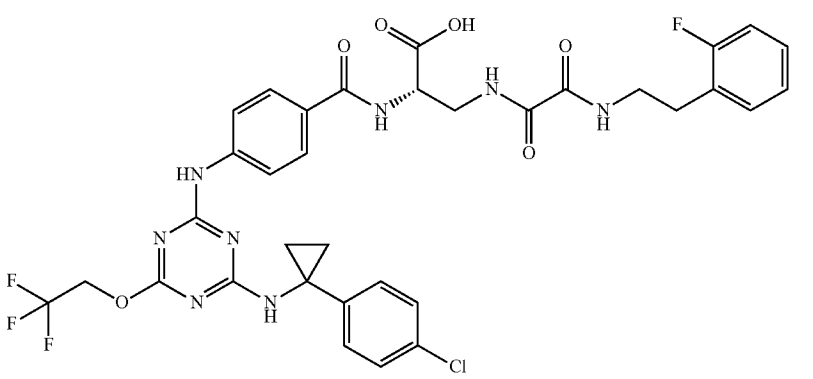 | | A |
| 1403 | Chiral 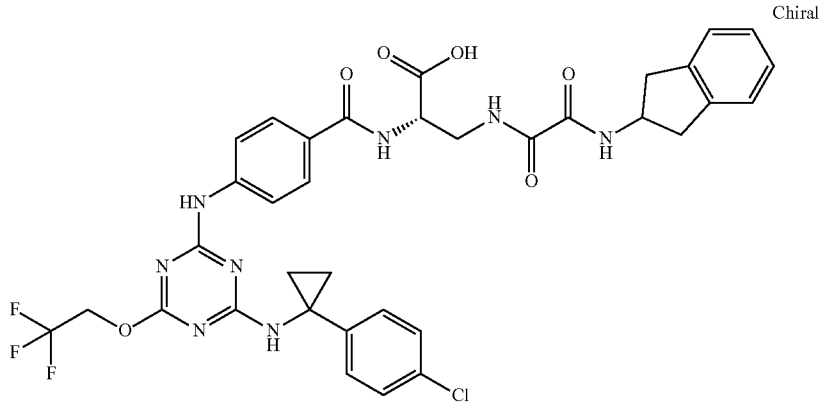 [SMILES: O=C(NC[C@H](NC(=O)c1ccc(Nc2nc(NC3(c4ccc(Cl)cc4)CC3)nc(OCC(F)(F)F)n2)cc1)C(=O)O)C(=O)NC1Cc2ccccc2C1] | | A |

TABLE 1-continued
| Compound | Structure | EC$_{50}$ | Activity |
|---|---|---|---|
| 1404 | 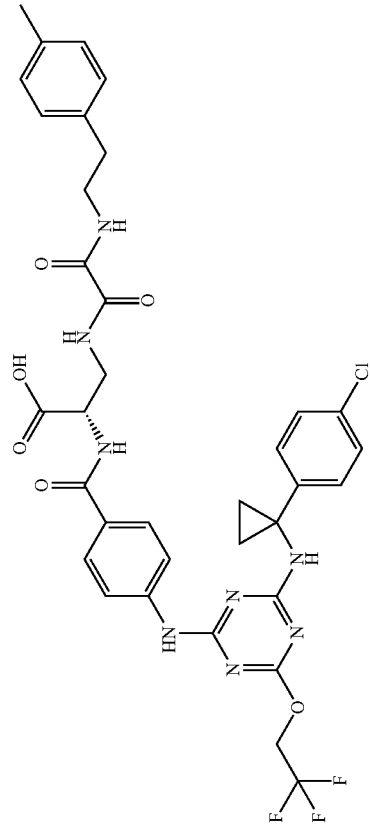 Chiral | | A |
| 1405 | 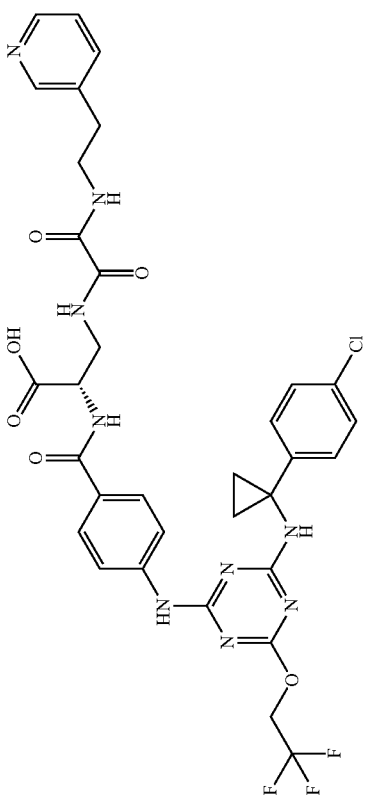 Chiral | | A |

TABLE 1-continued
| Compound | Structure | EC$_{50}$ | Activity |
|---|---|---|---|
| 1406 | 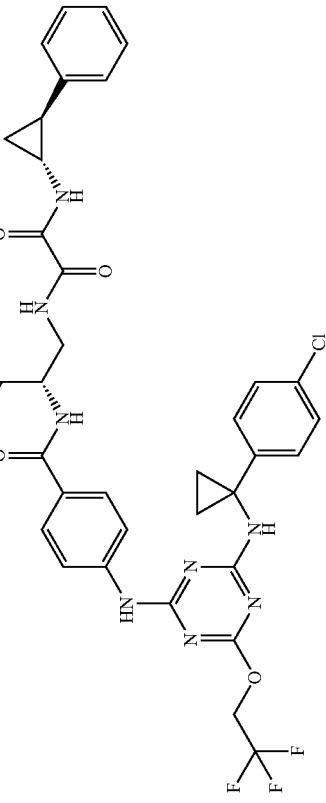 | | A |
| 1407 | 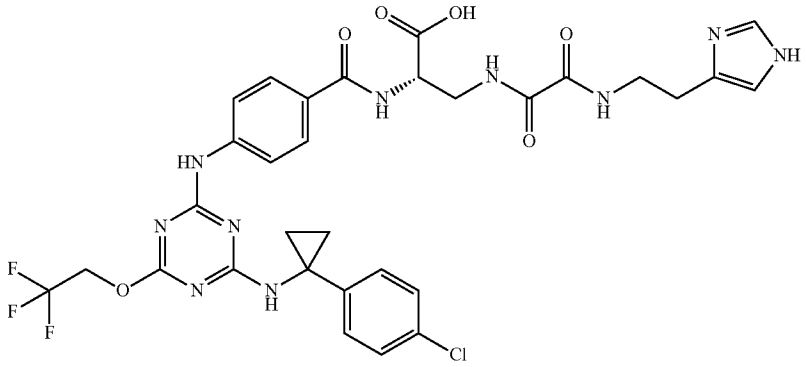 | | A |

TABLE 1-continued
| Compound | Structure | EC$_{50}$ | Activity |
|---|---|---|---|
| 1408 | 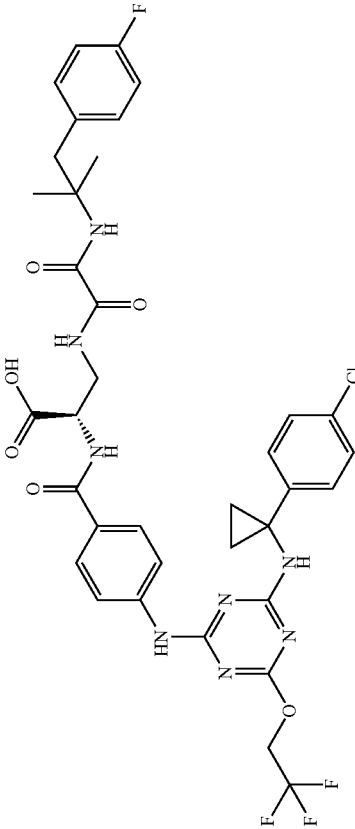 | | A |
| 1409 | 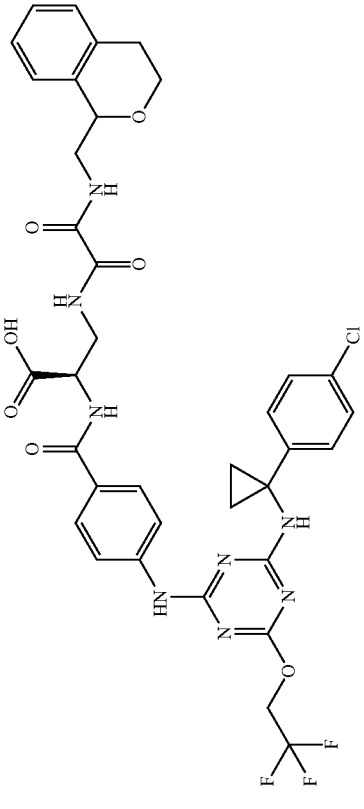 | | |

TABLE 1-continued
| Compound | Structure | EC$_{50}$ | Activity |
|---|---|---|---|
| 1410 | 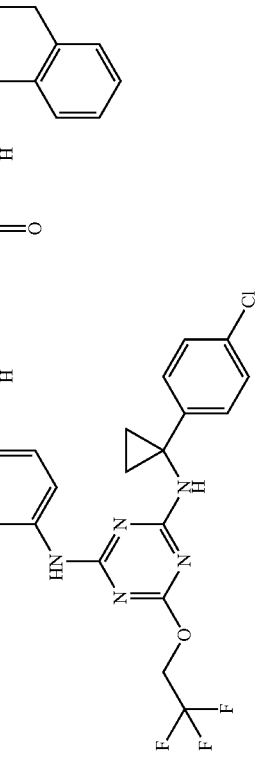 | | A |
| 1411 | 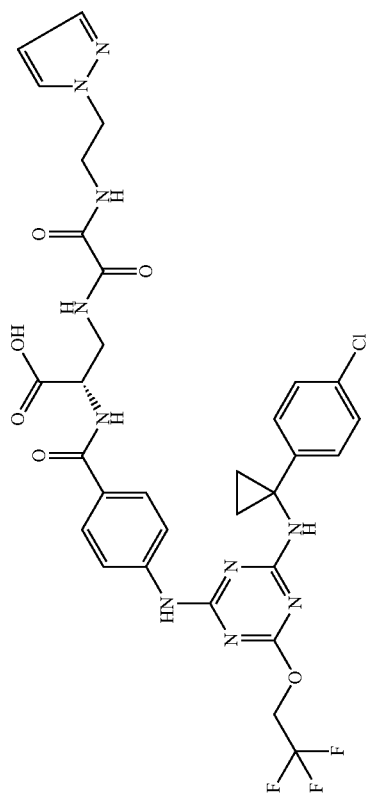 | | A |

TABLE 1-continued
| Compound | Structure | EC$_{50}$ | Activity |
|---|---|---|---|
| 1412 | 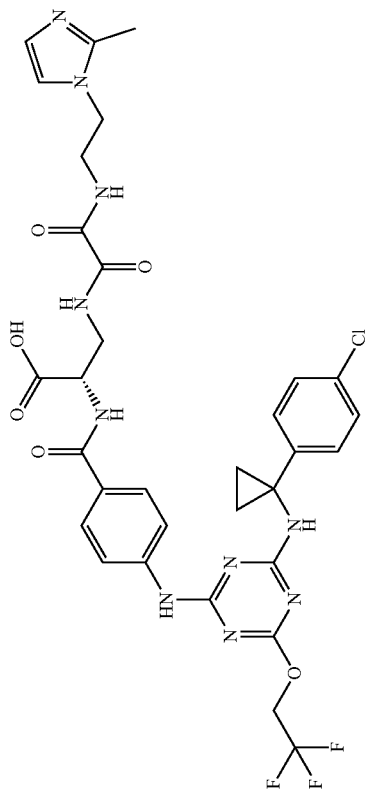 | | B |
| 1413 | 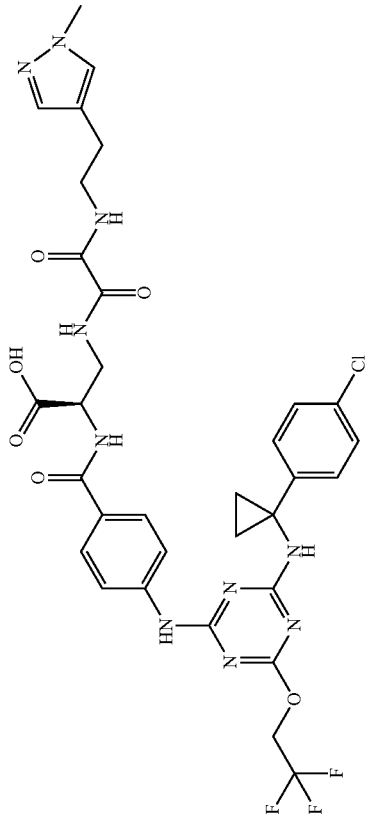 | | A |

TABLE 1-continued

| Compound | Structure | EC$_{50}$ | Activity |
|---|---|---|---|
| 1414 | 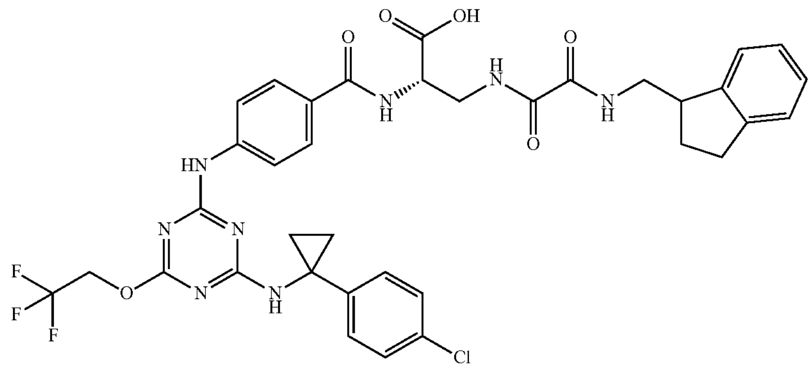 [SMILES: O=C(NCC1CCc2ccccc21)C(=O)NC[C@H](NC(=O)c1ccc(Nc2nc(NC3(c4ccc(Cl)cc4)CC3)nc(OCC(F)(F)F)n2)cc1)C(=O)O] | | A |
| 1415 | 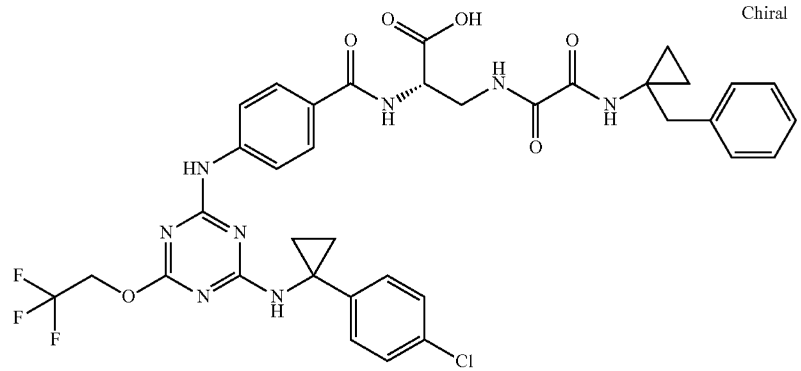 [SMILES: O=C(NC[C@H](NC(=O)c1ccc(Nc2nc(NC3(c4ccc(Cl)cc4)CC3)nc(OCC(F)(F)F)n2)cc1)C(=O)O)C(=O)NC1(Cc2ccccc2)CC1] | | A |

TABLE 1-continued

| Compound | Structure | EC$_{50}$ | Activity |
|---|---|---|---|
| 1416 | 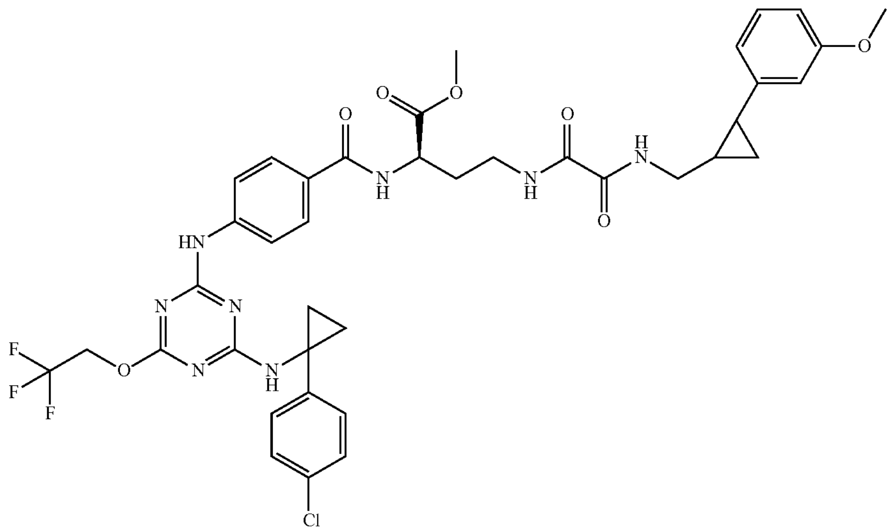 [SMILES: COC(=O)[C@@H](CCNC(=O)C(=O)NCC1CC1c1cccc(OC)c1)NC(=O)c1ccc(Nc2nc(NC3(c4ccc(Cl)cc4)CC3)nc(OCC(F)(F)F)n2)cc1] | | A |
| 1417 | 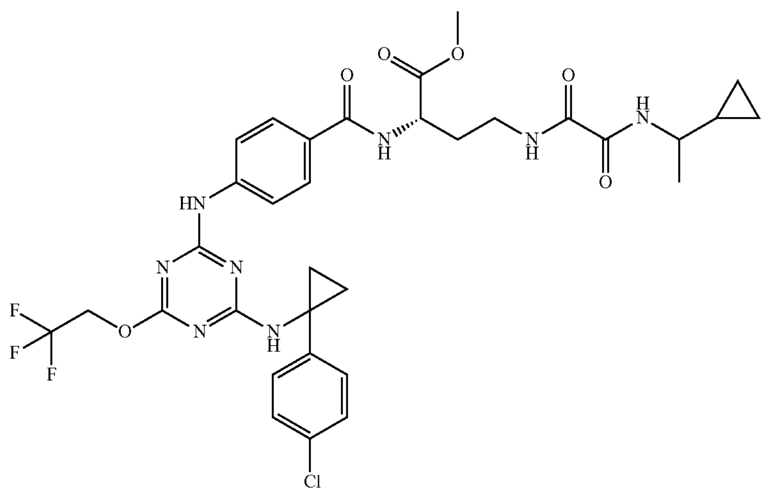 [SMILES: COC(=O)[C@H](CCNC(=O)C(=O)NC(C)C1CC1)NC(=O)c1ccc(Nc2nc(NC3(c4ccc(Cl)cc4)CC3)nc(OCC(F)(F)F)n2)cc1] | 0.16 | A |

TABLE 1-continued
| Compound | Structure | EC$_{50}$ | Activity |
|---|---|---|---|
| 1418 | 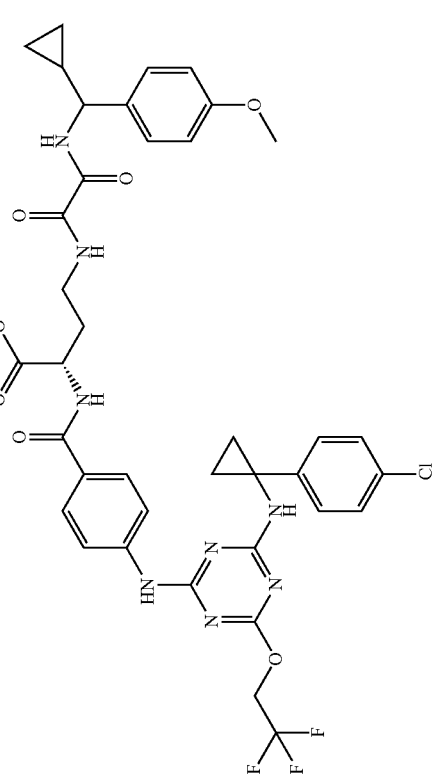 | 0.28 | A |
| 1419 | 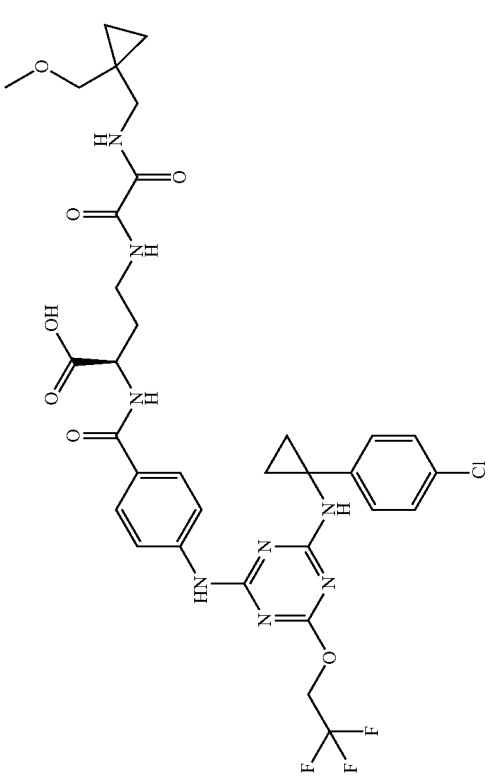 Chiral | | A |

TABLE 1-continued
| Compound | Structure | EC$_{50}$ | Activity |
|---|---|---|---|
| 1420 | 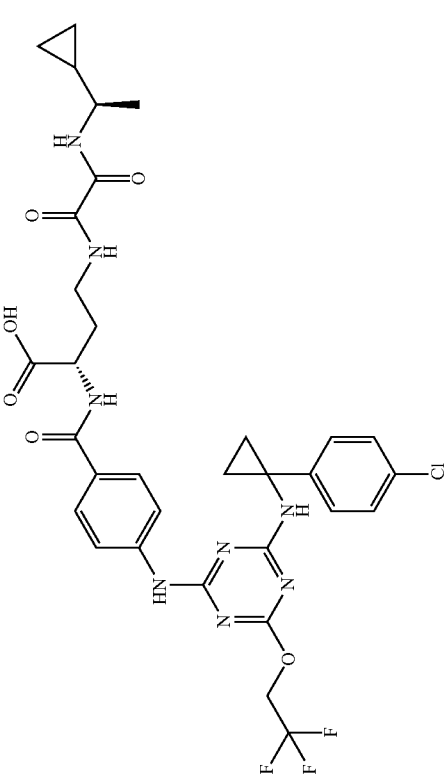 Chiral | | A |

TABLE 1-continued
| Compound | Structure | EC$_{50}$ | Activity |
|---|---|---|---|
| 1421 | 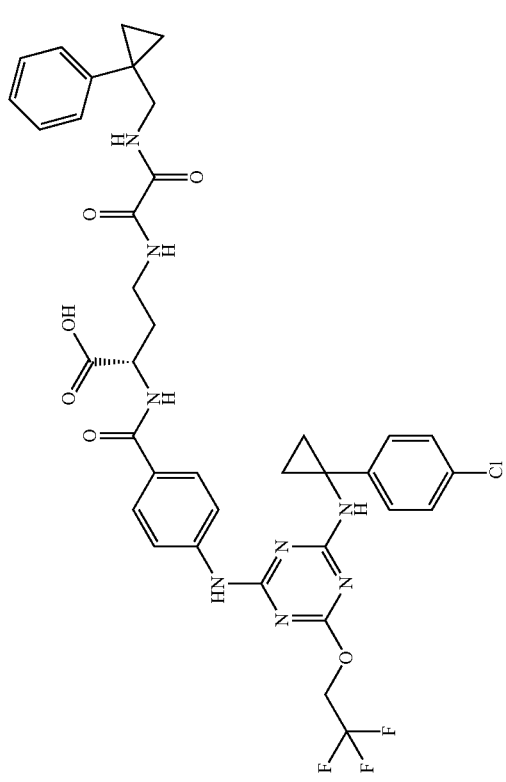 | | A |
| 1422 | 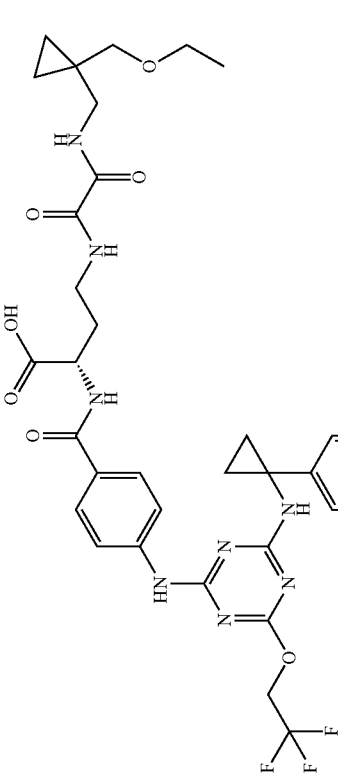 | | A |

TABLE 1-continued
| Compound | Structure | EC$_{50}$ | Activity |
|---|---|---|---|
| 1423 | 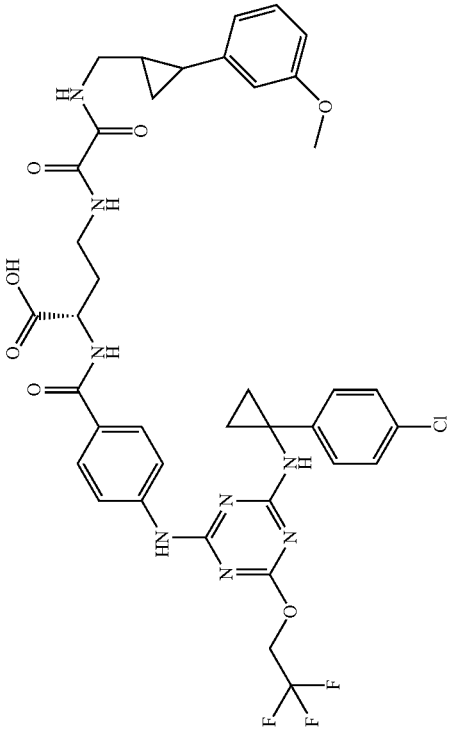 | | A |
| 1424 | 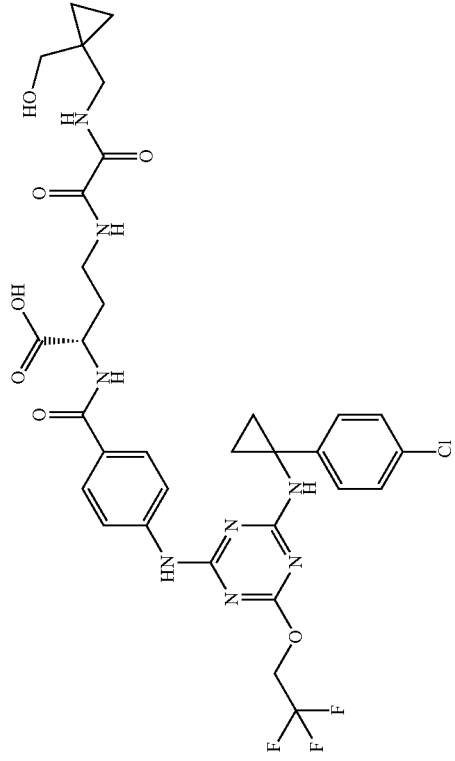 | | A |

TABLE 1-continued
| Compound | Structure | EC$_{50}$ | Activity |
|---|---|---|---|
| 1425 | 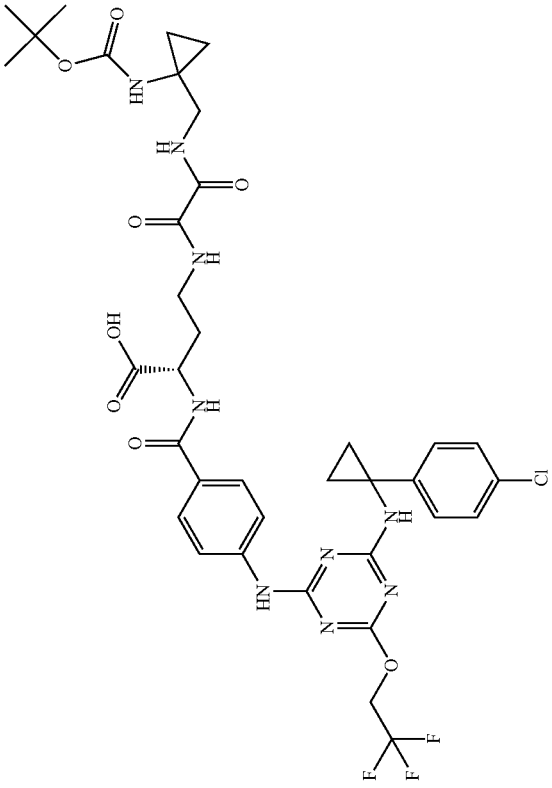 Chiral | | A |

TABLE 1-continued
| Compound | Structure | EC$_{50}$ | Activity |
|---|---|---|---|
| 1426 | 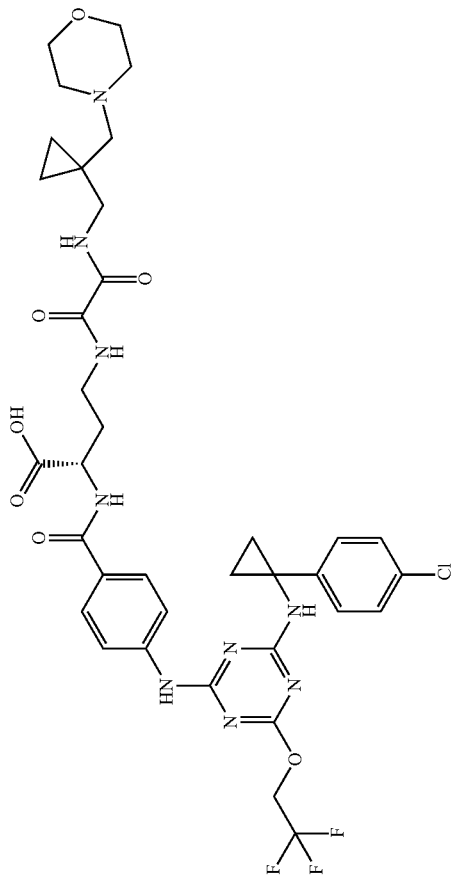 | | A |
| 1427 | 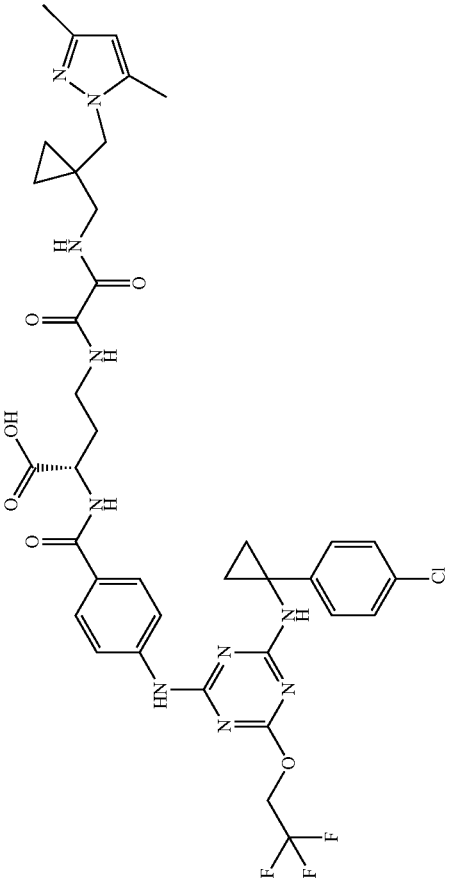 | | A |

TABLE 1-continued
| Compound | Structure | EC$_{50}$ | Activity |
|---|---|---|---|
| 1428 | 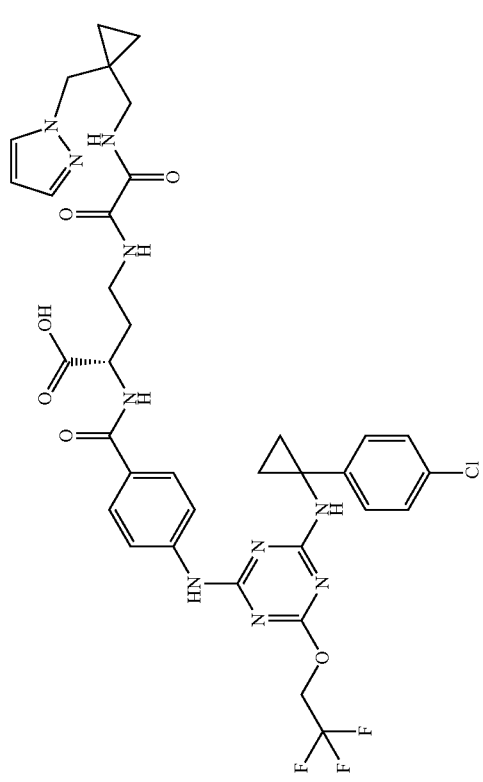 | | A |
| 1429 | 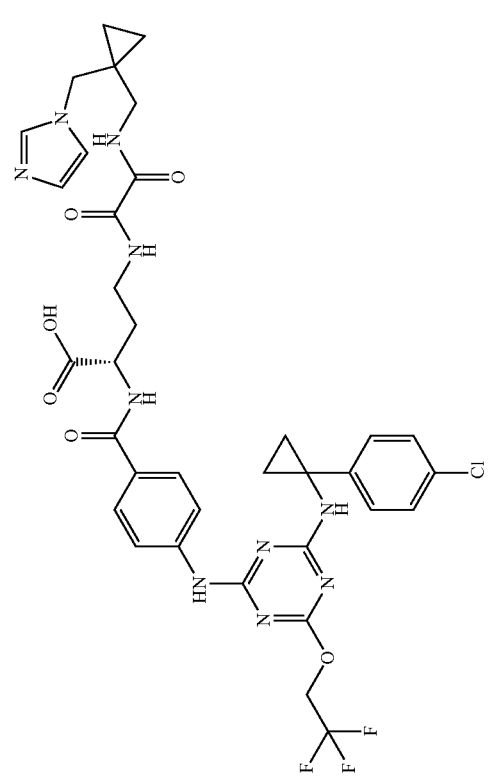 | | A |

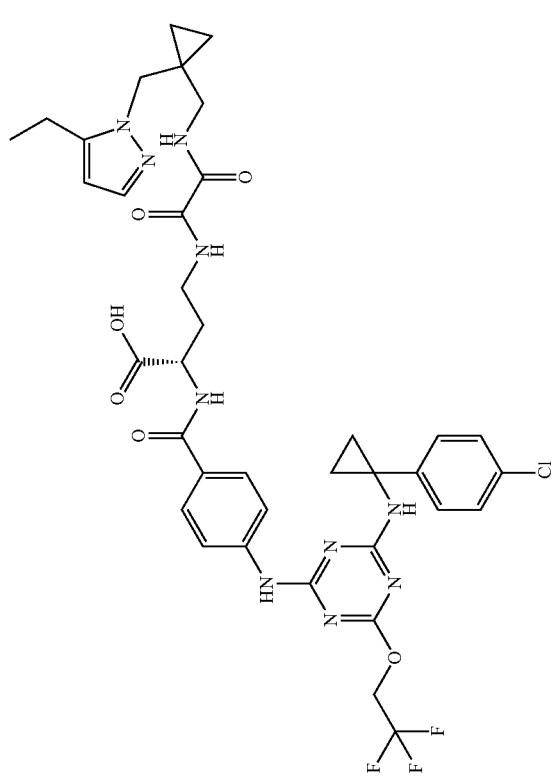

TABLE 1-continued
| Compound | Structure | EC$_{50}$ | Activity |
|---|---|---|---|
| 1432 | 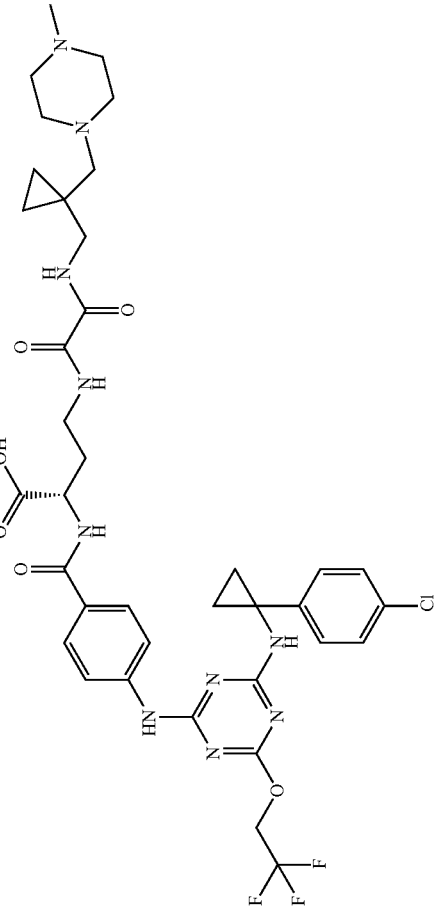 | | A |
| 1433 | 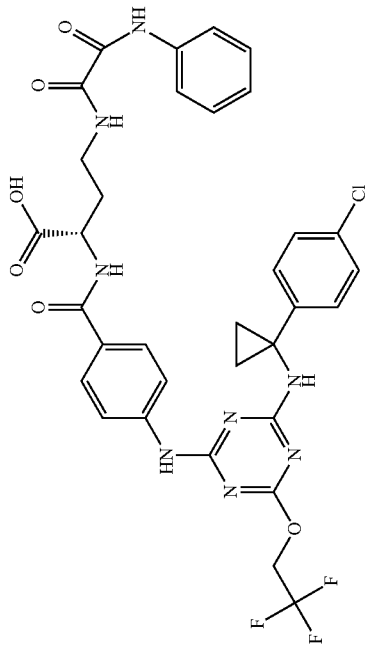 | | A |

TABLE 1-continued
| Compound | Structure | EC$_{50}$ | Activity |
|---|---|---|---|
| 1434 | 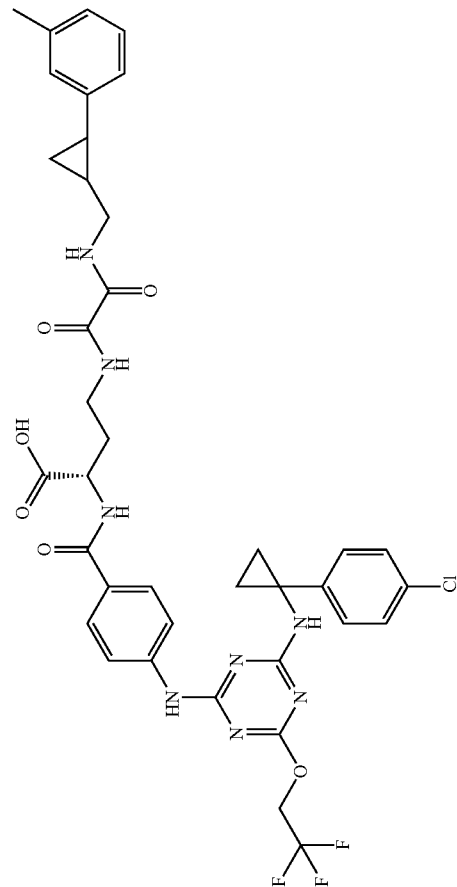 |  | A |
| 1435 | 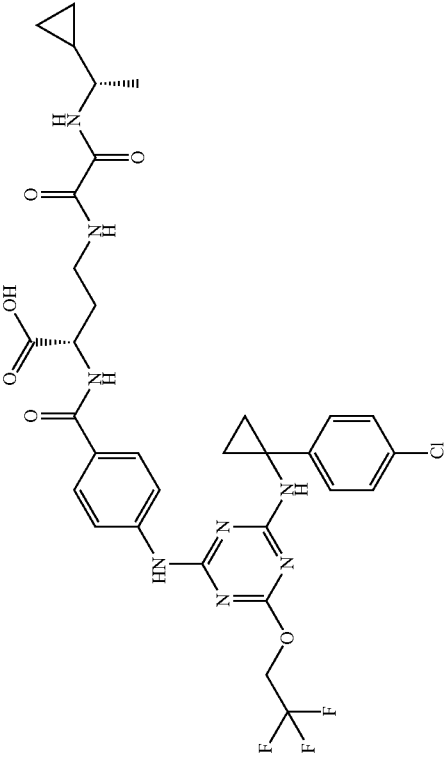 | 0.11 | A |

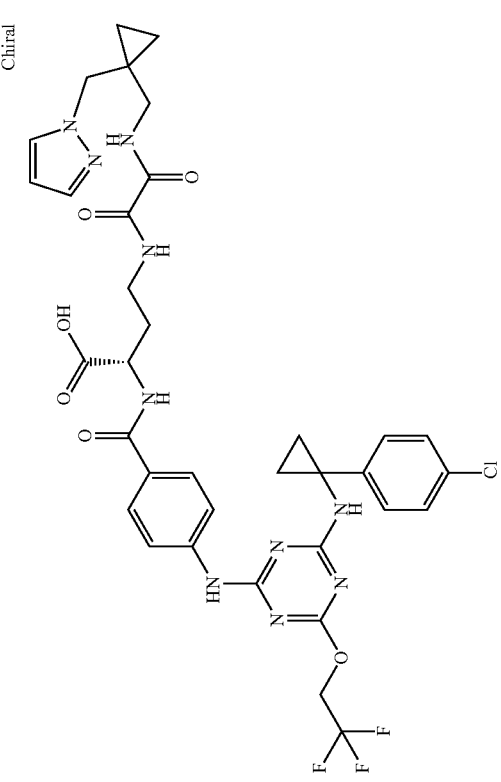

TABLE 1-continued
| Compound | Structure | EC$_{50}$ | Activity |
|---|---|---|---|
| 1438 | 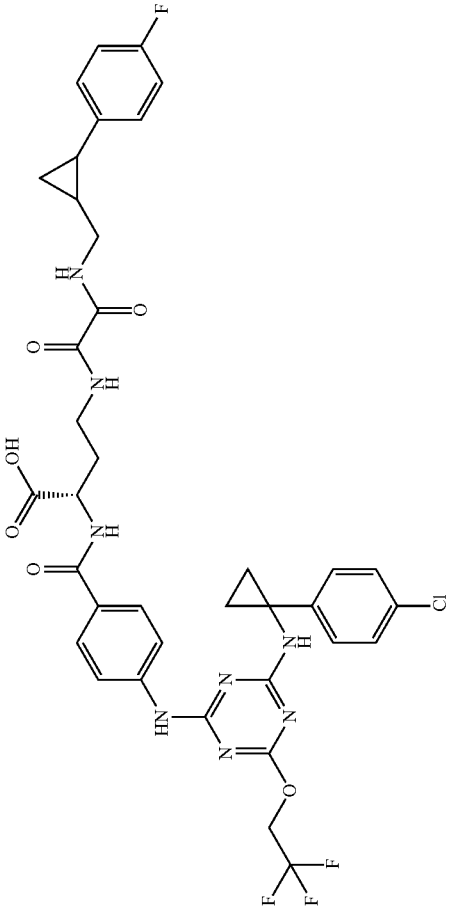 | | A |
| 1439 | 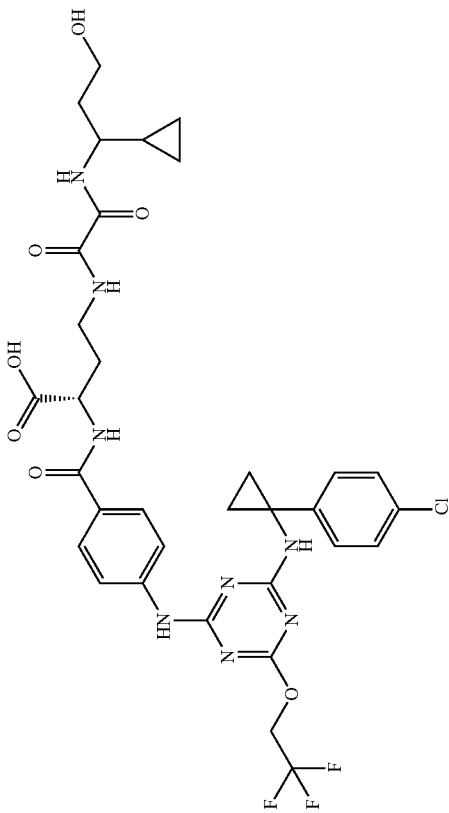 | | A |

TABLE 1-continued

| Compound | Structure | EC$_{50}$ | Activity |
|---|---|---|---|
| 1440 | 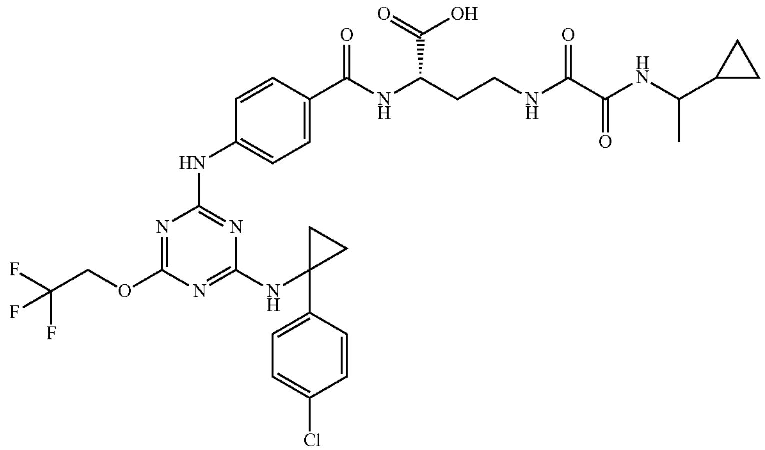 [SMILES: CC(NC(=O)C(=O)NCC[C@H](NC(=O)c1ccc(Nc2nc(NC3(c4ccc(Cl)cc4)CC3)nc(OCC(F)(F)F)n2)cc1)C(=O)O)C1CC1] | | A |
| 1441 | 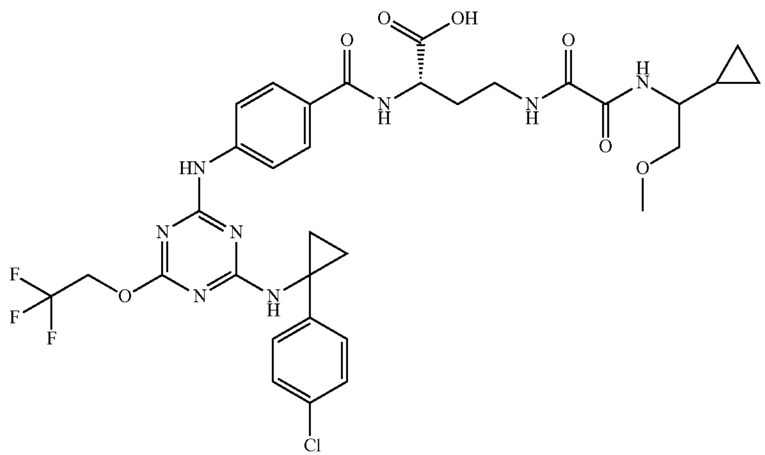 [SMILES: COCC(NC(=O)C(=O)NCC[C@H](NC(=O)c1ccc(Nc2nc(NC3(c4ccc(Cl)cc4)CC3)nc(OCC(F)(F)F)n2)cc1)C(=O)O)C1CC1] | | A |

TABLE 1-continued

| Compound | Structure | EC$_{50}$ | Activity |
|---|---|---|---|
| 1442 | 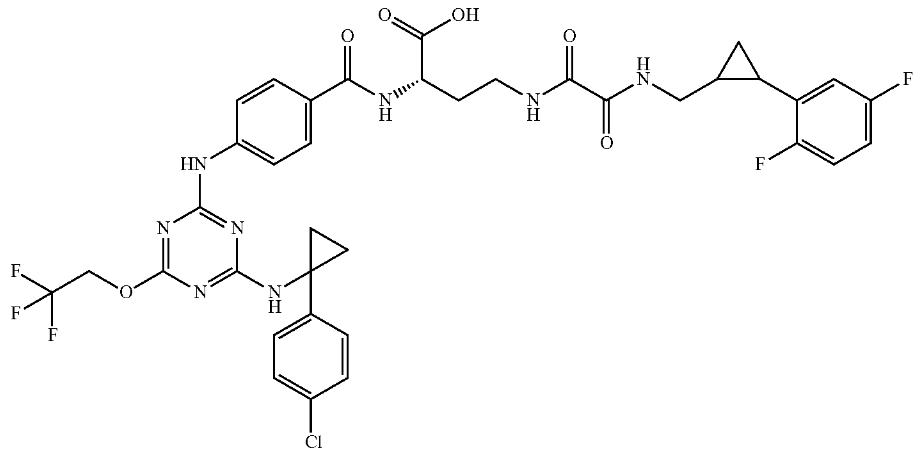 [SMILES: O=C(NCC[C@H](NC(=O)c1ccc(Nc2nc(NC3(c4ccc(Cl)cc4)CC3)nc(OCC(F)(F)F)n2)cc1)C(=O)O)C(=O)NCC1CC1c1cc(F)ccc1F] | | A |
| 1443 | 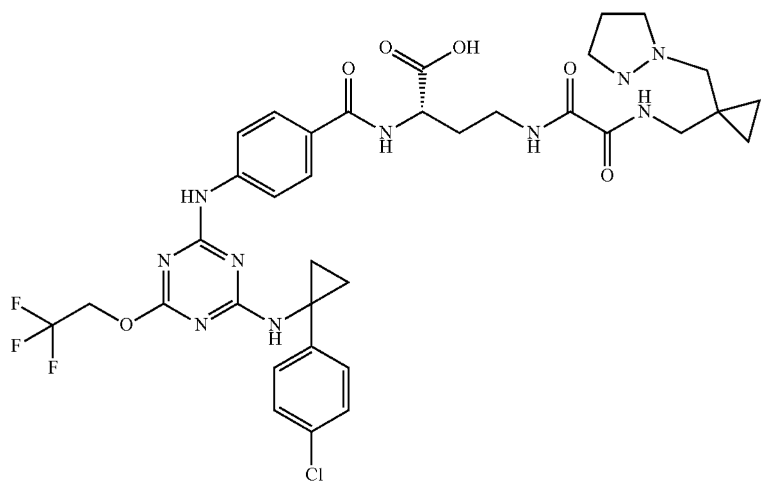 | | A |

TABLE 1-continued

| Compound | Structure | EC$_{50}$ | Activity |
|---|---|---|---|
| 1444 | Chiral | | A |
| 1445 | 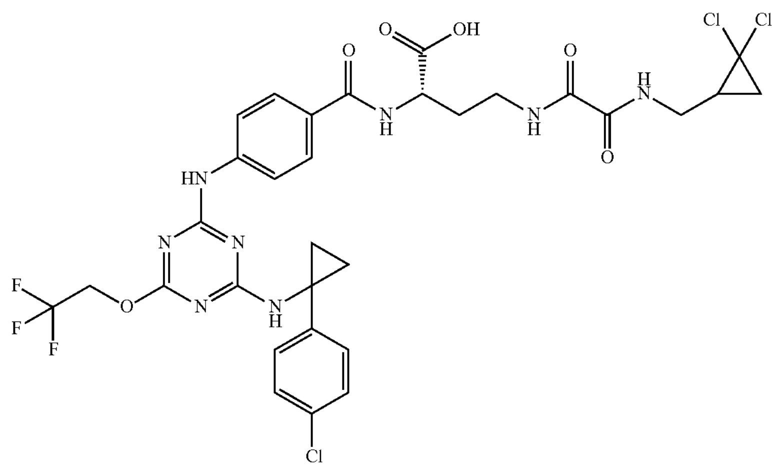 [SMILES: O=C(NCC[C@H](NC(=O)c1ccc(Nc2nc(NC3(c4ccc(Cl)cc4)CC3)nc(OCC(F)(F)F)n2)cc1)C(=O)O)C(=O)NCC1CC1(Cl)Cl] | | A |

TABLE 1-continued

| Compound | Structure | EC$_{50}$ | Activity |
|---|---|---|---|
| 1446 | 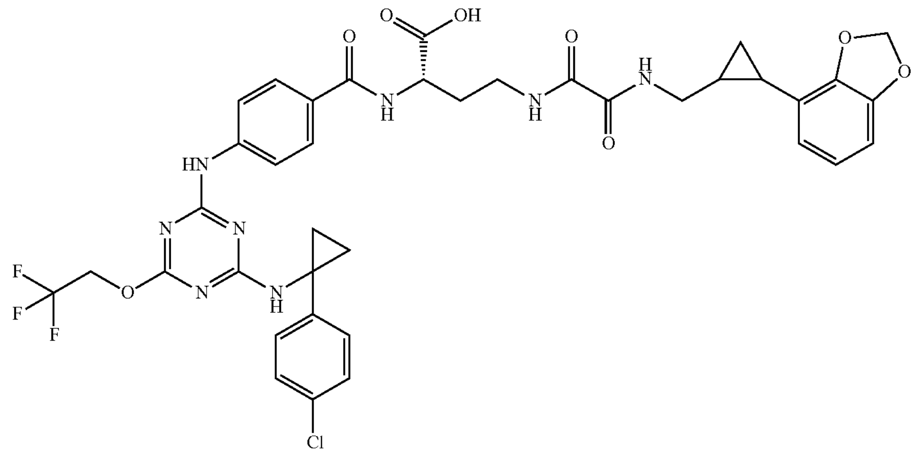 [SMILES: O=C(NCC[C@H](NC(=O)c1ccc(Nc2nc(NC3(c4ccc(Cl)cc4)CC3)nc(OCC(F)(F)F)n2)cc1)C(=O)O)C(=O)NCC1CC1c1cccc2c1OCO2] | | A |
| 1447 | 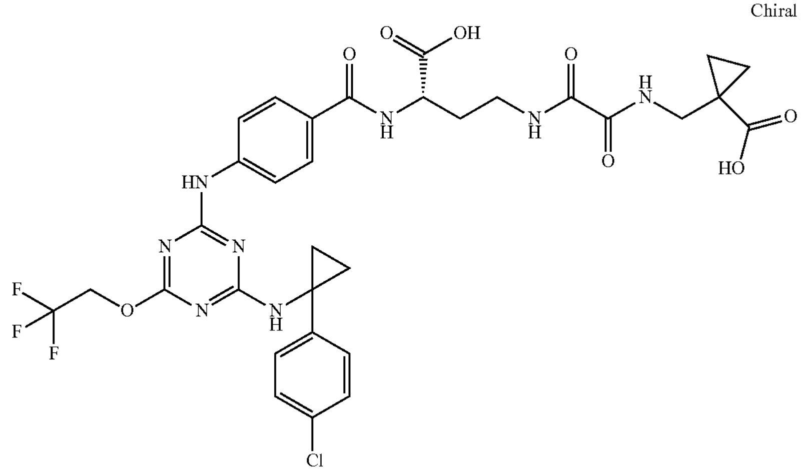 [SMILES: O=C(NCC[C@H](NC(=O)c1ccc(Nc2nc(NC3(c4ccc(Cl)cc4)CC3)nc(OCC(F)(F)F)n2)cc1)C(=O)O)C(=O)NCC1(C(=O)O)CC1] | 97.74 | B |

TABLE 1-continued
| Compound | Structure | EC$_{50}$ | Activity |
|---|---|---|---|
| 1448 | 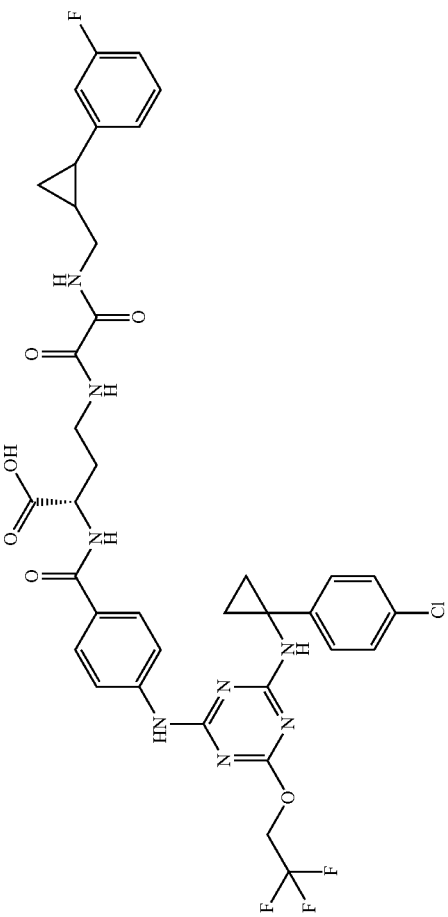 | | A |
| 1449 | 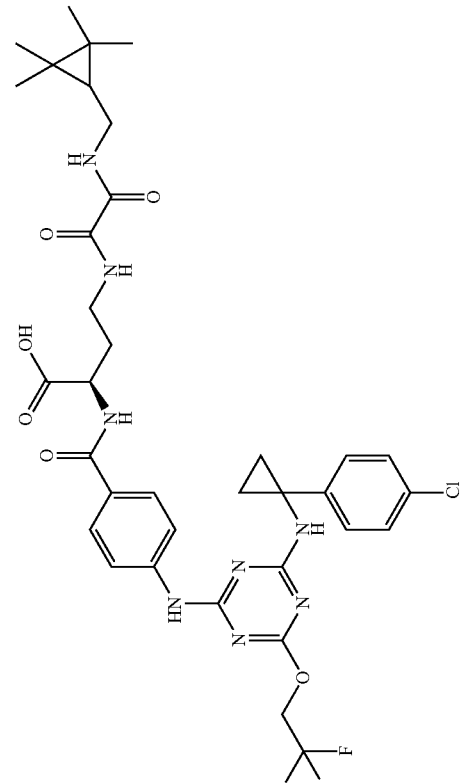 | | A |

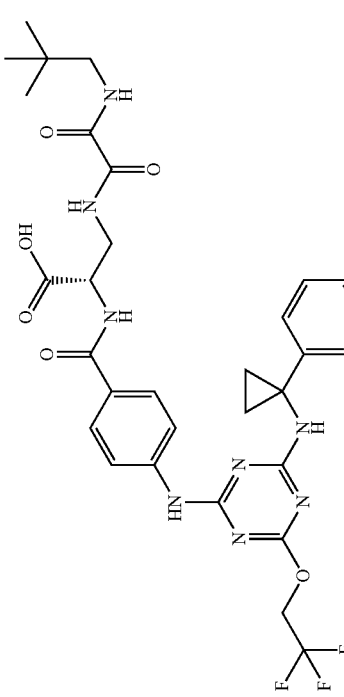

TABLE 1-continued

| Compound | Structure | EC$_{50}$ | Activity |
|---|---|---|---|
| 1452 | 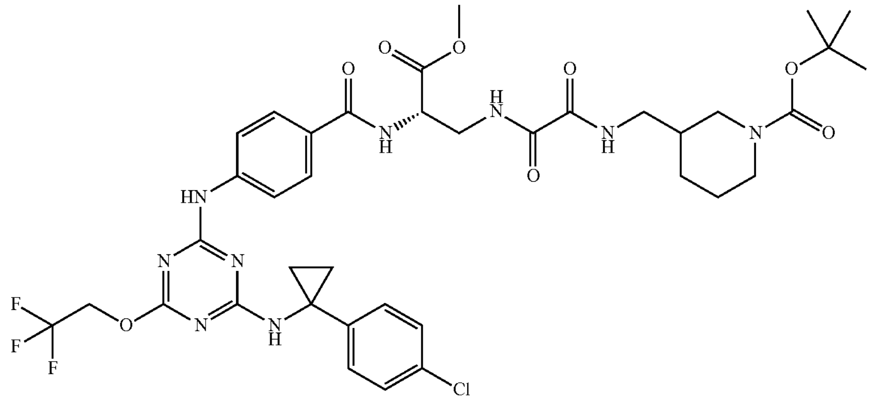 [SMILES: COC(=O)[C@H](CNC(=O)C(=O)NCC1CCCN(C(=O)OC(C)(C)C)C1)NC(=O)c1ccc(Nc2nc(NC3(c4ccc(Cl)cc4)CC3)nc(OCC(F)(F)F)n2)cc1] | 1.83 | A |
| 1453 | 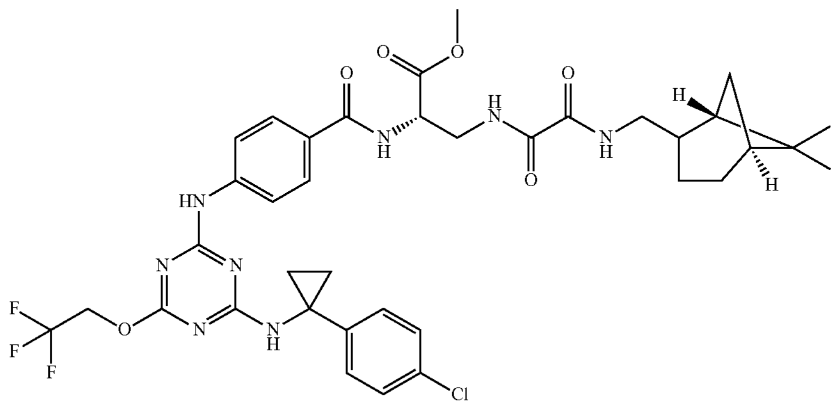 [SMILES: COC(=O)[C@H](CNC(=O)C(=O)NCC1CC[C@H]2C[C@@H]1C2(C)C)NC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 1454 | 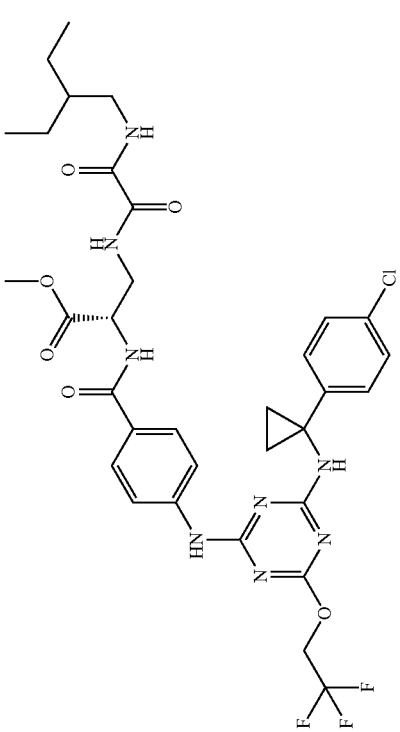 | | A |
| 1455 | 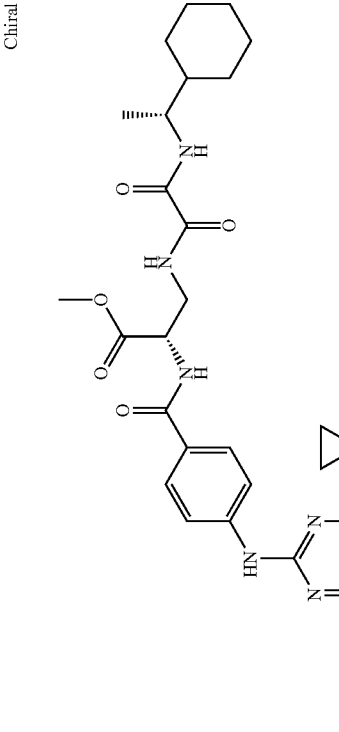 | | A |

TABLE 1-continued
| Compound | Structure | EC$_{50}$ | Activity |
|---|---|---|---|
| 1456 | 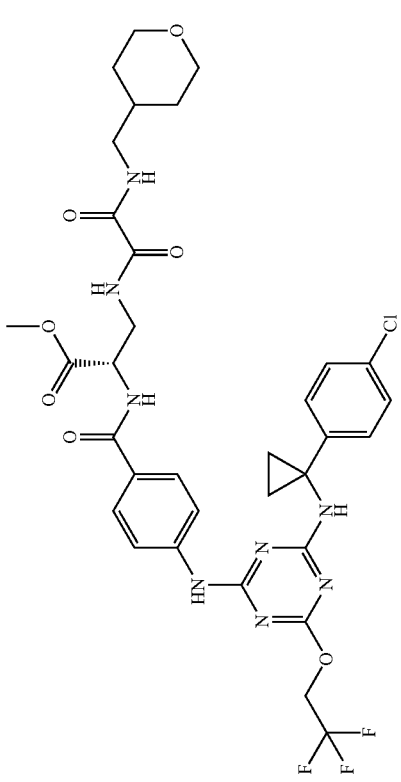 | 3.45 | A |
| 1457 | 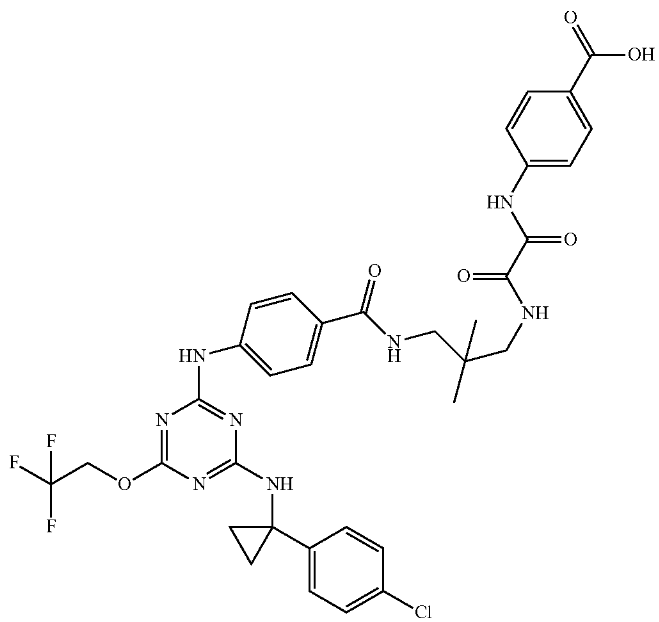 [SMILES: CC(C)(CNC(=O)C(=O)Nc1ccc(C(=O)O)cc1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 1458 | 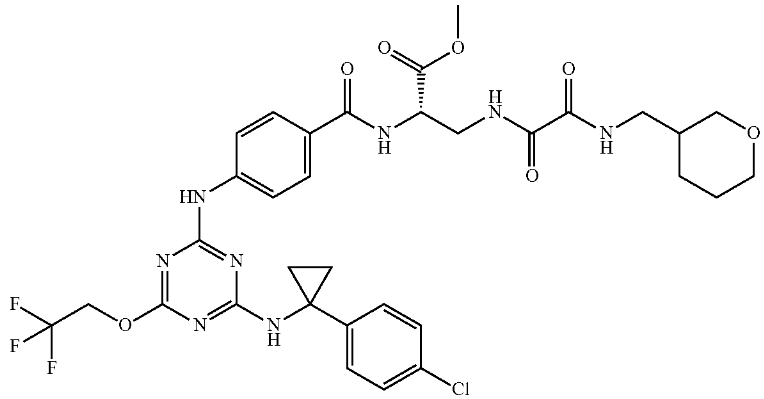 [SMILES: COC(=O)[C@H](CNC(=O)C(=O)NCC1CCCOC1)NC(=O)c1ccc(Nc2nc(NC3(c4ccc(Cl)cc4)CC3)nc(OCC(F)(F)F)n2)cc1] | 3.20 | A |
| 1459 | 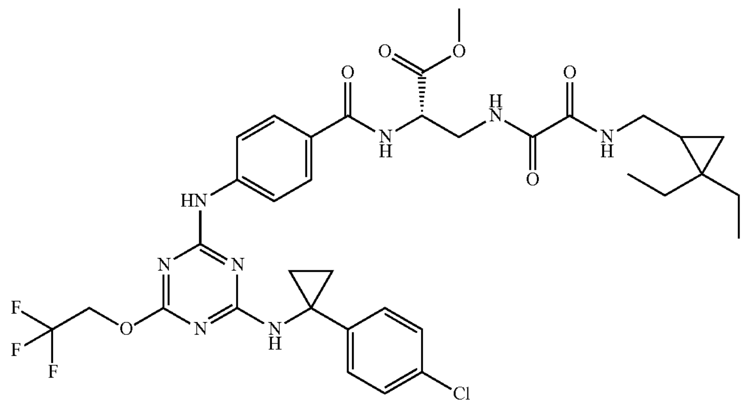 [SMILES: CCC1(CC)CC1CNC(=O)C(=O)NC[C@H](NC(=O)c1ccc(Nc2nc(NC3(c4ccc(Cl)cc4)CC3)nc(OCC(F)(F)F)n2)cc1)C(=O)OC] | | A |

TABLE 1-continued
| Compound | Structure | EC$_{50}$ | Activity |
|---|---|---|---|
| 1460 | 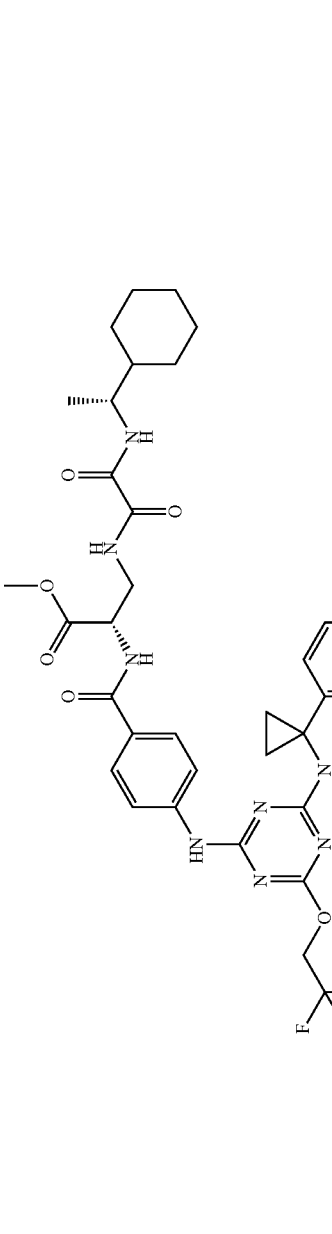 Chiral | | A |
| 1461 | 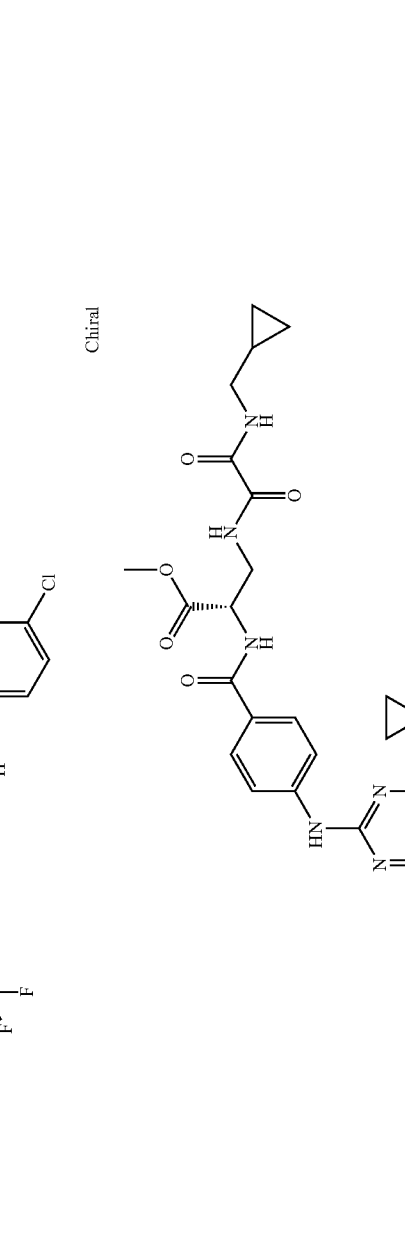 Chiral | | A |

| Compound | Structure | EC$_{50}$ | Activity |
|---|---|---|---|
| 1462 | 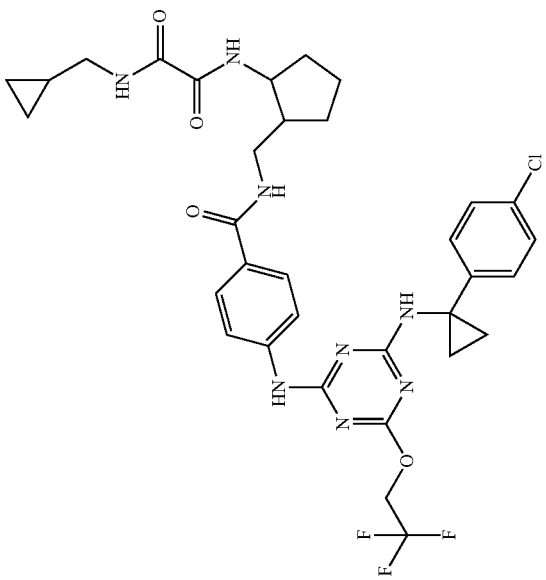 | | A |

TABLE 1-continued
| Compound | Structure | EC$_{50}$ | Activity |
|---|---|---|---|
| 1464 | 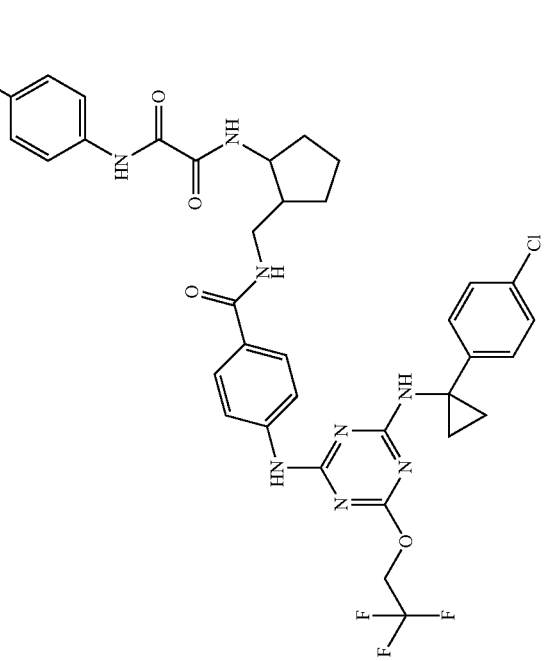 | 0.48 | A |

TABLE 1-continued
| Compound | Structure | EC$_{50}$ | Activity |
|---|---|---|---|
| 1465 | 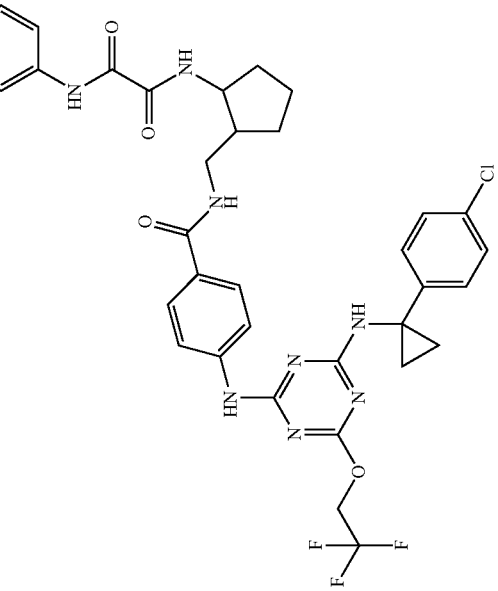 | | A |
| 1466 | 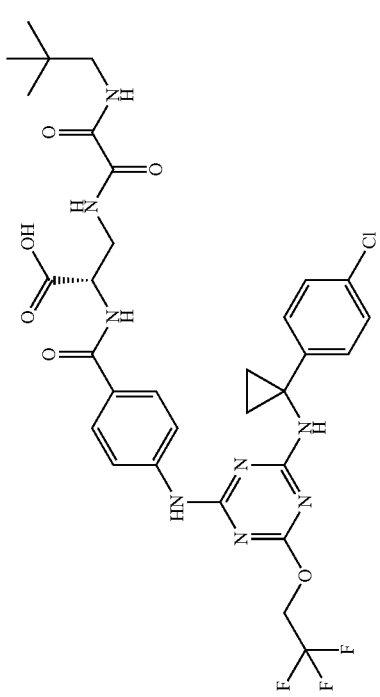 Chiral | | A |

TABLE 1-continued
| Compound | Structure | EC$_{50}$ | Activity |
|---|---|---|---|
| 1467 | 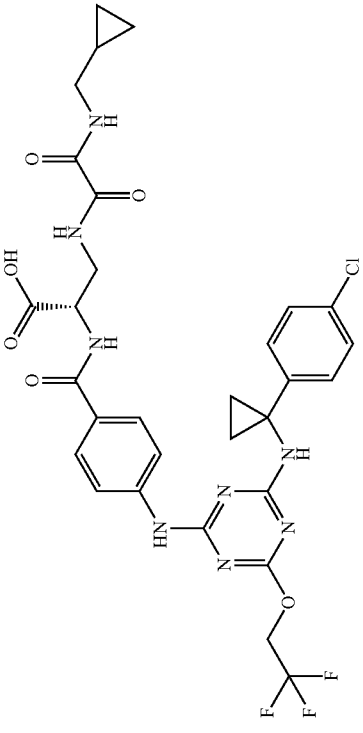 Chiral | | A |
| 1468 | 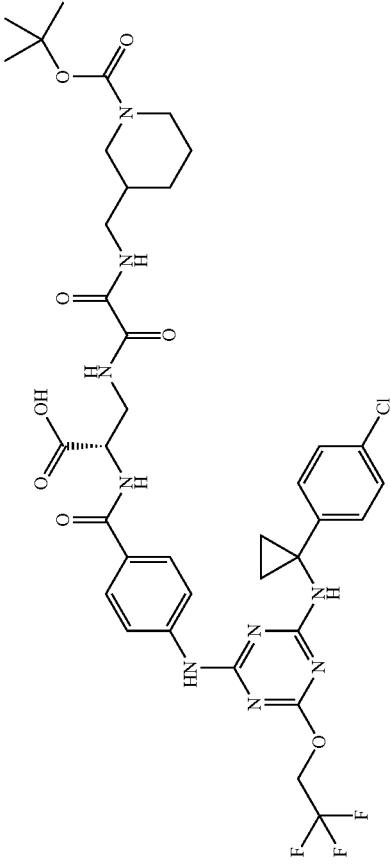 | | A |

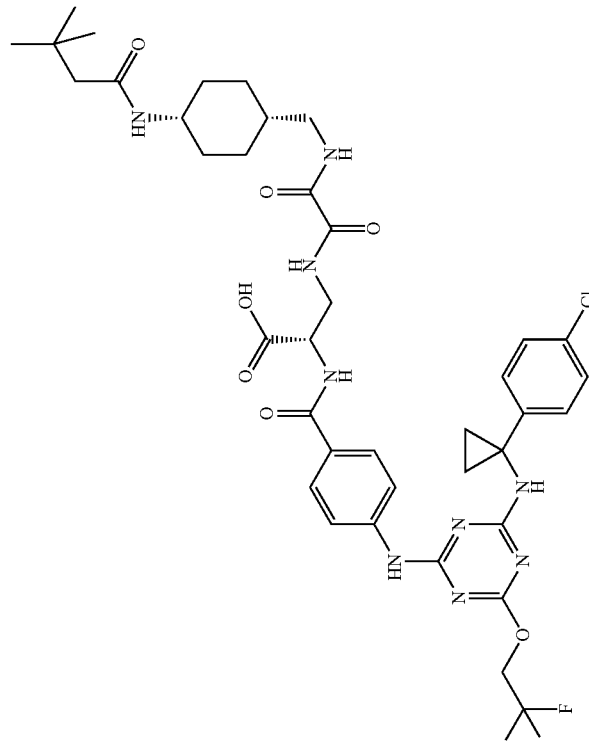

TABLE 1-continued
| Compound | Structure | EC$_{50}$ | Activity |
|---|---|---|---|
| 1471 | 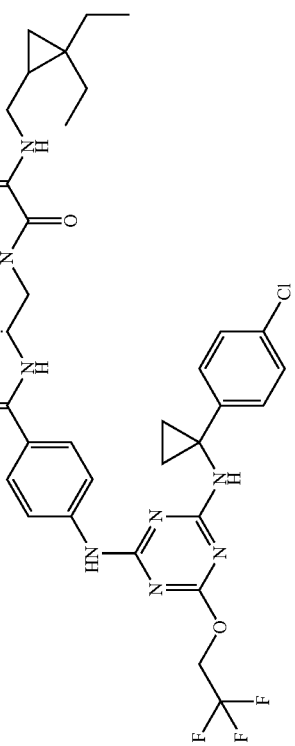 | | A |
| 1472 | 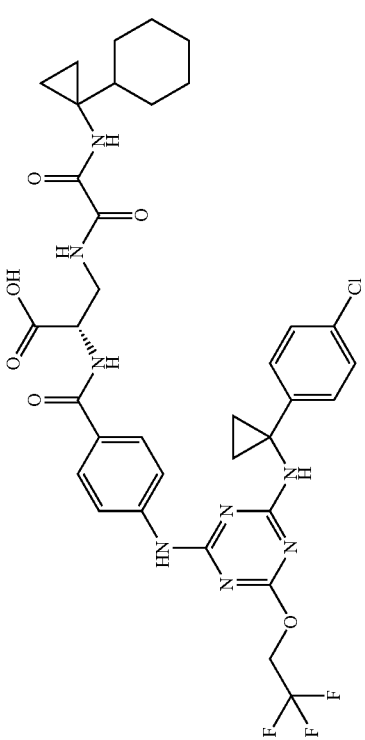 Chiral | | A |

TABLE 1-continued

| Compound | Structure | EC$_{50}$ | Activity |
|---|---|---|---|
| 1473 | 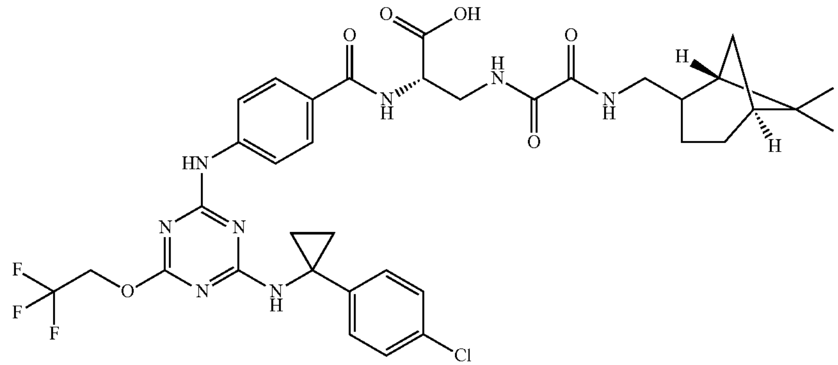 [SMILES: CC1(C)[C@H]2CCC(CNC(=O)C(=O)NC[C@H](NC(=O)c3ccc(Nc4nc(NC5(c6ccc(Cl)cc6)CC5)nc(OCC(F)(F)F)n4)cc3)C(=O)O)[C@@H]1C2] | | A |
| 1474 | 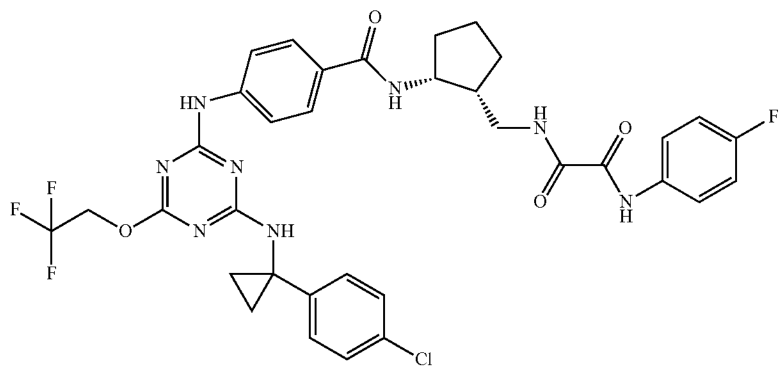 [SMILES: O=C(NC[C@H]1CCC[C@H]1NC(=O)c1ccc(Nc2nc(NC3(c4ccc(Cl)cc4)CC3)nc(OCC(F)(F)F)n2)cc1)C(=O)Nc1ccc(F)cc1] | | A |

TABLE 1-continued

| Compound | Structure | EC$_{50}$ | Activity |
|---|---|---|---|
| 1475 | 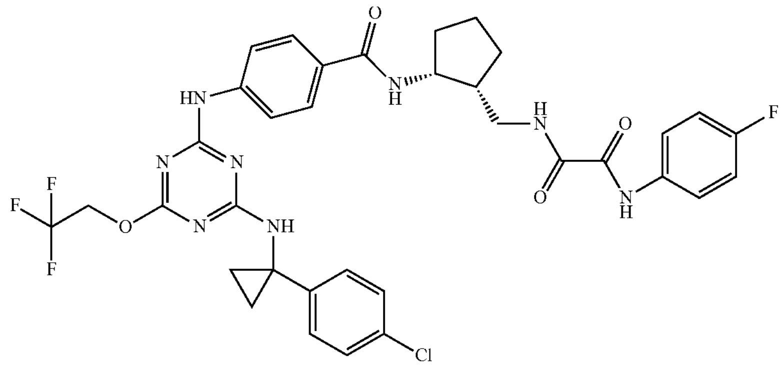 [SMILES: O=C(NC[C@H]1CCC[C@H]1NC(=O)c1ccc(Nc2nc(NC3(c4ccc(Cl)cc4)CC3)nc(OCC(F)(F)F)n2)cc1)C(=O)Nc1ccc(F)cc1] | | A |
| 1476 | (Chiral) | | A |

TABLE 1-continued

| Compound | Structure | EC$_{50}$ | Activity |
|---|---|---|---|
| 1477 | Chiral | | A |
| 1478 | Chiral | | A |

TABLE 1-continued
| Compound | Structure | EC50 | Activity |
|---|---|---|---|
| 1479 | 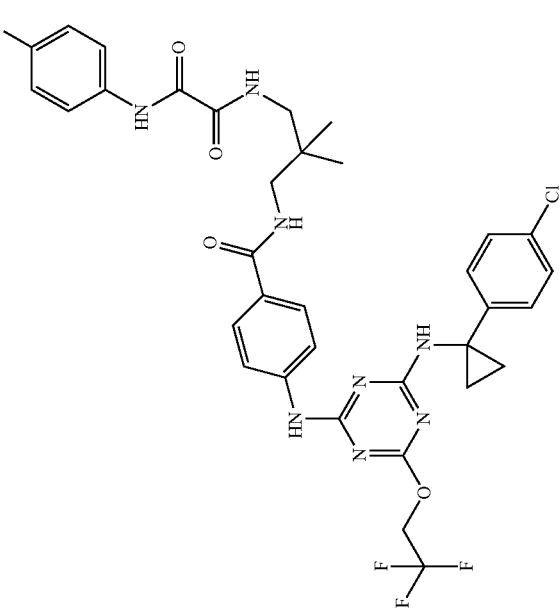 | | A |

TABLE 1-continued
| Compound | Structure | EC$_{50}$ | Activity |
|---|---|---|---|
| 1480 | 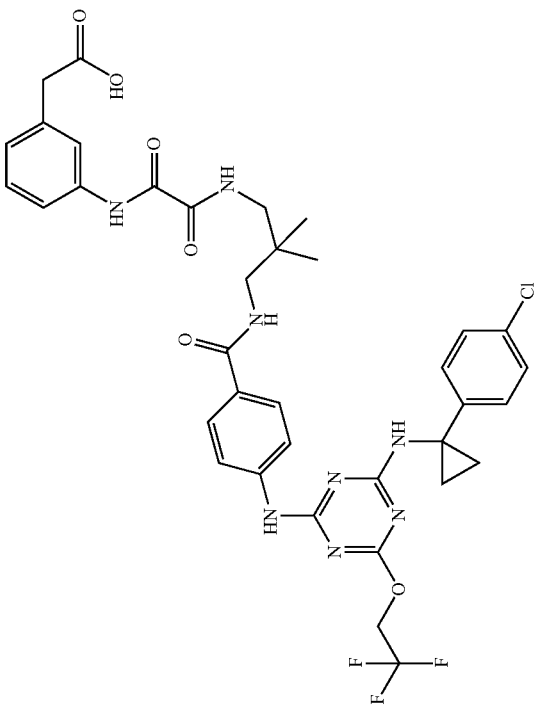 | | A |

TABLE 1-continued
| Compound | Structure | EC$_{50}$ | Activity |
|---|---|---|---|
| 1481 | 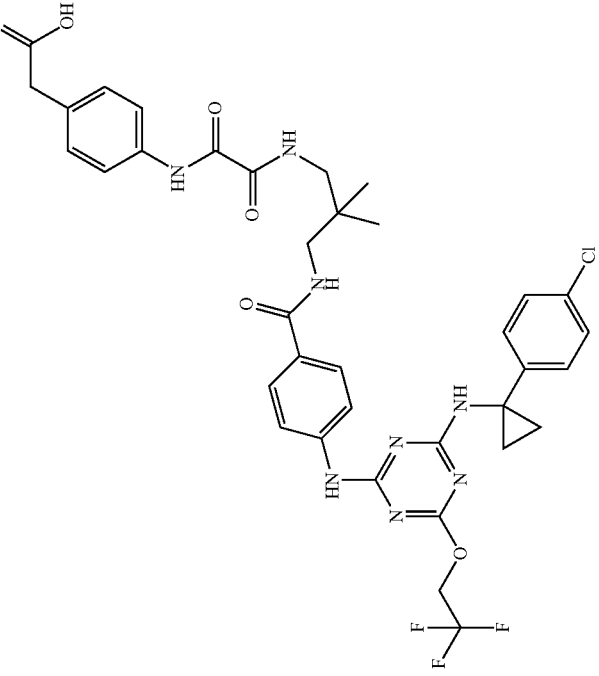 | | A |

| Compound | Structure | EC$_{50}$ | Activity |
|---|---|---|---|
| 1482 | 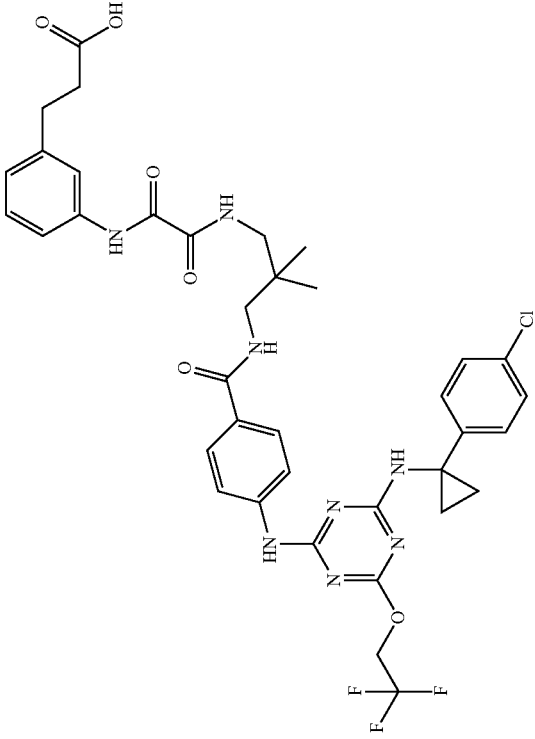 | 0.17 | A |
TABLE 1-continued TABLE 1-continued
| Compound | Structure | EC$_{50}$ | Activity |
|---|---|---|---|
| 1483 | 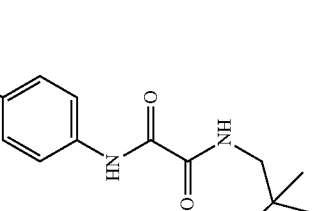 | | A |

TABLE 1-continued
| Compound | Structure | EC$_{50}$ | Activity |
|---|---|---|---|
| 1484 | 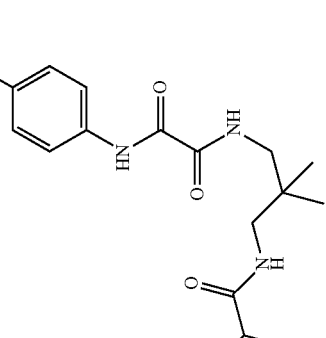 | | A |

TABLE 1-continued
| Compound | Structure | EC$_{50}$ | Activity |
|---|---|---|---|
| 1485 | 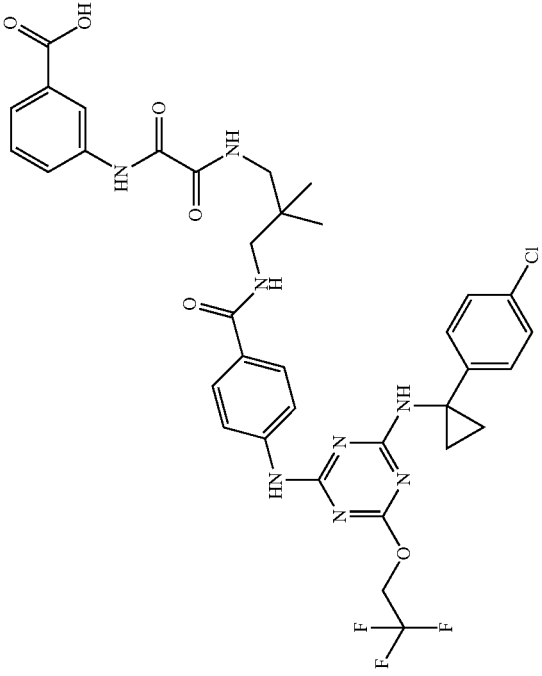 | | A |

TABLE 1-continued
| Compound | Structure | EC$_{50}$ | Activity |
|---|---|---|---|
| 1487 | 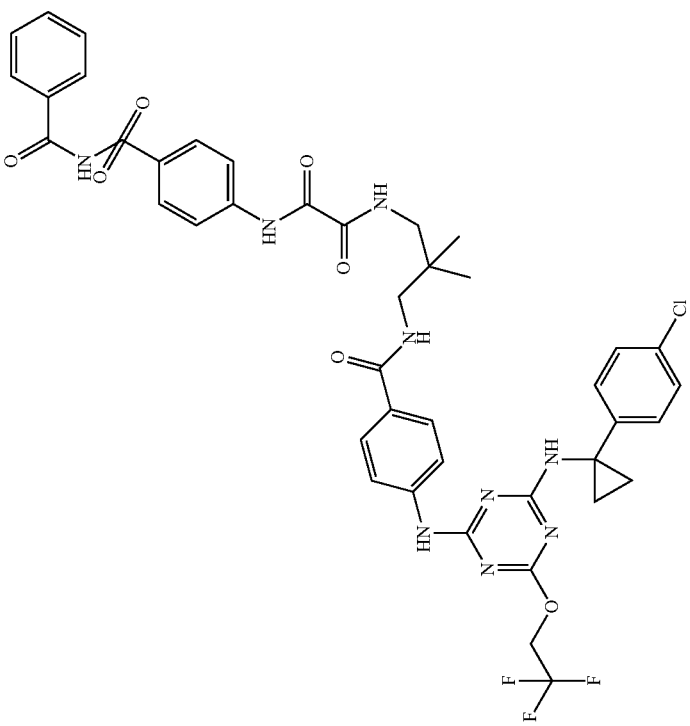 | 0.22 | A |

TABLE 1-continued
| Compound | Structure | EC$_{50}$ | Activity |
|---|---|---|---|
| 1488 | 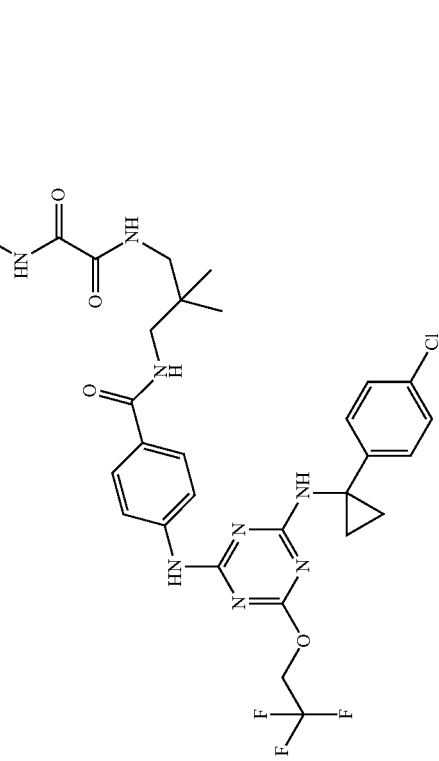 | | A |

TABLE 1-continued
| Compound | Structure | EC$_{50}$ | Activity |
|---|---|---|---|
| 1489 | 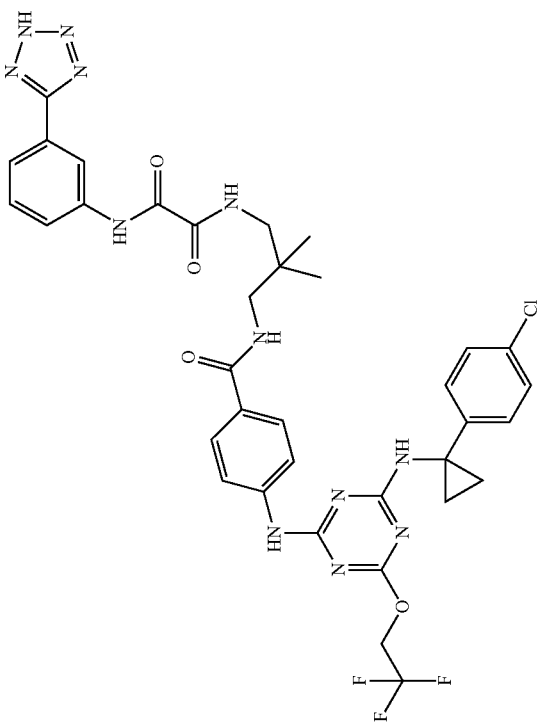 | | A |

TABLE 1-continued
| Compound | Structure | EC$_{50}$ | Activity |
|---|---|---|---|
| 1490 | 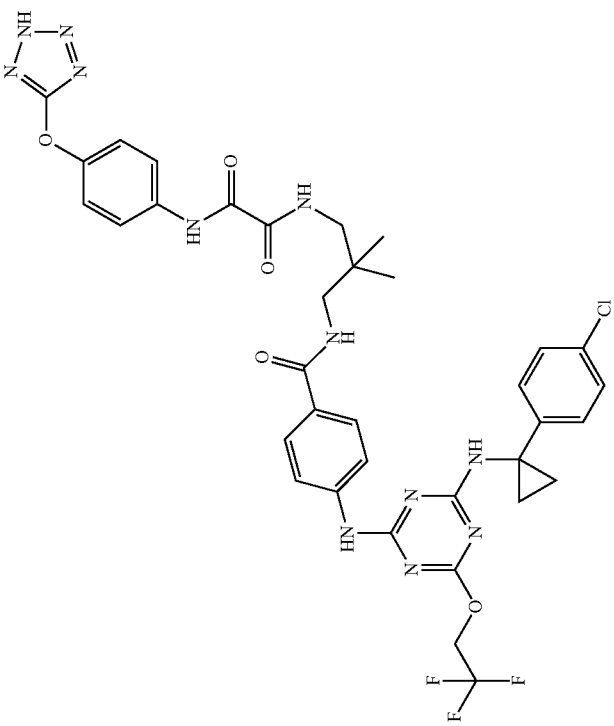 | | A |

TABLE 1-continued
| Compound | Structure | EC$_{50}$ | Activity |
|---|---|---|---|
| 1491 | 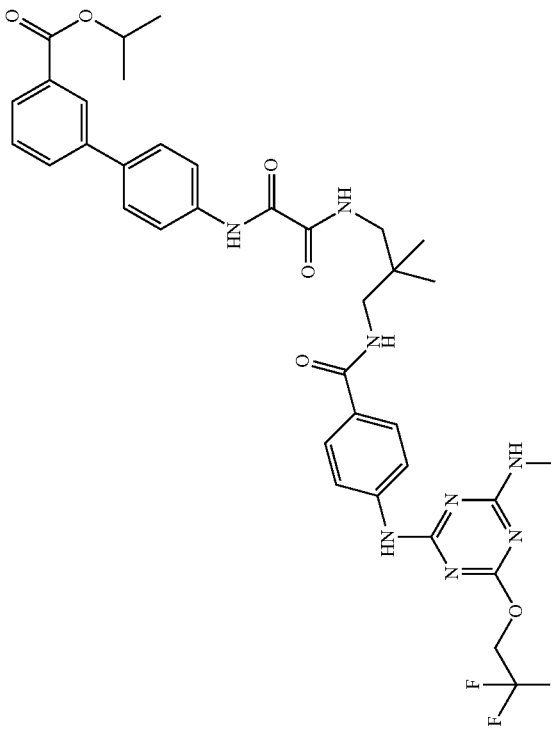 | | A |
| 1492 | 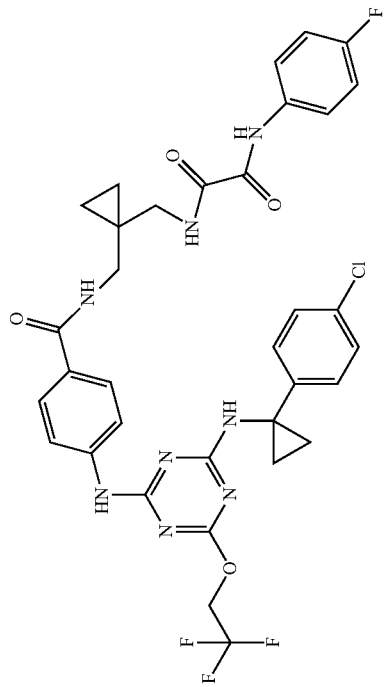 | | A |

TABLE 1-continued

| Compound | Structure | EC$_{50}$ | Activity |
|---|---|---|---|
| 1493 | 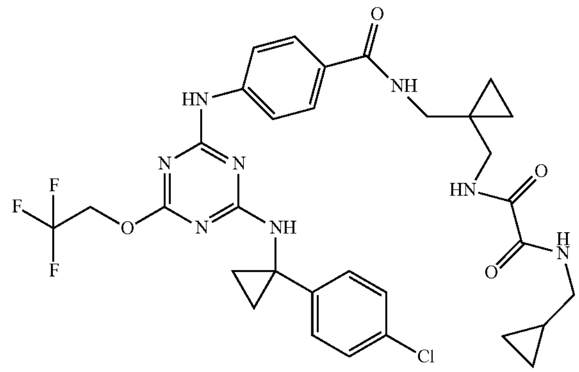 [SMILES: O=C(NCC1CC1)C(=O)NCC1(CNC(=O)c2ccc(Nc3nc(NC4(c5ccc(Cl)cc5)CC4)nc(OCC(F)(F)F)n3)cc2)CC1] | | A |
| 1494 | 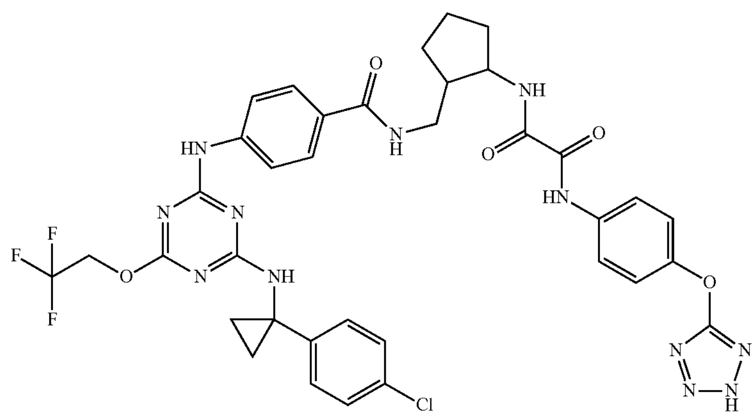 [SMILES: O=C(Nc1ccc(Oc2nn[nH]n2)cc1)C(=O)NC1CCCC1CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 1495 | 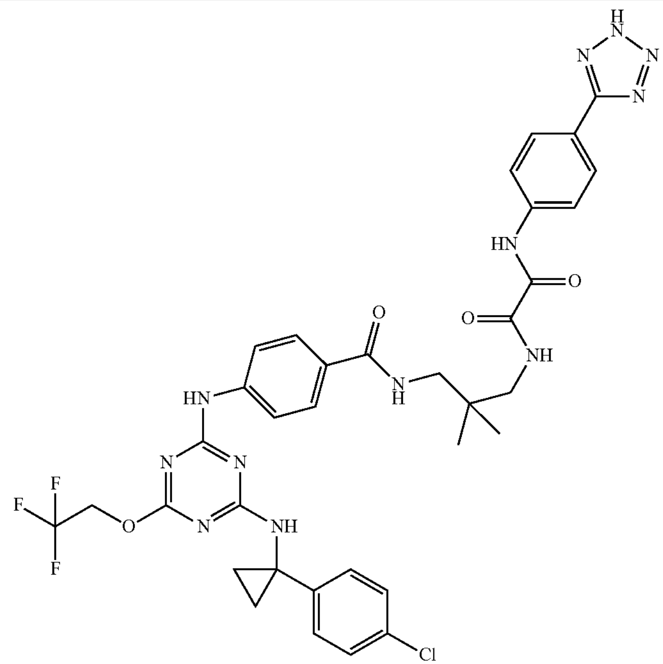 [SMILES: CC(C)(CNC(=O)C(=O)Nc1ccc(-c2nn[nH]n2)cc1)CNC(=O)c1ccc(Nc2nc(NC3(c4ccc(Cl)cc4)CC3)nc(OCC(F)(F)F)n2)cc1] | | A |
| 1496 | 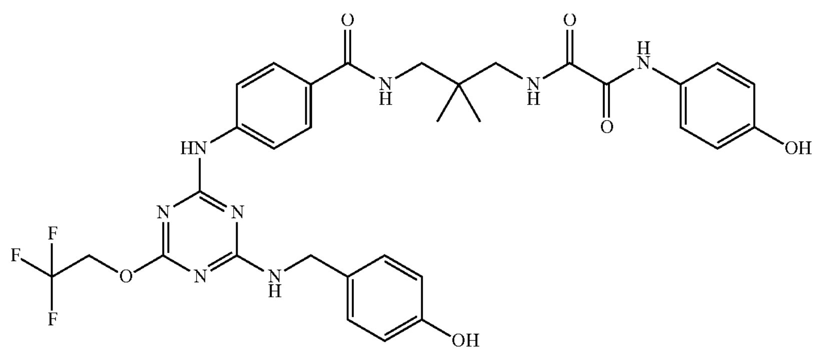 [SMILES: CC(C)(CNC(=O)C(=O)Nc1ccc(O)cc1)CNC(=O)c1ccc(Nc2nc(NCc3ccc(O)cc3)nc(OCC(F)(F)F)n2)cc1] | | A |

TABLE 1-continued
| Compound | Structure | EC$_{50}$ | Activity |
|---|---|---|---|
| 1497 | 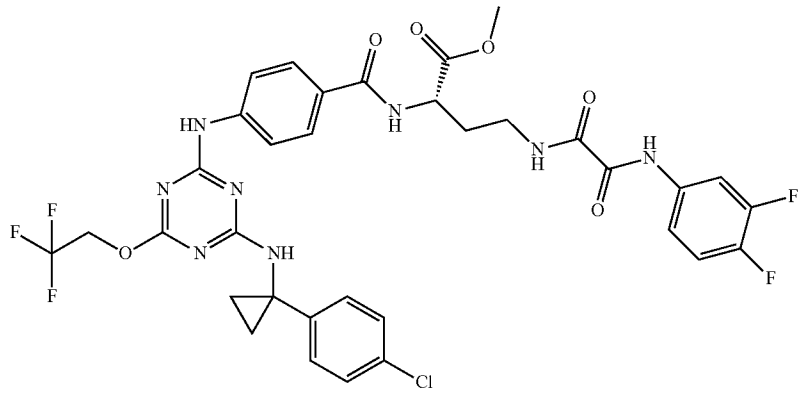 Chiral | | A |
| 1498 | 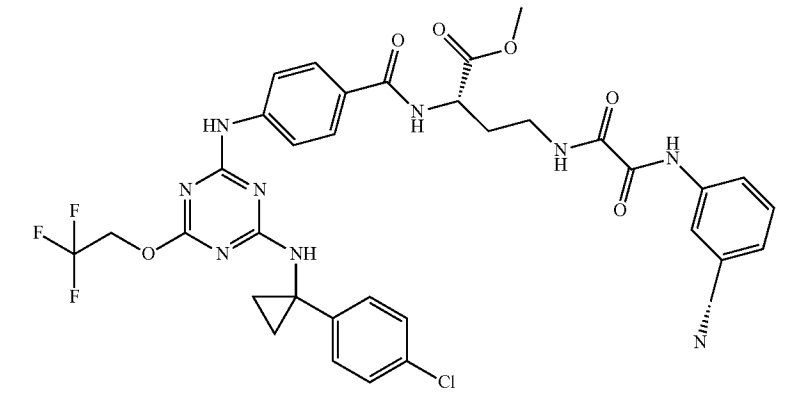 Chiral | 0.24 | A |

TABLE 1-continued
| Compound | Structure | EC$_{50}$ | Activity |
|---|---|---|---|
| 1499 | Chiral 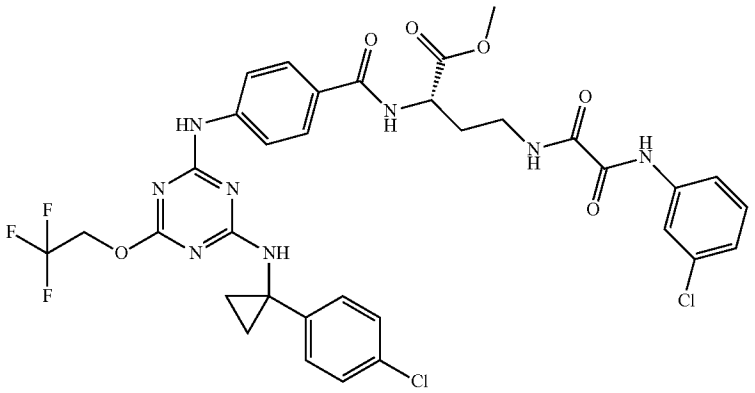 | | A |
| 1500 | Chiral 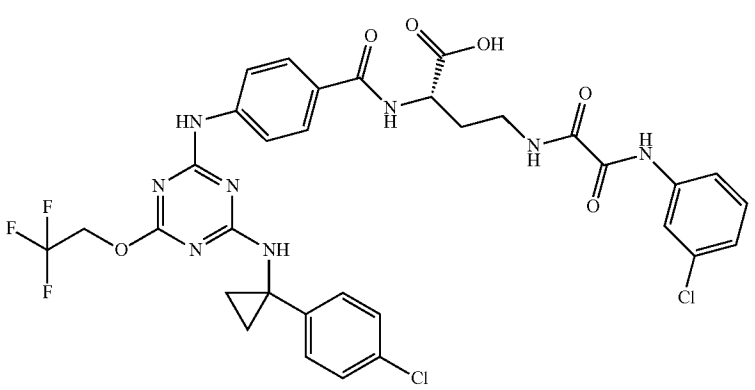 | | A |

TABLE 1-continued
| Compound | Structure | EC$_{50}$ | Activity |
|---|---|---|---|
| 1501 | 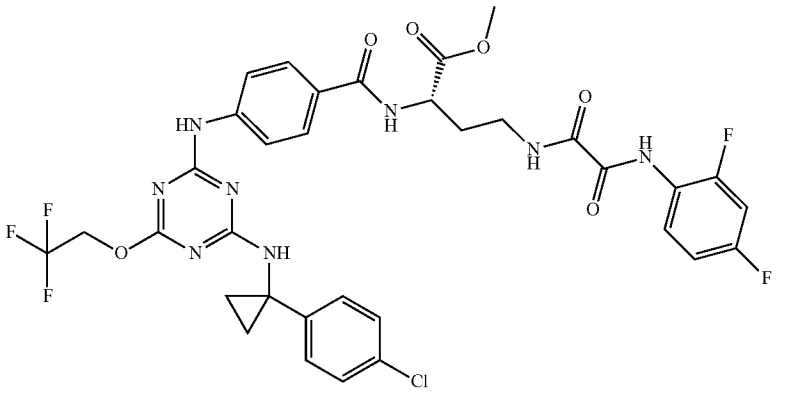 Chiral | | A |
| 1502 | 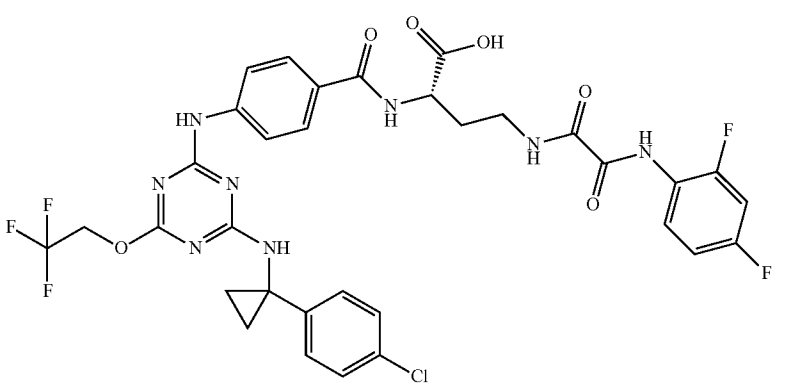 Chiral | | A |

TABLE 1-continued
| Compound | Structure | EC$_{50}$ | Activity |
|---|---|---|---|
| 1503 | 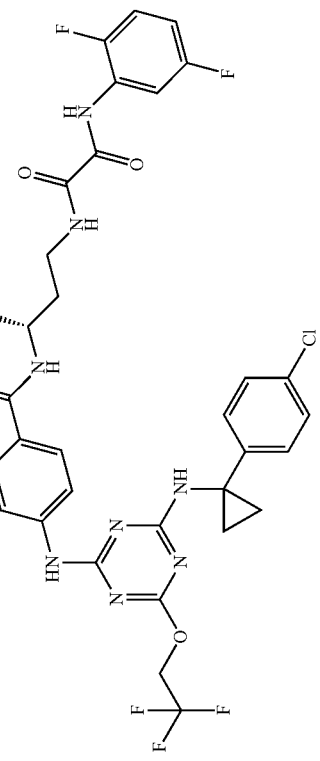 | | A |
| 1504 | 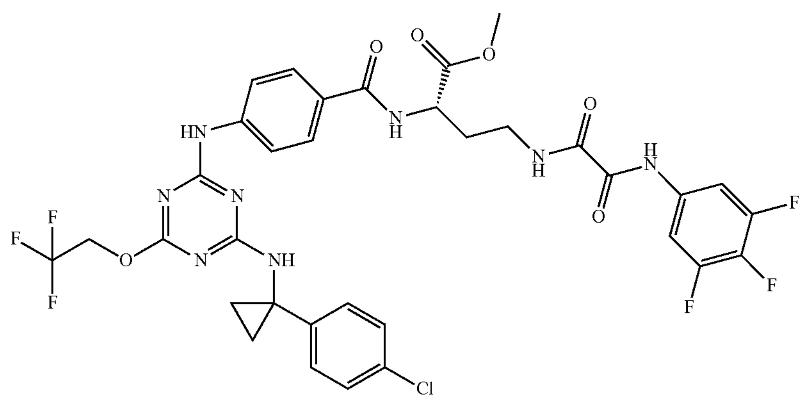 | <2.54 | A |

TABLE 1-continued
| Compound | Structure | EC$_{50}$ | Activity |
|---|---|---|---|
| 1505 | Chiral 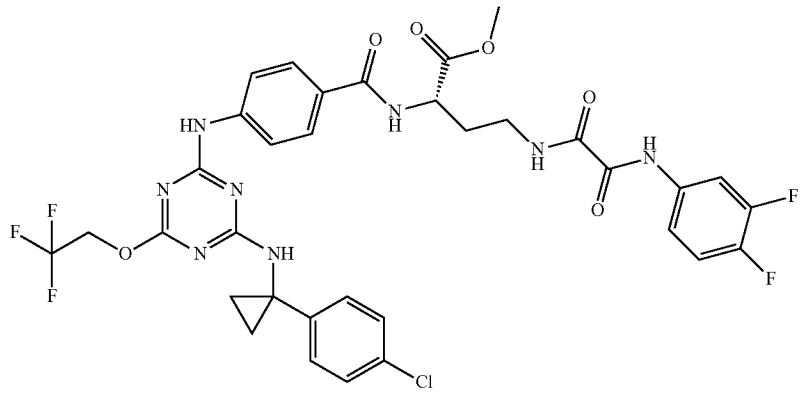 | | A |
| 1506 | Chiral 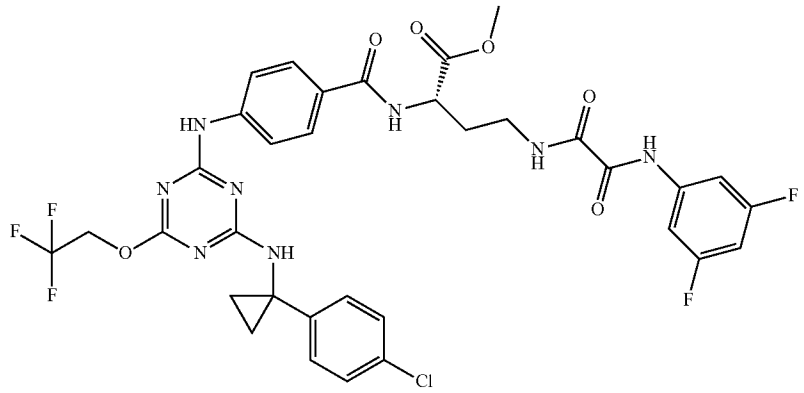 | | A |

| Compound | Structure | EC$_{50}$ | Activity |
|---|---|---|---|
| 1507 | 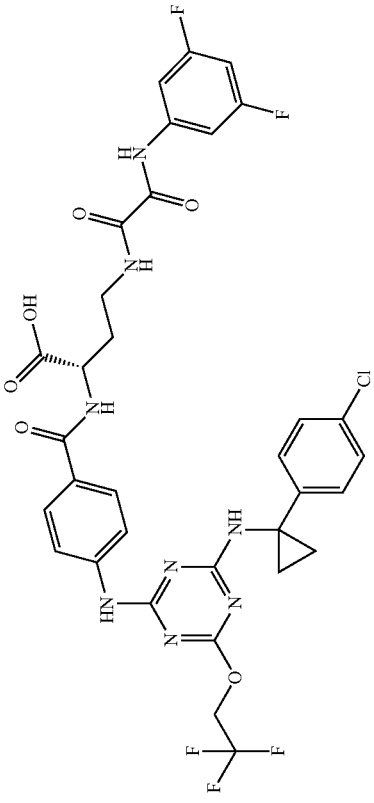 Chiral | | A |
| 1508 | 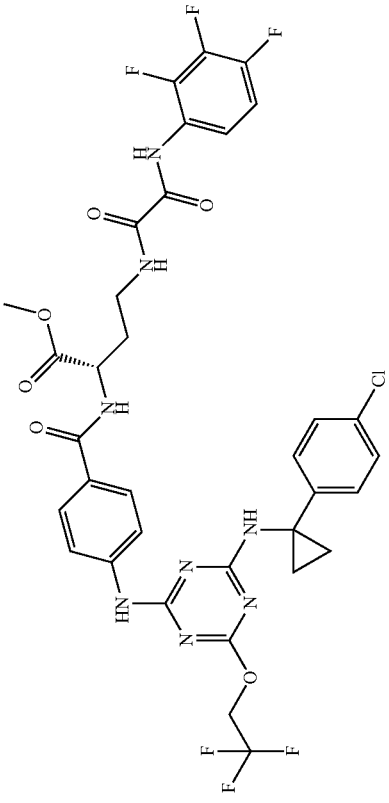 Chiral | | A |

TABLE 1-continued
| Compound | Structure | EC$_{50}$ | Activity |
|---|---|---|---|
| 1509 | 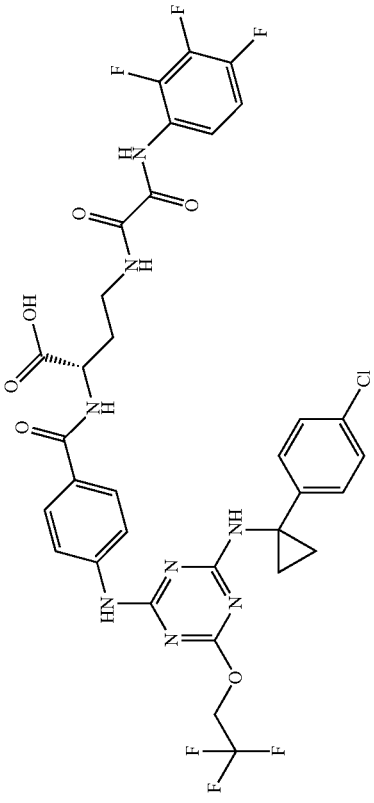 Chiral | | A |
| 1510 | 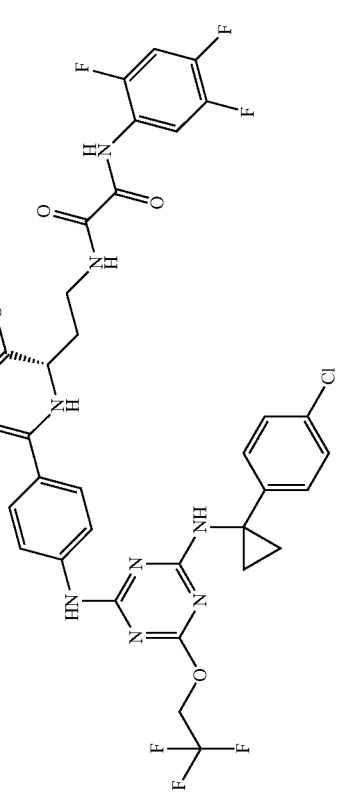 Chiral | | A |

TABLE 1-continued

| Compound | Structure | EC$_{50}$ | Activity |
|---|---|---|---|
| 1511 | Chiral | | A |
| 1512 | Chiral | | A |

TABLE 1-continued
| Compound | Structure | EC$_{50}$ | Activity |
|---|---|---|---|
| 1513 | 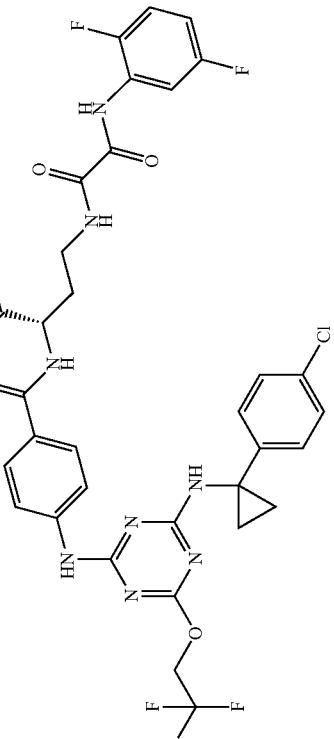 Chiral | | A |
| 1514 | 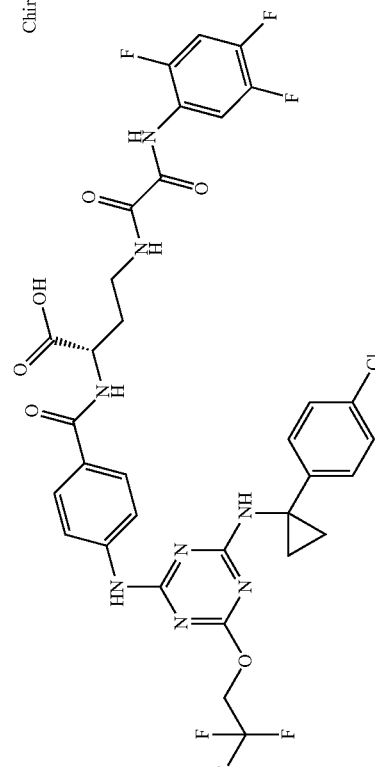 Chiral | 0.04 | A |

| Compound | Structure | | EC$_{50}$ | Activity |
|---|---|---|---|---|
| 1515 | Chiral | | | A |
| 1516 | Chiral | | 0.09 | A |
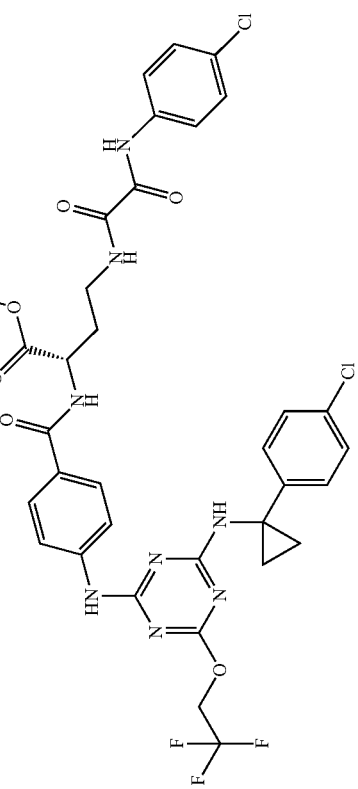
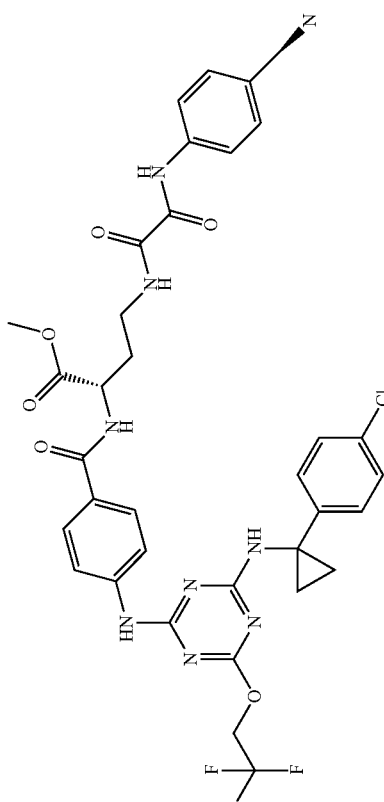

TABLE 1-continued

| Compound | Structure | EC$_{50}$ | Activity |
|---|---|---|---|
| 1517 | Chiral | | A |
| 1518 | Chiral | | A |

TABLE 1-continued

| Compound | Structure | EC$_{50}$ | Activity |
|---|---|---|---|
| 1519 | Chiral | | A |
| 1520 | Chiral | | A |

TABLE 1-continued
| Compound | Structure | EC$_{50}$ | Activity |
|---|---|---|---|
| 1521 | 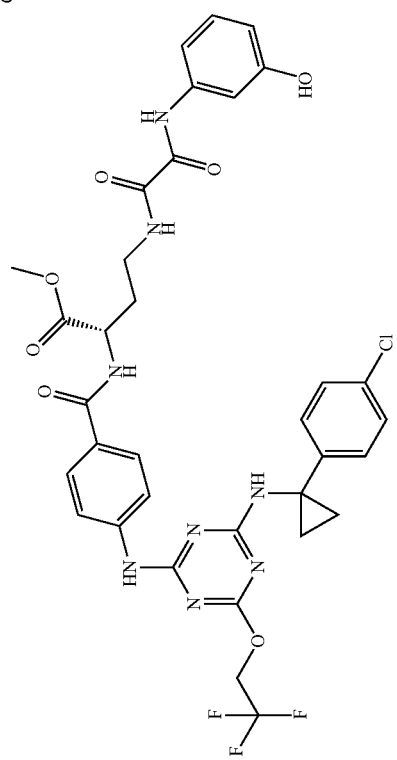 Chiral | | A |
| 1522 | 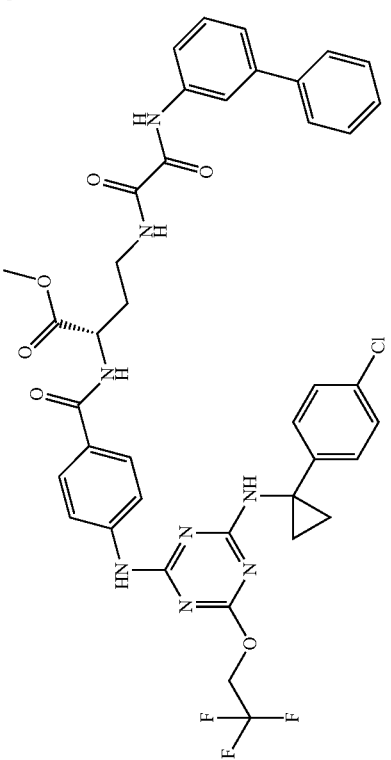 Chiral | 0.10 | A |

TABLE 1-continued
| Compound | Structure | EC$_{50}$ | Activity |
|---|---|---|---|
| 1523 | Chiral 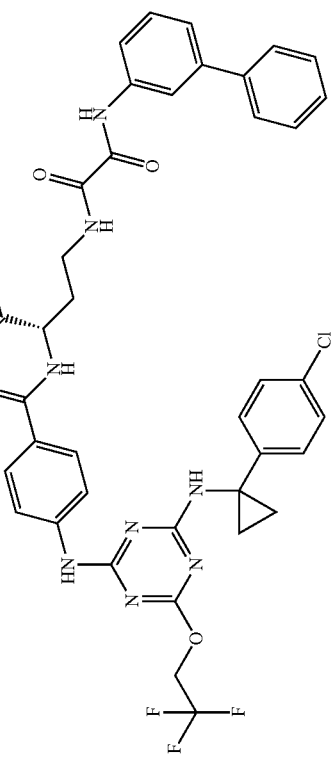 | 0.26 | A |
| 1524 | Chiral 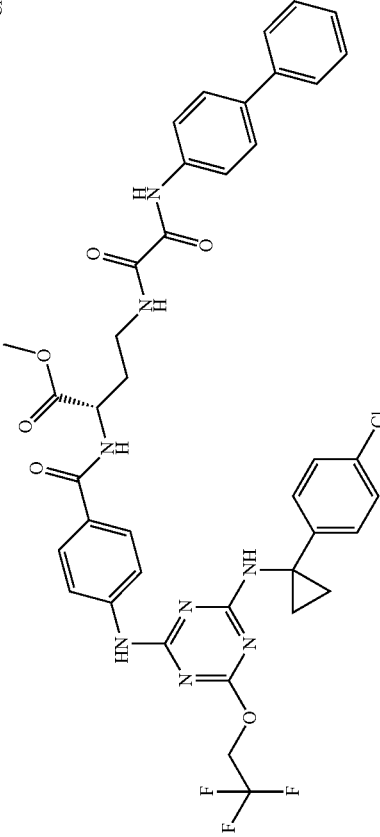 | | A |

TABLE 1-continued
| Compound | Structure | EC$_{50}$ | Activity |
|---|---|---|---|
| 1525 | 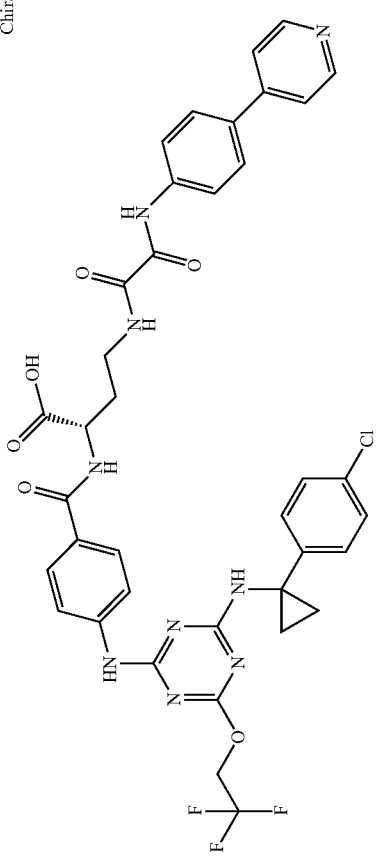 | | A |
| 1526 | 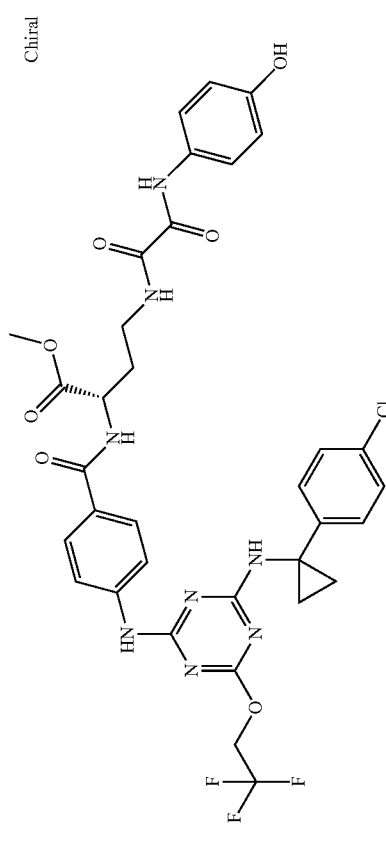 | | A |

TABLE 1-continued
| Compound | Structure | EC$_{50}$ | Activity |
|---|---|---|---|
| 1527 | 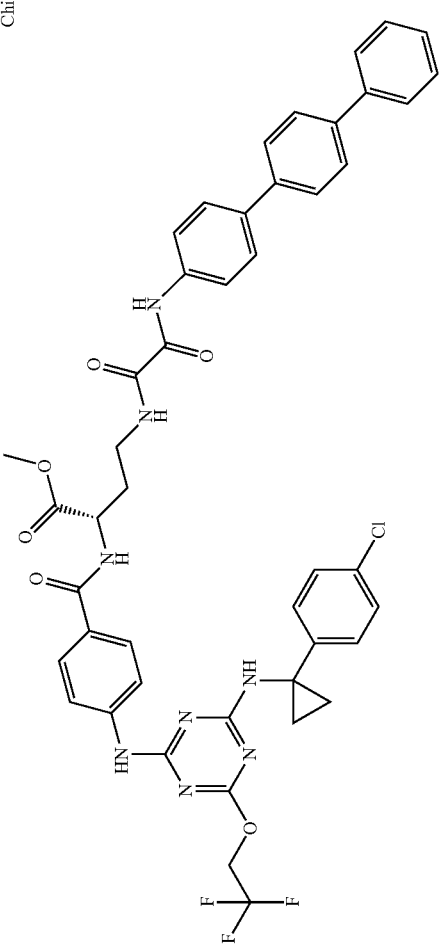 | 0.15 | A |
| 1528 | 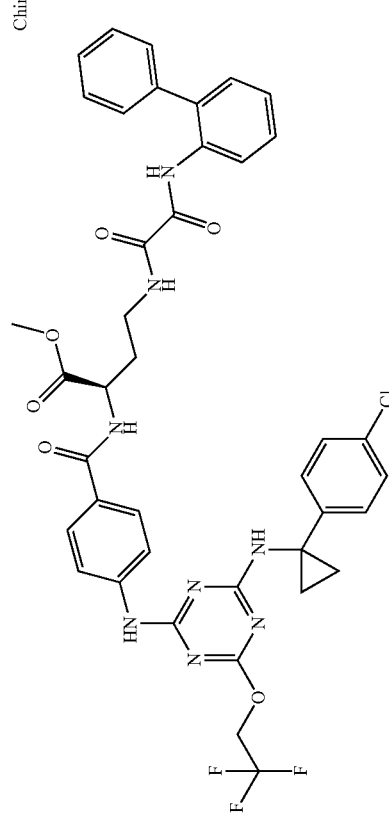 |  | A |

TABLE 1-continued
| Compound | Structure | EC$_{50}$ | Activity |
|---|---|---|---|
| 1529 | Chiral 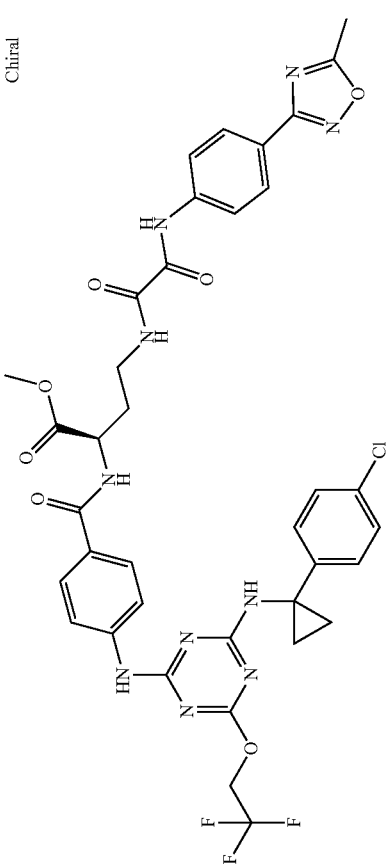 | | A |
| 1530 | Chiral 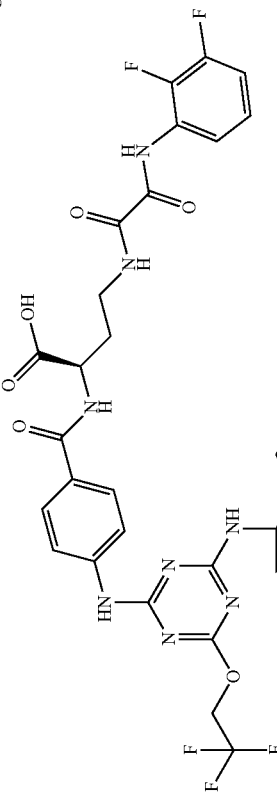 | | A |

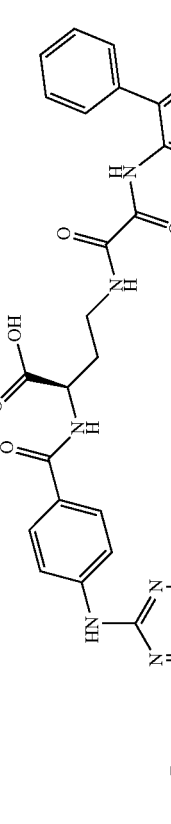

TABLE 1-continued

| Compound | Structure | EC$_{50}$ | Activity |
|---|---|---|---|
| 1534 | Chiral | | A |
| 1535 | Chiral | | A |

TABLE 1-continued
| Compound | Structure | EC$_{50}$ | Activity |
|---|---|---|---|
| 1536 | 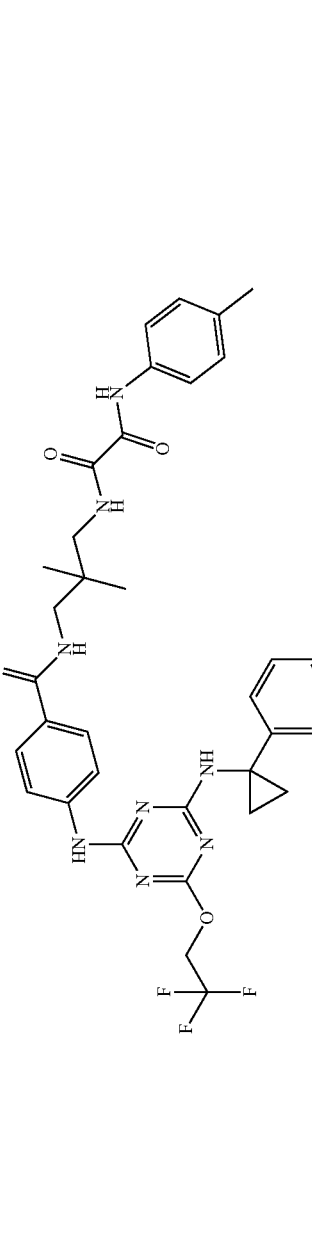 | | A |
| 1537 | 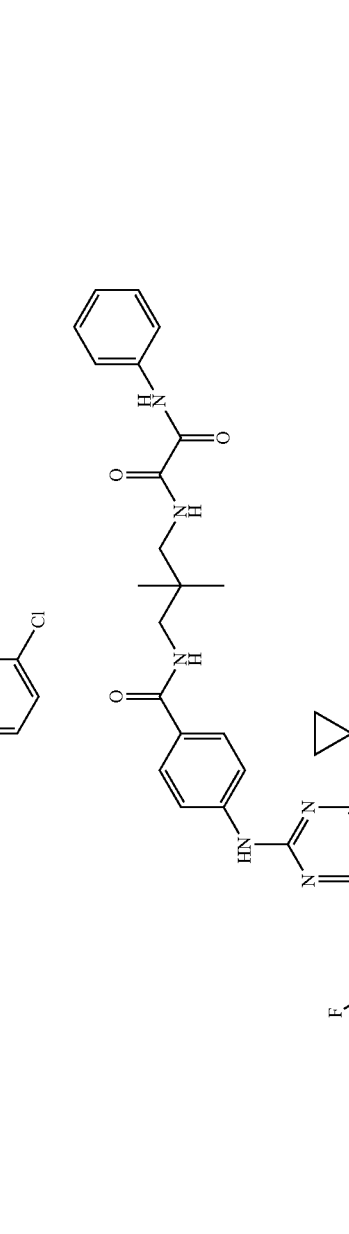 | | A |

TABLE 1-continued
| Compound | Structure | EC$_{50}$ | Activity |
|---|---|---|---|
| 1538 | Chiral 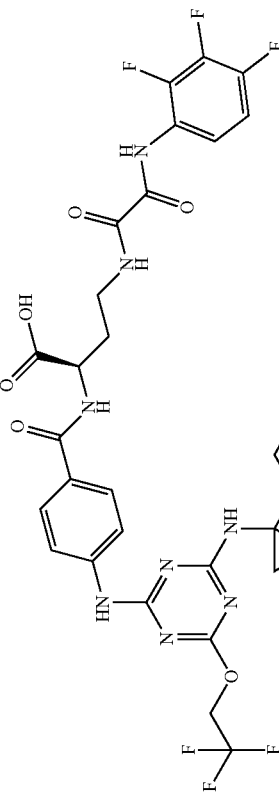 | | A |
| 1539 | 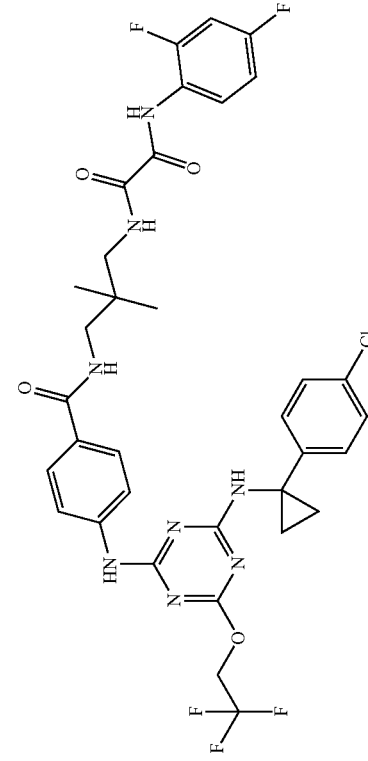 | | A |

TABLE 1-continued

| Compound | Structure | EC$_{50}$ | Activity |
|---|---|---|---|
| 1540 | 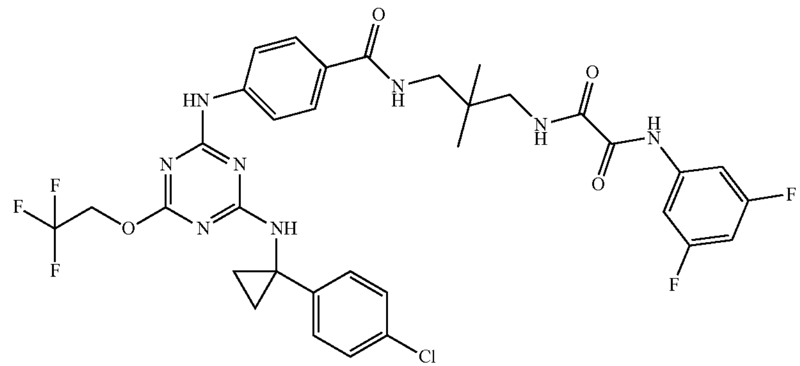 [SMILES: CC(C)(CNC(=O)C(=O)Nc1cc(F)cc(F)c1)CNC(=O)c1ccc(Nc2nc(NC3(c4ccc(Cl)cc4)CC3)nc(OCC(F)(F)F)n2)cc1] | | A |
| 1541 | 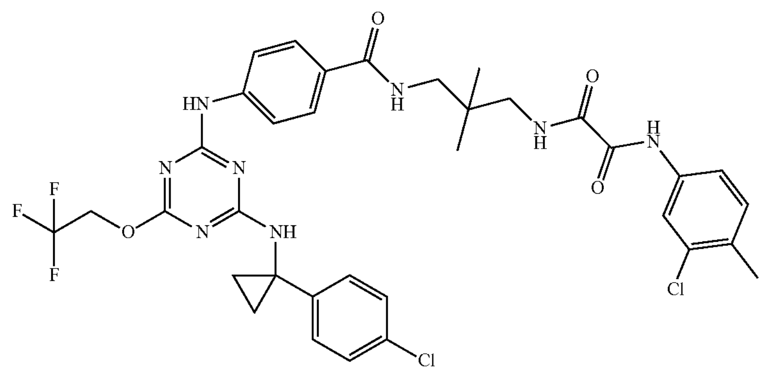 [SMILES: Cc1ccc(NC(=O)C(=O)NCC(C)(C)CNC(=O)c2ccc(Nc3nc(NC4(c5ccc(Cl)cc5)CC4)nc(OCC(F)(F)F)n3)cc2)cc1Cl] | | A |

TABLE 1-continued
| Compound | Structure | EC$_{50}$ | Activity |
|---|---|---|---|
| 1542 | 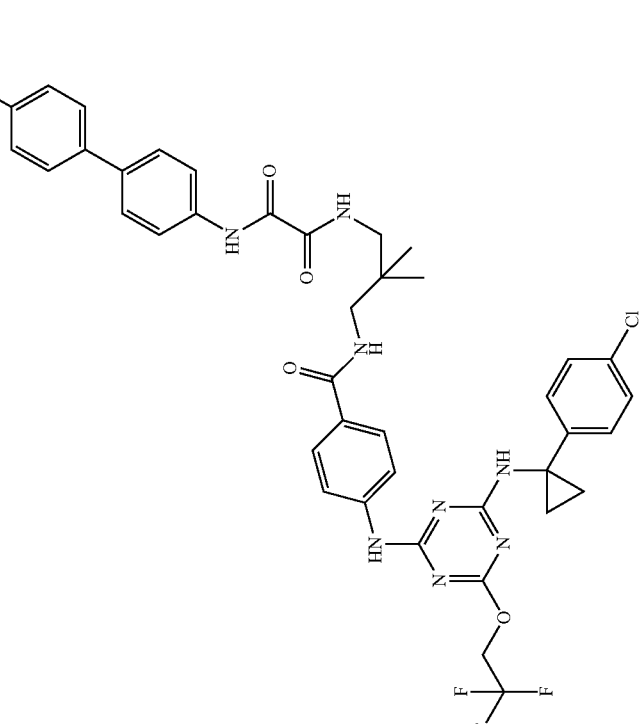 | | A |

TABLE 1-continued

| Compound | Structure | EC$_{50}$ | Activity |
|---|---|---|---|
| 1543 | 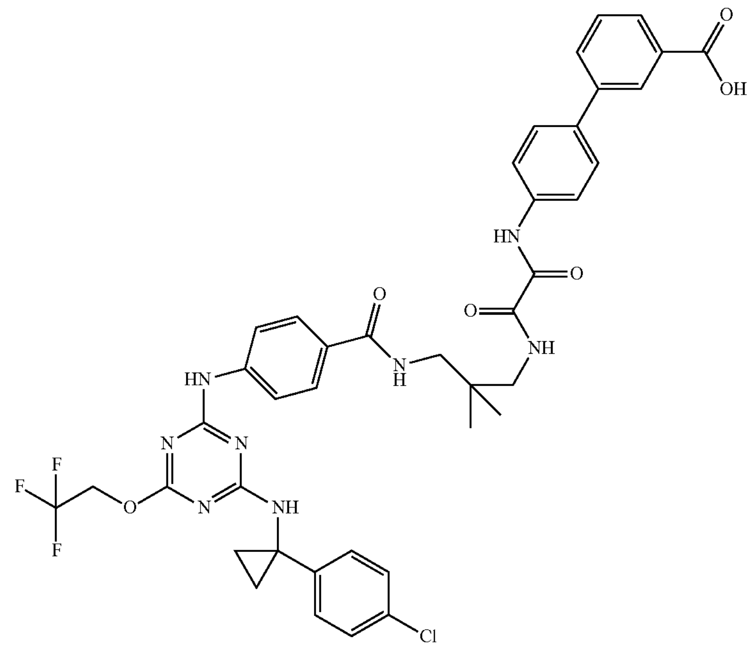 [SMILES: CC(C)(CNC(=O)C(=O)Nc1ccc(-c2cccc(C(=O)O)c2)cc1)CNC(=O)c1ccc(Nc2nc(NC3(c4ccc(Cl)cc4)CC3)nc(OCC(F)(F)F)n2)cc1] | | A |
| 1544 | 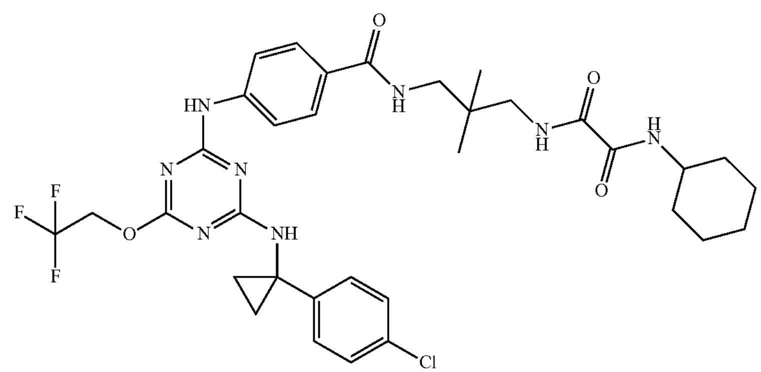 [SMILES: CC(C)(CNC(=O)C(=O)NC1CCCCC1)CNC(=O)c1ccc(Nc2nc(NC3(c4ccc(Cl)cc4)CC3)nc(OCC(F)(F)F)n2)cc1] | 0.08 | A |

TABLE 1-continued

| Compound | Structure | EC$_{50}$ | Activity |
|---|---|---|---|
| 1545 | 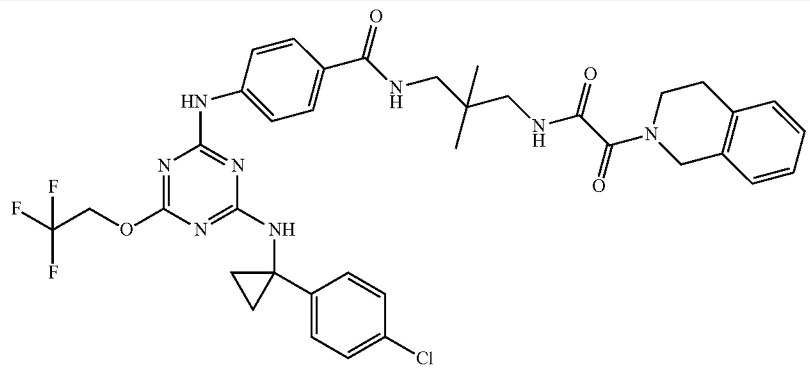 [SMILES: CC(C)(CNC(=O)C(=O)N1CCc2ccccc2C1)CNC(=O)c1ccc(Nc2nc(NC3(c4ccc(Cl)cc4)CC3)nc(OCC(F)(F)F)n2)cc1] | | A |
| 1546 | 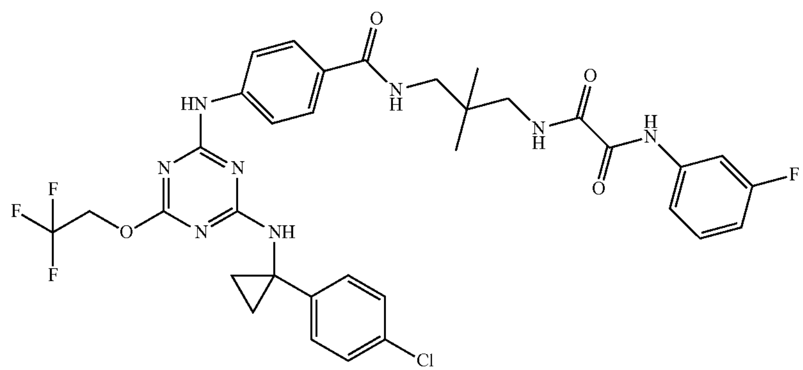 [SMILES: CC(C)(CNC(=O)C(=O)Nc1cccc(F)c1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 1547 | 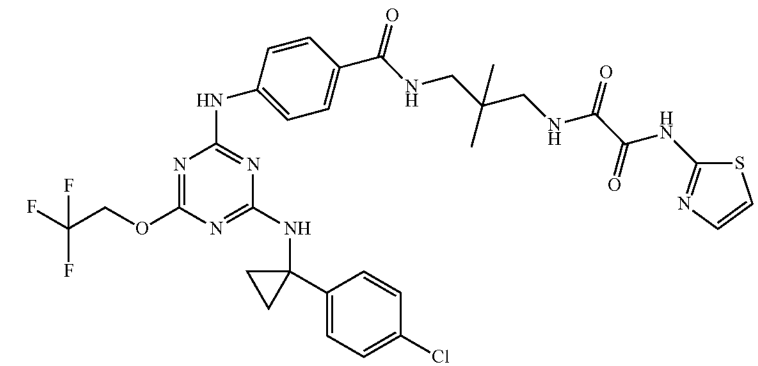 [SMILES: CC(C)(CNC(=O)C(=O)Nc1nccs1)CNC(=O)c1ccc(Nc2nc(NC3(c4ccc(Cl)cc4)CC3)nc(OCC(F)(F)F)n2)cc1] | 0.06 | A |
| 1548 | 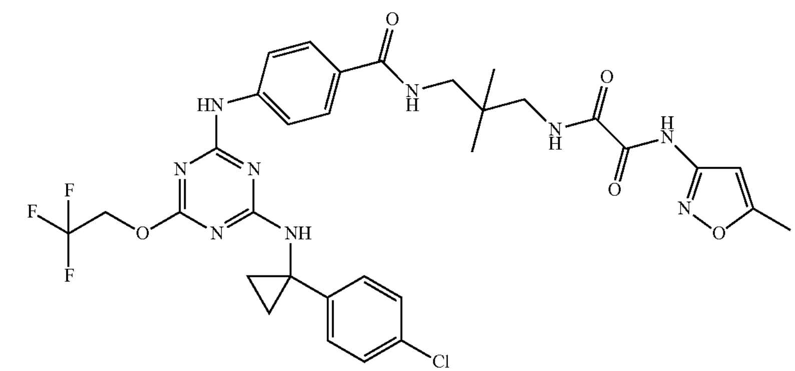 [SMILES: Cc1cc(NC(=O)C(=O)NCC(C)(C)CNC(=O)c2ccc(Nc3nc(NC4(c5ccc(Cl)cc5)CC4)nc(OCC(F)(F)F)n3)cc2)no1] | | A |

TABLE 1-continued

| Compound | Structure | EC$_{50}$ | Activity |
|---|---|---|---|
| 1549 | 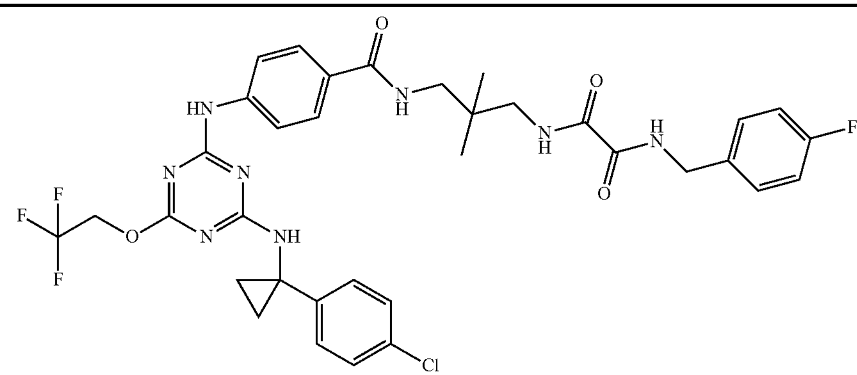 | | A |
| 1550 | 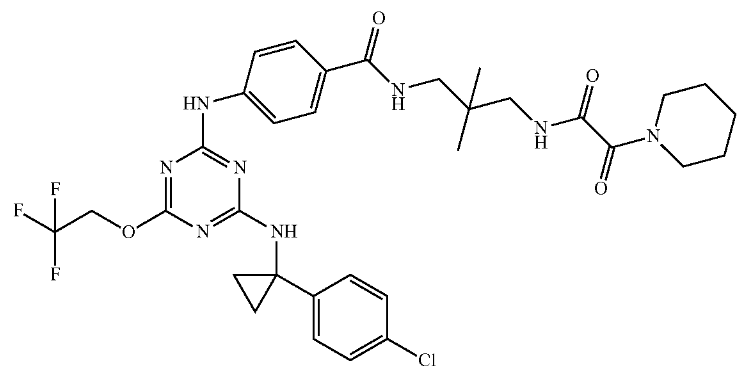 [SMILES: CC(C)(CNC(=O)C(=O)N1CCCCC1)CNC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 1551 | 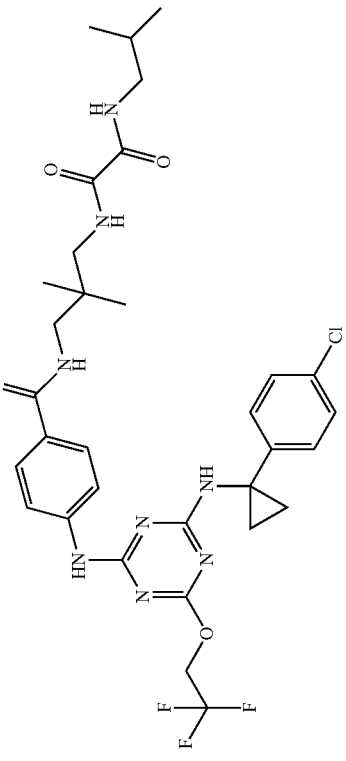 | | A |
| 1552 | 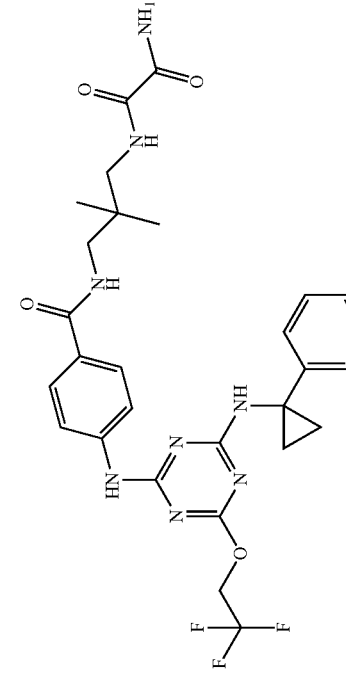 | | A |

TABLE 1-continued

| Compound | Structure | EC$_{50}$ | Activity |
|---|---|---|---|
| 1553 | 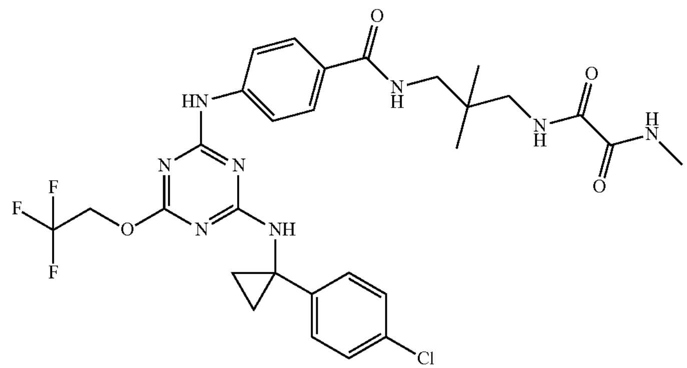 [SMILES: CNC(=O)C(=O)NCC(C)(C)CNC(=O)c1ccc(Nc2nc(NC3(c4ccc(Cl)cc4)CC3)nc(OCC(F)(F)F)n2)cc1] | | A |
| 1554 | Chiral | | A |

| Compound | Structure | EC$_{50}$ | Activity |
|---|---|---|---|
| 1555 | 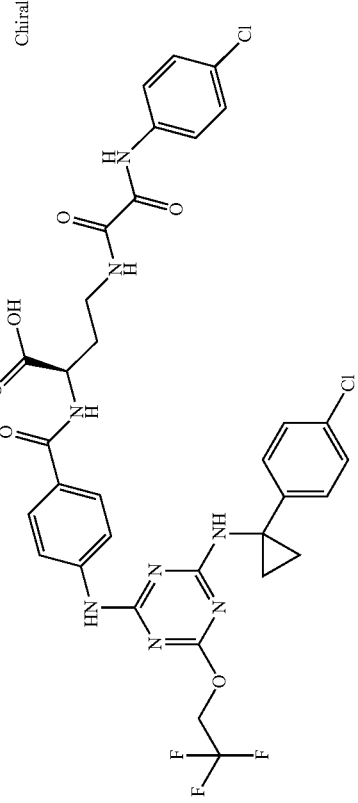 | | A |
| 1556 | 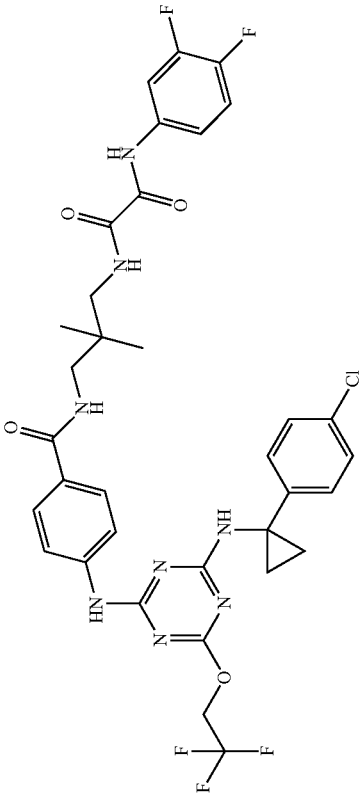 | | A |

TABLE 1-continued

| Compound | Structure | EC$_{50}$ | Activity |
|---|---|---|---|
| 1557 | (chiral structure) | | A |
| 1558 | (structure) | | A |

TABLE 1-continued

| Compound | Structure | EC$_{50}$ | Activity |
|---|---|---|---|
| 1559 | 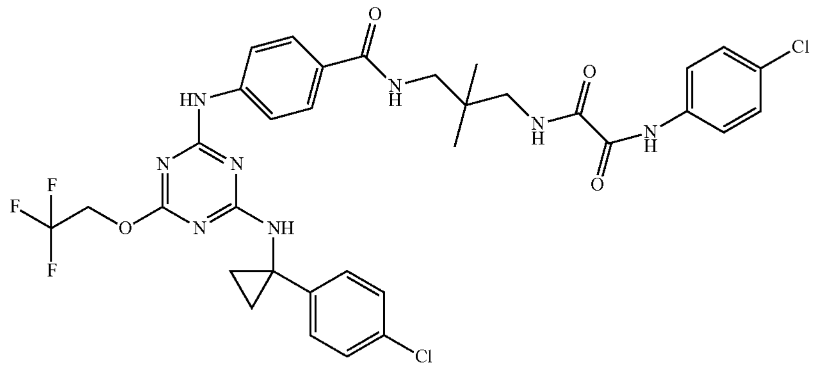 [SMILES: CC(C)(CNC(=O)C(=O)Nc1ccc(Cl)cc1)CNC(=O)c1ccc(Nc2nc(NC3(c4ccc(Cl)cc4)CC3)nc(OCC(F)(F)F)n2)cc1] | | A |
| 1560 | 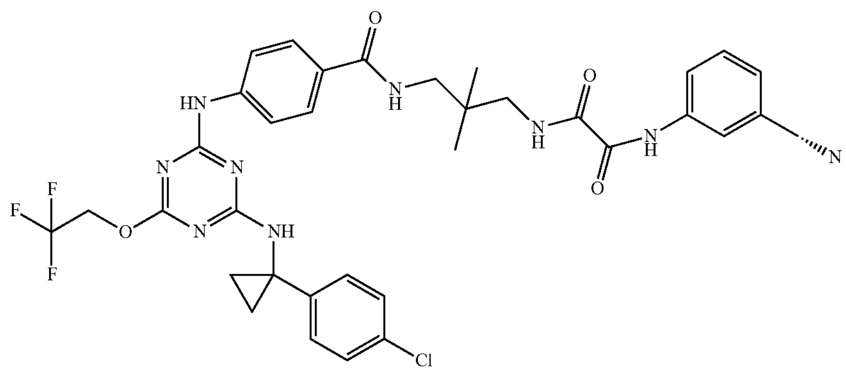 | | A |

TABLE 1-continued

| Compound | Structure | EC$_{50}$ | Activity |
|---|---|---|---|
| 1561 | 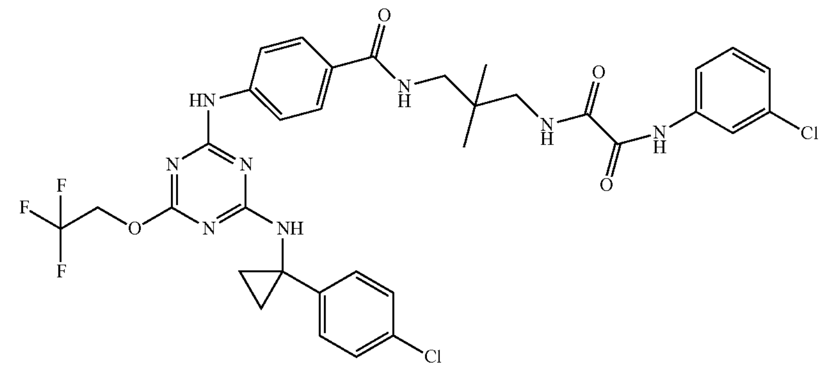 [SMILES: CC(C)(CNC(=O)C(=O)Nc1cccc(Cl)c1)CNC(=O)c1ccc(Nc2nc(NC3(c4ccc(Cl)cc4)CC3)nc(OCC(F)(F)F)n2)cc1] | | A |
| 1562 | 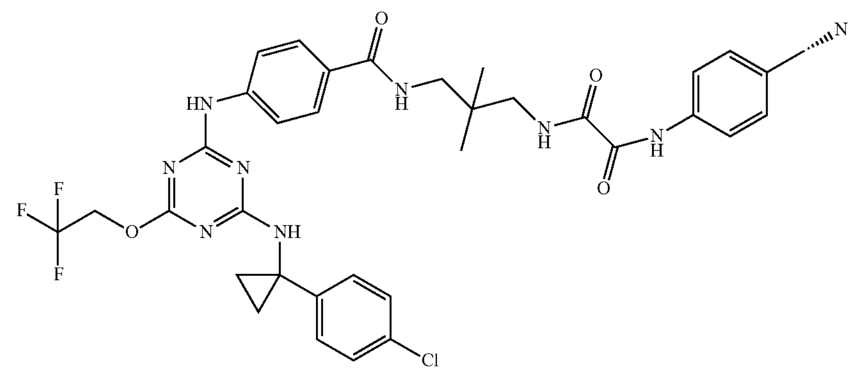 | | A |

TABLE 1-continued
| Compound | Structure | EC$_{50}$ | Activity |
|---|---|---|---|
| 1563 | 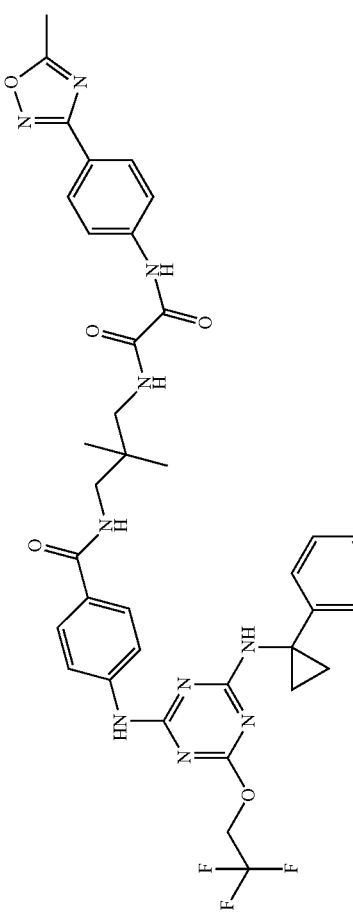 | | A |
| 1564 | 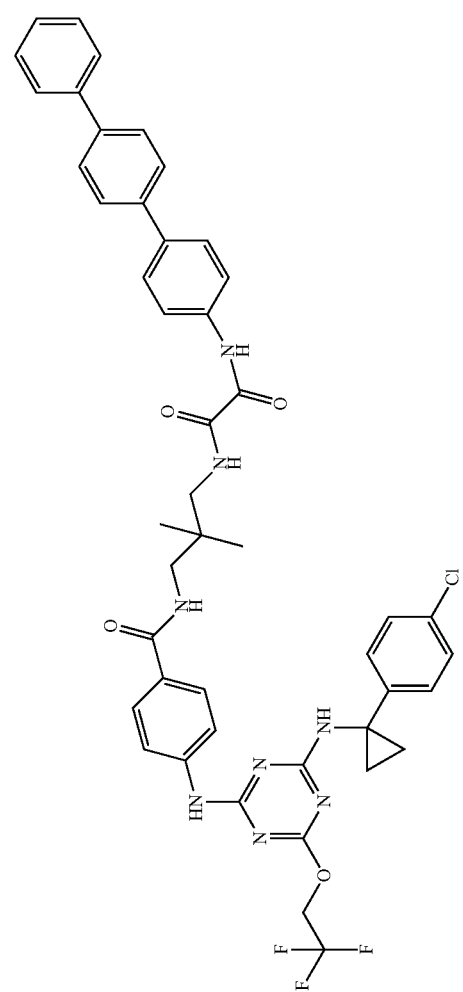 | | A |

TABLE 1-continued
| Compound | Structure | EC$_{50}$ | Activity |
|---|---|---|---|
| 1565 | 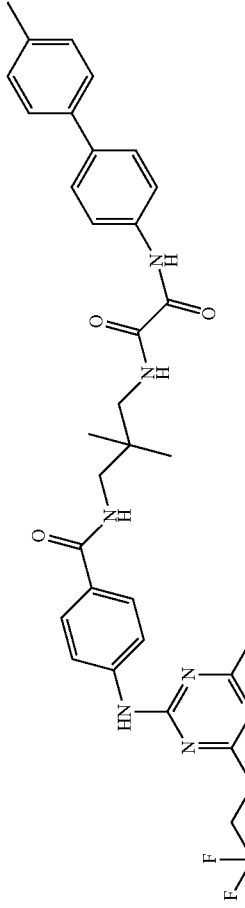 | 0.13 | A |
| 1566 | 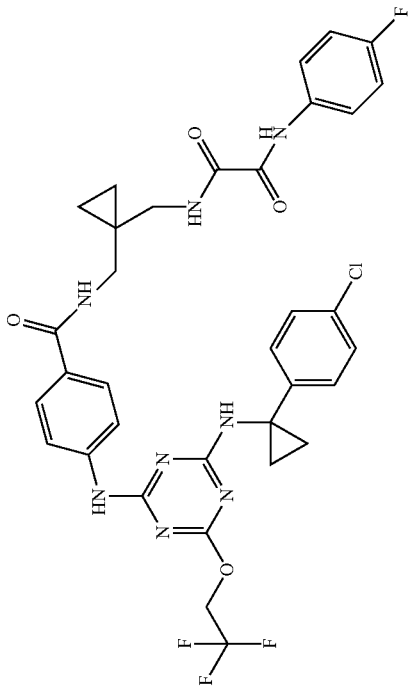 | | A |

TABLE 1-continued

| Compound | Structure | EC$_{50}$ | Activity |
|---|---|---|---|
| 1567 | 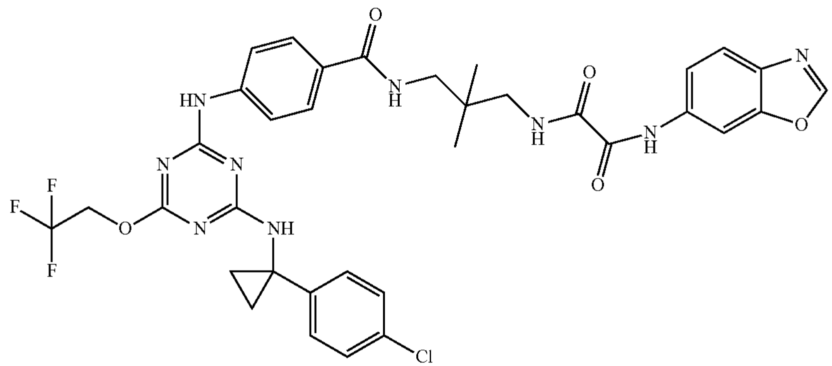 [SMILES: CC(C)(CNC(=O)C(=O)Nc1ccc2ncoc2c1)CNC(=O)c1ccc(Nc2nc(NC3(c4ccc(Cl)cc4)CC3)nc(OCC(F)(F)F)n2)cc1] | | A |
| 1568 | 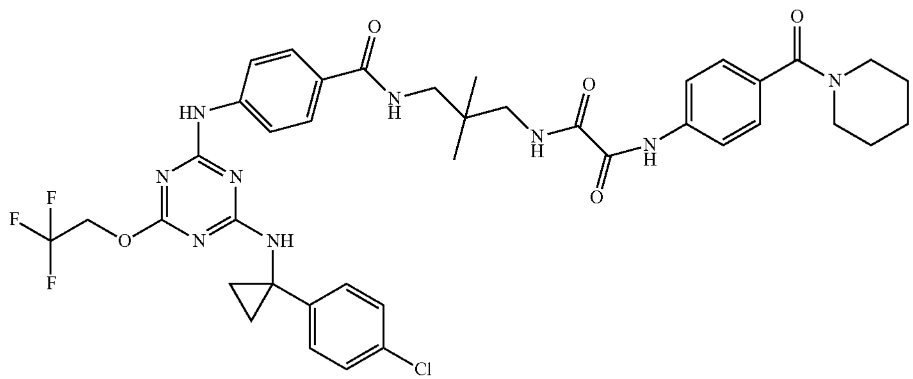 [SMILES: CC(C)(CNC(=O)C(=O)Nc1ccc(C(=O)N2CCCCC2)cc1)CNC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 1569 | 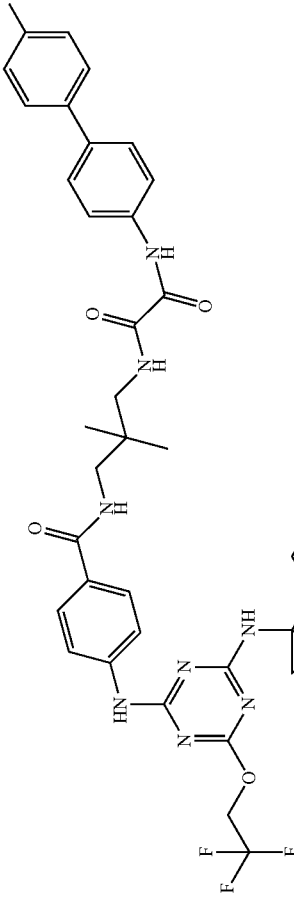 | | A |
| 1570 | 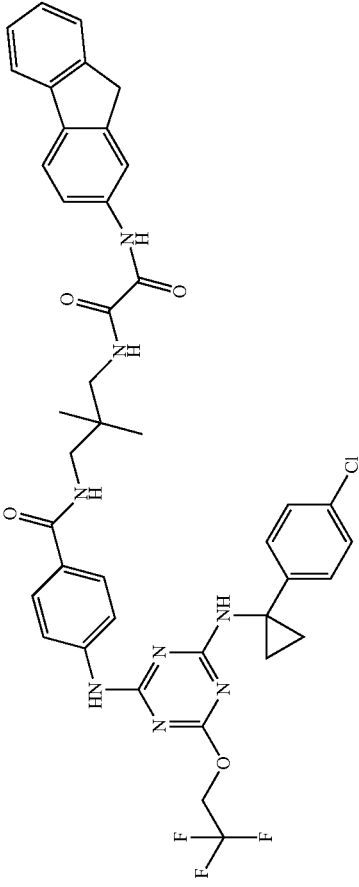 | 0.05 | A |

TABLE 1-continued

| Compound | Structure | EC$_{50}$ | Activity |
|---|---|---|---|
| 1571 | 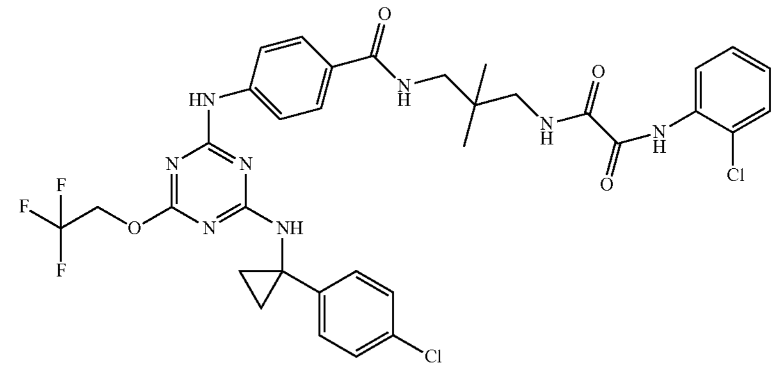 [SMILES: CC(C)(CNC(=O)C(=O)Nc1ccccc1Cl)CNC(=O)c1ccc(Nc2nc(NC3(c4ccc(Cl)cc4)CC3)nc(OCC(F)(F)F)n2)cc1] | 0.05 | A |
| 1572 | 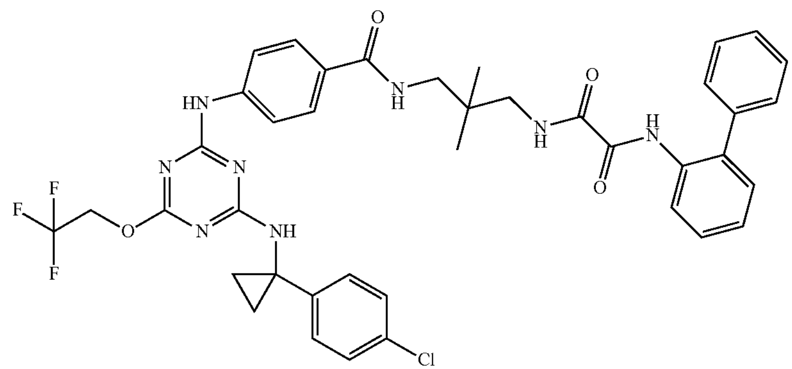 [SMILES: CC(C)(CNC(=O)C(=O)Nc1ccccc1-c1ccccc1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC₅₀ | Activity |
|---|---|---|---|
| 1573 | 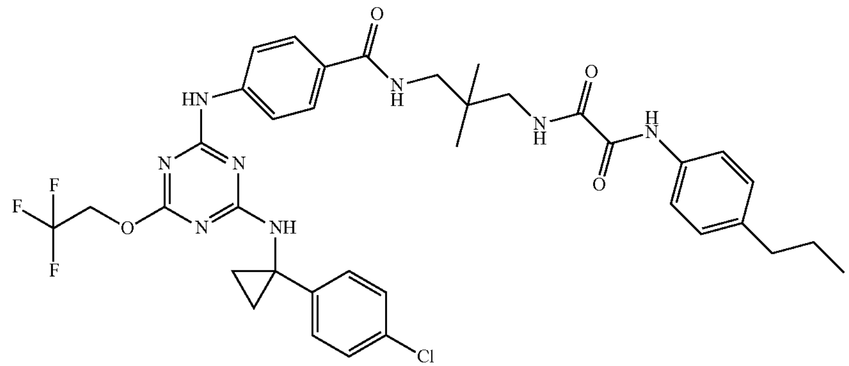 [SMILES: CCCc1ccc(NC(=O)C(=O)NCC(C)(C)CNC(=O)c2ccc(Nc3nc(NC4(c5ccc(Cl)cc5)CC4)nc(OCC(F)(F)F)n3)cc2)cc1] | | A |
| 1574 | 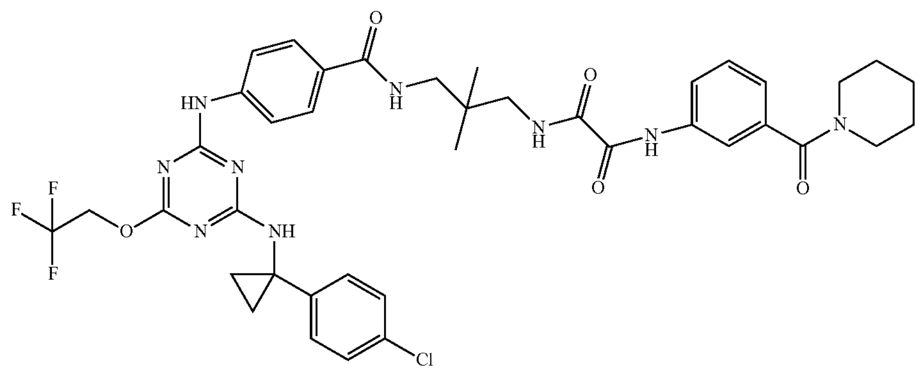 [SMILES: CC(C)(CNC(=O)C(=O)Nc1cccc(C(=O)N2CCCCC2)c1)CNC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 1576 | 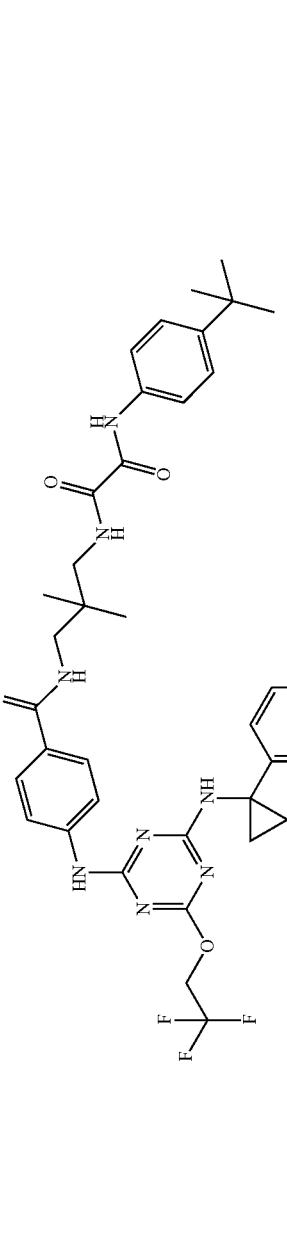 | | A |
| 1577 | 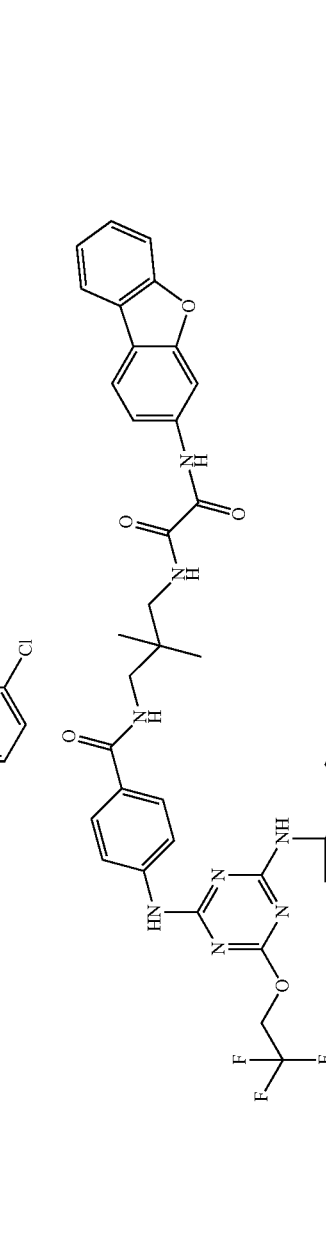 | | A |

TABLE 1-continued
| Compound | Structure | EC$_{50}$ | Activity |
|---|---|---|---|
| 1578 | 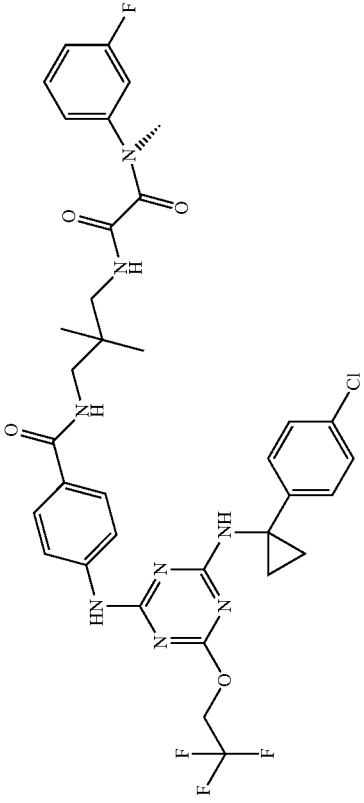 | | A |
| 1579 | 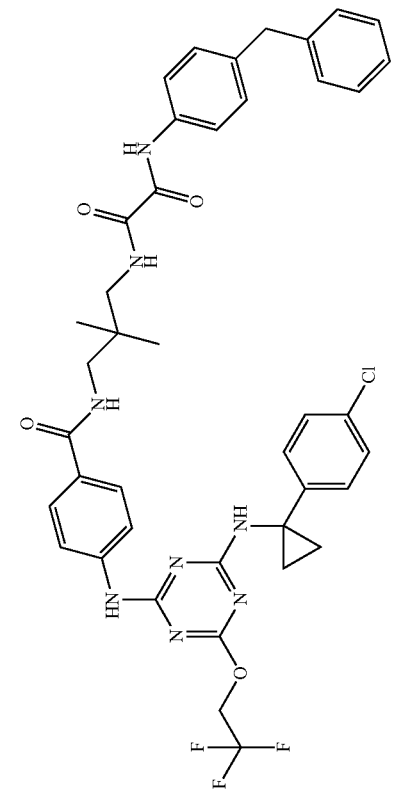 | | A |

TABLE 1-continued
| Compound | Structure | EC$_{50}$ | Activity |
|---|---|---|---|
| 1580 | 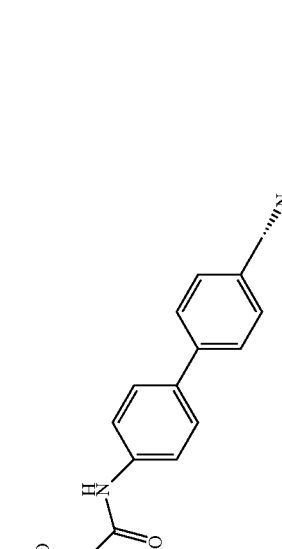 | 0.04 | A |
| 1581 | 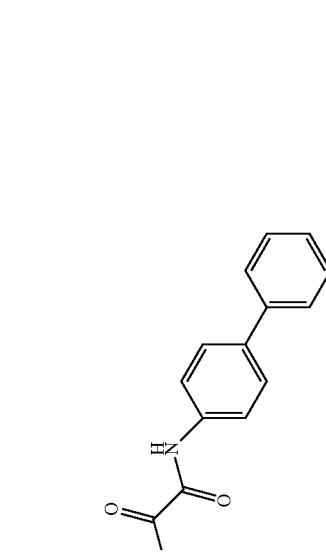 | | A |

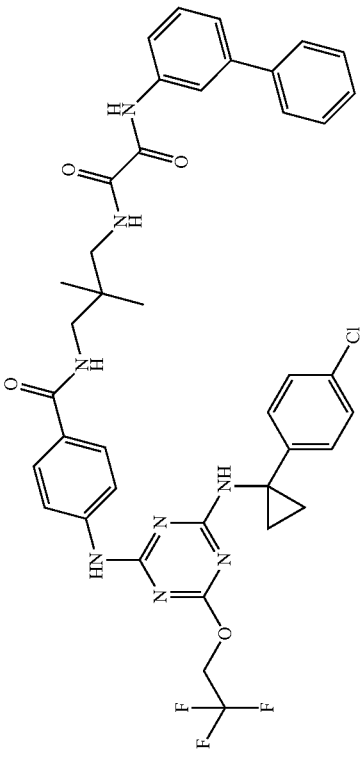

TABLE 1-continued

| Compound | Structure | EC$_{50}$ | Activity |
|---|---|---|---|
| 1584 | 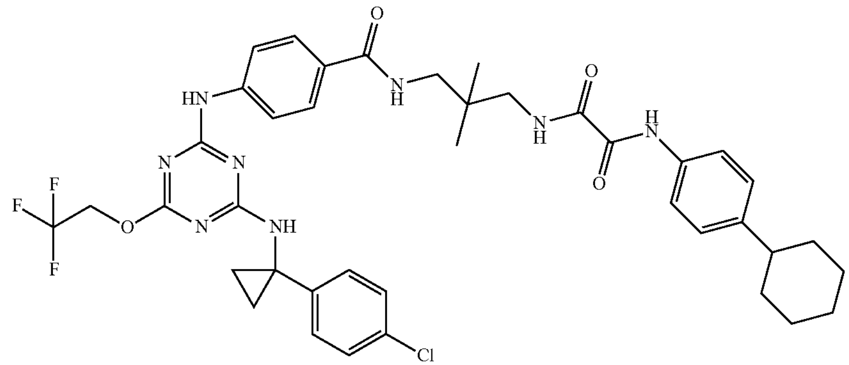 [SMILES: CC(C)(CNC(=O)C(=O)Nc1ccc(C2CCCCC2)cc1)CNC(=O)c1ccc(Nc2nc(NC3(c4ccc(Cl)cc4)CC3)nc(OCC(F)(F)F)n2)cc1] | | A |
| 1585 | 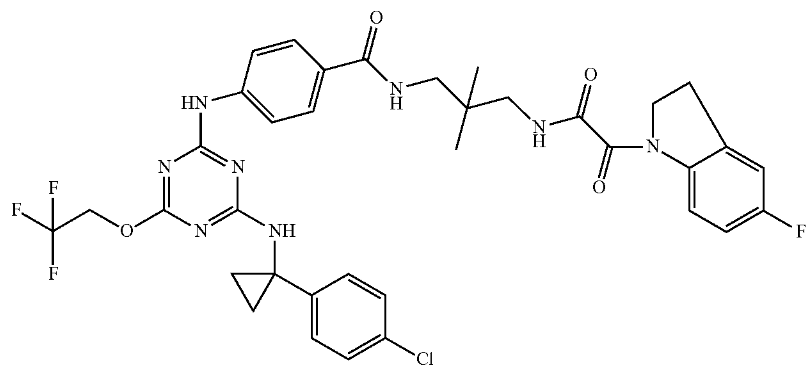 [SMILES: CC(C)(CNC(=O)C(=O)N1CCc2cc(F)ccc21)CNC(=O)c1ccc(Nc2nc(NC3(c4ccc(Cl)cc4)CC3)nc(OCC(F)(F)F)n2)cc1] | 0.03 | A |

TABLE 1-continued
| Compound | Structure | EC$_{50}$ | Activity |
|---|---|---|---|
| 1586 | 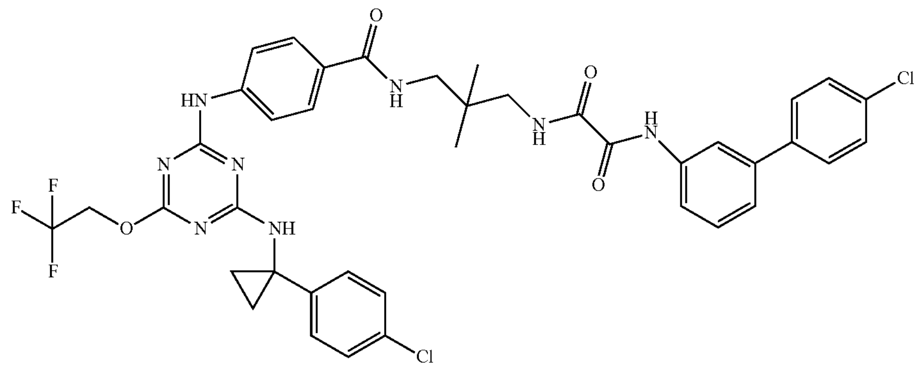 [SMILES: CC(C)(CNC(=O)C(=O)Nc1cccc(-c2ccc(Cl)cc2)c1)CNC(=O)c1ccc(Nc2nc(NC3(c4ccc(Cl)cc4)CC3)nc(OCC(F)(F)F)n2)cc1] | | A |
| 1587 | 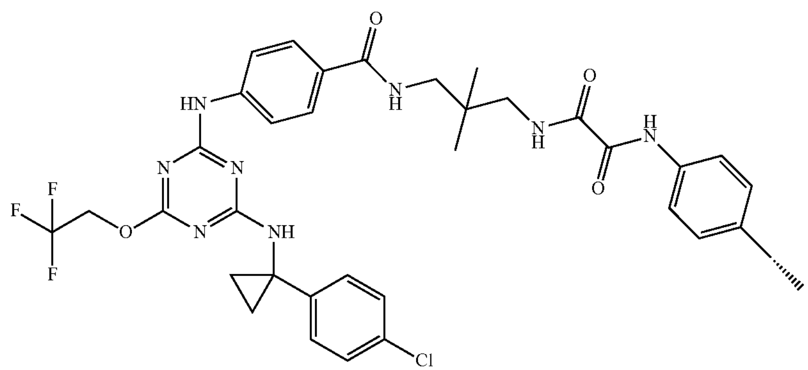 | | A |

TABLE 1-continued
| Compound | Structure | EC$_{50}$ | Activity |
|---|---|---|---|
| 1588 | 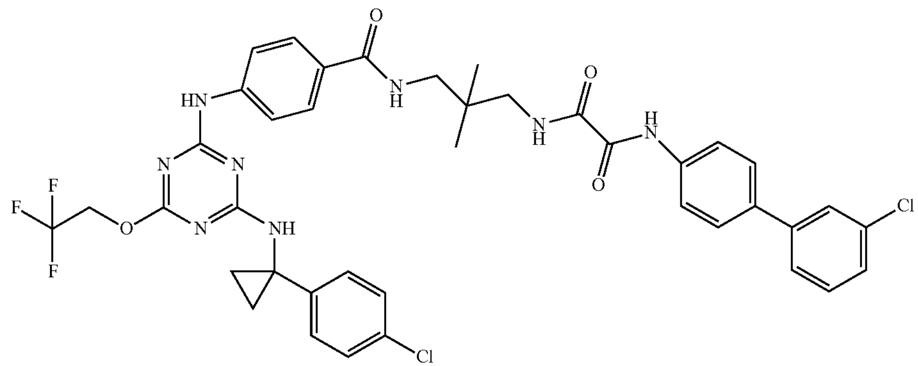 [SMILES: CC(C)(CNC(=O)C(=O)Nc1ccc(-c2cccc(Cl)c2)cc1)CNC(=O)c1ccc(Nc2nc(NC3(c4ccc(Cl)cc4)CC3)nc(OCC(F)(F)F)n2)cc1] | | A |
| 1589 | 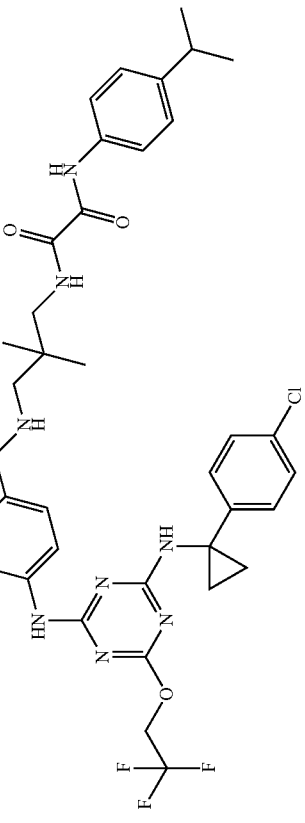 | | A |

| Compound | Structure | EC$_{50}$ | Activity |
|---|---|---|---|
| 1590 | 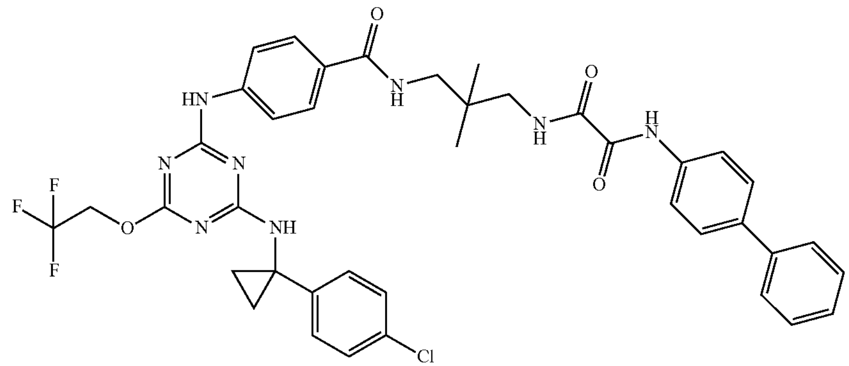 [SMILES: CC(C)(CNC(=O)C(=O)Nc1ccc(-c2ccccc2)cc1)CNC(=O)c1ccc(Nc2nc(NC3(c4ccc(Cl)cc4)CC3)nc(OCC(F)(F)F)n2)cc1] | | A |
| 1591 | 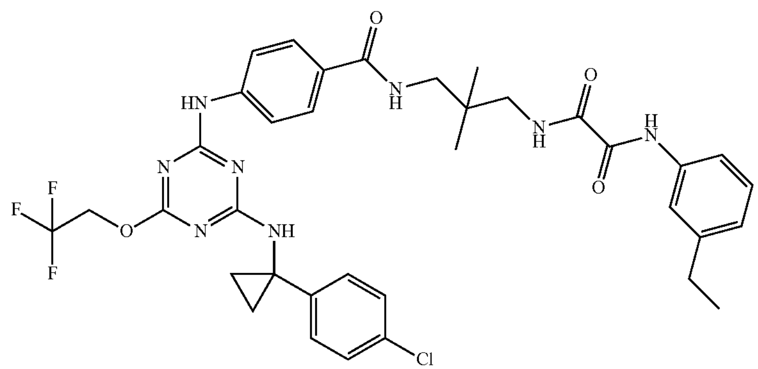 [SMILES: CCc1cccc(NC(=O)C(=O)NCC(C)(C)CNC(=O)c2ccc(Nc3nc(NC4(c5ccc(Cl)cc5)CC4)nc(OCC(F)(F)F)n3)cc2)c1] | | A |

TABLE 1-continued

| Compound | Structure | EC$_{50}$ | Activity |
|---|---|---|---|
| 1592 | 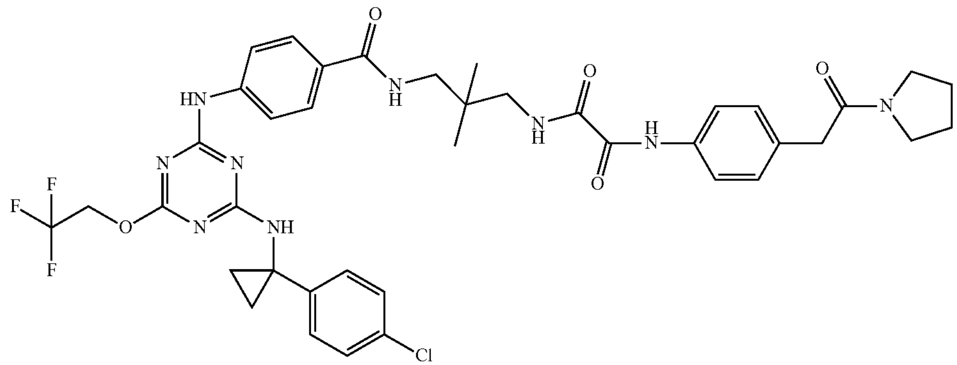 [SMILES: CC(C)(CNC(=O)C(=O)Nc1ccc(CC(=O)N2CCCC2)cc1)CNC(=O)c1ccc(Nc2nc(NC3(c4ccc(Cl)cc4)CC3)nc(OCC(F)(F)F)n2)cc1] | | A |
| 1593 | 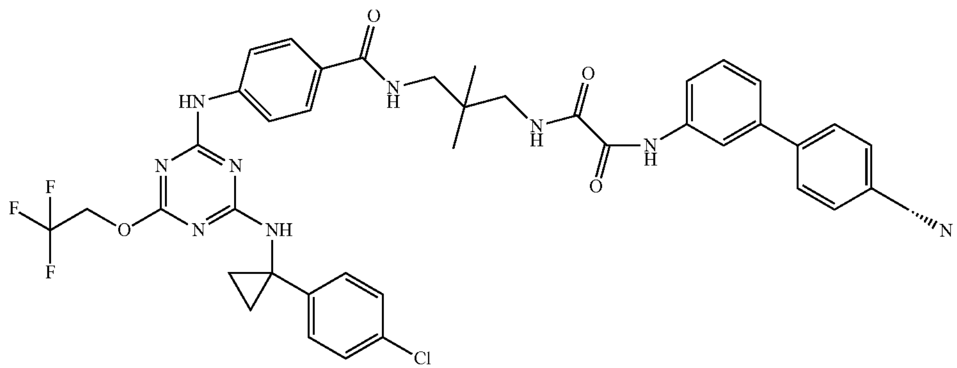 | | A |

TABLE 1-continued
| Compound | Structure | EC50 | Activity |
|---|---|---|---|
| 1594 | 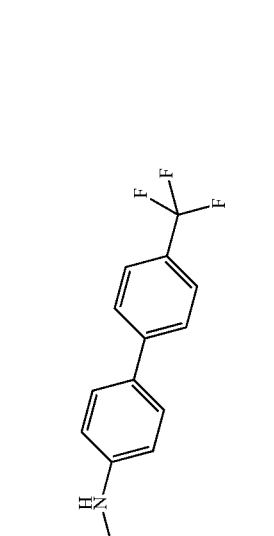 | 0.05 | A |
| 1595 | 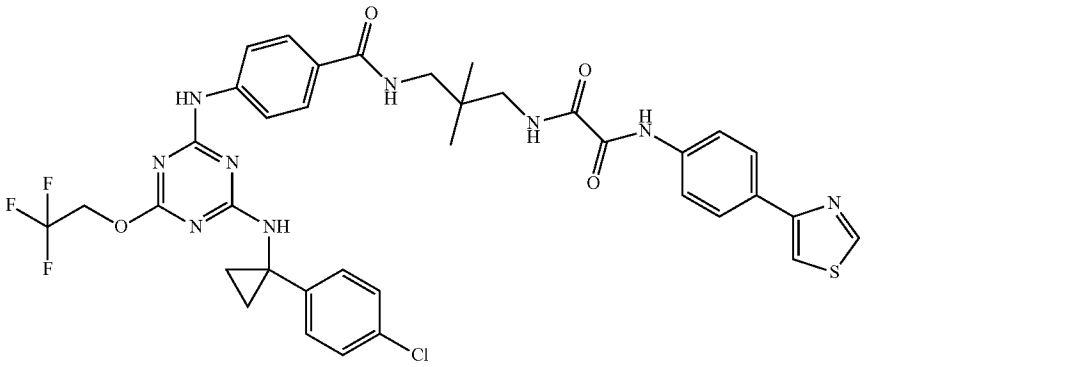 [SMILES: CC(C)(CNC(=O)C(=O)Nc1ccc(-c2cscn2)cc1)CNC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 1596 | 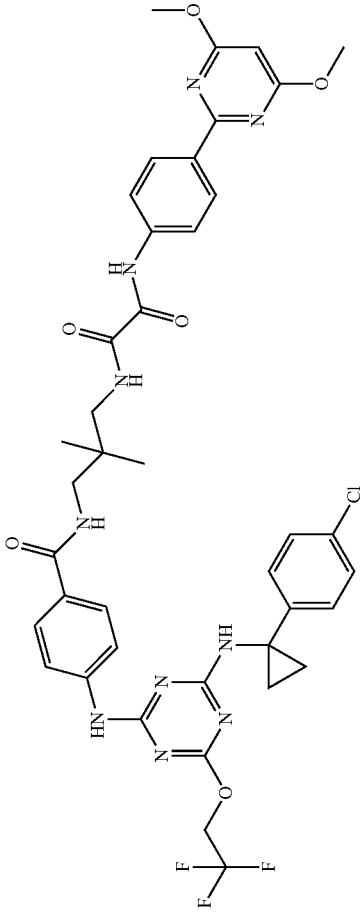 | | A |
| 1597 | 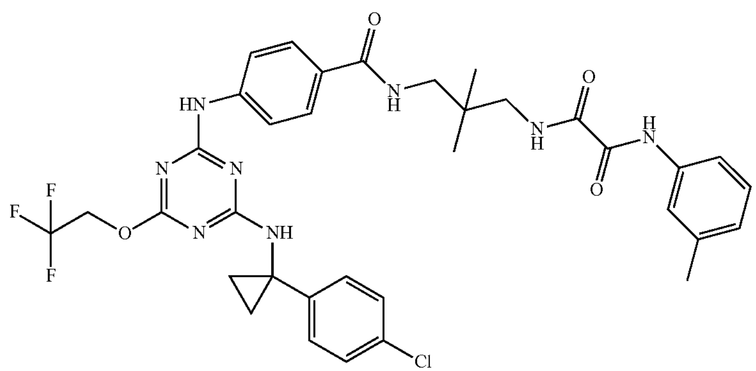 [SMILES: Cc1cccc(NC(=O)C(=O)NCC(C)(C)CNC(=O)c2ccc(Nc3nc(NC4(c5ccc(Cl)cc5)CC4)nc(OCC(F)(F)F)n3)cc2)c1] | | A |

TABLE 1-continued

| Compound | Structure | EC$_{50}$ | Activity |
|---|---|---|---|
| 1598 | 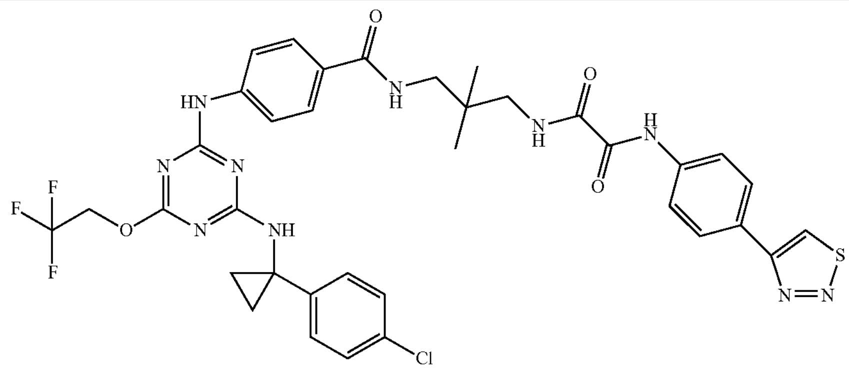 [SMILES: CC(C)(CNC(=O)C(=O)Nc1ccc(-c2csnn2)cc1)CNC(=O)c1ccc(Nc2nc(NC3(c4ccc(Cl)cc4)CC3)nc(OCC(F)(F)F)n2)cc1] | | A |
| 1599 | 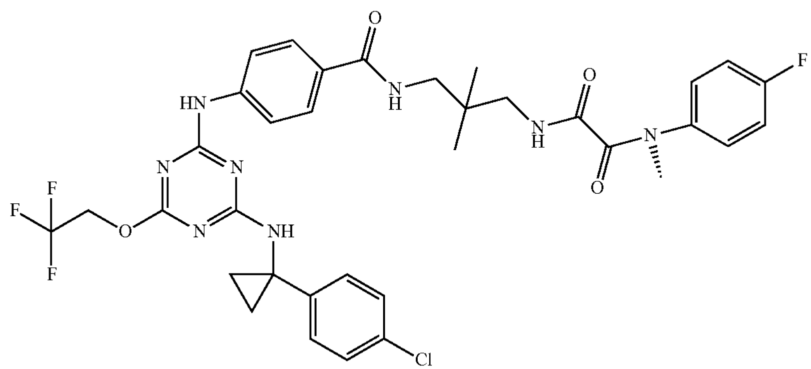 | | A |

TABLE 1-continued

| Compound | Structure | EC$_{50}$ | Activity |
|---|---|---|---|
| 1600 | 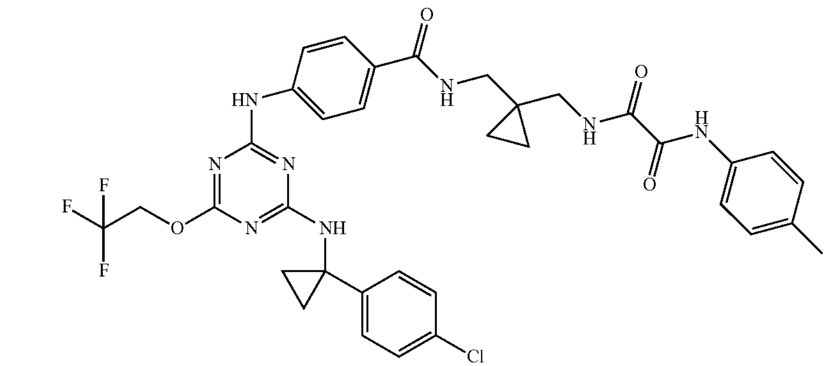 [SMILES: Cc1ccc(NC(=O)C(=O)NCC2(CNC(=O)c3ccc(Nc4nc(NC5(c6ccc(Cl)cc6)CC5)nc(OCC(F)(F)F)n4)cc3)CC2)cc1] | | A |
| 1601 | 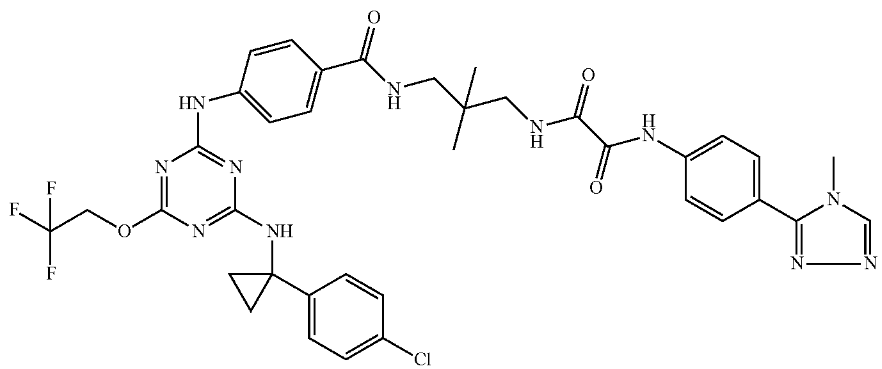 [SMILES: Cn1cnnc1-c1ccc(NC(=O)C(=O)NCC(C)(C)CNC(=O)c2ccc(Nc3nc(NC4(c5ccc(Cl)cc5)CC4)nc(OCC(F)(F)F)n3)cc2)cc1] | 0.03 | A |

TABLE 1-continued

| Compound | Structure | EC$_{50}$ | Activity |
|---|---|---|---|
| 1602 | 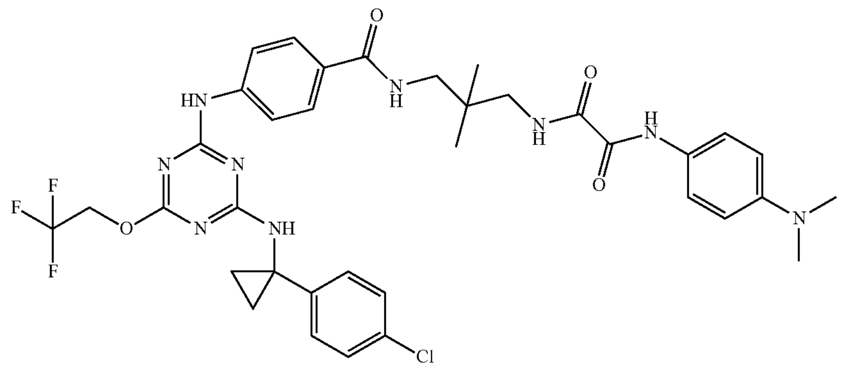 [SMILES: CN(C)c1ccc(NC(=O)C(=O)NCC(C)(C)CNC(=O)c2ccc(Nc3nc(NC4(c5ccc(Cl)cc5)CC4)nc(OCC(F)(F)F)n3)cc2)cc1] | | A |
| 1603 | 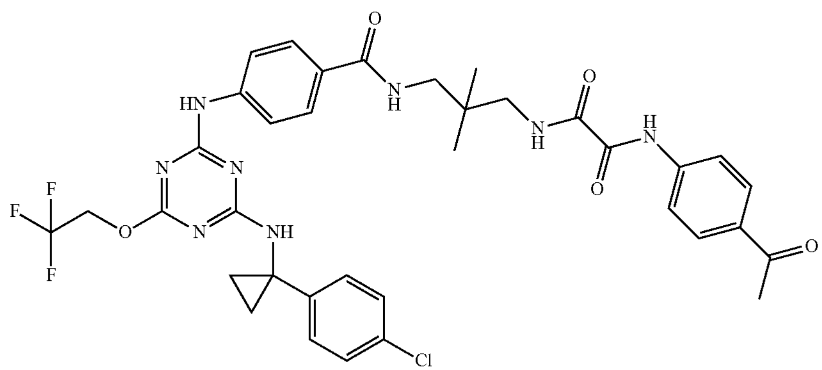 [SMILES: CC(=O)c1ccc(NC(=O)C(=O)NCC(C)(C)CNC(=O)c2ccc(Nc3nc(NC4(c5ccc(Cl)cc5)CC4)nc(OCC(F)(F)F)n3)cc2)cc1] | 0.04 | A |

TABLE 1-continued
| Compound | Structure | EC$_{50}$ | Activity |
|---|---|---|---|
| 1604 | 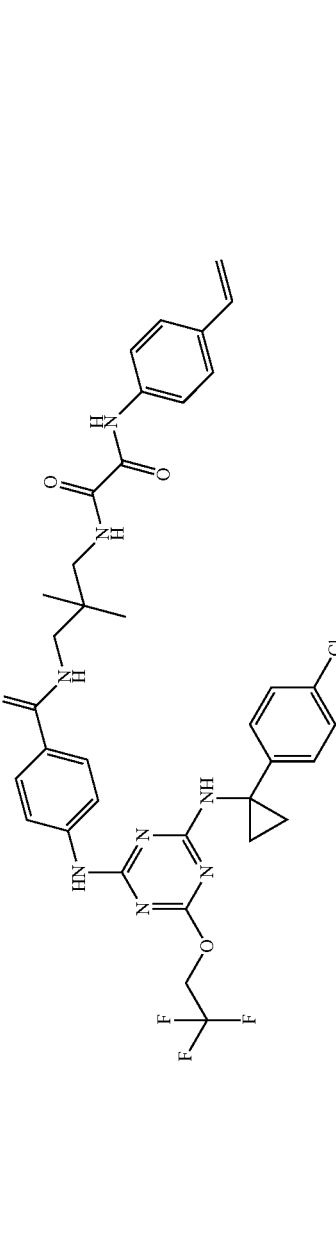 | 0.02 | A |
| 2001 | 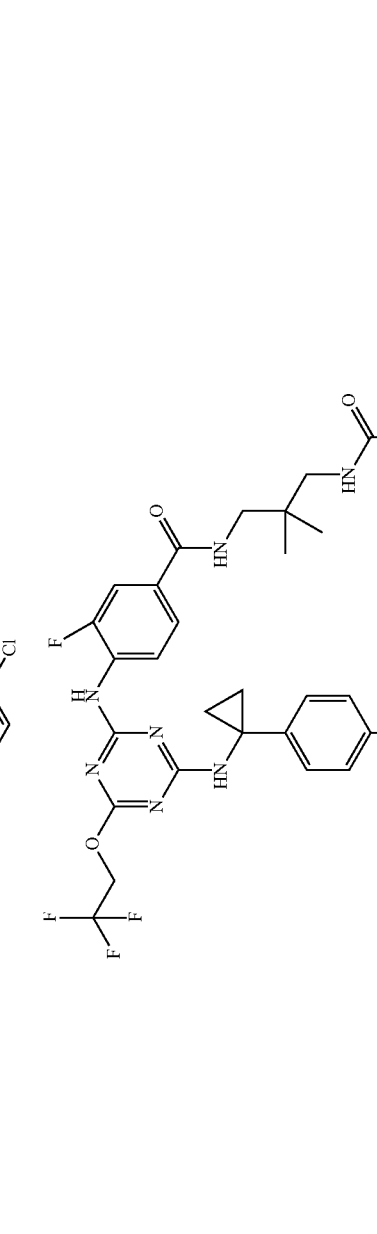 | | A |

TABLE 1-continued

| Compound | Structure | EC$_{50}$ | Activity |
|---|---|---|---|
| 2002 | 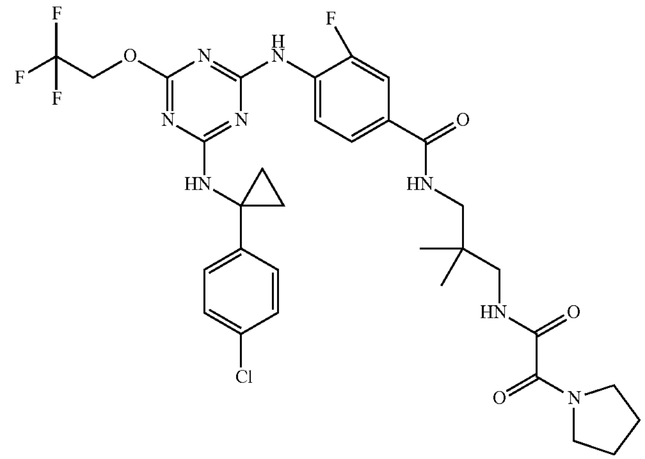 [SMILES: CC(C)(CNC(=O)C(=O)N1CCCC1)CNC(=O)c1ccc(Nc2nc(NC3(c4ccc(Cl)cc4)CC3)nc(OCC(F)(F)F)n2)c(F)c1] | | A |
| 3001 | 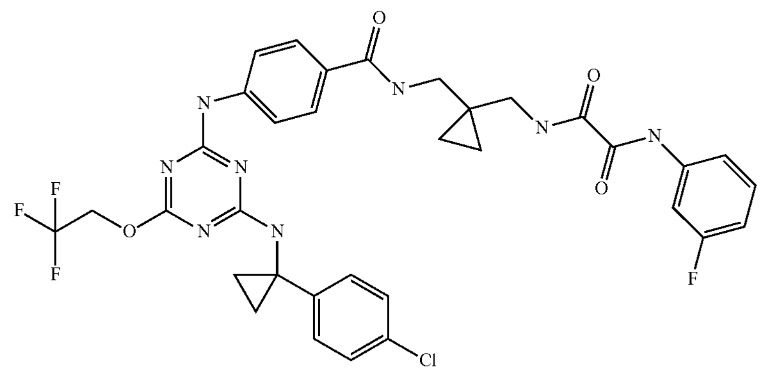 [SMILES: O=C(NCC1(CNC(=O)c2ccc(Nc3nc(NC4(c5ccc(Cl)cc5)CC4)nc(OCC(F)(F)F)n3)cc2)CC1)C(=O)Nc1cccc(F)c1] | | A |

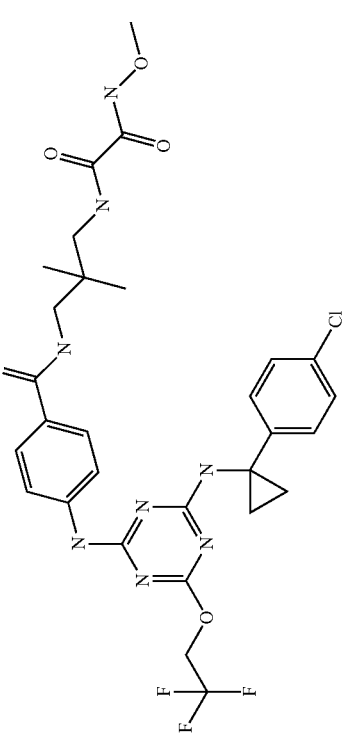

TABLE 1-continued

| Compound | Structure | EC$_{50}$ | Activity |
|---|---|---|---|
| 3004 | 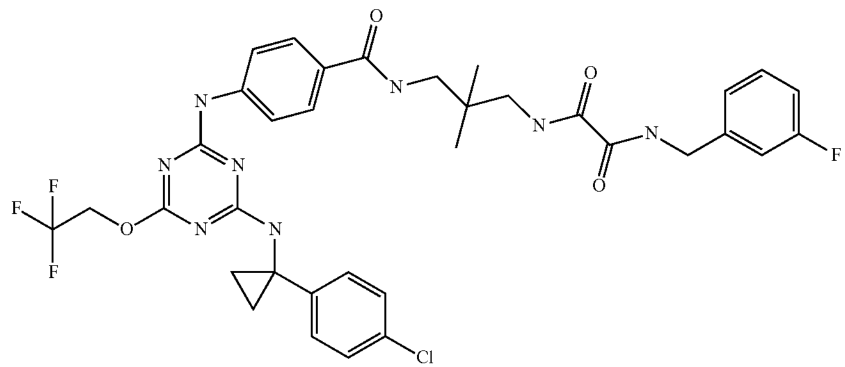 | | A |
| 3005 | 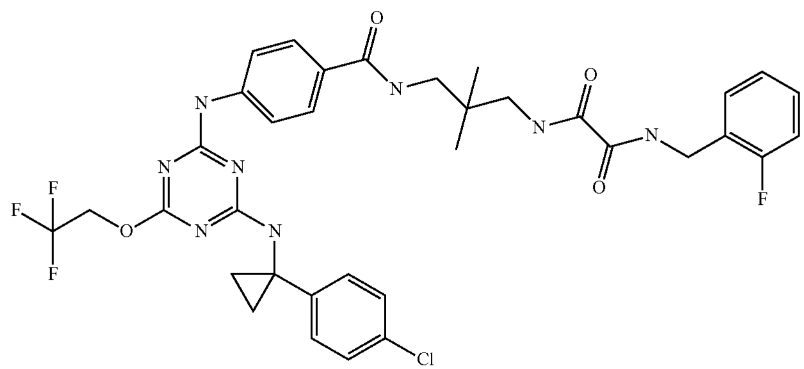 [SMILES: CC(C)(CNC(=O)C(=O)NCc1ccccc1Cl)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3006 | 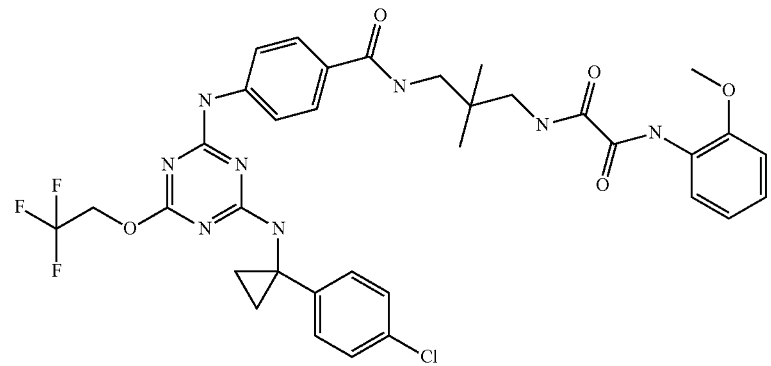 [SMILES: COc1ccccc1NC(=O)C(=O)NCC(C)(C)CNC(=O)c1ccc(Nc2nc(NC3(c4ccc(Cl)cc4)CC3)nc(OCC(F)(F)F)n2)cc1] | | A |
| 3007 | 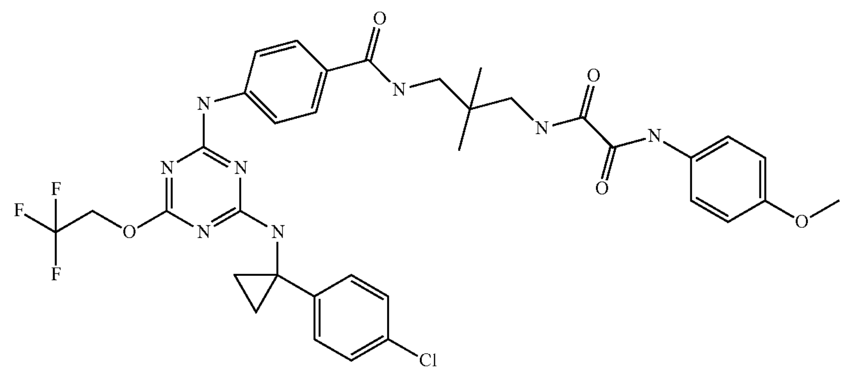 [SMILES: COc1ccc(NC(=O)C(=O)NCC(C)(C)CNC(=O)c2ccc(Nc3nc(NC4(c5ccc(Cl)cc5)CC4)nc(OCC(F)(F)F)n3)cc2)cc1] | | A |

TABLE 1-continued

| Compound | Structure | EC$_{50}$ | Activity |
|---|---|---|---|
| 3008 | 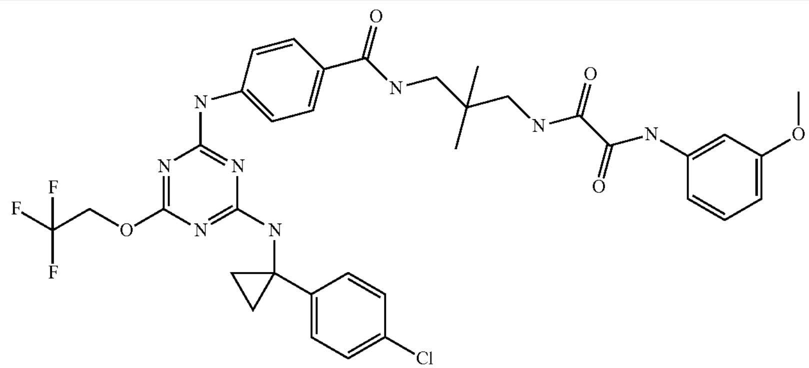 [SMILES: COc1cccc(NC(=O)C(=O)NCC(C)(C)CNC(=O)c2ccc(Nc3nc(NC4(c5ccc(Cl)cc5)CC4)nc(OCC(F)(F)F)n3)cc2)c1] | | A |
| 3009 | 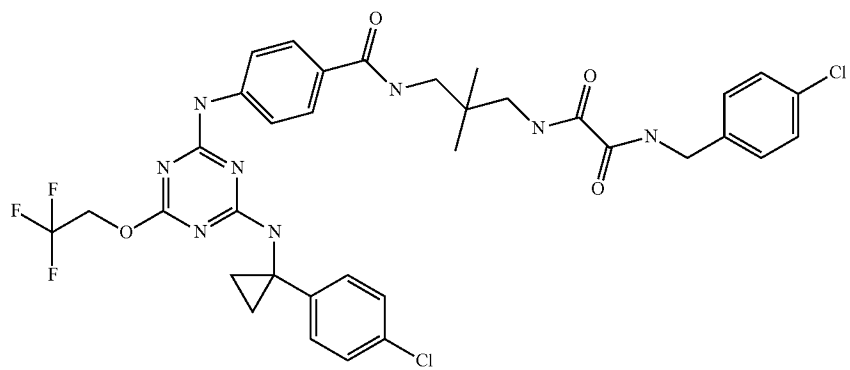 [SMILES: CC(C)(CNC(=O)C(=O)NCc1ccc(Cl)cc1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3010 | 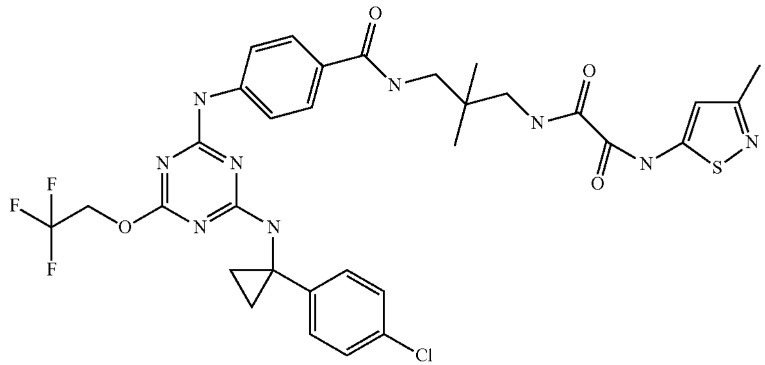 [SMILES: Cc1cc(NC(=O)C(=O)NCC(C)(C)CNC(=O)c2ccc(Nc3nc(NC4(c5ccc(Cl)cc5)CC4)nc(OCC(F)(F)F)n3)cc2)sn1] | 0.014 | A |
| 3011 | 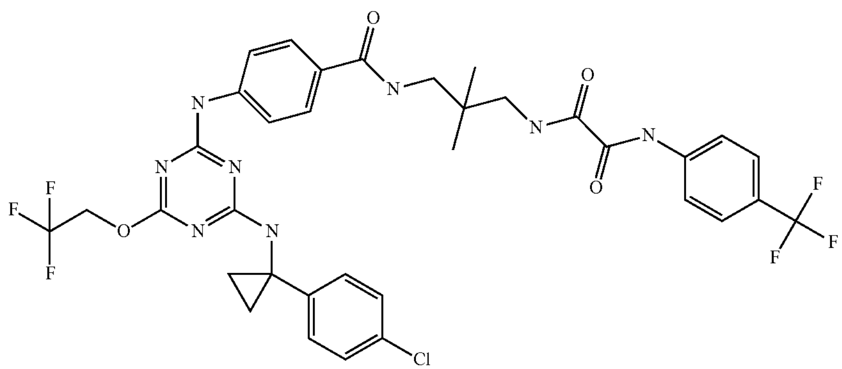 [SMILES: CC(C)(CNC(=O)C(=O)Nc1ccc(C(F)(F)F)cc1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3012 | 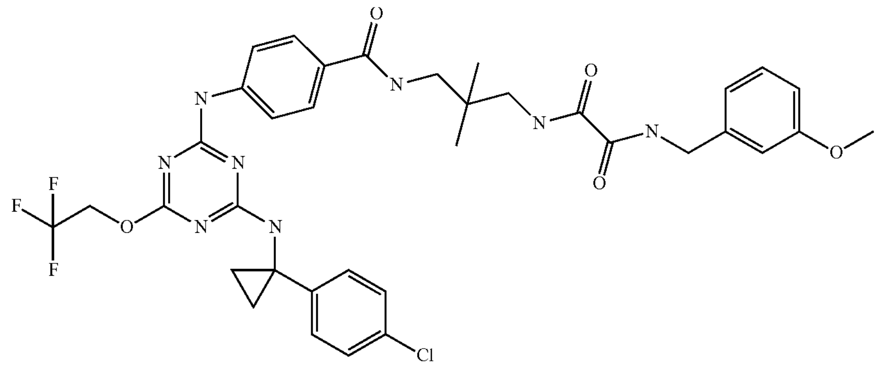 [SMILES: COc1cccc(CNC(=O)C(=O)NCC(C)(C)CNC(=O)c2ccc(Nc3nc(NC4(c5ccc(Cl)cc5)CC4)nc(OCC(F)(F)F)n3)cc2)c1] | | A |
| 3013 | 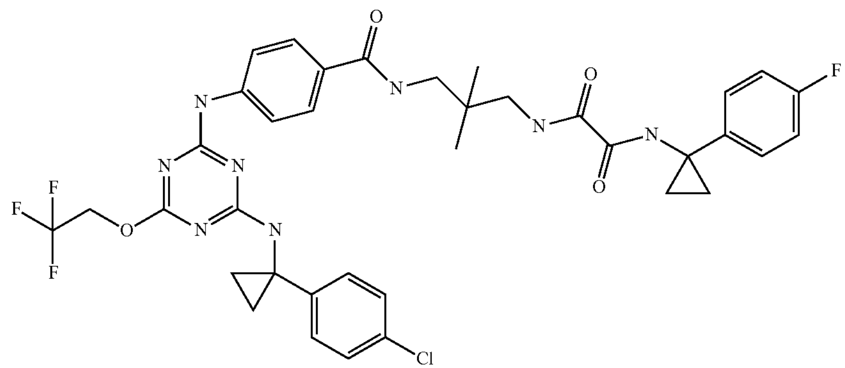 [SMILES: CC(C)(CNC(=O)C(=O)NC1(c2ccc(F)cc2)CC1)CNC(=O)c1ccc(Nc2nc(NC3(c4ccc(Cl)cc4)CC3)nc(OCC(F)(F)F)n2)cc1] | 0.066 | A |

TABLE 1-continued

| Compound | Structure | EC$_{50}$ | Activity |
|---|---|---|---|
| 3014 | 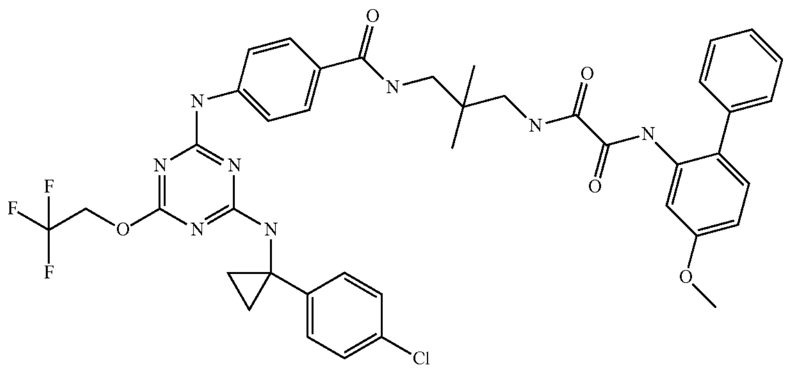 [SMILES: COc1ccc(-c2ccccc2)c(NC(=O)C(=O)NCC(C)(C)CNC(=O)c2ccc(Nc3nc(NC4(c5ccc(Cl)cc5)CC4)nc(OCC(F)(F)F)n3)cc2)c1] | | A |
| 3015 | 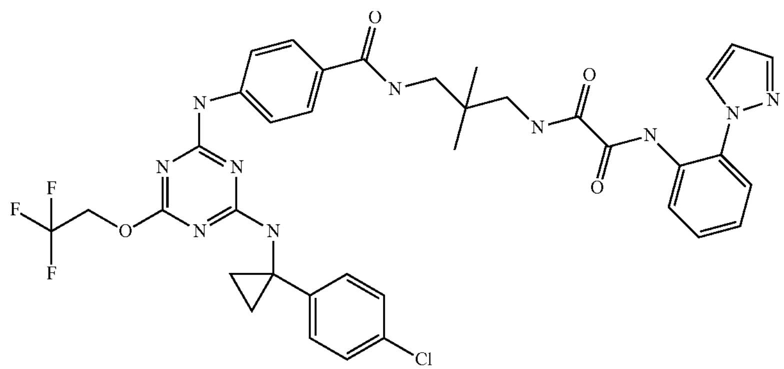 [SMILES: CC(C)(CNC(=O)C(=O)Nc1ccccc1-n1cccn1)CNC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 3016 | 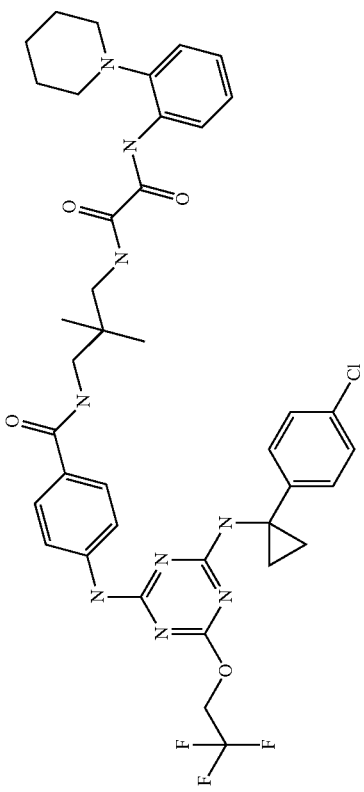 | | A |
| 3017 | 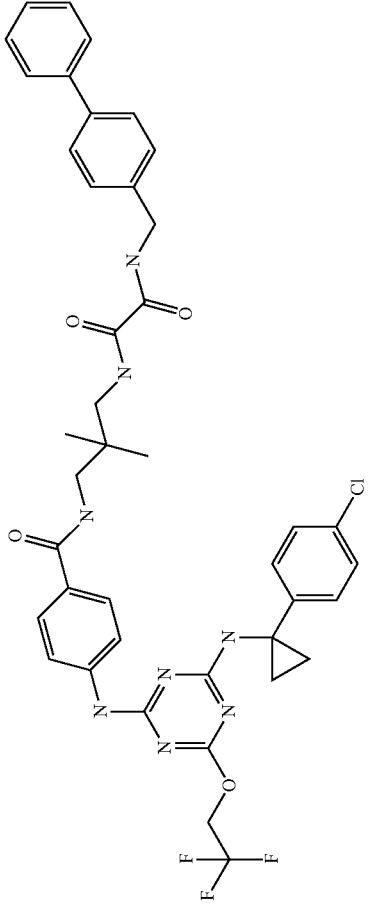 | | A |

TABLE 1-continued

| Compound | Structure | EC$_{50}$ | Activity |
|---|---|---|---|
| 3018 | 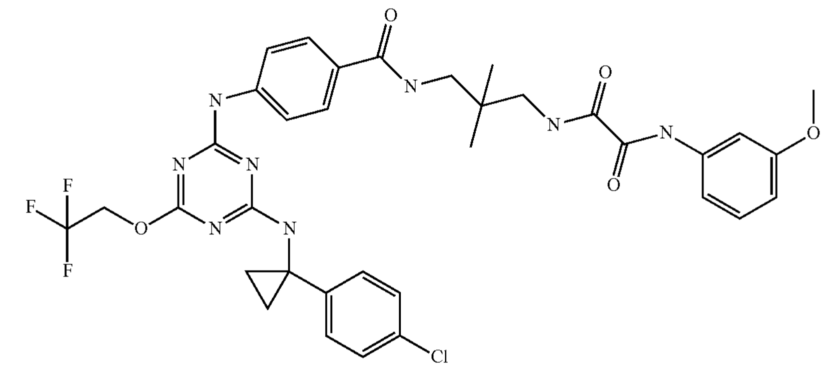 [SMILES: COc1cccc(NC(=O)C(=O)NCC(C)(C)CNC(=O)c2ccc(Nc3nc(NC4(c5ccc(Cl)cc5)CC4)nc(OCC(F)(F)F)n3)cc2)c1] | | A |
| 3019 | 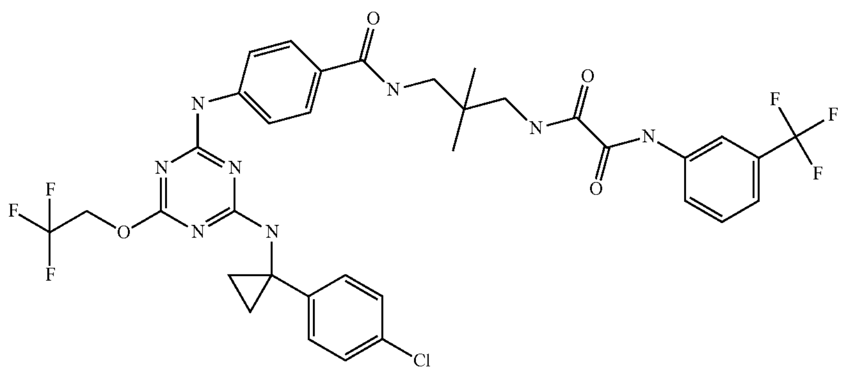 [SMILES: CC(C)(CNC(=O)C(=O)Nc1cccc(C(F)(F)F)c1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3020 | 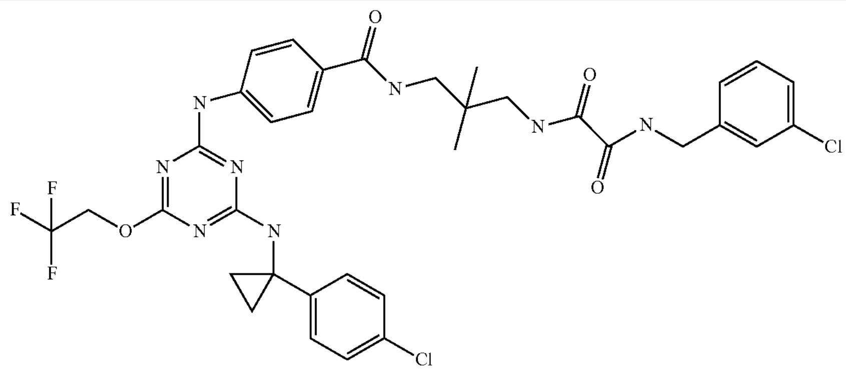 [SMILES: CC(C)(CNC(=O)C(=O)NCc1cccc(Cl)c1)CNC(=O)c1ccc(Nc2nc(NC3(c4ccc(Cl)cc4)CC3)nc(OCC(F)(F)F)n2)cc1] | | A |
| 3021 | 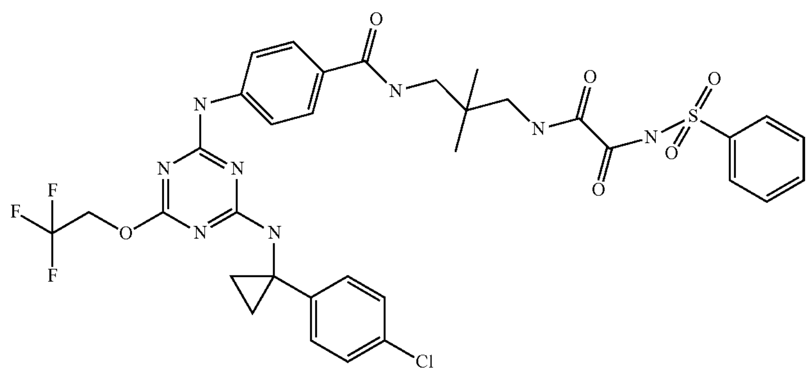 [SMILES: CC(C)(CNC(=O)C(=O)NS(=O)(=O)c1ccccc1)CNC(=O)c1ccc(Nc2nc(NC3(c4ccc(Cl)cc4)CC3)nc(OCC(F)(F)F)n2)cc1] | 0.73 | A |

TABLE 1-continued

| Compound | Structure | EC$_{50}$ | Activity |
|---|---|---|---|
| 3022 | 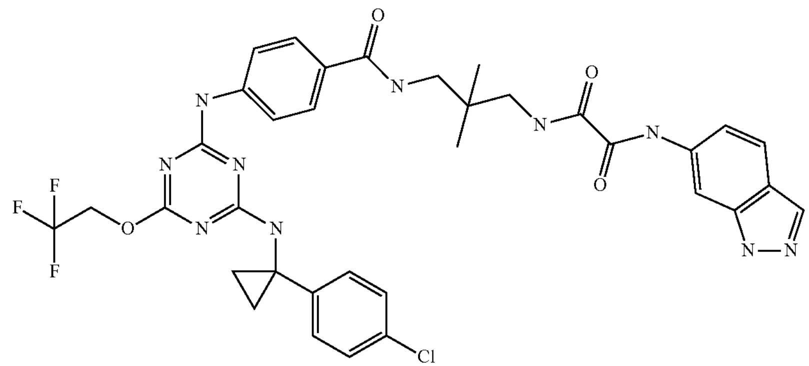 [SMILES: CC(C)(CNC(=O)C(=O)Nc1ccc2cn[nH]c2c1)CNC(=O)c1ccc(Nc2nc(NC3(c4ccc(Cl)cc4)CC3)nc(OCC(F)(F)F)n2)cc1] | | A |
| 3023 | 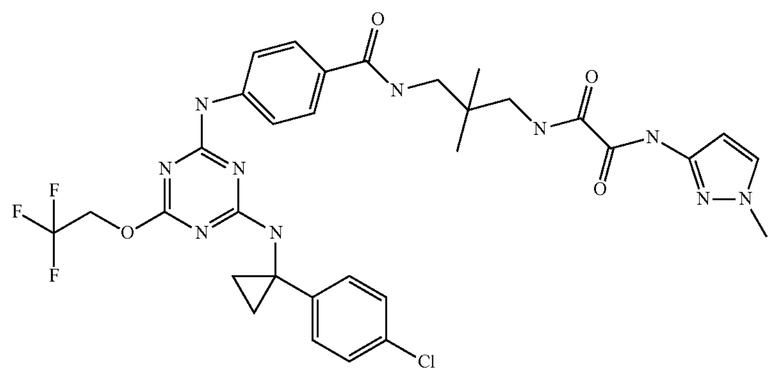 [SMILES: Cn1ccc(NC(=O)C(=O)NCC(C)(C)CNC(=O)c2ccc(Nc3nc(NC4(c5ccc(Cl)cc5)CC4)nc(OCC(F)(F)F)n3)cc2)n1] | | A |

TABLE 1-continued

| Compound | Structure | EC$_{50}$ | Activity |
|---|---|---|---|
| 3024 | 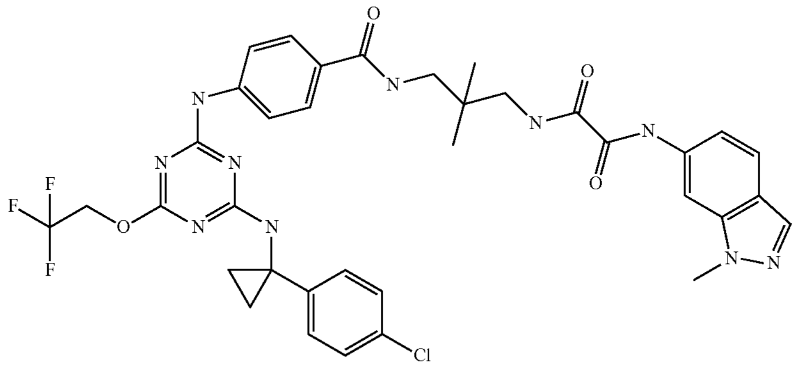 [SMILES: Cn1ncc2ccc(NC(=O)C(=O)NCC(C)(C)CNC(=O)c3ccc(Nc4nc(NC5(c6ccc(Cl)cc6)CC5)nc(OCC(F)(F)F)n4)cc3)cc21] | | A |
| 3025 | 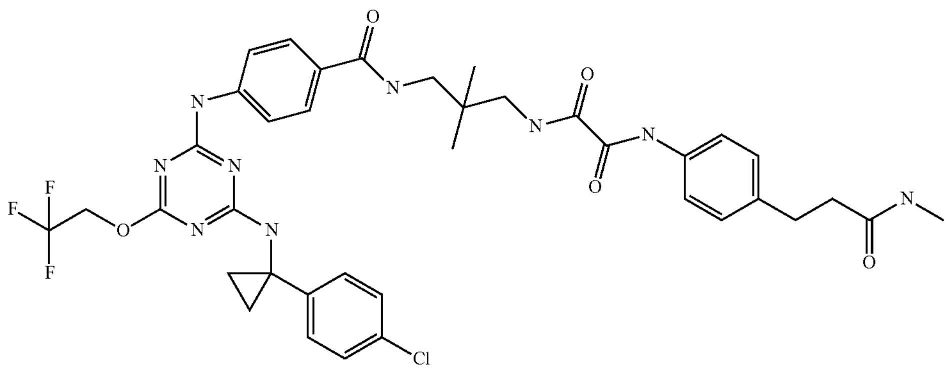 [SMILES: CNC(=O)CCc1ccc(NC(=O)C(=O)NCC(C)(C)CNC(=O)c2ccc(Nc3nc(NC4(c5ccc(Cl)cc5)CC4)nc(OCC(F)(F)F)n3)cc2)cc1] | | A |

TABLE 1-continued

| Compound | Structure | EC$_{50}$ | Activity |
|---|---|---|---|
| 3026 | 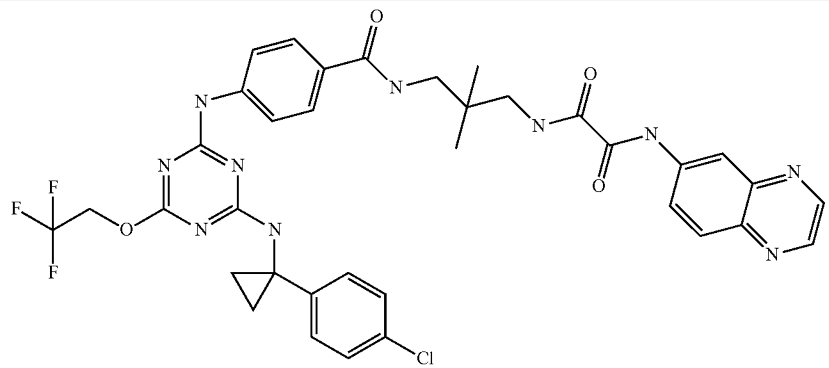 | | A |
| 3027 | 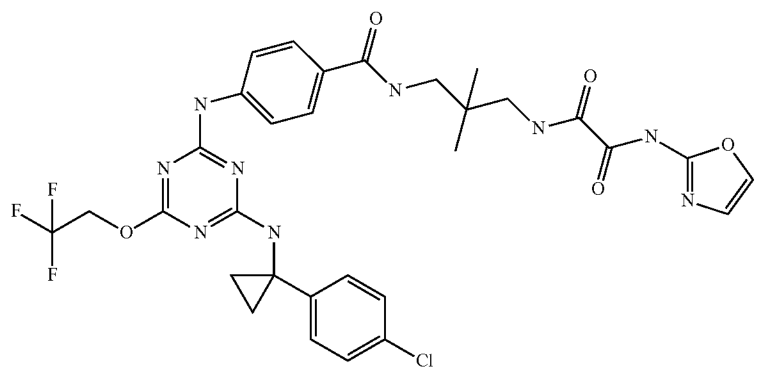 [SMILES: CC(C)(CNC(=O)C(=O)Nc1ncco1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3028 | 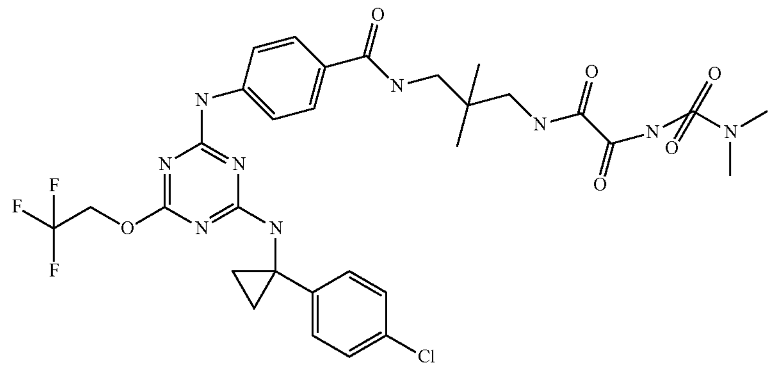 | | A |
| 3029 | 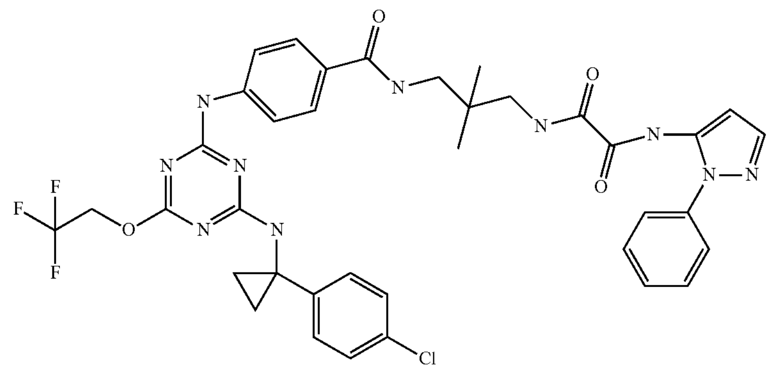 [SMILES: CC(C)(CNC(=O)C(=O)Nc1ccnn1-c1ccccc1)CNC(=O)c1ccc(Nc2nc(NC3(c4ccc(Cl)cc4)CC3)nc(OCC(F)(F)F)n2)cc1] | 0.071 | A |

TABLE 1-continued

| Compound | Structure | EC$_{50}$ | Activity |
|---|---|---|---|
| 3030 | 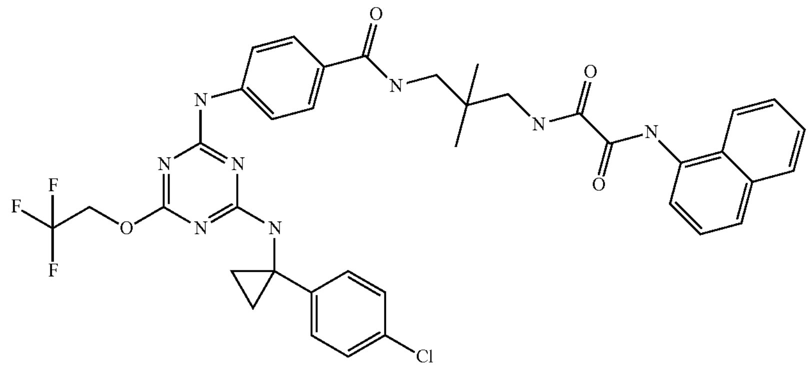 [SMILES: CC(C)(CNC(=O)C(=O)Nc1cccc2ccccc12)CNC(=O)c1ccc(Nc2nc(NC3(c4ccc(Cl)cc4)CC3)nc(OCC(F)(F)F)n2)cc1] | | A |
| 3031 | 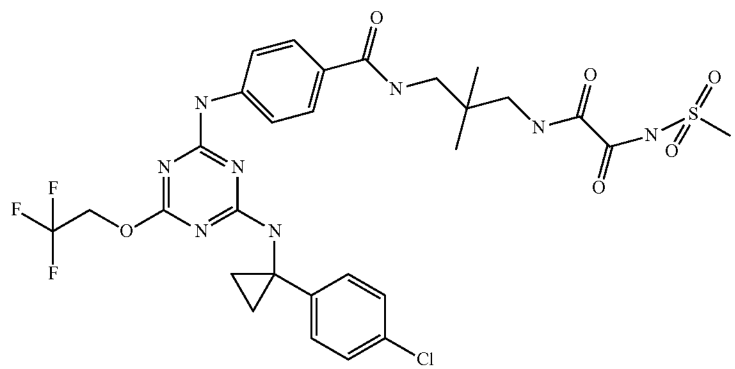 [SMILES: CC(C)(CNC(=O)C(=O)NS(C)(=O)=O)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3032 | 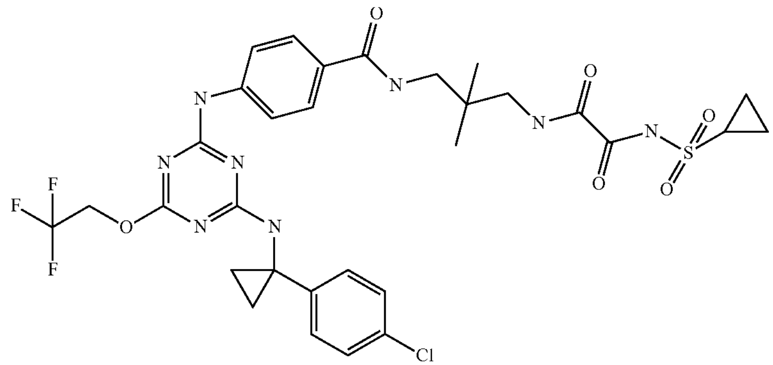 [SMILES: CC(C)(CNC(=O)C(=O)NS(=O)(=O)C1CC1)CNC(=O)c1ccc(Nc2nc(NC3(c4ccc(Cl)cc4)CC3)nc(OCC(F)(F)F)n2)cc1] | | A |
| 3033 | 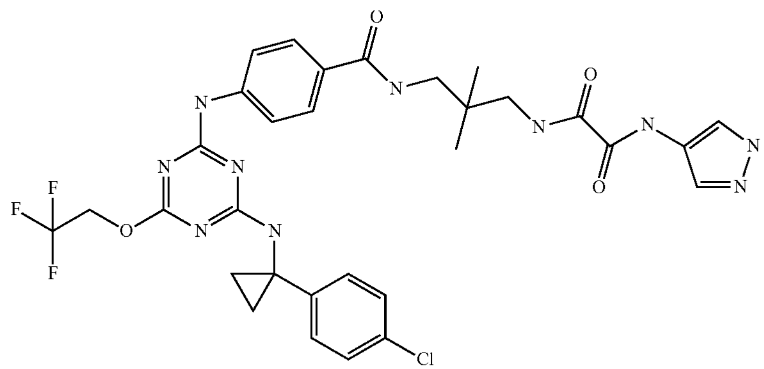 [SMILES: CC(C)(CNC(=O)C(=O)Nc1cn[nH]c1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3034 | 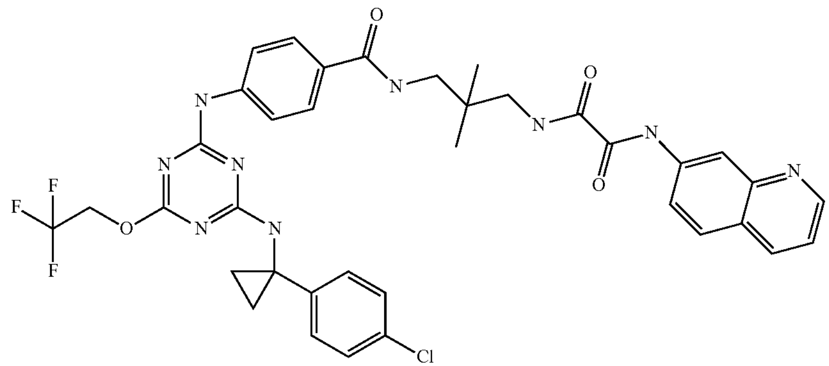 [SMILES: CC(C)(CNC(=O)C(=O)Nc1ccc2cccnc2c1)CNC(=O)c1ccc(Nc2nc(NC3(c4ccc(Cl)cc4)CC3)nc(OCC(F)(F)F)n2)cc1] | 0.040 | A |
| 3035 | 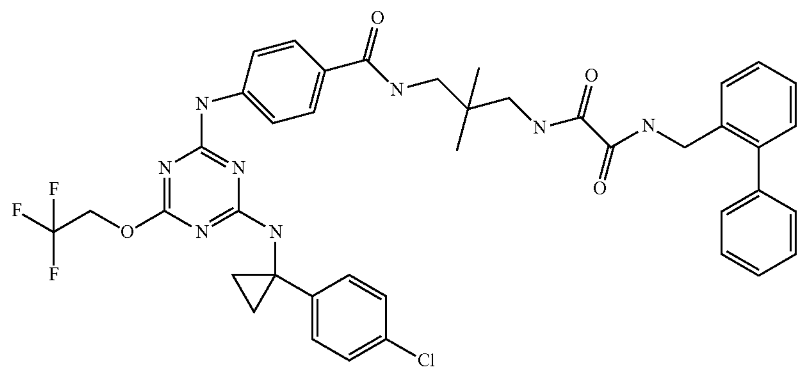 [SMILES: CC(C)(CNC(=O)C(=O)NCc1ccccc1-c1ccccc1)CNC(=O)c1ccc(Nc2nc(NC3(c4ccc(Cl)cc4)CC3)nc(OCC(F)(F)F)n2)cc1] | | A |

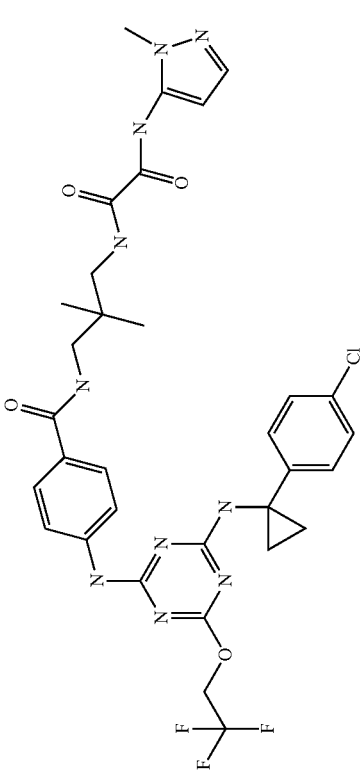

TABLE 1-continued

| Compound | Structure | EC$_{50}$ | Activity |
|---|---|---|---|
| 3038 | 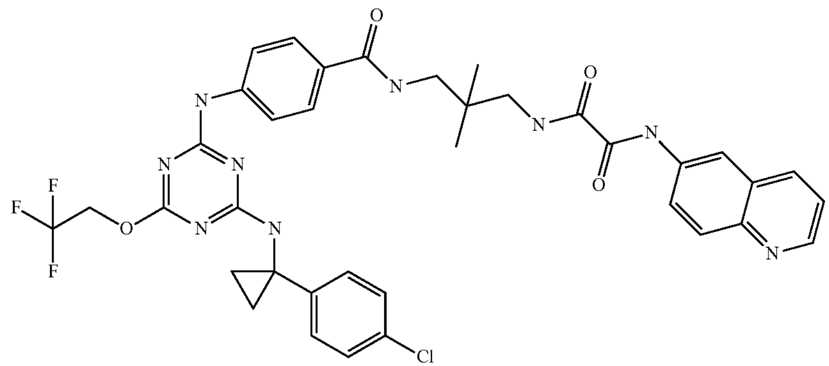 | | A |
| 3039 | 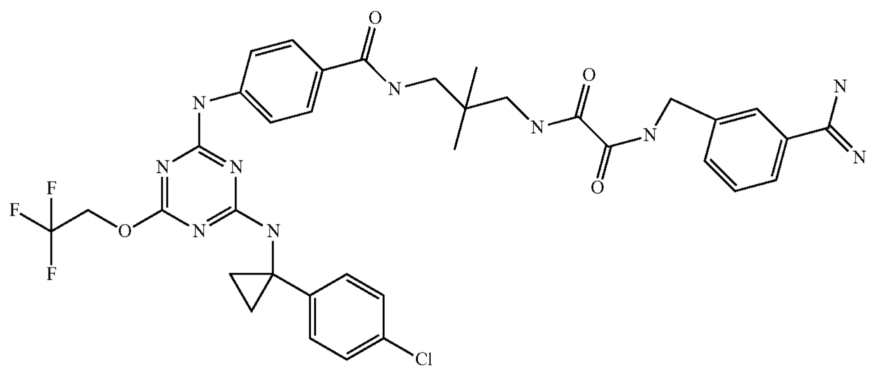 [SMILES: CC(C)(CNC(=O)C(=O)NCc1cccc(C(=N)N)c1)CNC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 3040 | 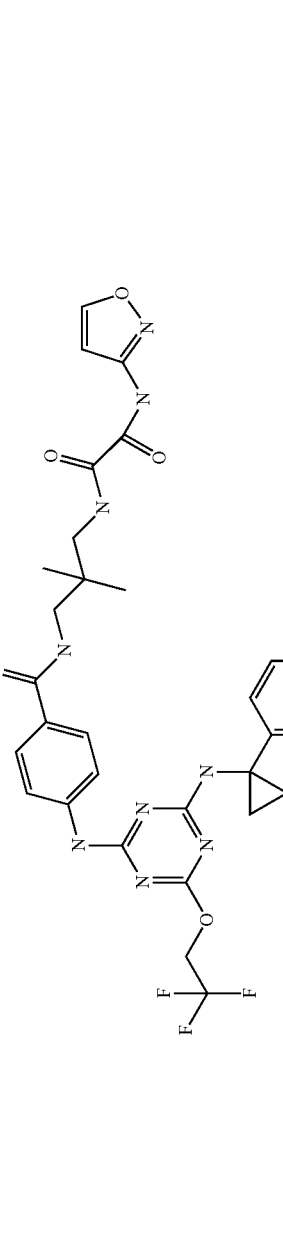 | | A |
| 3041 | 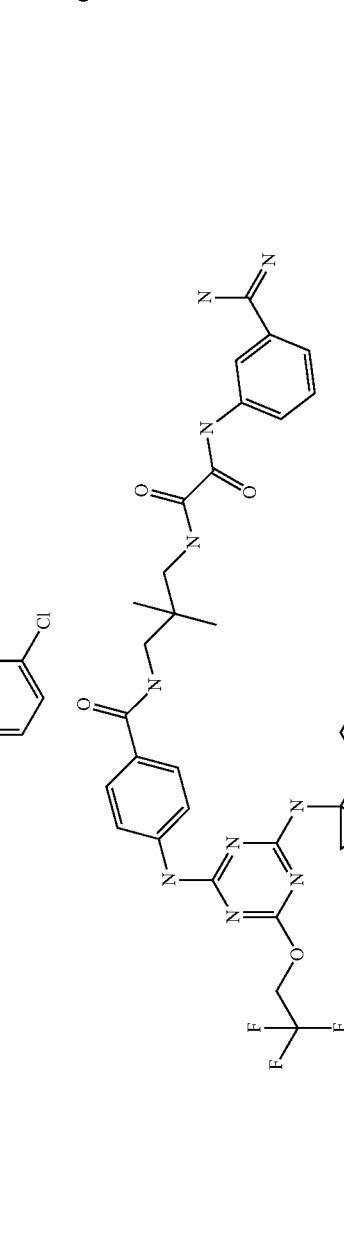 | 0.068 | A |

TABLE 1-continued

| Compound | Structure | EC$_{50}$ | Activity |
|---|---|---|---|
| 3042 | 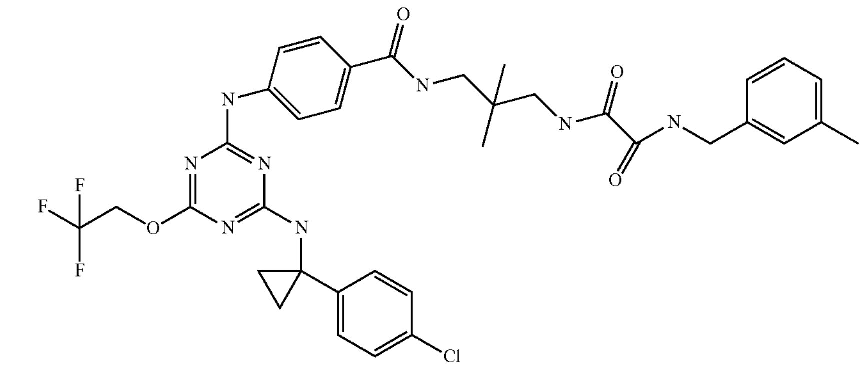 [SMILES: Cc1cccc(CNC(=O)C(=O)NCC(C)(C)CNC(=O)c2ccc(Nc3nc(NC4(c5ccc(Cl)cc5)CC4)nc(OCC(F)(F)F)n3)cc2)c1] | | A |
| 3043 | 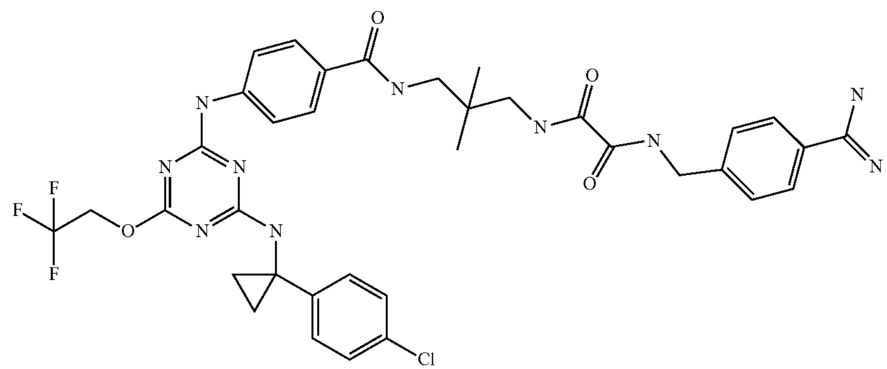 [SMILES: CC(C)(CNC(=O)C(=O)NCc1ccc(C(=N)N)cc1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3044 | 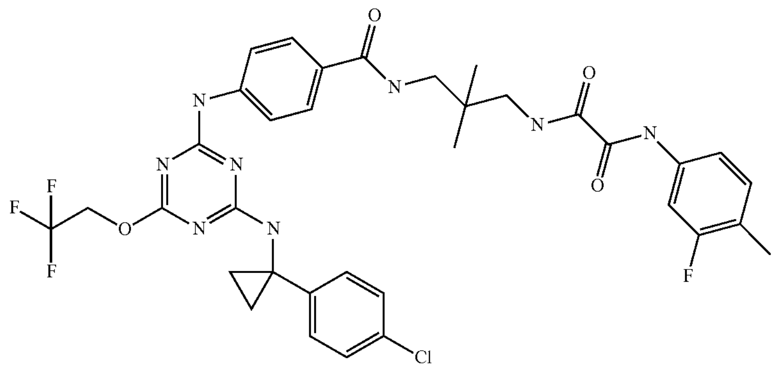 [SMILES: Cc1ccc(NC(=O)C(=O)NCC(C)(C)CNC(=O)c2ccc(Nc3nc(NC4(c5ccc(Cl)cc5)CC4)nc(OCC(F)(F)F)n3)cc2)cc1F] | | A |
| 3045 | 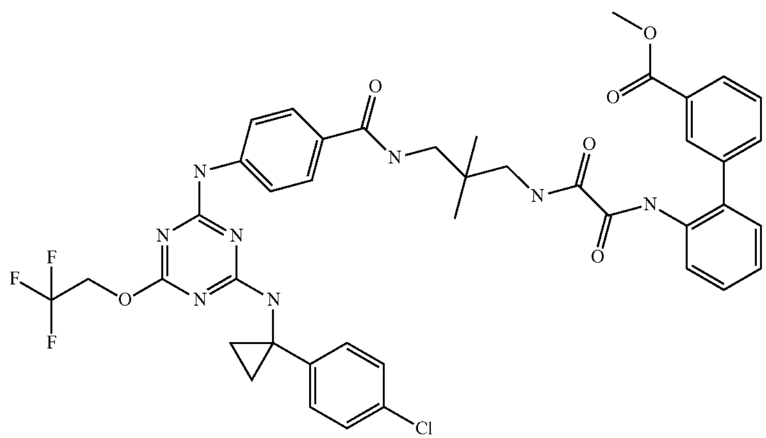 [SMILES: COC(=O)c1cccc(-c2ccccc2NC(=O)C(=O)NCC(C)(C)CNC(=O)c2ccc(Nc3nc(NC4(c5ccc(Cl)cc5)CC4)nc(OCC(F)(F)F)n3)cc2)c1] | | A |

TABLE 1-continued
| Compound | Structure | EC$_{50}$ | Activity |
|---|---|---|---|
| 3046 | 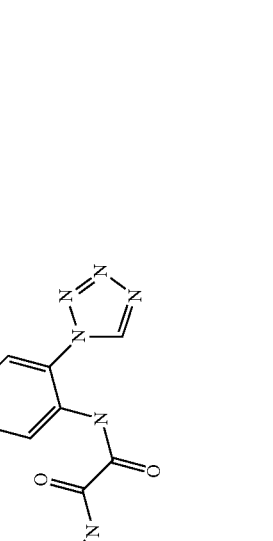 | | A |
| 3047 | 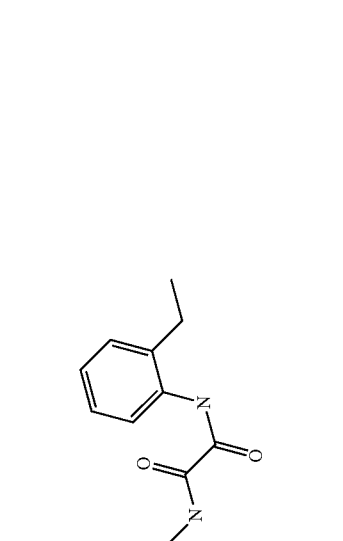 | | A |

TABLE 1-continued

| Compound | Structure | EC$_{50}$ | Activity |
|---|---|---|---|
| 3048 | 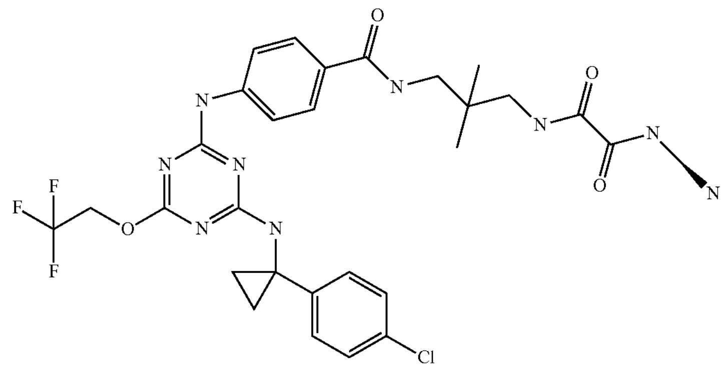 | 0.27 | A |
| 3049 | 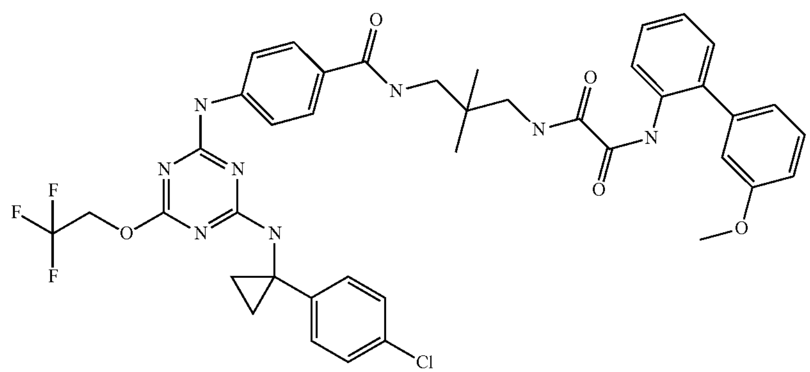 [SMILES: COc1cccc(-c2ccccc2NC(=O)C(=O)NCC(C)(C)CNC(=O)c2ccc(Nc3nc(NC4(c5ccc(Cl)cc5)CC4)nc(OCC(F)(F)F)n3)cc2)c1] | | A |

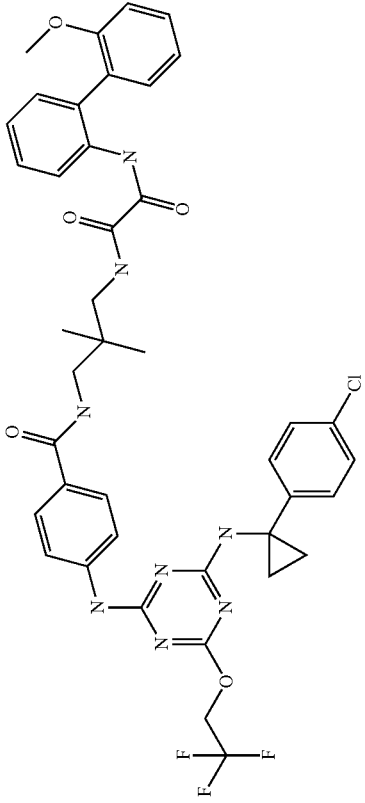

TABLE 1-continued

| Compound | Structure | EC₅₀ | Activity |
|---|---|---|---|
| 3052 | 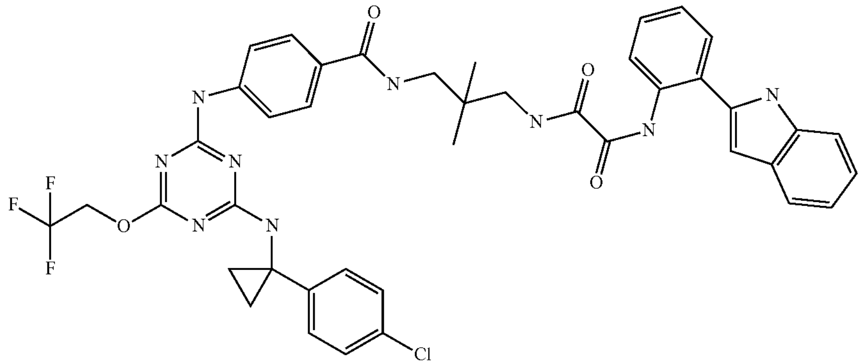 [SMILES: CC(C)(CNC(=O)C(=O)Nc1ccccc1-c1cc2ccccc2[nH]1)CNC(=O)c1ccc(Nc2nc(NC3(c4ccc(Cl)cc4)CC3)nc(OCC(F)(F)F)n2)cc1] | | A |
| 3053 | 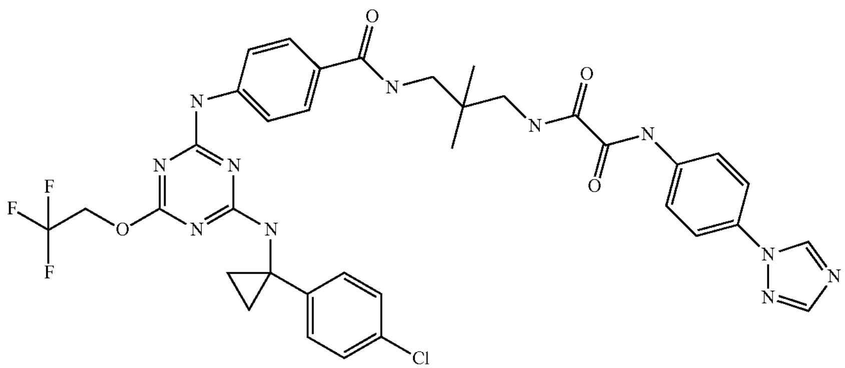 [SMILES: CC(C)(CNC(=O)C(=O)Nc1ccc(-n2cncn2)cc1)CNC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 3054 | 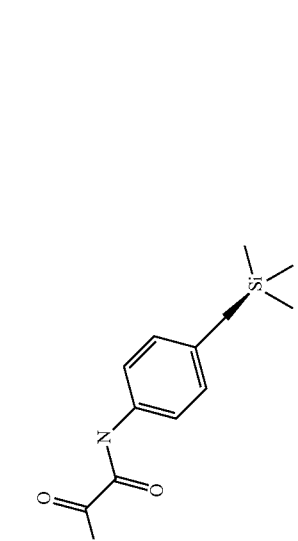 | | A |
| 3055 | 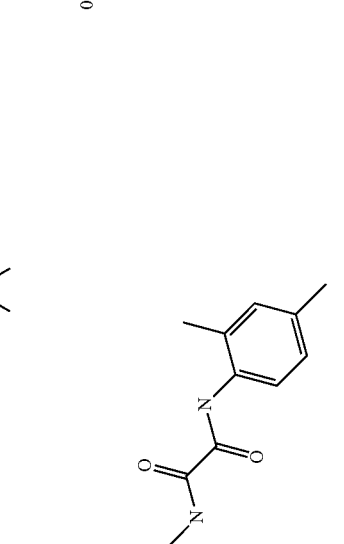 | 0.0095 | A |

TABLE 1-continued
| Compound | Structure | EC$_{50}$ | Activity |
|---|---|---|---|
| 3056 | 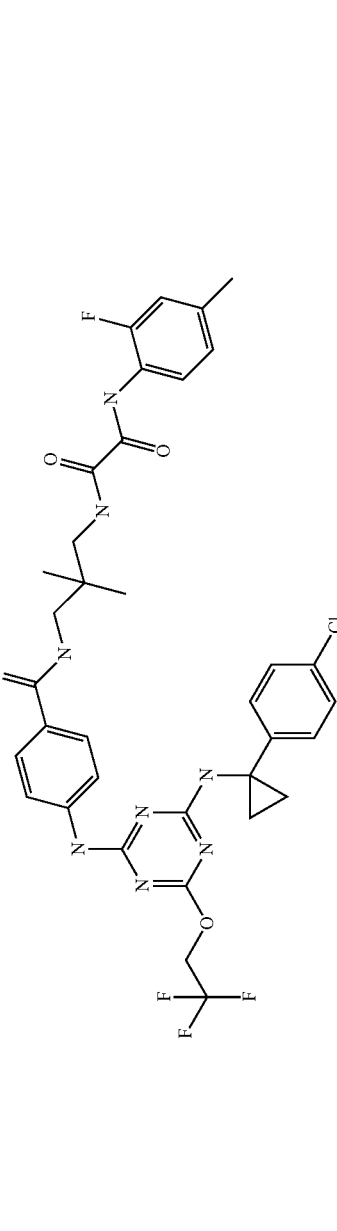 | 0.0070 | A |
| 3057 | 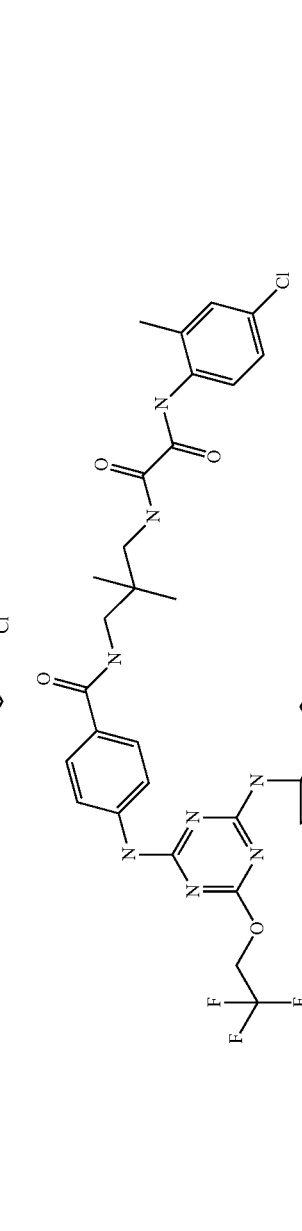 | | A |

TABLE 1-continued

| Compound | Structure | EC$_{50}$ | Activity |
|---|---|---|---|
| 3058 | 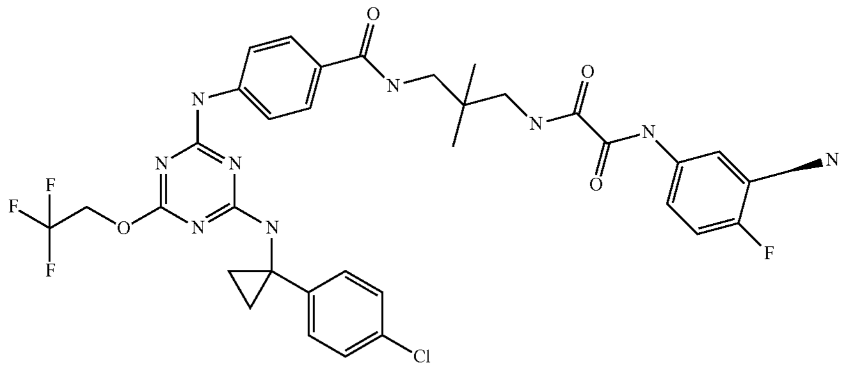 | | A |
| 3059 | 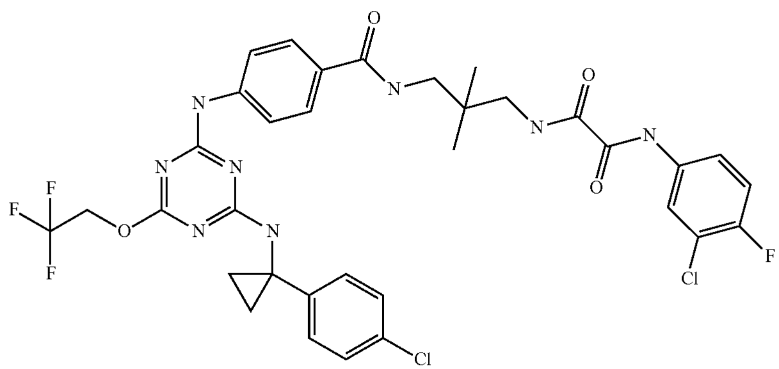 [SMILES: CC(C)(CNC(=O)C(=O)Nc1ccc(F)c(Cl)c1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3060 | 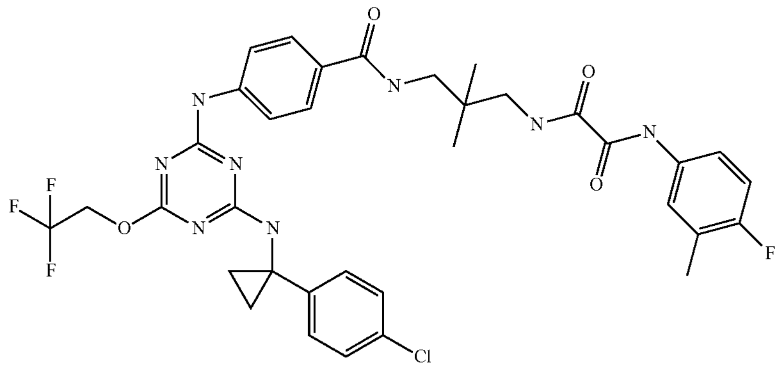 [SMILES: Cc1cc(NC(=O)C(=O)NCC(C)(C)CNC(=O)c2ccc(Nc3nc(NC4(c5ccc(Cl)cc5)CC4)nc(OCC(F)(F)F)n3)cc2)ccc1F] | | A |
| 3061 | 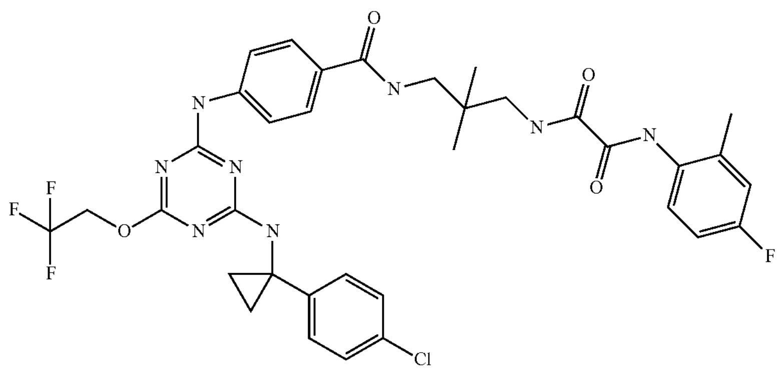 [SMILES: Cc1cc(F)ccc1NC(=O)C(=O)NCC(C)(C)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3062 | 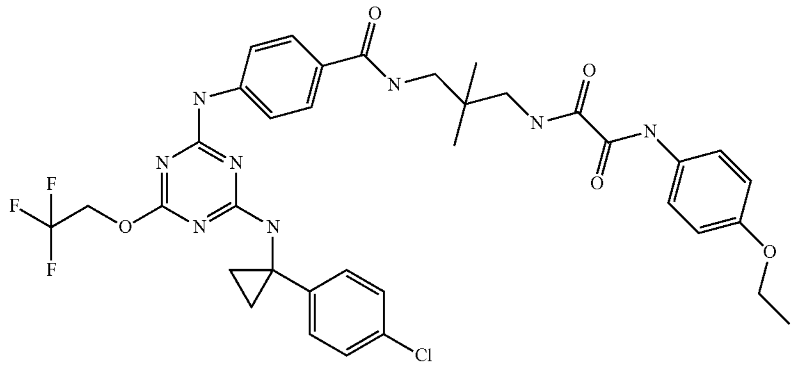 [SMILES: CCOc1ccc(NC(=O)C(=O)NCC(C)(C)CNC(=O)c2ccc(Nc3nc(NC4(c5ccc(Cl)cc5)CC4)nc(OCC(F)(F)F)n3)cc2)cc1] | | A |
| 3063 | 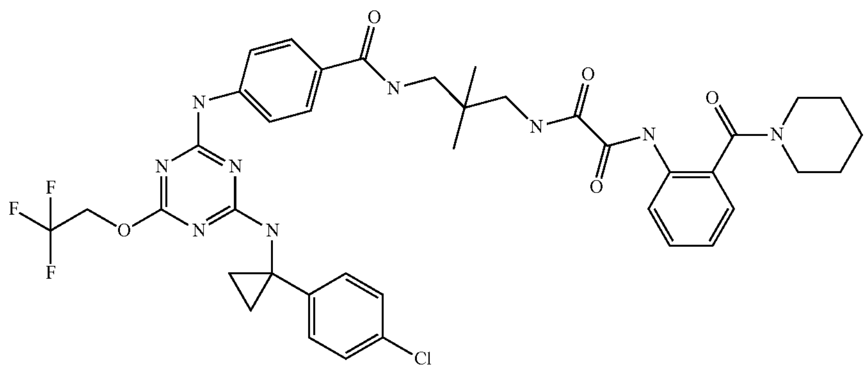 [SMILES: CC(C)(CNC(=O)C(=O)Nc1ccccc1C(=O)N1CCCCC1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3064 | 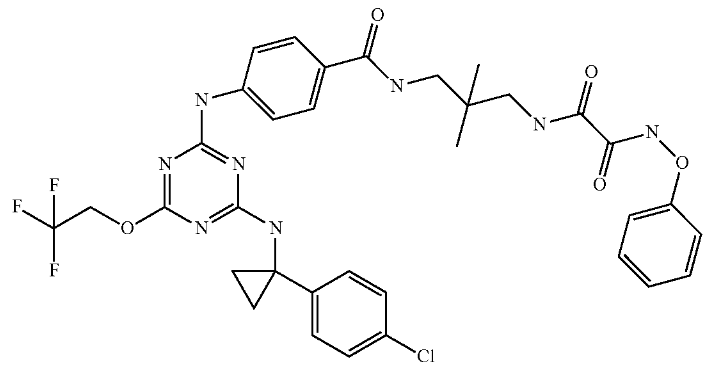 [SMILES: CC(C)(CNC(=O)C(=O)NOc1ccccc1)CNC(=O)c1ccc(Nc2nc(NC3(c4ccc(Cl)cc4)CC3)nc(OCC(F)(F)F)n2)cc1] | | A |
| 3065 | 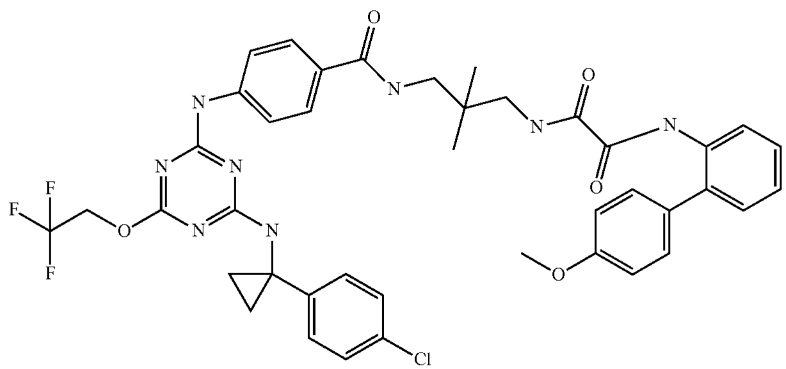 [SMILES: COc1ccc(-c2ccccc2NC(=O)C(=O)NCC(C)(C)CNC(=O)c2ccc(Nc3nc(NC4(c5ccc(Cl)cc5)CC4)nc(OCC(F)(F)F)n3)cc2)cc1] | | A |

TABLE 1-continued
| Compound | Structure | EC$_{50}$ | Activity |
|---|---|---|---|
| 3066 | 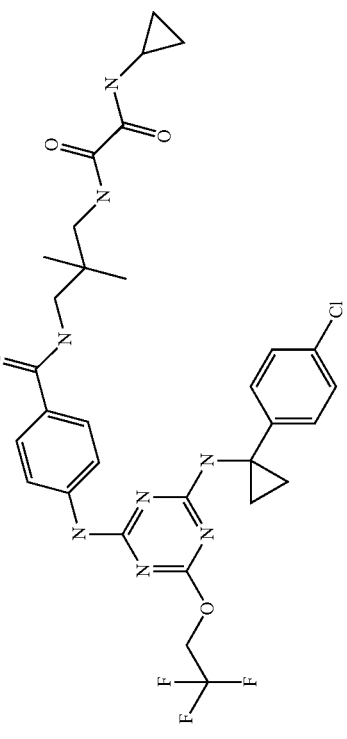 | 0.032 | A |
| 3067 | 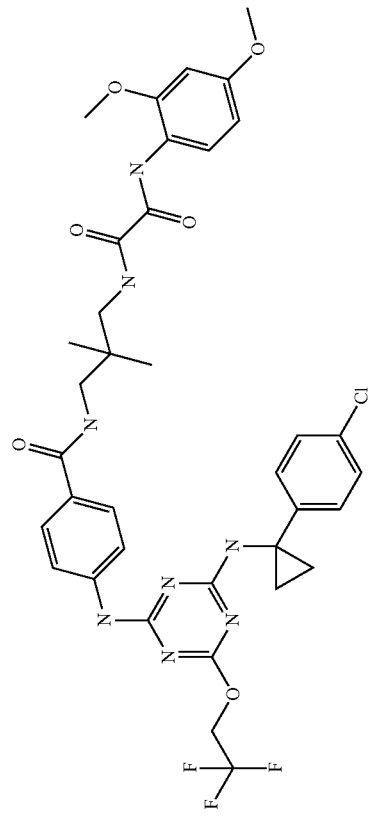 | | A |

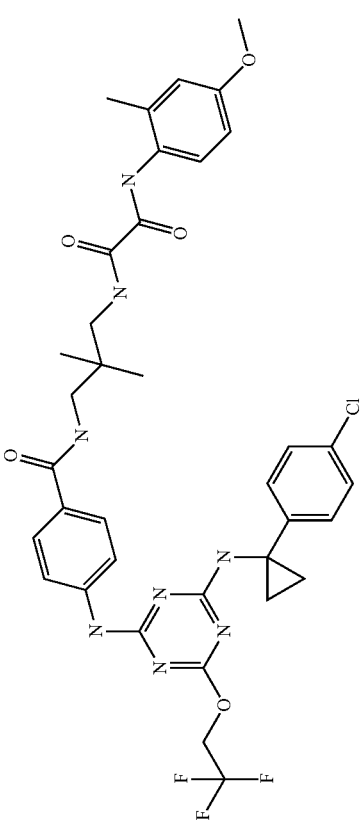

TABLE 1-continued
| Compound | Structure | EC$_{50}$ | Activity |
|---|---|---|---|
| 3070 | 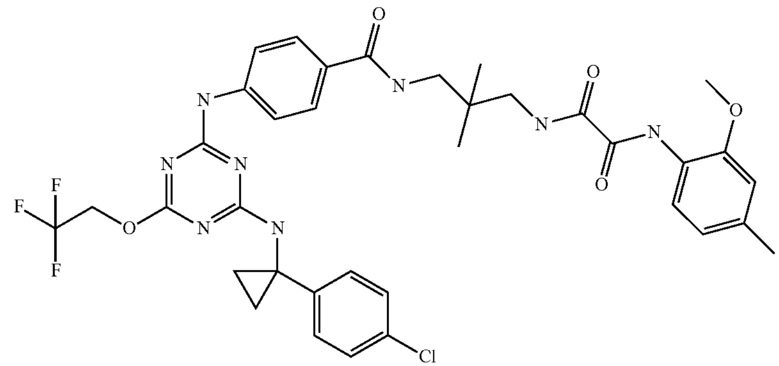 | | A |
| 3071 | 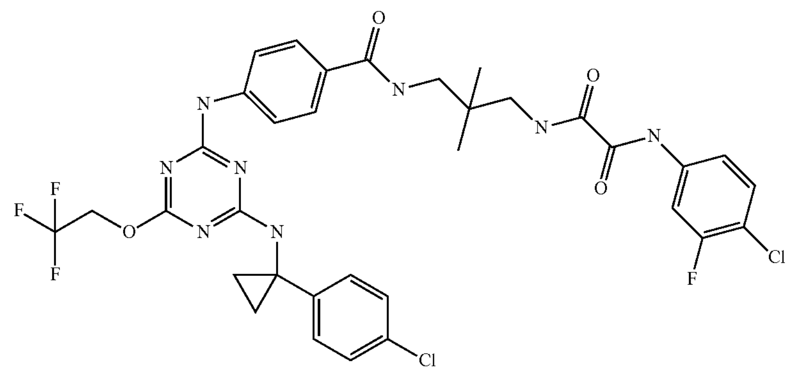 [SMILES: CC(C)(CNC(=O)C(=O)Nc1ccc(Cl)c(F)c1)CNC(=O)c1ccc(Nc2nc(NC3(c4ccc(Cl)cc4)CC3)nc(OCC(F)(F)F)n2)cc1] | | A |
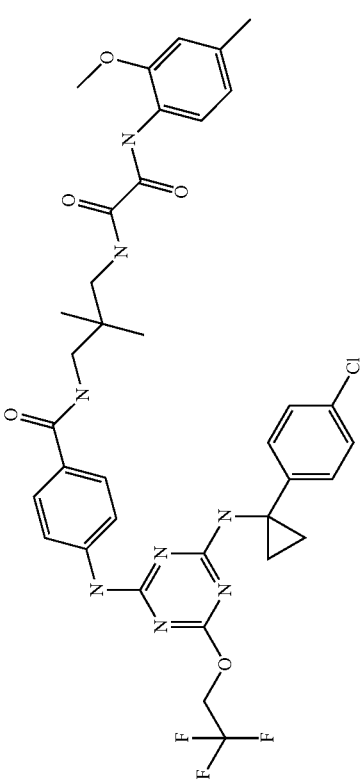

TABLE 1-continued

| Compound | Structure | EC$_{50}$ | Activity |
|---|---|---|---|
| 3072 | 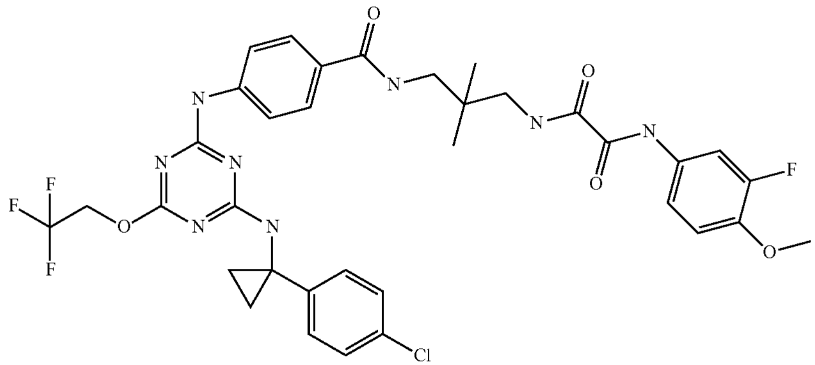 [SMILES: COc1ccc(NC(=O)C(=O)NCC(C)(C)CNC(=O)c2ccc(Nc3nc(NC4(c5ccc(Cl)cc5)CC4)nc(OCC(F)(F)F)n3)cc2)cc1F] | | A |
| 3073 | 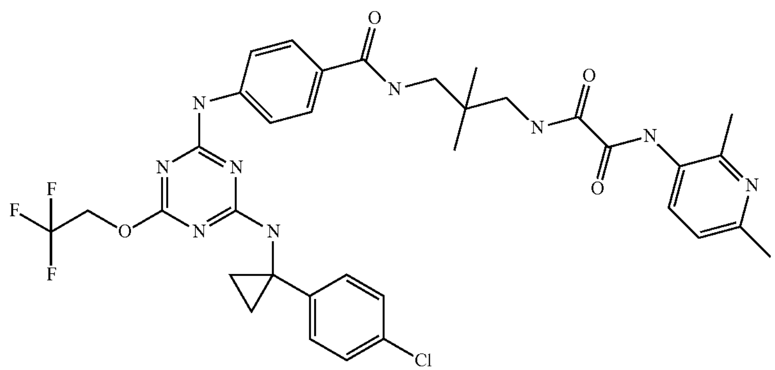 | | A |

TABLE 1-continued
| Compound | Structure | EC$_{50}$ | Activity |
|---|---|---|---|
| 3074 | 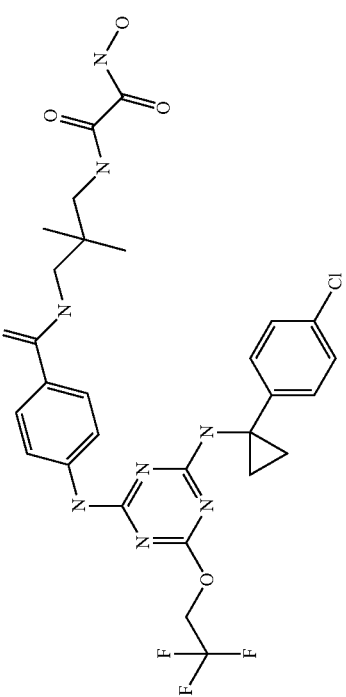 | 0.054 | A |
| 3075 | 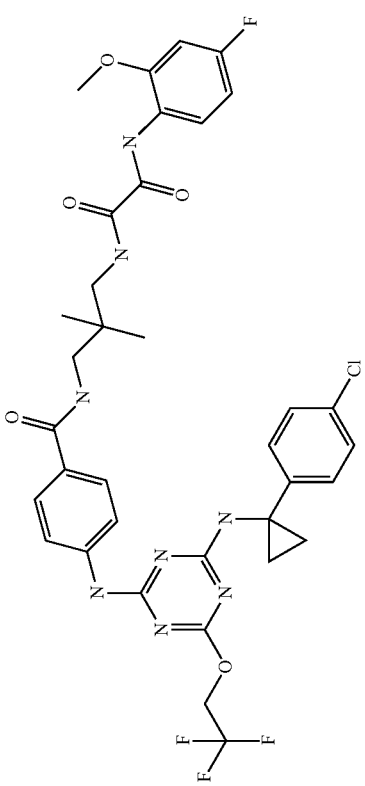 | | A |

TABLE 1-continued

| Compound | Structure | EC$_{50}$ | Activity |
|---|---|---|---|
| 3076 | 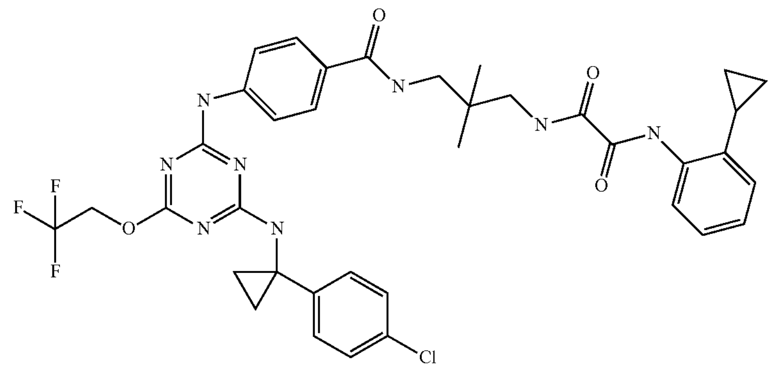 [SMILES: CC(C)(CNC(=O)C(=O)Nc1ccccc1C1CC1)CNC(=O)c1ccc(Nc2nc(NC3(c4ccc(Cl)cc4)CC3)nc(OCC(F)(F)F)n2)cc1] | | A |
| 3077 | 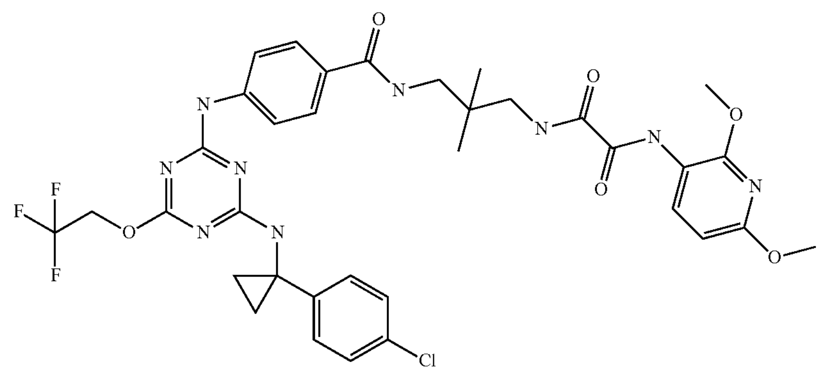 [SMILES: COc1ccc(NC(=O)C(=O)NCC(C)(C)CNC(=O)c2ccc(Nc3nc(NC4(c5ccc(Cl)cc5)CC4)nc(OCC(F)(F)F)n3)cc2)c(OC)n1] | | A |

TABLE 1-continued

| Compound | Structure | EC$_{50}$ | Activity |
|---|---|---|---|
| 3078 | 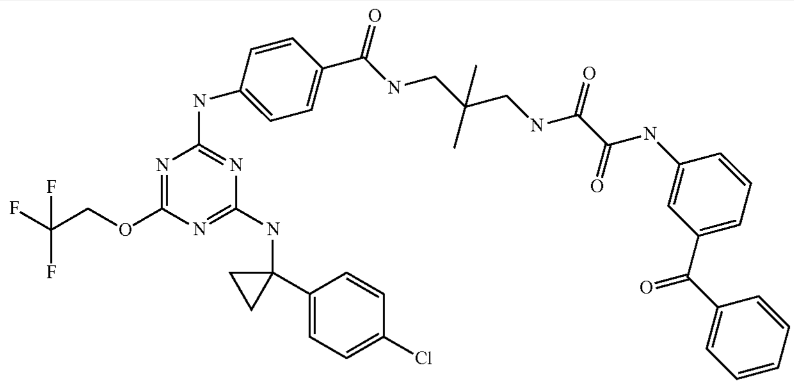 [SMILES: CC(C)(CNC(=O)C(=O)Nc1cccc(C(=O)c2ccccc2)c1)CNC(=O)c1ccc(Nc2nc(NC3(c4ccc(Cl)cc4)CC3)nc(OCC(F)(F)F)n2)cc1] | | A |
| 3079 | (Chiral) | 1.42 | A |

TABLE 1-continued
| Compound | Structure | EC$_{50}$ | Activity |
|---|---|---|---|
| 3080 | 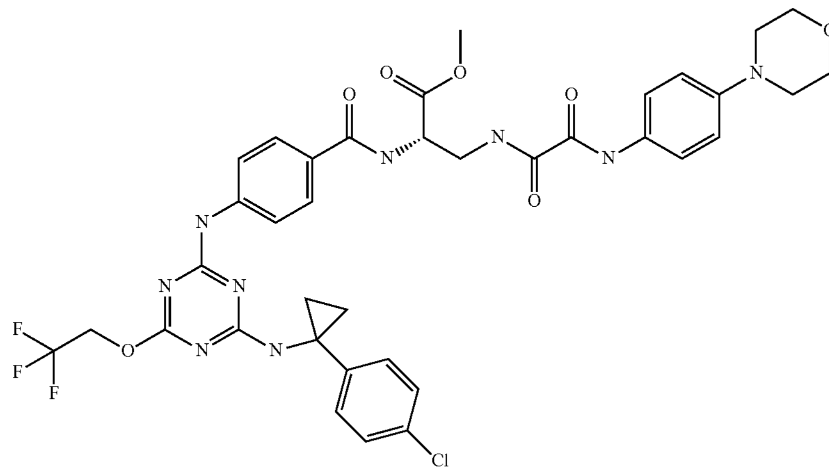 | | A |
| 3081 | 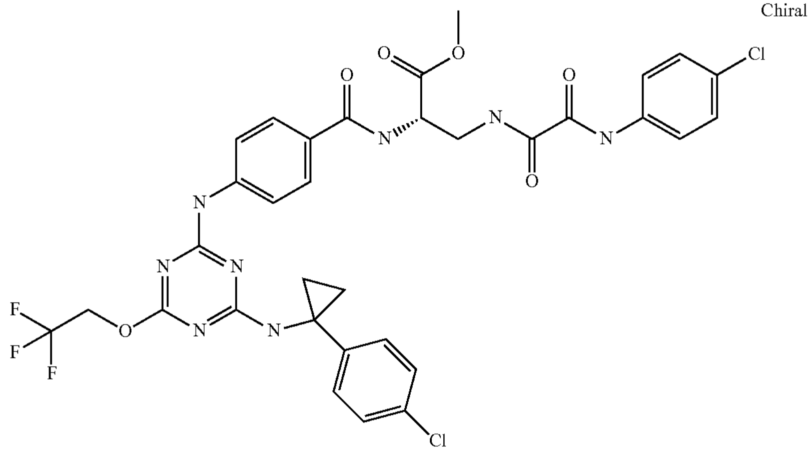 [SMILES: COC(=O)[C@H](CNC(=O)C(=O)Nc1ccc(Cl)cc1)NC(=O)c1ccc(Nc2nc(NC3(c4ccc(Cl)cc4)CC3)nc(OCC(F)(F)F)n2)cc1] | | A |
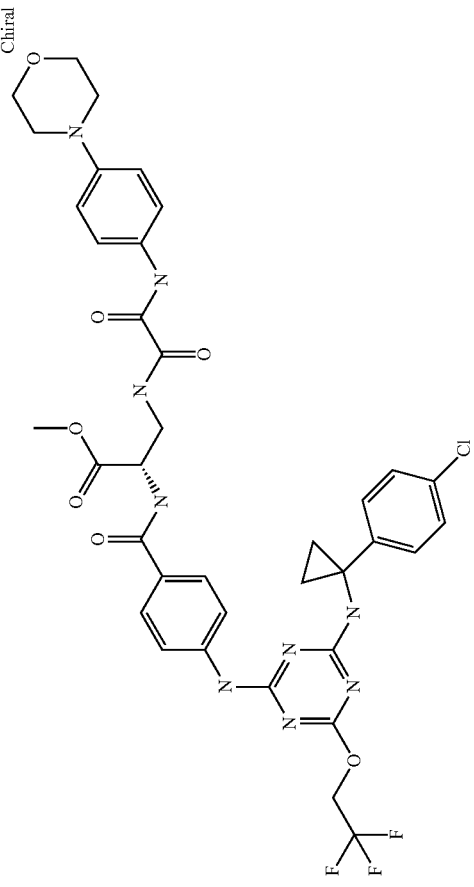

TABLE 1-continued
| Compound | Structure | EC$_{50}$ | Activity |
|---|---|---|---|
| 3082 | 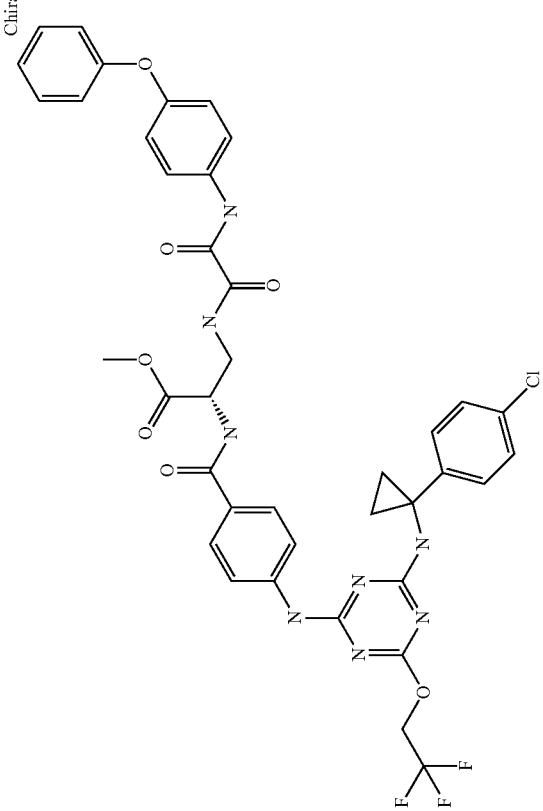 | | A |
| 3083 | 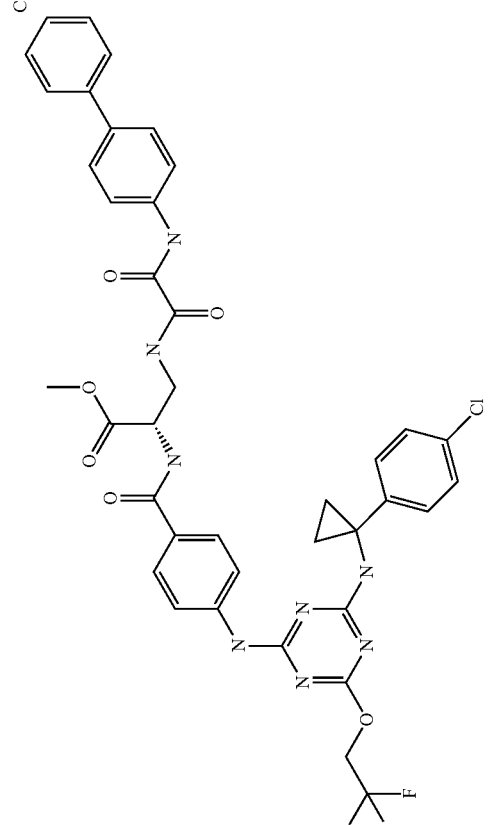 | | A |

TABLE 1-continued
| Compound | Structure | EC$_{50}$ | Activity |
|---|---|---|---|
| 3084 | 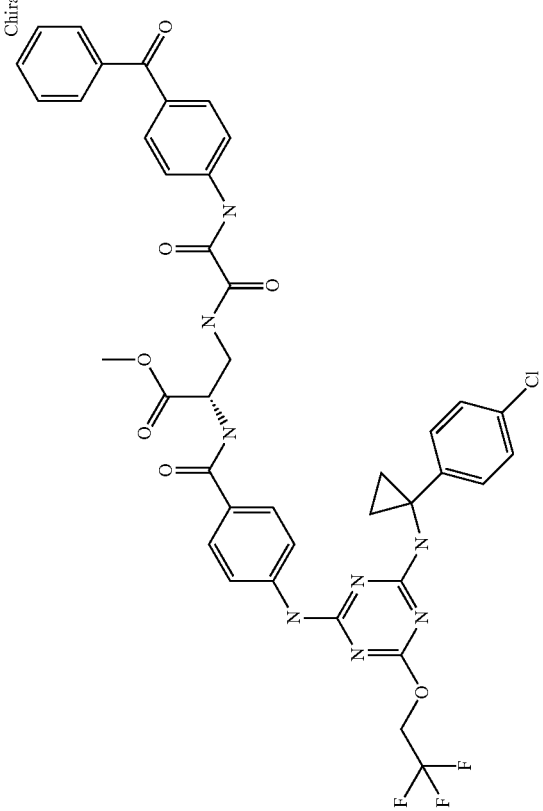 | 3.58 | A |
| 3085 | 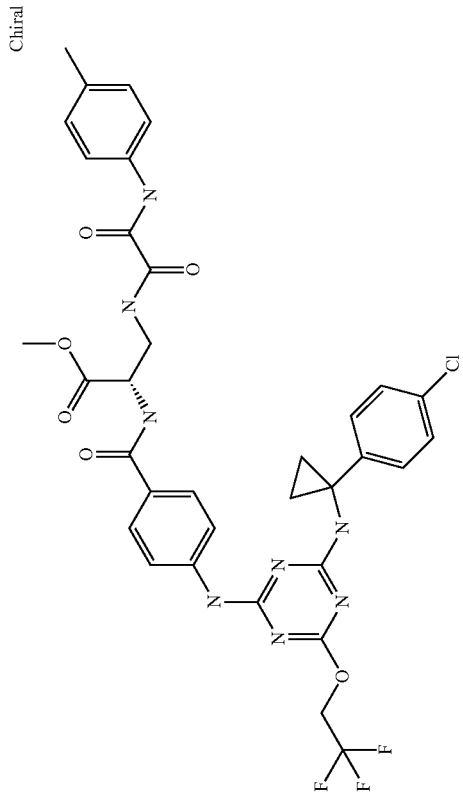 | | A |

TABLE 1-continued

| Compound | Structure | EC$_{50}$ | Activity |
|---|---|---|---|
| 3086 | 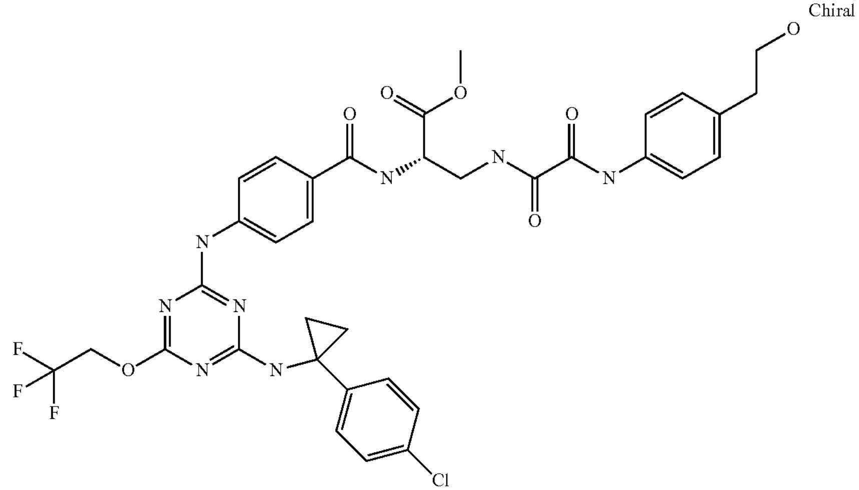 [SMILES: COC(=O)[C@H](CNC(=O)C(=O)Nc1ccc(CCO)cc1)NC(=O)c1ccc(Nc2nc(NC3(c4ccc(Cl)cc4)CC3)nc(OCC(F)(F)F)n2)cc1] | | A |
| 3087 | 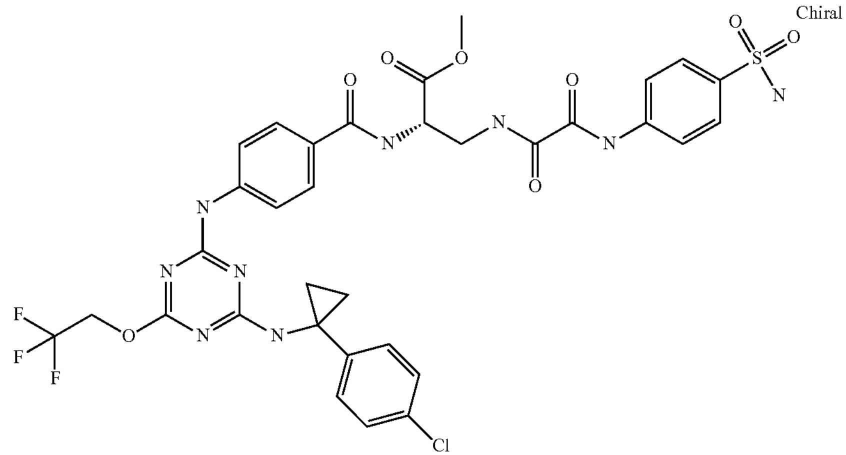 [SMILES: COC(=O)[C@H](CNC(=O)C(=O)Nc1ccc(S(N)(=O)=O)cc1)NC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 3088 | 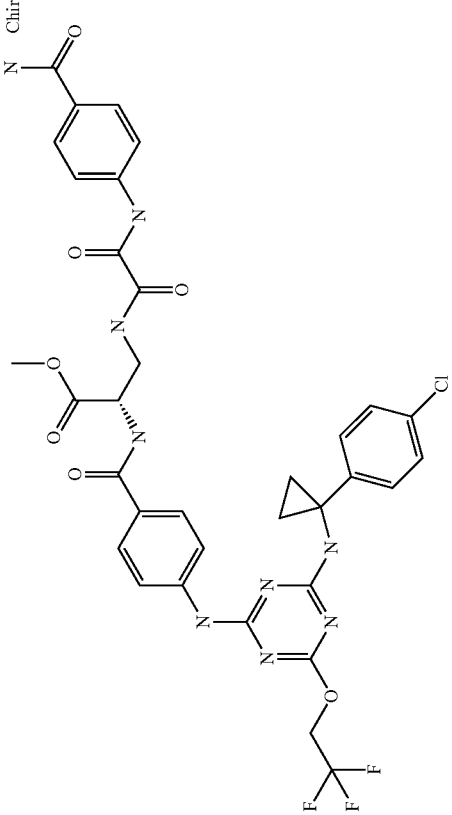 | | A |
| 3089 | 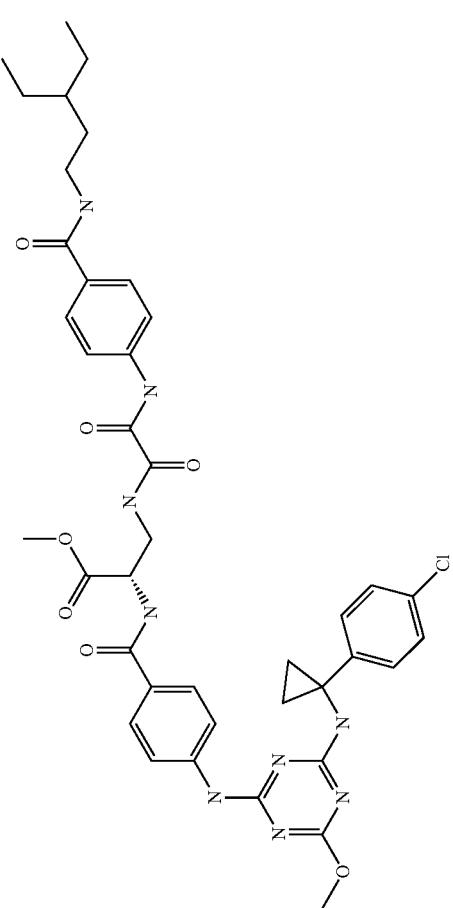 | | A |

TABLE 1-continued
| Compound | Structure | EC$_{50}$ | Activity |
|---|---|---|---|
| 3090 | 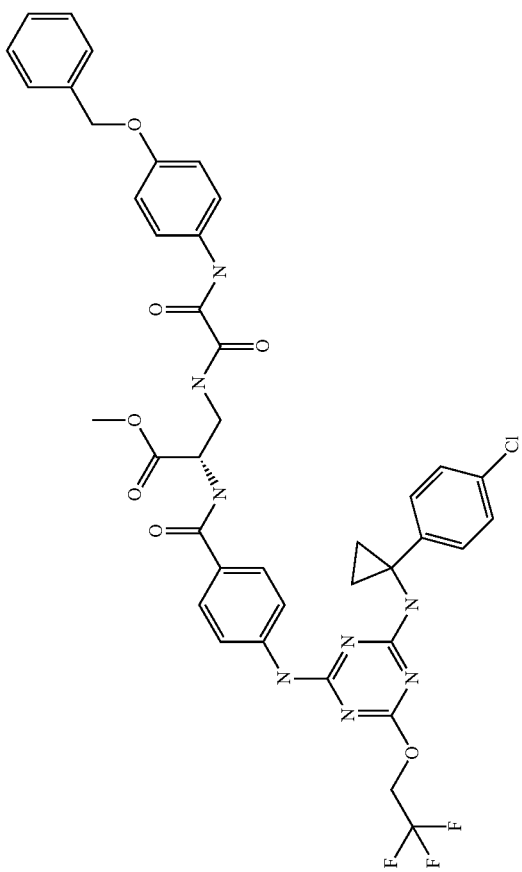 Chiral | | A |

TABLE 1-continued
| Compound | Structure | EC$_{50}$ | Activity |
|---|---|---|---|
| 3091 | 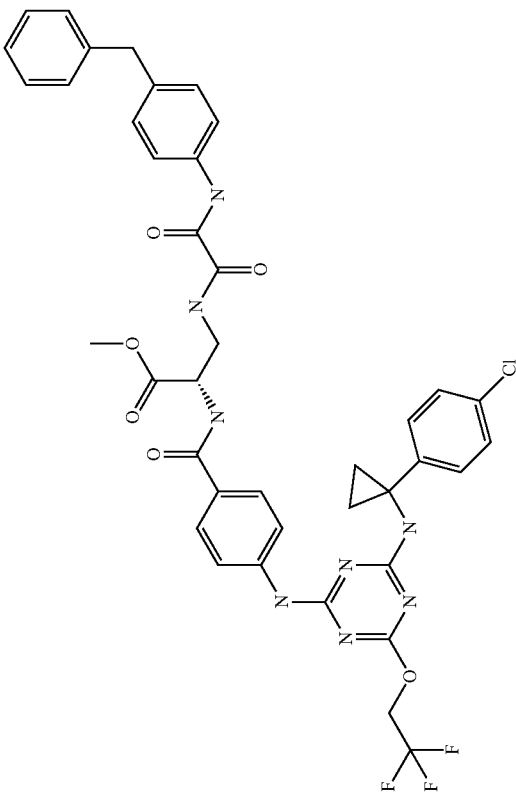 Chiral | 2.85 | A |

TABLE 1-continued

| Compound | Structure | EC$_{50}$ | Activity |
|---|---|---|---|
| 3092 | 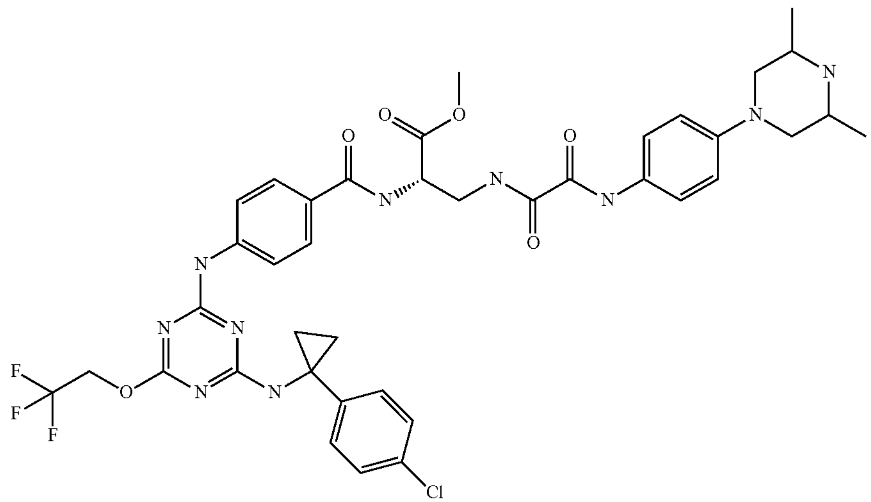 [SMILES: COC(=O)[C@H](CNC(=O)C(=O)Nc1ccc(N2CC(C)NC(C)C2)cc1)NC(=O)c1ccc(Nc2nc(NC3(c4ccc(Cl)cc4)CC3)nc(OCC(F)(F)F)n2)cc1] | | A |
| 3093 | Chiral | | A |

TABLE 1-continued
| Compound | Structure | EC$_{50}$ | Activity |
|---|---|---|---|
| 3094 | 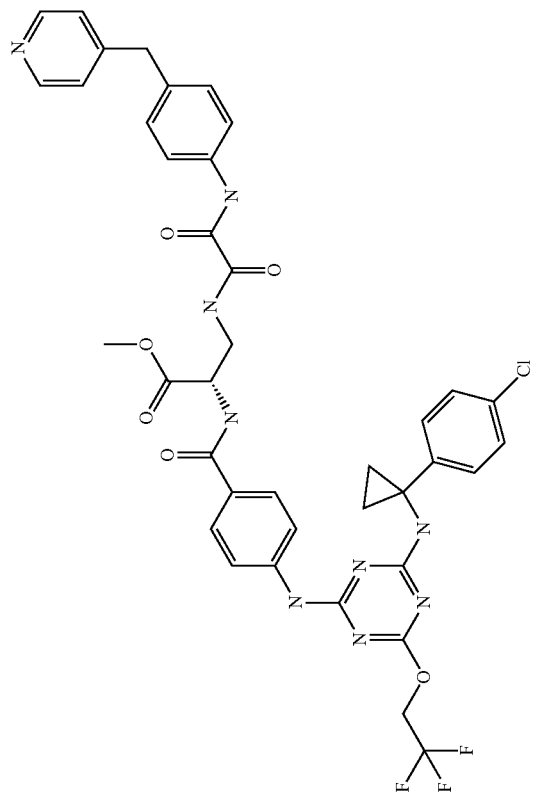 Chiral | | A |

TABLE 1-continued
| Compound | Structure | EC$_{50}$ | Activity |
|---|---|---|---|
| 3095 | Chiral 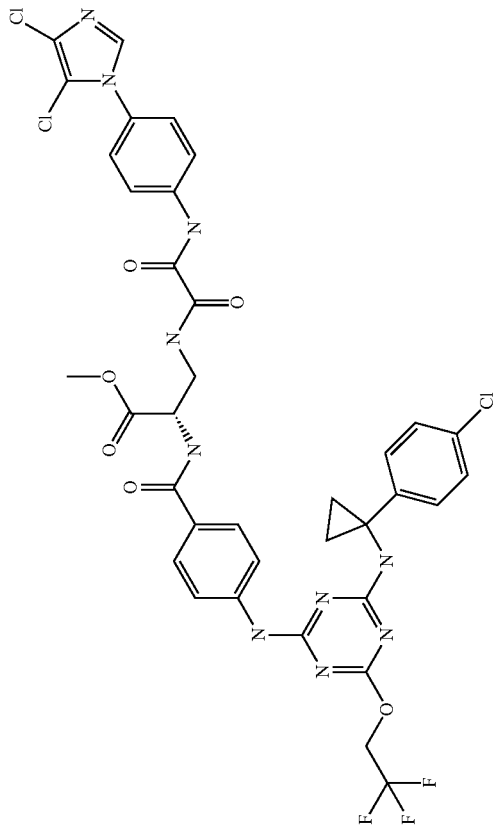 | | A |

TABLE 1-continued
| Compound | Structure | EC$_{50}$ | Activity |
|---|---|---|---|
| 3096 | 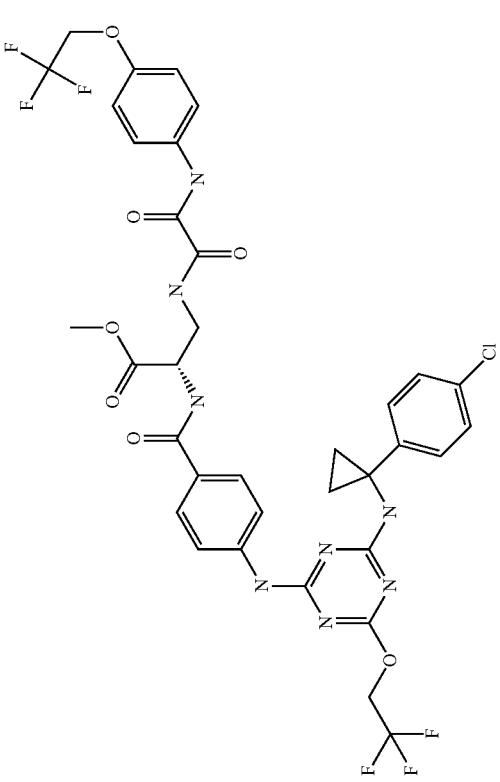 Chiral | | A |

| Compound | Structure | EC$_{50}$ | Activity |
|---|---|---|---|
| 3097 | Chiral 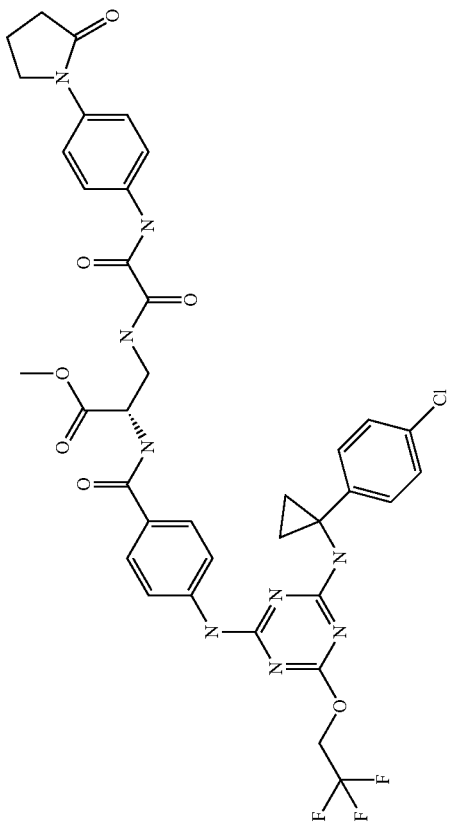 | | A |
| 3098 | Chiral 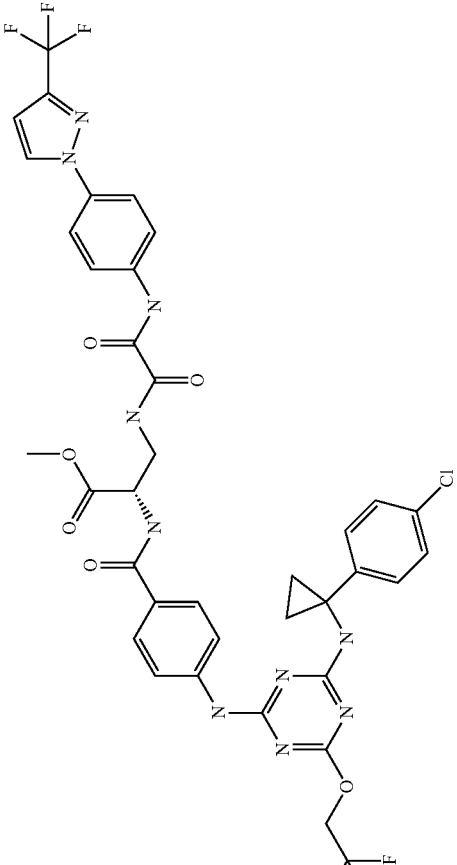 | | A |

TABLE 1-continued
| Compound | Structure | EC$_{50}$ | Activity |
|---|---|---|---|
| 3099 | 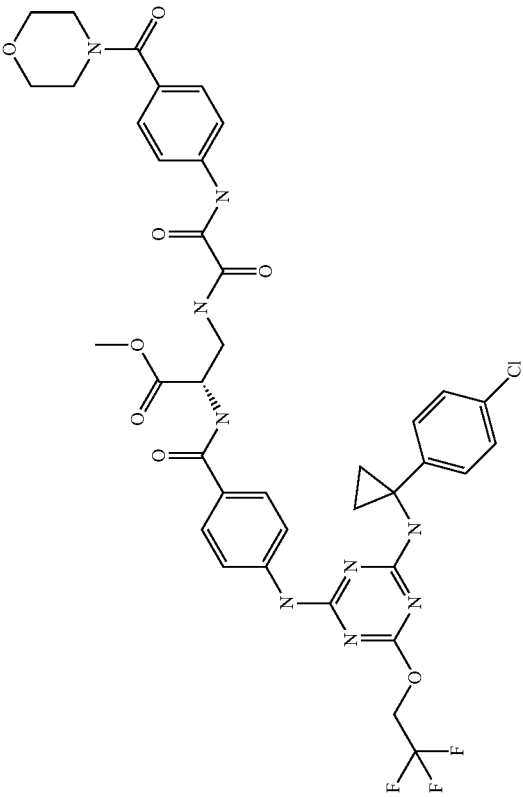 Chiral | | A |
| 3100 | 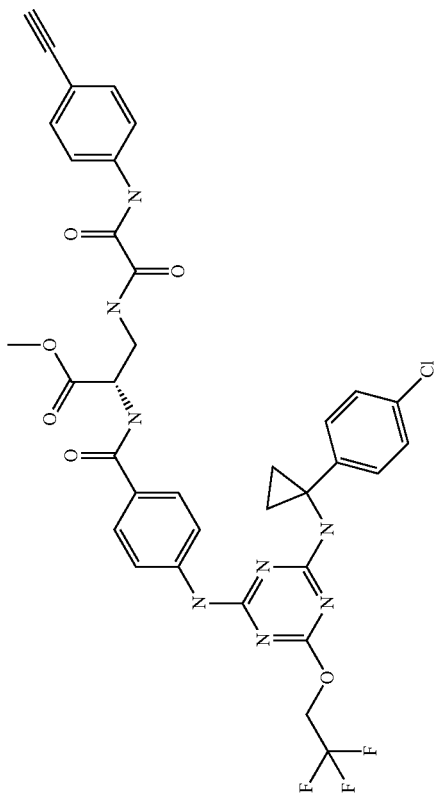 Chiral | 0.27 | A |

TABLE 1-continued
| Compound | Structure | EC$_{50}$ | Activity |
|---|---|---|---|
| 3101 | 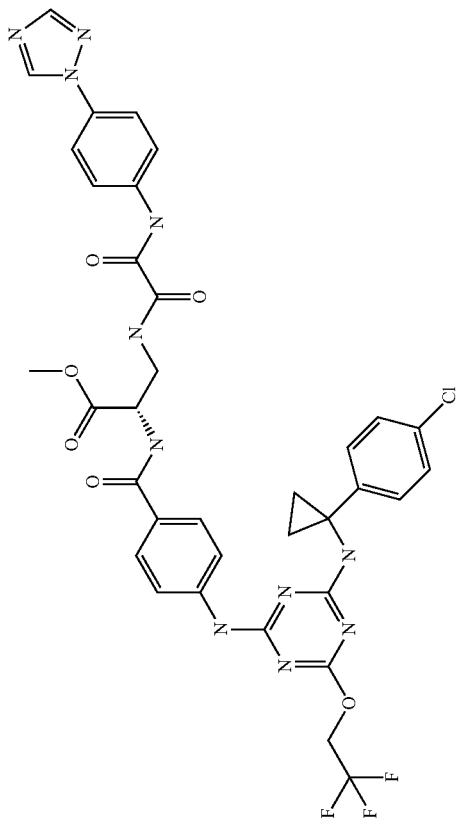 Chiral | | A |

TABLE 1-continued
| Compound | Structure | EC$_{50}$ | Activity |
|---|---|---|---|
| 3102 | 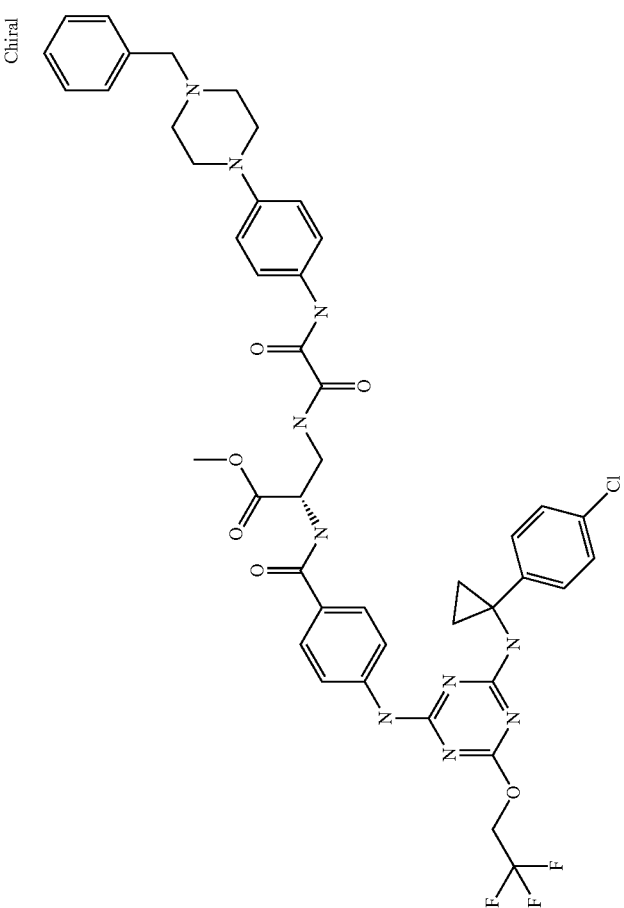 Chiral | | A |

TABLE 1-continued
| Compound | Structure | EC$_{50}$ | Activity |
|---|---|---|---|
| 3103 | 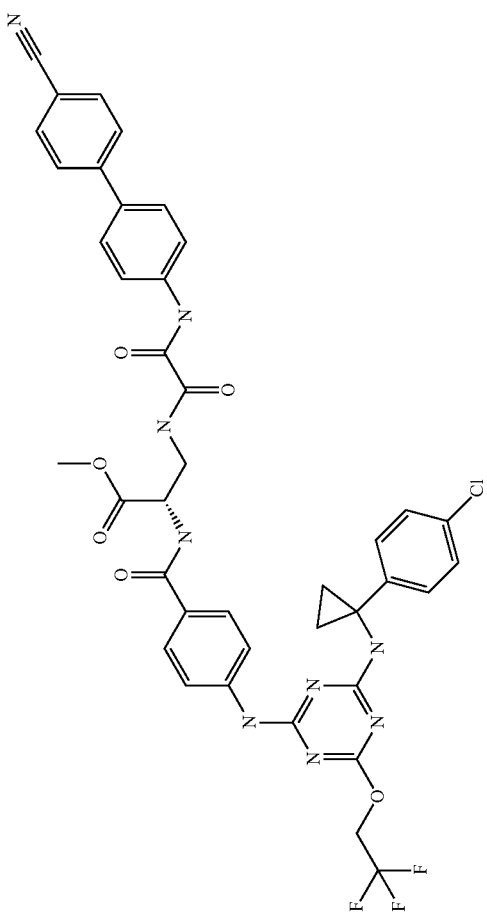 | | A |

TABLE 1-continued
| Compound | Structure | EC$_{50}$ | Activity |
|---|---|---|---|
| 3104 | 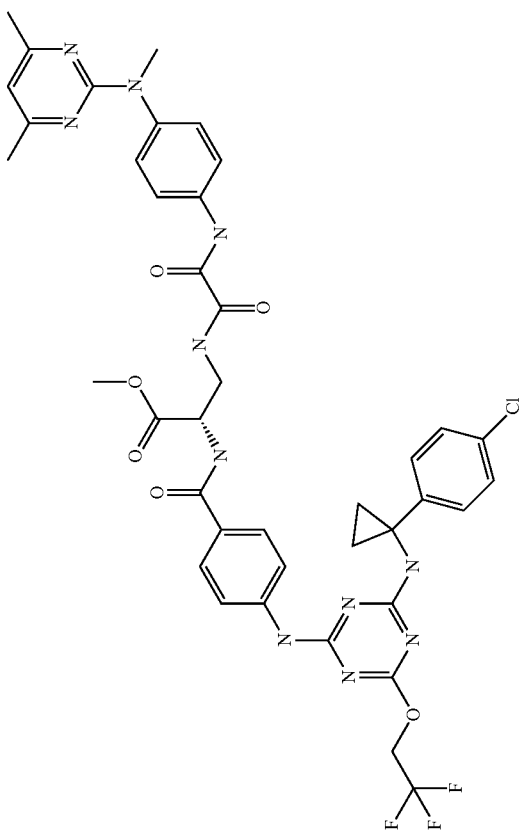 Chiral | | A |
| 3105 | 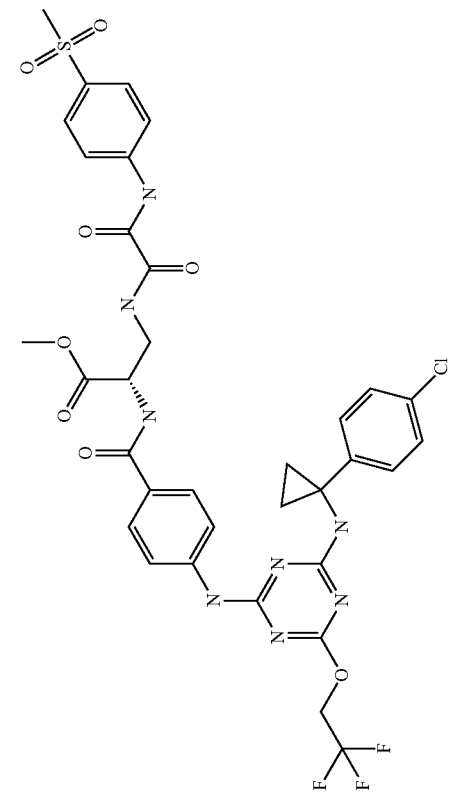 Chiral | | A |

TABLE 1-continued
| Compound | Structure | EC$_{50}$ | Activity |
|---|---|---|---|
| 3106 | 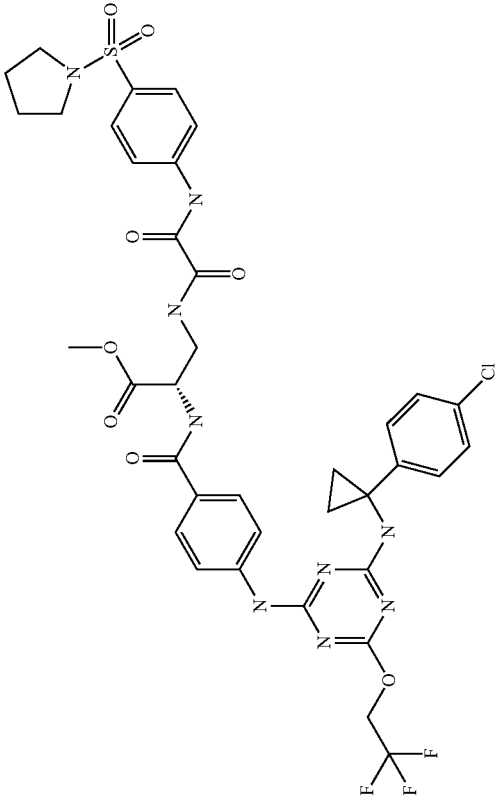 Chiral | | A |

TABLE 1-continued
| Compound | Structure | EC$_{50}$ | Activity |
|---|---|---|---|
| 3107 | 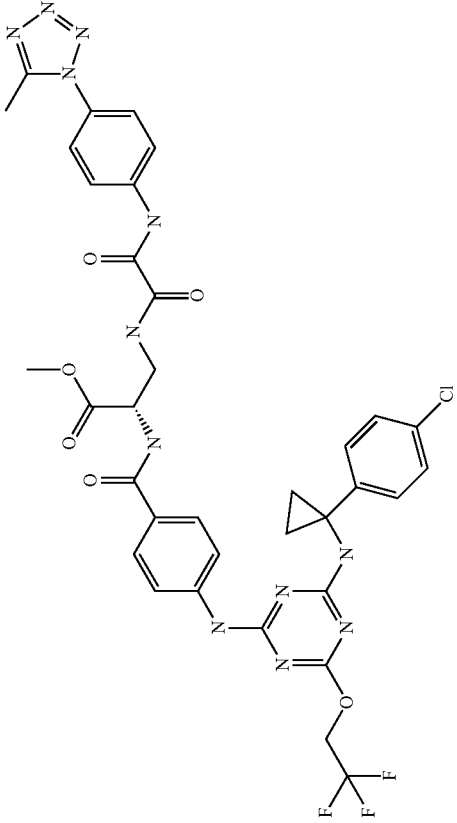 Chiral | 0.92 | A |
| 3108 | 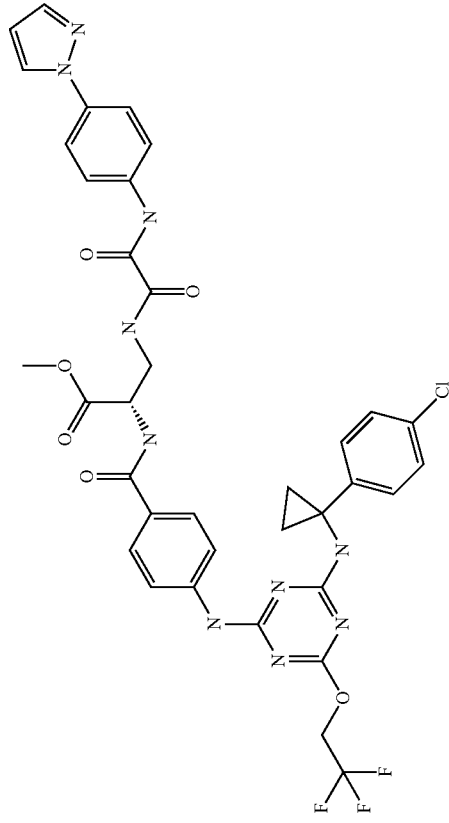 Chiral | | A |

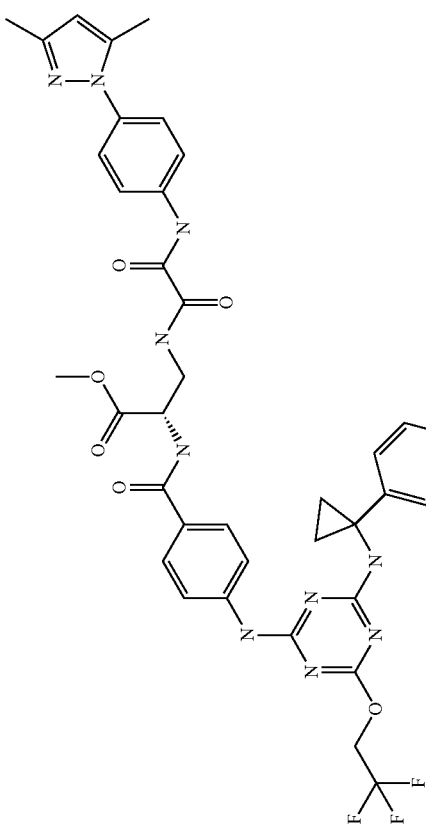

TABLE 1-continued
| Compound | Structure | EC$_{50}$ | Activity |
|---|---|---|---|
| 3111 | 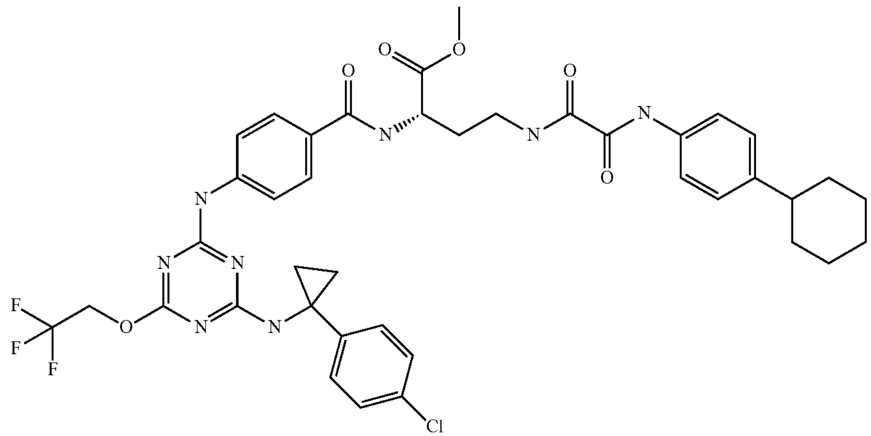 | | A |
| 3112 | 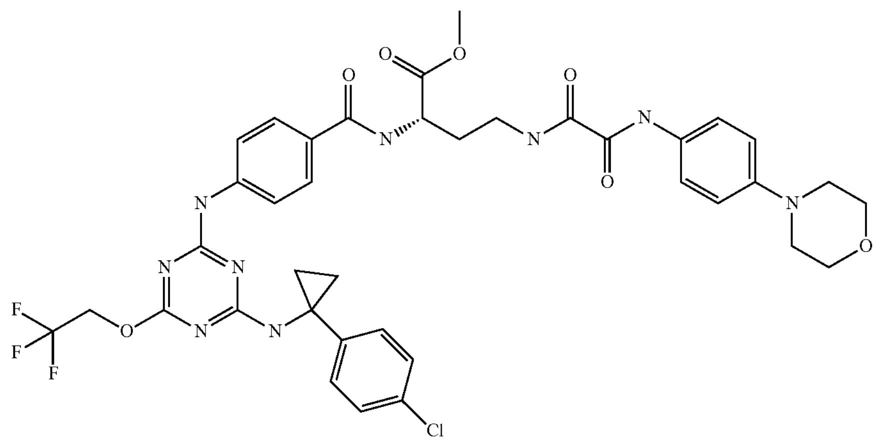 | | A |

TABLE 1-continued
| Compound | Structure | EC$_{50}$ | Activity |
|---|---|---|---|
| 3113 | 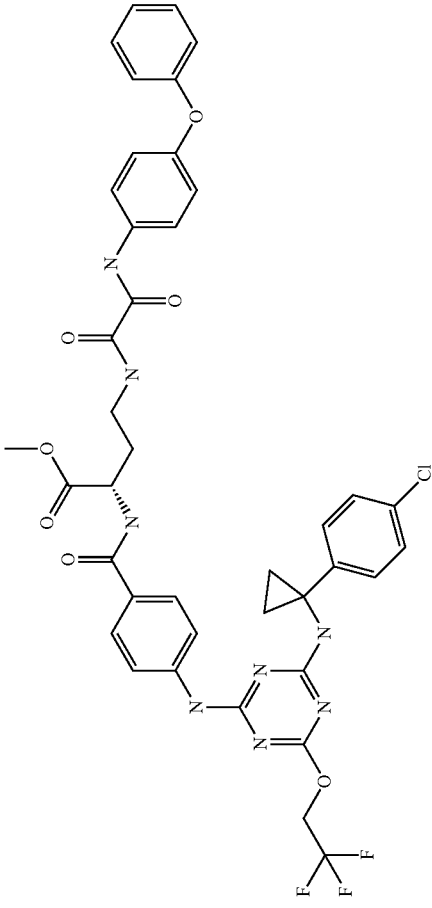 | 7.77 | A |
| 3114 | 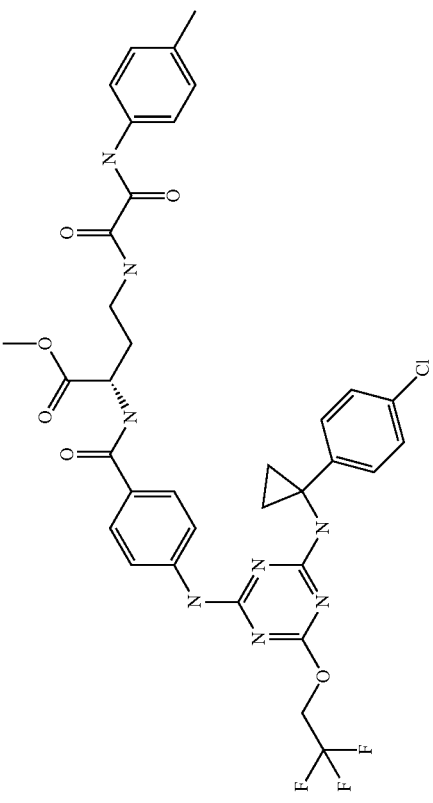 | 0.084 | A |

TABLE 1-continued
| Compound | Structure | EC$_{50}$ | Activity |
|---|---|---|---|
| 3115 | Chiral 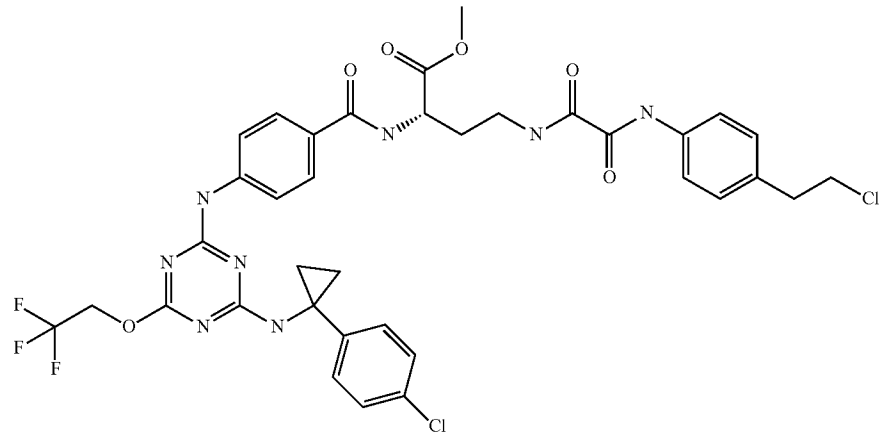 | | A |
| 3116 | Chiral 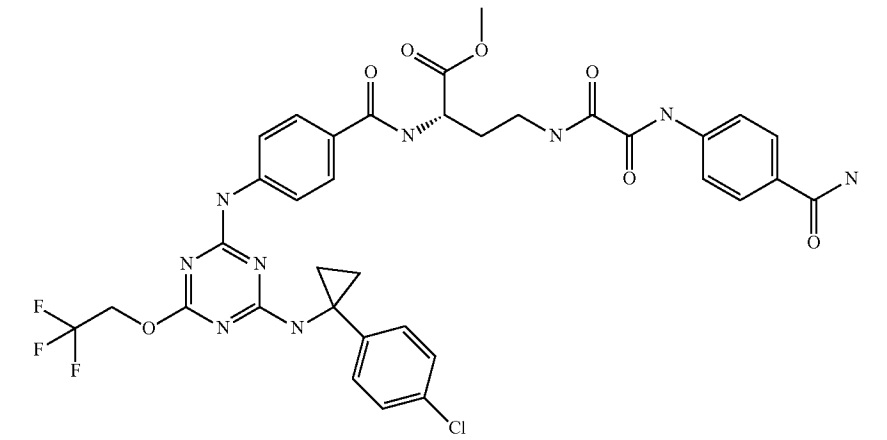 | | A |

TABLE 1-continued

| Compound | Structure | EC$_{50}$ | Activity |
|---|---|---|---|
| 3117 | Chiral | | A |
| 3118 | Chiral | | A |

TABLE 1-continued
| Compound | Structure | EC$_{50}$ | Activity |
|---|---|---|---|
| 3119 | 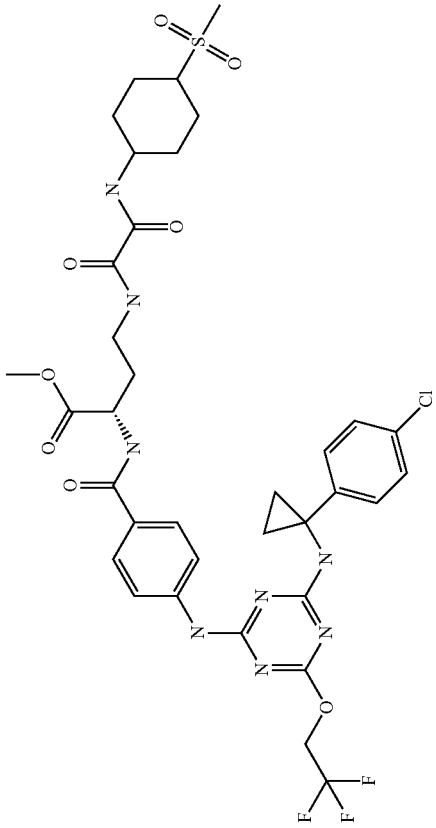 Chiral | | A |
| 3120 | 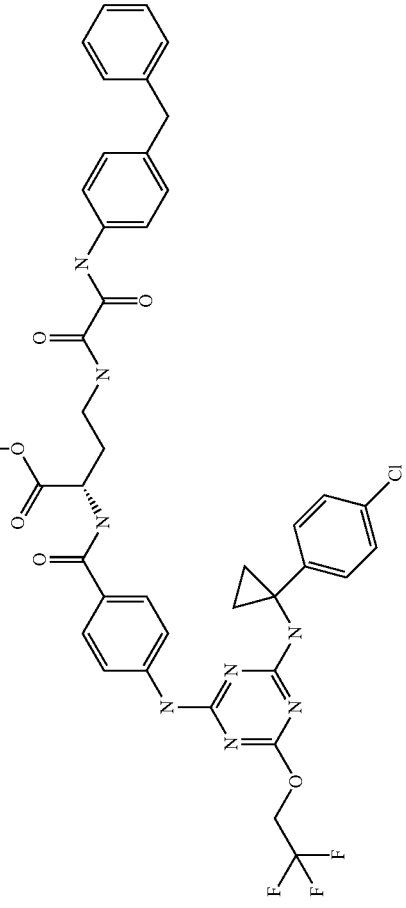 Chiral | | A |

TABLE 1-continued
| Compound | Structure | EC$_{50}$ | Activity |
|---|---|---|---|
| 3121 | 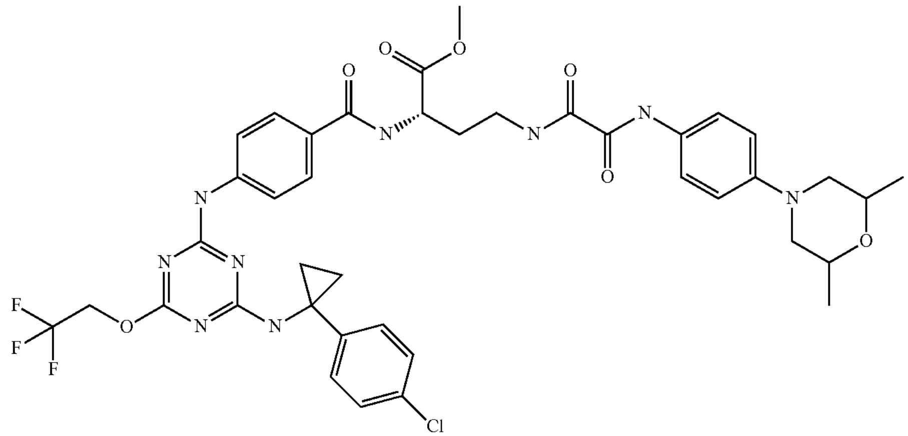 | 3.39 | A |
| 3122 | 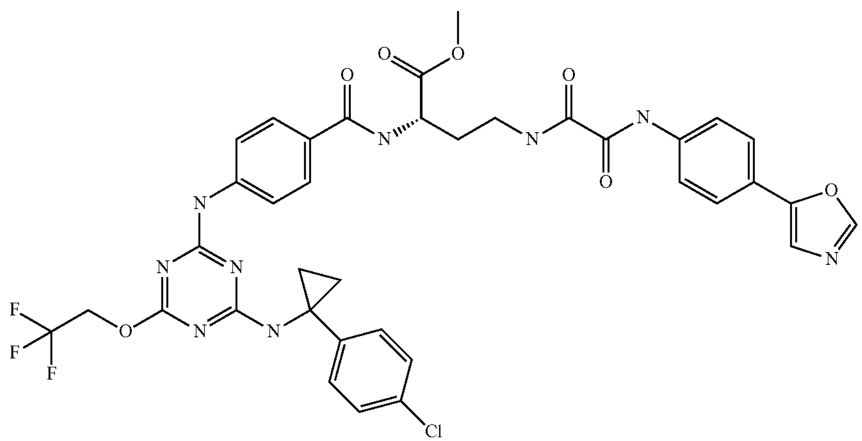 | | A |

TABLE 1-continued
| Compound | Structure | EC$_{50}$ | Activity |
|---|---|---|---|
| 3123 | Chiral 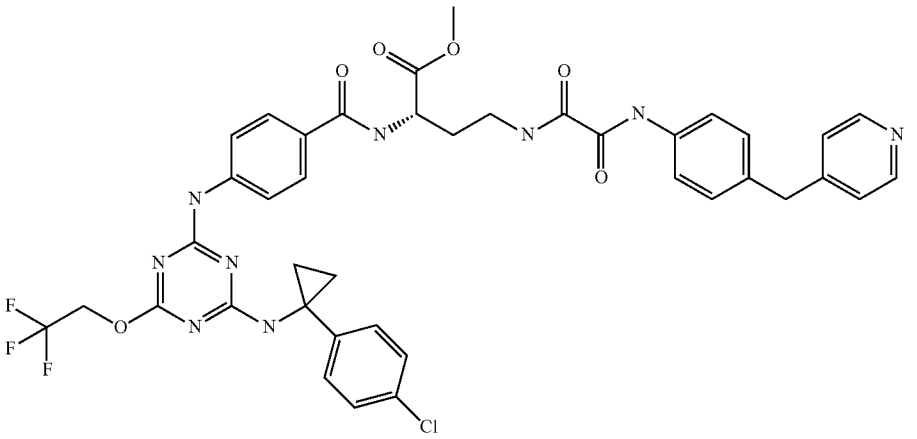 | | A |
| 3124 | Chiral 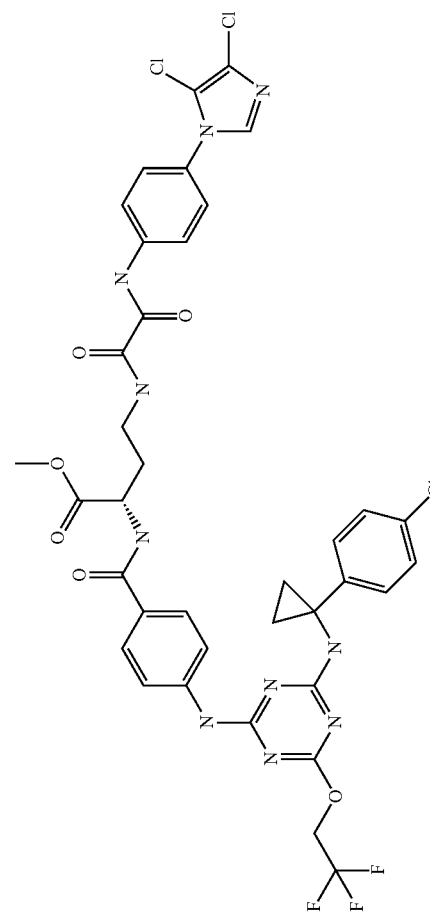 | 18.18 | A |

TABLE 1-continued
| Compound | Structure | EC$_{50}$ | Activity |
|---|---|---|---|
| 3125 | 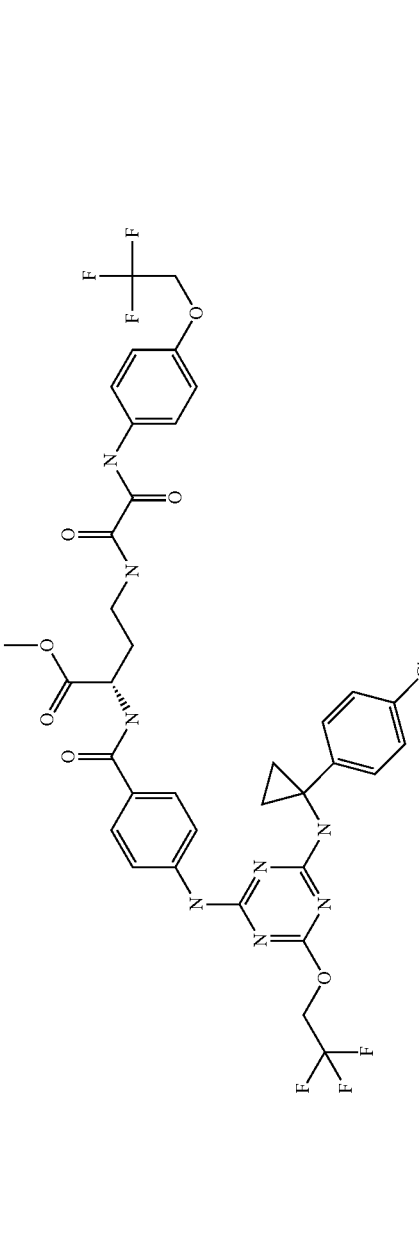 | | A |
| 3126 | 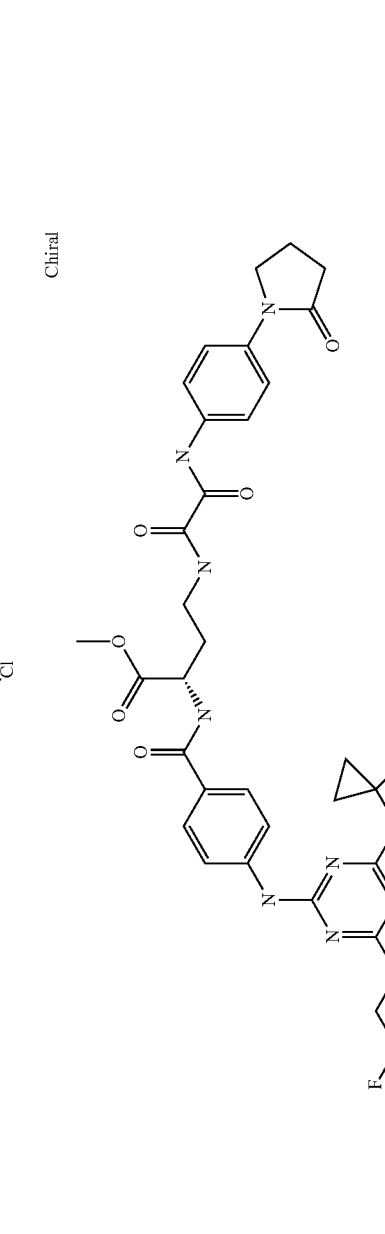 | | A |

TABLE 1-continued

| Compound | Structure | EC$_{50}$ | Activity |
|---|---|---|---|
| 3127 | Chiral | | A |
| 3128 | Chiral | | A |

TABLE 1-continued
| Compound | Structure | EC$_{50}$ | Activity |
|---|---|---|---|
| 3129 | 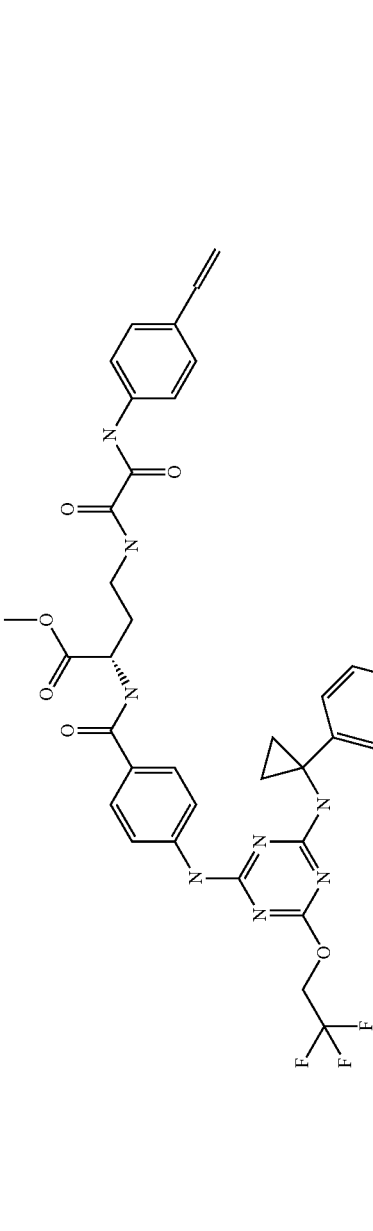 Chiral | 0.089 | A |
| 3130 | 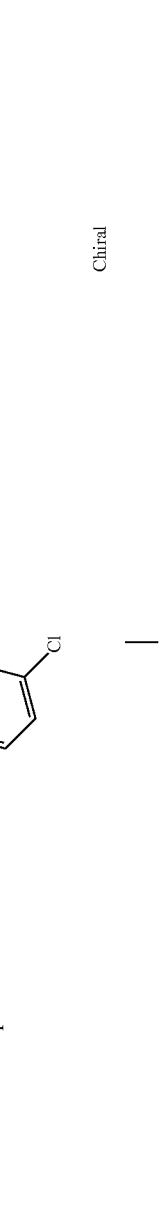 Chiral | | A |

TABLE 1-continued
| Compound | Structure | EC$_{50}$ | Activity |
|---|---|---|---|
| 3131 | 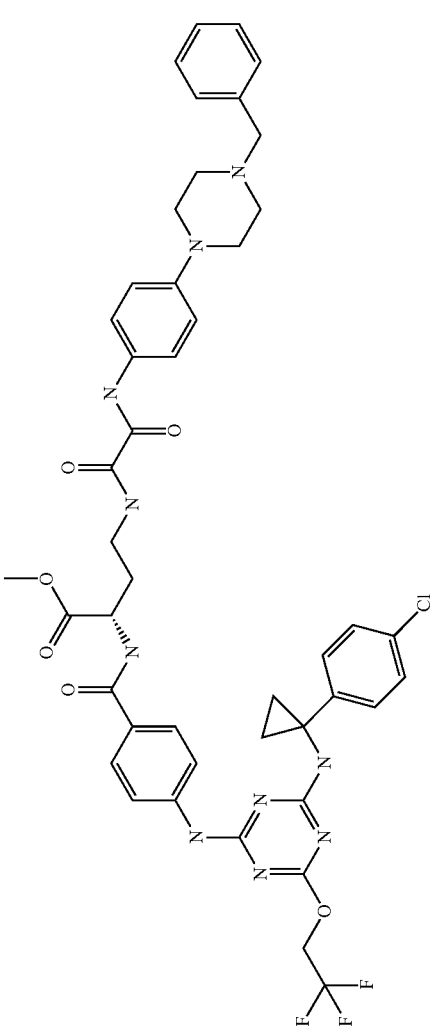 | | A |
| 3132 | 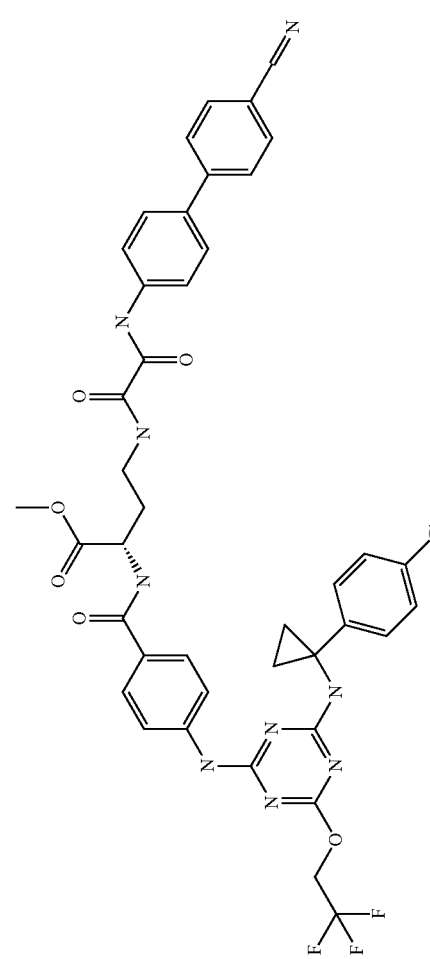 | | A |

TABLE 1-continued
| Compound | Structure | EC$_{50}$ | Activity |
|---|---|---|---|
| 3133 | Chiral 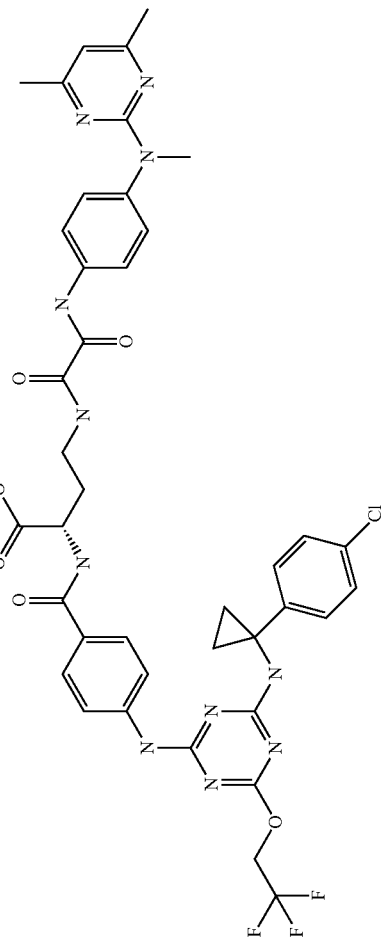 | | A |
| 3134 | Chiral 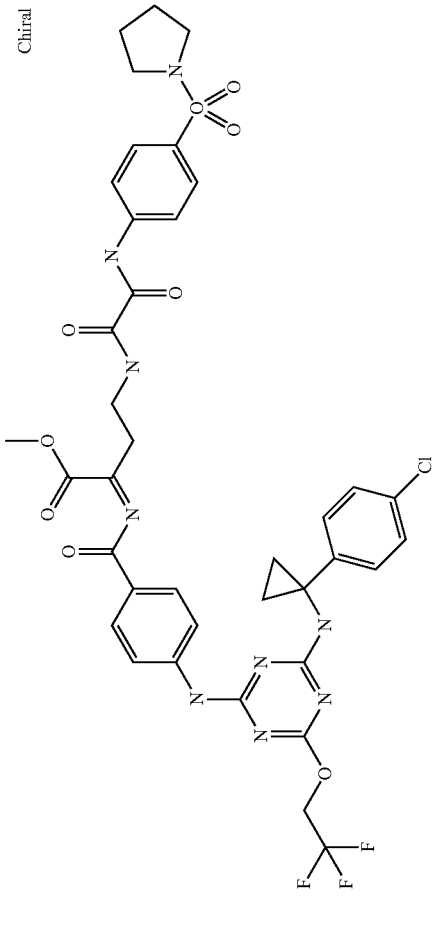 | | A |

TABLE 1-continued
| Compound | Structure | EC$_{50}$ | Activity |
|---|---|---|---|
| 3135 | 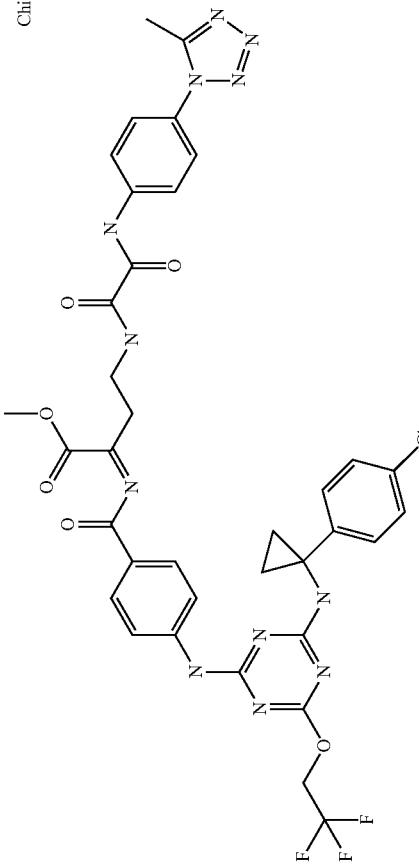 Chiral | 3.69 | A |
| 3136 | 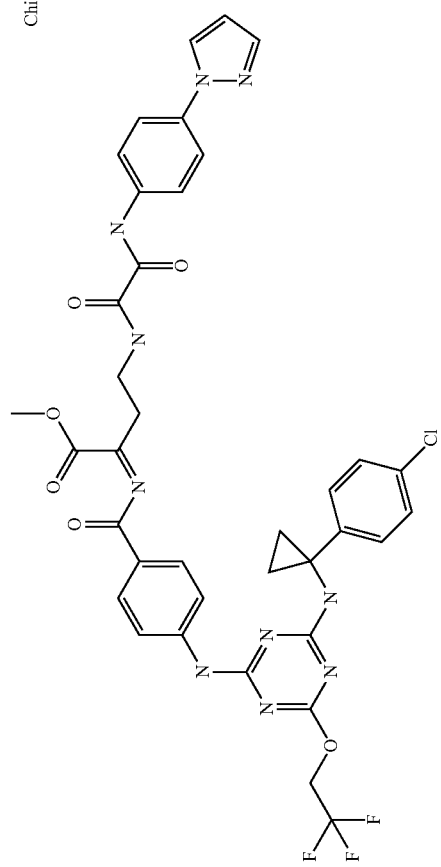 Chiral | | A |

TABLE 1-continued
| Compound | Structure | EC50 | Activity |
|---|---|---|---|
| 3137 | 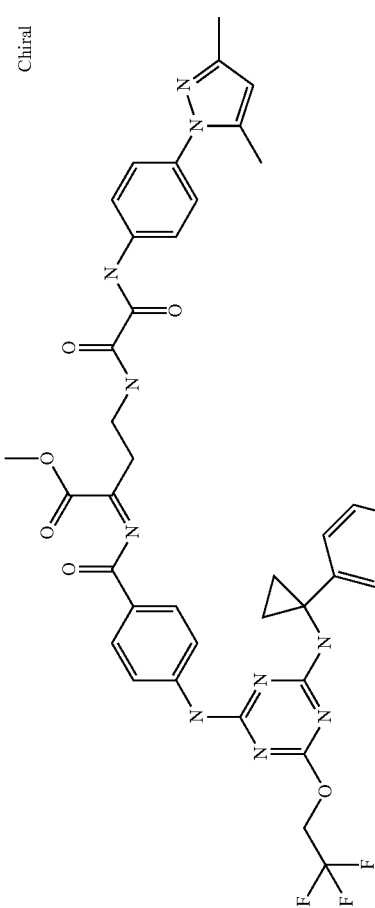 | | A |
| 3138 | 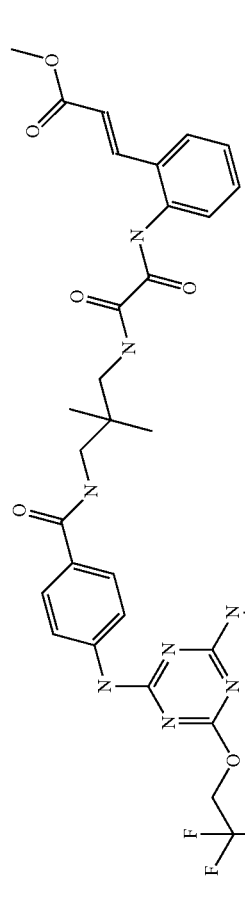 | 0.46 | A |

TABLE 1-continued

| Compound | Structure | EC$_{50}$ | Activity |
|---|---|---|---|
| 3139 | 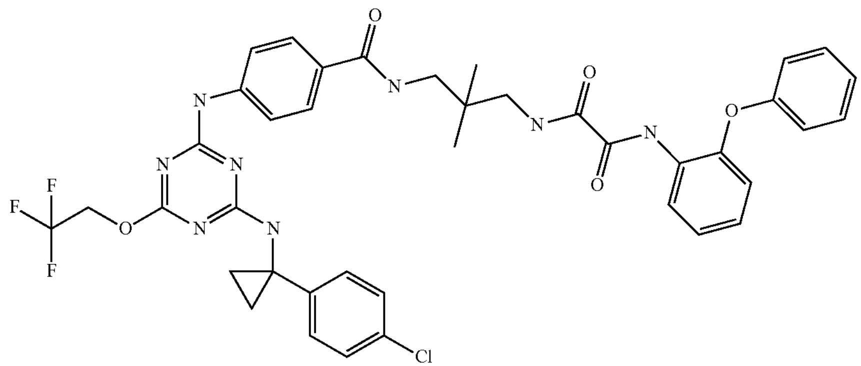 [SMILES: CC(C)(CNC(=O)C(=O)Nc1ccccc1Oc1ccccc1)CNC(=O)c1ccc(Nc2nc(NC3(c4ccc(Cl)cc4)CC3)nc(OCC(F)(F)F)n2)cc1] | | A |
| 3140 | 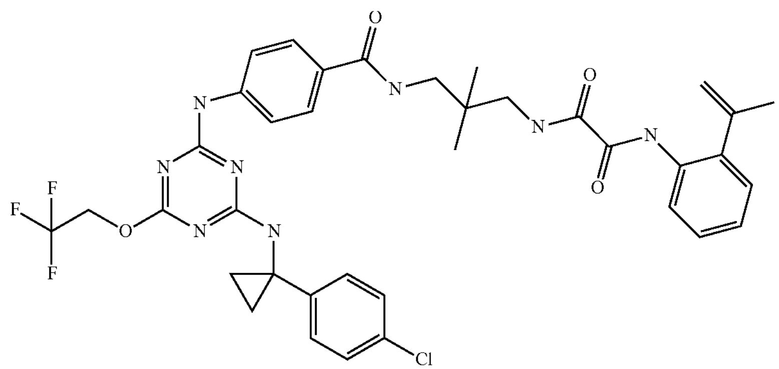 [SMILES: C=C(C)c1ccccc1NC(=O)C(=O)NCC(C)(C)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3141 | 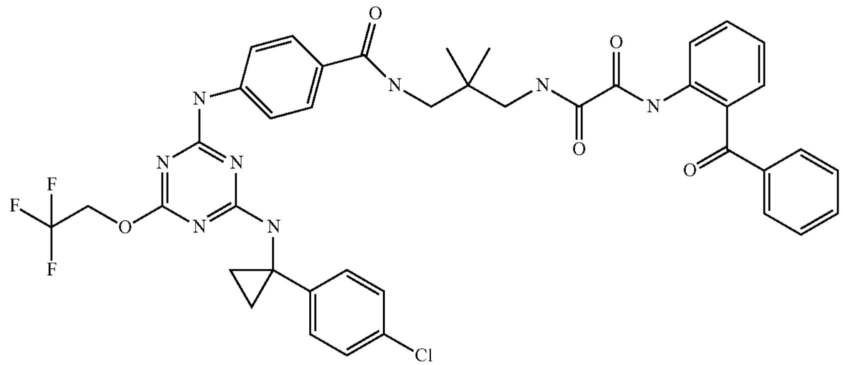 [SMILES: CC(C)(CNC(=O)C(=O)Nc1ccccc1C(=O)c1ccccc1)CNC(=O)c1ccc(Nc2nc(NC3(c4ccc(Cl)cc4)CC3)nc(OCC(F)(F)F)n2)cc1] | 0.11 | A |
| 3142 | 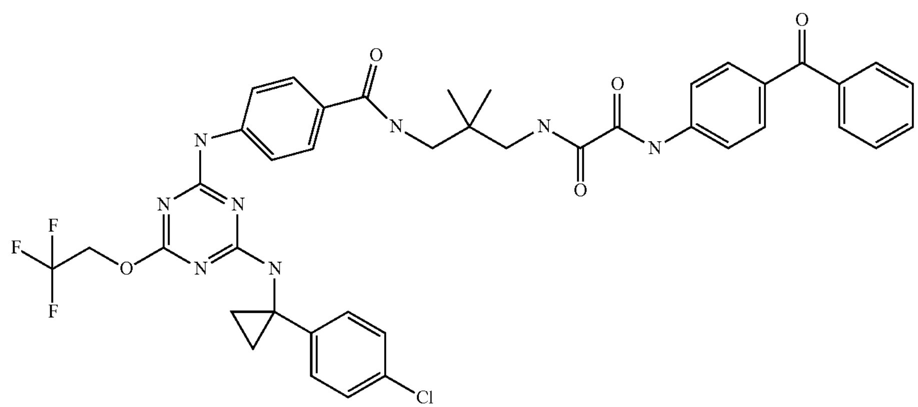 [SMILES: CC(C)(CNC(=O)C(=O)Nc1ccc(C(=O)c2ccccc2)cc1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC₅₀ | Activity |
|---|---|---|---|
| 3143 | 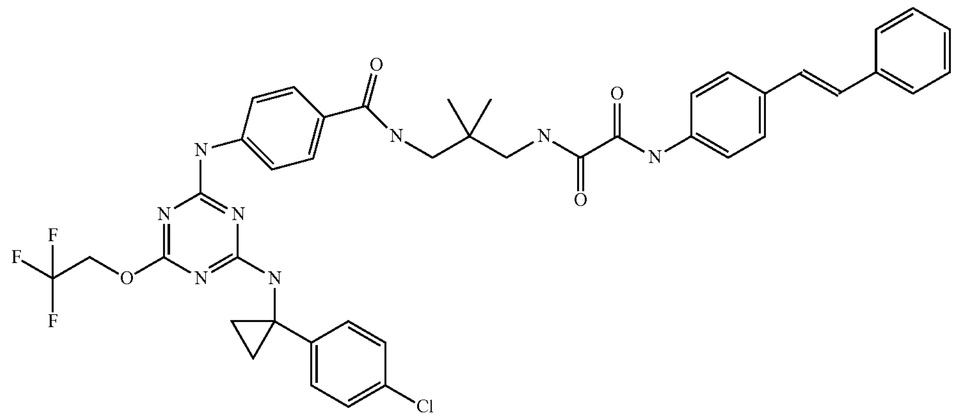 [SMILES: CC(C)(CNC(=O)C(=O)Nc1ccc(/C=C/c2ccccc2)cc1)CNC(=O)c1ccc(Nc2nc(NC3(c4ccc(Cl)cc4)CC3)nc(OCC(F)(F)F)n2)cc1] | | A |
| 3144 | 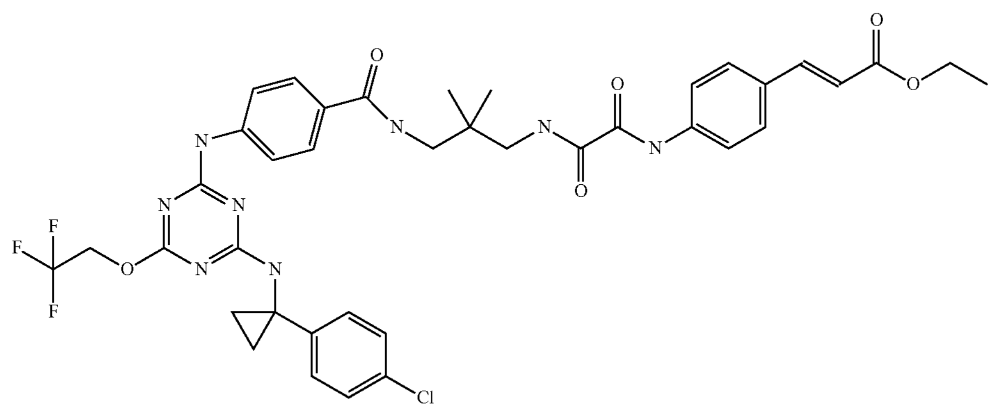 [SMILES: CCOC(=O)/C=C/c1ccc(NC(=O)C(=O)NCC(C)(C)CNC(=O)c2ccc(Nc3nc(NC4(c5ccc(Cl)cc5)CC4)nc(OCC(F)(F)F)n3)cc2)cc1] | | A |

TABLE 1-continued

| Compound | Structure | EC$_{50}$ | Activity |
|---|---|---|---|
| 3145 | 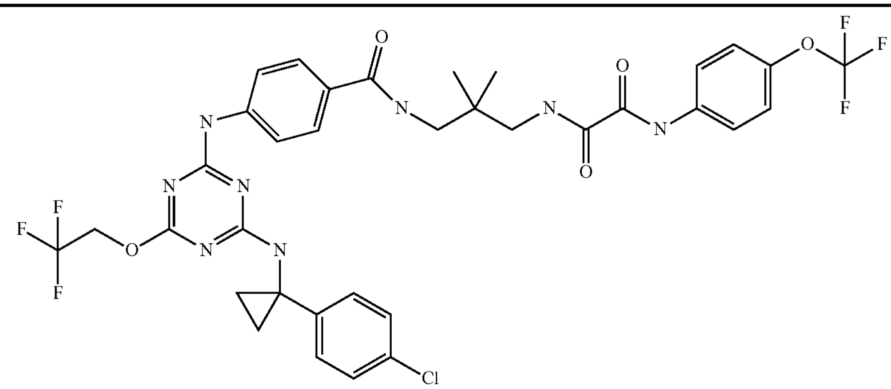 | | A |
| 3146 | 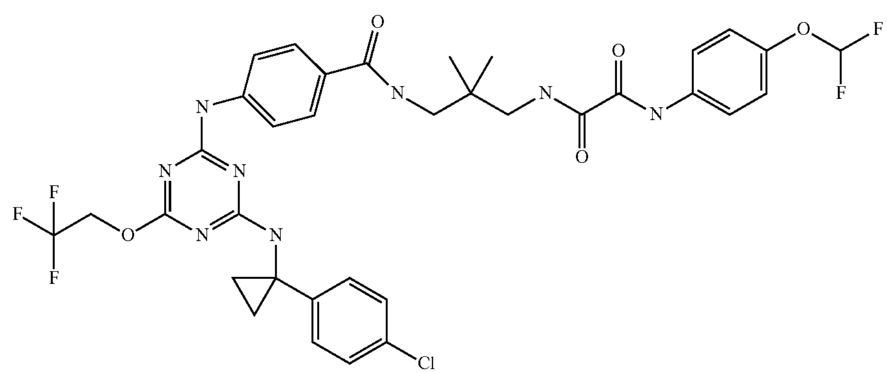 [SMILES: CC(C)(CNC(=O)C(=O)Nc1ccc(OC(F)F)cc1)CNC(=O)c1ccc(Nc2nc(NC3(c4ccc(Cl)cc4)CC3)nc(OCC(F)(F)F)n2)cc1] | 0.050 | A |

TABLE 1-continued
| Compound | Structure | EC$_{50}$ | Activity |
|---|---|---|---|
| 3147 | 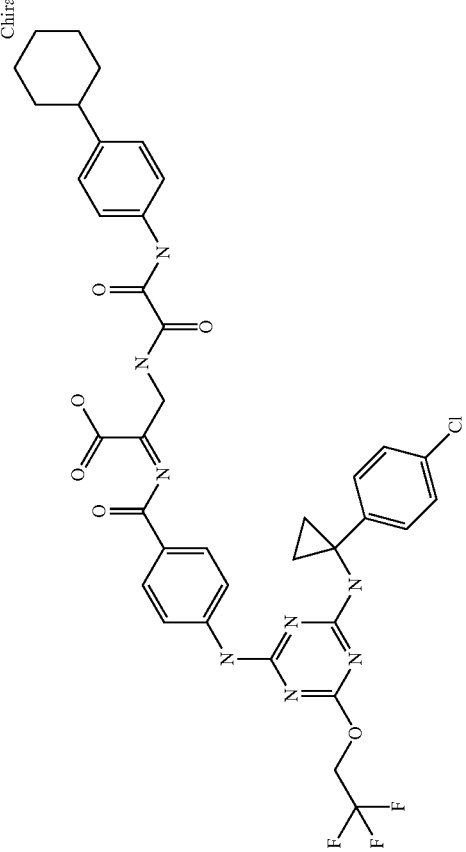 | | A |
| 3148 | 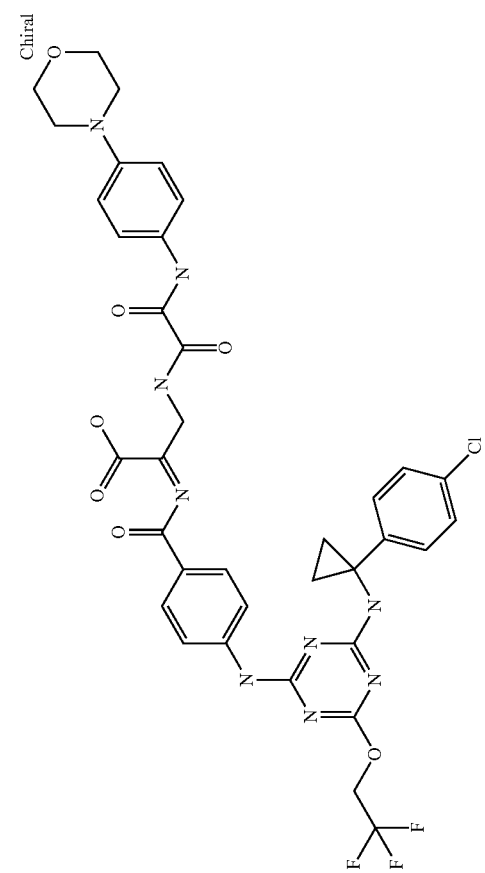 | | A |

TABLE 1-continued
| Compound | Structure | EC$_{50}$ | Activity |
|---|---|---|---|
| 3149 | 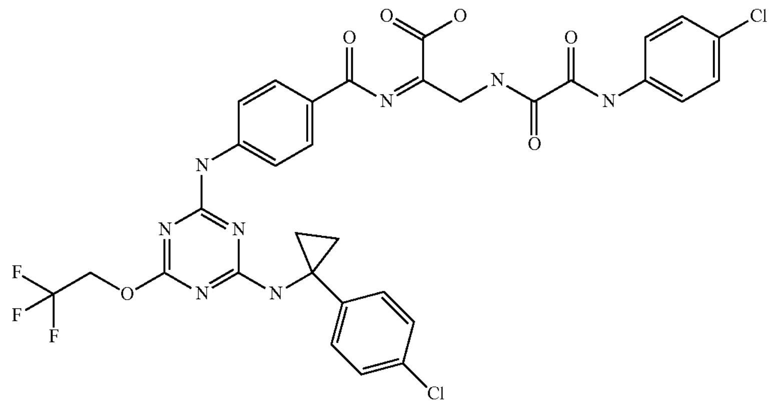 | | A |
| 3150 | 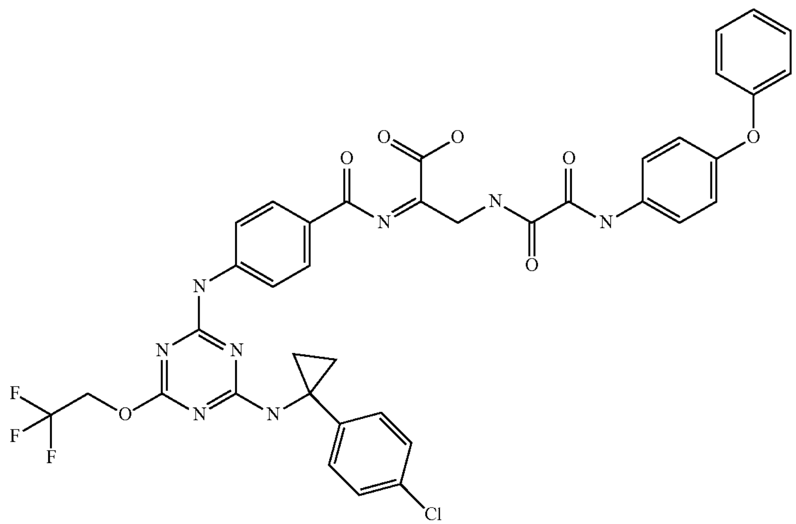 | | A |
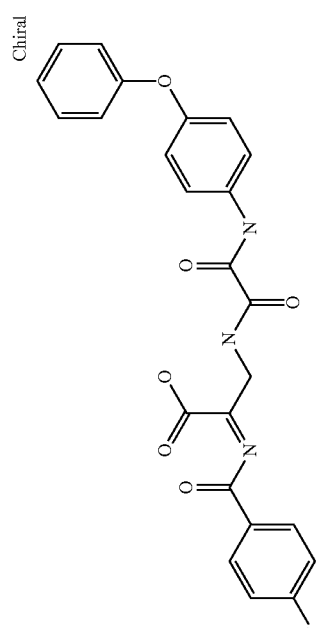

TABLE 1-continued
| Compound | Structure | EC$_{50}$ | Activity |
|---|---|---|---|
| 3151 | 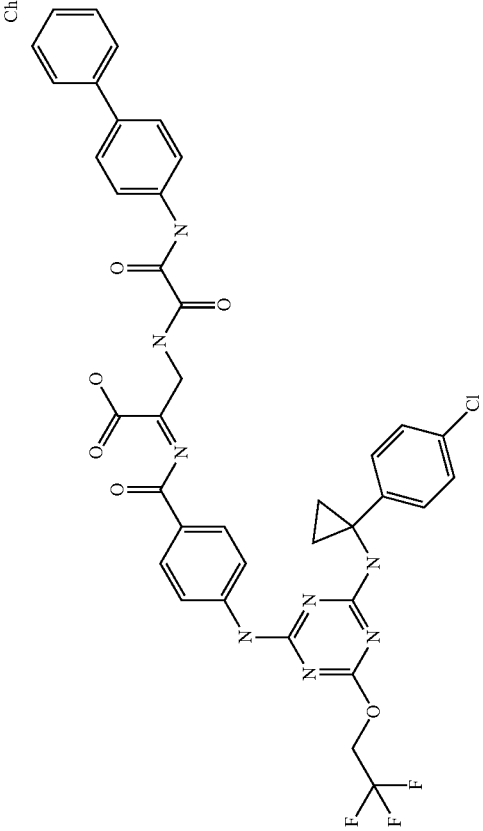 Chiral | | A |
| 3152 | 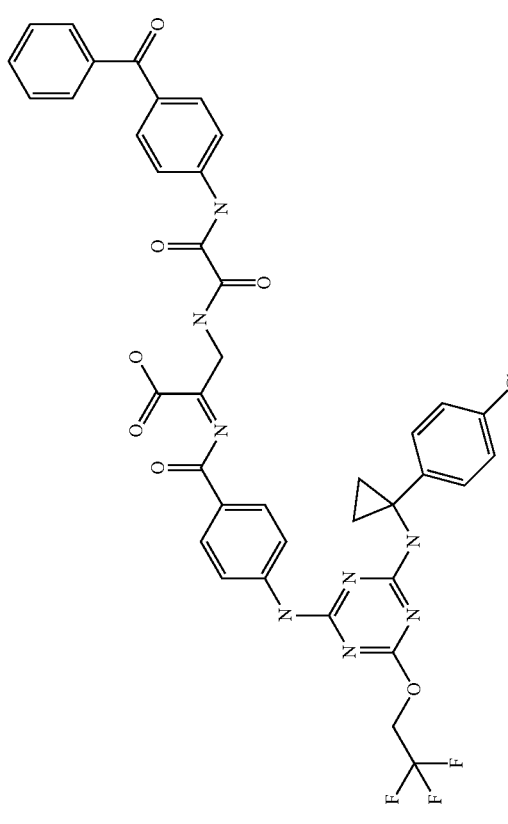 Chiral | | A |

TABLE 1-continued
| Compound | Structure | EC$_{50}$ | Activity |
|---|---|---|---|
| 3153 | 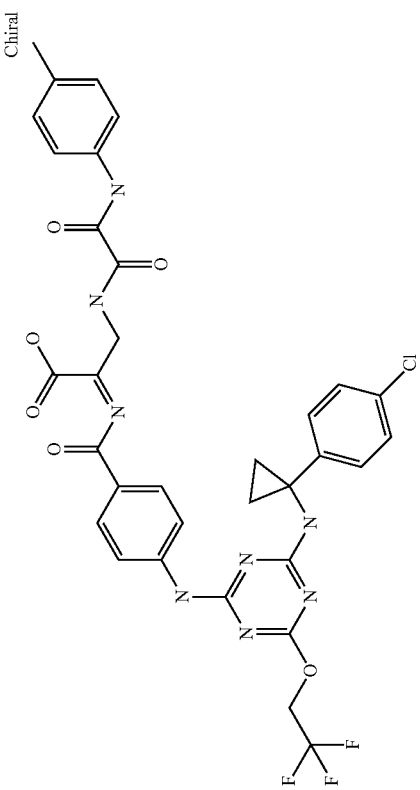 | | A |
| 3154 | 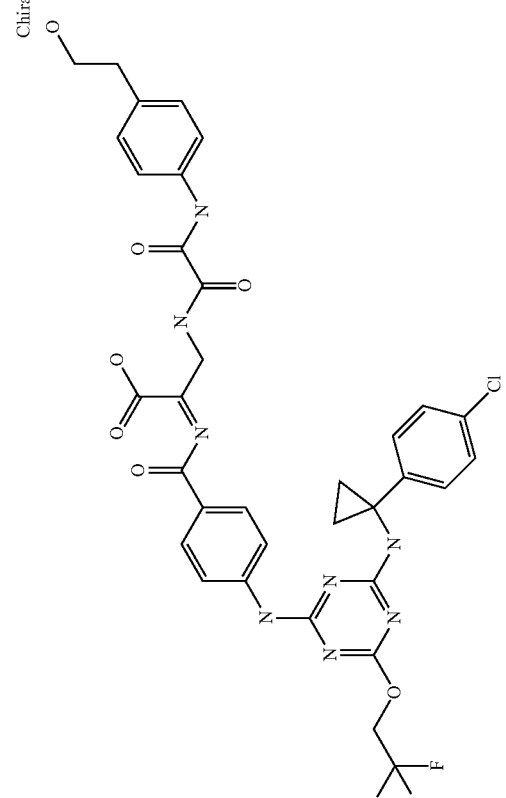 | 1.44 | A |

TABLE 1-continued

| Compound | Structure | EC$_{50}$ | Activity |
|---|---|---|---|
| 3155 | Chiral | | A |
| 3156 | Chiral | | A |

TABLE 1-continued
| Compound | Structure | EC$_{50}$ | Activity |
|---|---|---|---|
| 3157 | 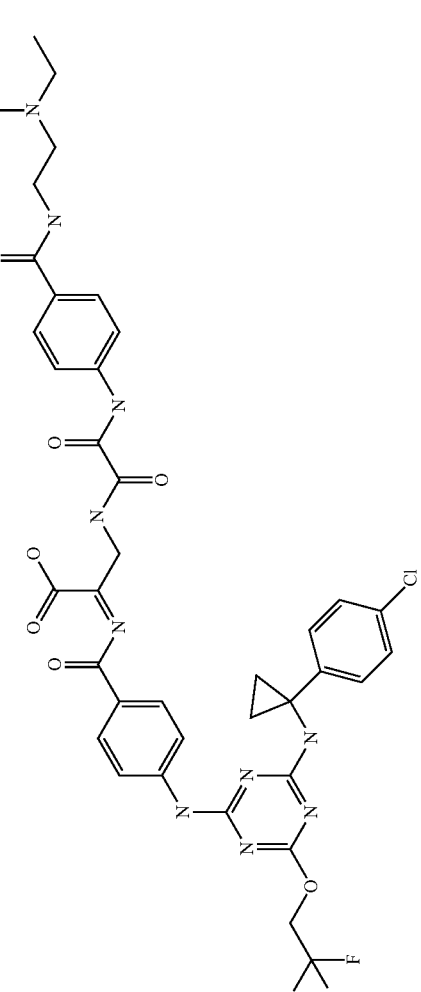 | | A |
| 3158 | 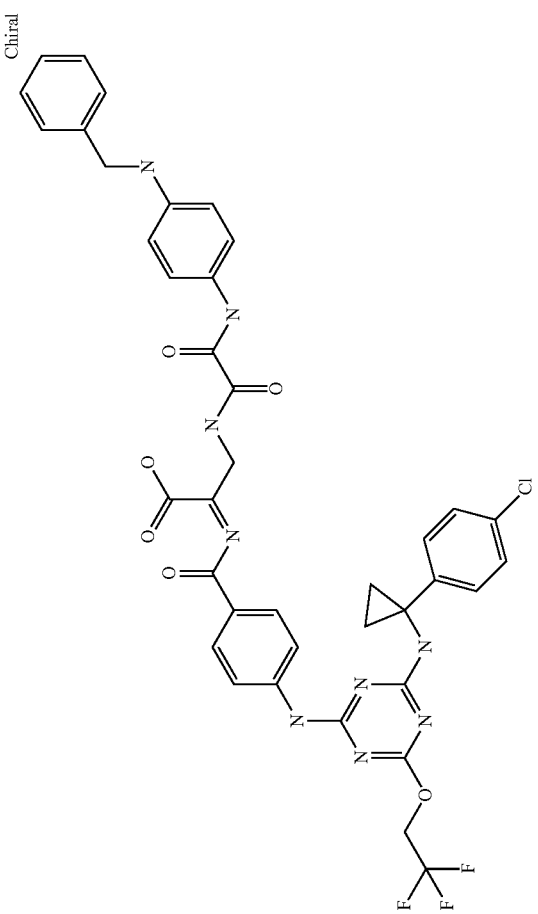 | | A |

TABLE 1-continued

| Compound | Structure | EC50 | Activity |
|---|---|---|---|
| 3159 | Chiral | | A |
| 3160 | 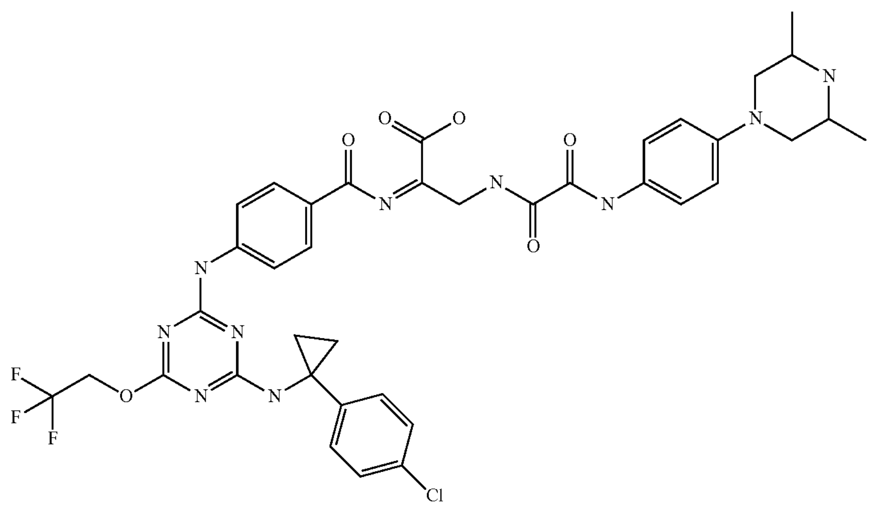 [SMILES: CC1CN(c2ccc(NC(=O)C(=O)NC/C(=N/C(=O)c3ccc(Nc4nc(NC5(c6ccc(Cl)cc6)CC5)nc(OCC(F)(F)F)n4)cc3)C(=O)O)cc2)CC(C)N1] | | A |

TABLE 1-continued
| Compound | Structure | EC$_{50}$ | Activity |
|---|---|---|---|
| 3161 | 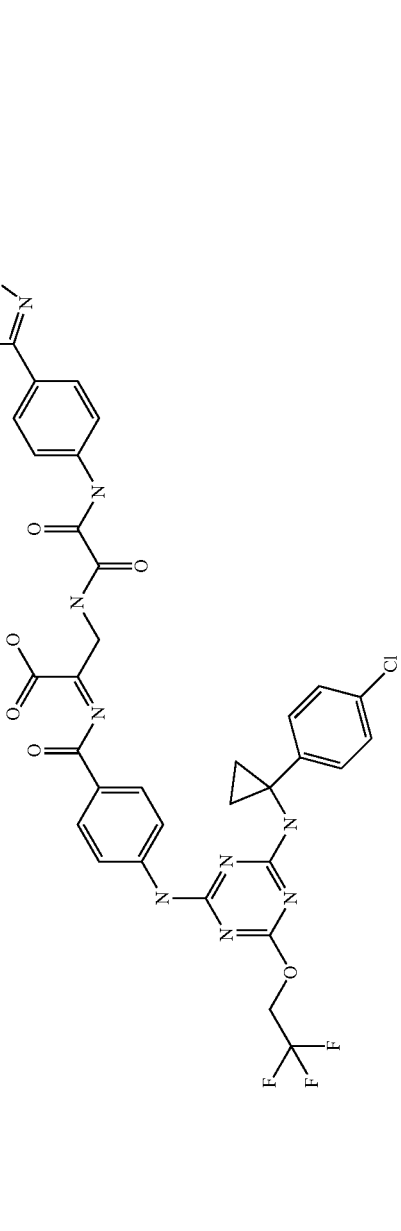 | | A |
| 3162 | 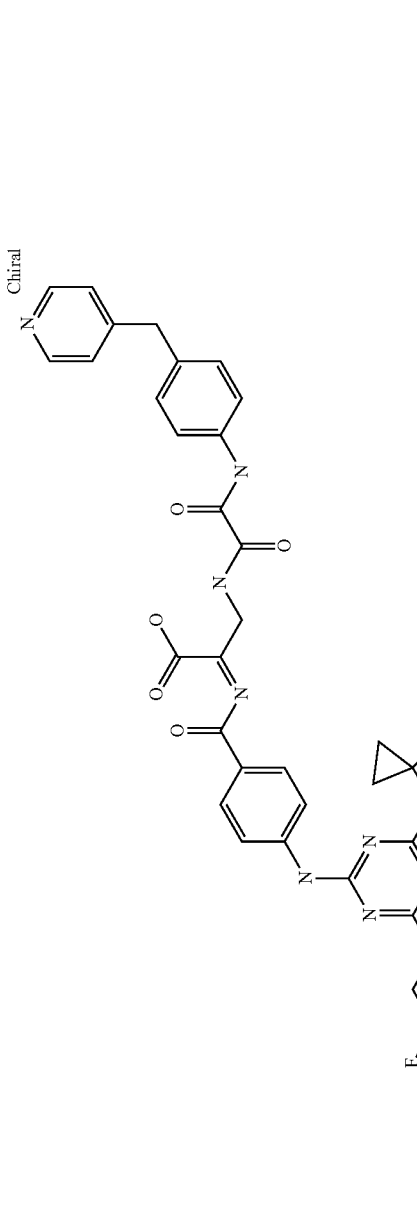 | | A |

TABLE 1-continued
| Compound | Structure | EC$_{50}$ | Activity |
|---|---|---|---|
| 3163 | 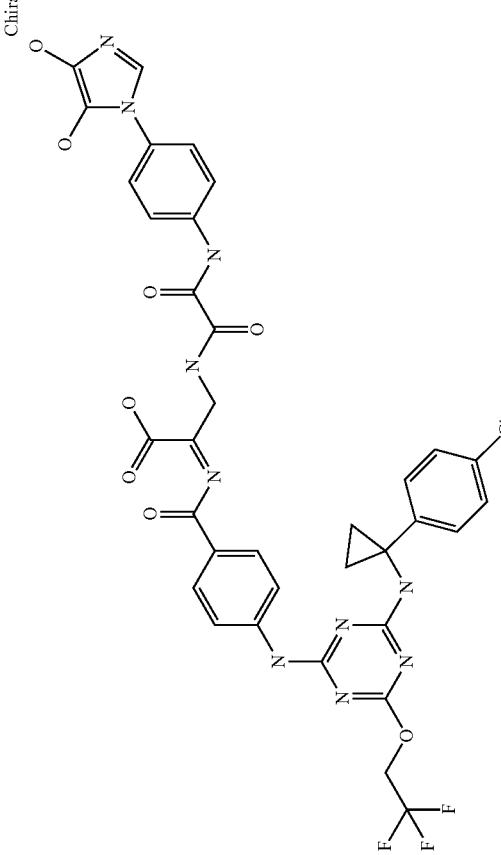 | | A |
| 3164 | 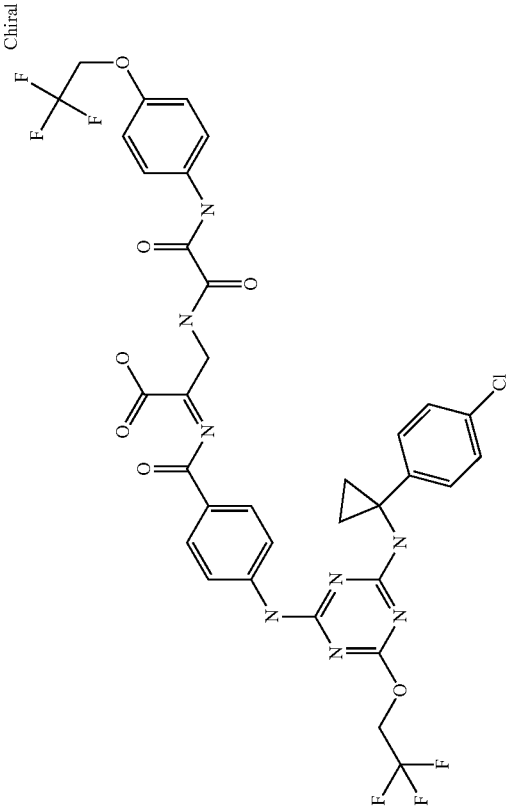 | 0.68 | A |

TABLE 1-continued
| Compound | Structure | EC$_{50}$ | Activity |
|---|---|---|---|
| 3165 | 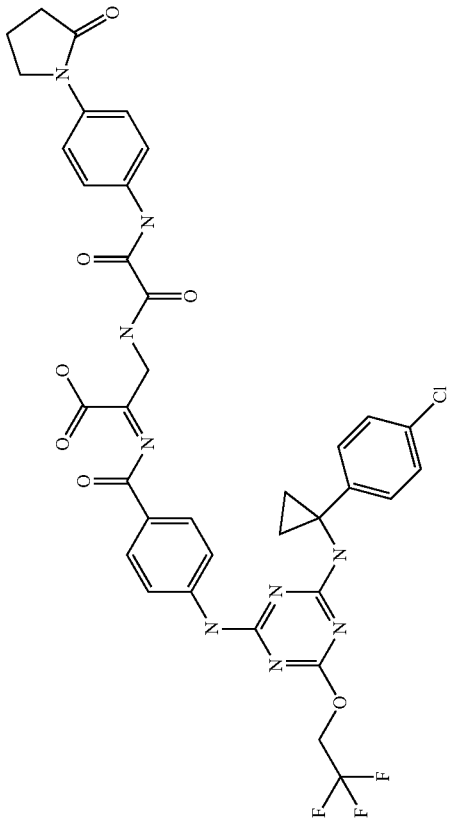 Chiral | | A |
| 3166 | 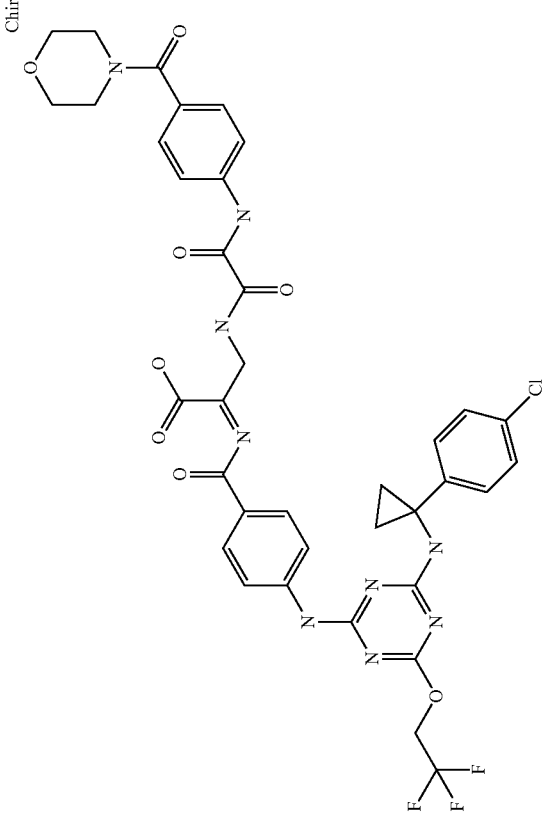 Chiral | | A |

TABLE 1-continued
| Compound | Structure | EC$_{50}$ | Activity |
|---|---|---|---|
| 3167 | 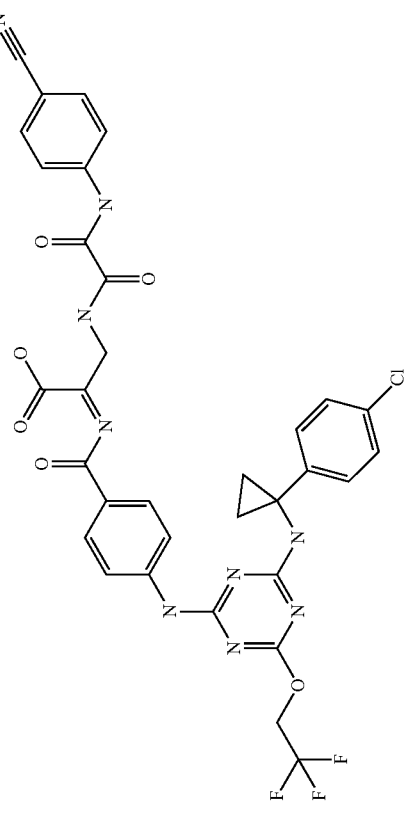 | | A |
| 3168 | 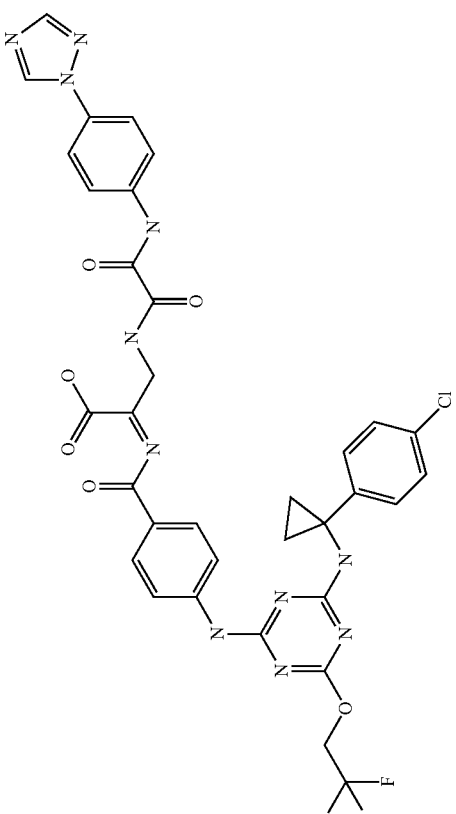 | | A |

TABLE 1-continued
| Compound | Structure | EC$_{50}$ | Activity |
|---|---|---|---|
| 3169 | 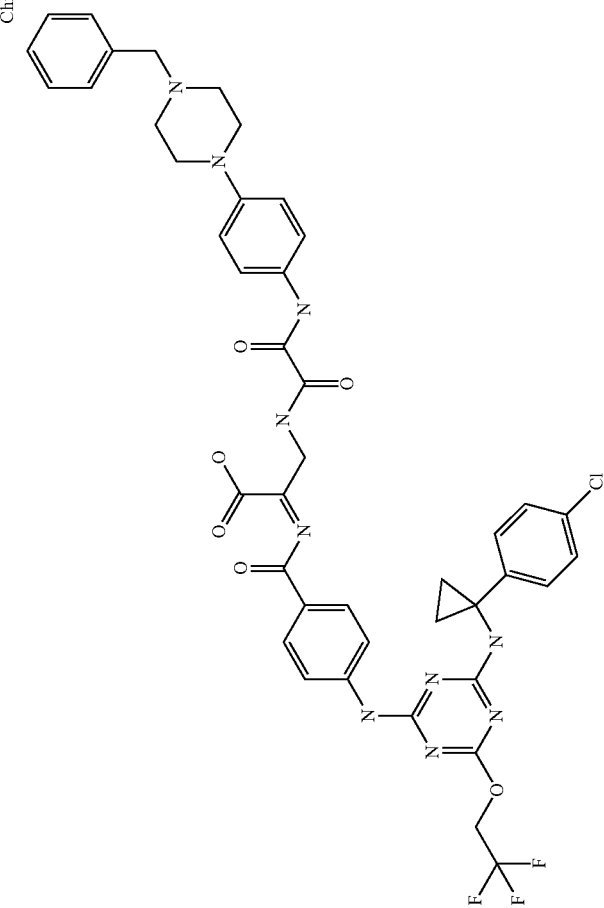 Chiral | | A |

TABLE 1-continued

| Compound | Structure | EC$_{50}$ | Activity |
|---|---|---|---|
| 3170 | Chiral | 0.63 | A |
| 3171 | Chiral | | A |

TABLE 1-continued
| Compound | Structure | EC$_{50}$ | Activity |
|---|---|---|---|
| 3172 | 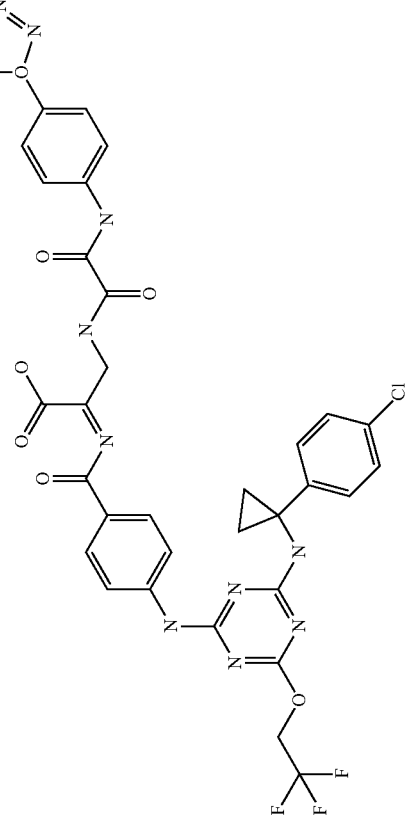 | | A |
| 3173 | 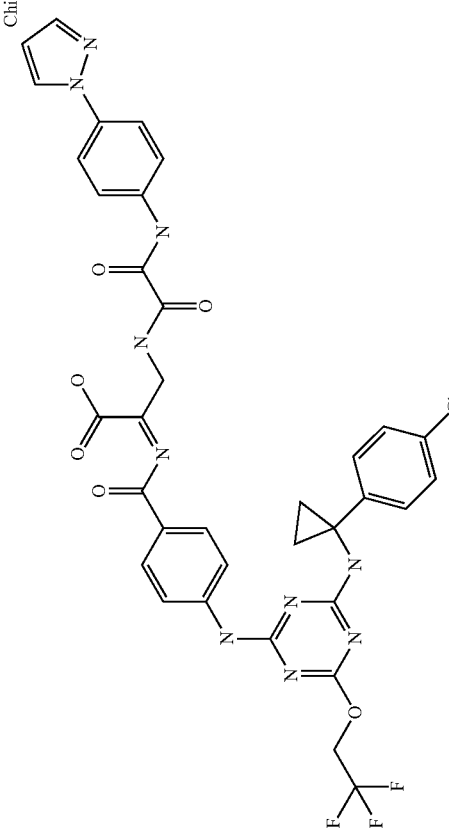 | | A |

TABLE 1-continued

| Compound | Structure | EC$_{50}$ | Activity |
|---|---|---|---|
| 3174 | (chiral structure) | | A |
| 3175 | (structure) | 0.11 | A |

TABLE 1-continued
| Compound | Structure | EC$_{50}$ | Activity |
|---|---|---|---|
| 3176 | 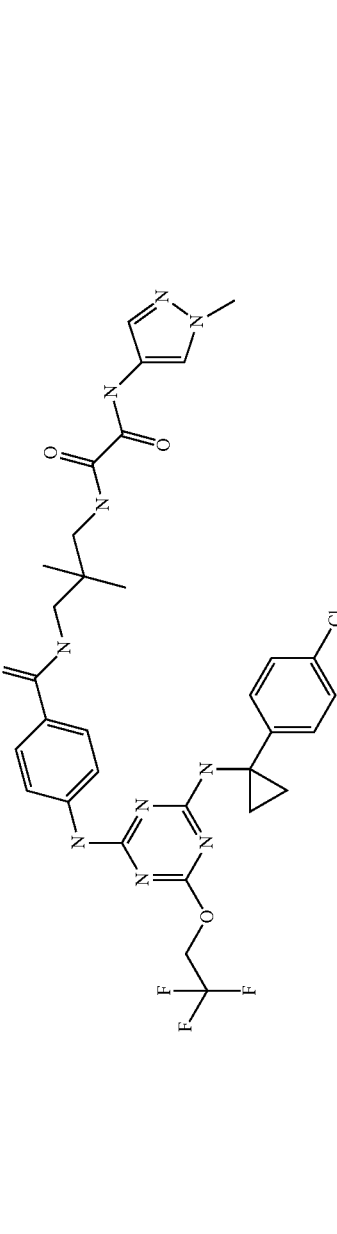 | | A |
| 3177 | 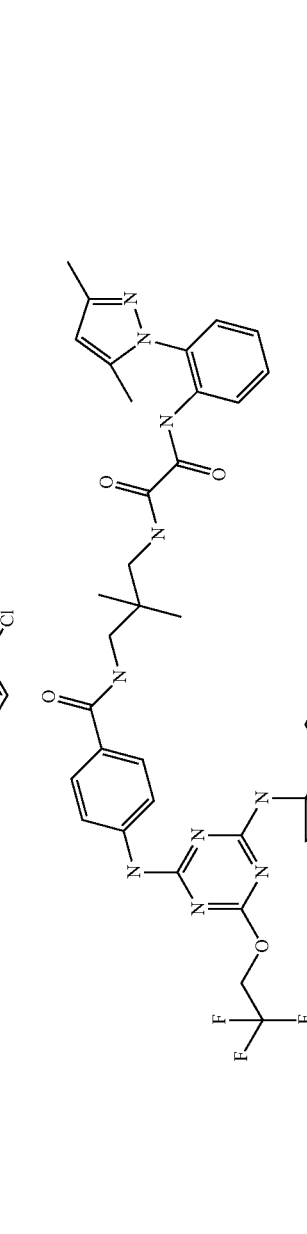 | | A |

TABLE 1-continued

| Compound | Structure | EC$_{50}$ | Activity |
|---|---|---|---|
| 3178 | 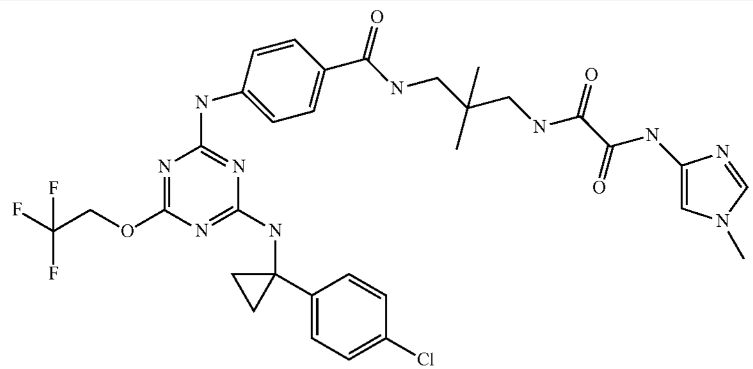 [SMILES: Cn1cnc(NC(=O)C(=O)NCC(C)(C)CNC(=O)c2ccc(Nc3nc(NC4(c5ccc(Cl)cc5)CC4)nc(OCC(F)(F)F)n3)cc2)c1] | | A |
| 3179 | Chiral | | A |

TABLE 1-continued
| Compound | Structure | EC$_{50}$ | Activity |
|---|---|---|---|
| 3180 | 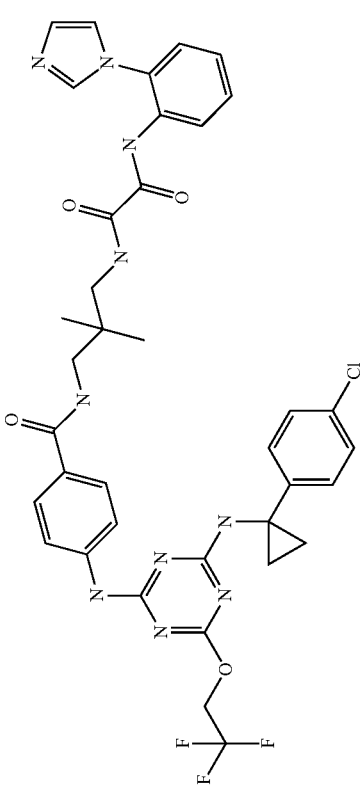 | | A |
| 3181 | 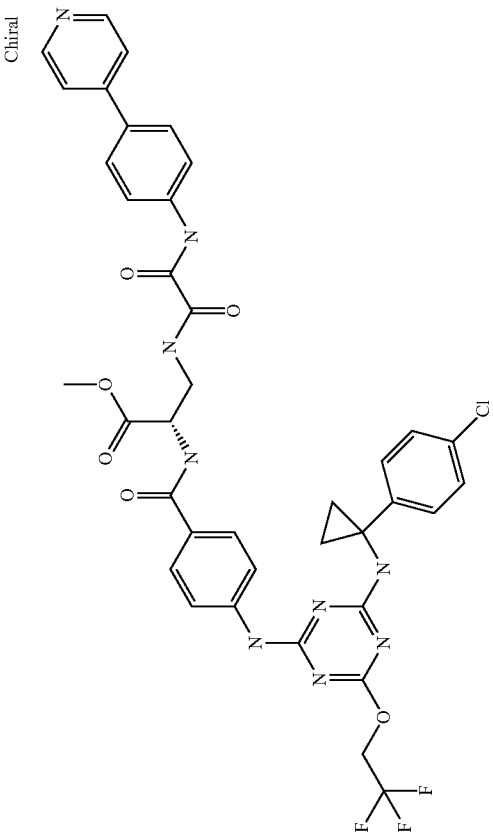 | | A |

TABLE 1-continued
| Compound | Structure | EC$_{50}$ | Activity |
|---|---|---|---|
| 3182 | 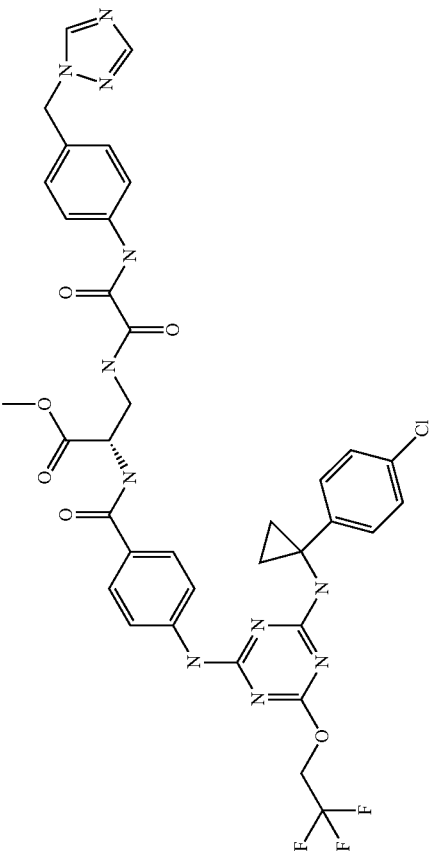 Chiral | | A |
| 3183 | 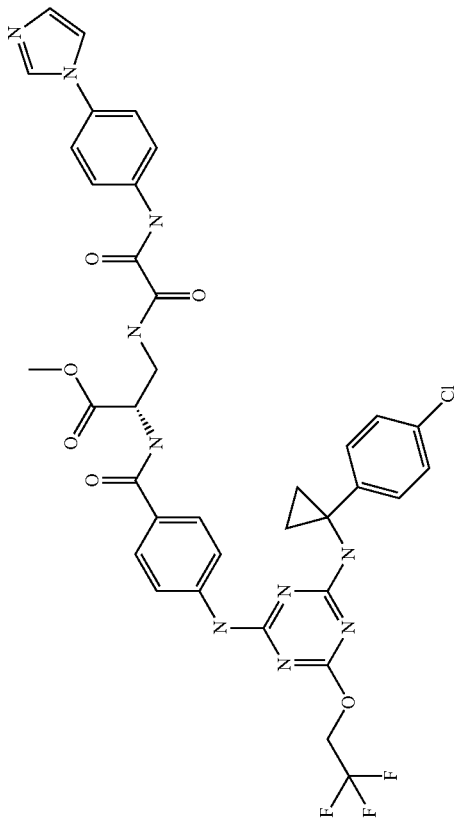 Chiral | | A |

TABLE 1-continued
| Compound | Structure | EC$_{50}$ | Activity |
|---|---|---|---|
| 3184 | 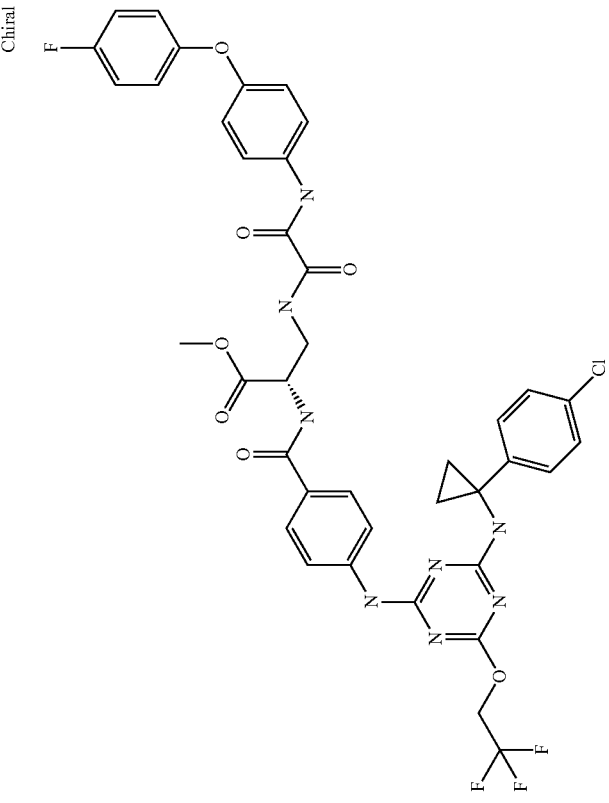 | | A |

TABLE 1-continued
| Compound | Structure | EC$_{50}$ | Activity |
|---|---|---|---|
| 3185 | 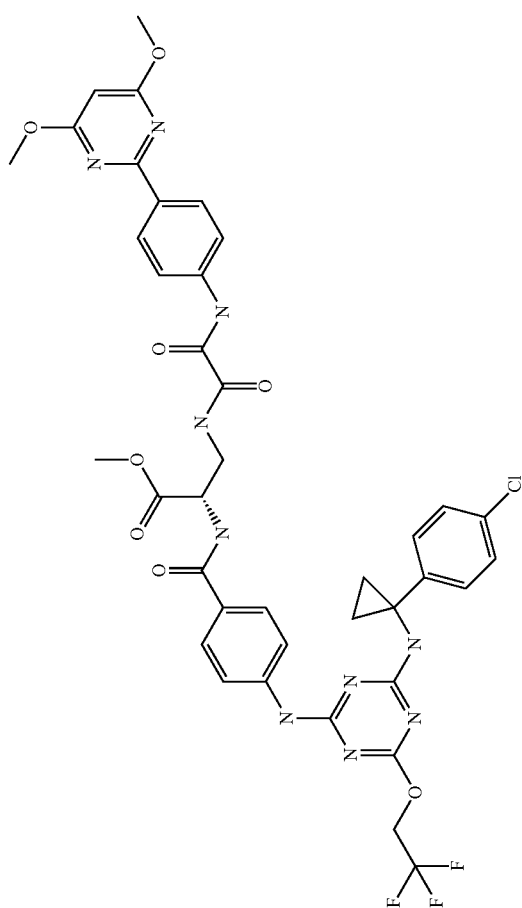 Chiral | | A |

TABLE 1-continued
| Compound | Structure | EC$_{50}$ | Activity |
|---|---|---|---|
| 3186 | 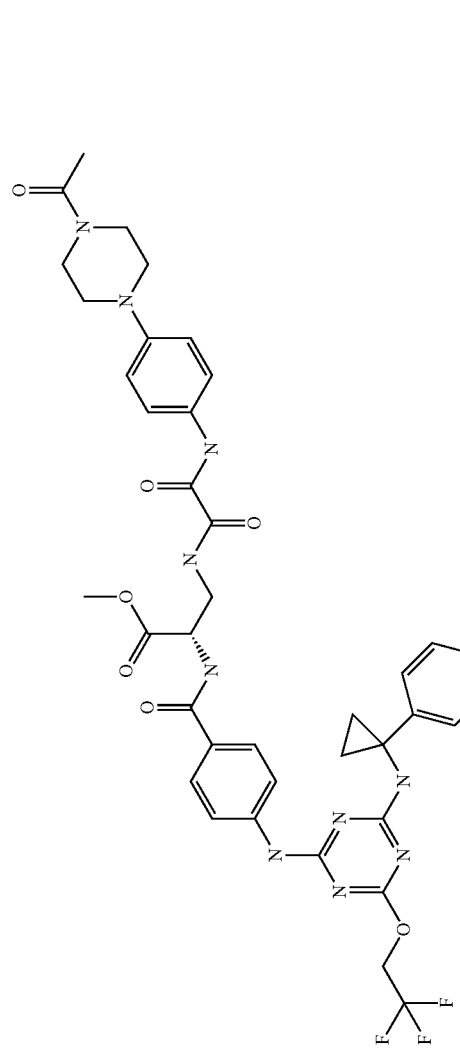 | 0.70 | A |
| 3187 | 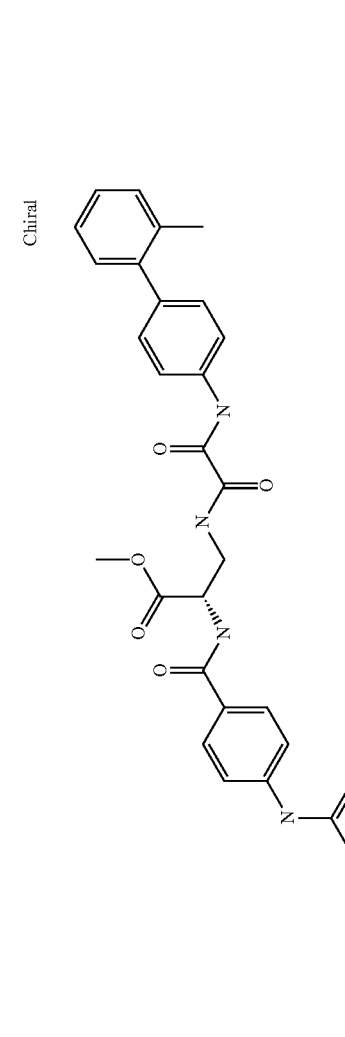 | | A |

TABLE 1-continued
| Compound | Structure | EC$_{50}$ | Activity |
|---|---|---|---|
| 3188 | 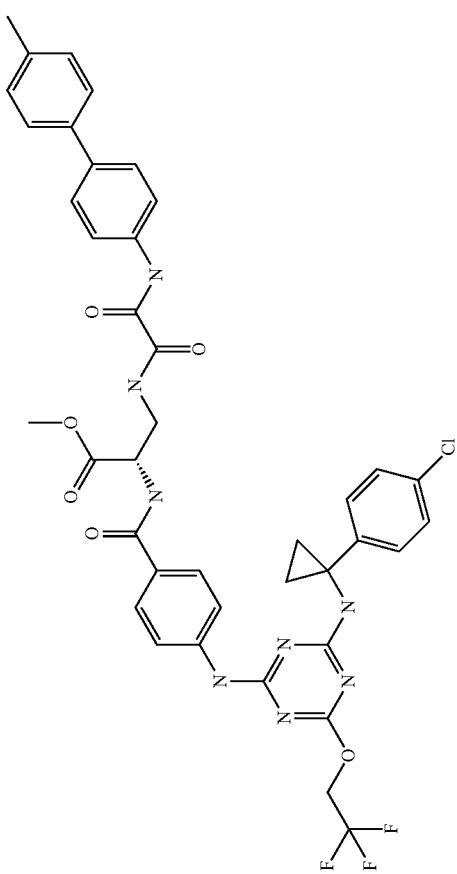 | | A |

TABLE 1-continued
| Compound | Structure | EC$_{50}$ | Activity |
|---|---|---|---|
| 3189 | 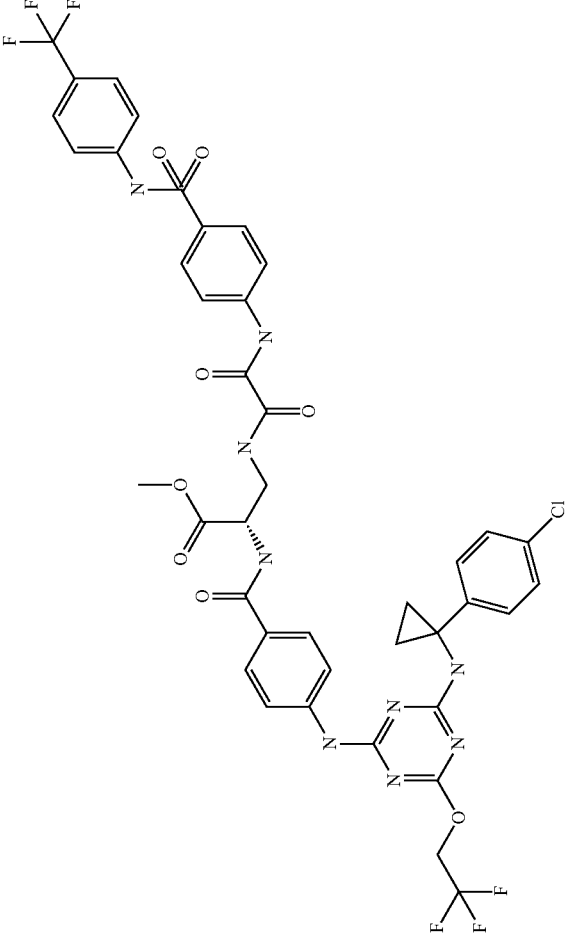 Chiral | | A |

TABLE 1-continued
| Compound | Structure | EC$_{50}$ | Activity |
|---|---|---|---|
| 3190 | 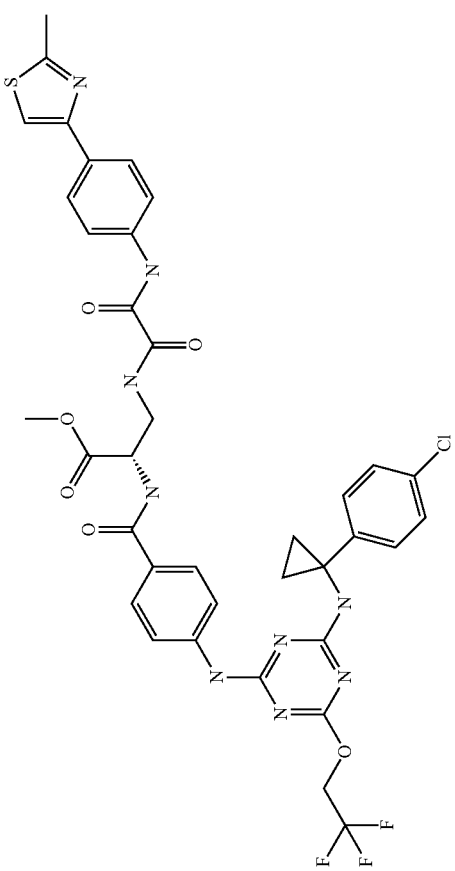 | | A |
| 3191 | 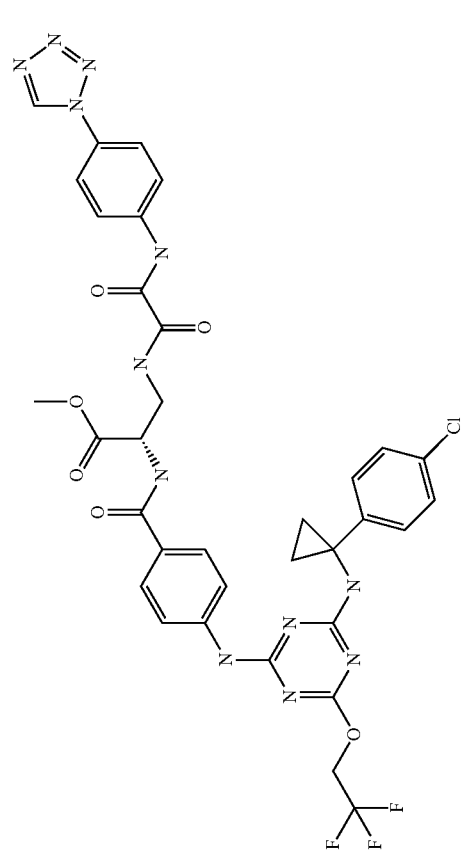 | 0.82 | A |

TABLE 1-continued
| Compound | Structure | EC$_{50}$ | Activity |
|---|---|---|---|
| 3192 | 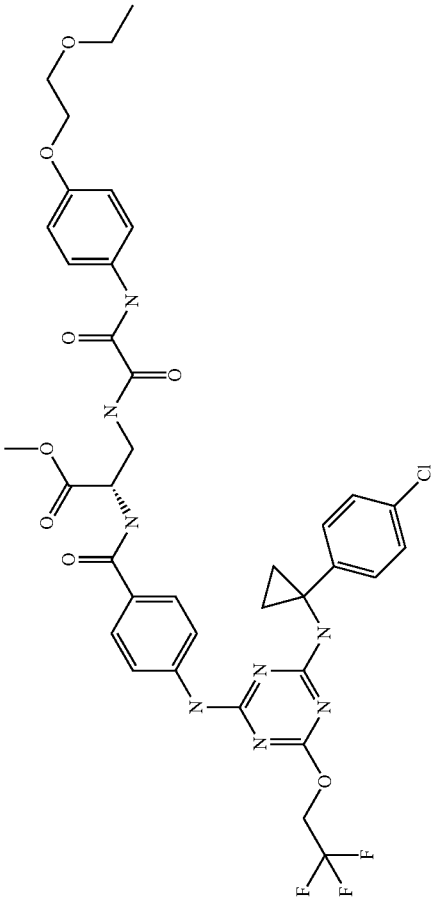 | | A |
| 3193 | 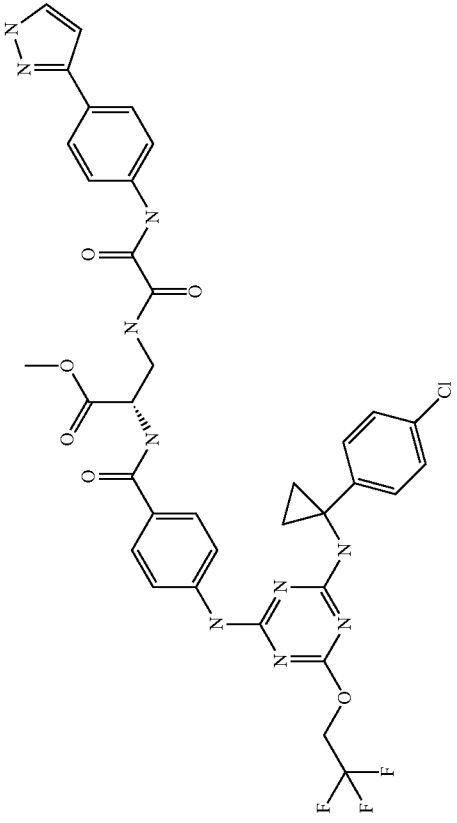 | 1.03 | A |

TABLE 1-continued
| Compound | Structure | EC$_{50}$ | Activity |
|---|---|---|---|
| 3194 | 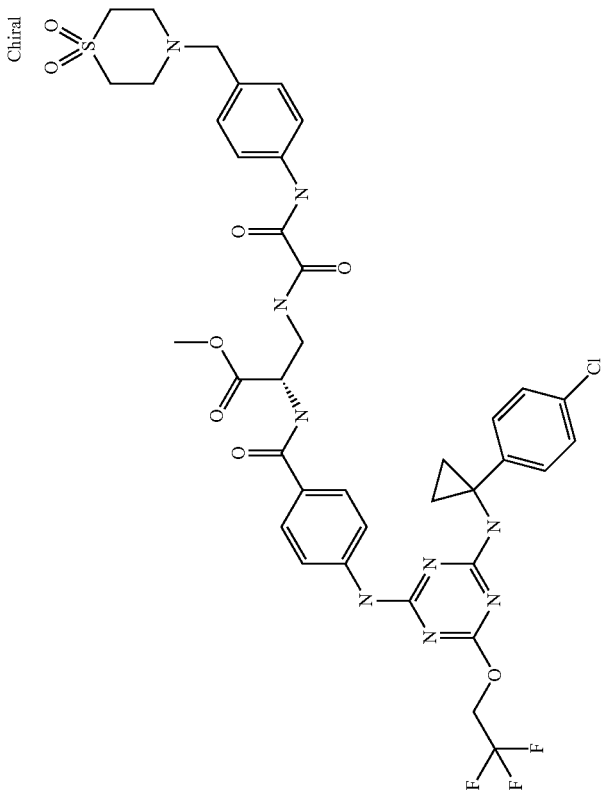 Chiral | | A |

TABLE 1-continued
| Compound | Structure | EC$_{50}$ | Activity |
|---|---|---|---|
| 3195 | Chiral 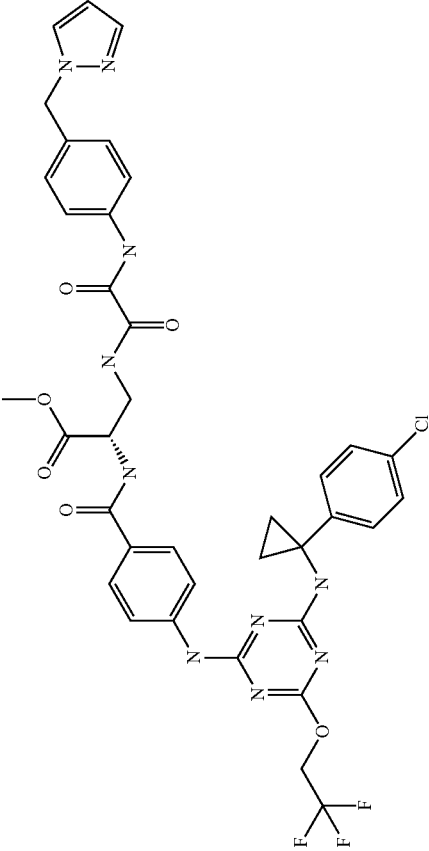 | | A |

TABLE 1-continued
| Compound | Structure | EC$_{50}$ | Activity |
|---|---|---|---|
| 3196 | 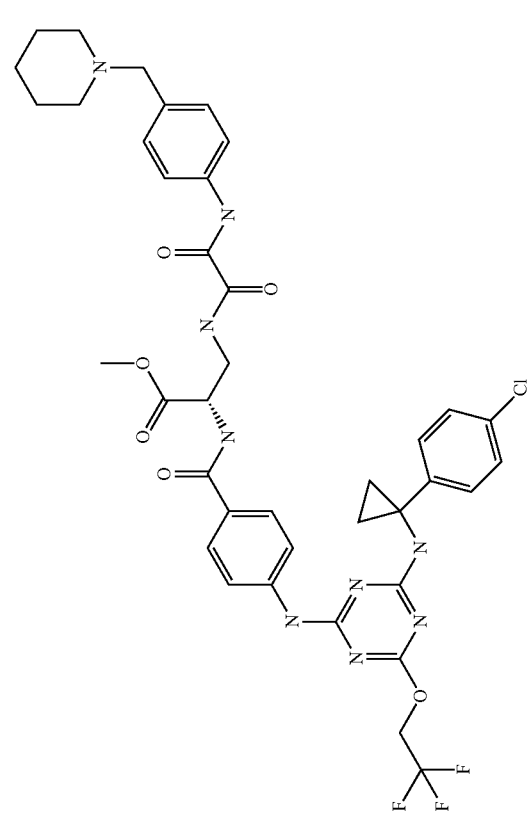 | | A |
| 3197 | 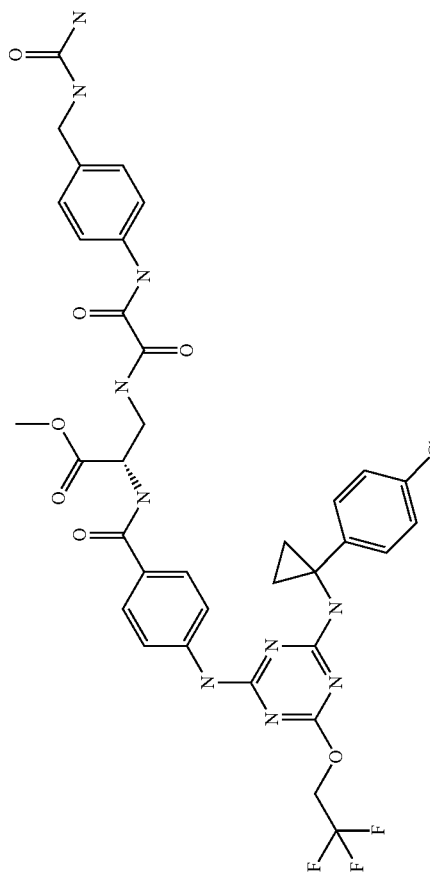 | | A |

TABLE 1-continued
| Compound | Structure | EC$_{50}$ | Activity |
|---|---|---|---|
| 3198 | 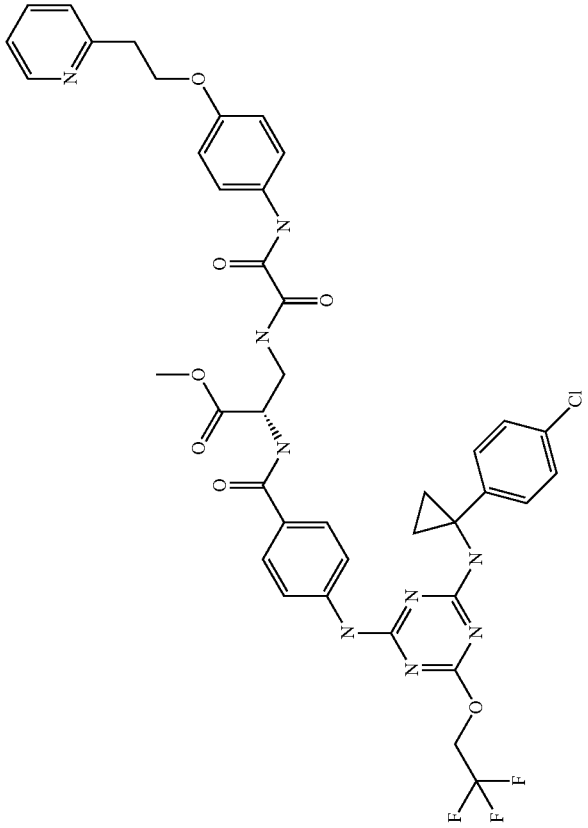 Chiral | 1.02 | A |

TABLE 1-continued

| Compound | Structure | EC$_{50}$ | Activity |
|---|---|---|---|
| 3199 | Chiral | | A |
| 3200 | Chiral | | A |

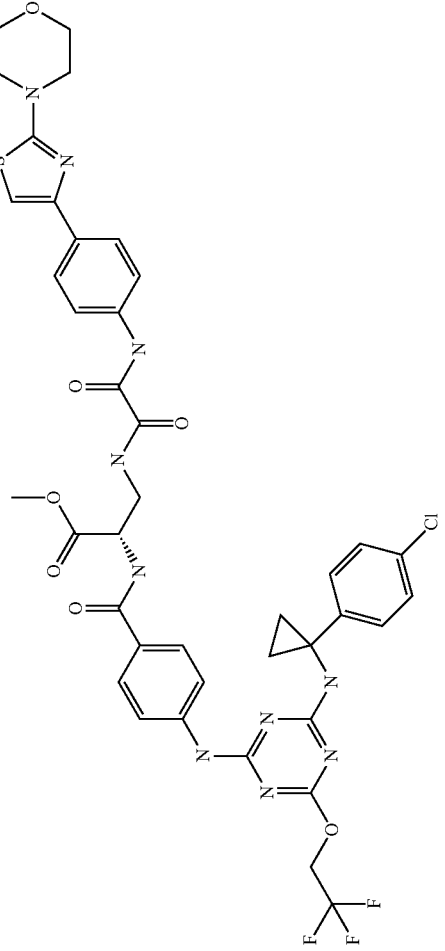

TABLE 1-continued
| Compound | Structure | EC50 | Activity |
|---|---|---|---|
| 3203 | 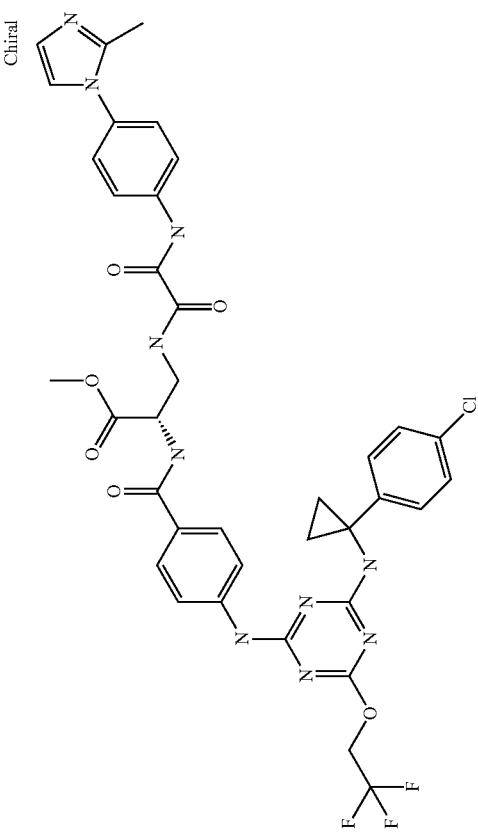 | 5.47 | A |
| 3204 | 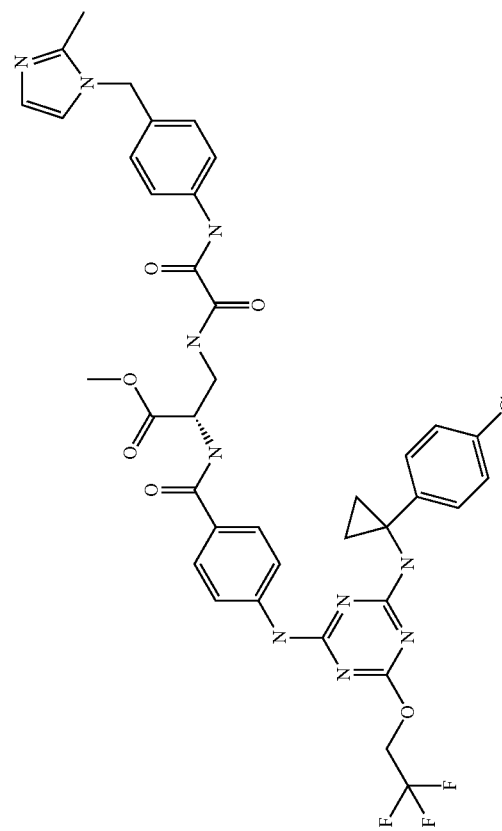 | | A |

TABLE 1-continued

| Compound | Structure | EC$_{50}$ | Activity |
|---|---|---|---|
| 3205 | Chiral | | A |
| 3206 | Chiral | | A |

| Compound | Structure | EC$_{50}$ | Activity |
|---|---|---|---|
| 3207 | Chiral 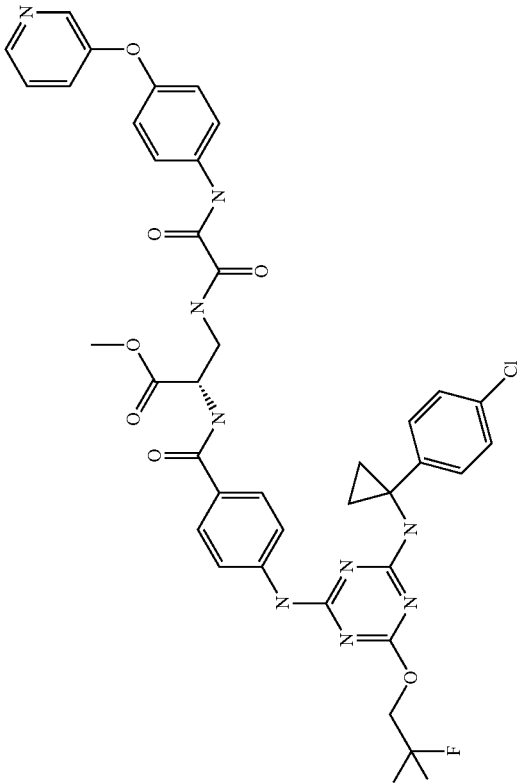 | | A |

TABLE 1-continued
| Compound | Structure | EC$_{50}$ | Activity |
|---|---|---|---|
| 3208 | 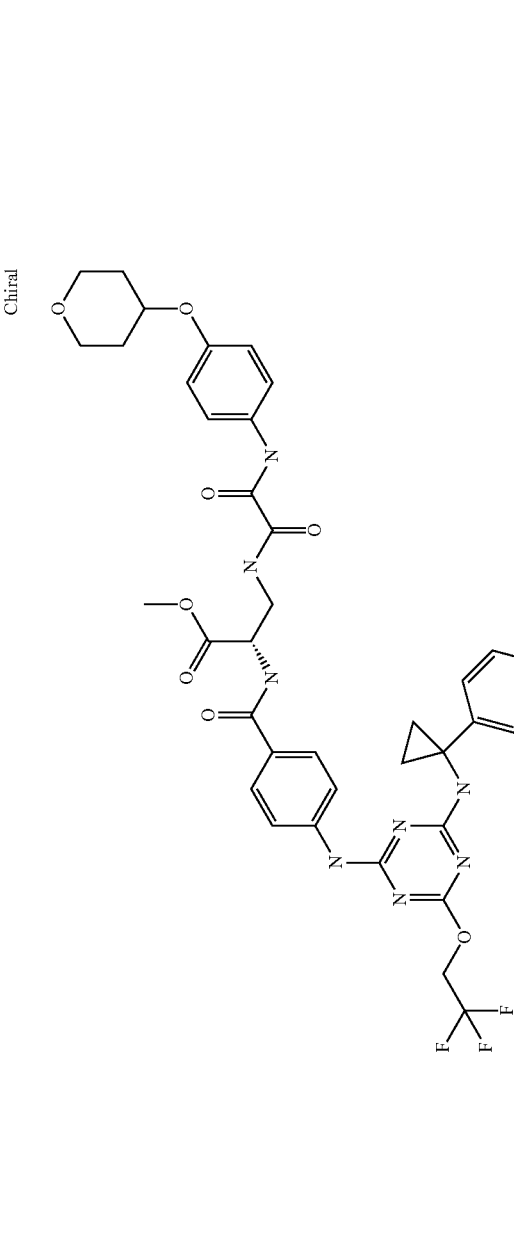 Chiral | | A |

TABLE 1-continued
| Compound | Structure | EC$_{50}$ | Activity |
|---|---|---|---|
| 3209 | 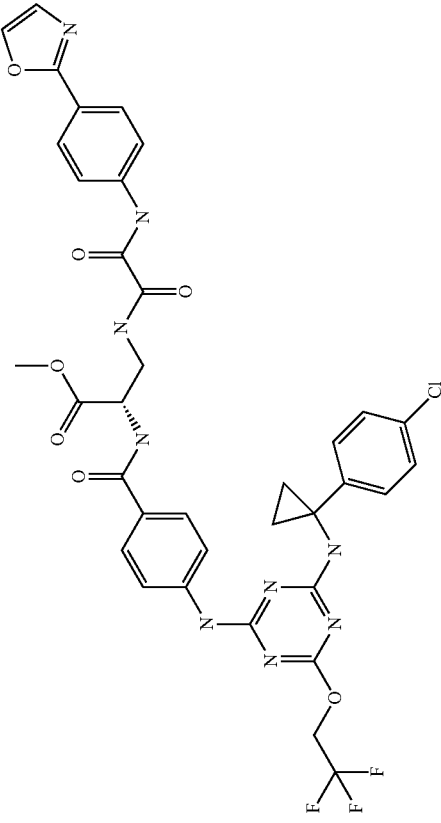 | | A |
| 3210 | 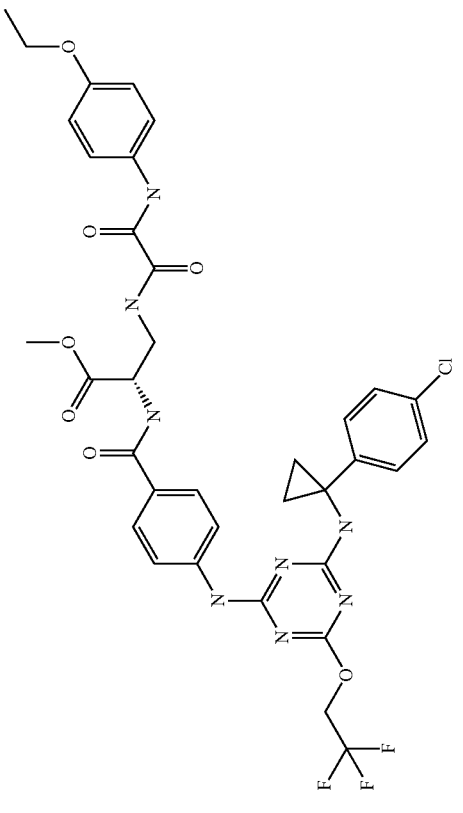 | 0.75 | A |

TABLE 1-continued
| Compound | Structure | EC$_{50}$ | Activity |
|---|---|---|---|
| 3211 | Chiral 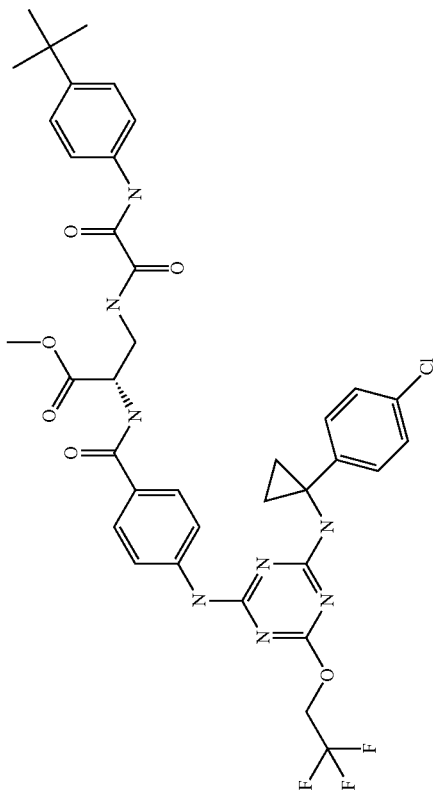 | | A |
| 3212 | Chiral 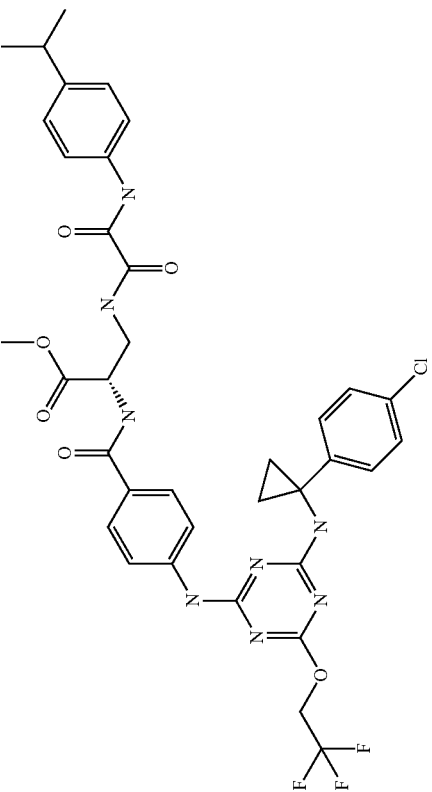 | | A |

TABLE 1-continued
| Compound | Structure | EC$_{50}$ | Activity |
|---|---|---|---|
| 3213 | 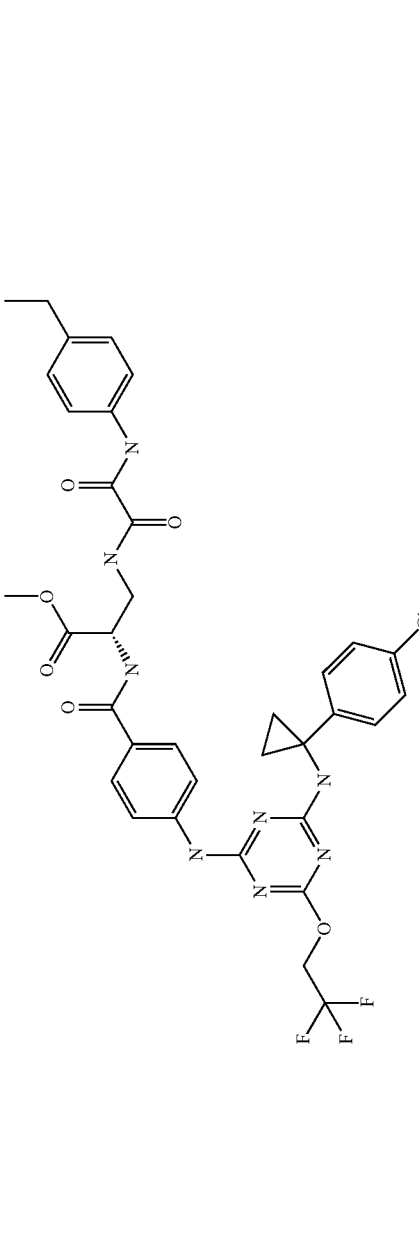 | | A |
| 3214 | 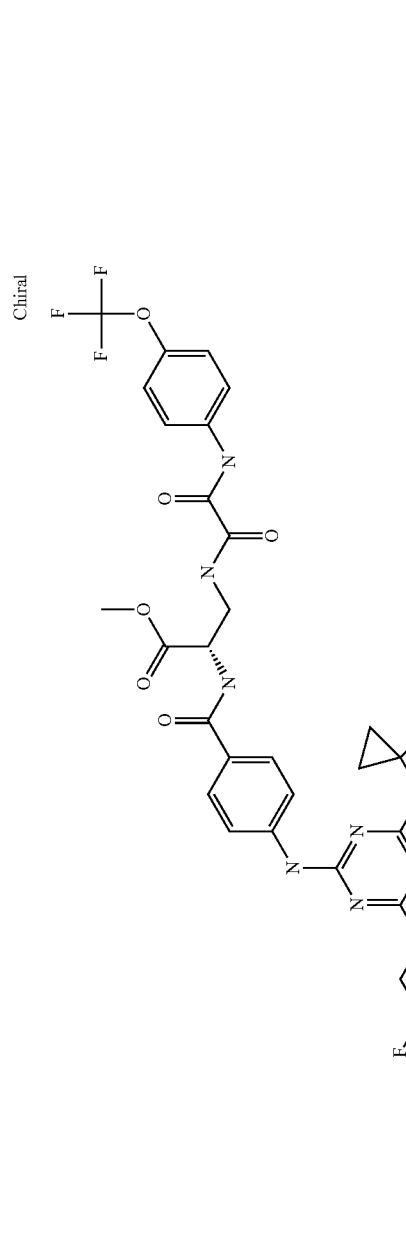 | | A |

TABLE 1-continued
| Compound | Structure | EC$_{50}$ | Activity |
|---|---|---|---|
| 3215 | 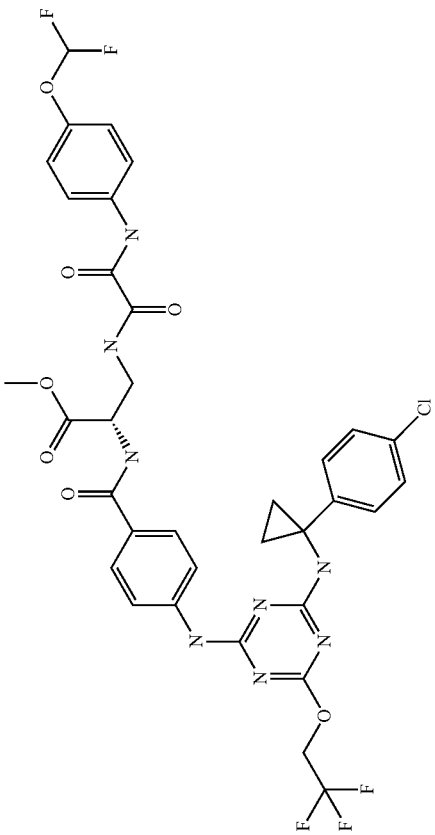 Chiral | | A |
| 3216 | 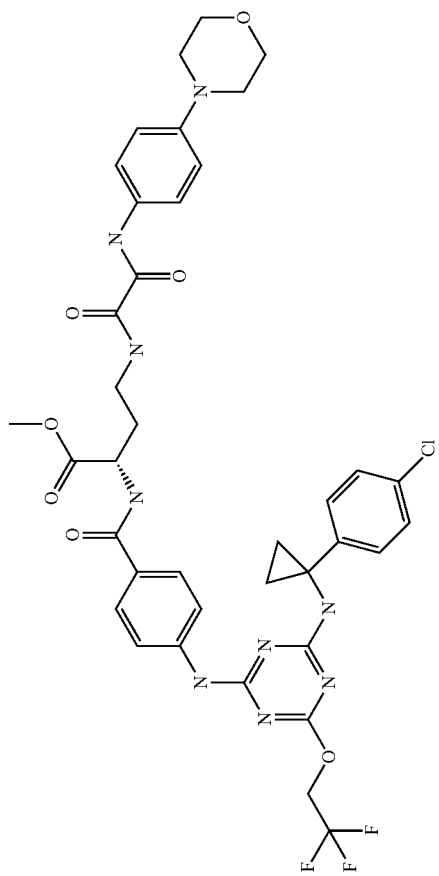 Chiral | | A |

TABLE 1-continued
| Compound | Structure | EC$_{50}$ | Activity |
|---|---|---|---|
| 3217 | Chiral 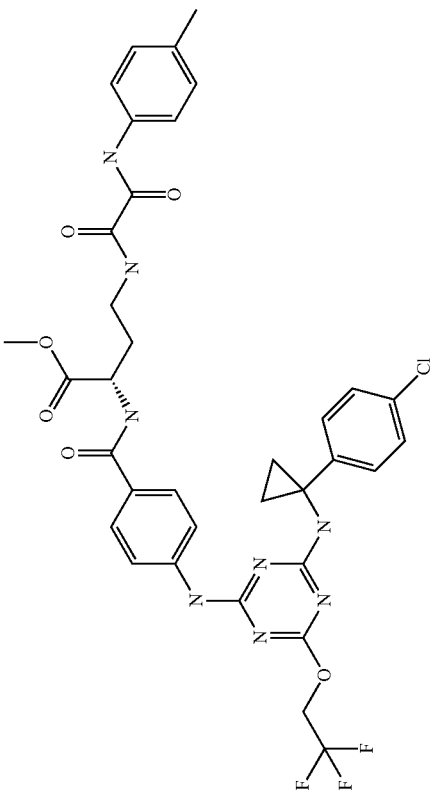 | 0.087 | A |
| 3218 | Chiral 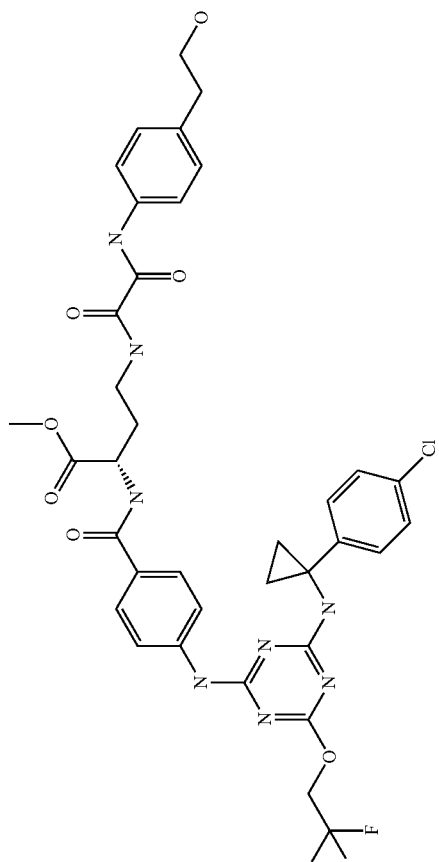 | | A |

TABLE 1-continued
| Compound | Structure | EC$_{50}$ | Activity |
|---|---|---|---|
| 3219 | 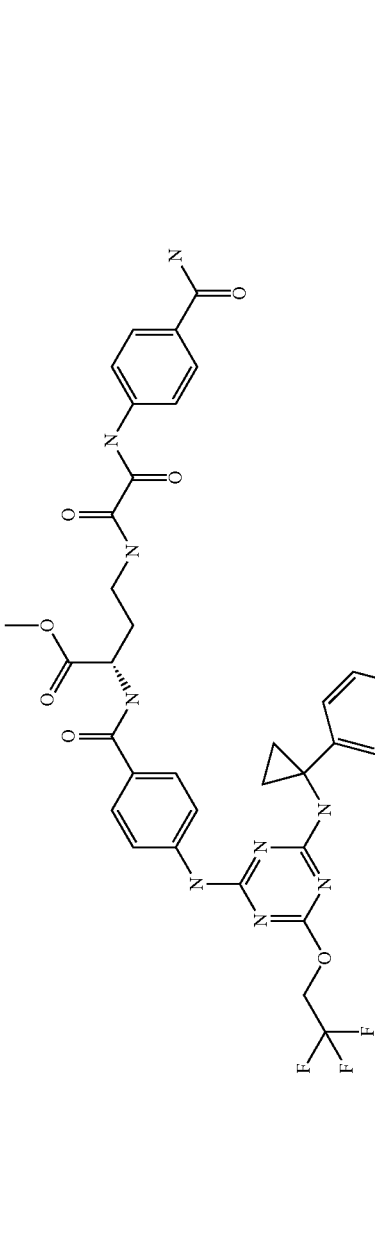 | | A |
| 3220 | 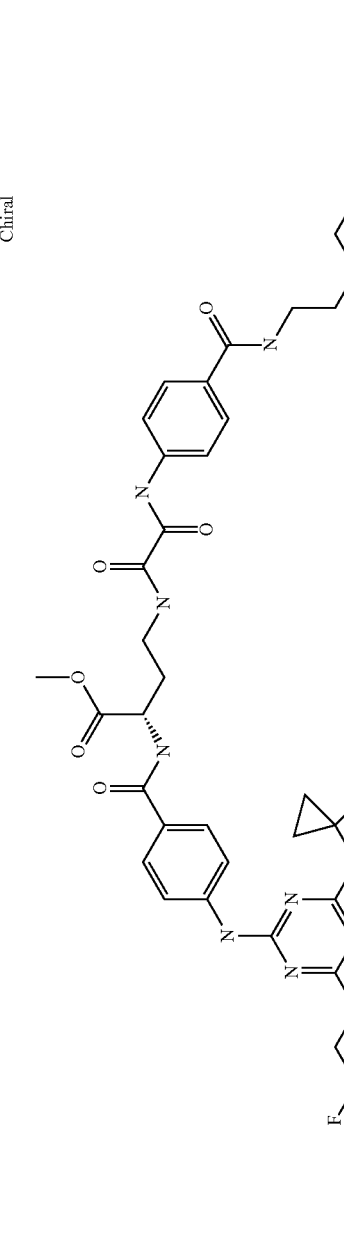 | | A |

TABLE 1-continued

| Compound | Structure | EC$_{50}$ | Activity |
|---|---|---|---|
| 3221 | Chiral | | A |
| 3222 | Chiral | | A |

TABLE 1-continued
| Compound | Structure | EC$_{50}$ | Activity |
|---|---|---|---|
| 3223 | 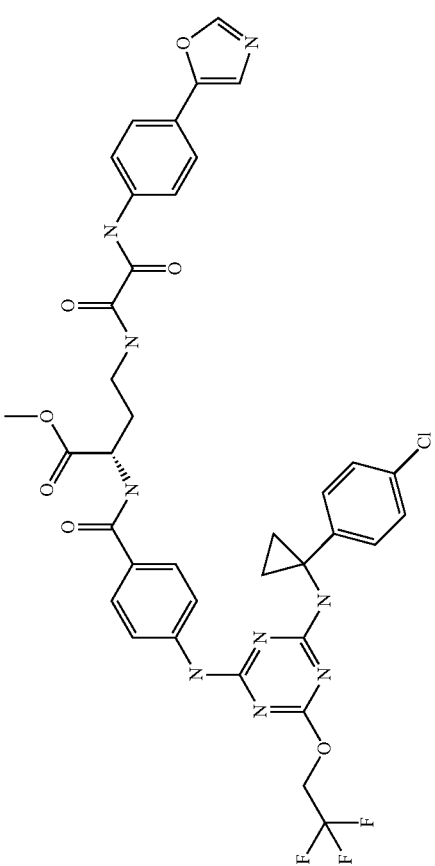 Chiral | | A |
| 3224 | 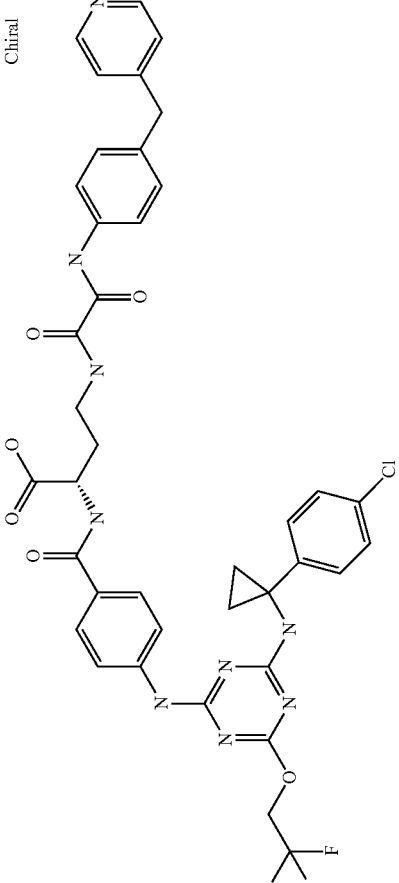 Chiral | | A |

TABLE 1-continued
| Compound | Structure | EC$_{50}$ | Activity |
|---|---|---|---|
| 3225 | 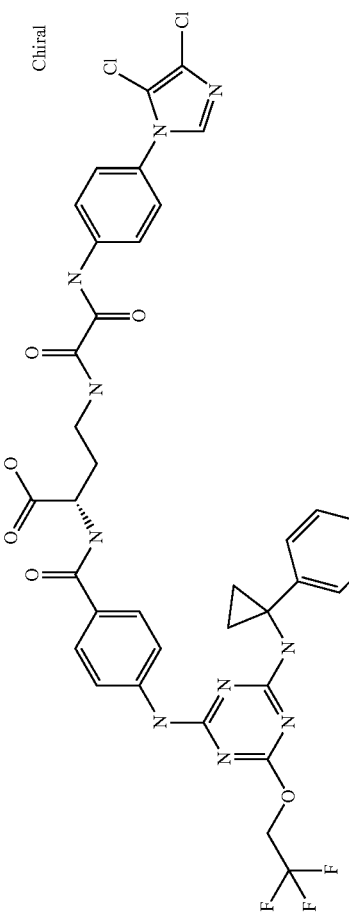 | 16.99 | B |
| 3226 | 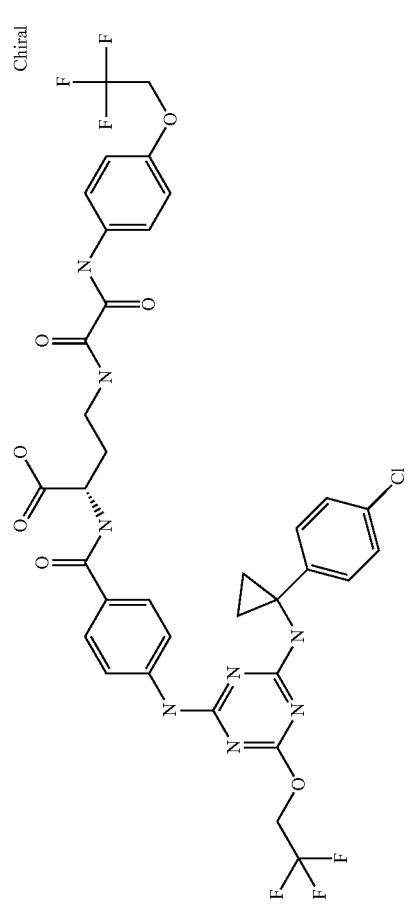 | | A |

TABLE 1-continued
| Compound | Structure | EC$_{50}$ | Activity |
|---|---|---|---|
| 3227 | 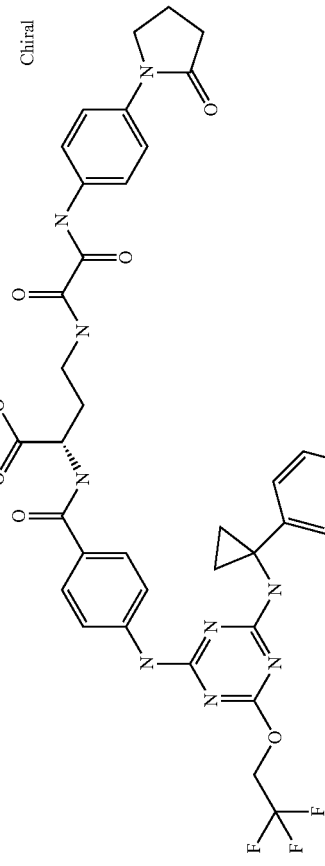 | | A |
| 3228 | 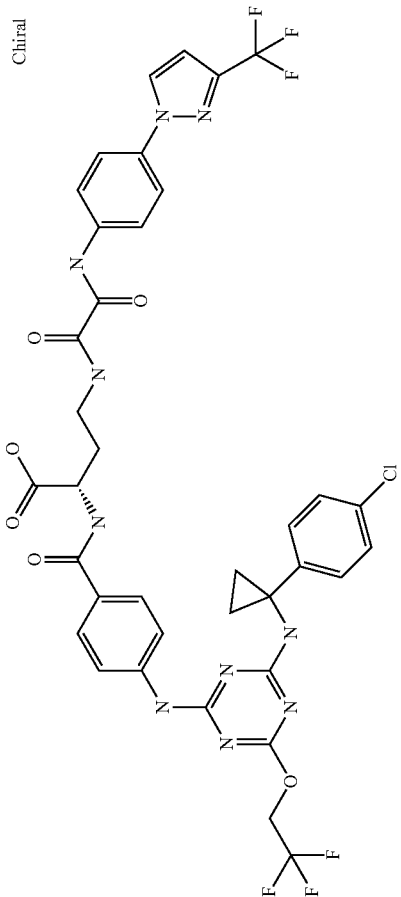 | | A |

TABLE 1-continued
| Compound | Structure | EC$_{50}$ | Activity |
|---|---|---|---|
| 3229 | 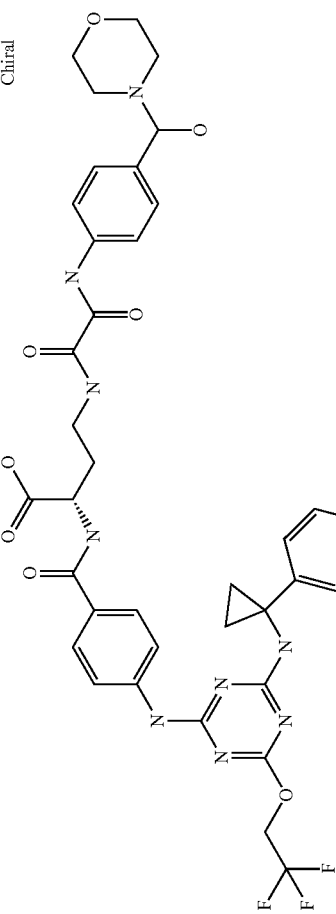 | | B |
| 3230 | 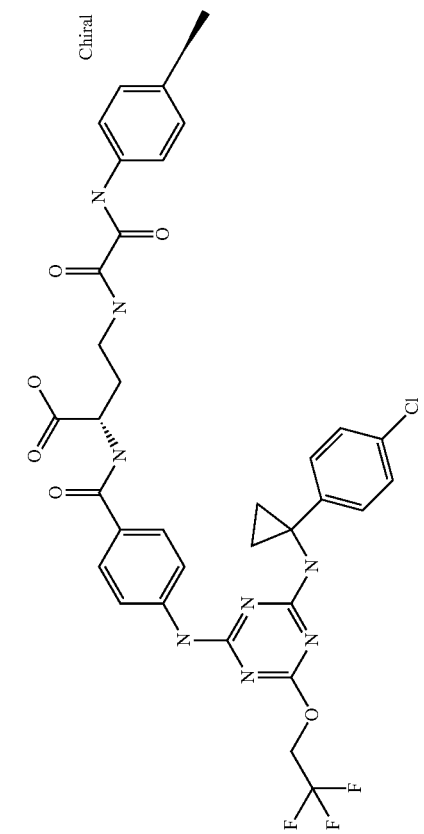 | | A |

TABLE 1-continued

| Compound | Structure | EC$_{50}$ | Activity |
|---|---|---|---|
| 3231 | (chiral structure) | | A |
| 3232 | (chiral structure) | | A |

TABLE 1-continued

| Compound | Structure | EC$_{50}$ | Activity |
|---|---|---|---|
| 3233 | 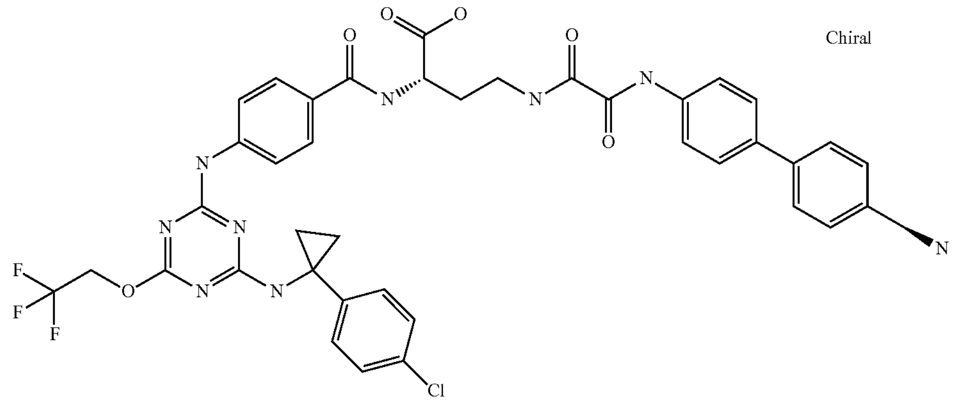 | | A |
| 3234 | 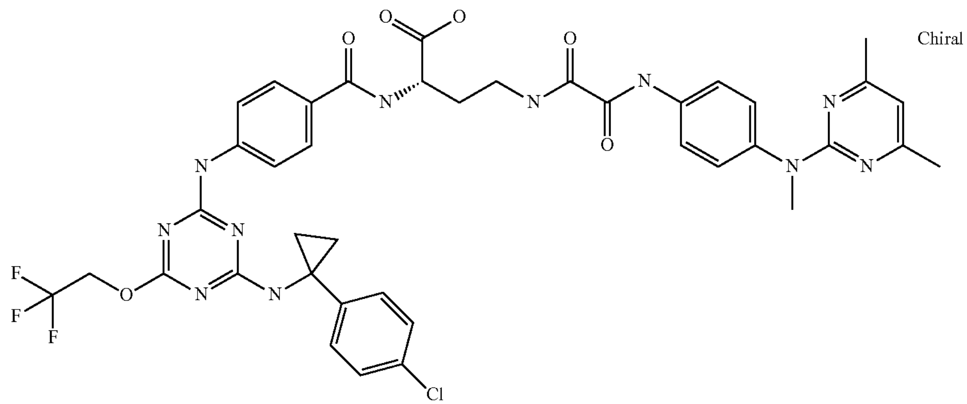 [SMILES: Cc1cc(C)nc(N(C)c2ccc(NC(=O)C(=O)NCC[C@H](NC(=O)c3ccc(Nc4nc(NC5(c6ccc(Cl)cc6)CC5)nc(OCC(F)(F)F)n4)cc3)C(=O)O)cc2)n1] | 0.24 | A |

TABLE 1-continued
| Compound | Structure | EC$_{50}$ | Activity |
|---|---|---|---|
| 3235 | 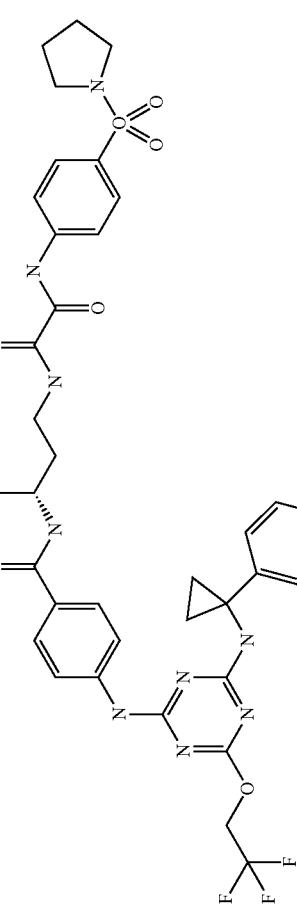 | | A |
| 3236 | 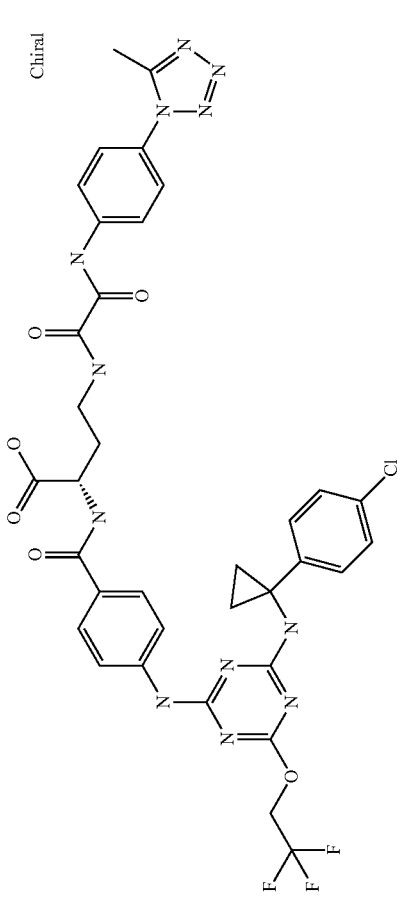 | | A |

TABLE 1-continued

| Compound | Structure | EC$_{50}$ | Activity |
|---|---|---|---|
| 3237 | Chiral | | A |
| 3238 | Chiral | | A |

TABLE 1-continued

| Compound | Structure | EC$_{50}$ | Activity |
|---|---|---|---|
| 3239 | 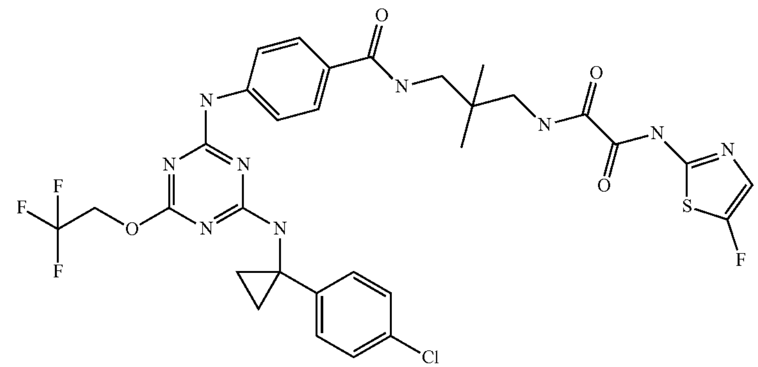 [SMILES: CC(C)(CNC(=O)C(=O)Nc1ncc(F)s1)CNC(=O)c1ccc(Nc2nc(NC3(c4ccc(Cl)cc4)CC3)nc(OCC(F)(F)F)n2)cc1] | | A |
| 3240 | 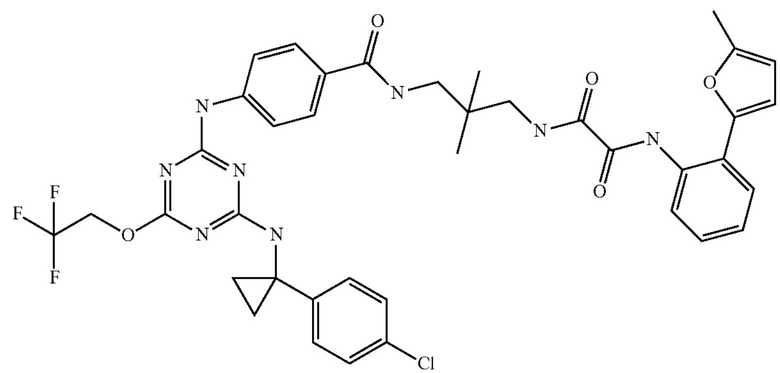 [SMILES: Cc1ccc(-c2ccccc2NC(=O)C(=O)NCC(C)(C)CNC(=O)c2ccc(Nc3nc(NC4(c5ccc(Cl)cc5)CC4)nc(OCC(F)(F)F)n3)cc2)o1] | | A |

TABLE 1-continued

| Compound | Structure | EC$_{50}$ | Activity |
|---|---|---|---|
| 3241 | 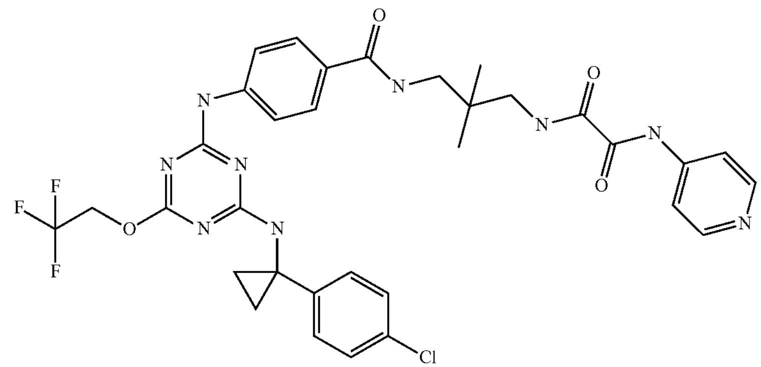 [SMILES: CC(C)(CNC(=O)C(=O)Nc1ccncc1)CNC(=O)c1ccc(Nc2nc(NC3(c4ccc(Cl)cc4)CC3)nc(OCC(F)(F)F)n2)cc1] | | A |
| 3242 | 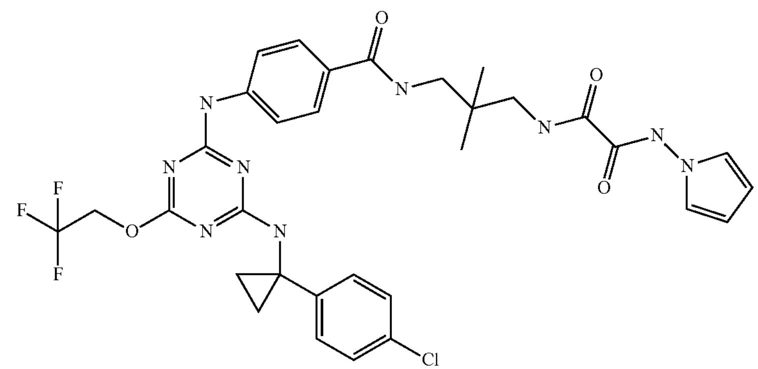 [SMILES: CC(C)(CNC(=O)C(=O)Nn1cccc1)CNC(=O)c1ccc(Nc2nc(NC3(c4ccc(Cl)cc4)CC3)nc(OCC(F)(F)F)n2)cc1] | 0.030 | A |

TABLE 1-continued

| Compound | Structure | EC$_{50}$ | Activity |
|---|---|---|---|
| 3243 | 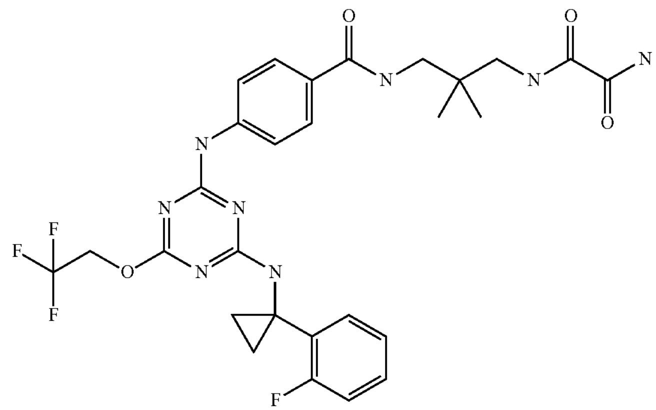 [SMILES: CC(C)(CNC(=O)C(N)=O)CNC(=O)c1ccc(Nc2nc(NC3(c4ccccc4F)CC3)nc(OCC(F)(F)F)n2)cc1] | | A |
| 3244 | 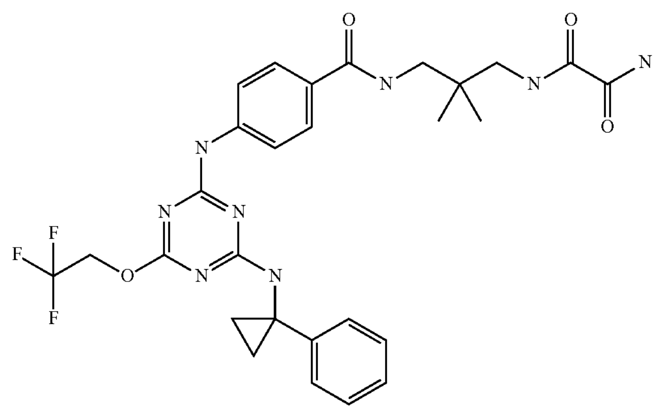 [SMILES: CC(C)(CNC(=O)C(N)=O)CNC(=O)c1ccc(Nc2nc(NC3(c4ccccc4)CC3)nc(OCC(F)(F)F)n2)cc1] | 0.070 | A |

TABLE 1-continued

| Compound | Structure | EC$_{50}$ | Activity |
|---|---|---|---|
| 3245 | 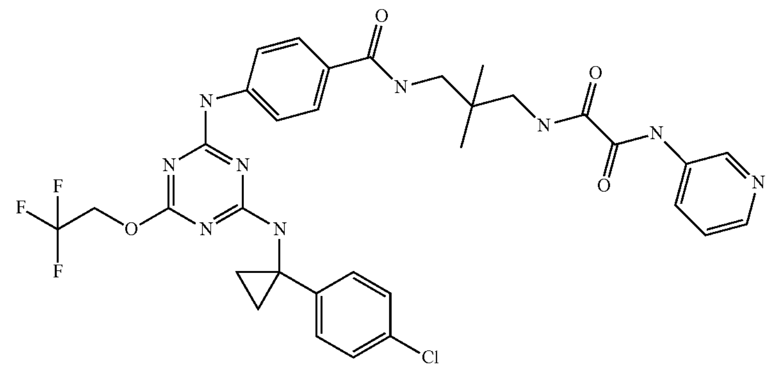 [SMILES: CC(C)(CNC(=O)C(=O)Nc1cccnc1)CNC(=O)c1ccc(Nc2nc(NC3(c4ccc(Cl)cc4)CC3)nc(OCC(F)(F)F)n2)cc1] | | A |
| 3246 | 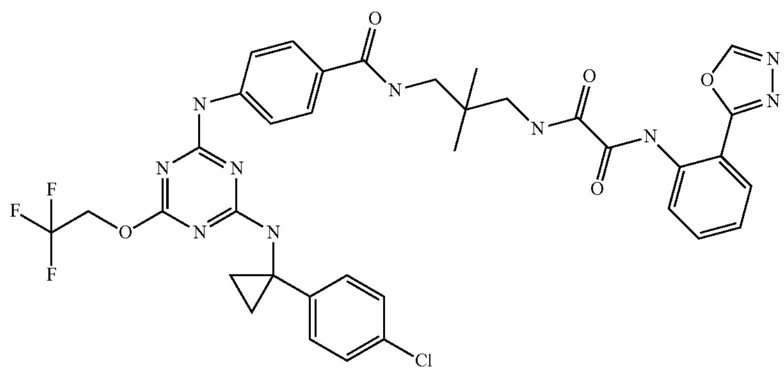 [SMILES: CC(C)(CNC(=O)C(=O)Nc1ccccc1-c1nnco1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3247 | 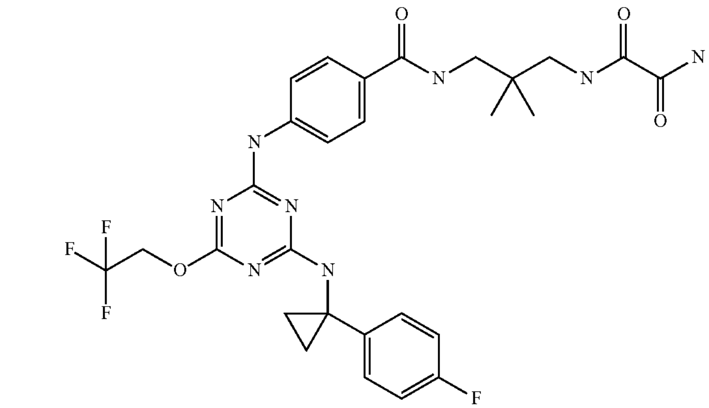 [SMILES: CC(C)(CNC(=O)C(N)=O)CNC(=O)c1ccc(Nc2nc(NC3(c4ccc(F)cc4)CC3)nc(OCC(F)(F)F)n2)cc1] | | A |
| 3248 | 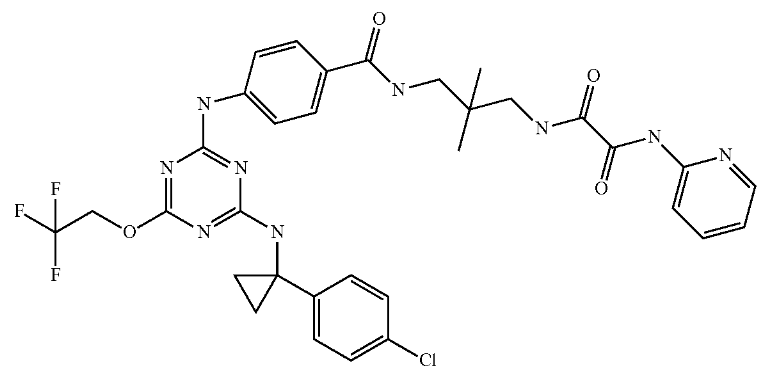 [SMILES: CC(C)(CNC(=O)C(=O)Nc1ccccn1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3249 | 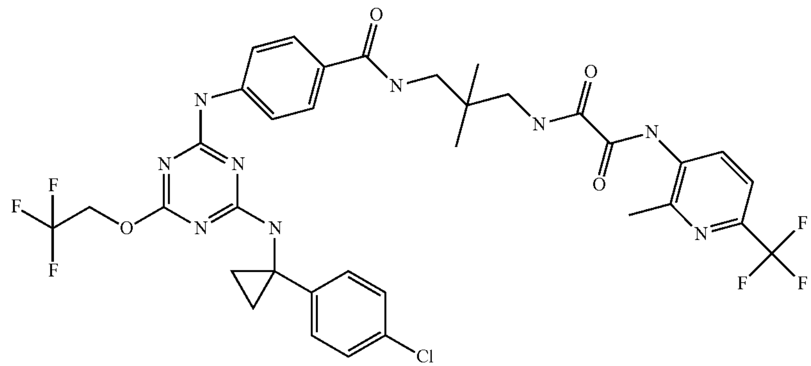 [SMILES: Cc1nc(C(F)(F)F)ccc1NC(=O)C(=O)NCC(C)(C)CNC(=O)c1ccc(Nc2nc(NC3(c4ccc(Cl)cc4)CC3)nc(OCC(F)(F)F)n2)cc1] | | A |
| 3250 | 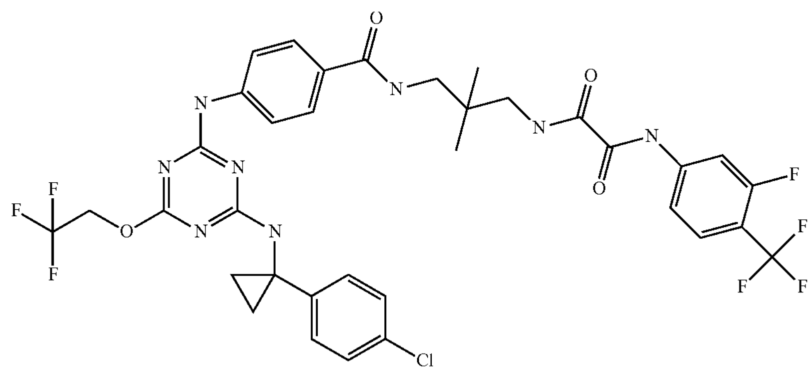 [SMILES: CC(C)(CNC(=O)C(=O)Nc1ccc(C(F)(F)F)c(F)c1)CNC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 3251 | 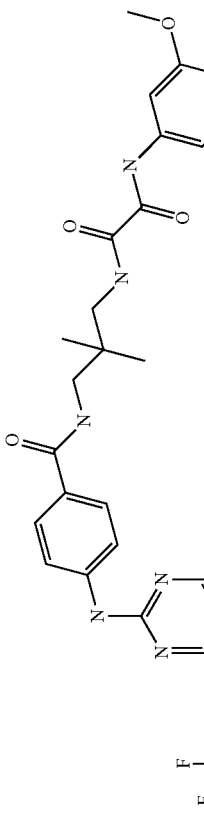 | | A |
| 3252 | 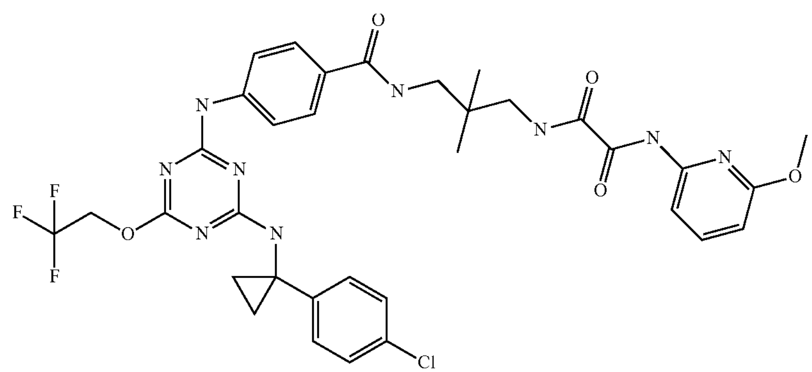 [SMILES: COc1cccc(NC(=O)C(=O)NCC(C)(C)CNC(=O)c2ccc(Nc3nc(NC4(c5ccc(Cl)cc5)CC4)nc(OCC(F)(F)F)n3)cc2)n1] | | A |

TABLE 1-continued
| Compound | Structure | EC$_{50}$ | Activity |
|---|---|---|---|
| 3253 | 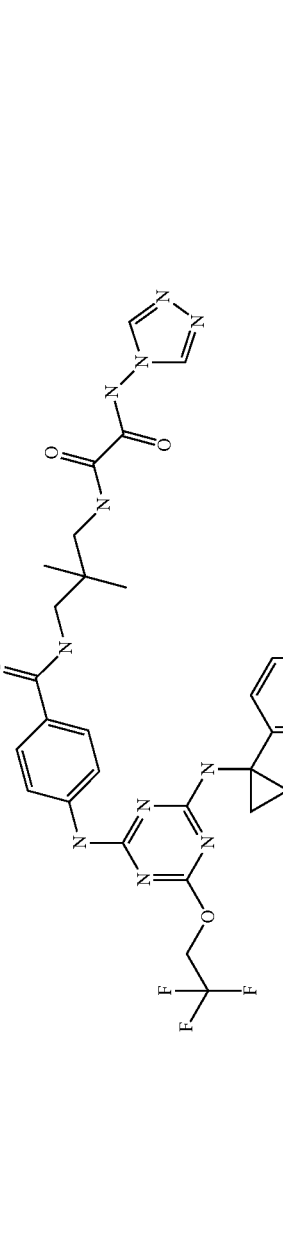 | | A |
| 3254 | 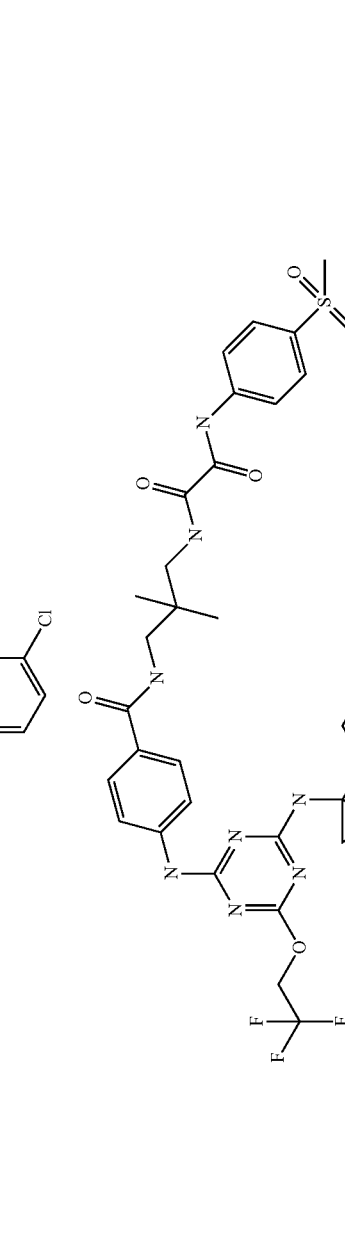 | | A |

TABLE 1-continued

| Compound | Structure | EC$_{50}$ | Activity |
|---|---|---|---|
| 3255 | 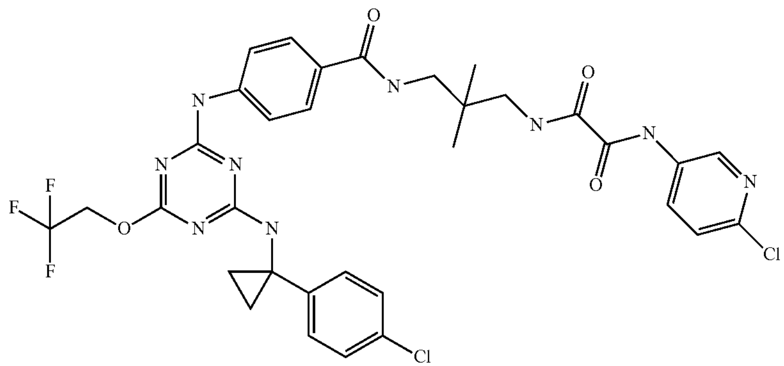 [SMILES: CC(C)(CNC(=O)C(=O)Nc1ccc(Cl)nc1)CNC(=O)c1ccc(Nc2nc(NC3(c4ccc(Cl)cc4)CC3)nc(OCC(F)(F)F)n2)cc1] | 0.029 | A |
| 3256 | 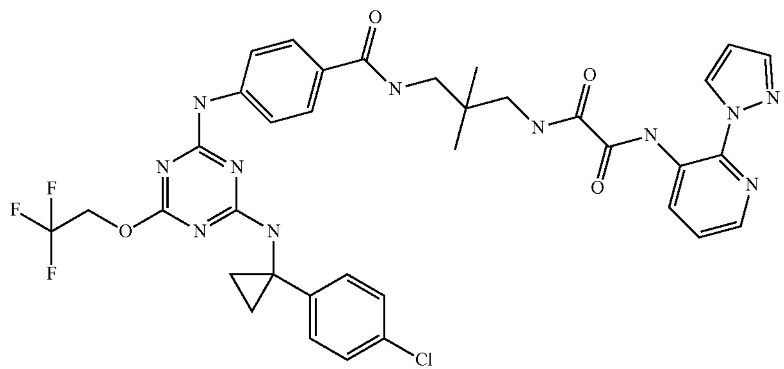 | | A |

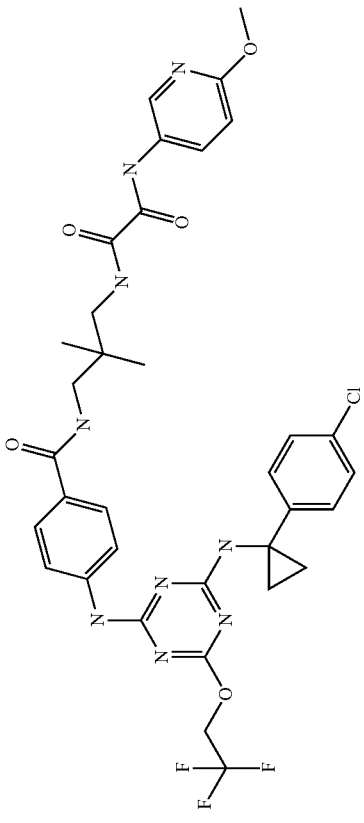

TABLE 1-continued

| Compound | Structure | EC$_{50}$ | Activity |
|---|---|---|---|
| 3259 | 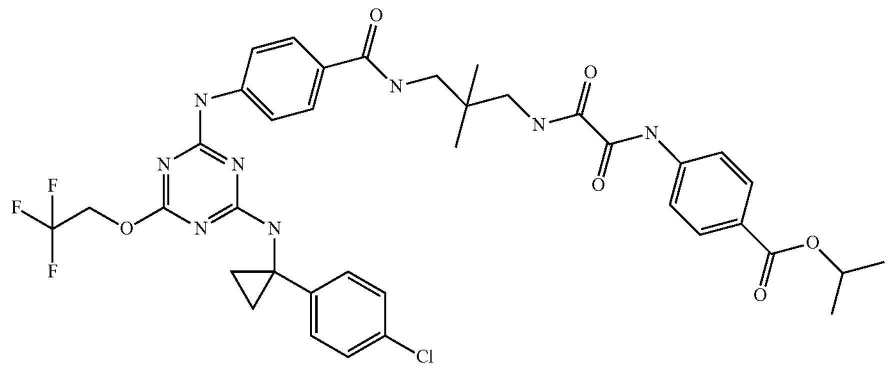 [SMILES: CC(C)OC(=O)c1ccc(NC(=O)C(=O)NCC(C)(C)CNC(=O)c2ccc(Nc3nc(NC4(c5ccc(Cl)cc5)CC4)nc(OCC(F)(F)F)n3)cc2)cc1] | | A |
| 3260 | 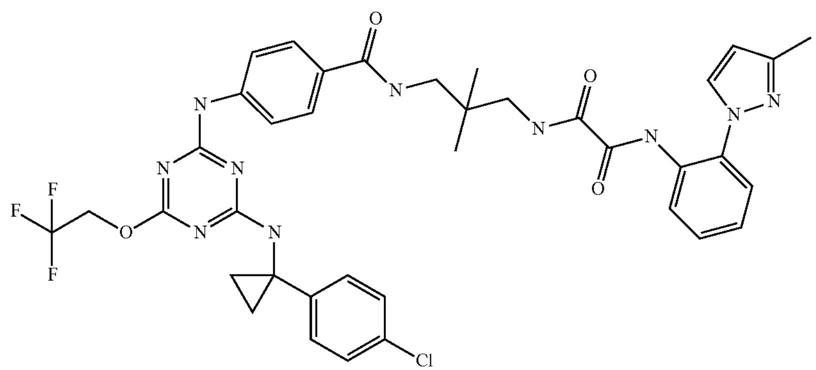 [SMILES: Cc1ccn(-c2ccccc2NC(=O)C(=O)NCC(C)(C)CNC(=O)c2ccc(Nc3nc(NC4(c5ccc(Cl)cc5)CC4)nc(OCC(F)(F)F)n3)cc2)n1] | | A |

TABLE 1-continued
| Compound | Structure | EC$_{50}$ | Activity |
|---|---|---|---|
| 3261 | 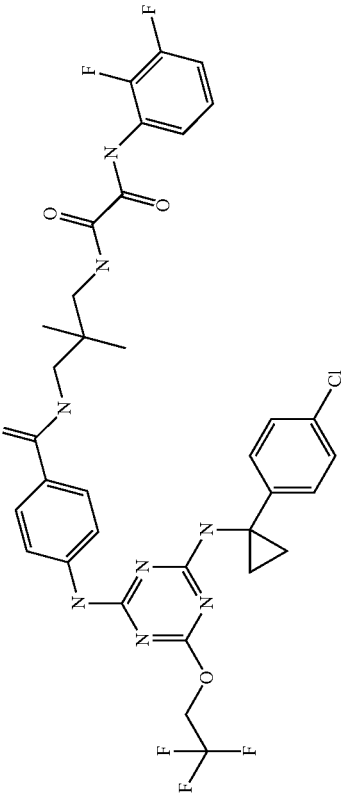 | 0.072 | A |
| 3262 | 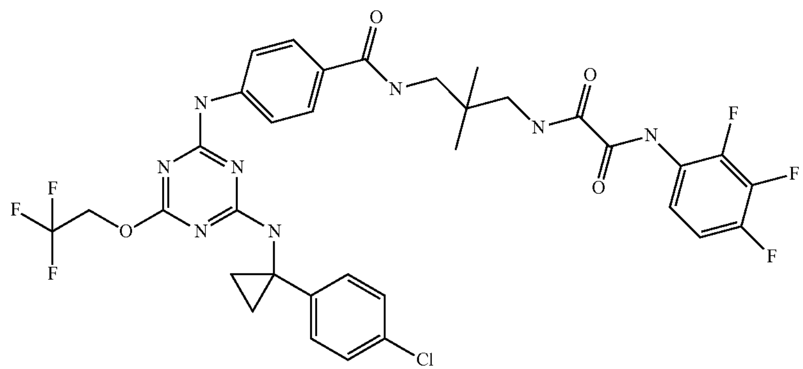 [SMILES: CC(C)(CNC(=O)C(=O)Nc1ccc(F)c(F)c1F)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3263 | 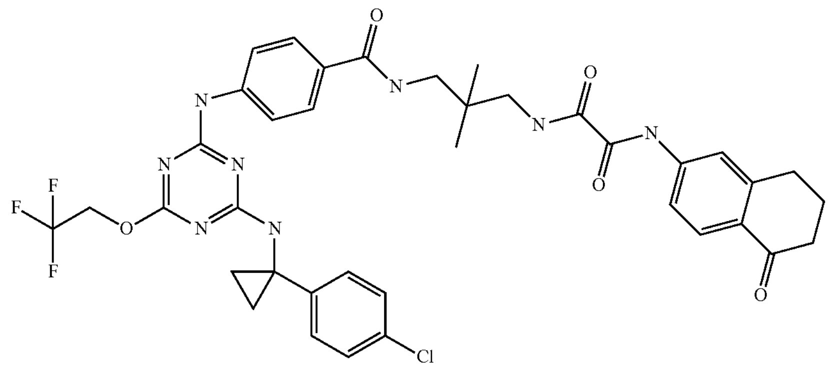 [SMILES: CC(C)(CNC(=O)C(=O)Nc1ccc2c(c1)CCCC2=O)CNC(=O)c1ccc(Nc2nc(NC3(c4ccc(Cl)cc4)CC3)nc(OCC(F)(F)F)n2)cc1] | | A |
| 3264 | 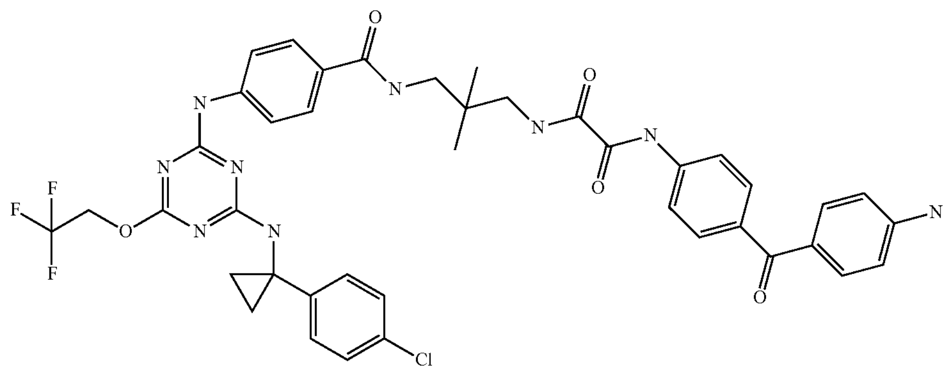 [SMILES: CC(C)(CNC(=O)C(=O)Nc1ccc(C(=O)c2ccc(N)cc2)cc1)CNC(=O)c1ccc(Nc2nc(NC3(c4ccc(Cl)cc4)CC3)nc(OCC(F)(F)F)n2)cc1] | 0.24 | A |

TABLE 1-continued

| Compound | Structure | EC$_{50}$ | Activity |
|---|---|---|---|
| 3265 | 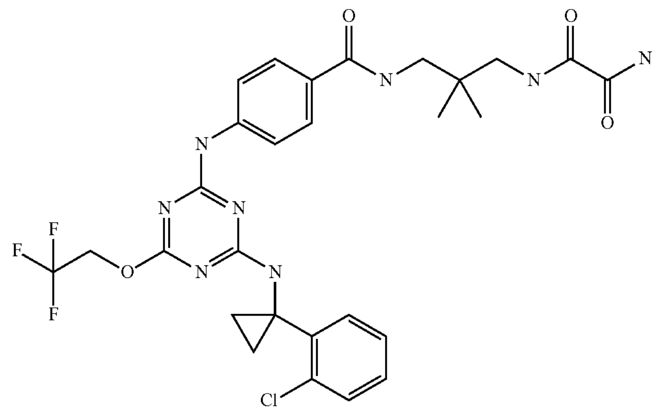 | | B |
| 3266 | 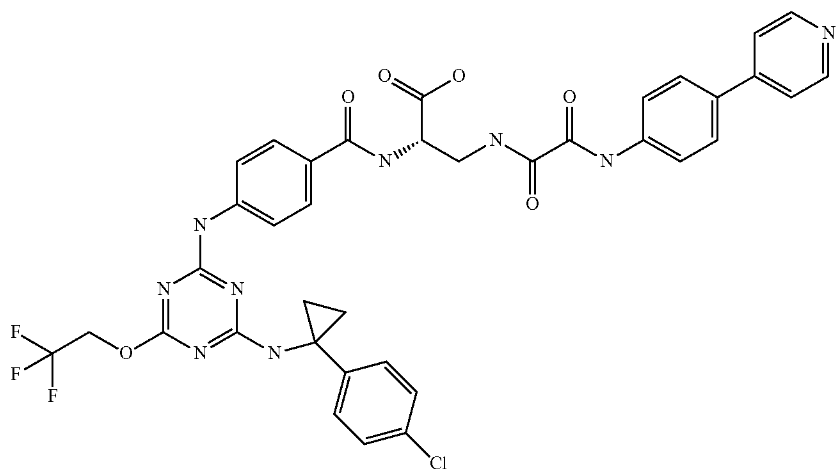 | | A |

TABLE 1-continued

| Compound | Structure | EC$_{50}$ | Activity |
|---|---|---|---|
| 3267 | Chiral | | A |
| 3268 | Chiral | | A |

| Compound | Structure | EC$_{50}$ | Activity |
|---|---|---|---|
| 3269 | 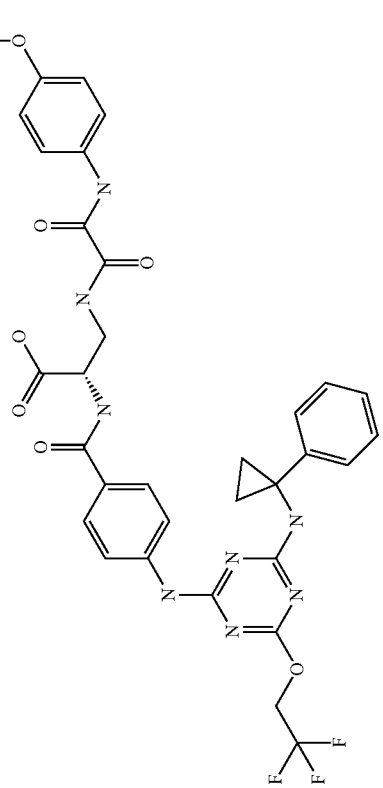 | | A |
| 3270 | 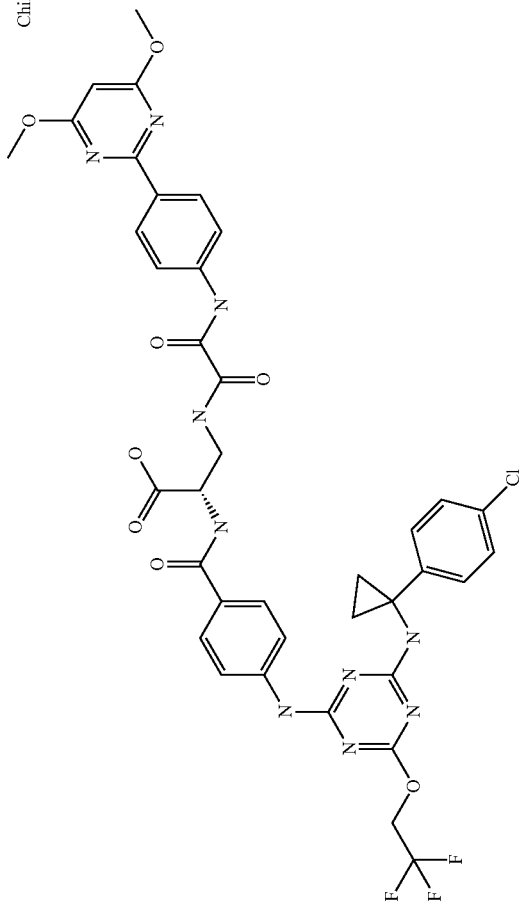 | | A |

TABLE 1-continued

| Compound | Structure | EC$_{50}$ | Activity |
|---|---|---|---|
| 3271 | 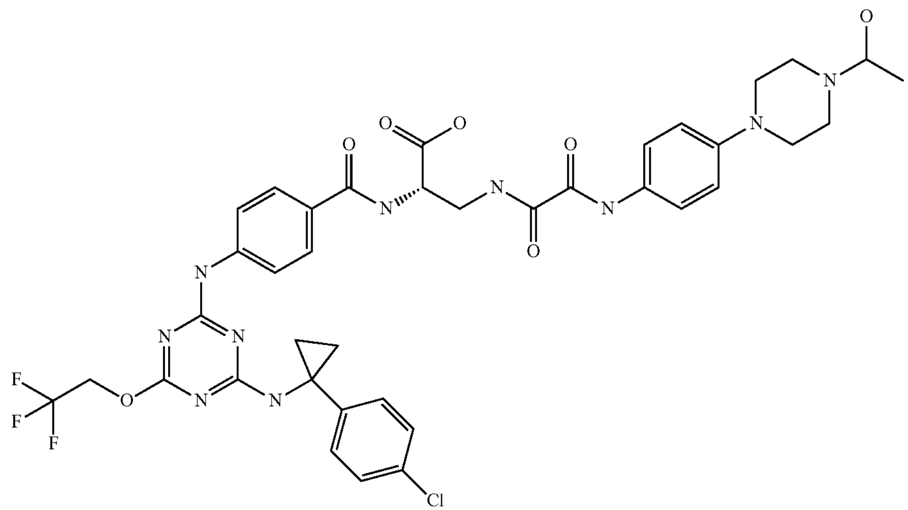 | 1.38 | A |
| 3272 | 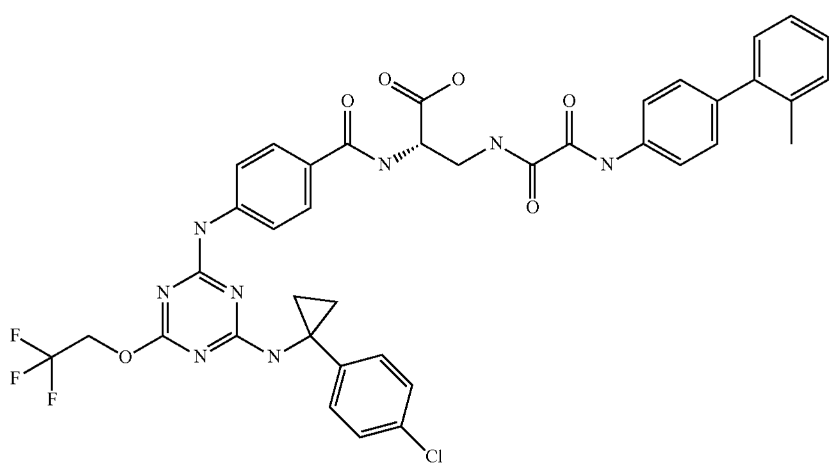 | | A |

TABLE 1-continued
| Compound | Structure | EC$_{50}$ | Activity |
|---|---|---|---|
| 3273 | 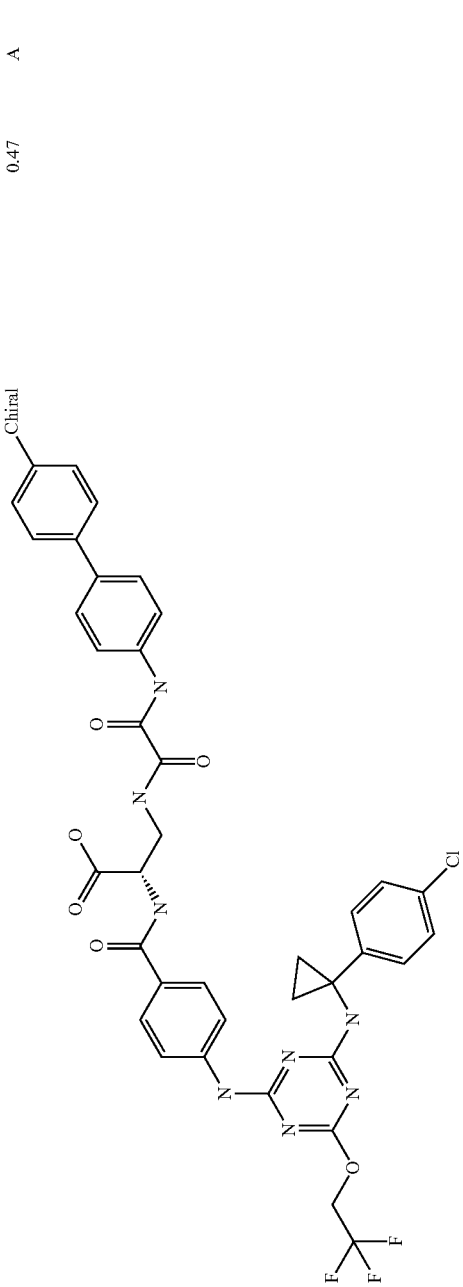 | 0.47 | A |
| 3274 | 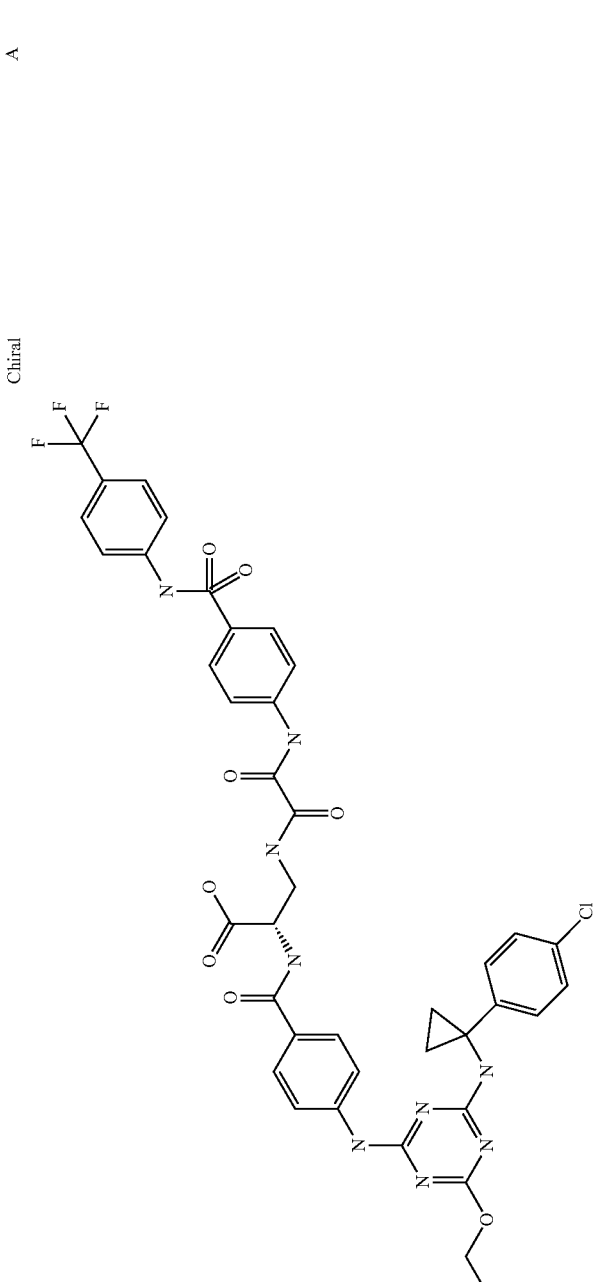 | | A |

| Compound | Structure | EC$_{50}$ | Activity |
|---|---|---|---|
| 3275 | 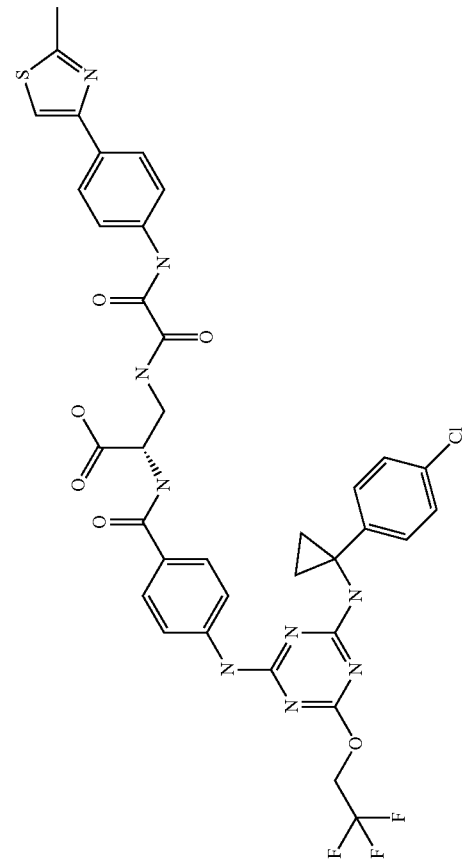 | | A |
| 3276 | 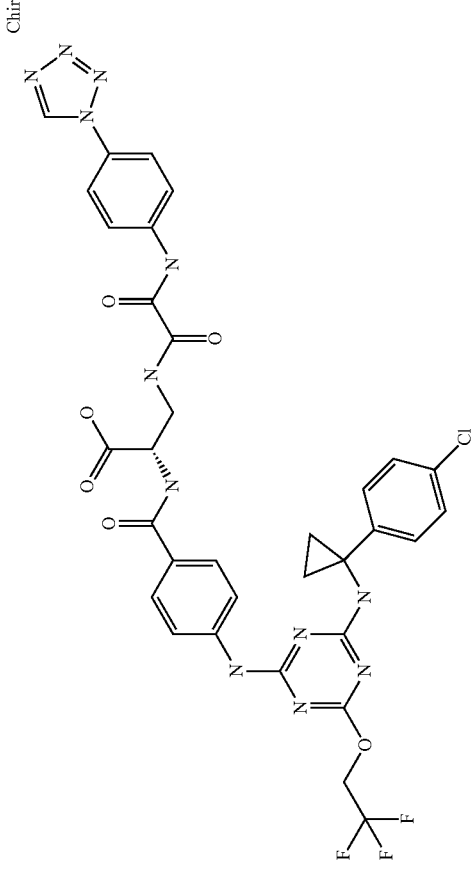 | | A |

TABLE 1-continued
| Compound | Structure | EC₅₀ | Activity |
|---|---|---|---|
| 3277 | 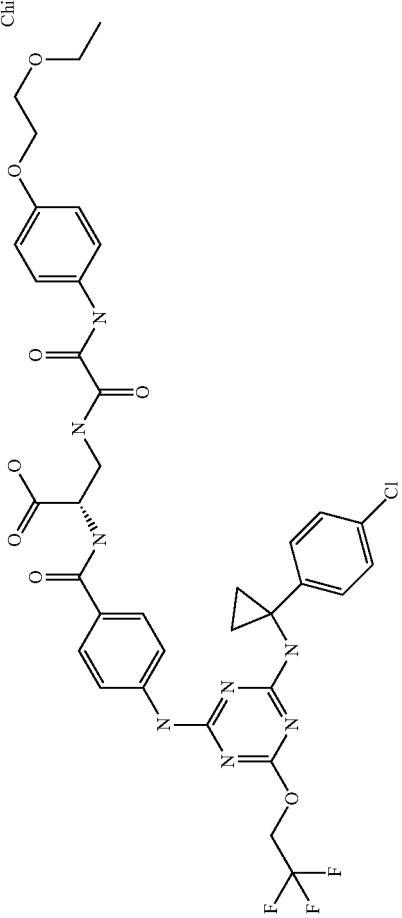 | | A |
| 3278 | 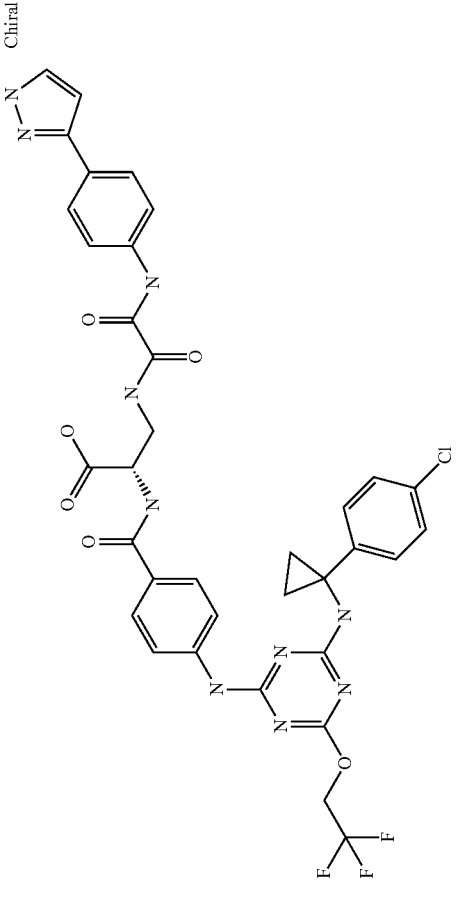 | | A |

TABLE 1-continued
| Compound | Structure | EC$_{50}$ | Activity |
|---|---|---|---|
| 3279 | 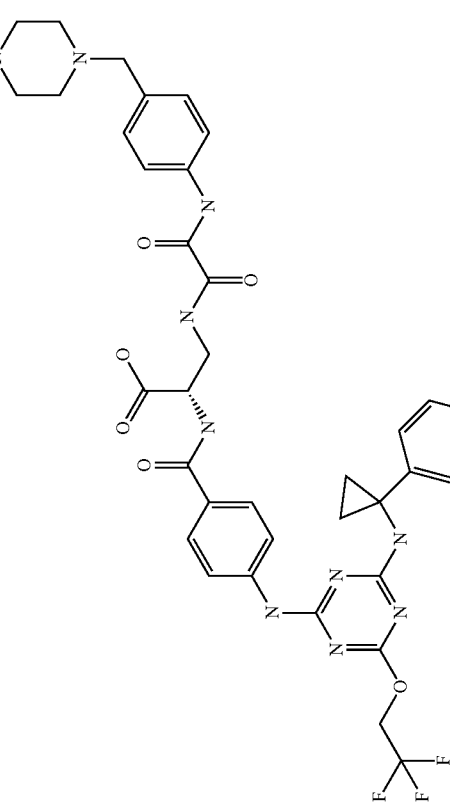 | | A |
| 3280 | 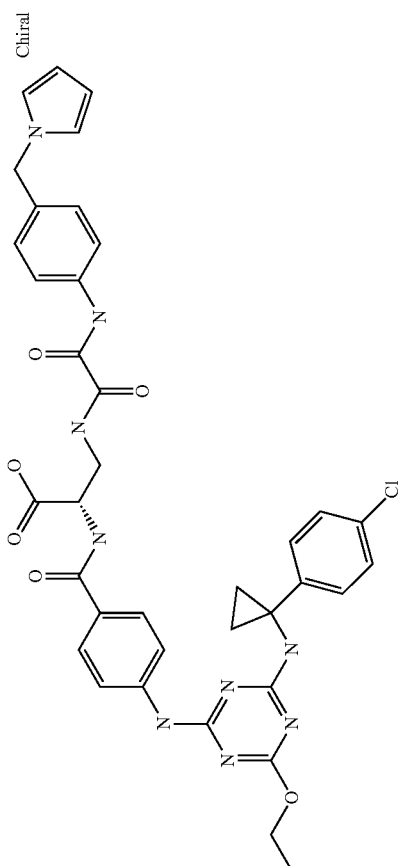 | | A |

TABLE 1-continued
| Compound | Structure | EC50 | Activity |
|---|---|---|---|
| 3281 | 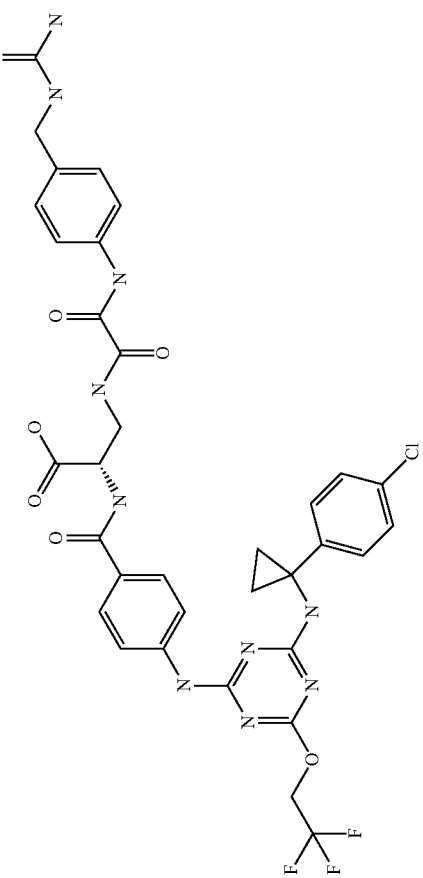 | 1.29 | A |
| 3282 | 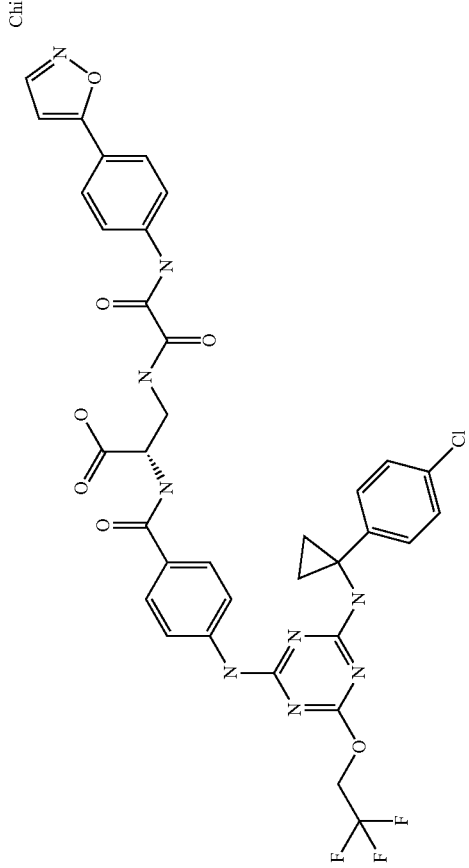 | | A |

TABLE 1-continued
| Compound | Structure | EC$_{50}$ | Activity |
|---|---|---|---|
| 3283 | 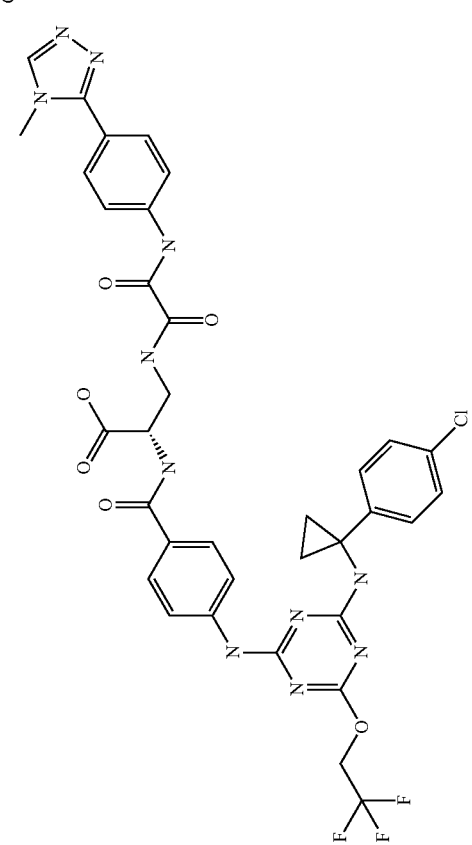 | | A |
| 3284 | 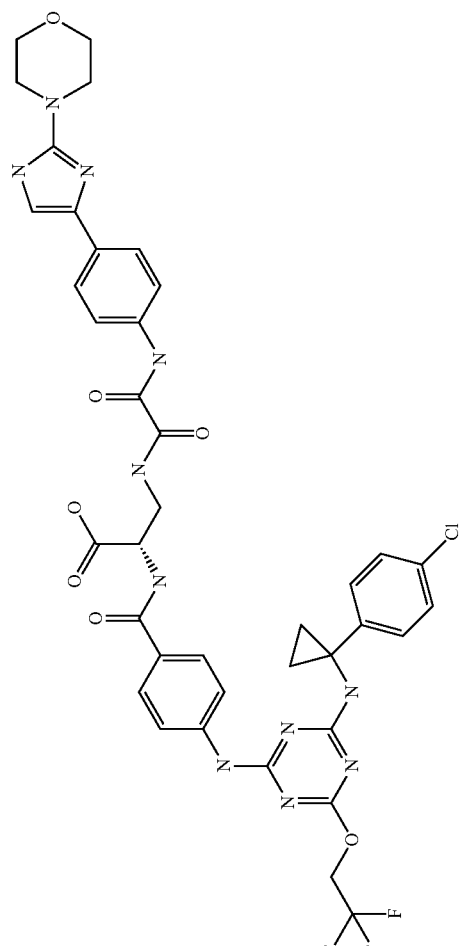 | | A |

| Compound | Structure | EC$_{50}$ | Activity |
|---|---|---|---|
| 3285 | Chiral 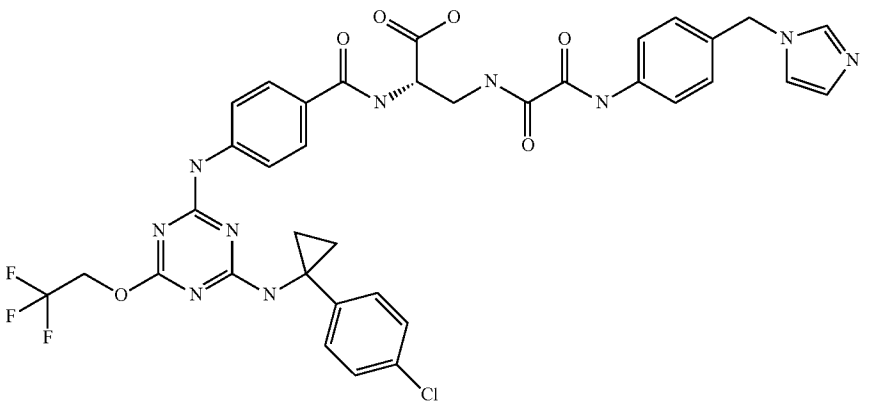 | | A |
| 3286 | Chiral 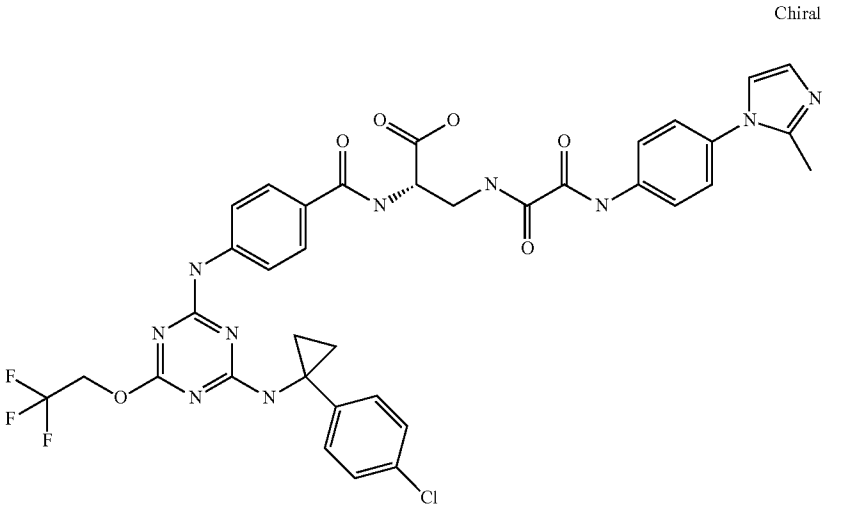 [SMILES: Cc1nccn1-c1ccc(NC(=O)C(=O)NC[C@H](NC(=O)c2ccc(Nc3nc(NC4(c5ccc(Cl)cc5)CC4)nc(OCC(F)(F)F)n3)cc2)C(=O)O)cc1] | | A |

| Compound | Structure | EC$_{50}$ | Activity |
|---|---|---|---|
| 3287 | Chiral | | A |
| 3288 | Chiral | | A |

TABLE 1-continued

| Compound | Structure | EC$_{50}$ | Activity |
|---|---|---|---|
| 3289 | Chiral | 2.53 | A |
| 3290 | Chiral | | A |

TABLE 1-continued
| Compound | Structure | EC$_{50}$ | Activity |
|---|---|---|---|
| 3291 | 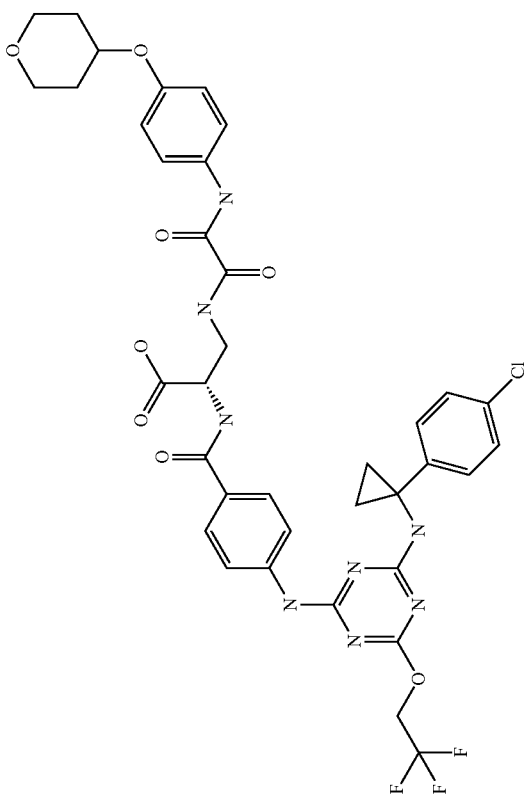 Chiral | | A |

TABLE 1-continued
| Compound | Structure | EC$_{50}$ | Activity |
|---|---|---|---|
| 3292 | 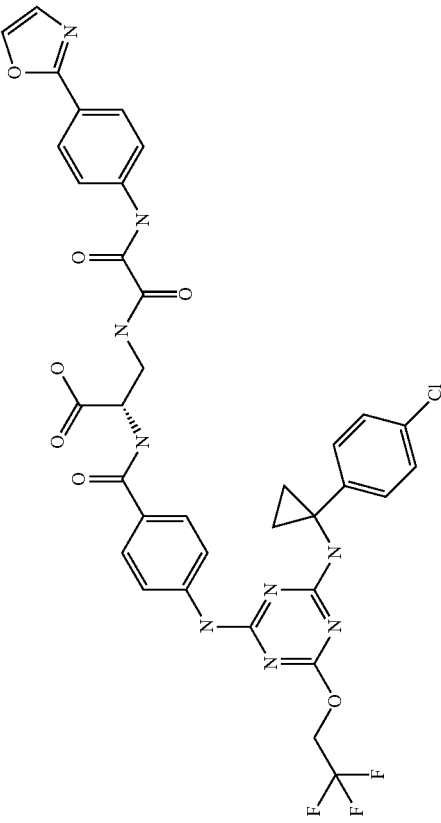 Chiral | | A |
| 3293 | 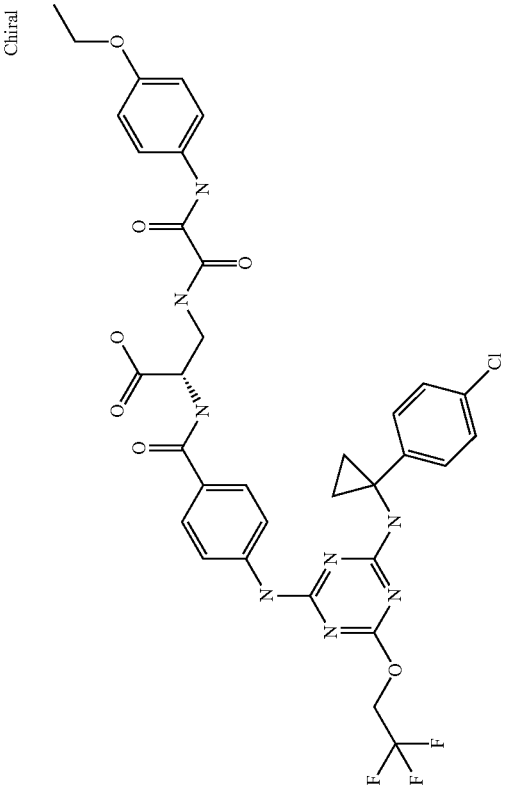 Chiral | | A |

| Compound | Structure | EC$_{50}$ | Activity |
|---|---|---|---|
| 3294 | 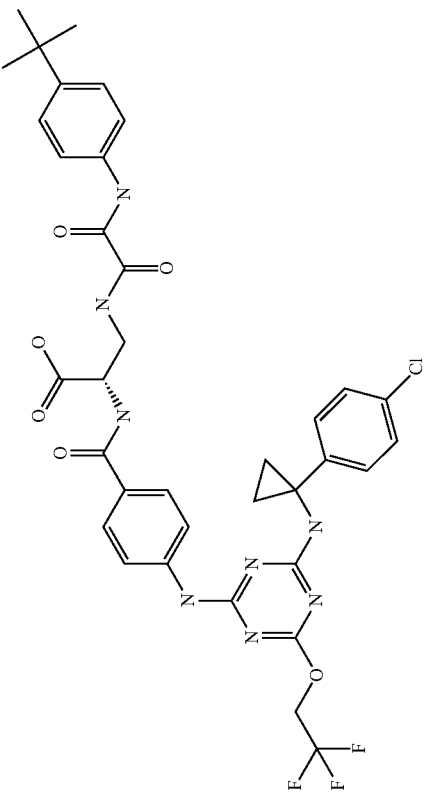 Chiral | | A |
| 3295 | 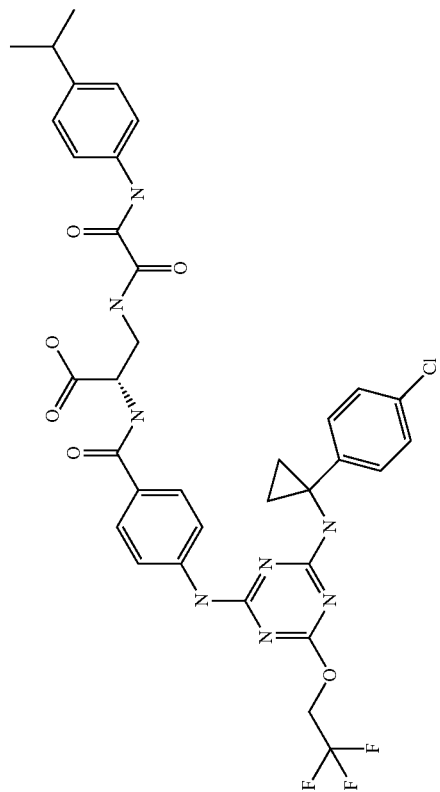 Chiral | | A |

TABLE 1-continued
| Compound | Structure | EC$_{50}$ | Activity |
|---|---|---|---|
| 3296 | 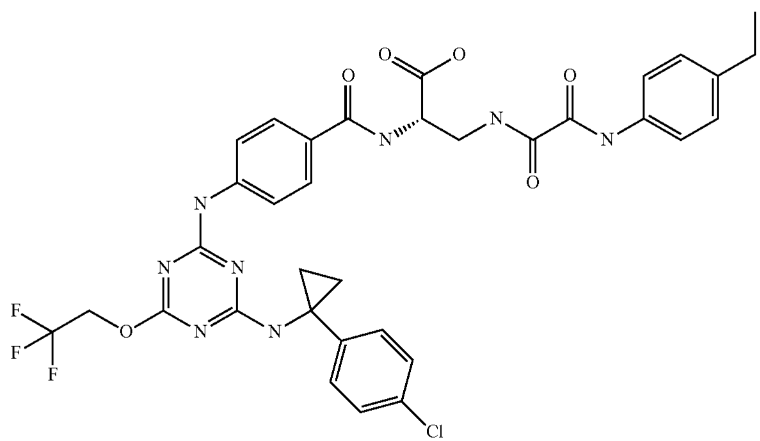 | 0.24 | A |
| 3297 | 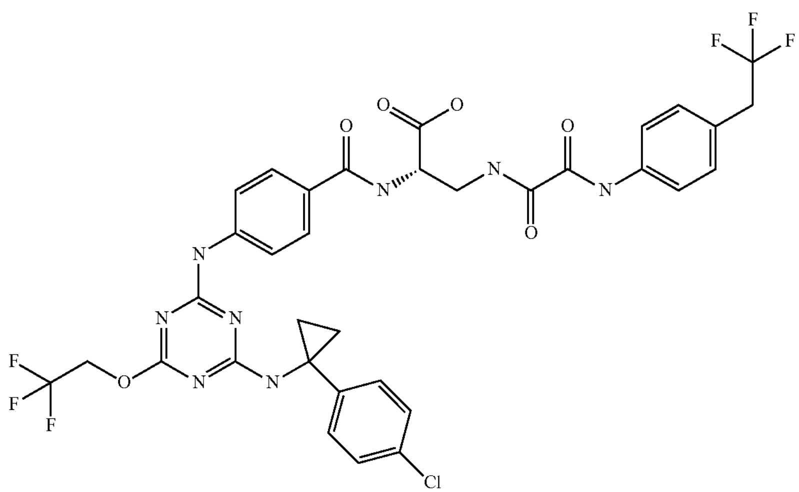 | | A |
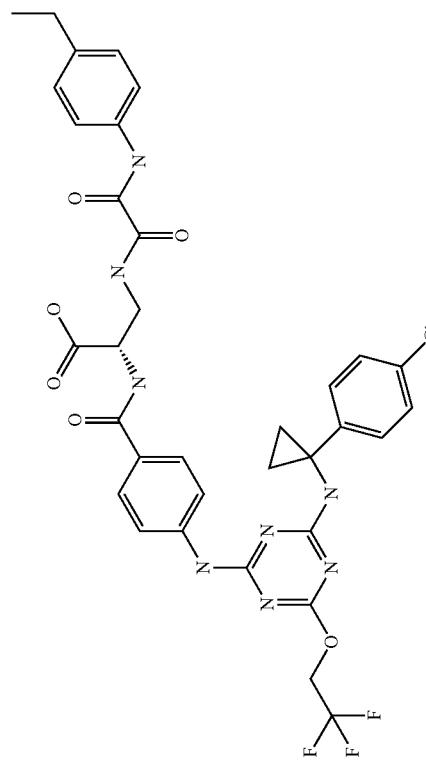

| Compound | Structure | | EC$_{50}$ | Activity |
|---|---|---|---|---|
| | TABLE 1-continued | | | |
| 3298 | Chiral 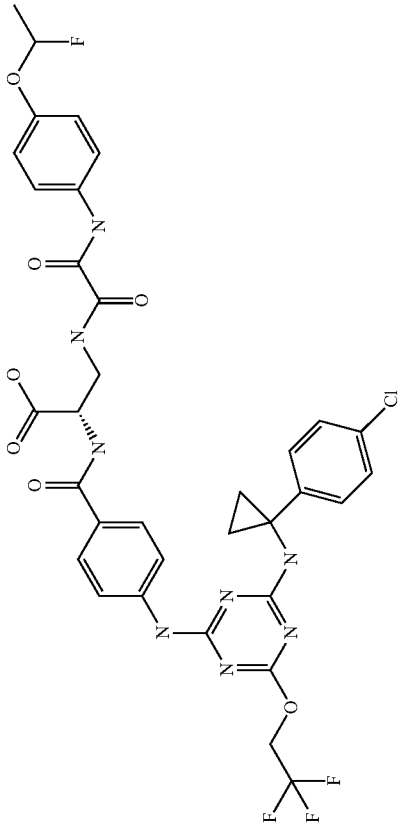 | | | A |
| 3299 | Chiral 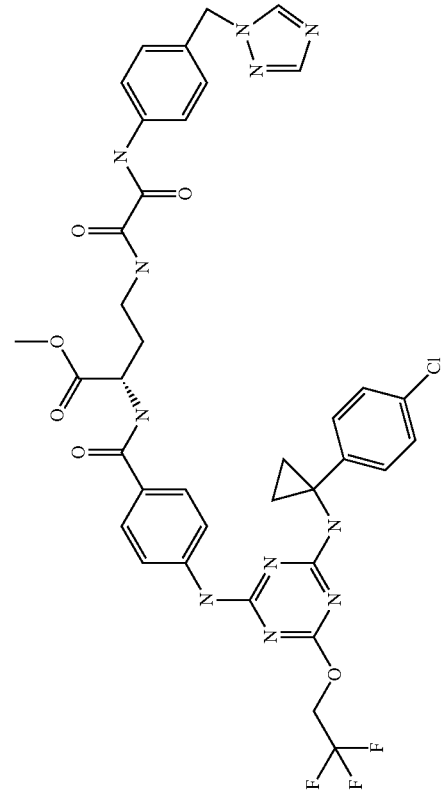 | | | A |

TABLE 1-continued
| Compound | Structure | EC$_{50}$ | Activity |
|---|---|---|---|
| 3300 | Chiral | | B |
| 3301 | Chiral | | A |
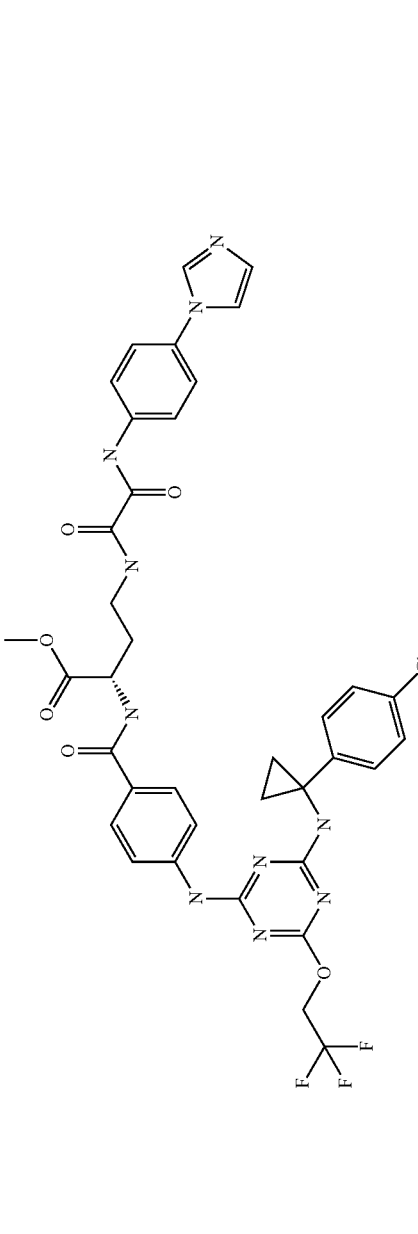
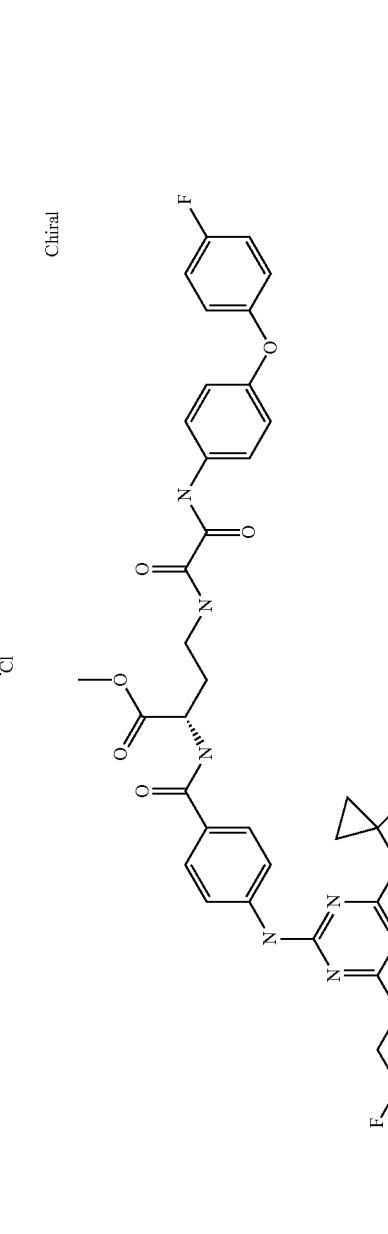

TABLE 1-continued
| Compound | Structure | EC50 | Activity |
|---|---|---|---|
| 3302 | 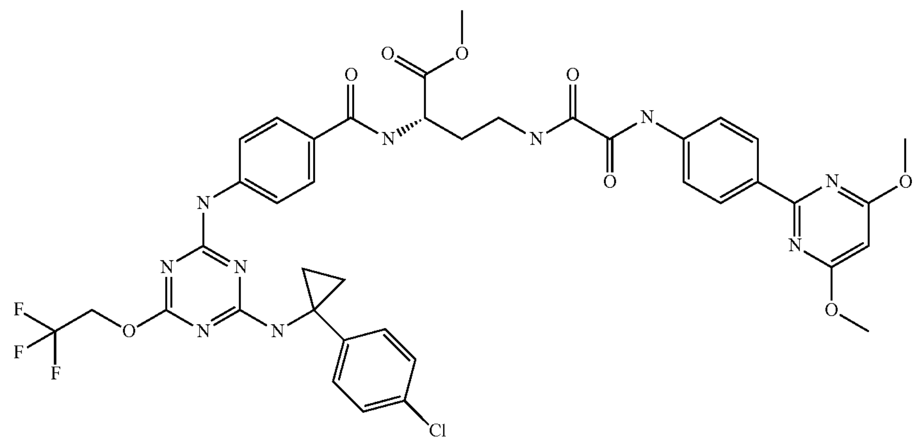 | | A |
| 3303 | 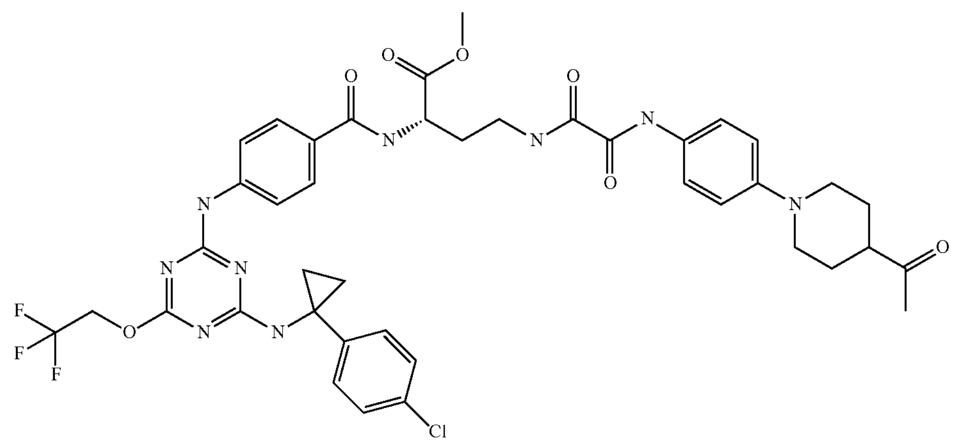 | 5.59 | A |

| Compound | Structure | EC$_{50}$ | Activity |
|---|---|---|---|
| 3304 | Chiral 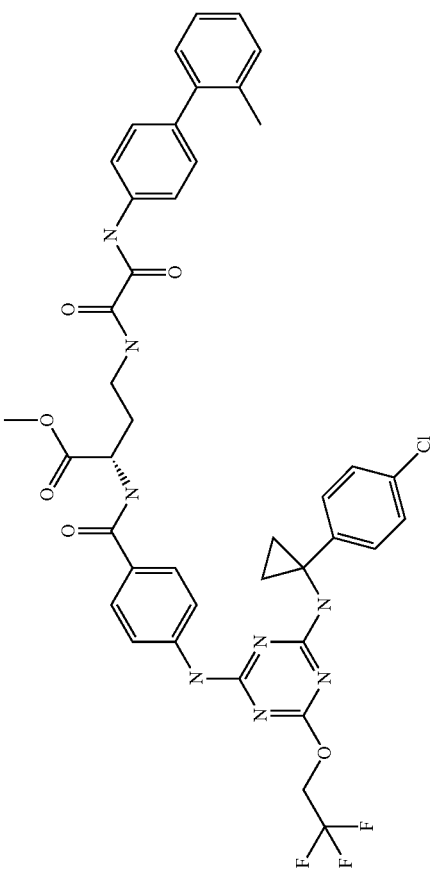 | | A |
| 3305 | Chiral 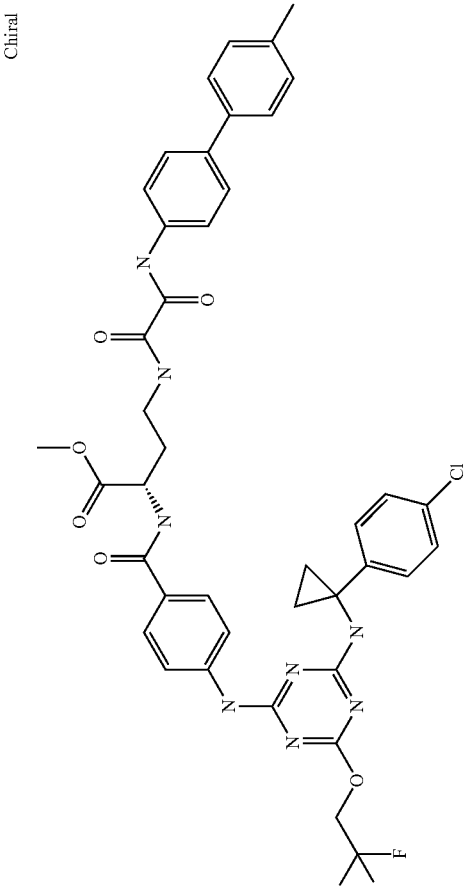 | | A |

TABLE 1-continued

| Compound | Structure | EC$_{50}$ | Activity |
|---|---|---|---|
| 3306 | Chiral | | A |
| 3307 | Chiral | | A |

TABLE 1-continued
| Compound | Structure | EC$_{50}$ | Activity |
|---|---|---|---|
| 3308 | Chiral 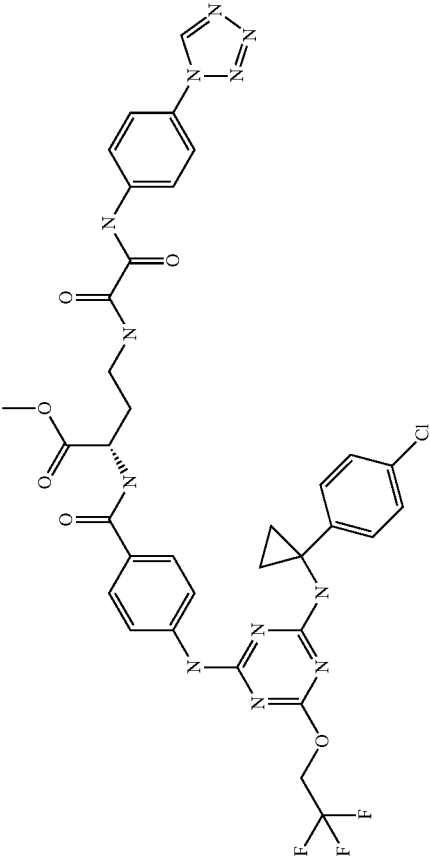 | | A |
| 3309 | Chiral 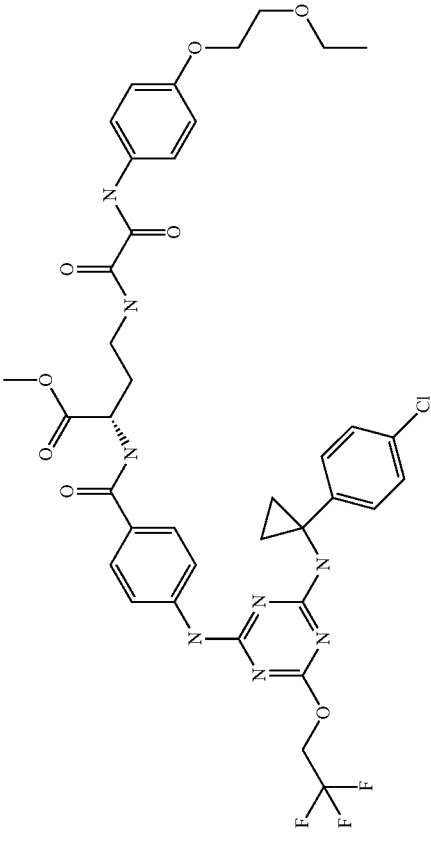 | | A |

TABLE 1-continued

| Compound | Structure | EC$_{50}$ | Activity |
|---|---|---|---|
| 3310 | Chiral | 2.15 | A |
| 3311 | Chiral | | A |

TABLE 1-continued

| Compound | Structure | EC$_{50}$ | Activity |
|---|---|---|---|
| 3312 | Chiral | | A |
| 3313 | Chiral | | A |

TABLE 1-continued
| Compound | Structure | EC$_{50}$ | Activity |
|---|---|---|---|
| 3314 | Chiral 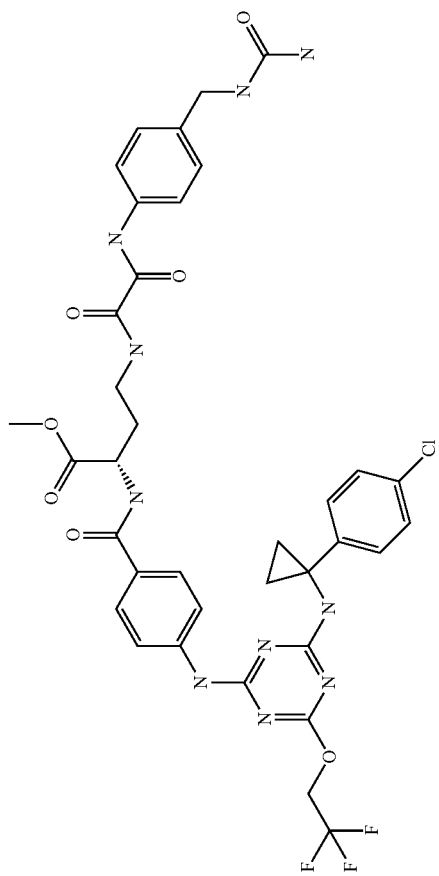 | | A |
| 3315 | Chiral 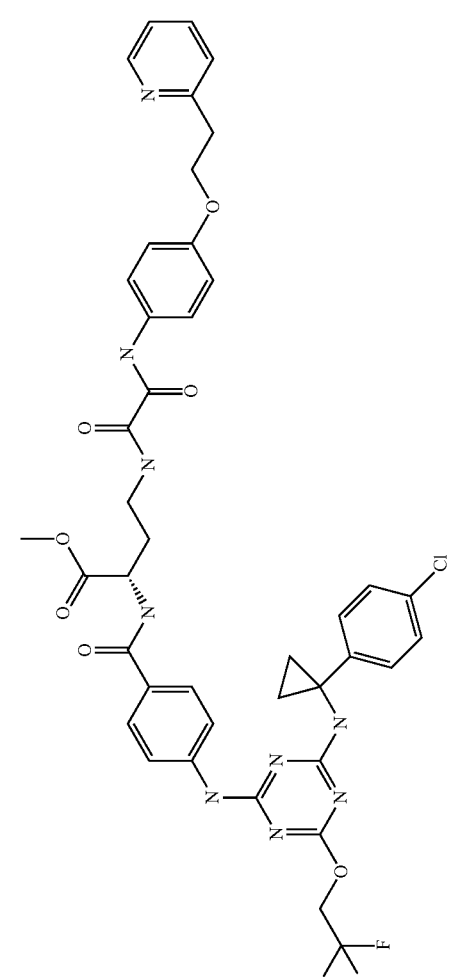 | | A |

TABLE 1-continued

| Compound | Structure | EC$_{50}$ | Activity |
|---|---|---|---|
| 3316 | Chiral | | A |
| 3317 | Chiral | | A |

TABLE 1-continued
| Compound | Structure | EC$_{50}$ | Activity |
|---|---|---|---|
| 3318 | Chiral 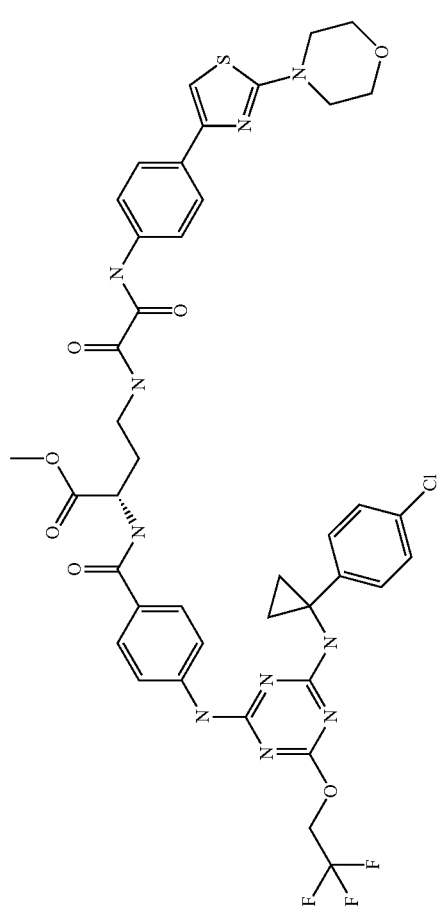 | | A |
| 3319 | Chiral | | A |

TABLE 1-continued
| Compound | Structure | EC$_{50}$ | Activity |
|---|---|---|---|
| 3320 | 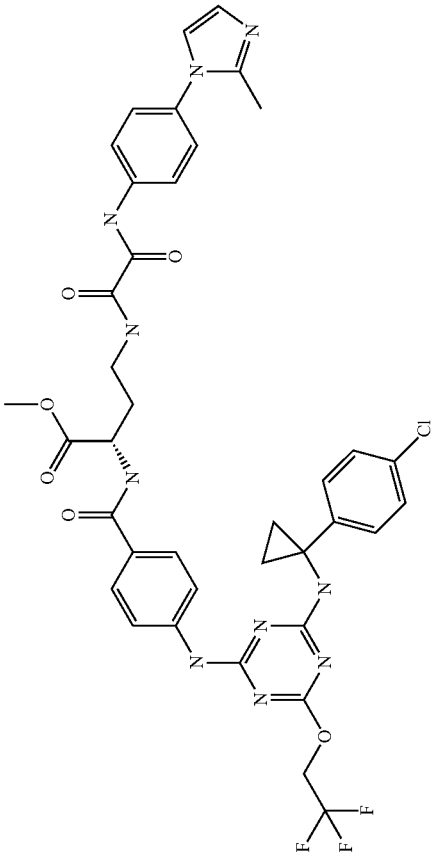 Chiral | 8.80 | A |
| 3321 | 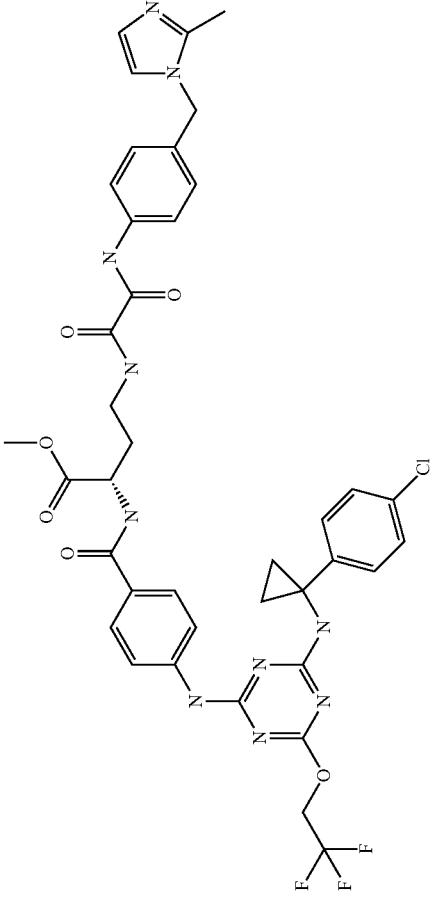 Chiral | | B |

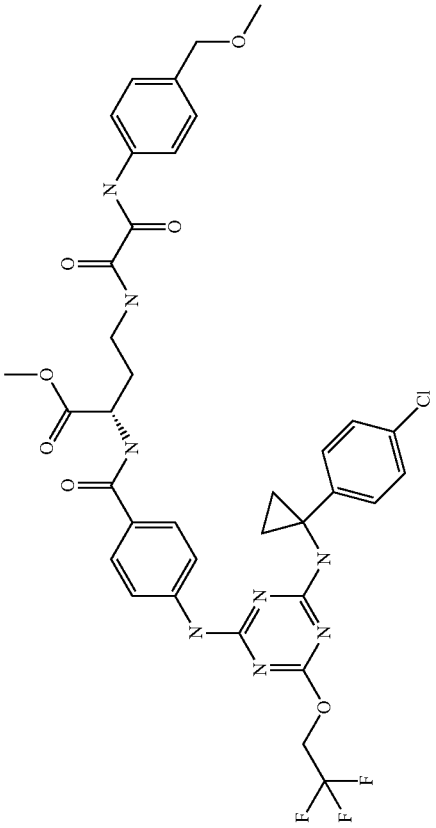

TABLE 1-continued
| Compound | Structure | EC50 | Activity |
|---|---|---|---|
| 3324 | 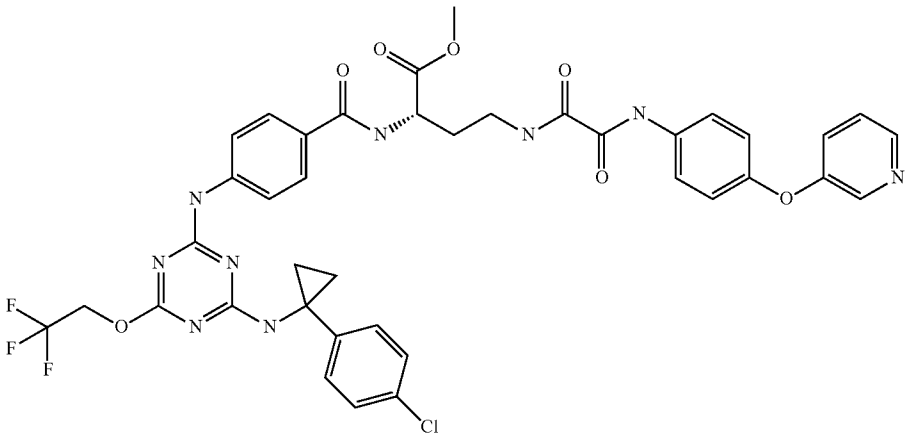 Chiral | | A |
| 3325 | 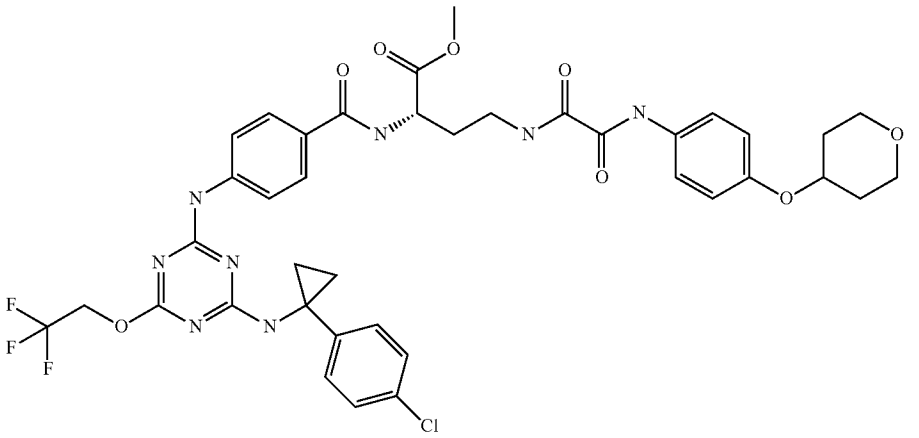 Chiral | 2.40 | A |

TABLE 1-continued
| Compound | Structure | EC$_{50}$ | Activity |
|---|---|---|---|
| 3326 | 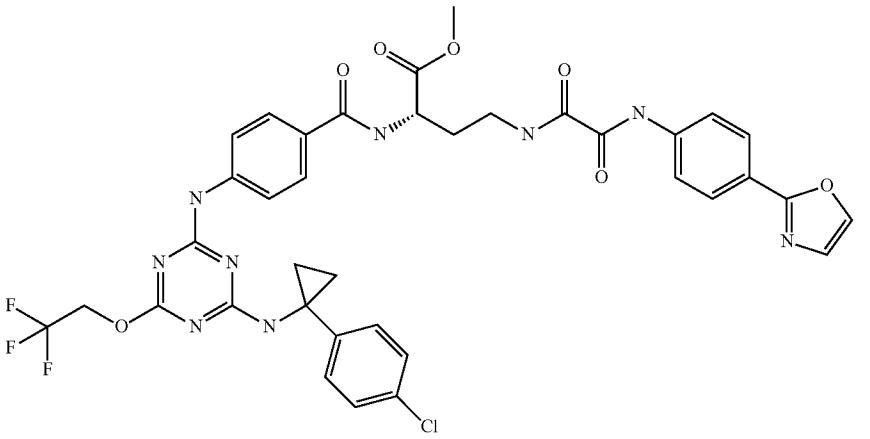 Chiral | | A |
| 3327 | 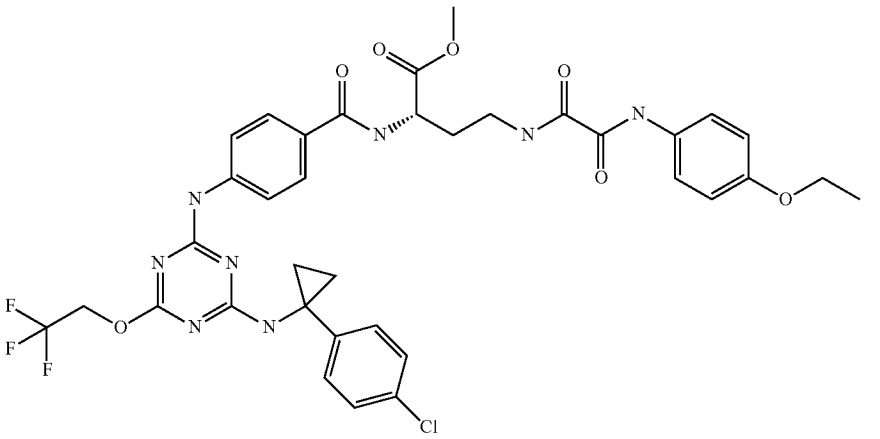 Chiral | | A |

TABLE 1-continued

| Compound | Structure | EC$_{50}$ | Activity |
|---|---|---|---|
| 3328 | Chiral | | A |
| 3329 | Chiral | | A |

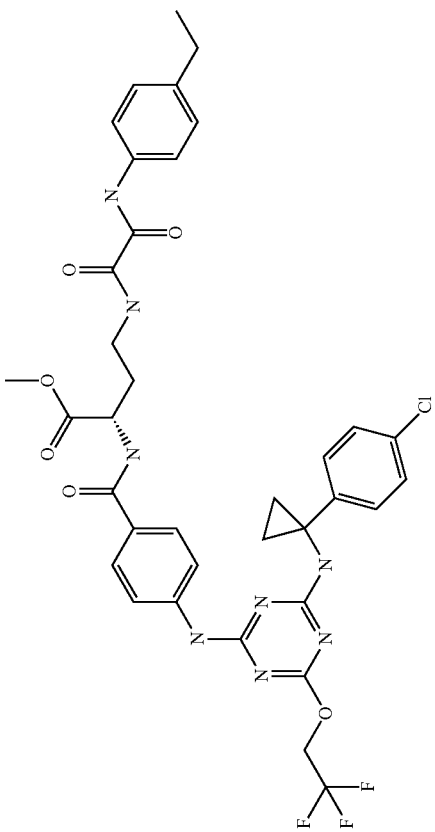

TABLE 1-continued
| Compound | Structure | EC$_{50}$ | Activity |
|---|---|---|---|
| 3332 | 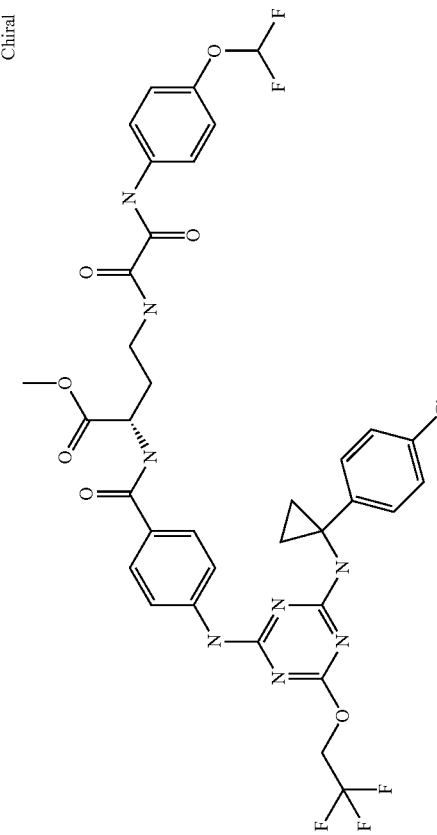 | | A |
| 3333 | 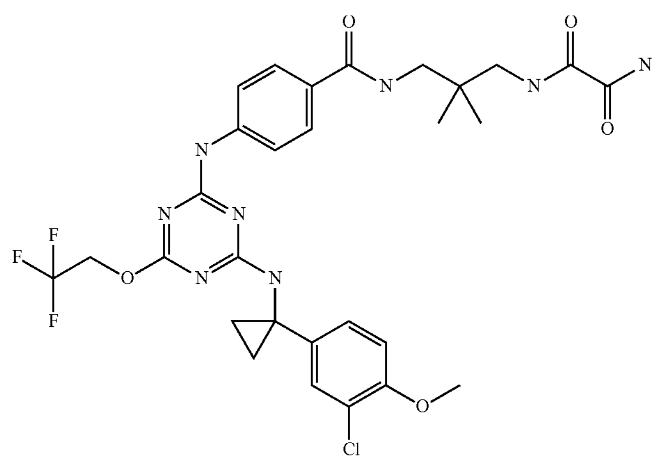 [SMILES: COc1ccc(C2(Nc3nc(Nc4ccc(C(=O)NCC(C)(C)CNC(=O)C(N)=O)cc4)nc(OCC(F)(F)F)n3)CC2)cc1Cl] | | A |

TABLE 1-continued

| Compound | Structure | EC$_{50}$ | Activity |
|---|---|---|---|
| 3334 | 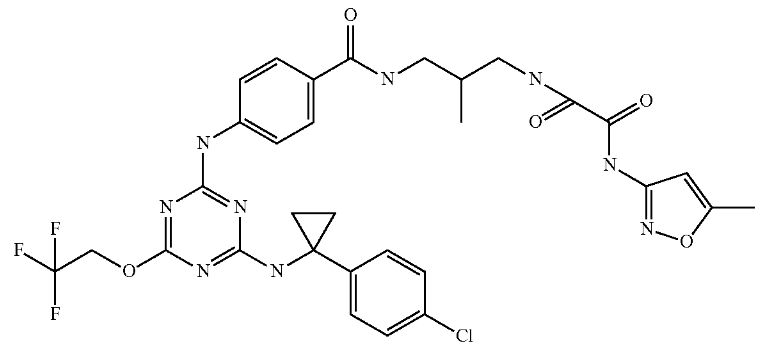 [SMILES: Cc1cc(NC(=O)C(=O)NCC(C)CNC(=O)c2ccc(Nc3nc(NC4(c5ccc(Cl)cc5)CC4)nc(OCC(F)(F)F)n3)cc2)no1] | 0.062 | A |
| 3335 | 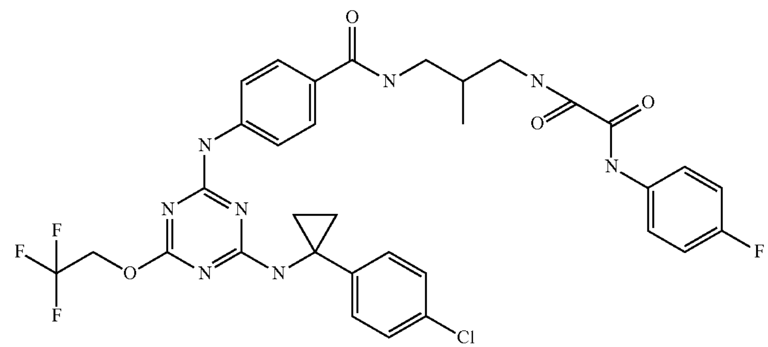 [SMILES: CC(CNC(=O)C(=O)Nc1ccc(F)cc1)CNC(=O)c1ccc(Nc2nc(NC3(c4ccc(Cl)cc4)CC3)nc(OCC(F)(F)F)n2)cc1] | | A |
| 3336 | 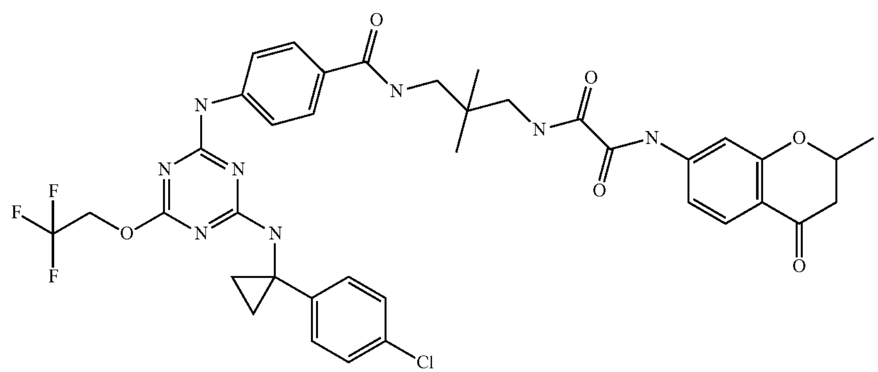 [SMILES: CC1CC(=O)c2ccc(NC(=O)C(=O)NCC(C)(C)CNC(=O)c3ccc(Nc4nc(NC5(c6ccc(Cl)cc6)CC5)nc(OCC(F)(F)F)n4)cc3)cc2O1] | 0.090 | A |

TABLE 1-continued

| Compound | Structure | EC$_{50}$ | Activity |
|---|---|---|---|
| 3337 | 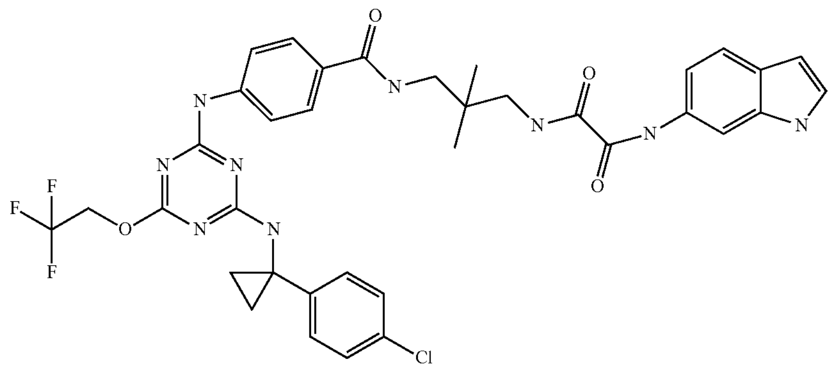 [SMILES: CC(C)(CNC(=O)C(=O)Nc1ccc2cc[nH]c2c1)CNC(=O)c1ccc(Nc2nc(NC3(c4ccc(Cl)cc4)CC3)nc(OCC(F)(F)F)n2)cc1] | | A |
| 3338 | 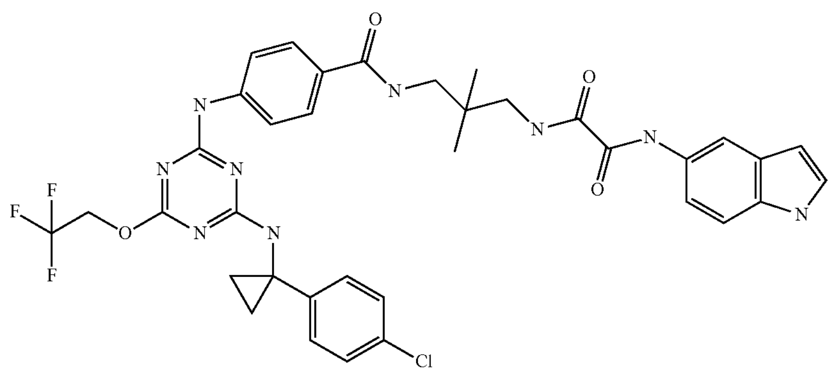 [SMILES: CC(C)(CNC(=O)C(=O)Nc1ccc2[nH]ccc2c1)CNC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 3339 | 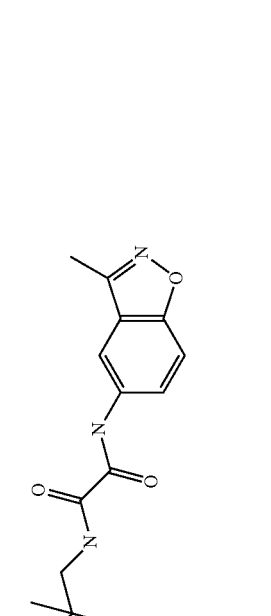 | | A |
| 3340 | 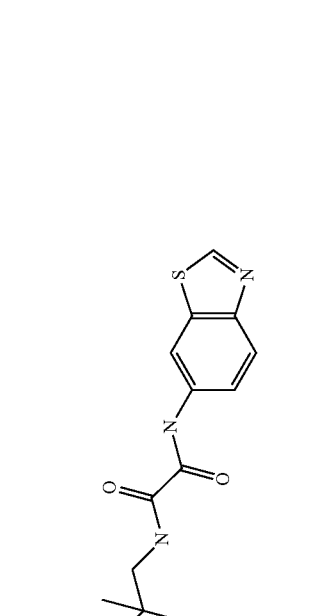 | | A |

TABLE 1-continued

| Compound | Structure | EC$_{50}$ | Activity |
|---|---|---|---|
| 3341 | 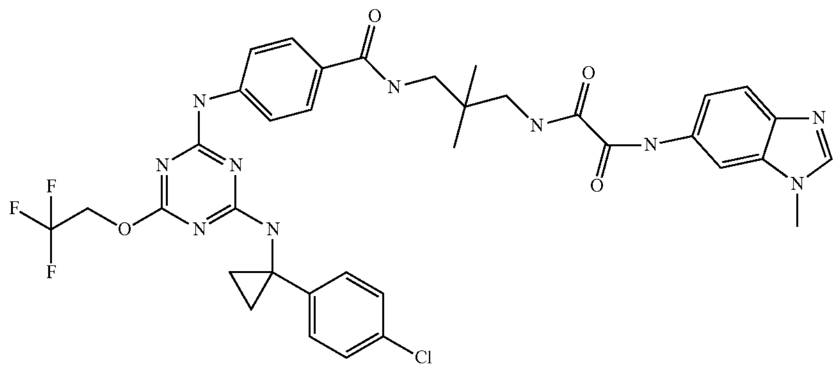 [SMILES: Cn1cnc2ccc(NC(=O)C(=O)NCC(C)(C)CNC(=O)c3ccc(Nc4nc(NC5(c6ccc(Cl)cc6)CC5)nc(OCC(F)(F)F)n4)cc3)cc21] | | A |
| 3342 | 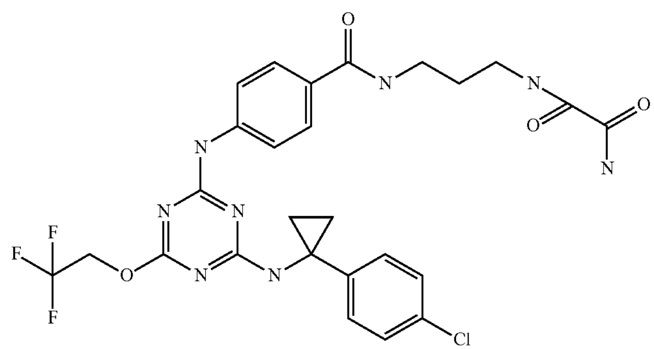 [SMILES: NC(=O)C(=O)NCCCNC(=O)c1ccc(Nc2nc(NC3(c4ccc(Cl)cc4)CC3)nc(OCC(F)(F)F)n2)cc1] | | A |
| 3343 | 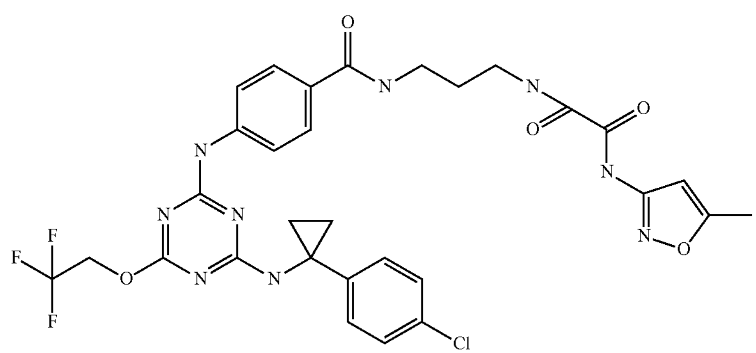 [SMILES: Cc1cc(NC(=O)C(=O)NCCCNC(=O)c2ccc(Nc3nc(NC4(c5ccc(Cl)cc5)CC4)nc(OCC(F)(F)F)n3)cc2)no1] | | A |

TABLE 1-continued

| Compound | Structure | EC$_{50}$ | Activity |
|---|---|---|---|
| 3344 | 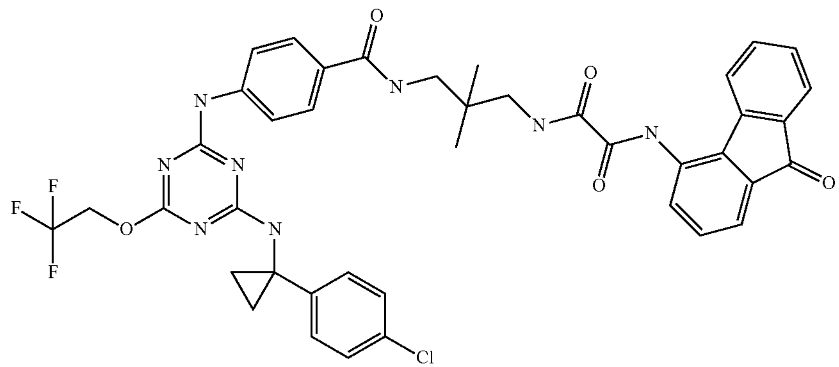 [SMILES: CC(C)(CNC(=O)C(=O)Nc1cccc2c1-c1ccccc1C2=O)CNC(=O)c1ccc(Nc2nc(NC3(c4ccc(Cl)cc4)CC3)nc(OCC(F)(F)F)n2)cc1] | | A |
| 3345 | 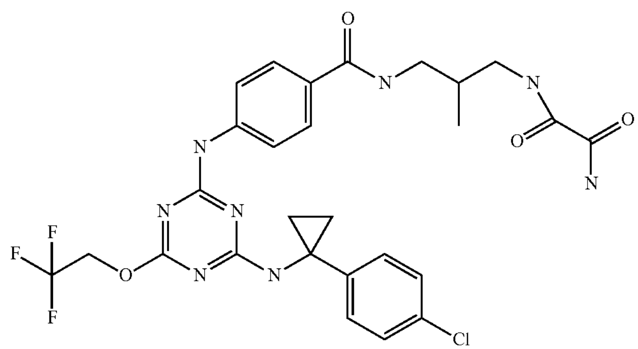 [SMILES: CC(CNC(=O)C(N)=O)CNC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 3346 | 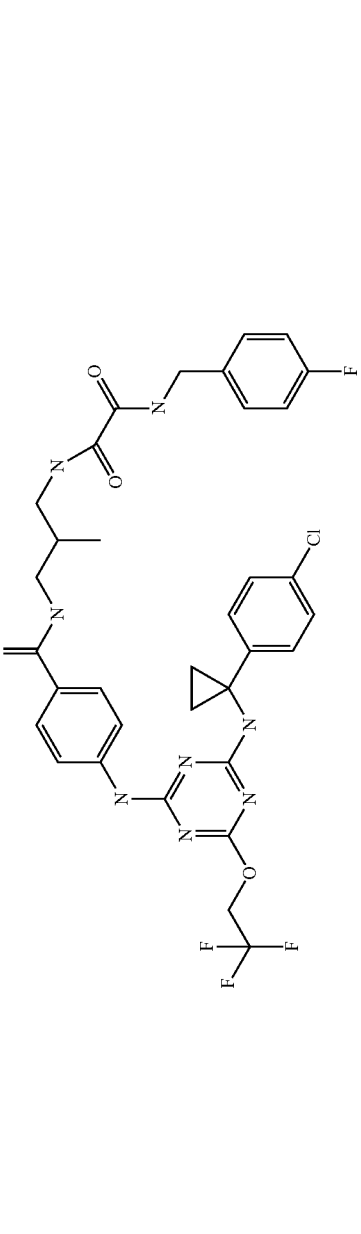 | 0.067 | A |
| 3347 | 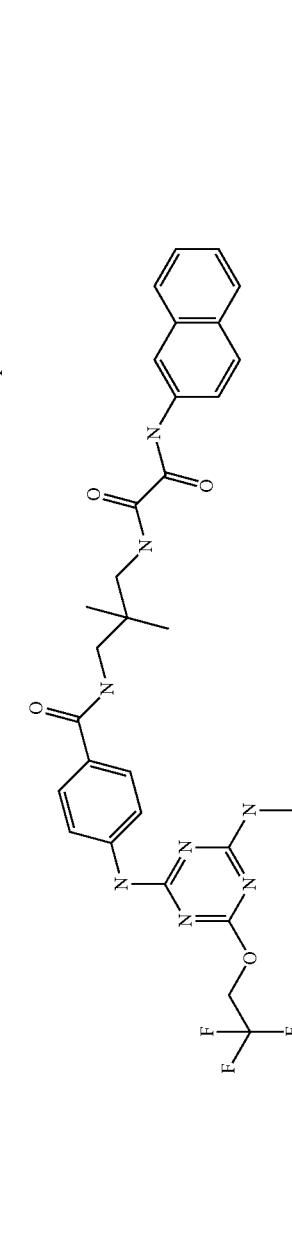 | | A |

TABLE 1-continued

| Compound | Structure | EC$_{50}$ | Activity |
|---|---|---|---|
| 3348 | 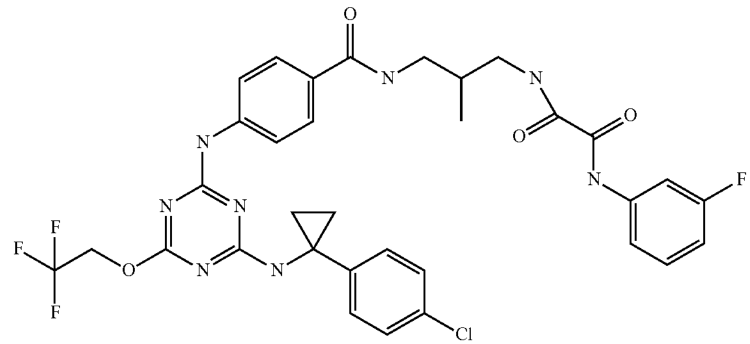 [SMILES: CC(CNC(=O)C(=O)Nc1cccc(F)c1)CNC(=O)c1ccc(Nc2nc(NC3(c4ccc(Cl)cc4)CC3)nc(OCC(F)(F)F)n2)cc1] | | A |
| 3349 | 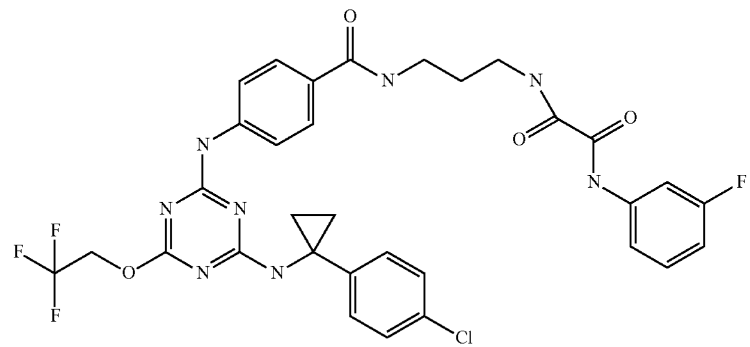 [SMILES: O=C(NCCCNC(=O)c1ccc(Nc2nc(NC3(c4ccc(Cl)cc4)CC3)nc(OCC(F)(F)F)n2)cc1)C(=O)Nc1cccc(F)c1] | 0.041 | A |
| 3350 | 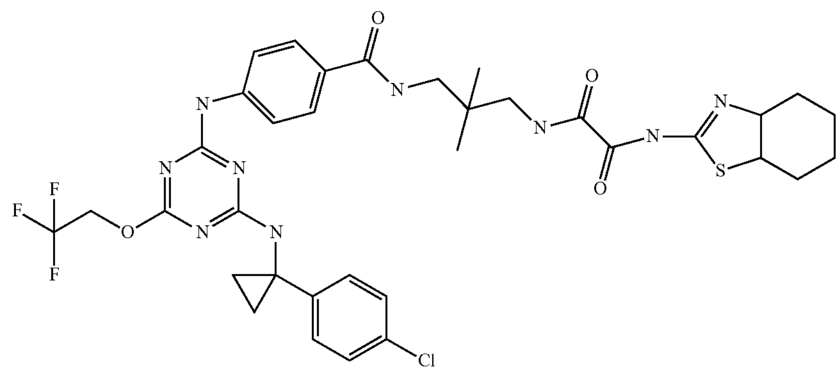 [SMILES: CC(C)(CNC(=O)C(=O)NC1=NC2CCCCC2S1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3351 | 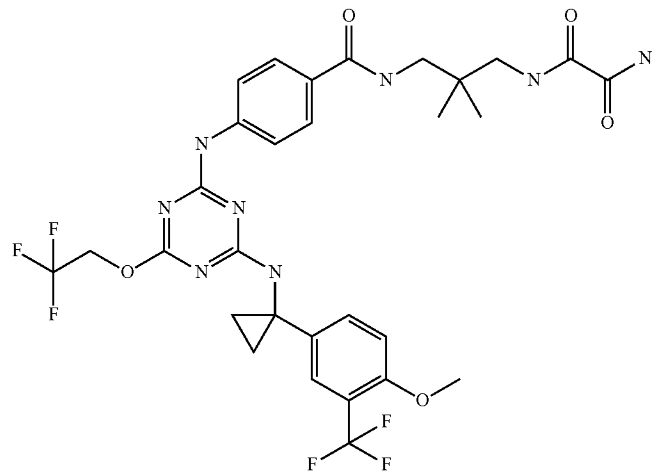 [SMILES: COc1ccc(C2(Nc3nc(Nc4ccc(C(=O)NCC(C)(C)CNC(=O)C(N)=O)cc4)nc(OCC(F)(F)F)n3)CC2)cc1C(F)(F)F] | | A |
| 3352 | 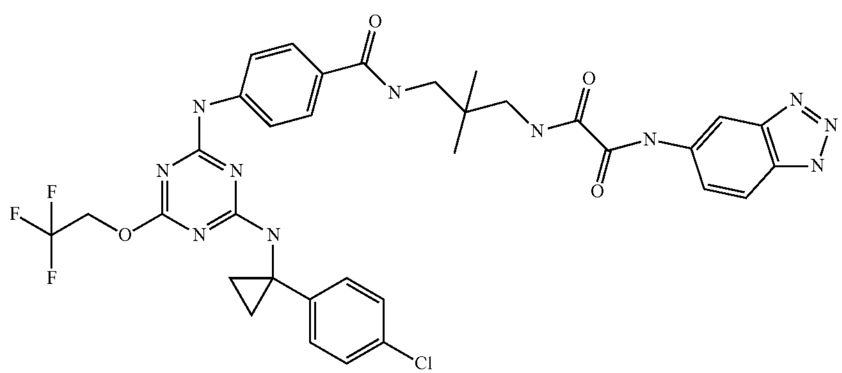 [SMILES: CC(C)(CNC(=O)C(=O)Nc1ccc2[nH]nnc2c1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3353 | 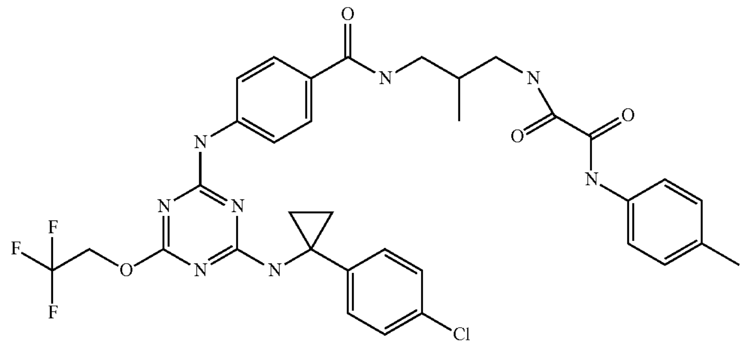 | | A |
| 3354 | 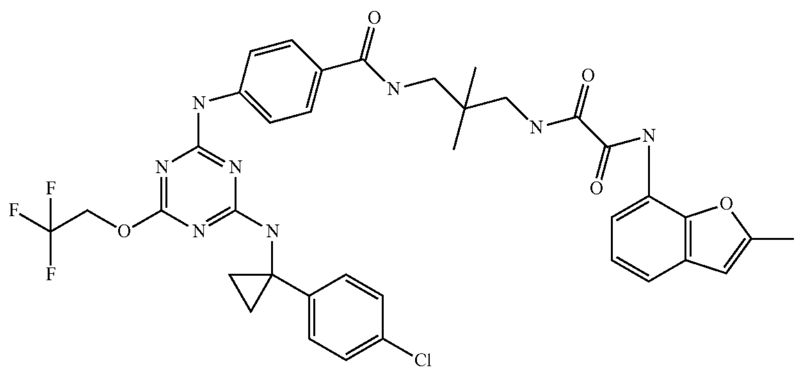 [SMILES: Cc1cc2cccc(NC(=O)C(=O)NCC(C)(C)CNC(=O)c3ccc(Nc4nc(NC5(c6ccc(Cl)cc6)CC5)nc(OCC(F)(F)F)n4)cc3)c2o1] | | A |

TABLE 1-continued

| Compound | Structure | EC$_{50}$ | Activity |
|---|---|---|---|
| 3355 | 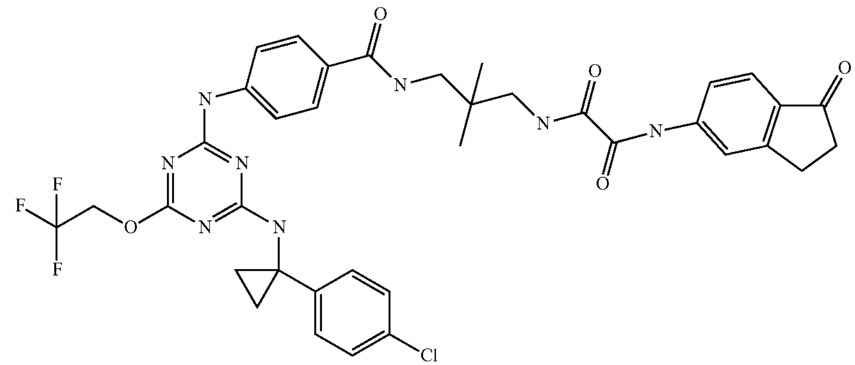 [SMILES: CC(C)(CNC(=O)C(=O)Nc1ccc2c(c1)CCC2=O)CNC(=O)c1ccc(Nc2nc(NC3(c4ccc(Cl)cc4)CC3)nc(OCC(F)(F)F)n2)cc1] | | A |
| 3356 | 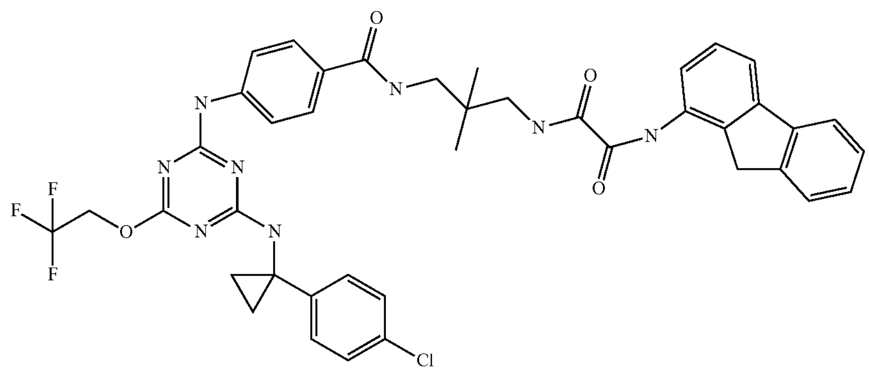 [SMILES: CC(C)(CNC(=O)C(=O)Nc1cccc2c1Cc1ccccc1-2)CNC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 3357 | 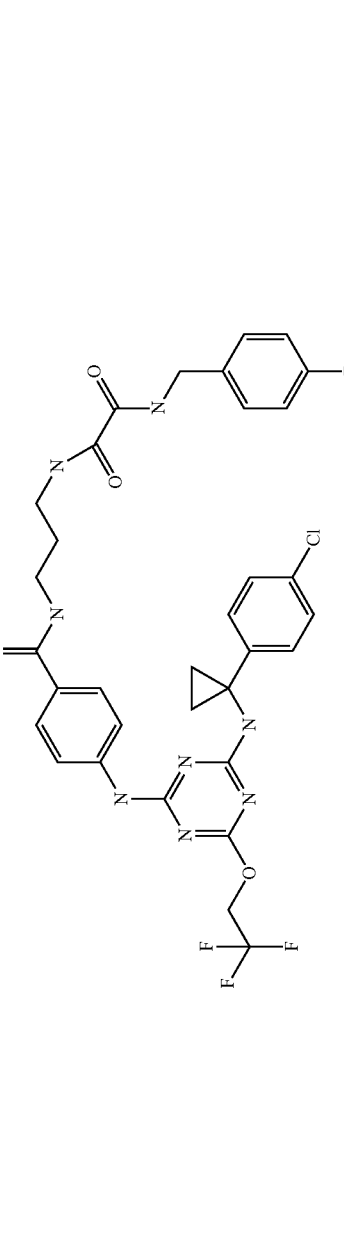 | | A |
| 3358 | 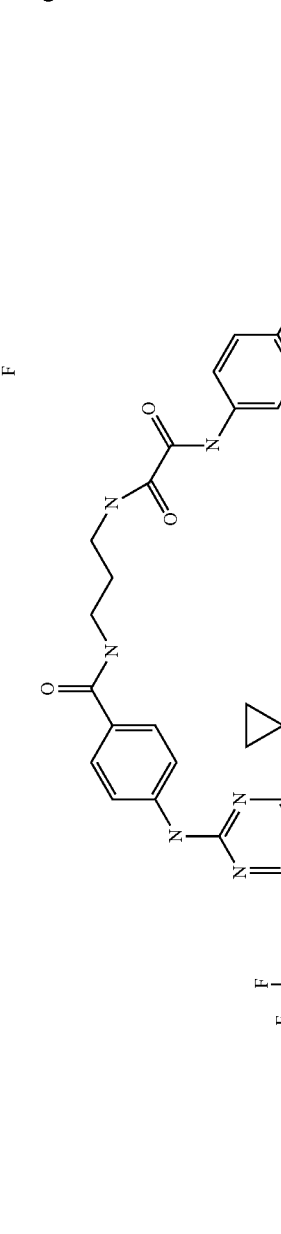 | 0.034 | A |

TABLE 1-continued
| Compound | Structure | EC$_{50}$ | Activity |
|---|---|---|---|
| 3359 | 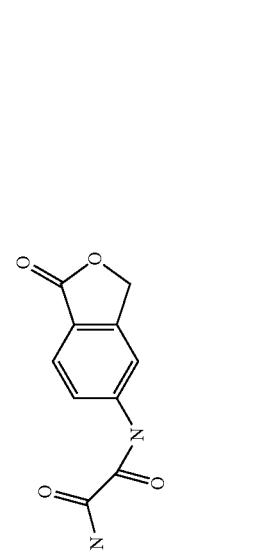 | | A |
| 3360 | 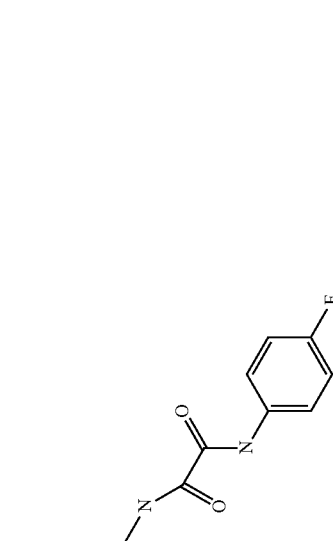 | | A |

TABLE 1-continued

| Compound | Structure | EC₅₀ | Activity |
|---|---|---|---|
| 3361 | 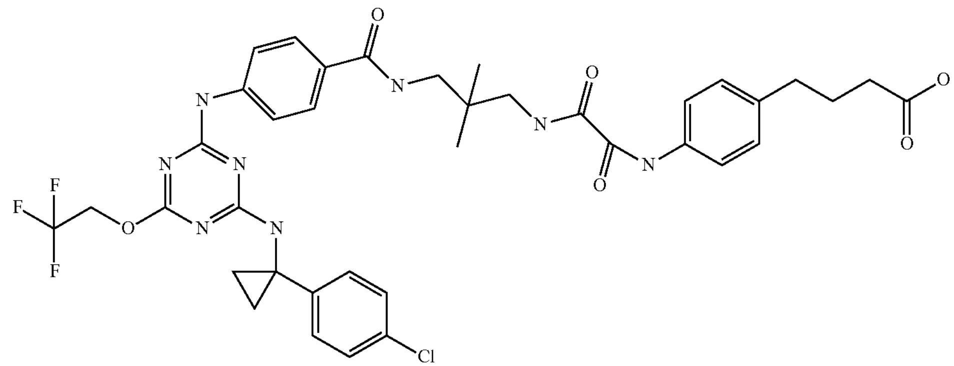 [SMILES: CC(C)(CNC(=O)C(=O)Nc1ccc(CCCC(=O)O)cc1)CNC(=O)c1ccc(Nc2nc(NC3(c4ccc(Cl)cc4)CC3)nc(OCC(F)(F)F)n2)cc1] | 0.16 | A |
| 3362 | 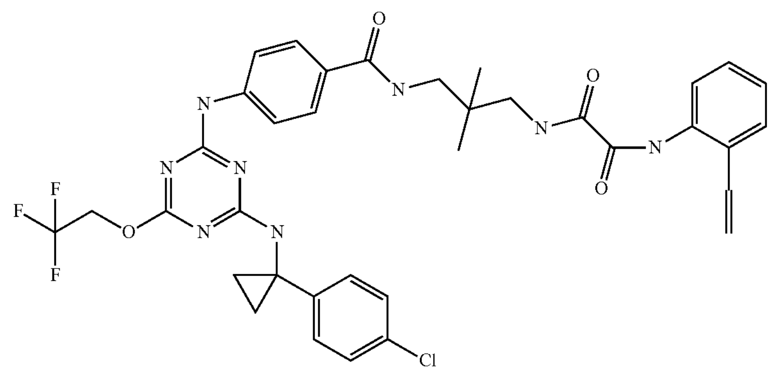 [SMILES: C=Cc1ccccc1NC(=O)C(=O)NCC(C)(C)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3363 | 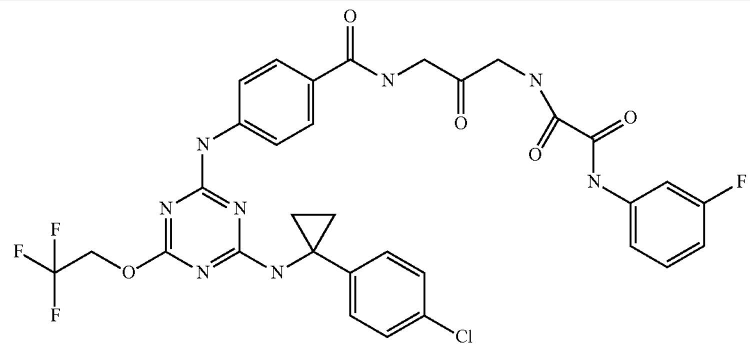 [SMILES: O=C(CNC(=O)C(=O)Nc1cccc(F)c1)CNC(=O)c1ccc(Nc2nc(NC3(c4ccc(Cl)cc4)CC3)nc(OCC(F)(F)F)n2)cc1] | | A |
| 3364 | 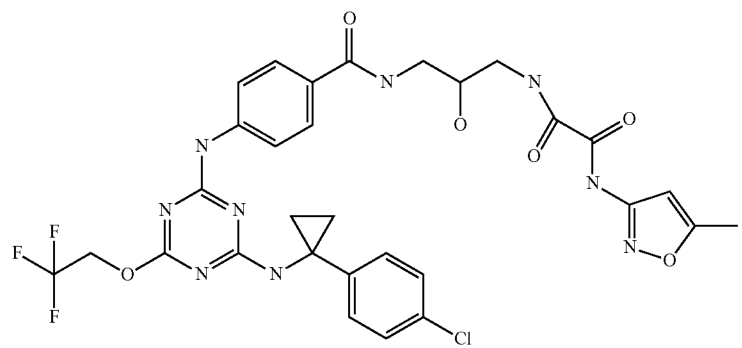 [SMILES: Cc1cc(NC(=O)C(=O)NCC(O)CNC(=O)c2ccc(Nc3nc(NC4(c5ccc(Cl)cc5)CC4)nc(OCC(F)(F)F)n3)cc2)no1] | | A |
| 3365 | 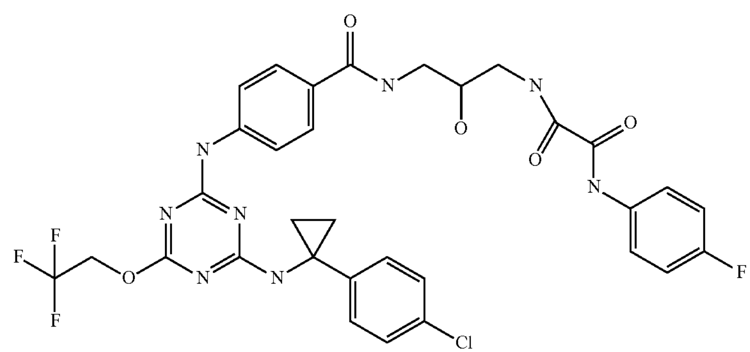 | 0.024 | A |

TABLE 1-continued
| Compound | Structure | EC$_{50}$ | Activity |
|---|---|---|---|
| 3366 | 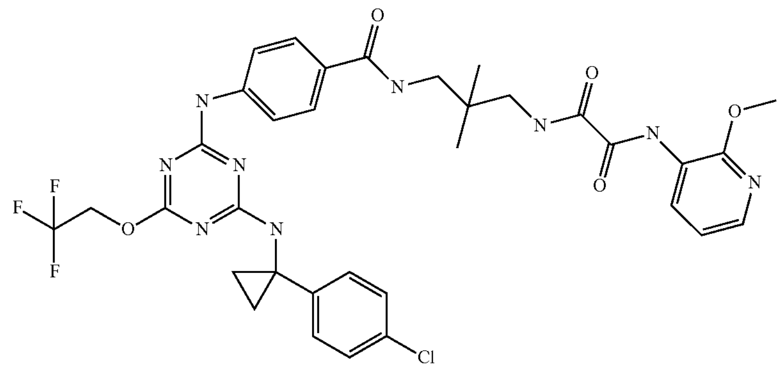 [SMILES: COc1ncccc1NC(=O)C(=O)NCC(C)(C)CNC(=O)c1ccc(Nc2nc(NC3(c4ccc(Cl)cc4)CC3)nc(OCC(F)(F)F)n2)cc1] | 0.14 | A |
| 3367 | 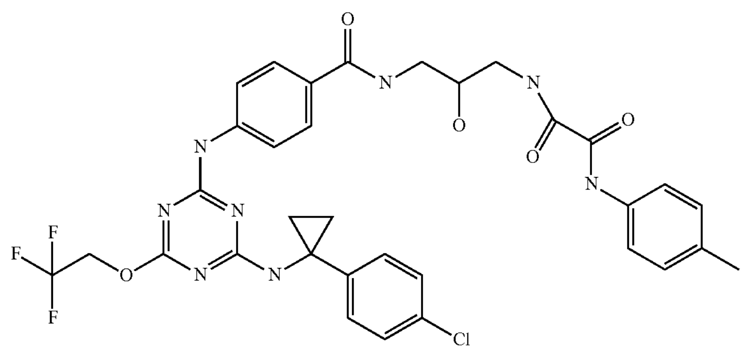 [SMILES: Cc1ccc(NC(=O)C(=O)NCC(O)CNC(=O)c2ccc(Nc3nc(NC4(c5ccc(Cl)cc5)CC4)nc(OCC(F)(F)F)n3)cc2)cc1] | | A |
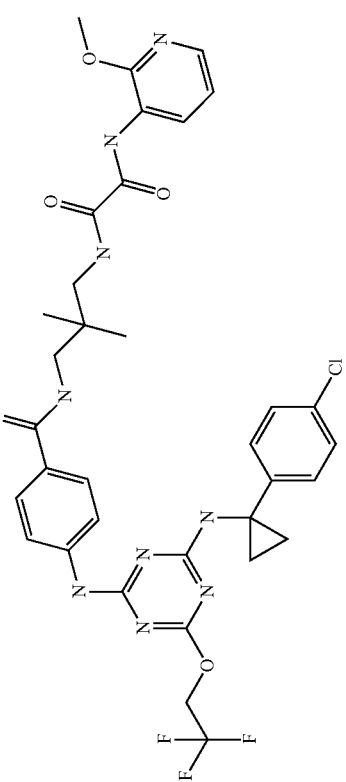

TABLE 1-continued

| Compound | Structure | EC$_{50}$ | Activity |
|---|---|---|---|
| 3368 | 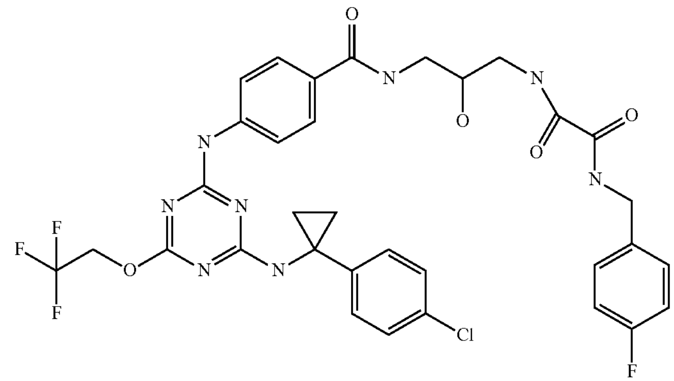 [SMILES: O=C(NCc1ccc(F)cc1)C(=O)NCC(O)CNC(=O)c1ccc(Nc2nc(NC3(c4ccc(Cl)cc4)CC3)nc(OCC(F)(F)F)n2)cc1] | | A |
| 3369 | 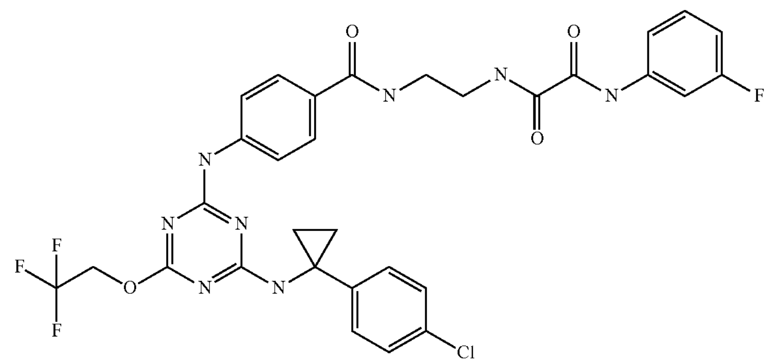 [SMILES: O=C(NCCNC(=O)c1ccc(Nc2nc(NC3(c4ccc(Cl)cc4)CC3)nc(OCC(F)(F)F)n2)cc1)C(=O)Nc1cccc(F)c1] | | A |

TABLE 1-continued

| Compound | Structure | EC$_{50}$ | Activity |
|---|---|---|---|
| 3370 | 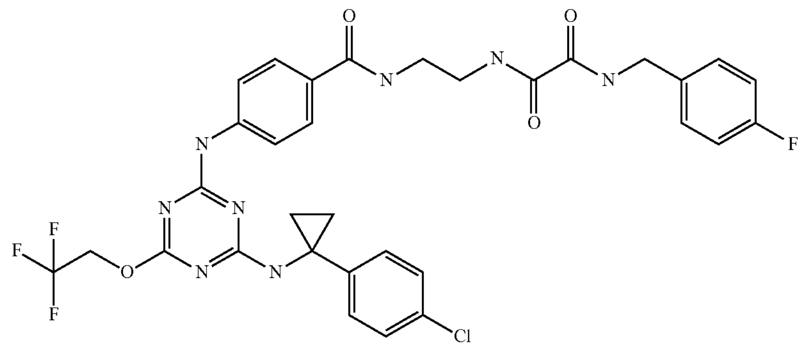 [SMILES: O=C(NCCNC(=O)c1ccc(Nc2nc(NC3(c4ccc(Cl)cc4)CC3)nc(OCC(F)(F)F)n2)cc1)C(=O)NCc1ccc(F)cc1] | | A |
| 3371 | 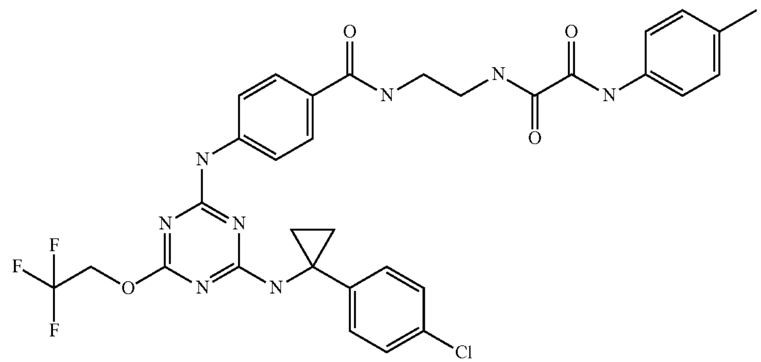 [SMILES: Cc1ccc(NC(=O)C(=O)NCCNC(=O)c2ccc(Nc3nc(NC4(c5ccc(Cl)cc5)CC4)nc(OCC(F)(F)F)n3)cc2)cc1] | | A |

TABLE 1-continued
| Compound | Structure | EC$_{50}$ | Activity |
|---|---|---|---|
| 3372 | 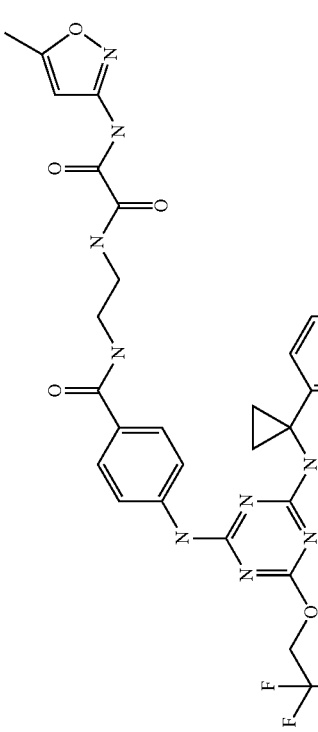 | | A |
| 3373 | 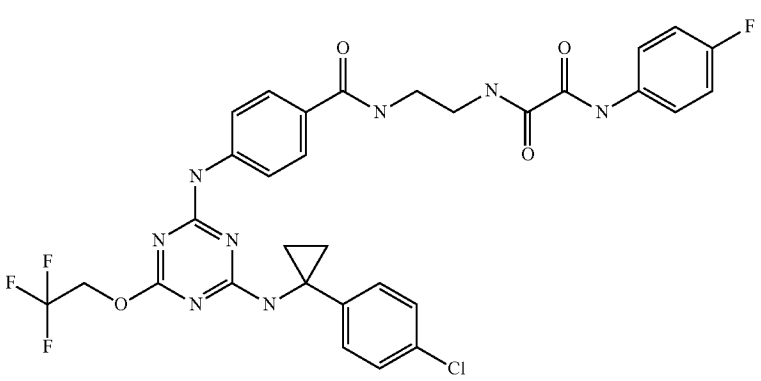 [SMILES: O=C(NCCNC(=O)c1ccc(Nc2nc(NC3(c4ccc(Cl)cc4)CC3)nc(OCC(F)(F)F)n2)cc1)C(=O)Nc1ccc(F)cc1] | 0.052 | A |

TABLE 1-continued

| Compound | Structure | EC$_{50}$ | Activity |
|---|---|---|---|
| 3374 | 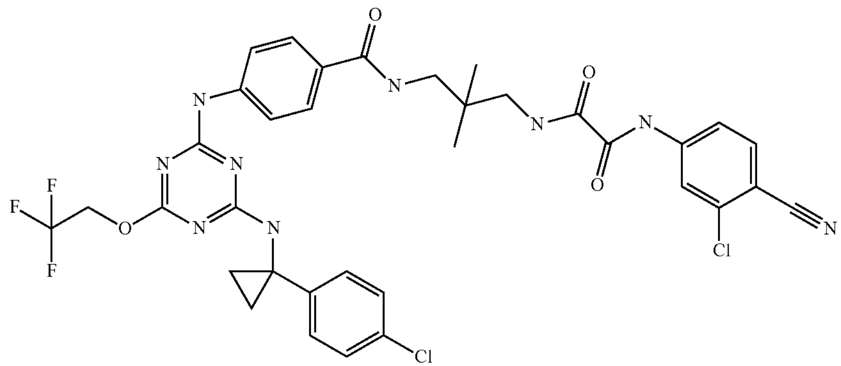 [SMILES: CC(C)(CNC(=O)C(=O)Nc1ccc(C#N)c(Cl)c1)CNC(=O)c1ccc(Nc2nc(NC3(c4ccc(Cl)cc4)CC3)nc(OCC(F)(F)F)n2)cc1] | | A |
| 3375 | 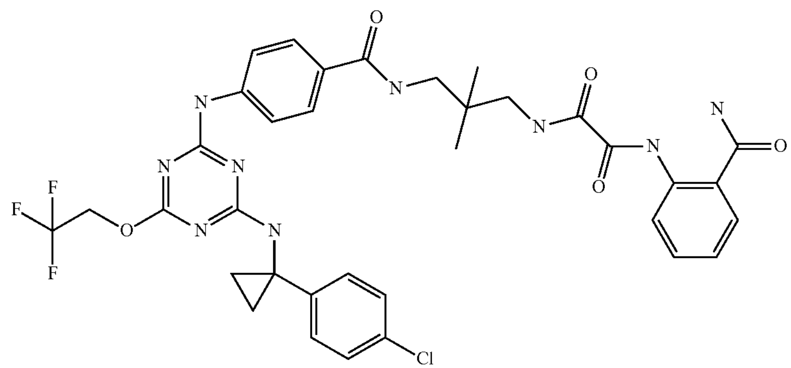 [SMILES: CC(C)(CNC(=O)C(=O)Nc1ccccc1C(N)=O)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3376 | 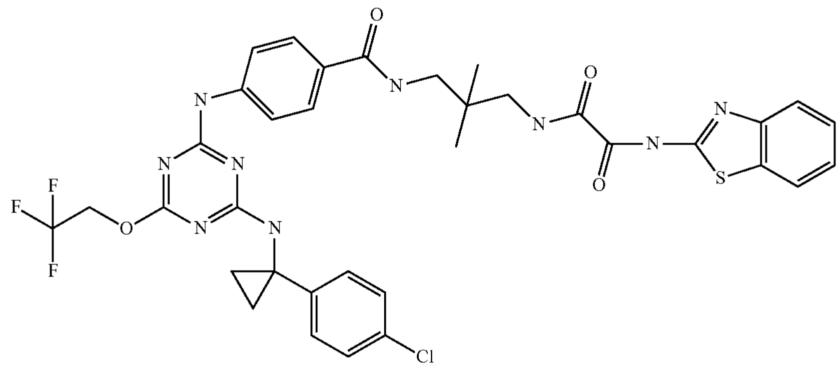 [SMILES: CC(C)(CNC(=O)C(=O)Nc1nc2ccccc2s1)CNC(=O)c1ccc(Nc2nc(NC3(c4ccc(Cl)cc4)CC3)nc(OCC(F)(F)F)n2)cc1] | | A |
| 3377 | 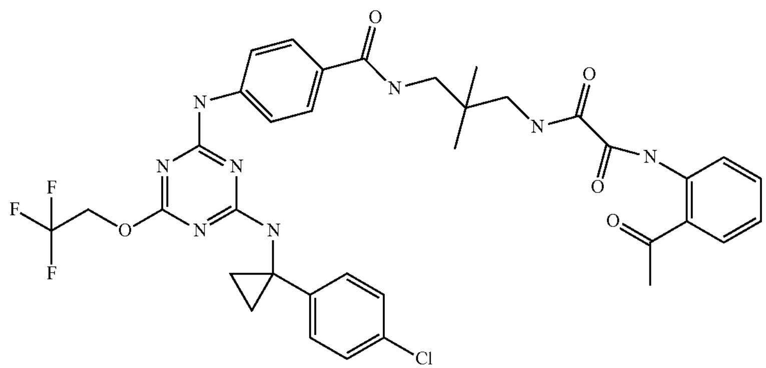 [SMILES: CC(=O)c1ccccc1NC(=O)C(=O)NCC(C)(C)CNC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 3378 | 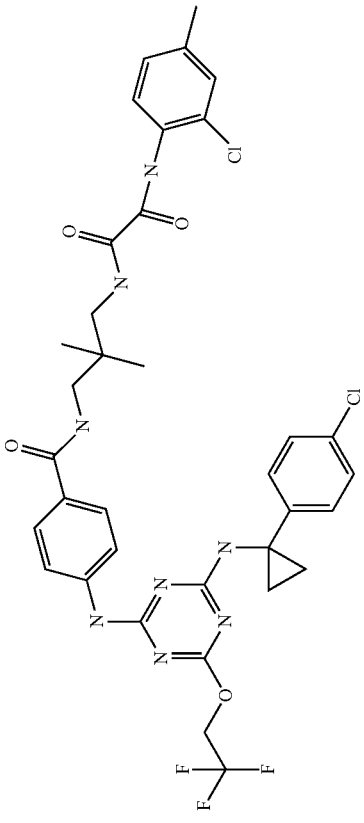 | | A |
| 3379 | 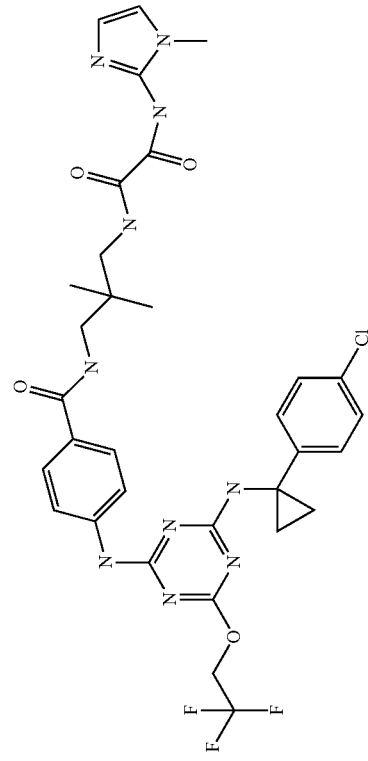 | 0.14 | A |

TABLE 1-continued

| Compound | Structure | EC$_{50}$ | Activity |
|---|---|---|---|
| 3380 | 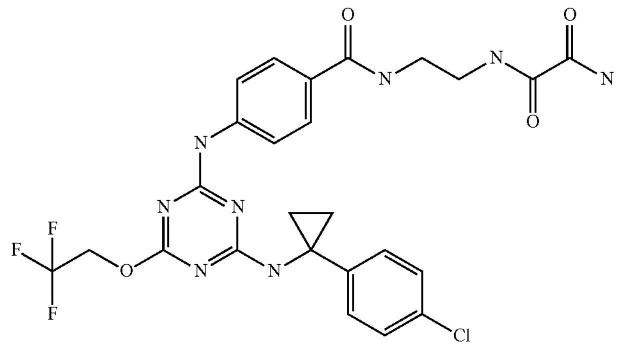 [SMILES: NC(=O)C(=O)NCCNC(=O)c1ccc(Nc2nc(NC3(c4ccc(Cl)cc4)CC3)nc(OCC(F)(F)F)n2)cc1] | | A |
| 3381 | 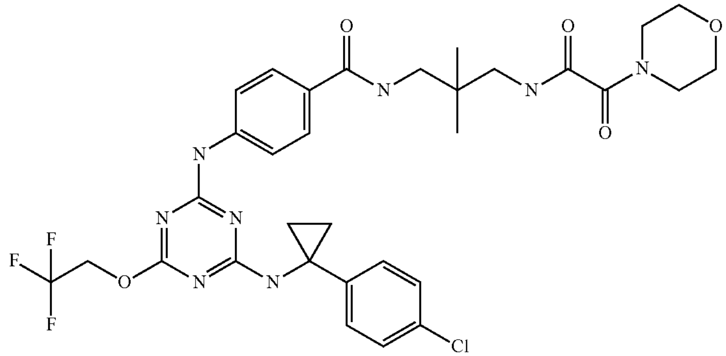 [SMILES: CC(C)(CNC(=O)C(=O)N1CCOCC1)CNC(=O)c1ccc(Nc2nc(NC3(c4ccc(Cl)cc4)CC3)nc(OCC(F)(F)F)n2)cc1] | | A |
| 3382 | 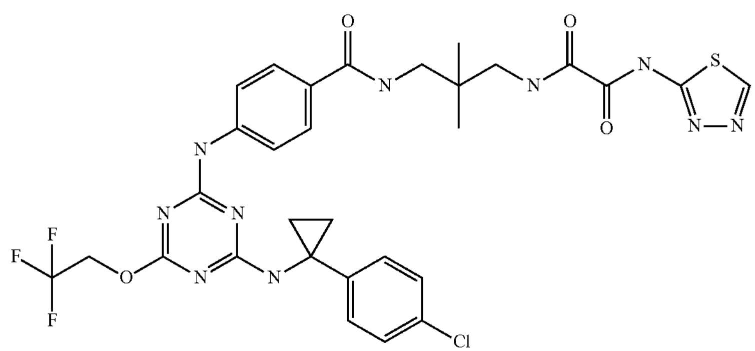 [SMILES: CC(C)(CNC(=O)C(=O)Nc1nncs1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3383 | 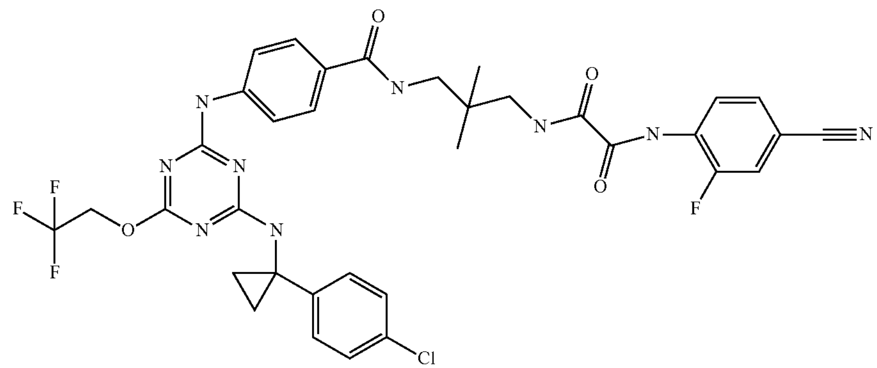 [SMILES: CC(C)(CNC(=O)C(=O)Nc1ccc(C#N)cc1F)CNC(=O)c1ccc(Nc2nc(NC3(c4ccc(Cl)cc4)CC3)nc(OCC(F)(F)F)n2)cc1] | | A |
| 3384 | 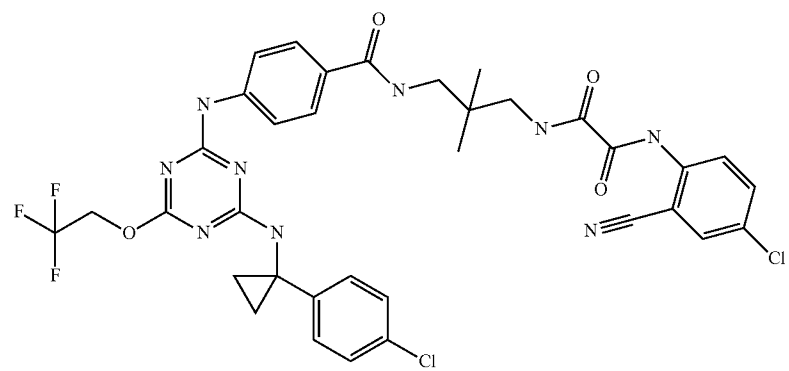 [SMILES: CC(C)(CNC(=O)C(=O)Nc1ccc(Cl)cc1C#N)CNC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 3385 | 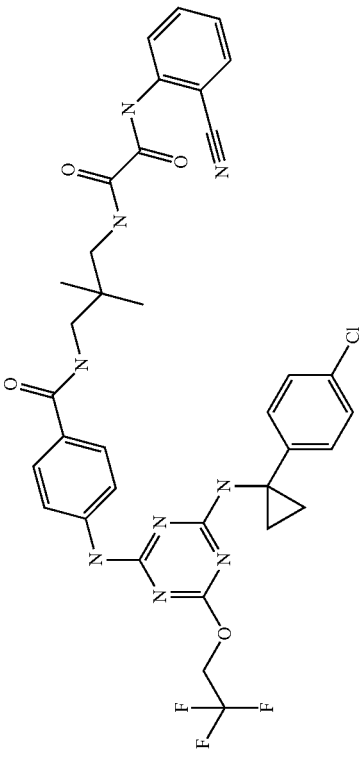 | | A |
| 3386 | 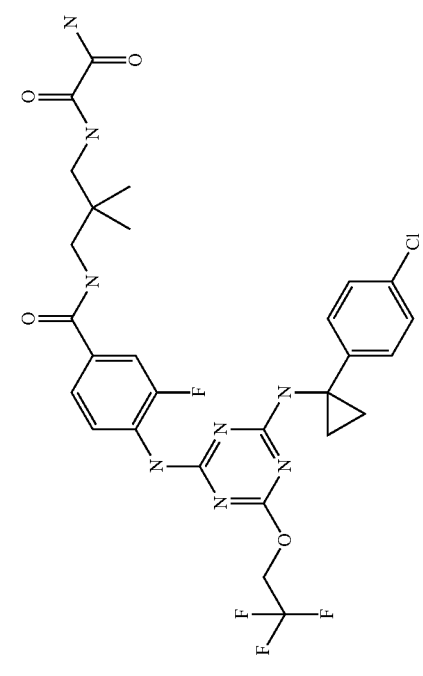 | | A |

TABLE 1-continued

| Compound | Structure | EC$_{50}$ | Activity |
|---|---|---|---|
| 3387 | 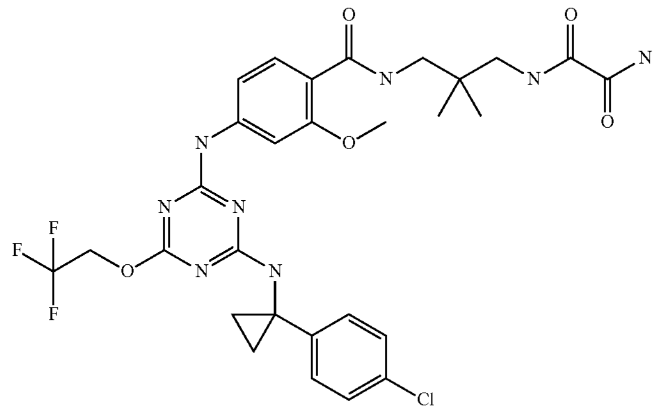 [SMILES: COc1cc(Nc2nc(NC3(c4ccc(Cl)cc4)CC3)nc(OCC(F)(F)F)n2)ccc1C(=O)NCC(C)(C)CNC(=O)C(N)=O] | 0.068 | A |
| 3388 | 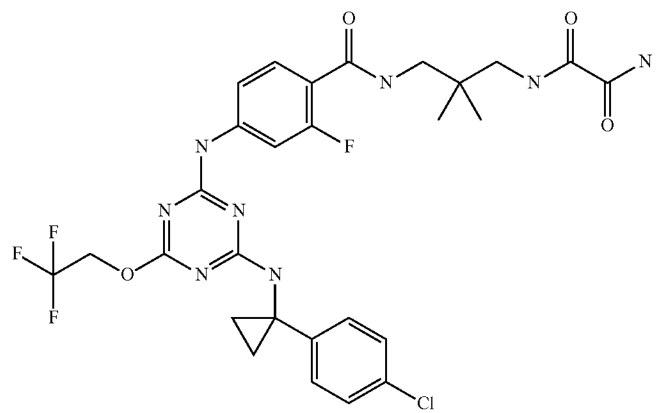 | 0.013 | A |

TABLE 1-continued

| Compound | Structure | EC$_{50}$ | Activity |
|---|---|---|---|
| 3389 | 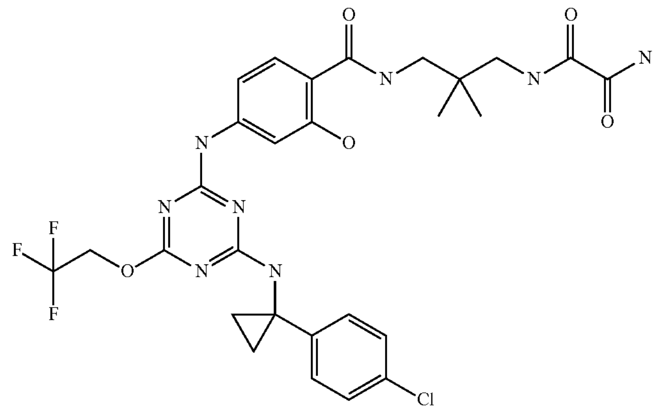 [SMILES: CC(C)(CNC(=O)C(N)=O)CNC(=O)c1ccc(Nc2nc(NC3(c4ccc(Cl)cc4)CC3)nc(OCC(F)(F)F)n2)cc1F] | | A |
| 3390 | 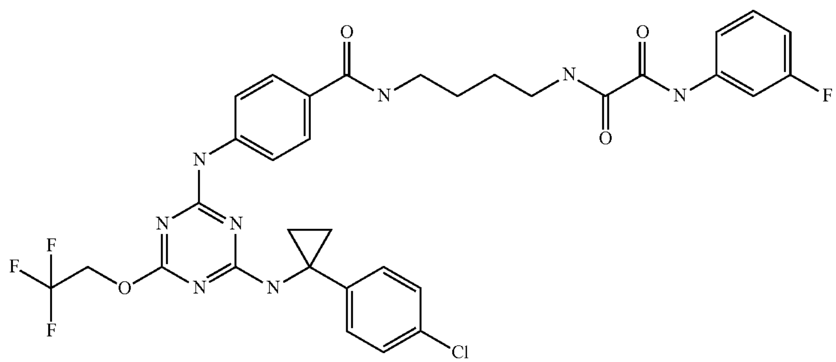 [SMILES: O=C(NCCCCNC(=O)c1ccc(Nc2nc(NC3(c4ccc(Cl)cc4)CC3)nc(OCC(F)(F)F)n2)cc1)C(=O)Nc1cccc(F)c1] | | A |

TABLE 1-continued

| Compound | Structure | EC$_{50}$ | Activity |
|---|---|---|---|
| 3391 | 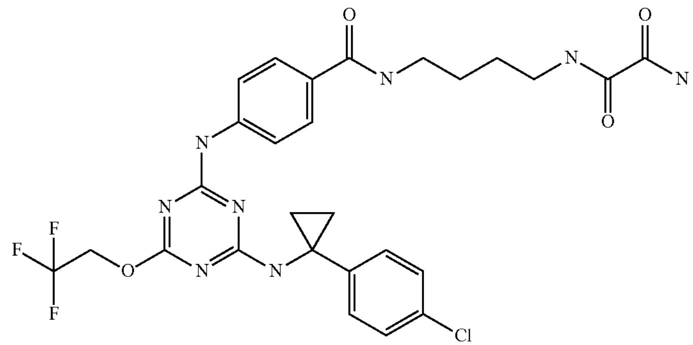 [SMILES: NC(=O)C(=O)NCCCCNC(=O)c1ccc(Nc2nc(NC3(c4ccc(Cl)cc4)CC3)nc(OCC(F)(F)F)n2)cc1] | | A |
| 3392 | 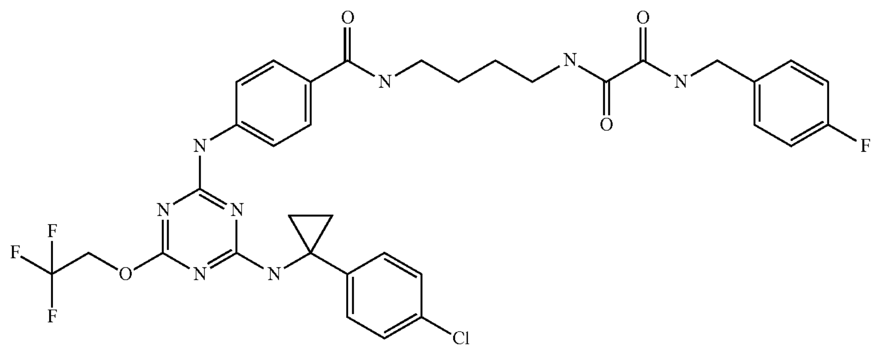 [SMILES: O=C(NCCCCNC(=O)c1ccc(Nc2nc(NC3(c4ccc(Cl)cc4)CC3)nc(OCC(F)(F)F)n2)cc1)C(=O)NCc1ccc(F)cc1] | | A |
| 3393 | 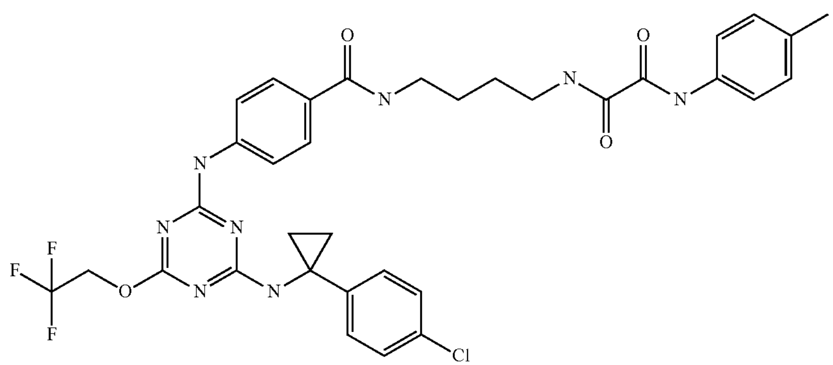 [SMILES: Cc1ccc(NC(=O)C(=O)NCCCCNC(=O)c2ccc(Nc3nc(NC4(c5ccc(Cl)cc5)CC4)nc(OCC(F)(F)F)n3)cc2)cc1] | | A |

TABLE 1-continued
| Compound | Structure | EC$_{50}$ | Activity |
|---|---|---|---|
| 3394 | 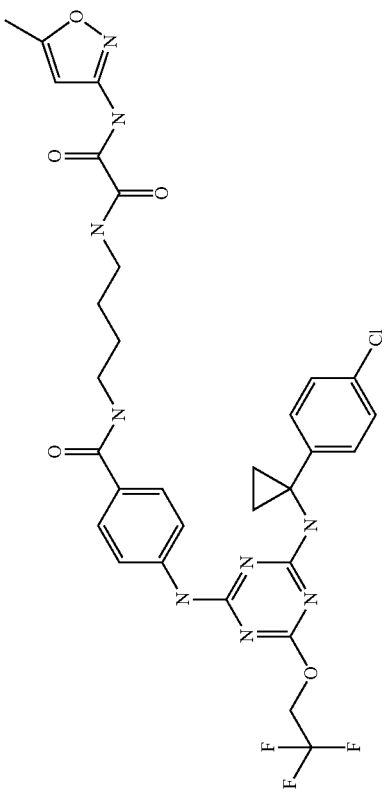 | | A |
| 3395 | 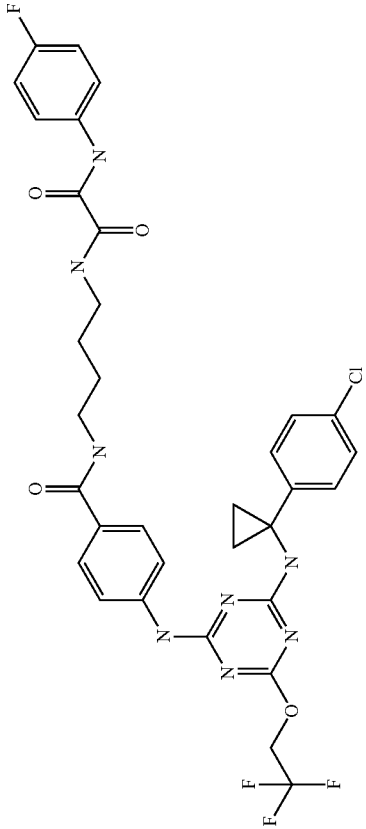 | | A |

TABLE 1-continued

| Compound | Structure | EC$_{50}$ | Activity |
|---|---|---|---|
| 3396 | 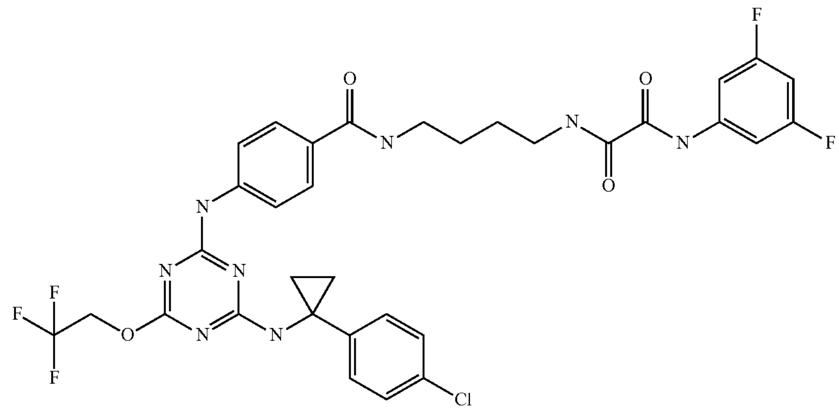 [SMILES: O=C(NCCCCNC(=O)c1ccc(Nc2nc(NC3(c4ccc(Cl)cc4)CC3)nc(OCC(F)(F)F)n2)cc1)C(=O)Nc1cc(F)cc(F)c1] | | A |
| 3397 | 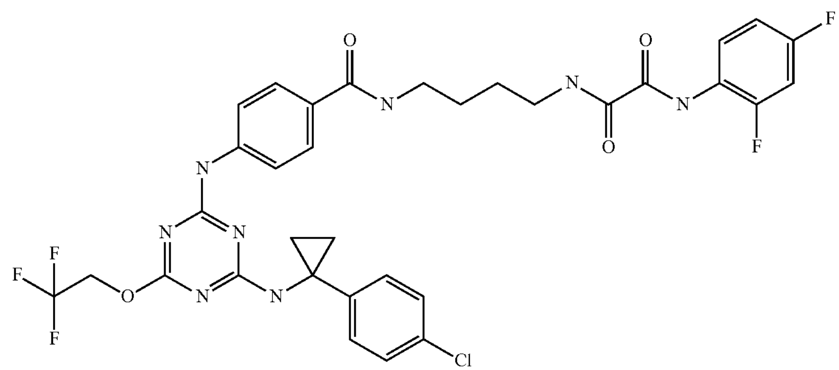 [SMILES: O=C(NCCCCNC(=O)c1ccc(Nc2nc(NC3(c4ccc(Cl)cc4)CC3)nc(OCC(F)(F)F)n2)cc1)C(=O)Nc1ccc(F)cc1F] | 0.082 | A |

TABLE 1-continued

| Compound | Structure | EC$_{50}$ | Activity |
|---|---|---|---|
| 3398 | 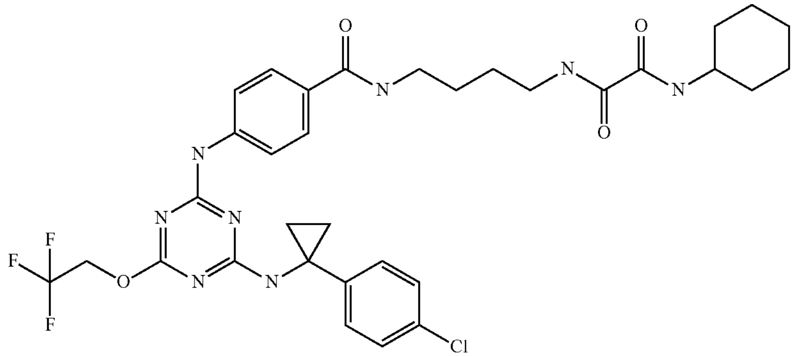 [SMILES: O=C(NCCCCNC(=O)c1ccc(Nc2nc(NC3(c4ccc(Cl)cc4)CC3)nc(OCC(F)(F)F)n2)cc1)C(=O)NC1CCCCC1] | | A |
| 3399 | 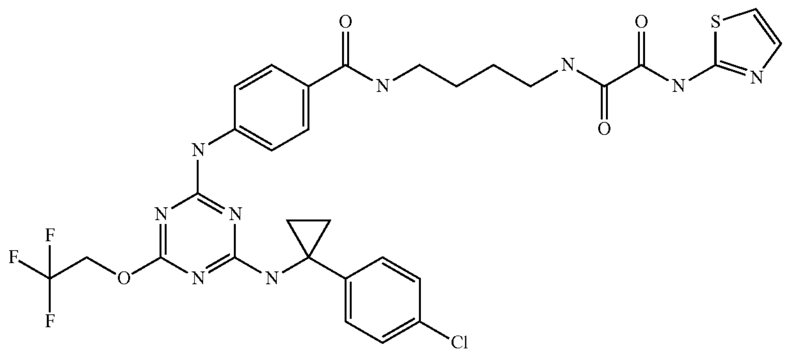 [SMILES: O=C(NCCCCNC(=O)c1ccc(Nc2nc(NC3(c4ccc(Cl)cc4)CC3)nc(OCC(F)(F)F)n2)cc1)C(=O)Nc1nccs1] | | A |

TABLE 1-continued

| Compound | Structure | EC$_{50}$ | Activity |
|---|---|---|---|
| 3400 | 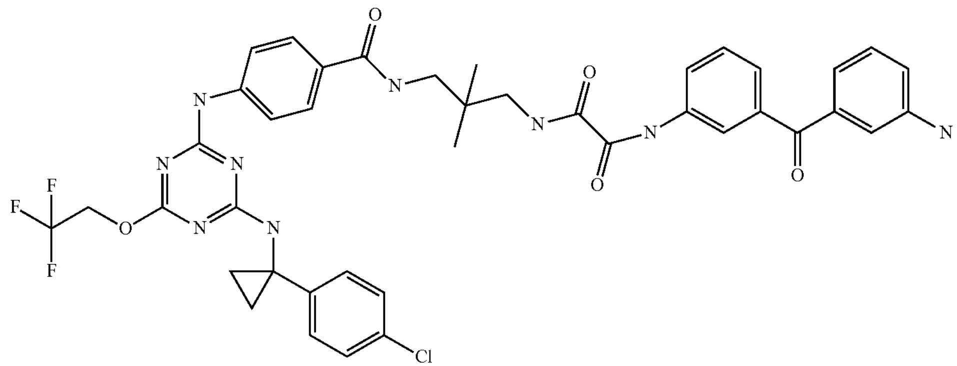 [SMILES: CC(C)(CNC(=O)C(=O)Nc1cccc(C(=O)c2cccc(N)c2)c1)CNC(=O)c1ccc(Nc2nc(NC3(c4ccc(Cl)cc4)CC3)nc(OCC(F)(F)F)n2)cc1] | | A |
| 3401 | 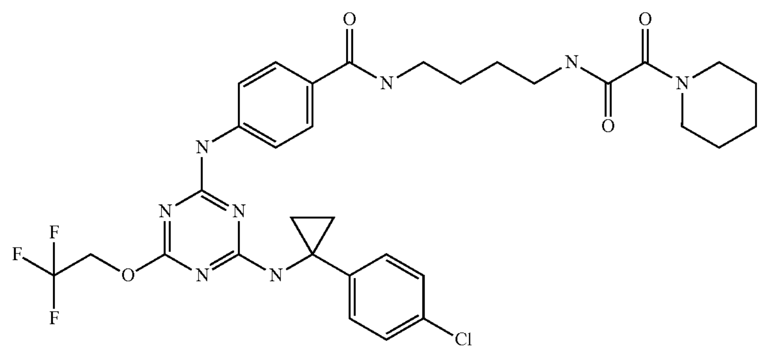 [SMILES: O=C(NCCCCNC(=O)c1ccc(Nc2nc(NC3(c4ccc(Cl)cc4)CC3)nc(OCC(F)(F)F)n2)cc1)C(=O)N1CCCCC1] | | A |
| 3402 | 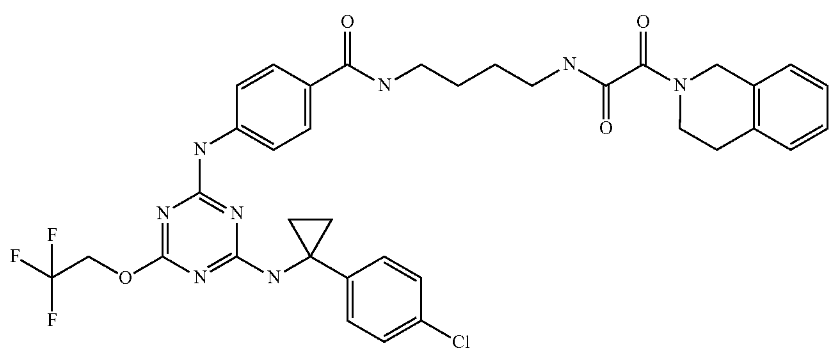 [SMILES: O=C(NCCCCNC(=O)c1ccc(Nc2nc(NC3(c4ccc(Cl)cc4)CC3)nc(OCC(F)(F)F)n2)cc1)C(=O)N1CCc2ccccc2C1] | 0.20 | A |

TABLE 1-continued

| Compound | Structure | EC$_{50}$ | Activity |
|---|---|---|---|
| 3403 | 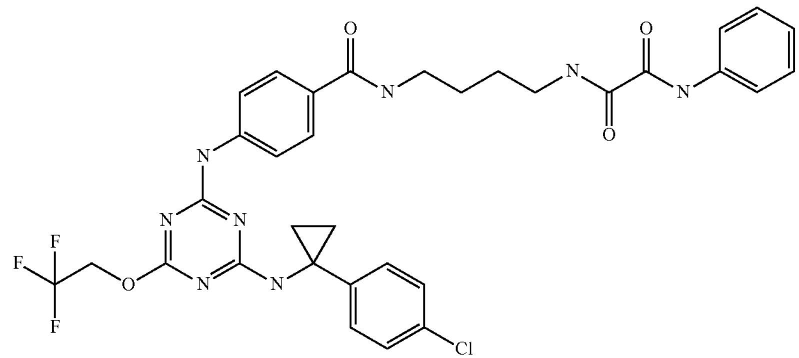 [SMILES: O=C(NCCCCNC(=O)c1ccc(Nc2nc(NC3(c4ccc(Cl)cc4)CC3)nc(OCC(F)(F)F)n2)cc1)C(=O)Nc1ccccc1] | | A |
| 3404 | 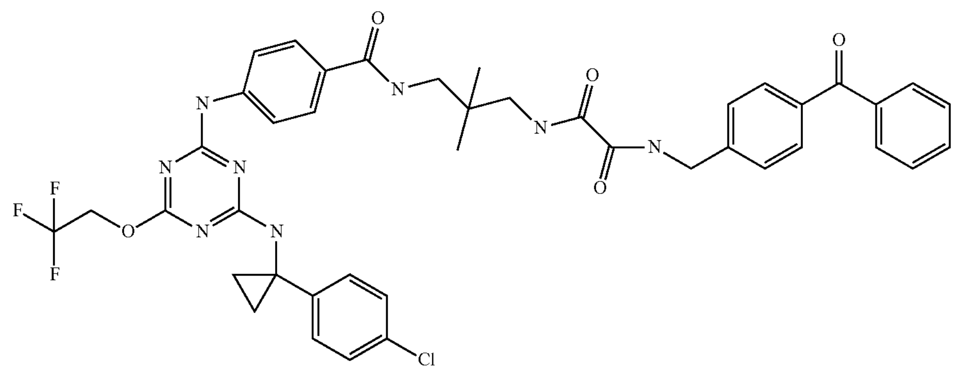 [SMILES: CC(C)(CNC(=O)C(=O)NCc1ccc(C(=O)c2ccccc2)cc1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3405 | 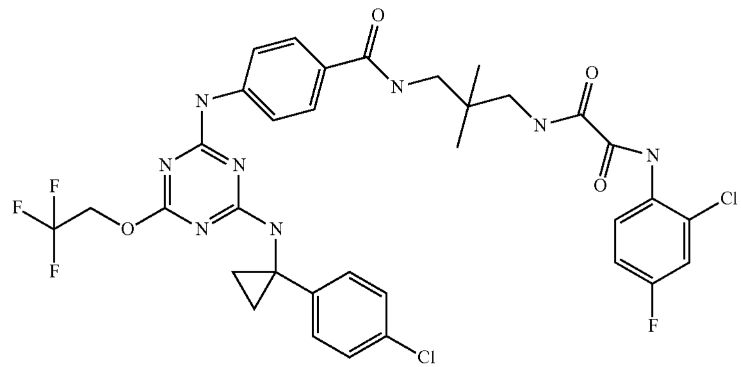 [SMILES: CC(C)(CNC(=O)C(=O)Nc1ccc(F)cc1Cl)CNC(=O)c1ccc(Nc2nc(NC3(c4ccc(Cl)cc4)CC3)nc(OCC(F)(F)F)n2)cc1] | | A |
| 3406 | 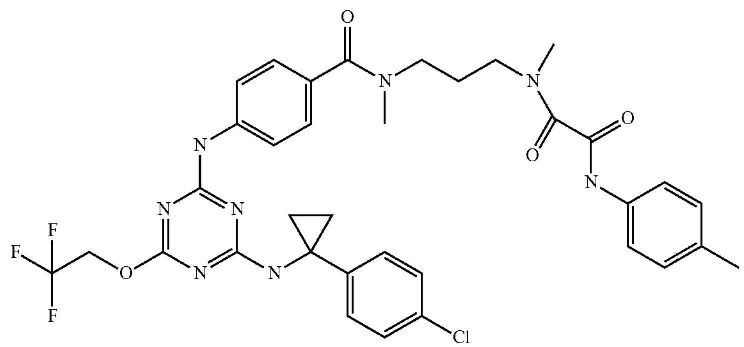 [SMILES: Cc1ccc(NC(=O)C(=O)N(C)CCCN(C)C(=O)c2ccc(Nc3nc(NC4(c5ccc(Cl)cc5)CC4)nc(OCC(F)(F)F)n3)cc2)cc1] | 1.91 | A |

TABLE 1-continued

| Compound | Structure | EC$_{50}$ | Activity |
|---|---|---|---|
| 3407 | 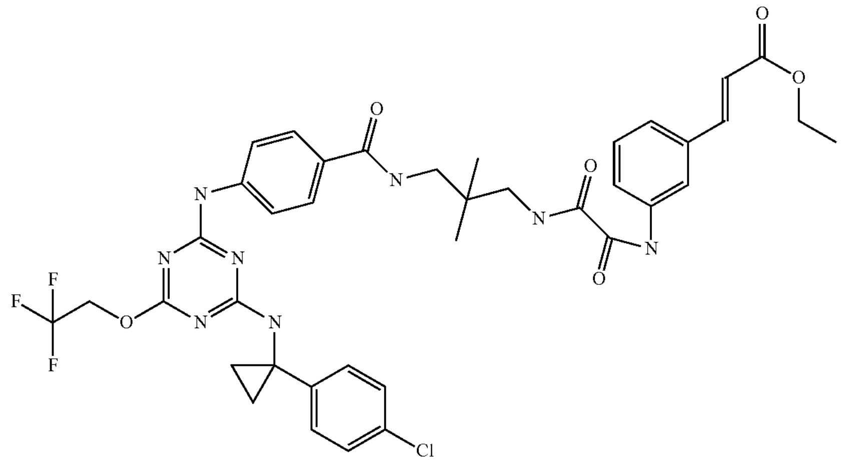 [SMILES: CCOC(=O)/C=C/c1cccc(NC(=O)C(=O)NCC(C)(C)CNC(=O)c2ccc(Nc3nc(NC4(c5ccc(Cl)cc5)CC4)nc(OCC(F)(F)F)n3)cc2)c1] | | A |
| 3408 | 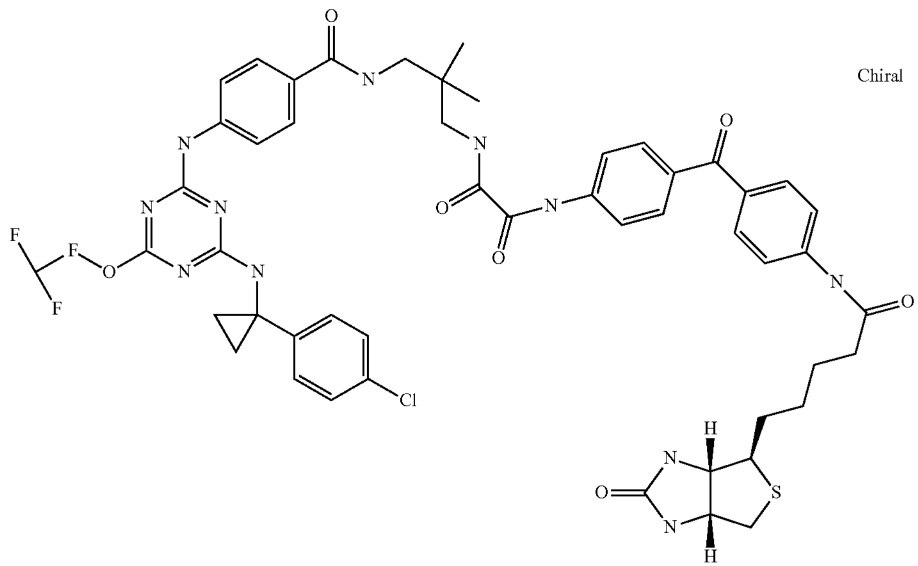 | | A |

TABLE 1-continued

| Compound | Structure | EC$_{50}$ | Activity |
|---|---|---|---|
| 3409 | 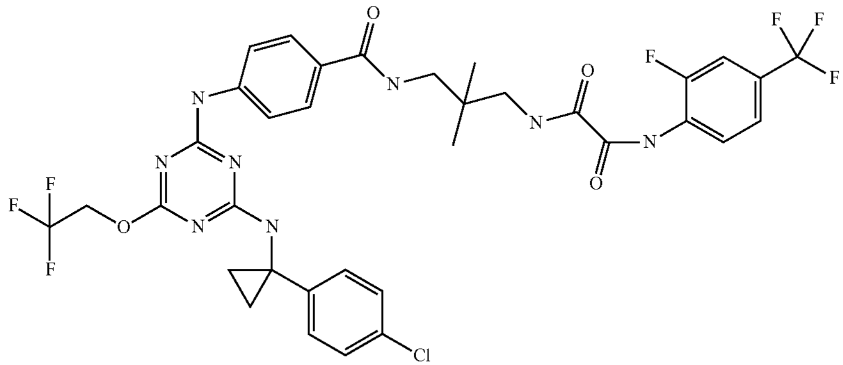 [SMILES: CC(C)(CNC(=O)C(=O)Nc1ccc(C(F)(F)F)cc1F)CNC(=O)c1ccc(Nc2nc(NC3(c4ccc(Cl)cc4)CC3)nc(OCC(F)(F)F)n2)cc1] | | A |
| 3410 | 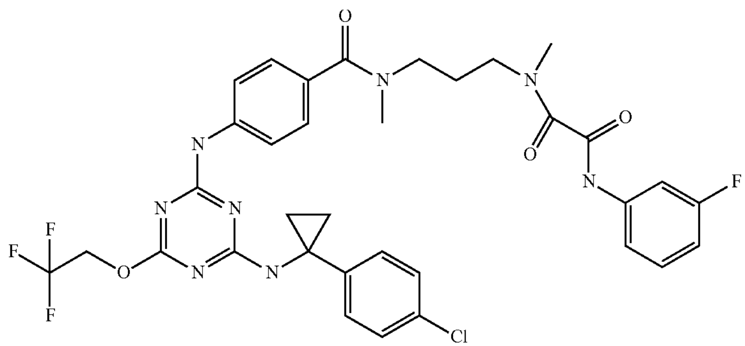 [SMILES: CN(CCCN(C)C(=O)c1ccc(Nc2nc(NC3(c4ccc(Cl)cc4)CC3)nc(OCC(F)(F)F)n2)cc1)C(=O)C(=O)Nc1cccc(F)c1] | | A |
| 3411 | 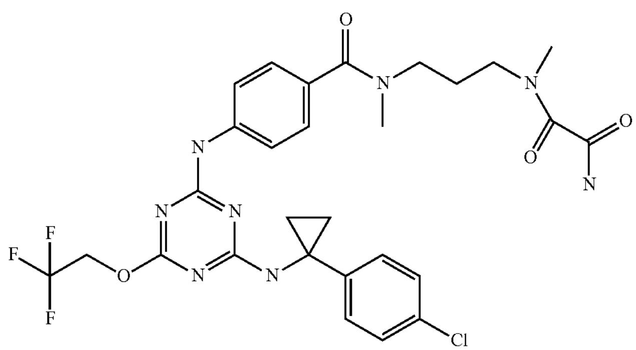 [SMILES: CN(CCCN(C)C(=O)c1ccc(Nc2nc(NC3(c4ccc(Cl)cc4)CC3)nc(OCC(F)(F)F)n2)cc1)C(=O)C(N)=O] | | A |

TABLE 1-continued

| Compound | Structure | EC$_{50}$ | Activity |
|---|---|---|---|
| 3412 | 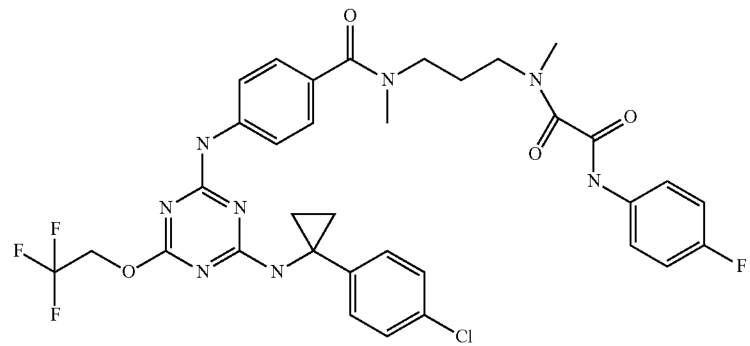 [SMILES: CN(CCCN(C)C(=O)c1ccc(Nc2nc(NC3(c4ccc(Cl)cc4)CC3)nc(OCC(F)(F)F)n2)cc1)C(=O)C(=O)Nc1ccc(F)cc1] | | A |
| 3413 | 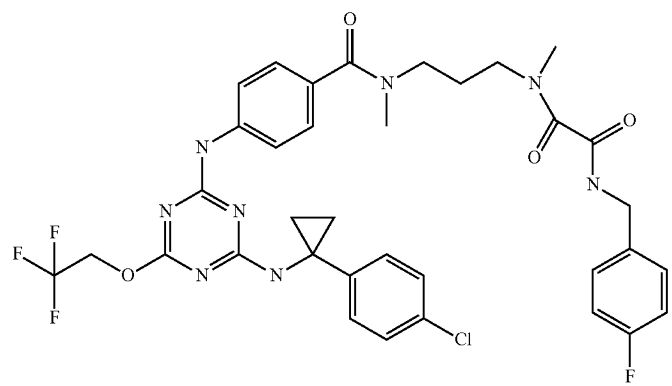 [SMILES: CN(CCCN(C)C(=O)c1ccc(Nc2nc(NC3(c4ccc(Cl)cc4)CC3)nc(OCC(F)(F)F)n2)cc1)C(=O)C(=O)NCc1ccc(F)cc1] | | B |

TABLE 1-continued

| Compound | Structure | EC$_{50}$ | Activity |
|---|---|---|---|
| 3414 | 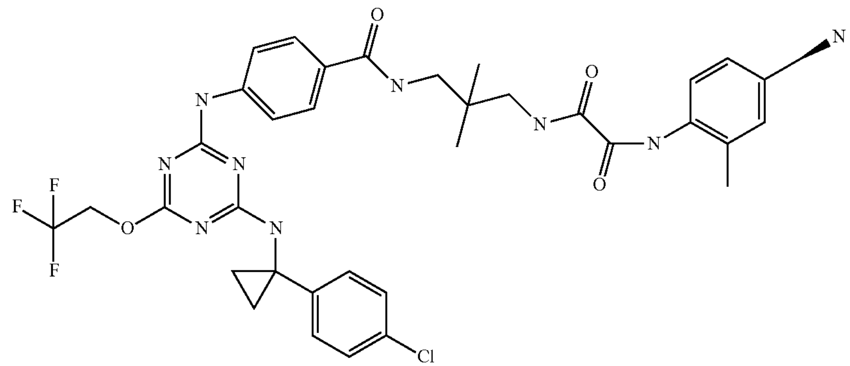 | | A |
| 3415 | 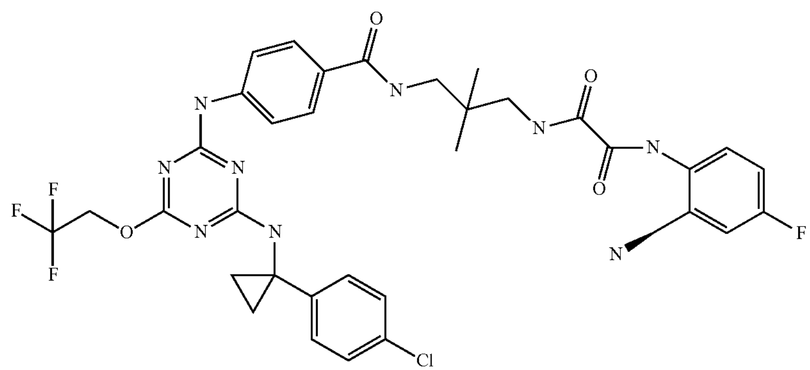 | | A |

TABLE 1-continued

| Compound | Structure | EC$_{50}$ | Activity |
|---|---|---|---|
| 3416 | 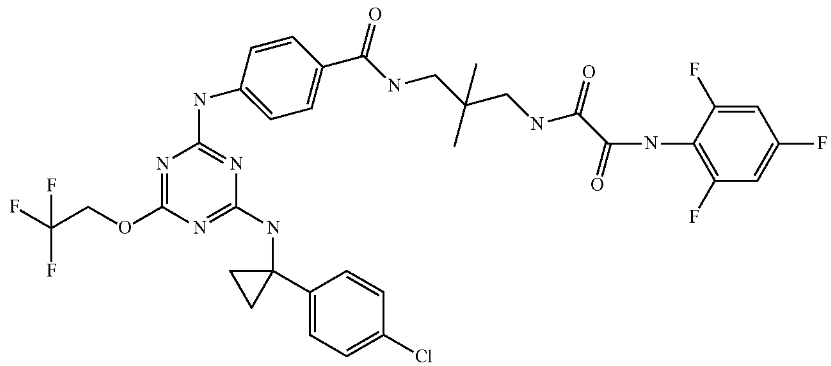 [SMILES: CC(C)(CNC(=O)C(=O)Nc1c(F)cc(F)cc1F)CNC(=O)c1ccc(Nc2nc(NC3(c4ccc(Cl)cc4)CC3)nc(OCC(F)(F)F)n2)cc1] | | A |
| 3417 | 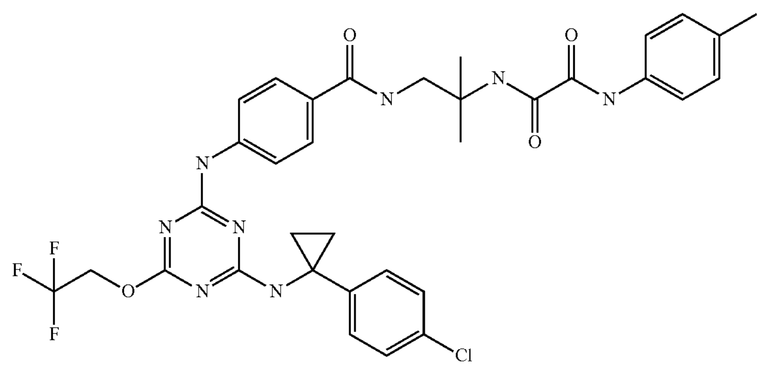 [SMILES: Cc1ccc(NC(=O)C(=O)NC(C)(C)CNC(=O)c2ccc(Nc3nc(NC4(c5ccc(Cl)cc5)CC4)nc(OCC(F)(F)F)n3)cc2)cc1] | 0.032 | A |

TABLE 1-continued

| Compound | Structure | EC$_{50}$ | Activity |
|---|---|---|---|
| 3418 | 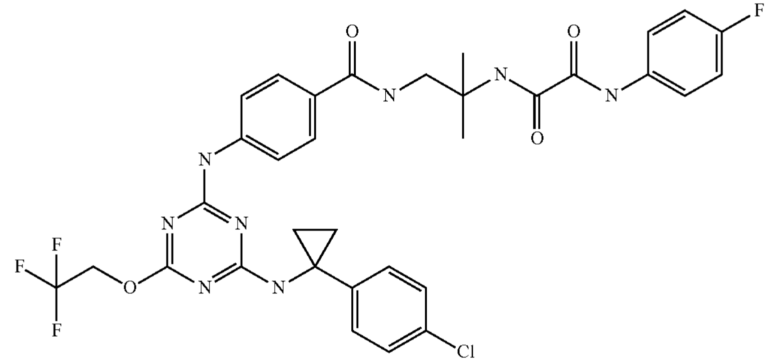 [SMILES: CC(C)(CNC(=O)c1ccc(Nc2nc(NC3(c4ccc(Cl)cc4)CC3)nc(OCC(F)(F)F)n2)cc1)NC(=O)C(=O)Nc1ccc(F)cc1] | | A |
| 3419 | 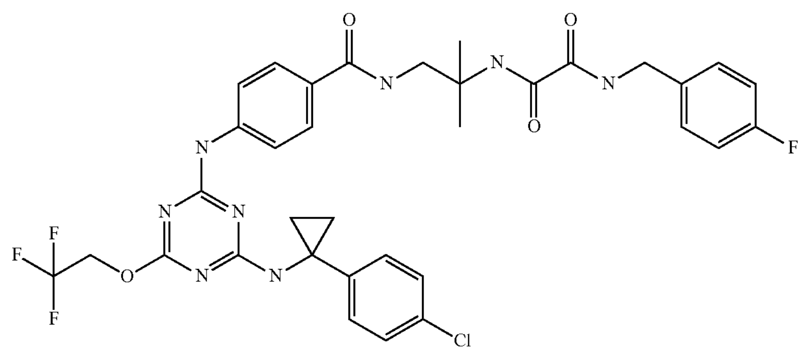 [SMILES: CC(C)(CNC(=O)c1ccc(Nc2nc(NC3(c4ccc(Cl)cc4)CC3)nc(OCC(F)(F)F)n2)cc1)NC(=O)C(=O)NCc1ccc(F)cc1] | | A |
| 3420 | 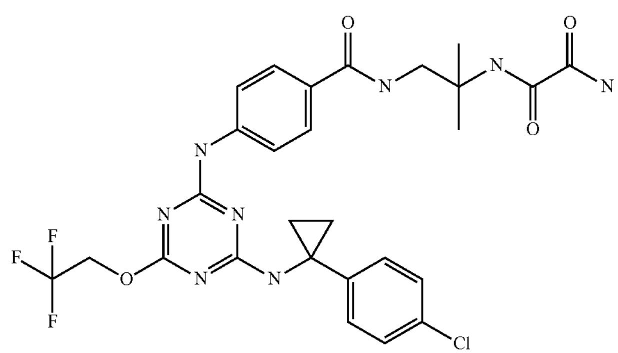 [SMILES: CC(C)(CNC(=O)c1ccc(Nc2nc(NC3(c4ccc(Cl)cc4)CC3)nc(OCC(F)(F)F)n2)cc1)NC(=O)C(N)=O] | | A |

TABLE 1-continued
| Compound | Structure | EC$_{50}$ | Activity |
|---|---|---|---|
| 3421 | 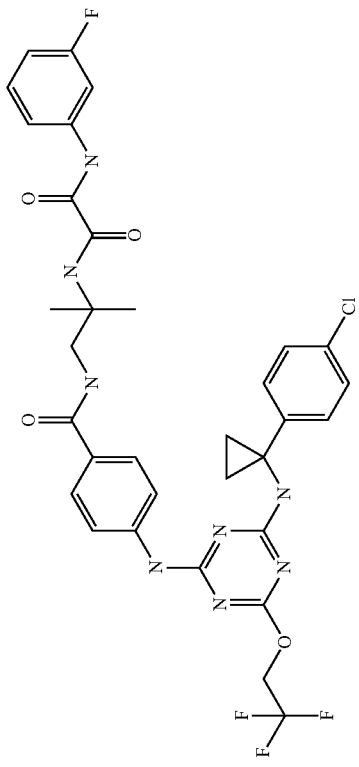 | | A |
| 3422 | 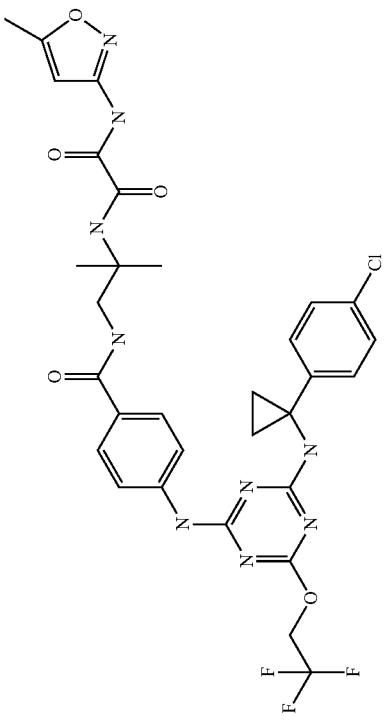 | | A |

TABLE 1-continued

| Compound | Structure | EC$_{50}$ | Activity |
|---|---|---|---|
| 3423 | 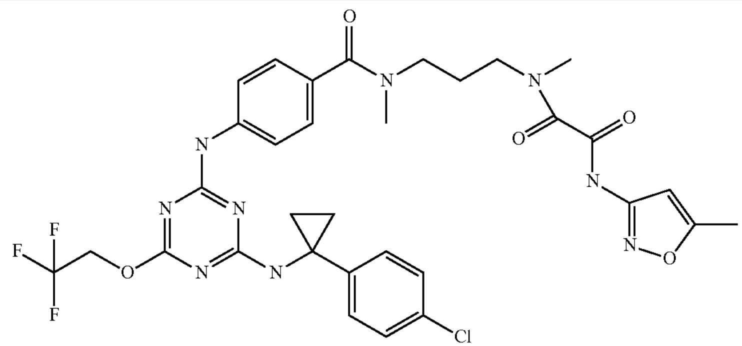 [SMILES: Cc1cc(NC(=O)C(=O)N(C)CCCN(C)C(=O)c2ccc(Nc3nc(NC4(c5ccc(Cl)cc5)CC4)nc(OCC(F)(F)F)n3)cc2)no1] | | A |
| 3424 | 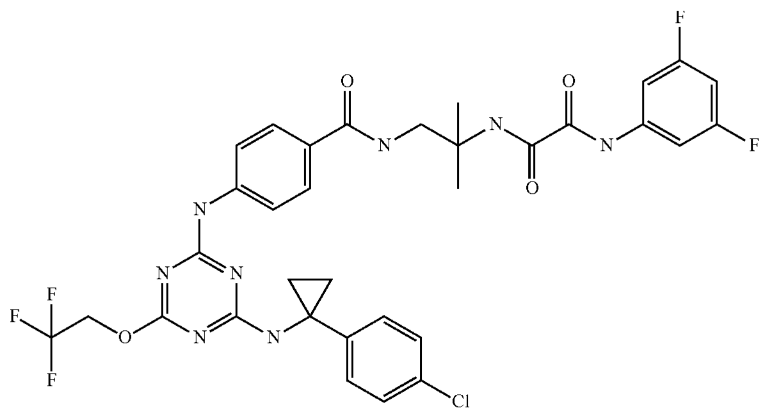 [SMILES: CC(C)(CNC(=O)c1ccc(Nc2nc(NC3(c4ccc(Cl)cc4)CC3)nc(OCC(F)(F)F)n2)cc1)NC(=O)C(=O)Nc1cc(F)cc(F)c1] | | A |

TABLE 1-continued

| Compound | Structure | EC₅₀ | Activity |
|---|---|---|---|
| 3425 | 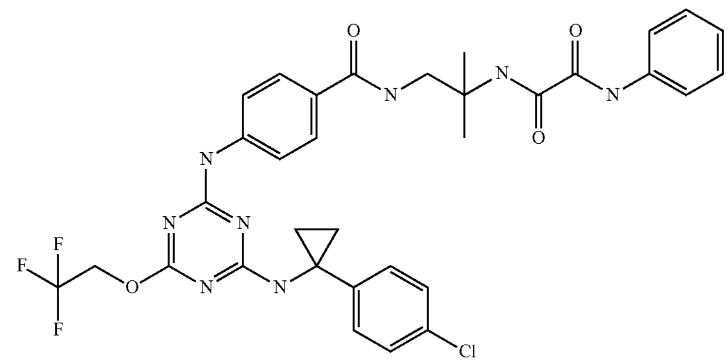 [SMILES: CC(C)(CNC(=O)c1ccc(Nc2nc(NC3(c4ccc(Cl)cc4)CC3)nc(OCC(F)(F)F)n2)cc1)NC(=O)C(=O)Nc1ccccc1] | 0.033 | A |
| 3426 | 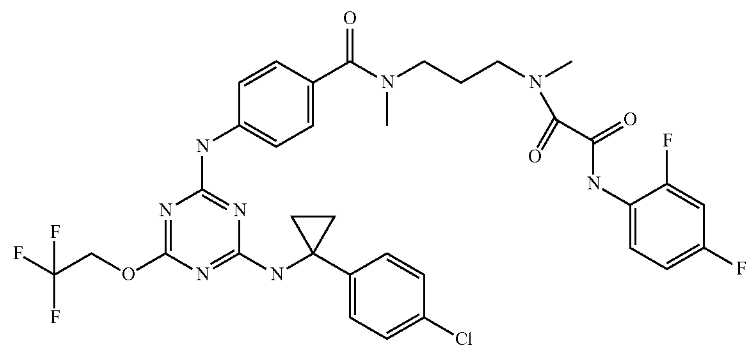 [SMILES: CN(CCCN(C)C(=O)c1ccc(Nc2nc(NC3(c4ccc(Cl)cc4)CC3)nc(OCC(F)(F)F)n2)cc1)C(=O)C(=O)Nc1ccc(F)cc1F] | | A |
| 3427 | 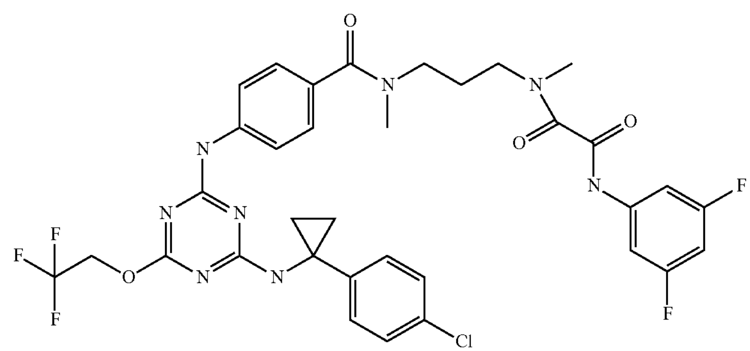 [SMILES: CN(CCCN(C)C(=O)c1ccc(Nc2nc(NC3(c4ccc(Cl)cc4)CC3)nc(OCC(F)(F)F)n2)cc1)C(=O)C(=O)Nc1cc(F)cc(F)c1] | | A |

TABLE 1-continued

| Compound | Structure | EC$_{50}$ | Activity |
|---|---|---|---|
| 3428 | 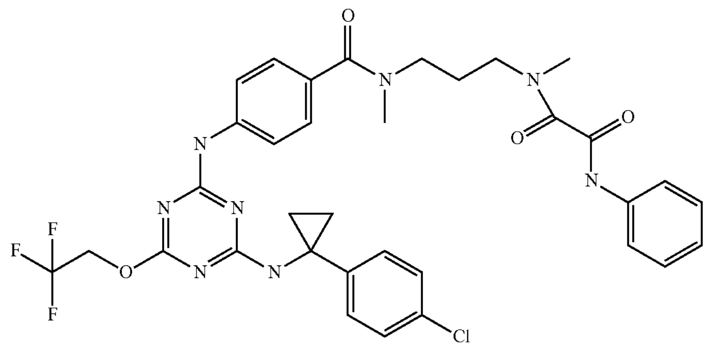 [SMILES: CN(CCCN(C)C(=O)c1ccc(Nc2nc(NC3(c4ccc(Cl)cc4)CC3)nc(OCC(F)(F)F)n2)cc1)C(=O)C(=O)Nc1ccccc1] | | A |
| 3429 | 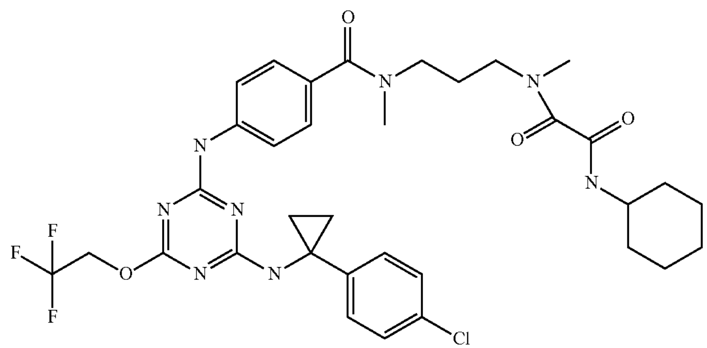 [SMILES: CN(CCCN(C)C(=O)c1ccc(Nc2nc(NC3(c4ccc(Cl)cc4)CC3)nc(OCC(F)(F)F)n2)cc1)C(=O)C(=O)NC1CCCCC1] | | A |
| 3430 | 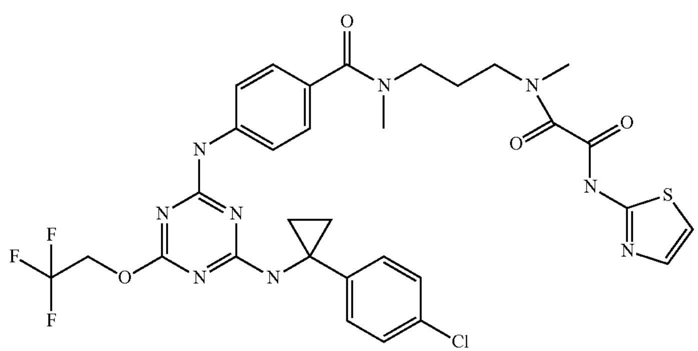 [SMILES: CN(CCCN(C)C(=O)c1ccc(Nc2nc(NC3(c4ccc(Cl)cc4)CC3)nc(OCC(F)(F)F)n2)cc1)C(=O)C(=O)Nc1nccs1] | 1.45 | A |

TABLE 1-continued

| Compound | Structure | EC$_{50}$ | Activity |
|---|---|---|---|
| 3431 | 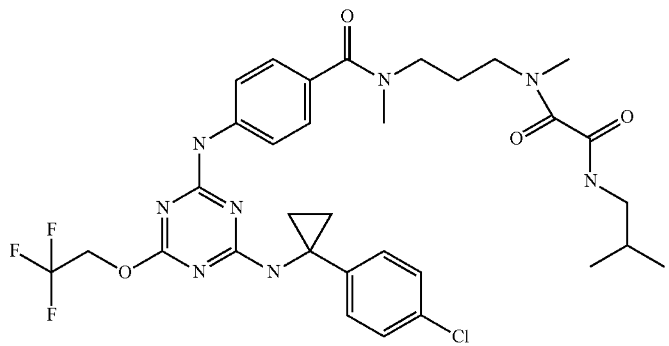 [SMILES: CC(C)CNC(=O)C(=O)N(C)CCCN(C)C(=O)c1ccc(Nc2nc(NC3(c4ccc(Cl)cc4)CC3)nc(OCC(F)(F)F)n2)cc1] | | A |
| 3432 | 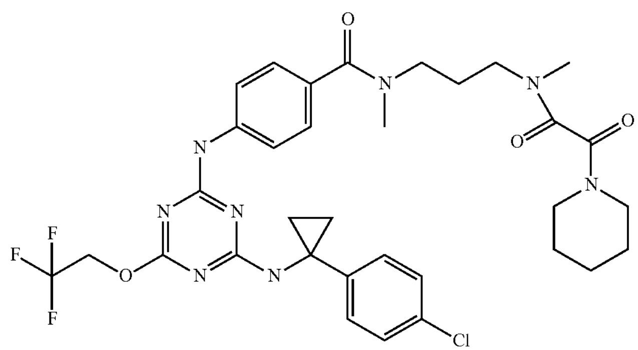 [SMILES: CN(CCCN(C)C(=O)c1ccc(Nc2nc(NC3(c4ccc(Cl)cc4)CC3)nc(OCC(F)(F)F)n2)cc1)C(=O)C(=O)N1CCCCC1] | | B |
| 3433 | 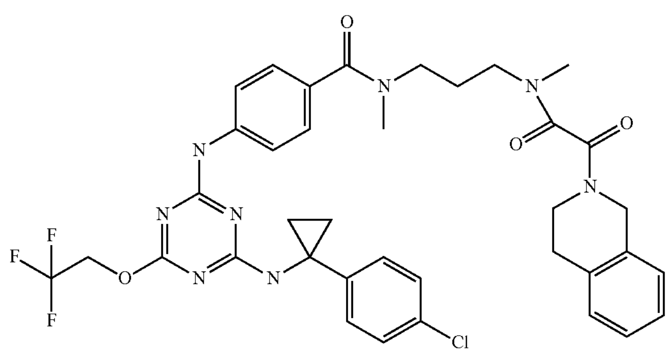 [SMILES: CN(CCCN(C)C(=O)c1ccc(Nc2nc(NC3(c4ccc(Cl)cc4)CC3)nc(OCC(F)(F)F)n2)cc1)C(=O)C(=O)N1CCc2ccccc2C1] | | B |

TABLE 1-continued

| Compound | Structure | EC$_{50}$ | Activity |
|---|---|---|---|
| 3434 | 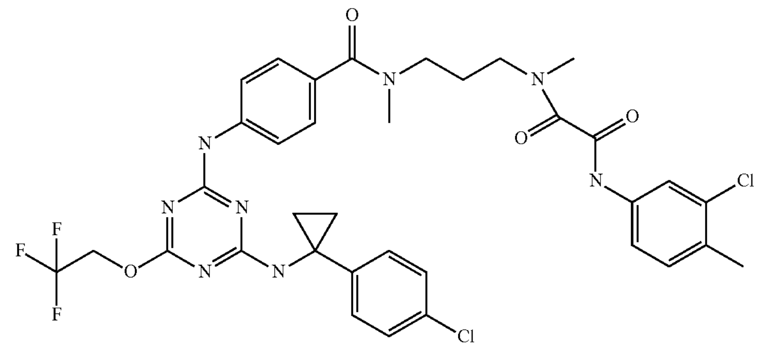 [SMILES: Cc1ccc(NC(=O)C(=O)N(C)CCCN(C)C(=O)c2ccc(Nc3nc(NC4(c5ccc(Cl)cc5)CC4)nc(OCC(F)(F)F)n3)cc2)cc1Cl] | | A |
| 3435 | 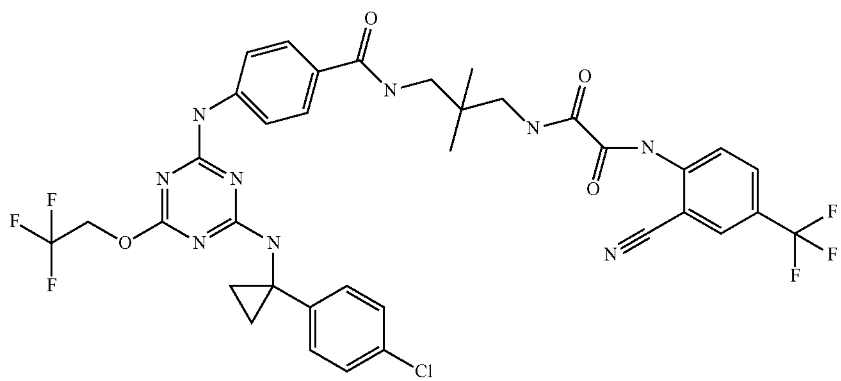 [SMILES: CC(C)(CNC(=O)C(=O)Nc1ccc(C(F)(F)F)cc1C#N)CNC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 3436 | 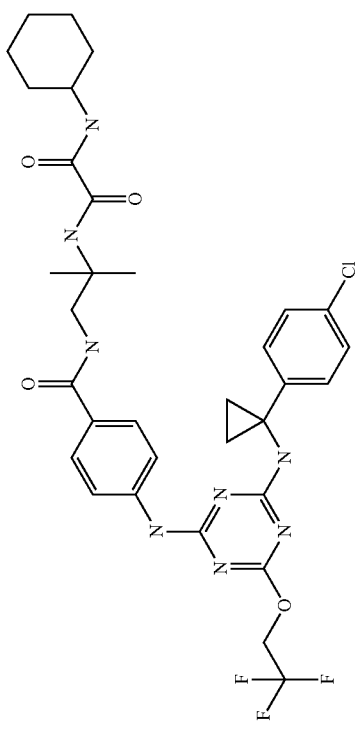 | 0.081 | A |
| 3437 | 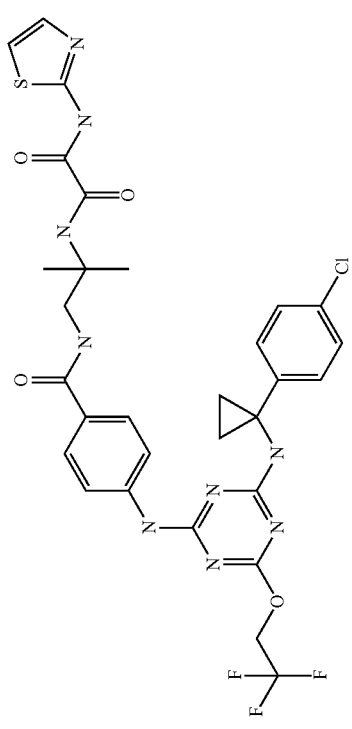 | | A |

TABLE 1-continued

| Compound | Structure | EC$_{50}$ | Activity |
|---|---|---|---|
| 3438 | 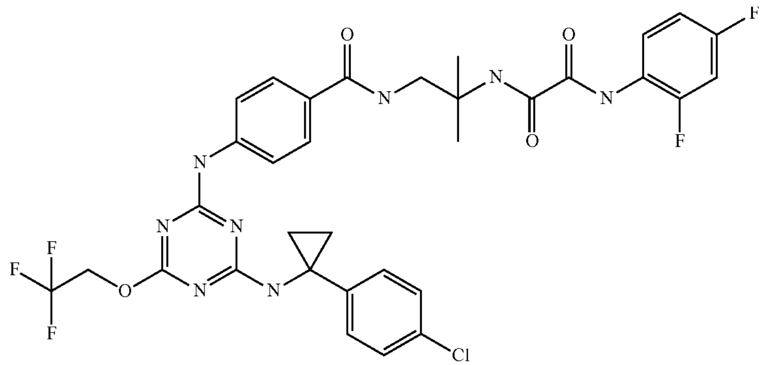 [SMILES: CC(C)(CNC(=O)c1ccc(Nc2nc(NC3(c4ccc(Cl)cc4)CC3)nc(OCC(F)(F)F)n2)cc1)NC(=O)C(=O)Nc1ccc(F)cc1F] | | A |
| 3439 | 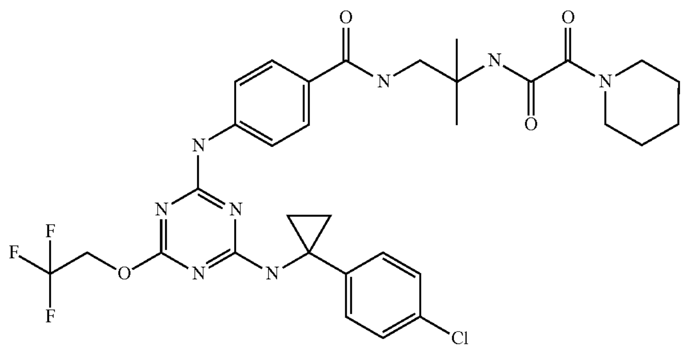 [SMILES: CC(C)(CNC(=O)c1ccc(Nc2nc(NC3(c4ccc(Cl)cc4)CC3)nc(OCC(F)(F)F)n2)cc1)NC(=O)C(=O)N1CCCCC1] | | A |
| 3440 | 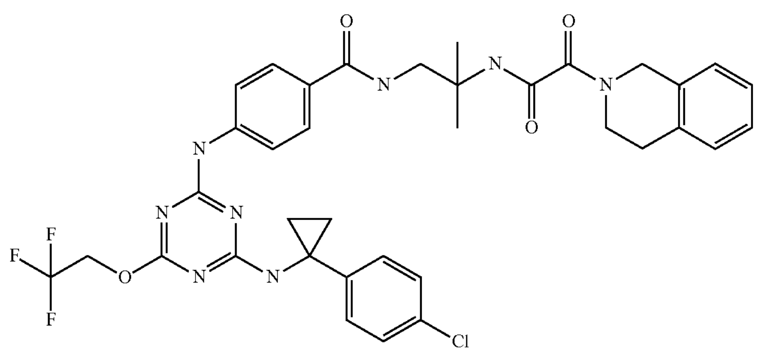 [SMILES: CC(C)(CNC(=O)c1ccc(Nc2nc(NC3(c4ccc(Cl)cc4)CC3)nc(OCC(F)(F)F)n2)cc1)NC(=O)C(=O)N1CCc2ccccc2C1] | | A |

TABLE 1-continued

| Compound | Structure | EC$_{50}$ | Activity |
|---|---|---|---|
| 3441 | 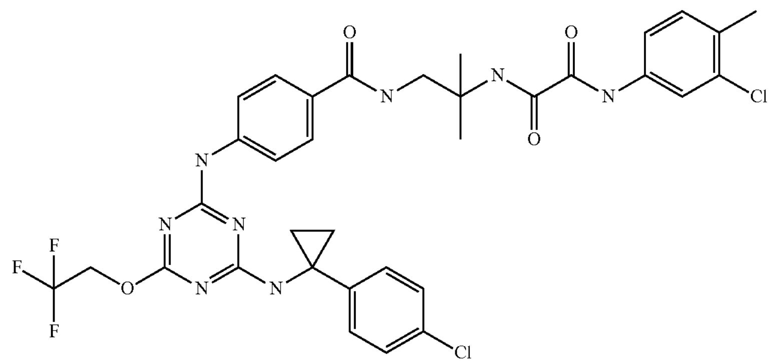 [SMILES: Cc1ccc(NC(=O)C(=O)NC(C)(C)CNC(=O)c2ccc(Nc3nc(NC4(c5ccc(Cl)cc5)CC4)nc(OCC(F)(F)F)n3)cc2)cc1Cl] | | A |
| 3442 | 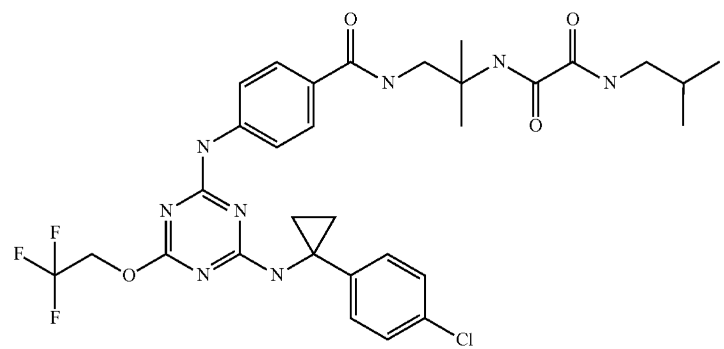 [SMILES: CC(C)CNC(=O)C(=O)NC(C)(C)CNC(=O)c1ccc(Nc2nc(NC3(c4ccc(Cl)cc4)CC3)nc(OCC(F)(F)F)n2)cc1] | | A |
| 3443 | 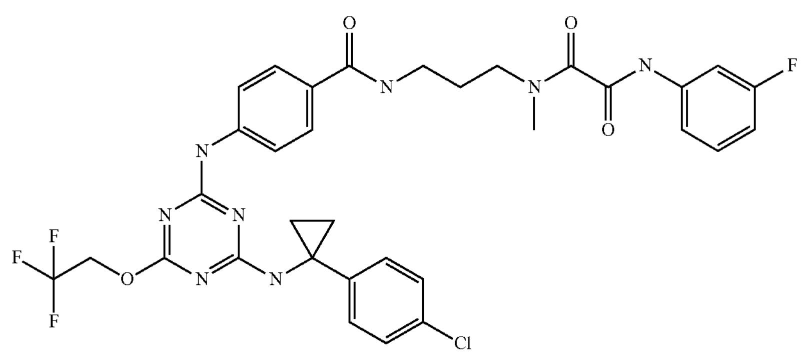 [SMILES: CN(CCCNC(=O)c1ccc(Nc2nc(NC3(c4ccc(Cl)cc4)CC3)nc(OCC(F)(F)F)n2)cc1)C(=O)C(=O)Nc1cccc(F)c1] | | A |

TABLE 1-continued

| Compound | Structure | EC$_{50}$ | Activity |
|---|---|---|---|
| 3444 | 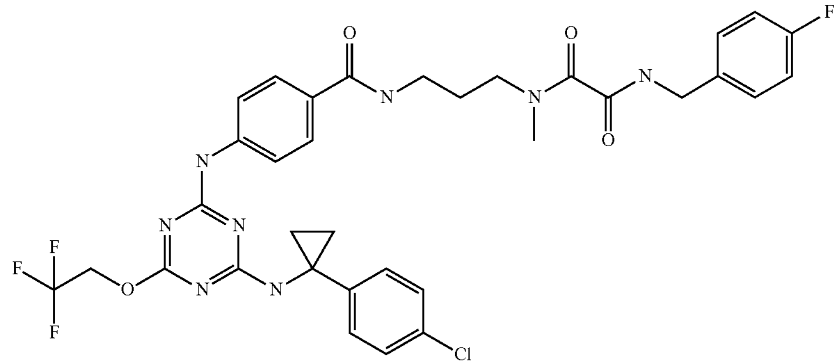 [SMILES: CN(CCCNC(=O)c1ccc(Nc2nc(NC3(c4ccc(Cl)cc4)CC3)nc(OCC(F)(F)F)n2)cc1)C(=O)C(=O)NCc1ccc(F)cc1] | | A |
| 3445 | 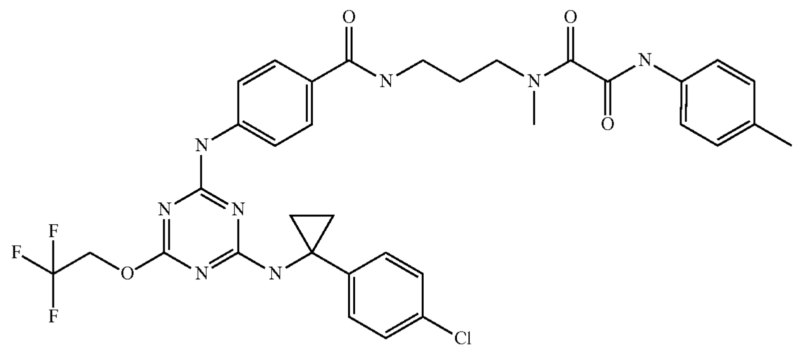 [SMILES: Cc1ccc(NC(=O)C(=O)N(C)CCCNC(=O)c2ccc(Nc3nc(NC4(c5ccc(Cl)cc5)CC4)nc(OCC(F)(F)F)n3)cc2)cc1] | 0.061 | A |

TABLE 1-continued

| Compound | Structure | EC₅₀ | Activity |
|---|---|---|---|
| 3446 | 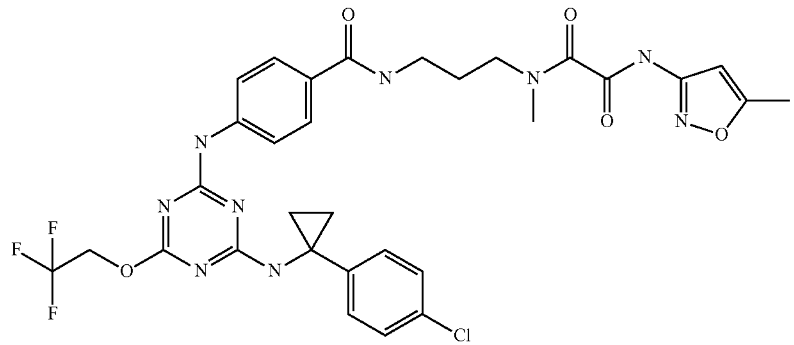 [SMILES: Cc1cc(NC(=O)C(=O)N(C)CCCNC(=O)c2ccc(Nc3nc(NC4(c5ccc(Cl)cc5)CC4)nc(OCC(F)(F)F)n3)cc2)no1] | | A |
| 3447 | 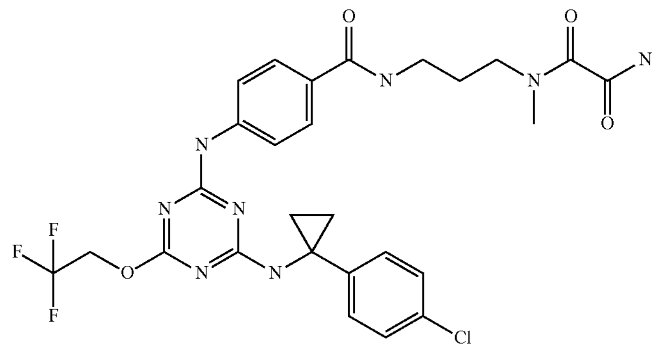 [SMILES: CN(CCCNC(=O)c1ccc(Nc2nc(NC3(c4ccc(Cl)cc4)CC3)nc(OCC(F)(F)F)n2)cc1)C(=O)C(N)=O] | | A |
| 3448 | 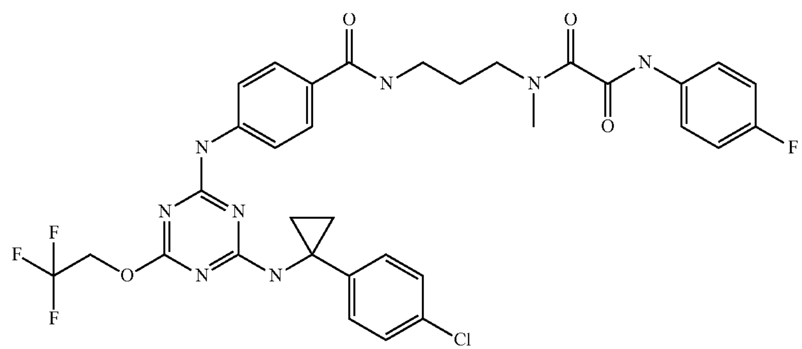 [SMILES: CN(CCCNC(=O)c1ccc(Nc2nc(NC3(c4ccc(Cl)cc4)CC3)nc(OCC(F)(F)F)n2)cc1)C(=O)C(=O)Nc1ccc(F)cc1] | 0.059 | A |

TABLE 1-continued

| Compound | Structure | EC$_{50}$ | Activity |
|---|---|---|---|
| 3449 | 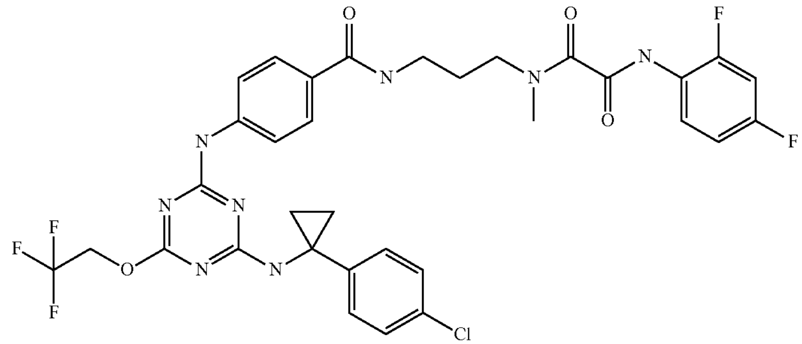 [SMILES: CN(CCCNC(=O)c1ccc(Nc2nc(NC3(c4ccc(Cl)cc4)CC3)nc(OCC(F)(F)F)n2)cc1)C(=O)C(=O)Nc1ccc(F)cc1F] | | A |
| 3450 | 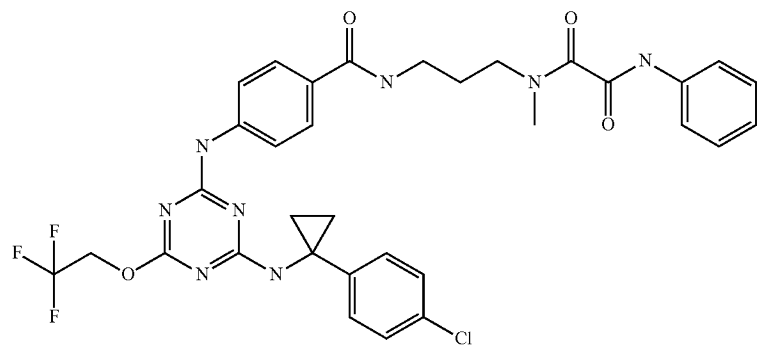 [SMILES: CN(CCCNC(=O)c1ccc(Nc2nc(NC3(c4ccc(Cl)cc4)CC3)nc(OCC(F)(F)F)n2)cc1)C(=O)C(=O)Nc1ccccc1] | | A |
| 3451 | 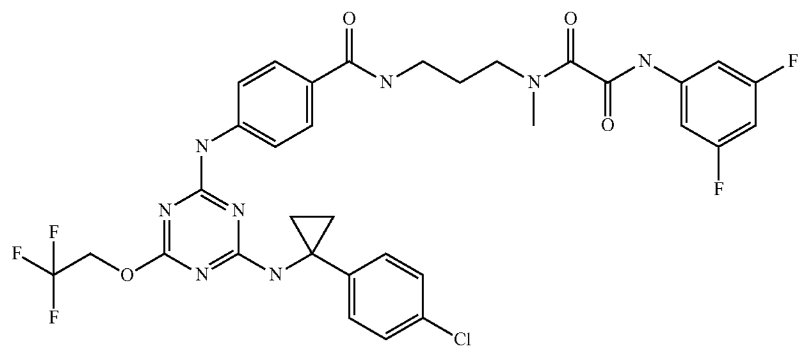 [SMILES: CN(CCCNC(=O)c1ccc(Nc2nc(NC3(c4ccc(Cl)cc4)CC3)nc(OCC(F)(F)F)n2)cc1)C(=O)C(=O)Nc1cc(F)cc(F)c1] | | A |

TABLE 1-continued
| Compound | Structure | EC$_{50}$ | Activity |
|---|---|---|---|
| 3452 | 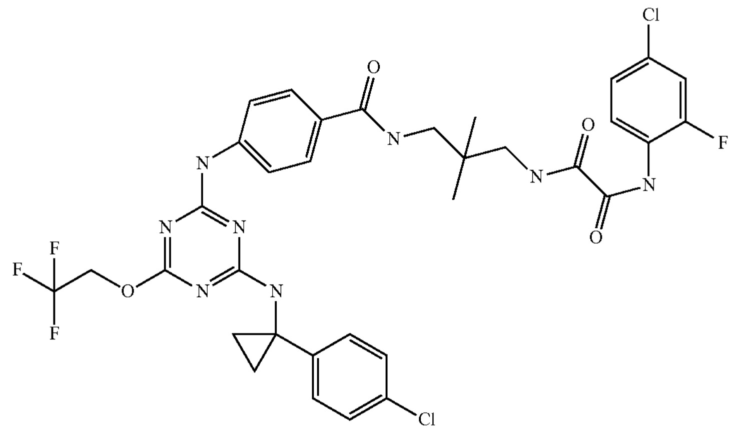 [SMILES: CC(C)(CNC(=O)C(=O)Nc1ccc(Cl)cc1F)CNC(=O)c1ccc(Nc2nc(NC3(c4ccc(Cl)cc4)CC3)nc(OCC(F)(F)F)n2)cc1] | | A |
| 3453 | 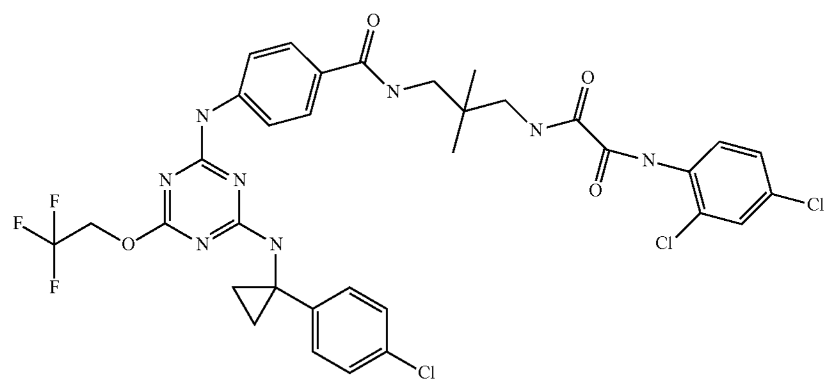 [SMILES: CC(C)(CNC(=O)C(=O)Nc1ccc(Cl)cc1Cl)CNC(=O)c1ccc(Nc2nc(NC3(c4ccc(Cl)cc4)CC3)nc(OCC(F)(F)F)n2)cc1] | | A |
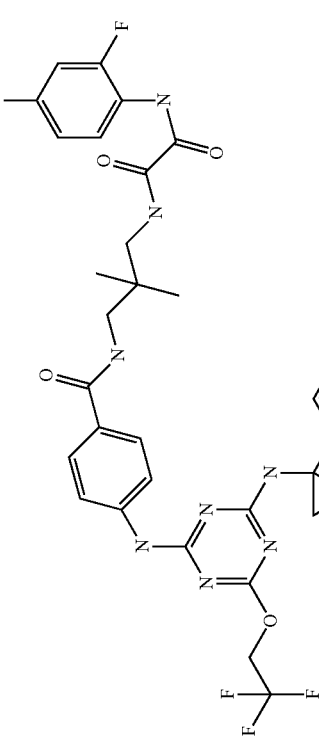

TABLE 1-continued

| Compound | Structure | EC$_{50}$ | Activity |
|---|---|---|---|
| 3454 | 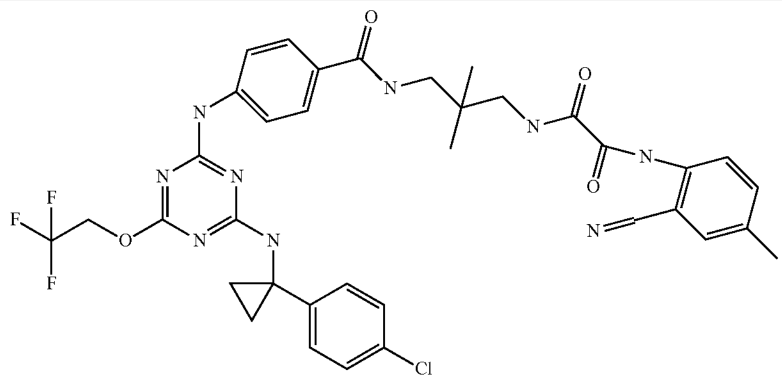 [SMILES: Cc1ccc(NC(=O)C(=O)NCC(C)(C)CNC(=O)c2ccc(Nc3nc(NC4(c5ccc(Cl)cc5)CC4)nc(OCC(F)(F)F)n3)cc2)c(C=N)c1] | | A |
| 3455 | 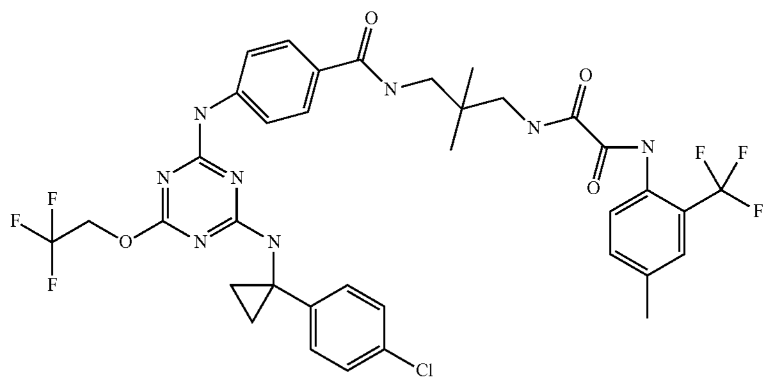 [SMILES: Cc1ccc(NC(=O)C(=O)NCC(C)(C)CNC(=O)c2ccc(Nc3nc(NC4(c5ccc(Cl)cc5)CC4)nc(OCC(F)(F)F)n3)cc2)c(C(F)(F)F)c1] | | A |

TABLE 1-continued
| Compound | Structure | EC$_{50}$ | Activity |
|---|---|---|---|
| 3456 | 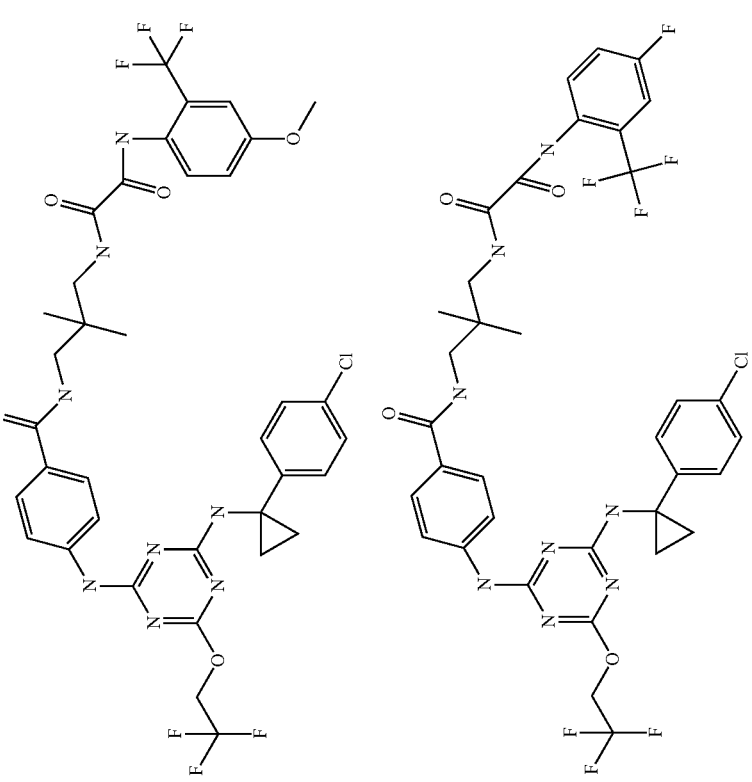 | | A |
| 3457 | 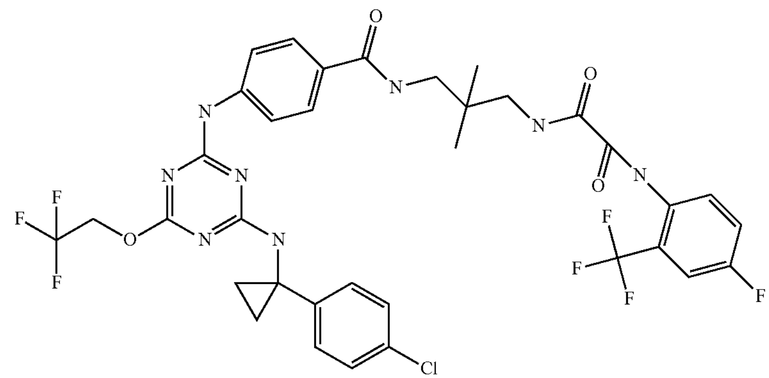 [SMILES: CC(C)(CNC(=O)C(=O)Nc1ccc(F)cc1C(F)(F)F)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3458 | 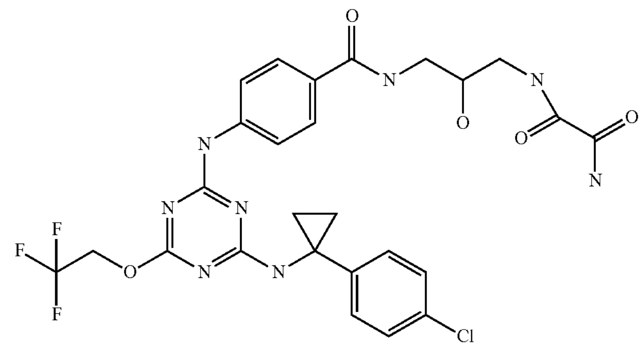 | | A |
| 3459 | 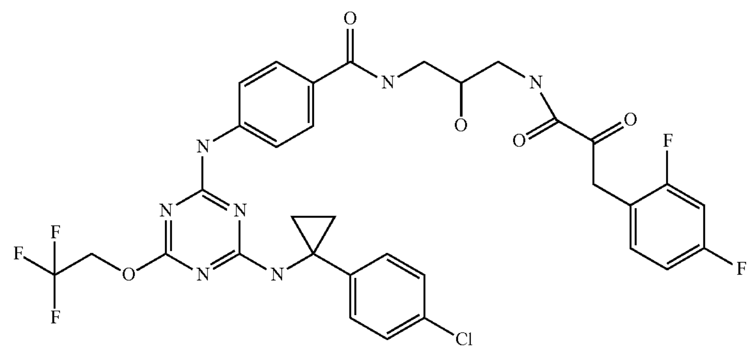 | | A |
| 3460 | 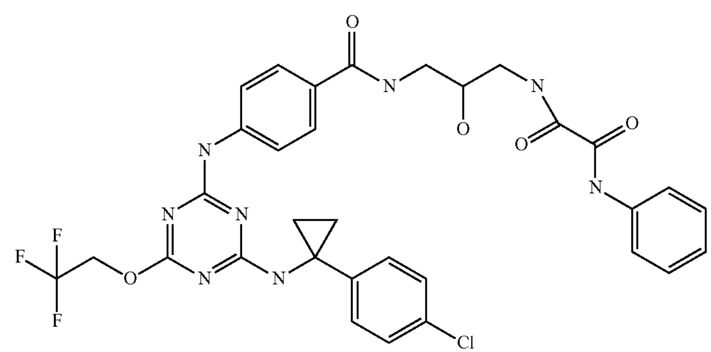 [SMILES: O=C(NCC(O)CNC(=O)c1ccc(Nc2nc(NC3(c4ccc(Cl)cc4)CC3)nc(OCC(F)(F)F)n2)cc1)C(=O)Nc1ccccc1] | 0.016 | A |

TABLE 1-continued

| Compound | Structure | EC$_{50}$ | Activity |
|---|---|---|---|
| 3461 | 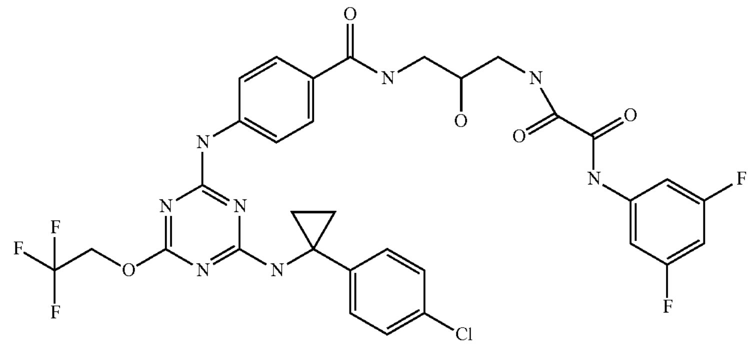 | 0.027 | A |
| 3462 | 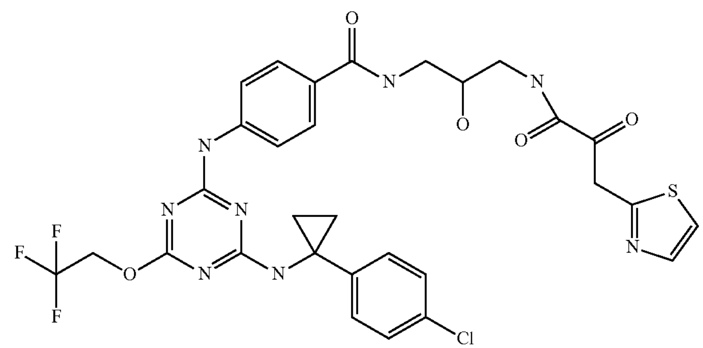 | | A |
| 3463 | 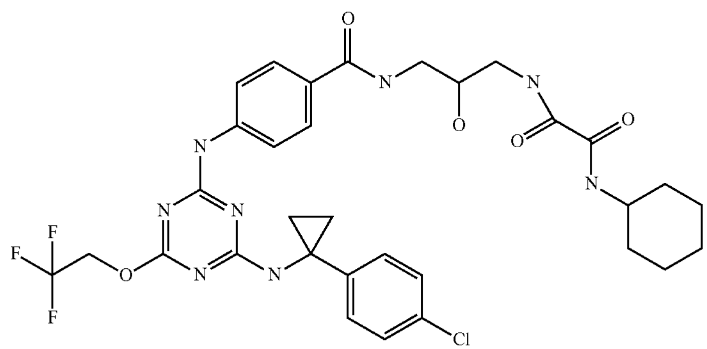 [SMILES: O=C(NCC(O)CNC(=O)c1ccc(Nc2nc(NC3(c4ccc(Cl)cc4)CC3)nc(OCC(F)(F)F)n2)cc1)C(=O)NC1CCCCC1] | | A |

TABLE 1-continued

| Compound | Structure | EC$_{50}$ | Activity |
|---|---|---|---|
| 3464 | 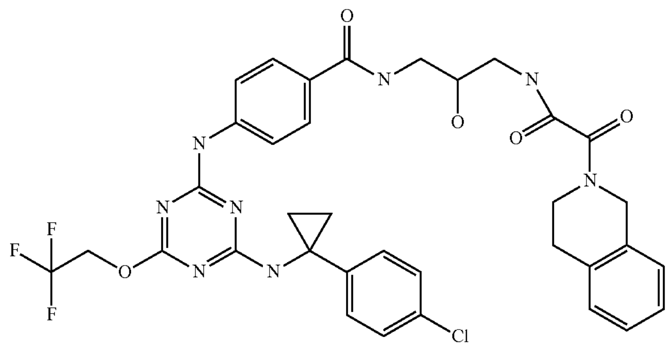 [SMILES: O=C(NCC(O)CNC(=O)c1ccc(Nc2nc(NC3(c4ccc(Cl)cc4)CC3)nc(OCC(F)(F)F)n2)cc1)C(=O)N1CCc2ccccc2C1] | | A |
| 3465 | 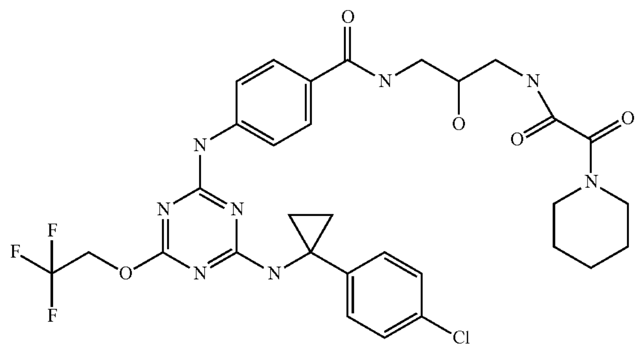 [SMILES: O=C(NCC(O)CNC(=O)c1ccc(Nc2nc(NC3(c4ccc(Cl)cc4)CC3)nc(OCC(F)(F)F)n2)cc1)C(=O)N1CCCCC1] | | A |
| 3466 | 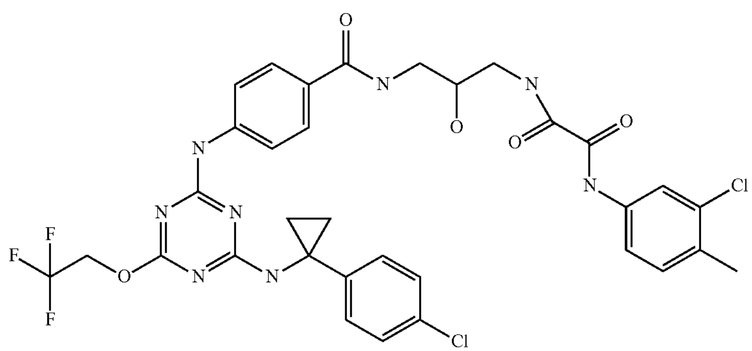 | | A |

TABLE 1-continued

| Compound | Structure | EC$_{50}$ | Activity |
|---|---|---|---|
| 3467 | 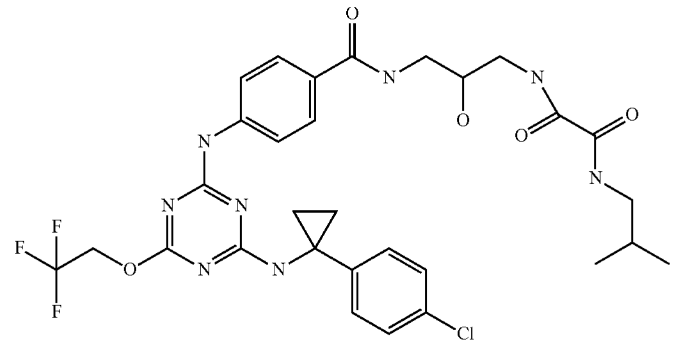 [SMILES: CC(C)CNC(=O)C(=O)NCC(O)CNC(=O)c1ccc(Nc2nc(NC3(c4ccc(Cl)cc4)CC3)nc(OCC(F)(F)F)n2)cc1] | | A |
| 3468 | 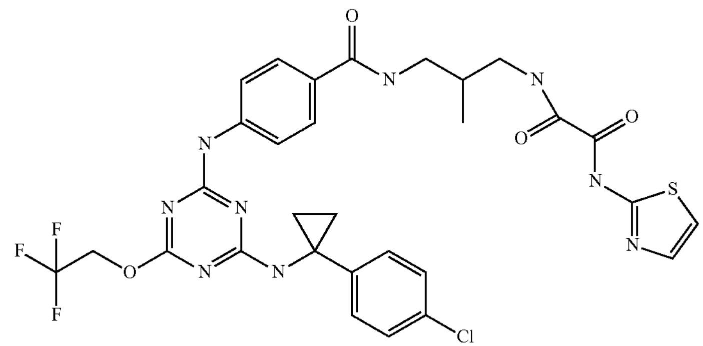 [SMILES: CC(CNC(=O)C(=O)Nc1nccs1)CNC(=O)c1ccc(Nc2nc(NC3(c4ccc(Cl)cc4)CC3)nc(OCC(F)(F)F)n2)cc1] | | A |
| 3469 | 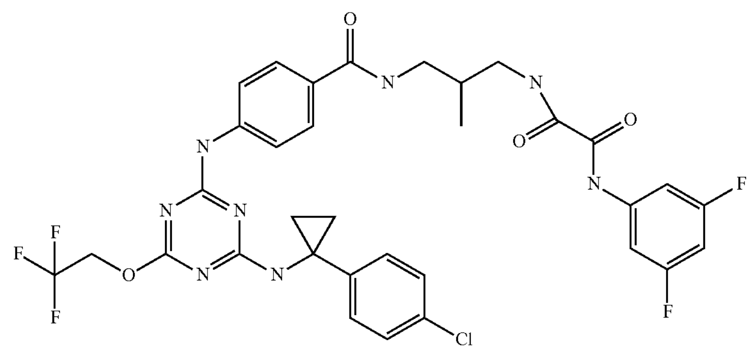 [SMILES: CC(CNC(=O)C(=O)Nc1cc(F)cc(F)c1)CNC(=O)c1ccc(Nc2nc(NC3(c4ccc(Cl)cc4)CC3)nc(OCC(F)(F)F)n2)cc1] | 0.035 | A |

TABLE 1-continued

| Compound | Structure | EC$_{50}$ | Activity |
|---|---|---|---|
| 3470 | 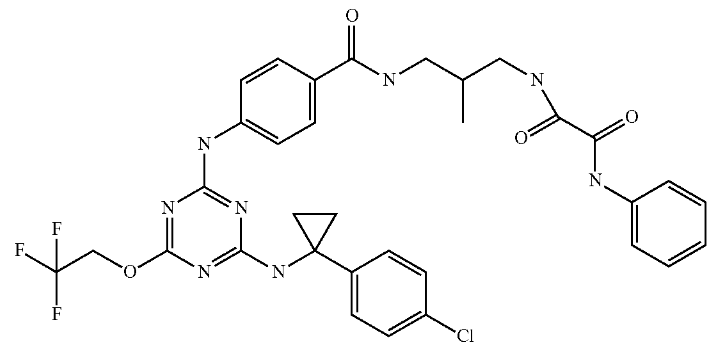 [SMILES: CC(CNC(=O)C(=O)Nc1ccccc1)CNC(=O)c1ccc(Nc2nc(NC3(c4ccc(Cl)cc4)CC3)nc(OCC(F)(F)F)n2)cc1] | | A |
| 3471 | 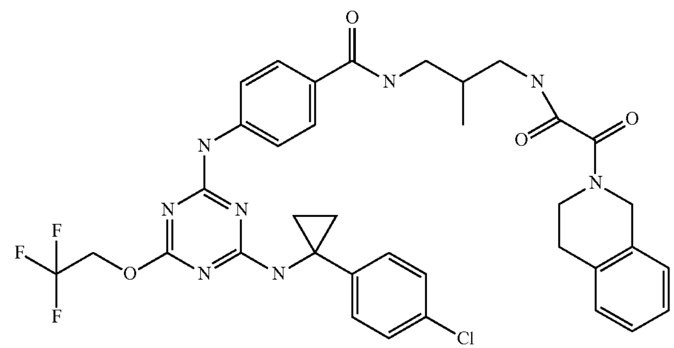 | | A |
| 3472 | 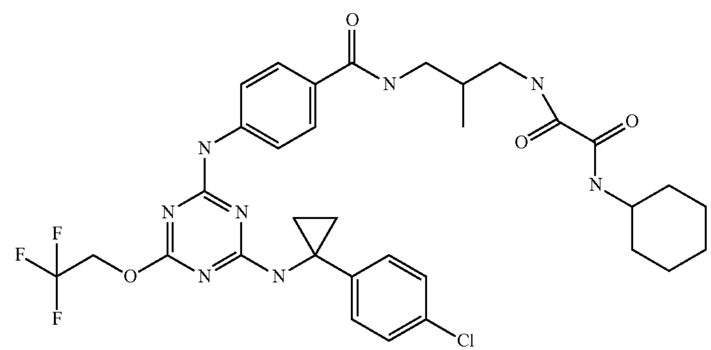 [SMILES: CC(CNC(=O)C(=O)NC1CCCCC1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3473 | 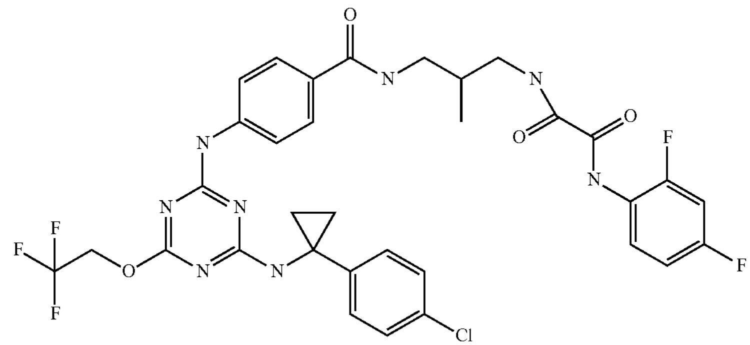 [SMILES: CC(CNC(=O)C(=O)Nc1ccc(F)cc1F)CNC(=O)c1ccc(Nc2nc(NC3(c4ccc(Cl)cc4)CC3)nc(OCC(F)(F)F)n2)cc1] | | A |
| 3474 | 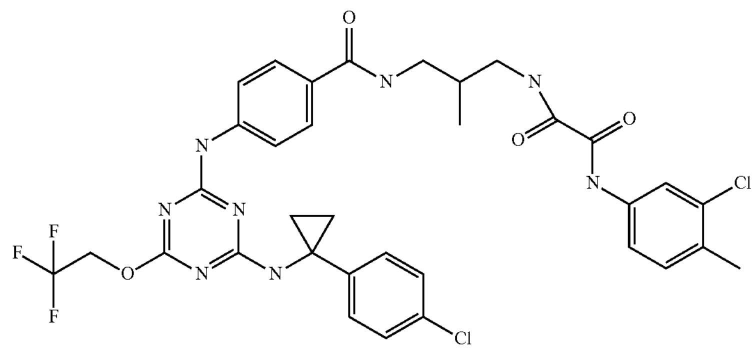 [SMILES: Cc1ccc(NC(=O)C(=O)NCC(C)CNC(=O)c2ccc(Nc3nc(NC4(c5ccc(Cl)cc5)CC4)nc(OCC(F)(F)F)n3)cc2)cc1Cl] | | A |
| 3475 | 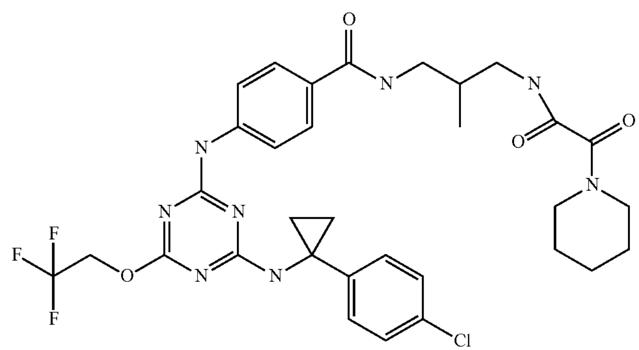 | | A |

TABLE 1-continued

| Compound | Structure | EC$_{50}$ | Activity |
|---|---|---|---|
| 3476 | 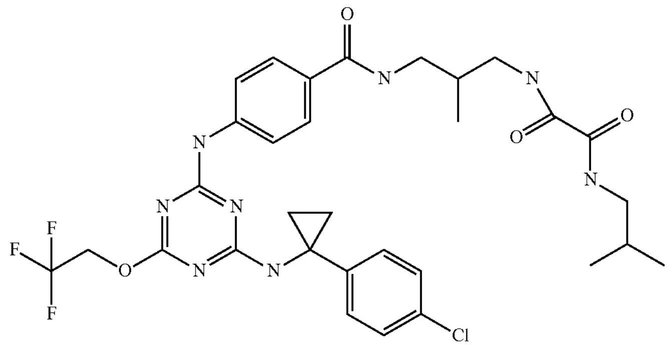 | | A |
| 3477 | 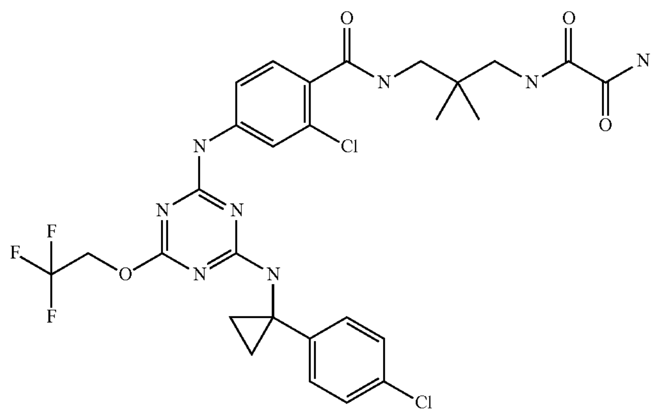 | 0.12 | A |

TABLE 1-continued
| Compound | Structure | EC$_{50}$ | Activity |
|---|---|---|---|
| 3478 | 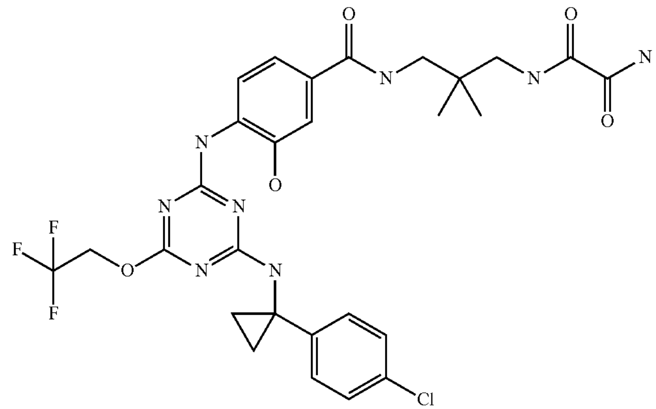 | | A |
| 3479 | 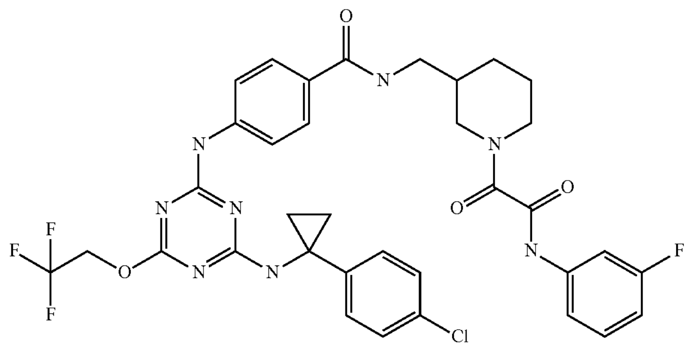 [SMILES: O=C(Nc1cccc(F)c1)C(=O)N1CCCC(CNC(=O)c2ccc(Nc3nc(NC4(c5ccc(Cl)cc5)CC4)nc(OCC(F)(F)F)n3)cc2)C1] | | A |
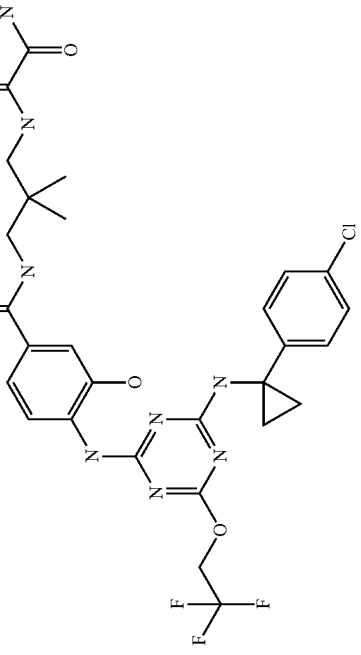

TABLE 1-continued

| Compound | Structure | EC₅₀ | Activity |
|---|---|---|---|
| 3480 | 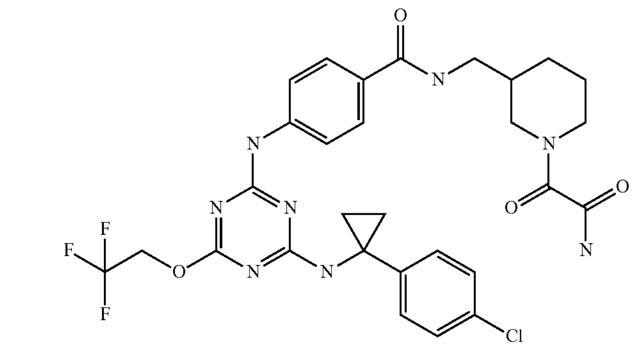 [SMILES: NC(=O)C(=O)N1CCCC(CNC(=O)c2ccc(Nc3nc(NC4(c5ccc(Cl)cc5)CC4)nc(OCC(F)(F)F)n3)cc2)C1] | | A |
| 3481 | 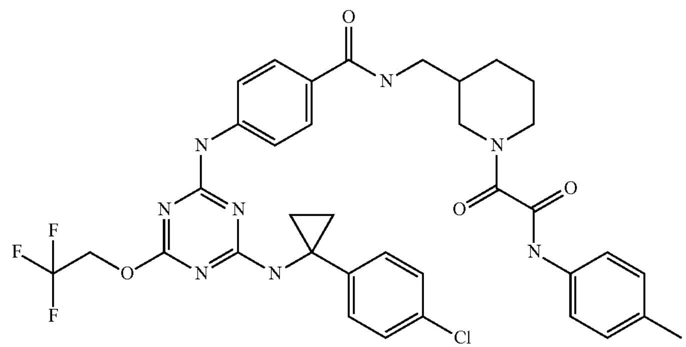 [SMILES: Cc1ccc(NC(=O)C(=O)N2CCCC(CNC(=O)c3ccc(Nc4nc(NC5(c6ccc(Cl)cc6)CC5)nc(OCC(F)(F)F)n4)cc3)C2)cc1] | 0.065 | A |
| 3482 | 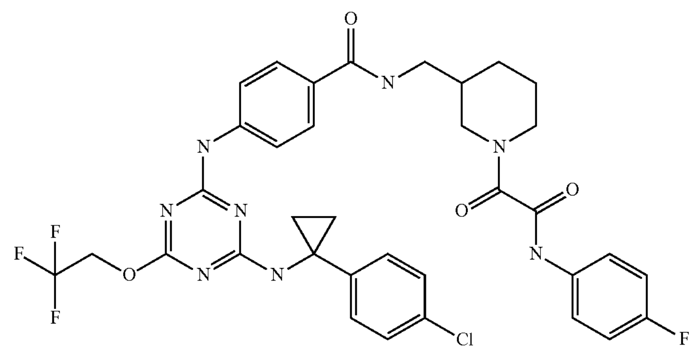 [SMILES: O=C(Nc1ccc(F)cc1)C(=O)N1CCCC(CNC(=O)c2ccc(Nc3nc(NC4(c5ccc(Cl)cc5)CC4)nc(OCC(F)(F)F)n3)cc2)C1] | | A |

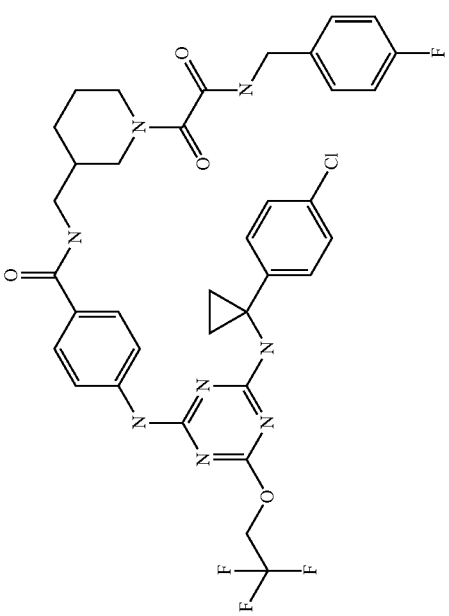

TABLE 1-continued

| Compound | Structure | EC$_{50}$ | Activity |
|---|---|---|---|
| 3485 | 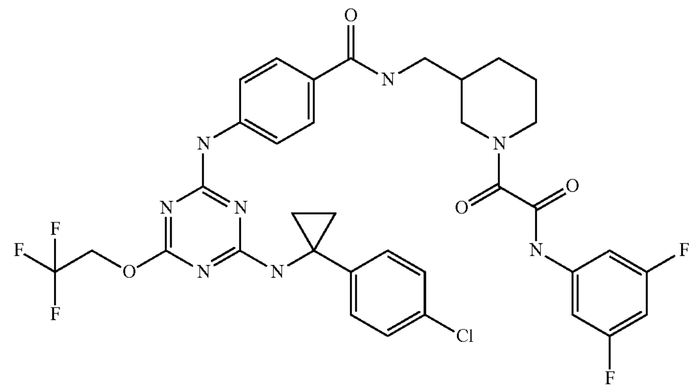 [SMILES: O=C(Nc1cc(F)cc(F)c1)C(=O)N1CCCC(CNC(=O)c2ccc(Nc3nc(NC4(c5ccc(Cl)cc5)CC4)nc(OCC(F)(F)F)n3)cc2)C1] | | A |
| 3486 | 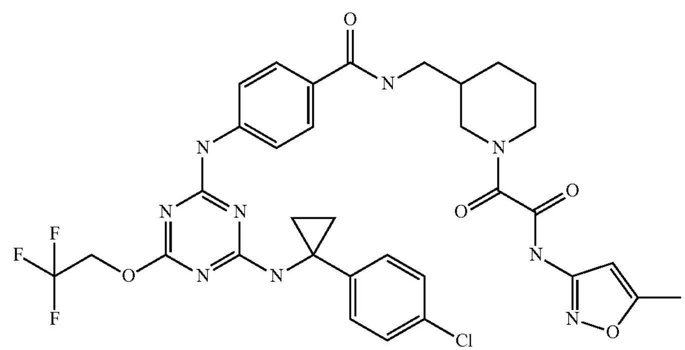 [SMILES: Cc1cc(NC(=O)C(=O)N2CCCC(CNC(=O)c3ccc(Nc4nc(NC5(c6ccc(Cl)cc6)CC5)nc(OCC(F)(F)F)n4)cc3)C2)no1] | 0.32 | A |

TABLE 1-continued

| Compound | Structure | EC$_{50}$ | Activity |
|---|---|---|---|
| 3487 | (structure) | | A |
| 3488 | (structure) | | A |
| 3489 | (structure) | | A |

TABLE 1-continued
| Compound | Structure | EC$_{50}$ | Activity |
|---|---|---|---|
| 3490 | 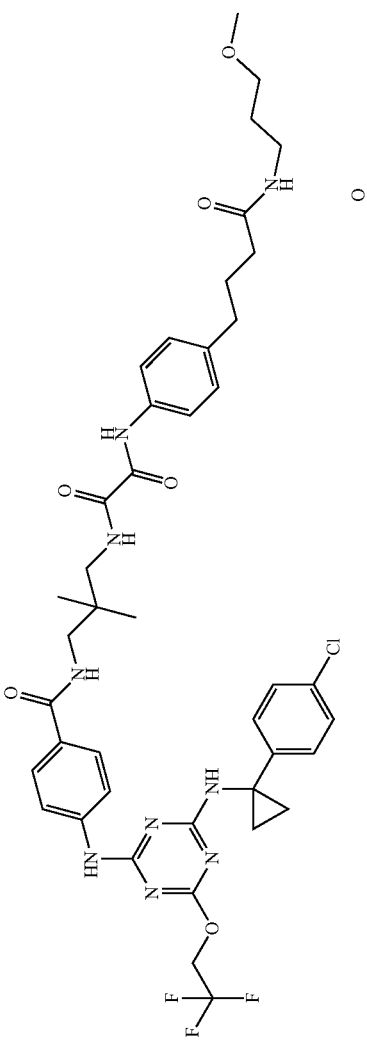 | 0.54 | A |
| 3491 | 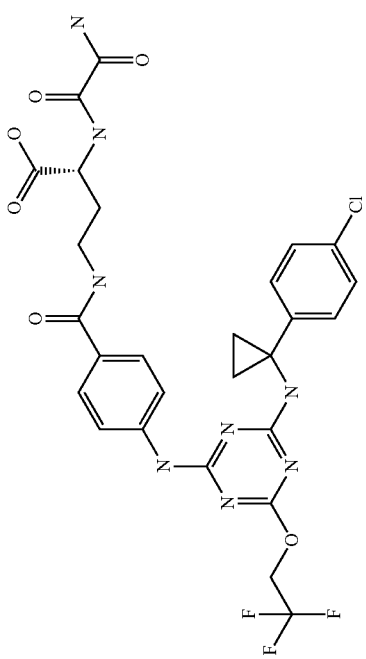 | | B |

TABLE 1-continued

| Compound | Structure | EC$_{50}$ | Activity |
|---|---|---|---|
| 3492 | 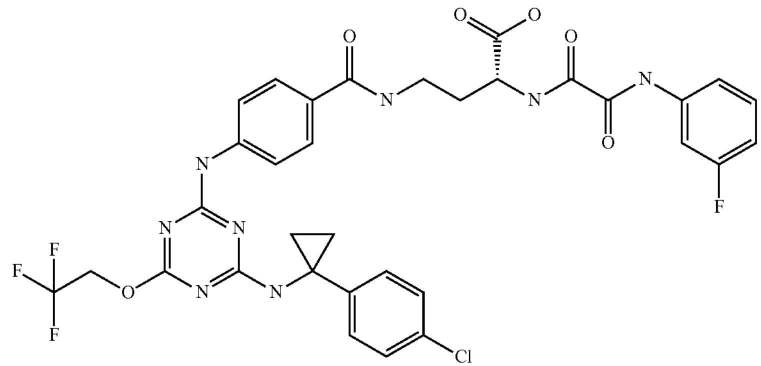 [SMILES: O=C(Nc1cccc(F)c1)C(=O)N[C@H](CCNC(=O)c1ccc(Nc2nc(NC3(c4ccc(Cl)cc4)CC3)nc(OCC(F)(F)F)n2)cc1)C(=O)O] | 0.33 | A |
| 3493 | 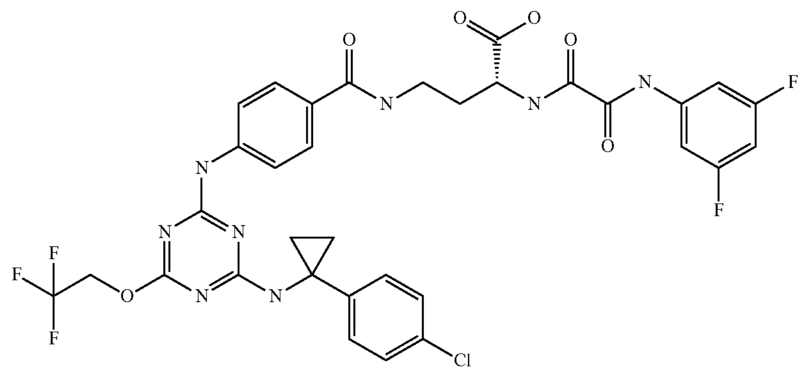 [SMILES: O=C(Nc1cc(F)cc(F)c1)C(=O)N[C@H](CCNC(=O)c1ccc(Nc2nc(NC3(c4ccc(Cl)cc4)CC3)nc(OCC(F)(F)F)n2)cc1)C(=O)O] | | A |

TABLE 1-continued

| Compound | Structure | EC$_{50}$ | Activity |
|---|---|---|---|
| 3494 | 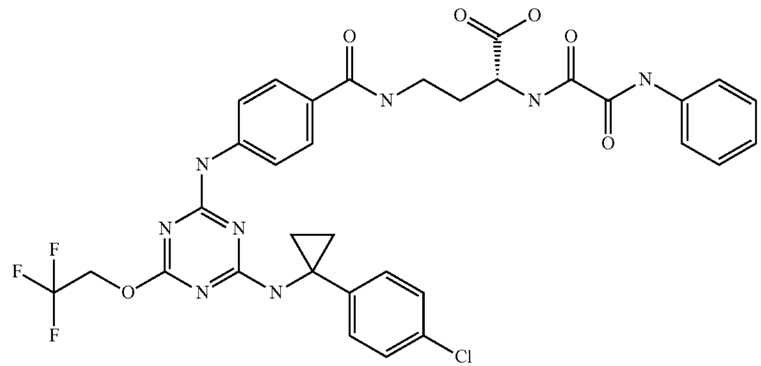 [SMILES: O=C(Nc1ccccc1)C(=O)N[C@H](CCNC(=O)c1ccc(Nc2nc(NC3(c4ccc(Cl)cc4)CC3)nc(OCC(F)(F)F)n2)cc1)C(=O)O] | | A |
| 3495 | 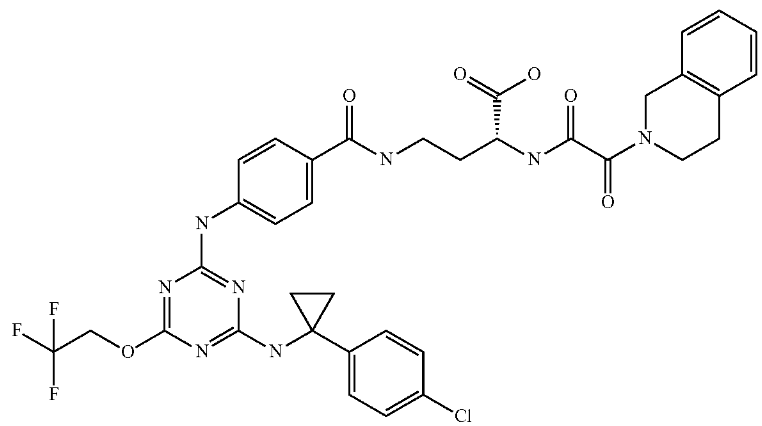 [SMILES: O=C(N[C@H](CCNC(=O)c1ccc(Nc2nc(NC3(c4ccc(Cl)cc4)CC3)nc(OCC(F)(F)F)n2)cc1)C(=O)O)C(=O)N1CCc2ccccc2C1] | | A |

TABLE 1-continued

| Compound | Structure | EC$_{50}$ | Activity |
|---|---|---|---|
| 3496 | 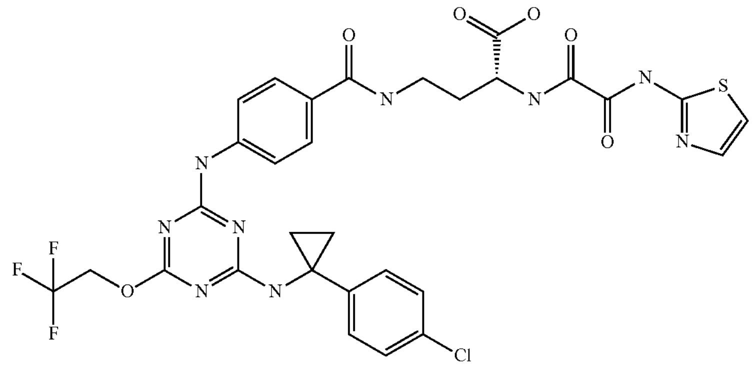 [SMILES: O=C(Nc1nccs1)C(=O)N[C@H](CCNC(=O)c1ccc(Nc2nc(NC3(c4ccc(Cl)cc4)CC3)nc(OCC(F)(F)F)n2)cc1)C(=O)O] | | B |
| 3497 | 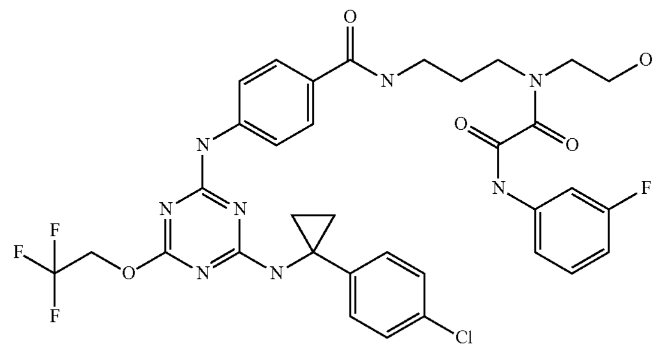 [SMILES: O=C(Nc1cccc(F)c1)C(=O)N(CCO)CCCNC(=O)c1ccc(Nc2nc(NC3(c4ccc(Cl)cc4)CC3)nc(OCC(F)(F)F)n2)cc1] | | A |
| 3498 | 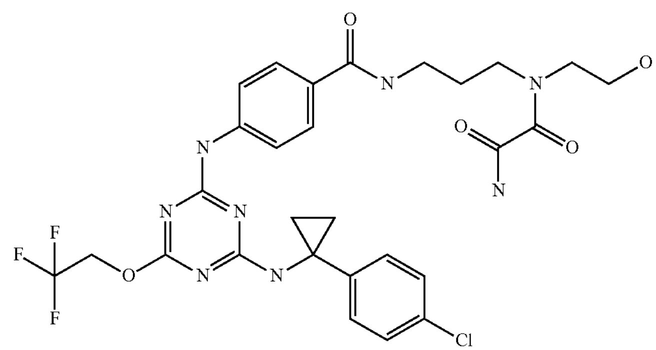 [SMILES: NC(=O)C(=O)N(CCO)CCCNC(=O)c1ccc(Nc2nc(NC3(c4ccc(Cl)cc4)CC3)nc(OCC(F)(F)F)n2)cc1] | | A |

| Compound | Structure | EC$_{50}$ | Activity |
|---|---|---|---|
| 3499 | 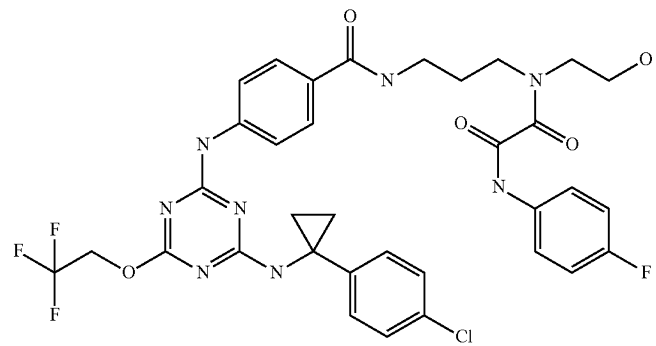 [SMILES: O=C(Nc1ccc(F)cc1)C(=O)N(CCO)CCCNC(=O)c1ccc(Nc2nc(NC3(c4ccc(Cl)cc4)CC3)nc(OCC(F)(F)F)n2)cc1] | 0.46 | A |
| 3500 | 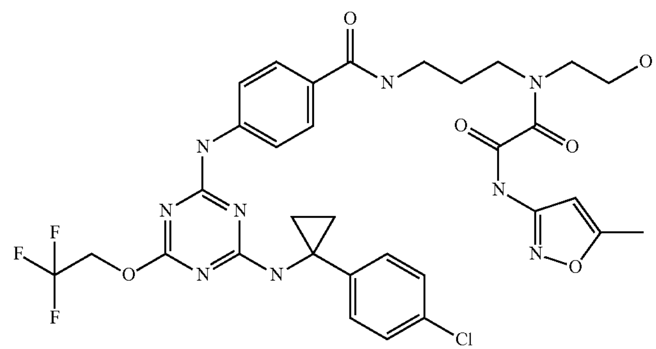 [SMILES: Cc1cc(NC(=O)C(=O)N(CCO)CCCNC(=O)c2ccc(Nc3nc(NC4(c5ccc(Cl)cc5)CC4)nc(OCC(F)(F)F)n3)cc2)no1] | | A |
| 3501 | 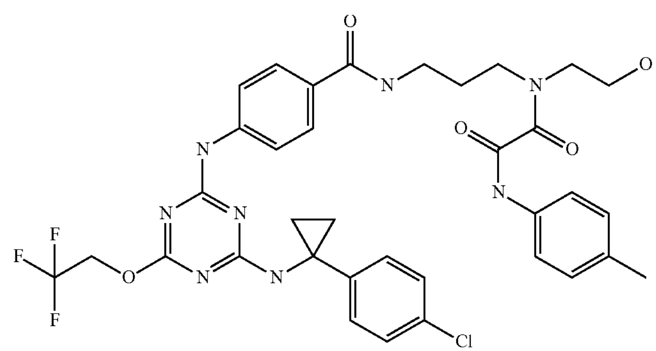 | | A |

TABLE 1-continued

| Compound | Structure | EC$_{50}$ | Activity |
|---|---|---|---|
| 3502 | 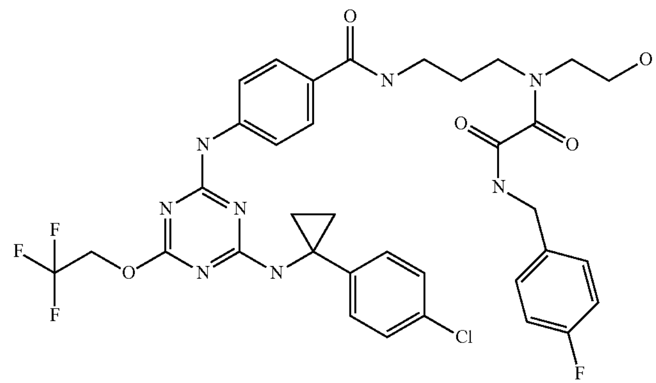 [SMILES: O=C(NCc1ccc(F)cc1)C(=O)N(CCO)CCCNC(=O)c1ccc(Nc2nc(NC3(c4ccc(Cl)cc4)CC3)nc(OCC(F)(F)F)n2)cc1] | | A |
| 3503 | 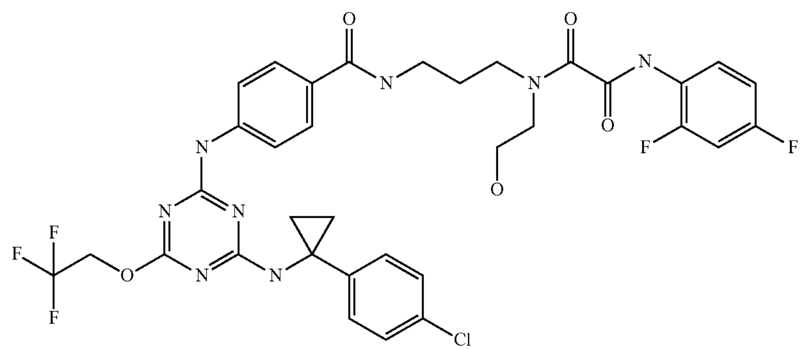 [SMILES: O=C(Nc1ccc(F)cc1F)C(=O)N(CCO)CCCNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3504 | 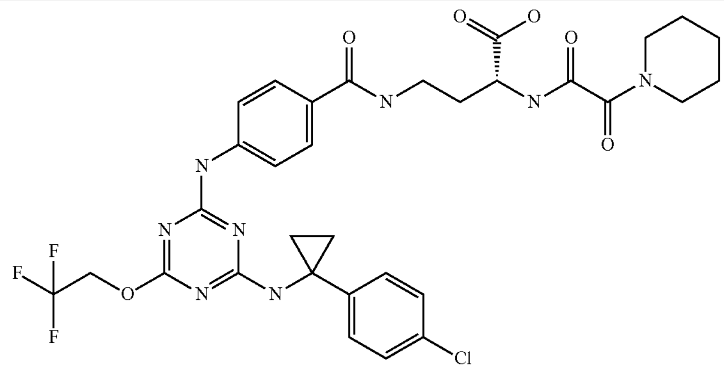 [SMILES: O=C(N[C@H](CCNC(=O)c1ccc(Nc2nc(NC3(c4ccc(Cl)cc4)CC3)nc(OCC(F)(F)F)n2)cc1)C(=O)O)C(=O)N1CCCCC1] | | A |
| 3505 | 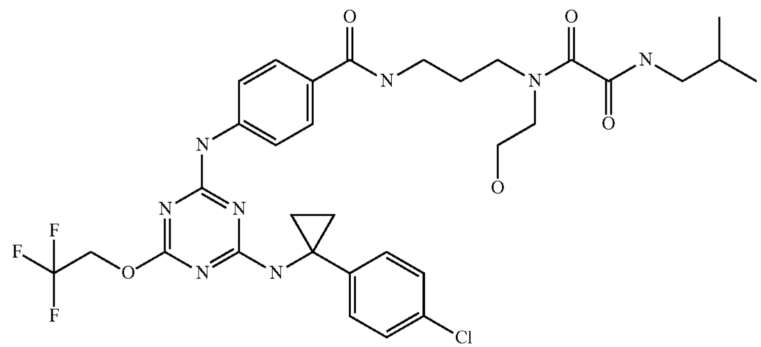 [SMILES: CC(C)CNC(=O)C(=O)N(CCO)CCCNC(=O)c1ccc(Nc2nc(NC3(c4ccc(Cl)cc4)CC3)nc(OCC(F)(F)F)n2)cc1] | | A |
| 3506 | 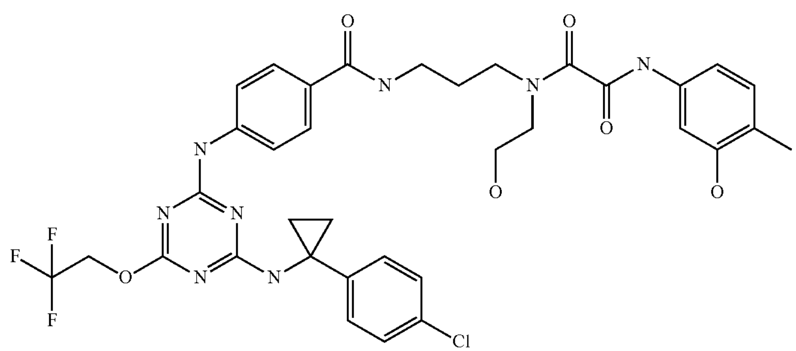 [SMILES: Cc1ccc(NC(=O)C(=O)N(CCO)CCCNC(=O)c2ccc(Nc3nc(NC4(c5ccc(Cl)cc5)CC4)nc(OCC(F)(F)F)n3)cc2)cc1O] | 0.51 | A |

TABLE 1-continued

| Compound | Structure | EC$_{50}$ | Activity |
|---|---|---|---|
| 3507 | 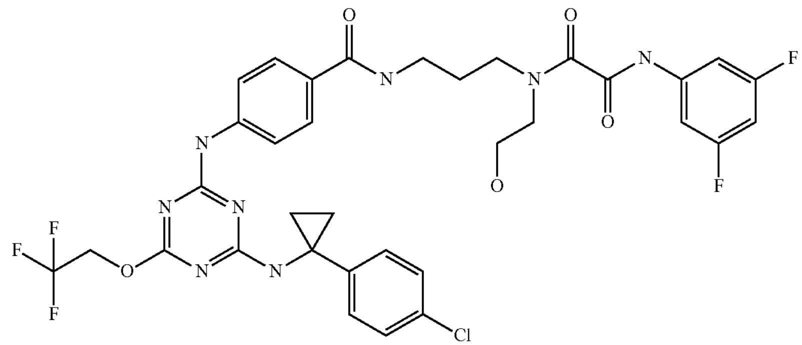 [SMILES: O=C(Nc1cc(F)cc(F)c1)C(=O)N(CCO)CCCNC(=O)c1ccc(Nc2nc(NC3(c4ccc(Cl)cc4)CC3)nc(OCC(F)(F)F)n2)cc1] | | A |
| 3508 | 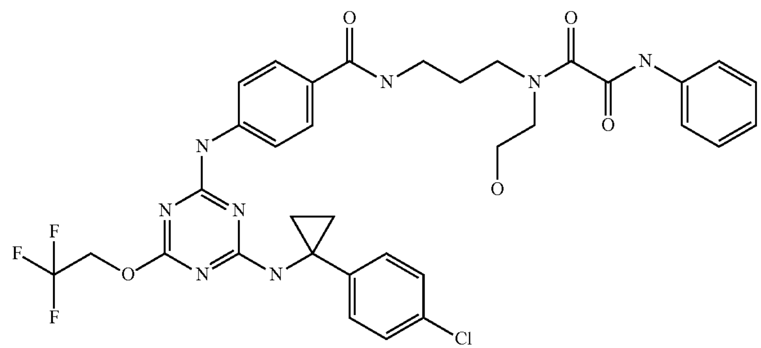 [SMILES: O=C(Nc1ccccc1)C(=O)N(CCO)CCCNC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 3509 | 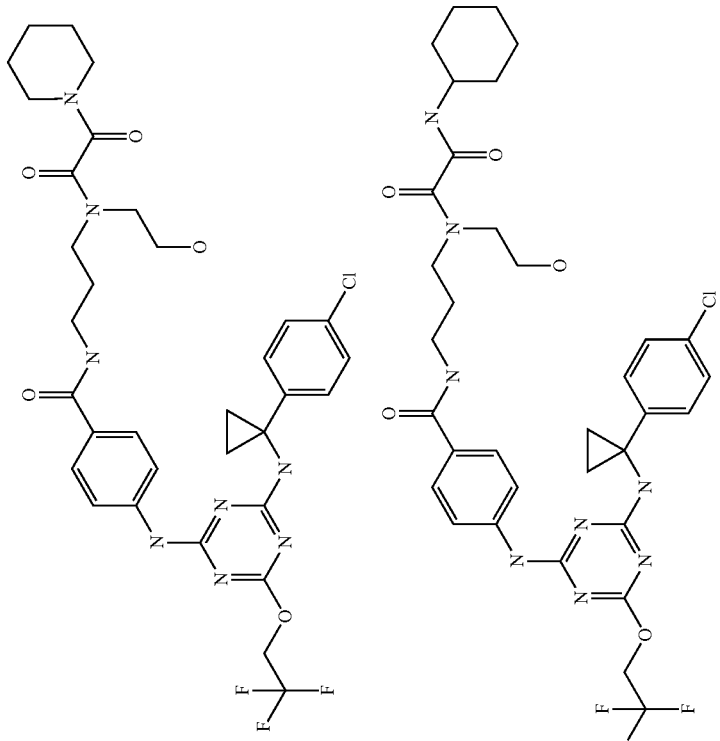 | | A |
| 3510 | 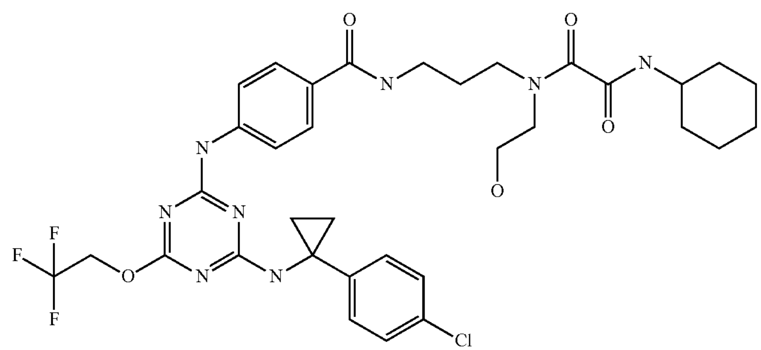 [SMILES: O=C(NC1CCCCC1)C(=O)N(CCO)CCCNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3511 | 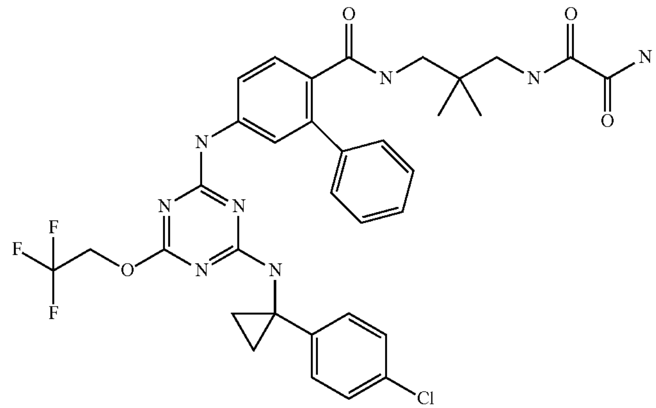 [SMILES: CC(C)(CNC(=O)C(N)=O)CNC(=O)c1ccc(Nc2nc(NC3(c4ccc(Cl)cc4)CC3)nc(OCC(F)(F)F)n2)cc1-c1ccccc1] | | A |
| 3512 | 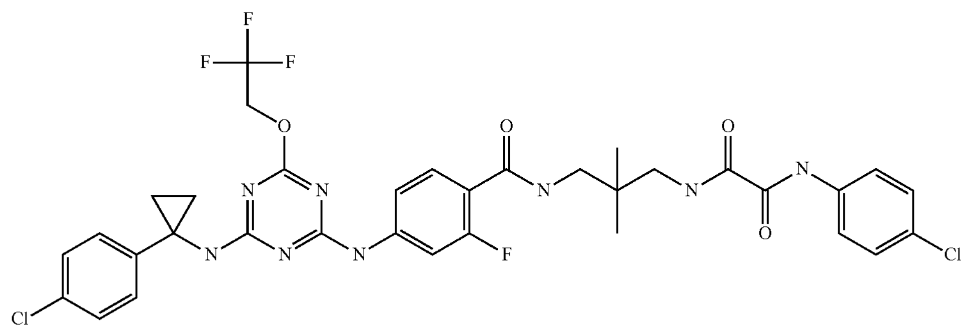 [SMILES: CC(C)(CNC(=O)C(=O)Nc1ccc(Cl)cc1)CNC(=O)c1ccc(Nc2nc(NC3(c4ccc(Cl)cc4)CC3)nc(OCC(F)(F)F)n2)cc1F] | | A |
| 3513 | 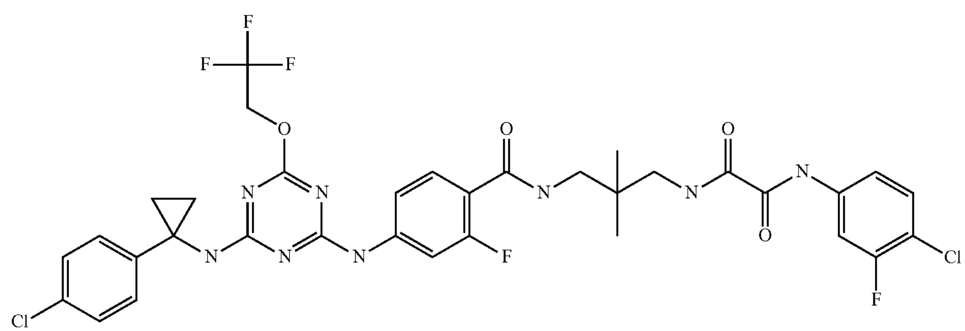 [SMILES: CC(C)(CNC(=O)C(=O)Nc1ccc(Cl)c(F)c1)CNC(=O)c1ccc(Nc2nc(NC3(c4ccc(Cl)cc4)CC3)nc(OCC(F)(F)F)n2)cc1F] | | A |

TABLE 1-continued

| Compound | Structure | EC$_{50}$ | Activity |
|---|---|---|---|
| 3514 | 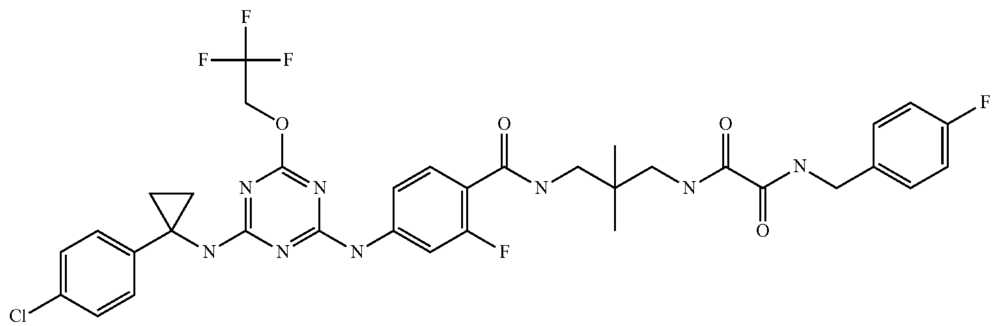 [SMILES: CC(C)(CNC(=O)C(=O)NCc1ccc(F)cc1)CNC(=O)c1ccc(Nc2nc(NC3(c4ccc(Cl)cc4)CC3)nc(OCC(F)(F)F)n2)cc1F] | | A |
| 3515 | 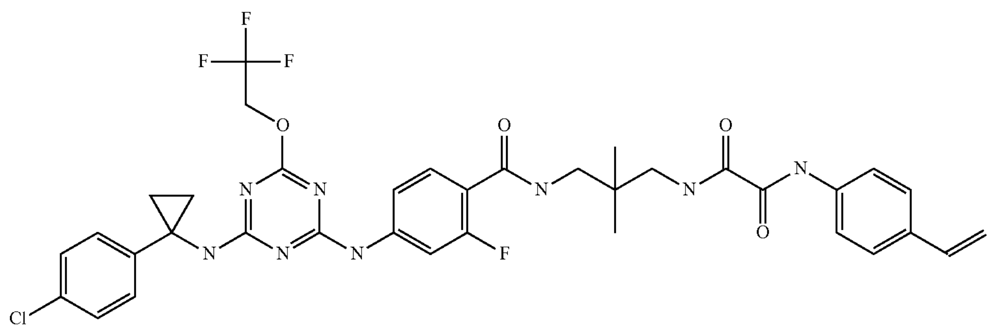 [SMILES: C=Cc1ccc(NC(=O)C(=O)NCC(C)(C)CNC(=O)c2ccc(Nc3nc(NC4(c5ccc(Cl)cc5)CC4)nc(OCC(F)(F)F)n3)cc2F)cc1] | 0.017 | A |
| 3516 | 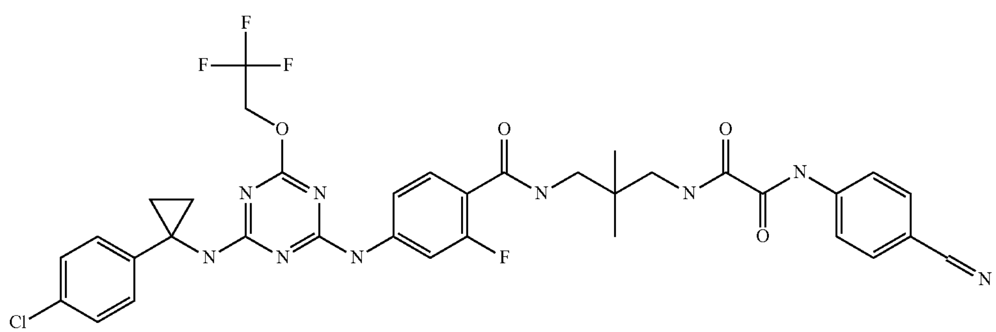 [SMILES: CC(C)(CNC(=O)C(=O)Nc1ccc(C=N)cc1)CNC(=O)c1ccc(Nc2nc(NC3(c4ccc(Cl)cc4)CC3)nc(OCC(F)(F)F)n2)cc1F] | | A |

TABLE 1-continued

| Compound | Structure | EC$_{50}$ | Activity |
|---|---|---|---|
| 3517 | 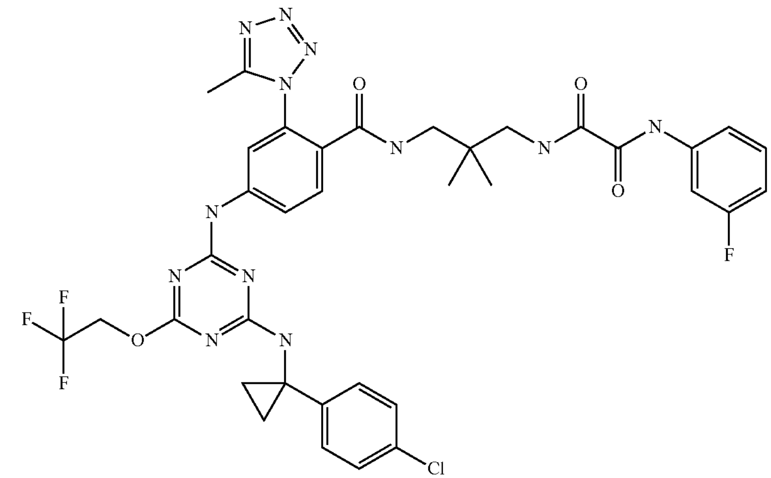 [SMILES: Cc1nnnn1-c1cc(Nc2nc(NC3(c4ccc(Cl)cc4)CC3)nc(OCC(F)(F)F)n2)ccc1C(=O)NCC(C)(C)CNC(=O)C(=O)Nc1cccc(F)c1] | | A |
| 3518 | 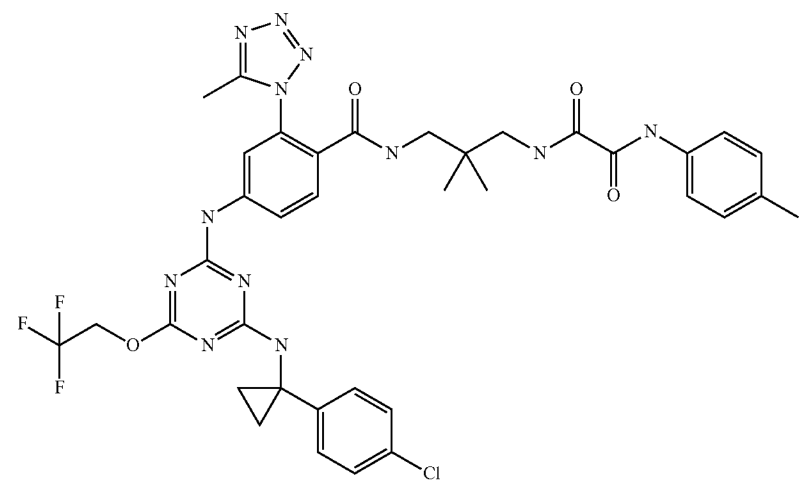 [SMILES: Cc1ccc(NC(=O)C(=O)NCC(C)(C)CNC(=O)c2ccc(Nc3nc(NC4(c5ccc(Cl)cc5)CC4)nc(OCC(F)(F)F)n3)cc2-n2nnnc2C)cc1] | 0.097 | A |

TABLE 1-continued

| Compound | Structure | EC$_{50}$ | Activity |
|---|---|---|---|
| 3519 | 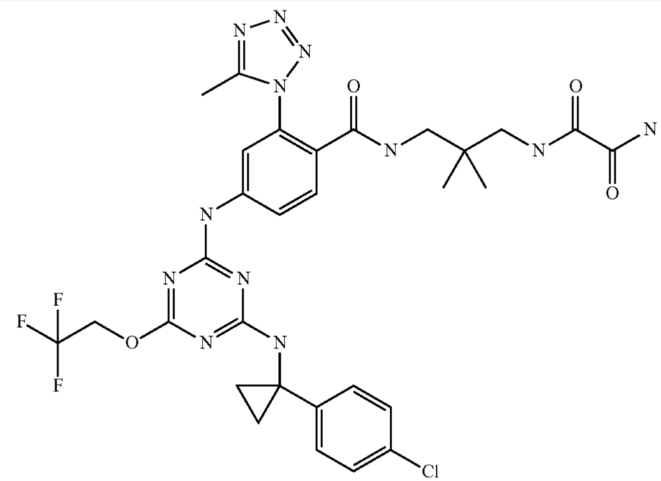 [SMILES: Cc1nnnn1-c1cc(Nc2nc(NC3(c4ccc(Cl)cc4)CC3)nc(OCC(F)(F)F)n2)ccc1C(=O)NCC(C)(C)CNC(=O)C(N)=O] | | A |
| 3520 | 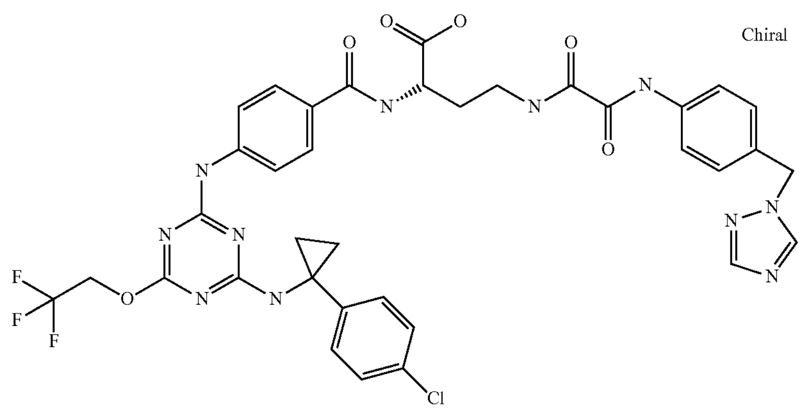 | | A |

TABLE 1-continued

| Compound | Structure | EC$_{50}$ | Activity |
|---|---|---|---|
| 3521 | (chiral structure) | | A |
| 3522 | (chiral structure) | | B |

TABLE 1-continued

| Compound | Structure | EC$_{50}$ | Activity |
|---|---|---|---|
| 3523 | Chiral | | A |
| 3524 | Chiral | | A |

TABLE 1-continued
| Compound | Structure | EC$_{50}$ | Activity |
|---|---|---|---|
| 3525 | 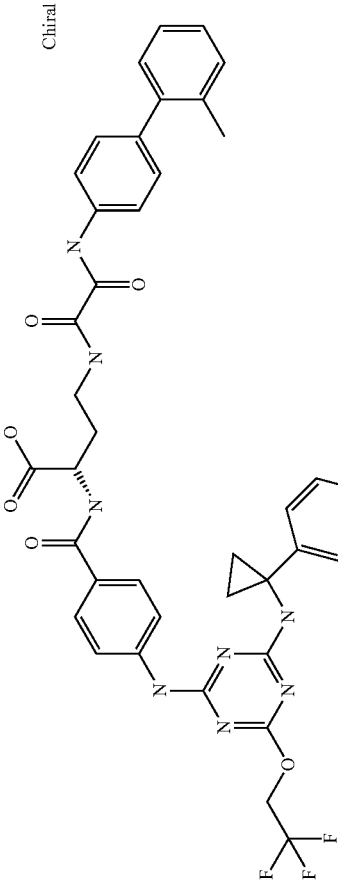 | | B |
| 3526 | 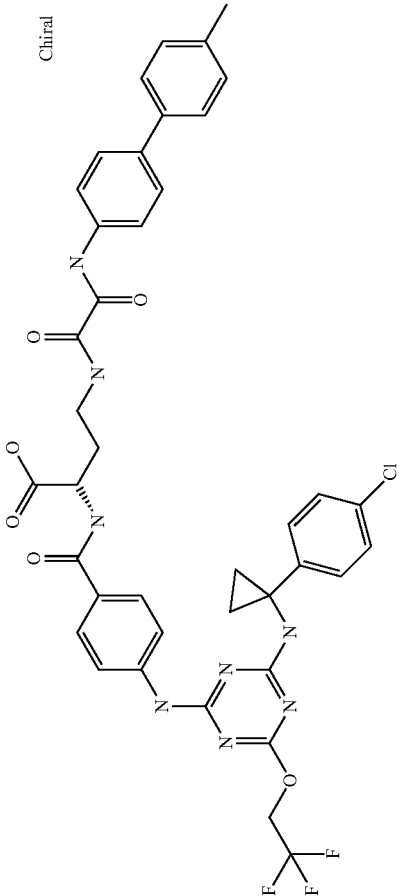 | | A |

TABLE 1-continued
| Compound | Structure | EC$_{50}$ | Activity |
|---|---|---|---|
| 3527 | 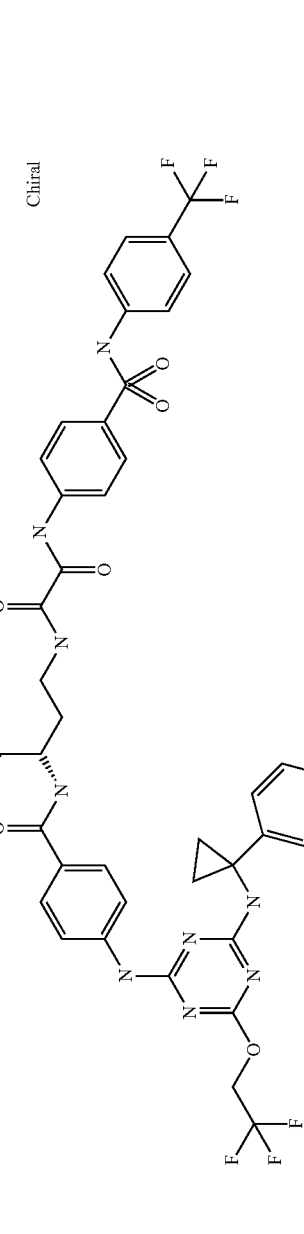 | 0.21 | A |
| 3528 | 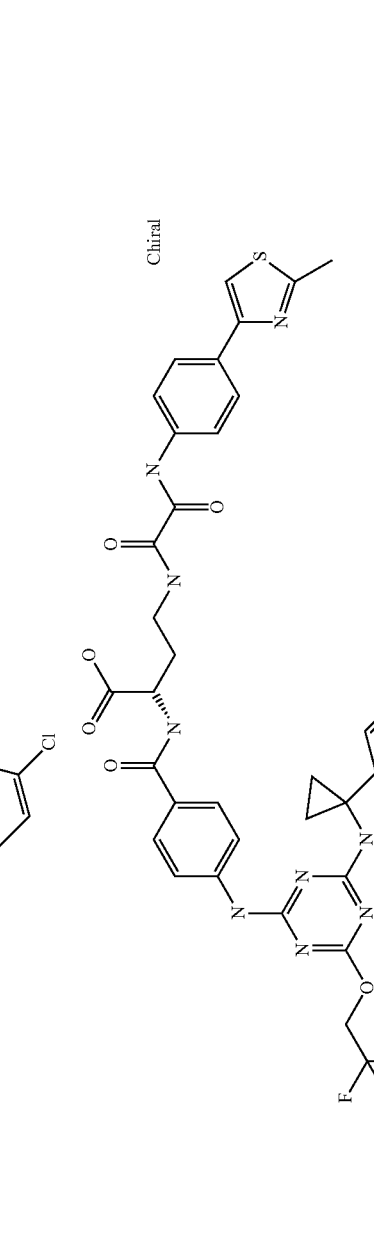 | | A |

TABLE 1-continued
| Compound | Structure | EC$_{50}$ | Activity |
|---|---|---|---|
| 3529 | 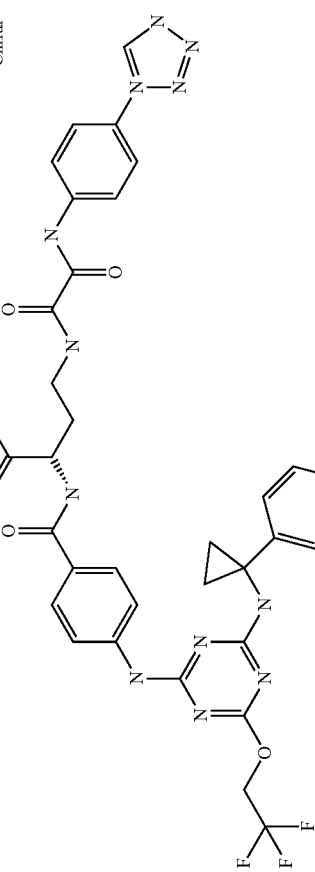 | | A |
| 3530 | 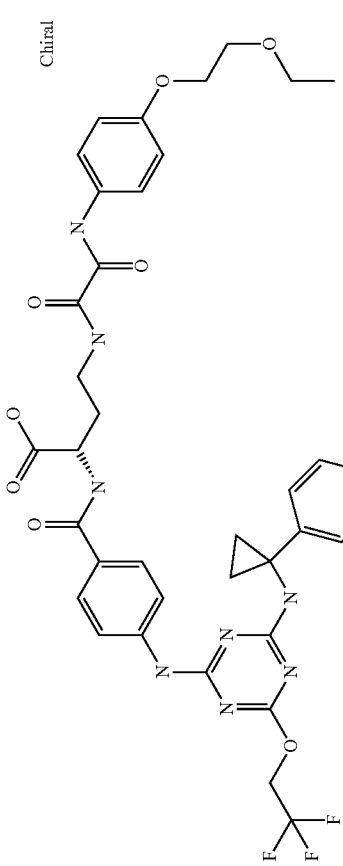 | | A |

TABLE 1-continued
| Compound | Structure | EC$_{50}$ | Activity |
|---|---|---|---|
| 3531 | 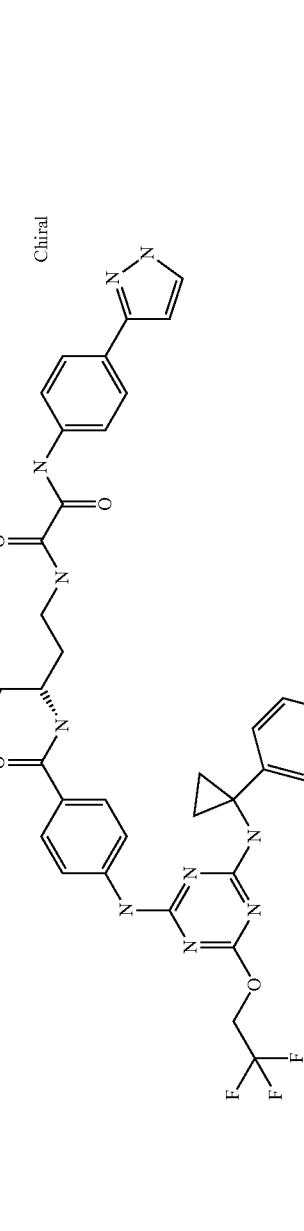 | | A |
| 3532 | 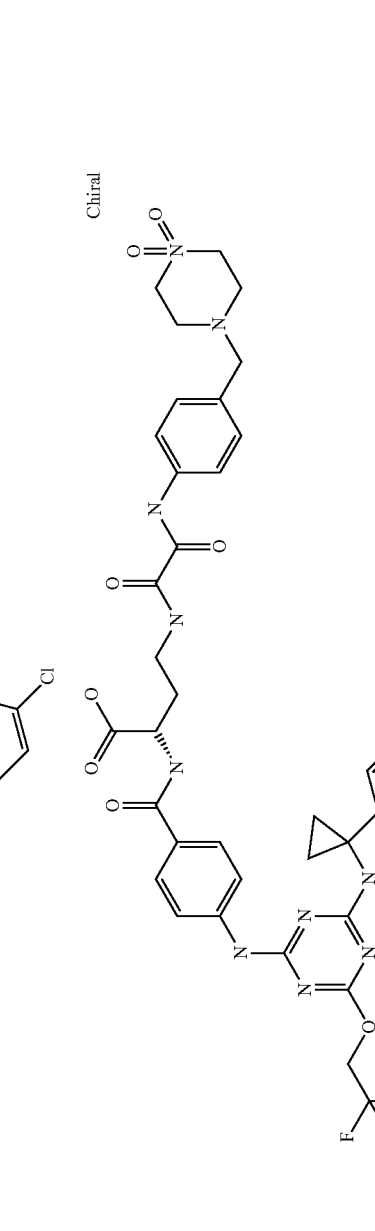 | | A |

TABLE 1-continued

| Compound | Structure | EC₅₀ | Activity |
|---|---|---|---|
| 3533 | (structure) | | A |
| 3534 | (structure) | 7.54 | A |

TABLE 1-continued

| Compound | Structure | EC$_{50}$ | Activity |
|---|---|---|---|
| 3535 | (chiral structure) | | A |
| 3536 | (chiral structure) | | A |

TABLE 1-continued
| Compound | Structure | EC$_{50}$ | Activity |
|---|---|---|---|
| 3537 | 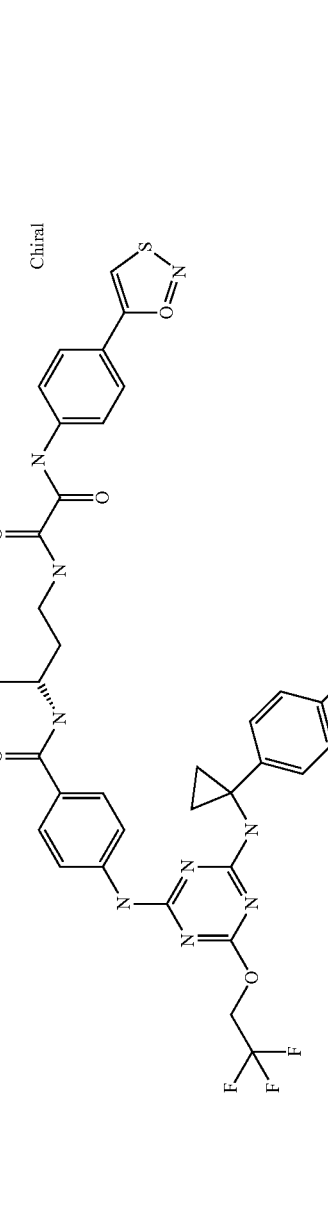 | | A |
| 3538 | 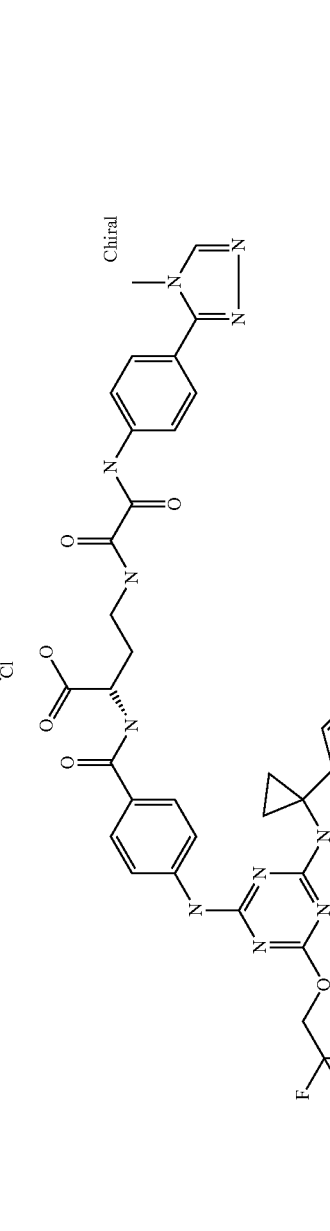 | | B |

TABLE 1-continued
| Compound | Structure | EC$_{50}$ | Activity |
|---|---|---|---|
| 3539 | 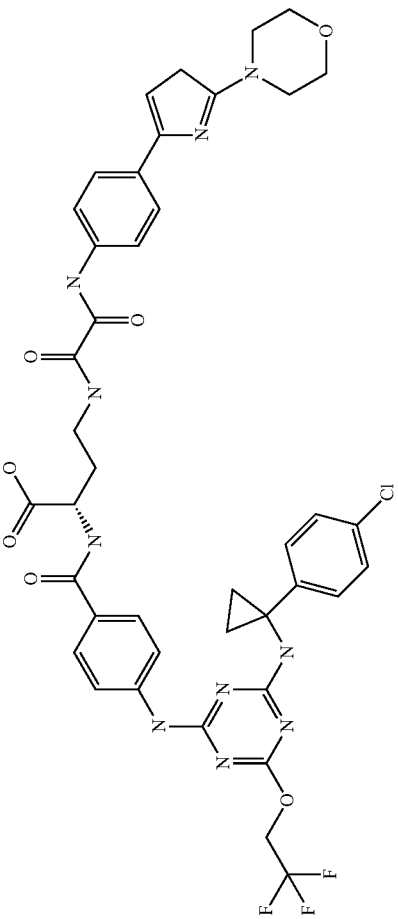 | | B |
| 3540 | 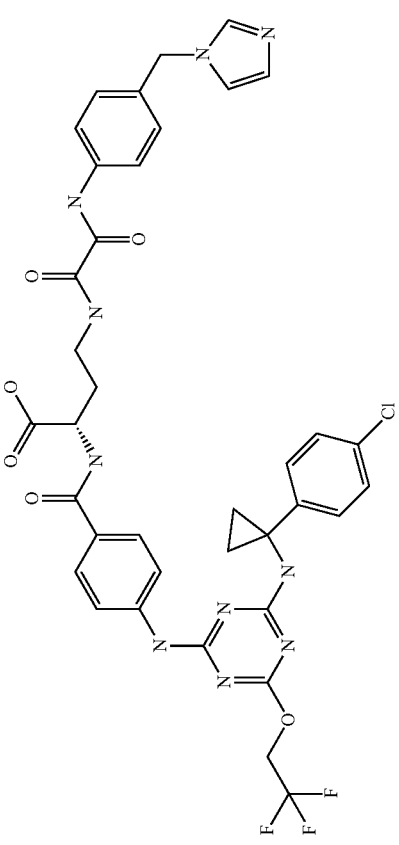 | 26.22 | B |

TABLE 1-continued
| Compound | Structure | EC$_{50}$ | Activity |
|---|---|---|---|
| 3541 | 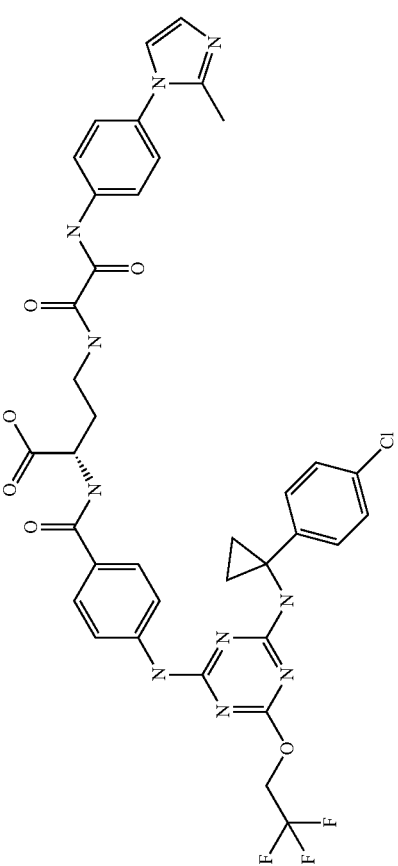 | | B |
| 3542 | 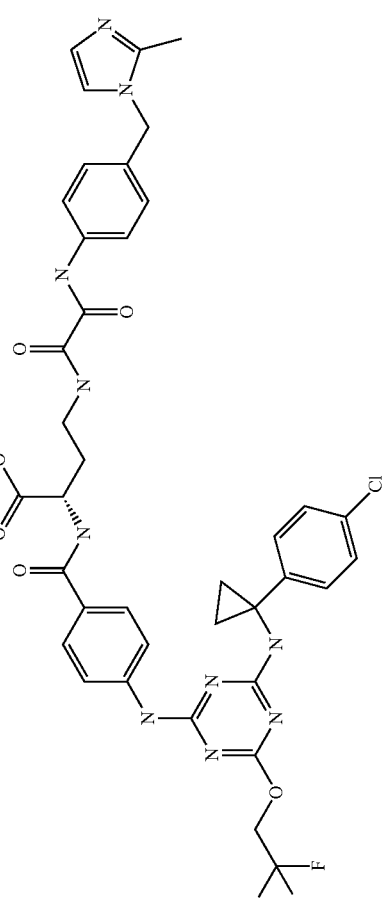 | | B |

TABLE 1-continued
| Compound | Structure | EC$_{50}$ | Activity |
|---|---|---|---|
| 3543 | Chiral 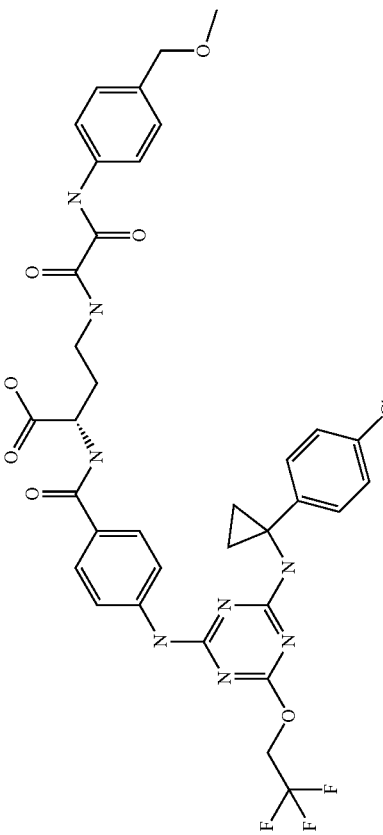 | | A |
| 3544 | Chiral 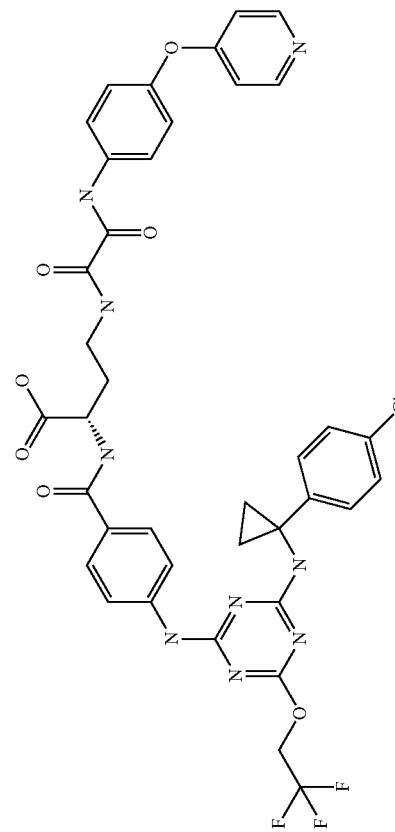 | | B |

TABLE 1-continued
| Compound | Structure | EC₅₀ | Activity |
|---|---|---|---|
| 3545 | 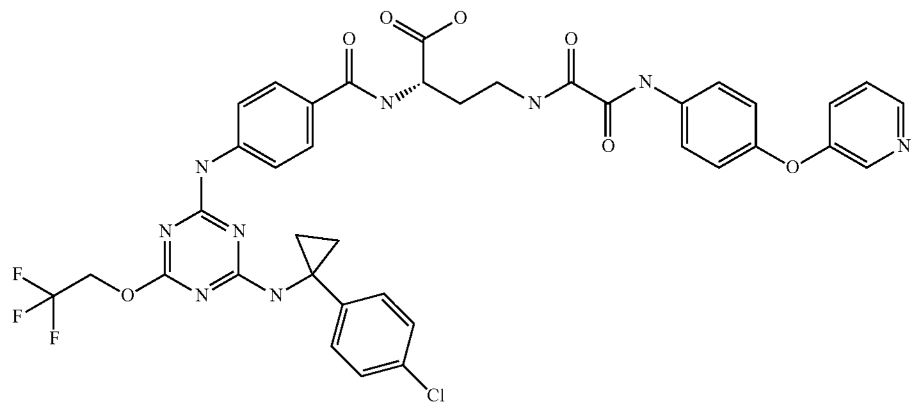 | | A |
| 3546 | 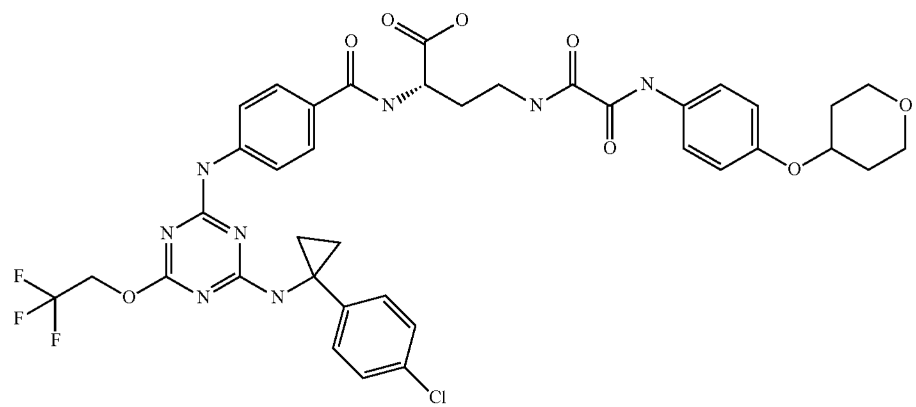 | | A |

TABLE 1-continued
| Compound | Structure | EC$_{50}$ | Activity |
|---|---|---|---|
| 3547 | 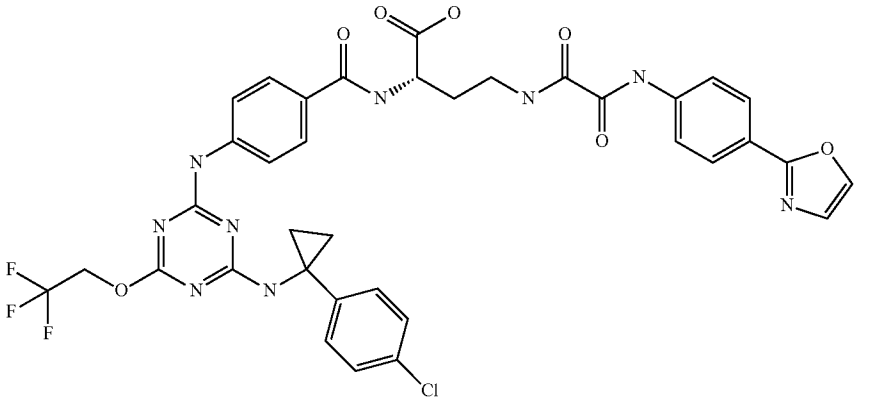 Chiral | 2.09 | A |
| 3548 | 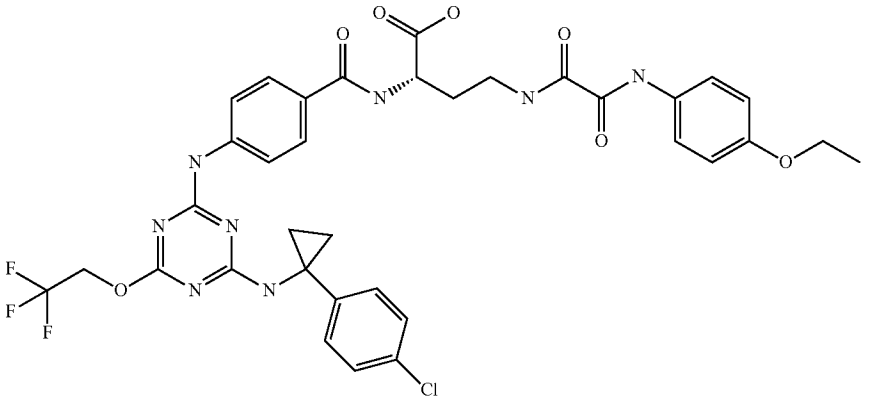 Chiral | | A |

TABLE 1-continued

| Compound | Structure | EC$_{50}$ | Activity |
|---|---|---|---|
| 3549 | Chiral | | A |
| 3550 | Chiral | | A |

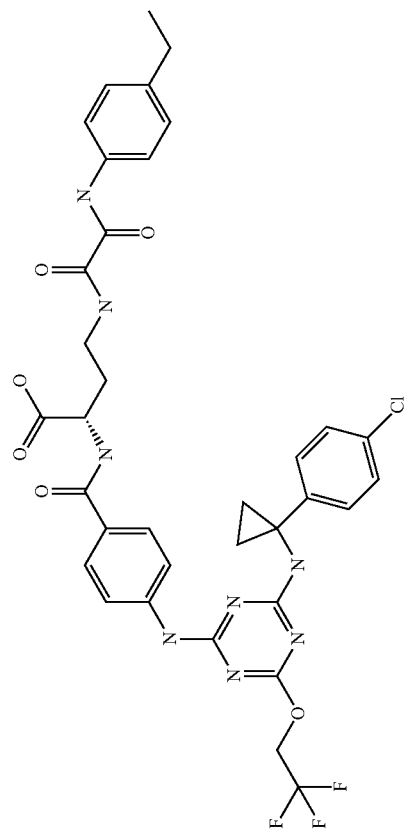

TABLE 1-continued

| Compound | Structure | EC$_{50}$ | Activity |
|---|---|---|---|
| 3553 | 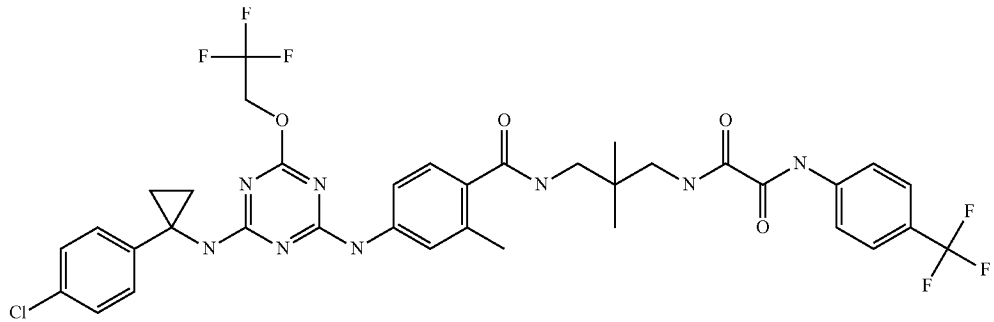 [SMILES: Cc1cc(Nc2nc(NC3(c4ccc(Cl)cc4)CC3)nc(OCC(F)(F)F)n2)ccc1C(=O)NCC(C)(C)CNC(=O)C(=O)Nc1ccc(C(F)(F)F)cc1] | | A |
| 3554 | 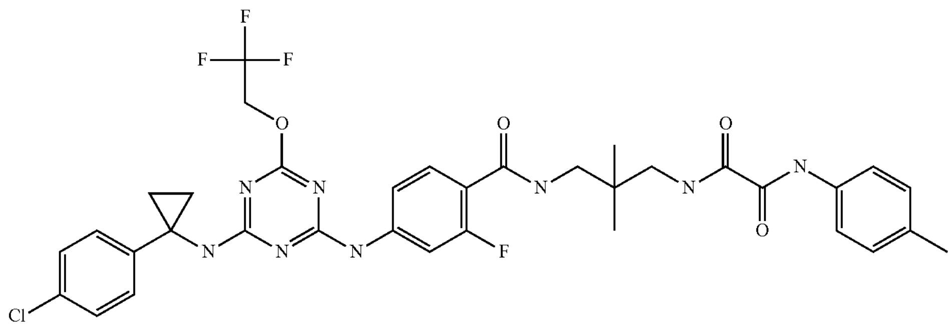 [SMILES: Cc1ccc(NC(=O)C(=O)NCC(C)(C)CNC(=O)c2ccc(Nc3nc(NC4(c5ccc(Cl)cc5)CC4)nc(OCC(F)(F)F)n3)cc2F)cc1] | 0.029 | A |
| 3555 | 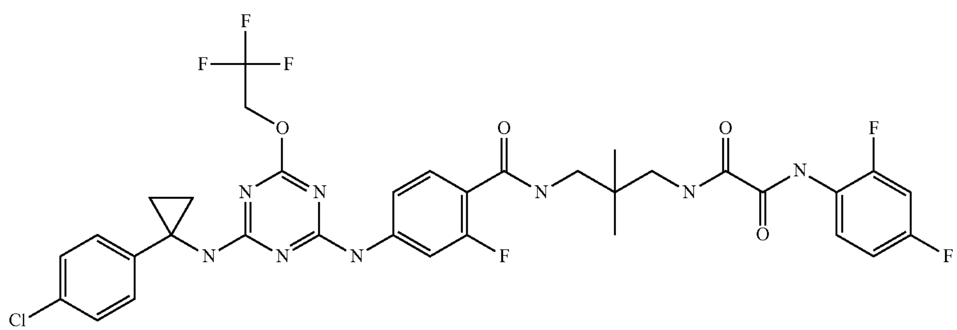 [SMILES: CC(C)(CNC(=O)C(=O)Nc1ccc(F)cc1F)CNC(=O)c1ccc(Nc2nc(NC3(c4ccc(Cl)cc4)CC3)nc(OCC(F)(F)F)n2)cc1F] | | A |

TABLE 1-continued
| Compound | Structure | EC$_{50}$ | Activity |
|---|---|---|---|
| 3556 | 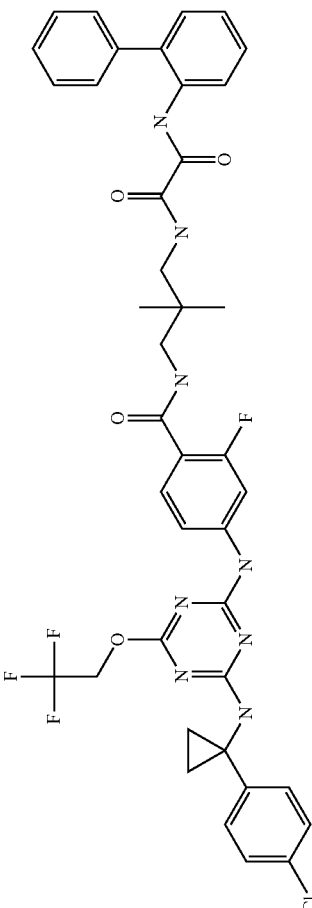 | | A |
| 3557 | 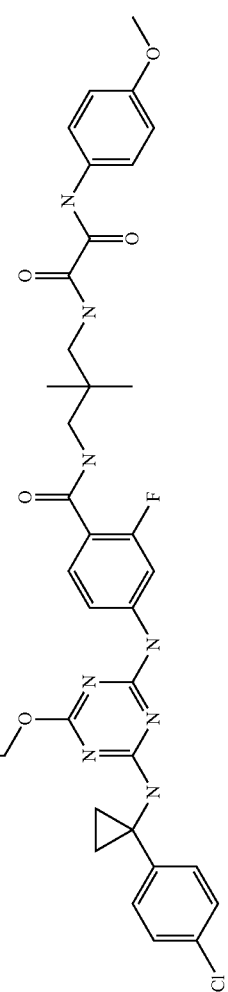 | | A |

TABLE 1-continued
| Compound | Structure | EC$_{50}$ | Activity |
|---|---|---|---|
| 3558 | 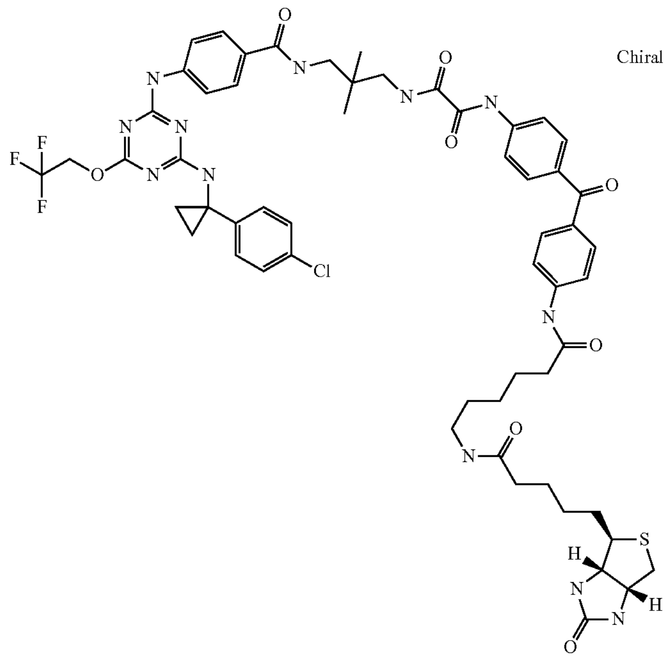 [SMILES: CC(C)(CNC(=O)C(=O)Nc1ccc(C(=O)c2ccc(NC(=O)CCCCCNC(=O)CCCC[C@H]3SC[C@@H]4NC(=O)N[C@@H]43)cc2)cc1)CNC(=O)c1ccc(Nc2nc(NC3(c4ccc(Cl)cc4)CC3)nc(OCC(F)(F)F)n2)cc1] | 0.26 | A |
| 3559 | 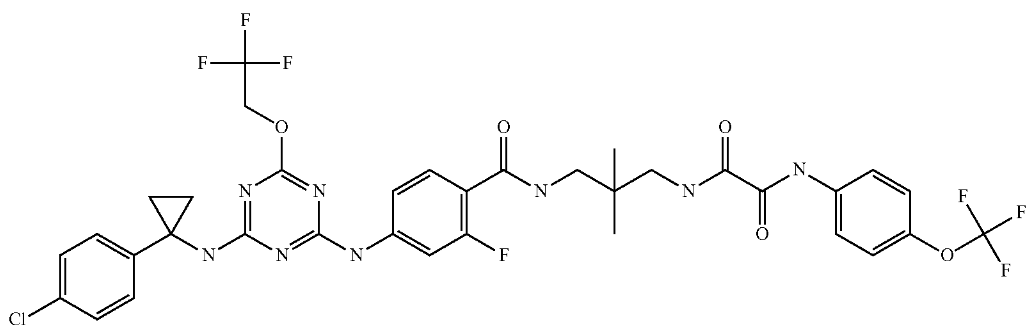 [SMILES: CC(C)(CNC(=O)C(=O)Nc1ccc(OC(F)(F)F)cc1)CNC(=O)c1ccc(Nc2nc(NC3(c4ccc(Cl)cc4)CC3)nc(OCC(F)(F)F)n2)cc1F] | | A |
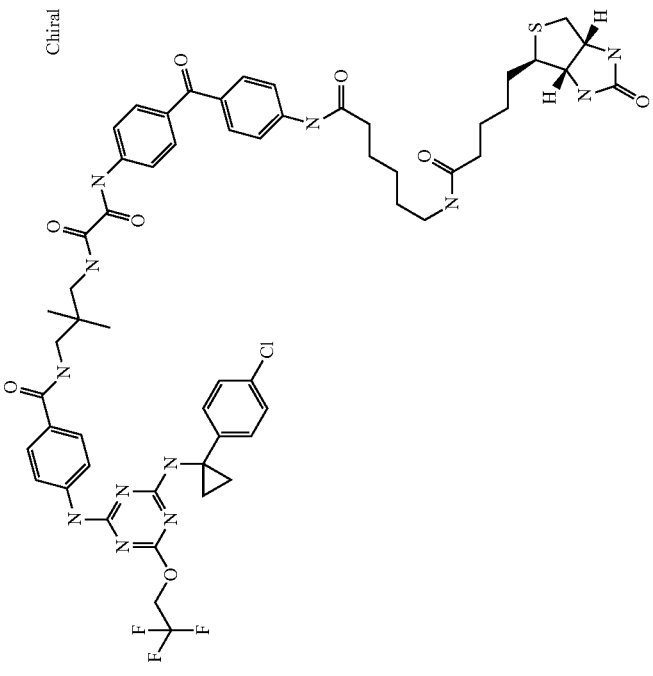

TABLE 1-continued

| Compound | Structure | EC$_{50}$ | Activity |
|---|---|---|---|
| 3560 | 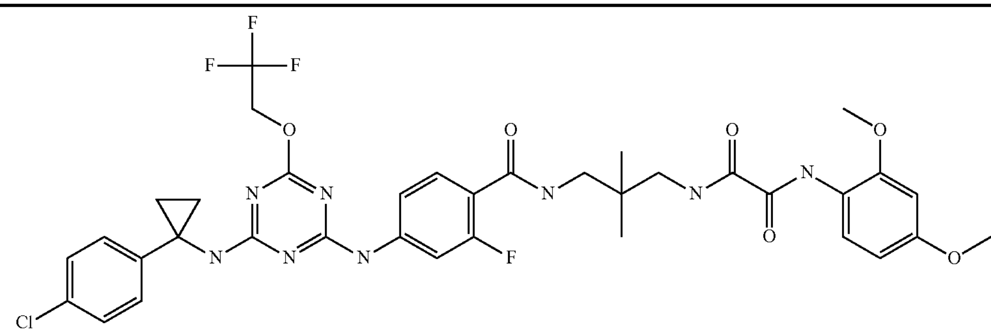 | | A |
| 3561 | 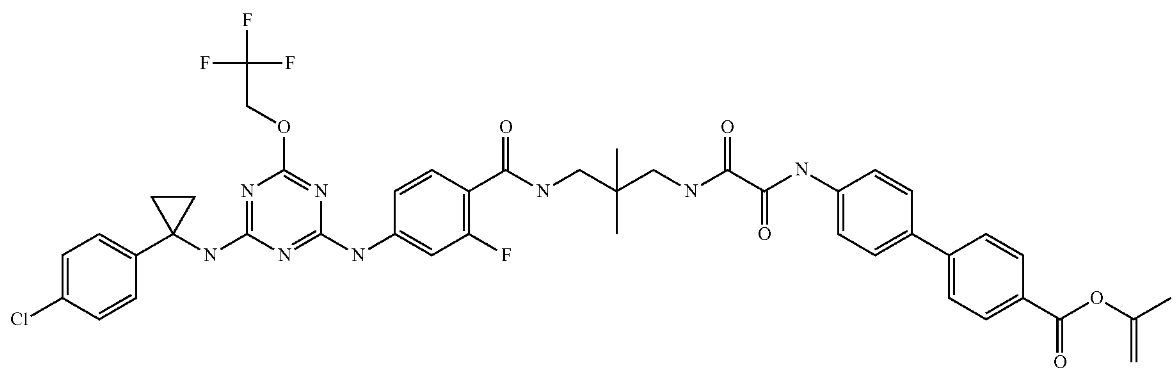 [SMILES: C=C(C)OC(=O)c1ccc(-c2ccc(NC(=O)C(=O)NCC(C)(C)CNC(=O)c3ccc(Nc4nc(NC5(c6ccc(Cl)cc6)CC5)nc(OCC(F)(F)F)n4)cc3F)cc2)cc1] | | A |
| 3562 | 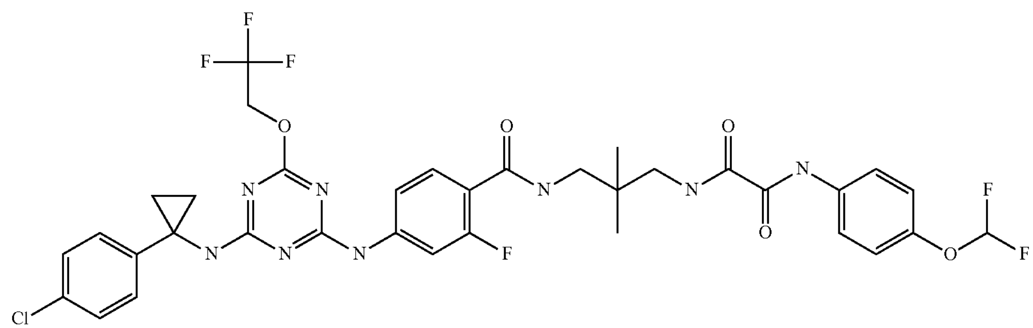 [SMILES: CC(C)(CNC(=O)C(=O)Nc1ccc(OC(F)F)cc1)CNC(=O)c1ccc(Nc2nc(NC3(c4ccc(Cl)cc4)CC3)nc(OCC(F)(F)F)n2)cc1F] | 0.018 | A |

TABLE 1-continued
| Compound | Structure | EC$_{50}$ | Activity |
|---|---|---|---|
| 3563 | 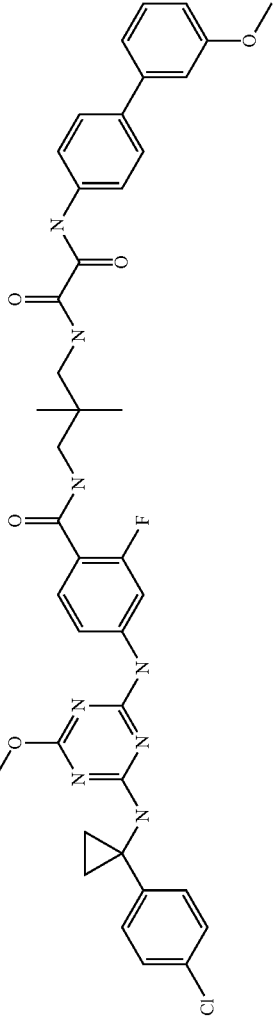 | | A |
| 3564 | 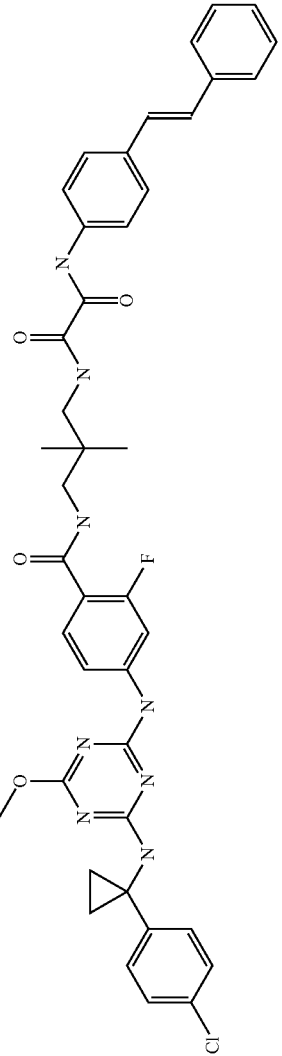 | | A |

TABLE 1-continued

| Compound | Structure | EC$_{50}$ | Activity |
|---|---|---|---|
| 3565 | 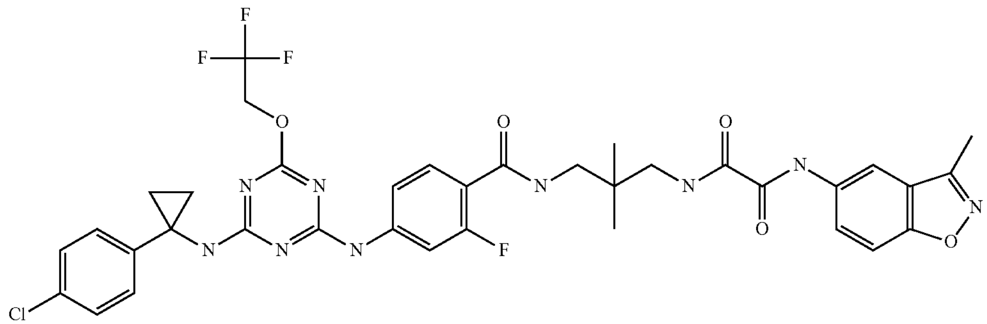 [SMILES: Cc1noc2ccc(NC(=O)C(=O)NCC(C)(C)CNC(=O)c3ccc(Nc4nc(NC5(c6ccc(Cl)cc6)CC5)nc(OCC(F)(F)F)n4)cc3F)cc12] | | A |
| 3566 | 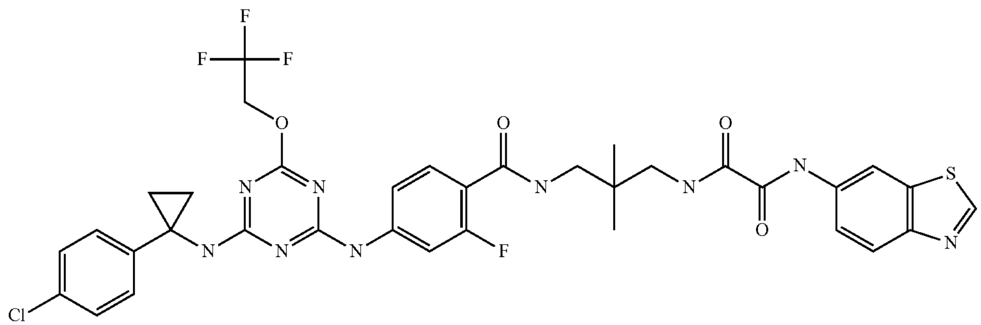 [SMILES: CC(C)(CNC(=O)C(=O)Nc1ccc2ncsc2c1)CNC(=O)c1ccc(Nc2nc(NC3(c4ccc(Cl)cc4)CC3)nc(OCC(F)(F)F)n2)cc1F] | | A |
| 3567 | 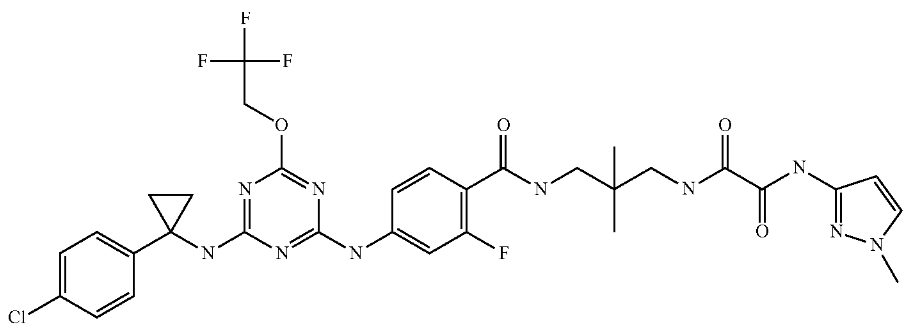 [SMILES: Cn1ccc(NC(=O)C(=O)NCC(C)(C)CNC(=O)c2ccc(Nc3nc(NC4(c5ccc(Cl)cc5)CC4)nc(OCC(F)(F)F)n3)cc2F)n1] | 0.035 | A |

TABLE 1-continued
| Compound | Structure | EC$_{50}$ | Activity |
|---|---|---|---|
| 3568 | 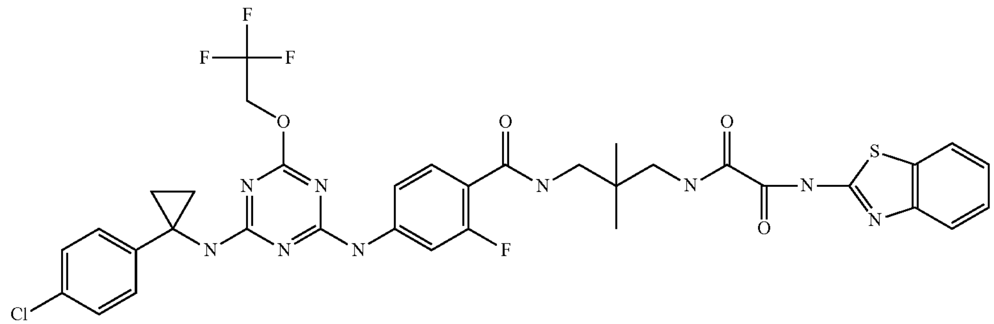 [SMILES: CC(C)(CNC(=O)C(=O)Nc1nc2ccccc2s1)CNC(=O)c1ccc(Nc2nc(NC3(c4ccc(Cl)cc4)CC3)nc(OCC(F)(F)F)n2)cc1F] | | A |
| 3569 |  Chiral | | A |

TABLE 1-continued
| Compound | Structure | EC$_{50}$ | Activity |
|---|---|---|---|
| 3570 | 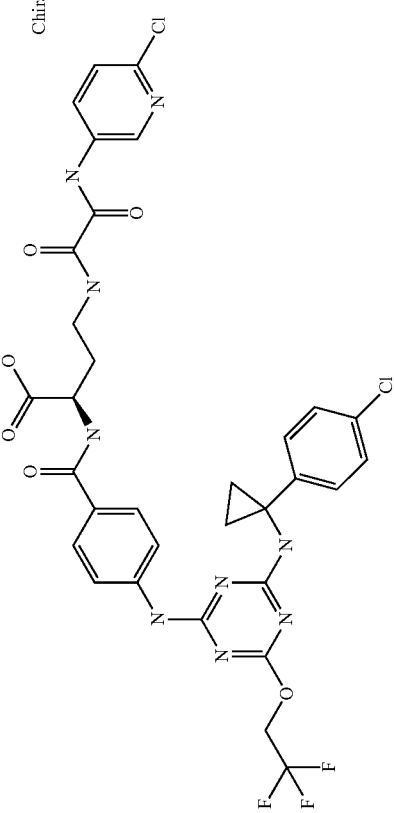 | | A |
| 351 | 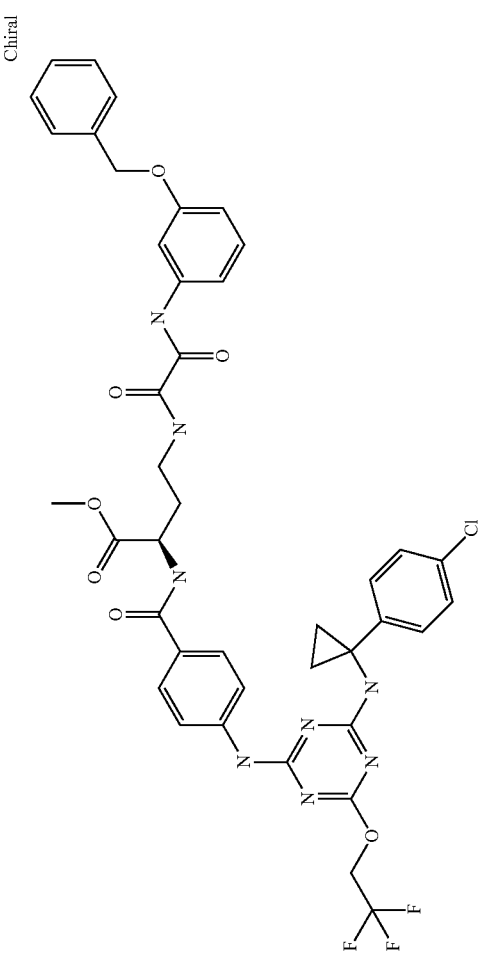 | | A |

| Compound | Structure | EC$_{50}$ | Activity |
|---|---|---|---|
| 3572 | 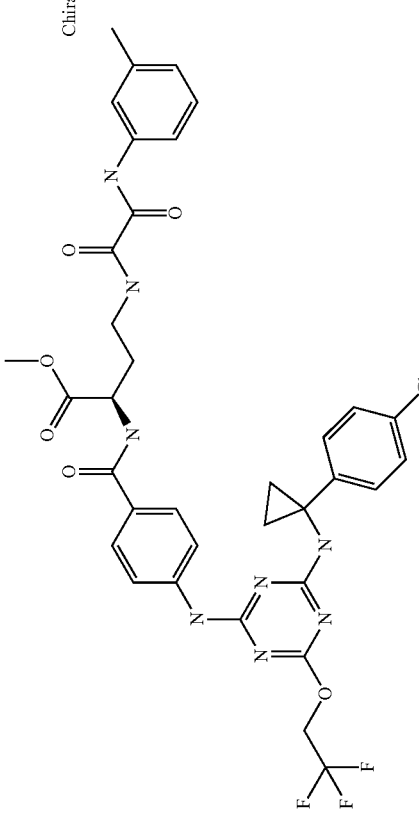 | | A |
| 3573 | 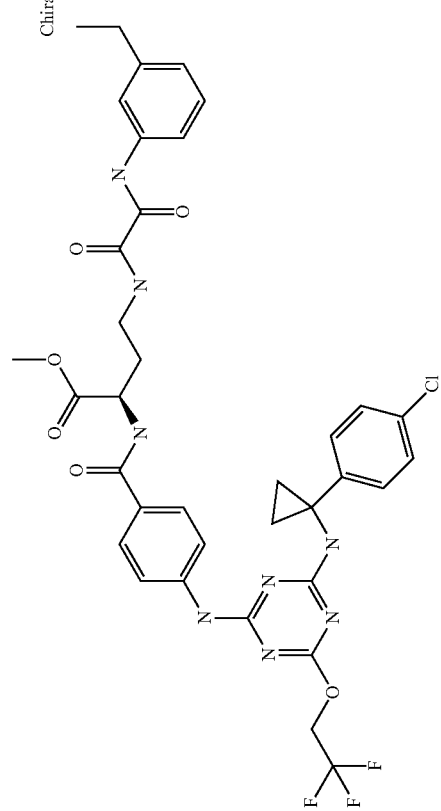 | | A |

TABLE 1-continued
| Compound | Structure | EC$_{50}$ | Activity |
|---|---|---|---|
| 3574 | 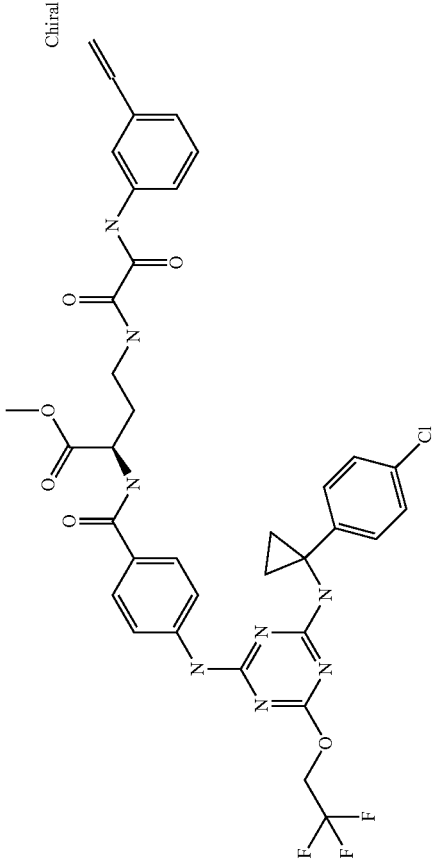 | | A |
| 3575 | 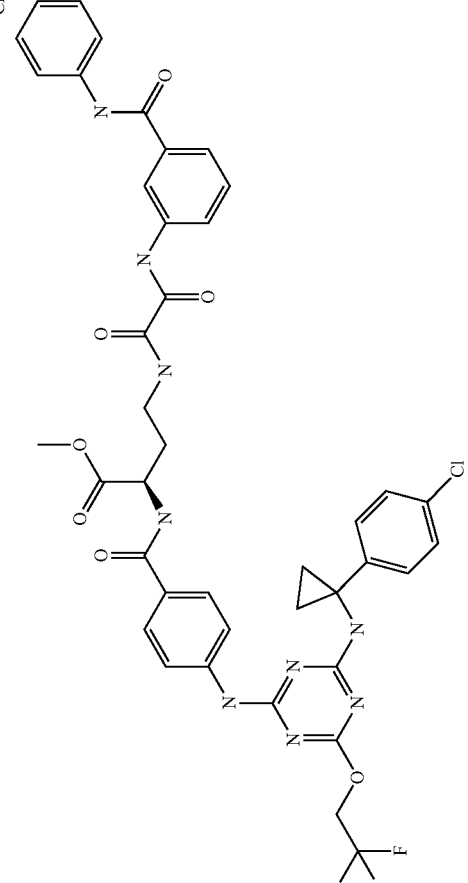 | | A |

TABLE 1-continued
| Compound | Structure | EC$_{50}$ | Activity |
|---|---|---|---|
| 3576 | Chiral 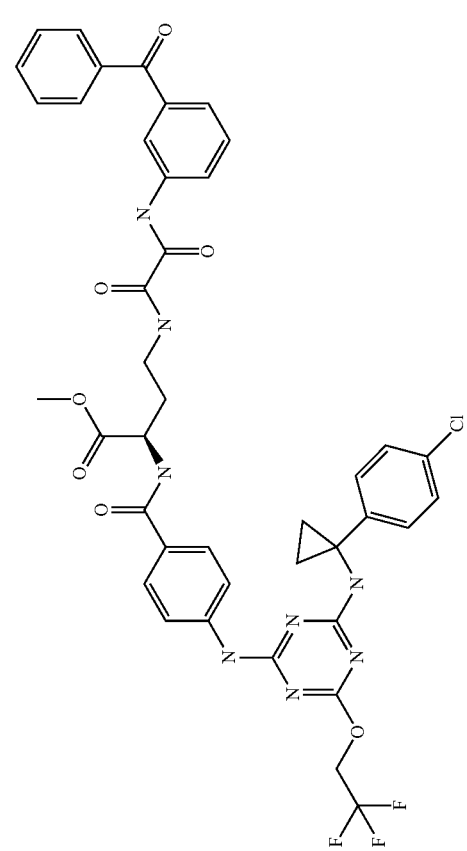 | | A |
| 3577 | Chiral 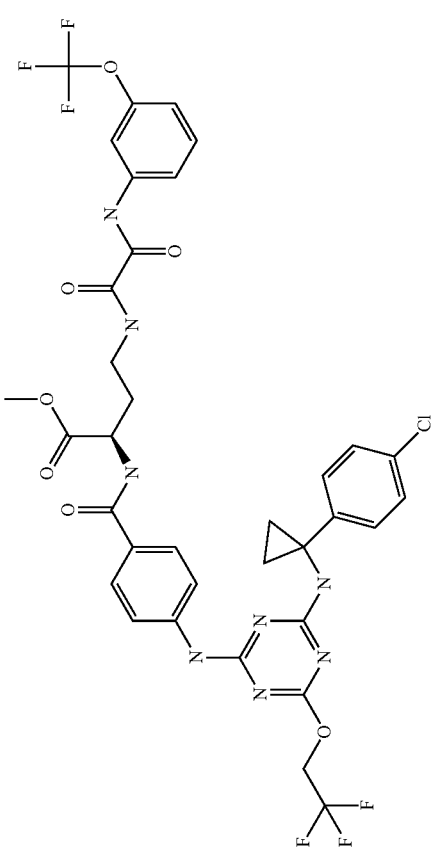 | 0.16 | A |

TABLE 1-continued
| Compound | Structure | EC$_{50}$ | Activity |
|---|---|---|---|
| 3578 | 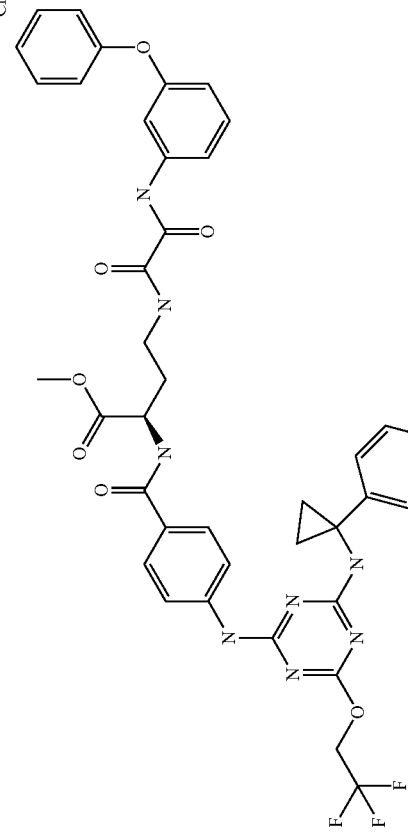 | | A |
| 3579 | 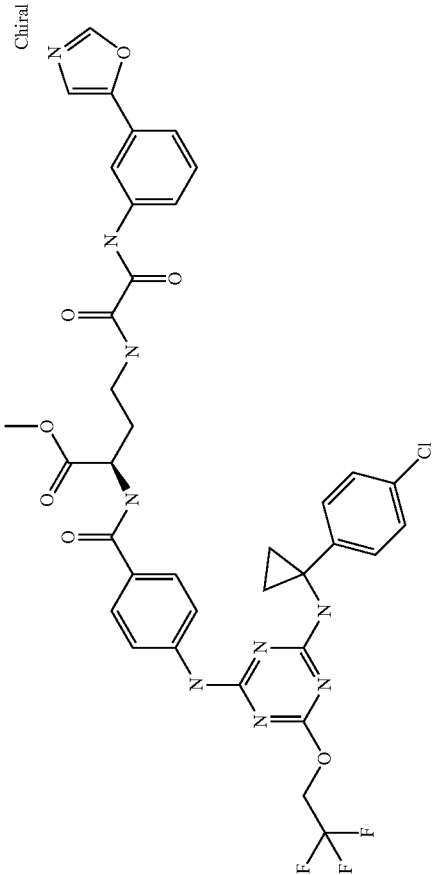 | | A |

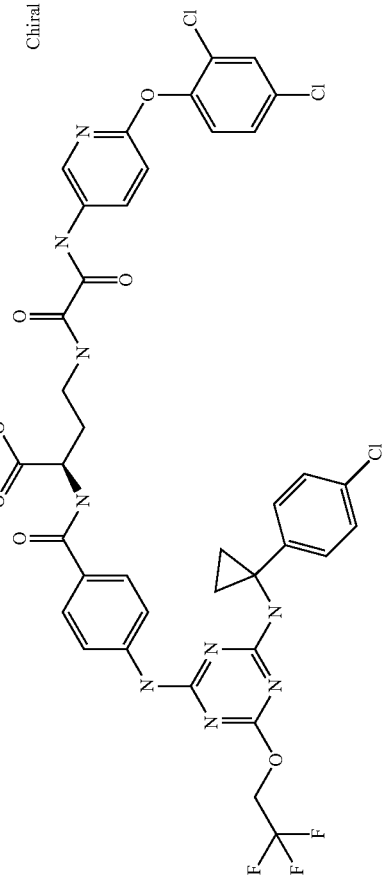

TABLE 1-continued
| Compound | Structure | EC50 | Activity |
|---|---|---|---|
| 3582 | 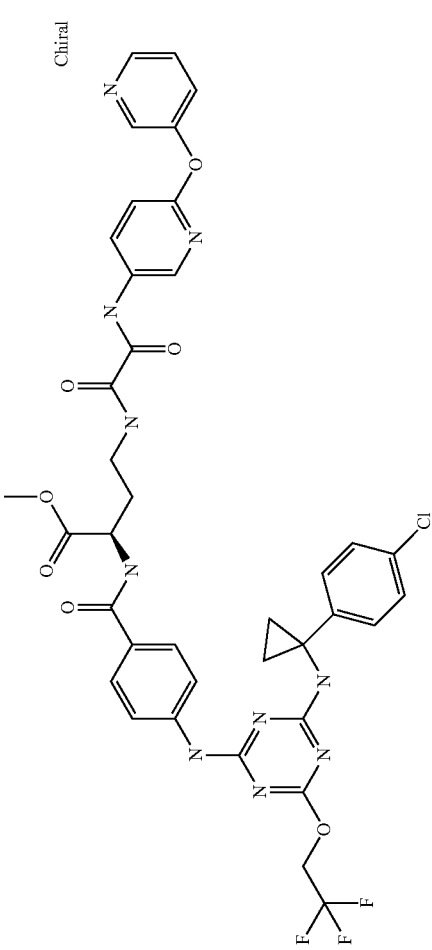 | 8.95 | A |
| 3583 | 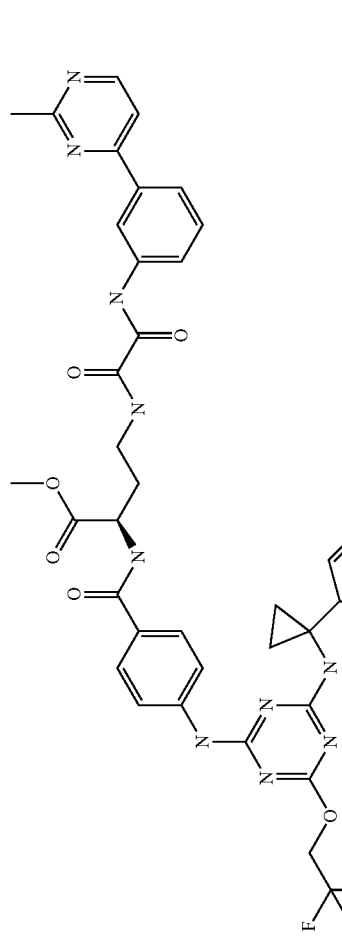 | | A |

TABLE 1-continued
| Compound | Structure | EC$_{50}$ | Activity |
|---|---|---|---|
| 3584 | 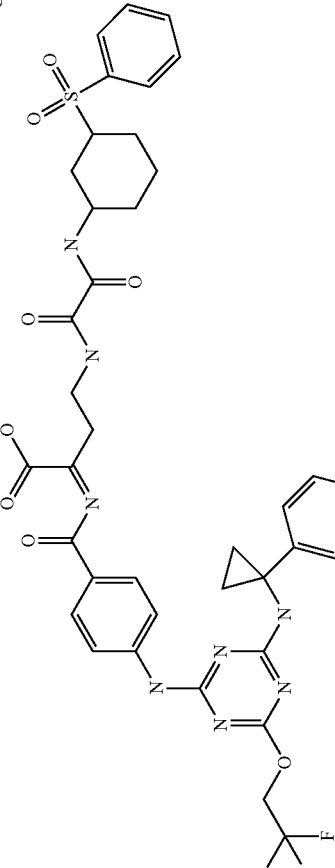 | | B |
| 3585 | 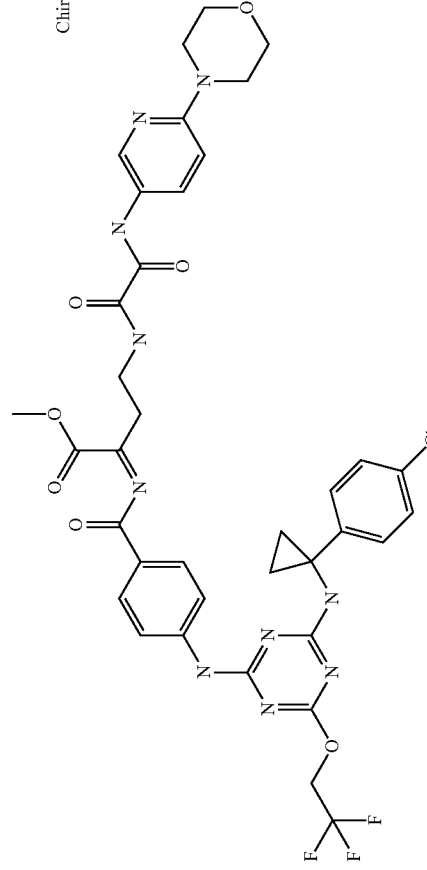 | | A |

TABLE 1-continued
| Compound | Structure | EC$_{50}$ | Activity |
|---|---|---|---|
| 3586 | 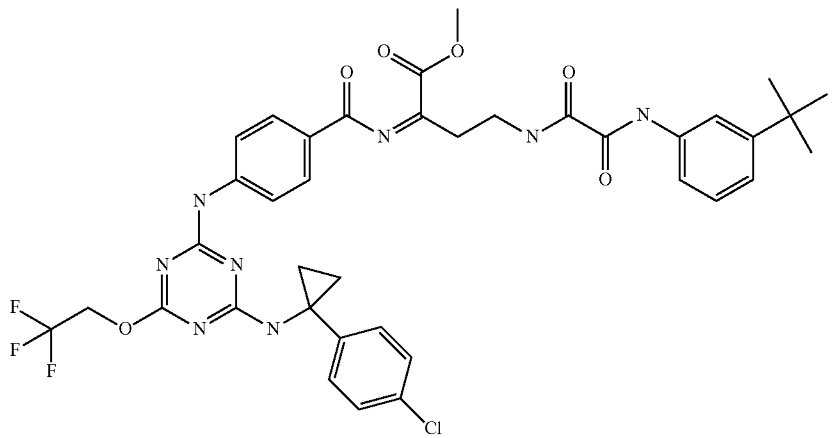 [SMILES: COC(=O)[C@@H](CCNC(=O)C(=O)Nc1ccc(Cl)nc1)NC(=O)c1ccc(Nc2nc(NC3(c4ccc(Cl)cc4)CC3)nc(OCC(F)(F)F)n2)cc1] | | A |
| 3587 | 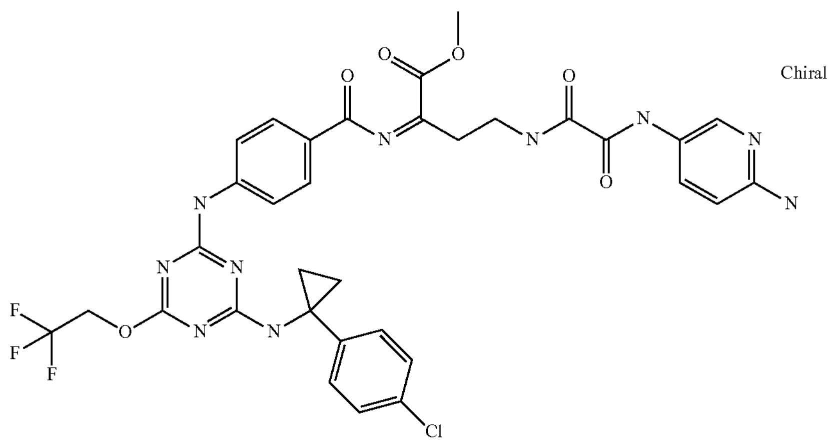 [SMILES: COC(=O)/C(CCNC(=O)C(=O)Nc1ccc(N)nc1)=N\C(=O)c1ccc(Nc2nc(NC3(c4ccc(Cl)cc4)CC3)nc(OCC(F)(F)F)n2)cc1] | | A |
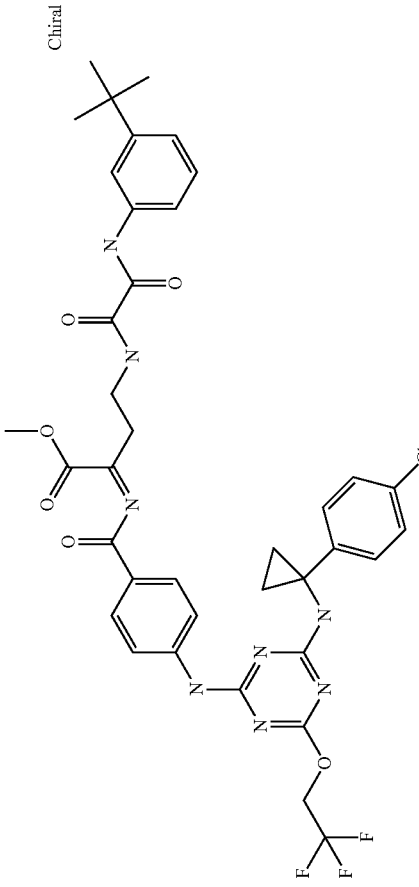

TABLE 1-continued
| Compound | Structure | EC$_{50}$ | Activity |
|---|---|---|---|
| 3588 | 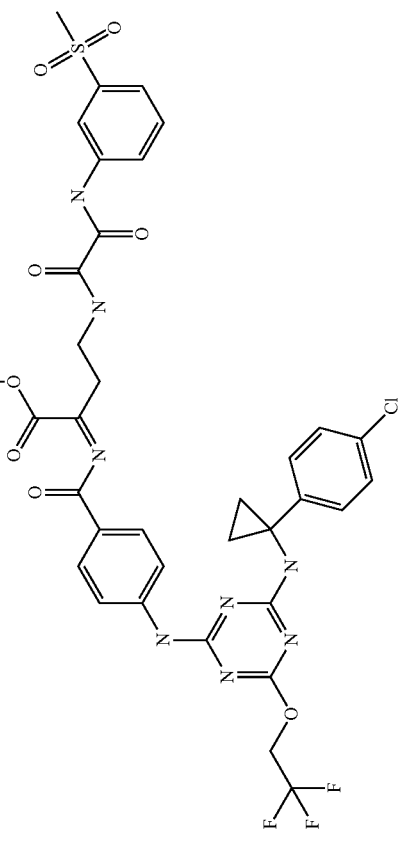 | | A |
| 3589 | 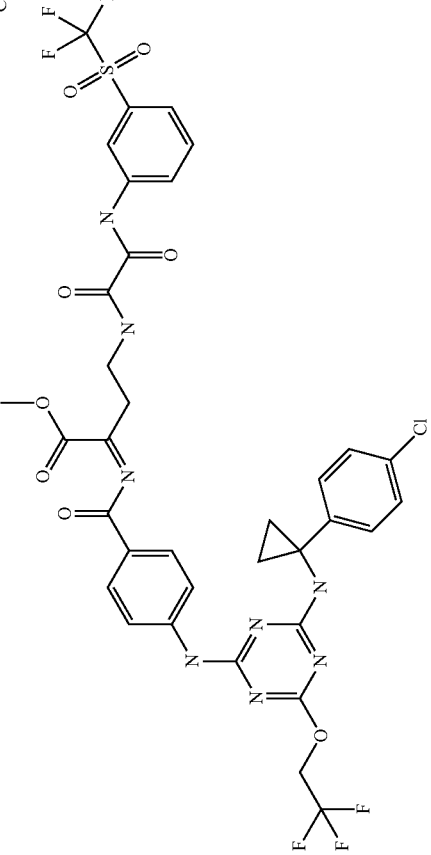 | | A |

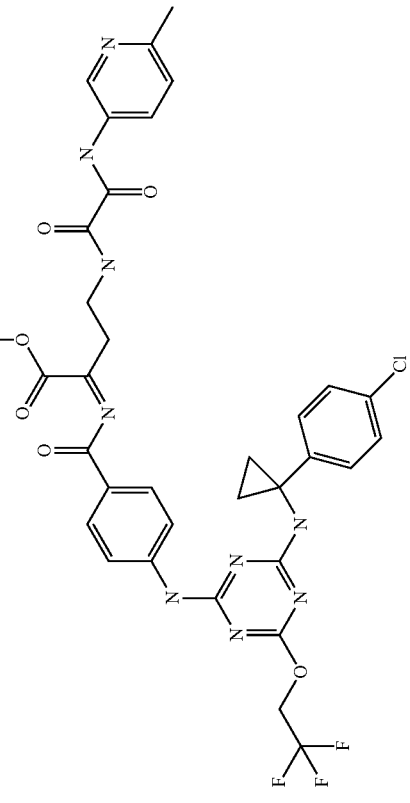

TABLE 1-continued

| Compound | Structure | EC$_{50}$ | Activity |
|---|---|---|---|
| 3592 | Chiral | | B |
| 3593 | Chiral | | A |

TABLE 1-continued
| Compound | Structure | EC$_{50}$ | Activity |
|---|---|---|---|
| 3594 | 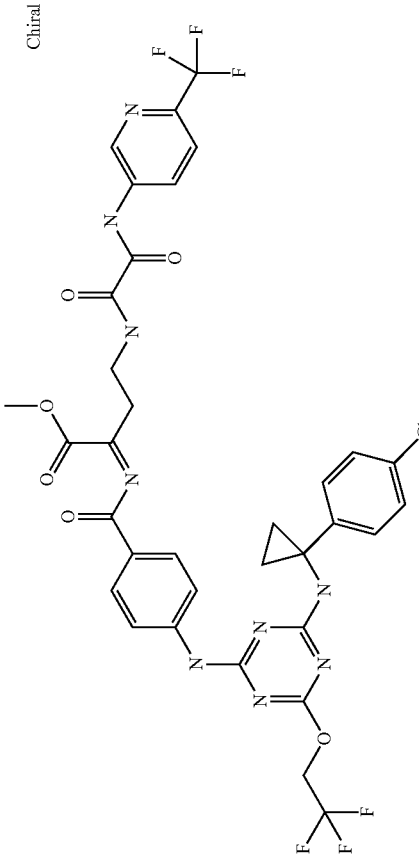 | | A |
| 3595 | 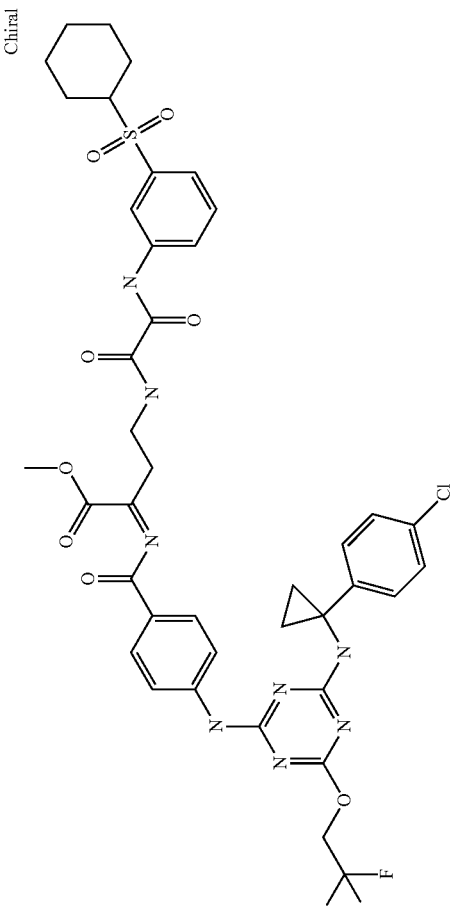 | | A |

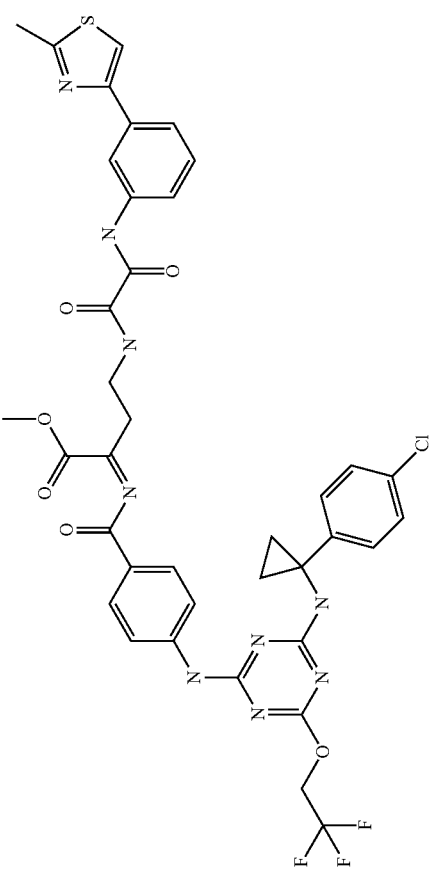

TABLE 1-continued

| Compound | Structure | EC$_{50}$ | Activity |
|---|---|---|---|
| 3598 | 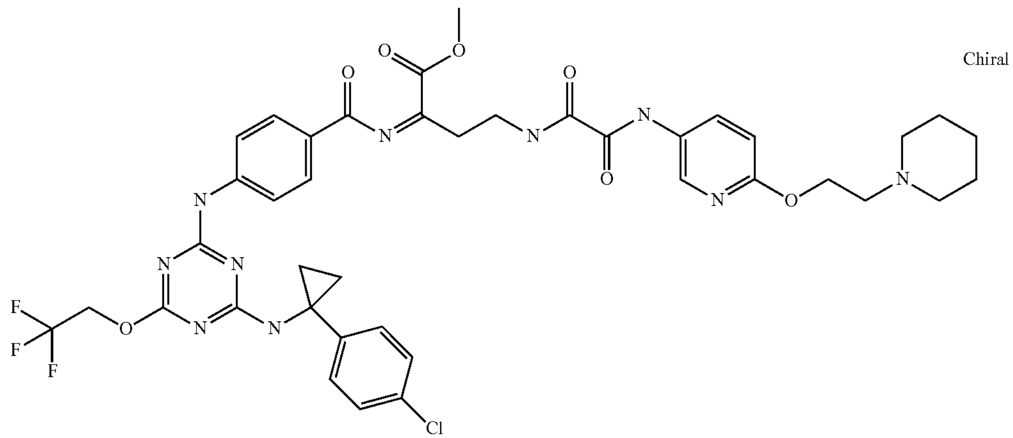 [SMILES: COC(=O)/C(CCNC(=O)C(=O)Nc1ccc(OCCN2CCCCC2)nc1)=N\C(=O)c1ccc(Nc2nc(NC3(c4ccc(Cl)cc4)CC3)nc(OCC(F)(F)F)n2)cc1] | | A |
| 3599 | 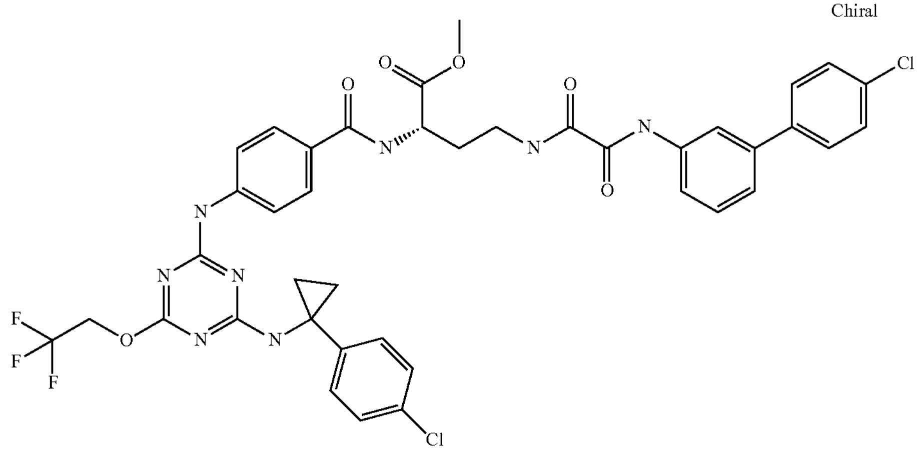 [SMILES: COC(=O)[C@H](CCNC(=O)C(=O)Nc1cccc(-c2ccc(Cl)cc2)c1)NC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 3600 | 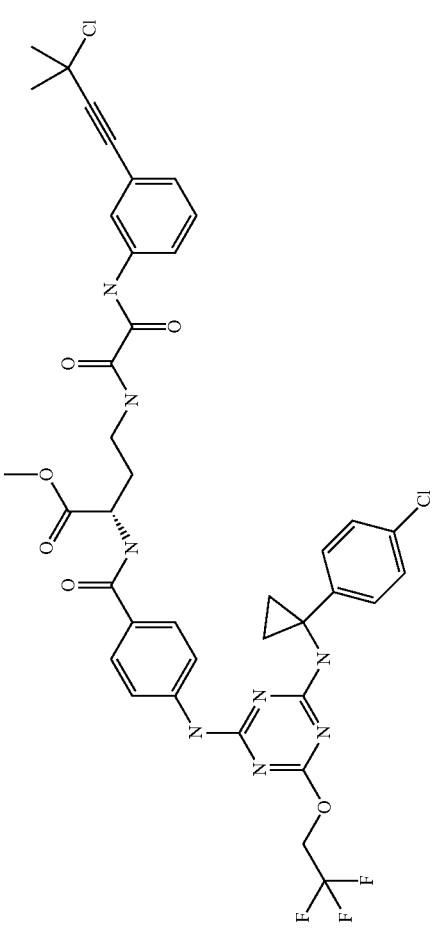 | | A |
| 3601 | 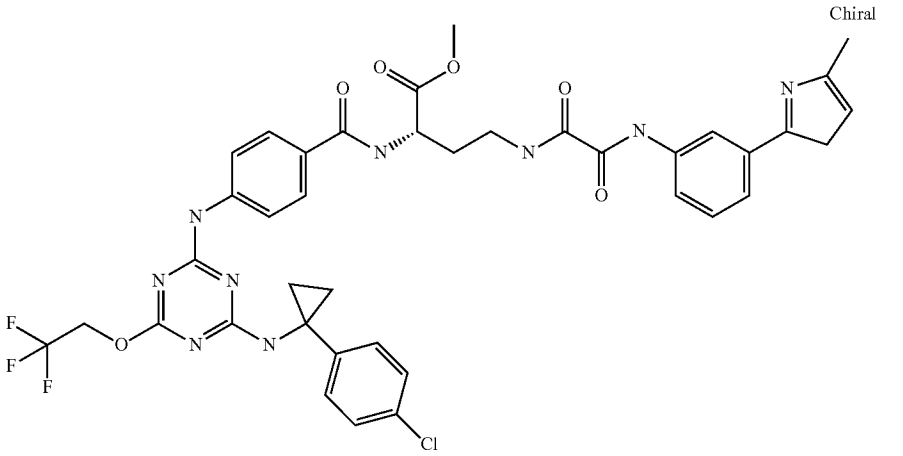 [SMILES: COC(=O)[C@H](CCNC(=O)C(=O)Nc1cccc(C2=NC(C)=CC2)c1)NC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3602 | 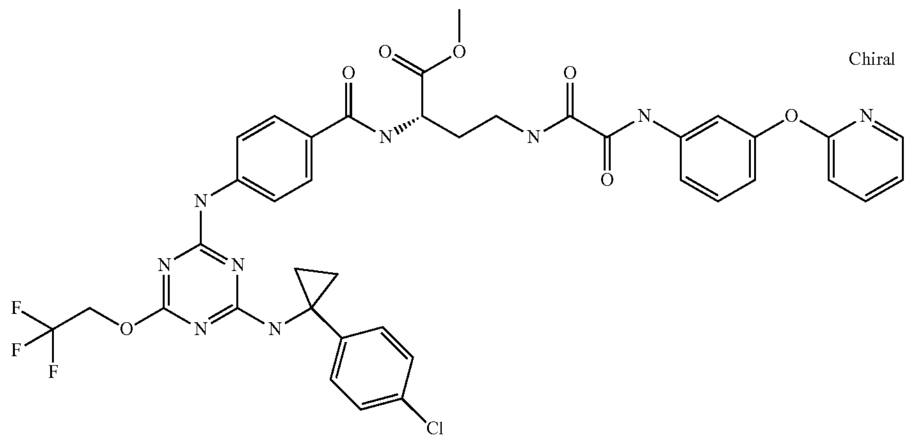 [SMILES: COC(=O)[C@H](CCNC(=O)C(=O)Nc1cccc(Oc2ccccn2)c1)NC(=O)c1ccc(Nc2nc(NC3(c4ccc(Cl)cc4)CC3)nc(OCC(F)(F)F)n2)cc1] | | A |
| 3603 | 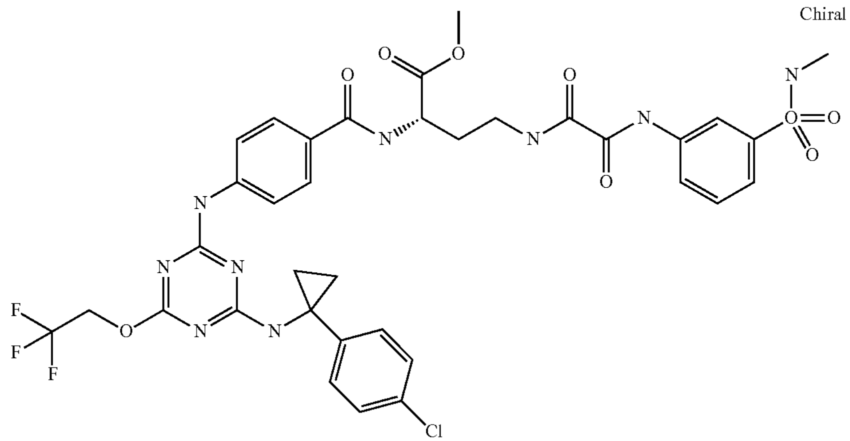 | 0.80 | A |

TABLE 1-continued
| Compound | Structure | EC$_{50}$ | Activity |
|---|---|---|---|
| 3604 | 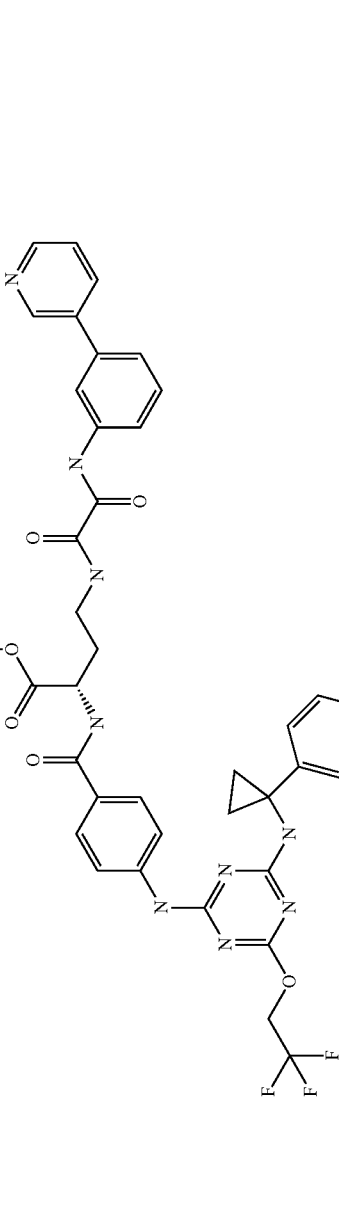 | | A |
| 3605 | 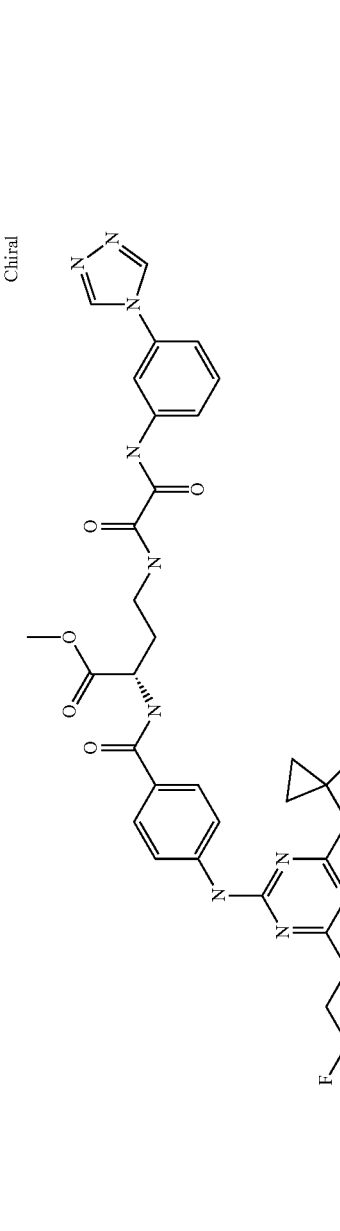 | | A |

| Compound | Structure | EC$_{50}$ | Activity |
|---|---|---|---|
| 3606 | 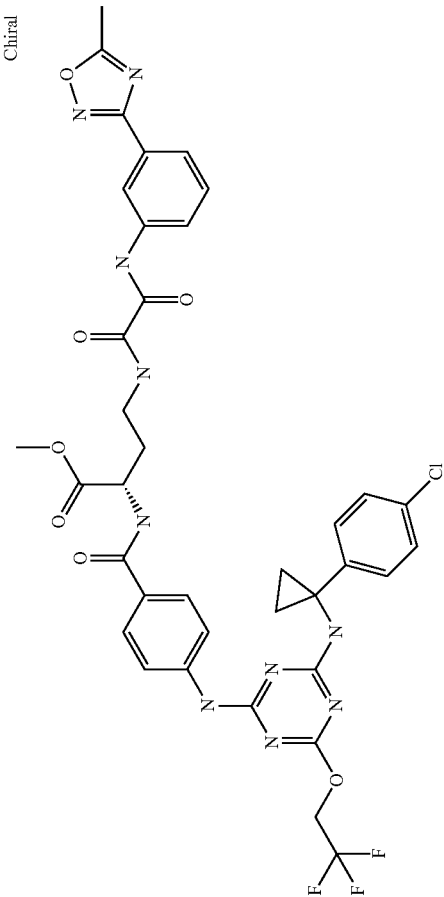 Chiral | | A |
| 3607 | 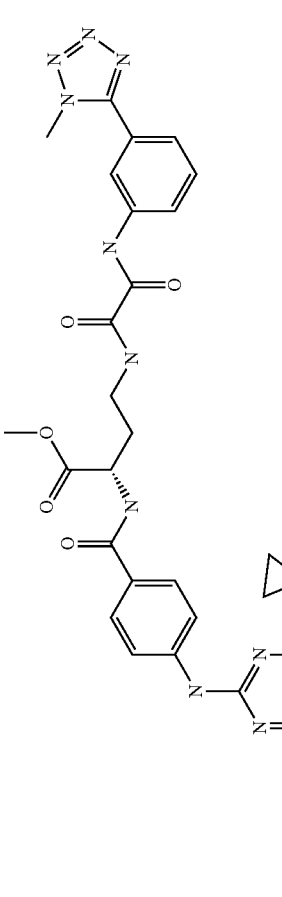 Chiral | | A |

TABLE 1-continued

| Compound | Structure | EC$_{50}$ | Activity |
|---|---|---|---|
| 3608 | Chiral | | A |
| 3609 | Chiral | | A |

TABLE 1-continued

| Compound | Structure | EC$_{50}$ | Activity |
|---|---|---|---|
| 3610 | 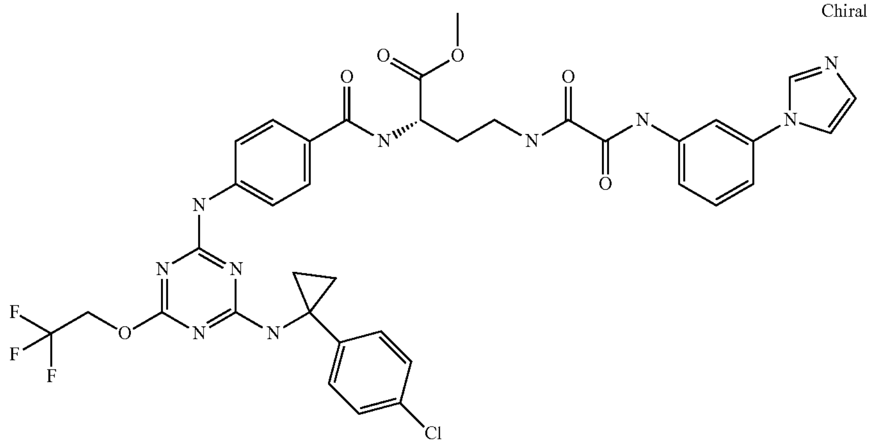 [SMILES: COC(=O)[C@H](CCNC(=O)C(=O)Nc1cccc(-n2ccnc2)c1)NC(=O)c1ccc(Nc2nc(NC3(c4ccc(Cl)cc4)CC3)nc(OCC(F)(F)F)n2)cc1] | | A |
| 3611 | 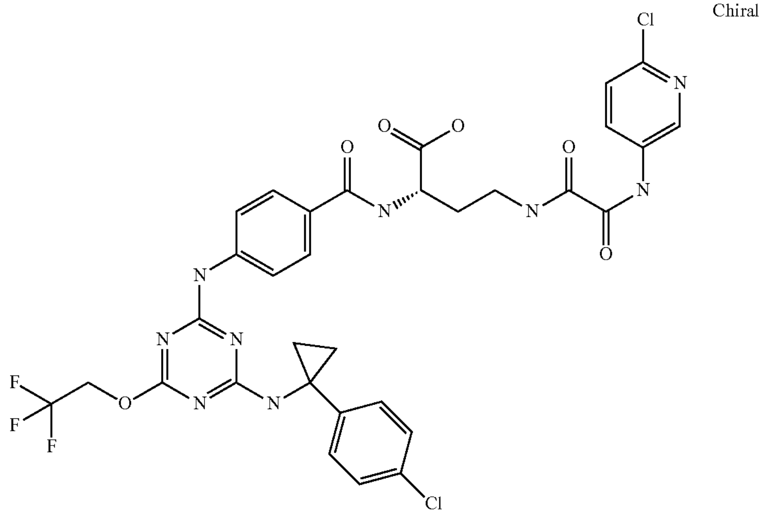 [SMILES: O=C(NCC[C@H](NC(=O)c1ccc(Nc2nc(NC3(c4ccc(Cl)cc4)CC3)nc(OCC(F)(F)F)n2)cc1)C(=O)O)C(=O)Nc1ccc(Cl)nc1] | | A |

TABLE 1-continued
| Compound | Structure | EC$_{50}$ | Activity |
|---|---|---|---|
| 3612 | 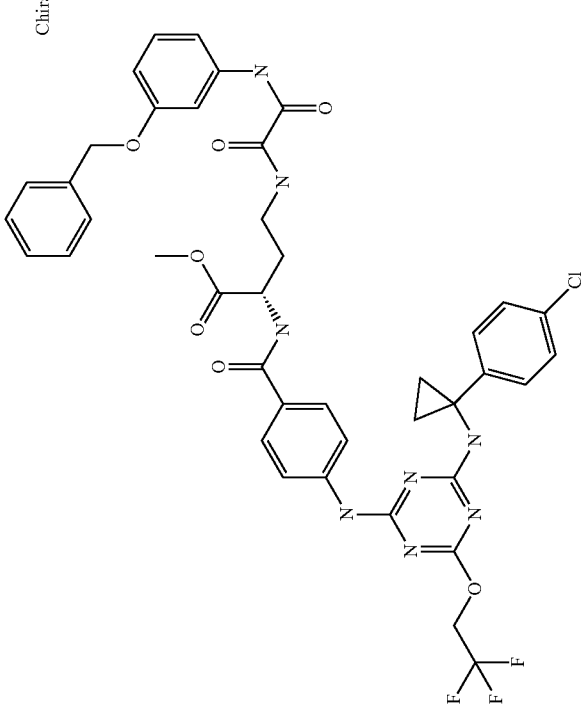 | | A |
| 3613 | 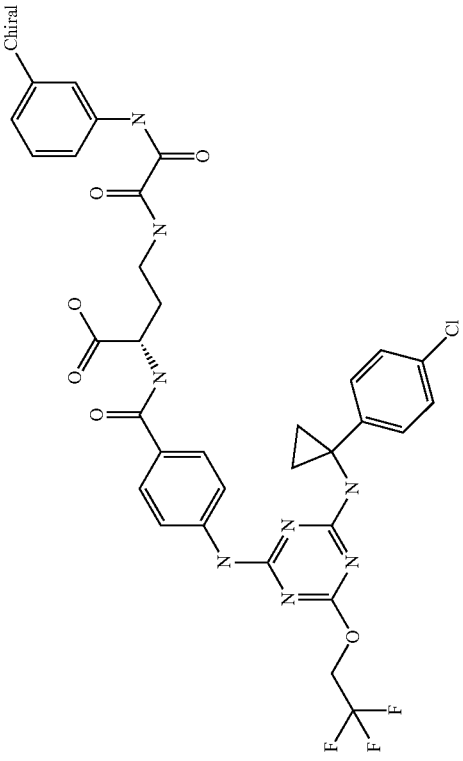 | 0.046 | A |

TABLE 1-continued
| Compound | Structure | EC$_{50}$ | Activity |
|---|---|---|---|
| 3614 | 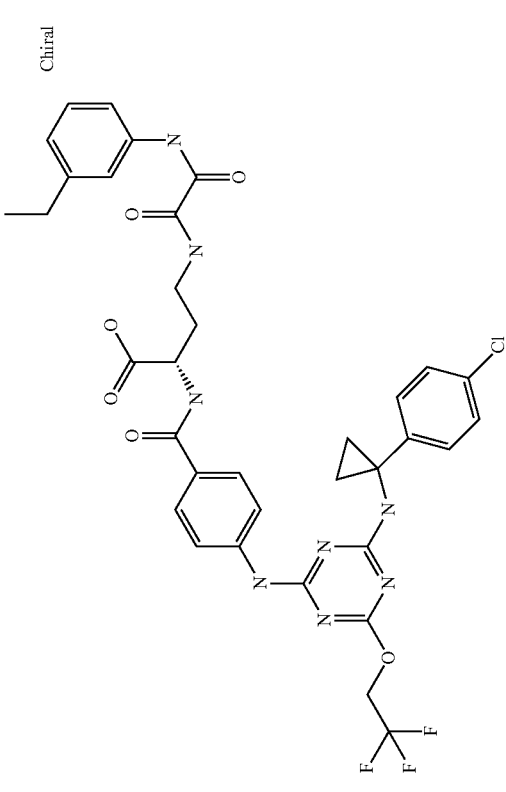 | | A |
| 3615 | 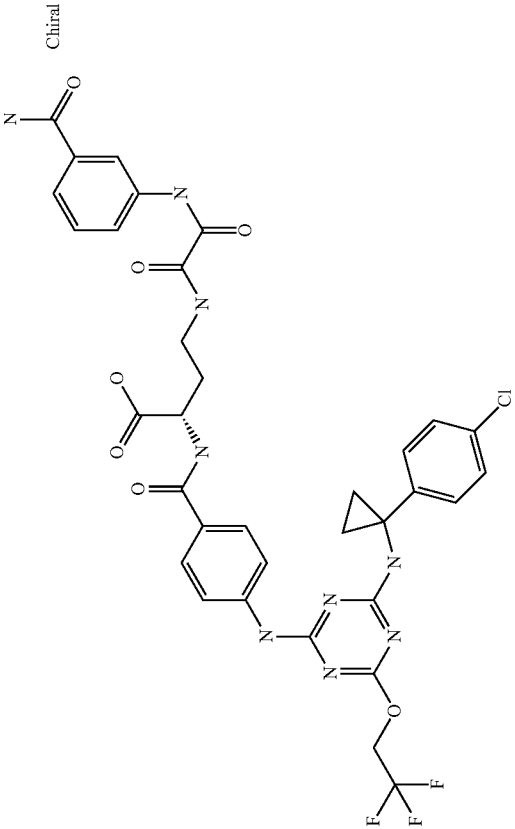 | | A |

TABLE 1-continued
| Compound | Structure | EC$_{50}$ | Activity |
|---|---|---|---|
| 3616 | 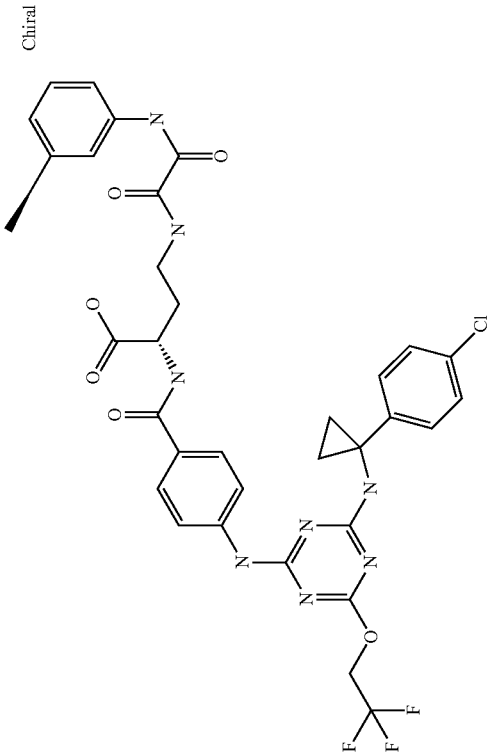 | | A |

TABLE 1-continued
| Compound | Structure | EC$_{50}$ | Activity |
|---|---|---|---|
| 3617 | 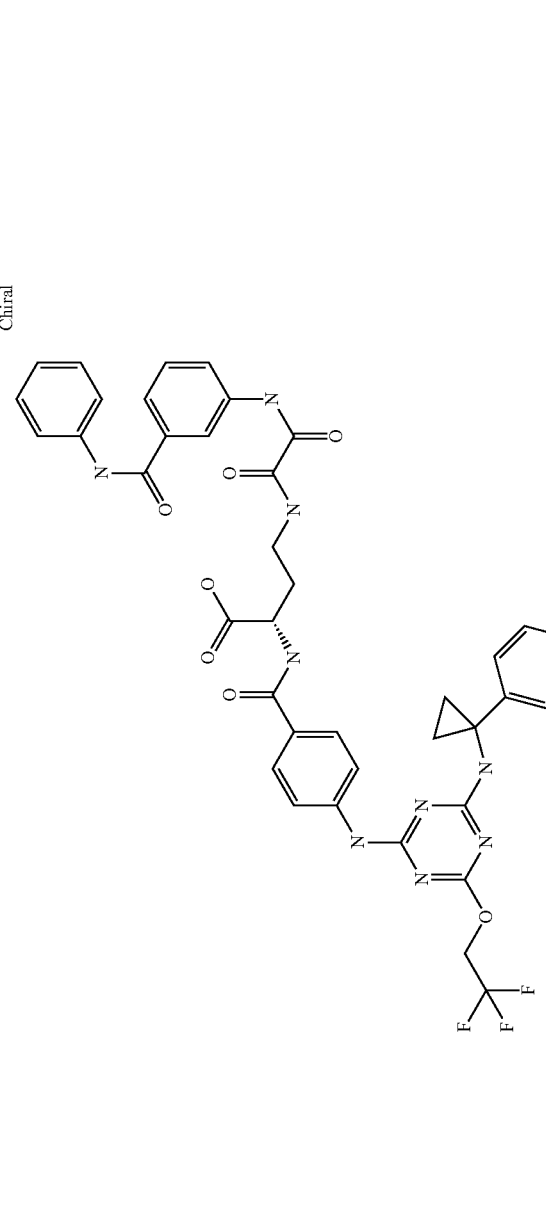 | | A |

TABLE 1-continued
| Compound | Structure | EC$_{50}$ | Activity |
|---|---|---|---|
| 3618 | 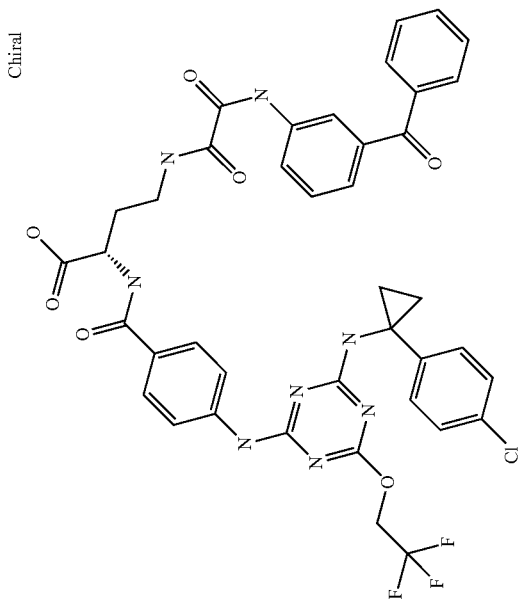 Chiral | | A |

TABLE 1-continued
| Compound | Structure | EC$_{50}$ | Activity |
|---|---|---|---|
| 3619 | 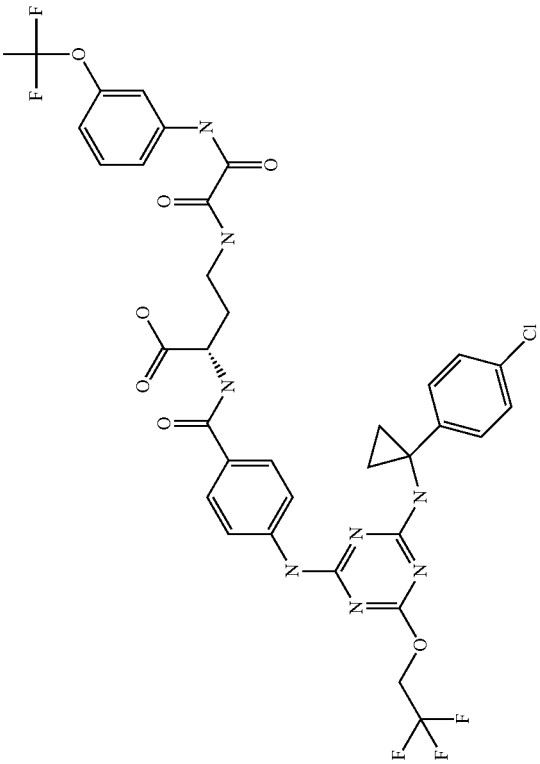 | 0.084 | A |
| 3620 | 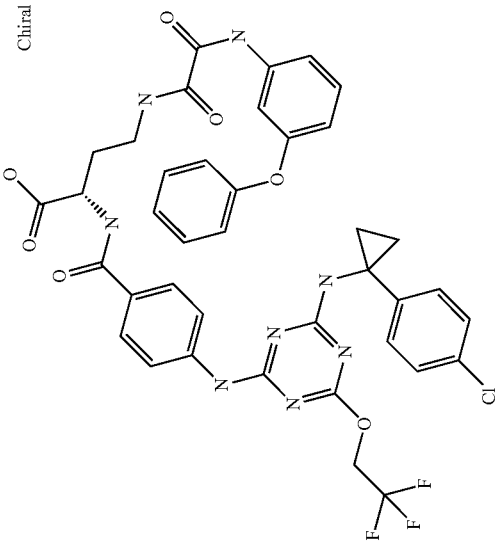 | | A |

TABLE 1-continued
| Compound | Structure | EC$_{50}$ | Activity |
|---|---|---|---|
| 3621 | 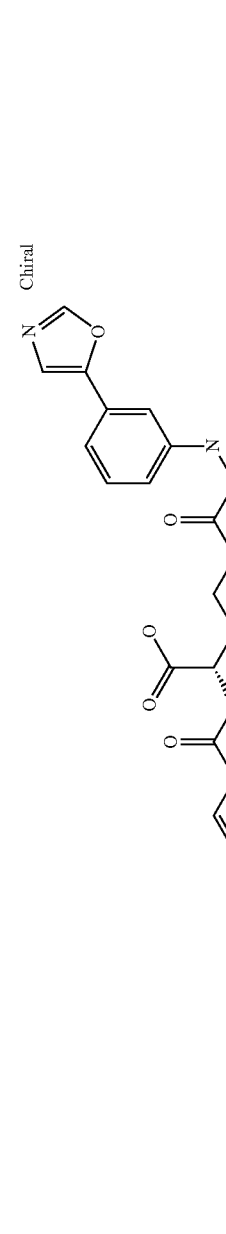 | | A |

TABLE 1-continued
| Compound | Structure | EC$_{50}$ | Activity |
|---|---|---|---|
| 3622 | 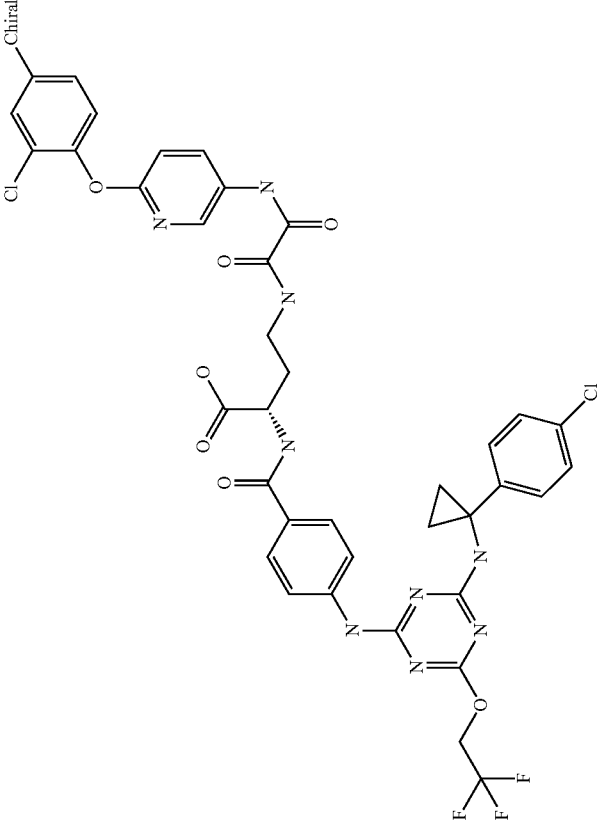 | | B |

TABLE 1-continued
| Compound | Structure | EC$_{50}$ | Activity |
|---|---|---|---|
| 3623 | 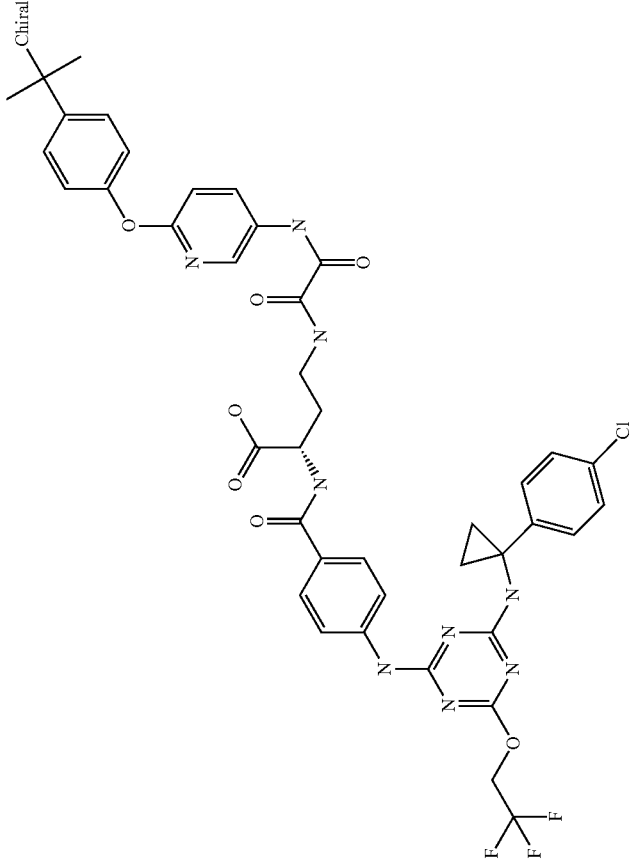 | | A |

TABLE 1-continued
| Compound | Structure | EC$_{50}$ | Activity |
|---|---|---|---|
| 3624 | 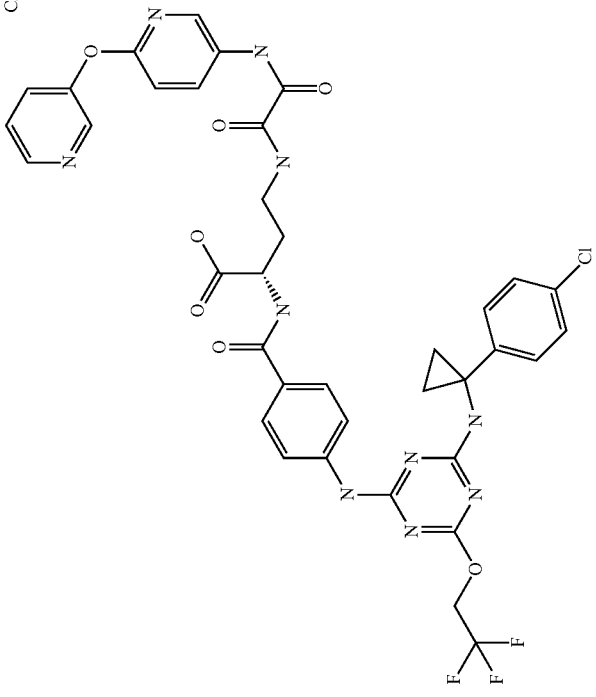 Chiral | | A |

TABLE 1-continued
| Compound | Structure | EC$_{50}$ | Activity |
|---|---|---|---|
| 3625 | 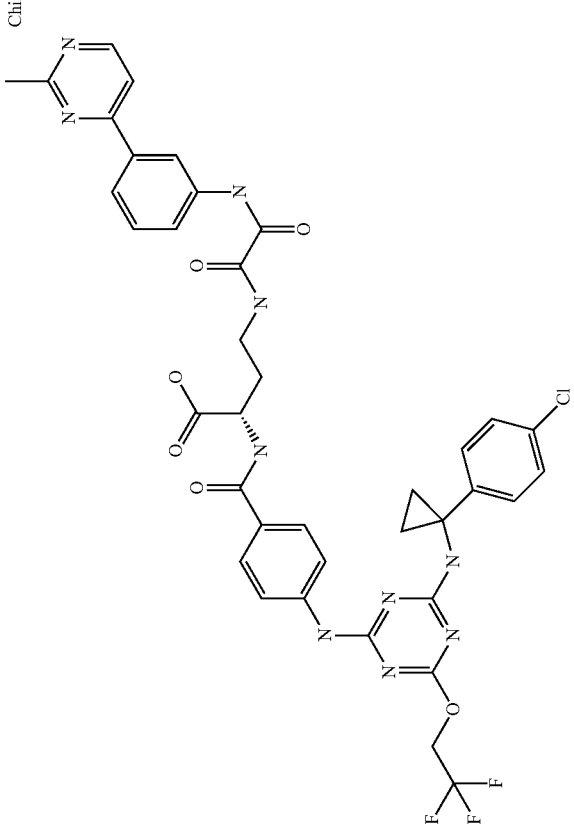 | | A |

TABLE 1-continued
| Compound | Structure | EC$_{50}$ | Activity |
|---|---|---|---|
| 3626 | 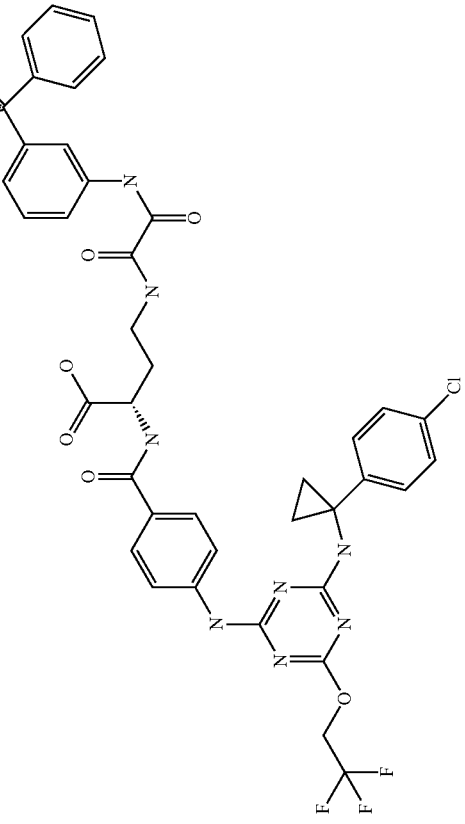 | | B |
| 3627 | 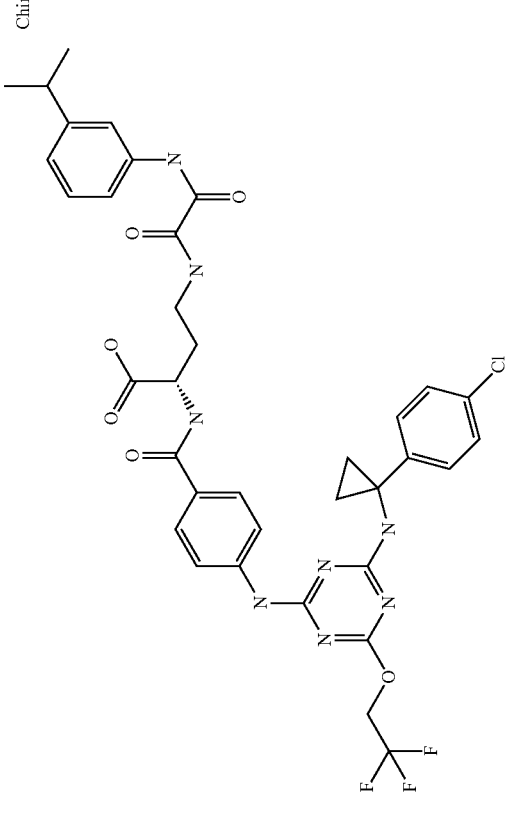 | 0.10 | A |

TABLE 1-continued
| Compound | Structure | EC$_{50}$ | Activity |
|---|---|---|---|
| 3628 | 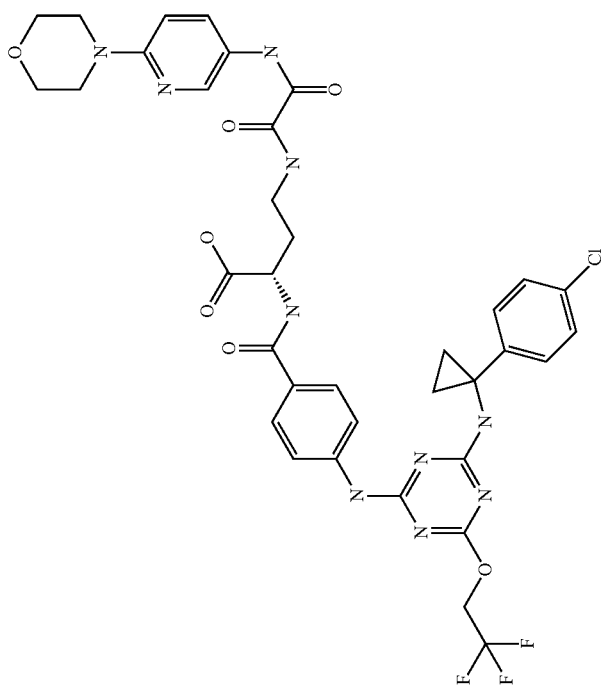 | | A |

| Compound | Structure | EC$_{50}$ | Activity |
|---|---|---|---|
| 3629 | 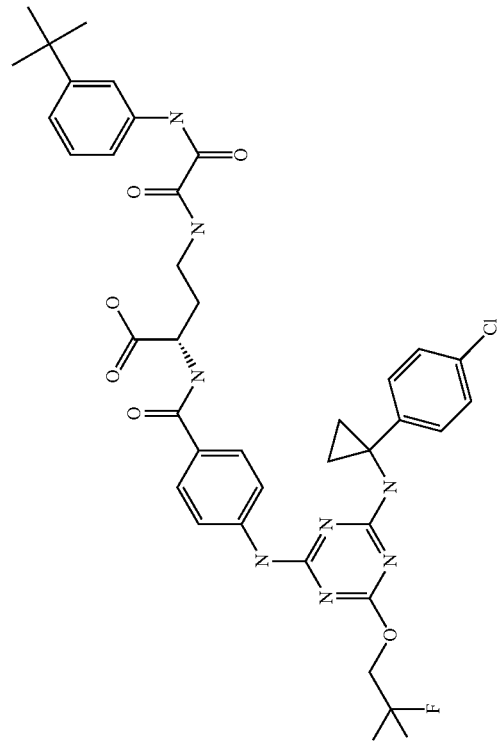 Chiral | | A |

TABLE 1-continued
| Compound | Structure | EC$_{50}$ | Activity |
|---|---|---|---|
| 3630 | 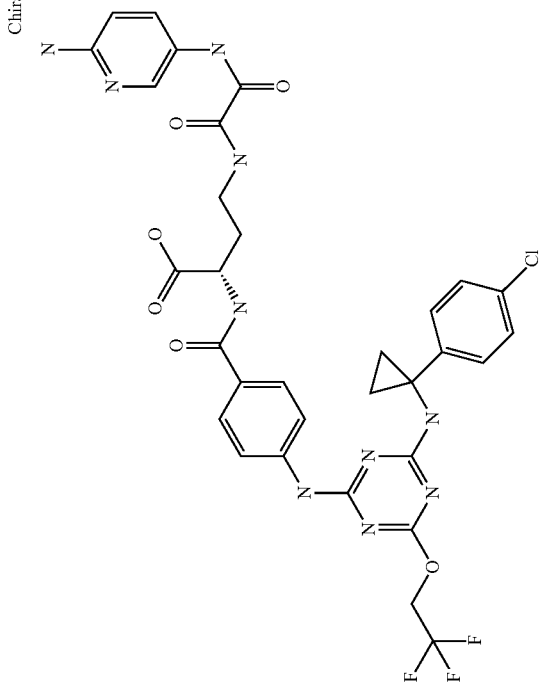 | | A |

TABLE 1-continued
| Compound | Structure | EC$_{50}$ | Activity |
|---|---|---|---|
| 3631 | Chiral 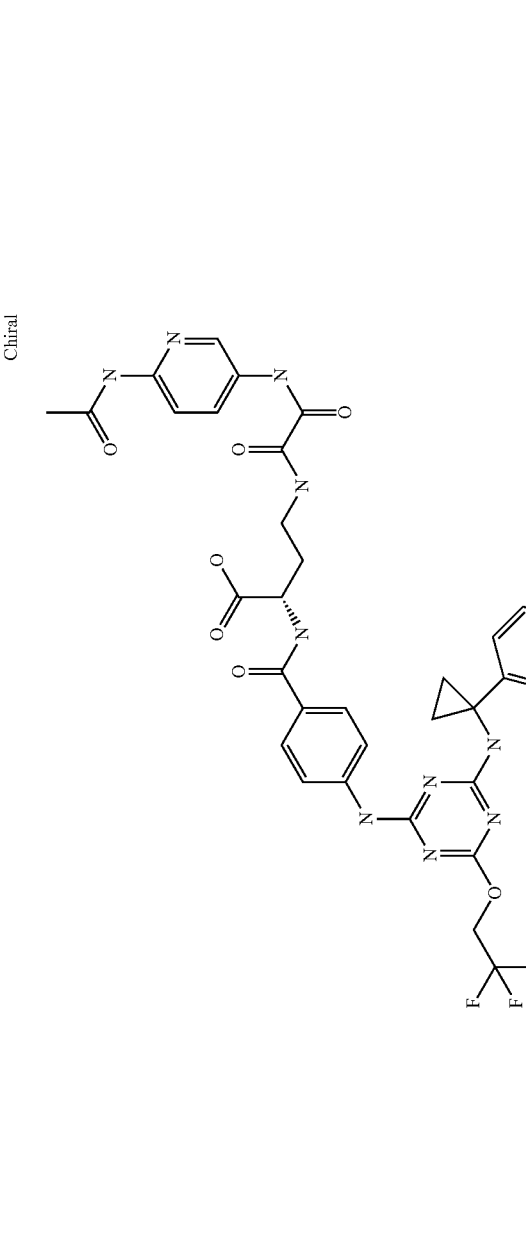 | | A |

TABLE 1-continued
| Compound | Structure | EC$_{50}$ | Activity |
|---|---|---|---|
| 3632 | 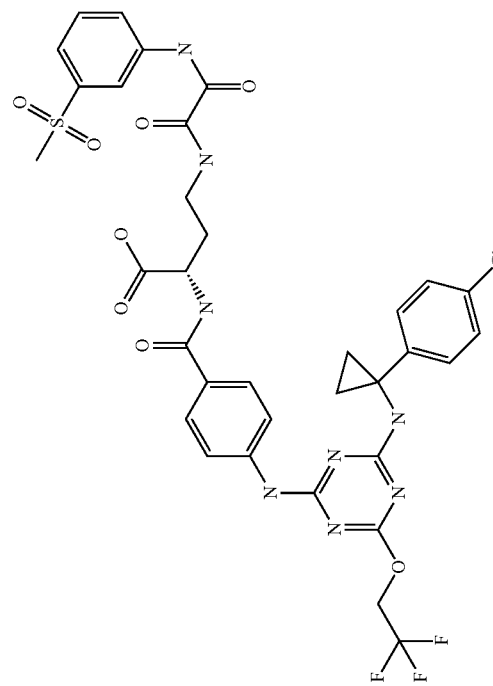 Chiral | | A |

TABLE 1-continued
| Compound | Structure | EC$_{50}$ | Activity |
|---|---|---|---|
| 3633 | 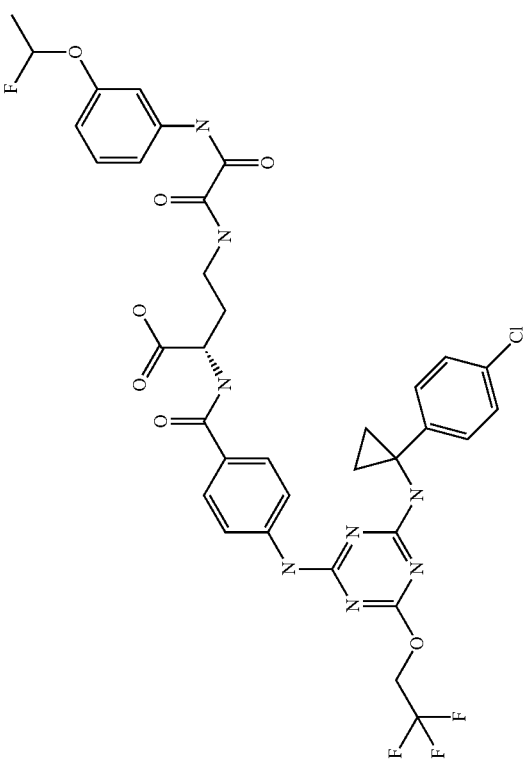 Chiral | 0.058 | A |

TABLE 1-continued
| Compound | Structure | EC$_{50}$ | Activity |
|---|---|---|---|
| 3634 | 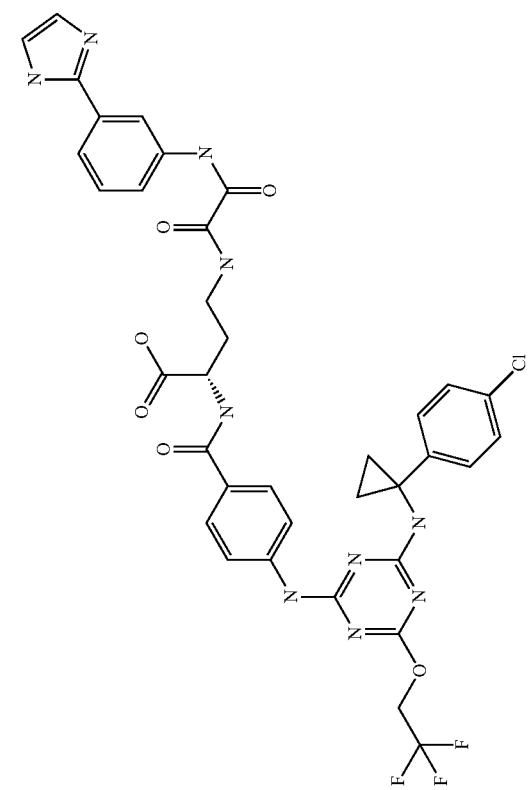 Chiral | | A |

TABLE 1-continued
| Compound | Structure | EC$_{50}$ | Activity |
|---|---|---|---|
| 3635 | 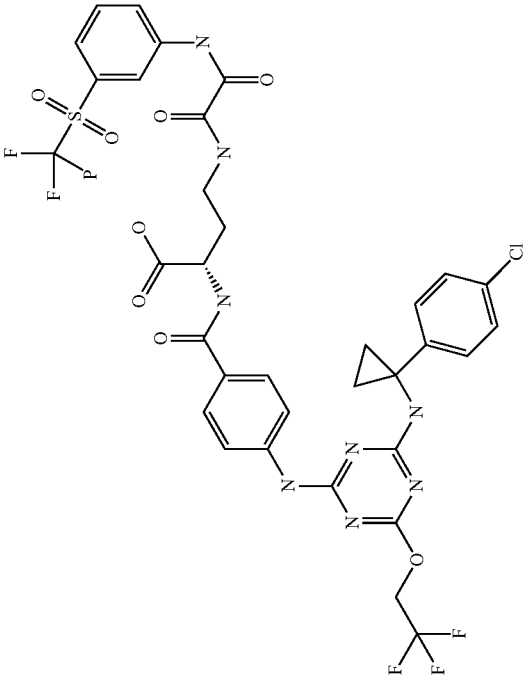 Chiral | | A |

TABLE 1-continued
| Compound | Structure | EC$_{50}$ | Activity |
|---|---|---|---|
| 3636 | Chiral 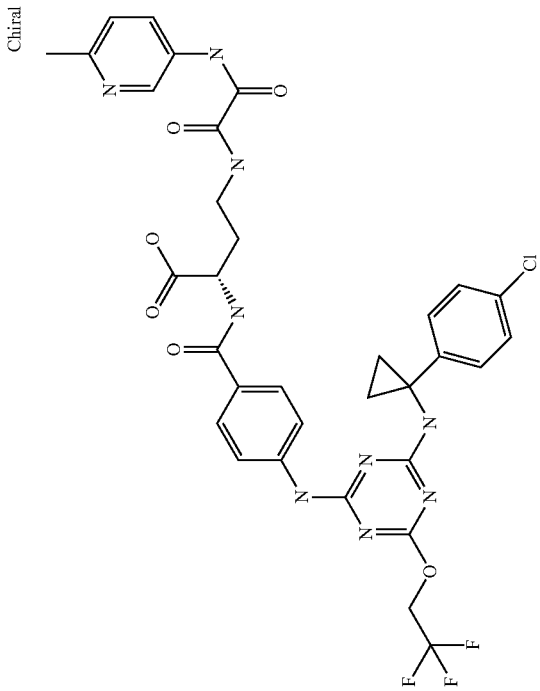 | | A |

TABLE 1-continued
| Compound | Structure | EC$_{50}$ | Activity |
|---|---|---|---|
| 3637 | Chiral 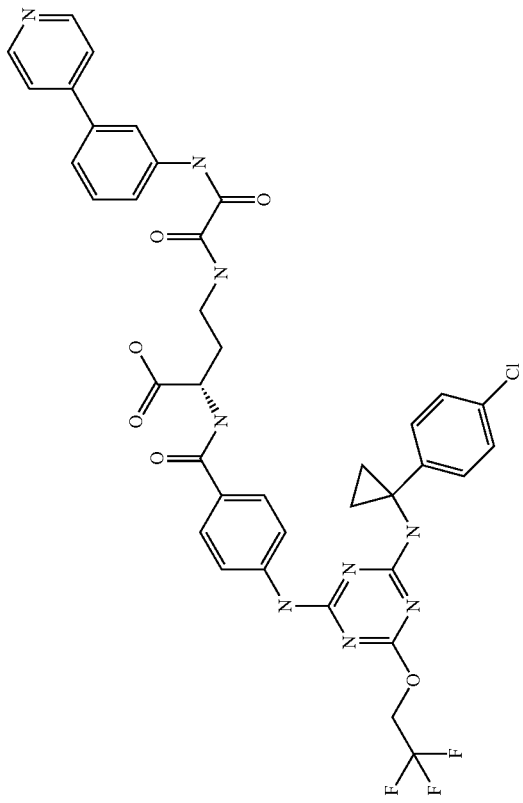 | | A |

TABLE 1-continued

| Compound | Structure | EC$_{50}$ | Activity |
|---|---|---|---|
| 3638 | Chiral | | A |
| 3639 | Chiral | | A |

TABLE 1-continued
| Compound | Structure | EC$_{50}$ | Activity |
|---|---|---|---|
| 3640 | 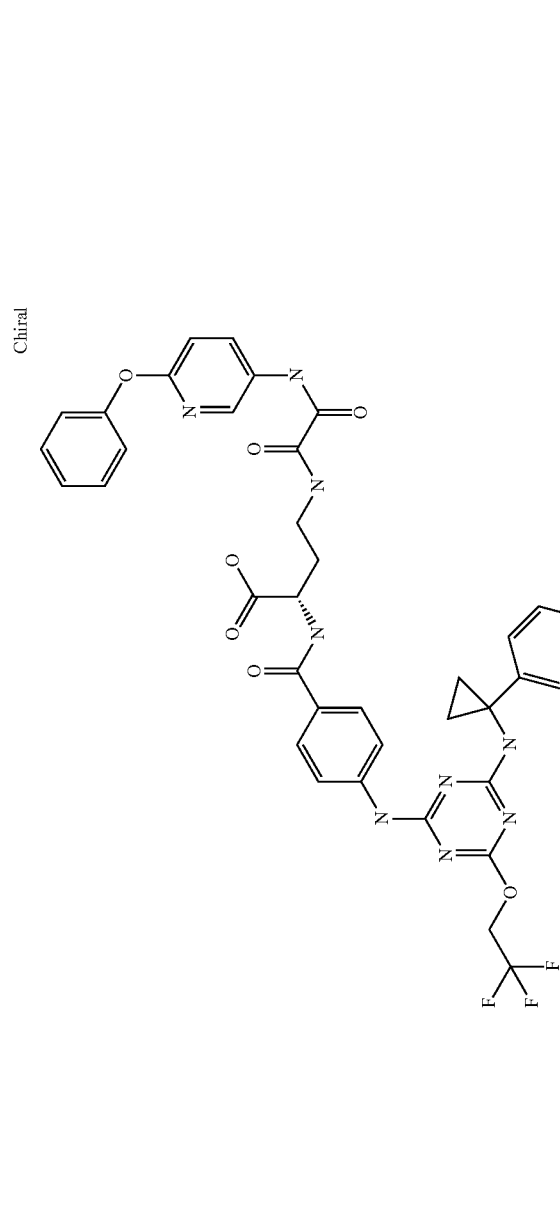 | 16.05 | B |

TABLE 1-continued
| Compound | Structure | EC$_{50}$ | Activity |
|---|---|---|---|
| 3641 | 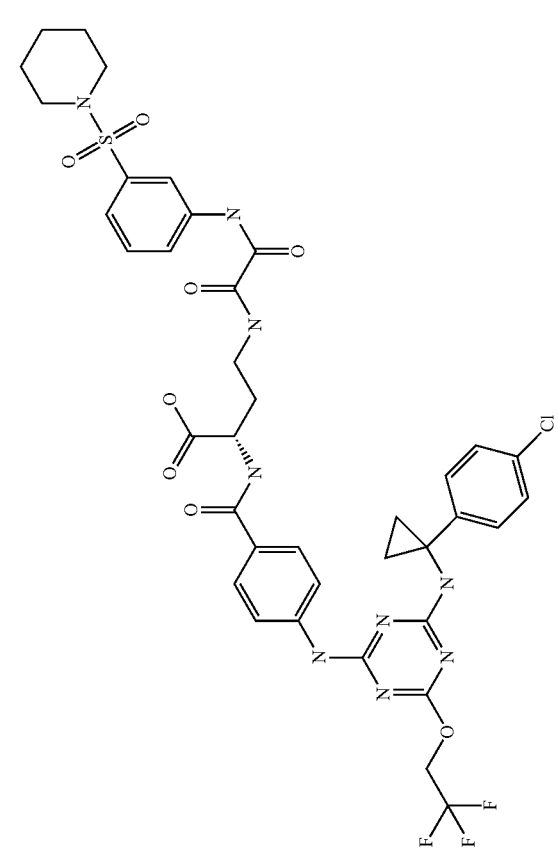 Chiral | | A |

TABLE 1-continued
| Compound | Structure | EC$_{50}$ | Activity |
|---|---|---|---|
| 3642 | 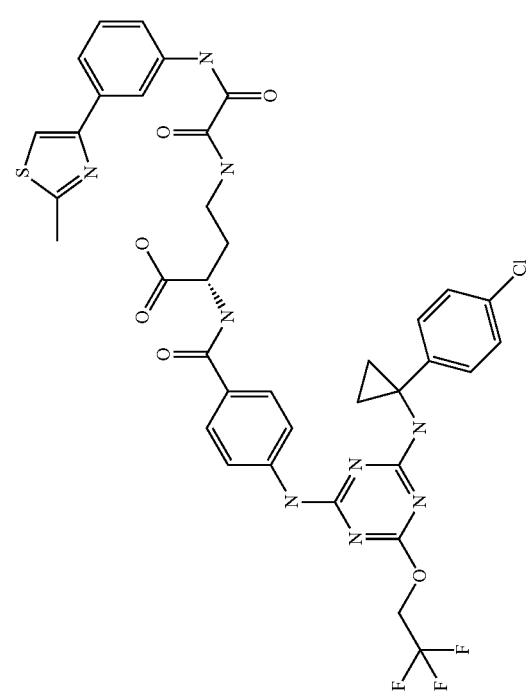 Chiral | | A |

TABLE 1-continued
| Compound | Structure | EC$_{50}$ | Activity |
|---|---|---|---|
| 3643 | 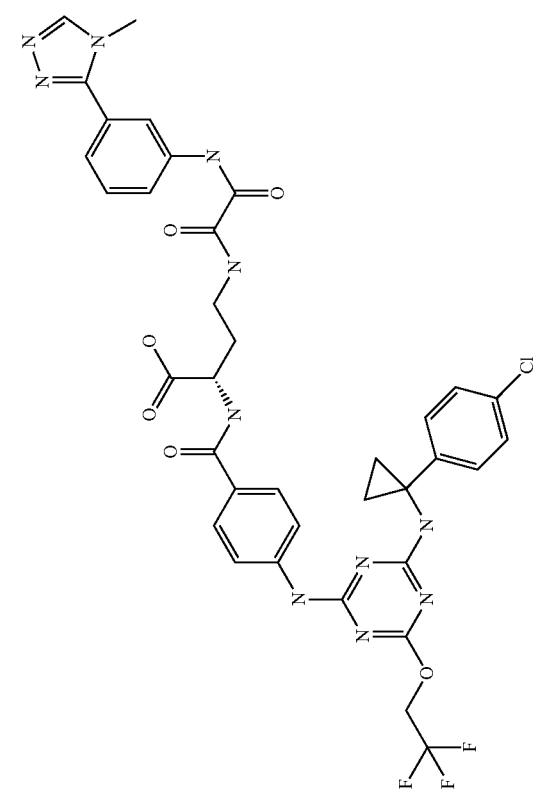 | | B |

TABLE 1-continued
| Compound | Structure | EC$_{50}$ | Activity |
|---|---|---|---|
| 3644 | 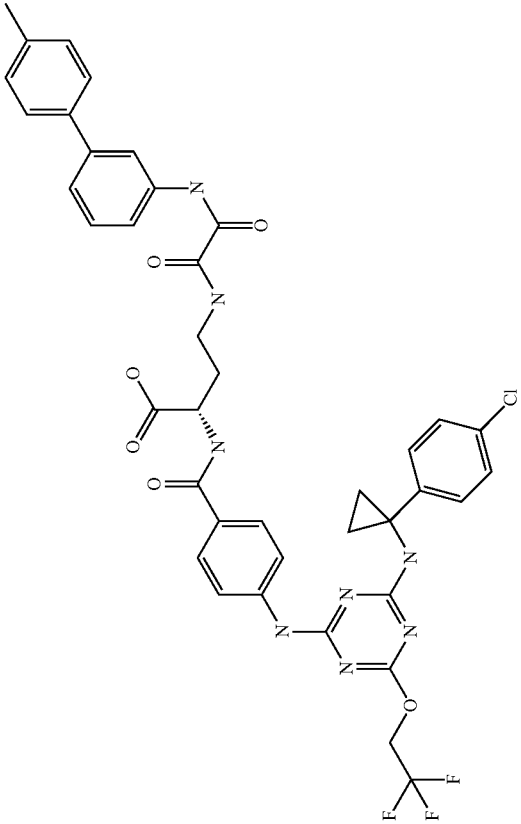 Chiral | | A |

TABLE 1-continued
| Compound | Structure | EC$_{50}$ | Activity |
|---|---|---|---|
| 3645 | 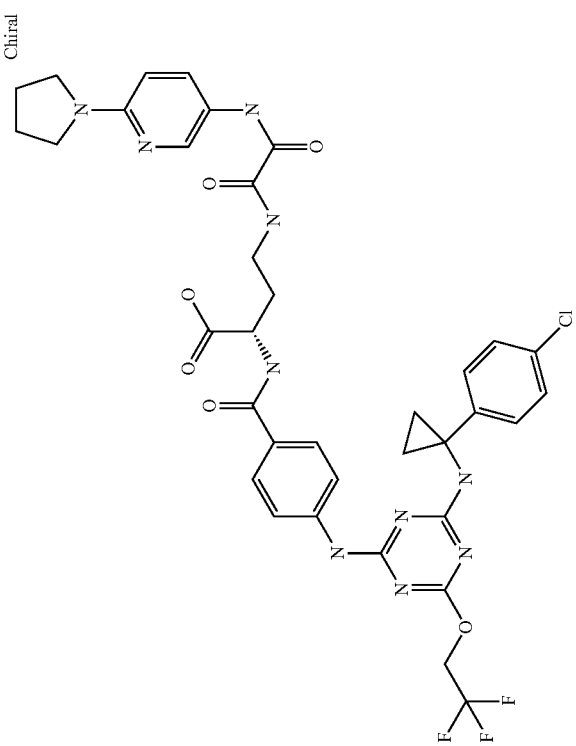 | | A |

TABLE 1-continued
| Compound | Structure | EC$_{50}$ | Activity |
|---|---|---|---|
| 3646 | 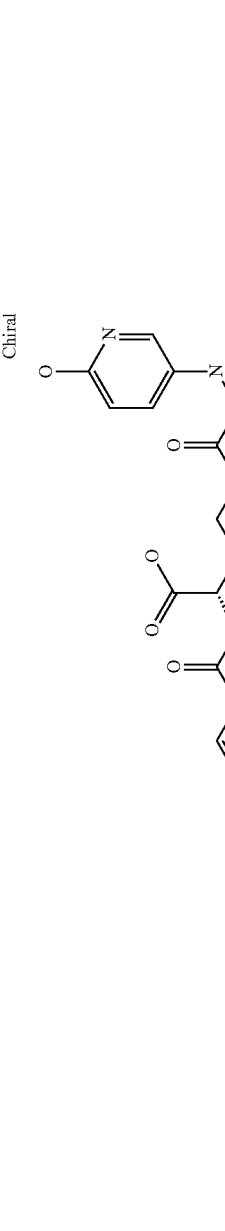 Chiral | | A |

TABLE 1-continued
| Compound | Structure | EC$_{50}$ | Activity |
|---|---|---|---|
| 3647 | 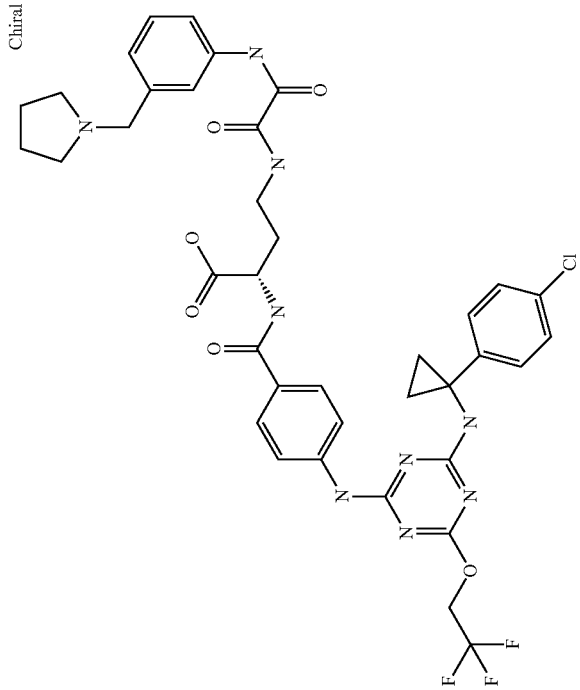 | | A |

TABLE 1-continued
| Compound | Structure | EC$_{50}$ | Activity |
|---|---|---|---|
| 3648 | 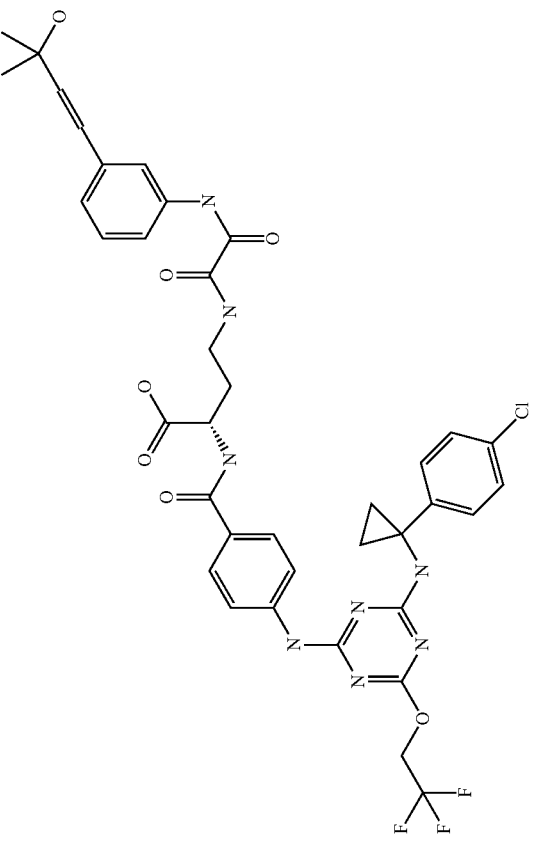 Chiral | 0.20 | A |

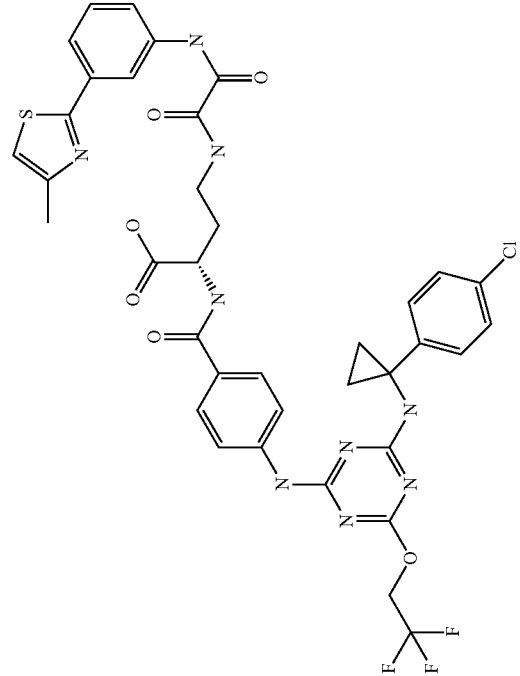

TABLE 1-continued
| Compound | Structure | EC$_{50}$ | Activity |
|---|---|---|---|
| 3651 | 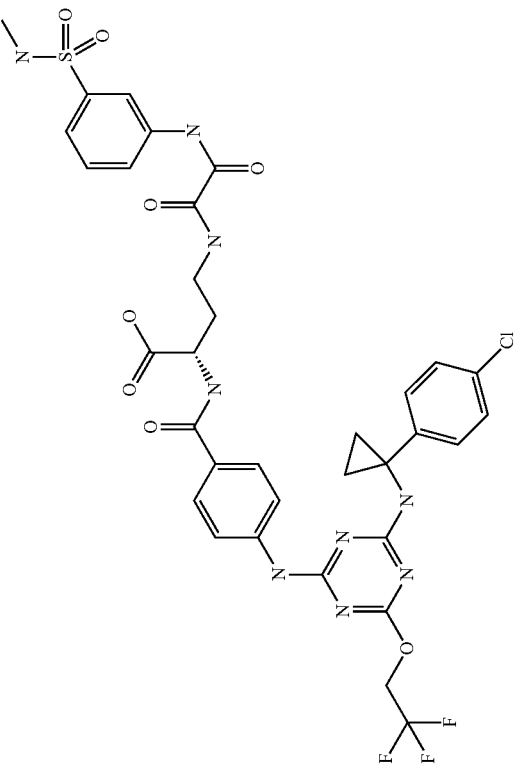 Chiral | | A |

TABLE 1-continued
| Compound | Structure | EC$_{50}$ | Activity |
|---|---|---|---|
| 3652 | 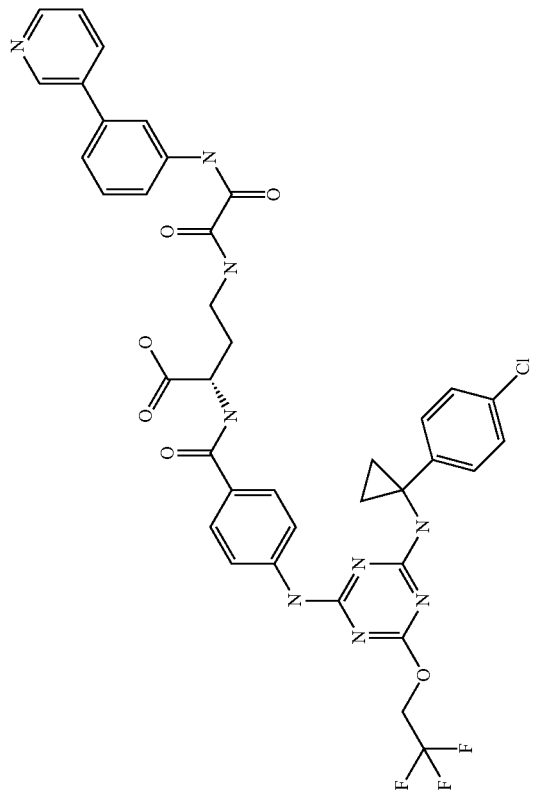 Chiral | 0.45 | A |

TABLE 1-continued
| Compound | Structure | EC₅₀ | Activity |
|---|---|---|---|
| 3653 | 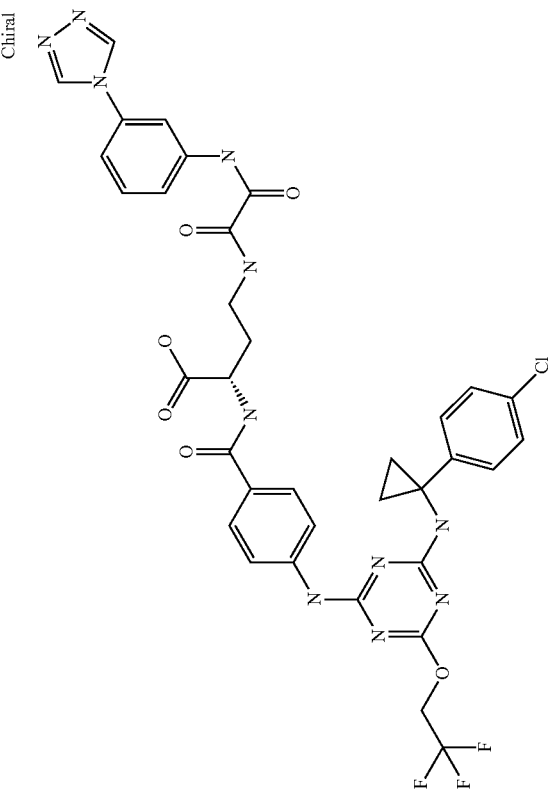 | | A |

TABLE 1-continued
| Compound | Structure | EC$_{50}$ | Activity |
|---|---|---|---|
| 3654 | 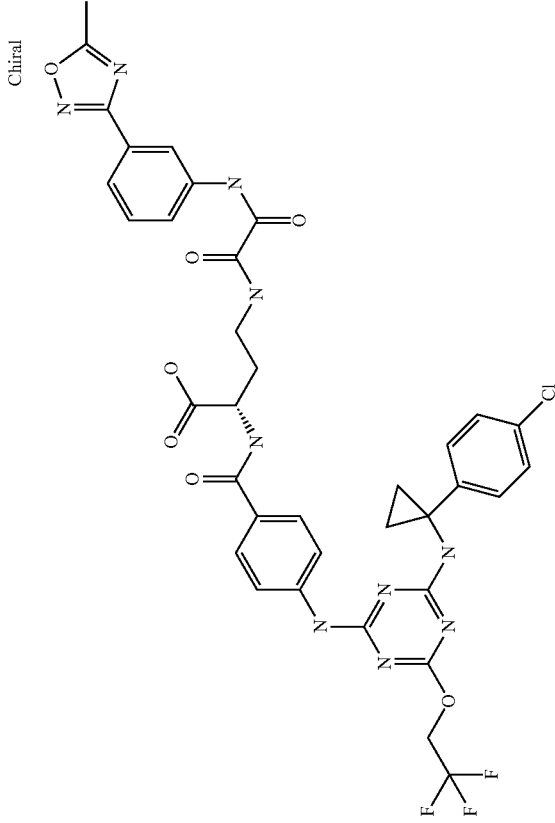 Chiral | | A |

TABLE 1-continued
| Compound | Structure | EC$_{50}$ | Activity |
|---|---|---|---|
| 3655 | 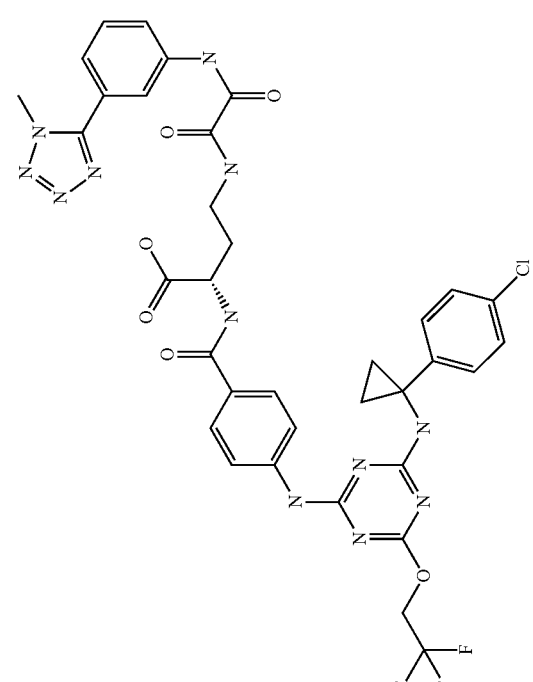 | | A |

TABLE 1-continued
| Compound | Structure | EC$_{50}$ | Activity |
|---|---|---|---|
| 3656 | Chiral 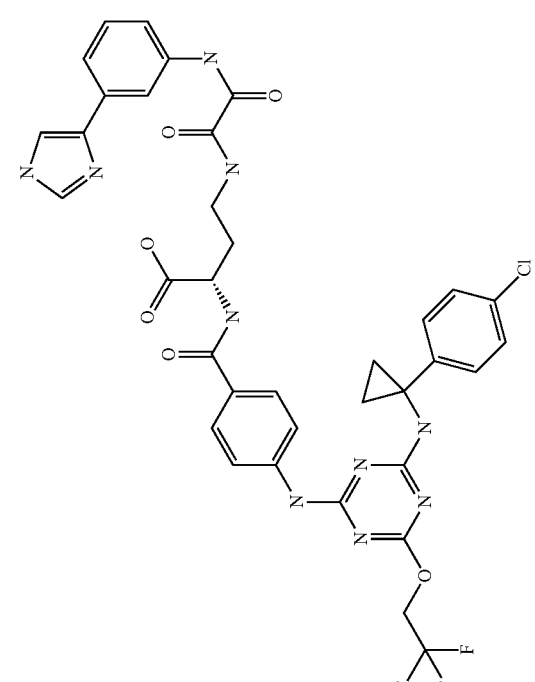 | | A |

TABLE 1-continued
| Compound | Structure | EC$_{50}$ | Activity |
|---|---|---|---|
| 3657 | 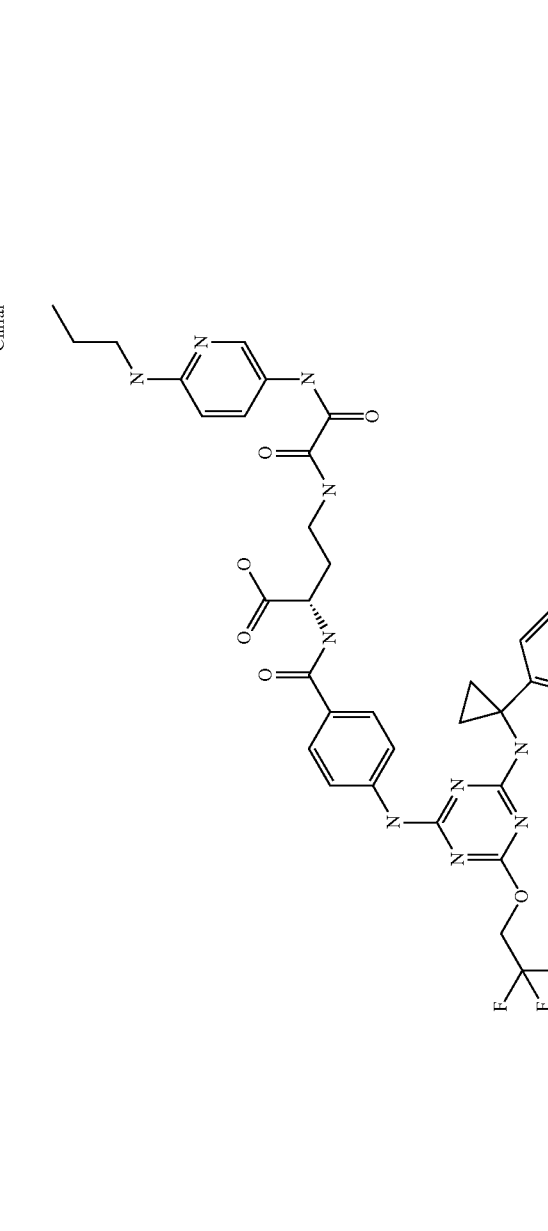 Chiral | | A |

TABLE 1-continued

| Compound | Structure | EC$_{50}$ | Activity |
|---|---|---|---|
| 3658 | Chiral | | A |

TABLE 1-continued
| Compound | Structure | EC$_{50}$ | Activity |
|---|---|---|---|
| 3659 | Chiral 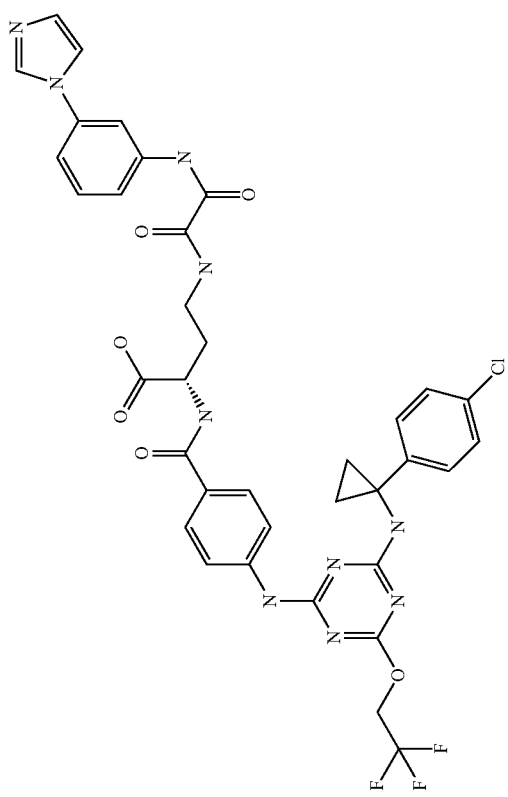 | | A |

TABLE 1-continued
| Compound | Structure | EC$_{50}$ | Activity |
|---|---|---|---|
| 3660 | 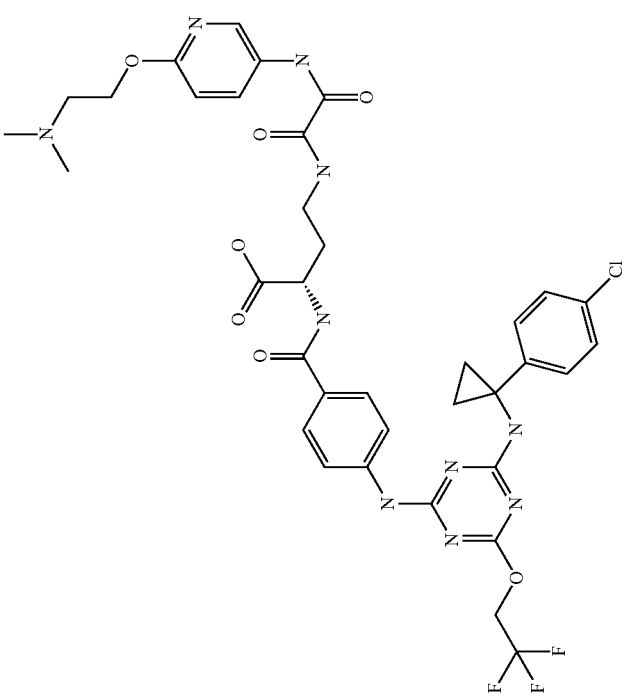 Chiral | 1.67 | A |

TABLE 1-continued
| Compound | Structure | EC$_{50}$ | Activity |
|---|---|---|---|
| 3661 | Chiral 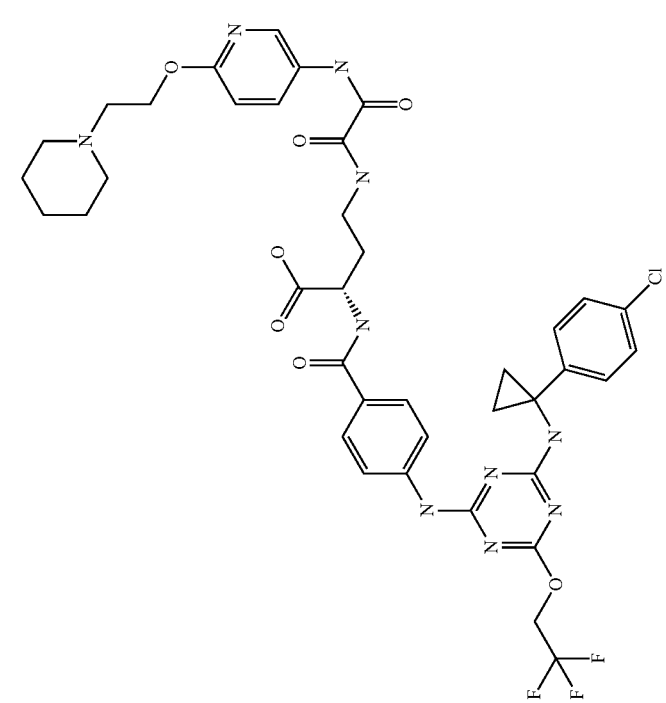 | | A |

| Compound | Structure | EC$_{50}$ | Activity |
|---|---|---|---|
| 3662 | 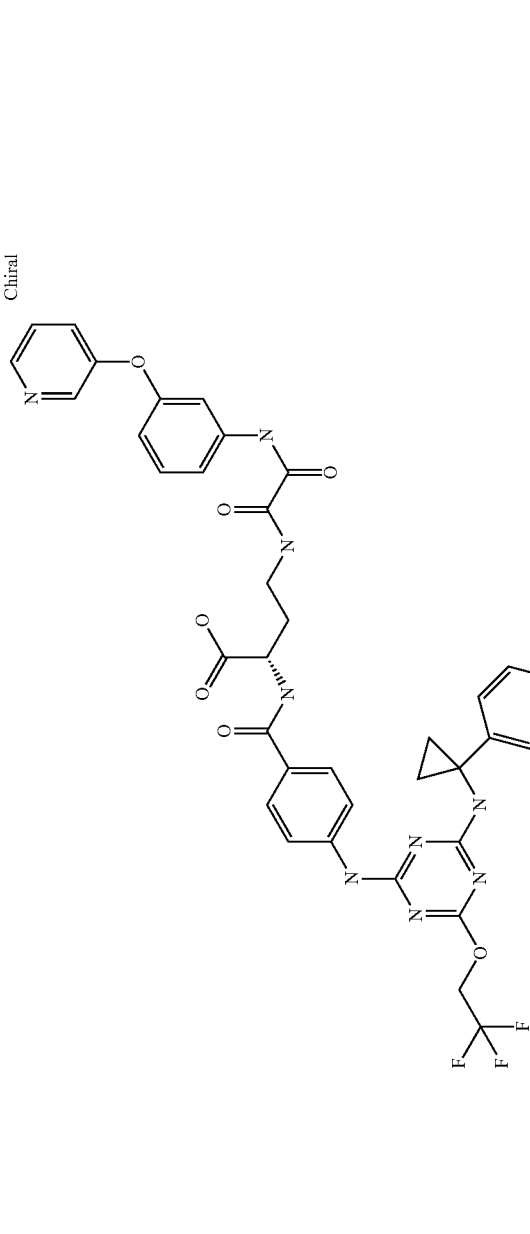 Chiral | | A |

TABLE 1-continued
| Compound | Structure | EC$_{50}$ | Activity |
|---|---|---|---|
| 3663 | 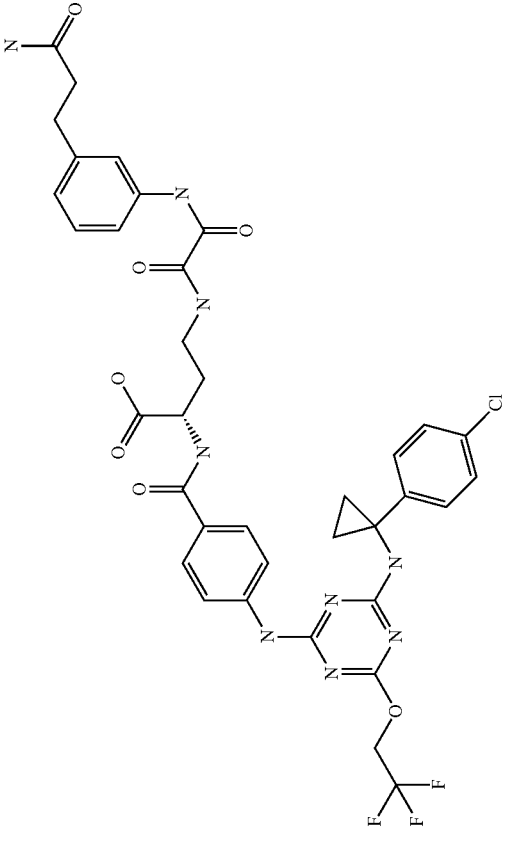 | | A |
| 3664 | 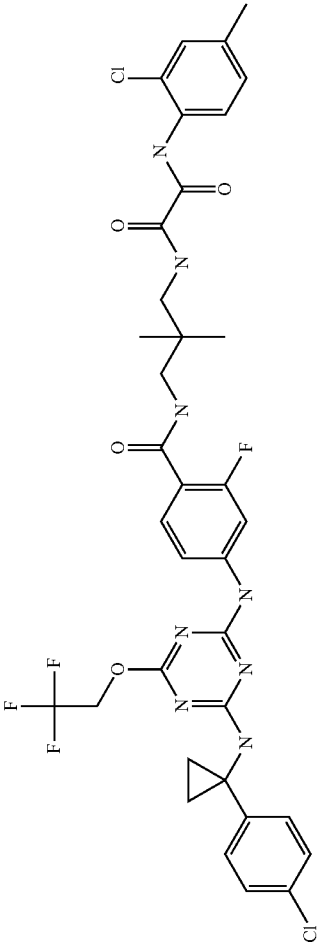 | 0.038 | A |

TABLE 1-continued

| Compound | Structure | EC$_{50}$ | Activity |
|---|---|---|---|
| 3665 | 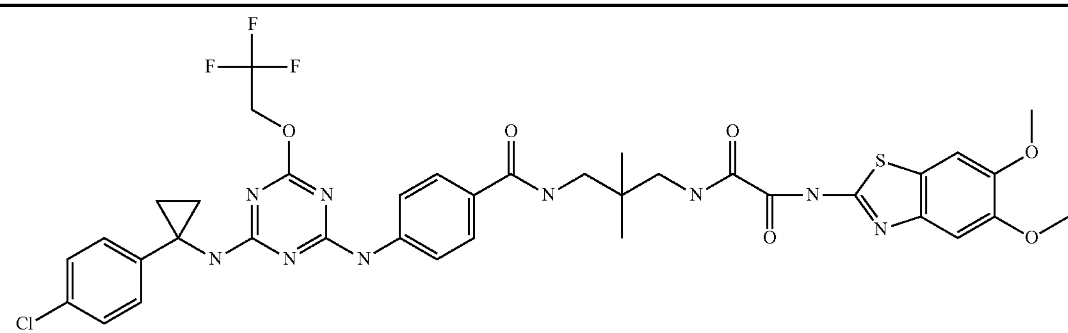 | | A |
| 3666 | 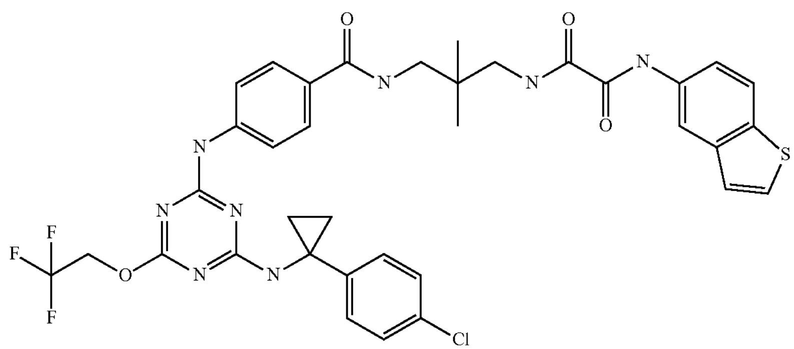 [SMILES: CC(C)(CNC(=O)C(=O)Nc1ccc2sccc2c1)CNC(=O)c1ccc(Nc2nc(NC3(c4ccc(Cl)cc4)CC3)nc(OCC(F)(F)F)n2)cc1] | | A |
| 3667 | 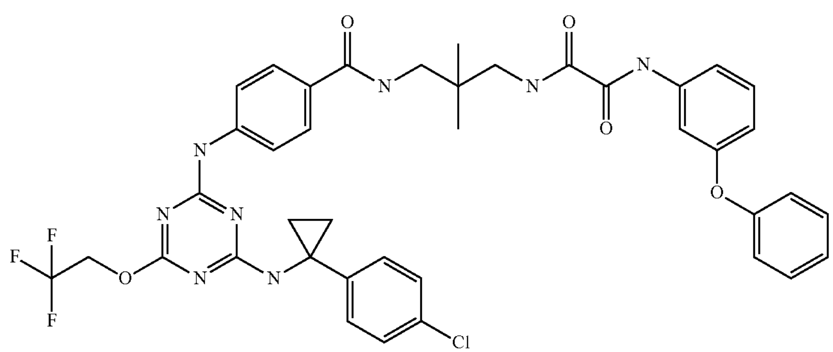 [SMILES: CC(C)(CNC(=O)C(=O)Nc1cccc(Oc2ccccc2)c1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3668 | 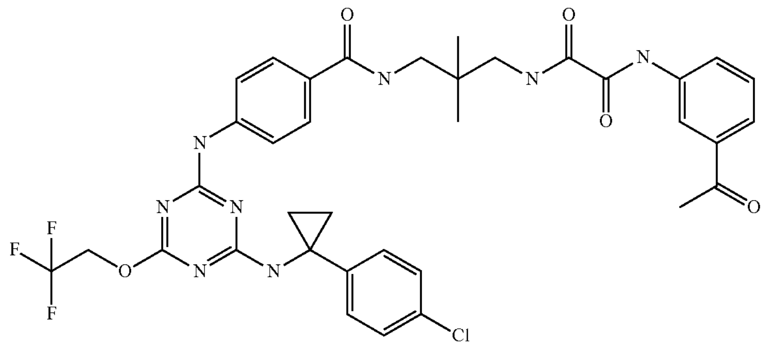 [SMILES: CC(=O)c1cccc(NC(=O)C(=O)NCC(C)(C)CNC(=O)c2ccc(Nc3nc(NC4(c5ccc(Cl)cc5)CC4)nc(OCC(F)(F)F)n3)cc2)c1] | | A |
| 3669 | 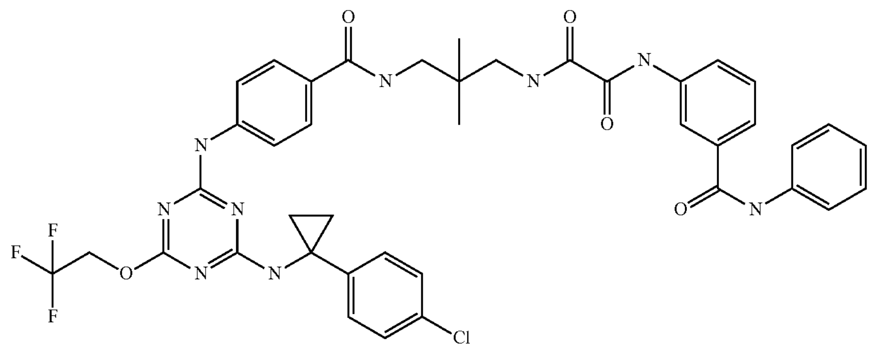 [SMILES: CC(C)(CNC(=O)C(=O)Nc1cccc(C(=O)Nc2ccccc2)c1)CNC(=O)c1ccc(Nc2nc(NC3(c4ccc(Cl)cc4)CC3)nc(OCC(F)(F)F)n2)cc1] | | A |
| 3670 | 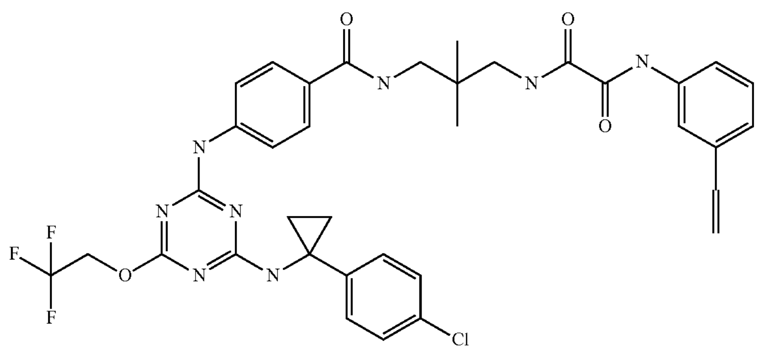 [SMILES: C=Cc1cccc(NC(=O)C(=O)NCC(C)(C)CNC(=O)c2ccc(Nc3nc(NC4(c5ccc(Cl)cc5)CC4)nc(OCC(F)(F)F)n3)cc2)c1] | | A |

TABLE 1-continued

| Compound | Structure | EC$_{50}$ | Activity |
|---|---|---|---|
| 3671 | 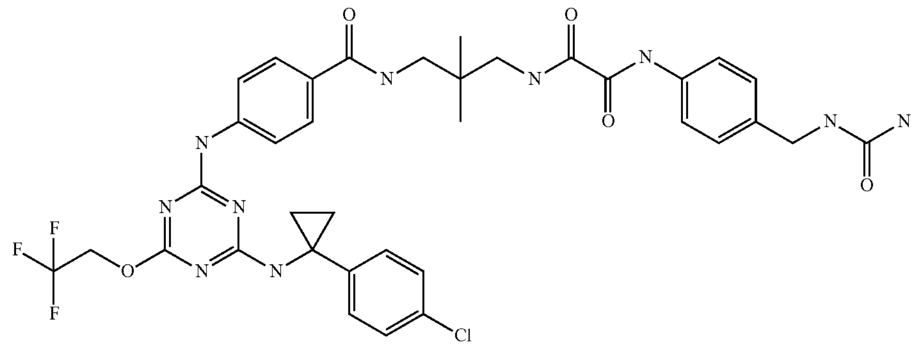 [SMILES: CC(C)(CNC(=O)C(=O)Nc1ccc(CNC(N)=O)cc1)CNC(=O)c1ccc(Nc2nc(NC3(c4ccc(Cl)cc4)CC3)nc(OCC(F)(F)F)n2)cc1] | | A |
| 3672 | 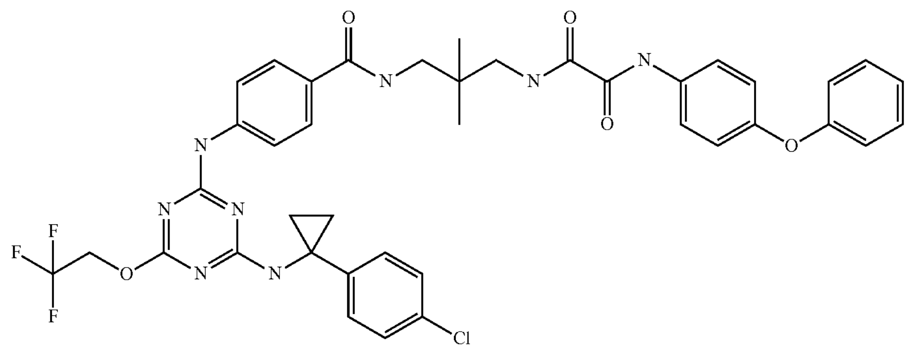 [SMILES: CC(C)(CNC(=O)C(=O)Nc1ccc(Oc2ccccc2)cc1)CNC(=O)c1ccc(Nc2nc(NC3(c4ccc(Cl)cc4)CC3)nc(OCC(F)(F)F)n2)cc1] | | A |
| 3673 | 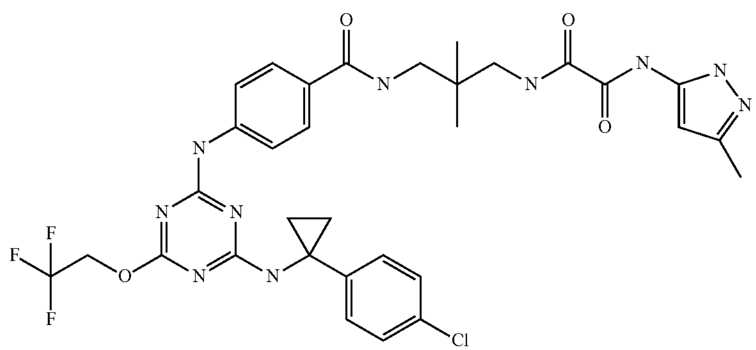 [SMILES: Cc1cc(NC(=O)C(=O)NCC(C)(C)CNC(=O)c2ccc(Nc3nc(NC4(c5ccc(Cl)cc5)CC4)nc(OCC(F)(F)F)n3)cc2)[nH]n1] | | A |

TABLE 1-continued

| Compound | Structure | EC$_{50}$ | Activity |
|---|---|---|---|
| 3674 | 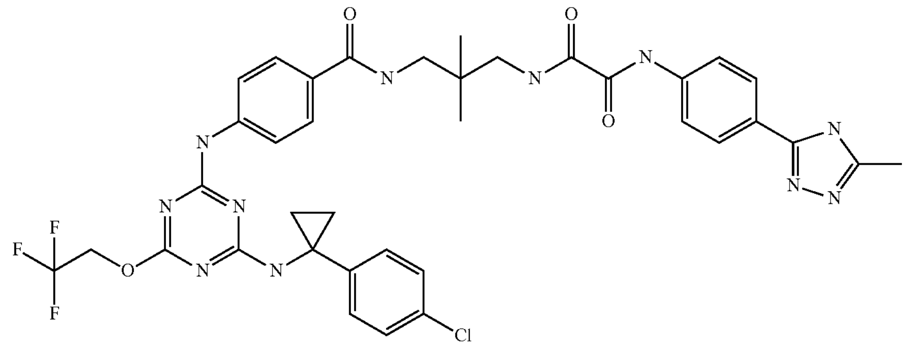 [SMILES: Cc1nnc(-c2ccc(NC(=O)C(=O)NCC(C)(C)CNC(=O)c3ccc(Nc4nc(NC5(c6ccc(Cl)cc6)CC5)nc(OCC(F)(F)F)n4)cc3)cc2)[nH]1] | 0.15 | A |
| 3675 | 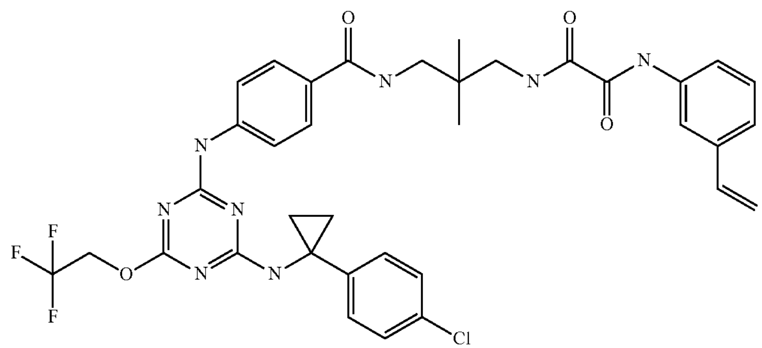 [SMILES: C=Cc1cccc(NC(=O)C(=O)NCC(C)(C)CNC(=O)c2ccc(Nc3nc(NC4(c5ccc(Cl)cc5)CC4)nc(OCC(F)(F)F)n3)cc2)c1] | | A |
| 3676 | 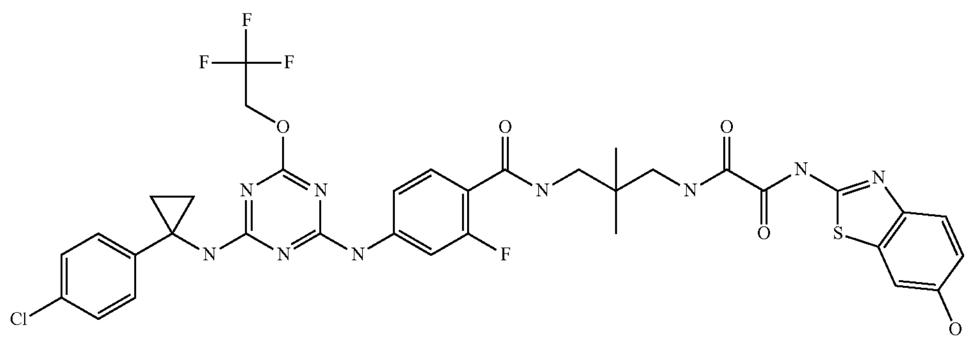 [SMILES: CC(C)(CNC(=O)C(=O)Nc1nc2ccc(O)cc2s1)CNC(=O)c1ccc(Nc2nc(NC3(c4ccc(Cl)cc4)CC3)nc(OCC(F)(F)F)n2)cc1F] | | A |

TABLE 1-continued

| Compound | Structure | EC$_{50}$ | Activity |
|---|---|---|---|
| 3677 | 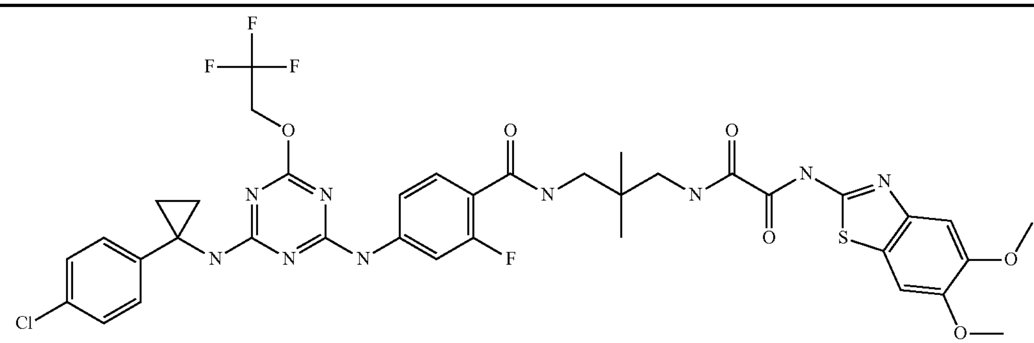 | | A |
| 3678 | 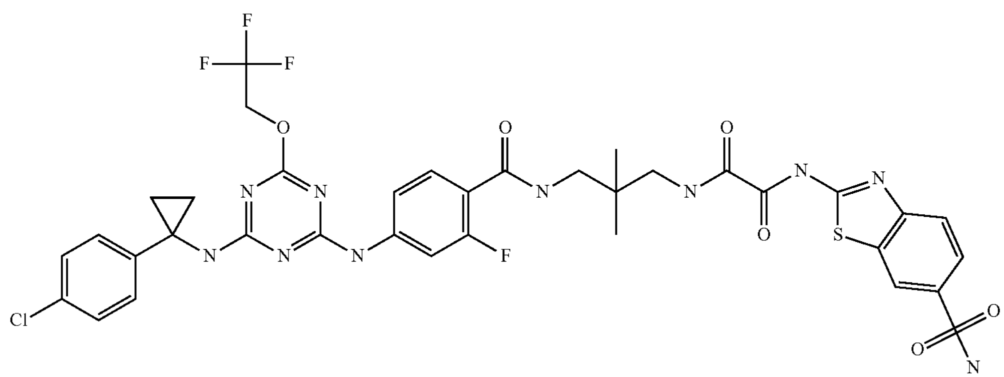 | | A |
| 3679 | 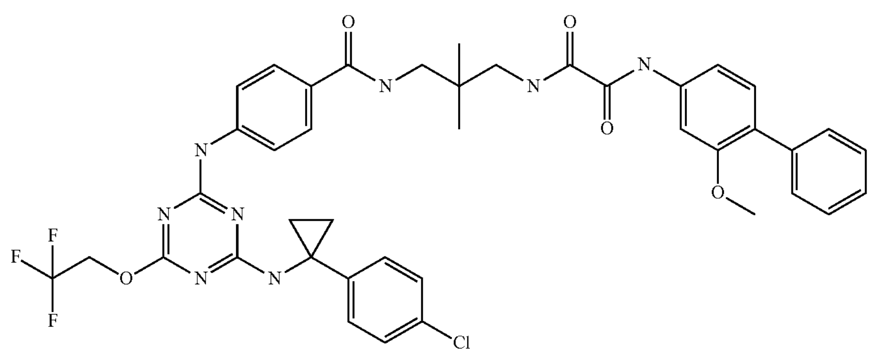 [SMILES: COc1cc(NC(=O)C(=O)NCC(C)(C)CNC(=O)c2ccc(Nc3nc(NC4(c5ccc(Cl)cc5)CC4)nc(OCC(F)(F)F)n3)cc2)ccc1-c1ccccc1] | | A |

TABLE 1-continued

| Compound | Structure | EC$_{50}$ | Activity |
|---|---|---|---|
| 3680 | 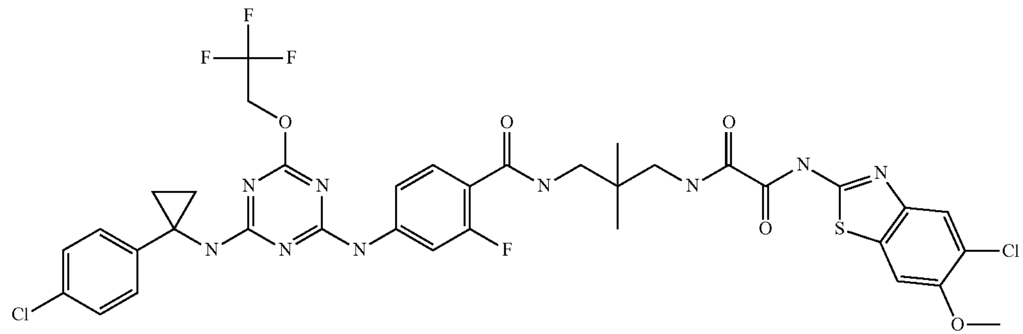 [SMILES: COc1cc2sc(NC(=O)C(=O)NCC(C)(C)CNC(=O)c3ccc(Nc4nc(NC5(c6ccc(Cl)cc6)CC5)nc(OCC(F)(F)F)n4)cc3F)nc2cc1Cl] | | A |
| 3681 | 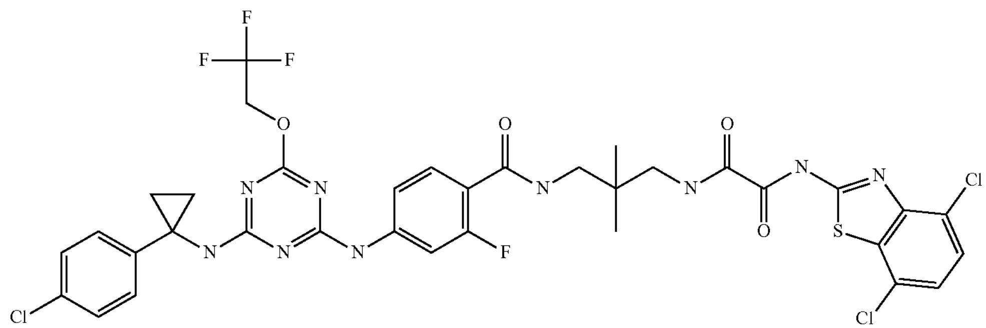 [SMILES: CC(C)(CNC(=O)C(=O)Nc1nc2c(Cl)ccc(Cl)c2s1)CNC(=O)c1ccc(Nc2nc(NC3(c4ccc(Cl)cc4)CC3)nc(OCC(F)(F)F)n2)cc1F] | | A |

TABLE 1-continued
| Compound | Structure | EC$_{50}$ | Activity |
|---|---|---|---|
| 3682 | 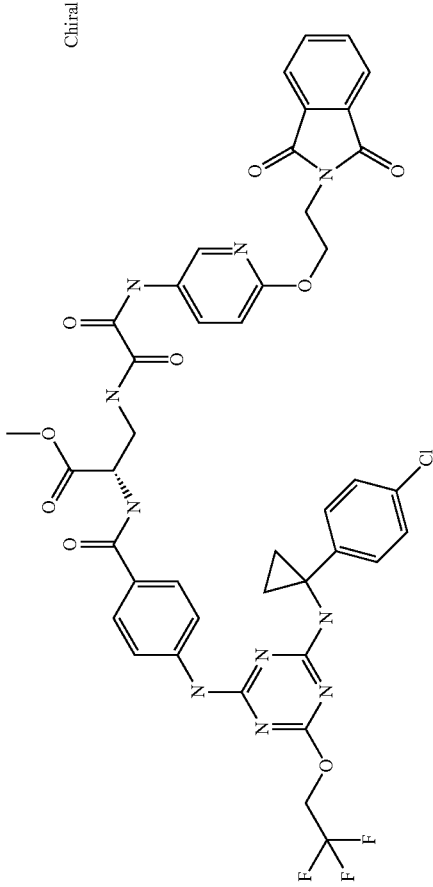 | 0.31 | A |
| 3683 | 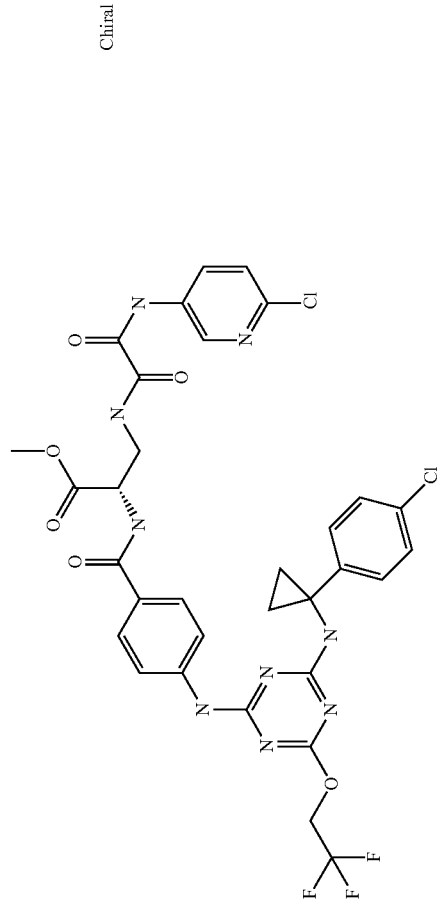 | | A |

TABLE 1-continued
| Compound | Structure | EC$_{50}$ | Activity |
|---|---|---|---|
| 3684 | 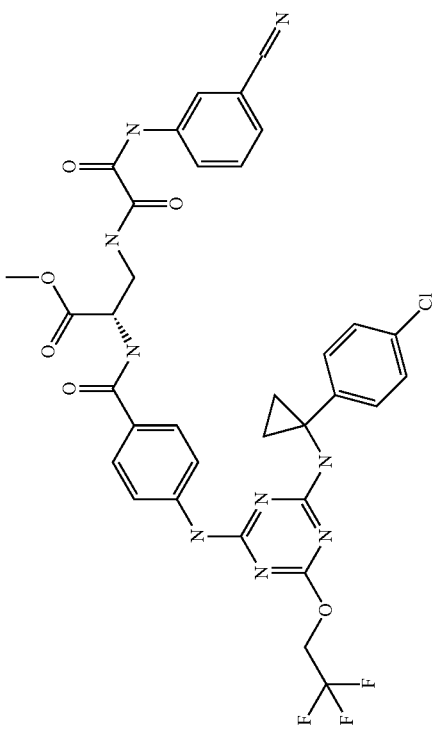 Chiral | | A |
| 3685 | 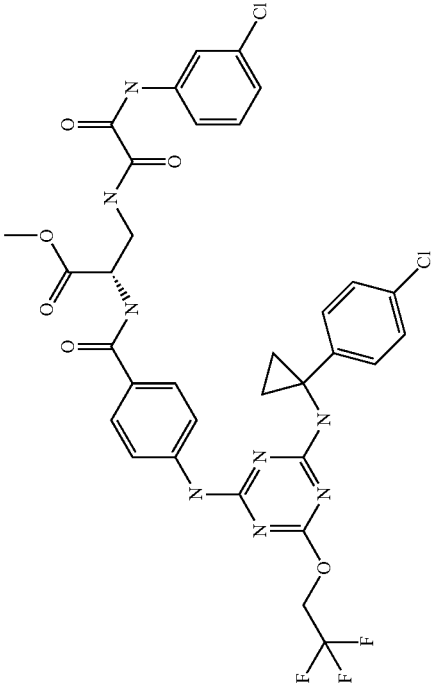 Chiral | | A |

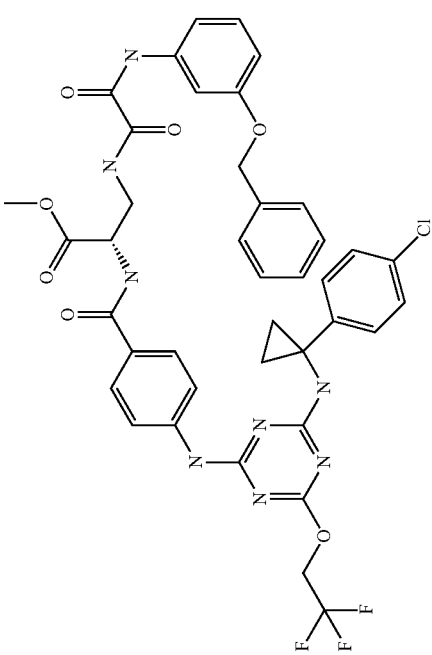

TABLE 1-continued
| Compound | Structure | EC$_{50}$ | Activity |
|---|---|---|---|
| 3688 | Chiral 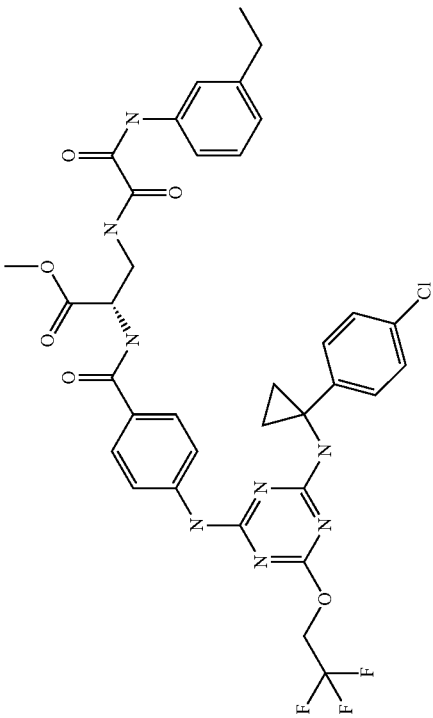 | 0.97 | A |
| 3689 | Chiral 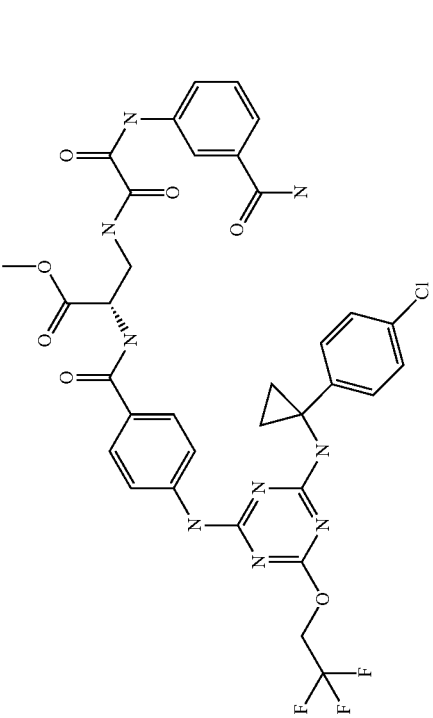 | | A |

TABLE 1-continued
| Compound | Structure | EC$_{50}$ | Activity |
|---|---|---|---|
| 3690 | 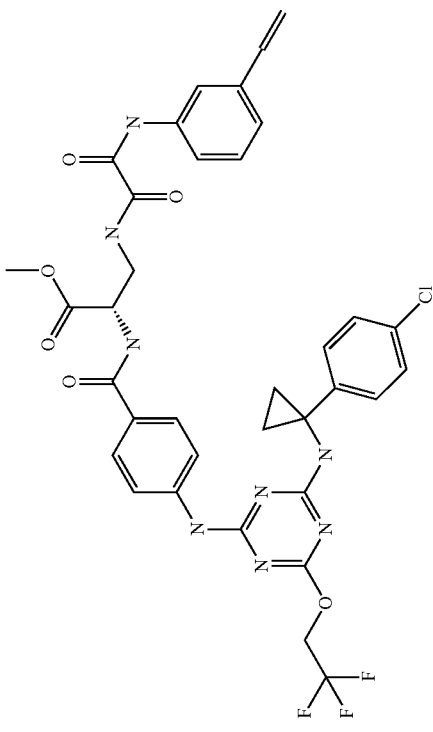 | | A |
| 3691 | 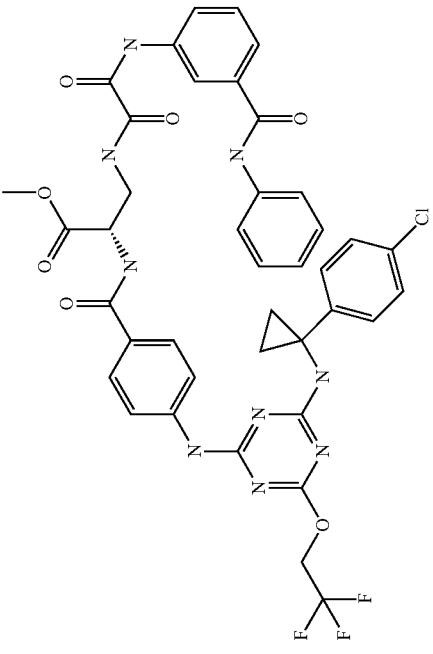 | | A |

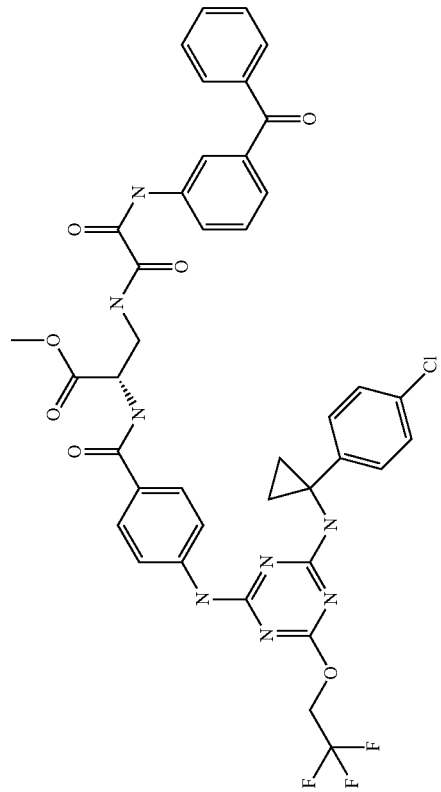

TABLE 1-continued

| Compound | Structure | EC$_{50}$ | Activity |
|---|---|---|---|
| 3694 | Chiral | 2.23 | A |
| 3695 | Chiral | | A |

TABLE 1-continued

| Compound | Structure | EC$_{50}$ | Activity |
|---|---|---|---|
| 3696 | Chiral | | A |
| 3697 | Chiral | | A |

TABLE 1-continued
| Compound | Structure | EC$_{50}$ | Activity |
|---|---|---|---|
| 3698 | 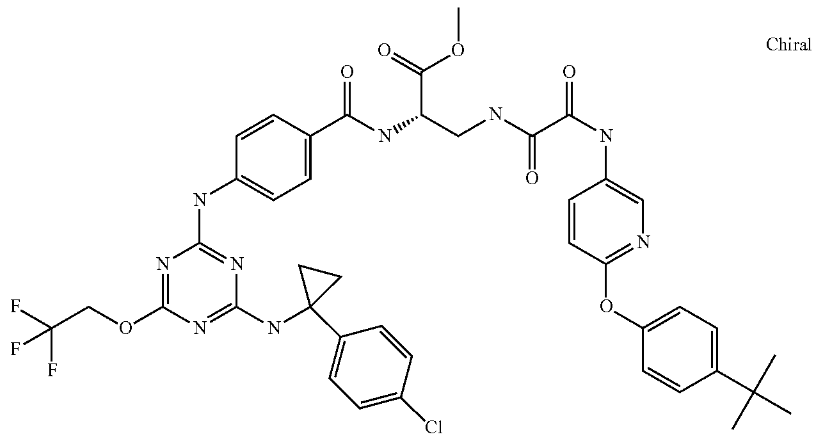 [SMILES: COC(=O)[C@H](CNC(=O)C(=O)Nc1ccc(Oc2ccc(C(C)(C)C)cc2)nc1)NC(=O)c1ccc(Nc2nc(NC3(c4ccc(Cl)cc4)CC3)nc(OCC(F)(F)F)n2)cc1] | | A |
| 3699 | 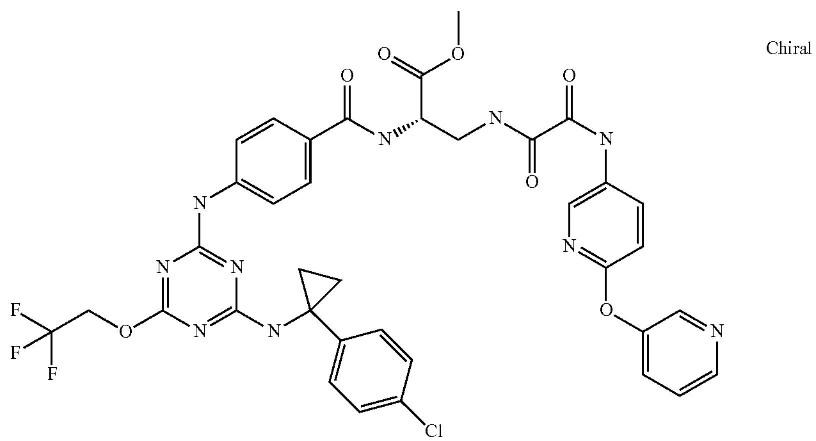 [SMILES: COC(=O)[C@H](CNC(=O)C(=O)Nc1ccc(Oc2cccnc2)nc1)NC(=O)c1ccc(Nc2nc(NC3(c4ccc(Cl)cc4)CC3)nc(OCC(F)(F)F)n2)cc1] | | A |
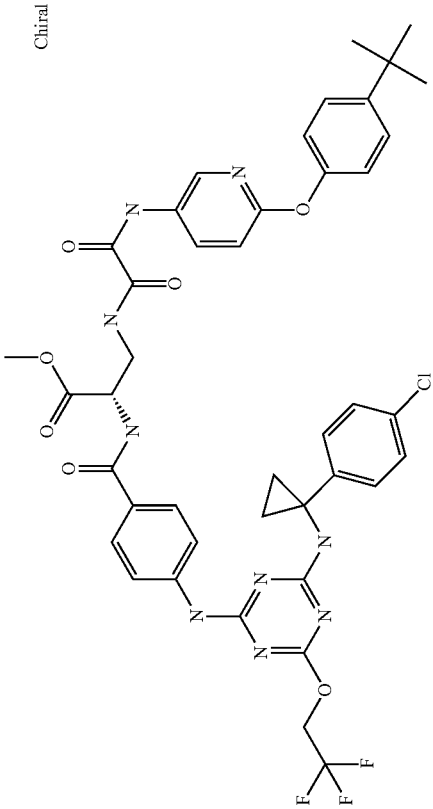

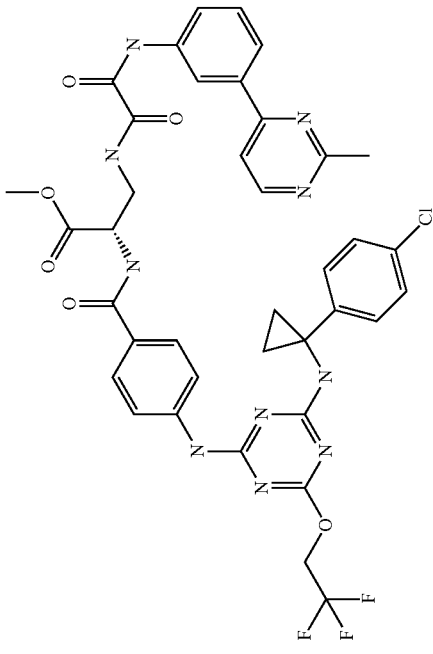

TABLE 1-continued
| Compound | Structure | EC$_{50}$ | Activity |
|---|---|---|---|
| 3702 | 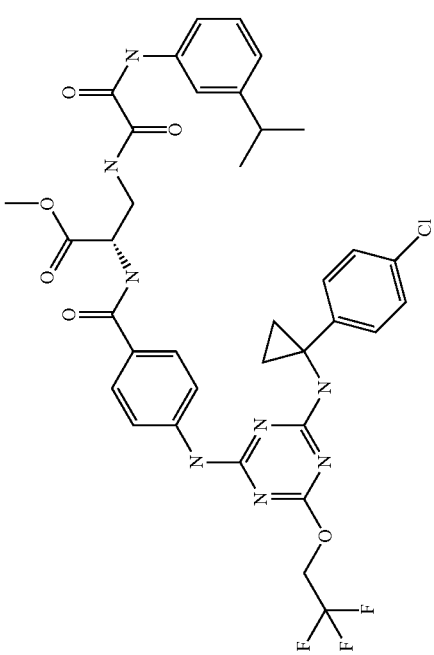 | | A |
| 3703 | 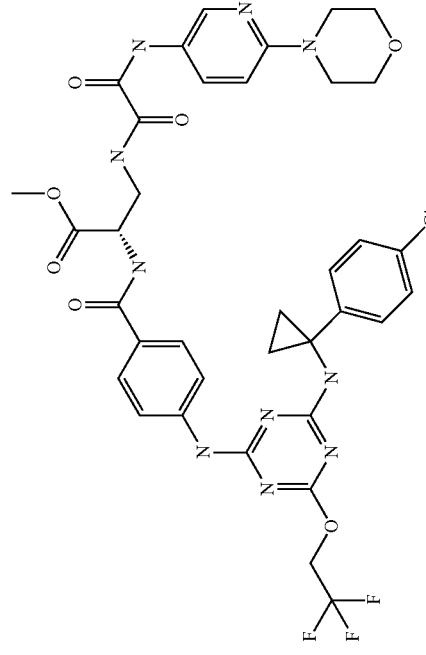 | 1.33 | A |

TABLE 1-continued
| Compound | Structure | EC$_{50}$ | Activity |
|---|---|---|---|
| 3704 | Chiral 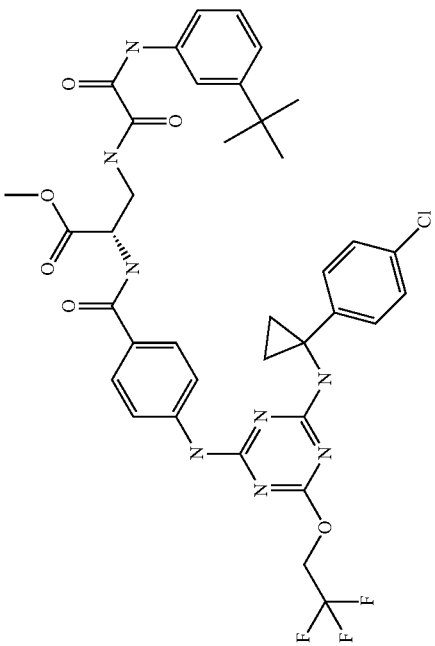 | | A |
| 3705 | Chiral 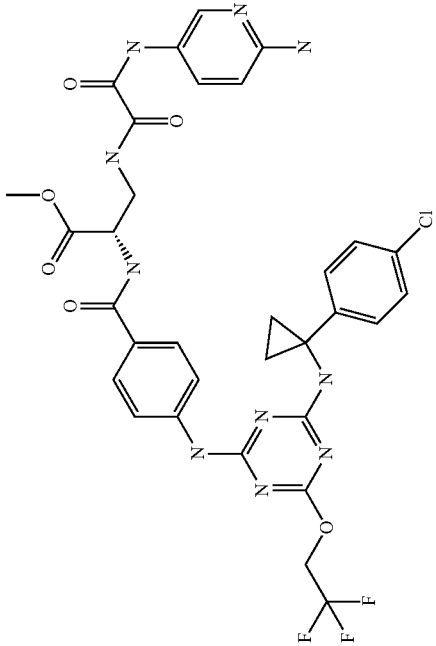 | | A |

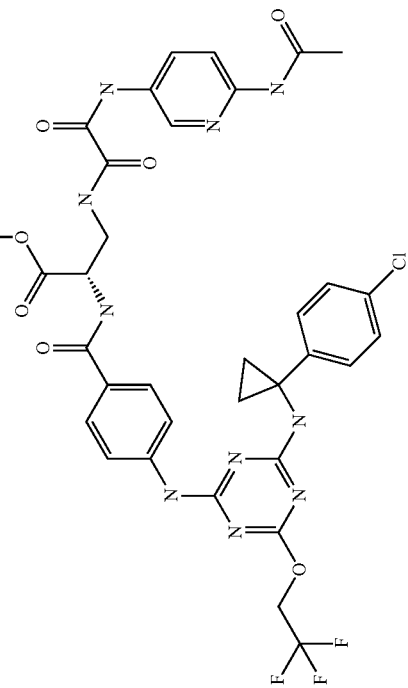

TABLE 1-continued
| Compound | Structure | EC$_{50}$ | Activity |
|---|---|---|---|
| 3708 | 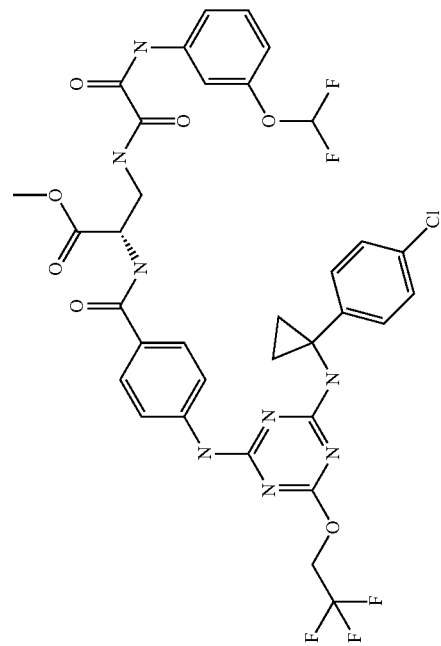 Chiral | | A |
| 3709 | 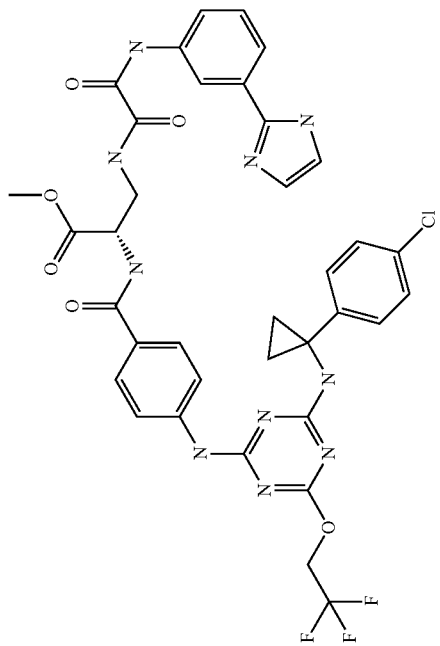 Chiral | 0.71 | A |

TABLE 1-continued
| Compound | Structure | EC$_{50}$ | Activity |
|---|---|---|---|
| 3710 | 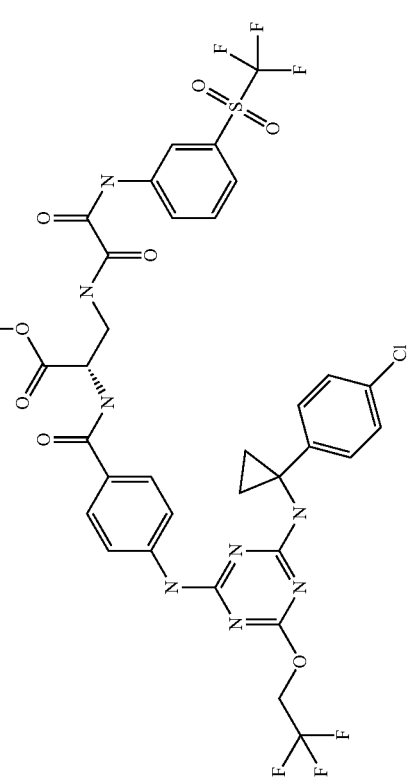 Chiral | | A |
| 3711 | 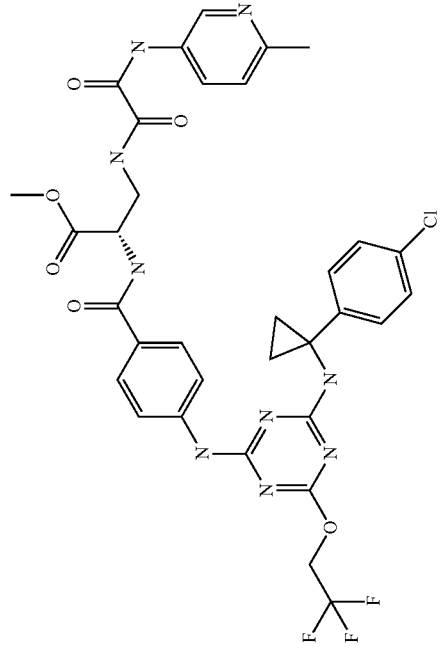 Chiral | | A |

TABLE 1-continued
| Compound | Structure | EC$_{50}$ | Activity |
|---|---|---|---|
| 3712 | 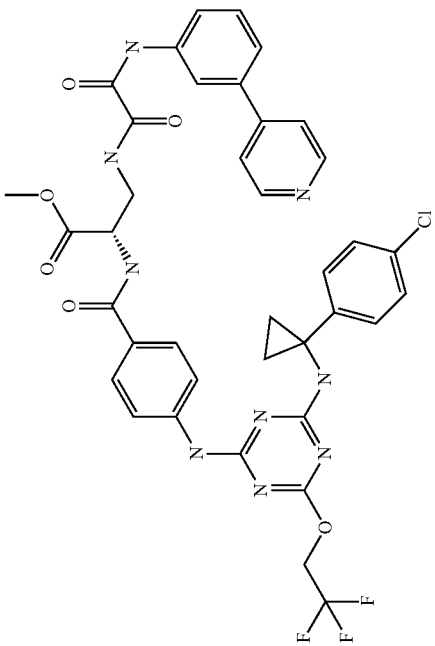 Chiral | | A |
| 3713 | 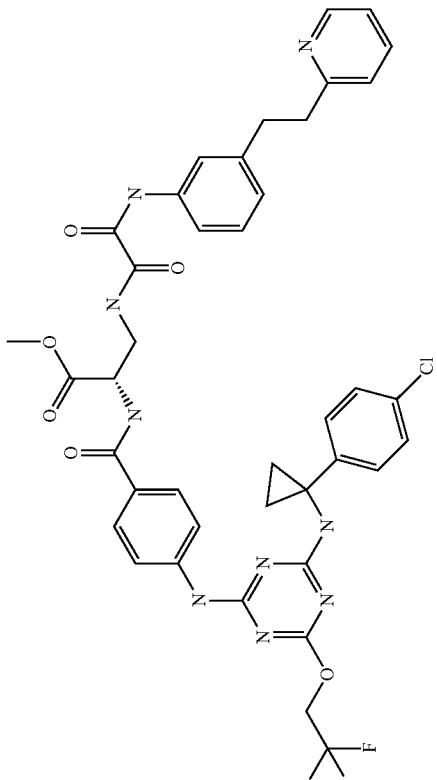 Chiral | | A |

TABLE 1-continued
| Compound | Structure | EC$_{50}$ | Activity |
|---|---|---|---|
| 3714 | Chiral 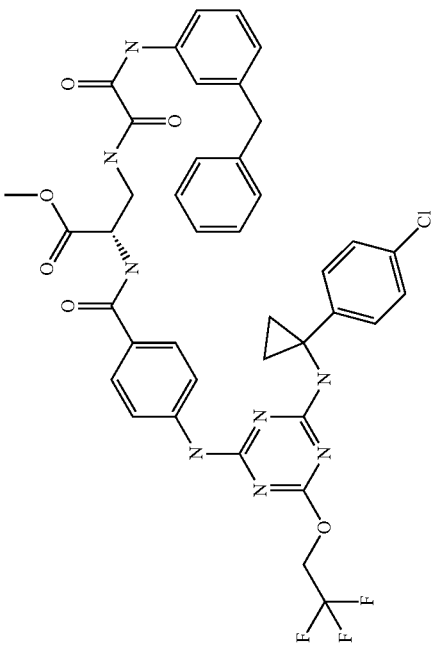 | | A |
| 3715 | Chiral 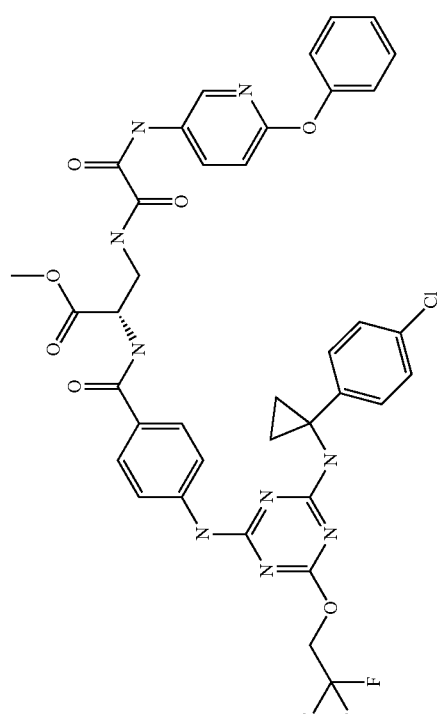 | | A |

TABLE 1-continued
| Compound | Structure | | EC$_{50}$ | Activity |
|---|---|---|---|---|
| 3716 | 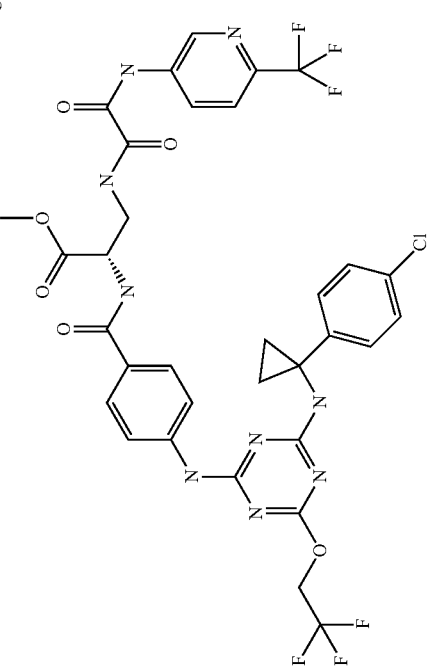 | Chiral | 0.62 | A |
| 3717 | 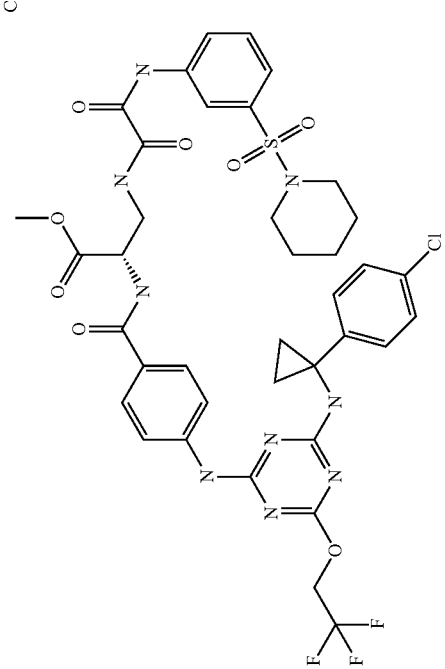 | Chiral | | A |

TABLE 1-continued
| Compound | Structure | EC$_{50}$ | Activity |
|---|---|---|---|
| 3718 | 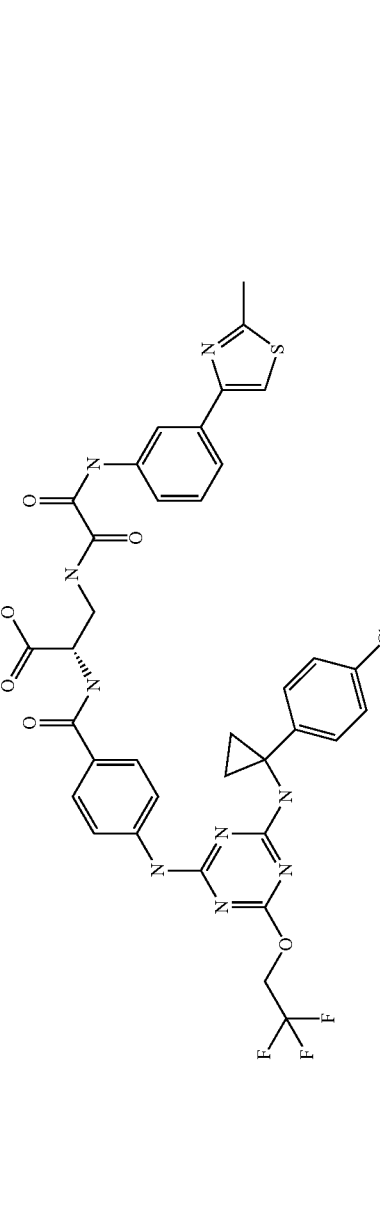 Chiral | | A |
| 3719 | 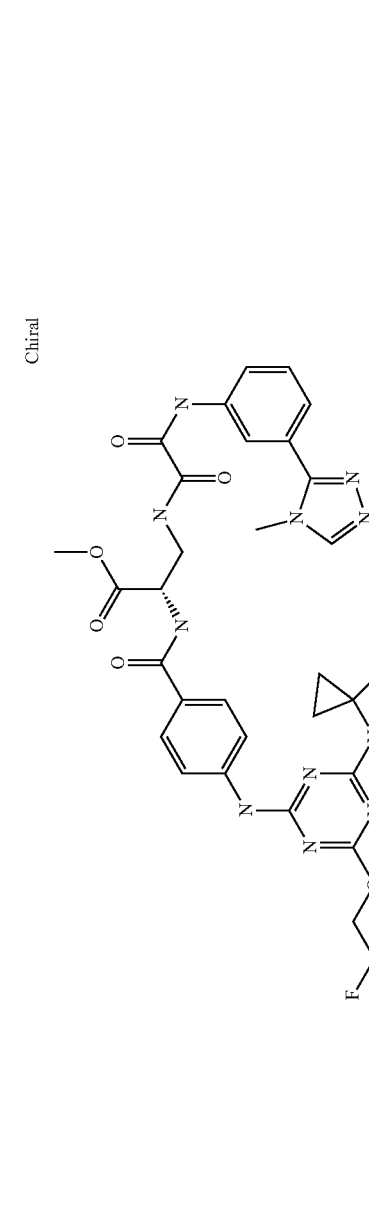 Chiral | | A |

| Compound | Structure | EC$_{50}$ | Activity |
|---|---|---|---|
| 3720 | Chiral 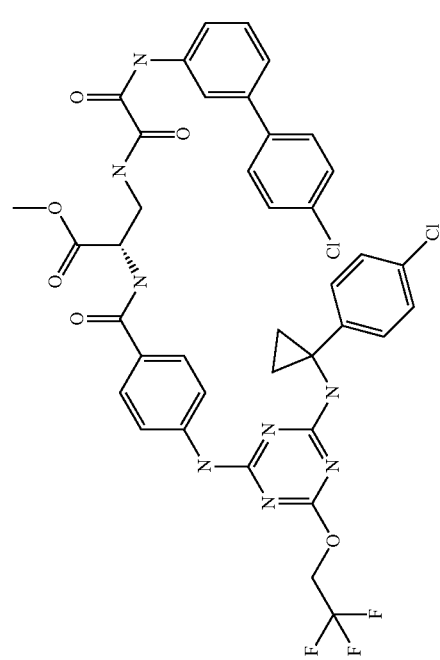 | | A |
| 3721 | Chiral 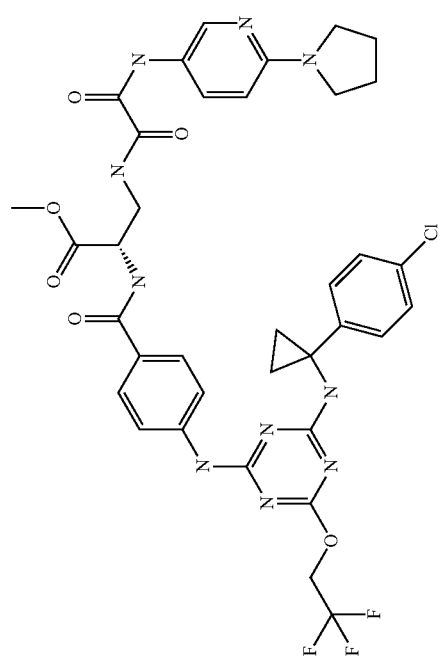 | | A |

TABLE 1-continued
| Compound | Structure | EC$_{50}$ | Activity |
|---|---|---|---|
| 3722 | 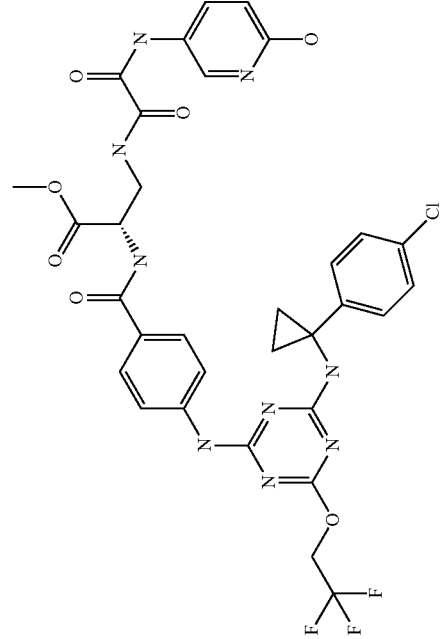 | | A |
| 3723 | 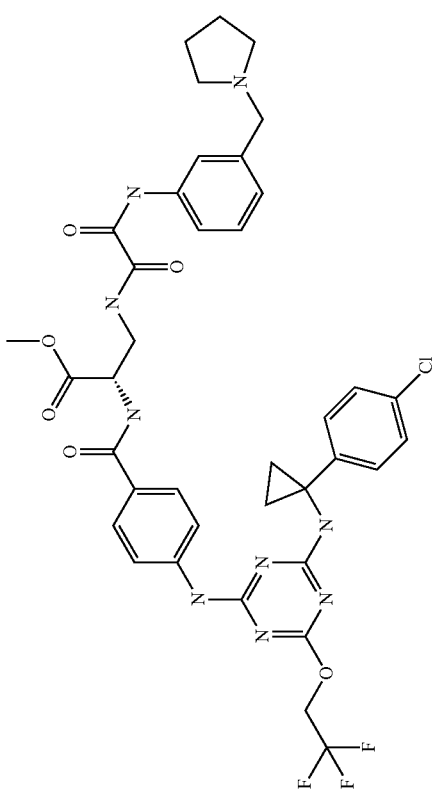 | 1.34 | A |

TABLE 1-continued
| Compound | Structure | EC$_{50}$ | Activity |
|---|---|---|---|
| 3724 | 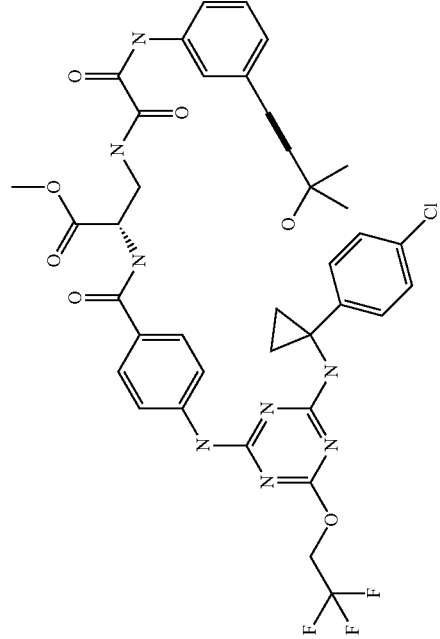 Chiral | | A |
| 3725 | 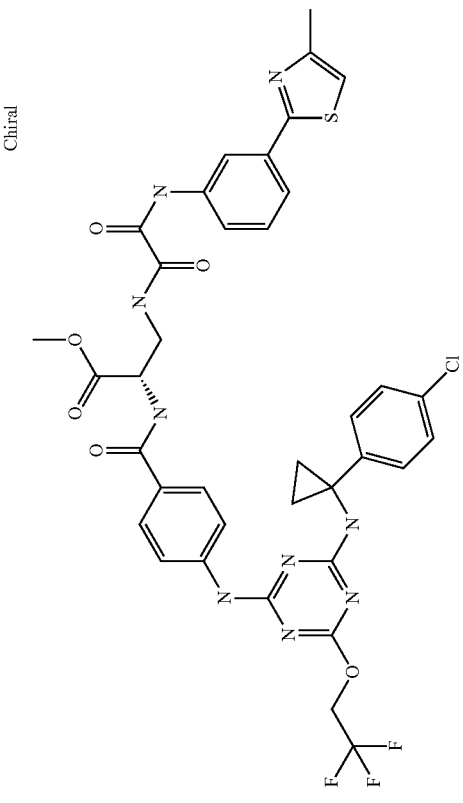 Chiral | | A |

TABLE 1-continued
| Compound | Structure | EC$_{50}$ | Activity |
|---|---|---|---|
| 3726 | 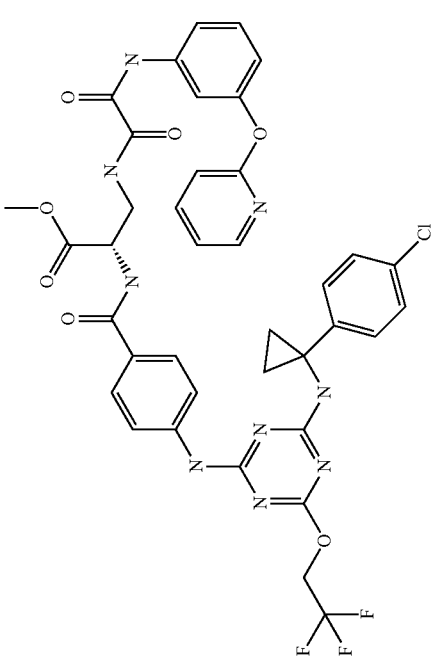 | | A |
| 3727 | 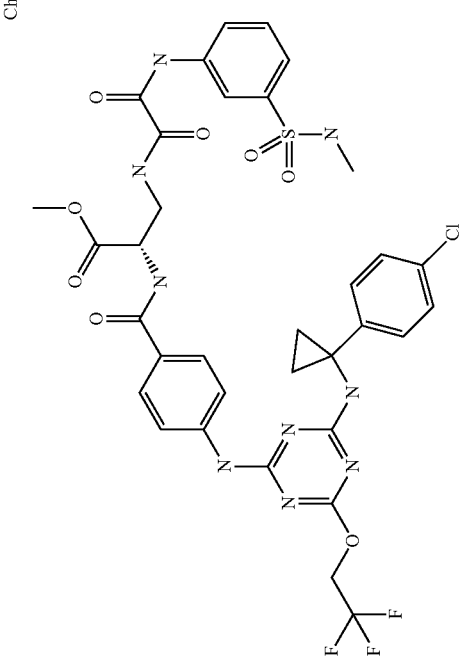 | | A |

TABLE 1-continued
| Compound | Structure | EC$_{50}$ | Activity |
|---|---|---|---|
| 3728 | 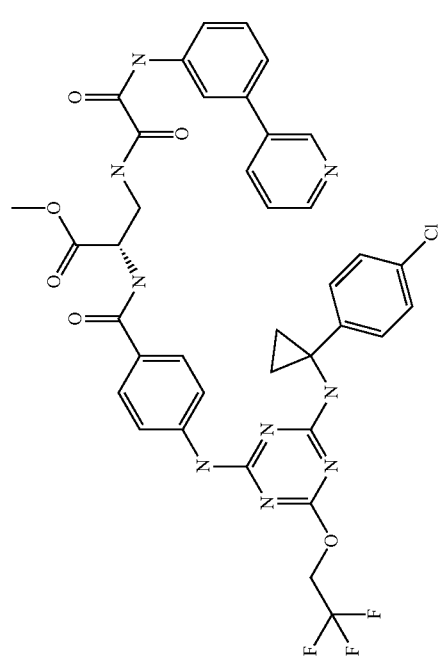 Chiral | | A |
| 3729 | 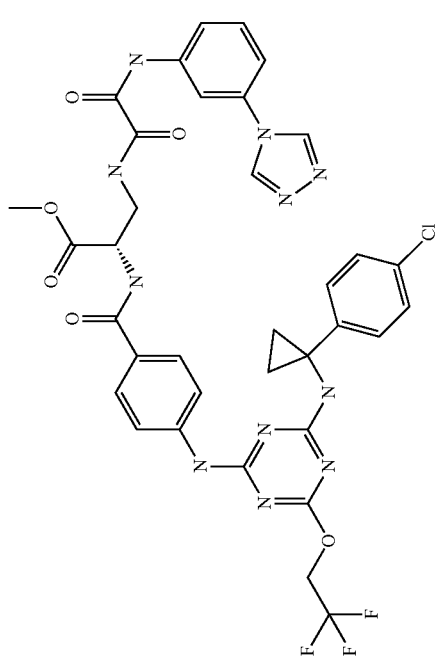 Chiral | | A |

TABLE 1-continued
| Compound | Structure | EC$_{50}$ | Activity |
|---|---|---|---|
| 3730 | Chiral 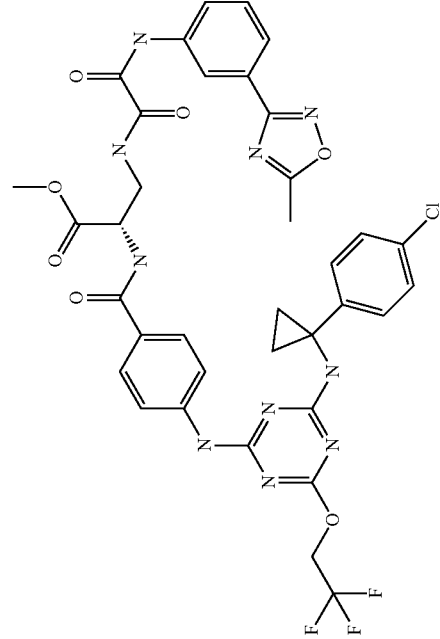 | 0.60 | A |
| 3731 | Chiral 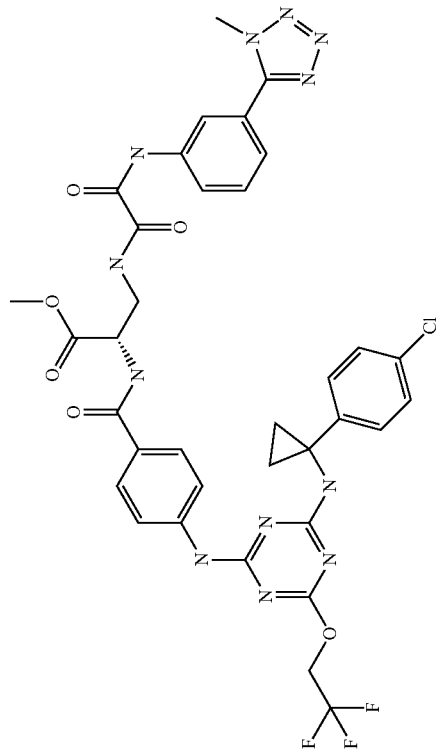 | | A |

| Compound | Structure | EC50 | Activity |
|---|---|---|---|
| 3732 | 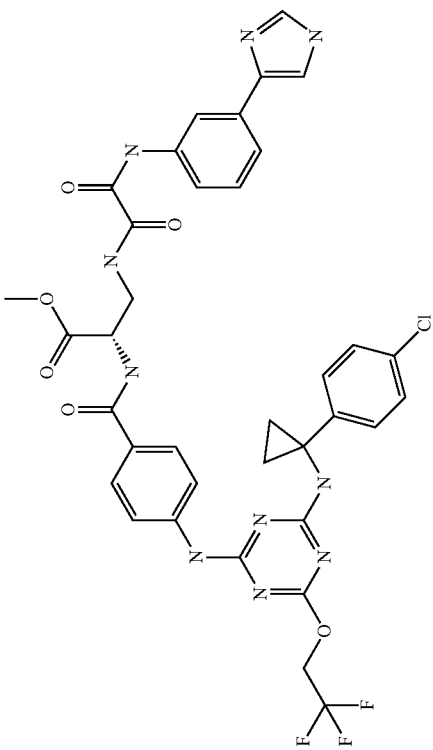 Chiral | | A |
| 3733 | 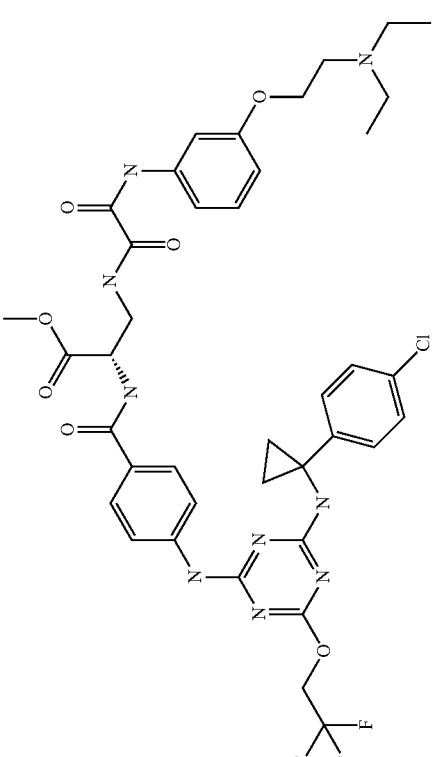 Chiral | | A |

TABLE 1-continued
| Compound | Structure | EC$_{50}$ | Activity |
|---|---|---|---|
| 3734 | 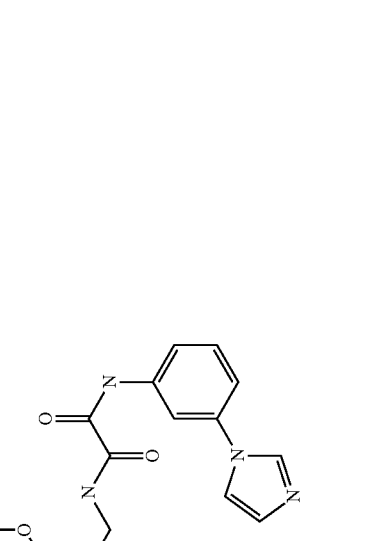 Chiral | | A |
| 3735 | 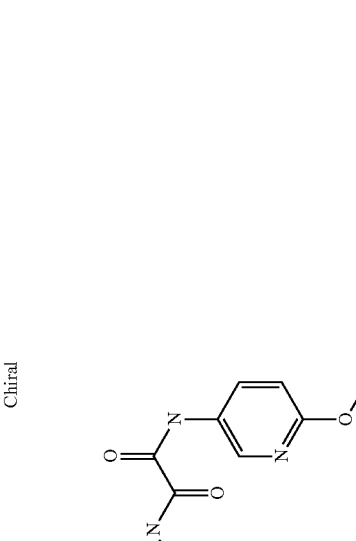 Chiral | | A |

TABLE 1-continued
| Compound | Structure | EC$_{50}$ | Activity |
|---|---|---|---|
| 3736 | 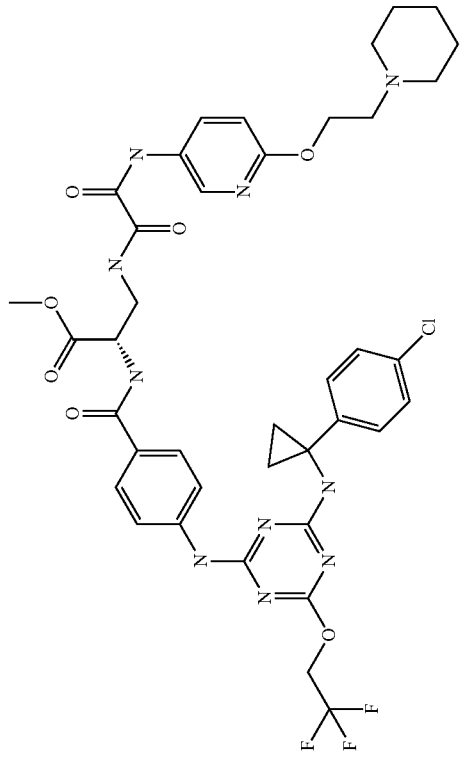 | | A |
| 3737 | 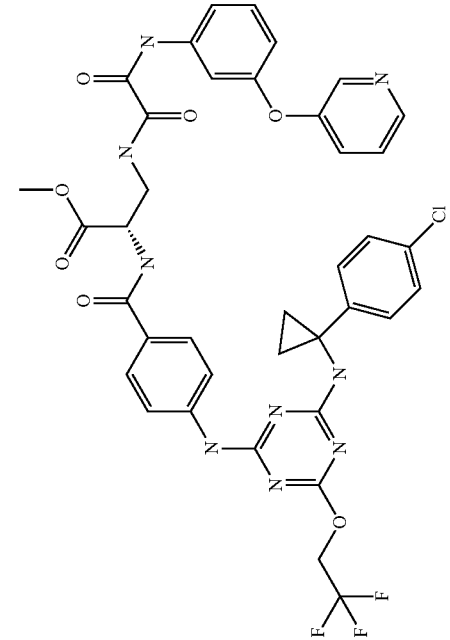 | 1.63 | A |

TABLE 1-continued

| Compound | Structure | EC50 | Activity |
|---|---|---|---|
| 3738 | Chiral | | A |
| 3739 | Chiral | | A |

TABLE 1-continued
| Compound | Structure | EC$_{50}$ | Activity |
|---|---|---|---|
| 3740 | 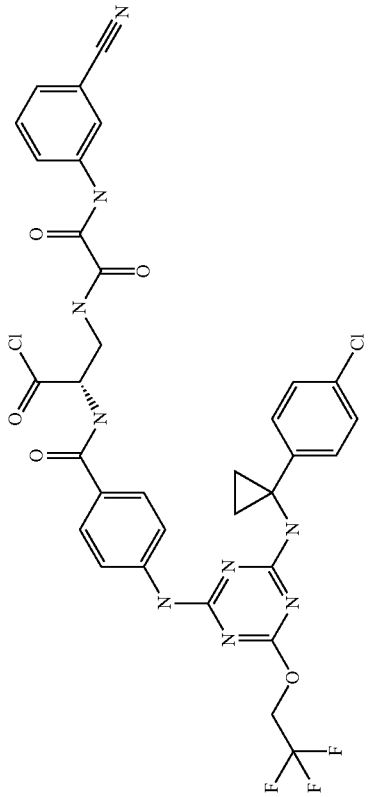 Chiral | | A |
| 3741 | 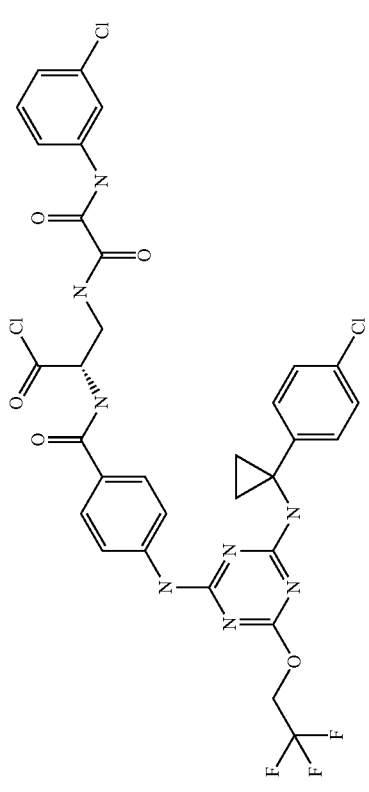 Chiral | | A |

TABLE 1-continued
| Compound | Structure | EC$_{50}$ | Activity |
|---|---|---|---|
| 3742 | 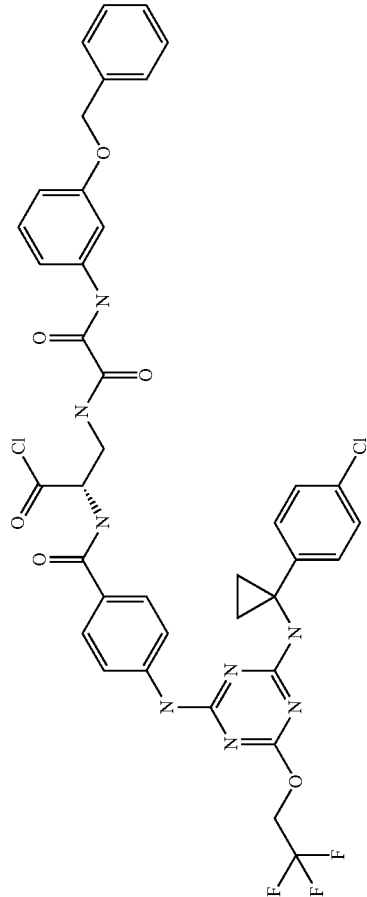 Chiral | | A |
| 3743 | 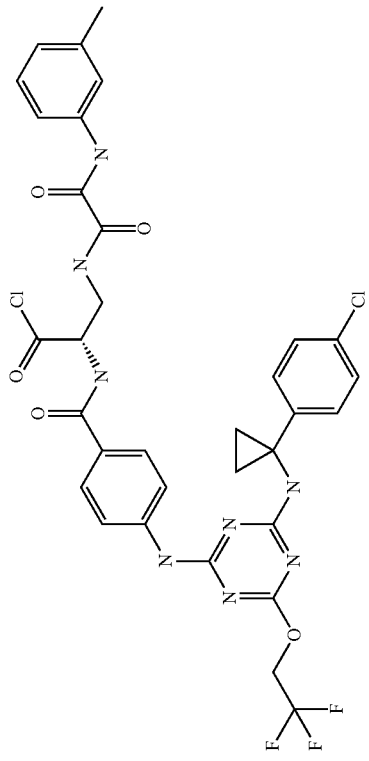 Chiral | | A |

TABLE 1-continued
| Compound | Structure | EC$_{50}$ | Activity |
|---|---|---|---|
| 3744 | 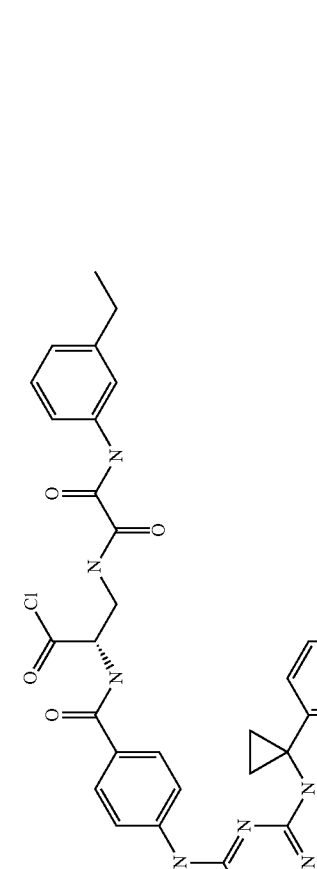 Chiral | 1.18 | A |
| 3745 | 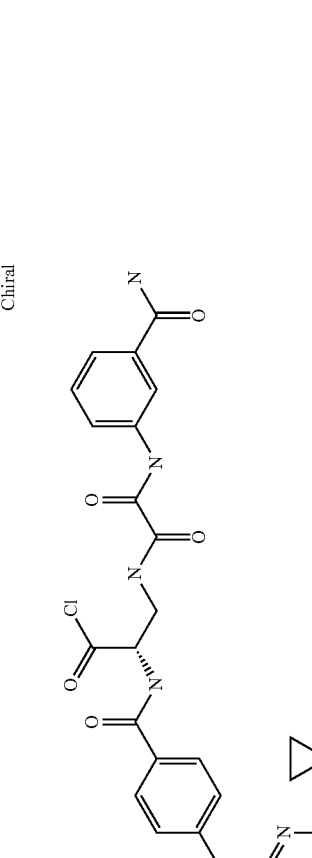 Chiral | | A |

TABLE 1-continued
| Compound | Structure | EC$_{50}$ | Activity |
|---|---|---|---|
| 3746 | 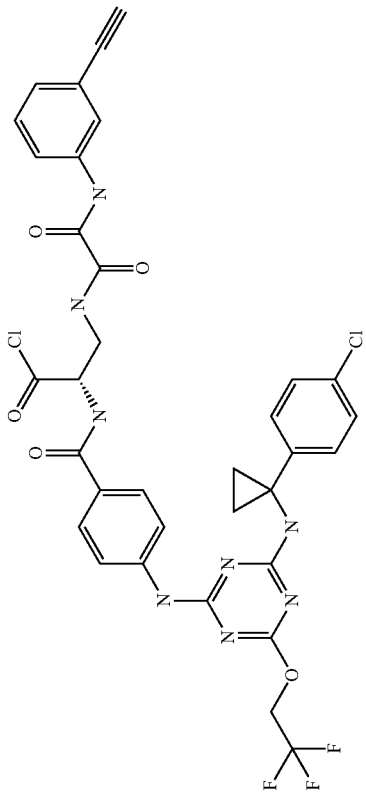 Chiral | | A |
| 3747 | 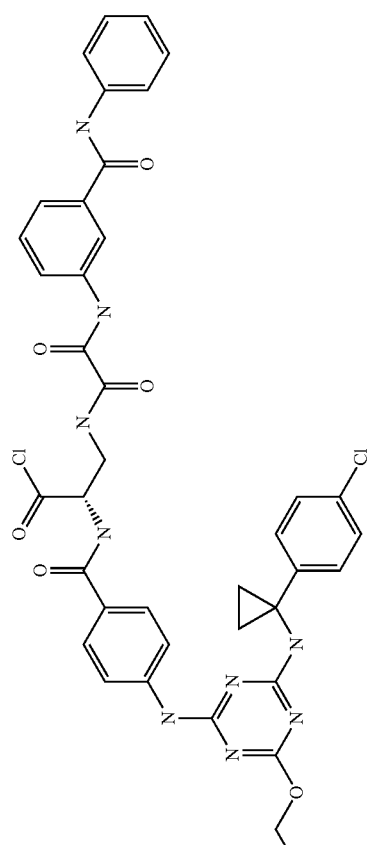 Chiral | | A |

TABLE 1-continued
| Compound | Structure | EC$_{50}$ | Activity |
|---|---|---|---|
| 3748 | 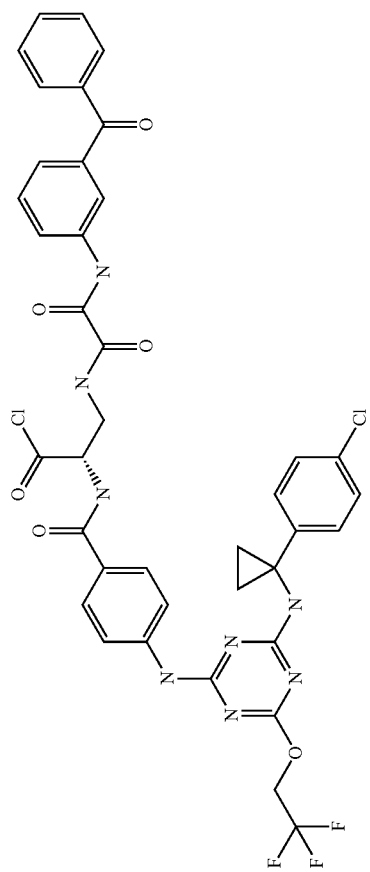 | | A |
| 3749 | 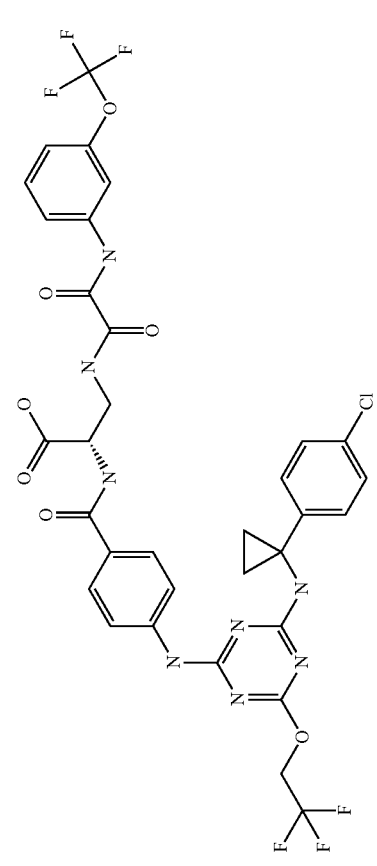 | | A |

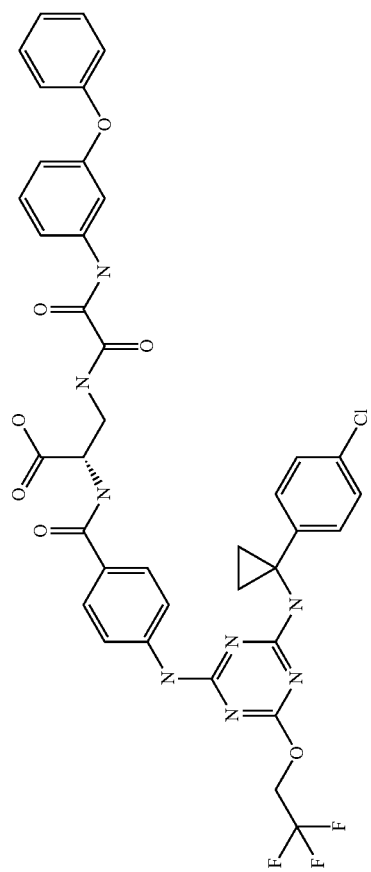
TABLE 1-continued
| Compound | Structure | EC$_{50}$ | Activity |
|---|---|---|---|
| 3750 | Chiral | | A |
| 3751 | Chiral | 0.14 | A |

TABLE 1-continued

| Compound | Structure | EC$_{50}$ | Activity |
|---|---|---|---|
| 3752 | Chiral | | A |
| 3753 | Chiral | | A |

TABLE 1-continued
| Compound | Structure | EC$_{50}$ | Activity |
|---|---|---|---|
| 3754 | 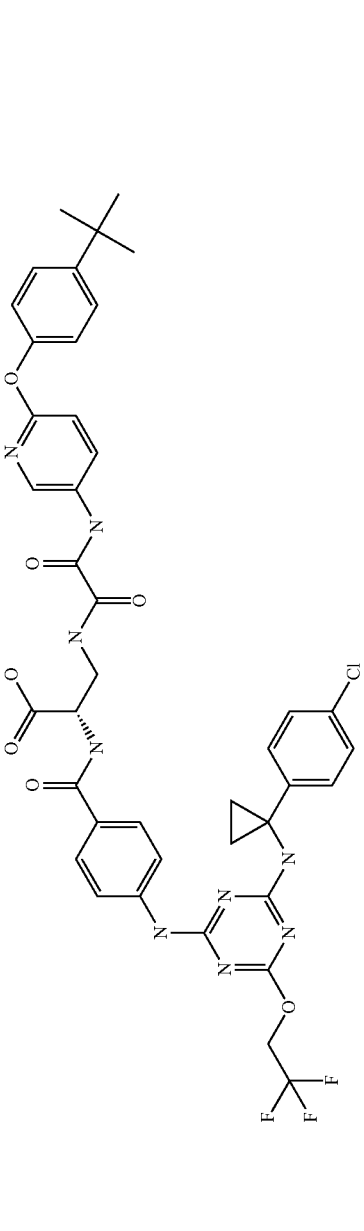 | | A |
| 3755 | 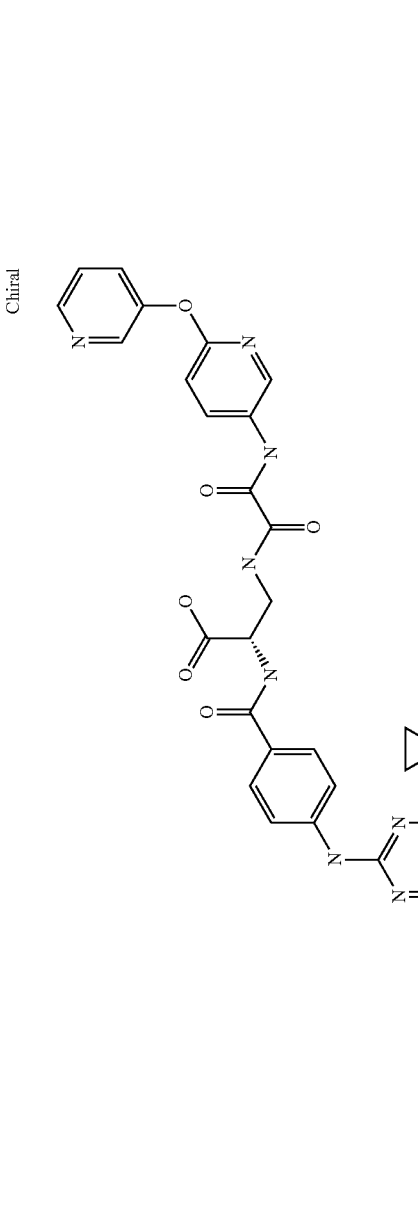 | | A |

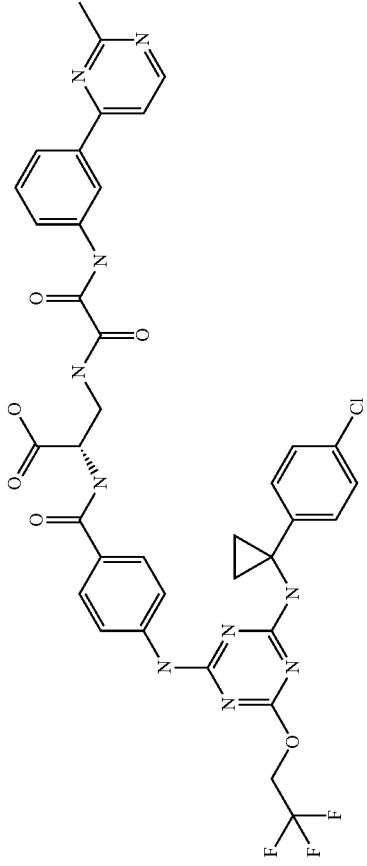

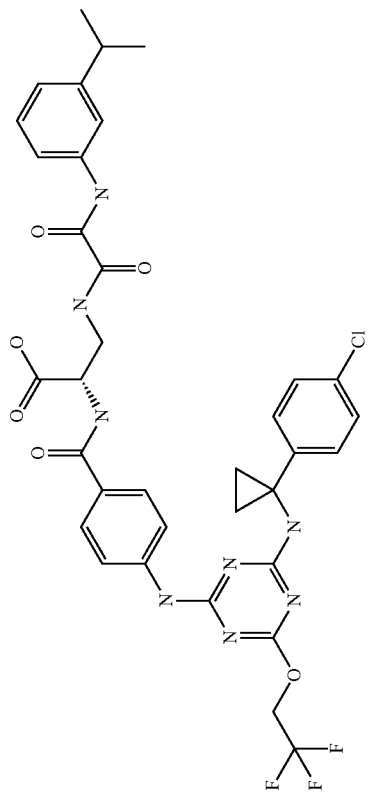

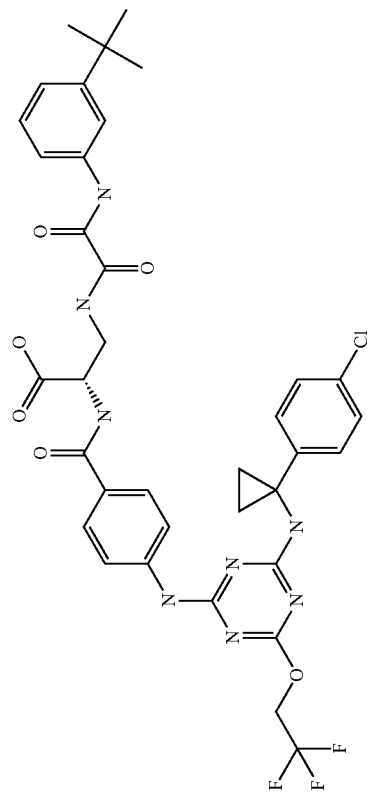

TABLE 1-continued
| Compound | Structure | EC$_{50}$ | Activity |
|---|---|---|---|
| 3762 | 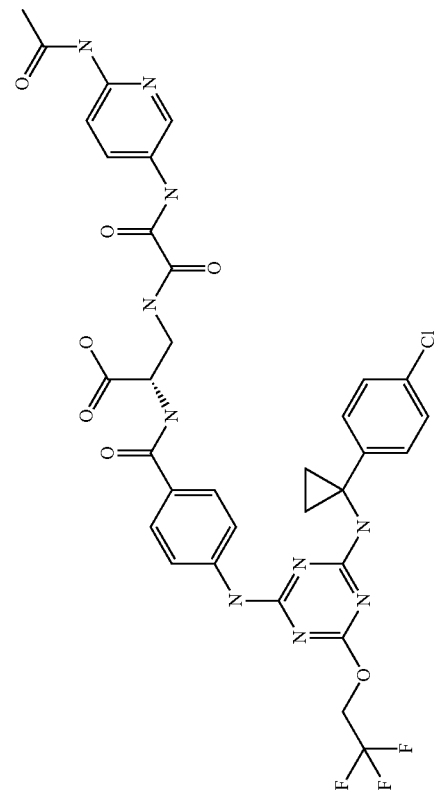 Chiral | | A |
| 3763 | 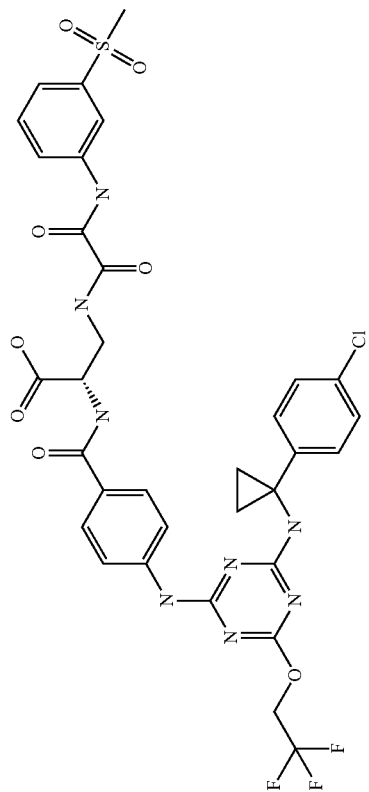 Chiral | | A |

TABLE 1-continued
| Compound | Structure | EC$_{50}$ | Activity |
|---|---|---|---|
| 3764 | Chiral | | A |
| 3765 | Chiral | 0.68 | A |
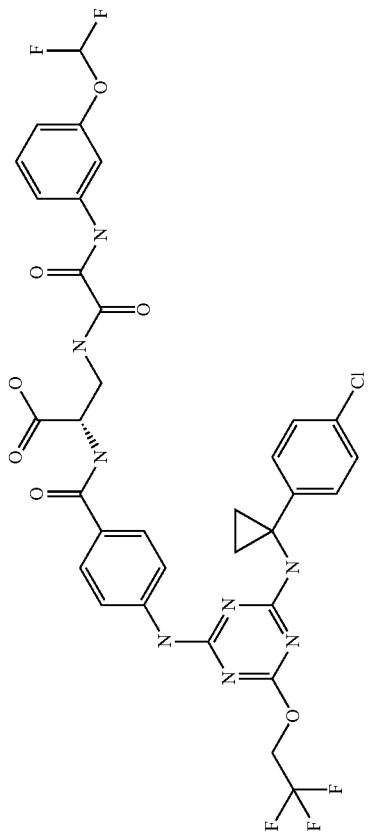
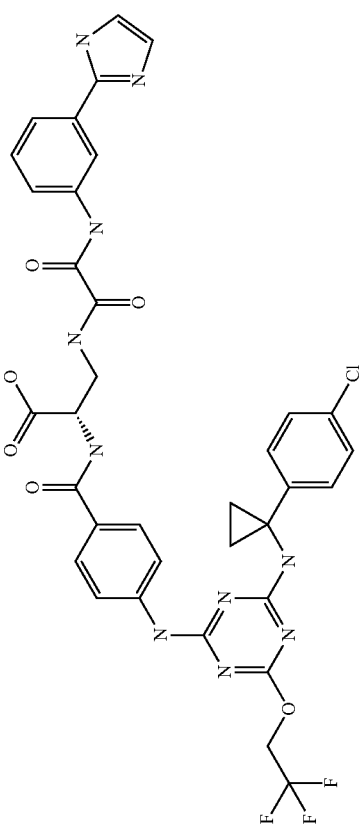

TABLE 1-continued
| Compound | Structure | EC$_{50}$ | Activity |
|---|---|---|---|
| 3766 | 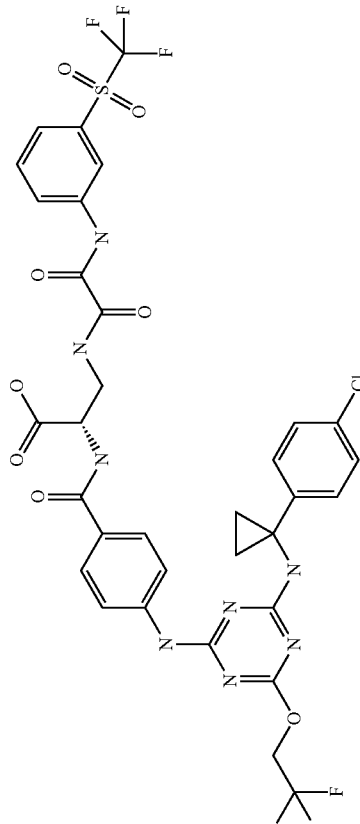 | | A |
| 3767 | 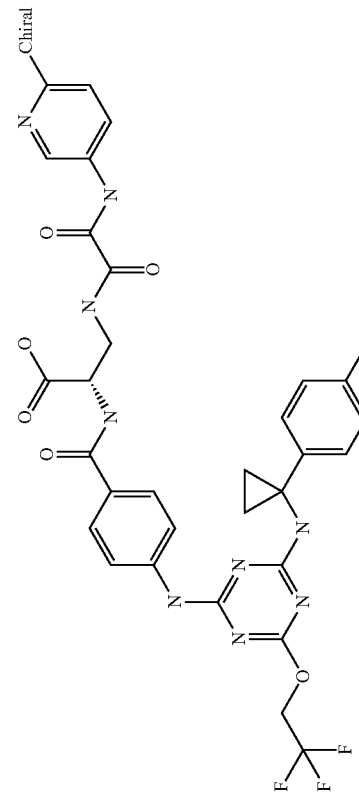 | | A |

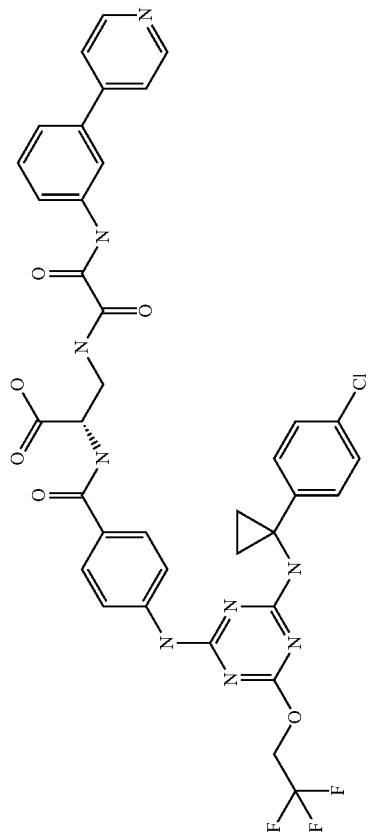

TABLE 1-continued

| Compound | Structure | EC$_{50}$ | Activity |
|---|---|---|---|
| 3770 | Chiral | | A |
| 3771 | Chiral | | A |

TABLE 1-continued
| Compound | Structure | EC$_{50}$ | Activity |
|---|---|---|---|
| 3772 | Chiral 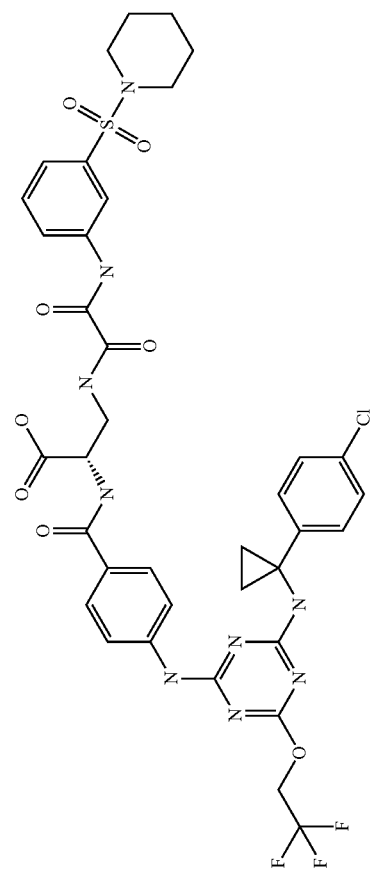 | 7.42 | A |
| 3773 | Chiral 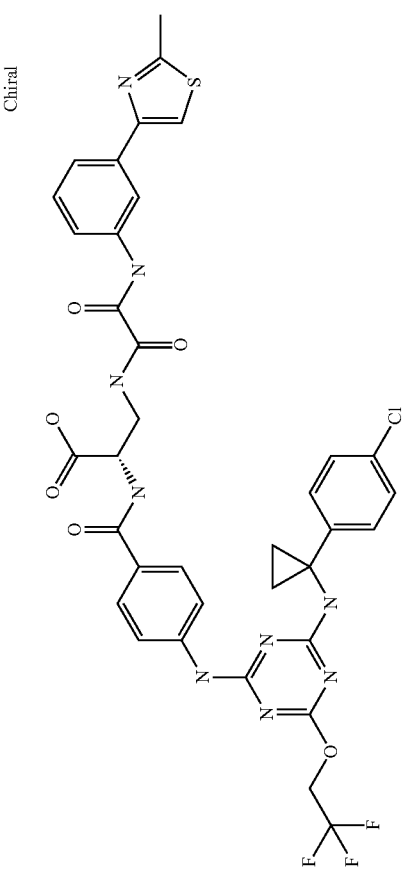 |  | A |

TABLE 1-continued
| Compound | Structure | EC$_{50}$ | Activity |
|---|---|---|---|
| 3774 | 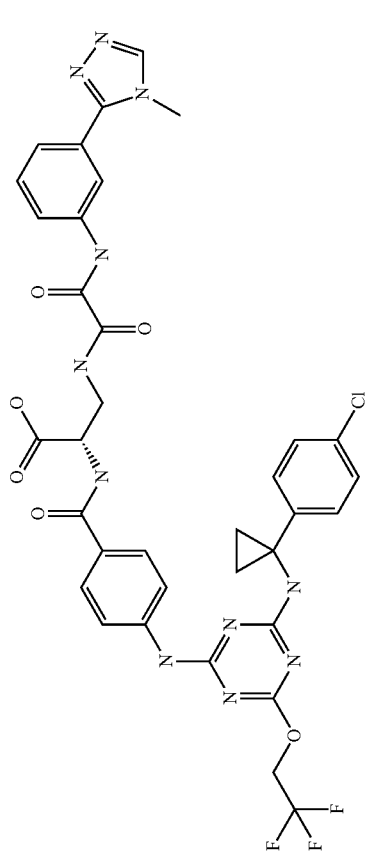 Chiral | | A |
| 3775 | 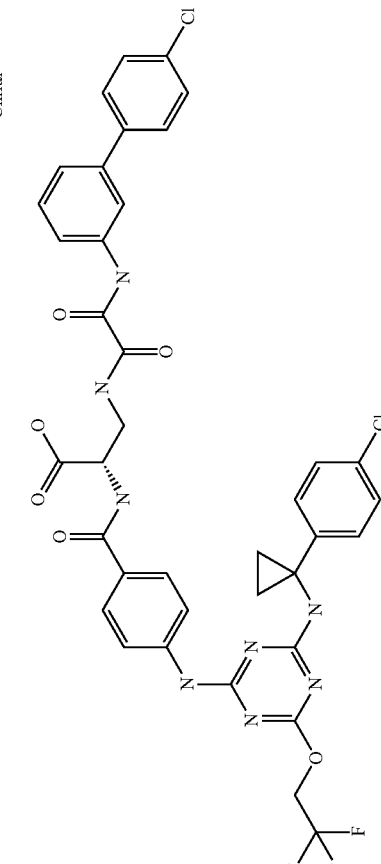 Chiral | | A |

TABLE 1-continued

| Compound | Structure | EC$_{50}$ | Activity |
|---|---|---|---|
| 3776 | Chiral | | A |
| 3777 | Chiral | | A |

TABLE 1-continued
| Compound | Structure | EC$_{50}$ | Activity |
|---|---|---|---|
| 3778 | 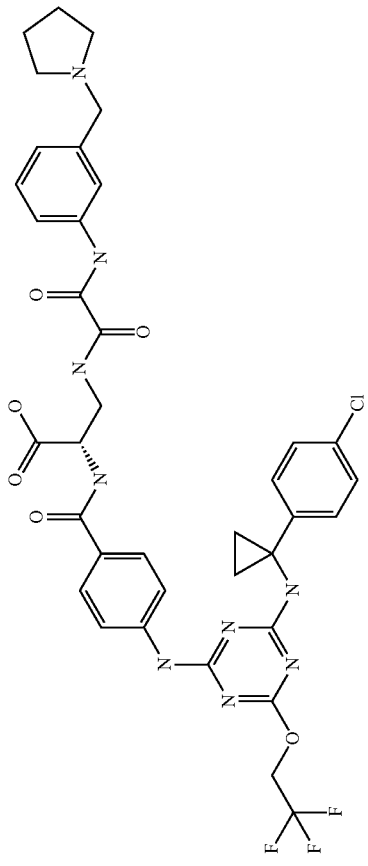 | | A |
| 3779 | 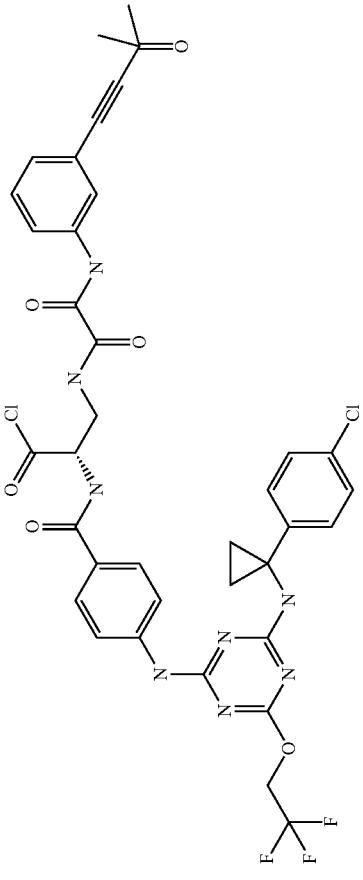 | 0.46 | A |

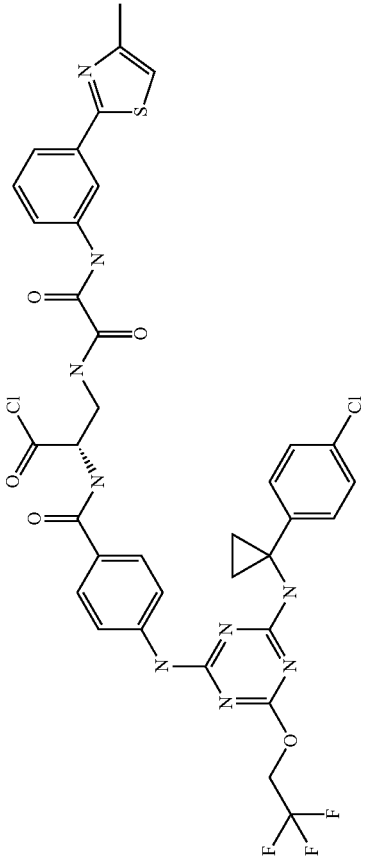

TABLE 1-continued

| Compound | Structure | EC$_{50}$ | Activity |
|---|---|---|---|
| 3782 | Chiral | | A |
| 3783 | Chiral | | A |

TABLE 1-continued
| Compound | Structure | EC$_{50}$ | Activity |
|---|---|---|---|
| 3784 | Chiral 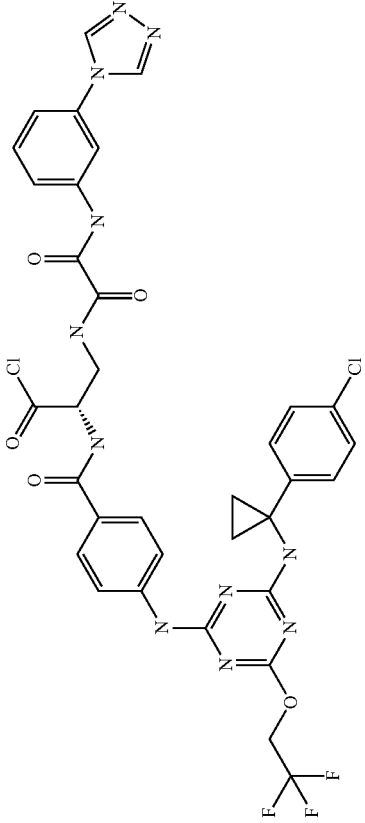 | | A |
| 3785 | Chiral 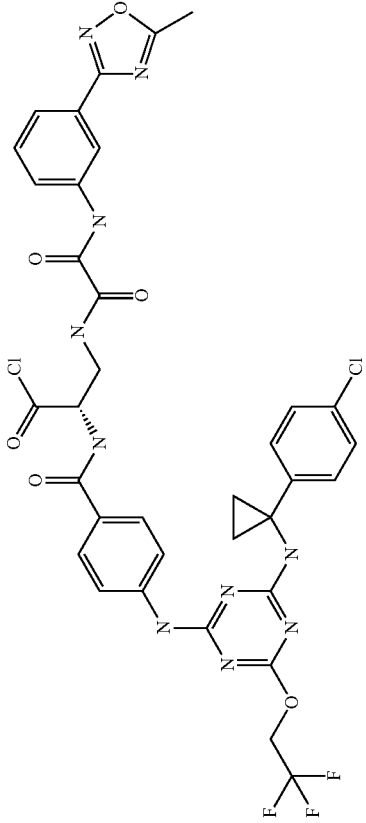 | | A |

TABLE 1-continued

| Compound | Structure | EC$_{50}$ | Activity |
|---|---|---|---|
| 3786 | Chiral | 0.55 | A |
| 3787 | Chiral | | A |

TABLE 1-continued

| Compound | Structure | EC$_{50}$ | Activity |
|---|---|---|---|
| 3788 | Chiral | | A |
| 3789 | Chiral | | A |

TABLE 1-continued
| Compound | Structure | EC$_{50}$ | Activity |
|---|---|---|---|
| 3790 | 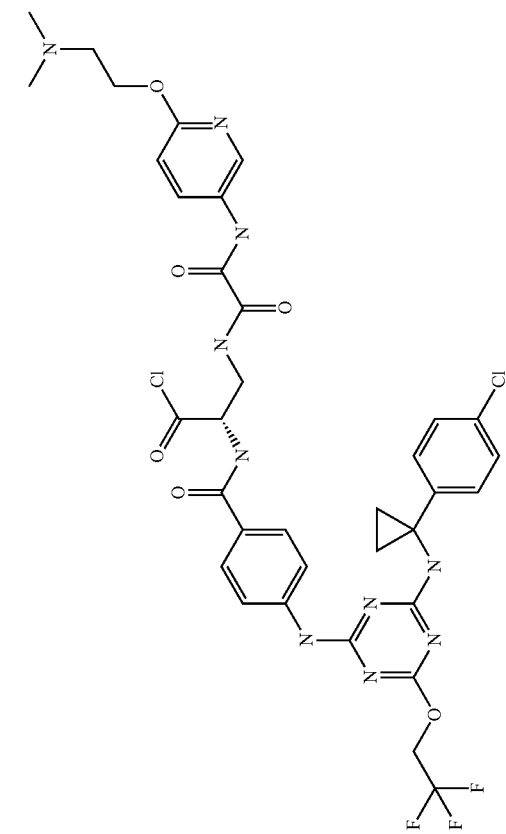 | | A |

TABLE 1-continued
| Compound | Structure | EC$_{50}$ | Activity |
|---|---|---|---|
| 3791 | 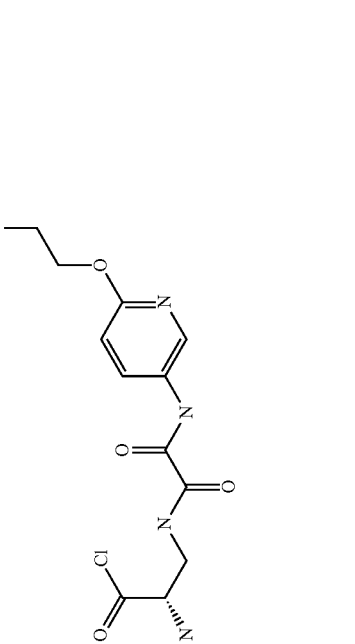 | | A |
| 3792 | 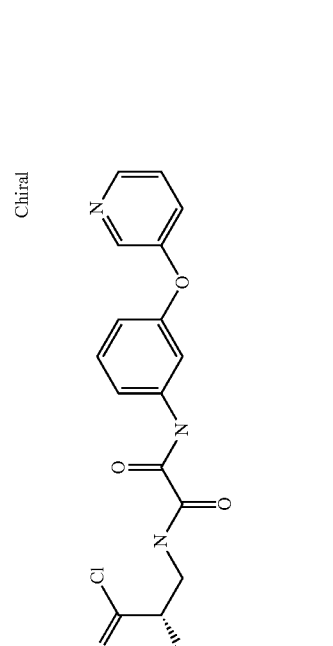 | | A |

TABLE 1-continued

| Compound | Structure | EC$_{50}$ | Activity |
|---|---|---|---|
| 3793 | 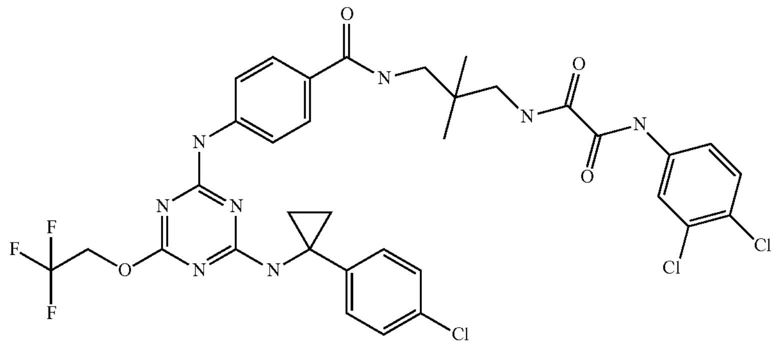 [SMILES: CC(C)(CNC(=O)C(=O)Nc1ccc(Cl)c(Cl)c1)CNC(=O)c1ccc(Nc2nc(NC3(c4ccc(Cl)cc4)CC3)nc(OCC(F)(F)F)n2)cc1] | | A |
| 3794 | 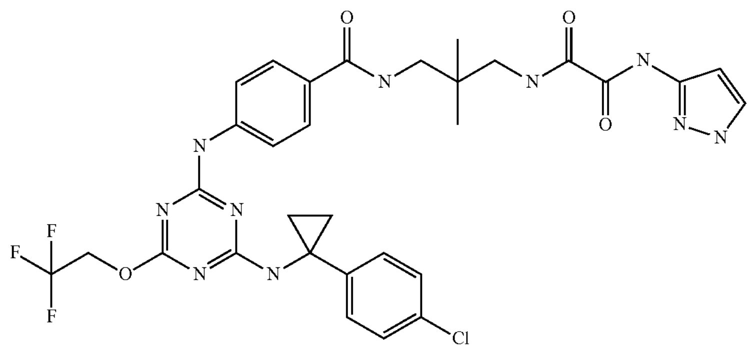 [SMILES: CC(C)(CNC(=O)C(=O)Nc1cc[nH]n1)CNC(=O)c1ccc(Nc2nc(NC3(c4ccc(Cl)cc4)CC3)nc(OCC(F)(F)F)n2)cc1] | 0.061 | A |
| 3795 | 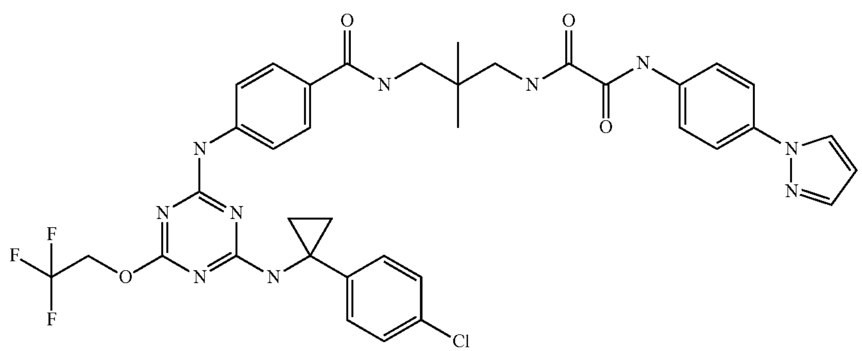 [SMILES: CC(C)(CNC(=O)C(=O)Nc1ccc(-n2cccn2)cc1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3796 | 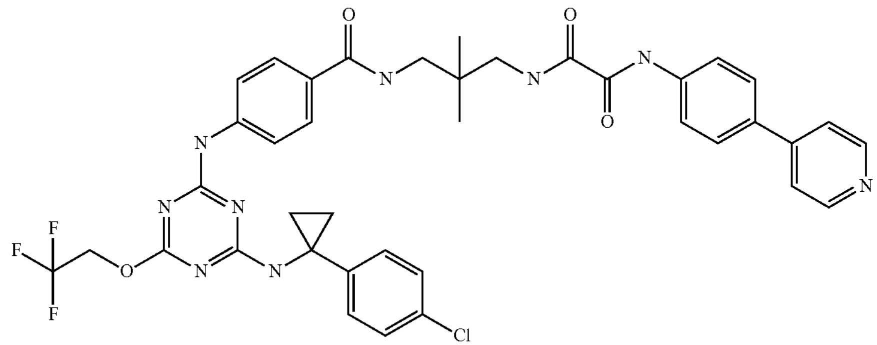 [SMILES: CC(C)(CNC(=O)C(=O)Nc1ccc(-c2ccncc2)cc1)CNC(=O)c1ccc(Nc2nc(NC3(c4ccc(Cl)cc4)CC3)nc(OCC(F)(F)F)n2)cc1] | | A |
| 3797 | 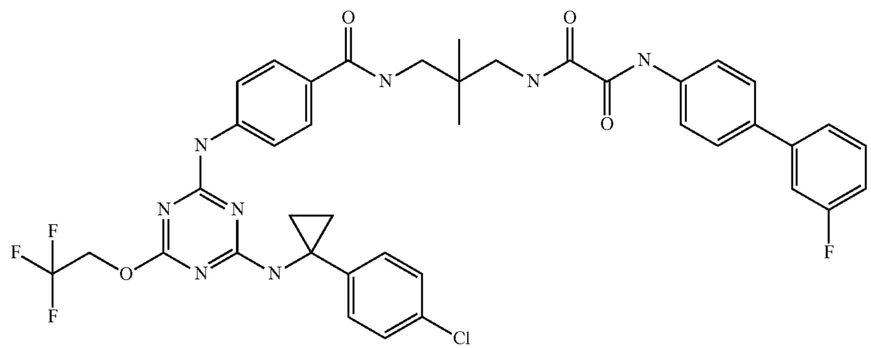 [SMILES: CC(C)(CNC(=O)C(=O)Nc1ccc(-c2cccc(F)c2)cc1)CNC(=O)c1ccc(Nc2nc(NC3(c4ccc(Cl)cc4)CC3)nc(OCC(F)(F)F)n2)cc1] | | A |
| 3798 | 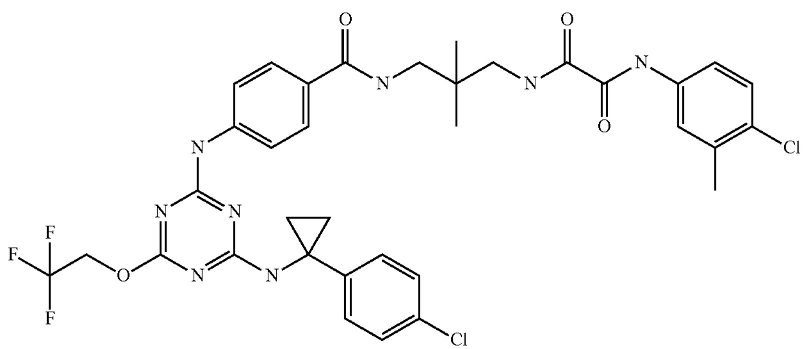 [SMILES: Cc1cc(NC(=O)C(=O)NCC(C)(C)CNC(=O)c2ccc(Nc3nc(NC4(c5ccc(Cl)cc5)CC4)nc(OCC(F)(F)F)n3)cc2)ccc1Cl] | | A |

TABLE 1-continued

| Compound | Structure | EC$_{50}$ | Activity |
|---|---|---|---|
| 3799 | 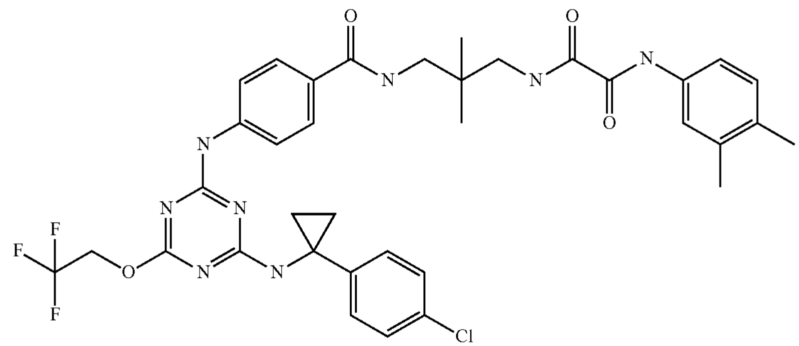 [SMILES: Cc1ccc(NC(=O)C(=O)NCC(C)(C)CNC(=O)c2ccc(Nc3nc(NC4(c5ccc(Cl)cc5)CC4)nc(OCC(F)(F)F)n3)cc2)cc1C] | | A |
| 3800 | 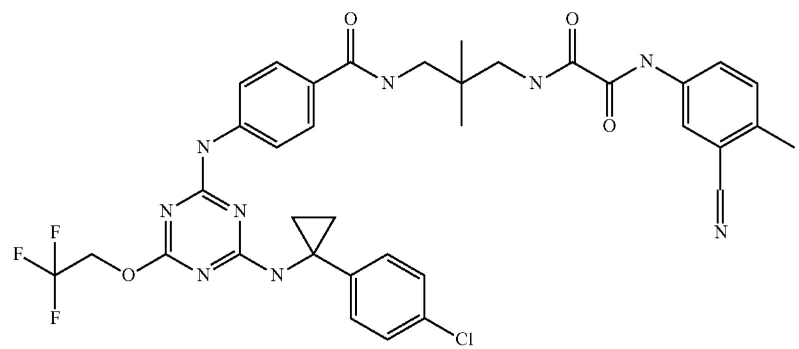 [SMILES: Cc1ccc(NC(=O)C(=O)NCC(C)(C)CNC(=O)c2ccc(Nc3nc(NC4(c5ccc(Cl)cc5)CC4)nc(OCC(F)(F)F)n3)cc2)cc1C=N] | 0.83 | A |
| 3801 | 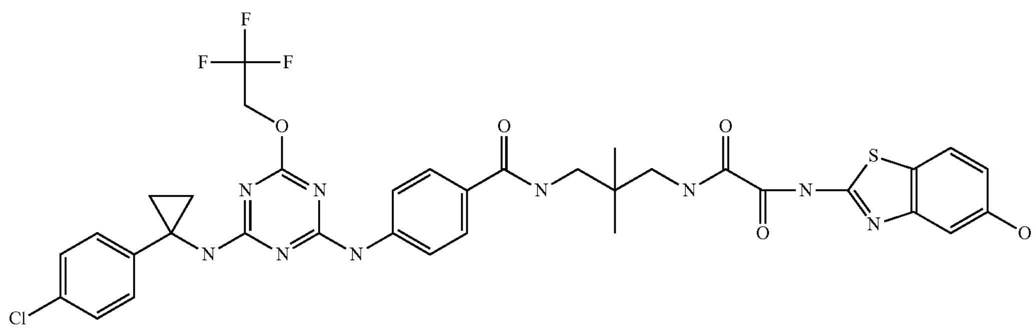 [SMILES: CC(C)(CNC(=O)C(=O)Nc1nc2cc(O)ccc2s1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC₅₀ | Activity |
|---|---|---|---|
| 3802 | 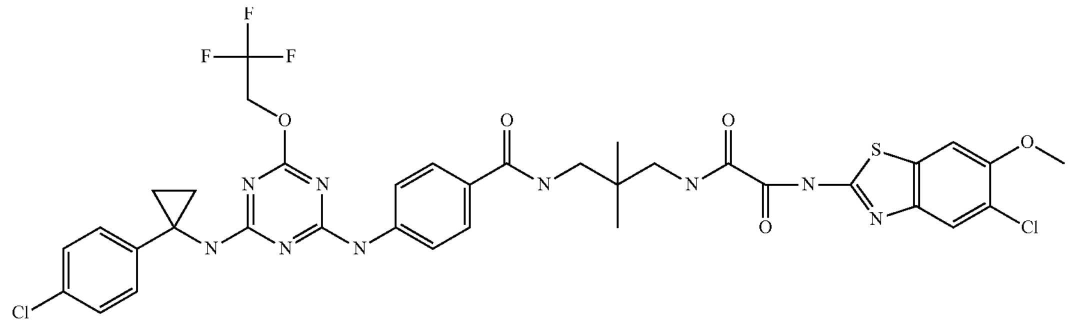 [SMILES: COc1cc2sc(NC(=O)C(=O)NCC(C)(C)CNC(=O)c3ccc(Nc4nc(NC5(c6ccc(Cl)cc6)CC5)nc(OCC(F)(F)F)n4)cc3)nc2cc1Cl] | | A |
| 3803 | 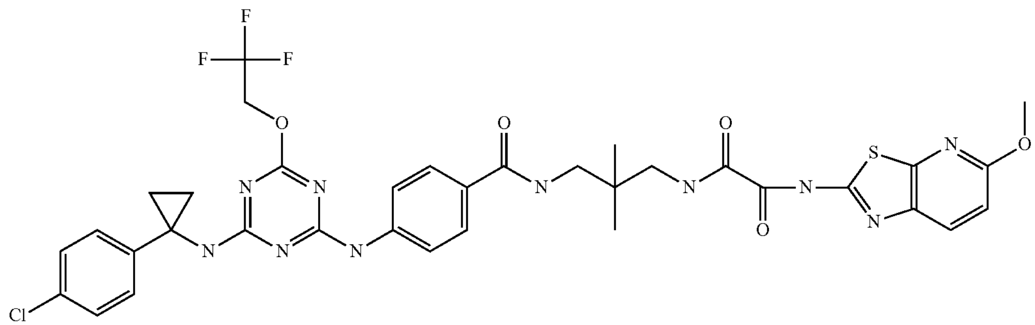 | | A |
| 3804 | 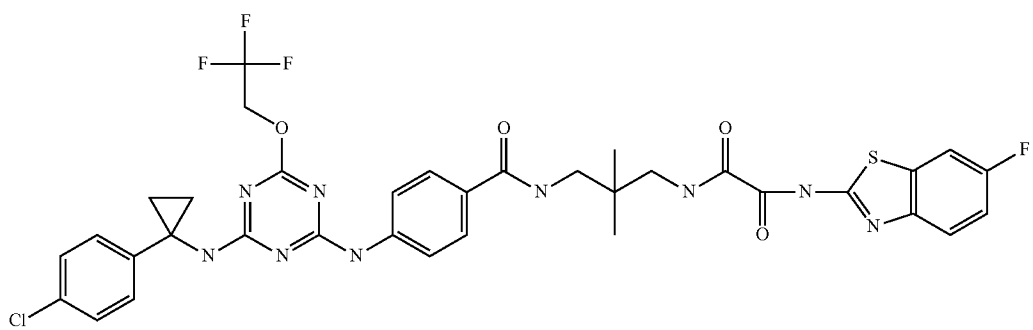 [SMILES: CC(C)(CNC(=O)C(=O)Nc1nc2ccc(F)cc2s1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3805 | 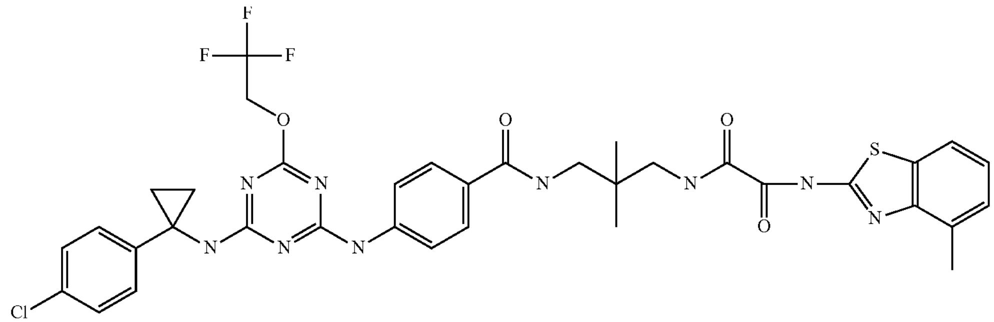 [SMILES: Cc1cccc2sc(NC(=O)C(=O)NCC(C)(C)CNC(=O)c3ccc(Nc4nc(NC5(c6ccc(Cl)cc6)CC5)nc(OCC(F)(F)F)n4)cc3)nc12] | | A |
| 3806 | 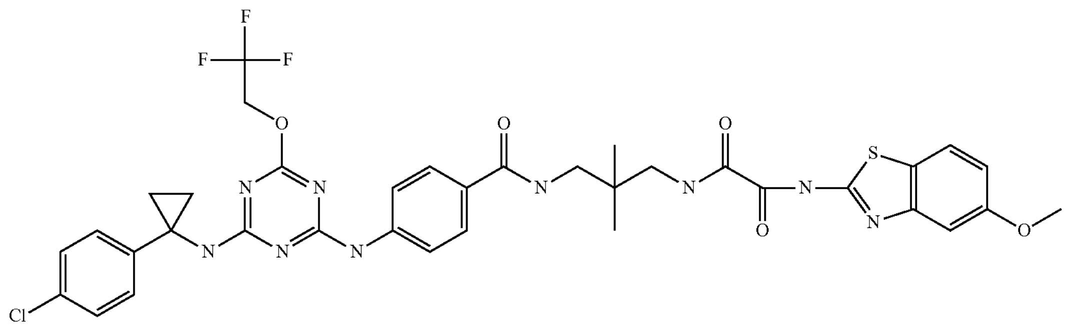 | | A |
| 3807 | 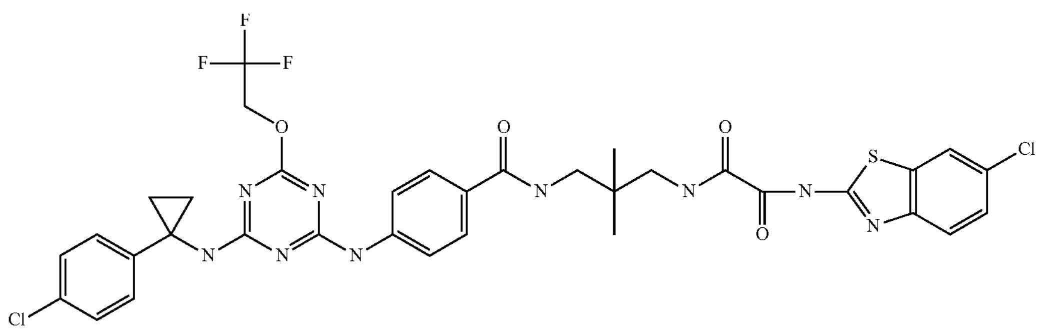 [SMILES: CC(C)(CNC(=O)C(=O)Nc1nc2ccc(Cl)cc2s1)CNC(=O)c1ccc(Nc2nc(NC3(c4ccc(Cl)cc4)CC3)nc(OCC(F)(F)F)n2)cc1] | 0.28 | A |

TABLE 1-continued

| Compound | Structure | EC$_{50}$ | Activity |
|---|---|---|---|
| 3808 | (structure) | | A |
| 3809 | (structure) | | A |
| 3810 | (structure) | | A |

TABLE 1-continued
| Compound | Structure | EC$_{50}$ | Activity |
|---|---|---|---|
| 3811 | 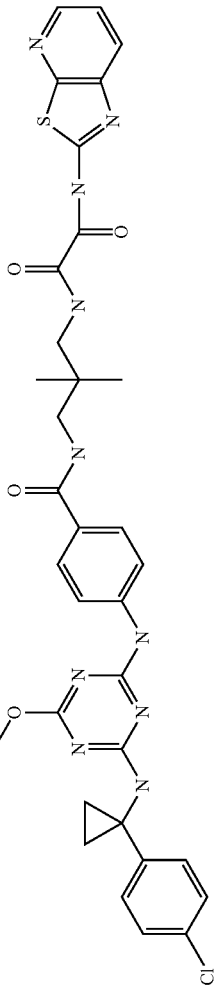 | | A |
| 3812 | 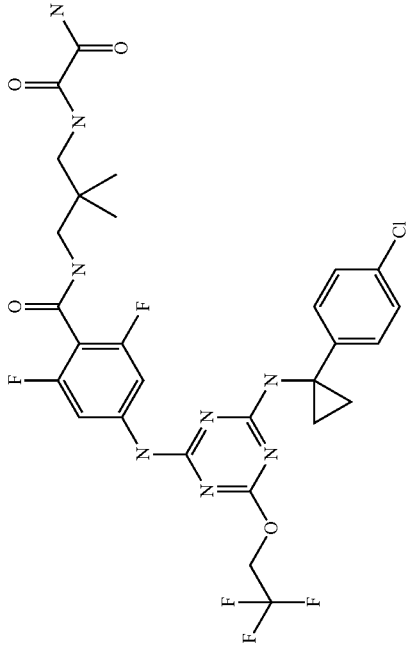 | 0.50 | A |
| 3813 | 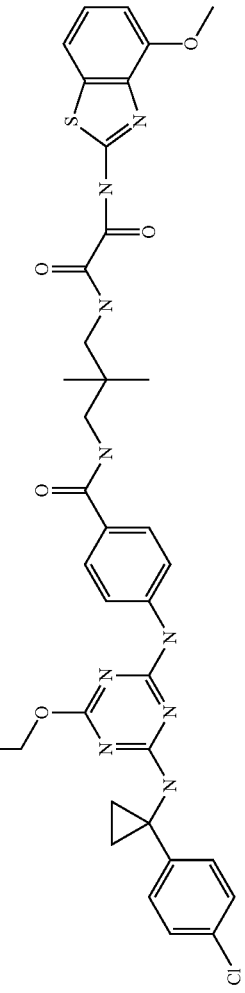 | | A |

TABLE 1-continued

| Compound | Structure | EC$_{50}$ | Activity |
|---|---|---|---|
| 3814 | 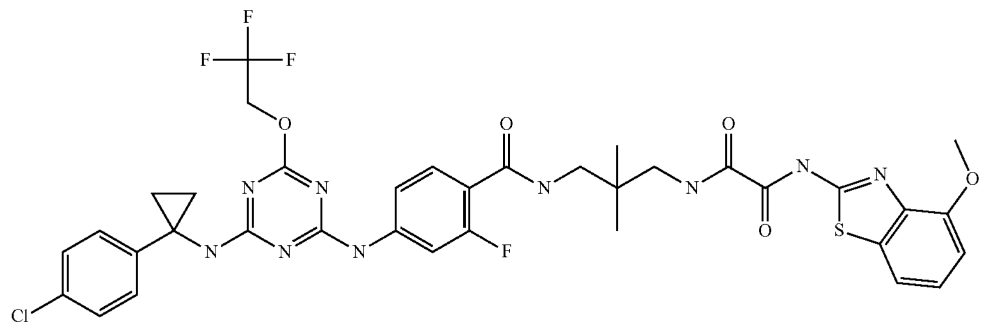 [SMILES: COc1cccc2sc(NC(=O)C(=O)NCC(C)(C)CNC(=O)c3ccc(Nc4nc(NC5(c6ccc(Cl)cc6)CC5)nc(OCC(F)(F)F)n4)cc3F)nc12] | | A |
| 3815 | 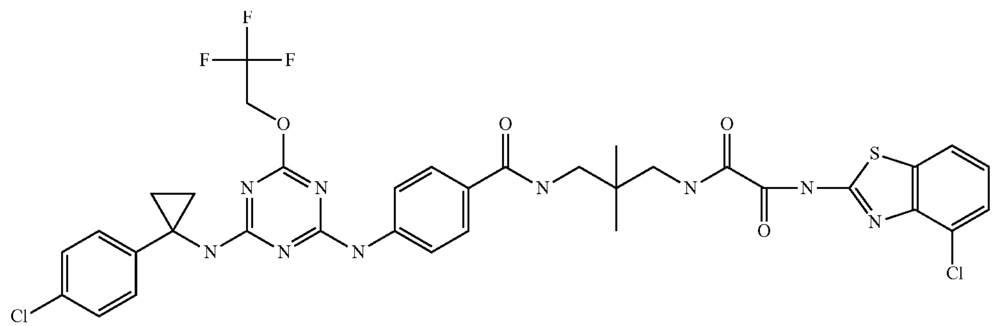 | | A |
| 3816 | 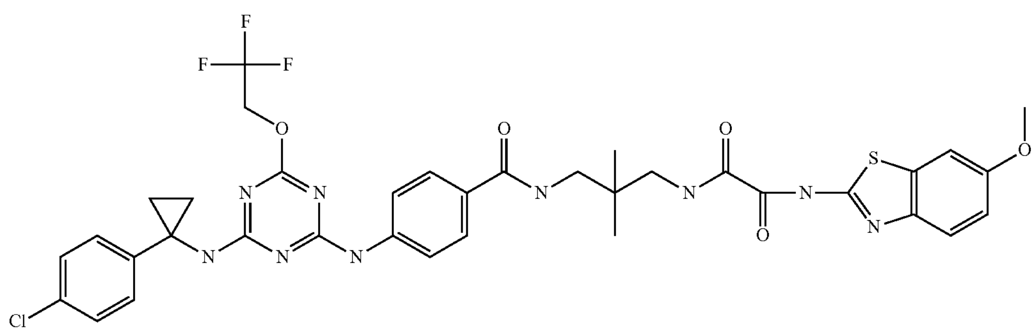 [SMILES: COc1ccc2nc(NC(=O)C(=O)NCC(C)(C)CNC(=O)c3ccc(Nc4nc(NC5(c6ccc(Cl)cc6)CC5)nc(OCC(F)(F)F)n4)cc3)sc2c1] | | A |

TABLE 1-continued
| Compound | Structure | EC$_{50}$ | Activity |
|---|---|---|---|
| 3817 | 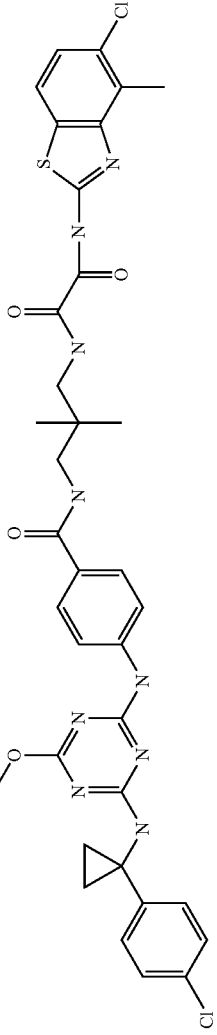 | 0.11 | A |
| 3818 | 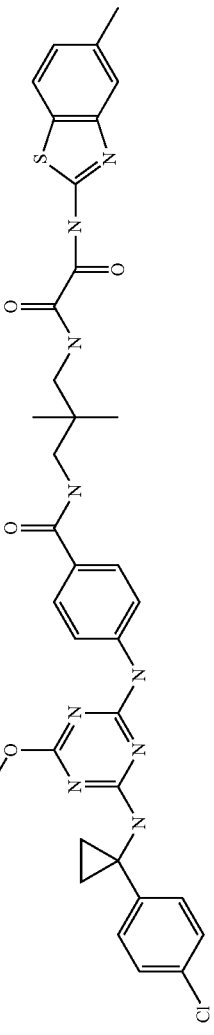 | | A |
| 3819 | 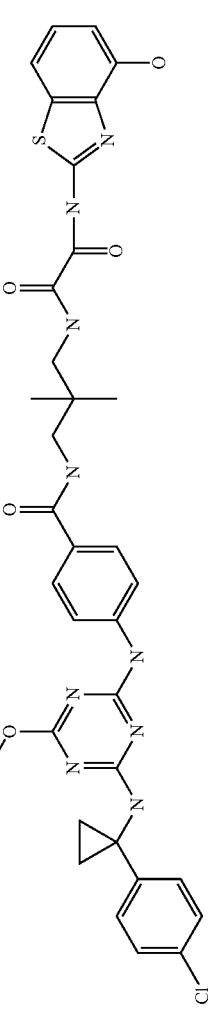 | | A |

TABLE 1-continued

| Compound | Structure | EC$_{50}$ | Activity |
|---|---|---|---|
| 3820 | 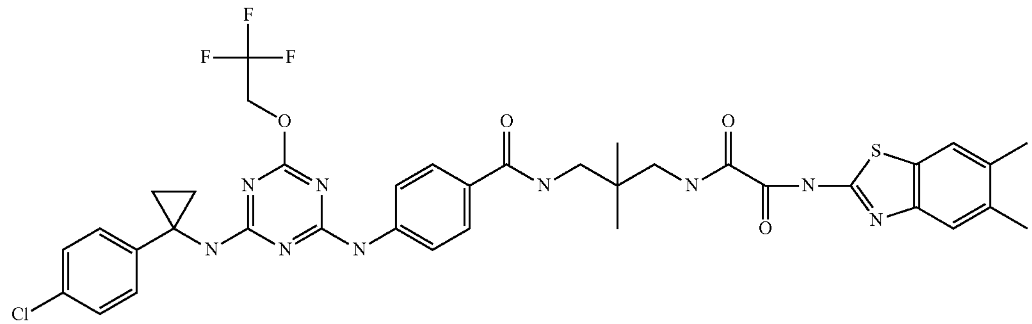 [SMILES: Cc1cc2nc(NC(=O)C(=O)NCC(C)(C)CNC(=O)c3ccc(Nc4nc(NC5(c6ccc(Cl)cc6)CC5)nc(OCC(F)(F)F)n4)cc3)sc2cc1C] | | A |
| 3821 | 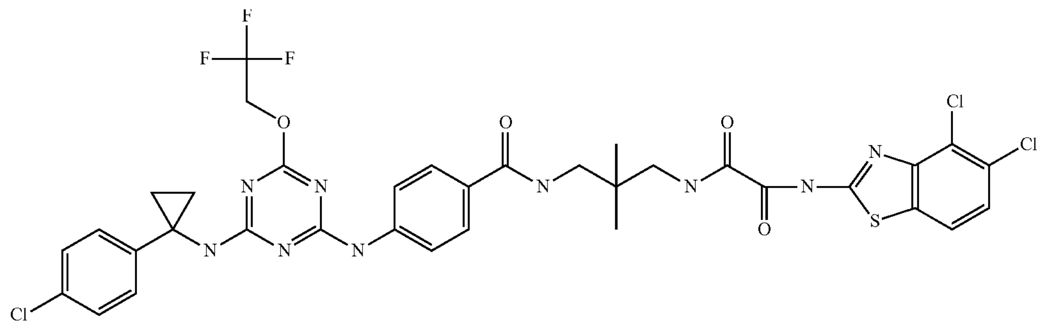 [SMILES: CC(C)(CNC(=O)C(=O)Nc1nc2c(Cl)c(Cl)ccc2s1)CNC(=O)c1ccc(Nc2nc(NC3(c4ccc(Cl)cc4)CC3)nc(OCC(F)(F)F)n2)cc1] | | A |
| 3822 | 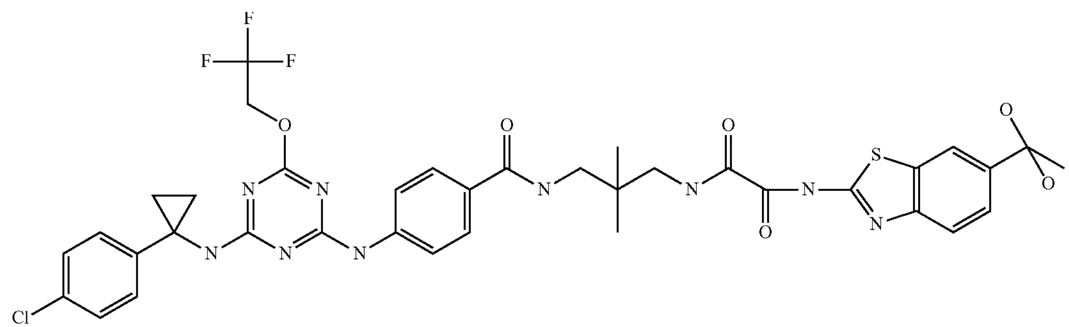 [SMILES: CC(C)(CNC(=O)C(=O)Nc1nc2ccc(C(C)(O)O)cc2s1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC₅₀ | Activity |
|---|---|---|---|
| 3823 | 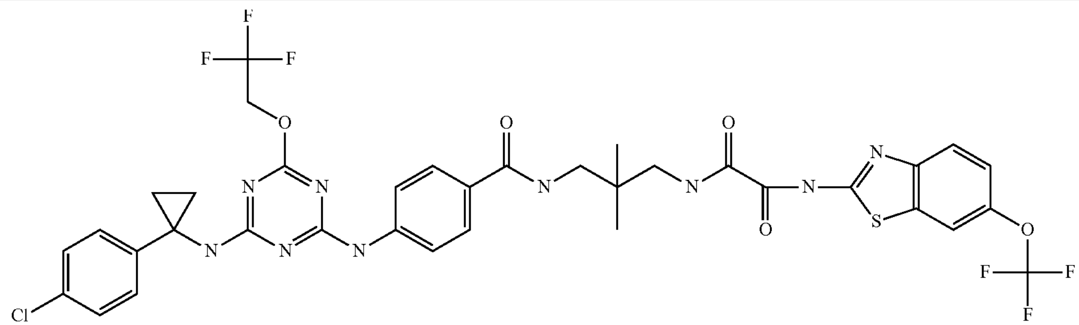 [SMILES: CC(C)(CNC(=O)C(=O)Nc1nc2ccc(OC(F)(F)F)cc2s1)CNC(=O)c1ccc(Nc2nc(NC3(c4ccc(Cl)cc4)CC3)nc(OCC(F)(F)F)n2)cc1] | | A |
| 3824 | 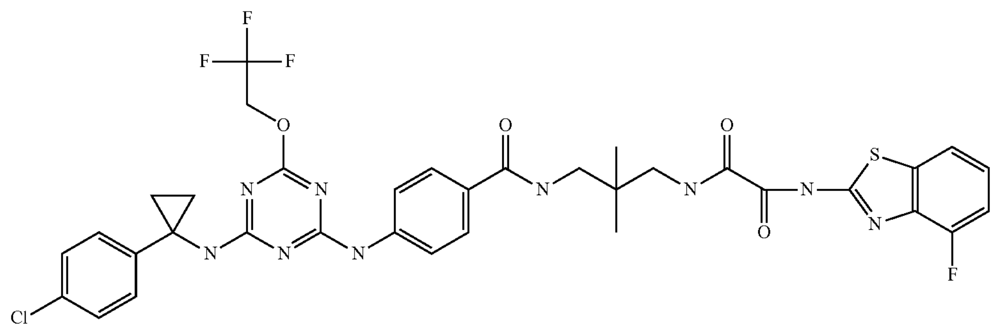 | 0.077 | A |
| 3825 | 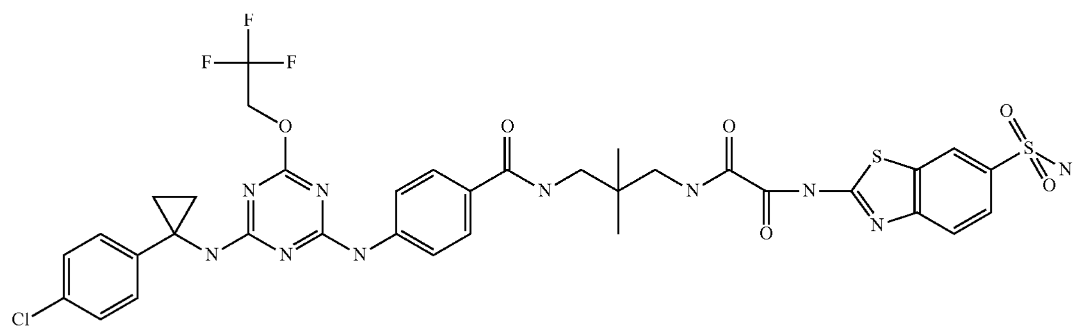 [SMILES: CC(C)(CNC(=O)C(=O)Nc1nc2ccc(S(N)(=O)=O)cc2s1)CNC(=O)c1ccc(Nc2nc(NC3(c4ccc(Cl)cc4)CC3)nc(OCC(F)(F)F)n2)cc1] | | A |

TABLE 1-continued
| Compound | Structure | EC$_{50}$ | Activity |
|---|---|---|---|
| 3826 | 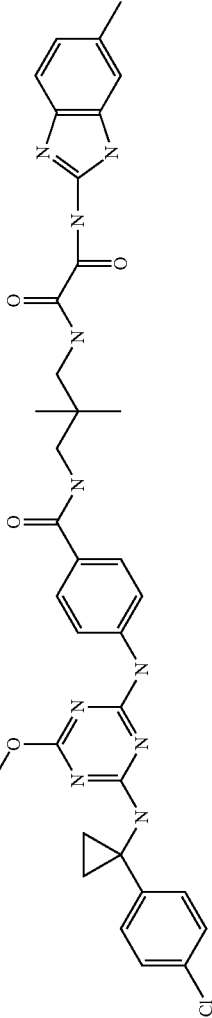 | | A |
| 3827 | 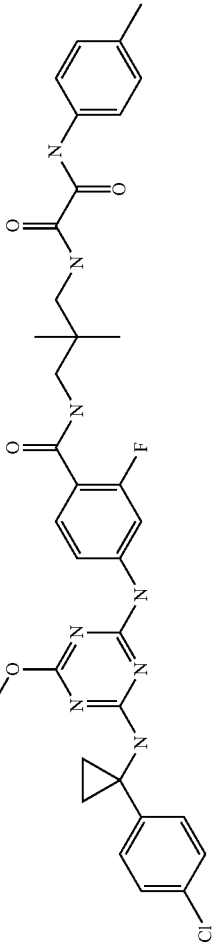 | | A |

TABLE 1-continued
| Compound | Structure | EC$_{50}$ | Activity |
|---|---|---|---|
| 3828 | 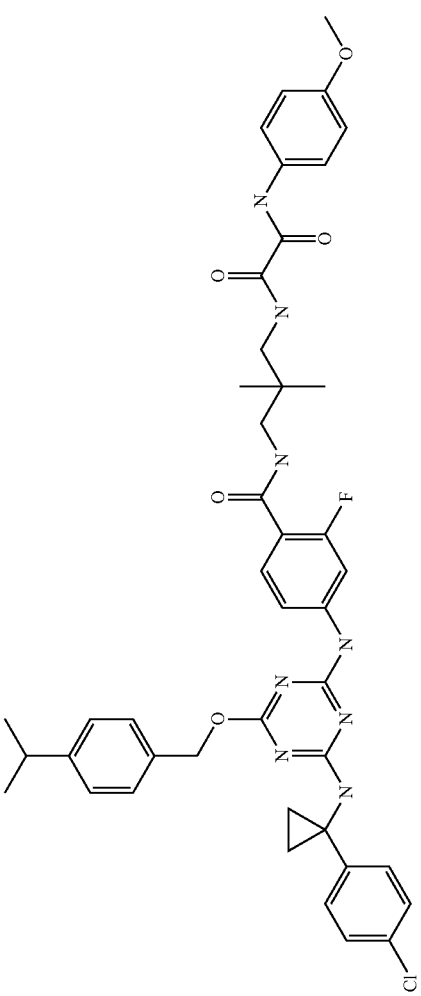 | 0.35 | A |
| 3829 | 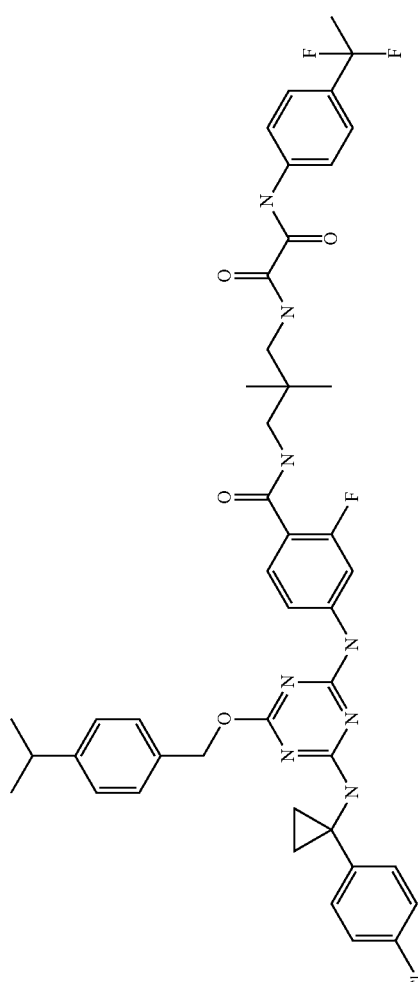 | | A |

TABLE 1-continued
| Compound | Structure | EC$_{50}$ | Activity |
|---|---|---|---|
| 3830 | 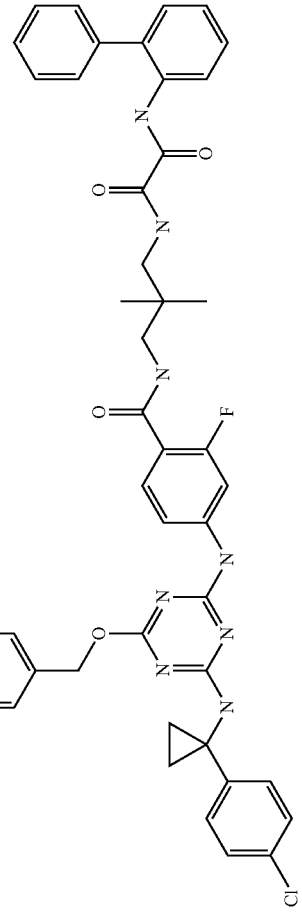 | | A |
| 3831 | 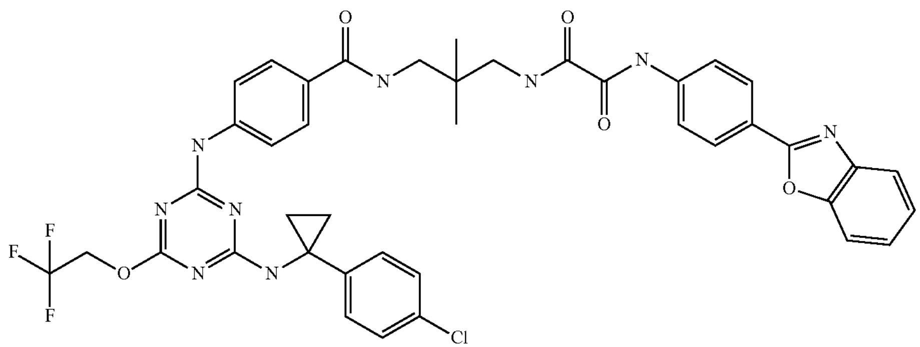 [SMILES: CC(C)(CNC(=O)C(=O)Nc1ccc(-c2nc3ccccc3o2)cc1)CNC(=O)c1ccc(Nc2nc(NC3(c4ccc(Cl)cc4)CC3)nc(OCC(F)(F)F)n2)cc1] | | A |

TABLE 1-continued

| Compound | Structure | EC$_{50}$ | Activity |
|---|---|---|---|
| 3832 | 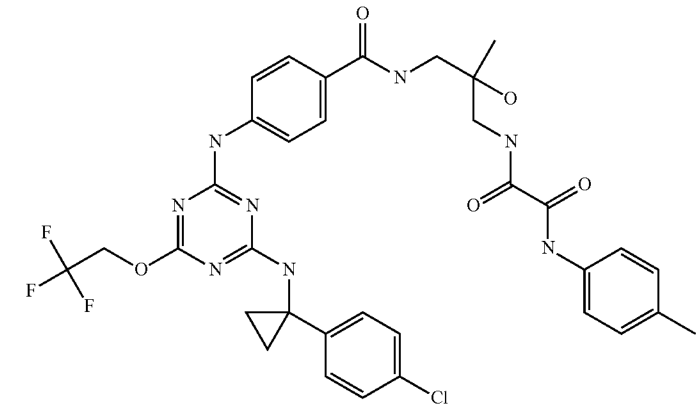 [SMILES: Cc1ccc(NC(=O)C(=O)NCC(C)(O)CNC(=O)c2ccc(Nc3nc(NC4(c5ccc(Cl)cc5)CC4)nc(OCC(F)(F)F)n3)cc2)cc1] | | A |
| 3833 | 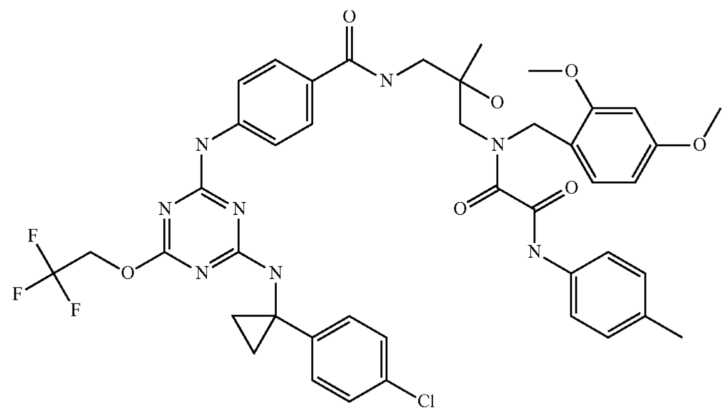 [SMILES: COc1ccc(CN(CC(C)(O)CNC(=O)c2ccc(Nc3nc(NC4(c5ccc(Cl)cc5)CC4)nc(OCC(F)(F)F)n3)cc2)C(=O)C(=O)Nc2ccc(C)cc2)c(OC)c1] | | A |

TABLE 1-continued

| Compound | Structure | EC$_{50}$ | Activity |
|---|---|---|---|
| 3834 | 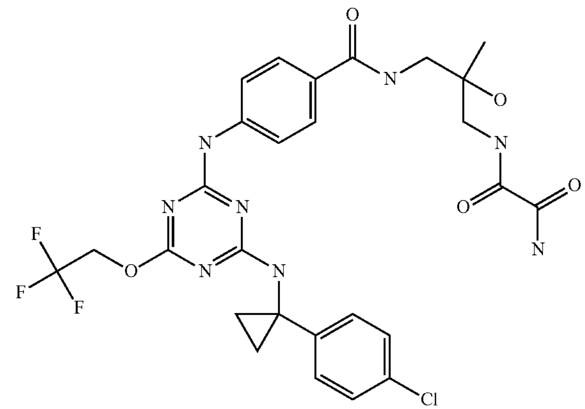 [SMILES: CC(O)(CNC(=O)C(N)=O)CNC(=O)c1ccc(Nc2nc(NC3(c4ccc(Cl)cc4)CC3)nc(OCC(F)(F)F)n2)cc1] | 0.086 | A |
| 3835 | 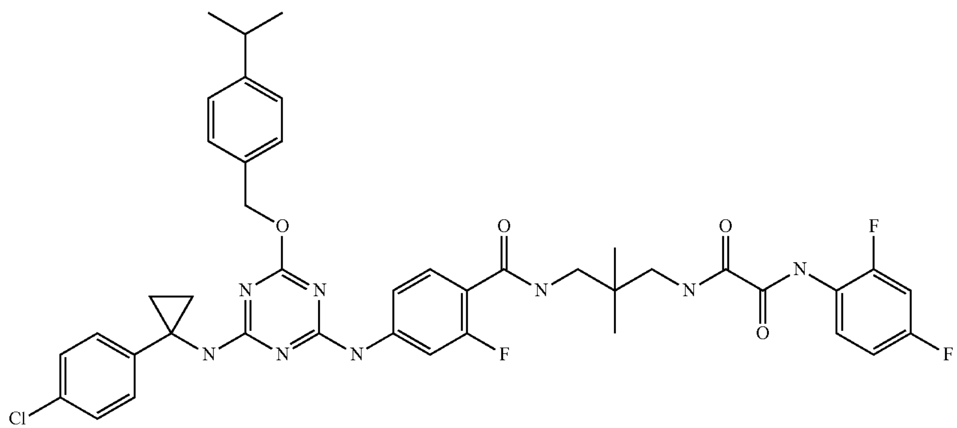 [SMILES: CC(C)c1ccc(COc2nc(Nc3ccc(C(=O)NCC(C)(C)CNC(=O)C(=O)Nc4ccc(F)cc4F)c(F)c3)nc(NC3(c4ccc(Cl)cc4)CC3)n2)cc1] | | A |

TABLE 1-continued

| Compound | Structure | EC$_{50}$ | Activity |
|---|---|---|---|
| 3836 | 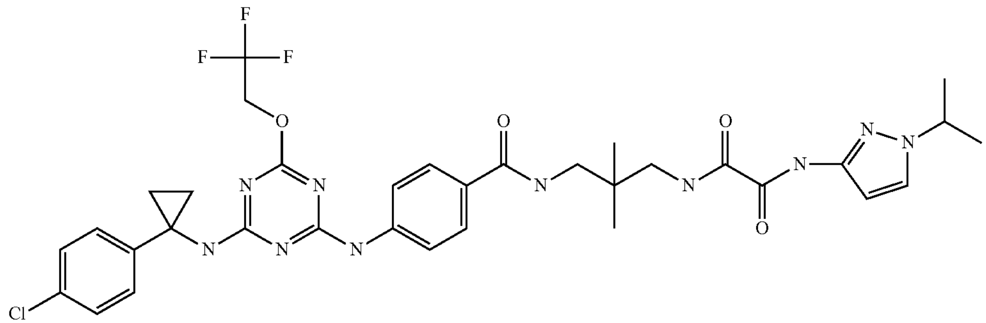 [SMILES: CC(C)n1ccc(NC(=O)C(=O)NCC(C)(C)CNC(=O)c2ccc(Nc3nc(NC4(c5ccc(Cl)cc5)CC4)nc(OCC(F)(F)F)n3)cc2)n1] | | A |
| 3837 | 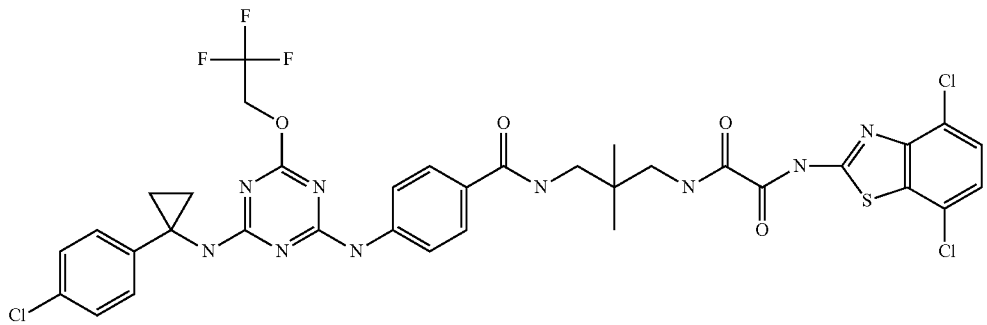 [SMILES: CC(C)(CNC(=O)C(=O)Nc1nc2c(Cl)ccc(Cl)c2s1)CNC(=O)c1ccc(Nc2nc(NC3(c4ccc(Cl)cc4)CC3)nc(OCC(F)(F)F)n2)cc1] | | A |
| 3838 | 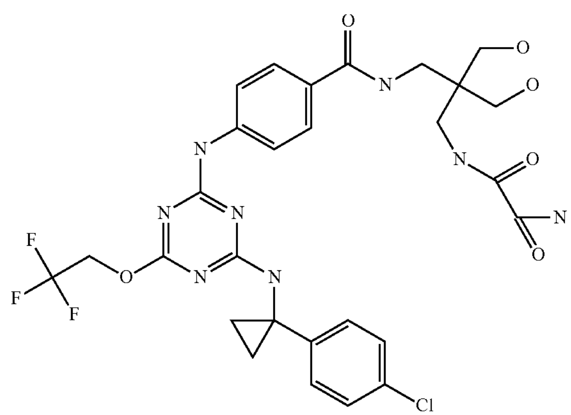 [SMILES: NC(=O)C(=O)NCC(CO)(CO)CNC(=O)c1ccc(Nc2nc(NC3(c4ccc(Cl)cc4)CC3)nc(OCC(F)(F)F)n2)cc1] | 0.052 | A |

TABLE 1-continued

| Compound | Structure | EC$_{50}$ | Activity |
|---|---|---|---|
| 3839 | 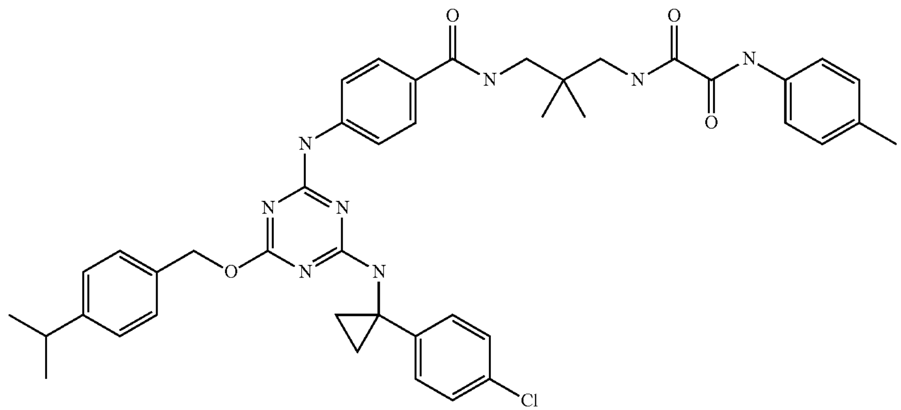 [SMILES: Cc1ccc(NC(=O)C(=O)NCC(C)(C)CNC(=O)c2ccc(Nc3nc(NC4(c5ccc(Cl)cc5)CC4)nc(OCc4ccc(C(C)C)cc4)n3)cc2)cc1] | 0.078 | A |
| 3840 | 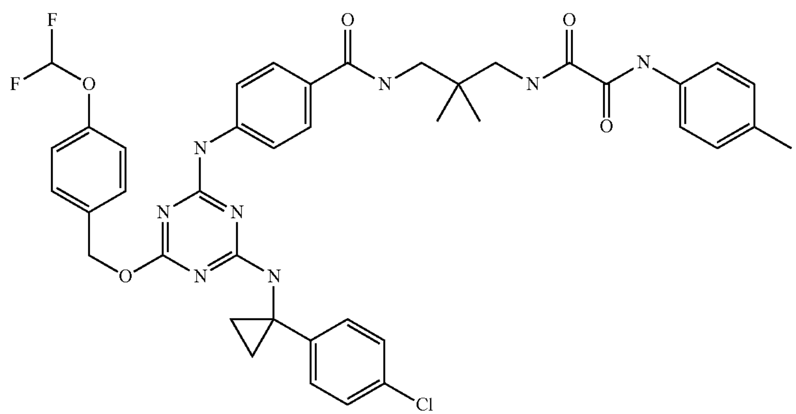 [SMILES: Cc1ccc(NC(=O)C(=O)NCC(C)(C)CNC(=O)c2ccc(Nc3nc(NC4(c5ccc(Cl)cc5)CC4)nc(OCc4ccc(OC(F)F)cc4)n3)cc2)cc1] | | A |

TABLE 1-continued
| Compound | Structure | EC$_{50}$ | Activity |
|---|---|---|---|
| 3841 | 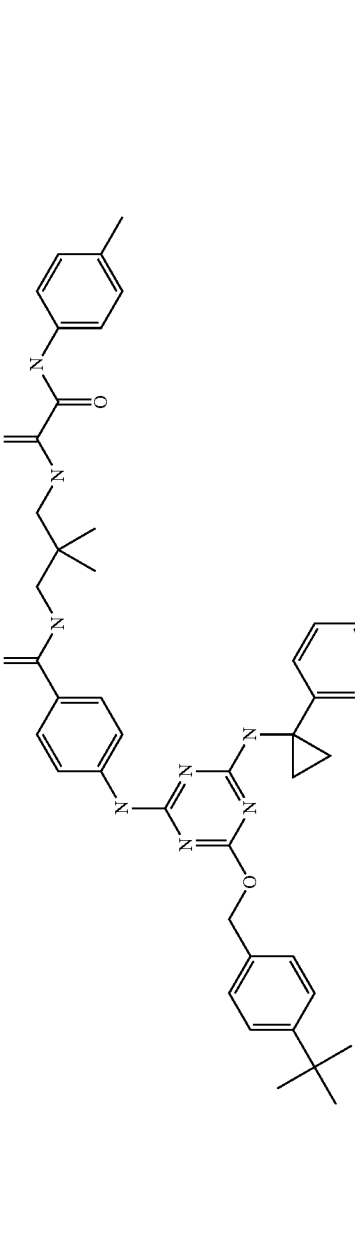 | | A |
| 3842 | 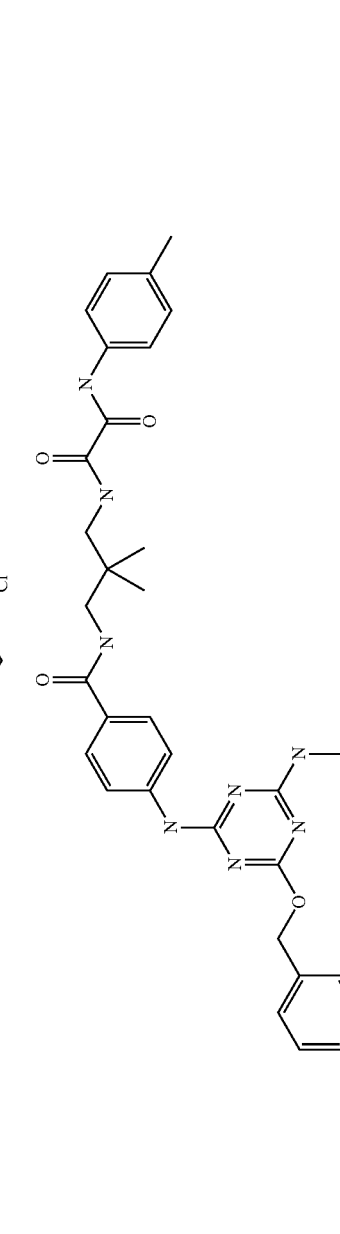 | | A |

TABLE 1-continued
| Compound | Structure | EC$_{50}$ | Activity |
|---|---|---|---|
| 3843 | 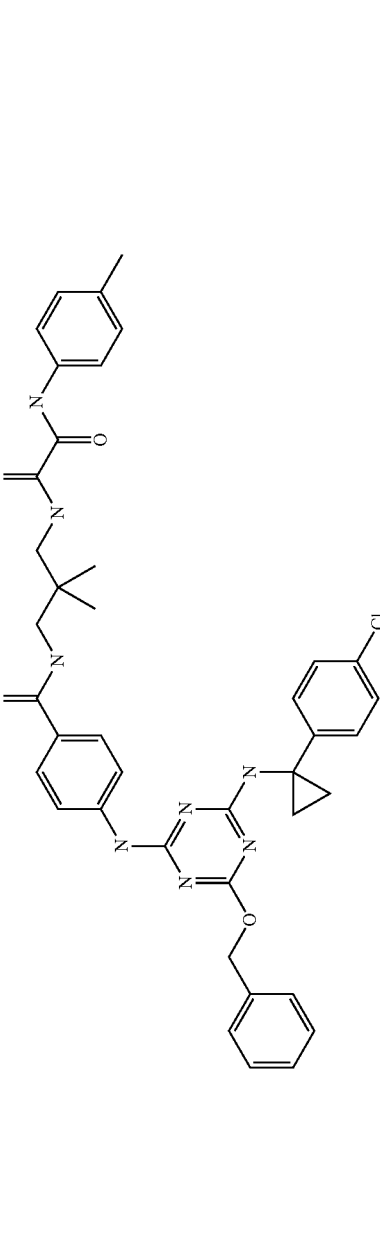 | | A |
| 3844 | 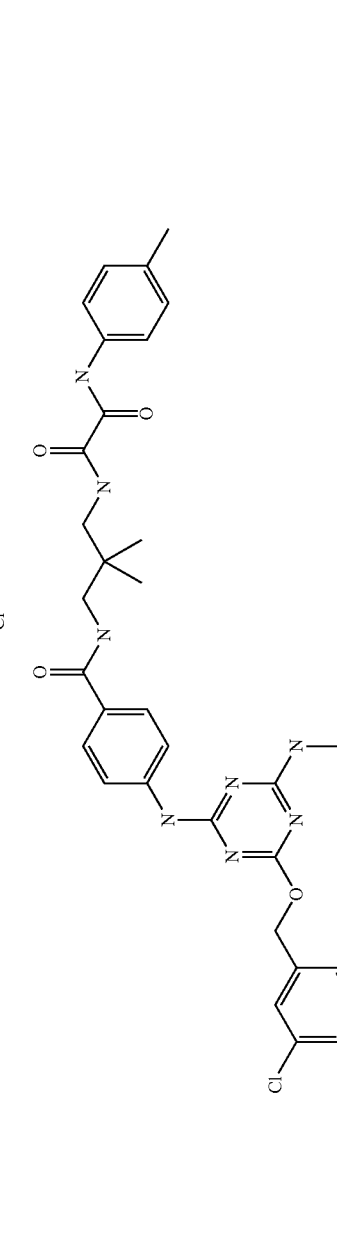 | | A |

TABLE 1-continued

| Compound | Structure | EC$_{50}$ | Activity |
|---|---|---|---|
| 3845 | 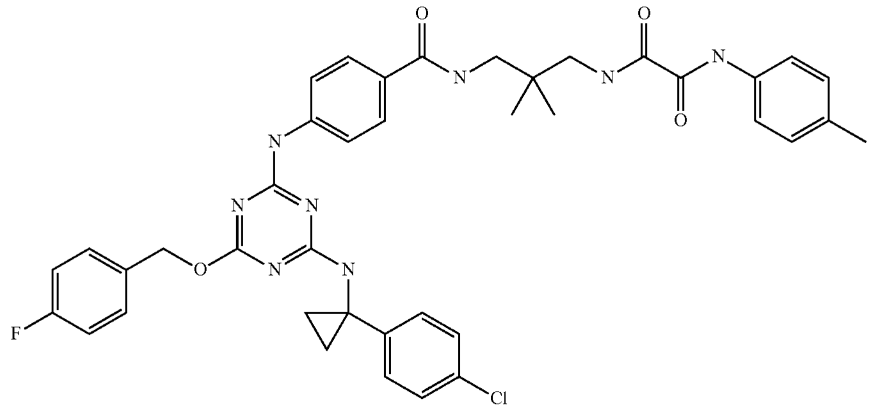 [SMILES: Cc1ccc(NC(=O)C(=O)NCC(C)(C)CNC(=O)c2ccc(Nc3nc(NC4(c5ccc(Cl)cc5)CC4)nc(OCc4ccc(F)cc4)n3)cc2)cc1] | 0.022 | A |
| 3846 | 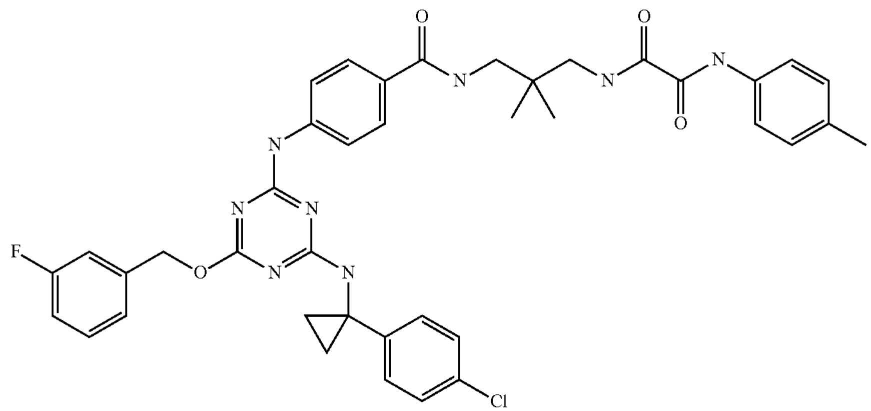 [SMILES: Cc1ccc(NC(=O)C(=O)NCC(C)(C)CNC(=O)c2ccc(Nc3nc(NC4(c5ccc(Cl)cc5)CC4)nc(OCc4cccc(F)c4)n3)cc2)cc1] | | A |

TABLE 1-continued
| Compound | Structure | EC$_{50}$ | Activity |
|---|---|---|---|
| 3847 | 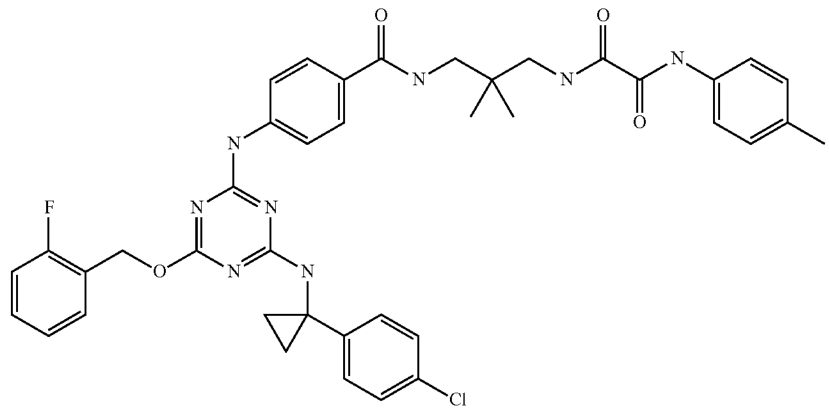 | 0.027 | A |
| 3848 | 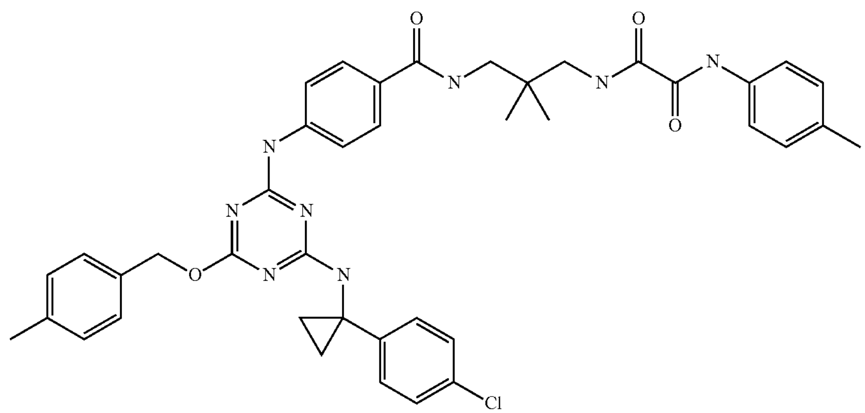 | | A |
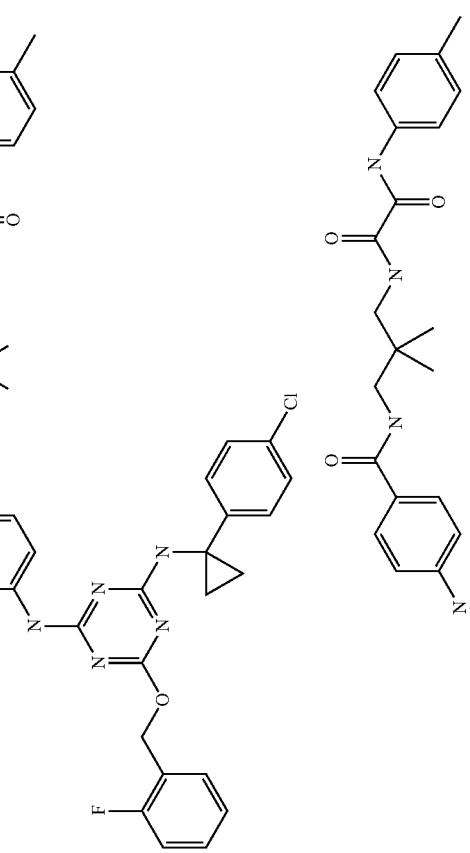

TABLE 1-continued
| Compound | Structure | EC$_{50}$ | Activity |
|---|---|---|---|
| 3849 | 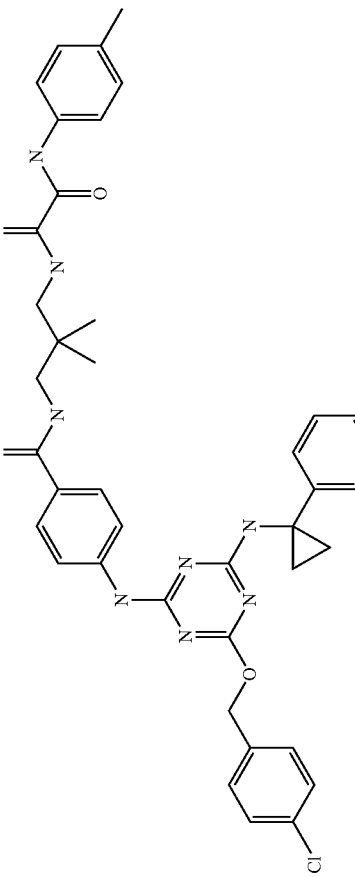 | | A |
| 3850 | 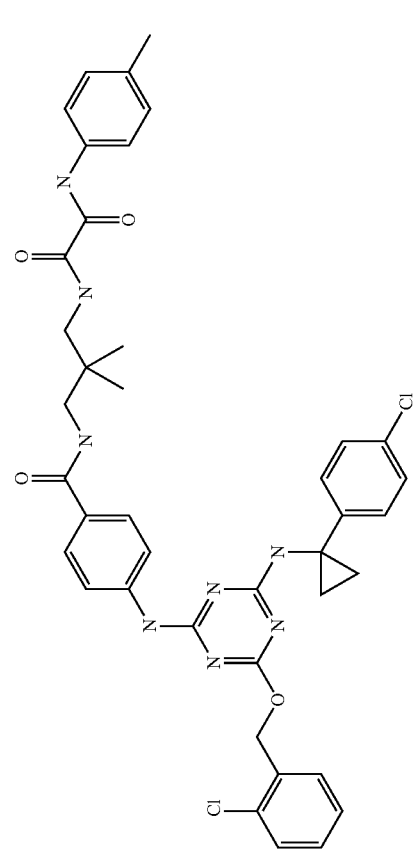 | | A |

TABLE 1-continued

| Compound | Structure | EC$_{50}$ | Activity |
|---|---|---|---|
| 3851 | 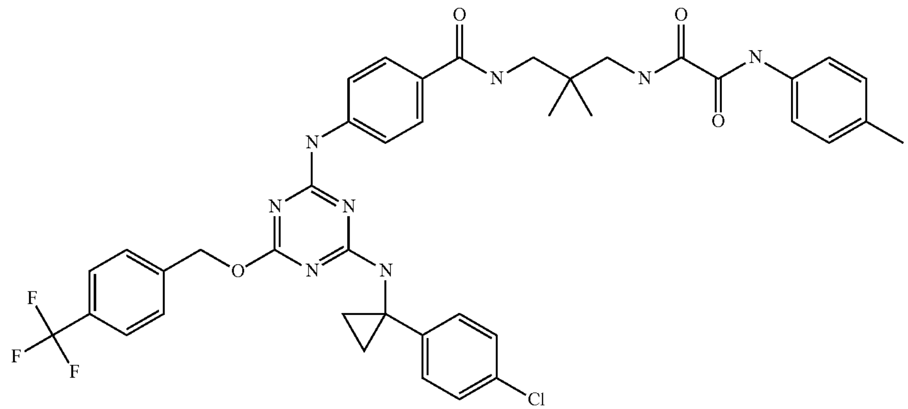 [SMILES: Cc1ccc(NC(=O)C(=O)NCC(C)(C)CNC(=O)c2ccc(Nc3nc(NC4(c5ccc(Cl)cc5)CC4)nc(OCc4ccc(C(F)(F)F)cc4)n3)cc2)cc1] | | A |
| 3852 | 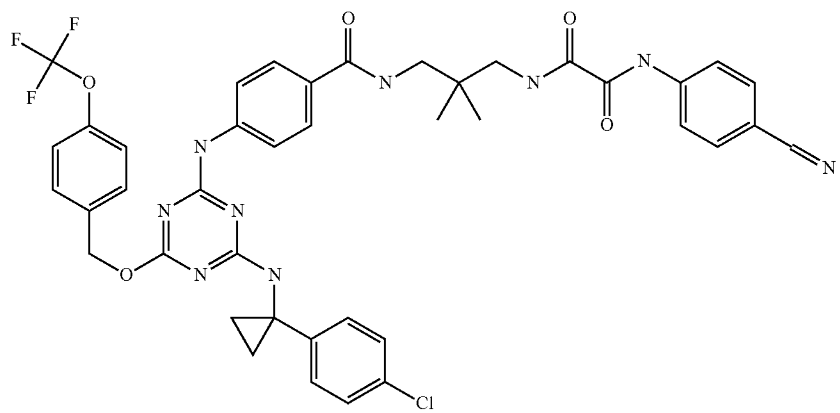 [SMILES: CC(C)(CNC(=O)C(=O)Nc1ccc(C=N)cc1)CNC(=O)c1ccc(Nc2nc(NC3(c4ccc(Cl)cc4)CC3)nc(OCc3ccc(OC(F)(F)F)cc3)n2)cc1] | | A |

TABLE 1-continued

| Compound | Structure | EC$_{50}$ | Activity |
|---|---|---|---|
| 3853 | 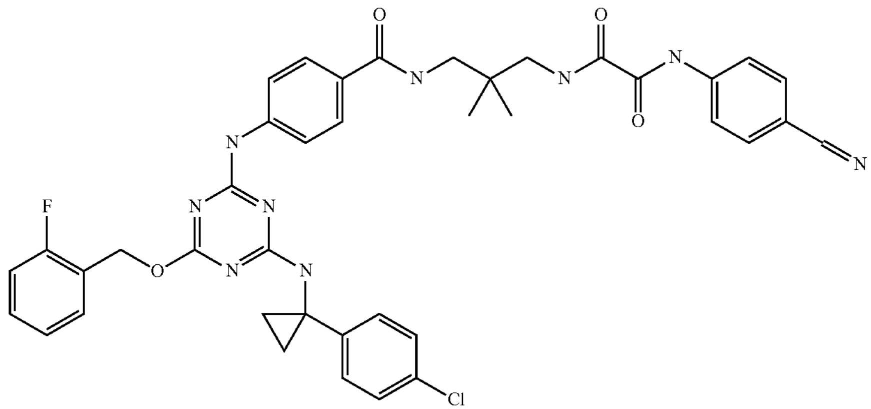 [SMILES: CC(C)(CNC(=O)C(=O)Nc1ccc(C=N)cc1)CNC(=O)c1ccc(Nc2nc(NC3(c4ccc(Cl)cc4)CC3)nc(OCc3ccccc3F)n2)cc1] | | A |

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon or a ribavirin. Another aspect of the invention is where the interferon is selected from interferon alpha 2B, pegylated interferon alpha, consensus interferon, interferon alpha 2A, interferon lambda, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon or a ribavirin.

Another aspect of the invention is the method where the interferon is selected from interferon alpha 2B, pegylated interferon alpha, consensus interferon, interferon alpha 2A, interferon lambda, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Physiological Class | Type of Inhibitor or Target | Source Company |
|---|---|---|---|
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 May 26, 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |

TABLE 2-continued

| Brand Name | Physiological Class | Type of Inhibitor or Target | Source Company |
|---|---|---|---|
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/ Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |

TABLE 2-continued

| Brand Name | Physiological Class | Type of Inhibitor or Target | Source Company |
|---|---|---|---|
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |
| PSI-7977 | Antiviral | Nucleotide NS5B Polymerase Inhibitor | Pharmasset, Princeton, NJ, USA |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/Bristol-Myers Squibb |

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3SO_2$—; and "TMOF" for trimethylorthoformate.

Abbreviations are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

LC/MS Method (i.e., Compound Identification).

All Liquid Chromatography (LC) data were recorded on a Shimadzu LC-10AS or LC-20AS liquid chromotograph using a SPD-10AV or SPD-20A UV-Vis detector and Mass Spectrometry (MS) data were determined with a Micromass Platform for LC in electrospray mode.

HPLC Method (i.e., Compound Isolation).

Compounds purified by preparative HPLC were diluted in methanol (1.2 mL) and purified using a Shimadzu LC-8A or LC-10A or Dionex APS-3000 or Waters Acquity™ automated preparative HPLC system.

Syntheses of Intermediates

Preparation of 4-(4-(1-(4-chlorophenyl)cyclopropylamino)-6-(2,2,2-trifluoroethoxy)-1,3,5-triazin-2-ylamino)benzoic acid, In-1001

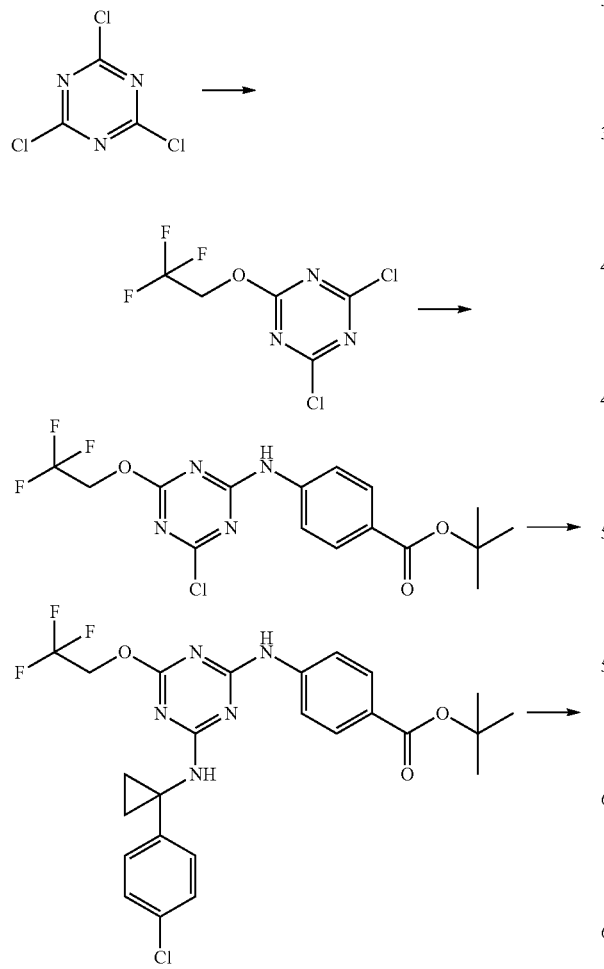

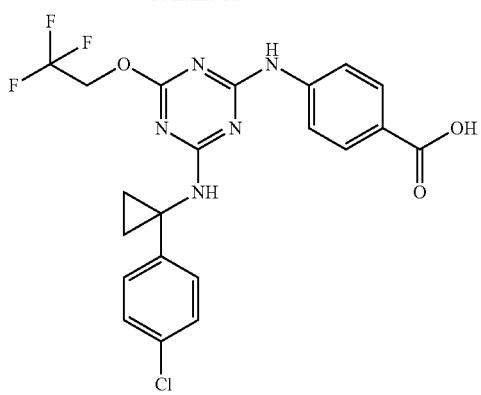

In-1001

Step 1:

To a solution of 2,4,6-trichloro-1,3,5-triazine (15 g) in THF (300 mL) was added 2,2,2-trifluoroethanol (8.14 g) and Hunig'sBase (15.63 mL). The resulting mixture was stirred for 16 hours. After removal of most THF and precipitate through a plug washing with THF, the filtrate was concentrate to give a crude that will be used as it is.

Step 2:

To a solution of the product in Step 1 above (10 g) in THF (100 mL) was added tert-butyl 4-aminobenzoate (7.79 g) and Hunig'sBase (7.04 mL). The resulting mixture was stirred for 16 h. The precipitate was filtered and washed with Et$_2$O, dried, then washed with water and dried to give 10.6 g of tert-butyl 4-(4-chloro-6-(2,2,2-trifluoroethoxy)-1,3,5-triazin-2-ylamino)benzoate as a solid.

| tert-butyl 4-(4-chloro-6-(2,2,2-trifluoroethoxy)-1,3,5-triazin-2-ylamino)benzoate | |
|---|---|
| MS (M + H)$^+$ Calcd. | 405.1 |
| MS (M + H)$^+$ Observ. | 405.0 |
| LC Condition | |
| Solvent A | 100% Water-0.1% TFA |
| Solvent B | 100% ACN-0.1% TFA |
| Start % B | 2 |
| Final % B | 98 |
| Gradient Time | 1.6 min |
| Stop Time | 1.8 min |
| Flow Rate | 0.8 mL/min |
| Wavelength | 220 |
| Solvent Pair | ACN-H$_2$O-0.1% TFA |
| Column | Aquity UPLC BEH C18 1.7 um |

Step 3:

To a slurry of tert-butyl 4-(4-chloro-6-(2,2,2-trifluoroethoxy)-1,3,5-triazin-2-ylamino)benzoate (3.6 g) and 1-(4-chlorophenyl)cyclopropanamine (1.49 g) in THF (50 mL) was stirred for 5 hours at 80° C. The precipitate was filtrated through a plug washing with THF to give acrude product that was purified by Biotage eluting with 4/1-hexane/ethyl acetate to give 1.8 g of tert-butyl 4-(4-(1-(4-chlorophenyl)cyclopropylamino)-6-(2,2,2-trifluoroethoxy)-1,3,5-triazin-2-ylamino)benzoate as a solid.

1511 tert-butyl 4-(4-(1-(4-chlorophenyl)cyclopropylamino)-6-(2,2,2-trifluoroethoxy)-1,3,5-triazin-2-ylamino)benzoate

| | |
|---|---|
| MS (M + H)+ Calcd. | 536.2 |
| MS (M + H)+ Observ. | 536.0 |
| | LC Condition |
| Solvent A | 100% Water-0.1% TFA |
| Solvent B | 100% ACN-0.1% TFA |
| Start % B | 2 |
| Final % B | 98 |
| Gradient Time | 1.6 min |
| Stop Time | 1.8 min |
| Flow Rate | 0.8 mL/min |
| Wavelength | 220 |
| Solvent Pair | ACN-H$_2$O-0.1% TFA |
| Column | Aquity UPLC BEH C18 1.7 um |

Step 4:

A solution of above tert-butyl 4-(4-(1-(4-chlorophenyl) cyclopropylamino)-6-(2,2,2-trifluoroethoxy)-1,3,5-triazin-2-ylamino)benzoate (4 g) and HCl in dioxane (7.46 ml, 4M) was stirred for 4 hours. Concentration gave 3.58 g of 4-(4-(1-(4-chlorophenyl)cyclopropylamino)-6-(2,2,2-trifluoroethoxy)-1,3,5-triazin-2-ylamino)benzoic acid as a solid.

4-(4-(1-(4-chlorophenyl)cyclopropylamino)-6-(2,2,2-trifluoroethoxy)-1,3,5-triazin-2-ylamino)benzoic acid, In-1001

| | |
|---|---|
| MS (M + H)+ Calcd. | 480.1 |
| MS (M + H)+ Observ. | 480.1 |
| | LC Condition |
| Solvent A | 100% Water-0.1% TFA |
| Solvent B | 100% ACN-0.1% TFA |
| Start % B | 2 |
| Final % B | 98 |
| Gradient Time | 1.6 min |
| Stop Time | 1.8 min |
| Flow Rate | 0.8 mL/min |
| Wavelength | 220 |
| Solvent Pair | ACN-H$_2$O-0.1% TFA |
| Column | Aquity UPLC BEH C18 1.7 um |

Preparation of (S)-methyl 3-amino-2-(4-(4-(1-(4-chlorophenyl)cyclopropylamino)-6-(2,2,2-trifluoroethoxy)-1,3,5-triazin-2-ylamino)benzamido)propanoate, In-1002

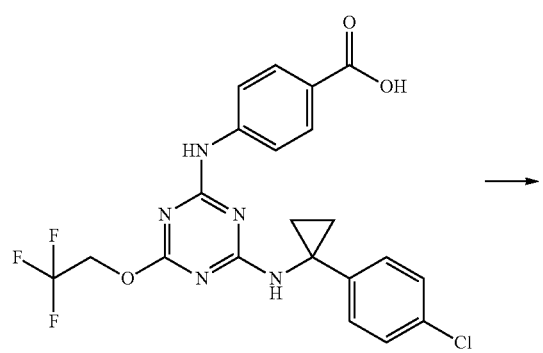

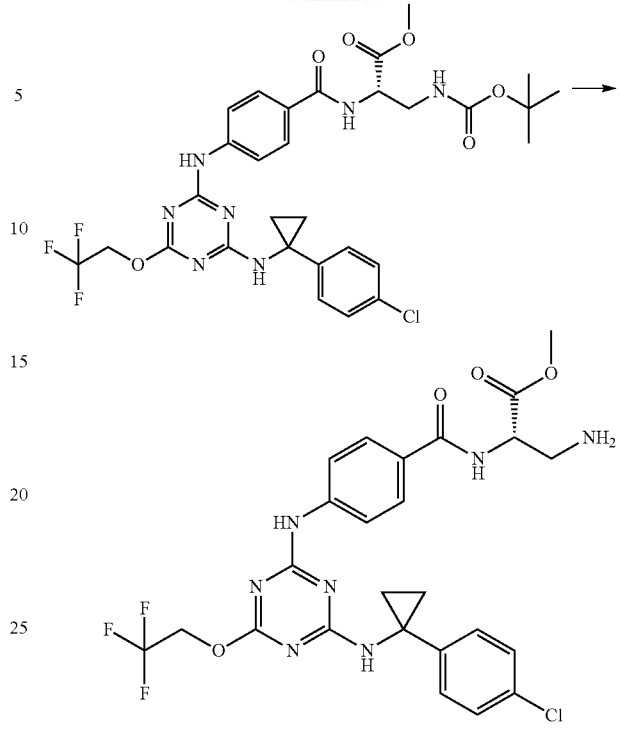

In-1002

Step 1:

To a solution of 4-(4-(1-(4-chlorophenyl)cyclopropylamino)-6-(2,2,2-trifluoroethoxy)-1,3,5-triazin-2-ylamino) benzoic acid (50 mg) in DMF (2 mL) was added O-(benzotriazol-1-yl-N,N,N',N'-tetramethyluronium tetrafluoroborate (23.82 mg) and (S)-methyl 2-amino-3-(tert-butoxycarbonylamino)propanoate hydrochloride (18.90 mg) and iPr$_2$NEt (0.052 ml). After stirring at rt for 4 h, the mixture was purified by preparative HPLC to give (S)-methyl 3-(tert-butoxycarbonylamino)-2-(4-(4-(1-(4-chlorophenyl)cyclopropylamino)-6-(2,2,2-trifluoroethoxy)-1,3,5-triazin-2-ylamino)benzamido)propanoate.

(S)-methyl 3-(tert-butoxycarbonylamino)-2-(4-(4-(1-(4-chlorophenyl)cyclopropylamino)-6-(2,2,2-trifluoroethoxy)-1,3,5-triazin-2-ylamino)benzamido)propanoate

| | |
|---|---|
| MS (M + H)+ Calcd. | 680.2 |
| MS (M + H)+ Observ. | 680.3 |
| Retention Time | 3.44 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex Luna C18, 50 × 2, 3 u |

Step 2:

To a solution of (S)-methyl 3-(tert-butoxycarbonylamino)-2-(4-(4-(1-(4-chlorophenyl)cyclopropylamino)-6-(2,2,2-trifluoroethoxy)-1,3,5-triazin-2-ylamino)benzamido)propanoate (1 g) in CH$_2$Cl$_2$ (10 mL) was added TFA (3 mL). The mixture was stirred at room temperature for 16 hours. All the solvents were removed under vacuum to give (S)-methyl 3-amino-2-(4-(4-(1-(4-chlorophenyl)cyclopropylamino)-6-(2,2,2-trifluoroethoxy)-1,3,5-triazin-2-ylamino)benzamido)propanoate (0.8 g).

| (S)-methyl 3-amino-2-(4-(4-(1-(4-chlorophenyl)cyclopropylamino)-6-(2,2,2-trifluoroethoxy)-1,3,5-triazin-2-ylamino)benzamido)propanoate, In-1002 | |
|---|---|
| MS (M + H)+ Calcd. | 580.2 |
| MS (M + H)+ Observ. | 580.0 |
| Retention Time | 1.35 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of (S)-methyl 4-amino-2-(4-(4-(1-(4-chlorophenyl)cyclopropylamino)-6-(2,2,2-trifluoroethoxy)-1,3,5-triazin-2-ylamino)benzamido)butanoate, In-1003

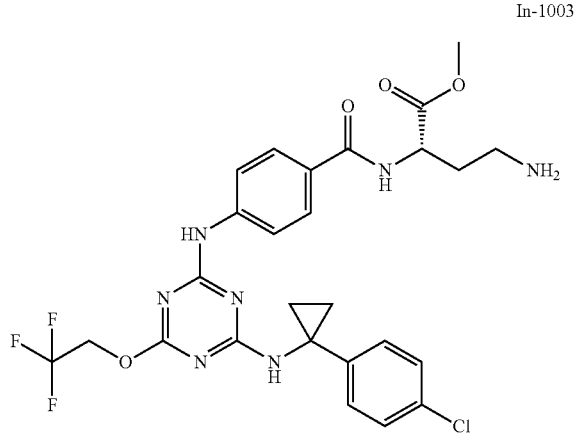 [SMILES: COC(=O)[C@H](CCN)NC(=O)c1ccc(Nc2nc(NC3(c4ccc(Cl)cc4)CC3)nc(OCC(F)(F)F)n2)cc1]

In-1003

In-1003 was prepared by using the same procedure of synthesizing In-1002, using (S)-methyl 2-amino-4-(tert-butoxycarbonylamino)butanoate as a starting material.

| (S)-methyl 4-amino-2-(4-(4-(1-(4-chlorophenyl)cyclopropylamino)-6-(2,2,2-trifluoroethoxy)-1,3,5-triazin-2-ylamino)benzamido)butanoate: | |
|---|---|
| MS (M + H)+ Calcd. | 594.2 |
| MS (M + H)+ Observ. | 594.4 |
| Retention Time | 1.64 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |

| (S)-methyl 4-amino-2-(4-(4-(1-(4-chlorophenyl)cyclopropylamino)-6-(2,2,2-trifluoroethoxy)-1,3,5-triazin-2-ylamino)benzamido)butanoate: | |
|---|---|
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3u |

Preparation of (S)-methyl 5-amino-2-(4-(4-(1-(4-chlorophenyl)cyclopropylamino)-6-(2,2,2-trifluoroethoxy)-1,3,5-triazin-2-ylamino)benzamido)pentanoate

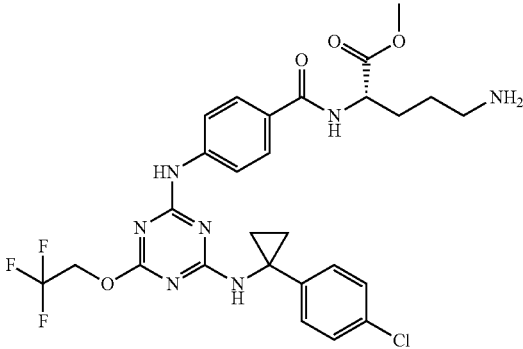

In-1004

In-1004 was prepared by using the same procedure of synthesizing In-1002, using (S)-methyl 2-amino-5-(tert-butoxycarbonylamino)pentanoate as a starting material.

| (S)-methyl 5-amino-2-(4-(4-(1-(4-chlorophenyl)cyclopropylamino)-6-(2,2,2-trifluoroethoxy)-1,3,5-triazin-2-ylamino)benzamido)pentanoate, In-1004 | |
|---|---|
| MS (M + H)+ Calcd. | 608.2 |
| MS (M + H)+ Observ. | 608.1 |
| Retention Time | 2.44 |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

1515

Preparation of N-(3-amino-2,2-dimethylpropyl)-4-(4-(1-(4-chlorophenyl)cyclopropylamino)-6-(2,2,2-trifluoroethoxy)-1,3,5-triazin-2-ylamino)benzamide, In-1005

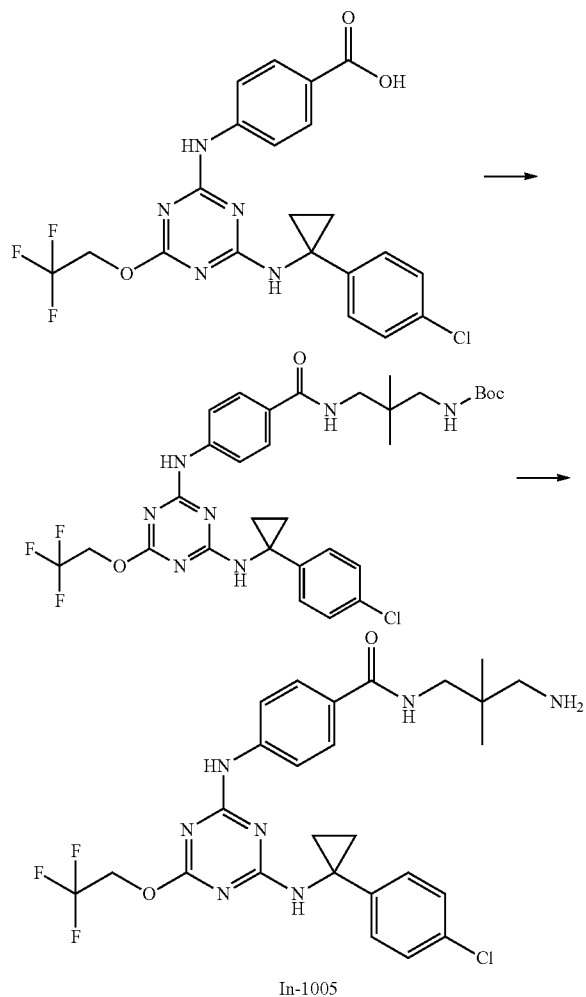

In-1005 iPr$_2$NEt (0.266 g) and O-benzotriazol-1-yl-N,N,N',N'-tetra-methyluronium tetrafluoroborate (0.610 g) were added into a solution of 4-(4-(1-(4-chlorophenyl)cyclopropylamino)-6-(2,2,2-trifluoroethoxy)-1,3,5-triazin-2-ylamino)benzoic acid (0.760 g) and tert-butyl 3-amino-2,2-dimethylpropylcarbamate (0.352 g) were dissolved in DMF (3 mL). The reaction was stirred at room temperature for 16 hrs before 200 mL of EtOAc was added. The organic phase was washed with water (2×25 mL) and brine (20 mL), dried over MgSO4, and concentrated to give crude product tert-butyl 3-(4-(4-(1-(4-chlorophenyl)cyclopropylamino)-6-(2,2,2-trifluoroethoxy)-1,3,5-triazin-2-ylamino)benzamido)-2,2-dimethylpropylcarbamate (0.75 g) which was dissolved in CH$_2$Cl$_2$ (3 mL) and TFA (1.3 mL). After being stirred at room temperature for 16 hours, the mixture was concentrated to give a crude product, N-(3-amino-2,2-dimethylpropyl)-4-(4-(1-(4-chlorophenyl)cyclopropylamino)-6-(2,2,2-trifluoroethoxy)-1,3,5-triazin-2-ylamino)benzamide (0.63 g).

1516

| tert-butyl 3-(4-(4-(1-(4-chlorophenyl)cyclopropylamino)-6-(2,2,2-trifluoroethoxy)-1,3,5-triazin-2-ylamino)-benzamido)-2,2-dimethylpropylcarbamate | |
|---|---|
| MS (M + H)$^+$ Calcd. | 664.3 |
| MS (M + H)$^+$ Observ. | 664.4 |
| Retention Time | 3.75 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3 u |

| N-(3-amino-2,2-dimethylpropyl)-4-(4-(1-(4-chlorophenyl)cyclopropylamino)-6-(2,2,2-trifluoroethoxy)-1,3,5-triazin-2-ylamino)benzamide, In-1005 | |
|---|---|
| MS (M + H)$^+$ Calcd. | 564.2 |
| MS (M + H)$^+$ Observ. | 564.3 |
| Retention Time | 3.02 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3 u |

Preparation of N-(3-amino-2,2-dimethylpropyl)-4-((4-((1-(4-chlorophenyl)cyclopropyl)amino)-6-(2,2,2-trifluoroethoxy)-1,3,5-triazin-2-yl)amino)-2-fluorobenzamide, In-1006

Intermediate In-1006 was prepared by using the same synthetic route of synthesizing In-1005, using methyl 4-amino-2-fluorobenzoate as one of the starting materials.

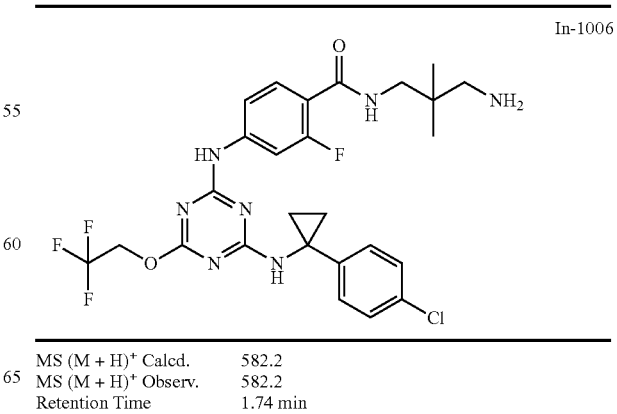

In-1006

| | |
|---|---|
| MS (M + H)$^+$ Calcd. | 582.2 |
| MS (M + H)$^+$ Observ. | 582.2 |
| Retention Time | 1.74 min |

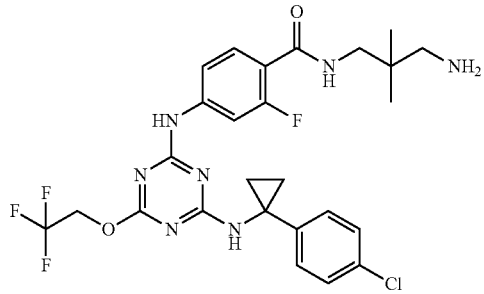 [SMILES: CC(C)(CN)CNC(=O)c1ccc(Nc2nc(NC3(c4ccc(Cl)cc4)CC3)nc(OCC(F)(F)F)n2)cc1F]

| LC Condition | |
|---|---|
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Synthesis of Compound 1001, (S)-methyl 2-(4-(4-(1-(4-chlorophenyl)cyclopropylamino)-6-(2,2,2-trifluoroethoxy)-1,3,5-triazin-2-ylamino)benzamido)-3-(2-ethoxy-2-oxoacetamido)propanoate

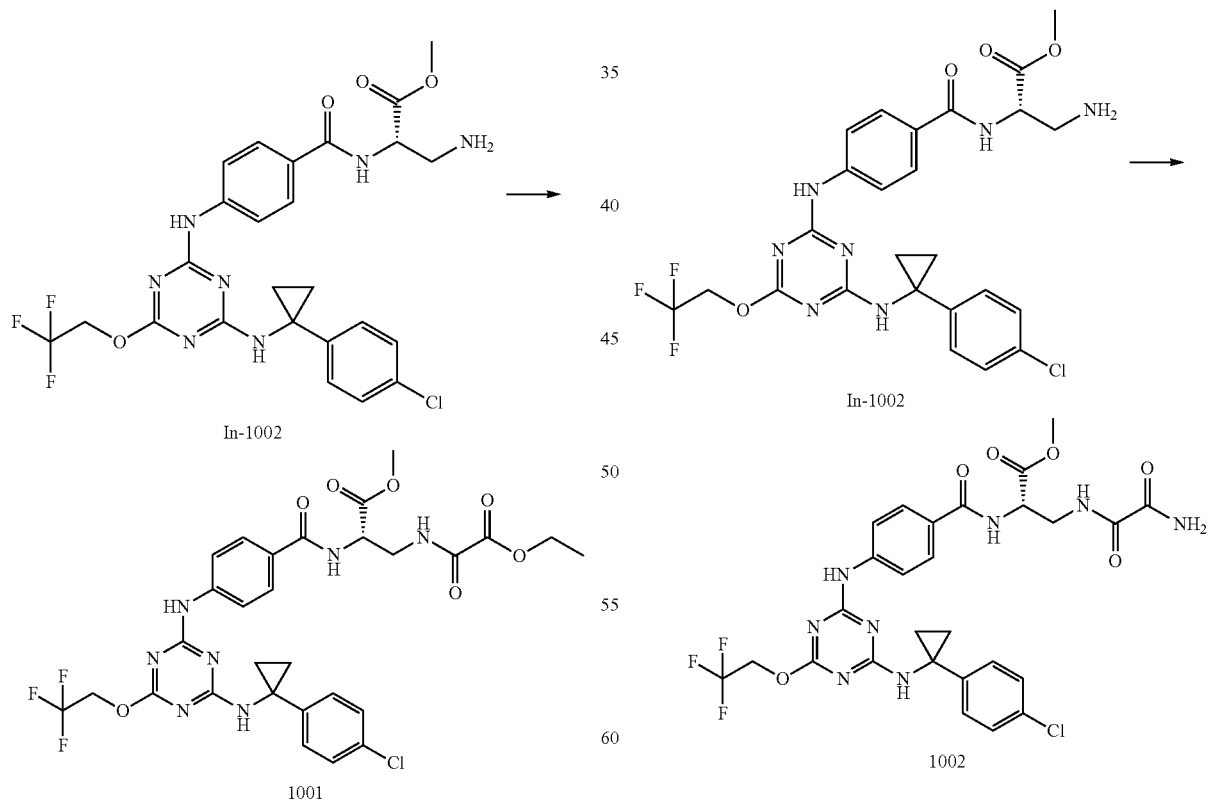

To a solution of In-1002 (25 mg) in CH$_2$Cl$_2$ (5 mL) was added ethyl 2-chloro-2-oxoacetate (5.89 mg). The mixture was stirred at room temperature for 4 hours. The reaction was quenched with the MeOH and all the solvents were removed under vacuum. The residue was purified by preparative HPLC to give 1001 (5 mg).

| (S)-methyl 2-(4-(4-(1-(4-chlorophenyl)cyclopropylamino)-6-(2,2,2-trifluoroethoxy)-1,3,5-triazin-2-ylamino)benzamido)-3-(2-ethoxy-2-oxoacetamido)propanoate, 1001 | |
|---|---|
| MS (M + H)$^+$ Calcd. | 680.2 |
| MS (M + H)$^+$ Observ. | 680.1 |
| Retention Time | 3.16 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1002, (S)-methyl 3-(2-amino-2-oxoacetamido)-2-(4-(4-(1-(4-chlorophenyl)cyclopropylamino)-6-(2,2,2-trifluoroethoxy)-1,3,5-triazin-2-ylamino)benzamido)propanoate

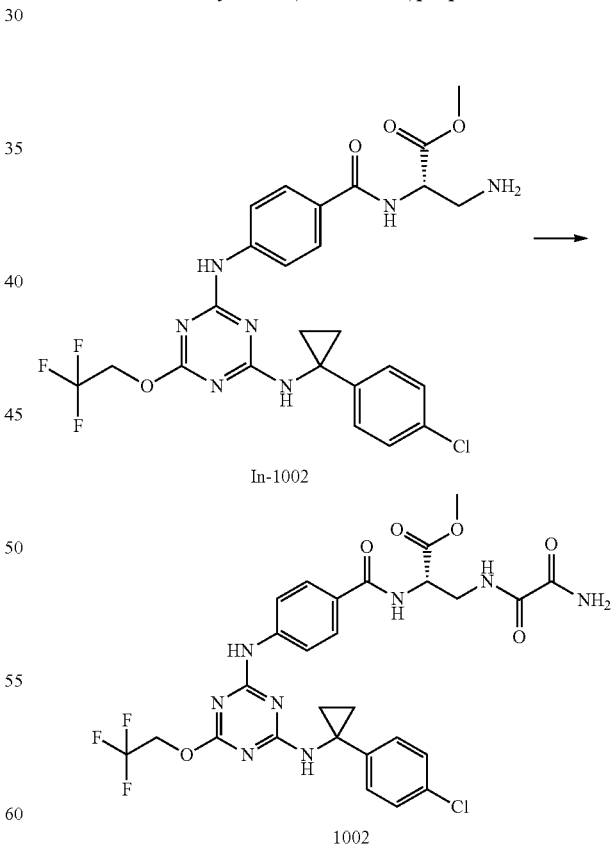

To a solution of 2-amino-2-oxoacetic acid (11.52 mg) and TBTU (41.5 mg) in DMF (2 mL) was added In-1002 (50 mg). After stirring at room temperature for 2 hours, the mixture was purified by preparative HPLC to give 1002 (14 mg).

| | |
|---|---|
| (S)-methyl 3-(2-amino-2-oxoacetamido)-2-(4-(4-(1-(4-chlorophenyl)cyclopropylamino)-6-(2,2,2-trifluoroethoxy)-1,3,5-triazin-2-ylamino)benzamido)propanoate, 1002 | |
| MS (M + H)+ Calcd. | 651.2 |
| MS (M + H)+ Observ. | 651.0 |
| Retention Time | 3.61 min |
| | LC Condition |
| Solvent A | 90% Water-10% Methanol-0.1% TFA |
| Solvent B | 10% Water-90% Methanol-0.1% TFA |
| Start % B | 40 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

| | |
|---|---|
| (S)-methyl 2-(4-(4-(1-(4-chlorophenyl)cyclopropylamino)-6-(2,2,2-trifluoroethoxy)-1,3,5-triazin-2-ylamino)benzamido)-3-(2-(methylamino)-2-oxoacetamido)propanoate, 1003 | |
| MS (M + H)+ Calcd. | 665.2 |
| MS (M + H)+ Observ. | 665.1 |
| Retention Time | 4.26 min |
| | LC Condition |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1003, (S)-methyl 2-(4-(4-(1-(4-chlorophenyl)cyclopropylamino)-6-(2,2,2-trifluoroethoxy)-1,3,5-triazin-2-ylamino)benzamido)-3-(2-(methylamino)-2-oxoacetamido)propanoate Synthesis of Compound 1004, (S)-methyl 2-(4-(4-(1-(4-chlorophenyl)cyclopropylamino)-6-(2,2,2-trifluoroethoxy)-1,3,5-triazin-2-ylamino)benzamido)-3-(2-(dimethylamino)-2-oxoacetamido)propanoate

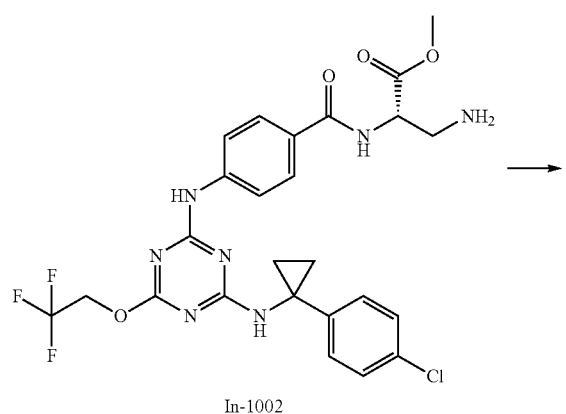

In-1002

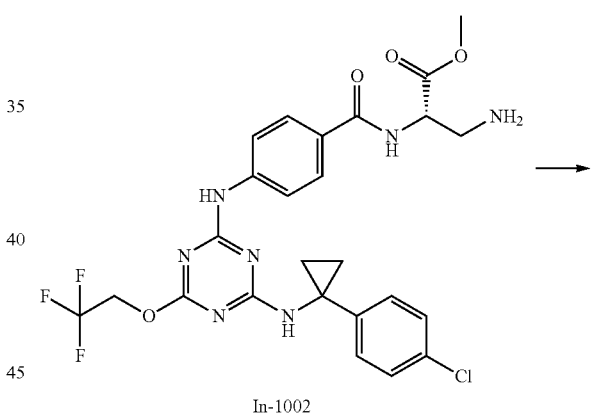

In-1002

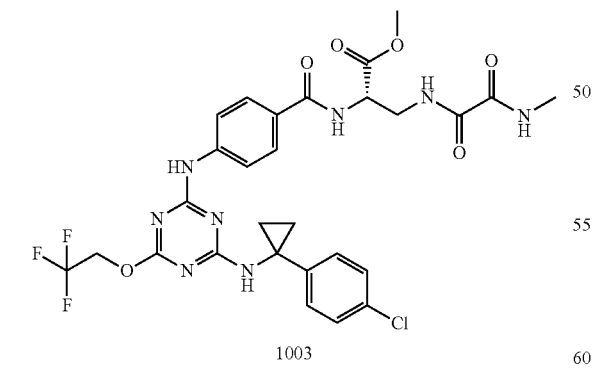

1003

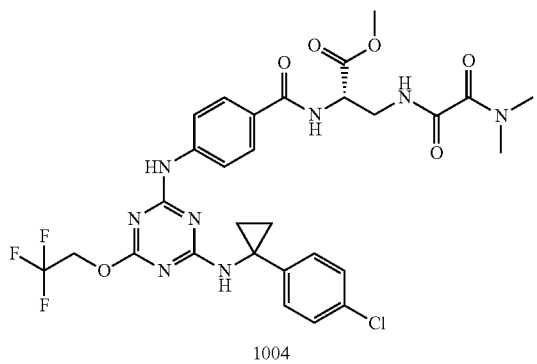

1004

To a solution of 2-(methylamino)-2-oxoacetic acid (13.33 mg) and TBTU (41.5 mg) in DMF (Volume: 2 mL) was added In-1002 (50 mg). After stirring at room temperature for 2 hours, the mixture was purified by preparative HPLC to give 1003 (20 mg).

To a solution of 2-(dimethylamino)-2-oxoacetic acid (15.14 mg) and TBTU (41.5 mg) in DMF (2 mL) was added In-1002 (50 mgl). After stirring at room temperature for 2 hours, the mixture was purified by preparative HPLC to give 1004 (28 mg).

1521

(S)-methyl 2-(4-(4-(1-(4-chlorophenyl)cyclopropylamino)-6-(2,2,2-trifluoroethoxy)-1,3,5-triazin-2-ylamino)benzamido)-3-(2-(dimethylamino)-2-oxoacetamido)propanoate, 1004

| | |
|---|---|
| MS (M + H)+ Calcd. | 679.2 |
| MS (M + H)+ Observ. | 679.1 |
| Retention Time | 3.61 min |
| LC Condition | |
| Solvent A | 90% Water-10% Methanol-0.1% TFA |
| Solvent B | 10% Water-90% Methanol-0.1% TFA |
| Start % B | 40 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1005, (S)-3-(2-amino-2-oxoacetamido)-2-(4-(4-(1-(4-chlorophenyl)cyclopropylamino)-6-(2,2,2-trifluoroethoxy)-1,3,5-triazin-2-ylamino)benzamido)propanoic acid

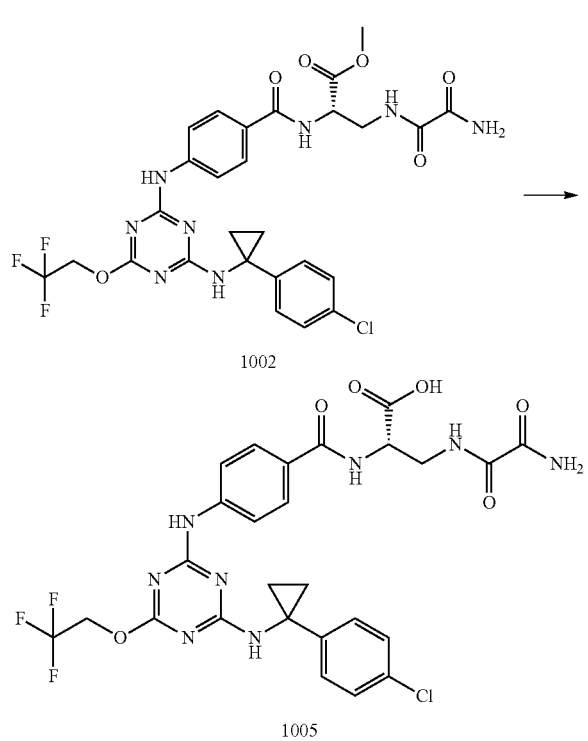

A suspension of 1002 (14 mg) and $K_2CO_3$ (8.92 mg) in acetone-water (1:1, 4 mL) was stirred at room temperature for 16 hours. All the solvents were removed under vacuum. The residue was purified by preparative HPLC to give 1005 (12.6 mg).

(S)-3-(2-amino-2-oxoacetamido)-2-(4-(4-(1-(4-chlorophenyl)cyclopropylamino)-6-(2,2,2-trifluoroethoxy)-1,3,5-triazin-2-ylamino)benzamido)propanoic acid, 1005

| | |
|---|---|
| MS (M + H)+ Calcd. | 637.2 |
| MS (M + H)+ Observ. | 637.0 |
| Retention Time | 2.83 min |

1522

-continued (S)-3-(2-amino-2-oxoacetamido)-2-(4-(4-(1-(4-chlorophenyl)cyclopropylamino)-6-(2,2,2-trifluoroethoxy)-1,3,5-triazin-2-ylamino)benzamido)propanoic acid, 1005

| | |
|---|---|
| LC Condition | |
| Solvent A | 90% Water-10% Methanol-0.1% TFA |
| Solvent B | 10% Water-90% Methanol-0.1% TFA |
| Start % B | 60 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1006, (S)-2-(4-(4-(1-(4-chlorophenyl)cyclopropylamino)-6-(2,2,2-trifluoroethoxy)-1,3,5-triazin-2-ylamino)benzamido)-3-(2-(methylamino)-2-oxoacetamido)propanoic acid

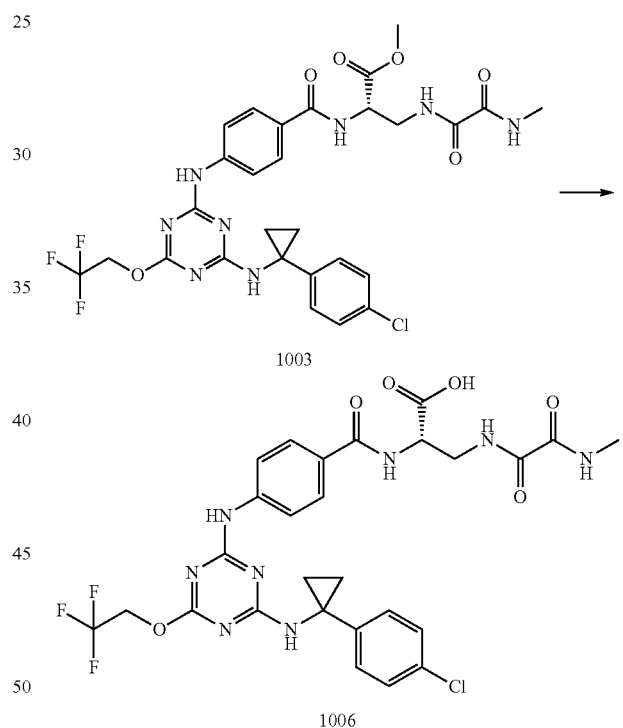

A suspension of 1003 (12 mg) and $K_2CO_3$ (7.48 mg) in acetone-water (1:1, 4 mL) was stirred at room temperature for 16 hours. All the solvents were removed under vacuum. The residue was purified by preparative HPLC to give 1006 (8.4 mg).

(S)-2-(4-(4-(1-(4-chlorophenyl)cyclopropylamino)-6-(2,2,2-trifluoroethoxy)-1,3,5-triazin-2-ylamino)benzamido)-3-(2-(methylamino)-2-oxoacetamido)propanoic acid, 1006

| | |
|---|---|
| MS (M + H)+ Calcd. | 651.2 |
| MS (M + H)+ Observ. | 651.1 |
| Retention Time | 3.01 min |

1523

-continued

| (S)-2-(4-(4-(1-(4-chlorophenyl)cyclopropylamino)-6-(2,2,2-trifluoroethoxy)-1,3,5-triazin-2-ylamino)benzamido)-3-(2-(methylamino)-2-oxoacetamido)propanoic acid, 1006 | |
|---|---|
| LC Condition | |
| Solvent A | 90% Water-10% Methanol-0.1% TFA |
| Solvent B | 10% Water-90% Methanol-0.1% TFA |
| Start % B | 60 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

1524

| (S)-2-(4-(4-(1-(4-chlorophenyl)cyclopropylamino)-6-(2,2,2-trifluoroethoxy)-1,3,5-triazin-2-ylamino)benzamido)-3-(2-(dimethylamino)-2-oxoacetamido)propanoic acid, 1007 | |
|---|---|
| MS (M + H)$^+$ Calcd. | 665.2 |
| MS (M + H)$^+$ Observ. | 665.1 |
| Retention Time | 3.10 min |
| LC Condition | |
| Solvent A | 90% Water-10% Methanol-0.1% TFA |
| Solvent B | 10% Water-90% Methanol-0.1% TFA |
| Start % B | 60 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1007, (S)-2-(4-(4-(1-(4-chlorophenyl)cyclopropylamino)-6-(2,2,2-trifluoroethoxy)-1,3,5-triazin-2-ylamino)benzamido)-3-(2-(dimethylamino)-2-oxoacetamido)propanoic acid Synthesis of Compound 1008, N1-(3-(4-(4-(1-(4-chlorophenyl)cyclopropylamino)-6-(2,2,2-trifluoroethoxy)-1,3,5-triazin-2-ylamino)benzamido)-2,2-dimethylpropyl)-N2,N2-dimethyloxalamide

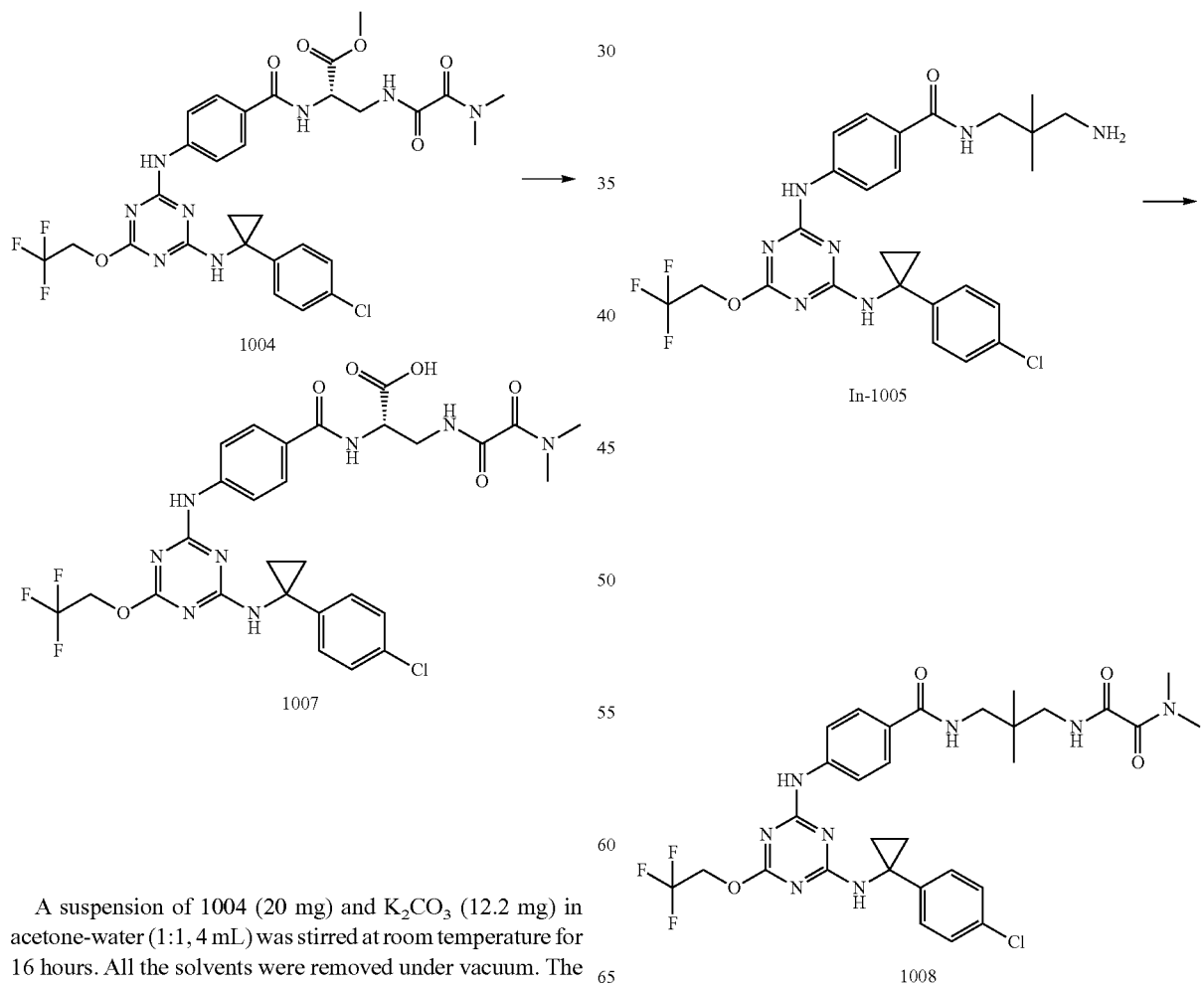

A suspension of 1004 (20 mg) and K$_2$CO$_3$ (12.2 mg) in acetone-water (1:1, 4 mL) was stirred at room temperature for 16 hours. All the solvents were removed under vacuum. The residue was purified by preparative HPLC to give 1007 (7 mg).

iPr₂NEt (0.037 g) and O-benzotriazol-1-yl-N,N,N',N'-tetra-methyluronium tetrafluoroborate (0.068 g) was added into the solution of crude In-1005 (0.080 g) and 2-(dimethylamino)-2-oxoacetic acid (0.017 g) in DMF (2 mL). The reaction was stirred at room temperature for 6 hours. All the solvents were removed under vacuum. The residue was purified by preparative HPLC to give 1008 (40 mg).

| N1-(3-(4-(4-(1-(4-chlorophenyl)cyclopropylamino)-6-(2,2,2-trifluoroethoxy)-1,3,5-triazin-2-ylamino)benzamido)-2,2-dimethylpropyl)-N2,N2-dimethyloxalamide, 1008 | |
|---|---|
| MS (M + H)⁺ Calcd. | 663.2 |
| MS (M + H)⁺ Observ. | 663.1 |
| Retention Time | 2.00 min |
| | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 5 mL/min |
| Wavelength | 220 |
| Solvent Pair | Water-Methanol-TFA |
| Column | PHENOMENEX-LUNA 4.6 × 50 mm S10 |

Synthesis of Compound 1479, N1-(3-(4-((4-(1-(4-chlorophenyl)cyclopropyl)amino)-6-(2,2,2-trifluoroethoxy)-1,3,5-triazin-2-yl)amino)benzamido)-2,2-dimethylpropyl)-N2-(4-fluorophenyl)oxalamide Compound 1479 was prepared by using the same procedure of synthesizing 1008, using 2-((4-fluorophenyl)amino)-2-oxoacetic acid as one of the starting materials. Its LCMS is shown in a later section.

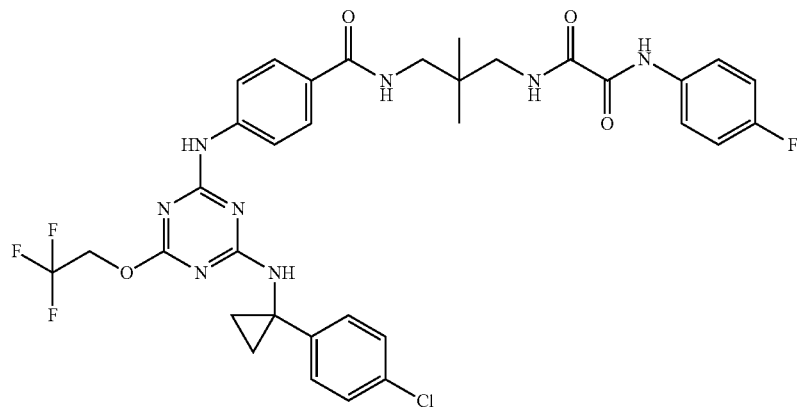 [SMILES: CC(C)(CNC(=O)C(=O)Nc1ccc(F)cc1)CNC(=O)c1ccc(Nc2nc(NC3(c4ccc(Cl)cc4)CC3)nc(OCC(F)(F)F)n2)cc1]

The following selected examples were prepared by using the same procedure of synthesizing 1479, using the corresponding mono-Boc diamines rather than mono-Boc 2,2-dimethylpropane-1,3-diamine as starting materials:

3335

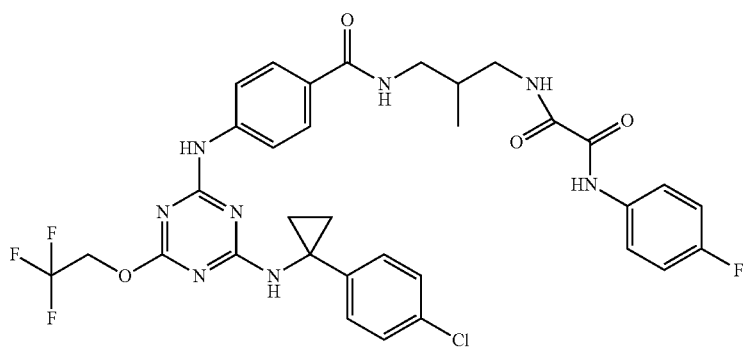 [SMILES: CC(CNC(=O)C(=O)Nc1ccc(F)cc1)CNC(=O)c1ccc(Nc2nc(NC3(c4ccc(Cl)cc4)CC3)nc(OCC(F)(F)F)n2)cc1]

| | |
|---|---|
| MS (M + H)+ Calcd. | 715.2 |
| MS (M + H)+ Observ. | 715.1 |
| Retention Time | 4.48 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

3360

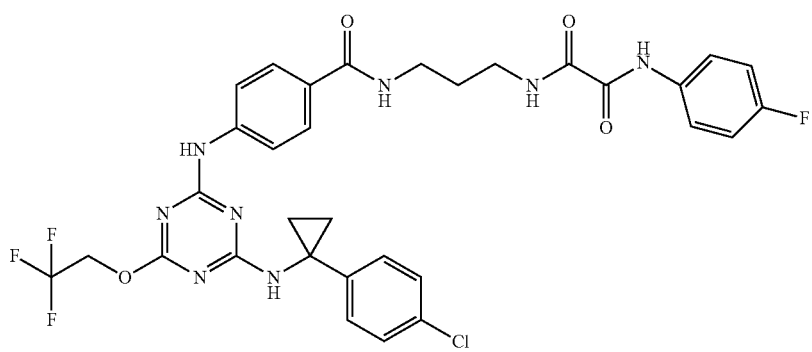 [SMILES: O=C(NCCCNC(=O)c1ccc(Nc2nc(NC3(c4ccc(Cl)cc4)CC3)nc(OCC(F)(F)F)n2)cc1)C(=O)Nc1ccc(F)cc1]

| | |
|---|---|
| MS (M + H)+ Calcd. | 701.2 |
| MS (M + H)+ Observ. | 701.0 |
| Retention Time | 4.42 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

-continued

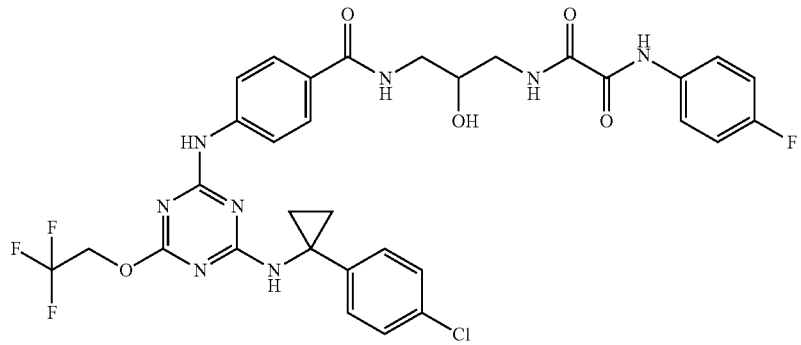 [SMILES: O=C(NCC(O)CNC(=O)c1ccc(Nc2nc(NC3(c4ccc(Cl)cc4)CC3)nc(OCC(F)(F)F)n2)cc1)C(=O)Nc1ccc(F)cc1]

3365

| | |
|---|---|
| MS (M + H)+ Calcd. | 717.2 |
| MS (M + H)+ Observ. | 717.2 |
| Retention Time | 4.42 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

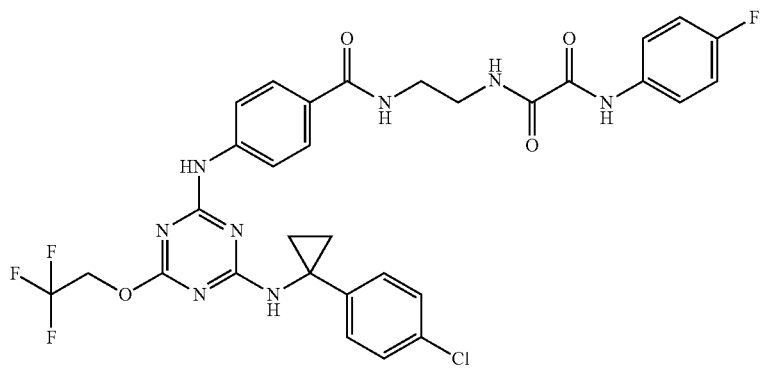 [SMILES: O=C(NCCNC(=O)c1ccc(Nc2nc(NC3(c4ccc(Cl)cc4)CC3)nc(OCC(F)(F)F)n2)cc1)C(=O)Nc1ccc(F)cc1]

3373

| | |
|---|---|
| MS (M + H)+ Calcd. | 687.2 |
| MS (M + H)+ Observ. | 687.0 |
| Retention Time | 4.40 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

-continued

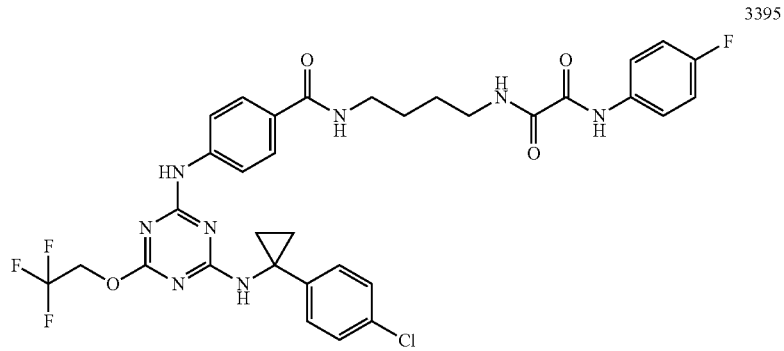
3395

| | |
|---|---|
| MS (M + H)+ Calcd. | 715.2 |
| MS (M + H)+ Observ. | 715.3 |
| Retention Time | 1.89 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

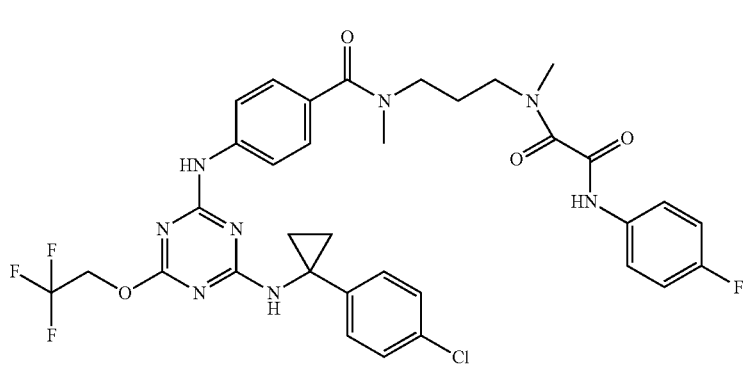 [SMILES: CN(CCCN(C)C(=O)c1ccc(Nc2nc(NC3(c4ccc(Cl)cc4)CC3)nc(OCC(F)(F)F)n2)cc1)C(=O)C(=O)Nc1ccc(F)cc1]
3412

| | |
|---|---|
| MS (M + H)+ Calcd. | 729.2 |
| MS (M + H)+ Observ. | 729.3 |
| Retention Time | 1.87 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

3418

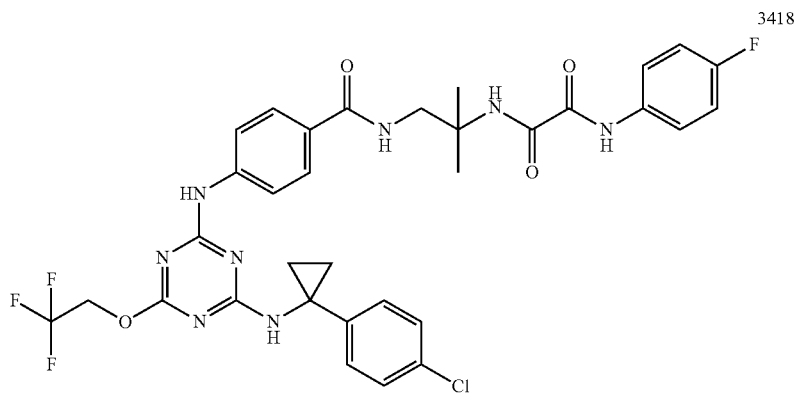

| | |
|---|---|
| MS (M + H)+ Calcd. | 715.2 |
| MS (M + H)+ Observ. | 715.3 |
| Retention Time | 2.01 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

3448

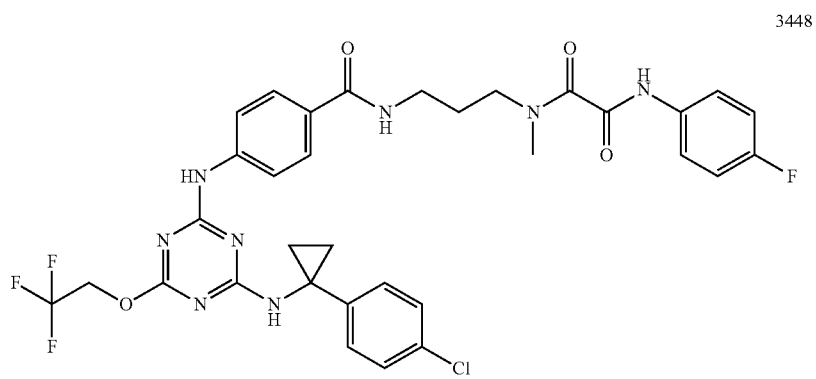

| | |
|---|---|
| MS (M + H)+ Calcd. | 715.2 |
| MS (M + H)+ Observ. | 715.5 |
| Retention Time | 2.36 min |
| LC Condition | |
| Solvent A | 90% Water -10% Methanol-0.1% TFA |
| Solvent B | 10% Water -90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

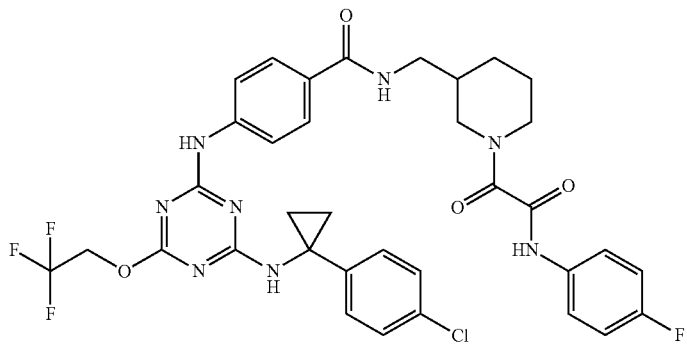 [SMILES: O=C(Nc1ccc(F)cc1)C(=O)N1CCCC(CNC(=O)c2ccc(Nc3nc(NC4(c5ccc(Cl)cc5)CC4)nc(OCC(F)(F)F)n3)cc2)C1]

3482

| | |
|---|---|
| MS (M + H)+ Calcd. | 741.2 |
| MS (M + H)+ Observ. | 741.3 |
| Retention Time | 1.89 min |

LC Condition

| | |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

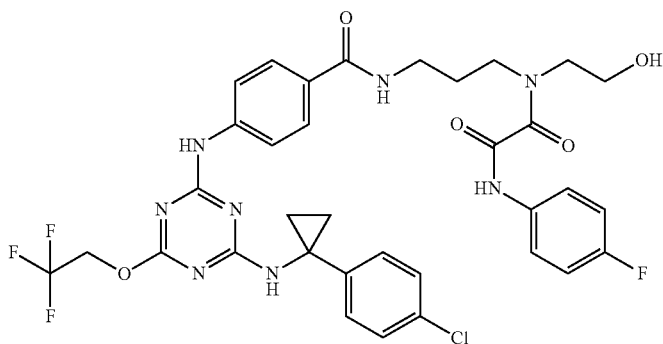 [SMILES: O=C(Nc1ccc(F)cc1)C(=O)N(CCO)CCCNC(=O)c1ccc(Nc2nc(NC3(c4ccc(Cl)cc4)CC3)nc(OCC(F)(F)F)n2)cc1]

3499

| | |
|---|---|
| MS (M + H)+ Calcd. | 745.2 |
| MS (M + H)+ Observ. | 745.3 |
| Retention Time | 3.18 min |

LC Condition

| | |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex Luna C18, 50 × 2, 3 u |

Synthesis of Compound 1009, (S)-methyl 4-(2-amino-2-oxoacetamido)-2-(4-(4-(1-(4-chlorophenyl)cyclopropylamino)-6-(2,2,2-trifluoroethoxy)-1,3,5-triazin-2-ylamino)benzamido)butanoate Synthesis of Compound 1010, (S)-methyl 2-(4-(4-(1-(4-chlorophenyl)cyclopropylamino)-6-(2,2,2-trifluoroethoxy)-1,3,5-triazin-2-ylamino)benzamido)-4-(2-(methylamino)-2-oxoacetamido)butanoate

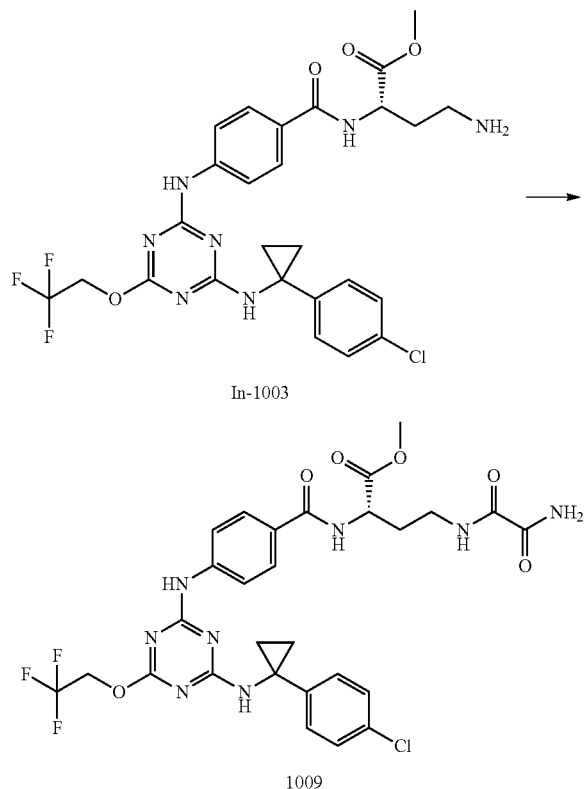

In-1003

1009

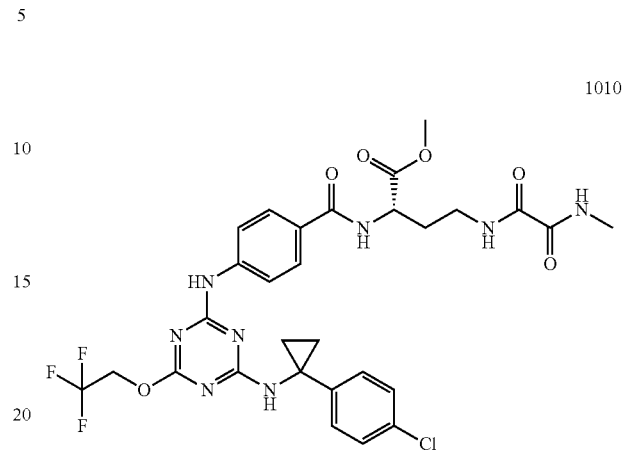

1010 was prepared by using the same procedure of synthesizing 1009, using 2-(methylamino)-2-oxoacetic acid as a starting material.

To a solution of In-1003 (50 mg) and 2-(1H-benzo[d][1,2,3]triazol-1-yl)-1,1,3,3-tetramethylisouronium tetrafluoroborate (54 mg) in DMF (1.5 mL) was added 2-amino-2-oxoacetic acid (15 mg). After stirring at room temperature for 4 hours, the mixture was purified by preparative HPLC to give 1009 (23 mg).

| (S)-methyl 4-(2-amino-2-oxoacetamido)-2-(4-(4-(1-(4-chlorophenyl)cyclopropylamino)-6-(2,2,2-trifluoroethoxy)-1,3,5-triazin-2-ylamino)benzamido)butanoate, 1009 | |
|---|---|
| MS (M + H)$^+$ Calcd. | 665.2 |
| MS (M + H)$^+$ Observ. | 665.1 |
| Retention Time | 3.61 min |
| | LC Condition |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

| (S)-methyl 2-(4-(4-(1-(4-chlorophenyl)cyclopropylamino)-6-(2,2,2-trifluoroethoxy)-1,3,5-triazin-2-ylamino)benzamido)-4-(2-(methylamino)-2-oxoacetamido)butanoate, 1010 | |
|---|---|
| MS (M + H)$^+$ Calcd. | 679.2 |
| MS (M + H)$^+$ Observ. | 679.1 |
| Retention Time | 3.57 min |
| | LC Condition |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1011, (S)-methyl 2-(4-(4-(1-(4-chlorophenyl)cyclopropylamino)-6-(2,2,2-trifluoroethoxy)-1,3,5-triazin-2-ylamino)benzamido)-4-(2-(dimethylamino)-2-oxoacetamido)butanoate

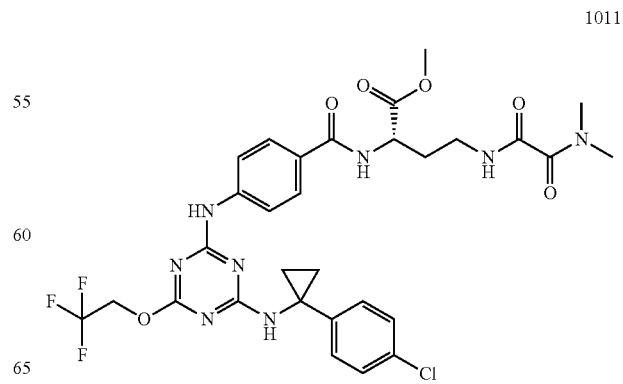

1011

1011 was prepared by using the same procedure of synthesizing 1009, using 2-(dimethylamino)-2-oxoacetic acid as a starting material.

| (S)-methyl 2-(4-(4-(1-(4-chlorophenyl)cyclopropylamino)-6-(2,2,2-trifluoroethoxy)-1,3,5-triazin-2-ylamino)benzamido)-4-(2-(dimethylamino)-2-oxoacetamido)butanoate, 1011 | |
|---|---|
| MS (M + H)+ Calcd. | 693.2 |
| MS (M + H)+ Observ. | 693.1 |
| Retention Time | 3.53 min |
| LC Condition | |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1012, (S)-methyl 5-(2-amino-2-oxoacetamido)-2-(4-(4-(1-(4-chlorophenyl)cyclopropylamino)-6-(2,2,2-trifluoroethoxy)-1,3,5-triazin-2-ylamino)benzamido)pentanoate

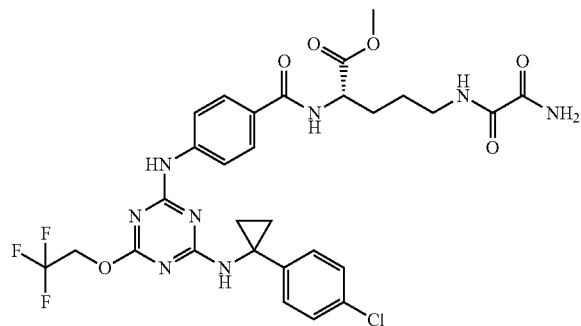

1012

1012 was prepared by using the same procedure of synthesizing 1009, using In-1004 as a starting material.

| (S)-methyl 5-(2-amino-2-oxoacetamido)-2-(4-(4-(1-(4-chlorophenyl)cyclopropylamino)-6-(2,2,2-trifluoroethoxy)-1,3,5-triazin-2-ylamino)benzamido)pentanoate, 1012 | |
|---|---|
| MS (M + H)+ Calcd. | 679.2 |
| MS (M + H)+ Observ. | 679.1 |
| Retention Time | 3.64 min |
| LC Condition | |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1013, (S)-4-(2-amino-2-oxoacetamido)-2-(4-(4-(1-(4-chlorophenyl)cyclopropylamino)-6-(2,2,2-trifluoroethoxy)-1,3,5-triazin-2-ylamino)benzamido)butanoic acid

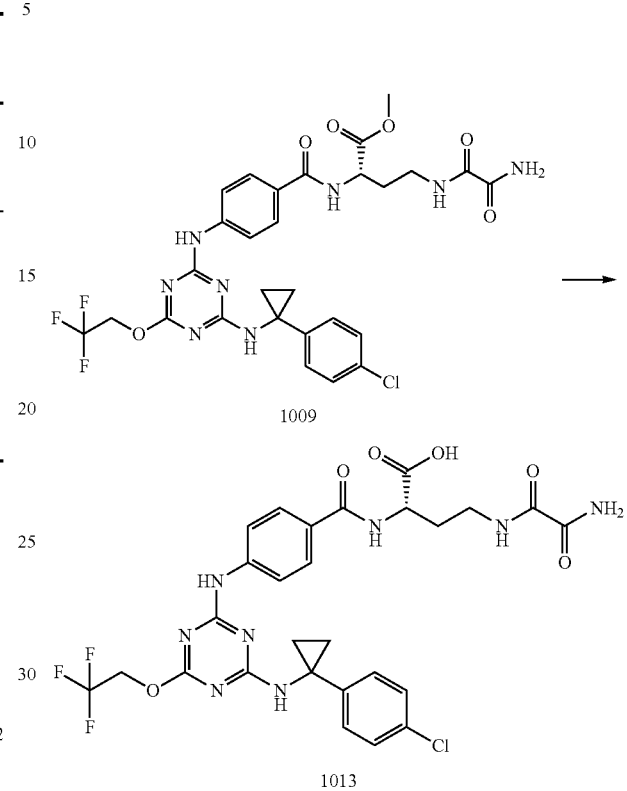

A mixture of 1009 (21 mg) and K₂CO₃ (18 mg) in acetone (2 mL)/water (2 mL) was stirred at room temperature for 16 hours. All the solvents were removed under vacuum. The residue was dissolved in MeOH and purified by preparative HPLC to give 1013 (7.5 mg).

| (S)-4-(2-amino-2-oxoacetamido)-2-(4-(4-(1-(4-chlorophenyl)-cyclopropylamino)-6-(2,2,2-trifluoroethoxy)-1,3,5-triazin-2-ylamino)benzamido)butanoic acid, 1013 | |
|---|---|
| MS (M + H)+ Calcd. | 651.2 |
| MS (M + H)+ Observ. | 651.1 |
| Retention Time | 3.53 min |
| LC Condition | |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1014, (S)-2-(4-(4-(1-(4-chlorophenyl)cyclopropylamino)-6-(2,2,2-trifluoroethoxy)-1,3,5-triazin-2-ylamino)benzamido)-4-(2-(methylamino)-2-oxoacetamido)butanoic acid

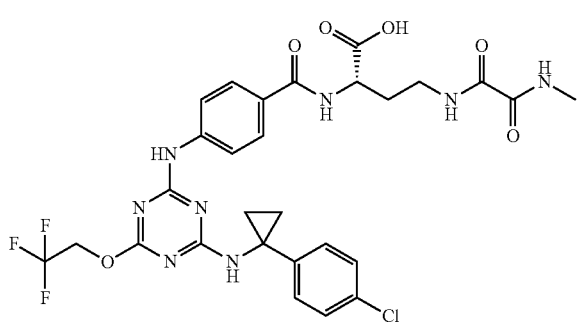

1014

1014 was prepared by using the same procedure of synthesizing 1013, using 1010 as a starting material.

| (S)-2-(4-(4-(1-(4-chlorophenyl)cyclopropylamino)-6-(2,2,2-trifluoroethoxy)-1,3,5-triazin-2-ylamino)benzamido)-4-(2-(methylamino)-2-oxoacetamido)butanoic acid, 1014 | |
|---|---|
| MS (M + H)+ Calcd. | 665.2 |
| MS (M + H)+ Observ. | 665.2 |
| Retention Time | 3.47 min |
| | LC Condition |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1015, (S)-2-(4-(4-(1-(4-chlorophenyl)cyclopropylamino)-6-(2,2,2-trifluoroethoxy)-1,3,5-triazin-2-ylamino)benzamido)-4-(2-(dimethylamino)-2-oxoacetamido)butanoic acid

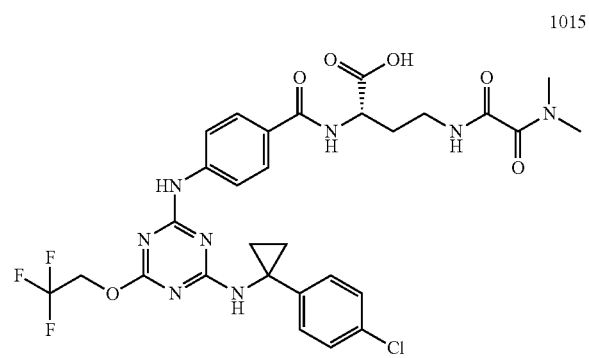 [SMILES: CNC(=O)C(=O)NCC[C@H](NC(=O)c1ccc(Nc2nc(NC3(c4ccc(Cl)cc4)CC3)nc(OCC(F)(F)F)n2)cc1)C(=O)O]

1015

1015 was prepared by using the same procedure of synthesizing 1013, using 1011 as a starting material.

| (S)-2-(4-(4-(1-(4-chlorophenyl)cyclopropylamino)-6-(2,2,2-trifluoroethoxy)-1,3,5-triazin-2-ylamino)benzamido)-4-(2-(dimethylamino)-2-oxoacetamido)butanoic acid, 1015 | |
|---|---|
| MS (M + H)+ Calcd. | 679.2 |
| MS (M + H)+ Observ. | 679.2 |
| Retention Time | 3.41 min |
| | LC Condition |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1016, (S)-5-(2-amino-2-oxoacetamido)-2-(4-(4-(1-(4-chlorophenyl)cyclopropylamino)-6-(2,2,2-trifluoroethoxy)-1,3,5-triazin-2-ylamino)benzamido)pentanoic acid

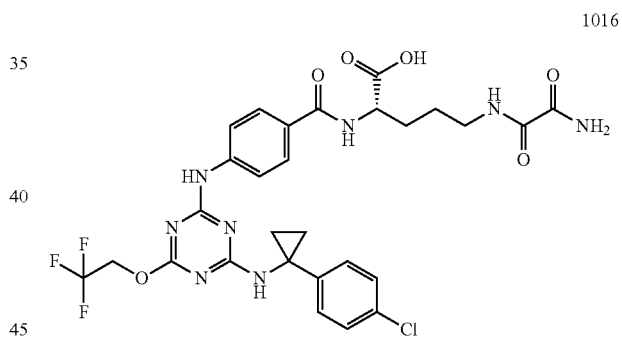

1016

1016 was prepared by using the same procedure of synthesizing 1013, using 1012 as a starting material.

| (S)-5-(2-amino-2-oxoacetamido)-2-(4-(4-(1-(4-chlorophenyl)-cyclopropylamino)-6-(2,2,2-trifluoroethoxy)-1,3,5-triazin-2-ylamino)benzamido)pentanoic acid, 1016 | |
|---|---|
| MS (M + H)+ Calcd. | 665.2 |
| MS (M + H)+ Observ. | 665.1 |
| Retention Time | 3.48 min |
| | LC Condition |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

1543

Synthesis of Compound 1017, methyl 2-(1-(2-amino-2-oxoacetyl)piperidin-3-yl)-2-(4-(4-(1-(4-chlorophenyl)cyclopropylamino)-6-(2,2,2-trifluoroethoxy)-1,3,5-triazin-2-ylamino)benzamido)acetate, and 1018, 2-(1-(2-amino-2-oxoacetyl)piperidin-3-yl)-2-(4-(4-(1-(4-chlorophenyl)cyclopropylamino)-6-(2,2,2-trifluoroethoxy)-1,3,5-triazin-2-ylamino)benzamido)acetic acid, and 1019, N-(1-(1-(2-amino-2-oxoacetyl)piperidin-3-yl)-2-oxo-2-(propylamino)ethyl)-4-(4-(1-(4-chlorophenyl)cyclopropylamino)-6-(2,2,2-trifluoroethoxy)-1,3,5-triazin-2-ylamino)benzamide

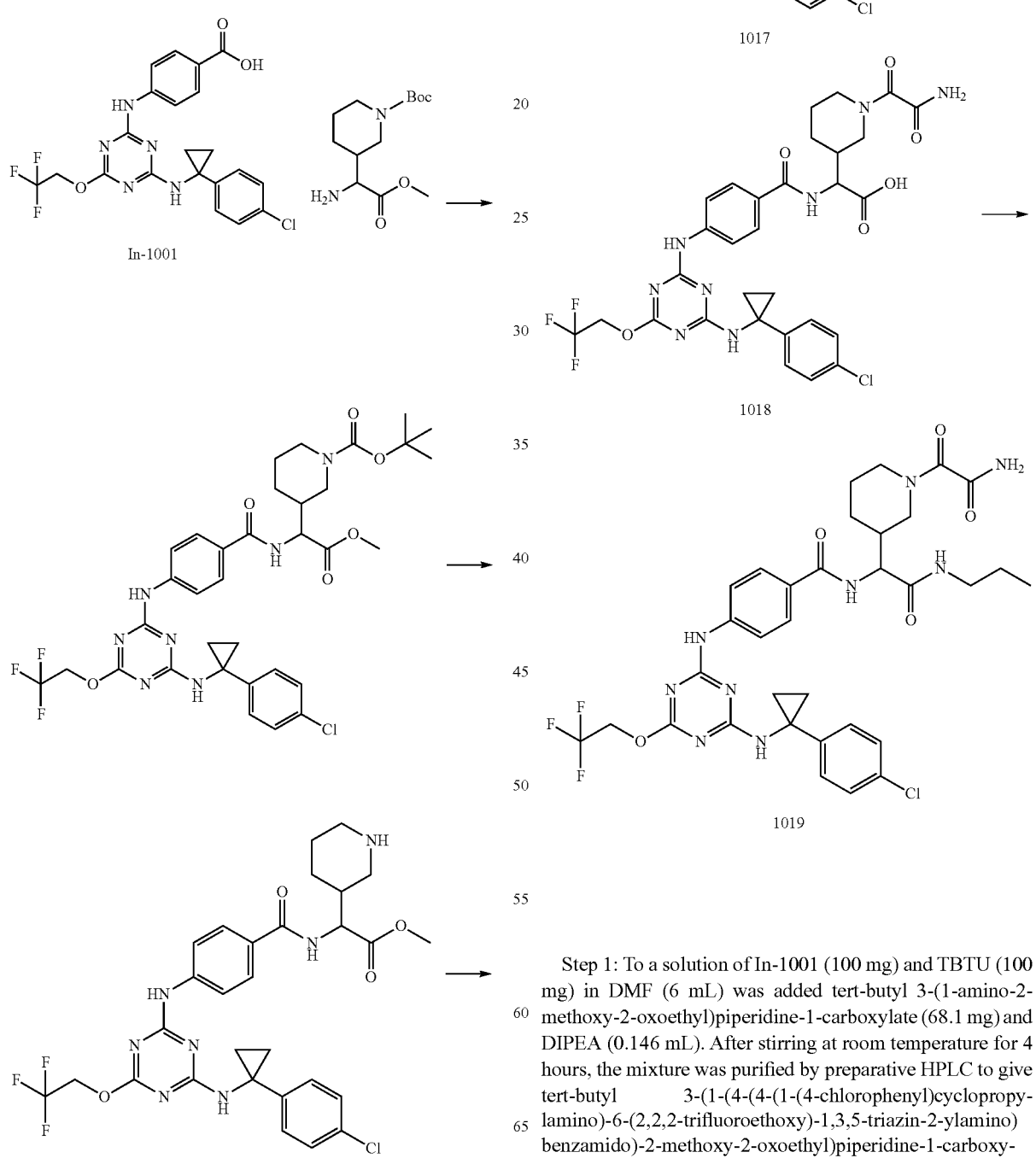

Step 1: To a solution of In-1001 (100 mg) and TBTU (100 mg) in DMF (6 mL) was added tert-butyl 3-(1-amino-2-methoxy-2-oxoethyl)piperidine-1-carboxylate (68.1 mg) and DIPEA (0.146 mL). After stirring at room temperature for 4 hours, the mixture was purified by preparative HPLC to give tert-butyl 3-(1-(4-(4-(1-(4-chlorophenyl)cyclopropylamino)-6-(2,2,2-trifluoroethoxy)-1,3,5-triazin-2-ylamino)benzamido)-2-methoxy-2-oxoethyl)piperidine-1-carboxylate (90 mg).

| tert-Butyl 3-(1-(4-(4-(1-(4-chlorophenyl)cyclopropylamino)-6-(2,2,2-trifluoroethoxy)-1,3,5-triazin-2-ylamino)benzamido)-2-methoxy-2-oxoethyl)piperidine-1-carboxylate | |
|---|---|
| MS (M + H)+ Calcd. | 734.2 |
| MS (M + H)+ Observ. | 734.1 |
| Retention Time | 4.00 min |
| | LC Condition |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Step 2: To a solution of tert-butyl 3-(1-(4-(4-(1-(4-chlorophenyl)cyclopropylamino)-6-(2,2,2-trifluoroethoxy)-1,3,5-triazin-2-ylamino)benzamido)-2-methoxy-2-oxoethyl)piperidine-1-carboxylate (85 mg) in DCM (5 mL) was added TFA (0.357 mL). The mixture was stirred at room temperature for 4 hours. All the solvents were removed under vacuum to give methyl 2-(4-(4-(1-(4-chlorophenyl)cyclopropylamino)-6-(2,2,2-trifluoroethoxy)-1,3,5-triazin-2-ylamino)benzamido)-2-(piperidin-3-yl)acetate (70 mg).

| Methyl 2-(4-(4-(1-(4-chlorophenyl)cyclopropylamino)-6-(2,2,2-trifluoroethoxy)-1,3,5-triazin-2-ylamino)benzamido)-2-(piperidin-3-yl)acetate | |
|---|---|
| MS (M + H)+ Calcd. | 634.2 |
| MS (M + H)+ Observ. | 634.1 |
| Retention Time | 2.60 min |
| | LC Condition |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Step 3: To a solution of 2-amino-2-oxoacetic acid (18.26 mg) and TBTU (65.8 mg) in DMF (2 mL) was added methyl 2-(4-(4-(1-(4-chlorophenyl)cyclopropylamino)-6-(2,2,2-trifluoroethoxy)-1,3,5-triazin-2-ylamino)benzamido)-2-(piperidin-3-yl)acetate (65 mg). After stirring at room temperature for 2 hours, the mixture was purified by preparative HPLC to give 1017 (35 mg).

| methyl 2-(1-(2-amino-2-oxoacetyl)piperidin-3-yl)-2-(4-(4-(1-(4-chlorophenyl)cyclopropylamino)-6-(2,2,2-trifluoroethoxy)-1,3,5-triazin-2-ylamino)benzamido)acetate, 1017 | |
|---|---|
| MS (M + H)+ Calcd. | 705.2 |
| MS (M + H)+ Observ. | 705.1 |
| Retention Time | 3.72 min |
| | LC Condition |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Step 4: A mixture of 1017 (35 mg) and K₂CO₃ (21 mg) in acetone (4 mL)/water (4.00 mL) was stirred at room temperature for 16 hours. All the solvents were removed under vacuum. The residue was purified by preparative HPLC to give 1018 (28 mg).

| 2-(1-(2-amino-2-oxoacetyl)piperidin-3-yl)-2-(4-(4-(1-(4-chlorophenyl)cyclopropylamino)-6-(2,2,2-trifluoroethoxy)-1,3,5-triazin-2-ylamino)benzamido)acetic acid, 1018 | |
|---|---|
| MS (M + H)+ Calcd. | 691.2 |
| MS (M + H)+ Observ. | 691.1 |
| Retention Time | 3.74 min |
| | LC Condition |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Step 5: To a solution of 1018 (15 mg) and TBTU (10.5 mg) in DMF (1.5 mL) was added propan-1-amine (6.42 mg). After stirring at room temperature for 16 hours, the mixture was diluted with water (200 mL) and extracted with EtOAc (2×300 mL). The organic layers were combined, washed with water (200 mL), brine (200 mL), dried over MgSO₄ and concentrated. The residue was purified by silica gel column to give 1019 (1.1 mg).

| N-(1-(1-(2-amino-2-oxoacetyl)piperidin-3-yl)-2-oxo-2-(propylamino)ethyl)-4-(4-(1-(4-chlorophenyl)cyclopropylamino)-6-(2,2,2-trifluoroethoxy)-1,3,5-triazin-2-ylamino)benzamide, 1019 | |
|---|---|
| MS (M + Na)+ Calcd. | 754.2 |
| MS (M + Na)+ Observ. | 754.2 |
| Retention Time | 3.65 min |
| | LC Condition |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1020, (S)-ethyl 2-(4-(4-(1-(4-chlorophenyl)cyclopropylamino)-6-(2,2,2-trifluoroethoxy)-1,3,5-triazin-2-ylamino)benzamido)-3-(2-(dimethylamino)-2-oxoacetamido)propanoate

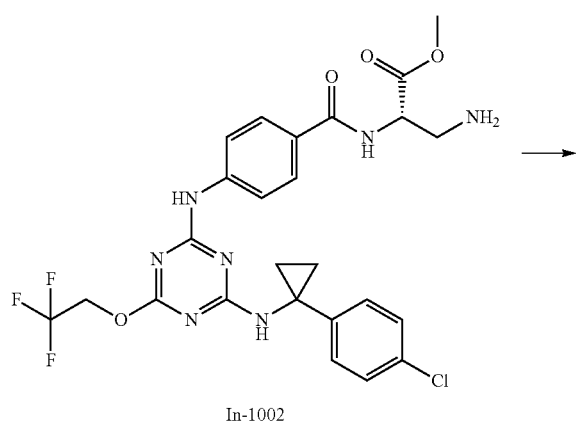

In-1002

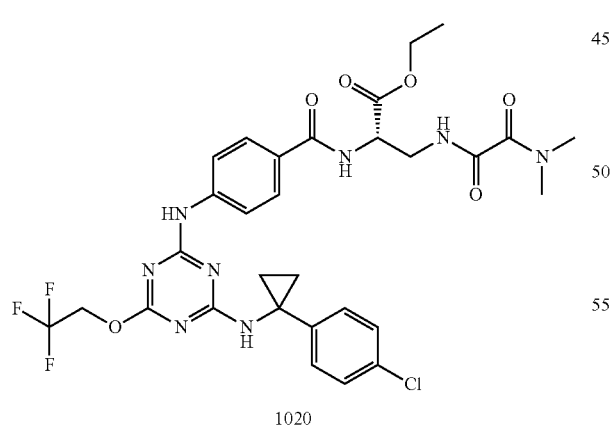

In-1101

1020

Step 1: A mixture of In-1002 (70 mg), K₂CO₃ (33.4 mg) and ethanol (2 mL) was stirred at room temperature for three days. The mixture was acidified by 1N HCl, diluted by MeOH and purified by preparative HPLC to give In-1101 (30 mg).

| (S)-ethyl 3-amino-2-(4-(4-(1-(4-chlorophenyl)-cyclopropylamino)-6-(2,2,2-trifluoroethoxy)-1,3,5-triazin-2-ylamino)benzamido)propanoate | |
|---|---|
| MS (M + Na)⁺ Calcd. | 594.2 |
| MS (M + Na)⁺ Observ. | 594.2 |
| Retention Time | 3.38 min |
| LC Condition | |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Step 2: To a solution of 2-(dimethylamino)-2-oxoacetic acid (7.6 mg) and TBTU (20.9 mg) in DMF (1 mL) was added In-1101 (30 mg) and DIPEA (0.03 mL). After stirring at room temperature for 2 hours, the mixture was purified by preparative HPLC to give 1020 (15.0 mg).

| (S)-ethyl 2-(4-(4-(1-(4-chlorophenyl)cyclopropylamino)-6-(2,2,2-trifluoroethoxy)-1,3,5-triazin-2-ylamino)benzamido)-3-(2-(dimethylamino)-2-oxoacetamido)propanoate, 1020 | |
|---|---|
| MS (M + H)⁺ Calcd. | 693.2 |
| MS (M + H)⁺ Observ. | 693.2 |
| Retention Time | 3.89 min |
| LC Condition | |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1021, (S)-isopropyl 2-(4-(4-(1-(4-chlorophenyl)cyclopropylamino)-6-(2,2,2-trifluoroethoxy)-1,3,5-triazin-2-ylamino)benzamido)-3-(2-(dimethylamino)-2-oxoacetamido)propanoate

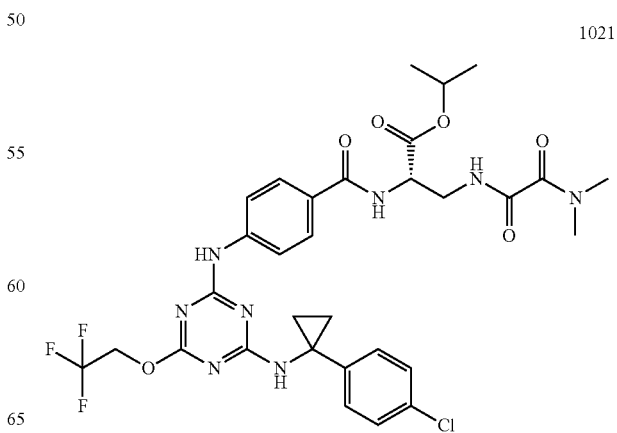

1021

1021 was prepared by using the same procedure of synthesizing 1020, using iPrOH as a starting material.

| (S)-isopropyl 2-(4-(4-(1-(4-chlorophenyl)cyclopropylamino)-6-(2,2,2-trifluoroethoxy)-1,3,5-triazin-2-ylamino)benzamido)-3-(2-(dimethylamino)-2-oxoacetamido)propanoate, 1021 | |
|---|---|
| MS (M + H)$^+$ Calcd. | 707.2 |
| MS (M + H)$^+$ Observ. | 707.2 |
| Retention Time | 4.03 min |
| | LC Condition |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1022, (S)-2-morpholinoethyl 2-(4-(4-(1-(4-chlorophenyl)cyclopropylamino)-6-(2,2,2-trifluoroethoxy)-1,3,5-triazin-2-ylamino)benzamido)-3-(2-(dimethylamino)-2-oxoacetamido)propanoate

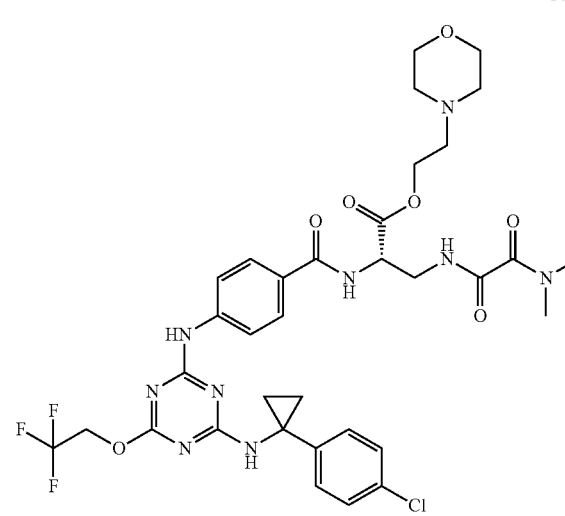

1022

1022 was prepared by using the same procedure of synthesizing 1020, using 2-morpholinoethanol as a starting material.

| (S)-2-morpholinoethyl 2-(4-(4-(1-(4-chlorophenyl)cyclopropylamino)-6-(2,2,2-trifluoroethoxy)-1,3,5-triazin-2-ylamino)benzamido)-3-(2-(dimethylamino)-2-oxoacetamido)propanoate, 1022 | |
|---|---|
| MS (M + H)$^+$ Calcd. | 778.3 |
| MS (M + H)$^+$ Observ. | 778.3 |
| Retention Time | 3.22 min |
| | LC Condition |
| Solvent A | 90% Water-10% Methanol-0.1% TFA |
| Solvent B | 10% Water-90% Methanol-0.1% TFA |
| Start % B | 30 |
| Final % B | 100 |

-continued

| (S)-2-morpholinoethyl 2-(4-(4-(1-(4-chlorophenyl)cyclopropylamino)-6-(2,2,2-trifluoroethoxy)-1,3,5-triazin-2-ylamino)benzamido)-3-(2-(dimethylamino)-2-oxoacetamido)propanoate, 1022 | |
|---|---|
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1023, (S)-2-(2-hydroxyethoxy)ethyl 2-(4-(4-(1-(4-chlorophenyl)cyclopropylamino)-6-(2,2,2-trifluoroethoxy)-1,3,5-triazin-2-ylamino)benzamido)-3-(2-(dimethylamino)-2-oxoacetamido)propanoate

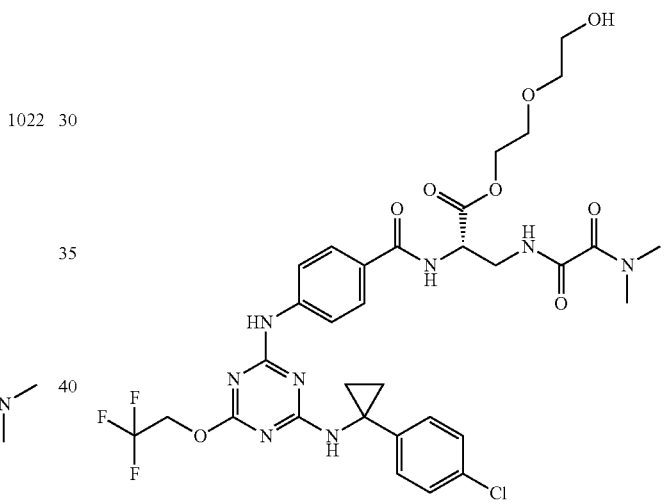

1023

1023 was prepared by using the same procedure of synthesizing 1020, using 2-morpholinoethanol as a starting material.

| (S)-2-(2-hydroxyethoxy)ethyl 2-(4-(4-(1-(4-chlorophenyl)cyclopropylamino)-6-(2,2,2-trifluoroethoxy)-1,3,5-triazin-2-ylamino)benzamido)-3-(2-(dimethylamino)-2-oxoacetamido)propanoate, 1023 | |
|---|---|
| MS (M + H)$^+$ Calcd. | 753.2 |
| MS (M + H)$^+$ Observ. | 753.3 |
| Retention Time | 3.64 min |
| | LC Condition |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1024, (S)-ethyl 2-(4-(4-(1-(4-chlorophenyl)cyclopropylamino)-6-(2,2,2-trifluoroethoxy)-1,3,5-triazin-2-ylamino)benzamido)-3-(2-(methylamino)-2-oxoacetamido)propanoate

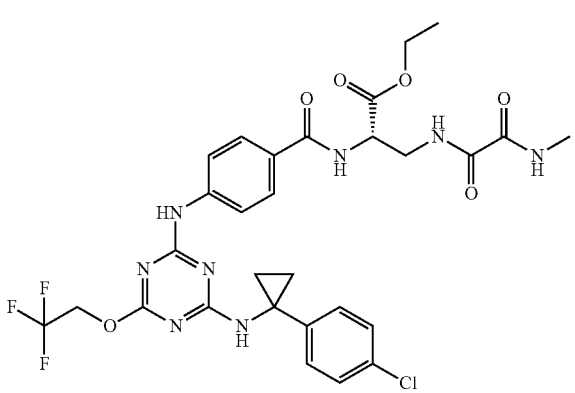

1024

1024 was prepared by using the same procedure of synthesizing 1020, using 2-(methylamino)-2-oxoacetic acid as a starting material.

| ((S)-ethyl 2-(4-(4-(1-(4-chlorophenyl)cyclopropylamino)-6-(2,2,2-trifluoroethoxy)-1,3,5-triazin-2-ylamino)benzamido)-3-(2-(methylamino)-2-oxoacetamido)propanoate, 1024 | |
|---|---|
| MS (M + H)+ Calcd. | 679.2 |
| MS (M + H)+ Observ. | 679.1 |
| Retention Time | 3.93 min |
| | LC Condition |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1025, (S)-ethyl 3-(2-amino-2-oxoacetamido)-2-(4-(4-(1-(4-chlorophenyl)cyclopropylamino)-6-(2,2,2-trifluoroethoxy)-1,3,5-triazin-2-ylamino)benzamido)propanoate

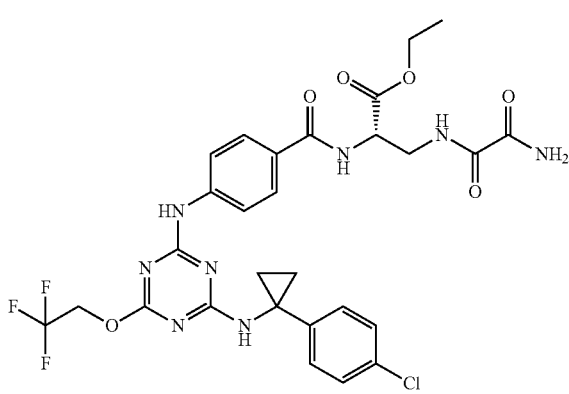

1025

1025 was prepared by using the same procedure of synthesizing 1020, using 2-amino-2-oxoacetic acid as a starting material.

| (S)-ethyl 3-(2-amino-2-oxoacetamido)-2-(4-(4-(1-(4-chlorophenyl)cyclopropylamino)-6-(2,2,2-trifluoroethoxy)-1,3,5-triazin-2-ylamino)benzamido)propanoate, 1025 | |
|---|---|
| MS (M + H)+ Calcd. | 665.2 |
| MS (M + H)+ Observ. | 665.1 |
| Retention Time | 3.78 min |
| | LC Condition |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1552, N¹-(3-(4-((4-((1-(4-chlorophenyl)cyclopropyl)amino)-6-(2,2,2-trifluoroethoxy)-1,3,5-triazin-2-yl)amino)benzamido)-2,2-dimethylpropyl)oxalamide

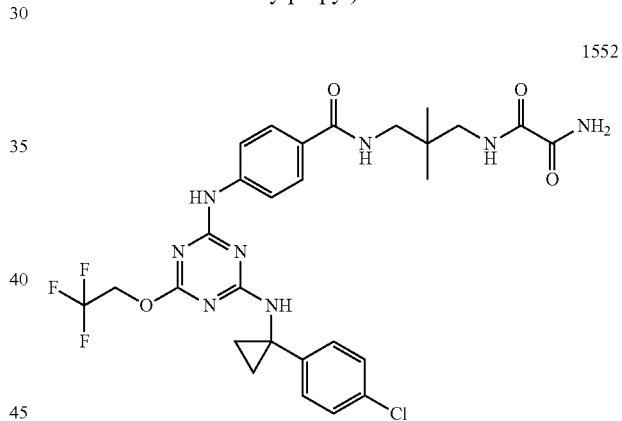

1552

1552 was prepared by using the same procedure of synthesizing 1025, using In-1005 instead of In-1101.

| Compound 1552 | |
|---|---|
| MS (M + H)+ Calcd. | 635.2 |
| MS (M + H)+ Observ. | 635.5 |
| Retention Time | 1.83 min |
| | LC Condition |
| Solvent A | 5% ACN: 95% Water: 10 mM Ammonium Actetate |
| Solvent B | 95% ACN: 5% Water: 10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN: Water: Ammonium Actetate |
| Column | Phenomenex Luna C18, 30 × 2, 3u |

Synthesis of Compound 1026, (S)-ethyl 2-(4-(4-(1-(4-chlorophenyl)cyclopropylamino)-6-(2,2,2-trifluoroethoxy)-1,3,5-triazin-2-ylamino)benzamido)-4-(2-(dimethylamino)-2-oxoacetamido)butanoate

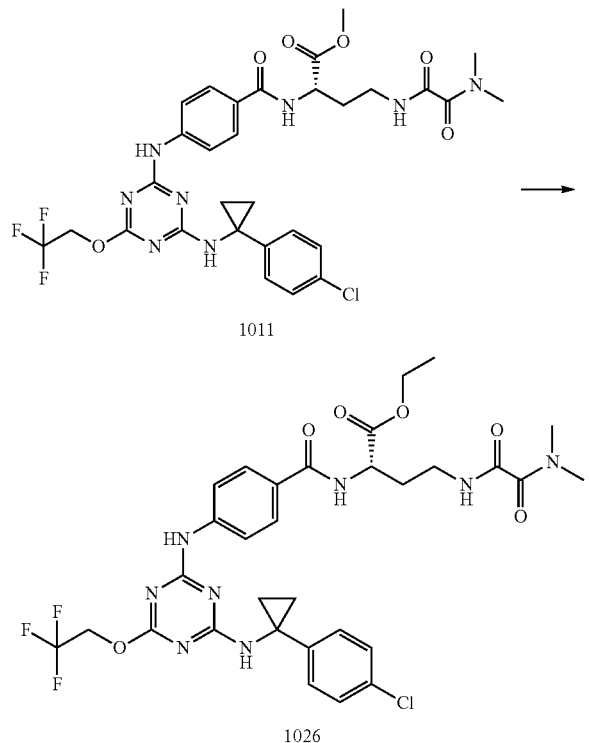

To a solution of 1011 (20 mg) in ethanol (2 mL) was added K$_2$CO$_3$ (20 mg). The mixture was stirred at room temperature for 2 days and then purified by preparative HPLC to give 1026 (5.2 mg).

| (S)-ethyl 2-(4-(4-(1-(4-chlorophenyl)cyclopropylamino)-6-(2,2,2-trifluoroethoxy)-1,3,5-triazin-2-ylamino)benzamido)-4-(2-(dimethylamino)-2-oxoacetamido)butanoate, 1026 | |
|---|---|
| MS (M + H)$^+$ Calcd. | 707.2 |
| MS (M + H)$^+$ Observ. | 707.1 |
| Retention Time | 3.60 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1027, (S)-ethyl 2-(4-(4-(1-(4-chlorophenyl)cyclopropylamino)-6-(2,2,2-trifluoroethoxy)-1,3,5-triazin-2-ylamino)benzamido)-4-(2-(methylamino)-2-oxoacetamido)butanoate

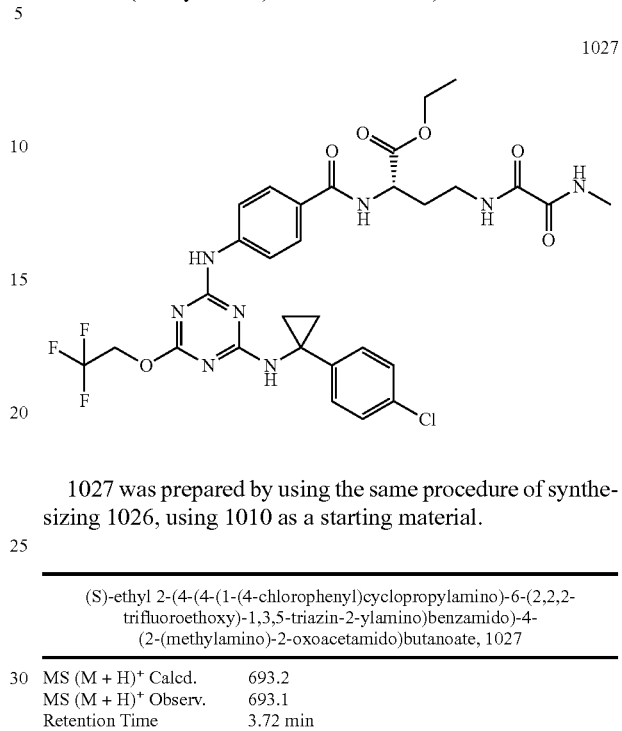

1027 was prepared by using the same procedure of synthesizing 1026, using 1010 as a starting material.

| (S)-ethyl 2-(4-(4-(1-(4-chlorophenyl)cyclopropylamino)-6-(2,2,2-trifluoroethoxy)-1,3,5-triazin-2-ylamino)benzamido)-4-(2-(methylamino)-2-oxoacetamido)butanoate, 1027 | |
|---|---|
| MS (M + H)$^+$ Calcd. | 693.2 |
| MS (M + H)$^+$ Observ. | 693.1 |
| Retention Time | 3.72 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1028, (S)-ethyl 4-(2-amino-2-oxoacetamido)-2-(4-(4-(1-(4-chlorophenyl)cyclopropylamino)-6-(2,2,2-trifluoroethoxy)-1,3,5-triazin-2-ylamino)benzamido)butanoate

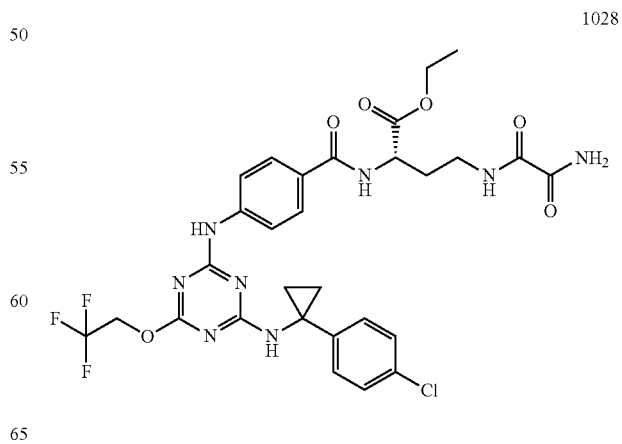

1028 was prepared by using the same procedure of synthesizing 1026, using 1009 as a starting material.

| (S)-ethyl 4-(2-amino-2-oxoacetamido)-2-(4-(4-(1-(4-chlorophenyl)cyclopropylamino)-6-(2,2,2-trifluoroethoxy)-1,3,5-triazin-2-ylamino)benzamido)butanoate, 1028 | |
|---|---|
| MS (M + H)+ Calcd. | 679.2 |
| MS (M + H)+ Observ. | 679.1 |
| Retention Time | 3.56 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1029, (S)-ethyl 5-(2-amino-2-oxoacetamido)-2-(4-(4-(1-(4-chlorophenyl)cyclopropylamino)-6-(2,2,2-trifluoroethoxy)-1,3,5-triazin-2-ylamino)benzamido)pentanoate

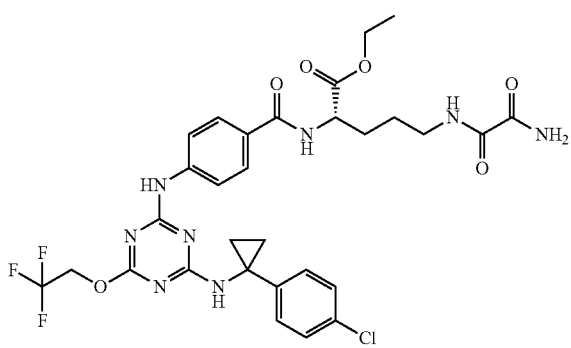

1029

1029 was prepared by using the same procedure of synthesizing 1026, using 1012 as a starting material.

| (S)-ethyl 5-(2-amino-2-oxoacetamido)-2-(4-(4-(1-(4-chlorophenyl)cyclopropylamino)-6-(2,2,2-trifluoroethoxy)-1,3,5-triazin-2-ylamino)benzamido)pentanoate, 1029 | |
|---|---|
| MS (M + H)+ Calcd. | 693.2 |
| MS (M + H)+ Observ. | 693.1 |
| Retention Time | 3.54 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1030, (S)-ethyl 2-(4-(4-(1-(4-chlorophenyl)cyclopropylamino)-6-(2,2,2-trifluoroethoxy)-1,3,5-triazin-2-ylamino)benzamido)-5-(2-(methylamino)-2-oxoacetamido)pentanoate

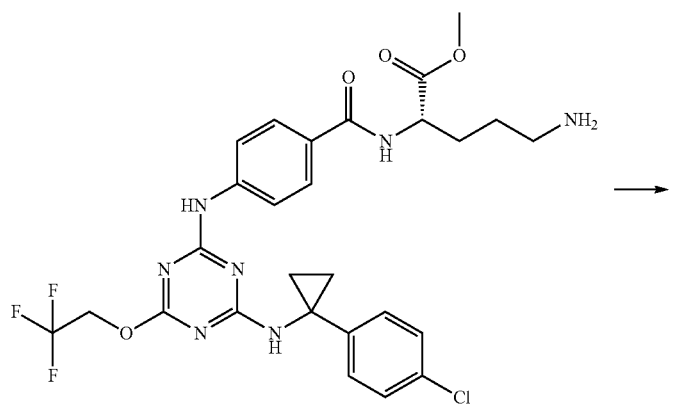

In-1004

-continued

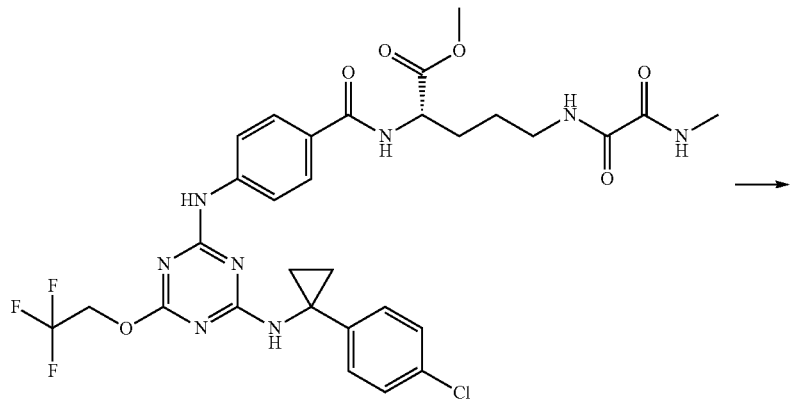

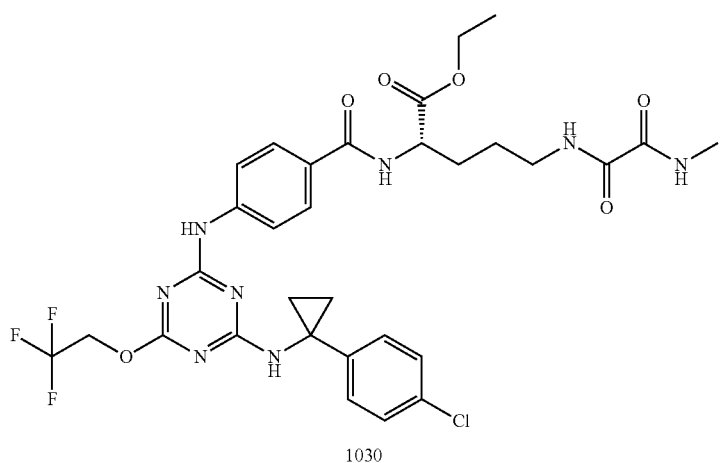

1030

Step 1: To a solution of 2-(methylamino)-2-oxoacetic acid (16.1 mg) and TBTU (50.1 mg) in DMF (1 mL) was added In-1004 (100 mg) and DIPEA (0.15 mL). After stirring at room temperature for 2 hours, the mixture was purified by preparative HPLC to give (S)-methyl 2-(4-(4-(1-(4-chlorophenyl)cyclopropylamino)-6-(2,2,2-trifluoroethoxy)-1,3,5-triazin-2-ylamino)benzamido)-5-(2-(methylamino)-2-oxoacetamido)pentanoate (58 mg).

| (S)-methyl 2-(4-(4-(1-(4-chlorophenyl)cyclopropylamino)-6-(2,2,2-trifluoroethoxy)-1,3,5-triazin-2-ylamino)benzamido)-5-(2-(methylamino)-2-oxoacetamido)pentanoate | |
|---|---|
| MS (M + H)+ Calcd. | 693.2 |
| MS (M + H)+ Observ. | 693.1 |
| Retention Time | 3.54 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 4 min |
| Flow Rate | 0.8 mL/min |
| Wavelength | 220 |

-continued

| (S)-methyl 2-(4-(4-(1-(4-chlorophenyl)cyclopropylamino)-6-(2,2,2-trifluoroethoxy)-1,3,5-triazin-2-ylamino)benzamido)-5-(2-(methylamino)-2-oxoacetamido)pentanoate | |
|---|---|
| Solvent Pair | Water-Methanol-TFA |
| Column | PHENOMENEX-LUNA 2.0 × 50 mm 3 um |

Step 2: 1030 was prepared by using the same procedure of synthesizing 1026, using (S)-methyl 2-(4-(4-(1-(4-chlorophenyl)cyclopropylamino)-6-(2,2,2-trifluoroethoxy)-1,3,5-triazin-2-ylamino)benzamido)-5-(2-(methylamino)-2-oxoacetamido)pentanoate as a starting material.

| (S)-ethyl 2-(4-(4-(1-(4-chlorophenyl)cyclopropylamino)-6-(2,2,2-trifluoroethoxy)-1,3,5-triazin-2-ylamino)benzamido)-5-(2-(methylamino)-2-oxoacetamido)pentanoate, 1030 | |
|---|---|
| MS (M + H)+ Calcd. | 707.2 |
| MS (M + H)+ Observ. | 707.1 |
| Retention Time | 3.68 min |
| LC Condition | |
| Solvent A | 90% Water-10% Methanol-0.1% TFA |
| Solvent B | 10% Water-90% Methanol-0.1% TFA |

(S)-ethyl 2-(4-(4-(1-(4-chlorophenyl)cyclopropylamino)-6-(2,2,2-trifluoroethoxy)-1,3,5-triazin-2-ylamino)benzamido)-5-(2-(methylamino)-2-oxoacetamido)pentanoate, 1030

| | |
|---|---|
| Start % B | 50 |
| Final % B | 100 |
| Gradient Time | 4 min |
| Flow Rate | 0.8 mL/min |
| Wavelength | 220 |

(S)-ethyl 2-(4-(4-(1-(4-chlorophenyl)cyclopropylamino)-6-(2,2,2-trifluoroethoxy)-1,3,5-triazin-2-ylamino)benzamido)-5-(2-(methylamino)-2-oxoacetamido)pentanoate, 1030

| | |
|---|---|
| Solvent Pair | Water-Methanol-TFA |
| Column | PHENOMENEX-LUNA 2.0 × 50 mm 3 um |

Synthesis of Compound 1031, (S)-ethyl 2-(4-(4-(1-(4-chlorophenyl)cyclopropylamino)-6-(2,2,2-trifluoroethoxy)-1,3,5-triazin-2-ylamino)benzamido)-5-(2-(dimethylamino)-2-oxoacetamido)pentanoate

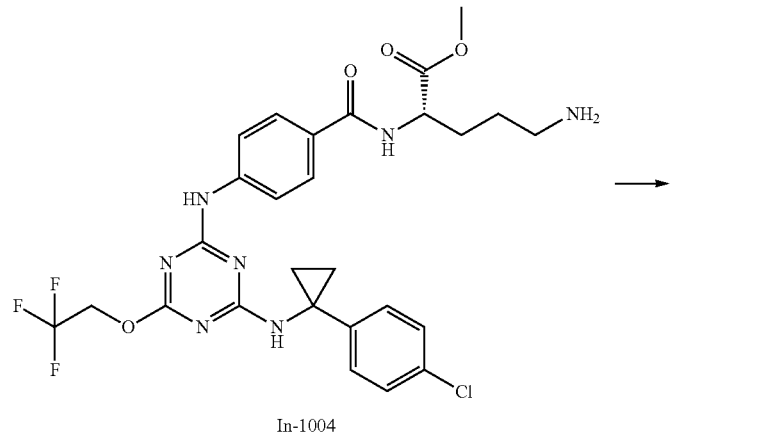

In-1004

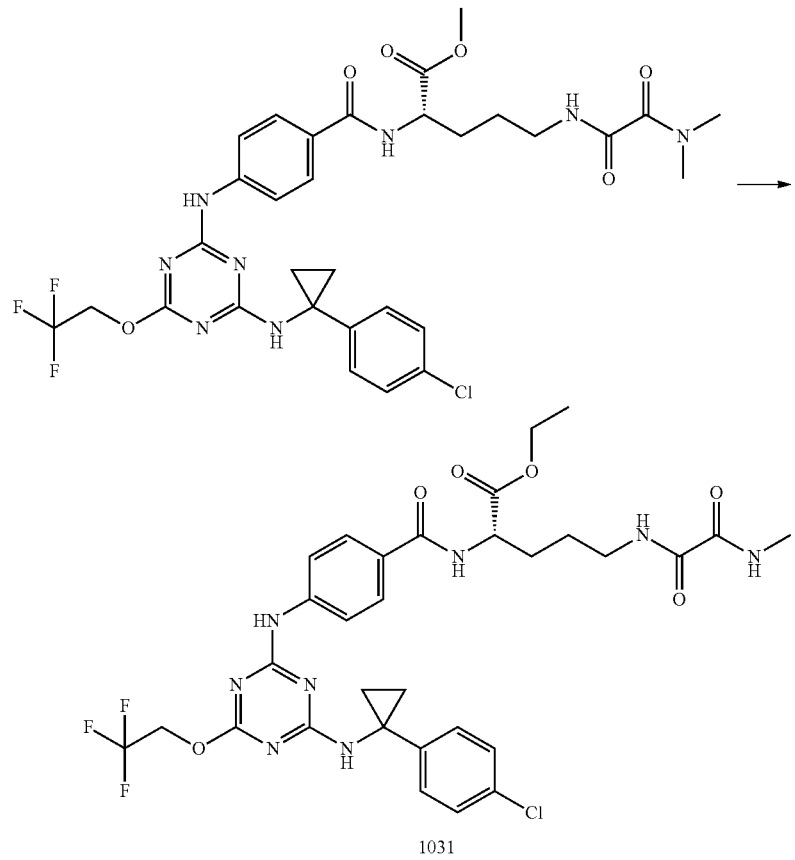

1031

1561

Step 1: To a solution of 2-(dimethylamino)-2-oxoacetic acid (18.3 mg) and TBTU (50 mg) in DMF (1 mL) was added In-1004 (100 mg) and DIPEA (0.15 mL). After stirring at room temperature for 2 hours, the mixture was purified by preparative HPLC to give (S)-methyl 2-(4-((4-(((1-(4-chlorophenyl)cyclopropyl)amino)-6-(2,2,2-trifluoroethoxy)-1,3,5-triazin-2-yl)amino)benzamido)-5-(2-(dimethylamino)-2-oxoacetamido)pentanoate (48 mg).

| (S)-methyl 2-(4-((4-((1-(4-chlorophenyl)cyclopropyl)amino)-6-(2,2,2-trifluoroethoxy)-1,3,5-triazin-2-yl)amino)benzamido)-5-(2-(dimethylamino)-2-oxoacetamido)pentanoate | |
|---|---|
| MS (M + H)$^+$ Calcd. | 707.2 |
| MS (M + H)$^+$ Observ. | 707.1 |
| Retention Time | 3.44 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Step 2: 1031 was prepared by using the same procedure of synthesizing 1026, using (S)-methyl 2-(4-((4-(((1-(4-chlorophenyl)cyclopropyl)amino)-6-(2,2,2-trifluoroethoxy)-1,3,5-triazin-2-yl)amino)benzamido)-5-(2-(dimethylamino)-2-oxoacetamido)pentanoate as a starting material.

| (S)-ethyl 2-(4-(4-(1-(4-chlorophenyl)cyclopropylamino)-6-(2,2,2-trifluoroethoxy)-1,3,5-triazin-2-ylamino)benzamido)-5-(2-(dimethylamino)-2-oxoacetamido)pentanoate, 1031 | |
|---|---|
| MS (M + H)$^+$ Calcd. | 721.2 |
| MS (M + H)$^+$ Observ. | 721.1 |
| Retention Time | 3.70 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1032, cyclopropylmethyl 2-(3-(4-(4-(1-(4-chlorophenyl)cyclopropylamino)-6-(2,2,2-trifluoroethoxy)-1,3,5-triazin-2-ylamino)benzamido)-2,2-dimethylpropylamino)-2-oxoacetate

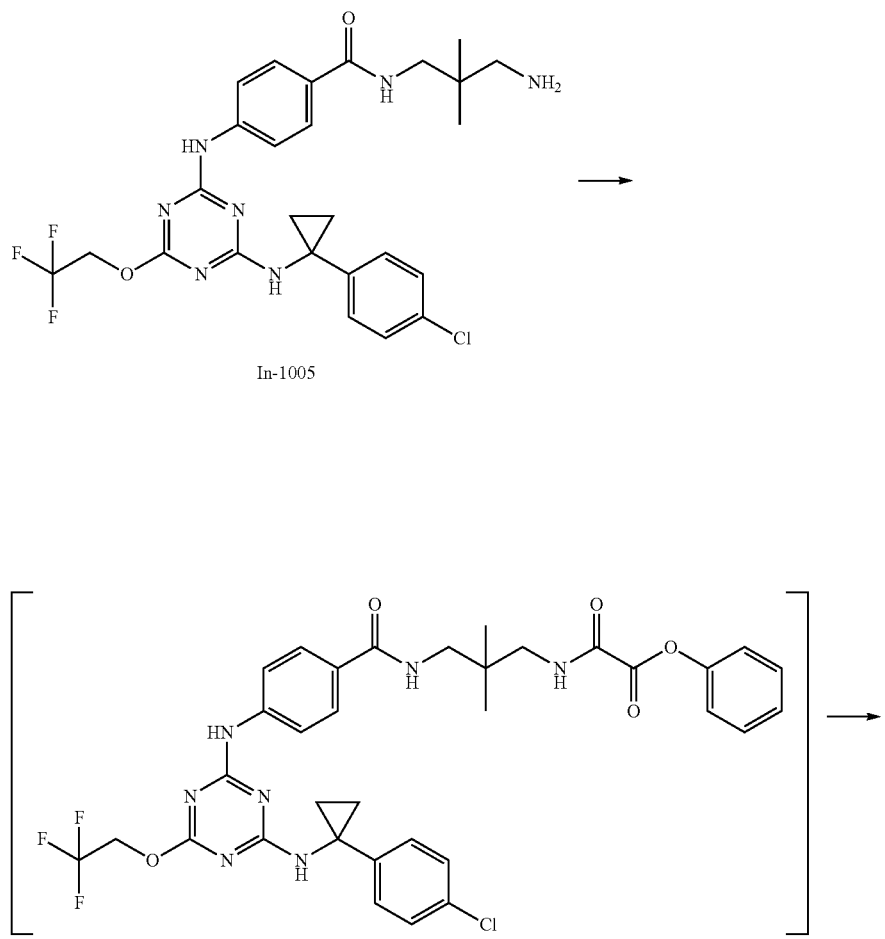

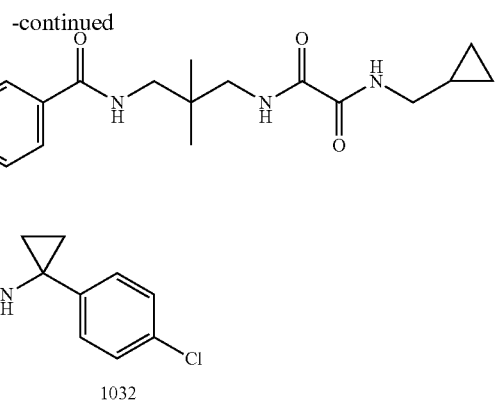

1032

A mixture of In-1005 (50 mg) and diphenyl oxalate (100 mg) in THF (5 mL) was stirred at room temperature for 16 hours, before cyclopropylmethanamine hydrochloride (191 mg) and iPr2NEt (0.5 mL) were added. The reaction was carried out at room temperature for 4 hours. Removal of solvents gave a residue which was purified by preparative HPLC to offer 1032 (20.7 mg).

| cyclopropylmethyl 2-(3-(4-(4-(1-(4-chlorophenyl)cyclopropylamino)-6-(2,2,2-trifluoroethoxy)-1,3,5-triazin-2-ylamino)benzamido)-2,2-dimethylpropylamino)-2-oxoacetate, 1032 | |
|---|---|
| MS (M + Na)+ Calcd. | 712.2 |
| MS (M + Na)+ Observ. | 712.2 |
| Retention Time | 2.38 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Synthesis of Compound 1033, N1-(3-(4-(4-(1-(4-chlorophenyl)cyclopropylamino)-6-(2,2,2-trifluoroethoxy)-1,3,5-triazin-2-ylamino)benzamido)-2,2-dimethylpropyl)-N2-cycloheptyloxalamide

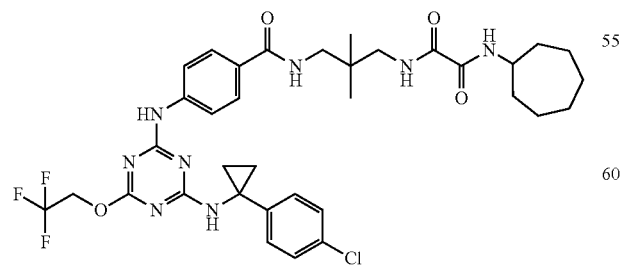

1033

1033 was prepared by using the same procedure of synthesizing 1032, using cycloheptanamine as a starting material.

| N1-(3-(4-(4-(1-(4-chlorophenyl)cyclopropylamino)-6-(2,2,2-trifluoroethoxy)-1,3,5-triazin-2-ylamino)benzamido)-2,2-dimethylpropyl)-N2-cycloheptyloxalamide, 1033 | |
|---|---|
| MS (M + H)+ Calcd. | 731.3 |
| MS (M + H)+ Observ. | 731.4 |
| Retention Time | 2.53 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Synthesis of Compound 1034, N1-(3-(4-(4-(1-(4-chlorophenyl)cyclopropylamino)-6-(2,2,2-trifluoroethoxy)-1,3,5-triazin-2-ylamino)benzamido)-2,2-dimethylpropyl)-N2-(2,4-difluorobenzyl)oxalamide

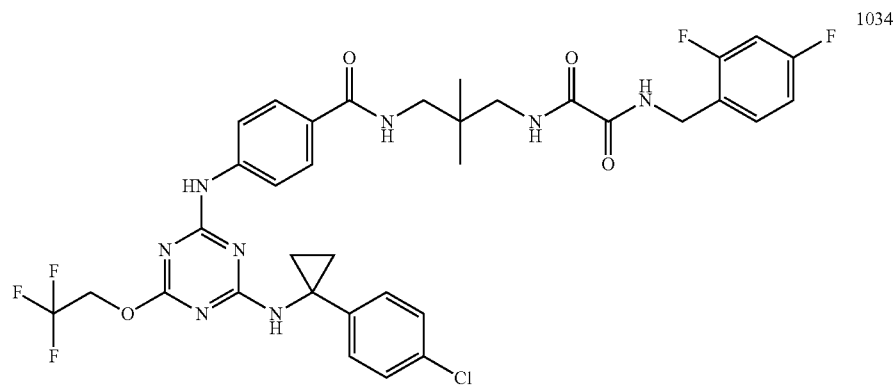 [SMILES: CC(C)(CNC(=O)C(=O)NCc1ccc(F)cc1F)CNC(=O)c1ccc(Nc2nc(NC3(c4ccc(Cl)cc4)CC3)nc(OCC(F)(F)F)n2)cc1]

1034

1034 was prepared by using the same procedure of synthesizing 1032, using (2,4-difluorophenyl)methanamine as a starting material.

| N1-(3-(4-(4-(1-(4-chlorophenyl)cyclopropylamino)-6-(2,2,2-trifluoroethoxy)-1,3,5-triazin-2-ylamino)benzamido)-2,2-dimethylpropyl)-N2-(2,4-difluorobenzyl)oxalamide, 1034 | |
|---|---|
| MS (M + H)+ Calcd. | 761.2 |
| MS (M + H)+ Observ. | 761.3 |
| Retention Time | 2.47 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Synthesis of Compound 1035, N1-(3-(4-(4-(1-(4-chlorophenyl)cyclopropylamino)-6-(2,2,2-trifluoroethoxy)-1,3,5-triazin-2-ylamino)benzamido)-2,2-dimethylpropyl)-N2-phenyloxalamide

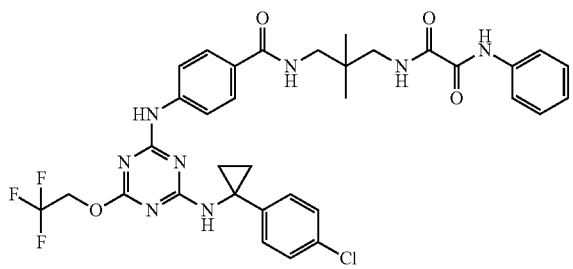

1035

1035 was prepared by using the same procedure of synthesizing 1032, using aniline as a starting material.

| N1-(3-(4-(4-(1-(4-chlorophenyl)cyclopropylamino)-6-(2,2,2-trifluoroethoxy)-1,3,5-triazin-2-ylamino)benzamido)-2,2-dimethylpropyl)-N2-phenyloxalamide, 1035 | |
|---|---|
| MS (M + H)+ Calcd. | 711.2 |
| MS (M + H)+ Observ. | 711.3 |
| Retention Time | 2.45 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Synthesis of Compound 1036, N1-(3-(4-(4-(1-(4-chlorophenyl)cyclopropylamino)-6-(2,2,2-trifluoroethoxy)-1,3,5-triazin-2-ylamino)benzamido)-2,2-dimethylpropyl)-N2-(1-(pyrrolidin-1-ylmethyl)cyclopropyl)methyl)oxalamide 1036 was prepared by using the same procedure of synthesizing 1032, using (1-(pyrrolidin-1-ylmethyl)cyclopropyl)methanamine as a starting material.

| N1-(3-(4-(4-(1-(4-chlorophenyl)cyclopropylamino)-6-(2,2,2-trifluoroethoxy)-1,3,5-triazin-2-ylamino)benzamido)-2,2-dimethylpropyl)-N2-((1-(pyrrolidin-1-ylmethyl)cyclopropyl)methyl)oxalamide, 1036 | |
|---|---|
| MS (M + H)+ Calcd. | 772.3 |
| MS (M + H)+ Observ. | 772.4 |
| Retention Time | 2.11 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

The following selected examples were prepared by using the same procedure of synthesizing 1032, using the corresponding amines rather than cyclopropylmethanamine hydrochloride as starting materials:

| LC Condition A | |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

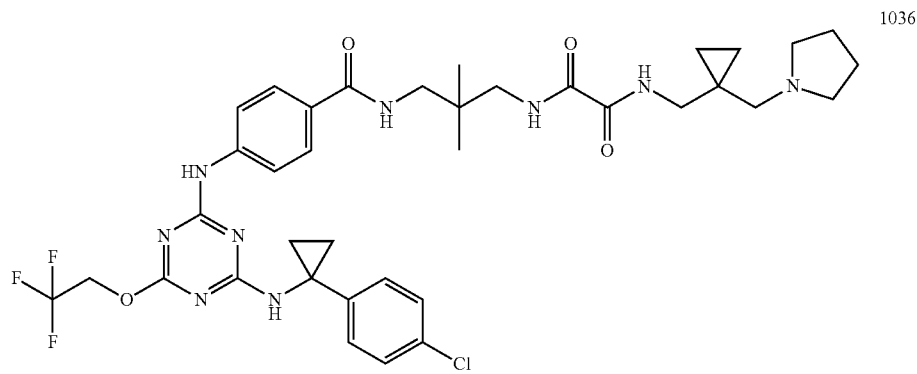 [SMILES: CC(C)(CNC(=O)C(=O)NCC1(CN2CCCC2)CC1)CNC(=O)c1ccc(Nc2nc(NC3(c4ccc(Cl)cc4)CC3)nc(OCC(F)(F)F)n2)cc1]

1036

| Compd. # | Structure | MS (M + H)+ Calcd. | MS (M + H)+ Obs. | HPLC Rt (min) | Method |
|---|---|---|---|---|---|
| 1479 | 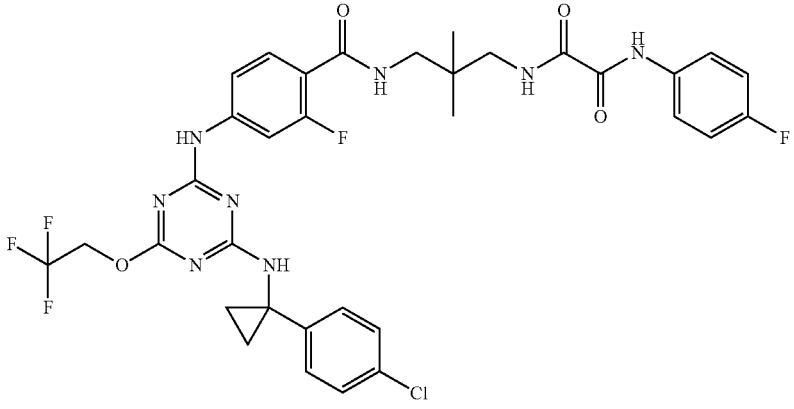 [SMILES: CC(C)(CNC(=O)C(=O)Nc1ccc(F)cc1)CNC(=O)c1ccc(Nc2nc(NC3(c4ccc(Cl)cc4)CC3)nc(OCC(F)(F)F)n2)cc1F] | 729.2 | 729.5 | 2.07 | A |
| 1536 | 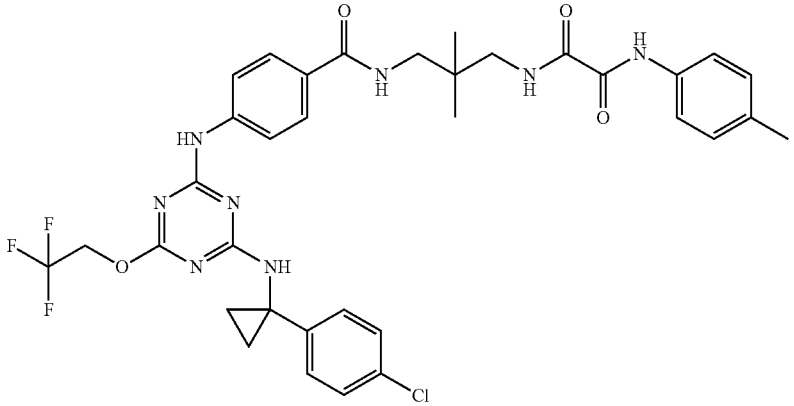 [SMILES: Cc1ccc(NC(=O)C(=O)NCC(C)(C)CNC(=O)c2ccc(Nc3nc(NC4(c5ccc(Cl)cc5)CC4)nc(OCC(F)(F)F)n3)cc2)cc1] | 725.3 | 725.3 | 2.12 | A |
| 3002 | 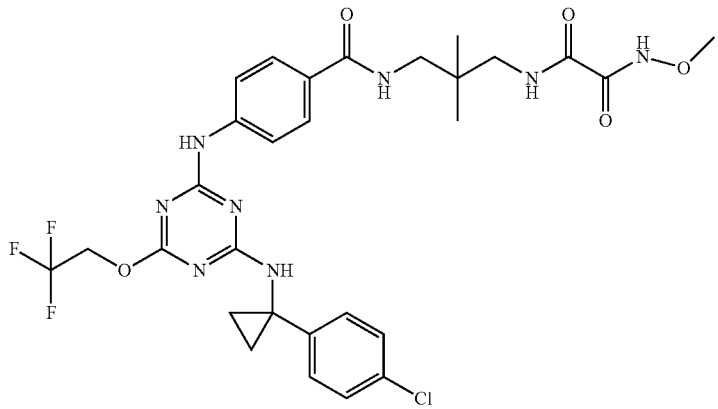 [SMILES: CONC(=O)C(=O)NCC(C)(C)CNC(=O)c1ccc(Nc2nc(NC3(c4ccc(Cl)cc4)CC3)nc(OCC(F)(F)F)n2)cc1] | 665.2 | 665.5 | 1.78 | A |

-continued

| Compd. # | Structure | MS (M + H)+ Calcd. | MS (M + H)+ Obs. | HPLC Rt (min) | Method |
|---|---|---|---|---|---|
| 3006 | 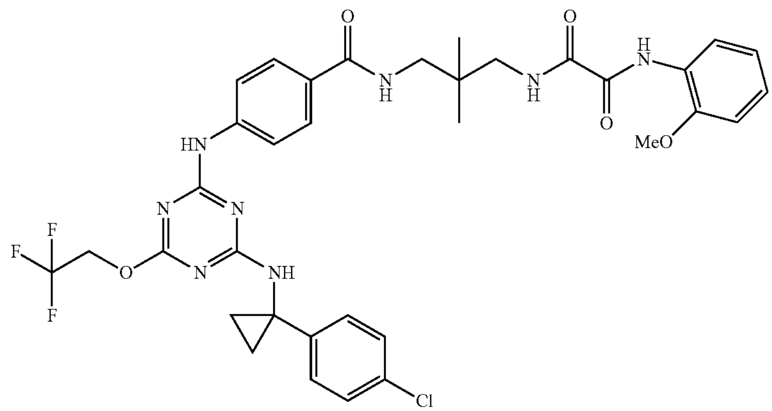 [SMILES: COc1ccccc1NC(=O)C(=O)NCC(C)(C)CNC(=O)c1ccc(Nc2nc(NC3(c4ccc(Cl)cc4)CC3)nc(OCC(F)(F)F)n2)cc1] | 741.2 | 741.6 | 2.11 | A |
| 3007 | 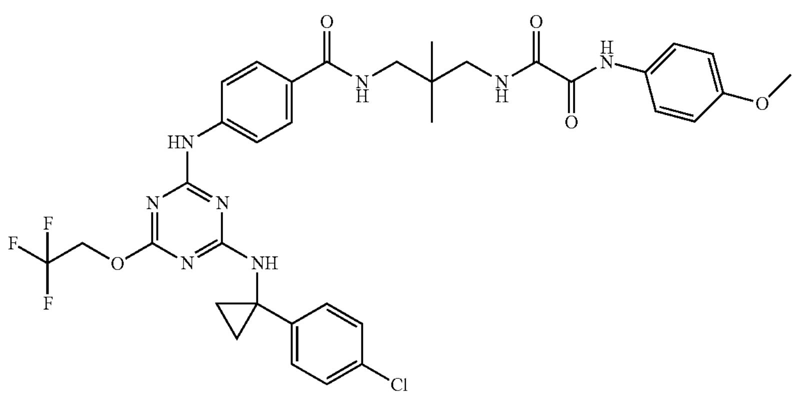 [SMILES: COc1ccc(NC(=O)C(=O)NCC(C)(C)CNC(=O)c2ccc(Nc3nc(NC4(c5ccc(Cl)cc5)CC4)nc(OCC(F)(F)F)n3)cc2)cc1] | 741.2 | 741.5 | 2.03 | A |
| 3009 | 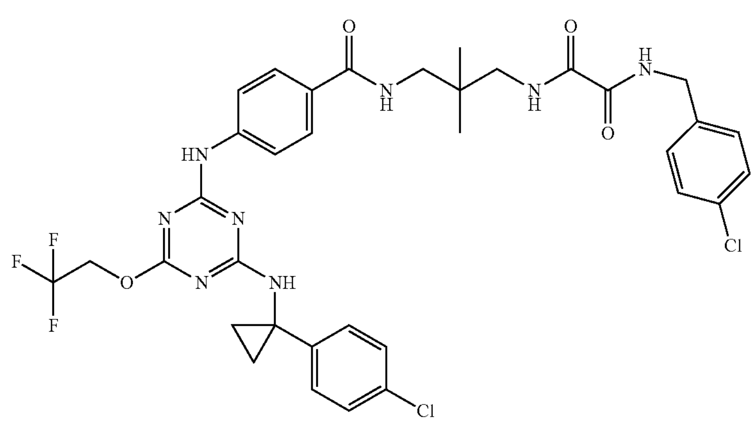 [SMILES: CC(C)(CNC(=O)C(=O)NCc1ccc(Cl)cc1)CNC(=O)c1ccc(Nc2nc(NC3(c4ccc(Cl)cc4)CC3)nc(OCC(F)(F)F)n2)cc1] | 759.2 | 759.5 | 2.07 | A |

-continued

| Compd. # | Structure | MS (M + H)+ Calcd. | MS (M + H)+ Obs. | HPLC Rt (min) | Method |
|---|---|---|---|---|---|
| 3010 | 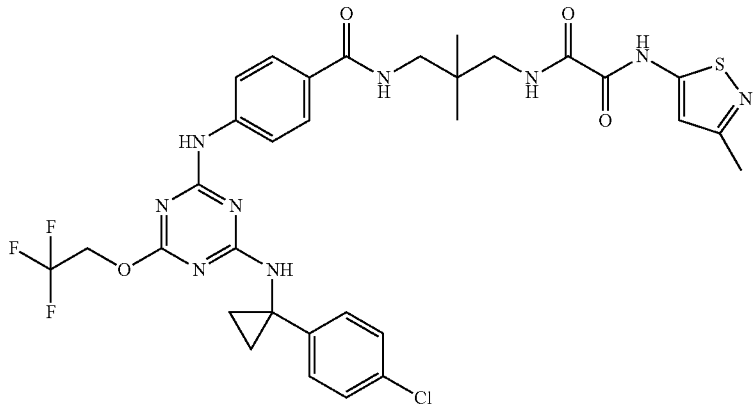 [SMILES: Cc1cc(NC(=O)C(=O)NCC(C)(C)CNC(=O)c2ccc(Nc3nc(NC4(c5ccc(Cl)cc5)CC4)nc(OCC(F)(F)F)n3)cc2)sn1] | 732.2 | 732.5 | 1.91 | A |
| 3012 | 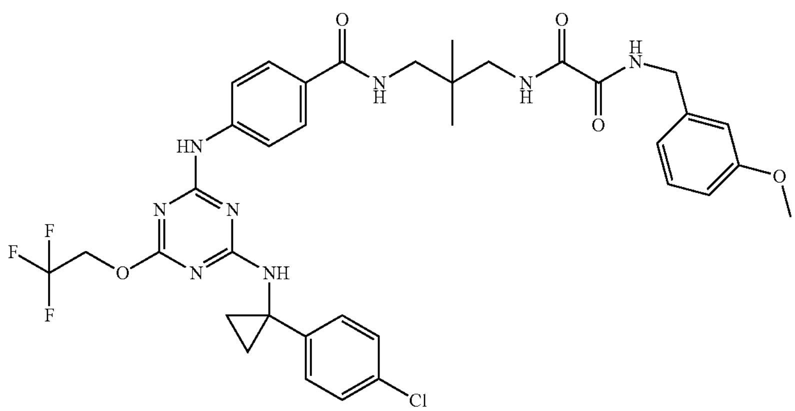 [SMILES: COc1cccc(CNC(=O)C(=O)NCC(C)(C)CNC(=O)c2ccc(Nc3nc(NC4(c5ccc(Cl)cc5)CC4)nc(OCC(F)(F)F)n3)cc2)c1] | 755.3 | 755.5 | 1.99 | A |
| 3013 | 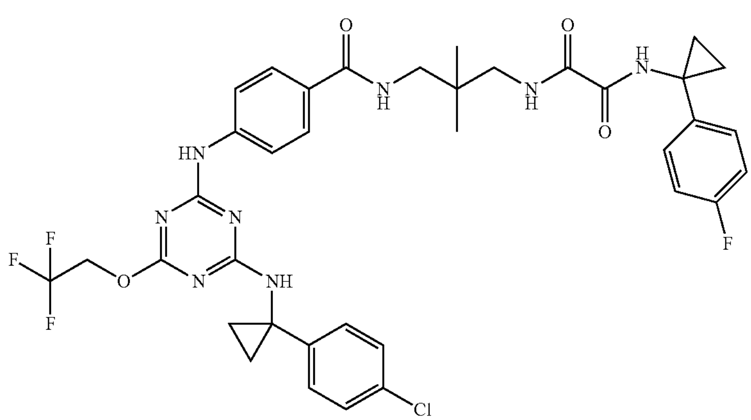 [SMILES: CC(C)(CNC(=O)C(=O)NC1(c2ccc(F)cc2)CC1)CNC(=O)c1ccc(Nc2nc(NC3(c4ccc(Cl)cc4)CC3)nc(OCC(F)(F)F)n2)cc1] | 769.3 | 769.6 | 2.04 | A |

| Compd. # | Structure | MS (M + H)+ Calcd. | MS (M + H)+ Obs. | HPLC Rt (min) | Method |
|---|---|---|---|---|---|
| 3017 | 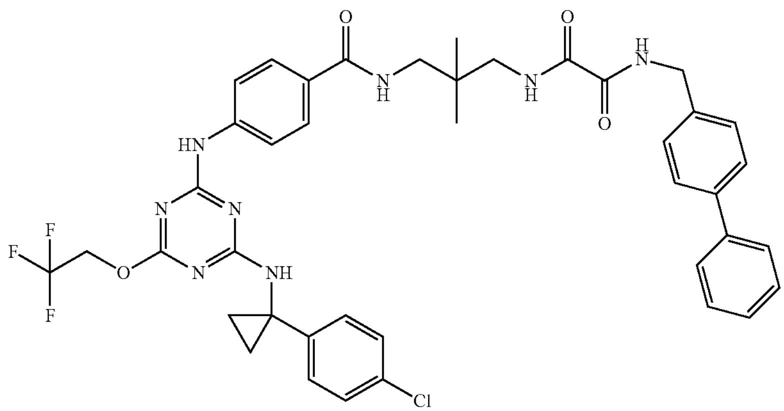 [SMILES: CC(C)(CNC(=O)C(=O)NCc1ccc(-c2ccccc2)cc1)CNC(=O)c1ccc(Nc2nc(NC3(c4ccc(Cl)cc4)CC3)nc(OCC(F)(F)F)n2)cc1] | 801.3 | 801.5 | 2.19 | A |
| 3032 | 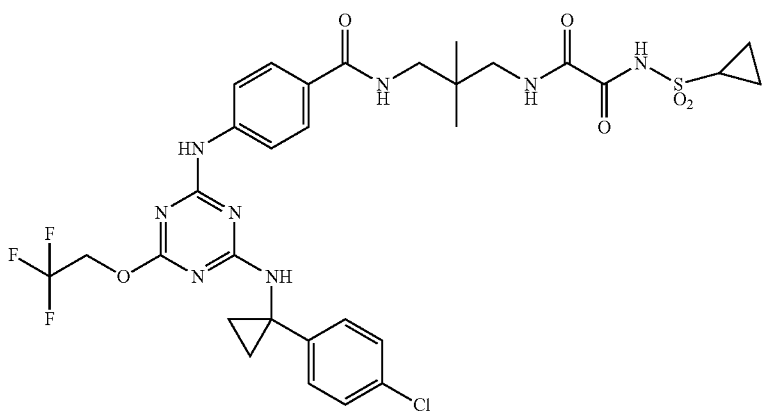 [SMILES: CC(C)(CNC(=O)C(=O)NS(=O)(=O)C1CC1)CNC(=O)c1ccc(Nc2nc(NC3(c4ccc(Cl)cc4)CC3)nc(OCC(F)(F)F)n2)cc1] | 739.2 | 739.5 | 1.54 | A |
| 3033 | 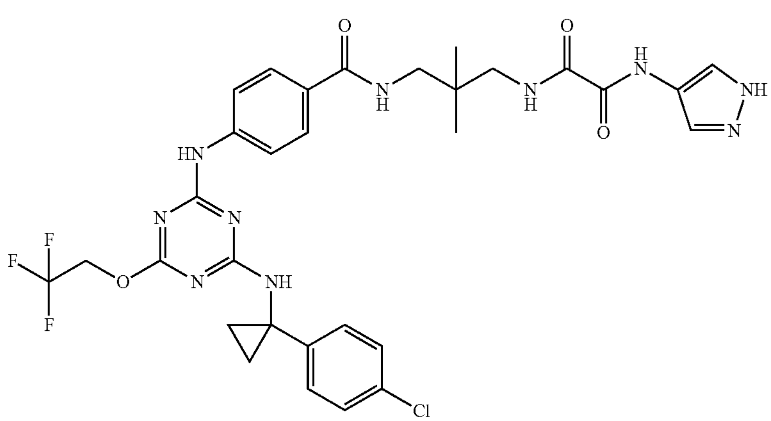 [SMILES: CC(C)(CNC(=O)C(=O)Nc1cn[nH]c1)CNC(=O)c1ccc(Nc2nc(NC3(c4ccc(Cl)cc4)CC3)nc(OCC(F)(F)F)n2)cc1] | 701.2 | 701.5 | 1.73 | A |

-continued
| Compd. # | Structure | MS (M + H)+ Calcd. | MS (M + H)+ Obs. | HPLC Rt (min) | Method |
|---|---|---|---|---|---|
| 3036 | 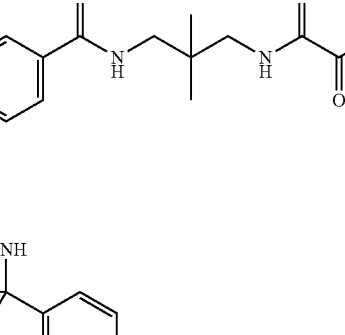 | 715.2 | 715.5 | 1.81 | A |
| 3037 | 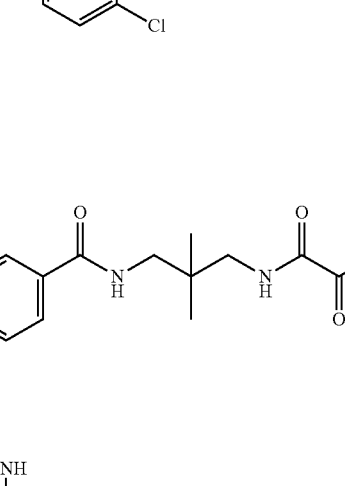 | 796.3 | 796.5 | 1.91 | A |
| 3038 | 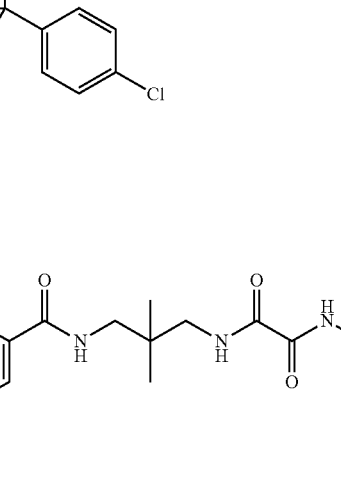 | 762.3 | 762.5 | 1.94 | A |

| Compd. # | Structure | MS (M + H)+ Calcd. | MS (M + H)+ Obs. | HPLC Rt (min) | Method |
|---|---|---|---|---|---|
| 3040 | 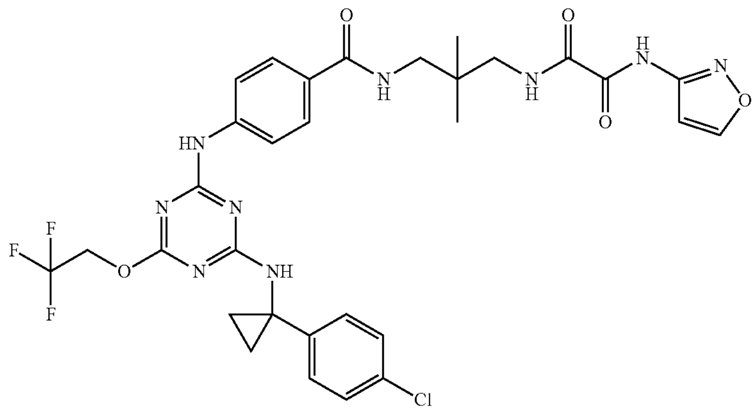 [SMILES: CC(C)(CNC(=O)C(=O)Nc1ccon1)CNC(=O)c1ccc(Nc2nc(NC3(c4ccc(Cl)cc4)CC3)nc(OCC(F)(F)F)n2)cc1] | 702.2 | 702.4 | 1.89 | A |
| 3041 | 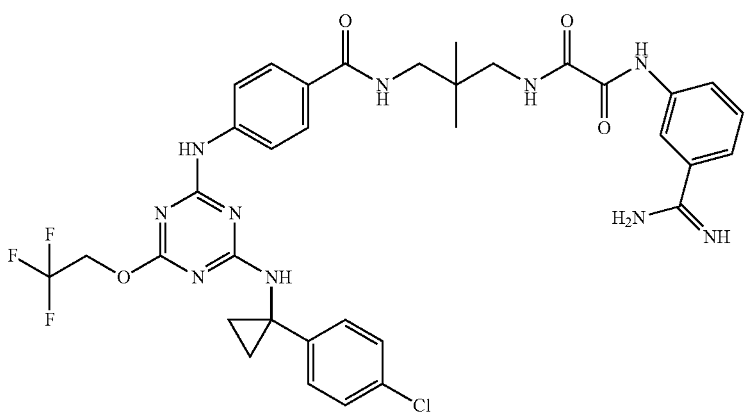 [SMILES: CC(C)(CNC(=O)C(=O)Nc1cccc(C(=N)N)c1)CNC(=O)c1ccc(Nc2nc(NC3(c4ccc(Cl)cc4)CC3)nc(OCC(F)(F)F)n2)cc1] | 753.3 | 753.5 | 1.73 | A |
| 3043 | 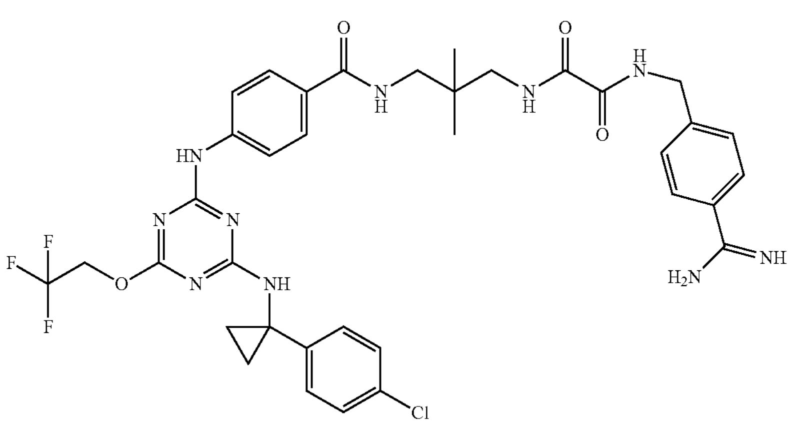 [SMILES: CC(C)(CNC(=O)C(=O)NCc1ccc(C(=N)N)cc1)CNC(=O)c1ccc(Nc2nc(NC3(c4ccc(Cl)cc4)CC3)nc(OCC(F)(F)F)n2)cc1] | 767.3 | 767.5 | 1.64 | A |

-continued

| Compd. # | Structure | MS (M + H)+ Calcd. | MS (M + H)+ Obs. | HPLC Rt (min) | Method |
|---|---|---|---|---|---|
| 3071 | 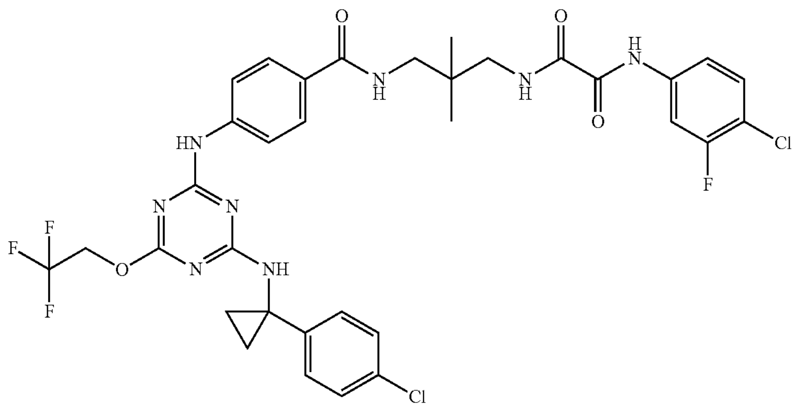 [SMILES: CC(C)(CNC(=O)C(=O)Nc1ccc(Cl)c(F)c1)CNC(=O)c1ccc(Nc2nc(NC3(c4ccc(Cl)cc4)CC3)nc(OCC(F)(F)F)n2)cc1] | 763.2 | 763.2 | 2.25 | A |
| 3074 | 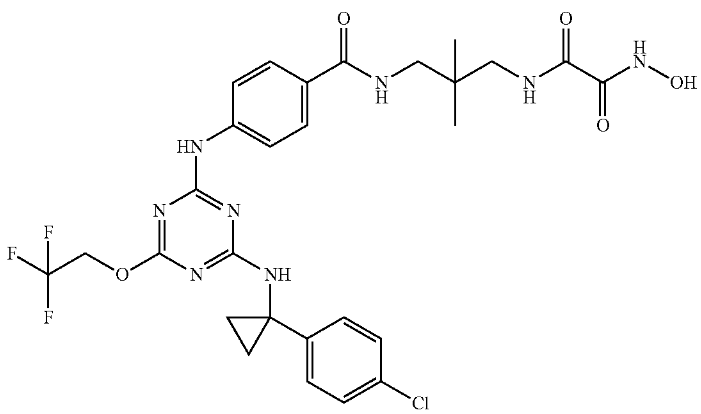 [SMILES: CC(C)(CNC(=O)C(=O)NO)CNC(=O)c1ccc(Nc2nc(NC3(c4ccc(Cl)cc4)CC3)nc(OCC(F)(F)F)n2)cc1] | 651.2 | 651.4 | 1.76 | A |
| 3141 | 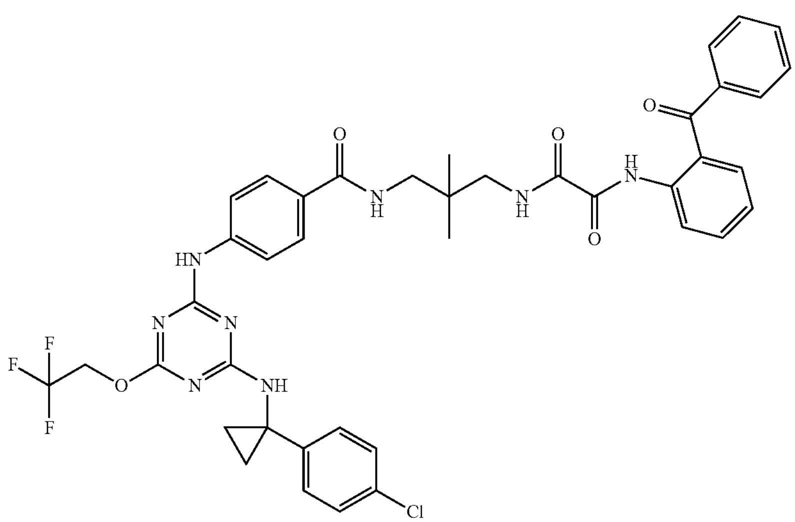 [SMILES: CC(C)(CNC(=O)C(=O)Nc1ccccc1C(=O)c1ccccc1)CNC(=O)c1ccc(Nc2nc(NC3(c4ccc(Cl)cc4)CC3)nc(OCC(F)(F)F)n2)cc1] | 815.3 | 815.4 | 2.15 | A |

| Compd. # | Structure | MS (M + H)+ Calcd. | MS (M + H)+ Obs. | HPLC Rt (min) | Method |
|---|---|---|---|---|---|
| 3143 | 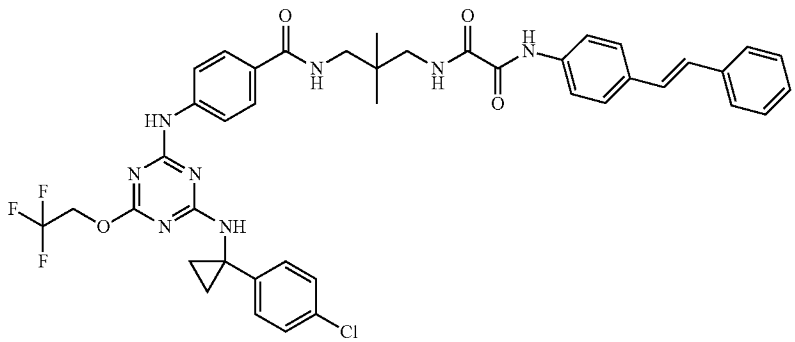 [SMILES: CC(C)(CNC(=O)C(=O)Nc1ccc(/C=C/c2ccccc2)cc1)CNC(=O)c1ccc(Nc2nc(NC3(c4ccc(Cl)cc4)CC3)nc(OCC(F)(F)F)n2)cc1] | 813.3 | 813.4 | 2.27 | A |
| 3146 | 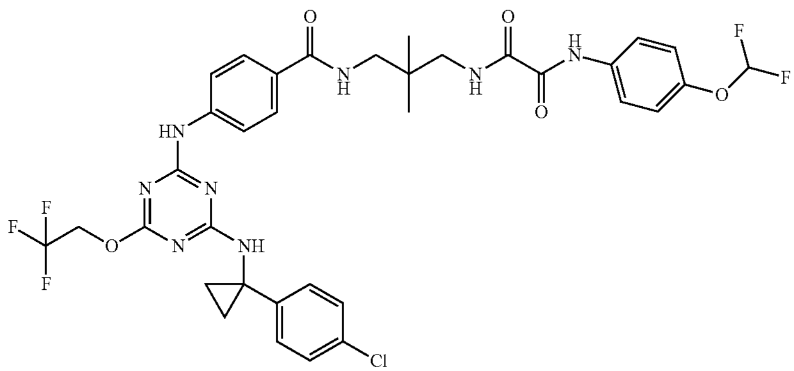 [SMILES: CC(C)(CNC(=O)C(=O)Nc1ccc(OC(F)F)cc1)CNC(=O)c1ccc(Nc2nc(NC3(c4ccc(Cl)cc4)CC3)nc(OCC(F)(F)F)n2)cc1] | 777.2 | 777.3 | 2.01 | A |
| 3176 | 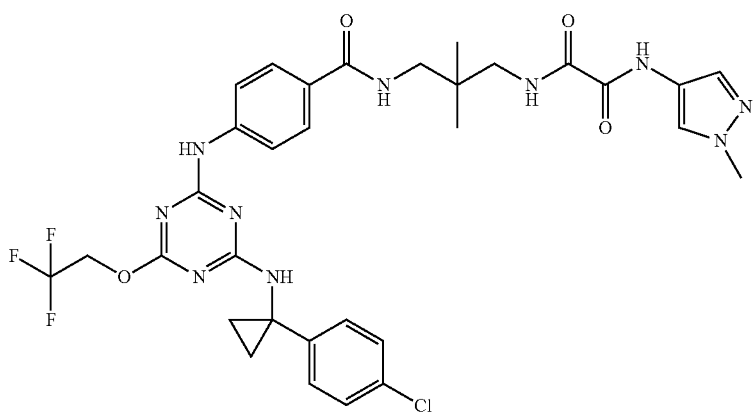 [SMILES: Cn1cc(NC(=O)C(=O)NCC(C)(C)CNC(=O)c2ccc(Nc3nc(NC4(c5ccc(Cl)cc5)CC4)nc(OCC(F)(F)F)n3)cc2)cn1] | 715.2 | 715.4 | 1.80 | A |
| 3178 | 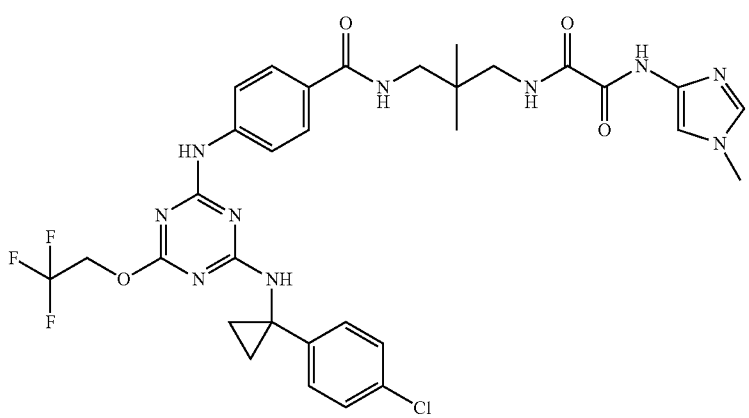 [SMILES: Cn1cnc(NC(=O)C(=O)NCC(C)(C)CNC(=O)c2ccc(Nc3nc(NC4(c5ccc(Cl)cc5)CC4)nc(OCC(F)(F)F)n3)cc2)c1] | 715.2 | 715.4 | 1.77 | A |

-continued

| Compd. # | Structure | MS (M + H)+ Calcd. | MS (M + H)+ Obs. | HPLC Rt (min) | Method |
|---|---|---|---|---|---|
| 3239 | 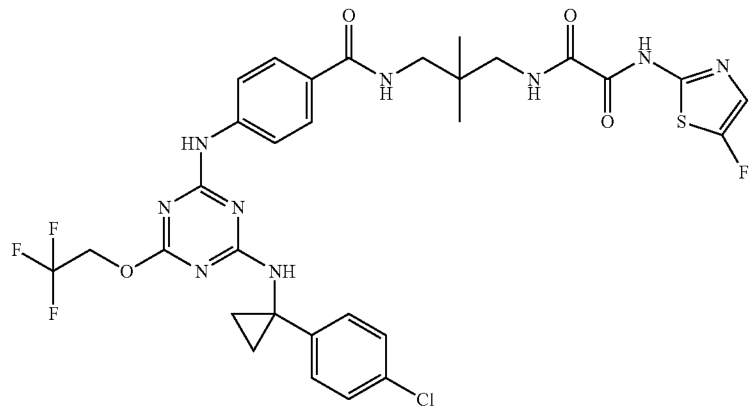 [SMILES: CC(C)(CNC(=O)C(=O)Nc1ncc(F)s1)CNC(=O)c1ccc(Nc2nc(NC3(c4ccc(Cl)cc4)CC3)nc(OCC(F)(F)F)n2)cc1] | 736.2 | 736.3 | 1.98 | A |
| 3241 | 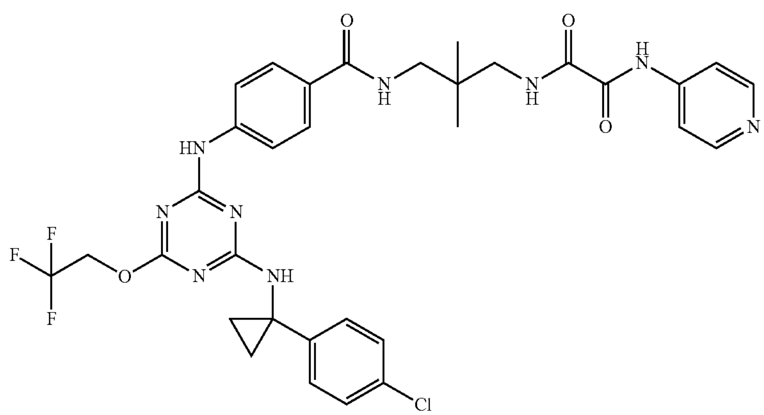 [SMILES: CC(C)(CNC(=O)C(=O)Nc1ccncc1)CNC(=O)c1ccc(Nc2nc(NC3(c4ccc(Cl)cc4)CC3)nc(OCC(F)(F)F)n2)cc1] | 712.2 | 712.3 | 1.83 | A |
| 3245 | 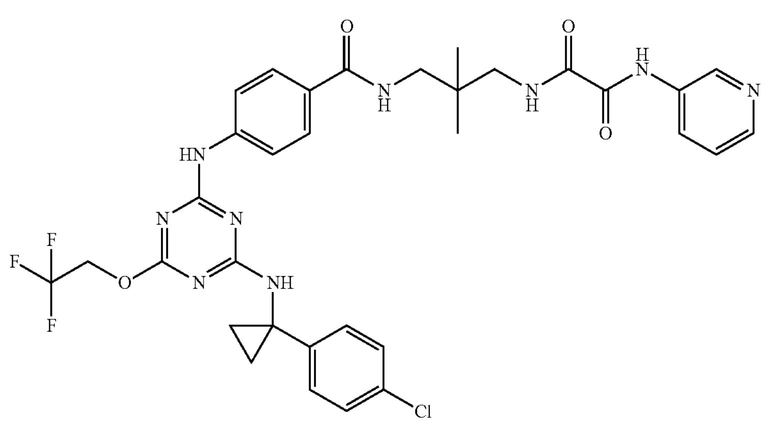 [SMILES: CC(C)(CNC(=O)C(=O)Nc1cccnc1)CNC(=O)c1ccc(Nc2nc(NC3(c4ccc(Cl)cc4)CC3)nc(OCC(F)(F)F)n2)cc1] | 712.2 | 712.3 | 1.86 | A |

-continued

| Compd. # | Structure | MS (M + H)+ Calcd. | MS (M + H)+ Obs. | HPLC Rt (min) | Method |
|---|---|---|---|---|---|
| 3248 | 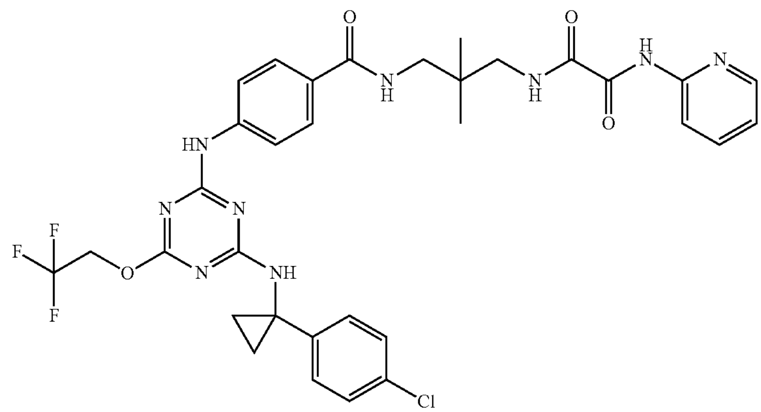 [SMILES: CC(C)(CNC(=O)C(=O)Nc1ccccn1)CNC(=O)c1ccc(Nc2nc(NC3(c4ccc(Cl)cc4)CC3)nc(OCC(F)(F)F)n2)cc1] | 712.2 | 712.3 | 1.97 | A |
| 3250 | 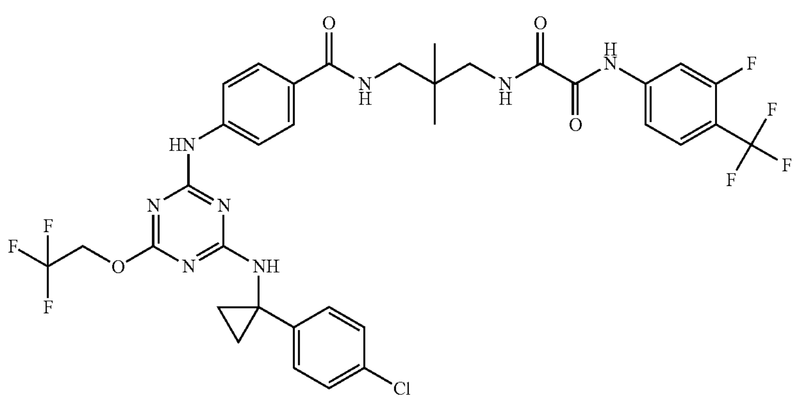 [SMILES: CC(C)(CNC(=O)C(=O)Nc1ccc(C(F)(F)F)c(F)c1)CNC(=O)c1ccc(Nc2nc(NC3(c4ccc(Cl)cc4)CC3)nc(OCC(F)(F)F)n2)cc1] | 797.2 | 797.3 | 2.25 | A |
| 3253 | 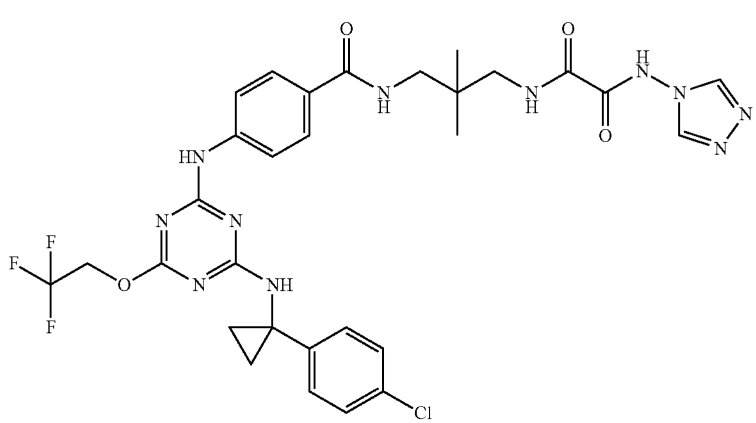 [SMILES: CC(C)(CNC(=O)C(=O)Nn1cnnc1)CNC(=O)c1ccc(Nc2nc(NC3(c4ccc(Cl)cc4)CC3)nc(OCC(F)(F)F)n2)cc1] | 702.2 | 702.3 | 1.52 | A |

| Compd. # | Structure | MS (M + H)+ Calcd. | MS (M + H)+ Obs. | HPLC Rt (min) | Method |
|---|---|---|---|---|---|
| 3256 | 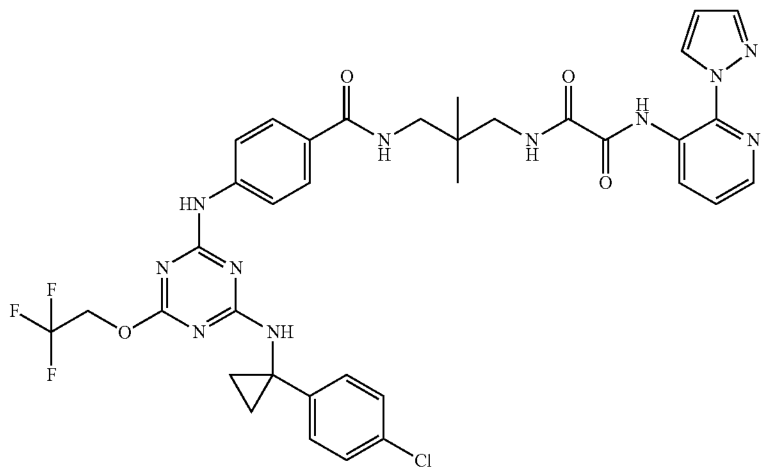 [SMILES: CC(C)(CNC(=O)C(=O)Nc1cccnc1-n1cccn1)CNC(=O)c1ccc(Nc2nc(NC3(c4ccc(Cl)cc4)CC3)nc(OCC(F)(F)F)n2)cc1] | 778.3 | 778.4 | 2.14 | A |
| 3262 | 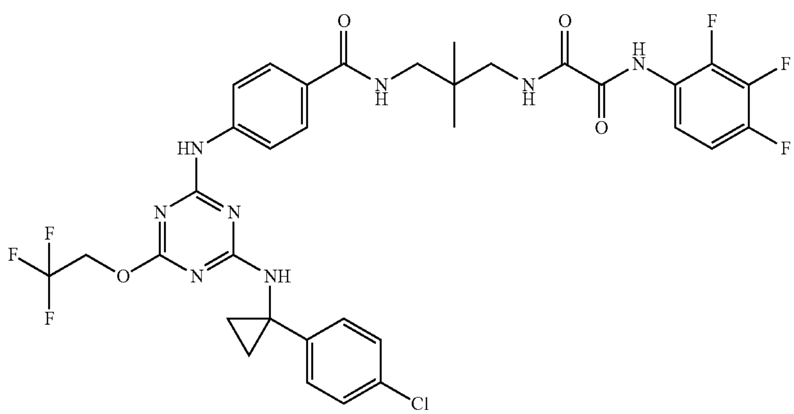 [SMILES: CC(C)(CNC(=O)C(=O)Nc1ccc(F)c(F)c1F)CNC(=O)c1ccc(Nc2nc(NC3(c4ccc(Cl)cc4)CC3)nc(OCC(F)(F)F)n2)cc1] | 765.2 | 765.3 | 2.10 | A |
| 3337 | 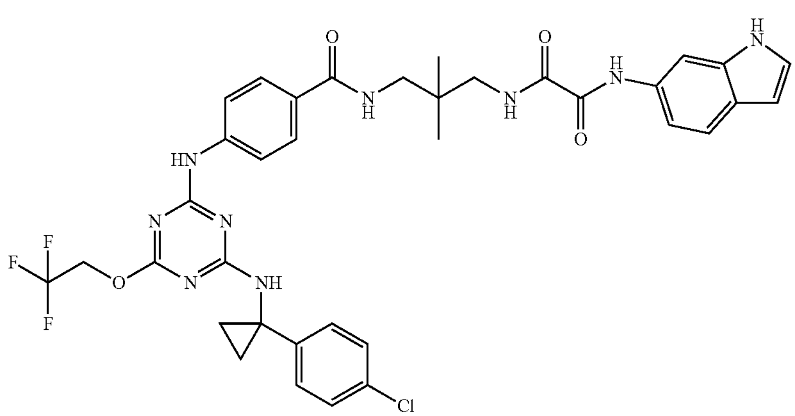 [SMILES: CC(C)(CNC(=O)C(=O)Nc1ccc2cc[nH]c2c1)CNC(=O)c1ccc(Nc2nc(NC3(c4ccc(Cl)cc4)CC3)nc(OCC(F)(F)F)n2)cc1] | 750.3 | 750.3 | 2.00 | A |

| Compd. # | Structure | MS (M + H)+ Calcd. | MS (M + H)+ Obs. | HPLC Rt (min) | Method |
|---|---|---|---|---|---|
| 3350 | 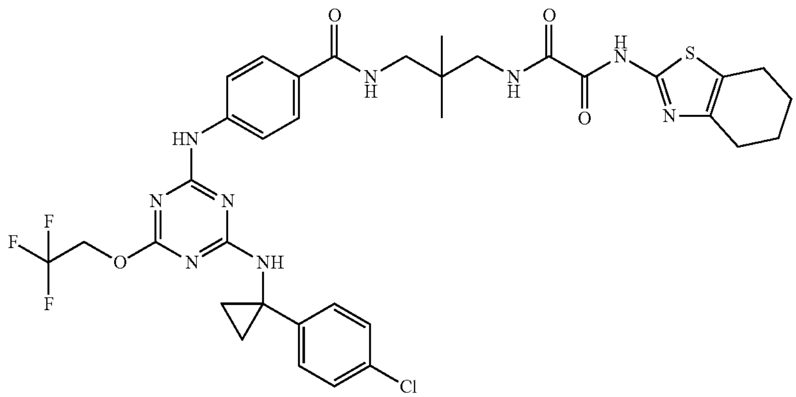 [SMILES: CC(C)(CNC(=O)C(=O)Nc1nc2c(s1)CCCC2)CNC(=O)c1ccc(Nc2nc(NC3(c4ccc(Cl)cc4)CC3)nc(OCC(F)(F)F)n2)cc1] | 772.2 | 772.4 | 2.15 | A |
| 3352 | 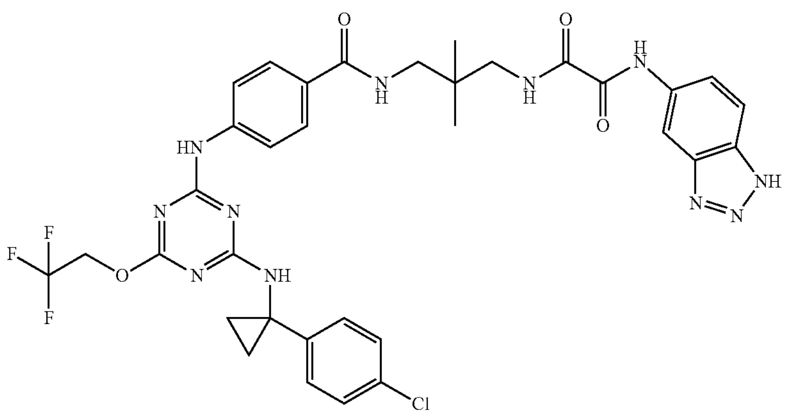 [SMILES: CC(C)(CNC(=O)C(=O)Nc1ccc2[nH]nnc2c1)CNC(=O)c1ccc(Nc2nc(NC3(c4ccc(Cl)cc4)CC3)nc(OCC(F)(F)F)n2)cc1] | 752.2 | 752.4 | 1.80 | A |
| 3355 | 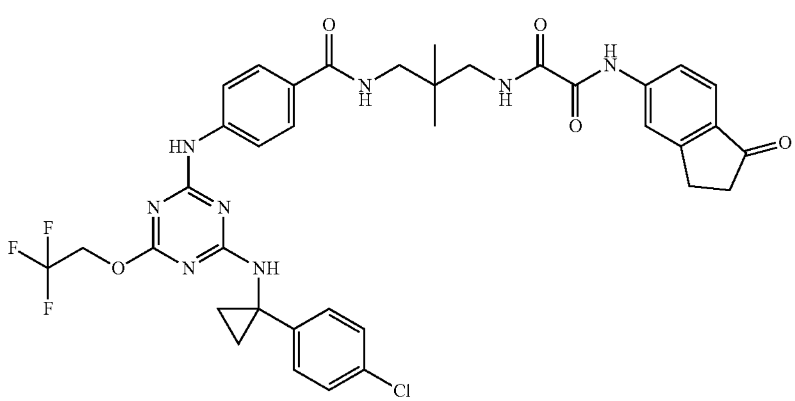 [SMILES: CC(C)(CNC(=O)C(=O)Nc1ccc2c(c1)CCC2=O)CNC(=O)c1ccc(Nc2nc(NC3(c4ccc(Cl)cc4)CC3)nc(OCC(F)(F)F)n2)cc1] | 765.2 | 765.4 | 2.04 | A |

-continued
| Compd. # | Structure | MS (M + H)+ Calcd. | MS (M + H)+ Obs. | HPLC Rt (min) | Method |
|---|---|---|---|---|---|
| 3359 | 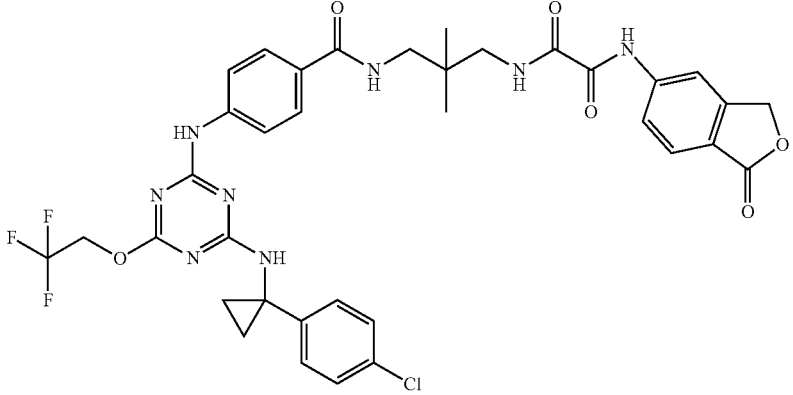 [SMILES: CC(C)(CNC(=O)C(=O)Nc1ccc2c(c1)COC2=O)CNC(=O)c1ccc(Nc2nc(NC3(c4ccc(Cl)cc4)CC3)nc(OCC(F)(F)F)n2)cc1] | 767.2 | 767.3 | 1.96 | A |
| 3361 | 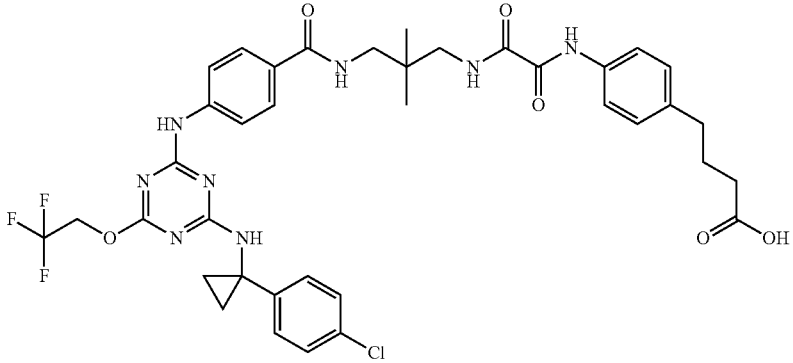 [SMILES: CC(C)(CNC(=O)C(=O)Nc1ccc(CCCC(=O)O)cc1)CNC(=O)c1ccc(Nc2nc(NC3(c4ccc(Cl)cc4)CC3)nc(OCC(F)(F)F)n2)cc1] | 797.3 | 797.4 | 1.75 | A |
| 3375 | 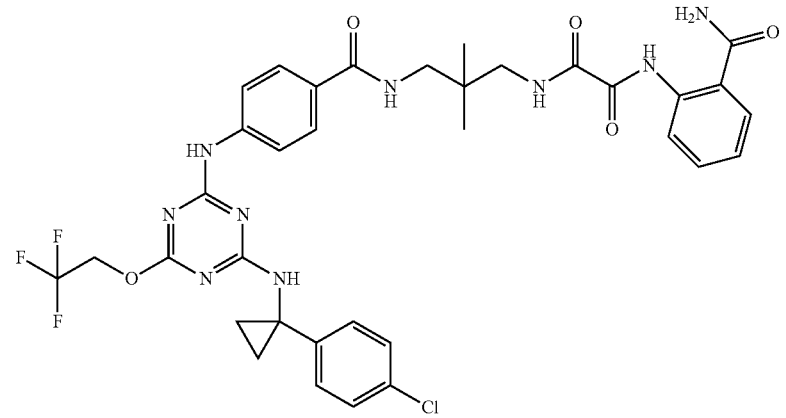 [SMILES: CC(C)(CNC(=O)C(=O)Nc1ccccc1C(N)=O)CNC(=O)c1ccc(Nc2nc(NC3(c4ccc(Cl)cc4)CC3)nc(OCC(F)(F)F)n2)cc1] | 754.2 | 754.4 | 1.88 | A |

| Compd. # | Structure | MS (M + H)+ Calcd. | MS (M + H)+ Obs. | HPLC Rt (min) | Method |
|---|---|---|---|---|---|
| 3376 | 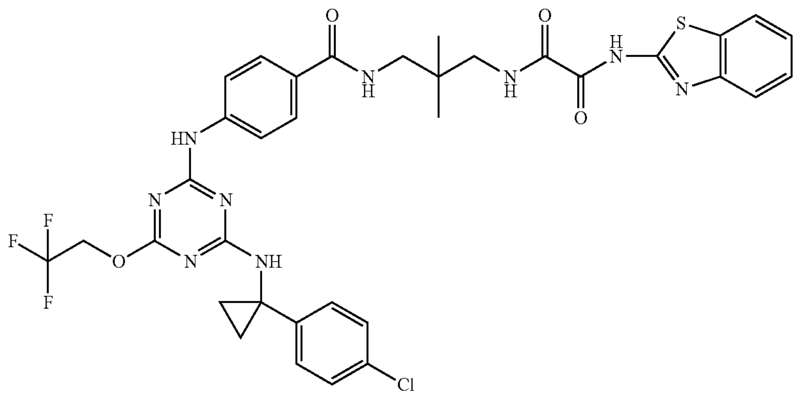 [SMILES: CC(C)(CNC(=O)C(=O)Nc1nc2ccccc2s1)CNC(=O)c1ccc(Nc2nc(NC3(c4ccc(Cl)cc4)CC3)nc(OCC(F)(F)F)n2)cc1] | 768.2 | 768.4 | 2.16 | A |
| 3378 | 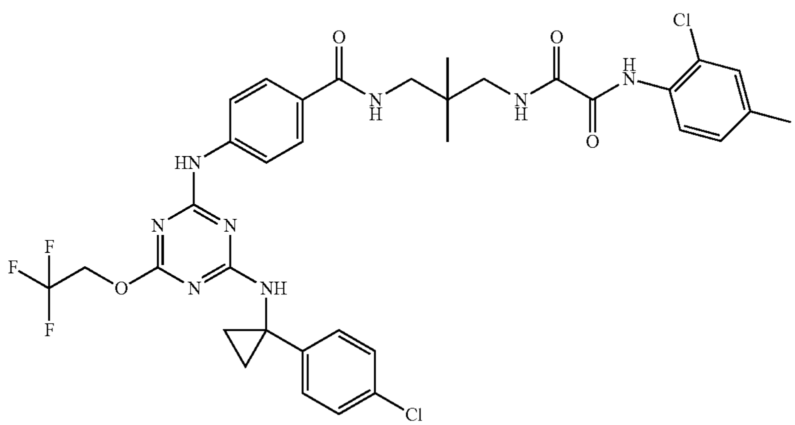 [SMILES: Cc1ccc(NC(=O)C(=O)NCC(C)(C)CNC(=O)c2ccc(Nc3nc(NC4(c5ccc(Cl)cc5)CC4)nc(OCC(F)(F)F)n3)cc2)c(Cl)c1] | 759.2 | 759.4 | 2.31 | A |
| 3400 | 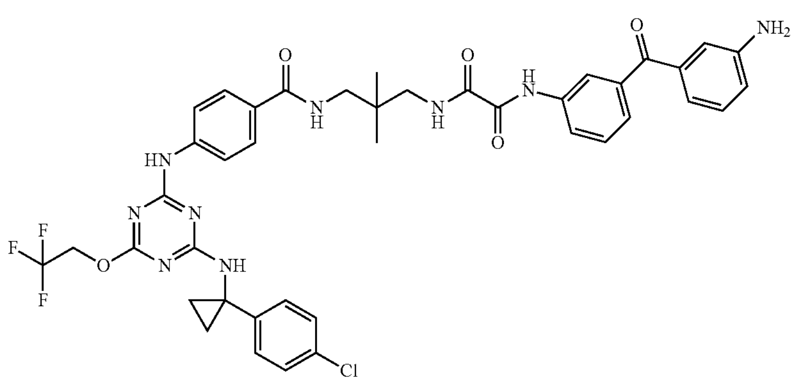 [SMILES: CC(C)(CNC(=O)C(=O)Nc1cccc(C(=O)c2cccc(N)c2)c1)CNC(=O)c1ccc(Nc2nc(NC3(c4ccc(Cl)cc4)CC3)nc(OCC(F)(F)F)n2)cc1] | 830.3 | 830.4 | 2.05 | A |

| Compd. # | Structure | MS (M + H)+ Calcd. | MS (M + H)+ Obs. | HPLC Rt (min) | Method |
|---|---|---|---|---|---|
| 3404 | 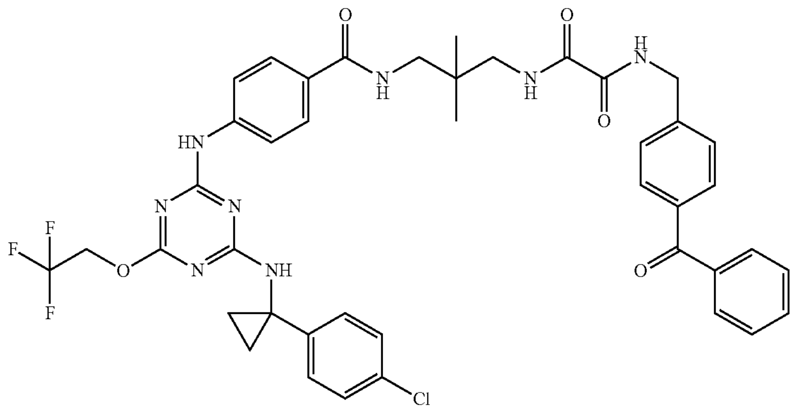 [SMILES: CC(C)(CNC(=O)C(=O)NCc1ccc(C(=O)c2ccccc2)cc1)CNC(=O)c1ccc(Nc2nc(NC3(c4ccc(Cl)cc4)CC3)nc(OCC(F)(F)F)n2)cc1] | 829.3 | 829.4 | 2.06 | A |
| 3452 | 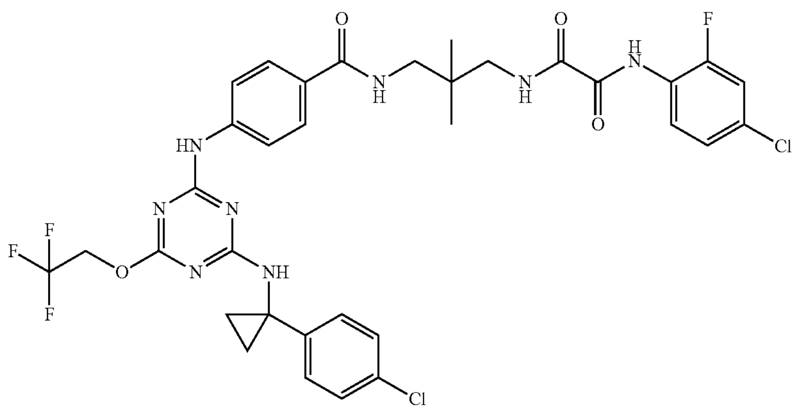 [SMILES: CC(C)(CNC(=O)C(=O)Nc1ccc(Cl)cc1F)CNC(=O)c1ccc(Nc2nc(NC3(c4ccc(Cl)cc4)CC3)nc(OCC(F)(F)F)n2)cc1] | 763.2 | 763.4 | 2.17 | A |
| 3454 | 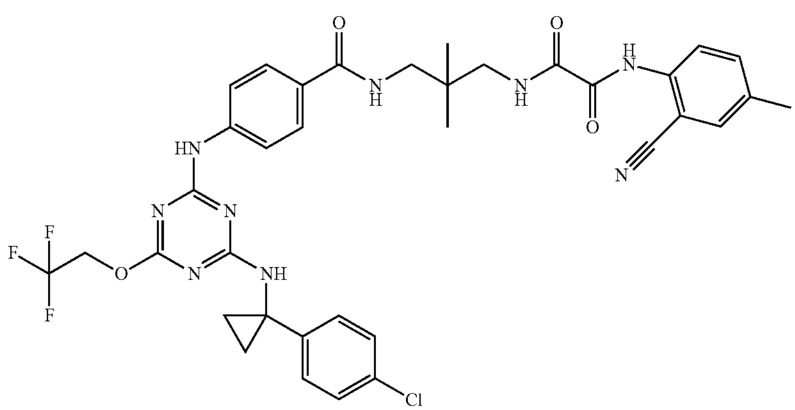 [SMILES: Cc1ccc(NC(=O)C(=O)NCC(C)(C)CNC(=O)c2ccc(Nc3nc(NC4(c5ccc(Cl)cc5)CC4)nc(OCC(F)(F)F)n3)cc2)c(C#N)c1] | 750.3 | 750.4 | 2.09 | A |
| 3805 | 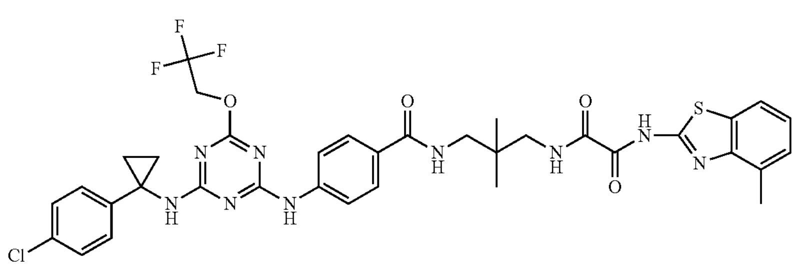 [SMILES: Cc1cccc2sc(NC(=O)C(=O)NCC(C)(C)CNC(=O)c3ccc(Nc4nc(NC5(c6ccc(Cl)cc6)CC5)nc(OCC(F)(F)F)n4)cc3)nc12] | 782.2 | 782.2 | 2.23 | A |

-continued

| Compd. # | Structure | MS (M + H)+ Calcd. | MS (M + H)+ Obs. | HPLC Rt (min) | Method |
|---|---|---|---|---|---|
| 3808 | 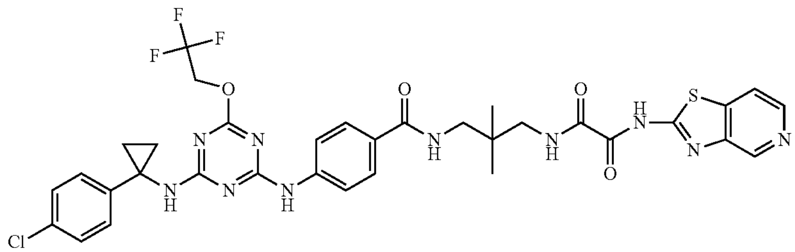 [SMILES: CC(C)(CNC(=O)C(=O)Nc1nc2cnccc2s1)CNC(=O)c1ccc(Nc2nc(NC3(c4ccc(Cl)cc4)CC3)nc(OCC(F)(F)F)n2)cc1] | 769.2 | 769.3 | 1.89 | A |
| 2824 | 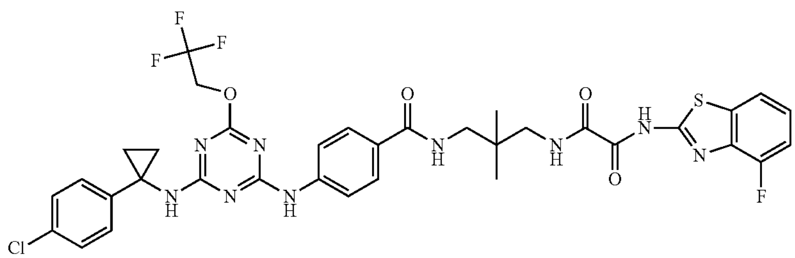 | 785.2 | 786.2 | 2.10 | A |
| 3826 | 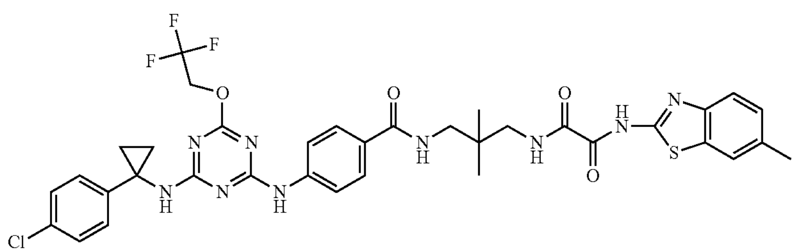 [SMILES: Cc1ccc2nc(NC(=O)C(=O)NCC(C)(C)CNC(=O)c3ccc(Nc4nc(NC5(c6ccc(Cl)cc6)CC5)nc(OCC(F)(F)F)n4)cc3)sc2c1] | 782.2 | 782.2 | 2.13 | A |
| 3836 | 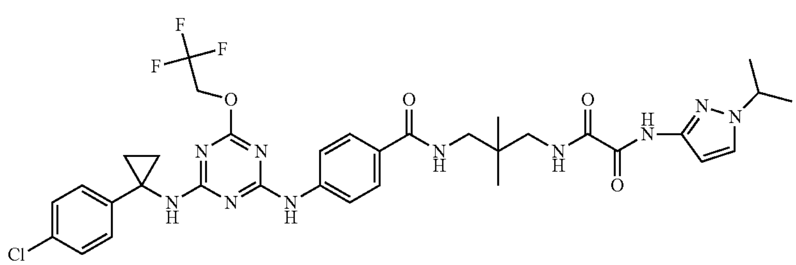 [SMILES: CC(C)n1ccc(NC(=O)C(=O)NCC(C)(C)CNC(=O)c2ccc(Nc3nc(NC4(c5ccc(Cl)cc5)CC4)nc(OCC(F)(F)F)n3)cc2)n1] | 743.3 | 743.3 | 1.99 | A |

Preparation of 1465, N¹-(2-((4-((4-((1-(4-chlorophenyl)cyclopropyl)amino)-6-(2,2,2-trifluoroethoxy)-1,3,5-triazin-2-yl)amino)benzamido)methyl)cyclopentyl)-N²-(4-fluorophenyl)oxalamide iPr₂NEt (0.2 mL) and 4-fluoroaniline (39.2 mg) added into the solution of ethyl 2-((2-((4-((4-((1-(4-chlorophenyl)cyclopropyl)amino)-6-(2,2,2-trifluoroethoxy)-1,3,5-triazin-2-yl)amino)benzamido)methyl)cyclopentyl)amino)-2-oxoacetate (40 mg) in EtOH (2 mL) and the reaction was stirred at 155° C. for 3 days. The product was isolated by preparative HPLC system.

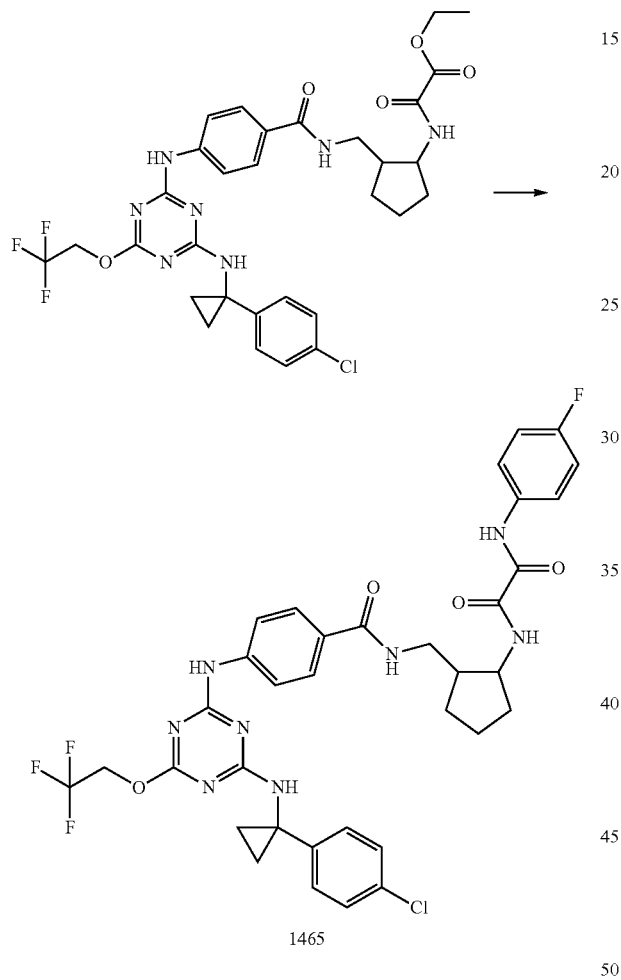

1465

| Compound 1465 | |
|---|---|
| MS (M + H)⁺ Calcd. | 741.2 |
| MS (M + H)⁺ Observ. | 741.5 |
| Retention Time | 2.07 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

Preparation of 1492, N¹-((1-((4-((4-((1-(4-chlorophenyl)cyclopropyl)amino)-6-(2,2,2-trifluoroethoxy)-1,3,5-triazin-2-yl)amino)benzamido)methyl)cyclopropyl)methyl)-N²-(4-fluorophenyl)oxalamide To a solution of 2-(((1-((4-((4-((1-(4-chlorophenyl)cyclopropyl)amino)-6-(2,2,2-trifluoroethoxy)-1,3,5-triazin-2-yl)amino)benzamido)methyl)cyclopropyl)methyl)amino)-2-oxoacetic acid (17 mg) and TBTU (10.33 mg) in DMF (2 mL) was added 4-fluoroaniline (3.58 mg). The mixture was stirred at room temperature for 16 hours, before being purified by preparative HPLC.

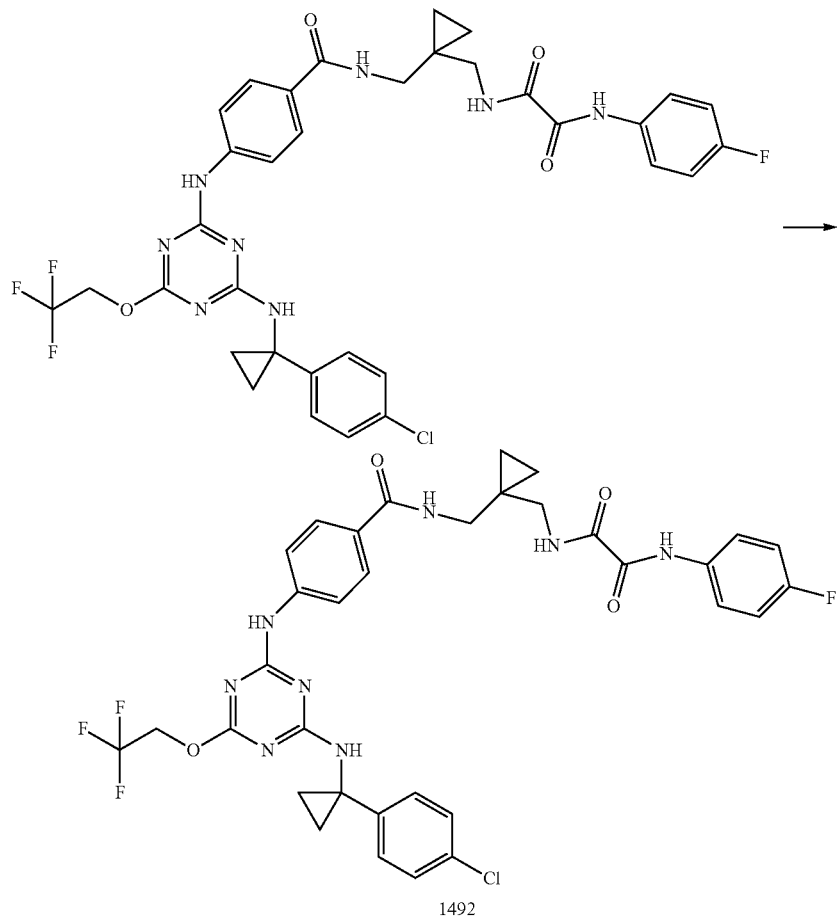

1492

| Compound 1492 | |
|---|---|
| MS (M + H)⁺ Calcd. | 727.3 |
| MS (M + H)⁺ Observ. | 727.2 |
| Retention Time | 2.09 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of 3388, N¹-(3-(4-((4-((1-(4-chlorophenyl)cyclopropyl)amino)-6-(2,2,2-trifluoroethoxy)-1,3,5-triazin-2-yl)amino)-2-fluorobenzamido)-2,2-dimethylpropyl)oxalamide

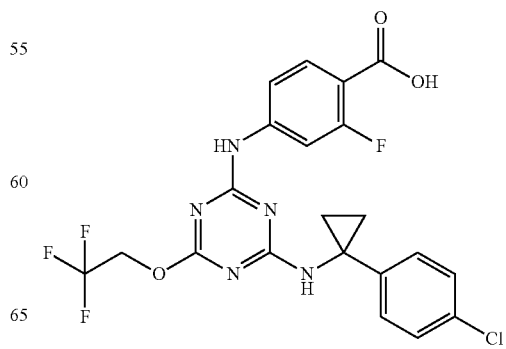

1605

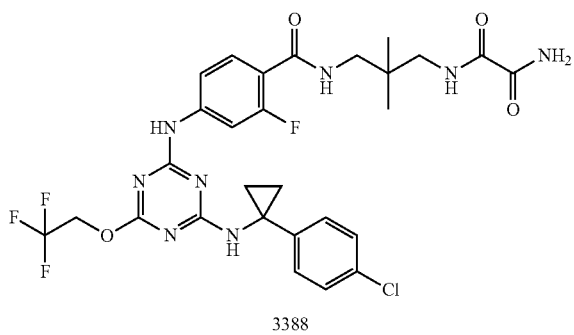

3388

To a solution of 4-((4-((1-(4-chlorophenyl)cyclopropyl)amino)-6-(2,2,2-trifluoroethoxy)-1,3,5-triazin-2-yl)amino)-2-fluorobenzoic acid (10 mg) and TBTU (7.74 mg) in DMF (1 mL) was added $N^1$-(3-amino-2,2-dimethylpropyl)oxalamide (4.18 mg) and DIPEA (0.018 mL). The mixture was stirred at room temperature for 2 hours. The product was isolated by using preparative HPLC system.

| Compound 3388 | |
|---|---|
| MS (M + H)⁺ Calcd. | 653.2 |
| MS (M + H)⁺ Observ. | 653.0 |
| Retention Time | 2.11 min |
| LC Condition | |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 2 min |

1606

| Compound 3388 | |
|---|---|
| Flow Rate | 1 mL/min |
| Wavelength | 220 |
| Solvent Pair | Water-Methanol-TFA |
| Column | PHENOMENEX-LUNA 2.0 × 30 mm 3 um |

The following selected examples were prepared by using the same synthetic route of synthesizing 3388, using the corresponding substituted alkyl 4-aminobenzoates rather than methyl 4-amino-2-fluorobenzoate or substituted benzamines rather than 1-(4-chlorophenyl)cyclopropanamine as starting materials:

| LC Condition A | |
|---|---|
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

| LC Condition B | |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex Luna C18, 50 × 2, 3 u |

| Compd. # | Structure | MS (M + H)⁺ Calcd. | MS (M + H)⁺ Obs. | HPLC Rt (min) | Method |
|---|---|---|---|---|---|
| 3386 | 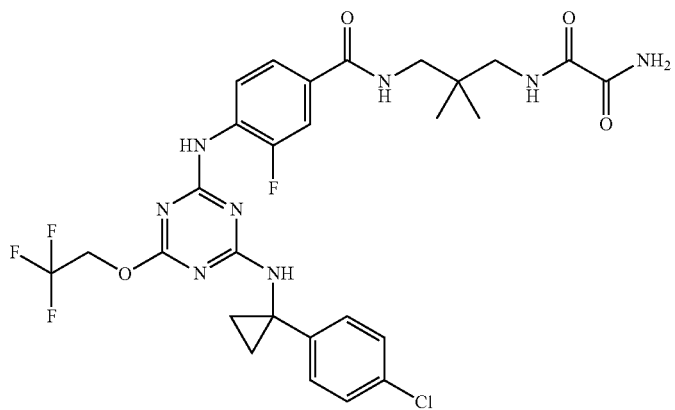 [SMILES: CC(C)(CNC(=O)C(N)=O)CNC(=O)c1ccc(Nc2nc(NC3(c4ccc(Cl)cc4)CC3)nc(OCC(F)(F)F)n2)c(F)c1] | 653.2 | 653.0 | 2.08 | A |

| Compd. # | Structure | MS (M + H)+ Calcd. | MS (M + H)+ Obs. | HPLC Rt (min) | Method |
|---|---|---|---|---|---|
| 3387 | 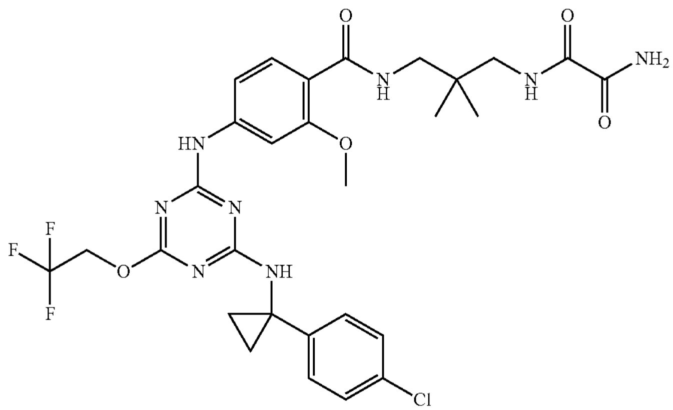 [SMILES: COc1cc(Nc2nc(NC3(c4ccc(Cl)cc4)CC3)nc(OCC(F)(F)F)n2)ccc1C(=O)NCC(C)(C)CNC(=O)C(N)=O] | 665.2 | 665.0 | 2.11 | A |
| 3389 | 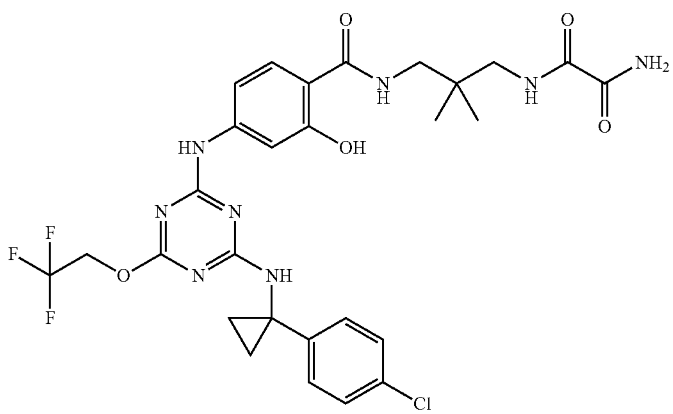 | 651.2 | 651.0 | 2.16 | A |
| 3477 | 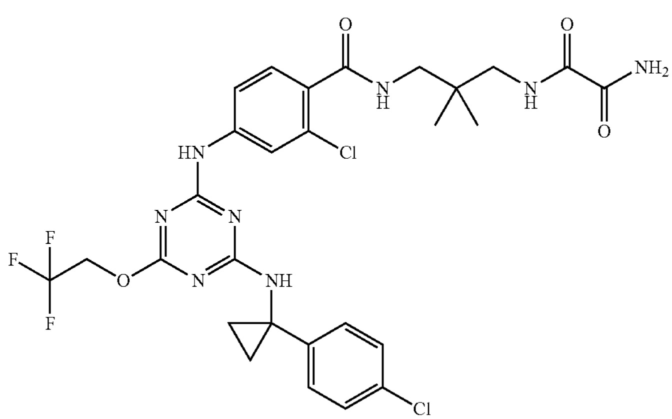 [SMILES: CC(C)(CNC(=O)C(N)=O)CNC(=O)c1ccc(Nc2nc(NC3(c4ccc(Cl)cc4)CC3)nc(OCC(F)(F)F)n2)cc1Cl] | 669.2 | 669.3 | 2.16 | A |

| Compd. # | Structure | MS (M + H)+ Calcd. | MS (M + H)+ Obs. | HPLC Rt (min) | Method |
|---|---|---|---|---|---|
| 3478 | 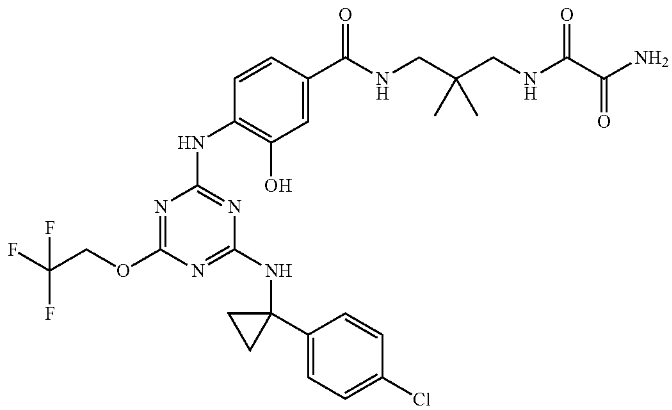 [SMILES: CC(C)(CNC(=O)C(N)=O)CNC(=O)c1ccc(Nc2nc(NC3(c4ccc(Cl)cc4)CC3)nc(OCC(F)(F)F)n2)c(O)c1] | 651.2 | 651.3 | 2.07 | A |
| 3511 | 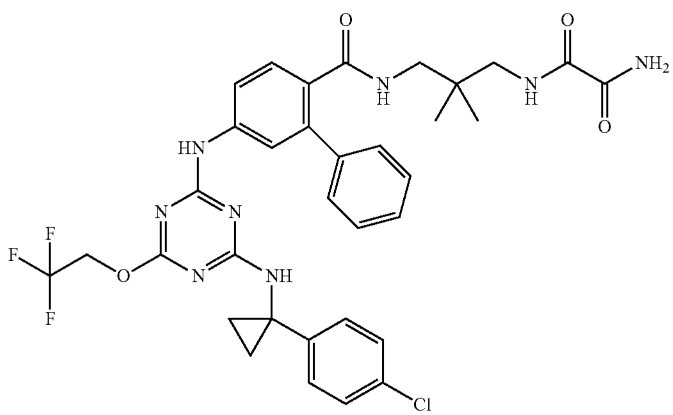 [SMILES: CC(C)(CNC(=O)C(N)=O)CNC(=O)c1ccc(Nc2nc(NC3(c4ccc(Cl)cc4)CC3)nc(OCC(F)(F)F)n2)cc1-c1ccccc1] | 711.2 | 711.4 | 2.08 | A |
| 3519 | 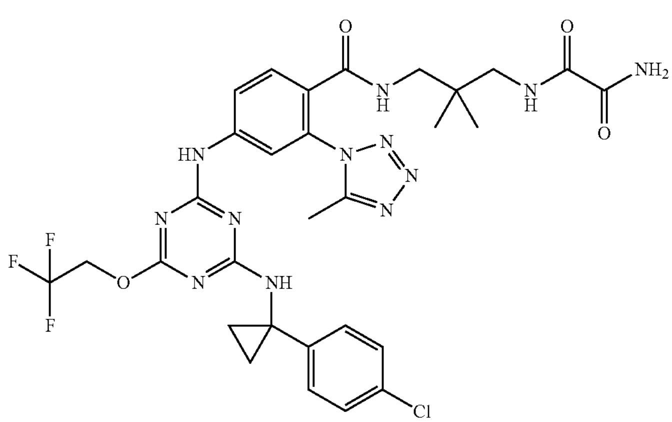 [SMILES: Cc1nnnn1-c1cc(Nc2nc(NC3(c4ccc(Cl)cc4)CC3)nc(OCC(F)(F)F)n2)ccc1C(=O)NCC(C)(C)CNC(=O)C(N)=O] | 717.2 | 717.4 | 1.88 | A |

| Compd. # | Structure | MS (M + H)+ Calcd. | MS (M + H)+ Obs. | HPLC Rt (min) | Method |
|---|---|---|---|---|---|
| 3812 | 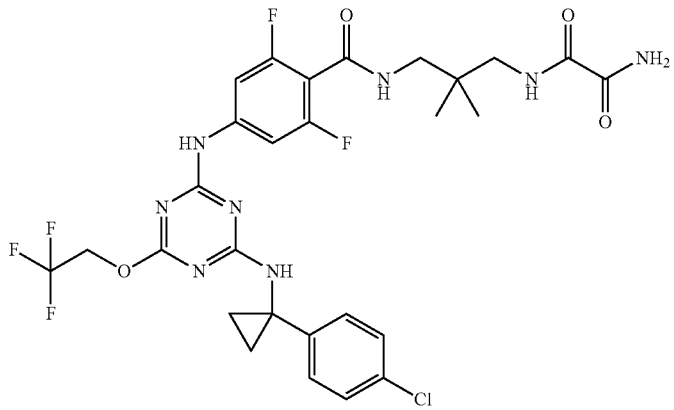 [SMILES: CC(C)(CNC(=O)C(N)=O)CNC(=O)c1c(F)cc(Nc2nc(NC3(c4ccc(Cl)cc4)CC3)nc(OCC(F)(F)F)n2)cc1F] | 671.2 | 671.2 | 3.25 | B |
| 3243 | 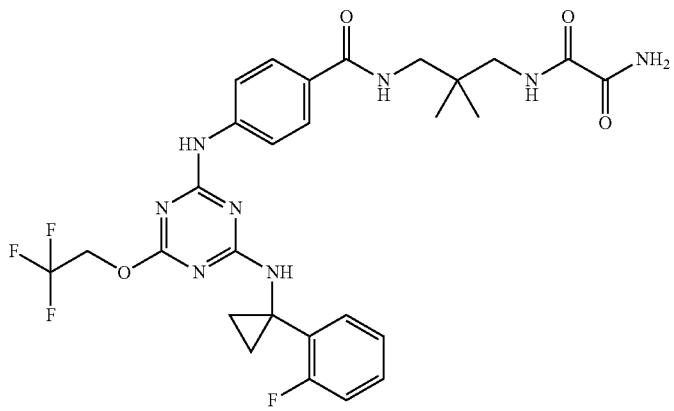 [SMILES: CC(C)(CNC(=O)C(N)=O)CNC(=O)c1ccc(Nc2nc(NC3(c4ccccc4F)CC3)nc(OCC(F)(F)F)n2)cc1] | 619.2 | 619.1 | 2.12 | A |
| 3244 | 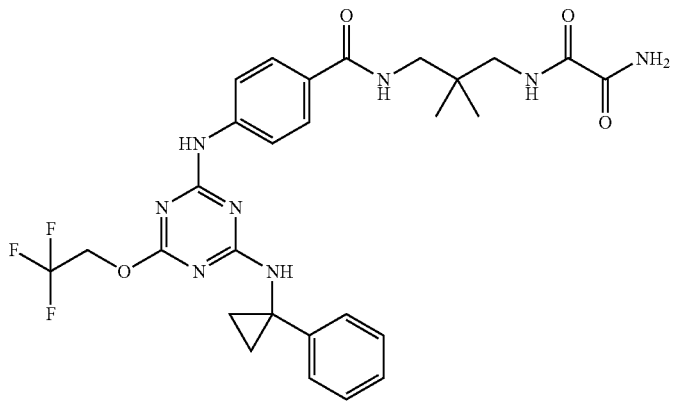 [SMILES: CC(C)(CNC(=O)C(N)=O)CNC(=O)c1ccc(Nc2nc(NC3(c4ccccc4)CC3)nc(OCC(F)(F)F)n2)cc1] | 601.2 | 601.2 | 2.06 | A |

-continued
| Compd. # | Structure | MS (M + H)+ Calcd. | MS (M + H)+ Obs. | HPLC Rt (min) | Method |
|---|---|---|---|---|---|
| 3247 | 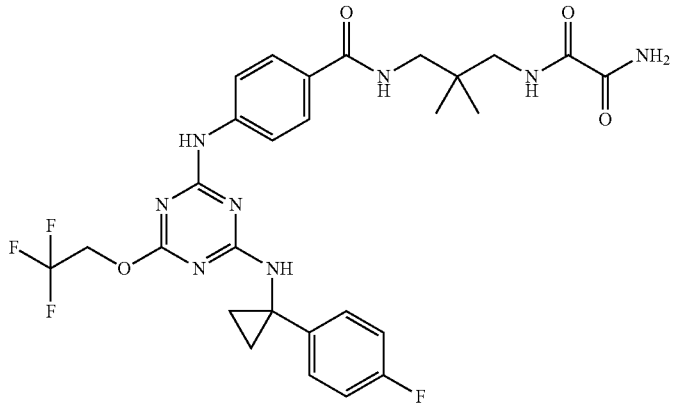 [SMILES: CC(C)(CNC(=O)C(N)=O)CNC(=O)c1ccc(Nc2nc(NC3(c4ccc(F)cc4)CC3)nc(OCC(F)(F)F)n2)cc1] | 619.2 | 619.1 | 2.10 | A |
| 3265 | 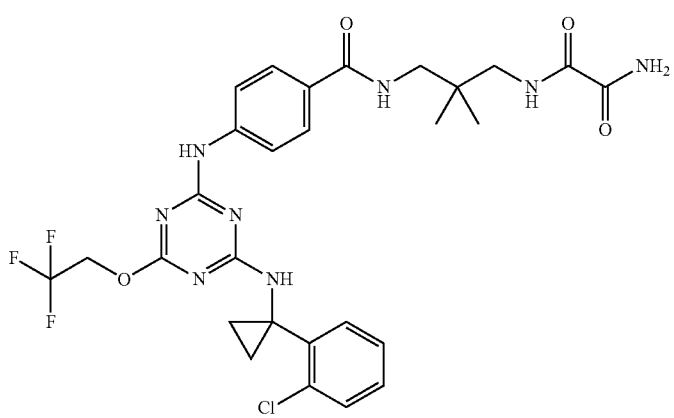 [SMILES: CC(C)(CNC(=O)C(N)=O)CNC(=O)c1ccc(Nc2nc(NC3(c4ccccc4Cl)CC3)nc(OCC(F)(F)F)n2)cc1] | 635.2 | 635.1 | 2.11 | A |
| 3333 | 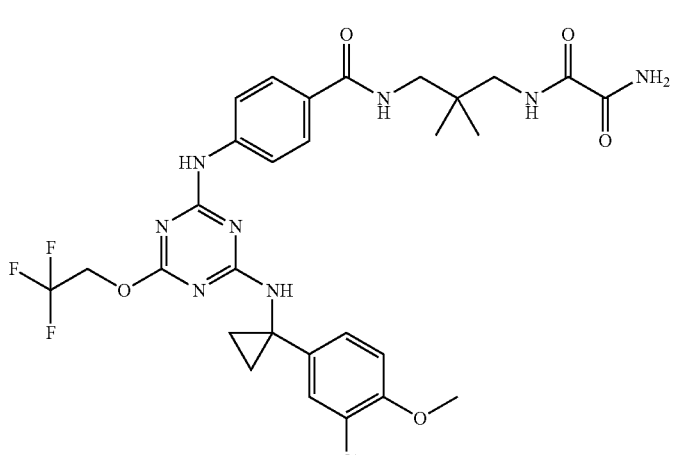 | 665.2 | 665.1 | 1.94 | A |

| Compd. # | Structure | MS (M + H)+ Calcd. | MS (M + H)+ Obs. | HPLC Rt (min) | Method |
|---|---|---|---|---|---|
| 3351 | 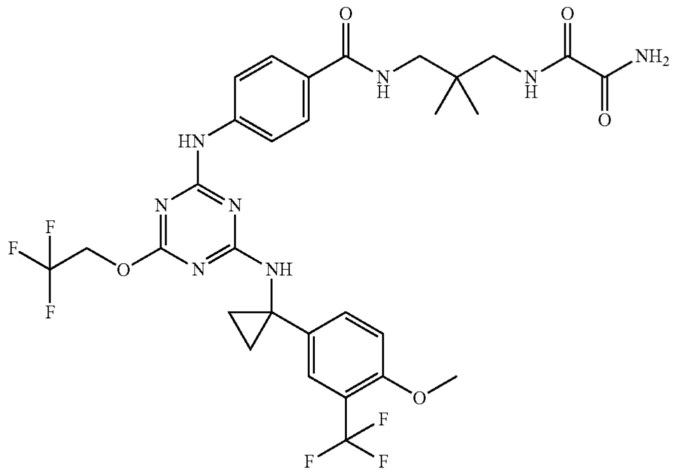 [SMILES: COc1ccc(C2(Nc3nc(Nc4ccc(C(=O)NCC(C)(C)CNC(=O)C(N)=O)cc4)nc(OCC(F)(F)F)n3)CC2)cc1C(F)(F)F] | 699.2 | 699.2 | 2.01 | A |
| 4001 | 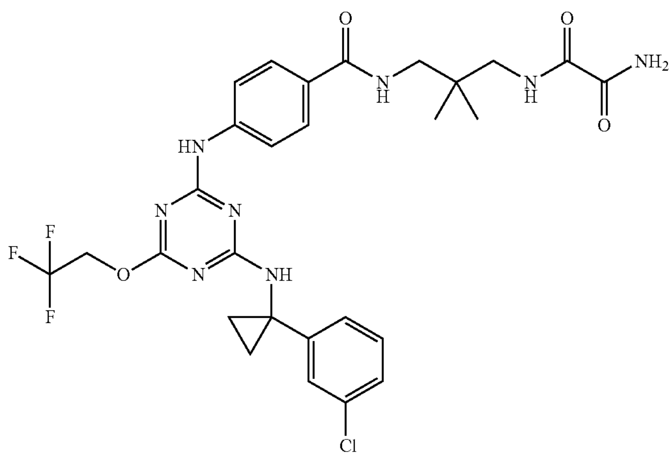 [SMILES: CC(C)(CNC(=O)C(N)=O)CNC(=O)c1ccc(Nc2nc(NC3(c4cccc(Cl)c4)CC3)nc(OCC(F)(F)F)n2)cc1] | 635.2 | 635.1 | 2.02 | A |

The following selected examples were prepared by using the same synthetic route of synthesizing 1032, using In-1006 rather than In-1005 as one of the starting materials, alone with the corresponding amines or their salts instead of cyclopropylmethanamine hydrochloride:

| LC Condition A | |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

| Compd. # | Structure | MS (M+H)+ Calcd. | MS (M+H)+ Obs. | HPLC Rt (min) | Method |
|---|---|---|---|---|---|
| 3512 | 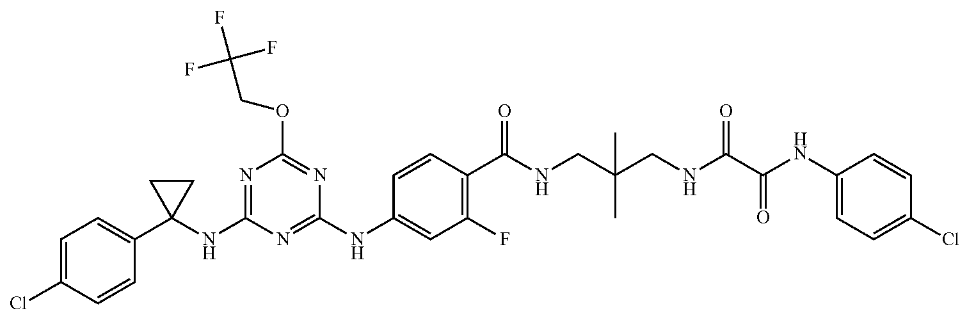 | 763.2 | 763.2 | 2.16 | A |
| 3513 | 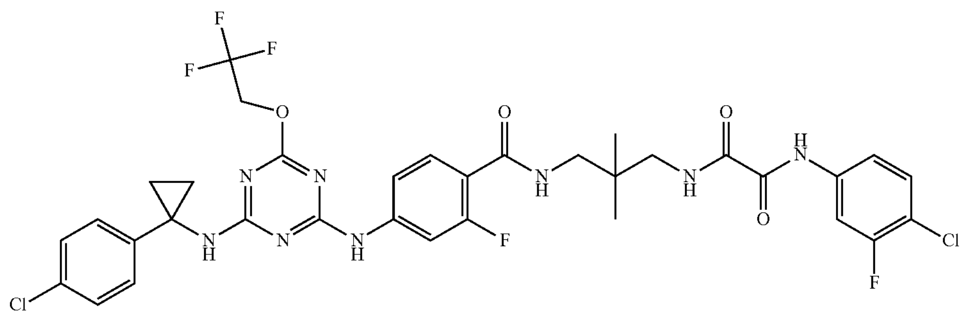 [SMILES: CC(C)(CNC(=O)C(=O)Nc1ccc(Cl)c(F)c1)CNC(=O)c1ccc(Nc2nc(NC3(c4ccc(Cl)cc4)CC3)nc(OCC(F)(F)F)n2)cc1F] | 781.2 | 781.1 | 2.19 | A |
| 3514 | 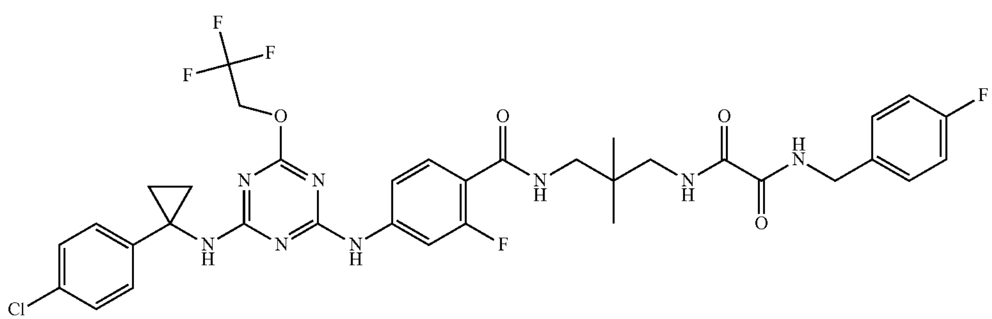 [SMILES: CC(C)(CNC(=O)C(=O)NCc1ccc(F)cc1)CNC(=O)c1ccc(Nc2nc(NC3(c4ccc(Cl)cc4)CC3)nc(OCC(F)(F)F)n2)cc1F] | 761.2 | 761.3 | 2.05 | A |

-continued

| Compd. # | Structure | MS (M + H)+ Calcd. | MS (M + H)+ Obs. | HPLC Rt (min) | Method |
|---|---|---|---|---|---|
| 3515 | 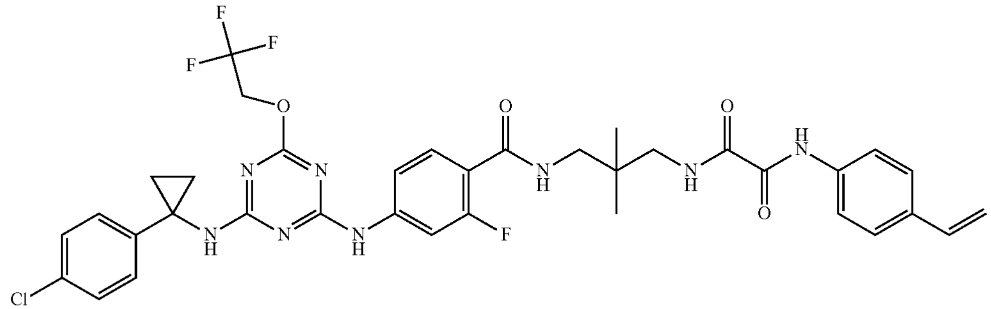 [SMILES: C=Cc1ccc(NC(=O)C(=O)NCC(C)(C)CNC(=O)c2ccc(Nc3nc(NC4(c5ccc(Cl)cc5)CC4)nc(OCC(F)(F)F)n3)cc2F)cc1] | 755.2 | 755.3 | 2.54 | A |
| 3516 | 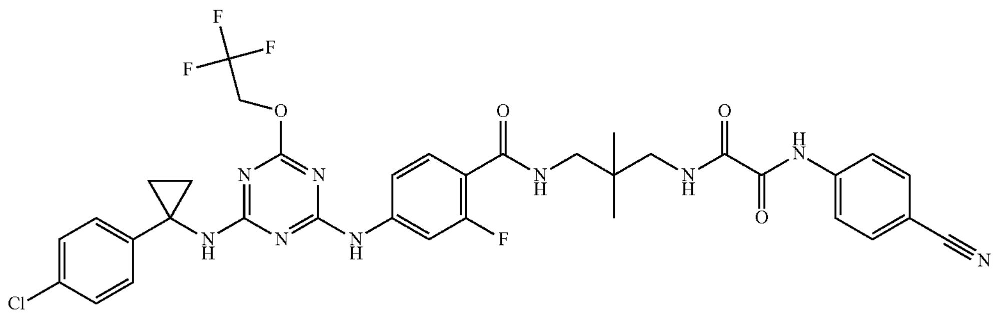 [SMILES: CC(C)(CNC(=O)C(=O)Nc1ccc(C#N)cc1)CNC(=O)c1ccc(Nc2nc(NC3(c4ccc(Cl)cc4)CC3)nc(OCC(F)(F)F)n2)cc1F] | 754.2 | 754.3 | 2.13 | A |
| 3553 | 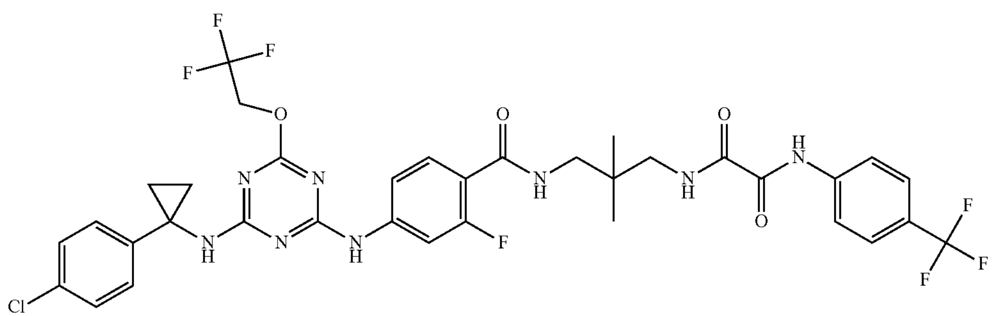 [SMILES: CC(C)(CNC(=O)C(=O)Nc1ccc(C(F)(F)F)cc1)CNC(=O)c1ccc(Nc2nc(NC3(c4ccc(Cl)cc4)CC3)nc(OCC(F)(F)F)n2)cc1F] | 797.2 | 797.3 | 2.23 | A |

| Compd. # | Structure | MS (M + H)+ Calcd. | MS (M + H)+ Obs. | HPLC Rt (min) | Method |
|---|---|---|---|---|---|
| 3554 | 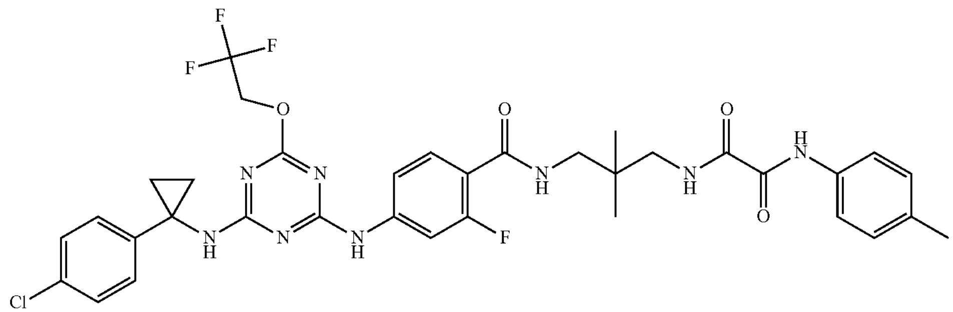 [SMILES: Cc1ccc(NC(=O)C(=O)NCC(C)(C)CNC(=O)c2ccc(Nc3nc(NC4(c5ccc(Cl)cc5)CC4)nc(OCC(F)(F)F)n3)cc2F)cc1] | 743.2 | 743.3 | 2.18 | A |
| 3555 | 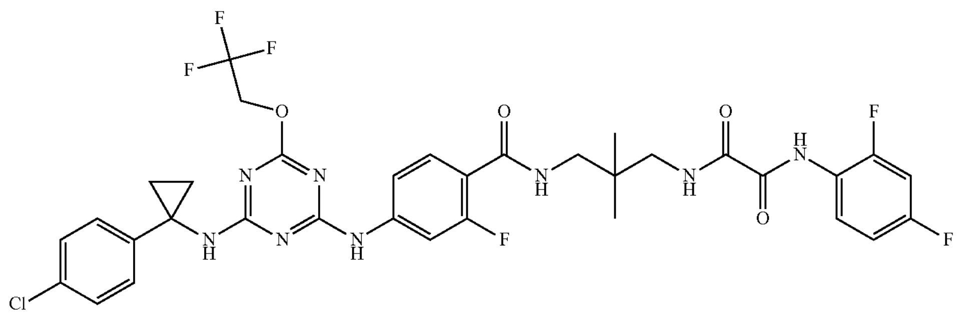 [SMILES: CC(C)(CNC(=O)C(=O)Nc1ccc(F)cc1F)CNC(=O)c1ccc(Nc2nc(NC3(c4ccc(Cl)cc4)CC3)nc(OCC(F)(F)F)n2)cc1F] | 765.2 | 765.2 | 2.23 | A |
| 3556 | 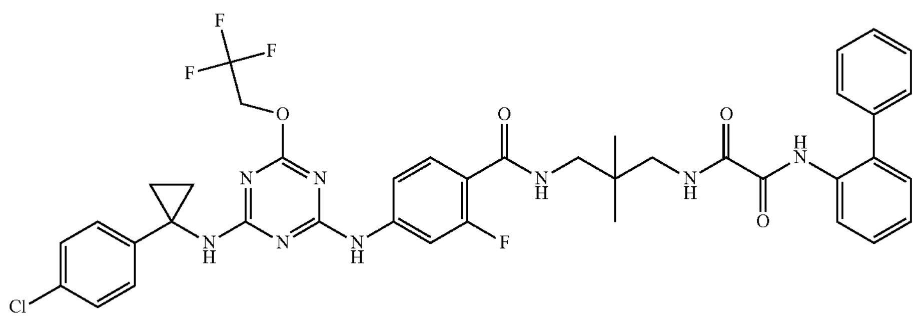 [SMILES: CC(C)(CNC(=O)C(=O)Nc1ccccc1-c1ccccc1)CNC(=O)c1ccc(Nc2nc(NC3(c4ccc(Cl)cc4)CC3)nc(OCC(F)(F)F)n2)cc1F] | 805.3 | 805.3 | 2.28 | A |

| Compd. # | Structure | MS (M + H)⁺ Calcd. | MS (M + H)⁺ Obs. | HPLC Rt (min) | Method |
|---|---|---|---|---|---|
| 3557 | 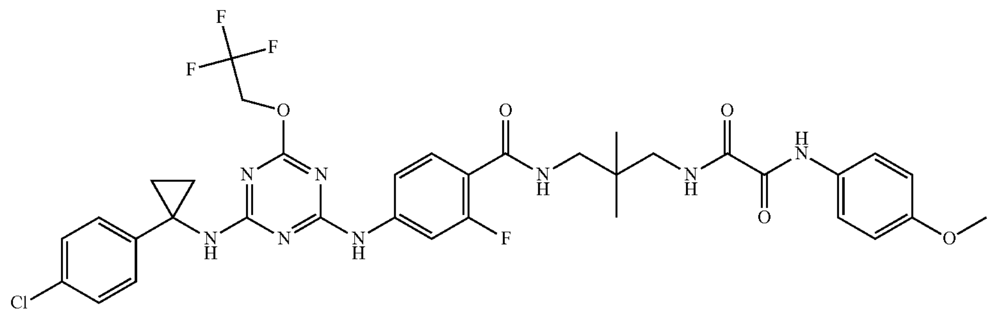 [SMILES: COc1ccc(NC(=O)C(=O)NCC(C)(C)CNC(=O)c2ccc(Nc3nc(NC4(c5ccc(Cl)cc5)CC4)nc(OCC(F)(F)F)n3)cc2F)cc1] | 759.2 | 759.3 | 2.06 | A |
| 3559 | 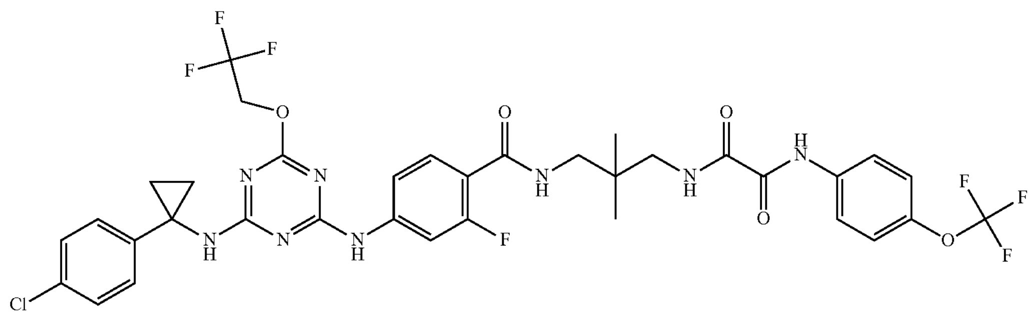 [SMILES: CC(C)(CNC(=O)C(=O)Nc1ccc(OC(F)(F)F)cc1)CNC(=O)c1ccc(Nc2nc(NC3(c4ccc(Cl)cc4)CC3)nc(OCC(F)(F)F)n2)cc1F] | 813.2 | 813.2 | 2.24 | A |
| 3560 | 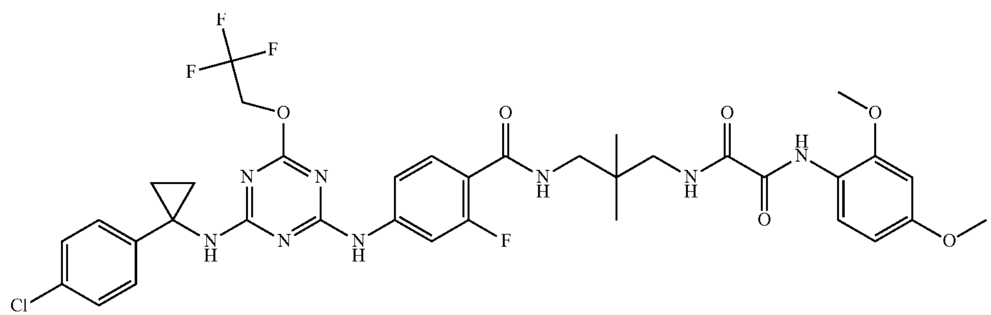 [SMILES: COc1ccc(NC(=O)C(=O)NCC(C)(C)CNC(=O)c2ccc(Nc3nc(NC4(c5ccc(Cl)cc5)CC4)nc(OCC(F)(F)F)n3)cc2F)c(OC)c1] | 789.3 | 789.3 | 2.12 | A |

-continued

| Compd. # | Structure | MS (M + H)+ Calcd. | MS (M + H)+ Obs. | HPLC Rt (min) | Method |
|---|---|---|---|---|---|
| 3561 | 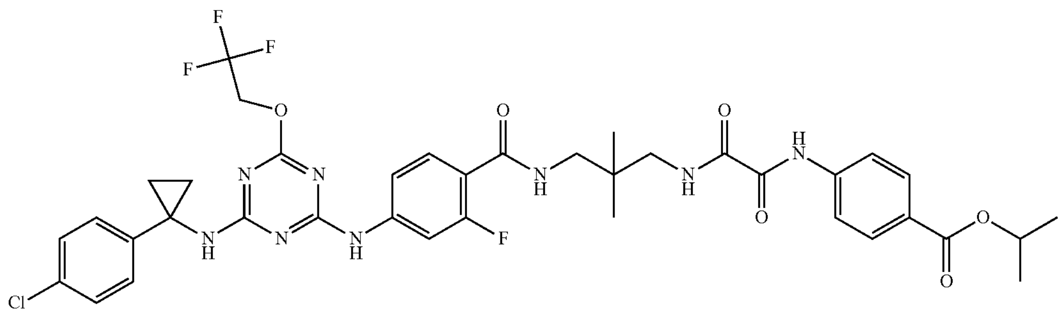 [SMILES: CC(C)OC(=O)c1ccc(NC(=O)C(=O)NCC(C)(C)CNC(=O)c2ccc(Nc3nc(NC4(c5ccc(Cl)cc5)CC4)nc(OCC(F)(F)F)n3)cc2F)cc1] | 891.3 | 891.3 | 2.35 | A |
| 3562 | 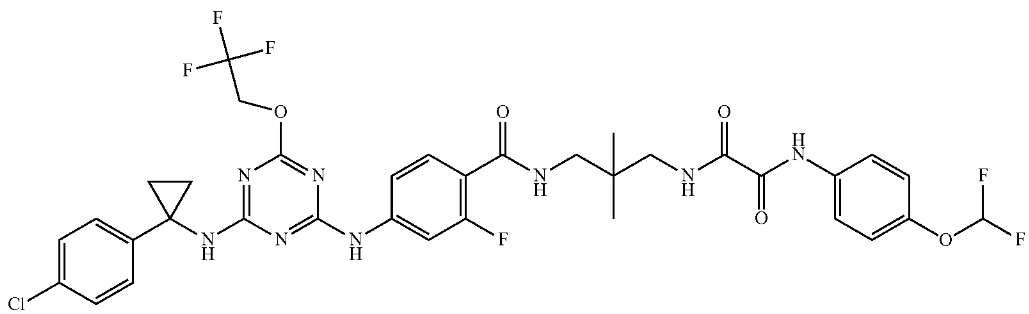 [SMILES: CC(C)(CNC(=O)C(=O)Nc1ccc(OC(F)F)cc1)CNC(=O)c1ccc(Nc2nc(NC3(c4ccc(Cl)cc4)CC3)nc(OCC(F)(F)F)n2)cc1F] | 795.2 | 795.3 | 2.08 | A |
| 3563 | 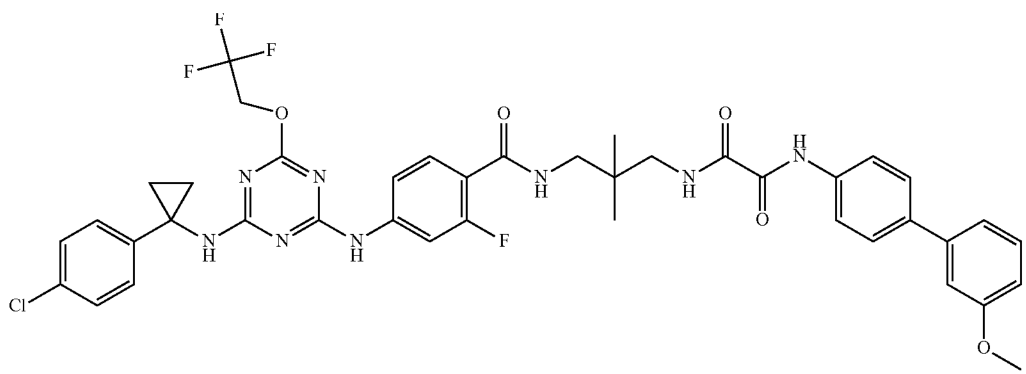 [SMILES: COc1cccc(-c2ccc(NC(=O)C(=O)NCC(C)(C)CNC(=O)c3ccc(Nc4nc(NC5(c6ccc(Cl)cc6)CC5)nc(OCC(F)(F)F)n4)cc3F)cc2)c1] | 835.3 | 835.2 | 2.21 | A |

| Compd. # | Structure | MS (M+H)+ Calcd. | MS (M+H)+ Obs. | HPLC Rt (min) | Method |
|---|---|---|---|---|---|
| 3564 | 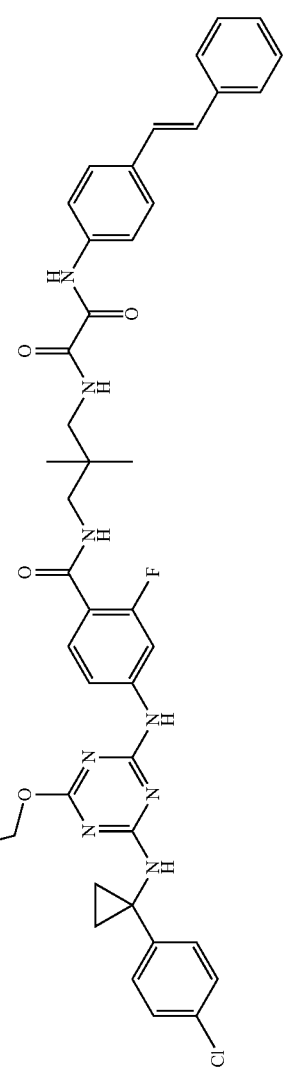 | 831.3 | 831.3 | 2.31 | A |
| 3565 | 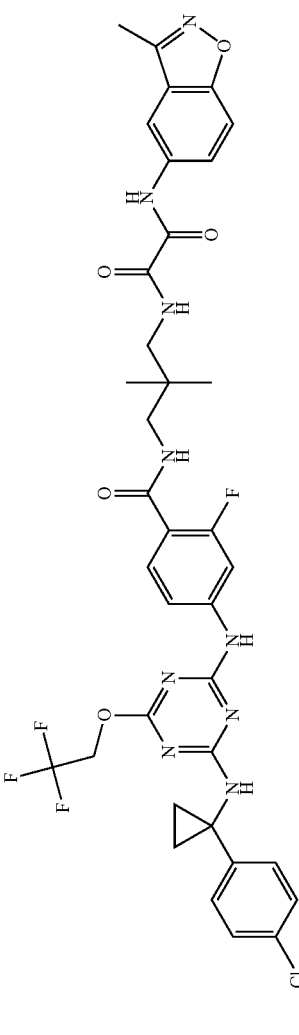 | 784.2 | 784.3 | 1.97 | A |
| 3566 | 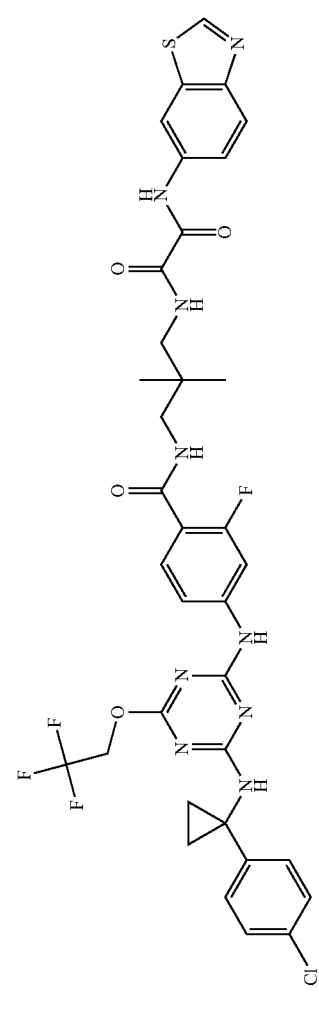 | 786.2 | 786.2 | 2.00 | A |

| Compd. # | Structure | MS (M + H)+ Calcd. | MS (M + H)+ Obs. | HPLC Rt (min) | Method |
|---|---|---|---|---|---|
| 3567 | 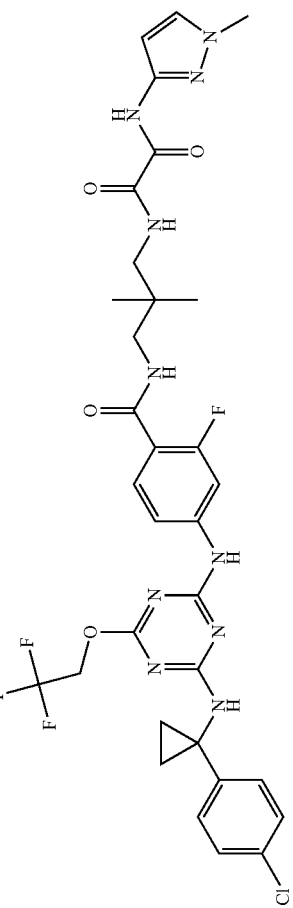 | 733.2 | 733.2 | 1.87 | A |
| 3568 | 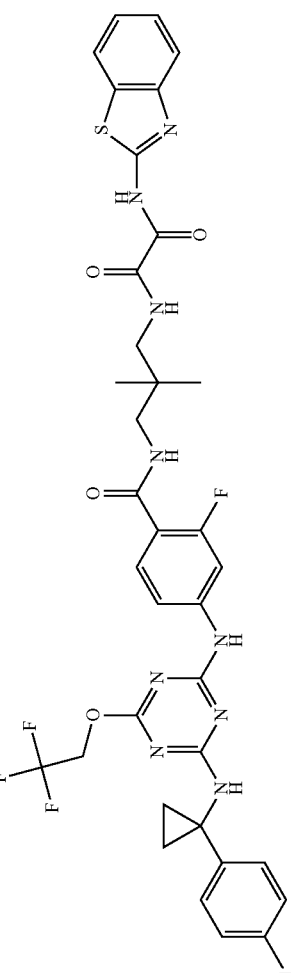 | 786.2 | 786.2 | 2.09 | A |
| 3664 | 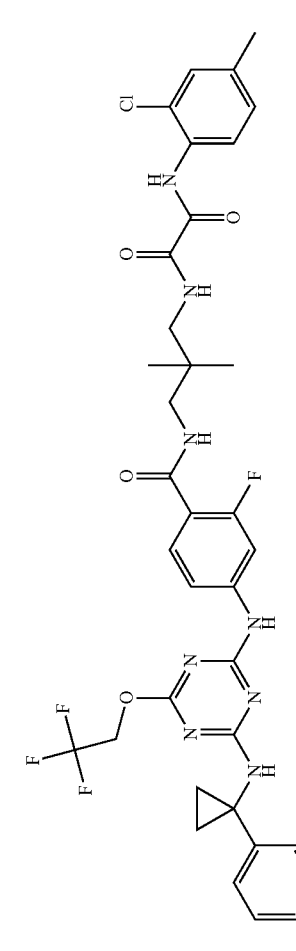 | 777.2 | 777.1 | 2.26 | A |

| Compd. # | Structure | MS (M + H)+ Calcd. | MS (M + H)+ Obs. | HPLC Rt (min) | Method |
|---|---|---|---|---|---|
| 3676 | 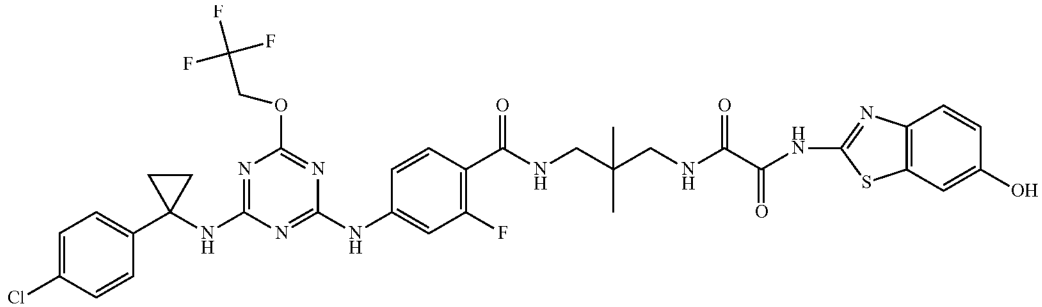 [SMILES: CC(C)(CNC(=O)C(=O)Nc1nc2ccc(O)cc2s1)CNC(=O)c1ccc(Nc2nc(NC3(c4ccc(Cl)cc4)CC3)nc(OCC(F)(F)F)n2)cc1F] | 802.2 | 802.3 | 1.87 | A |
| 3677 | 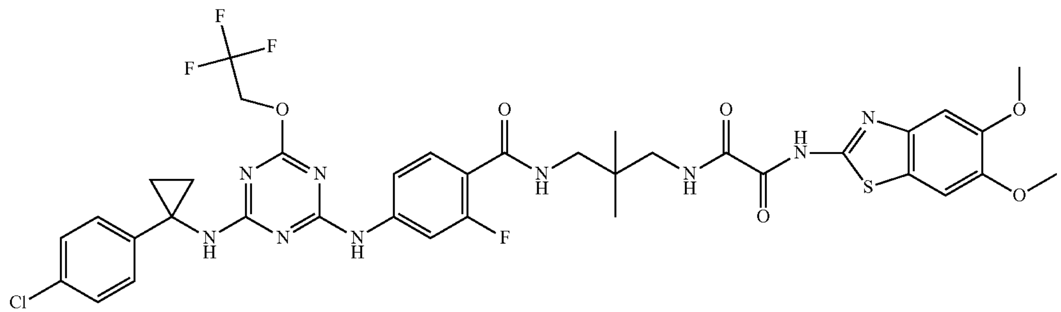 [SMILES: COc1cc2nc(NC(=O)C(=O)NCC(C)(C)CNC(=O)c3ccc(Nc4nc(NC5(c6ccc(Cl)cc6)CC5)nc(OCC(F)(F)F)n4)cc3F)sc2cc1OC] | 846.2 | 846.2 | 2.13 | A |
| 3678 | 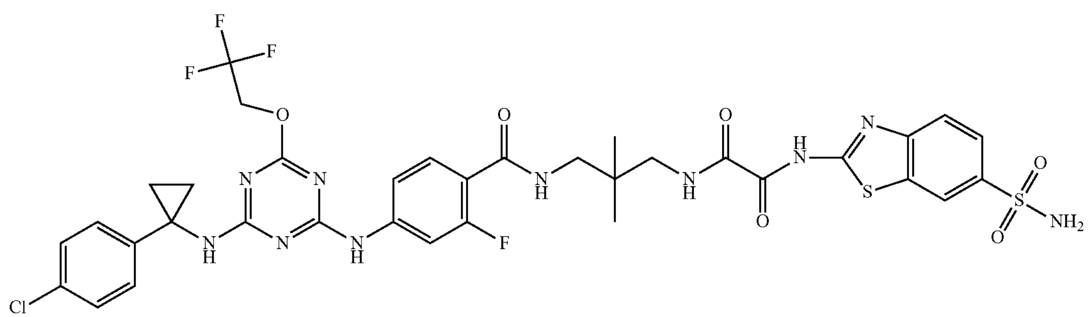 [SMILES: CC(C)(CNC(=O)C(=O)Nc1nc2ccc(S(N)(=O)=O)cc2s1)CNC(=O)c1ccc(Nc2nc(NC3(c4ccc(Cl)cc4)CC3)nc(OCC(F)(F)F)n2)cc1F] | 865.2 | 865.1 | 2.10 | A |

| Compd. # | Structure | MS (M + H)+ Calcd. | MS (M + H)+ Obs. | HPLC Rt (min) | Method |
|---|---|---|---|---|---|
| 3680 | 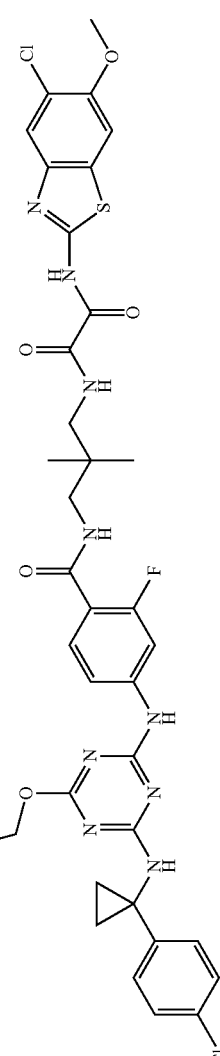 | 850.2 | 850.1 | 2.16 | A |
| 3681 | 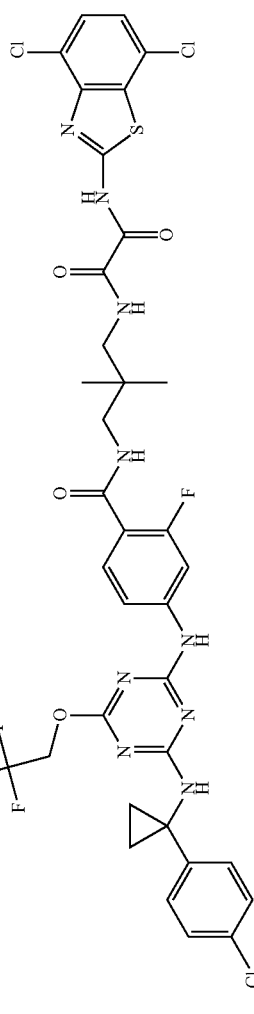 | 854.2 | 854.1 | 2.29 | A |
| 3814 | 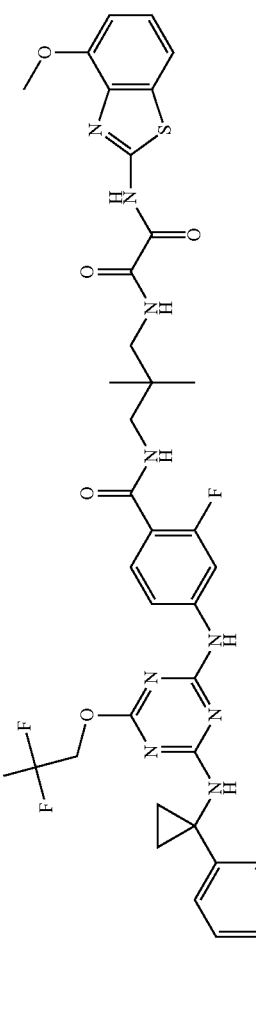 | 816.2 | 816.2 | 2.08 | A |

General Procedure for Parallel Synthesis of Oxalamides

Method 1 and Method 2

Method 1:

A 0.08 M stock solution of the (S)-methyl 2-(4-((4-((1-(4-chlorophenyl)cyclopropyl)amino)-6-(2,2,2-trifluoroethoxy)-1,3,5-triazin-2-yl)amino)benzamido)-4-(2-ethoxy-2-oxoacetamido)butanoate in DMF was prepared and DIPEA (5.0 eq) was charged in. To each of the amines (15 eq) weighed into 16×100 mm threaded vials was added 1000 μLs of the (S)-methyl 2-(4-((4-((1-(4-chlorophenyl)cyclopropyl)amino)-6-(2,2,2-trifluoroethoxy)-1,3,5-triazin-2-yl)amino)benzamido)-3-(2-ethoxy-2-oxoacetamido)propanoate/DIPEA solution. The reactions were agitated at 350 rpm on an Innova platform shaker at room temperature for 48 hours. Mixtures were transferred to a 96 well filter plate collecting into a 96 well deep-well plate. Each reaction vial was rinsed with 500 μLs of DMF and rinses were transferred to the appropriate wells of the filter plate. The desired products were isolated by preparative HPLC.

Method 2:

A 0.08 M stock solution of the (S)-methyl 2-(4-((4-((1-(4-chlorophenyl)cyclopropyl)amino)-6-(2,2,2-trifluoroethoxy)-1,3,5-triazin-2-yl)amino)benzamido)-4-(2-ethoxy-2-oxoacetamido)butanoate in NMP was prepared and DIPEA (5.0 eq) was charged in. To each of the amines (15 eq) weighed into 16×100 mm threaded vials was added 1000 μLs of the (S)-methyl 2-(4-((4-((1-(4-chlorophenyl)cyclopropyl)amino)-6-(2,2,2-trifluoroethoxy)-1,3,5-triazin-2-yl)amino)benzamido)-3-(2-ethoxy-2-oxoacetamido)propanoate/DIPEA solution. The reactions were agitated at 350 rpm on an Innova platform shaker at room temperature for 48 hours. Samples were blown down using a Zymark tabletop dryer at 30° C. for 3 hours. A 1.8M solution of potassium carbonate in water was prepared. To each of the reaction vials was added 0.5 mL of acetone followed by 0.5 mls of the potassium carbonate solution. Vials were capped and agitated at 350 rpm on an Innova platform shaker at room temperature for 72 hours. Samples were blown down using a Zymark tabletop dryer at 30° C. for 3 hours before redissolving in 1 mL DMF each. Mixtures were transferred to a 96 well filter plate collecting into a 96 well deep-well plate. Reaction vials were rinsed with 500 μLs of DMF each and rinses were transferred to the appropriate wells of the filter plate. The desired products were isolated by preparative HPLC.

Analytical Methods

A:

Column. Supelco Ascentis Express C18, 4.6×50 mm, 2.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.;

Gradient: 0-100% B over 8 minutes, then a 1-minute hold at 100% B, then 100-0% B over 1 minute; Flow: 1 mL/min.

B:

Column: Waters Sunfire C18, 4.6×100 mm, 3.5-μm particles; Mobile Phase A: water with 0.1% TFA; Mobile Phase B: acetonitrile:water with 0.1% TFA;

Temperature: 40° C.; Gradient: 10-95% B over 6 minutes, then a 2-minute hold at 95% B, then 95-10% B over 0.50 minutes, then a 1.5 minute hold at 10% B; Flow: 1.2 mL/min.

C:

Column. Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B;

Flow: 1 mL/min.

D:

Column. Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0-100% B over 4 minutes, then a 1-minute hold at 100% B; Flow: 0.83 mL/min.

E:

Column. Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0-100% B over 4 minutes, then a 1-minute hold at 100% B; Flow: 1 mL/min.

F:

Column. Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B;

Flow: 0.5 mL/min.

General Procedure for Parallel Synthesis of Oxalamides

Method 3

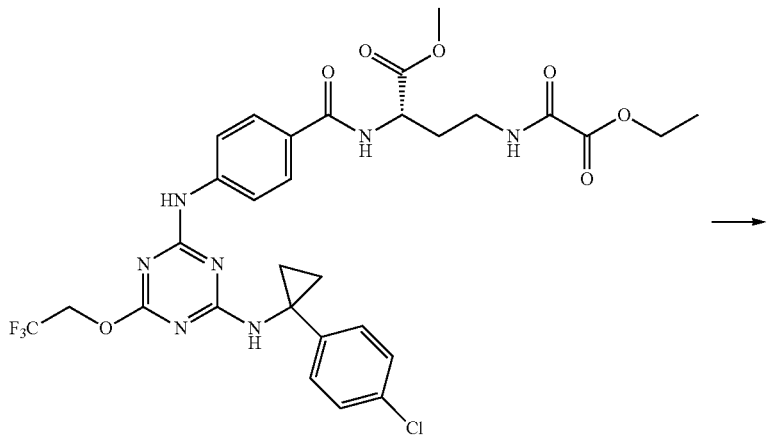

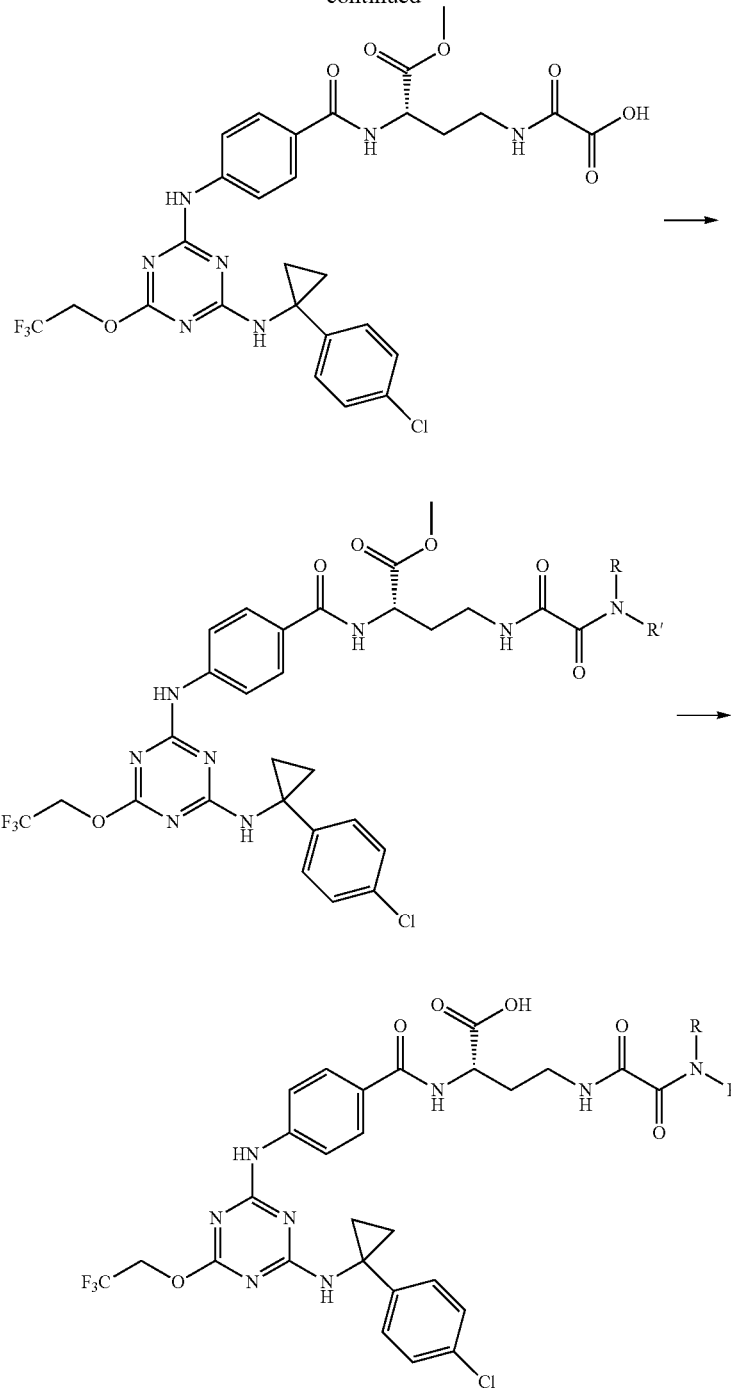

Step 1: To a solution of (S)-methyl 2-(4-(4-(1-(4-chlorophenyl)cyclopropylamino)-6-(2,2,2-trifluoroethoxy)-1,3,5-triazin-2-ylamino)benzamido)-4-(2-ethoxy-2-oxoacetamido)butanoate (1.0 g) in methanol (10 mL) was added Et$_3$N (10.0 mL) at room temperature. The reaction mixture was heated to 55° C. for 24 hours. The solvent was concentrated in vacuo. The reaction mixture was diluted with water and acidified with 1.5; N HCl. The aqueous layer was extracted with ethylacetate (3×100 mL). The combined organic layer was dried over anhydrous Na$_2$SO$_4$, filtered and concentrated in vacuo to afford desired crude acid as white solid (850 mg).

Step 2: To a solution of (S)-2-(3-(4-(4-(1-(4-chlorophenyl)cyclopropylamino)-6-(2,2,2-trifluoroethoxy)-1,3,5-triazin-2-ylamino)benzamido)-4-methoxy-4-oxobutylamino)-2-oxoacetic acid (20 mg) in DMF (1.0 mL) were added HCTU (17.91 mg) and DIPEA (16 µL) at rt and stirred for 15 minutes. Amine (1.2 eq.) was added to above solution and stirred at room temperature for 2 hour. Initial LCMS analysis showed formation of desired product. The solvent was evaporated and crude mixture was purified using preparative HPLC to afford desired product.

Step 3: To a solution of crude amide from step 2 in MeOH: H$_2$O (5:1, 1.0 mL) was added K$_2$CO$_3$ (8.3 mg) and stirred for 24 hours at room temperature. The crude mixture was purified using preparative HPLC to afford desired product.

General Procedure for Parallel Synthesis of Oxalamides

Method 4

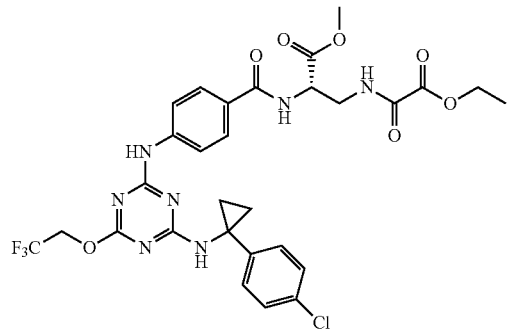

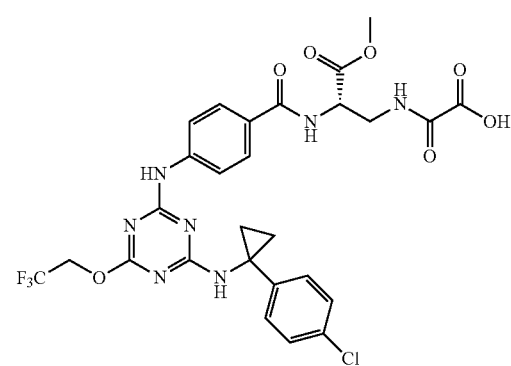

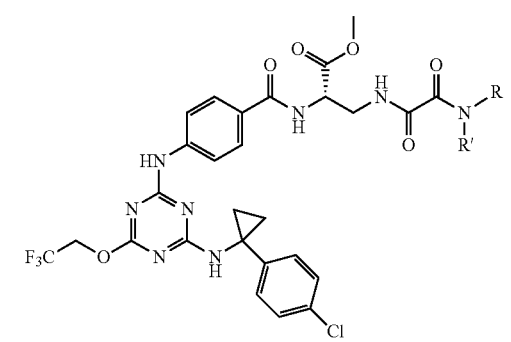

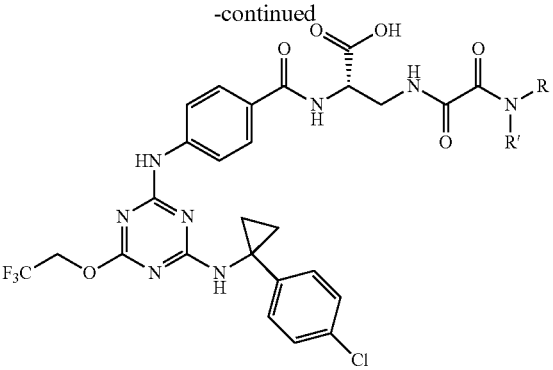

Step 1: To a solution of (S)-methyl 2-(4-(4-(1-(4-chlorophenyl)cyclopropylamino)-6-(2,2,2-trifluoroethoxy)-1,3,5-triazin-2-ylamino)benzamido)-3-(2-ethoxy-2-oxoacetamido)propanoate (1.5 g) in methanol (15 mL) was added Et₃N (15.0 mL) at room temperature. The reaction mixture was heated to 55° C. for 24 hours. The solvent was concentrated in vacuo. The reaction mixture was diluted with water and acidified with 1.5N HCl. The aqueous layer was extracted with ethylacetate (3×100 mL). The combined organic layer was dried over anhydrous Na₂SO₄, filtered and concentrated in vacuo to afford desired crude acid as white solid (1.35 g).

Step 2: To a solution of (S)-2-(2-(4-(4-(1-(4-chlorophenyl)cyclopropylamino)-6-(2,2,2-trifluoroethoxy)-1,3,5-triazin-2-ylamino)benzamido)-3-methoxy-3-oxopropylamino)-2-oxoacetic acid (20 mg) in DMF (1.0 mL) were added HCTU (17.91 mg) and DIPEA (16 μL) at room temperature and stirred for 15 minutes. Amine (1.2 eq.) was added to above solution and stirred at room temperature for 2 hours. Initial LCMS analysis showed formation of desired product. The solvent was evaporated and crude mixture was purified using preparative HPLC to afford desired product.

Step 3: To a solution of crude amide from step 2 in MeOH:H₂O (5:1, 1.0 mL) was added K₂CO₃ (8.3 mg) and stirred for 24 hours at room temperature. The crude mixture was purified using preparative HPLC to afford desired product.

Preparation of Compound 2001, 4-(4-(1-(4-chlorophenyl)cyclopropylamino)-6-(2,2,2-trifluoroethoxy)-1,3,5-triazin-2-ylamino)-N-(2,2-dimethyl-3-(2-oxo-2-(pyrrolidin-1-yl)acetamido)propyl)-3-fluorobenzamide

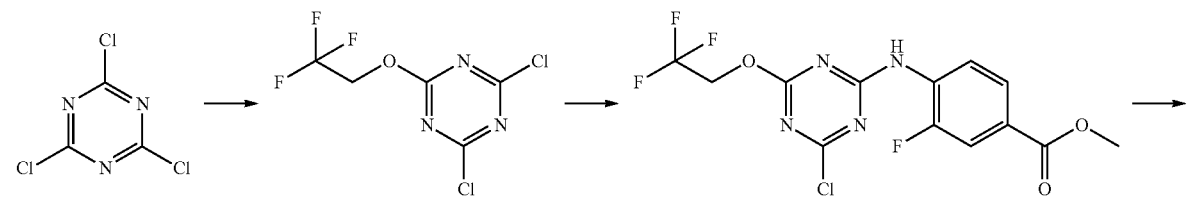

1641                                                    1642
-continued
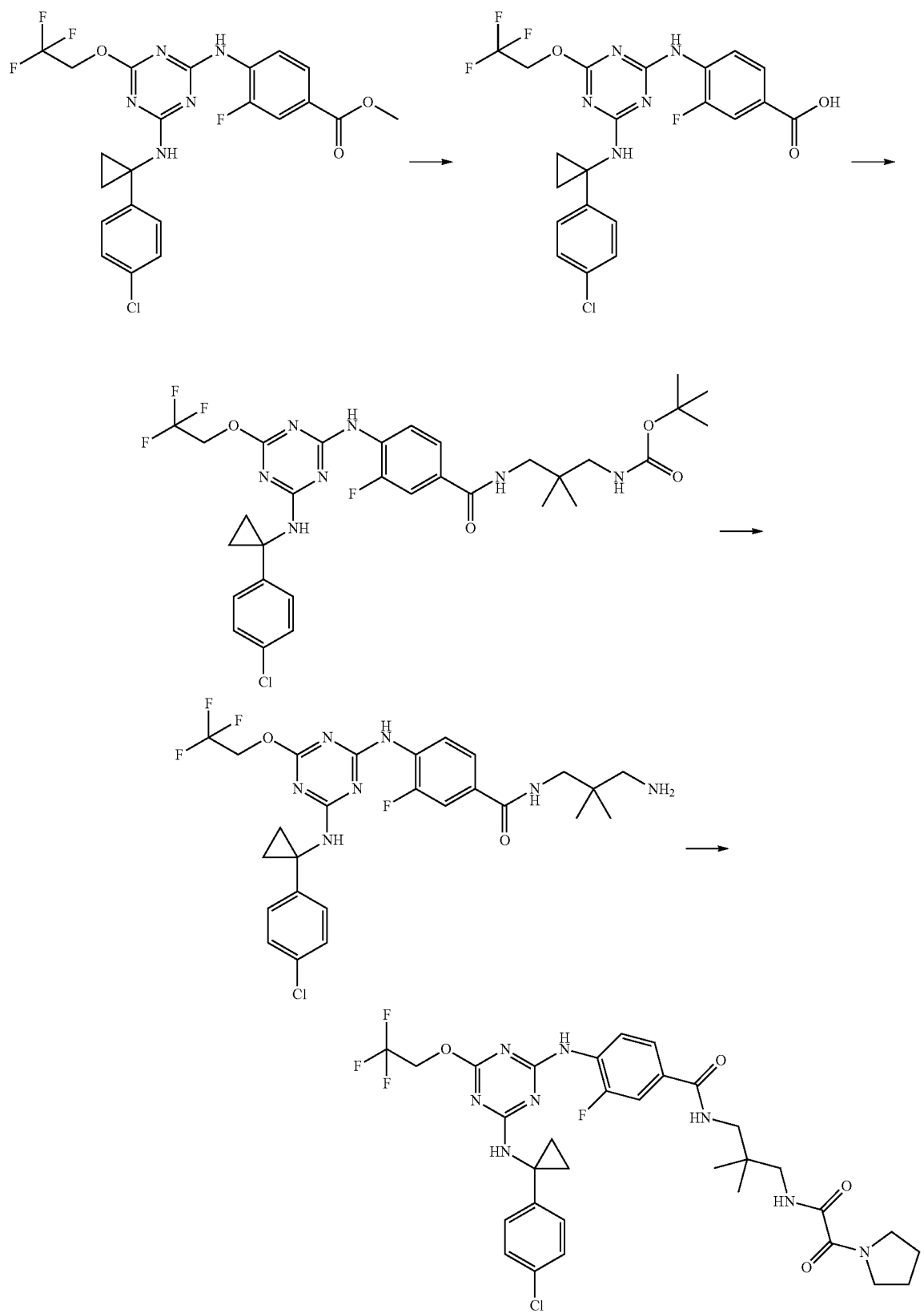

Step 1:
To a solution of 2,4,6-trichloro-1,3,5-triazine (15 g) in THF (300 mL) was added 2,2,2-trifluoroethanol (8.14 g) and Hunig'sBase (15.63 mL). The resulting mixture was stirred for 16 hours. After removal of most THF and precipitate through a plug washing with THF, the filtrate was concentrate to give a crude that will be used as it is.

Step 2:
To a solution of the product in Step 1 above (1.47 g, 5.91 mmol) in THF (10 mL) was added methyl 4-amino-3-fluorobenzoate (1 g, 5.91 mmol) and Hunig'sBase (3.10 mL, 17.74 mmol). The resulting mixture was stirred for 16 h. The precipitate was filtered and washed with THF and water and dried to give 1.5 g of methyl 4-(4-chloro-6-(2,2,2-trifluoroethoxy)-1,3,5-triazin-2-ylamino)-3-fluorobenzoate as a solid.

| methyl 4-(4-chloro-6-(2,2,2-trifluoroethoxy)-1,3,5-triazin-2-ylamino)-3-fluorobenzoate | |
|---|---|
| MS (M + H)$^+$ Calcd. | 381.7 |
| MS (M + H)$^+$ Observ. | 381.0 |
| Retention Time | 1.0 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 uM |

Step 3:
To a solution of methyl 4-(4-chloro-6-(2,2,2-trifluoroethoxy)-1,3,5-triazin-2-ylamino)-3-fluorobenzoate (0.93 g, 2.45 mmol) in THF (10 mL) was added 1-(4-chlorophenyl)cyclopropanamine (0.5 g, 2.45 mmol) and Hunig's Base (1.71 mL, 9.8 mmol). The resulting mixture was refluxed at 80° C. for 16 hs. The precipitate was filtrated through a plug washing with THF to give a crude product that was purified by Biotage eluting with 4/1 to 3/2 hexane/ethyl acetate to give 1.2 g of methyl 4-(4-(1-(4-chlorophenyl)cyclopropylamino)-6-(2,2,2-trifluoro ethoxy)-1,3,5-triazin-2-ylamino)-3-fluorobenzoate as product.

| methyl 4-(4-(1-(4-chlorophenyl)cyclopropylamino)-6-(2,2,2-trifluoroethoxy)-1,3,5-triazin-2-ylamino)-3-fluorobenzoate | |
|---|---|
| MS (M + H)$^+$ Calcd. | 512.9 |
| MS (M + H)$^+$ Observ. | 512.1 |
| Retention Time | 1.10 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 uM |

Step 4:
To a solution of methyl 4-(4-(1-(4-chlorophenyl)cyclopropylamino)-6-(2,2,2-trifluoroethoxy)-1,3,5-triazin-2-ylamino)-3-fluorobenzoate (1.2 g, 2.34 mmol) in THF/water (1:1, 10 mL) was added LiOH (0.6 g, 25.0 mmol). The reaction mixture was refluxed at 80° C. for 7 hours. After cooling to room temperature, the reaction solution was acidified with 1N HCl. The product was extracted by EtOAc. The organic layer was washed with brine, dried over Na$_2$SO$_4$ and concentrated under vacuum. The crude product 4-(4-(1-(4-chlorophenyl)cyclopropylamino)-6-(2,2,2-trifluoroethoxy)-1,3,5-triazin-2-ylamino)-3-fluorobenzoic acid was used directly in the next step.

| 4-(4-(1-(4-chlorophenyl)cyclopropylamino)-6-(2,2,2-trifluoroethoxy)-1,3,5-triazin-2-ylamino)-3-fluorobenzoic acid | |
|---|---|
| MS (M + H)$^+$ Calcd. | 498.8 |
| MS (M + H)$^+$ Observ. | 498.0 |
| Retention Time | 1.00 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 uM |

Step 5:
To a solution of 4-(4-(1-(4-chlorophenyl)cyclopropylamino)-6-(2,2,2-trifluoroethoxy)-1,3,5-triazin-2-ylamino)-3-fluorobenzoic acid (200 mg, 0.42 mmol) in DCM (3 mL) was added tert-butyl 3-amino-2,2-dimethylpropylcarbamate (98 mg, 0.48 mmol), HATU (229 mg, 0.60 mol) and iPr$_2$NEt (0.35 mL, 2.00 mmol). The mixture was stirred at r.t. for 16 hours before all the solvents were removed under vacuum. All solvents were removed under vacuum and the residue was purified by silica gel column (EtOAC/Hexanes=20% to 40%) to give tert-butyl 3-(4-(4-(1-(4-chlorophenyl)cyclopropylamino)-6-(2,2,2-trifluoroethoxy)-1,3,5-triazin-2-ylamino)-3-fluorobenzamido)-2,2-dimethylpropylcarbamate (270 mg, 100%) as a white solid.

| tert-butyl 3-(4-(4-(1-(4-chlorophenyl)cyclopropylamino)-6-(2,2,2-trifluoroethoxy)-1,3,5-triazin-2-ylamino)-3-fluorobenzamido)-2,2-dimethylpropylcarbamate | |
|---|---|
| MS (M + H)$^+$ Calcd. | 683.1 |
| MS (M + H)$^+$ Observ. | 682.3 |
| Retention Time | 1.15 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 uM |

Step 6:
tert-butyl 3-(4-(4-(1-(4-chlorophenyl)cyclopropylamino)-6-(2,2,2-trifluoroethoxy)-1,3,5-triazin-2-ylamino)-3-fluorobenzamido)-2,2-dimethylpropylcarbamate (270 mg, 0.40 mmol) was dissolved in 4 M HCl in dioxane (5 mL) solution. After being stirred at room temperature for 3 hours, the mixture was concentrated to give N-(3-amino-2,2-dimethylpropyl)-4-(4-(1-(4-chlorophenyl)cyclopropylamino)-6-(2,2,2-trifluoroethoxy)-1,3,5-triazin-2-ylamino)-3-fluorobenzamide as crude product.

N-(3-amino-2,2-dimethylpropyl)-4-(4-(1-(4-chlorophenyl) cyclopropylamino)-6-(2,2,2-trifluoroethoxy)-1,3,5-triazin-2-ylamino)-3-fluorobenzamide

| | |
|---|---|
| MS (M + H)+ Calcd. | 583.0 |
| MS (M + H)+ Observ. | 582.2 |
| Retention Time | 0.92 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 uM |

Step 7:

To a solution of N-(3-amino-2,2-dimethylpropyl)-4-(4-(1-(4-chlorophenyl)cyclopropylamino)-6-(2,2,2-trifluoroethoxy)-1,3,5-triazin-2-ylamino)-3-fluorobenzamide (80 mg, 0.14 mmol) and 2-oxo-2-(pyrrolidin-1-yl)acetic acid (20 mg, 0.137 mmol) in DMF (2 mL) were added O-(benzotriazol-1-yl-N,N,N',N'-tetramethyluronium tetrafluoroborate (66 mg, 0.21 mmol) and iPr$_2$NEt (0.050 ml, 0.28 mmol). After stirring at rt for 16 hs, the mixture was purified by preparative HPLC to give 4-(4-(1-(4-chlorophenyl)cyclopropylamino)-6-(2,2,2-trifluoroethoxy)-1,3,5-triazin-2-ylamino)-N-(2,2-dimethyl-3-(2-oxo-2-(pyrrolidin-1-yl)acetamido)propyl)-3-fluorobenzamide (14.4 mg, 14%) as product. $^1$H NMR (400 MHz, CHLOROFORM-d) δ ppm 1.01 (6H, s), 1.42 (4H, m), 1.81-2.02 (4H, m), 3.14 (2H, m), 3.29 (2H, d, J=6.0 Hz), 3.60 (2H, t, J=6.9 Hz), 3.91-4.12 (2H, m), 4.70-4.80 (2H, m), 7.14-7.38 (3H, m), 7.48-7.59 (1H, m), 7.69-7.80 (1H, m), 7.94-8.06 (1H, m), 8.24-8.31 (1H, m).

4-(4-(1-(4-chlorophenyl)cyclopropylamino)-6-(2,2,2-trifluoroethoxy)-1,3,5-triazin-2-ylamino)-N-(2,2-dimethyl-3-(2-oxo-2-(pyrrolidin-1-yl)acetamido)propyl)-3-fluorobenzamide

| | |
|---|---|
| MS (M + H)+ Calcd. | 708.1 |
| MS (M + H)+ Observ. | 707.3 |
| Retention Time | 1.07 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 uM |

Preparation of Compound 2002, N1-(3-(4-(4-(1-(4-chlorophenyl)cyclopropylamino)-6-(2,2,2-trifluoroethoxy)-1,3,5-triazin-2-ylamino)-3-fluorobenzamido)-2,2-dimethylpropyl)-N2,N2-dimethyloxalamide

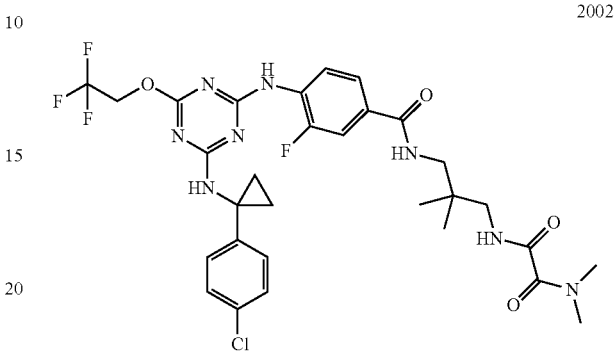

2002

To a solution of N-(3-amino-2,2-dimethylpropyl)-4-(4-(1-(4-chlorophenyl)cyclopropylamino)-6-(2,2,2-trifluoroethoxy)-1,3,5-triazin-2-ylamino)-3-fluorobenzamide (20 mg, 0.034 mmol) and 2-(dimethylamino)-2-oxoacetic acid (4.83 mg, 0.041 mmol) in DMF (1 mL) were added O-(benzotriazol-1-yl-N,N,N',N'-tetramethyluronium tetrafluoroborate (16.5 mg, 0.052 mmol) and iPr$_2$NEt (0.012 ml, 0.069 mmol). After stirring at rt for 16 hs, the mixture was purified by preparative HPLC to give N1-(3-(4-(4-(1-(4-chlorophenyl)cyclopropylamino)-6-(2,2,2-trifluoroethoxy)-1,3,5-triazin-2-ylamino)-3-fluorobenzamido)-2,2-dimethylpropyl)-N2,N2-dimethyloxalamide (13.8 mg, 56%) as product. $^1$H NMR (400 MHz, CHLOROFORM-d) δ ppm 1.03 (6H, s), 1.31-1.53 (4H, m), 3.06 (3H, s), 3.10-3.21 (2H, m), 3.29 (2H, d, J=6.0 Hz), 3.39 (3H, s), 4.75 (2H, m), 7.14-7.29 (3H, m), 7.33-7.48 (1H, m), 7.70-7.81 (1H, m), 7.92-8.04 (1H, m), 8.07-8.15 (1H, m).

N1-(3-(4-(4-(1-(4-chlorophenyl)cyclopropylamino)-6-(2,2,2-trifluoroethoxy)-1,3,5-triazin-2-ylamino)-3-fluorobenzamido)-2,2-dimethylpropyl)-N2,N2-dimethyloxalamide

| | |
|---|---|
| MS (M + H)+ Calcd. | 682.1 |
| MS (M + H)+ Observ. | 681.3 |
| Retention Time | 1.02 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |

Displacement of CF₃CH₂O moiety by benzyl alcohol:

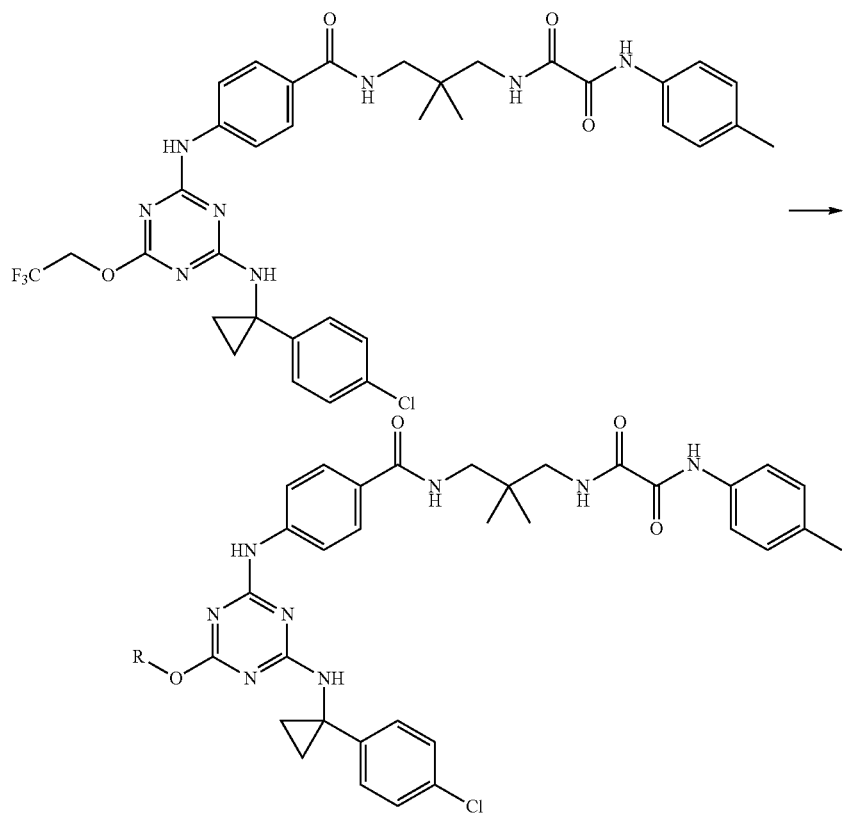

A solution of N1-(3-(4-((4-((1-(4-chlorophenyl)cyclopropyl)amino)-6-(2,2,2-trifluoroethoxy)-1,3,5-triazin-2-yl)amino)benzamido)-2,2-dimethylpropyl)-N2-(p-tolyl)oxalamide (520 mg) in THF was prepared. NaH (19.86 mg) and 500 μL of the N₁-(3-(4-((4-((1-(4-chlorophenyl)cyclopropyl)amino)-6-(2,2,2-trifluoroethoxy)-1,3,5-triazin-2-yl)amino)benzamido)-2,2-dimethylpropyl)-N₂-(p-tolyl)oxalamide solution was added into 16×48 mm each threaded vial containing an individual alcohol (5-10 eq.). Vials were capped and allowed to shake at room temperature for 3 days. Samples were blown down in the Zymark tabletop dryer at 35° C. for 2 hours and products were purified by preparative HPLC systems.

Method M=Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient 0.5 min hold at 0% B, 0-100% B over 4 minutes, then a 0.5-minute hold at 100% B; Flow: 0.5 mL/min.

Method A=Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min.

| Compd. # | Structure | MS (M + H)+ Calcd. | MS (M + H)+ Obs. | HPLC Rt (min) | Method |
|---|---|---|---|---|---|
| 3840 | 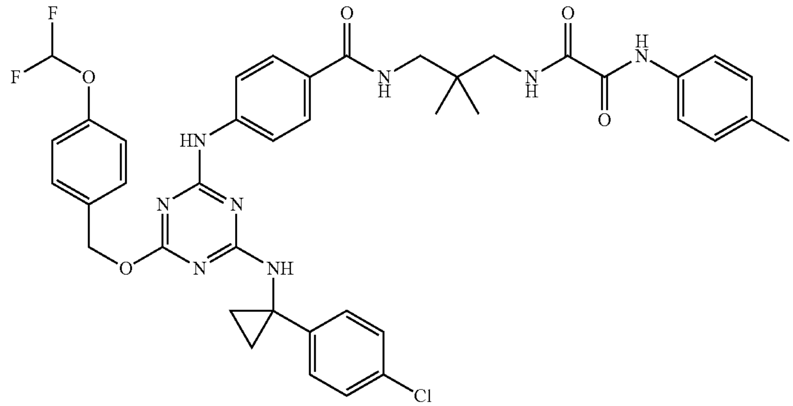 [SMILES: Cc1ccc(NC(=O)C(=O)NCC(C)(C)CNC(=O)c2ccc(Nc3nc(NC4(c5ccc(Cl)cc5)CC4)nc(OCc4ccc(OC(F)F)cc4)n3)cc2)cc1] | 799.3 | 798.9 | 3.61 | A |
| 3841 | 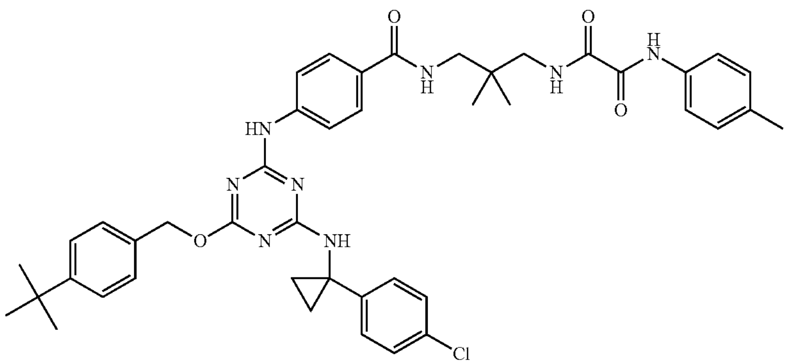 [SMILES: Cc1ccc(NC(=O)C(=O)NCC(C)(C)CNC(=O)c2ccc(Nc3nc(NC4(c5ccc(Cl)cc5)CC4)nc(OCc4ccc(C(C)(C)C)cc4)n3)cc2)cc1] | 789.4 | 789.8 | 4.86 | M |
| 3842 | 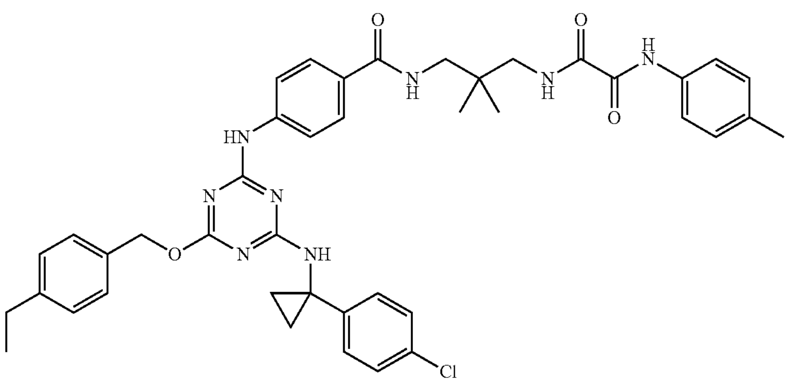 | 761.3 | 761.8 | 4.75 | M |
| 3843 | 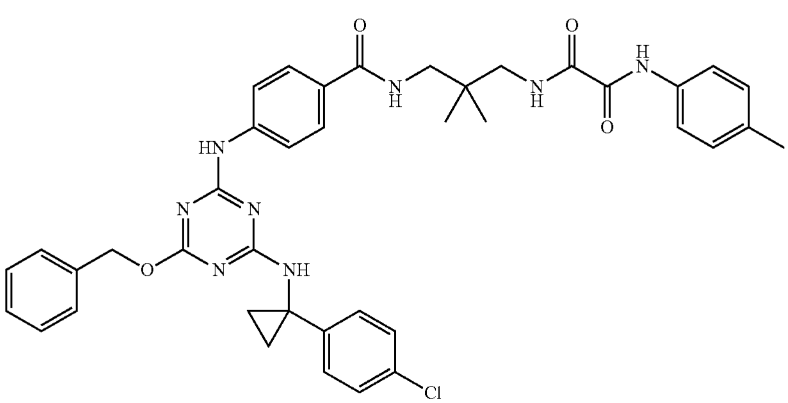 [SMILES: Cc1ccc(NC(=O)C(=O)NCC(C)(C)CNC(=O)c2ccc(Nc3nc(NC4(c5ccc(Cl)cc5)CC4)nc(OCc4ccccc4)n3)cc2)cc1] | 733.3 | 733.7 | 4.60 | M |

-continued

| Compd. # | Structure | MS (M + H)+ Calcd. | MS (M + H)+ Obs. | HPLC Rt (min) | Method |
|---|---|---|---|---|---|
| 3844 | 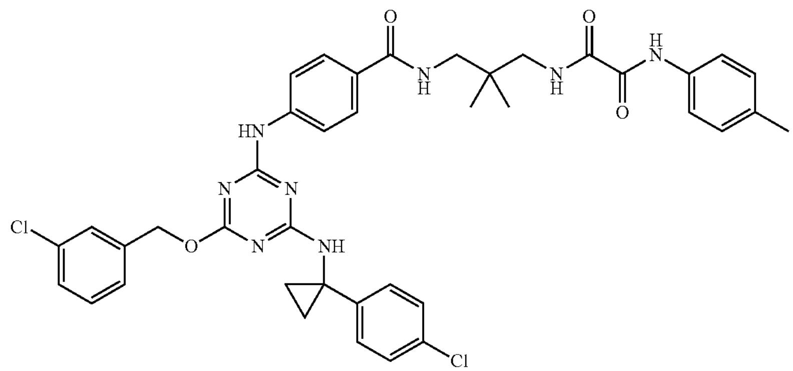 [SMILES: Cc1ccc(NC(=O)C(=O)NCC(C)(C)CNC(=O)c2ccc(Nc3nc(NC4(c5ccc(Cl)cc5)CC4)nc(OCc4cccc(Cl)c4)n3)cc2)cc1] | 767.3 | 767.9 | 4.68 | M |
| 3845 | 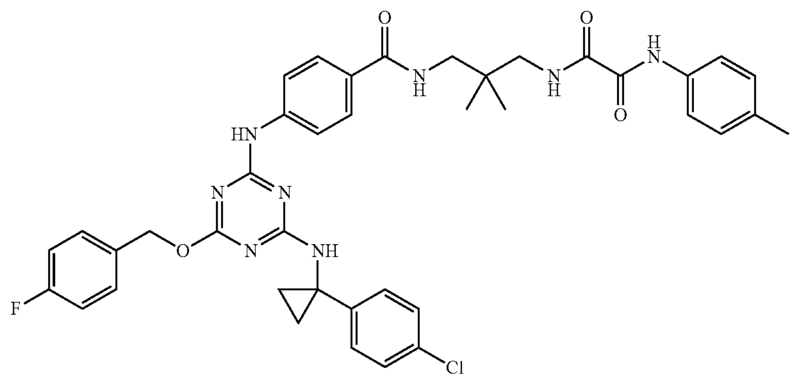 [SMILES: Cc1ccc(NC(=O)C(=O)NCC(C)(C)CNC(=O)c2ccc(Nc3nc(NC4(c5ccc(Cl)cc5)CC4)nc(OCc4ccc(F)cc4)n3)cc2)cc1] | 751.3 | 751.7 | 4.58 | M |
| 3846 | 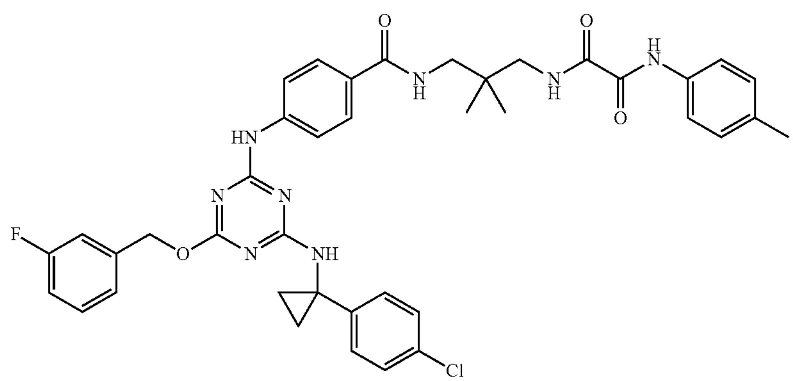 [SMILES: Cc1ccc(NC(=O)C(=O)NCC(C)(C)CNC(=O)c2ccc(Nc3nc(NC4(c5ccc(Cl)cc5)CC4)nc(OCc4cccc(F)c4)n3)cc2)cc1] | 751.3 | 751.8 | 4.59 | M |
| 3847 | 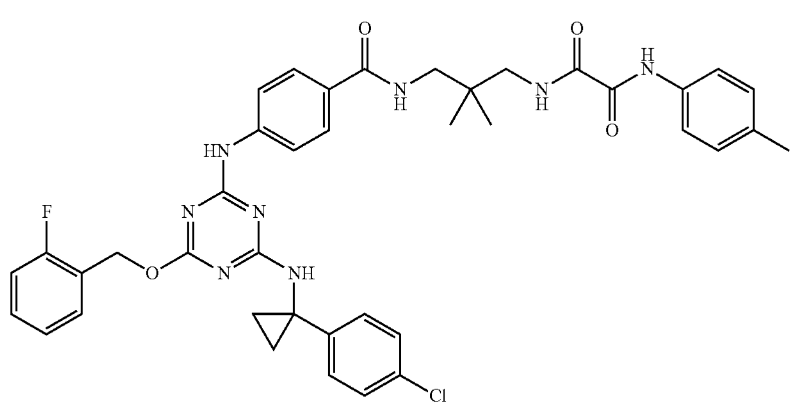 [SMILES: Cc1ccc(NC(=O)C(=O)NCC(C)(C)CNC(=O)c2ccc(Nc3nc(NC4(c5ccc(Cl)cc5)CC4)nc(OCc4ccccc4F)n3)cc2)cc1] | 751.3 | 751.9 | 4.60 | M |

-continued

| Compd. # | Structure | MS (M + H)+ Calcd. | MS (M + H)+ Obs. | HPLC Rt (min) | Method |
|---|---|---|---|---|---|
| 3848 | 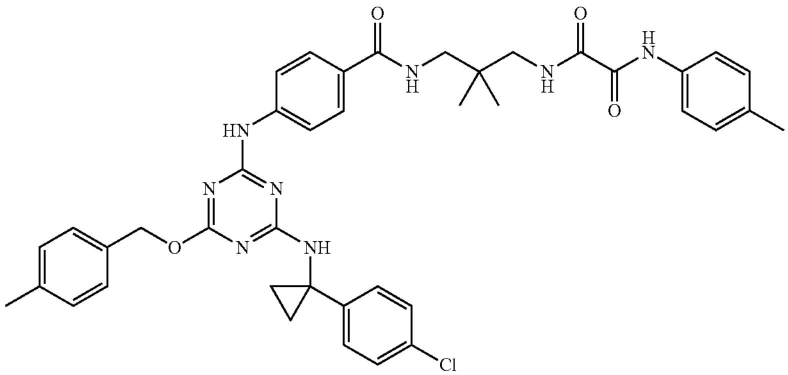 | 747.3 | 747.8 | 4.68 | M |
| 3849 | 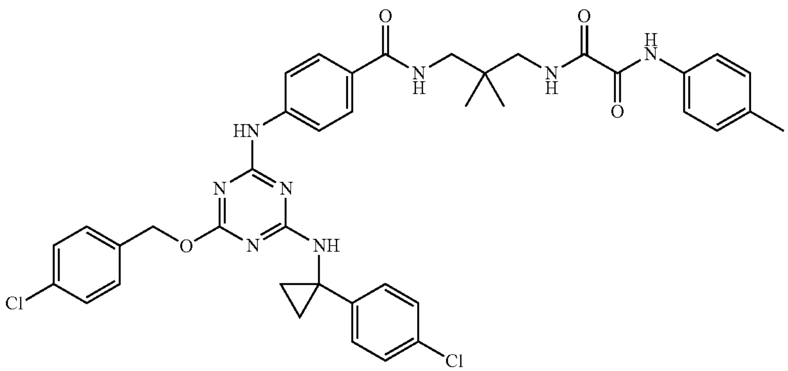 [SMILES: Cc1ccc(NC(=O)C(=O)NCC(C)(C)CNC(=O)c2ccc(Nc3nc(NC4(c5ccc(Cl)cc5)CC4)nc(OCc4ccc(Cl)cc4)n3)cc2)cc1] | 767.3 | 767.7 | 4.68 | M |
| 3850 | 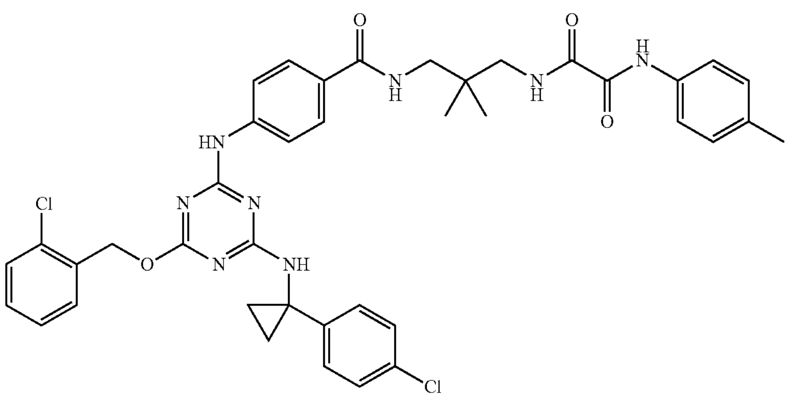 | 767.3 | 767.7 | 4.71 | M |
| 3851 | 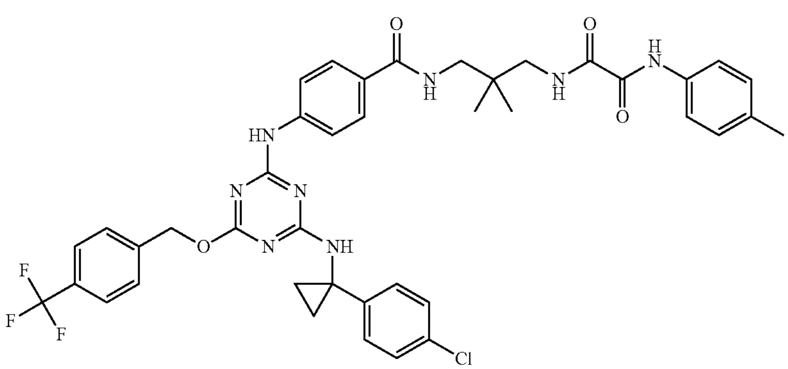 [SMILES: Cc1ccc(NC(=O)C(=O)NCC(C)(C)CNC(=O)c2ccc(Nc3nc(NC4(c5ccc(Cl)cc5)CC4)nc(OCc4ccc(C(F)(F)F)cc4)n3)cc2)cc1] | 801.3 | 800.8 | 3.76 | A |

-continued

| Compd. # | Structure | MS (M + H)+ Calcd. | MS (M + H)+ Obs. | HPLC Rt (min) | Method |
|---|---|---|---|---|---|
| 3852 | 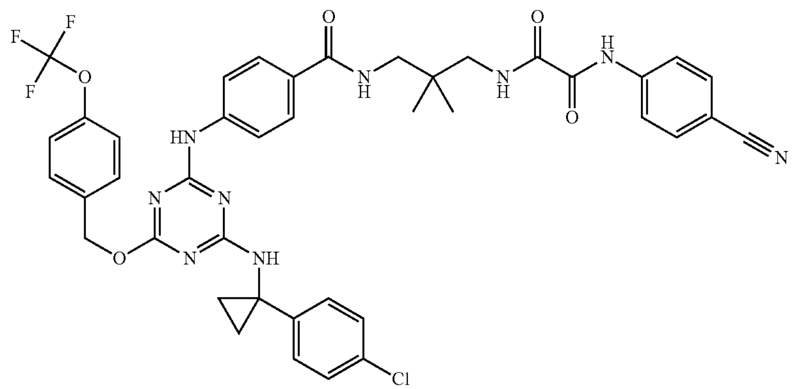 [SMILES: CC(C)(CNC(=O)C(=O)Nc1ccc(C#N)cc1)CNC(=O)c1ccc(Nc2nc(NC3(c4ccc(Cl)cc4)CC3)nc(OCc3ccc(OC(F)(F)F)cc3)n2)cc1] | 828.3 | 828.0 | 4.54 | M |
| 3853 | 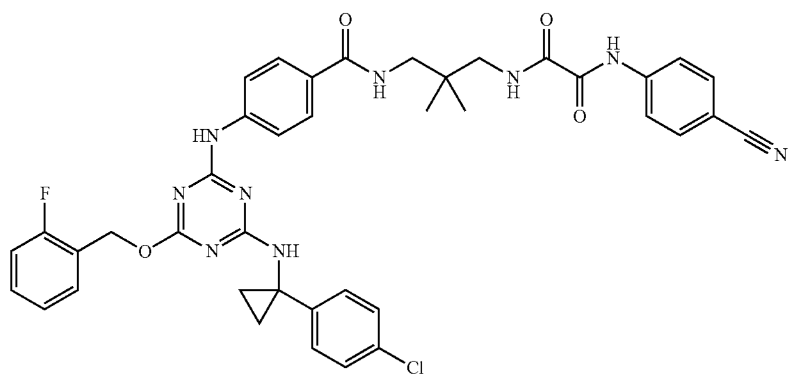 [SMILES: CC(C)(CNC(=O)C(=O)Nc1ccc(C#N)cc1)CNC(=O)c1ccc(Nc2nc(NC3(c4ccc(Cl)cc4)CC3)nc(OCc3ccccc3F)n2)cc1] | 762.3 | 762.8 | 4.43 | M |
| 3839 | 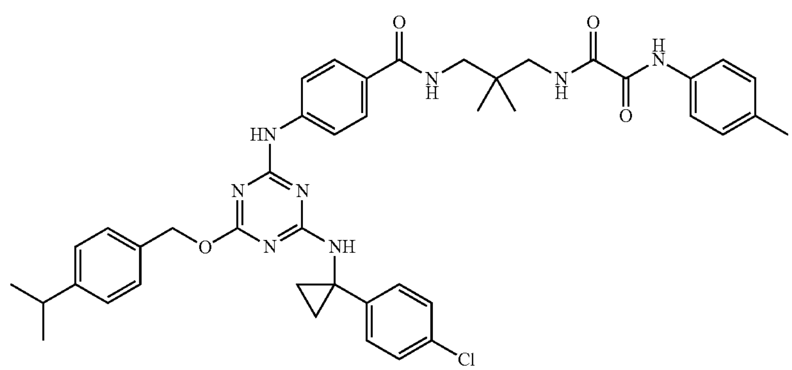 [SMILES: Cc1ccc(NC(=O)C(=O)NCC(C)(C)CNC(=O)c2ccc(Nc3nc(NC4(c5ccc(Cl)cc5)CC4)nc(OCc4ccc(C(C)C)cc4)n3)cc2)cc1] | 775.3 | 775.8 | 3.92 | A |
| 4002 | 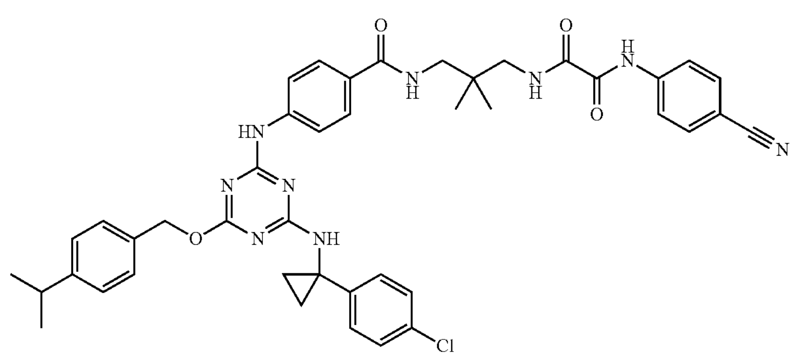 [SMILES: CC(C)c1ccc(COc2nc(Nc3ccc(C(=O)NCC(C)(C)CNC(=O)C(=O)Nc4ccc(C#N)cc4)cc3)nc(NC3(c4ccc(Cl)cc4)CC3)n2)cc1] | 786.3 | 786.8 | 3.75 | A |

Preparation of 3827, $N^1$-(3-(4-((4-((1-(4-chlorophenyl)cyclopropyl)amino)-6-((4-isopropylbenzyl)oxy)-1,3,5-triazin-2-yl)amino)-2-fluorobenzamido)-2,2-dimethylpropyl)-$N^2$-(p-tolyl)oxalamide

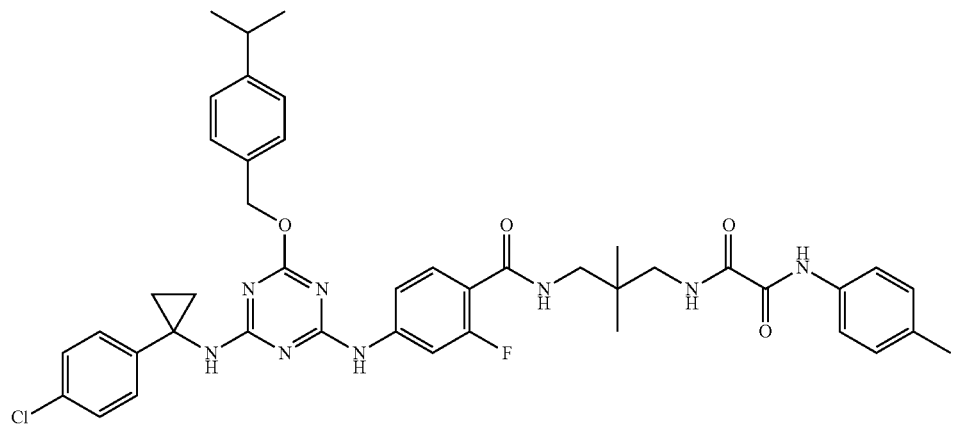

3827

To a suspension of (4-isopropylphenyl)methanol (24.46 mg) and NaH (5.92 mg) in THF (10 mL) was added $N^1$-(3-(4-((4-((1-(4-chlorophenyl)cyclopropyl)amino)-6-(2,2,2-trifluoroethoxy)-1,3,5-triazin-2-yl)amino)-2-fluorobenzamido)-2,2-dimethylpropyl)-$N^2$-(p-tolyl)oxalamide (11 mg). The mixture was heated to reflux for 3 hours. The reaction was quenched by 5% NaHCO$_3$/H$_2$O and extracted with EtOAc (2×10 mL). The organic layers were combined, washed with brine (10 mL), dried over MgSO$_4$ and concentrated. The residue was purified by preparative HPLC system to give Compound 3827.

| Compound 3827 | |
|---|---|
| MS (M + H)$^+$ Calcd. | 793.3 |
| MS (M + H)$^+$ Observ. | 793.4 |
| Retention Time | 2.38 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

Preparations of 3828, 3829, 3830 and 3835

Compounds 3828, 3829, 3830 and 3835 were prepared under the same condition for the synthesis of Compound 3827, using $N^1$-(3-(4-((4-((1-(4-chlorophenyl)cyclopropyl)amino)-6-(2,2,2-trifluoroethoxy)-1,3,5-triazin-2-yl)amino)-2-fluorobenzamido)-2,2-dimethylpropyl)-$N^2$-(4-methoxyphenyl)oxalamide, $N^1$-(3-(4-((4-((1-(4-chlorophenyl)cyclopropyl)amino)-6-(2,2,2-trifluoroethoxy)-1,3,5-triazin-2-yl)amino)-2-fluorobenzamido)-2,2-dimethylpropyl)-$N^2$-(4-(trifluoromethyl)phenyl)oxalamide, $N^1$-([1, 1'-biphenyl]-2-yl)-$N^2$-(3-(4-((4-((1-(4-chlorophenyl)cyclopropyl)amino)-6-((4-isopropylbenzyl)oxy)-1,3,5-triazin-2-yl)amino)-2-fluorobenzamido)-2,2-dimethylpropyl)oxalamide and $N^1$-(3-(4-((4-((1-(4-chlorophenyl)cyclopropyl)amino)-6-((4-isopropylbenzyl)oxy)-1,3,5-triazin-2-yl)amino)-2-fluorobenzamido)-2,2-dimethylpropyl)-$N^2$-(2,4-difluorophenyl)oxalamide as starting materials.

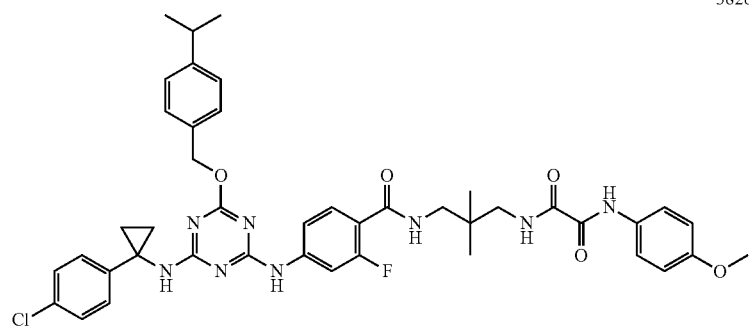

3828

| | |
|---|---|
| MS (M + H)$^+$ Calcd. | 809.3 |
| MS (M + H)$^+$ Observ. | 809.3 |

-continued

| | |
|---|---|
| Retention Time | 2.32 min |

LC Condition

| | |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

3829

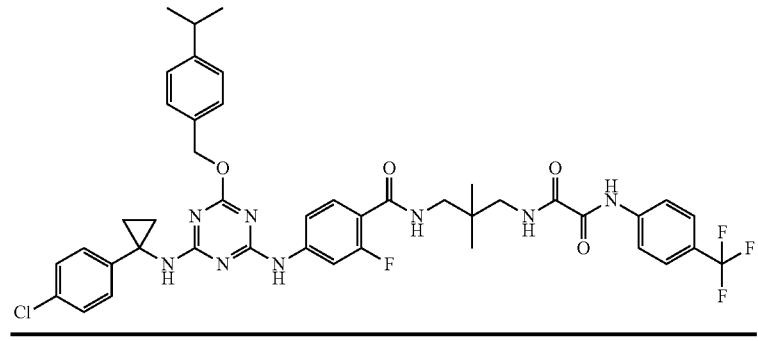

| | |
|---|---|
| MS (M + H)+ Calcd. | 847.3 |
| MS (M + H)+ Observ. | 847.3 |
| Retention Time | 2.44 min |

LC Condition

| | |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

3830

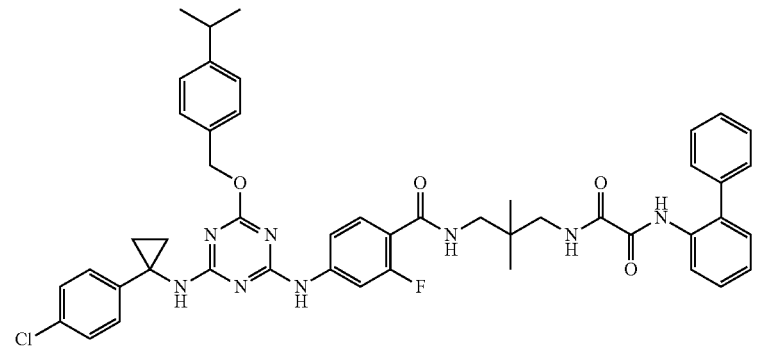 [SMILES: CC(C)c1ccc(COc2nc(Nc3ccc(C(=O)NCC(C)(C)CNC(=O)C(=O)Nc4ccccc4-c4ccccc4)c(F)c3)nc(NC3(c4ccc(Cl)cc4)CC3)n2)cc1]

| | |
|---|---|
| MS (M + H)+ Calcd. | 855.4 |
| MS (M + H)+ Observ. | 855.3 |
| Retention Time | 2.51 min |

LC Condition

| | |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

3835

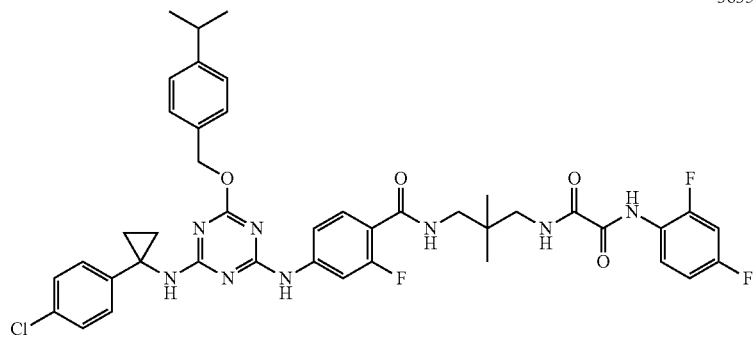

| | |
|---|---|
| MS (M + H)+ Calcd. | 815.3 |
| MS (M + H)+ Observ. | 815.3 |
| Retention Time | 2.29 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3u |

Preparations of 3834 and 4003

Step 1: iPr₂NEt (4 mL) was added into a solution of 2-(chloromethyl)-2-methyloxirane (0.745 g) and (2,4-dimethoxyphenyl)methanamine (2.338 g) in EtOH (20 mL). The reaction was stirred at room temperature for 16 hours, then 115° C. for 72 hours before being quenched by water. After removal of solvents under vacuum, the residue was purified by silica gel chromatography or preparative HPLC.

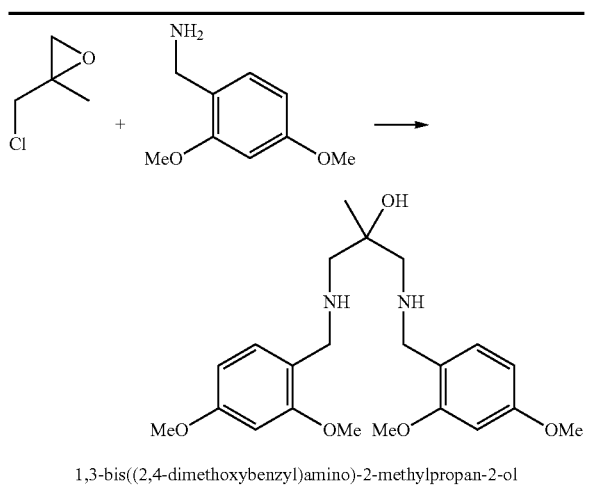

1,3-bis((2,4-dimethoxybenzyl)amino)-2-methylpropan-2-ol

| | |
|---|---|
| MS (M + H)+ Calcd. | 405.2 |
| MS (M + H)+ Observ. | 405.2 |
| Retention Time | 2.79 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |

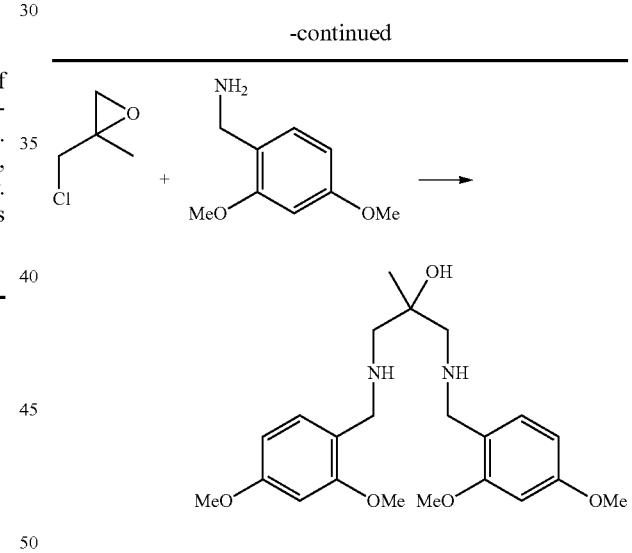

1,3-bis((2,4-dimethoxybenzyl)amino)-2-methylpropan-2-ol

| | |
|---|---|
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Step 2: iPr₂NEt (0.5 mL) and HATU (238 mg) were added into the solution of 4-((4-((1-(4-chlorophenyl)cyclopropyl)amino)-6-(2,2,2-trifluoroethoxy)-1,3,5-triazin-2-yl)amino)benzoic acid (300 mg) and 1,3-bis((2,4-dimethoxybenzyl)amino)-2-methylpropan-2-ol (253 mg) in THF (10 mL). The reaction was stirred at room temperature for 24 hours. The product was isolated by silica gel chromatography.

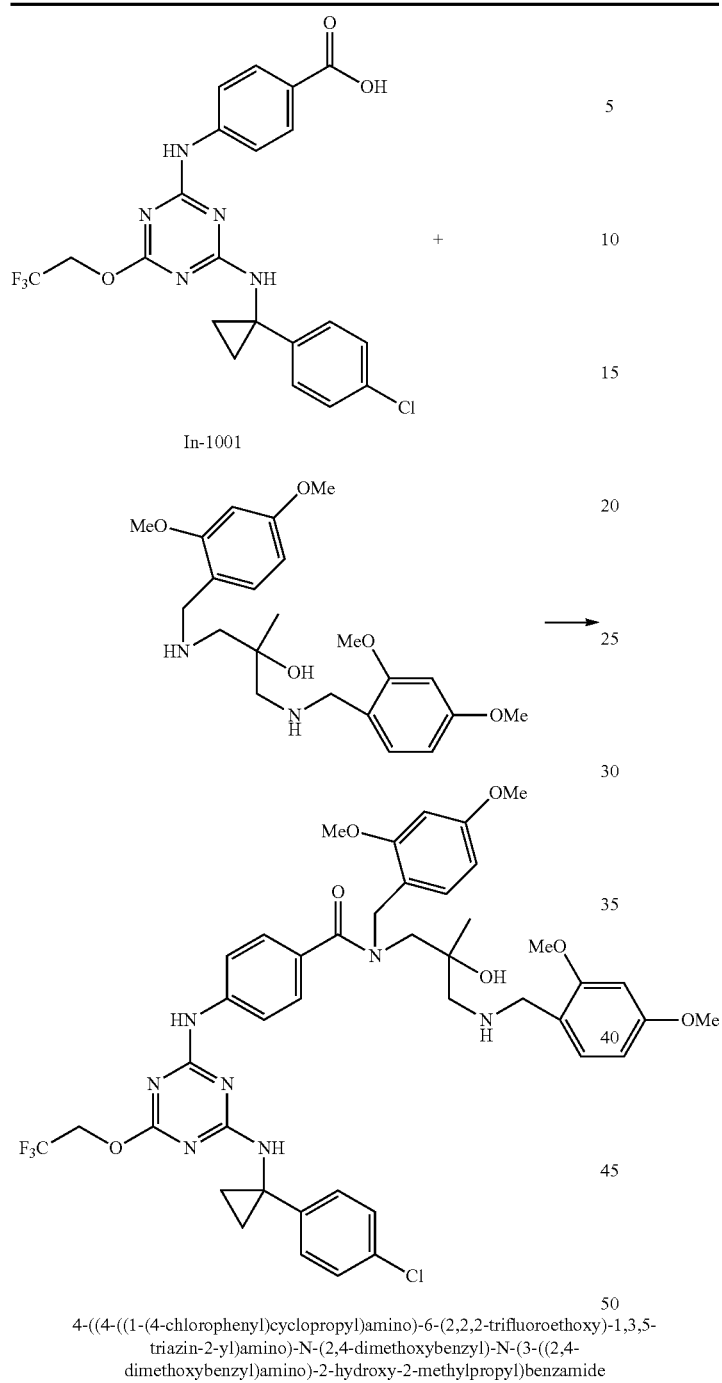

4-((4-((1-(4-chlorophenyl)cyclopropyl)amino)-6-(2,2,2-trifluoroethoxy)-1,3,5-triazin-2-yl)amino)-N-(2,4-dimethoxybenzyl)-N-(3-((2,4-dimethoxybenzyl)amino)-2-hydroxy-2-methylpropyl)benzamide

| | |
|---|---|
| MS (M + H)+ Calcd. | 866.3 |
| MS (M + H)+ Observ. | 866.3 |
| Retention Time | 2.01 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

Step 3: iPr$_2$NEt (0.5 mL), HATU (21.93 mg) were added into the solution of 4-((4-((1-(4-chlorophenyl)cyclopropyl)amino)-6-(2,2,2-trifluoroethoxy)-1,3,5-triazin-2-yl)amino)-N-(2,4-dimethoxybenzyl)-N-(3-((2,4-dimethoxybenzyl)amino)-2-hydroxy-2-methylpropyl)benzamide (50 mg) in THF (10 mL). The reaction was stirred at room temperature for 24 hours, before being quenched by NaHCO3 aqueous solution (10 mL). The aqueous phase was extracted by EtOAc (3×10 mL). The combined organic layer was dried over MgSO$_4$ and concentrated under vacuum to give a residue which was used as was.

Step 4: TFA (0.2 mL) was added into a solution of N$^1$-(3-(4-((4-((1-(4-chlorophenyl)cyclopropyl)amino)-6-(2,2,2-trifluoroethoxy)-1,3,5-triazin-2-yl)amino)-N-(2,4-dimethoxybenzyl)benzamido)-2-hydroxy-2-methylpropyl)-N$^1$-(2,4-dimethoxybenzyl)oxalamide (50 mg) in CH$_2$Cl$_2$ (2 mL). The reaction was stirred at room temperature for 24 hours, before all the solvents were removed under vacuum. The residue was purified by preparative HPLC system.

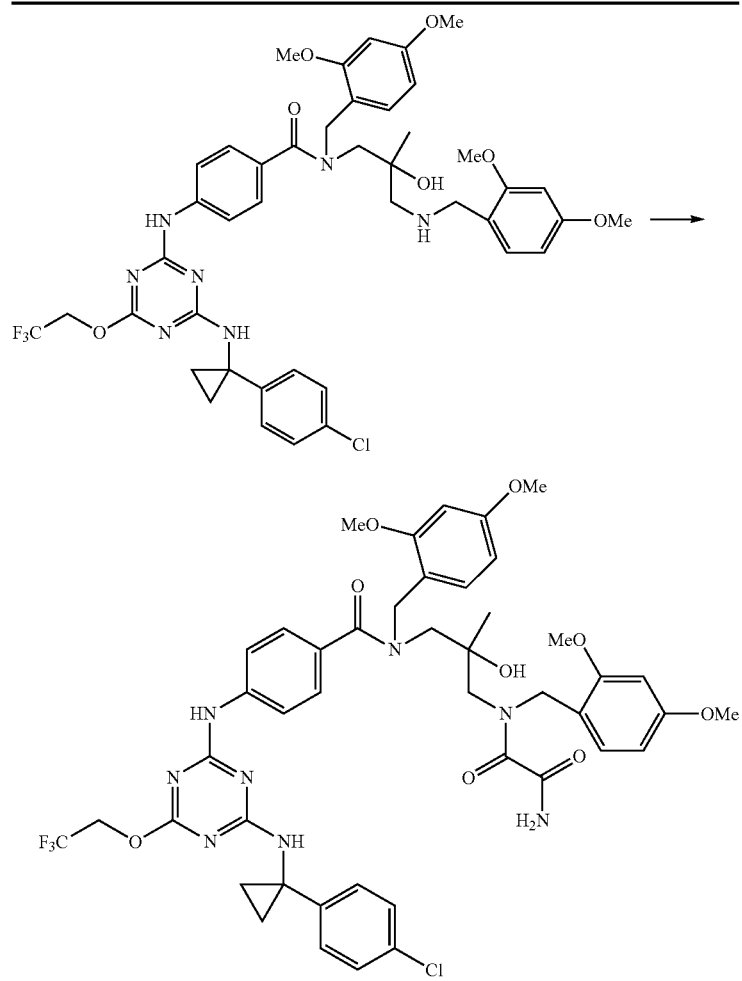

N$^1$-(3-(4-((4-((1-(4-chlorophenyl)cyclopropyl)amino)-6-(2,2,2-trifluoroethoxy)-1,3,5-triazin-2-yl)amino)-N-(2,4-dimethoxybenzyl)benzamido)-2-hydroxy-2-methylpropyl)-N$^1$-(2,4-dimethoxybenzyl)oxalamide

| | |
|---|---|
| MS (M + H)$^+$ Calcd. | 937.3 |
| MS (M + H)$^+$ Observ. | 937.3 |
| Retention Time | 1.93 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

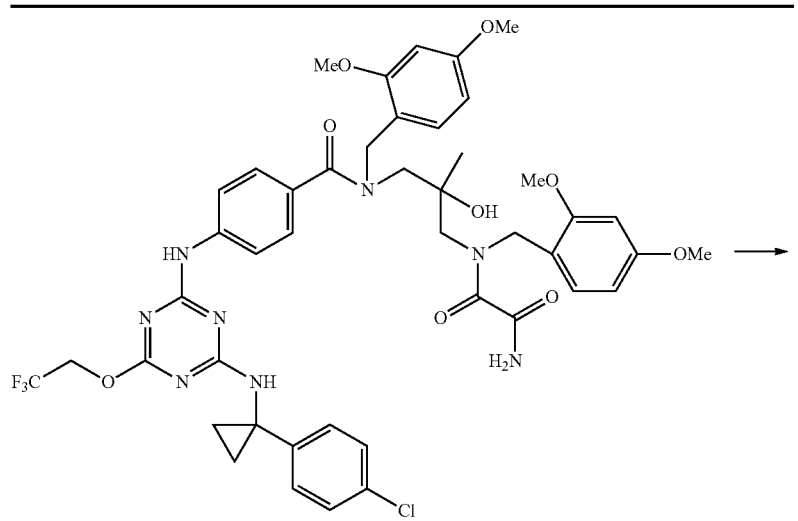
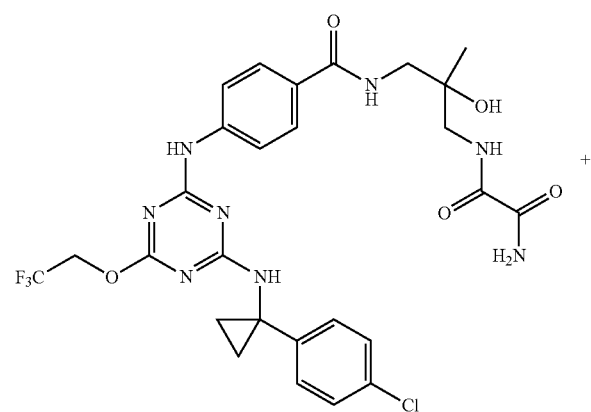
3834
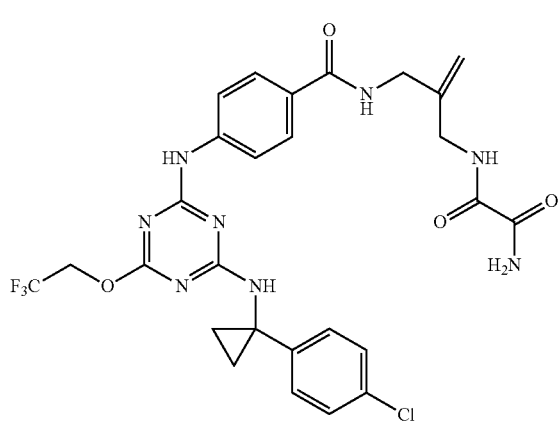
4003
| Compound 3834 | |
|---|---|
| MS (M + H)+ Calcd. | 637.2 |
| MS (M + H)+ Observ. | 637.1 |
| Retention Time | 1.58 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |

-continued
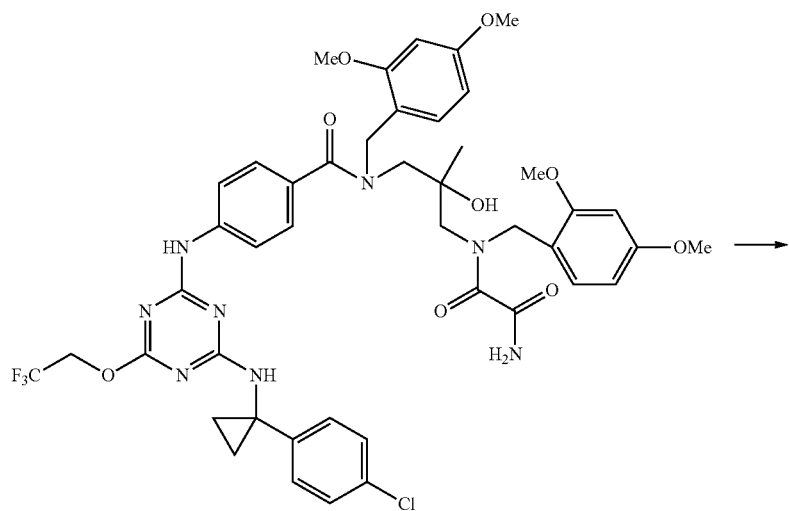 [SMILES: COc1ccc(CN(CC(C)(O)CN(Cc2ccc(OC)cc2OC)C(=O)c2ccc(Nc3nc(NC4(c5ccc(Cl)cc5)CC4)nc(OCC(F)(F)F)n3)cc2)C(=O)C(N)=O)c(OC)c1] →
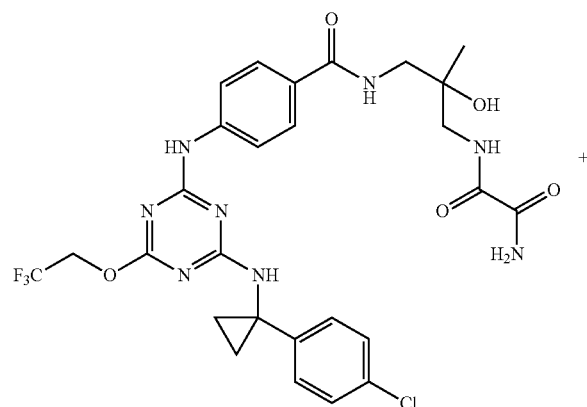 +
3834
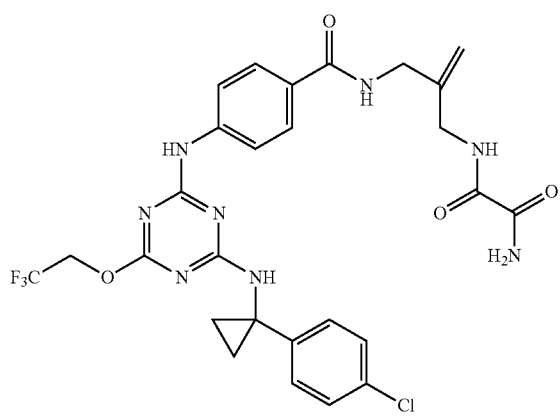
4003
| | |
|---|---|
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

-continued
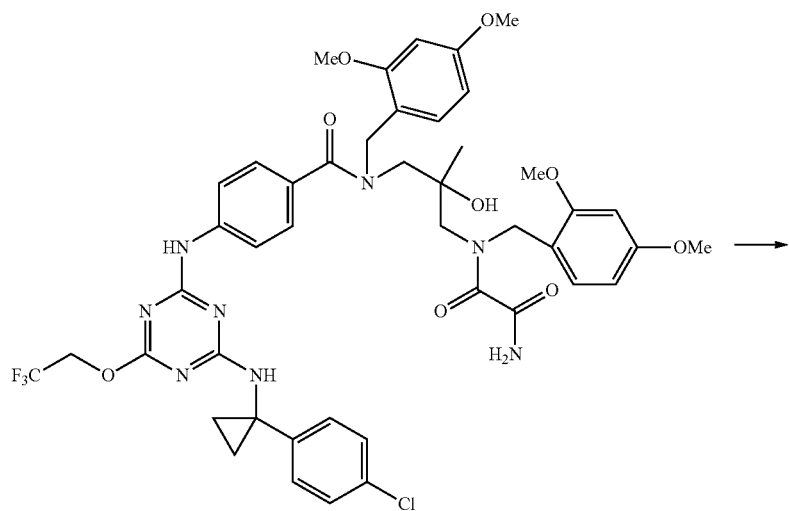 [SMILES: COc1ccc(CN(CC(C)(O)CN(Cc2ccc(OC)cc2OC)C(=O)c2ccc(Nc3nc(NC4(c5ccc(Cl)cc5)CC4)nc(OCC(F)(F)F)n3)cc2)C(=O)C(N)=O)c(OC)c1]
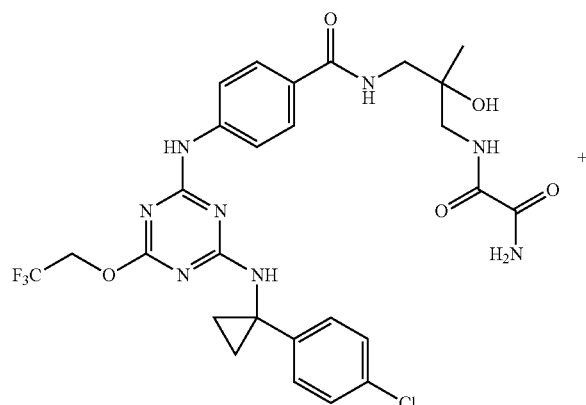
3834
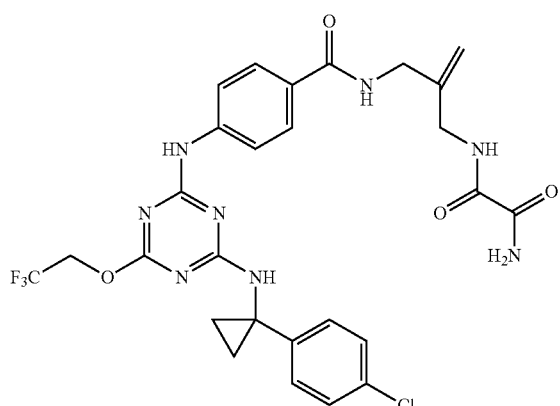
4003
| Compound 4003 | |
|---|---|
| MS (M + H)+ Calcd. | 619.2 |
| MS (M + H)+ Observ. | 619.1 |
| Retention Time | 1.72 min |

-continued
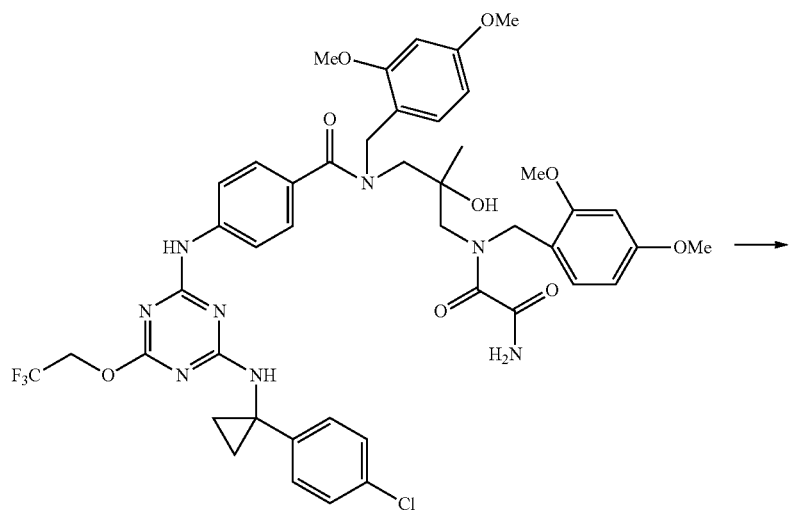
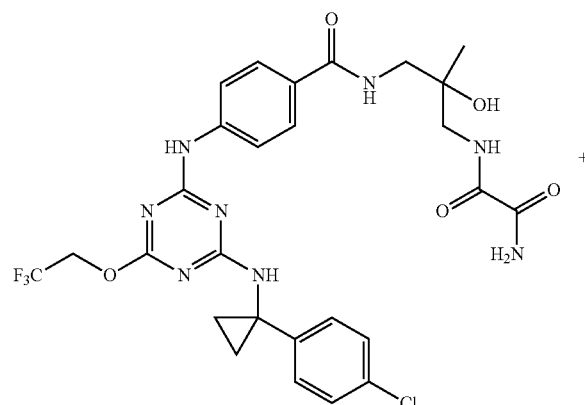
3834
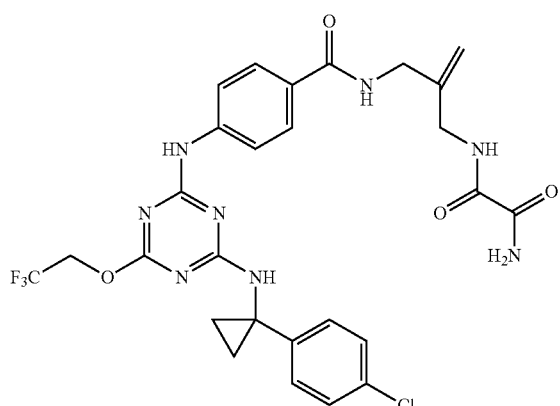
4003
| LC Condition | |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |

-continued
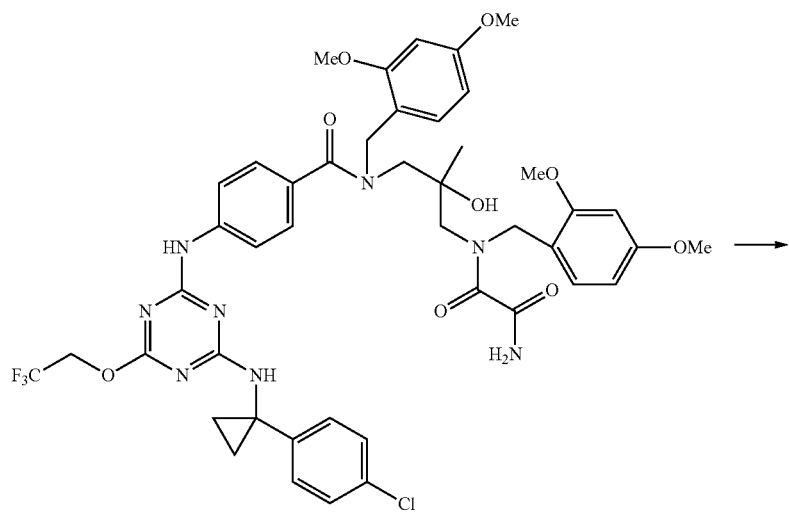 →
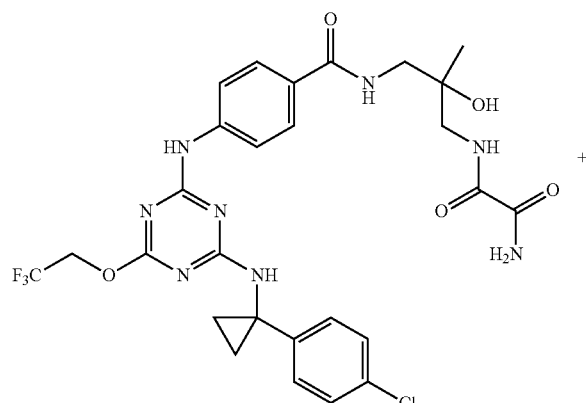 +
3834
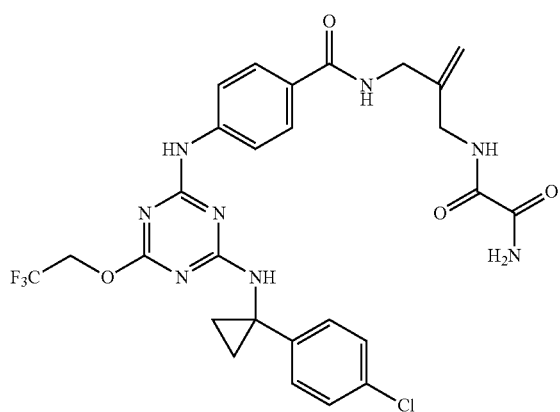
4003
| | |
|---|---|
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

Preparation of 3838, $N^1$-(3-(4-((4-((1-(4-chlorophenyl)cyclopropyl)amino)-6-(2,2,2-trifluoroethoxy)-1,3,5-triazin-2-yl)amino)benzamido)-2,2-bis(hydroxymethyl)propyl)oxalamide

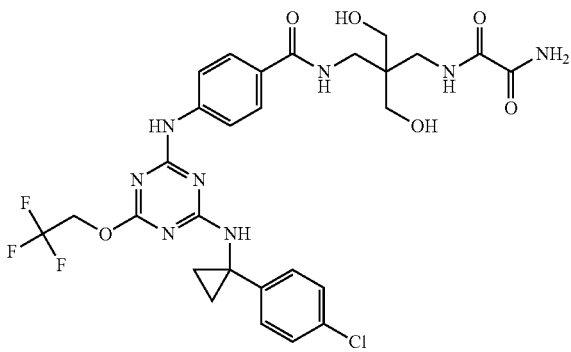

3838

Compound 3838 was prepared by using the same synthetic route of synthesizing 3834, using 2,2-bis(((2,4-dimethoxybenzyl)amino)methyl)propane-1,3-diol instead of 1,3-bis((2,4-dimethoxybenzyl)amino)-2-methylpropan-2-ol as one of the starting materials. And, 2,2-bis(((2,4-dimethoxybenzyl)amino)methyl)propane-1,3-diol was prepared by using the same procedure of synthesizing 1,3-bis((2,4-dimethoxybenzyl)amino)-2-methylpropan-2-ol by using 2,2-bis(bromomethyl)propane-1,3-diol rather than 2-(chloromethyl)-2-methyloxirane as one of the starting materials.

| Compound 3838 | |
|---|---|
| MS (M + H)+ Calcd. | 667.2 |
| MS (M + H)+ Observ. | 667.3 |
| Retention Time | 1.55 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

Preparations of 4004, $N^2$-((2-(4-((4-((1-(4-chlorophenyl)cyclopropyl)amino)-6-(2,2,2-trifluoroethoxy)-1,3,5-triazin-2-yl)amino)benzamido)cyclopentyl)methyl)-$N^2$-(4-fluorophenyl)oxalamide and 4005, $N^1$-((2-(4-((4-((1-(4-chlorophenyl)cyclopropyl)amino)-6-(2,2,2-trifluoroethoxy)-1,3,5-triazin-2-yl)amino)benzamido)cyclopentyl)methyl)-$N^2$-(cyclopropylmethyl)oxalamide Step 1: iPr$_2$NEt (0.5 mL) was added into a solution of tert-butyl (2-(aminomethyl)cyclopentyl)carbamate (300 mg) and ethyl 2-chloro-2-oxoacetate (191 mg) in THF (10 mL). The reaction was stirred at room temperature for 16 hours before being quenched by water. The aqueous layer was extracted with EtOAc (3×20 mL). The combined organic phase was dried over MgSO$_4$ and concentrated under vacuum to give the crude ethyl 2-(((2-((tert-butoxycarbonyl)amino)cyclopentyl)methyl)amino)-2-oxoacetate which was used as was.

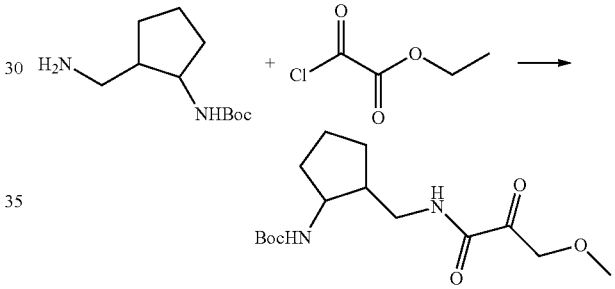

Step 2: Ethyl 2-(((2-((tert-butoxycarbonyl)amino)cyclopentyl)methyl)amino)-2-oxoacetate (440 mg) in TFA (1 mL) and CH$_2$Cl$_2$ (10 mL) was stirred at room temperature for 16 hours. After removal of solvents, the crude ethyl 2-(((2-aminocyclopentyl)methyl)amino)-2-oxoacetate was used as was.

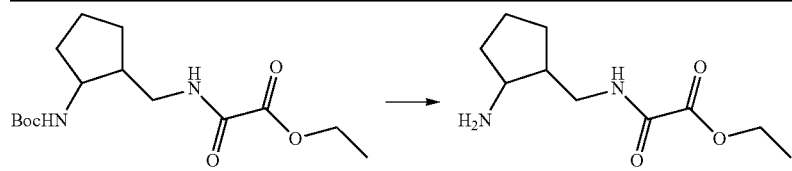

ethyl 2-(((2-aminocyclopentyl)methyl)amino)-2-oxoacetate

| MS (M + H)+ Calcd. | 215.1 |
|---|---|
| MS (M + H)+ Observ. | 215.2 |
| Retention Time | 0.65 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

Step 3: iPr₂NEt (0.5 mL) was added into a solution of 4-((4-((1-(4-chlorophenyl)cyclopropyl)amino)-6-(2,2,2-trifluoroethoxy)-1,3,5-triazin-2-yl)amino)benzoic acid (300 mg), ethyl 2-(((2-aminocyclopentyl)methyl)amino)-2-oxoacetate (205 mg) and TBTU (201 mg) in THF (10 mL). The reaction was stirred at room temperature for 16 hours before being quenched by water. The aqueous layer was extracted with EtOAc (3×20 mL). The combined organic phase was dried over MgSO₄ and concentrated under vacuum to give the crude ethyl 2-(((2-(4-((4-((1-(4-chlorophenyl)cyclopropyl)amino)-6-(2,2,2-trifluoroethoxy)-1,3,5-triazin-2-yl)amino)benzamido)cyclopentyl)methyl)amino)-2-oxoacetate which was used as was.

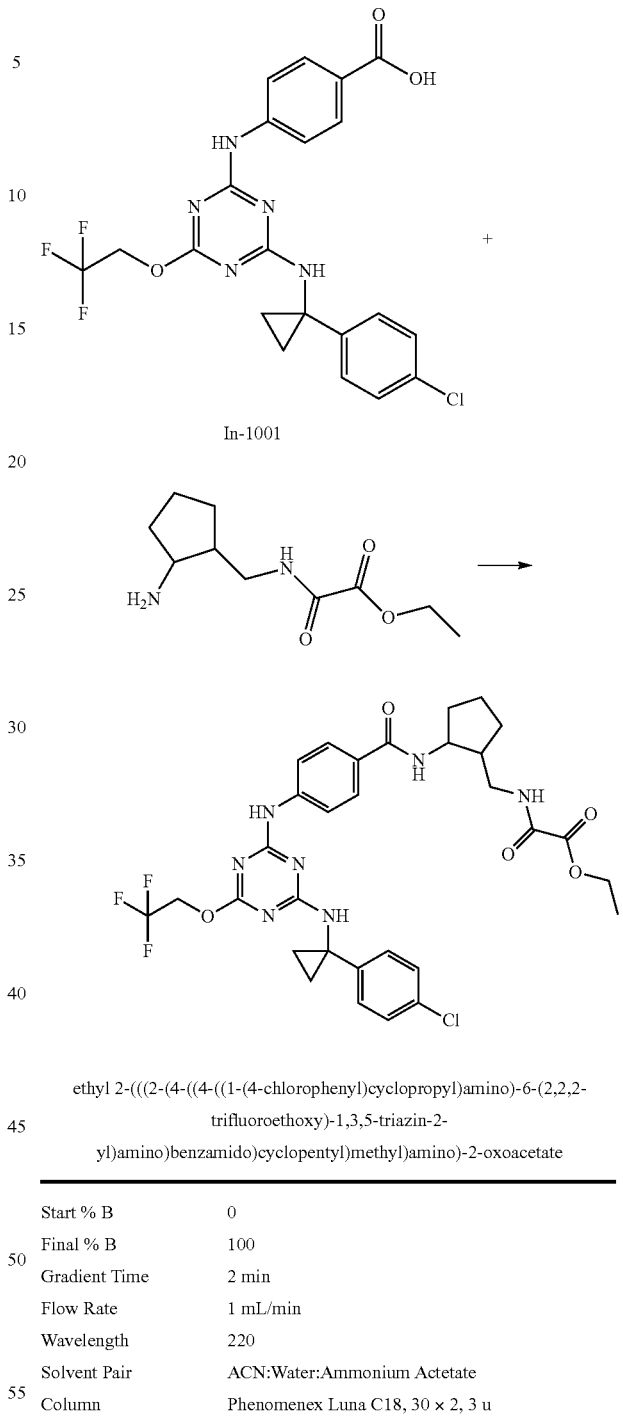

In-1001

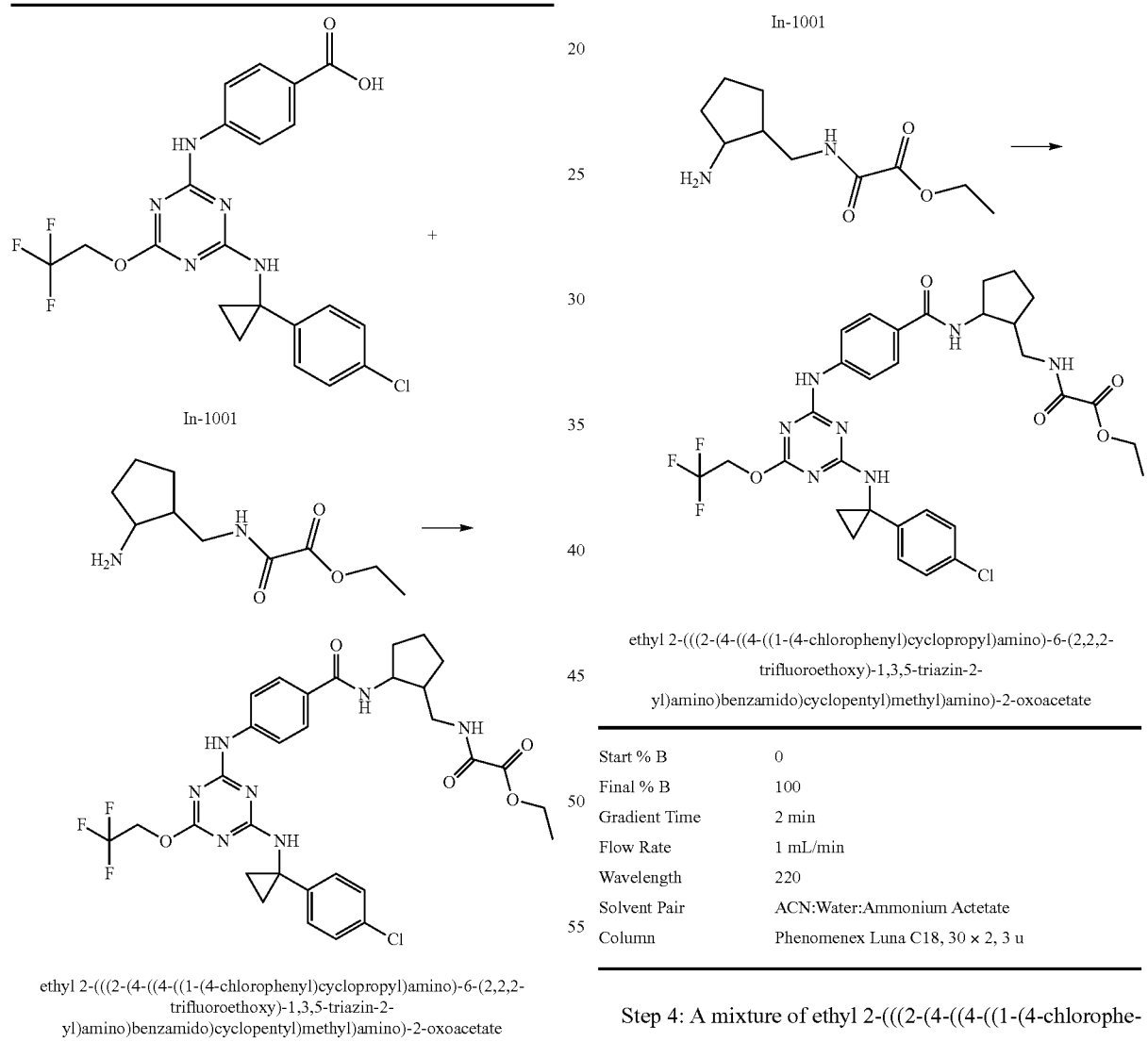

ethyl 2-(((2-(4-((4-((1-(4-chlorophenyl)cyclopropyl)amino)-6-(2,2,2-trifluoroethoxy)-1,3,5-triazin-2-yl)amino)benzamido)cyclopentyl)methyl)amino)-2-oxoacetate

| | |
|---|---|
| MS (M + H)⁺ Calcd. | 676.2 |
| MS (M + H)⁺ Observ. | 676.4 |
| Retention Time | 1.82 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

Step 4: A mixture of ethyl 2-(((2-(4-((4-((1-(4-chlorophenyl)cyclopropyl)amino)-6-(2,2,2-trifluoroethoxy)-1,3,5-triazin-2-yl)amino)benzamido)cyclopentyl)methyl)amino)-2-oxoacetate (30 mg) and 4-fluoroaniline (49.3 mg) in EtOH (2 mL) was stirred at room temperature for 16 hours, then at 155° C. for 16 hours. Then, the product 4004 was isolated by preparative HPLC system.

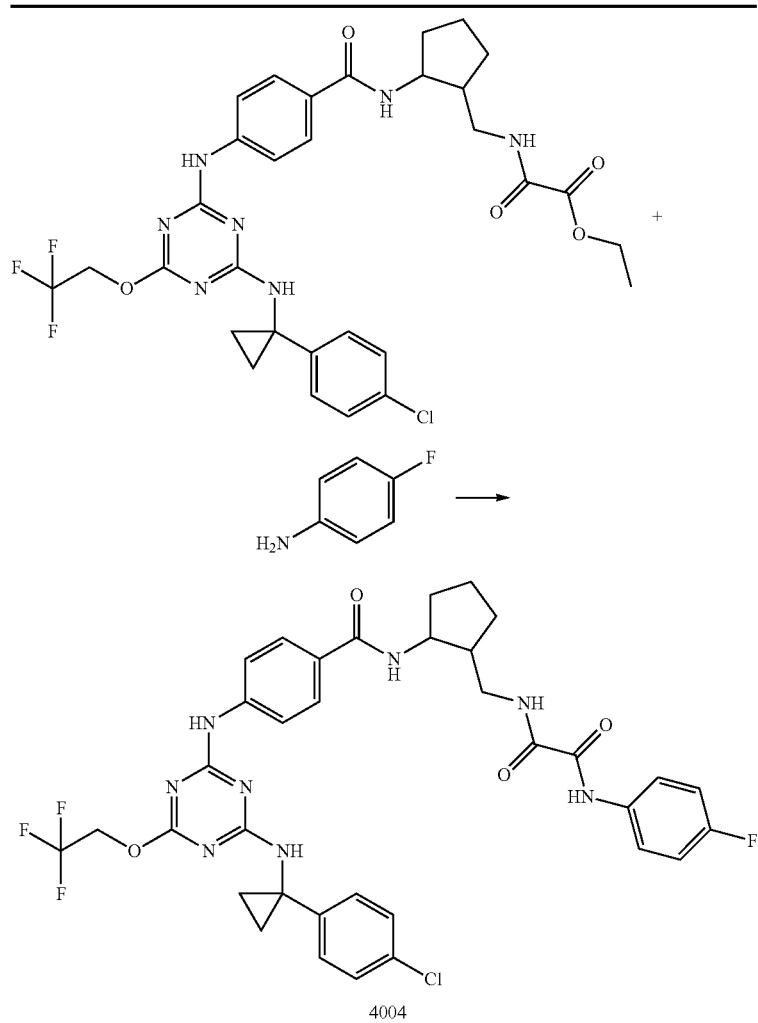

| Compound 4004 | |
|---|---|
| MS (M + H)+ Calcd. | 741.2 |
| MS (M + H)+ Observ. | 741.5 |
| Retention Time | 2.09 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

Preparation of 4005, $N^2$-((2-(4-((4-((1-(4-chlorophenyl)cyclopropyl)amino)-6-(2,2,2-trifluoroethoxy)-1,3,5-triazin-2-yl)amino)benzamido)cyclopentyl)methyl)-$N^2$-(cyclopropylmethyl)oxalamide A mixture of ethyl 2-(((2-(4-((4-((1-(4-chlorophenyl)cyclopropyl)amino)-6-(2,2,2-trifluoroethoxy)-1,3,5-triazin-2-yl)amino)benzamido)cyclopentyl)methyl)amino)-2-oxoacetate (30 mg) and cyclopropylmethanamine (31.6 mg) in EtOH (2 mL) was stirred at room temperature for 16 hours. Then, the product 4005 was isolated by preparative HPLC system.

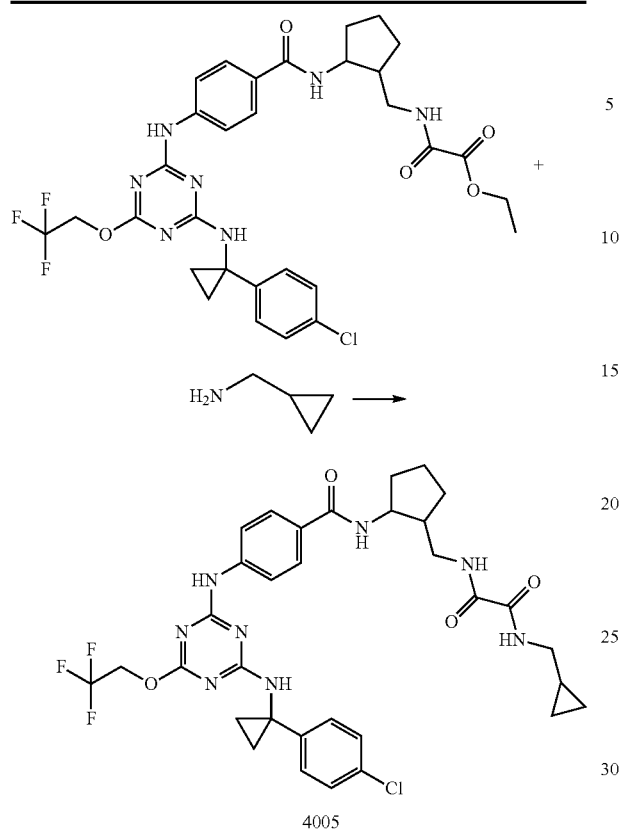

4005

| Compound 4005 | |
|---|---|
| MS (M + H)+ Calcd. | 701.3 |
| MS (M + H)+ Observ. | 701.5 |
| Retention Time | 1.98 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

Preparation of 3492, (R)-4-(4-((4-((1-(4-chlorophenyl)cyclopropyl)amino)-6-(2,2,2-trifluoroethoxy)-1,3,5-triazin-2-yl)amino)benzamido)-2-(2-((3-fluorophenyl)amino)-2-oxoacetamido)butanoic acid Step 1: N,N-Di-iso-propylethylamine (0.054 g) and 2-(3H-[1,2,3]triazolo[4,5-b]pyridin-3-yl)-1,1,3,3-tetramethylisouronium hexafluorophosphate(V) (0.079 g) were added into a solution of 4-((4-((1-(4-chlorophenyl)cyclopropyl)amino)-6-(2,2,2-trifluoroethoxy)-1,3,5-triazin-2-yl)amino)benzoic acid (0.1 g) and (R)-4-amino-2-((tert-butoxycarbonyl)amino)butanoic acid (0.045 g) in DMF (1 mL). The reaction was stirred at room temperature for 16 hours and (R)-2-((tert-butoxycarbonyl)amino)-4-(4-((4-((1-(4-chlorophenyl)cyclopropyl)amino)-6-(2,2,2-trifluoroethoxy)-1,3,5-triazin-2-yl)amino)benzamido)butanoic acid was isolated by using preparative HPLC system.

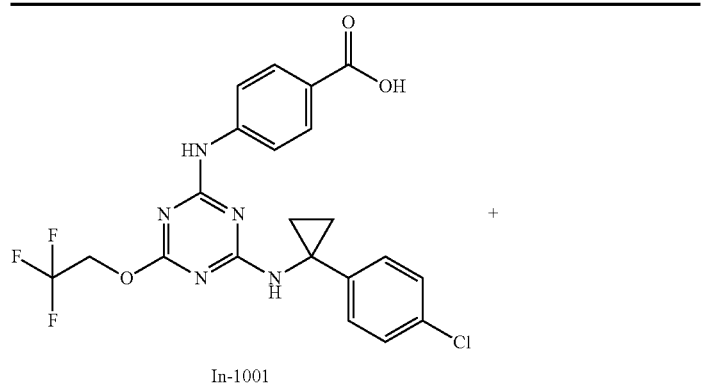

In-1001

+

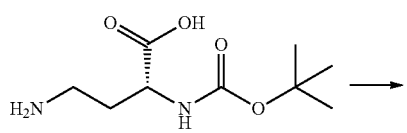

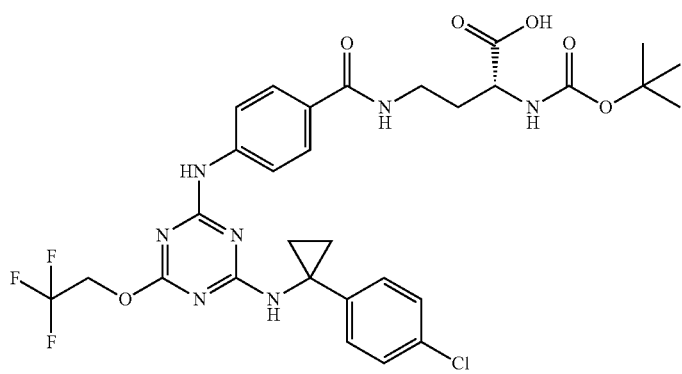 [SMILES: CC(C)(C)OC(=O)N[C@H](CCNC(=O)c1ccc(Nc2nc(NC3(c4ccc(Cl)cc4)CC3)nc(OCC(F)(F)F)n2)cc1)C(=O)O]

(R)-2-((tert-butoxycarbonyl)amino)-4-(4-((4-((1-(4-chlorophenyl)cyclopropyl)amino)-6-(2,2,2-trifluoroethoxy)-1,3,5-triazin-2-yl)amino)benzamido)butanoic acid

| | |
|---|---|
| MS (M + H)+ Calcd. | 680.2 |
| MS (M + H)+ Observ. | 680.2 |
| Retention Time | 1.55 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

Step 2: TFA (0.340 mL) was added into a solution of (R)-2-((tert-butoxycarbonyl)amino)-4-(4-((4-((1-(4-chlorophenyl)cyclopropyl)amino)-6-(2,2,2-trifluoroethoxy)-1,3,5-triazin-2-yl)amino)benzamido)butanoic acid (0.2 g) in DCM (1 mL). The reaction was stirred at room temperature for 2 hours. After removal of solvents, the residue was purified by preparative HPLC system.

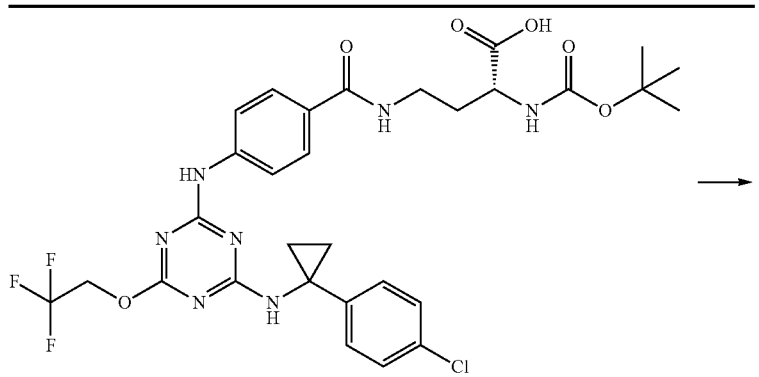

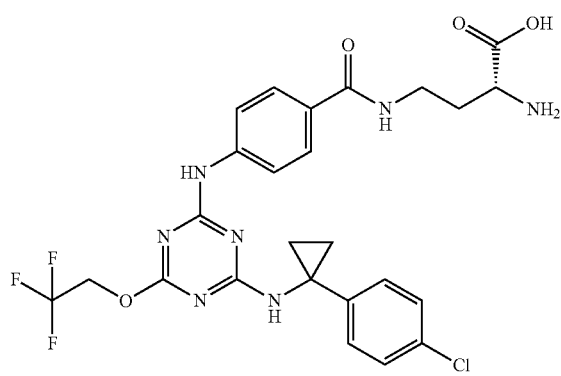 [SMILES: N[C@H](CCNC(=O)c1ccc(Nc2nc(NC3(c4ccc(Cl)cc4)CC3)nc(OCC(F)(F)F)n2)cc1)C(=O)O]

(R)-2-amino-4-(4-((4-((1-(4-chlorophenyl)cyclopropyl)amino)-6-(2,2,2-trifluoroethoxy)-1,3,5-triazin-2-yl)amino)benzamido)butanoic acid

| | |
|---|---|
| MS (M + H)+ Calcd. | 580.2 |
| MS (M + H)+ Observ. | 580.2 |
| Retention Time | 1.52 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

Step 3: iPr$_2$NEt (8.91 mg) and 2-(3H-[1,2,3]triazolo[4,5-b]pyridin-3-yl)-1,1,3,3-tetramethylisouronium hexafluorophosphate(V) (0.013 g) were added into a solution of (R)-2-amino-4-(4-((4-((1-(4-chlorophenyl)cyclopropyl)amino)-6-(2,2,2-trifluoroethoxy)-1,3,5-triazin-2-yl)amino)benzamido)butanoic acid (0.020 g) and 2-((3-fluorophenyl)amino)-2-oxoacetic acid (6.32 mg) in DMF (1 mL). The reaction was stirred at room temperature for 1 hour and compound 3492 was isolated by using preparative HPLC system.

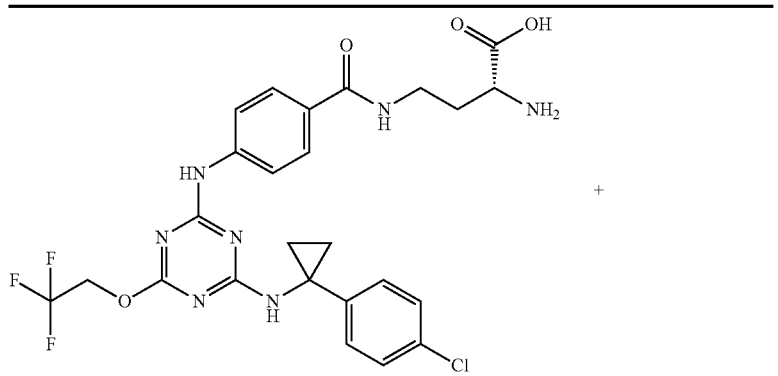

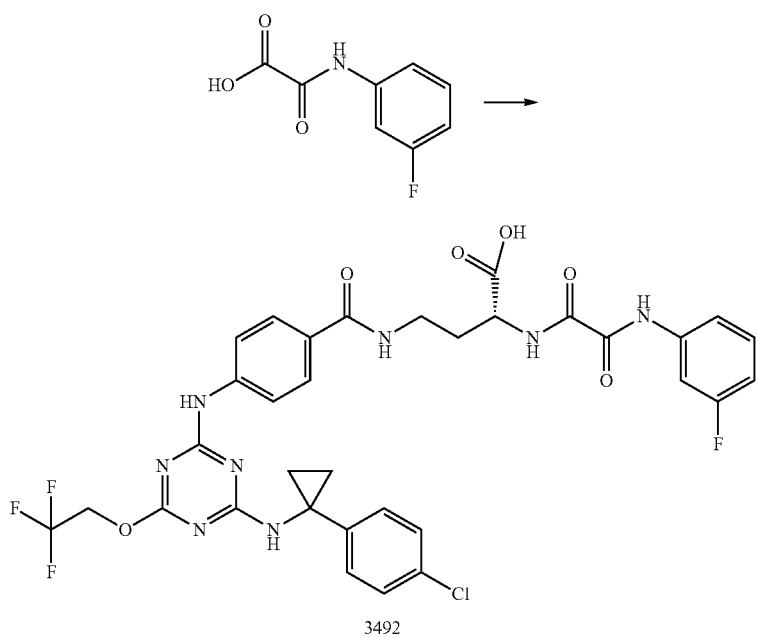

3492

| Compound 3492 | |
|---|---|
| MS (M + H)+ Calcd. | 745.2 |
| MS (M + H)+ Observ. | 745.2 |
| Retention Time | 1.61 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex Luna C18, 30 × 2, 3 u |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of formula I

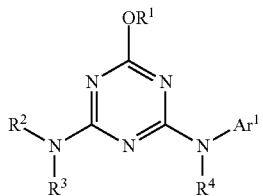

where:
R¹ is alkyl, hydroxyalkyl, alkoxyalkyl, haloalkyl, cycloalkyl, hydroxycycloalkyl, alkoxycycloalkyl, halocycloalkyl, cycloalkenyl, indanyl, alkylcarbonyl, or benzyl wherein the benzyl moiety is substituted with 0-3 substituents selected from cyano, halo, alkyl, haloalkyl, cycloalkyl, alkenyl, alkynyl, hydroxy, alkoxy, and haloalkoxy;
R² is alkyl, cycloalkyl, (Ar²)alkyl, (Ar²)cycloalkyl, ((Ar²)cycloalkyl)alkyl, ((Ar²)alkyl)cycloalkyl, or (((Ar²)alkyl)cycloalkyl)alkyl;
R³ is hydrogen, alkyl, or cycloalkyl;
R⁴ is hydrogen, alkyl, or cycloalkyl;
R⁵ is

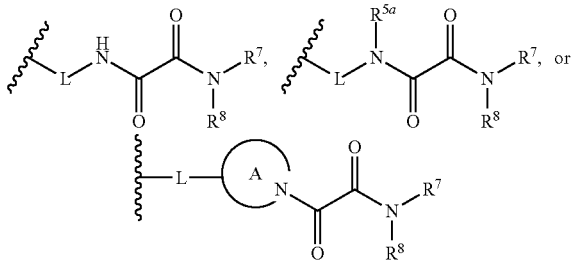

where ring A is a 4 to 7 membered alkylene ring attached to the indicated nitrogen atom and bonded to L;
R⁵ᵃ is alkyl or benzyl wherein the benzyl is substituted with 0-3 substituents selected from the group consisting of halo, alkyl, haloalkyl, cycloalkyl, hydroxyalkyl, alkoxyalkyl, hydroxy, alkoxy, and haloalkoxy;
R⁶ is hydrogen, alkyl, or cycloalkyl;
R⁷ is alkyl, cycloalkyl, benzocycloalkyl, bicycloalkyl, (cycloalkyl)alkyl, (alkyl)cycloalkyl, ((alkyl))cycloalkyl)alkyl, or bridged bicycloalkyl, and is substituted with 0-4 substituents selected from the group consisting of halo, alkyl, cycloalkyl, benzocycloalkyl, bicycloalkyl, hydroxyalkyl, alkoxyalkyl, hydroxy, alkoxy, benzyloxy, $NR^9CO_2R^{11}$, $N(R^{10})(R^{11})$, $CO_2R^9$, $CON(R^{10})(R^{11})$, $NR^9CON(R^{10})(R^{11})$, $SO_2N(R^{10})(R^{11})$, tetrahydrofuranyl, tetrahydropyranyl, $Ar^3$, $OAr^3$, $NR^{13}Ar^3$, $N(R^{13})COAr^3$, $N(R^{13})COAr^3$, and $N(R^{13})SO_2Ar^3$;
or R⁷ is hydrogen, N-alkoxycarbonylpiperidinyl, piperidinonyl, or Ar⁴;
R⁸ is hydrogen, alkyl, or cycloalkyl wherein alkyl or cycloalkyl is substituted with 0-4 substituents selected from the group consisting of halo, alkyl, cycloalkyl, fused bicycloalkyl, bridged bicycloalkyl, spirocycloalkyl, hydroxyalkyl, alkoxyalkyl, hydroxy, alkoxy, benzyloxy, $CO_2R^9$, $N(R^{10})(R^{11})$, tetrahydrofuranyl, tetrahydropyranyl, $Ar^3$, $OAr^3$, $NR^{13}Ar^3$, $N(R^{13})COAr^3$, and $N(R^{13})SO_2Ar^3$;

or R⁷ and R⁸ taken together with the nitrogen to which they are attached is azetidinyl, pyrrolidinyl, piperidinyl, piperazinyl, morpholinyl, thiomorpholinyl, 1,1-dioxothiomorpholinyl, tetrahydroquinolinyl, tetrahydroisoquinolinyl, indolinyl, or isoindolinyl, and is substituted with 0-2 substituents selected from alkyl, alkylcarbonyl, and alkoxycarbonyl;
R⁹ is hydrogen, alkyl, cycloalkyl, hydroxyalkyl, alkoxyalkyl, ((hydroxyalkyl)alkoxy)alkoxy, ((alkoxy)alkoxy)alkoxy, or Ar³;
R¹⁰ is hydrogen, alkyl, cycloalkyl, alkylcarbonyl, alkoxycarbonyl, or Ar⁶;
R¹¹ is hydrogen, alkyl, cycloalkyl, or Ar⁶;
or R¹⁰ and R¹¹ taken together with the nitrogen to which they are attached is azetidinyl, pyrrolidinyl, piperidinyl, piperazinyl, morpholinyl, thiomorpholinyl, 1,1-dioxothiomorpholinyl, tetrahydroquinolinyl, tetrahydroisoquinolinyl, indolinyl, or isoindolinyl, and is substituted with 0-2 substituents selected from alkyl, alkylcarbonyl, and alkoxycarbonyl;
R¹² is hydrogen, alkyl, cycloalkyl, or Ar⁶;
R¹³ is hydrogen, alkyl, cycloalkyl, alkylcarbonyl, alkoxycarbonyl, or Ar⁶, and is substituted with 0-3 substituents selected from cyano, halo, alkyl, alkyenyl, haloalkyl, alkoxy, and haloalkoxy, $N(R^{15})(R^{16})$, and alkylCO;
R¹⁴ is hydrogen, alkyl, cycloalkyl, or Ar⁶;
or R¹³ and R¹⁴ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl, or isoindolinyl, and is substituted with 0-2 substituents selected from alkyl, alkylcarbonyl, and alkoxycarbonyl;
R¹⁵ is hydrogen, alkyl, cycloalkyl, alkylcarbonyl, or alkoxycarbonyl;
R¹⁶ is hydrogen, alkyl or cycloalkyl;
or R¹⁵ and R¹⁶ taken together with the nitrogen to which they are attached is azetidinyl, pyrrolidinyl, piperidinyl, piperazinyl, morpholinyl, thiomorpholinyl, thiomorpholine 1,1-dioxide, tetrahydroquinolinyl, tetrahydroisoquinolinyl, indolinyl, or isoindolinyl, and is substituted with 0-2 substituents selected from alkyl, alkylcarbonyl, and alkoxycarbonyl;
L is alkylene, cycloalkylene, (cycloalkyl)alkyl, (alkyl)cycloalkyl, or alkyl(cycloalkyl)alkyl, and is substituted with 0-2 substituents selected from alkoxy, hydroxy, $CO_2R^{12}$ and $CONR^{13}R^{14}$;
Ar¹ is phenyl substituted with 1 $CON(R^5)(R^6)$ and with 0-3 substituents selected from cyano, halo, alkyl, haloalkyl, cycloalkyl, hydroxy, alkoxy, haloalkoxy, and Ar³;
Ar² is phenyl substituted with 0-3 substituents selected from cyano, halo, alkyl, haloalkyl, alkenyl, alkynyl, cycloalkyl, hydroxy, alkoxy, and haloalkoxy;
Ar³ is phenyl, biphenyl, terphenyl, naphthalenyl, furanyl, benzofuranyl, fluorenyl, fluorenonyl, thiophenyl, benzothiophenyl, pyrrolyl, indolyl, indanyl, pyridinyl, quinolinyl, azaquinolinyl, isoquinolinyl, azaisoquinolinyl, quinoxalinyl, azaquinoxalinyl, pyrimidinyl, quinazolinyl, azaquinazolinyl, pyrazolyl, indazolyl, azaindolyl, oxazolyl, benzoxazolyl, azabenzoxazolyl, isoxazolyl, benzoisoxazolyl, azabenzoisoxazolyl, imidazolyl, benzoimidazolyl, azabenzoimidazolyl, thiazolyl, benzothiazolyl, azabenzothiazolyl, isothiazolyl, benzoisothiazolyl, azabenzoisothiazolyl, oxadiazolyl, thiadiazolyl, triazolyl, benzotriazolyl, azabenzotriazolyl, tetrazolyl, indolinyl, chromenonyl, or dibenzofuranyl, and is substituted with 0-5 substituents selected from cyano, halo, alkyl, cycloalkyl, alkenyl, alkynyl, haloalkyl, cycloalkyl, $(CO_2R^{12})$alkyl, $(CO_2R^{12})$alkenyl, $(CON(R^{13})(R^{14}))$alkyl, phenyl, hydroxy, alkoxy, $Ar^5$, $OAr^5$, $NR^{13}Ar^5$, $N(R^{13})COAr^5$, $N(R^{13})SO_2Ar^5$, alkylthio, haloalkoxy, haloalkylthio, alkylcarbonyl, $CO_2R^{12}$, $COR^{12}$, $SO_2R^{12}$, $CON(R^{13})(R^{14})$, $SO_2N(R^{13})(R^{14})$, $N(R^{13})(R^{14})$, and $PhCONHSO_2$;

or $Ar^3$ is phenyl substituted with 1 substituent selected from benzyl, phenoxy, pyridyloxy, pyrimidyloxy, tetrazolyloxy, thiazolyl, phenylpyrazolyl, methyloxadiazolyl, thiadiazolyl, triazolyl, methyltriazolyl, tetrazolyl, pyridinyl, dimethoxypyrimdinyl, indolyl, indolinyl, and isoindolinyl;

$Ar^4$ is phenyl, indanyl, tetrahydronaphthyl, isochromanyl, benzodioxolyl, pyridinyl, pyrazolyl, imidazolyl, or triazolyl, and is substituted with 0-3 substituents selected from cyano, halo, alkyl, alkyenyl, haloalkyl, alkoxy, haloalkoxy, $N(R^{13})(R^{14})$, and alkylCO;

$Ar^5$ is phenyl, naphthalenyl, furanyl, benzofuranyl, azabenzofuranyl, thiophenyl, benzothiophenyl, azabenzothiophenyl, pyrrolyl, indolyl, azaindolyl, indanyl, pyridinyl, quinolinyl, azaquinolinyl, isoquinolinyl, azaisoquinolinyl, quinoxalinyl, azaquinoxalinyl, pyrimidinyl, quinazolinyl, azaquinazolinyl, pyrazolyl, indazolyl, azaindazolyl, oxazolyl, benzoxazolyl, azabenzoxazolyl, isoxazolyl, benzoisoxazolyl, azabenzoisoxazolyl, imidazolyl, benzoimidazolyl, azabenzoimidazolyl, thiazolyl, benzothiazolyl, azabenzothiazolyl, isothiazolyl, benzoisothiazolyl, azabenzothiazolyl, oxadiazolyl, thiadiazolyl, triazolyl, benzotriazolyl, azabenzotriazolyl, tetrazolyl, or indolinyl, and is substituted with 0-5 substituents selected from cyano, halo, alkyl, cycloalkyl, alkenyl, alkynyl, haloalkyl, cycloalkyl, $(CO_2R^{12})$alkyl, $(CO_2R^{12})$alkenyl, $(CON(R^{13})(R^{14}))$alkyl, phenyl, hydroxy, alkoxy, $OAr^6$, $NR^{13}Ar^6$, alkylthio, haloalkoxy, haloalkylthio, alkylcarbonyl, $CO_2R^{12}$, $COR^{12}$, $SO_2R^{12}$, $CON(R^{13})(R^{14})$, $SO_2N(R^{13})(R^{14})$, and $N(R^{13})(R^{14})$;

$Ar^6$ is phenyl, naphthalenyl, furanyl, benzofuranyl, azabenzofuranyl, thiophenyl, benzothiophenyl, azabenzothiophenyl, pyrrolyl, indolyl, azaindolyl, indanyl, pyridinyl, quinolinyl, azaquinolinyl, isoquinolinyl, azaisoquinolinyl, quinoxalinyl, azaquinoxalinyl, pyrimidinyl, quinazolinyl, azaquinazolinyl, pyrazolyl, indazolyl, azaindazolyl, oxazolyl, benzoxazolyl, azabenzoxazolyl, isoxazolyl, benzoisoxazolyl, azabenzoisoxazolyl, imidazolyl, benzoimidazolyl, azabenzoimidazolyl, thiazolyl, benzothiazolyl, azabenzothiazolyl, isothiazolyl, benzoisothiazolyl, azabenzothiazolyl, oxadiazolyl, thiadiazolyl, triazolyl, benzotriazolyl, azabenzotriazolyl, tetrazolyl, or indolinyl, and is substituted with 0-5 substituents selected from cyano, halo, alkyl, cycloalkyl, alkenyl, alkynyl, haloalkyl, cycloalkyl, phenyl, hydroxy, alkoxy, aryloxy, alkylthio, haloalkoxy, haloalkylthio, and alkylcarbonyl;

or a pharmaceutically acceptable salt thereof.

2. A compound of claim 1 where $R^1$ is haloalkyl or benzyl wherein the benzyl moiety is substituted with 0-3 substituents selected from halo, alkyl, haloalkyl, alkoxy, and haloalkoxy; $R^2$ is $(Ar^2)$alkyl or $(Ar^2)$cycloalkyl; $R^3$ is hydrogen; $R^4$ is hydrogen; $R^7$ is alkyl, cycloalkyl, (cycloalkyl)alkyl, (alkyl)cycloalkyl, ((alkyl))cycloalkyl)alkyl, or bridged bicycloalkyl, and is substituted with 0-4 substituents selected from the group consisting of halo, alkyl, cycloalkyl, hydroxyalkyl, alkoxyalkyl, hydroxy, alkoxy, benzyloxy, $CO_2R^9$, $N(R^{10})(R^{11})$, tetrahydrofuranyl, tetrahydropyranyl, $Ar^3$, $OAr^3$, $NR^{13}Ar^3$, $N(R^{13})COAr^3$, $N(R^{13})COAr^3$, $N(R^{13})SO_2Ar^3$ and $Ar^4$; L is

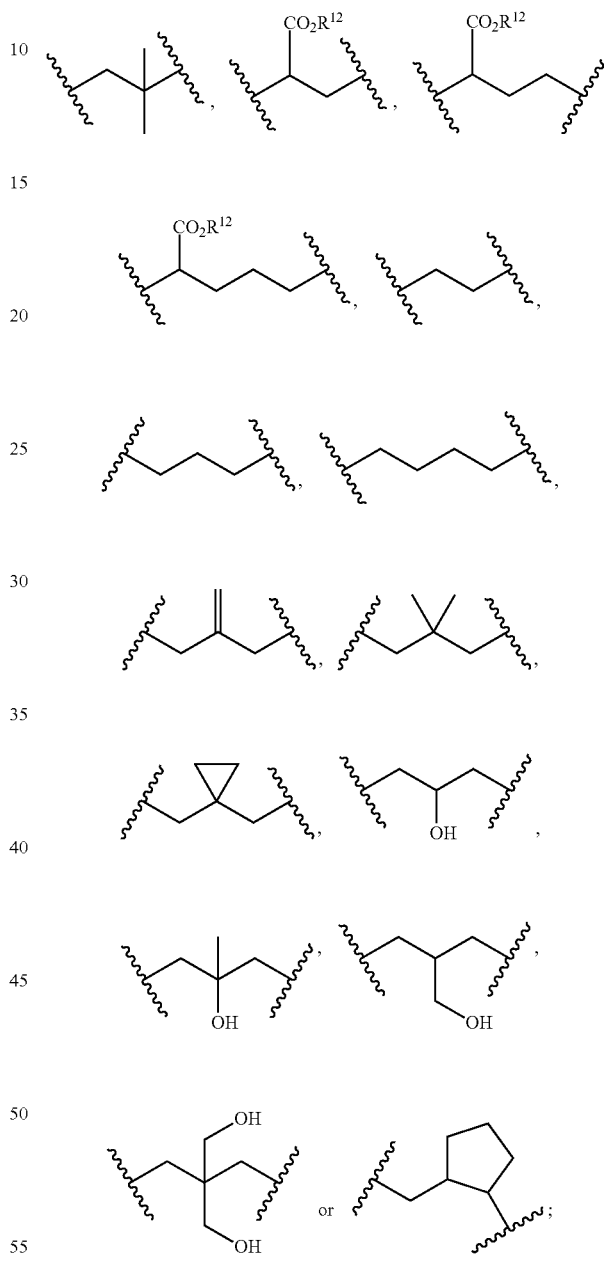

and $Ar^1$ is phenyl para-substituted with 1 $CON(R^5)(R^6)$, or a pharmaceutically acceptable salt thereof.

3. A compound of claim 2 where $R^1$ is haloalkyl or benzyl wherein the benzyl moiety is substituted with 0-3 substituents selected from halo, alkyl, haloalkyl, alkoxy, and haloalkoxy; $R^2$ is $(Ar^2)$alkyl or $(Ar^2)$cycloalkyl; $R^3$ is hydrogen; $R^4$ is hydrogen; $R^7$ is $Ar^3$ or $Ar^4$; L is

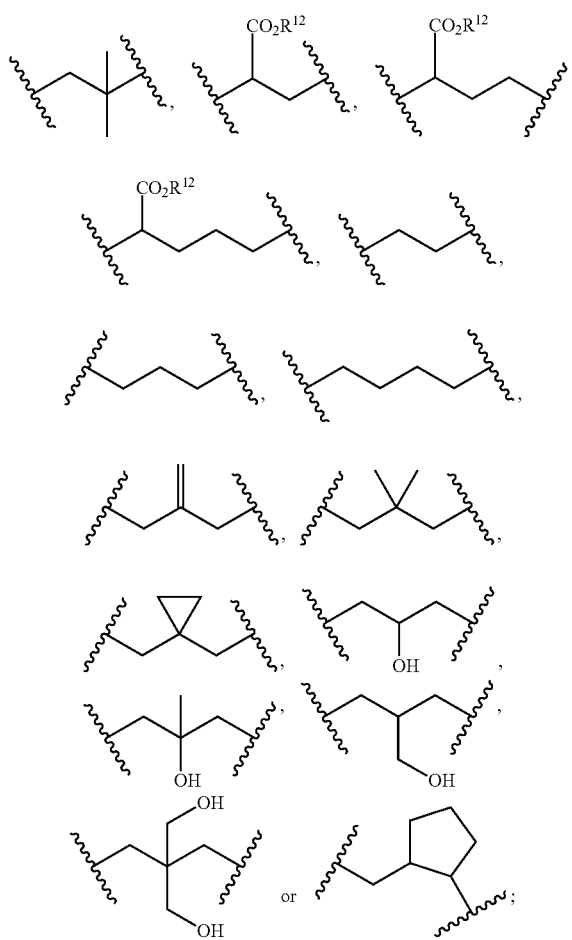

and Ar¹ is phenyl para-substituted with 1 $CON(R^5)(R^6)$, or a pharmaceutically acceptable salt thereof.

4. A compound of claim 1 where $R^1$ is trifluoroethyl or a pharmaceutically acceptable salt thereof.

5. A compound of claim 1 where $R^1$ is benzyl substituted with 0-5 halo, alkyl, alkenyl, haloalkyl, alkoxy or haloalkoxy substituents, or a pharmaceutically acceptable salt thereof.

6. A compound of claim 1 where $R^2$ is $(Ar^2)$alkyl or $(Ar^2)$ cycloalkyl, or a pharmaceutically acceptable salt thereof.

7. A compound of claim 1 where $R^3$ is hydrogen and $R^4$ is hydrogen, or a pharmaceutically acceptable salt thereof.

8. A compound of claim 1 where $R^7$ is $Ar^3$, or a pharmaceutically acceptable salt thereof.

9. A compound of claim 1 where $R^7$ is $Ar^4$, or a pharmaceutically acceptable salt thereof.

10. A compound of claim 1 where L is

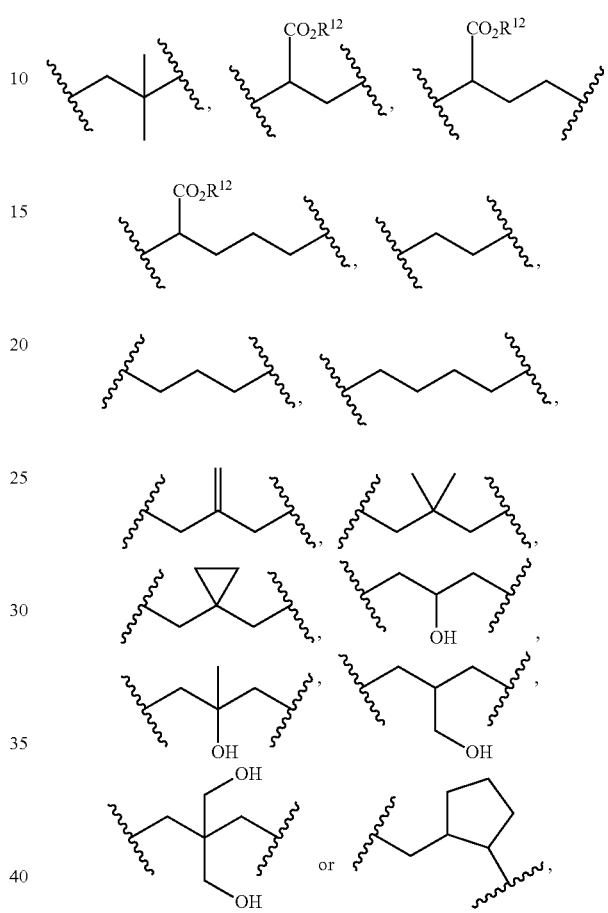

or a pharmaceutically acceptable salt thereof.

11. A compound of claim 1 where $Ar^1$ is phenyl para-substituted with 1 $CON(R^5)(R^6)$, or a pharmaceutically acceptable salt thereof.

12. A compound of claim 1 selected from the group consisting of

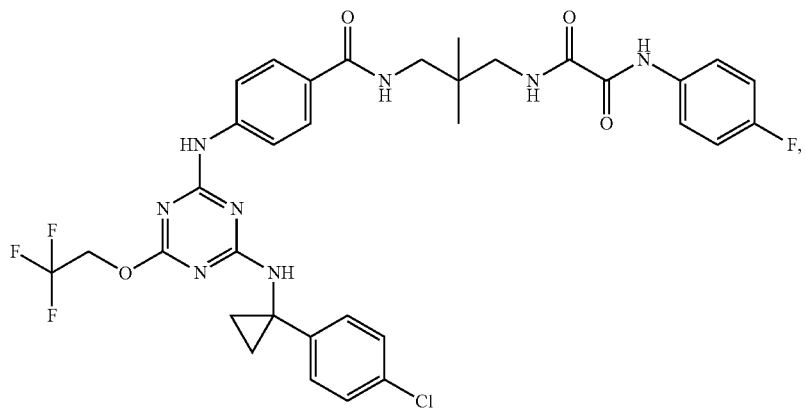

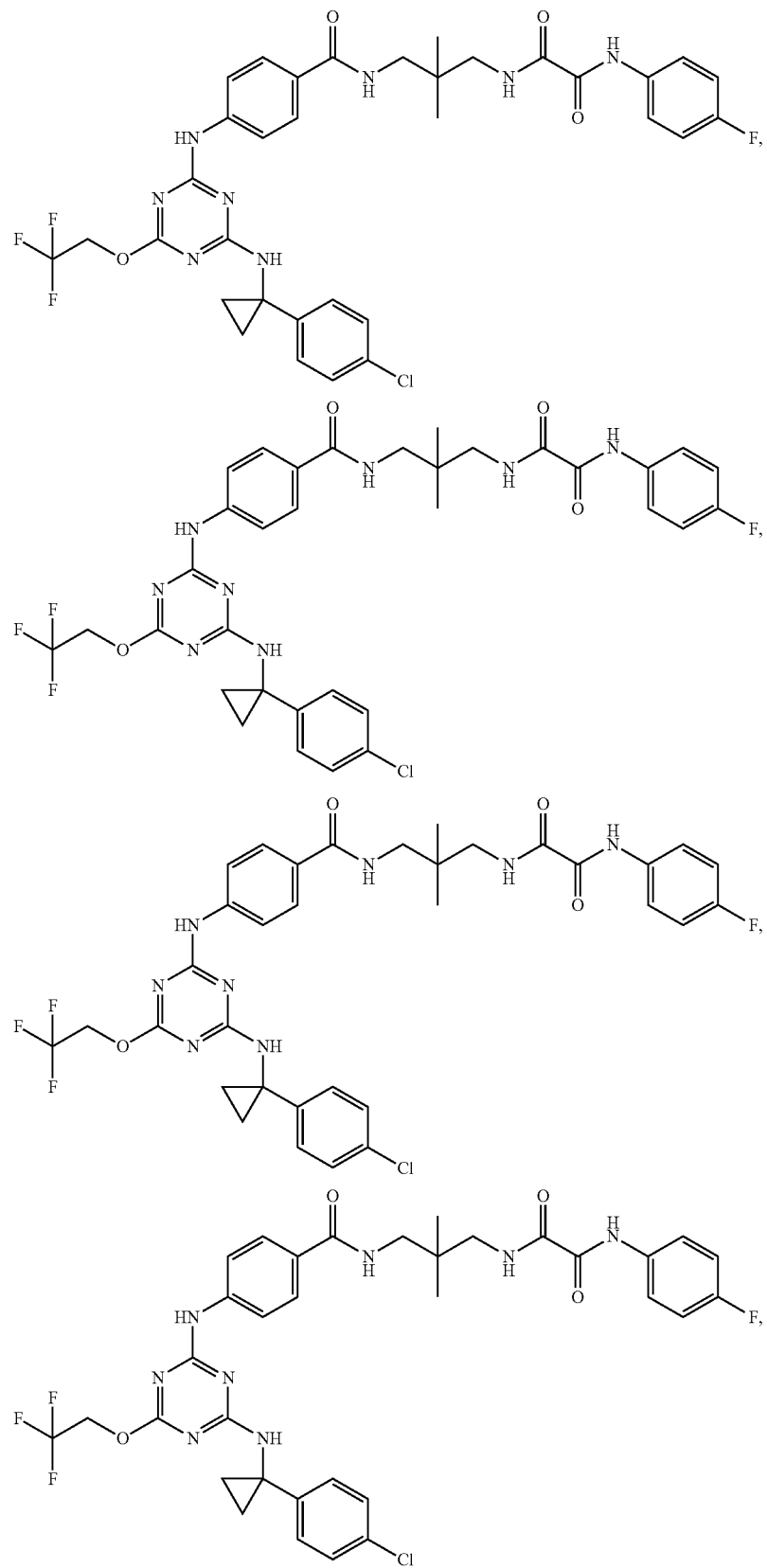

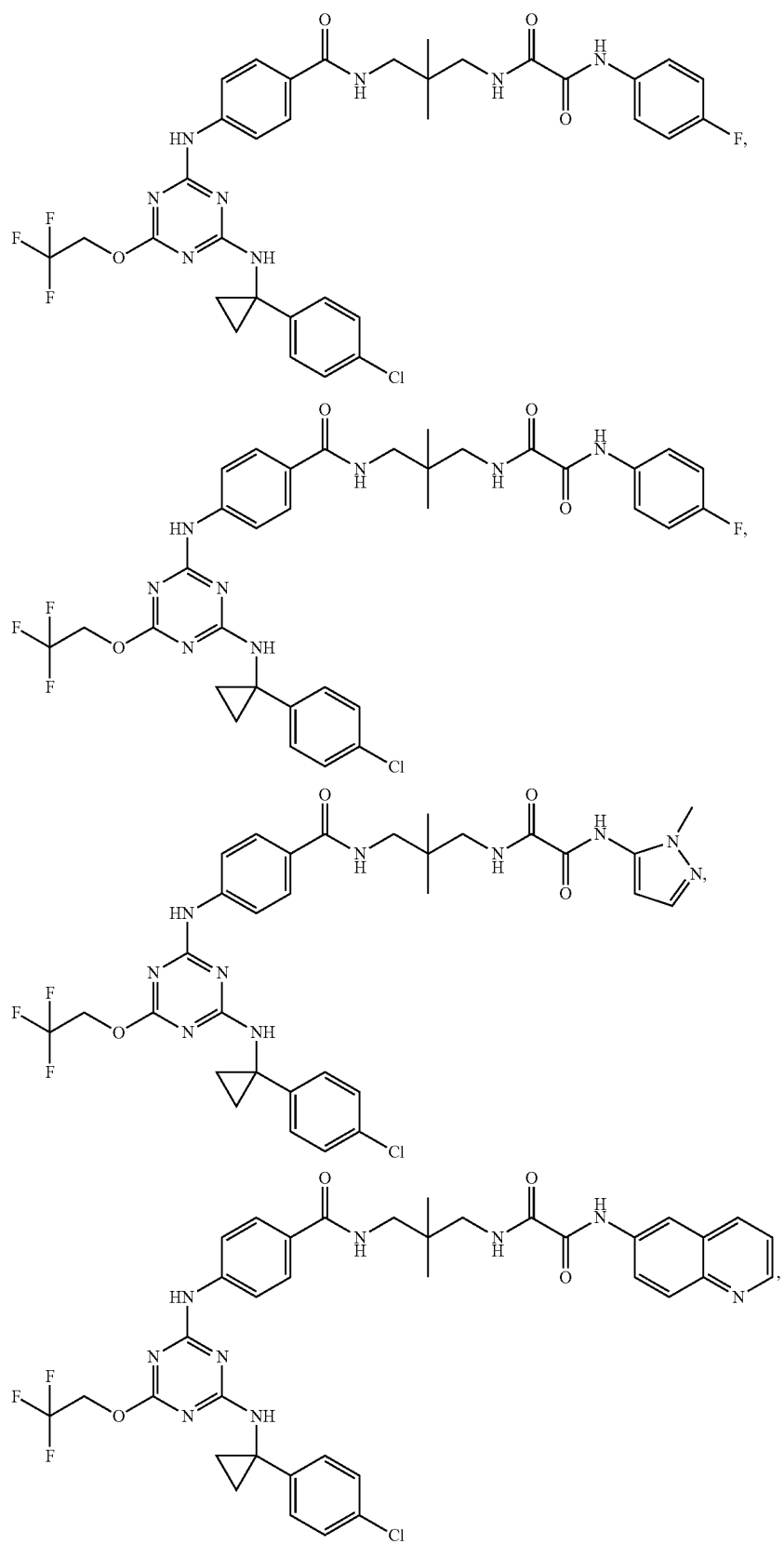

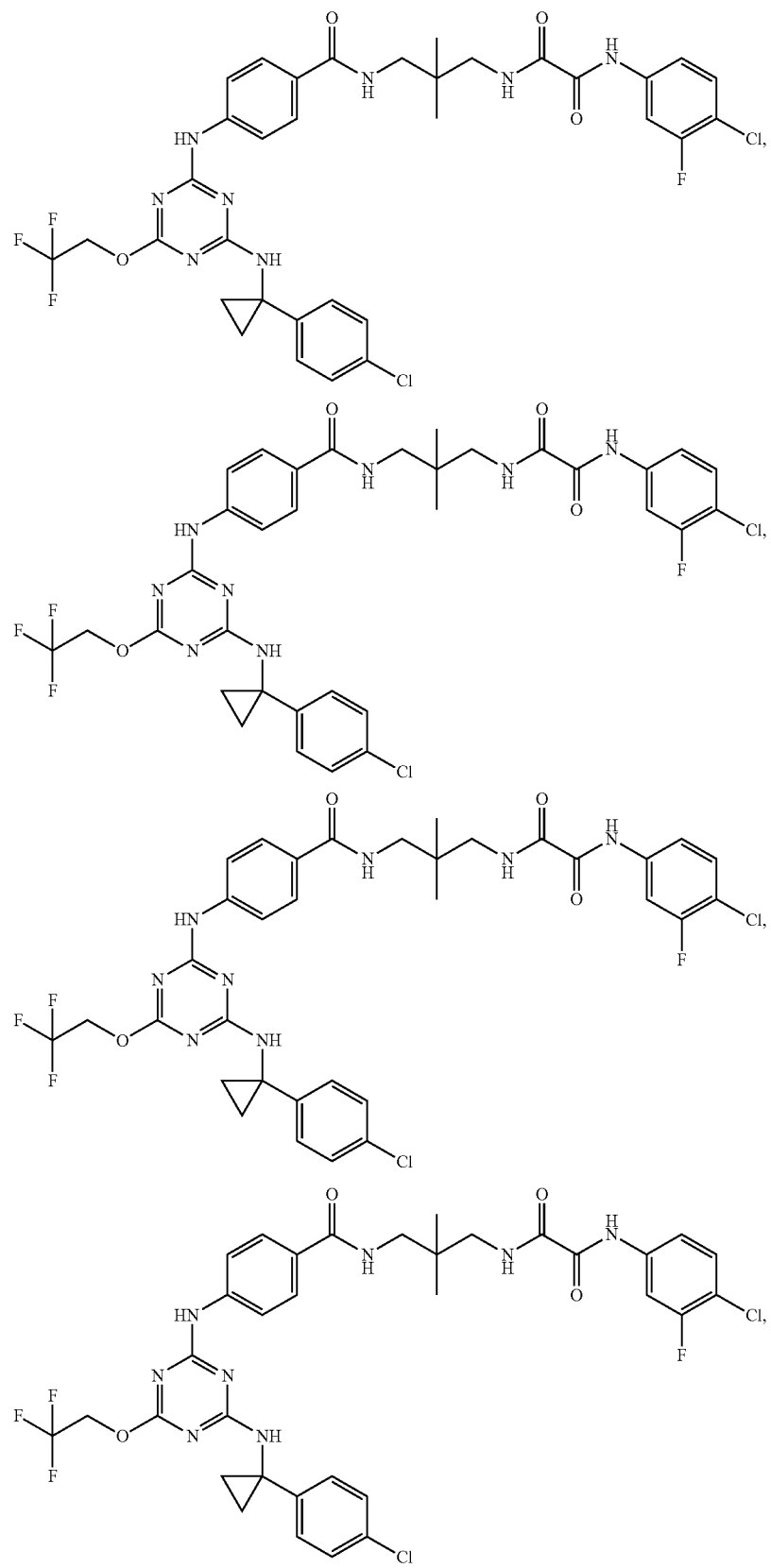

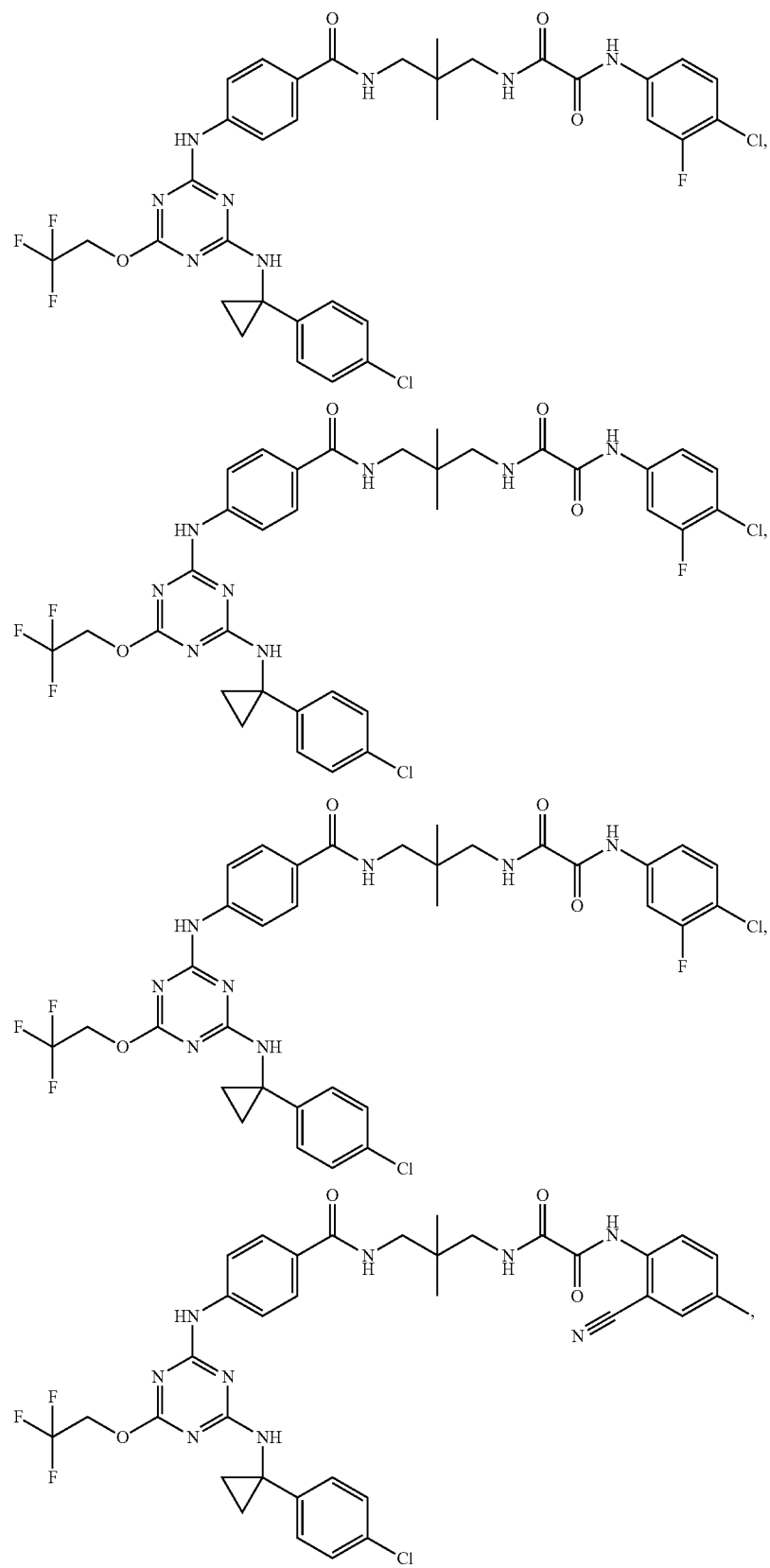

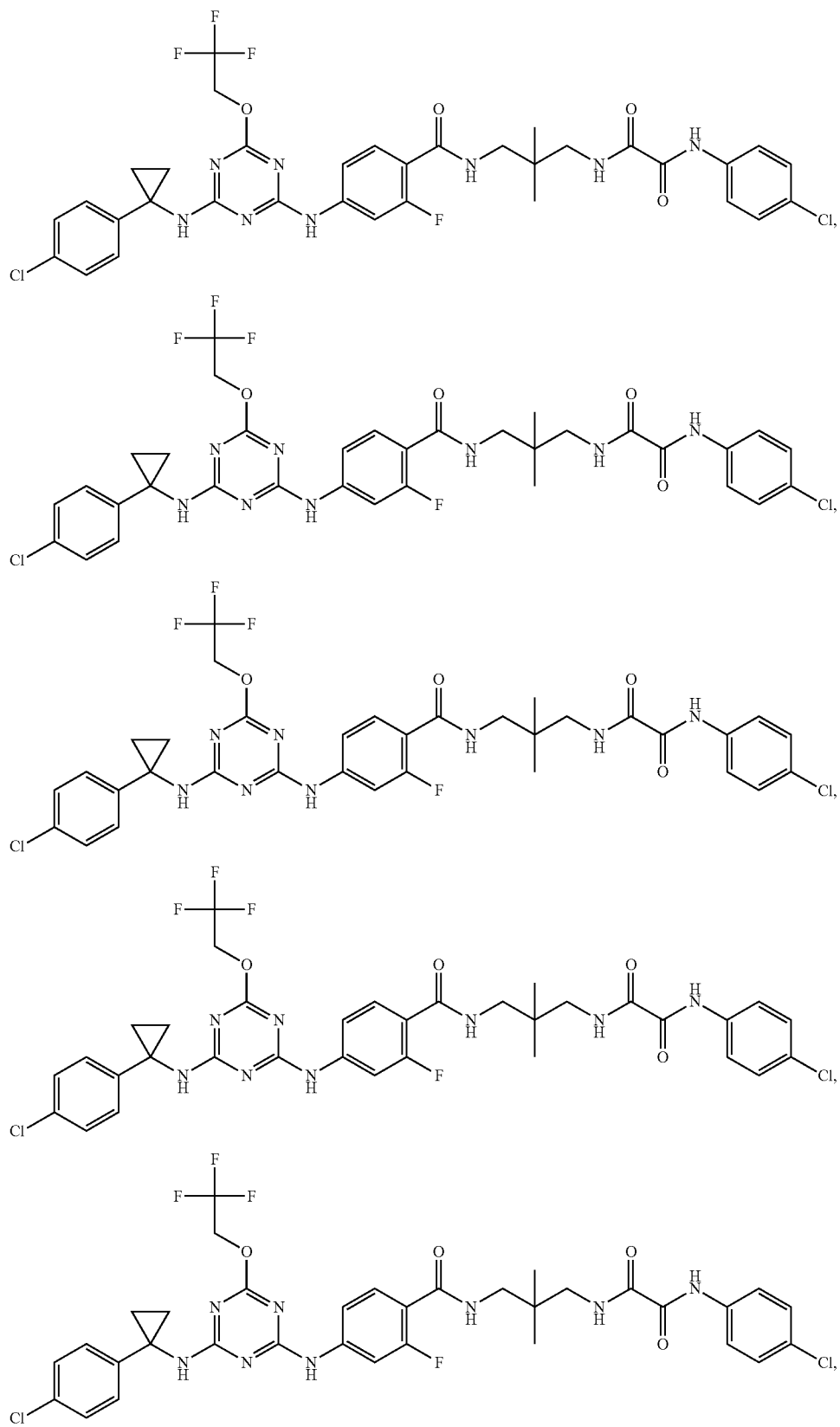

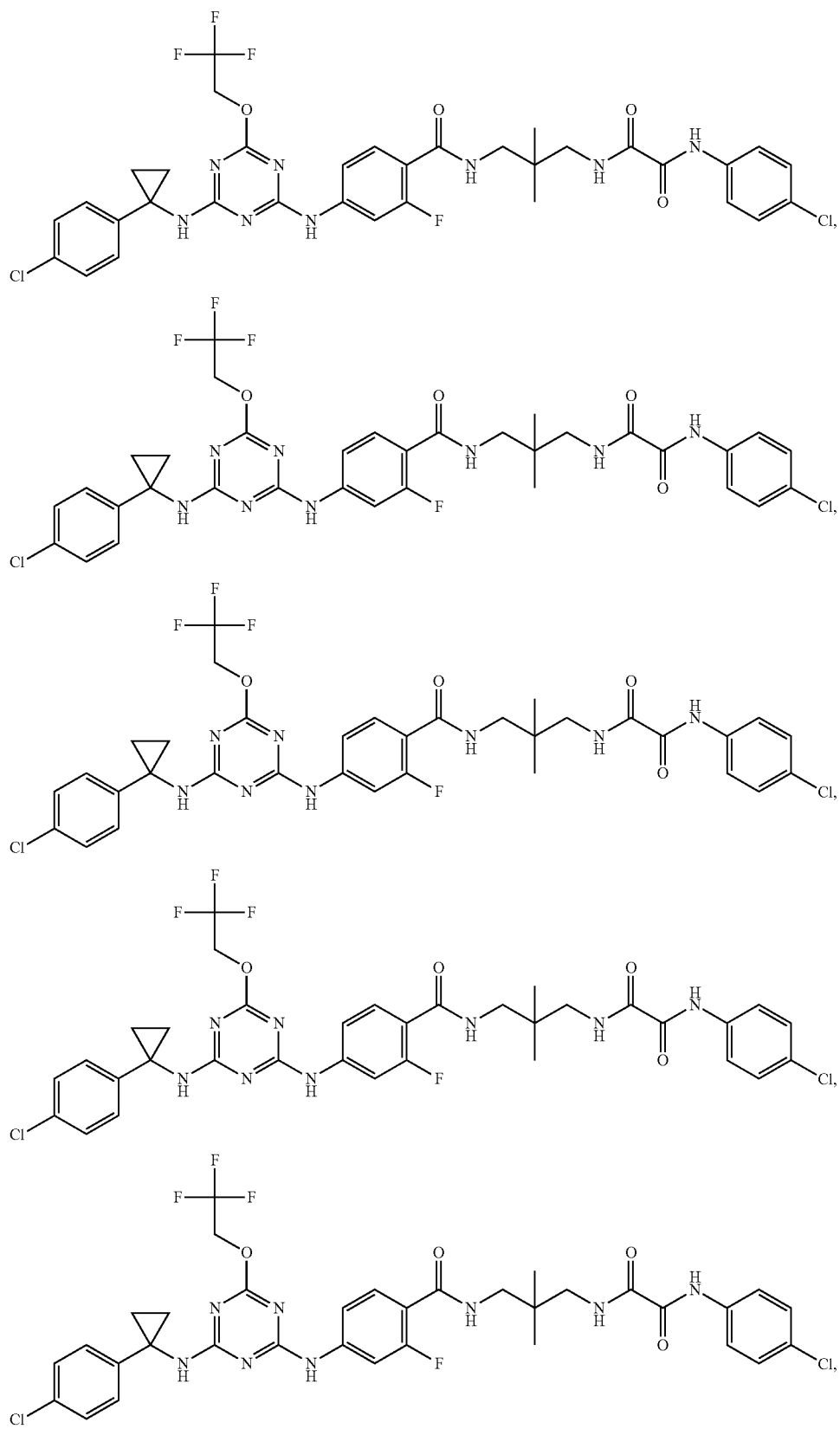

-continued
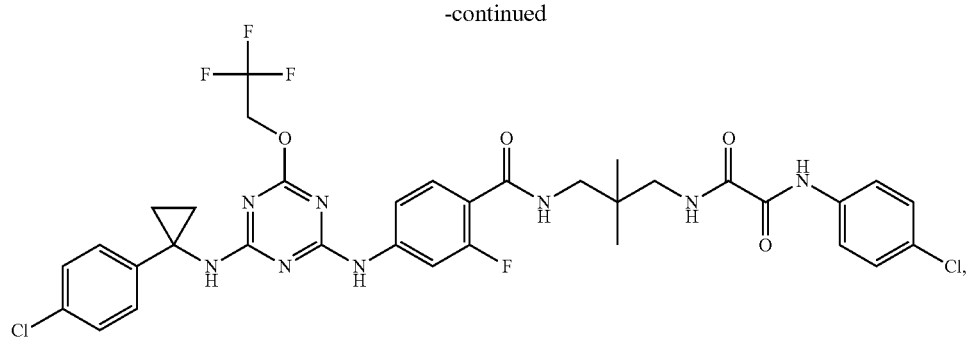
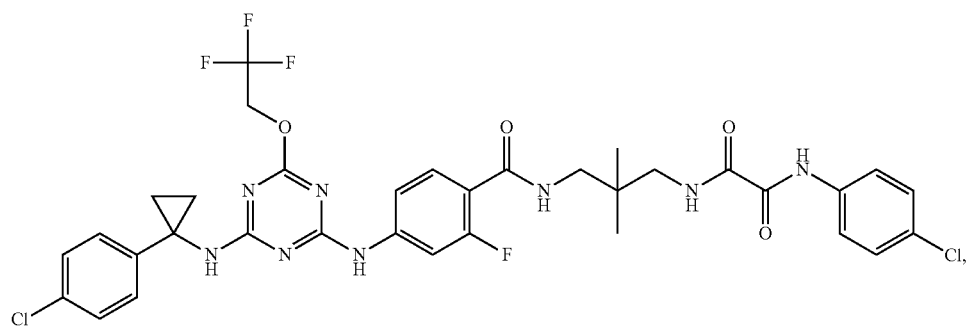
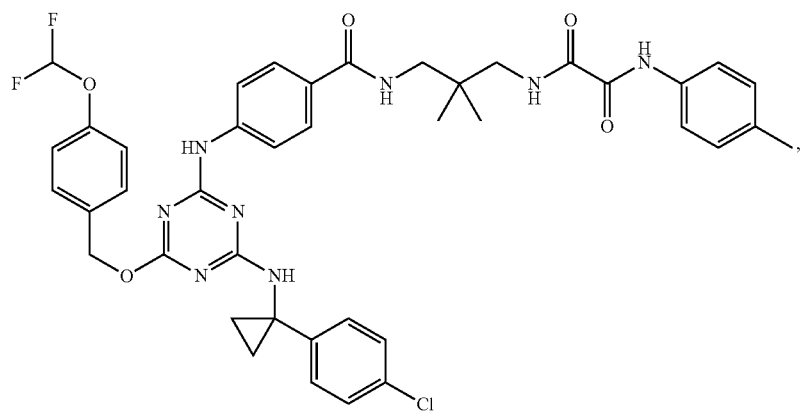
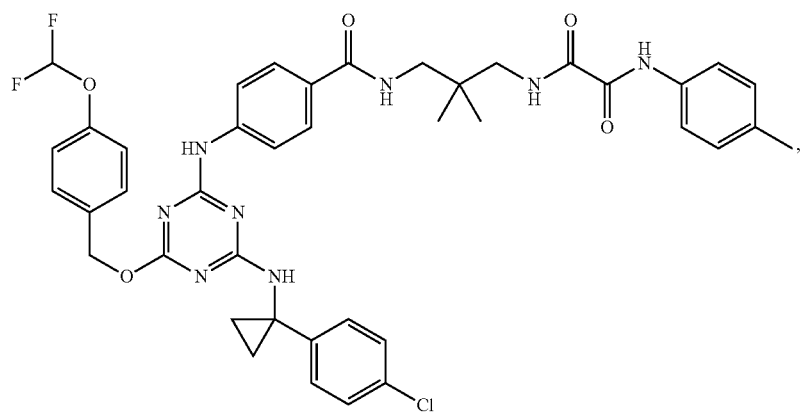

1711
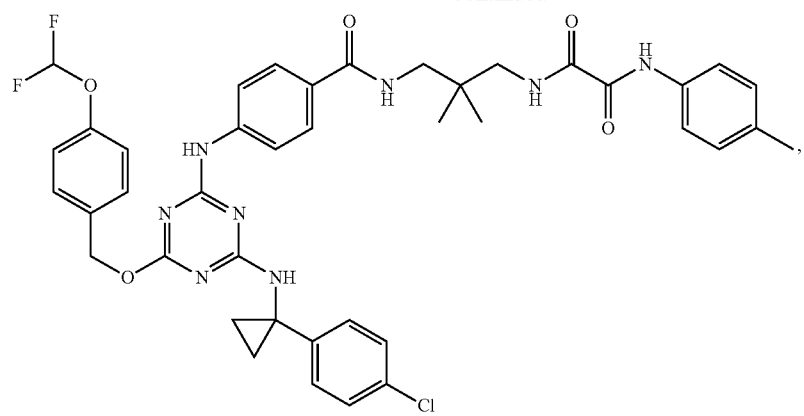
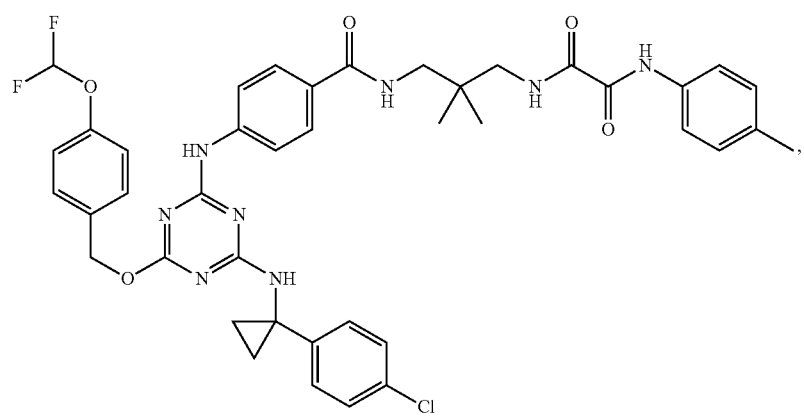
1712
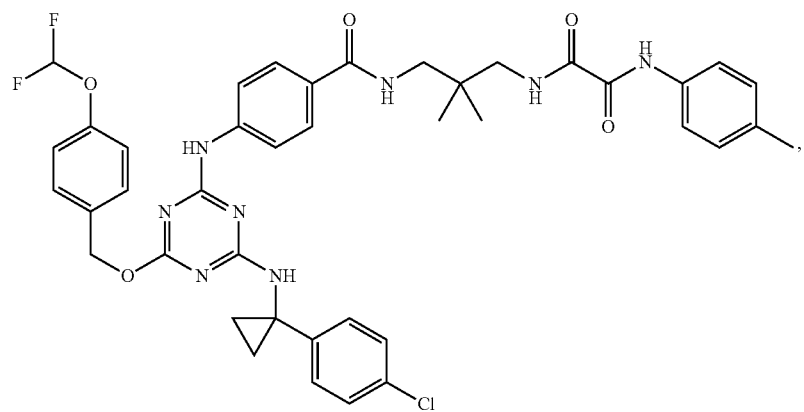
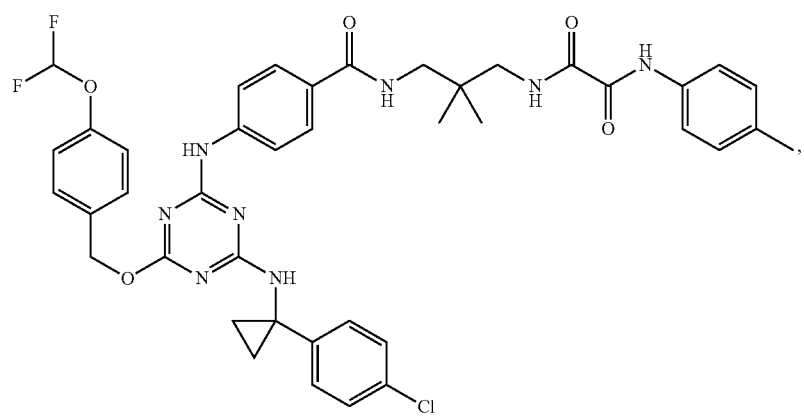

1713
-continued
1714
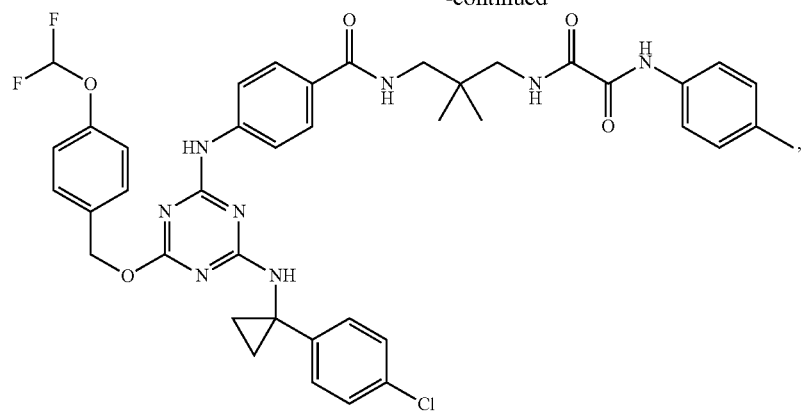
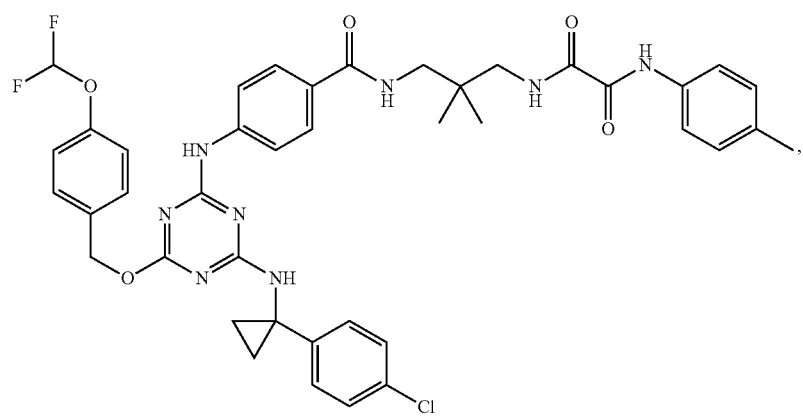
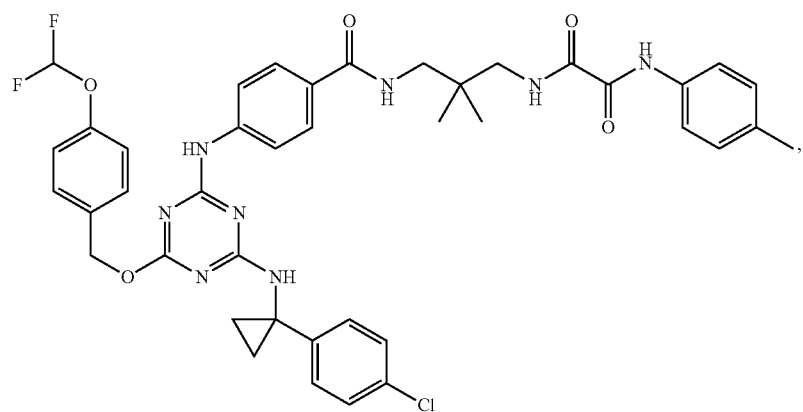
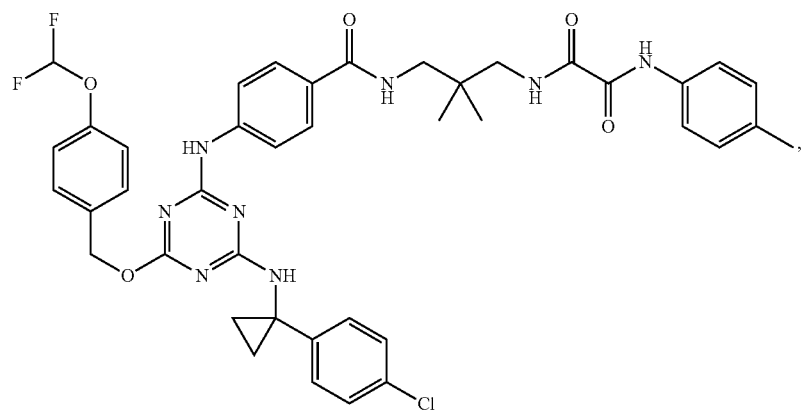

-continued
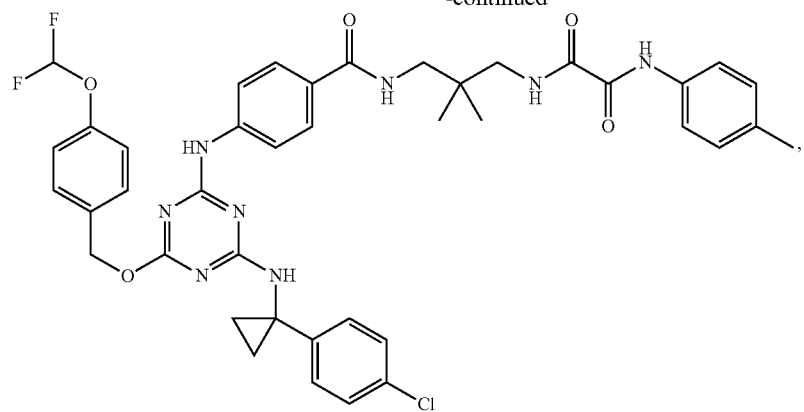
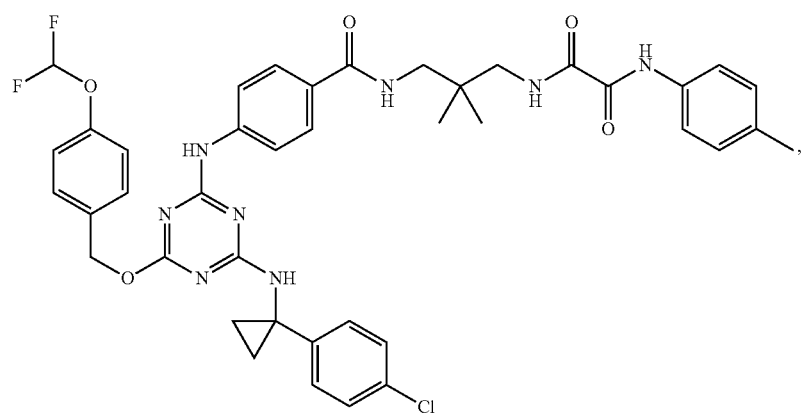
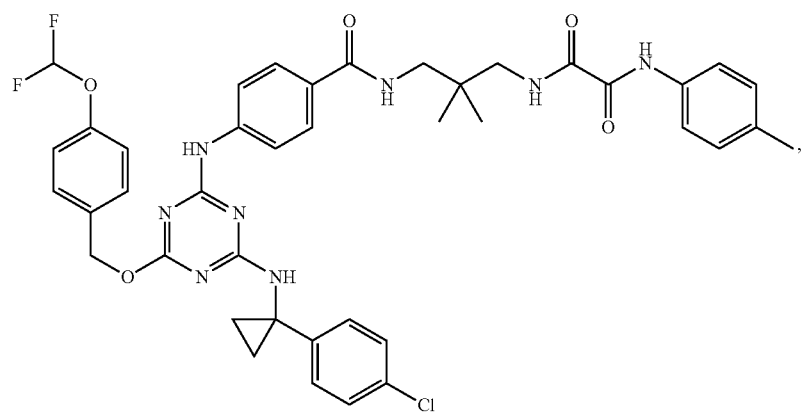
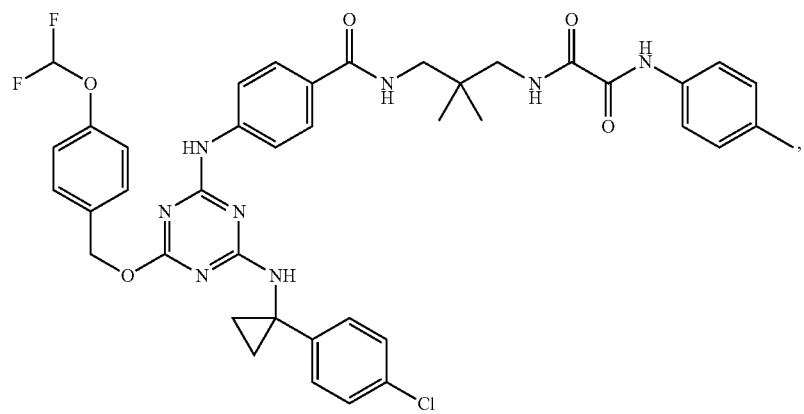

-continued
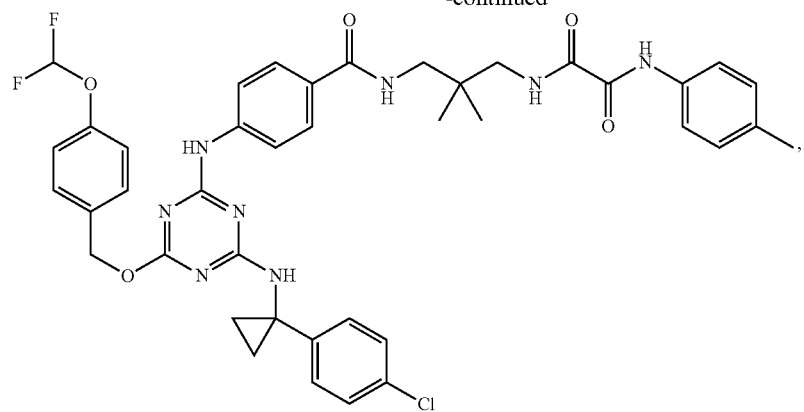
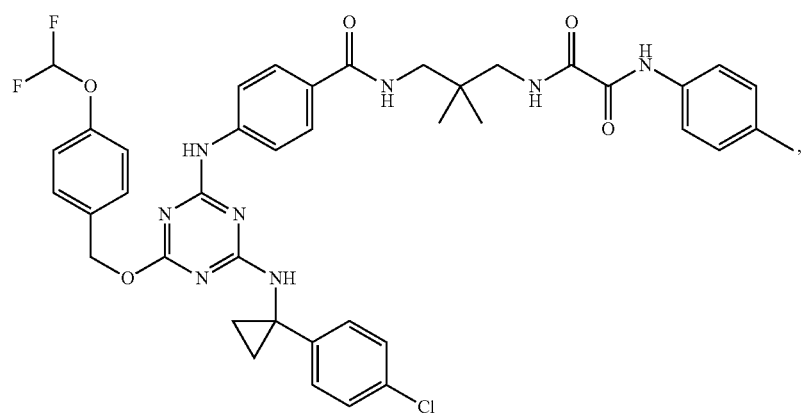
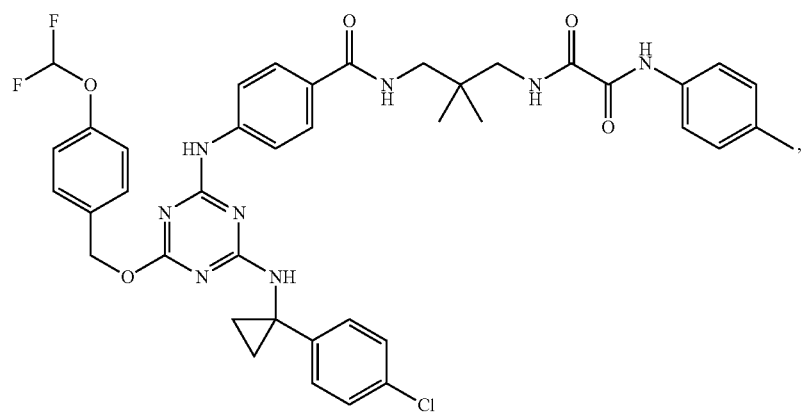
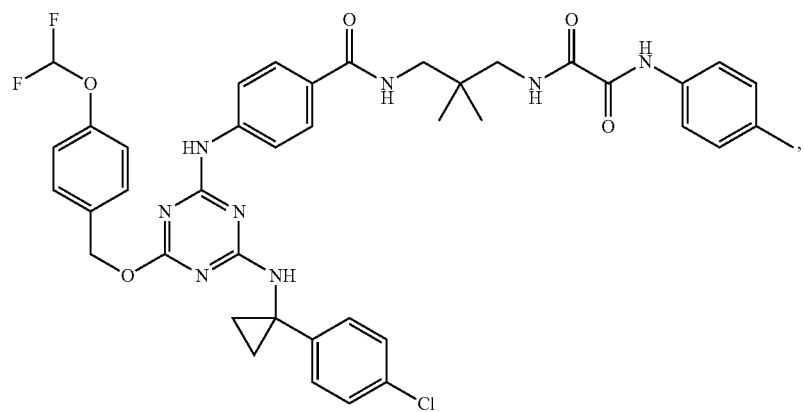

-continued

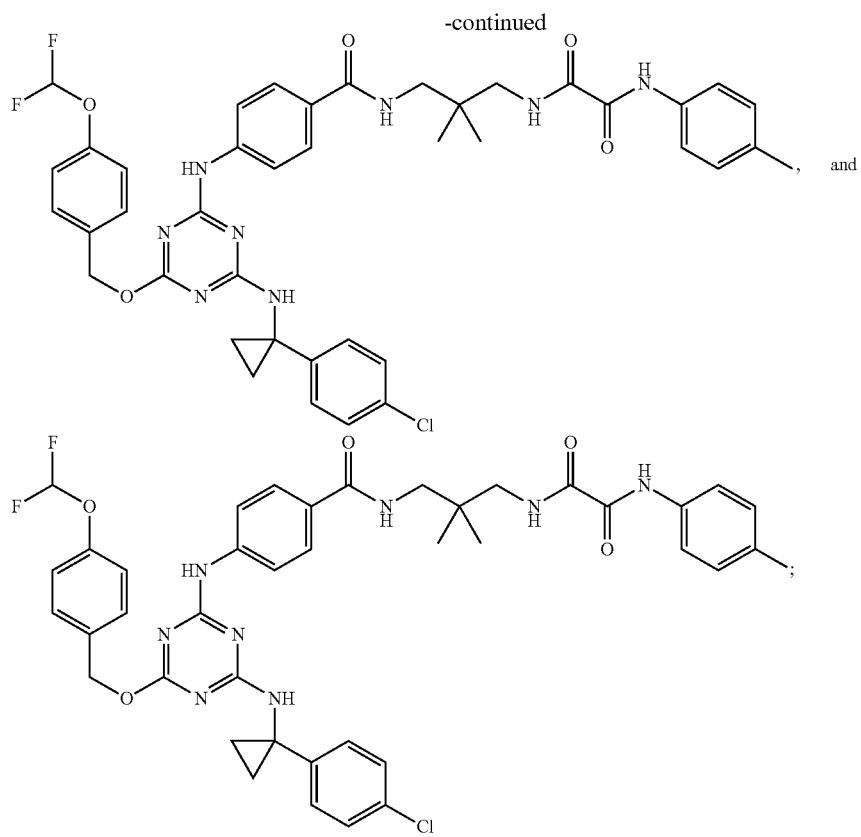

or a pharmaceutically acceptable salt thereof.

13. A composition comprising a compound of claim 1, or a pharmaceutically acceptable salt thereof, and a pharmaceutically acceptable carrier.

14. A method of treating hepatitis C infection comprising administering a therapeutically effective amount of a compound of claim 1 to a patient infected with the HCV virus and suitable for therapy as understood by practitioners in the field of hepatitis and HCV infection.

* * * * *